United States Patent
Nakano et al.

(10) Patent No.: US 12,410,182 B2
(45) Date of Patent: Sep. 9, 2025

(54) COMPOUND, ORGANIC ELECTROLUMINESCENCE DEVICE AND ELECTRONIC APPARATUS

(71) Applicant: IDEMITSU KOSAN CO., LTD., Tokyo (JP)

(72) Inventors: Yuki Nakano, Tokyo (JP); Taro Yamaki, Tokyo (JP); Satomi Tasaki, Tokyo (JP); Tomoki Kato, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 18/946,939

(22) Filed: Nov. 14, 2024

(65) Prior Publication Data

US 2025/0092059 A1    Mar. 20, 2025

Related U.S. Application Data

(63) Continuation of application No. 18/891,132, filed on Sep. 20, 2024, which is a continuation of application No. 17/282,347, filed as application No. PCT/JP2019/039846 on Oct. 9, 2019, now Pat. No. 12,202,837, which is a continuation-in-part of application No. 16/593,743, filed on Oct. 4, 2019, now Pat. No. 10,804,474, and a continuation-in-part of application No. 16/557,675, filed on Aug. 30, 2019, now Pat. No. 10,763,444.

(30) Foreign Application Priority Data

| Oct. 9, 2018 | (JP) | 2018-190838 |
| Oct. 9, 2018 | (JP) | 2018-191224 |
| May 30, 2019 | (JP) | 2019-101578 |
| May 30, 2019 | (JP) | 2019-101675 |

(51) Int. Cl.
| C07D 493/00 | (2006.01) |
| H10K 50/11  | (2023.01) |
| H10K 85/40  | (2023.01) |
| H10K 85/60  | (2023.01) |
| H10K 101/10 | (2023.01) |

(52) U.S. Cl.
CPC ......... *C07D 493/00* (2013.01); *H10K 85/40* (2023.02); *H10K 85/622* (2023.02); *H10K 85/623* (2023.02); *H10K 85/626* (2023.02); *H10K 85/633* (2023.02); *H10K 85/636* (2023.02); *H10K 85/6574* (2023.02); *H10K 85/6576* (2023.02); *H10K 50/11* (2023.02); *H10K 2101/10* (2023.02)

(58) Field of Classification Search
None
See application file for complete search history.

(56) References Cited

U.S. PATENT DOCUMENTS

| 10,763,444 B2 | 9/2020  | Nakano et al. |
| 10,804,474 B2 | 10/2020 | Nakano et al. |
| 11,482,675 B1 | 10/2022 | Tasaki et al. |

(Continued)

FOREIGN PATENT DOCUMENTS

| CN | 110317186 A | 10/2019 |
| CN | 111937173 A | 11/2020 |

(Continued)

OTHER PUBLICATIONS

Lee et al., Journal of Nanoscience and Nanotechnology, vol. 16, (2016), pp. 8460-8464.
Third-Party Submission issued in corresponding Korean Patent Application No. 10-2021-7010371, dated Nov. 16, 2022 (42 pages).

(Continued)

*Primary Examiner* — Jeffrey D Washville
(74) *Attorney, Agent, or Firm* — Foley & Lardner LLP

(57) ABSTRACT

A compound having structures represented by the following formulas (1) or (2): wherein in the formulas (1) and (2), at least one of $R_1$ to $R_8$ is a deuterium atom.

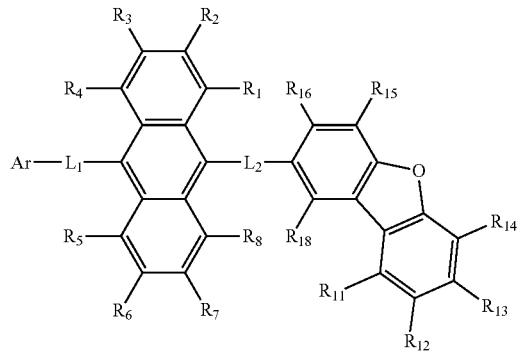

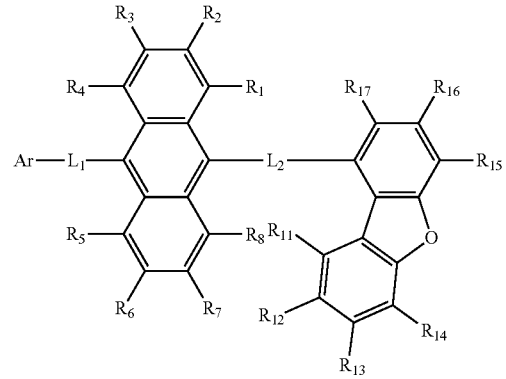

23 Claims, No Drawings

(56) References Cited

U.S. PATENT DOCUMENTS

| | | |
|---|---|---|
| 2014/0001459 A1 | 1/2014 | Gao |
| 2015/0236274 A1 | 8/2015 | Hatakeyama et al. |
| 2016/0079542 A1 | 3/2016 | Itoi |
| 2016/0204355 A1 | 7/2016 | Kim et al. |
| 2016/0351817 A1 | 12/2016 | Kim et al. |
| 2016/0351818 A1 | 12/2016 | Kim et al. |
| 2017/0018723 A1 | 1/2017 | Cha et al. |
| 2017/0025608 A1 | 1/2017 | Herron et al. |
| 2017/0125686 A1 | 5/2017 | Heil et al. |
| 2017/0324045 A1 | 11/2017 | Takahashi et al. |
| 2018/0009776 A1 | 1/2018 | Cha et al. |
| 2018/0019430 A1 | 1/2018 | Cha et al. |
| 2018/0123055 A1 | 5/2018 | Park et al. |
| 2018/0198076 A1 | 7/2018 | Takahashi et al. |
| 2018/0233669 A1 | 8/2018 | Lee et al. |
| 2018/0277771 A1 | 9/2018 | Park et al. |
| 2018/0301629 A1 | 10/2018 | Hatakeyama et al. |
| 2019/0058124 A1 | 2/2019 | Hatakeyama et al. |
| 2019/0097142 A1 | 3/2019 | Takahashi et al. |
| 2019/0207112 A1 | 7/2019 | Hatakeyama et al. |
| 2019/0305227 A1 | 10/2019 | Yoon et al. |
| 2019/0341556 A1 | 11/2019 | Takahashi et al. |
| 2019/0393420 A1 | 12/2019 | Takeda et al. |
| 2019/0393429 A1 | 12/2019 | Takahashi et al. |
| 2021/0053998 A1 | 2/2021 | Kim et al. |
| 2021/0296590 A1 | 9/2021 | Cha et al. |
| 2022/0246864 A1 | 8/2022 | Yoon et al. |

FOREIGN PATENT DOCUMENTS

| | | | |
|---|---|---|---|
| CN | 112005392 A | | 11/2020 |
| EP | 3 524 660 A1 | | 8/2019 |
| JP | 2006-151844 A | | 6/2006 |
| JP | 2015-153911 A | | 8/2015 |
| JP | 2017-514807 A | | 6/2017 |
| JP | 2018-157209 A | | 10/2018 |
| KR | 2009-0086015 A | | 8/2009 |
| KR | 2013-0022071 A | | 3/2013 |
| KR | 2014-0058290 A | | 5/2014 |
| KR | 2016-0102881 A | | 8/2016 |
| KR | 2017-0039020 A | | 4/2017 |
| KR | 2019-0056338 A | | 5/2019 |
| KR | 2019-0113498 A | | 10/2019 |
| KR | 2019-0139794 A | | 12/2019 |
| KR | 2020-0019272 A | | 2/2020 |
| KR | 2020-0095429 A | | 8/2020 |
| KR | 2020-0030003 A | | 12/2020 |
| WO | WO-2010/066830 A1 | | 6/2010 |
| WO | WO-2010/071362 A2 | | 6/2010 |
| WO | WO-2010/099534 A2 | | 9/2010 |
| WO | WO-2010/135395 A1 | | 11/2010 |
| WO | WO-2013/106041 A1 | | 7/2013 |
| WO | WO-2015/102118 A1 | | 7/2015 |
| WO | WO-2015/181667 A1 | | 12/2015 |
| WO | WO-2016/117848 A1 | | 7/2016 |
| WO | WO-2016/152544 A1 | | 9/2016 |
| WO | WO-2017/023021 A1 | | 2/2017 |
| WO | WO-2017/188111 A1 | | 11/2017 |
| WO | WO-2018/151065 A1 | | 8/2018 |
| WO | WO-2020/022751 A1 | | 1/2020 |

OTHER PUBLICATIONS

Third Party Submission issued in corresponding Korean Patent Application No. 10-2021-7010371, dated Dec. 19, 2022.

Wu, C.L. et al., 2014. High efficiency non-dopant blue organic light-emitting diodes based on anthracene-based fluorophores with molecular design of charge transport and red-shifted emission proof. Journal of Materials Chemistry C, 2(35), pp. 7188-7200. (2014).

Tsuji et al., "The hydrogen/deuterium isotope effect of the host material on the lifetime of organic light-emitting diodes." Chemical Communications, vol. 50, Sep. 15, 2014, pp. 14870-14872.

Yao et al. "Lifetime Enhancement and Degradation Study of Blue OLEDs Using Deuterated Materials" ACS Applied Materials & Interfaces, vol. 15, Jan. 26, 2023, pp. 7255-7262.

Office Action issued in corresponding Chinese Patent Application No. 201980066851.7 dated Dec. 5, 2023 (10 pages).

International Preliminary Report on Patentability (including the Written Opinion), dated Apr. 22, 2021, issued in corresponding PCT Application No. PCT/JP2019/039846 (9 pages).

International Preliminary Report on Patentability (including the Written Opinion), dated Apr. 22, 2021, issued in corresponding PCT Application No. PCT/JP2019/039870 (9 pages).

International Search Report and Written Opinion, dated Dec. 24, 2019, issued in corresponding PCT Application No. PCT/JP2019/039870 (18 pages).

COMPOUND, ORGANIC ELECTROLUMINESCENCE DEVICE AND ELECTRONIC APPARATUS

CROSS-REFERENCE TO RELATED APPLICATIONS

The present application is a Track One continuation of U.S. patent application Ser. No. 18/891,132, filed on Sep. 20, 2024, which is a continuation of U.S. patent application Ser. No. 17/282,347, filed on Apr. 1, 2021, which claims priority under 35 U.S.C. § 371 to International Patent Application No. PCT/JP2019/039846, filed Oct. 9, 2019, which claims priority to and the benefit of U.S. patent application Ser. No. 16/557,675, filed on Aug. 30, 2019 (issued as U.S. Pat. No. 10,763,444, on Sep. 1, 2020), and U.S. patent application Ser. No. 16/593,743, filed on Oct. 4, 2019 (issued as U.S. Pat. No. 10,804,474, on Oct. 4, 2019), and Japanese Patent Application No. 2019-101578, filed on May 30, 2019, and Japanese Patent Application No. 2019-101675, filed on May 30, 2019, and Japanese Patent Application No. 2018-191224, filed on Oct. 9, 2018, and Japanese Patent Application No. 2018-190838, filed on Oct. 9, 2018. The contents of these applications are hereby incorporated by reference in their entireties.

TECHNICAL FIELD

The invention relates to a new compound, an organic electroluminescence device and an electronic apparatus.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

Although materials for an organic EL device are being improved gradually to increase the performances of the organic EL device (for example, Patent Documents 1 to 9), high performances are further offered. In particular, improvement in lifetime of an organic EL device is an important task relating to a lifetime of commercial products provided with the organic EL device, and thus a material enabling to realize along-lifetime organic EL device is required.

RELATED ART DOCUMENTS

Patent Documents

Patent Document 1: WO2017/023021
Patent Document 2: WO2013/106041
Patent Document 3: Publication of US Patent Application No. 20170025608
Patent Document 4: WO2017/023021
Patent Document 5: JP-A-2006-151844
Patent Document 6: WO2010/099534
Patent Document 7: WO2010/135395
Patent Document 8: WO2010/071362
Patent Document 9: WO2010/066830

SUMMARY OF THE INVENTION

An object of the invention is to provide a compound capable of producing an organic EL device having along lifetime, an organic EL device having along lifetime and an electronic apparatus provided with the organic EL device.

As a result of extensive studies, the inventors have found that an organic EL device having along lifetime can be obtained by using compounds having a specific structure represented by formula (1) or (2), and they have achieved the invention.

According to the invention, the following compound, organic EL device and electric apparatus can be provided.

1. A compound having structures represented by the following formulas (1) or (2):

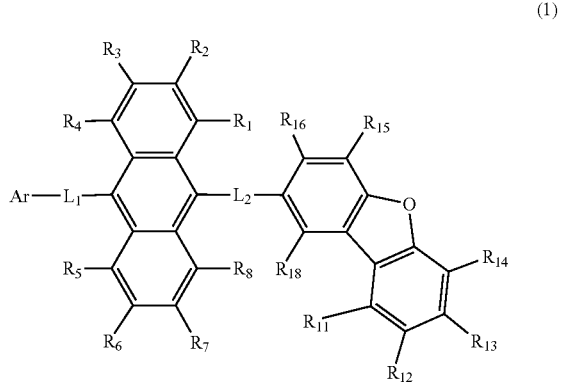

(1)

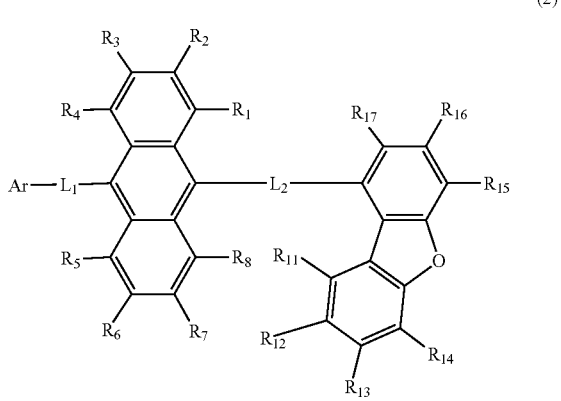

(2)

wherein in the formulas (1) and (2),
$R_1$ to $R_6$ and $R_{11}$ to $R_{14}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si$(R_{901})(R_{902})(R_{903})$,
—O—$(R_{904})$,
—S—$(R_{905})$,
—N$(R_{906})(R_{907})$,
a halogen atom, a cyano group, a nitro group,
a substituted or unsubstituted aryl group having 6 to 50 ring carbon atoms, or
a substituted or unsubstituted monovalent heterocylic group having 5 to 50 ring atoms;
$R_{15}$ to $R_{18}$ are hydrogen atoms;
$R_{901}$ to $R_{907}$ are independently a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_{901}$ to $R_{907}$ is a deuterium atom;
two or more adjacent groups of $R_1$ to $R_4$, two or more adjacent groups of $R_5$ to $R_6$ and two or more adjacent groups of $R_{11}$ to $R_{14}$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms; Ar is
a substituted or unsubstituted aryl group having 6 to 50 ring carbon atoms, or
a substituted or unsubstituted monovalent heterocyclic group having 5 to 50 ring atoms.

2. An organic electroluminescence device comprising:
a cathode, an anode, and one or two or more organic layer disposed between the cathode and the anode, wherein at least one organic layer comprises the compound according to the above 1.

3. An electronic apparatus provided with the organic electroluminescence device according to the above 2.

According to the invention, a compound capable of producing an organic EL device having along lifetime, an organic EL device having along lifetime, and an electronic apparatus provided with the organic EL device can be provided.

MODE FOR CARRYING OUT THE INVENTION

Definition

In this specification, a hydrogen atom means an atom including isotopes different in the number of neutrons, namely, a protium, a deuterium and a tritium.

In this specification, to a bondable position in which a symbol such as "R", or "D" representing a deuterium atom is not specified in a chemical formula, a hydrogen atom, that is, alight hydrogen atom, a deuterium atom, or a tritium atom is bonded thereto.

In this specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocylic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, abenzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In this specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocylic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In this specification, a term "XX to YY carbon atoms" in an expression of "substituted or unsubstituted ZZ group including XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In this specification, a term "XX to YY atoms" in an expression of "substituted or unsubstituted ZZ group including XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternately, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9-spirobifluorenyl group,
a benzofluorenyl group,
a dibenzofluorenyl group,
a fluoranthenyl group,
a benzofluoranthenyl group, and
a perylenyl group.

A substituted aryl group:
an o-tolyl group,
a m-tolyl group,
a p-tolyl group,
a p-xyy group,
a m-xylyl group,
an o-xylyl group,
a p-isopropyl phenyl group,
a m-isopropylphenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group including at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocylic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocylic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed herein are merely one example, and the "substituted heterocylic group" described herein also includes a group in which "unsubstituted heterocyclic group" which has a substituent further has a substituent, and a group in which "substituted heterocyclic group" further has a substituent, and the like.

An unsubstituted heterocyclic group including a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acidinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group including an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group including a sulfur atom:
a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group including a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methybenzimidazolyl group,
an ethylbenzimidazolyl group,
a phenyltriazinyl group,
a biphenylyltriazinyl group,
a diphenyltriazinyl group,
a phenyquinazolinyl group, and
a biphenylylquinazolinyl group.

A substituted heterocyclic group including an oxygen atom:
a phenyldibenzofuranyl group,
a methyldibenzofuranyl group,
a t-butyldibenzofuranyl group, and
a monovalent residue of spiro[9H-xanthene-9,9-[9H]fluorene].

A substituted heterocyclic group including a sulfur atom:
a phenyldibenzothiophenyl group,
a methyldibenzothiophenyl group,
a t-butyldibenzothiophenyl group, and
a monovalent residue of spiro[9H-thioxanthene-9,9-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:

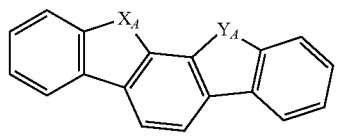

(XY-1)

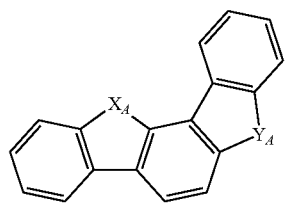

(XY-2)

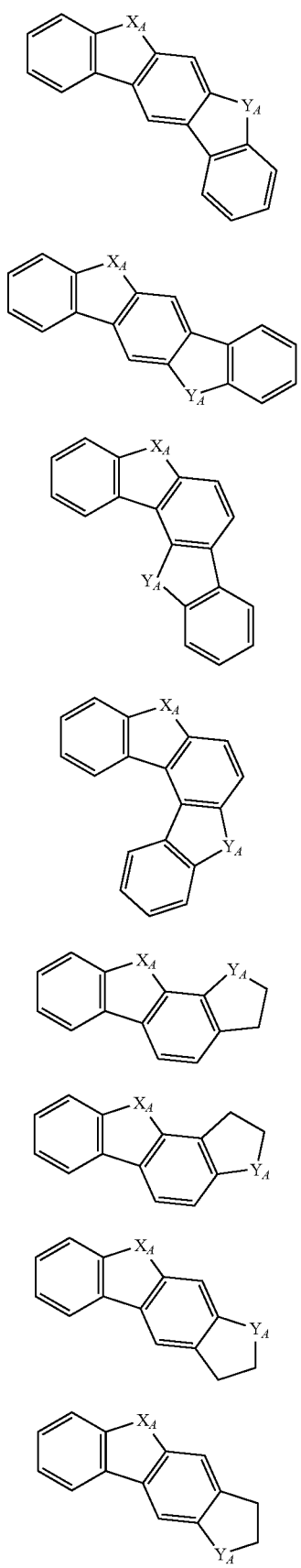
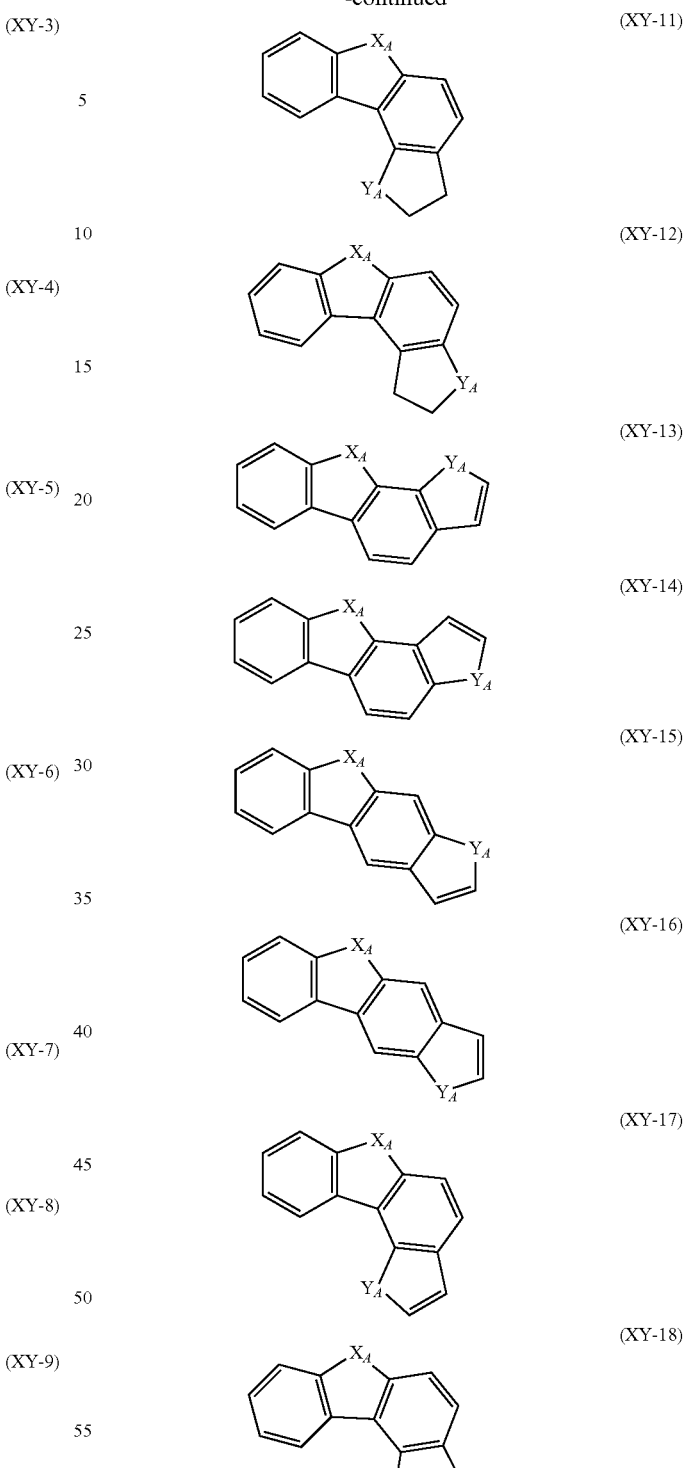
In the formulas (XY-1) to (XY-18), $X_A$ and $Y_A$ are independently an oxygen atom, a sulfur atom, NH or CH$_2$. However, at least one of $X_A$ and $Y_A$ is an oxygen atom, a sulfur atom or NH.
The heterocyclic ring represented by the formulas (XY-1) to (XY-18) becomes a monovalent heterocyclic group including a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:
a methyl group,
an ethyl group,
a n-propyl group,
an isopropyl group,
a n-butyl group,
an isobutyl group,
a s-butyl group, and
a t-butyl group.

A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described herein include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein are merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbonmyl group, and
a 2-norbonmyl group.

A substituted cycloalkyl group:
a 4-methylcyclohexyl group.

Specific examples (specific example group G7) of the group represented by —Si(R901)(R902)(R903) described herein include
—Si(G1)(G1)(G1),
—Si(G1)(G2)(G2), —Si(G1)(G1)(G2),
—Si(G2)(G2)(G2),
—Si(G3)(G3)(G3),
—Si(G5)(G5)(G5) and
—Si(G6)(G6)(G6).

In which,

G1 is the "aryl group" described in the specific example group G1.

G2 is the "heterocyclic group" described in the specific example group G2.

G3 is the "alkyl group" described in the specific example group G3.

G5 is the "alkynyl group" described in the specific example group G5.

G6 is the "cycloalkyl group" described in the specific example group G6.

Specific examples (specific example group G8) of the group represented by —O—(R904) described herein include
—O(G1),
—O(G2),
—O(G3) and
—O(G6).

In which,

G1 is the "aryl group" described in the specific example group G1.

G2 is the "heterocyclic group" described in the specific example group G2.

G3 is the "alkyl group" described in the specific example group G3.

G6 is the "cycloalkyl group" described in the specific example group G6.

Specific examples (specific example group G9) of the group represented by —S—(R905) described herein include
—S(G1),
—S(G2),
—S(G3) and
—S(G6).

In which,

G1 is the "aryl group" described in the specific example group G1.

G2 is the "heterocyle group" described in the specific example group G2.

G3 is the "alkyl group" described in the specific example group G3.

G6 is the "cycloalkyl group" described in the specific example group G6.

Specific examples (specific example group G10) of the group represented by —N($R_{906}$)($R_{907}$) described herein include
—N(G1)(G1),
—N(G2)(G2),
—N(G1)(G2),
—N(G3)(G3) and
—N(G6) (G6).

In which,

G1 is the "aryl group" described in the specific example group G1.

G2 is the "heterocyle group" described in the specific example group G2.

G3 is the "alkyl group" described in the specific example group G3.

G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthiol group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthiol group" described herein include a group represented by —S(G1), where G1 is the "aryl group" described in the specific example group G1. The number of ring carbon atoms of the "unsubstituted arylthio group" are 6 to 50, preferably 6 b 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, am-biphenyl group, an o-biphenyl group, a p-terphenyl-4-yl group, a p-terphenyl-3-yl group, a p-terphenyl-2-yl group, am-terphenyl-4-yl group, am-terphenyl-3-yl group, am-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, an aphthobenzothiophenyl group, an azadibenzothiophenyl group, a diazadibenzothiophenyl group, a (9-phenyl)carbazolyl group (a(9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazoyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, a n imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

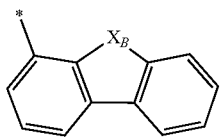
(XY-76)

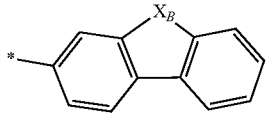
(XY-77)

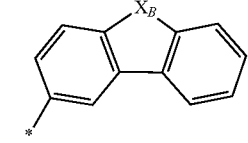
(XY-78)

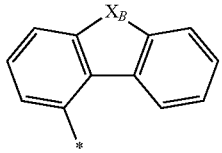
(XY-79)

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group G13) of the "substituted or unsubstituted divalent heterocyclic group" include a group in which the "heterocyclic group" described in the specific example group G2 is converted into divalence. Namely, specific examples (specific example group G13) of the "substituted or unsubstituted divalent heterocyclic group" refer to a group derived from the "heterocyclic group" described in specific example group G2 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group G14) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described herein is any group described below, unless otherwise specified.

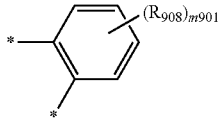
(XY-20)

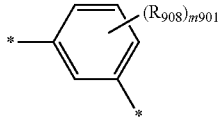
(XY-21)

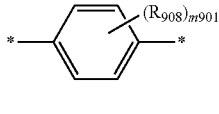
(XY-22)

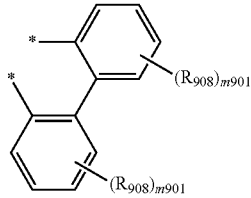
(XY-23)

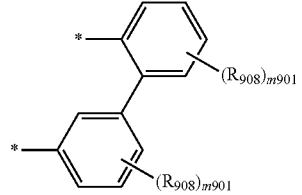
(XY-24)

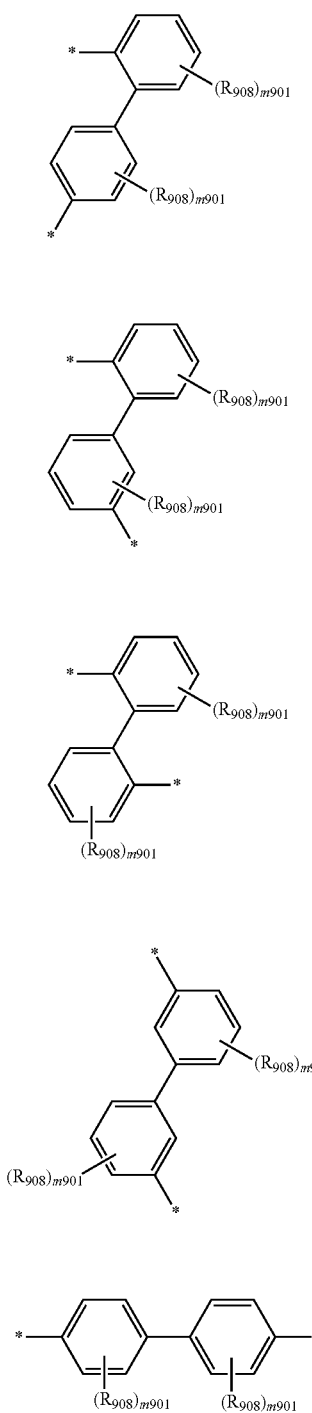
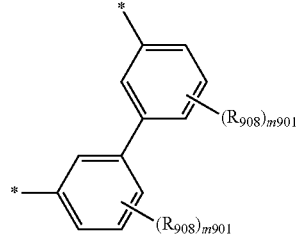
In the formulas (XY-20) to (XY-29), (XY-83) and (XY-84), $R_{908}$ is a substituent.
Then, m901 is an integer of 0 to 4, and when m901 is 2 or more, a plurality of $R_{908}$ may be the same with or different from each other.

(XY-37)
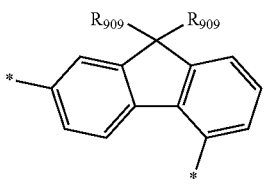

(XY-38)
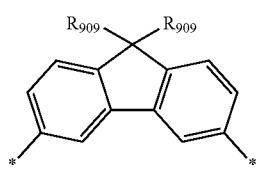

(XY-39)
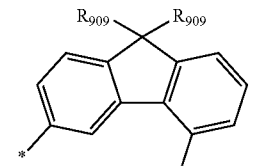

(XY-40)
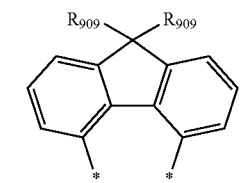

In the formulas (XY-30) to (XY-40), $R_{909}$ is independently a hydrogen atom or a substituent. Two of $R_{909}$ may form a ring by bonding with each other through a single bond.

(XY-41)
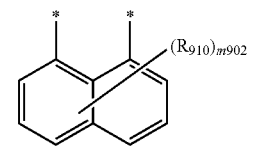

(XY-42)
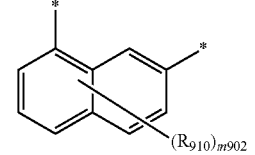

(XY-43)
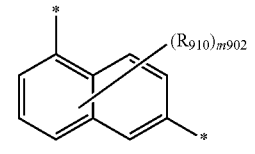

(XY-44)
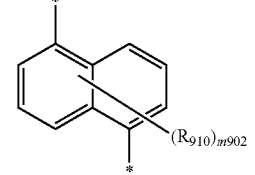

(XY-45)
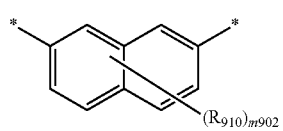

(XY-46)
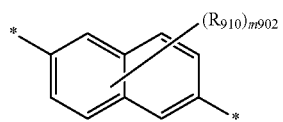

In the formulas (XY-41) to (XY-46), $R_{910}$ is a substituent.

Then, m902 is an integer of 0 to 6. When m902 is 2 or more, a plurality of $R_{910}$ may be the same with or different from each other.

The substituted or unsubstituted divalent heterocyclic group described herein is preferably any group described below, unless otherwise specified.

(XY-50)
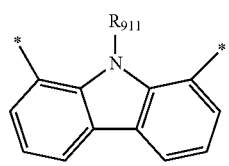

(XY-51)
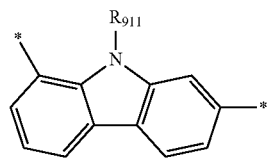

(XY-52)
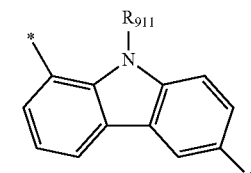

(XY-53)
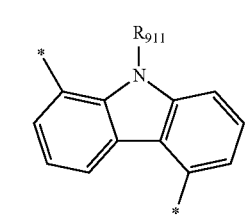

(XY-54)
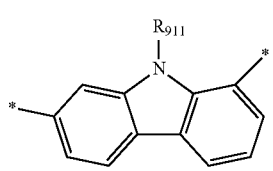

(XY-55)
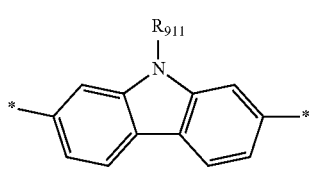

(XY-56) 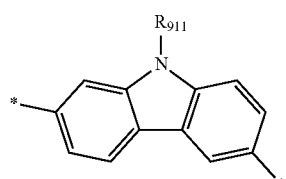
(XY-57) 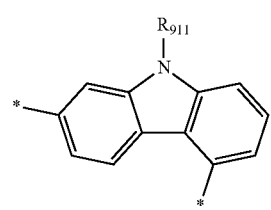
(XY-58) 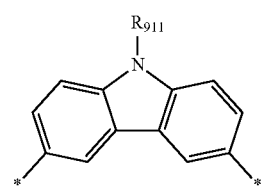
(XY-59) 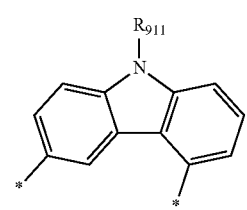
(XY-60) 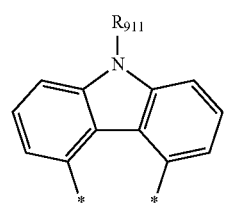
(XY-61) 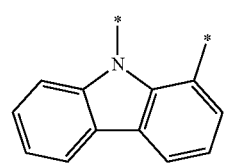
(XY-62) 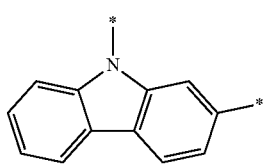
(XY-63) 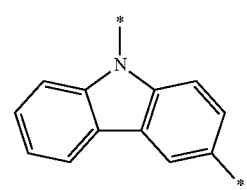
(XY-64) 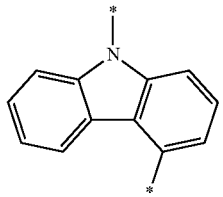
In the formulas (XY-50) to (XY-60), $R_{911}$ is a hydrogen atom or a substituent.
(XY-65) 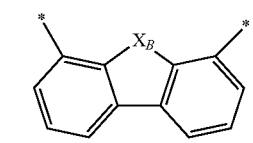
(XY-66) 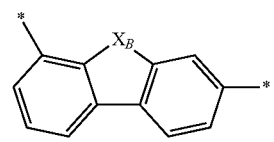
(XY-67) 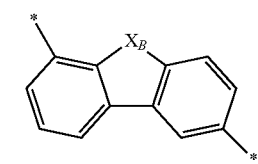
(XY-68) 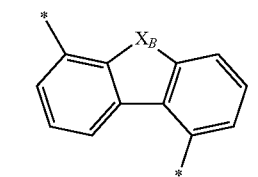
(XY-69) 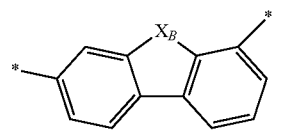
(XY-70) 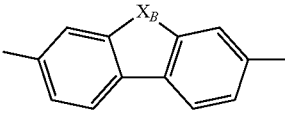
(XY-71) 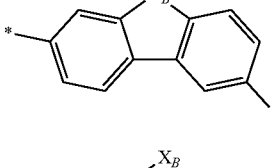
(XY-72) 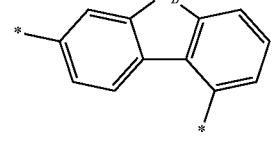

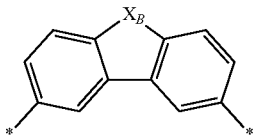
(XY-73)

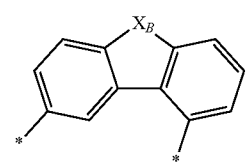
(XY-74)

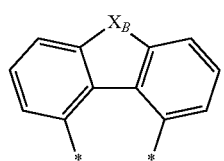
(XY-75)

In the formulas (XY-65) to (XY-75), $X_B$ is an oxygen atom or a sulfur atom.

Herein, a case where "one or more sets of two or more groups adjacent to each other form a substituted or unsubstituted and saturated or unsaturated ring by bonding with each other" will be described by taking, as an example, a case of an anthracene compound represented by the following formula (XY-80) in which a mother skeleton is an anthracene ring.

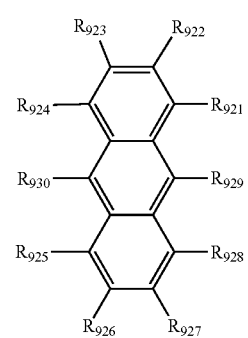
(XY-80)

For example, two adjacent to each other into one set when "one or more sets of two or more groups adjacent to each other form the ring by bonding with each other" among $R_{921}$ to $R_{930}$ include $R_{921}$ and $R_{922}$, $R_{9222}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ form a ring A by bonding with each other, and simultaneously $R_{925}$ and $R_{926}$ form a ring B by bonding with each other is represented by the following formula (XY-81).

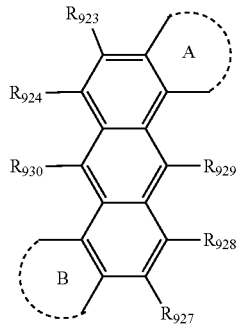
(XY-81)

A case where "two or more groups adjacent to each other" form a ring means that, for example, $R_{921}$ and $R_{922}$ form a ring A by bonding with each other, and $R_{922}$ and $R_{923}$ form a ring C by bonding with each other. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

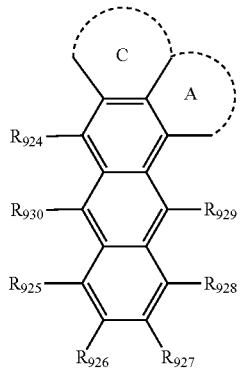
(XY-82)

The rings A to C formed in the formulas (XY81) and (XY82) area saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by w and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into abenzene ring. Further, when a saturated ring is formed, the ring is formed into a cyclohexane ring.

Here, "arbitrary elements" are preferably a C element, a N element, an O element and a S element In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of this specification, the substituent (hereinafter; referred to as an "arbitrary substituent" in several cases) in the case of the "substituted or unsubstituted" is a group selected from the group consisting of
  an unsubstituted alkyl group including 1 to 50 carbon atoms,
  an unsubstituted alkenyl group including 2 to 50 carbon atoms,
  an unsubstituted alkynyl group including 2 to 50 carbon atoms,
  an unsubstituted cycloalkyl group including 3 to 50 ring carbon atoms,
  —Si($R_{901}$)($R_{902}$)($R_{903}$),
  —O—($R_{904}$),
  —S—($R_{905}$)
  —N($R_{906}$)($R_{907}$)
  wherein,
  $R_{901}$ to $R_{907}$ are independently
  a hydrogen atom,
  a substituted or unsubstituted alkyl group including 1 to 50 carbon atoms,
  a substituted or unsubstituted cycloalkyl group including 3 to 50 ring carbon atoms,
  a substituted or unsubstituted aryl group including 6 to 50 ring carbon atoms, or
  a substituted or unsubstituted monovalent heterocyclic group including 5 to 50 ring atoms; and when two or more of $R_{901}$ to $R_{907}$ exist, two or more of $R_{901}$ to $R_{907}$ may be the same with or different from each other,
  a halogen atom, a cyano group, a nitro group,
  an unsubstituted aryl group including 6 to 50 ring carbon atoms, and
  an unsubstituted monovalent heterocyclic group including 5 to 50 ring atoms.

In one embodiment, the substituent in the case of "substituted or unsubstituied" is a group selected from the group consisting of
  an alkyl group including 1 to 50 carbon atoms,
  an aryl group including 6 to 50 ring carbon atoms, and
  a monovalent heterocyclic group including 5 to 50 ring atoms.

In one embodiment, the substituent in the case of "substituted or unsubstituied" is a group selected from the group consisting of
  an alkyl group including 1 to 18 carbon atoms,
  an aryl group including 6 to 18 ring carbon atoms, and
  a monovalent heterocyclic group including 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably abenzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[New Compound]

The compound according to one aspect of the invention is represented by the following formula (1) or (2).

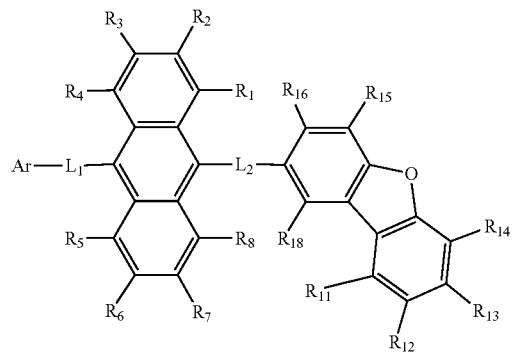

(1)

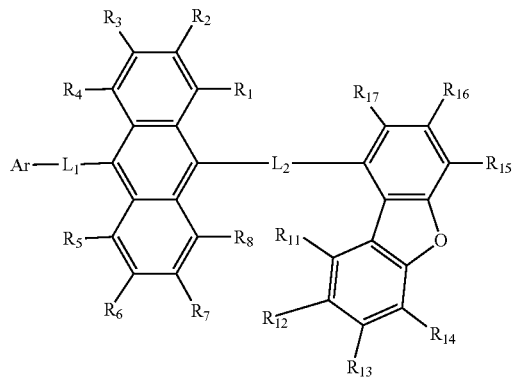

(2)

In the formulas (1) and (2),
$R_1$ to $R_8$ and $R_{11}$ to $R_{14}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, —Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{15}$ to $R_{18}$ are hydrogen atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$, two or more adjacent groups of $R_5$ to $R_6$ and two or more adjacent groups of $R_{11}$ to $R_{14}$ do not form a ring;
$L_1$ and $L_2$ are independently
a single bond,
a substituted or unsubstituted arylene group having 6 to 30 ring carbon atoms, or
a substituted or unsubstituted divalent heterocyclic group having 5 to 30 ring atoms;
Ar is
a substituted or unsubstituted aryl group having 6 to 50 ring carbon atoms, or
a substituted or unsubstituted monovalent heterocyclic group having 5 to 50 ring atoms.

By having the above structure, the compound according to one aspect of the invention can enhance the device performance when the compound is used in an organic EL device. Specifically, it is possible to provide an organic EL device with longer life.

According to one aspect of the present invention, a method for improving a performance of an organic EL device can also be provided. the method is characterized in that the above compound is used in the emitting layer of the organic EL device. Specifically, the method can improve an organic EL device performance as compared with the case where a compound having the same structure as formula (1) or (2) except that only protium atoms are contained as hydrogen atoms (hereinafter also referred to as "protium compound") is used as a host material. The case where the protium compound is used means that a host material in an emitting layer consists essentially of the protium compound (the ratio of the protium compound to the sum of the protium compound and the compound represented by formula (1) or (2) is 90 mol % or more, 95 mol % or more, or 99 mol % or more).

That is, it is possible to increase a performance of an organic EL device by, instead of a protium compound or in addition to a protium compound, using a compound obtained by replacing at least one protium atoms on an anthracene skeleton of the protium compound with a deuterium atom (a compound represented by formula (1) or (2)) as a host material.

All of $R_1$ to $R_8$ may be deuterium atoms or apart of them (e.g., one or two or more of $R_1$ to $R_8$) may be deuterium atoms.

$R_1$ to $R_8$ that are not deuterium atoms are preferably hydrogen atoms (protium atoms).

In one embodiment, at least one hydrogen atom contained in one or more groups selected from a group consisting of $L_1$ and $L_2$ is a deuterium atom. In more detail, in one embodiment, one or more groups selected from the group consisting of $L_1$ and $L_2$ are an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

In one embodiment, $L_1$ and $L_2$ are independently a single bond, or a substituted or unsubstituted arylene group having 6 to 14 ring carbon atoms. It is preferable that at least one of $L_1$ and $L_2$ is a single bond.

In one embodiment, $R_{11}$ to $R_{14}$ are hydrogen atoms.

In one embodiment, at least one $R_{11}$ to $R_{18}$ is a deuterium atom.

In one embodiment, at least one hydrogen atom contained in one or more Ar is a deuterium atom. In more detail, in one embodiment, Ar is an unsubstituted aryl group having 6 to 50 ring carbon atoms in which at least one hydrogen atom is a deuterium atom, or an unsubstituted monovalent heterocyclic group having 5 to 50 ring atoms in which at least one hydrogen atom is a deuterium atom.

Ar is preferably a substituted or unsubstituted aryl group having 6 to 50 ring carbon atoms, more preferably selected from groups represented by the following formulas (a1) to (a4).

(a1)

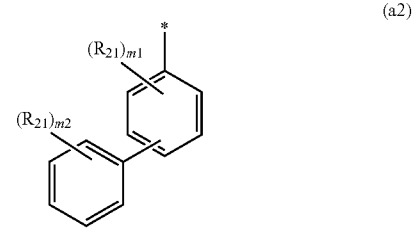

(a2)

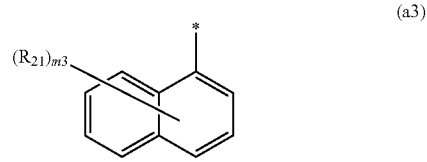

(a3)

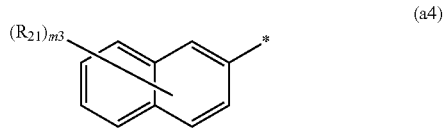

(a4)

In the formulas (a1) to (a4), * is a single bond bonding to $L_1$; $R_2$, is independently
a halogen atom, a cyano group, a nitro group,
a substituted or unsubstituted alkyl group having 1 to 50 carbon atoms, a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);
m1 is independently an integer of 0 to 4;
m2 is independently an integer of 0 to 5;
m3 is independently an integer of 0 to 7;
when each of m1 to m3 is 2 or more, the plural $R_{21}$s may be the same or different; and
when each of m1 to m3 is 2 or more, adjacent plural $R_{21}$s are bonded with each other to form a substituted or unsubstituted, saturated or unsaturated ring, or do not form a substituted or unsubstituted, saturated or unsaturated ring.

A bond position on $L_2$ side on the dibenzofuran skeleton, that is, at positions 1, 3, and 4 of dibenzofuran in formula (1), and at positions 2, 3, and 4 of dibenzofuran in formula (2), all of which are bonded to hydrogen atom, may be deuterium atom, or may be one or more (for example, positions 1 and 4 in formula (1), and positions 2 and 4 in formula (2)).

Existence of a deuterium atom in the compound is confirmed by Mass Spectrometry or 1H-NMR Spectrometry. The bonding position of a deuterium atom in the compound is identified by $^1$H-NMR Spectrometry. In concrete terms, it is confirmed as follows.

If it is identified that, by Mass Spectrometry, a molecular weight of a target compound is greater by "one" than a molecular weight of a corresponding compound in which all hydrogen atoms are protium atoms, it is confirmed that one deuterium atom exists in the target compound. Further, the number of deuterium atoms in a molecule can be confirmed by an integration value obtained by $^1$H-NMR analysis on the target compound, since no signal is observed by performing 1H-NMR analysis on a deuterium atom. The bonding position of a deuterium can be identified by performing $^1$H-NMR analysis on the target compound and assigning signals.

The composition according to one aspect of the invention contains the compound represented by formula (1) or (2), and the content ratio of the protium compound to the total of the compound represented by formula (1) or (2) and the protium compound is preferably 99 mol % or less. The content ratio of the protium compound is confirmed by Mass Spectrometry.

In the composition according to one aspect of the invention, the content ratio of the compound represented by formula (1) or (2) to the total of the compound represented by formula (1) or (2) and the protium compound is 30 mol % or more, 50 mol % or more, 70 mol % or more, 90 mol % or more, 95 mol % or more, 99 mol % or more, or 100 mol %.

In one embodiment, the compound represented by the formula (1) is a compound represented by following formula (1-1) and the compound represented by the formula (2) is a compound represented by following formula (2-1).

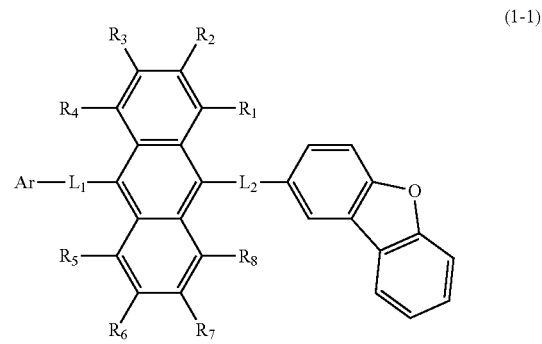

(1-1)

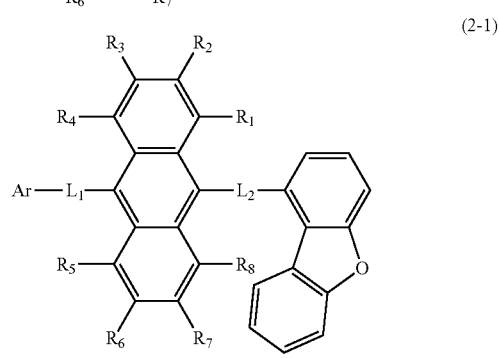

(2-1)

In the formulas (1-1) and (2-1), $R_1$ to $R_8$, Ar, $L_1$ and $L_2$ are as defined in the formula (1).

In one embodiment, the compound represented by the formula (1) is a compound represented by following formula (1-2) and the compound represented by the formula (2) is a compound represented by following formula (2-2).

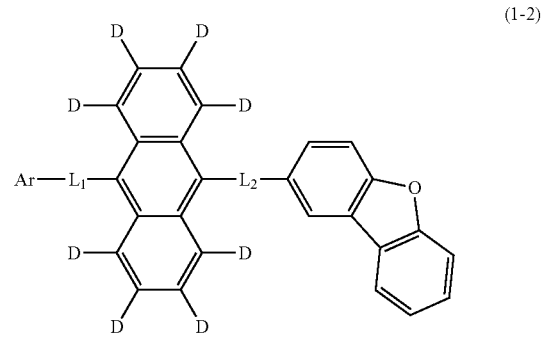

(1-2)

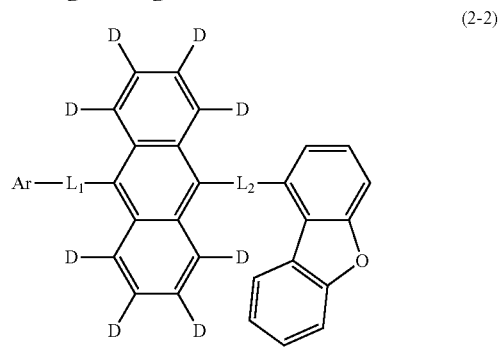

(2-2)

In the formulas (1-2) and (2-2), Ar, $L_1$ and $L_2$ are as defined in the formula (1).

The compound represented by the formula (1) or (2) can be synthesized in accordance with the synthesis process described in Examples by using publicly known alternative reactions or materials corresponding to a target compound.
Examples of the compound according to one aspect of the invention include the following compounds. In the specific examples, D represents deuterium atom.
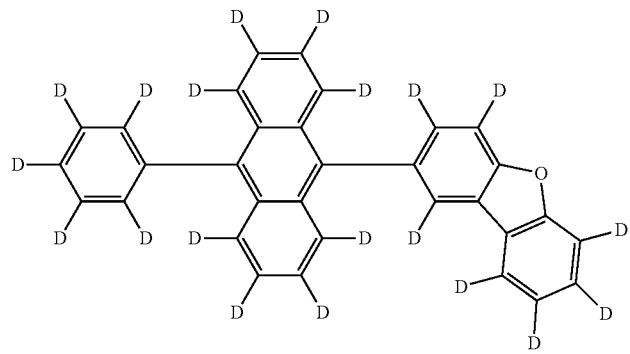
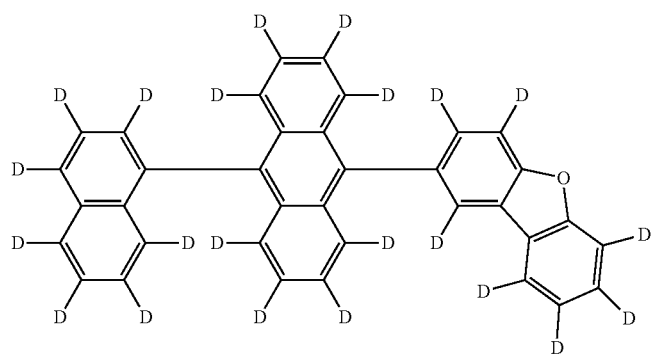
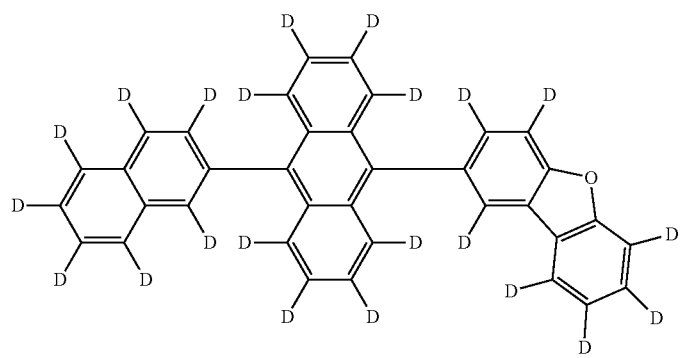
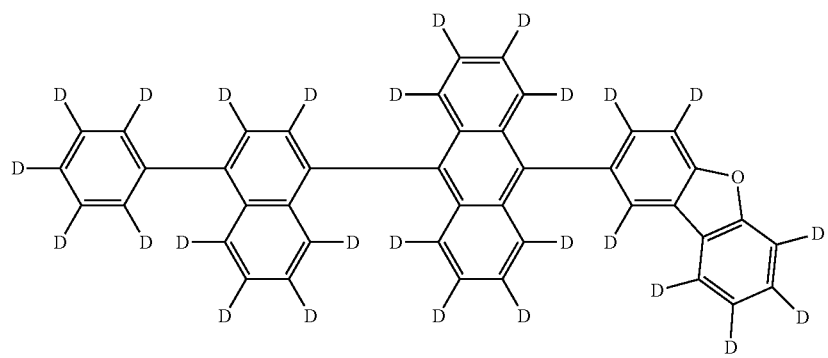

-continued
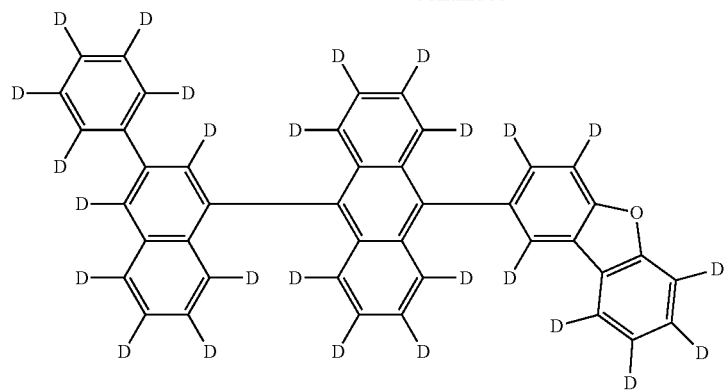
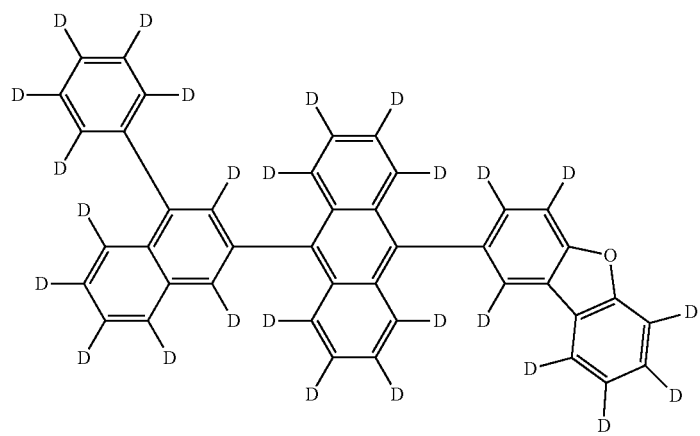
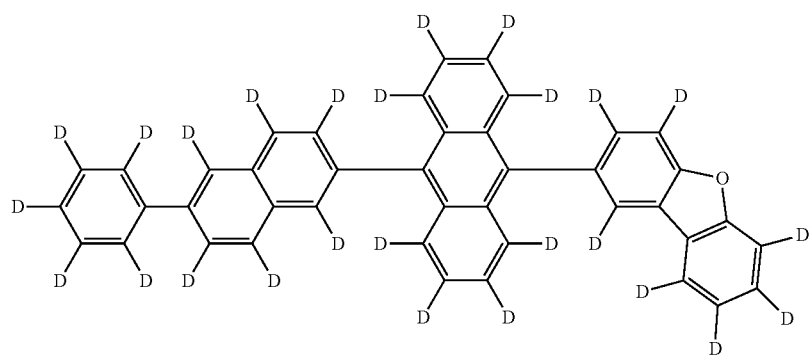
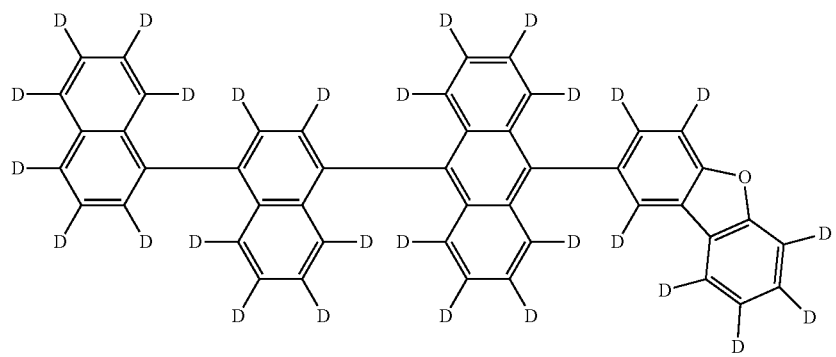

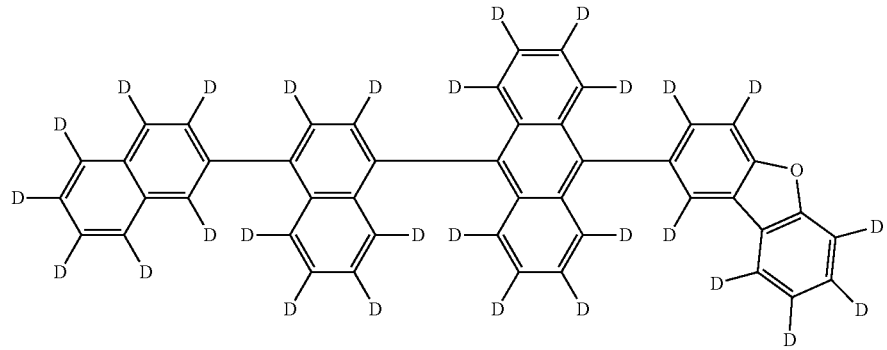
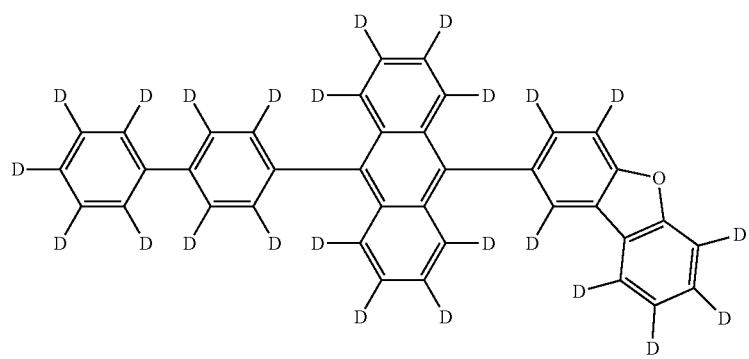
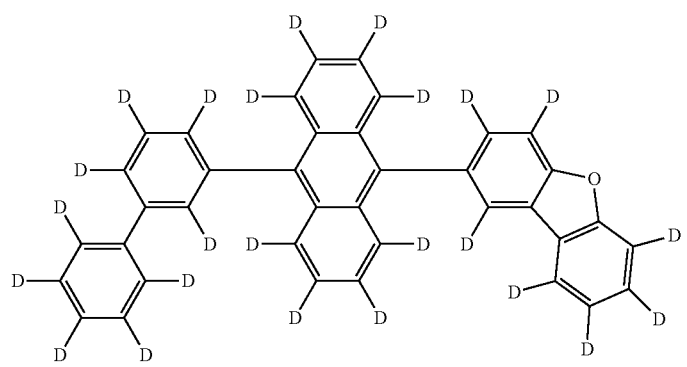

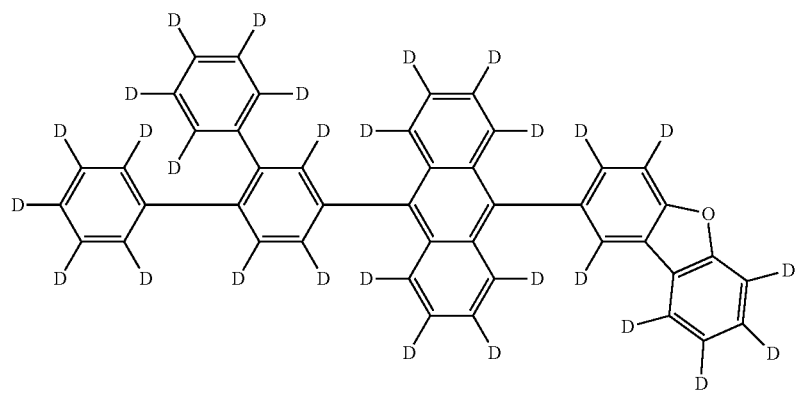
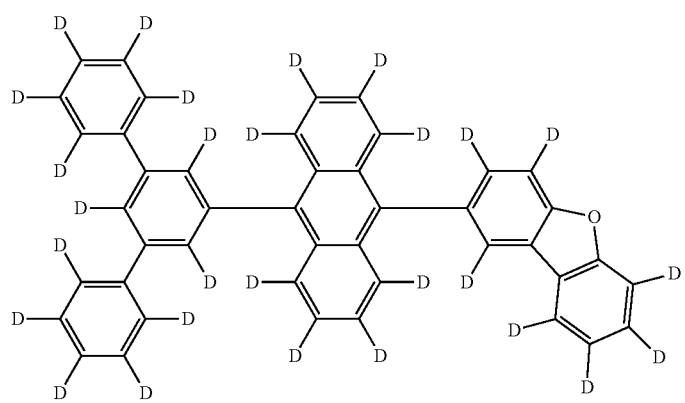
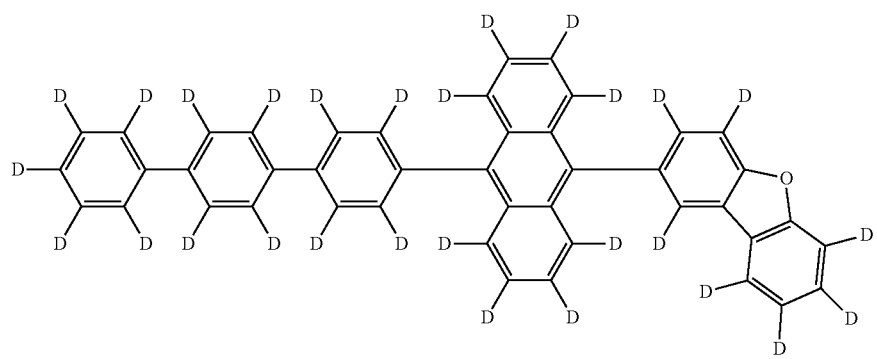
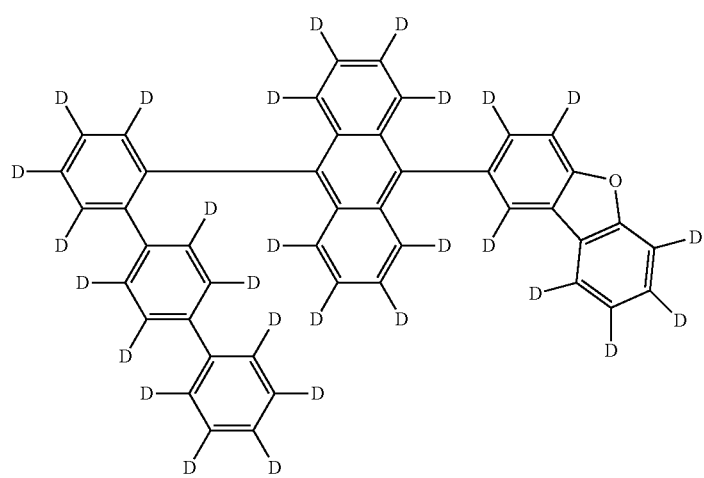

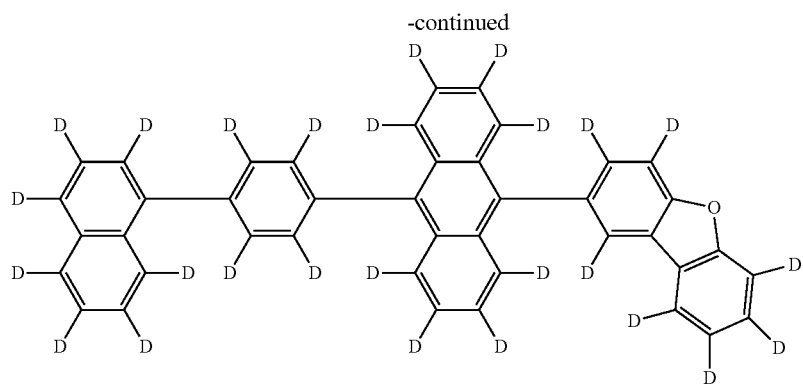
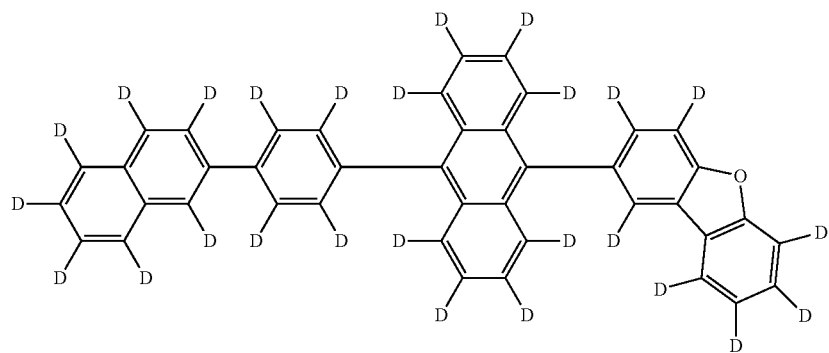
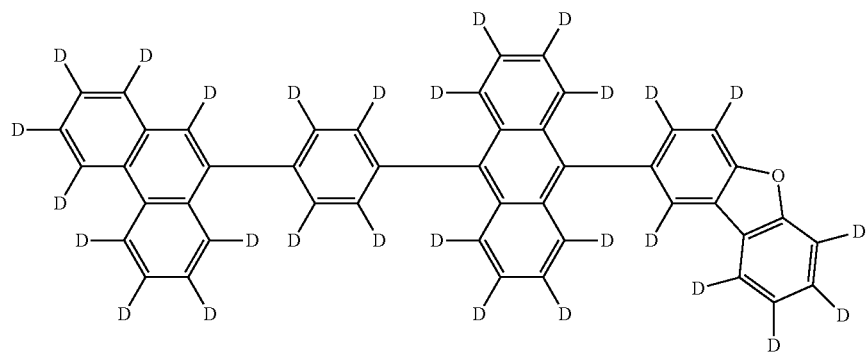
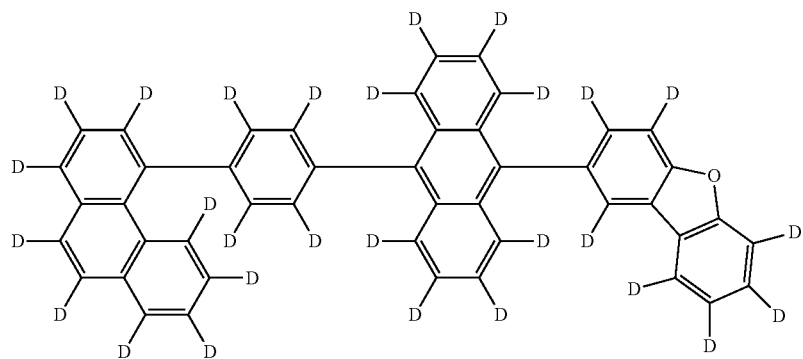

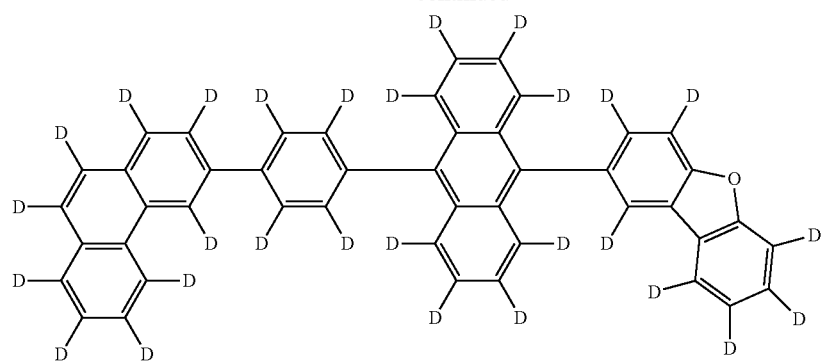
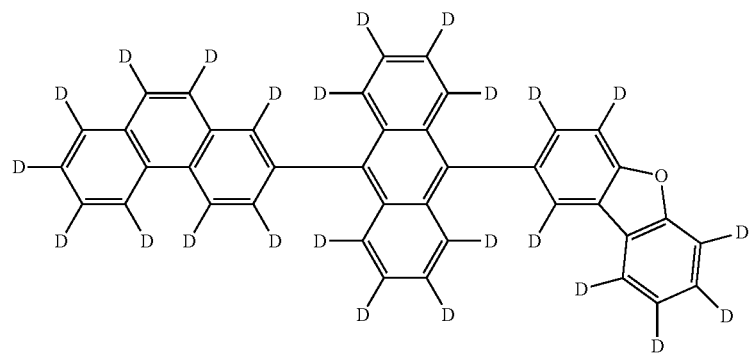
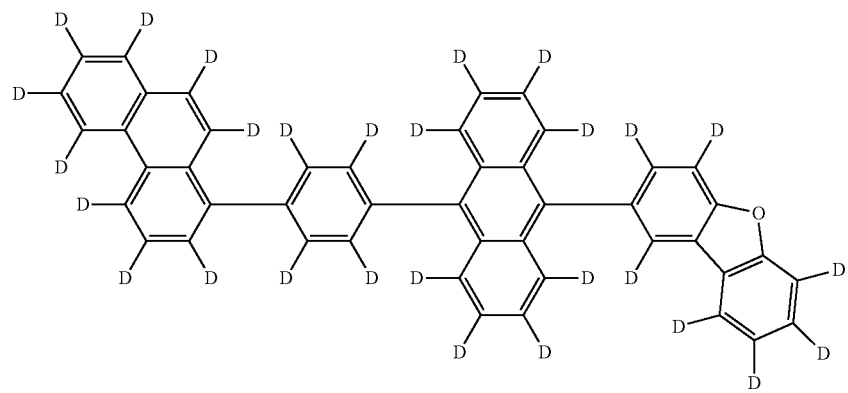
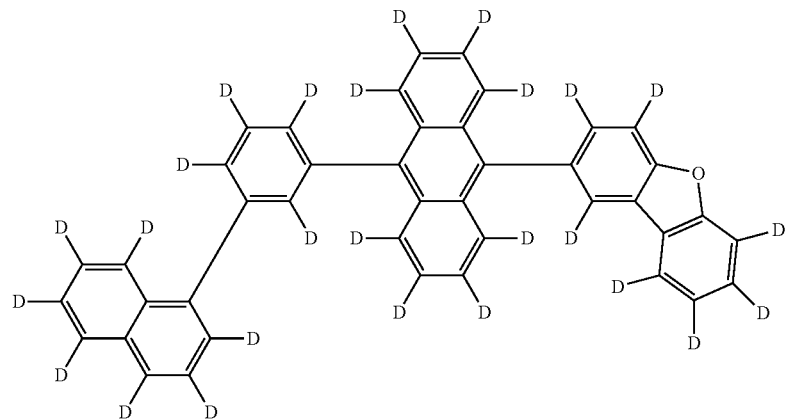

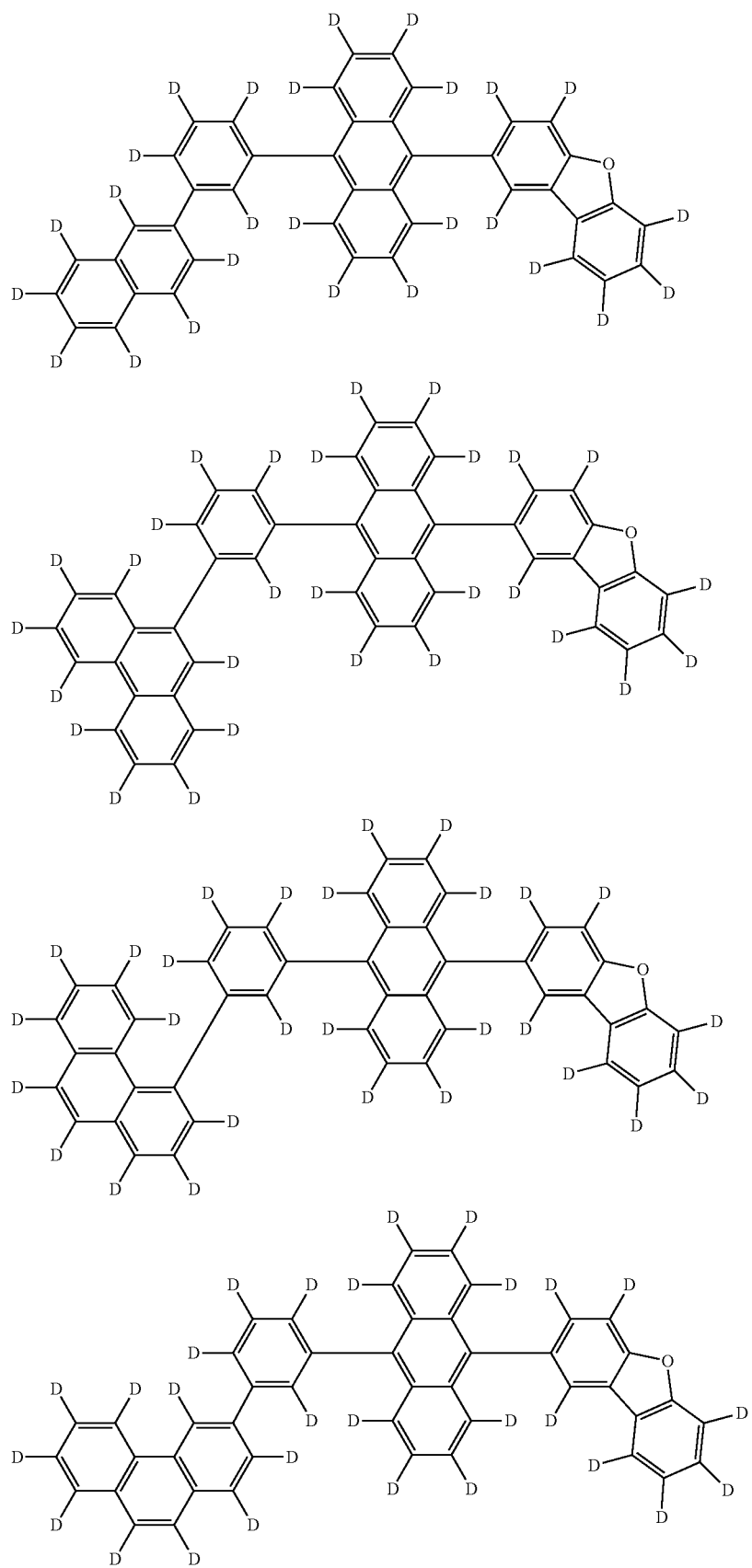

-continued
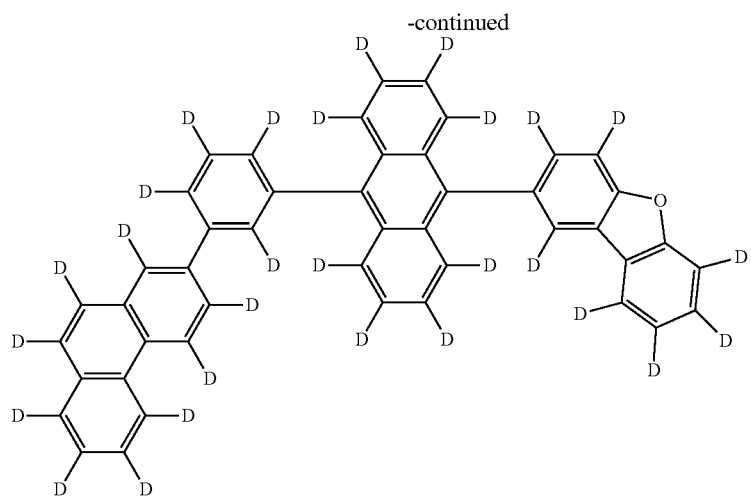
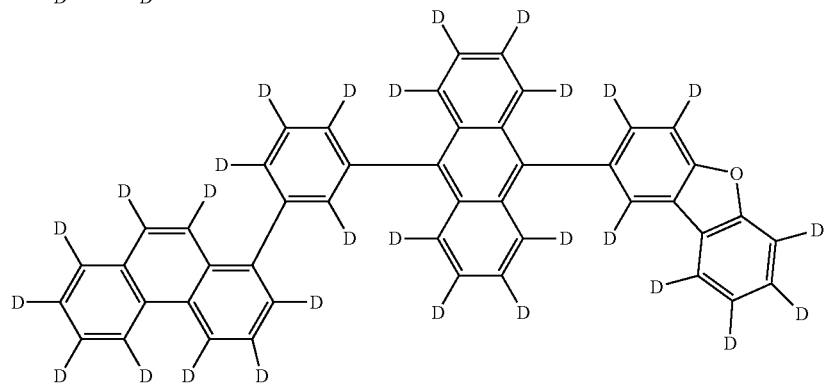
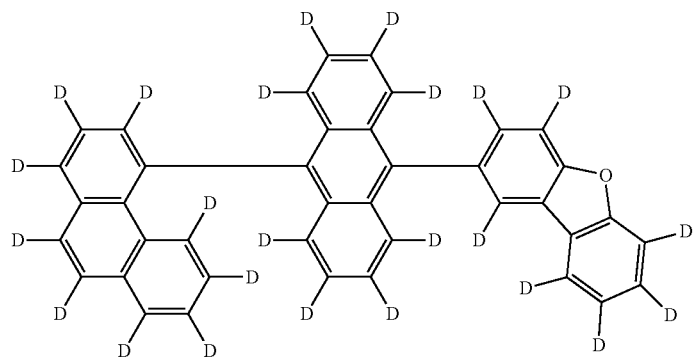
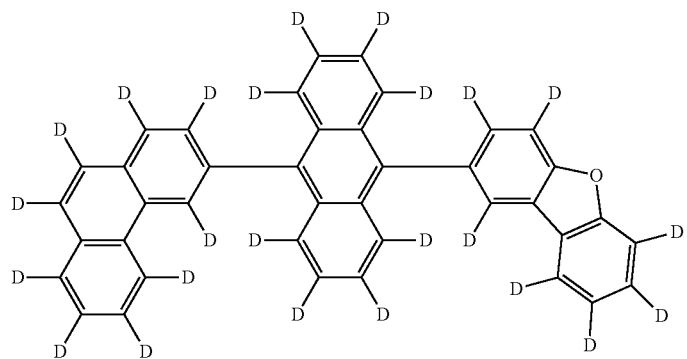

-continued
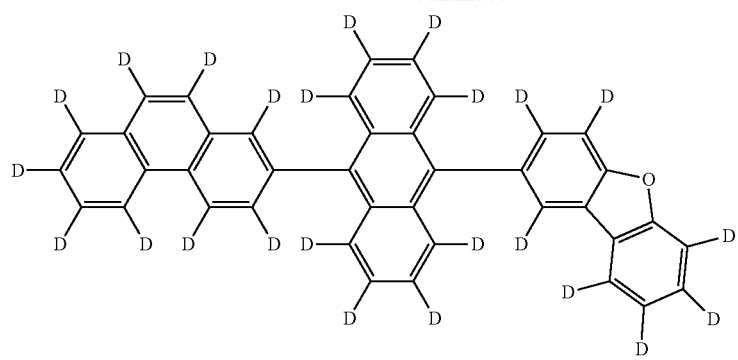
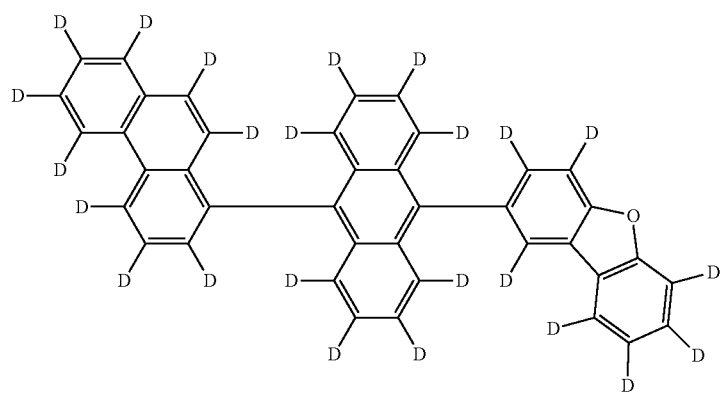
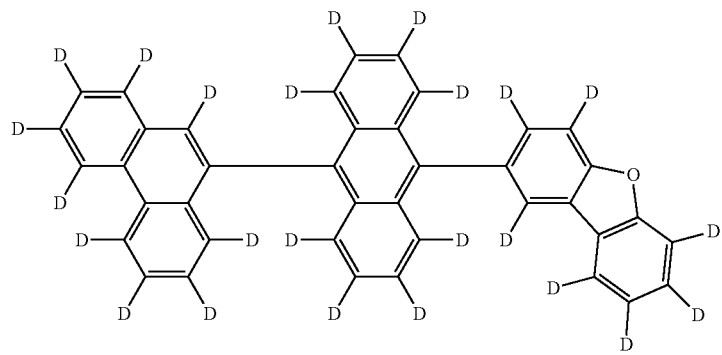
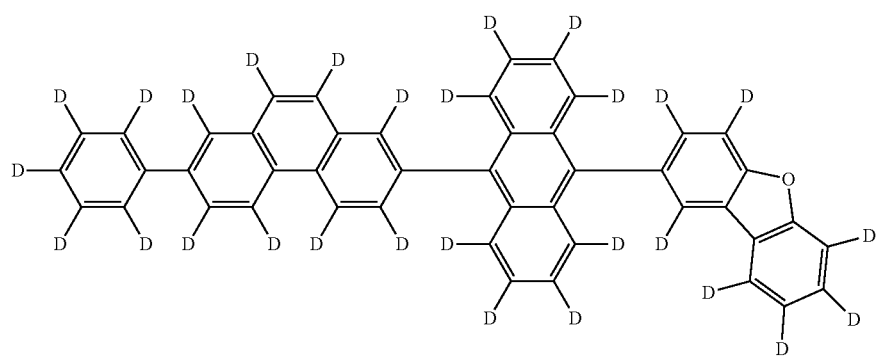

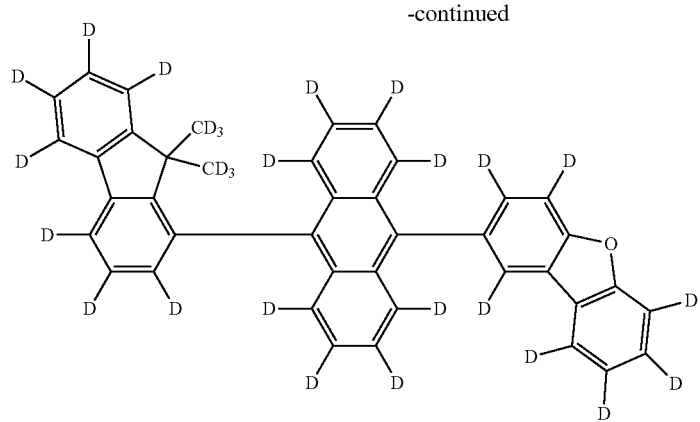
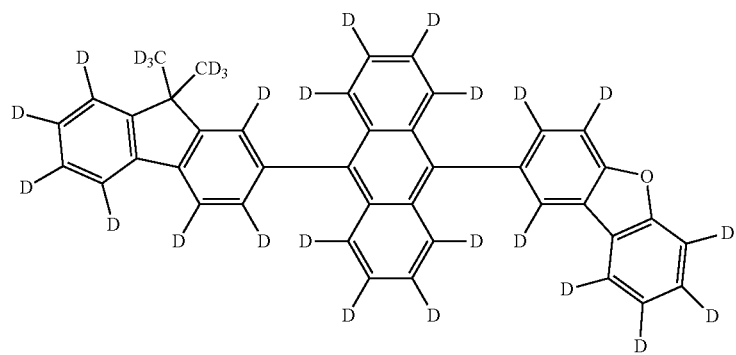
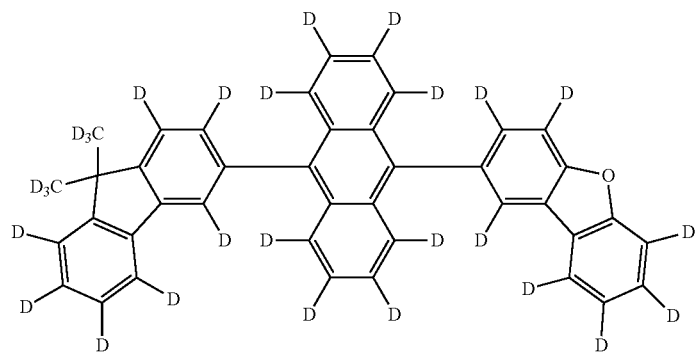
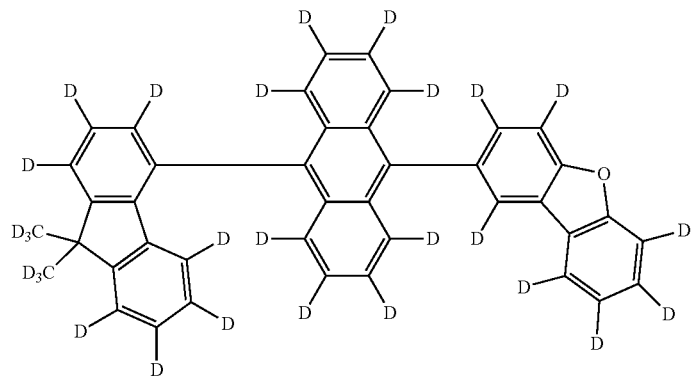

-continued
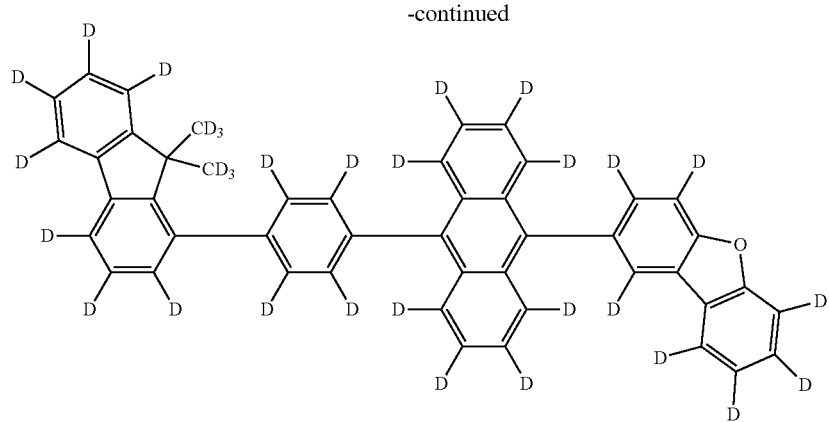
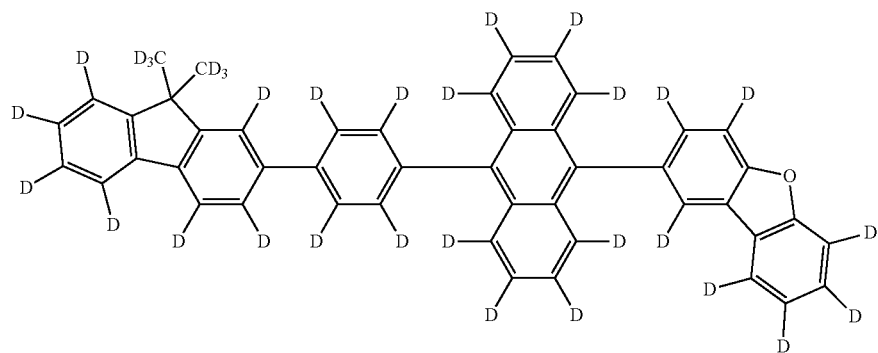
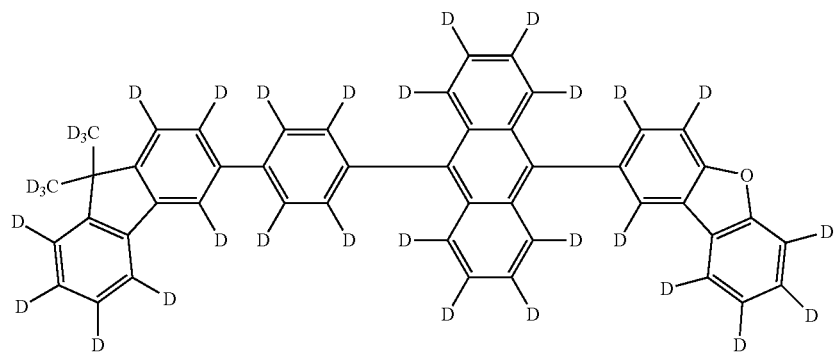
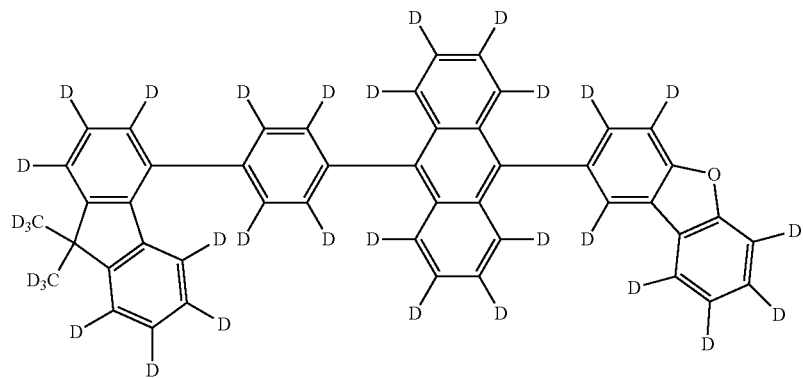

-continued
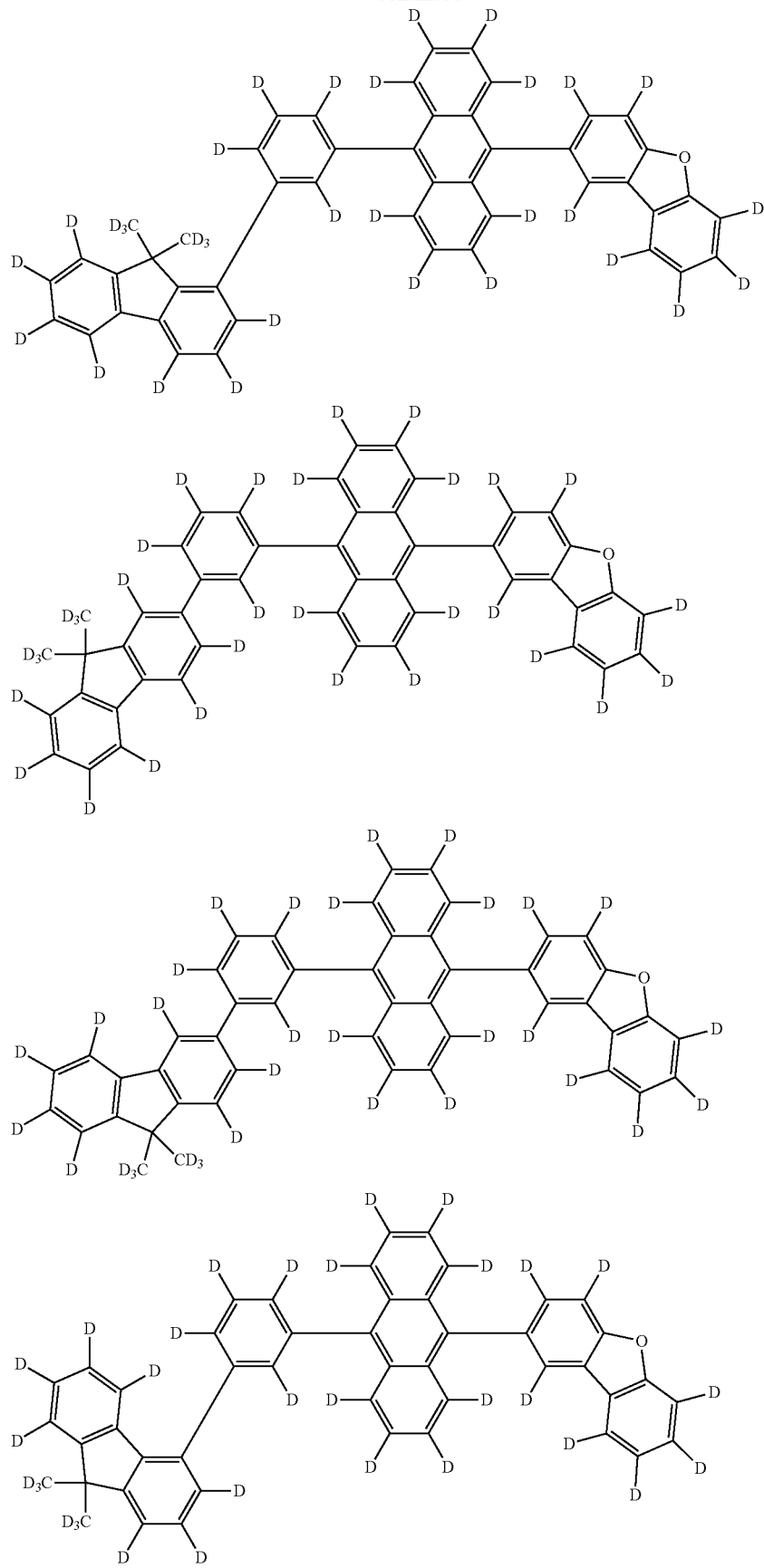

-continued
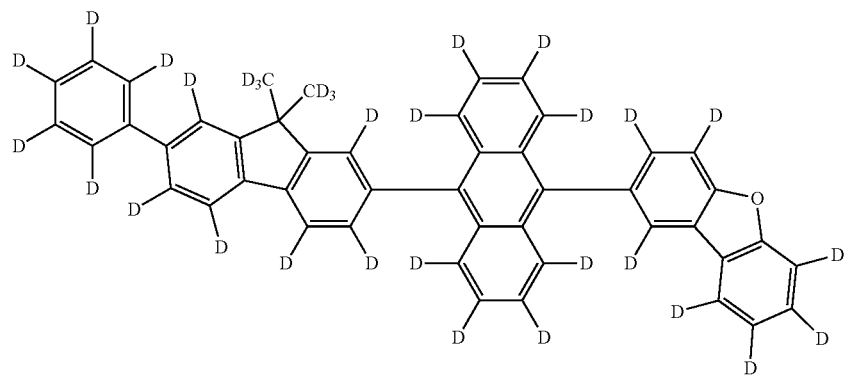
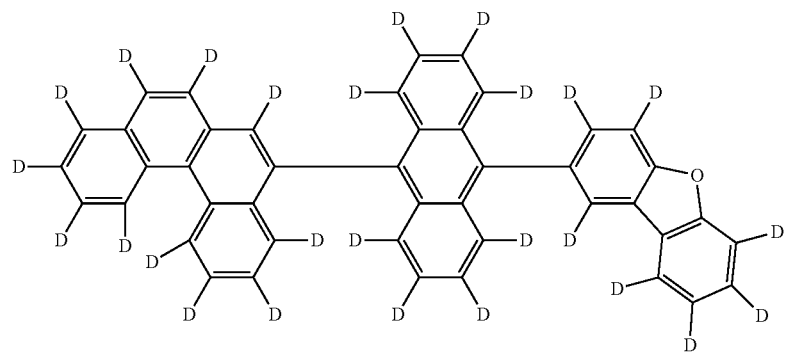
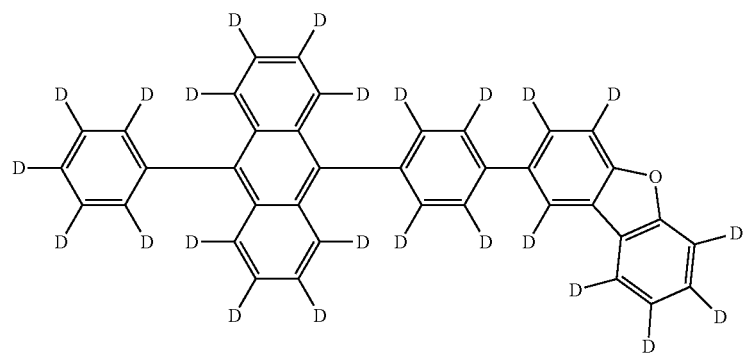
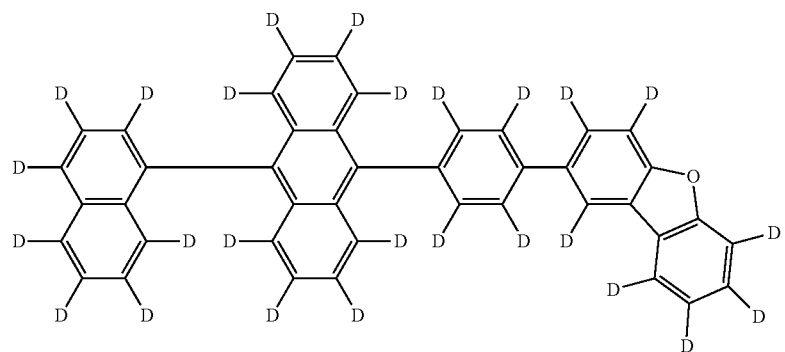

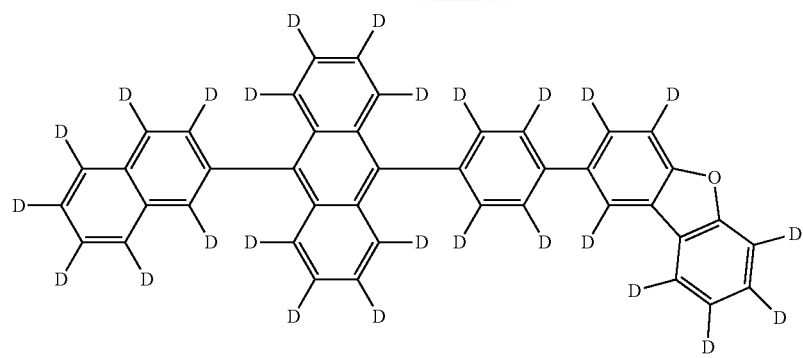
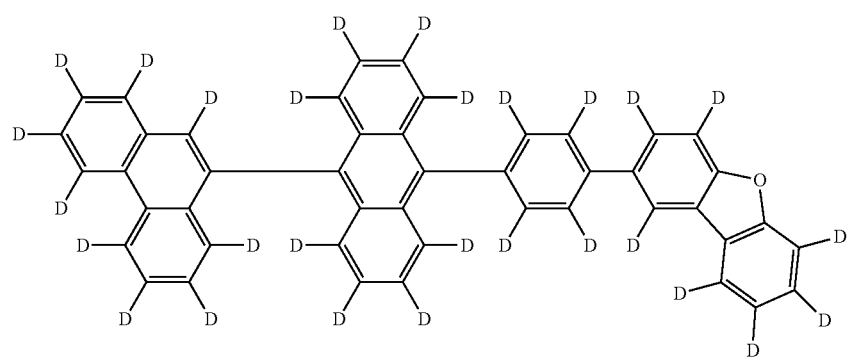
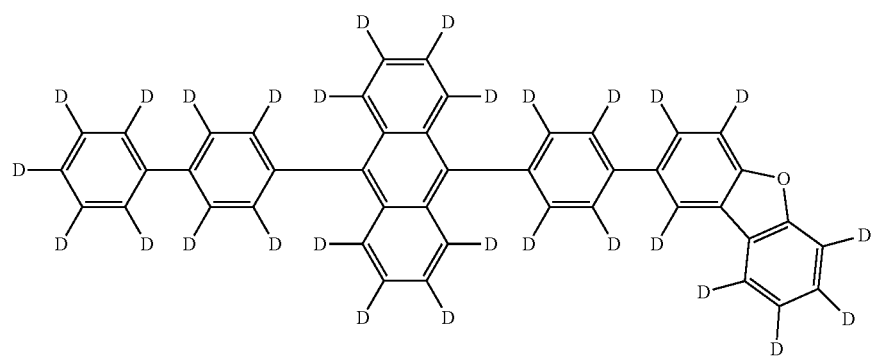
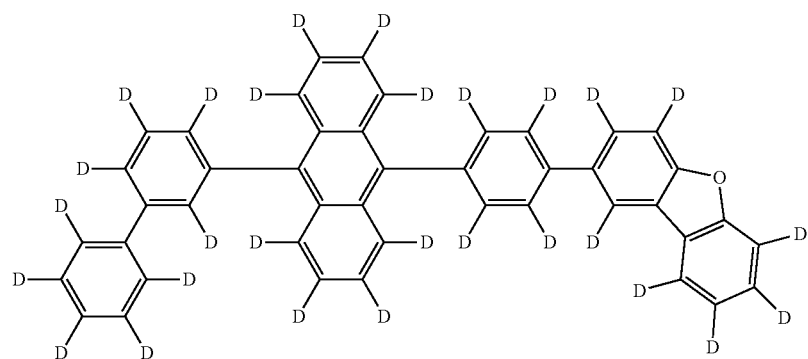

-continued
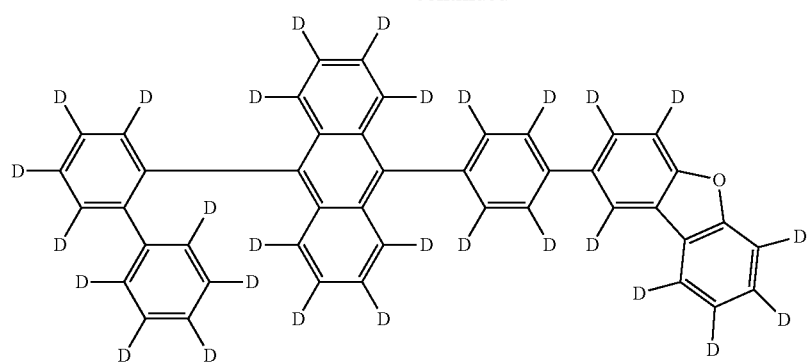
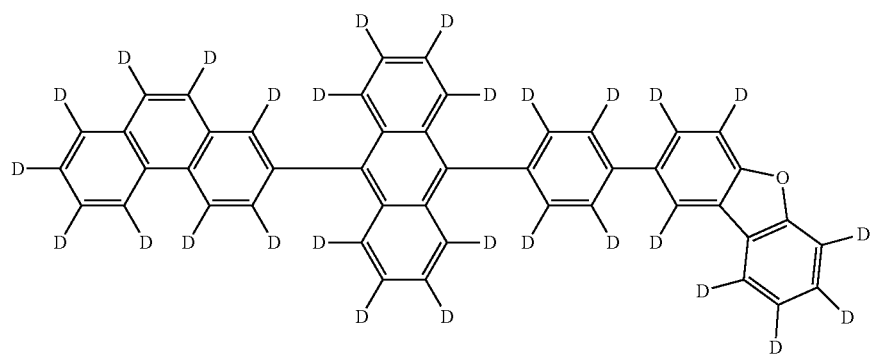
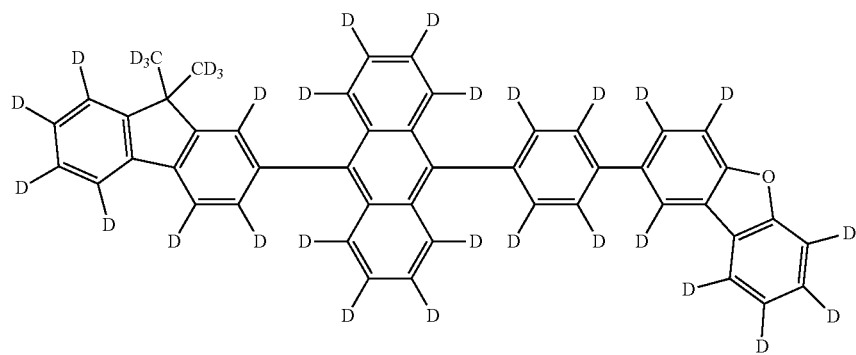
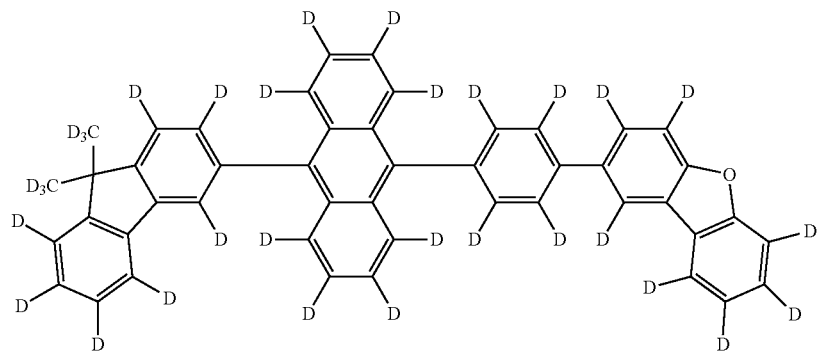

-continued
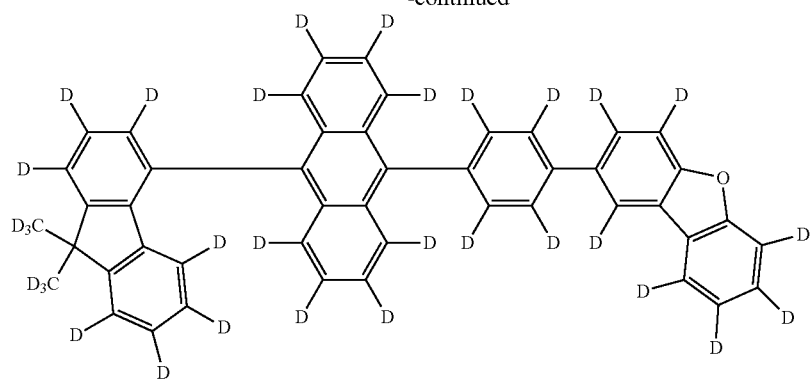
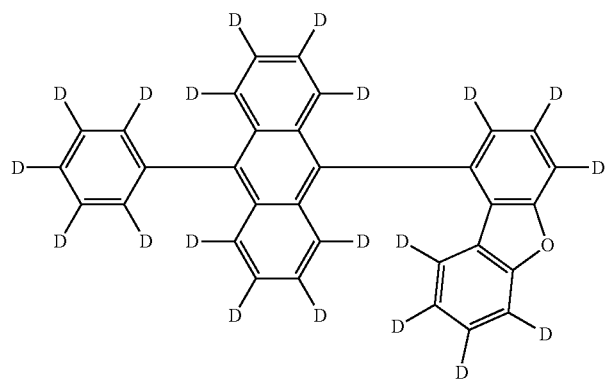
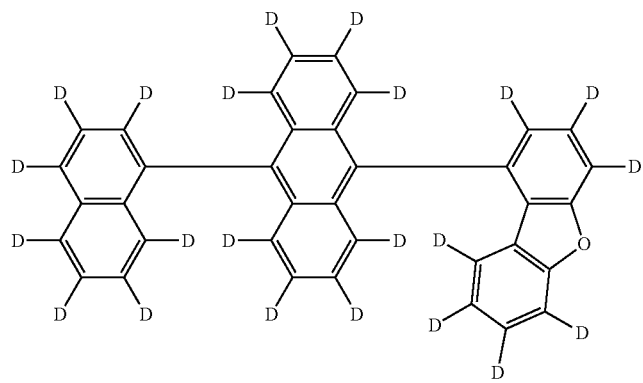
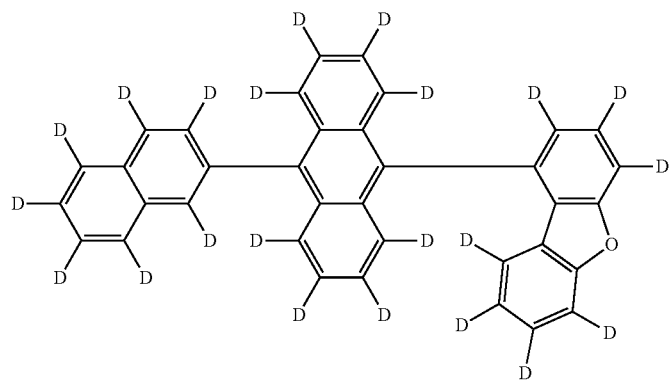

-continued
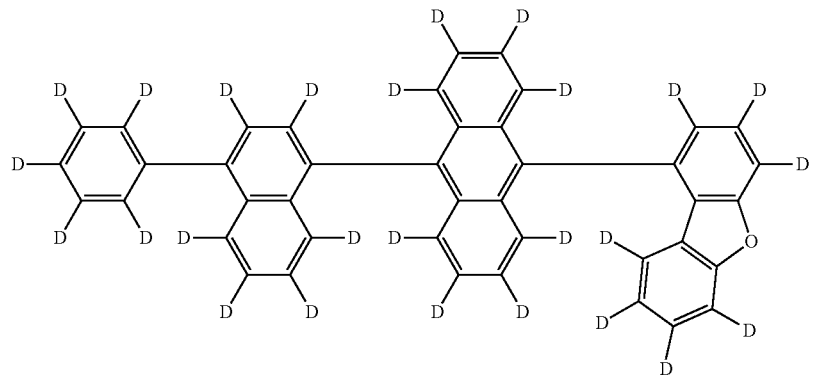
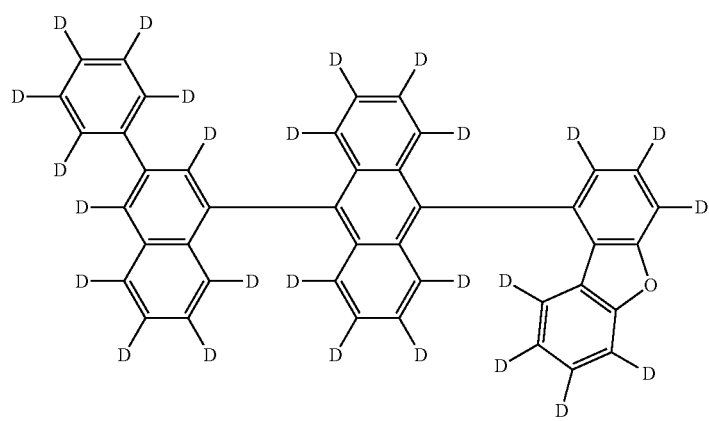
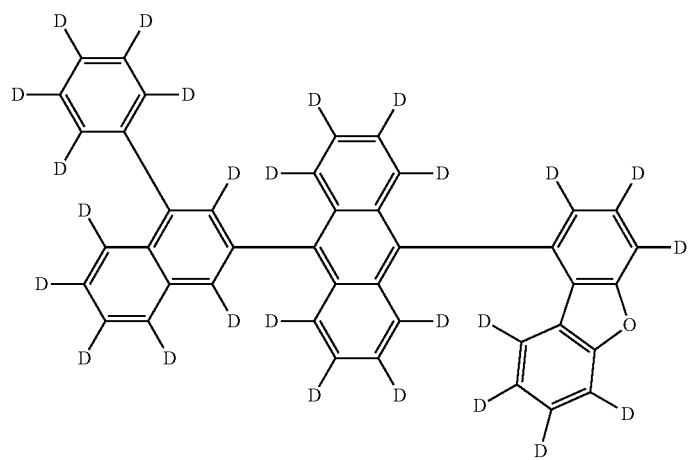
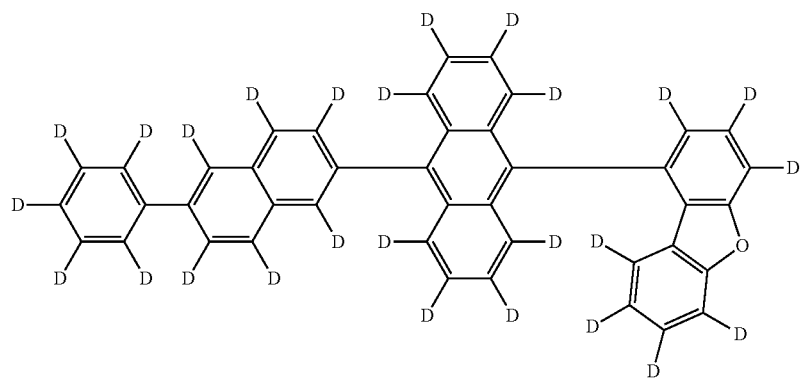

-continued
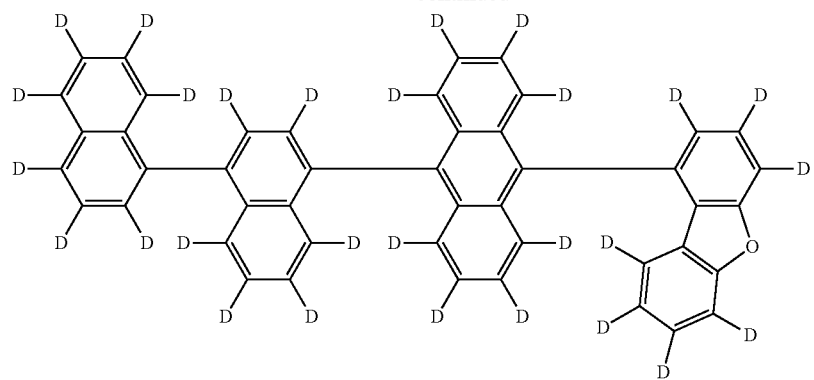
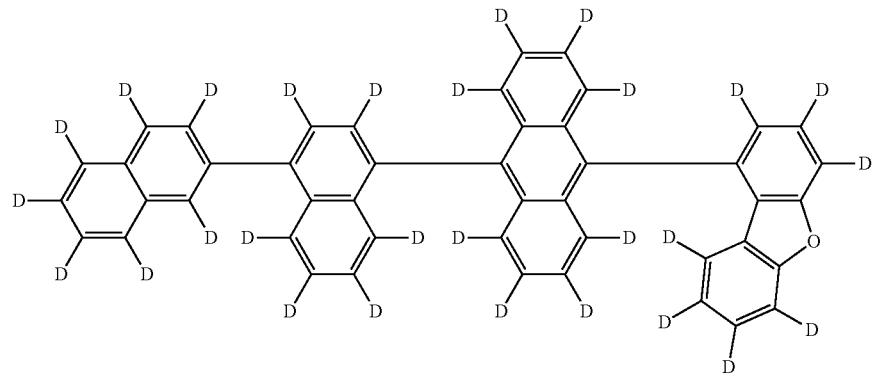
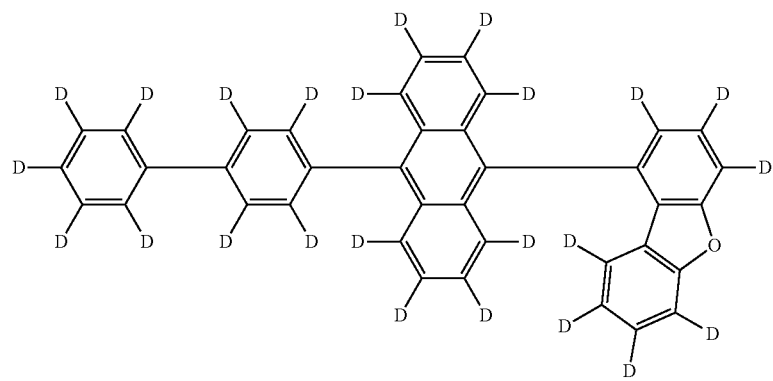
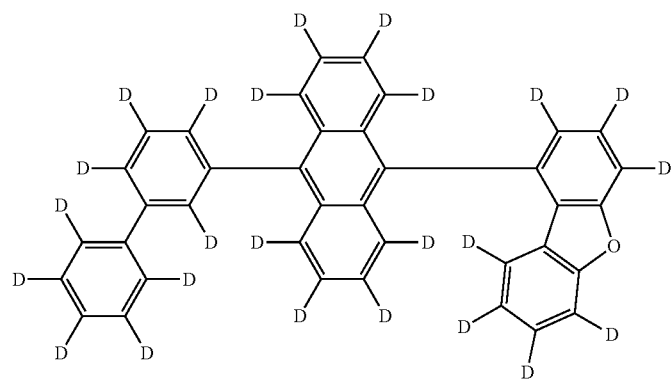

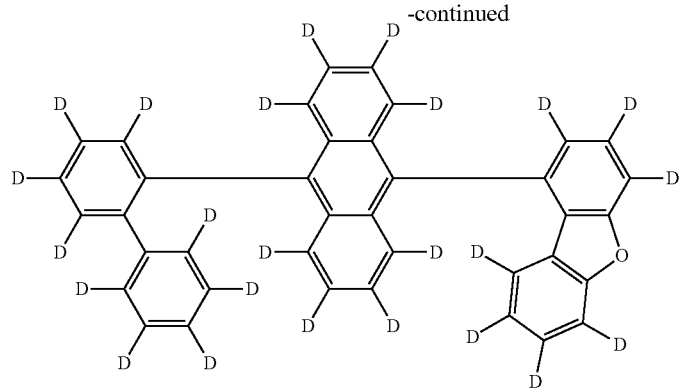
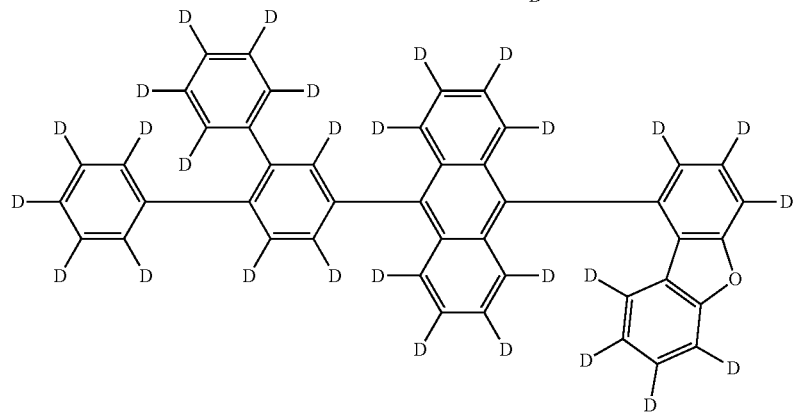
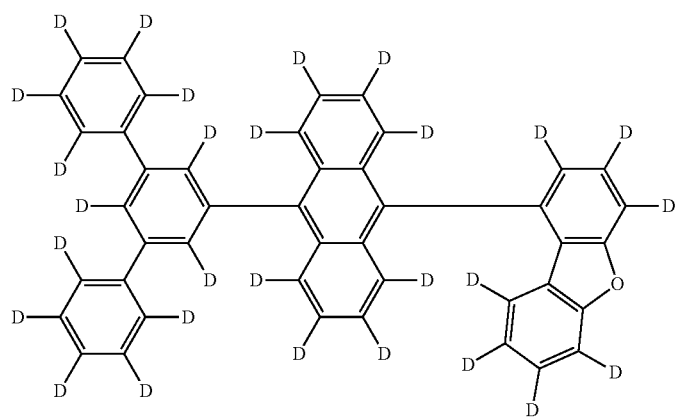
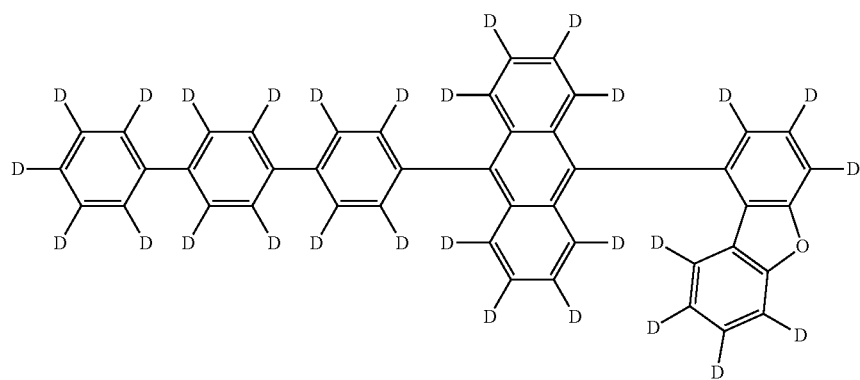

-continued
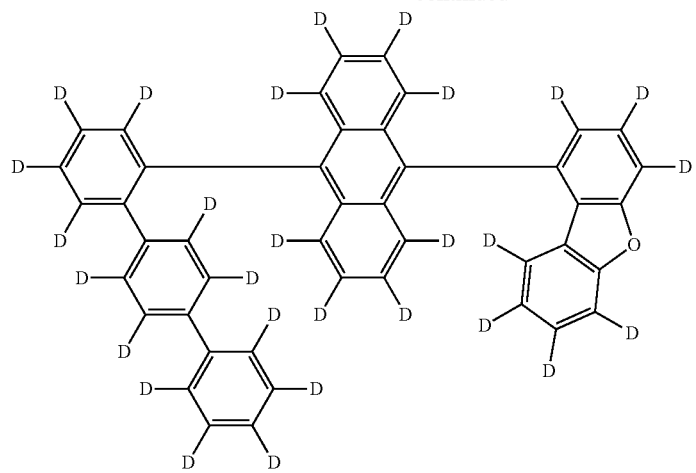
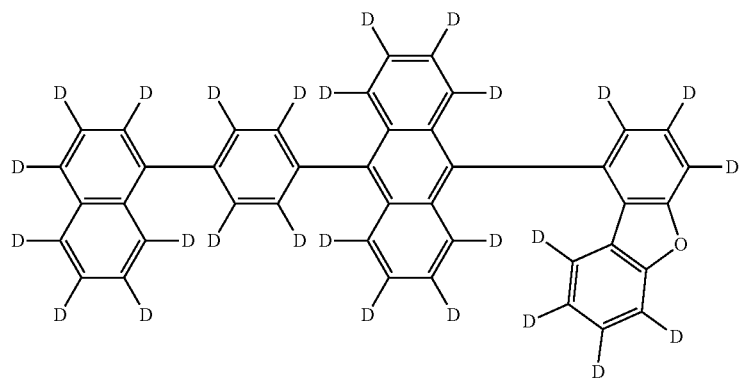
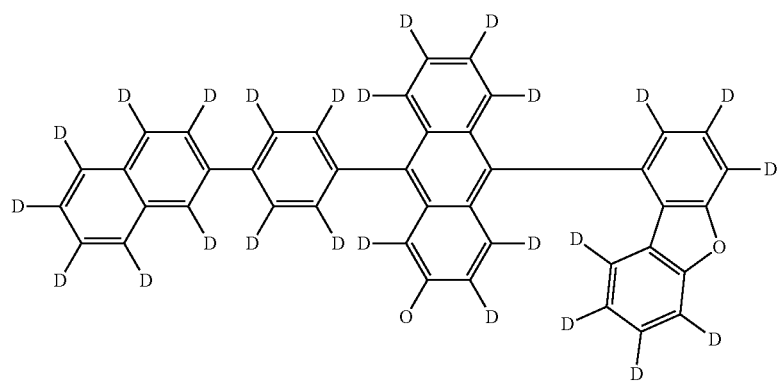
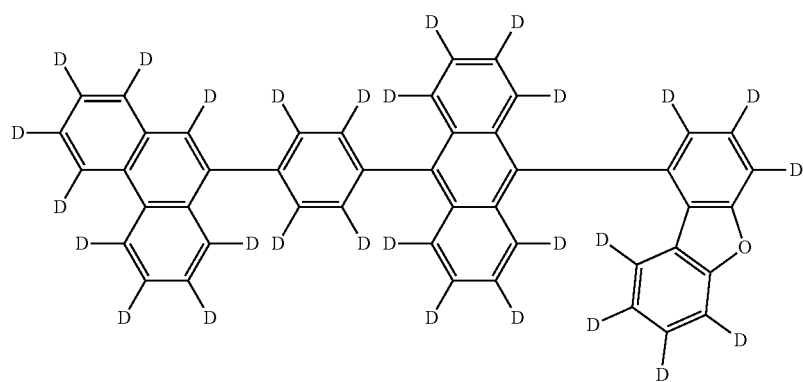

-continued
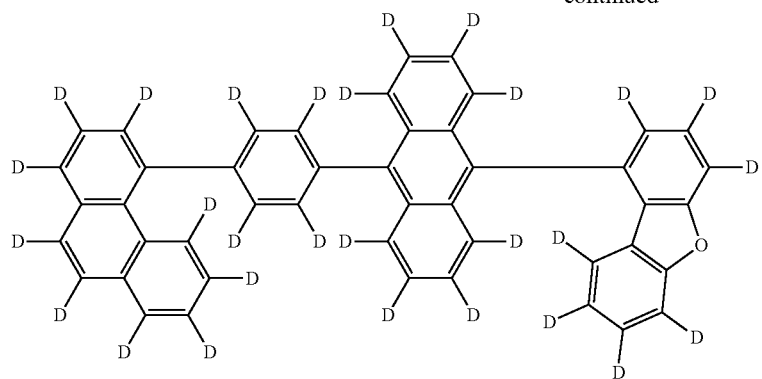
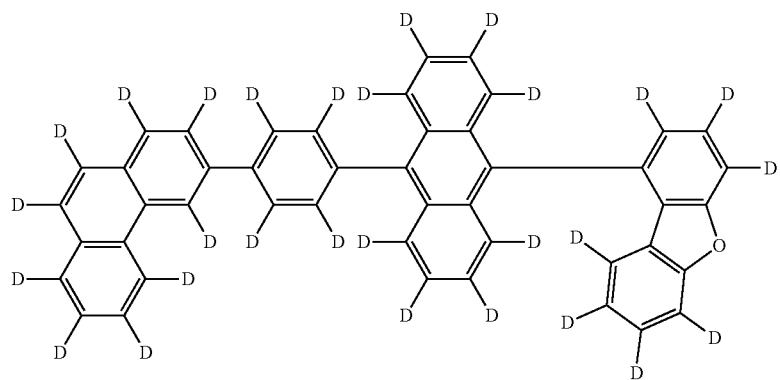
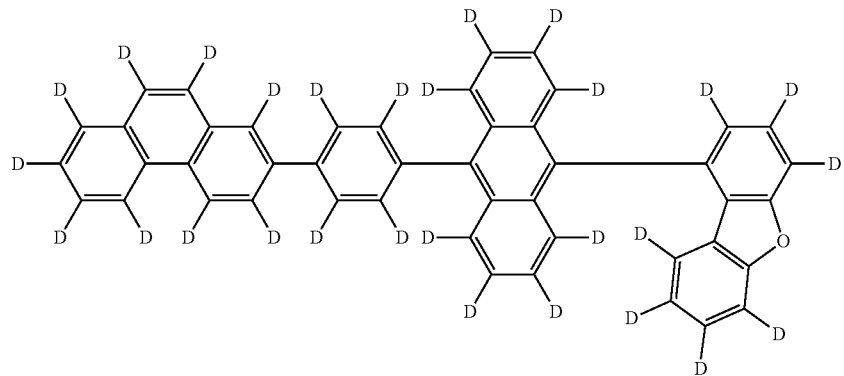
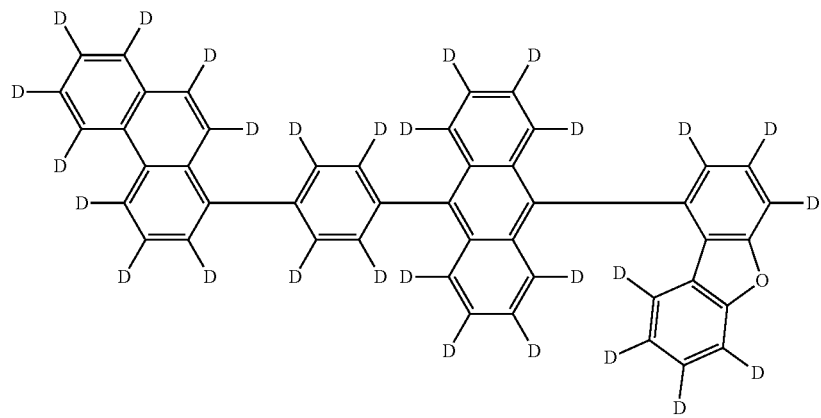

-continued
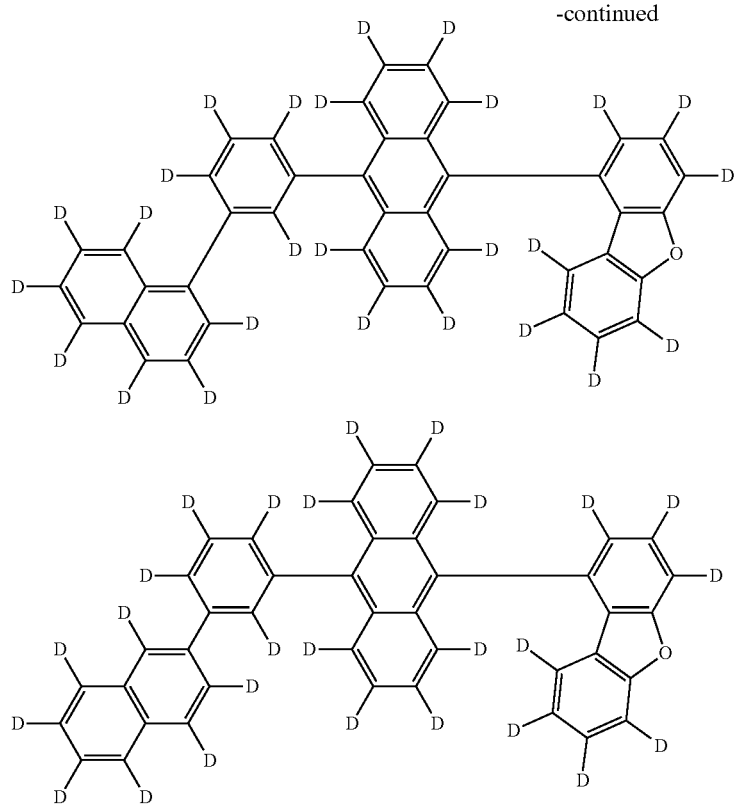
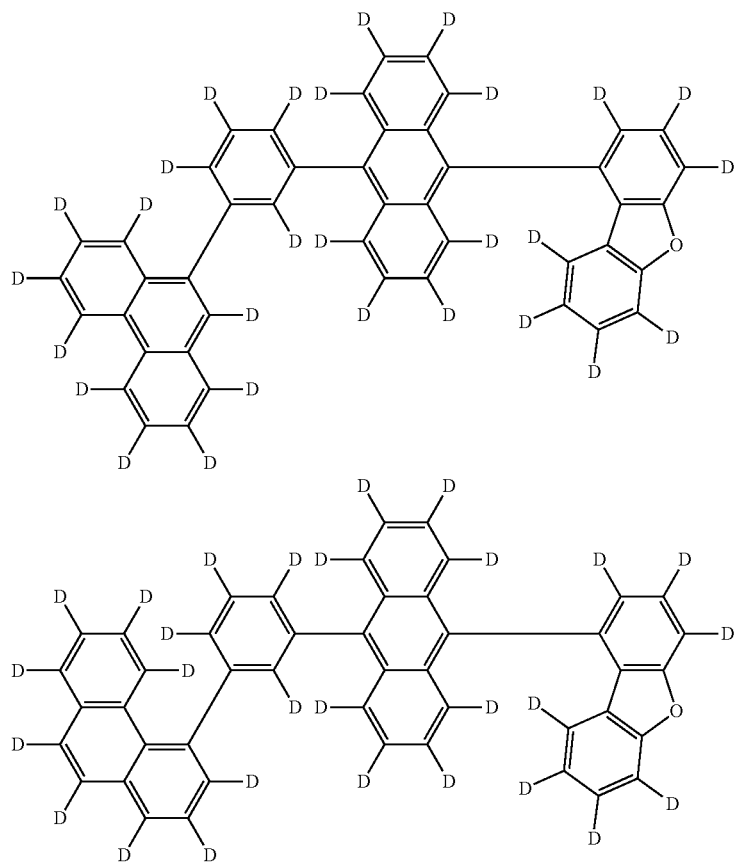

-continued
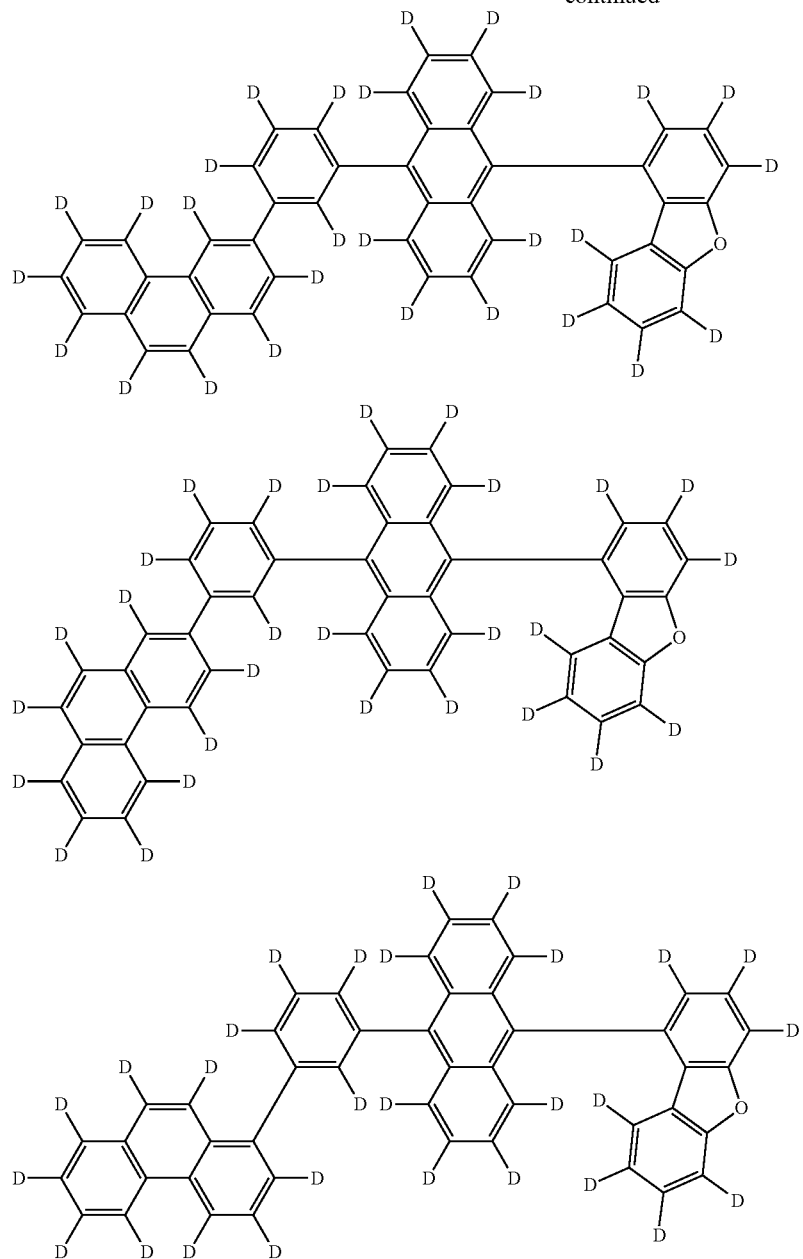
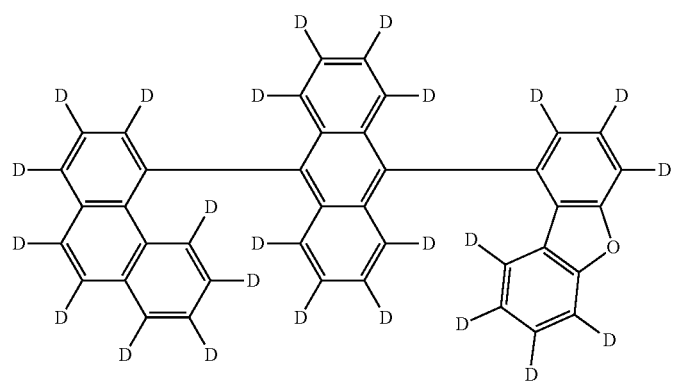

-continued
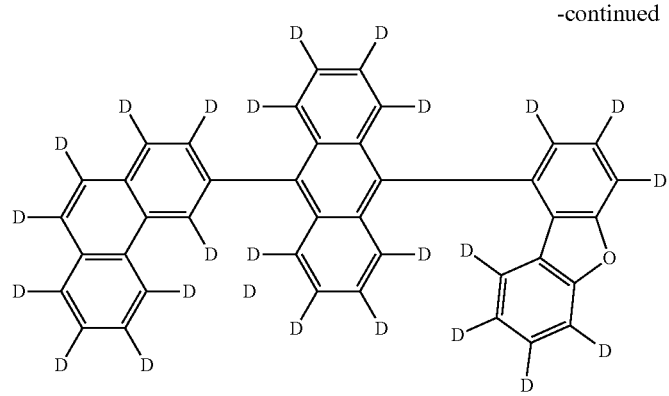
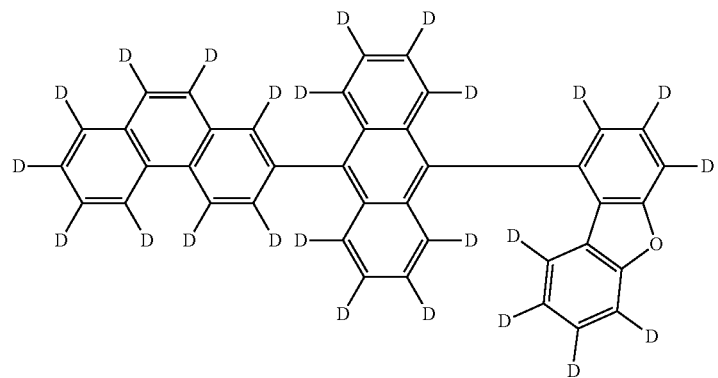
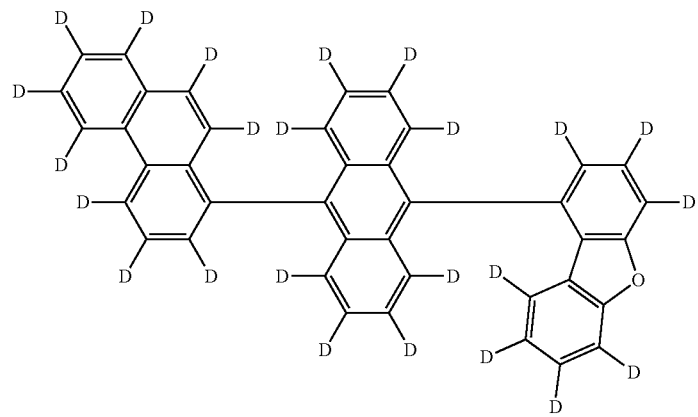
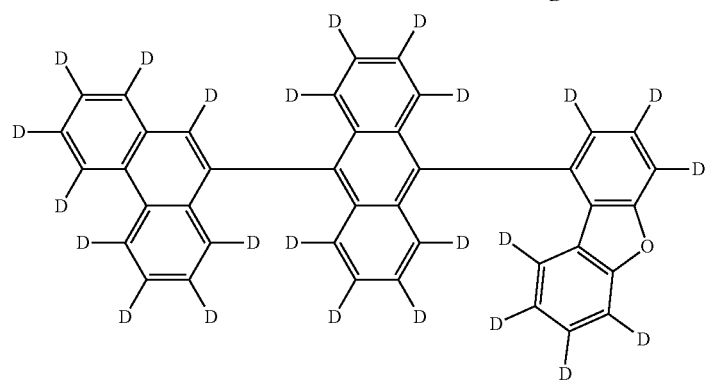

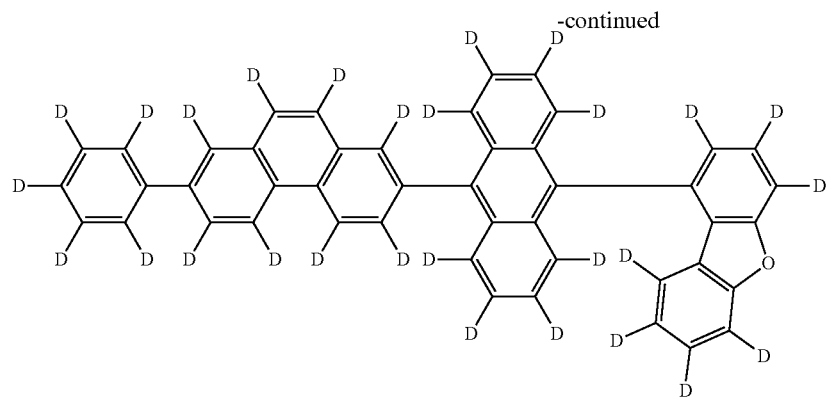
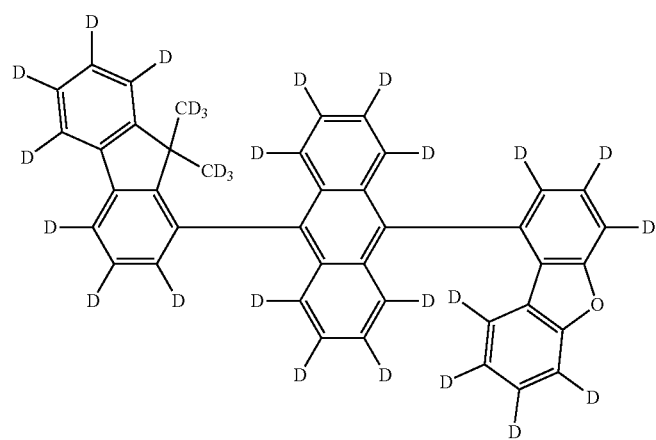
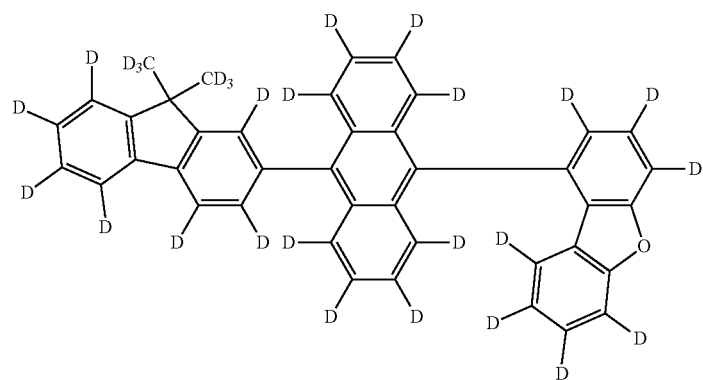
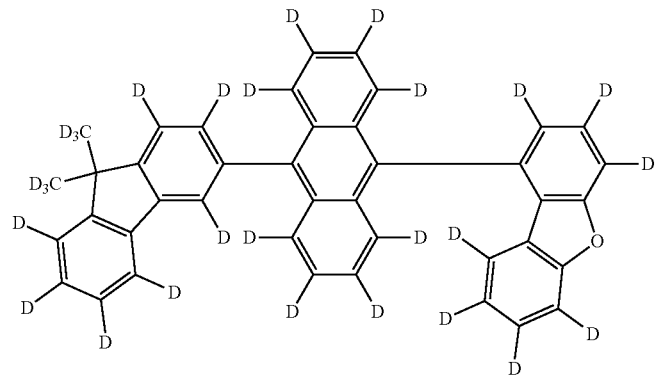

-continued
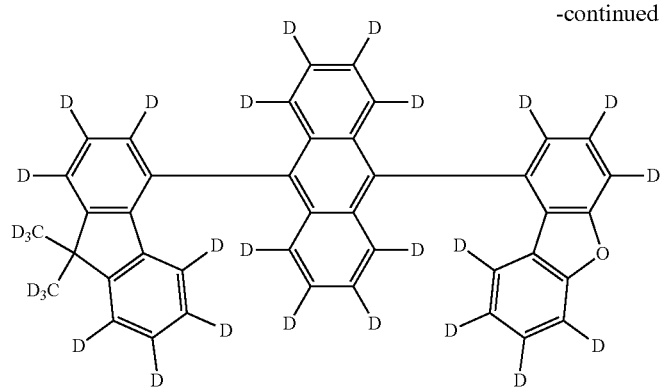
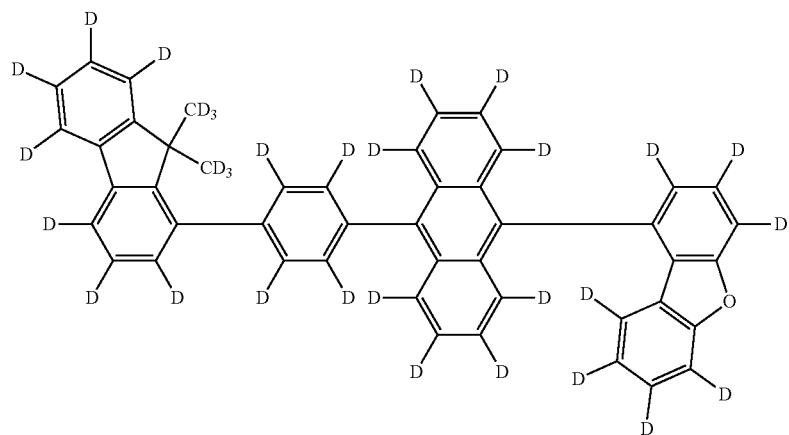
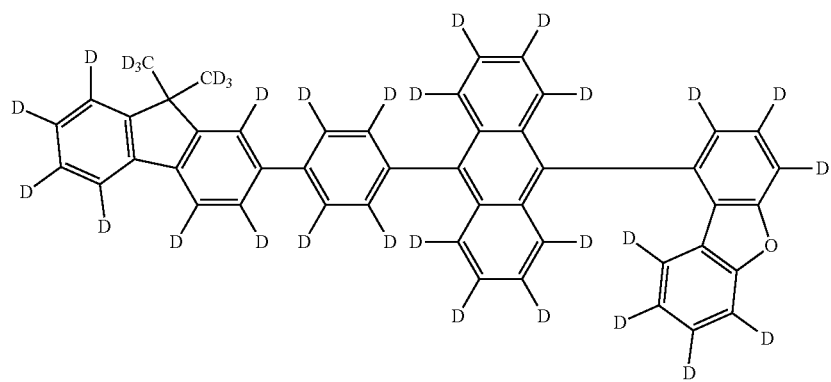
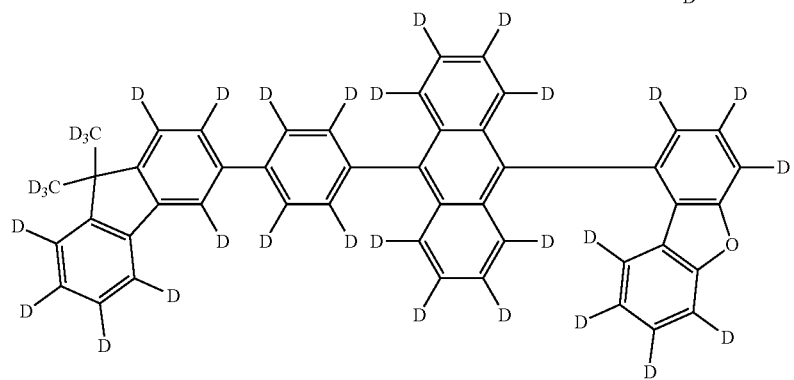

-continued
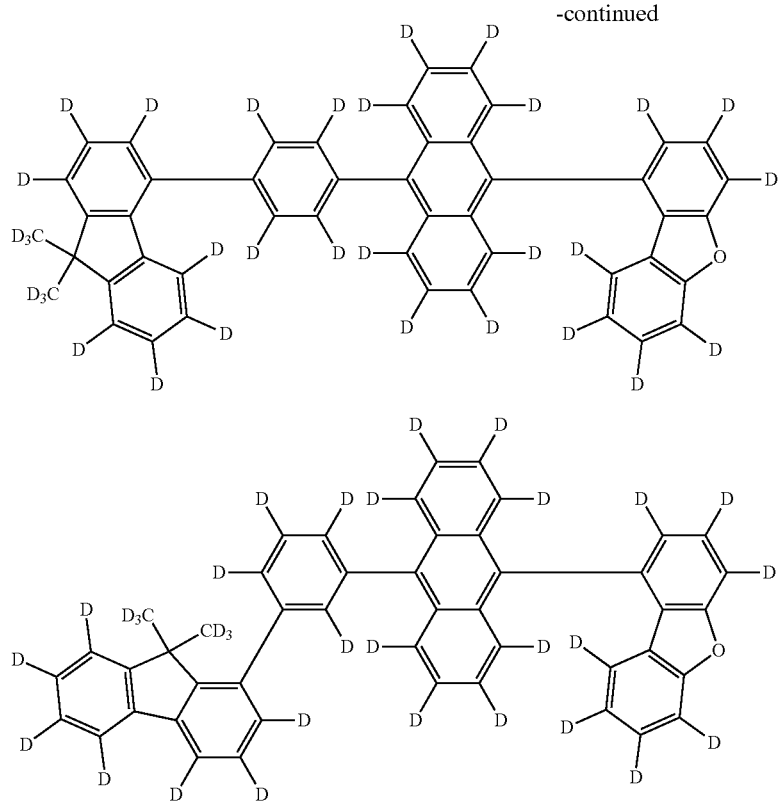
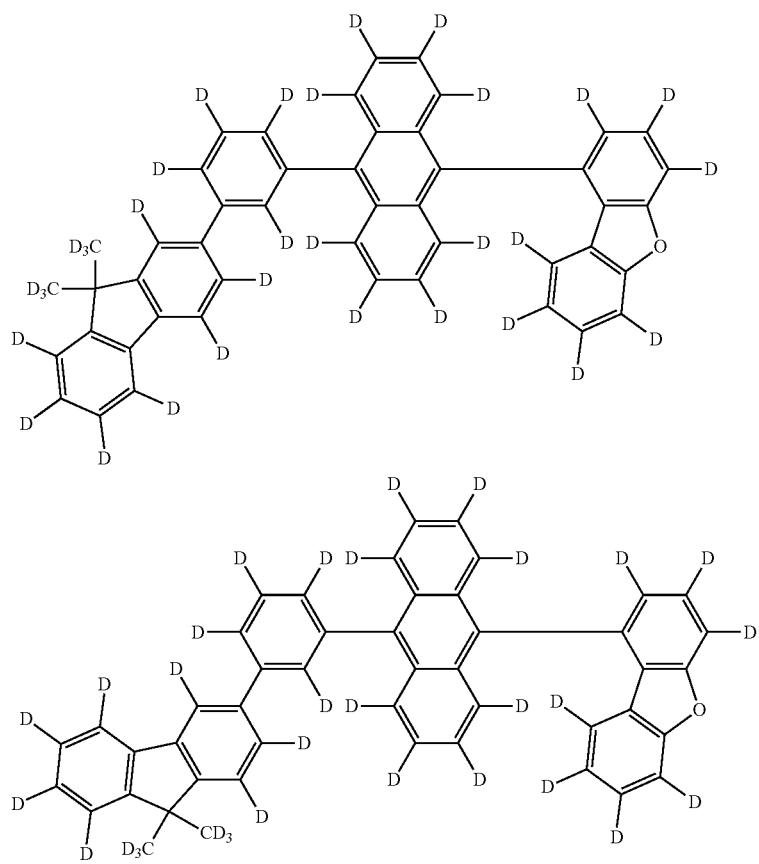

-continued
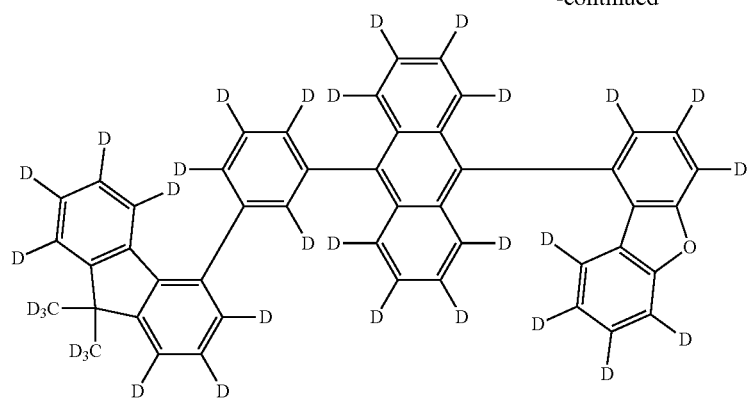
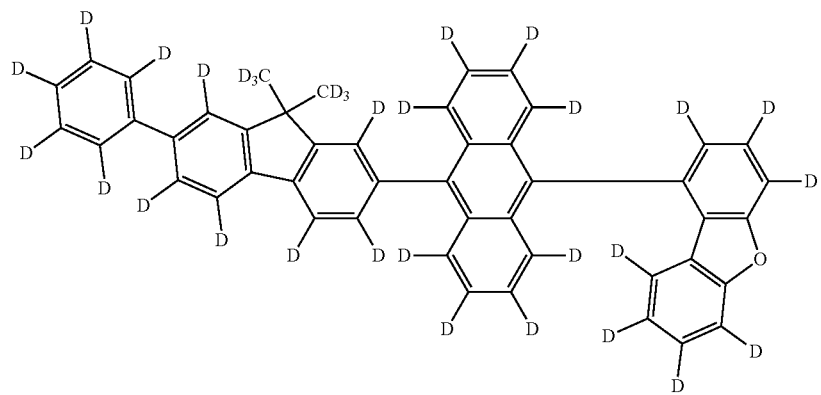
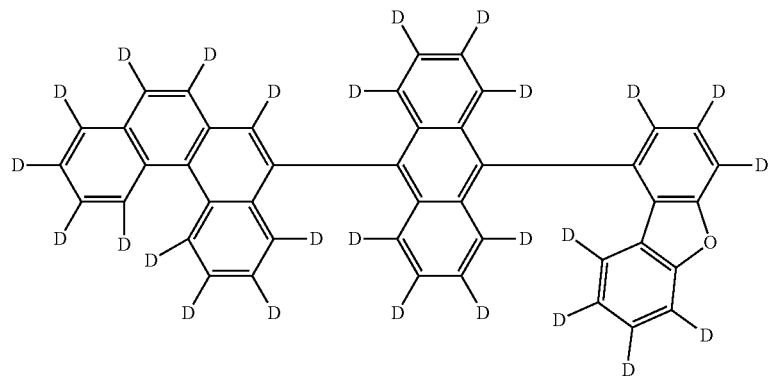
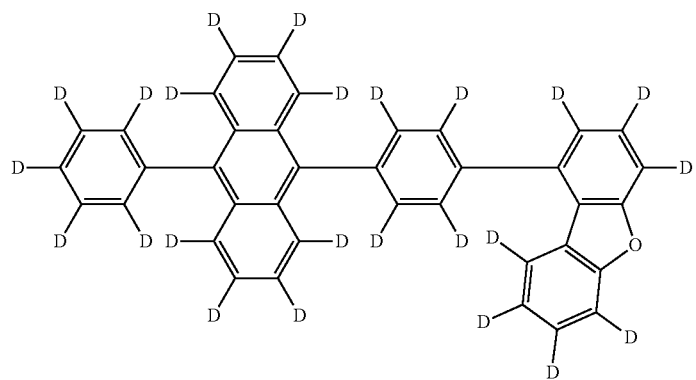

-continued
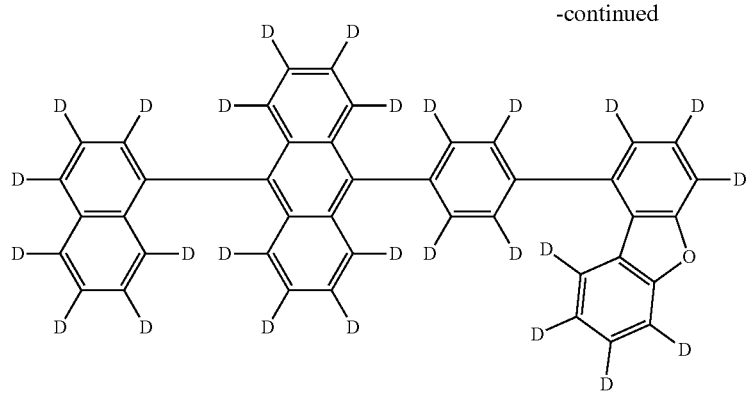
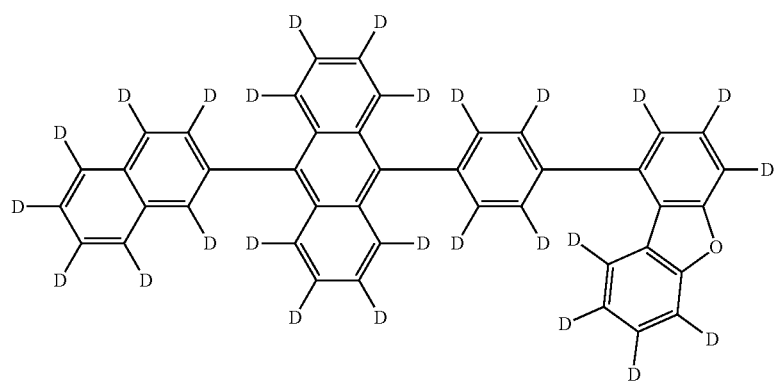
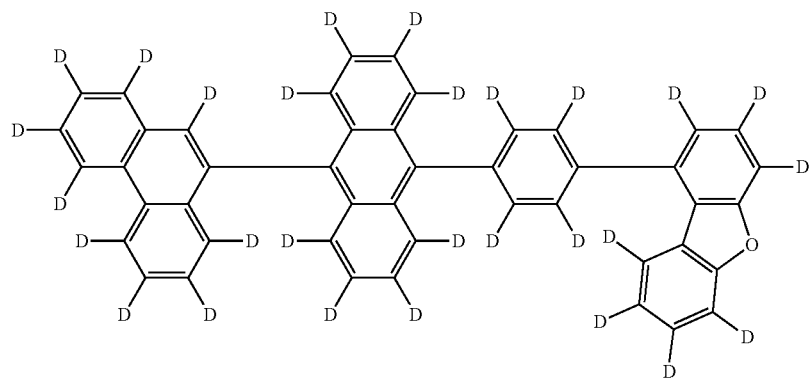
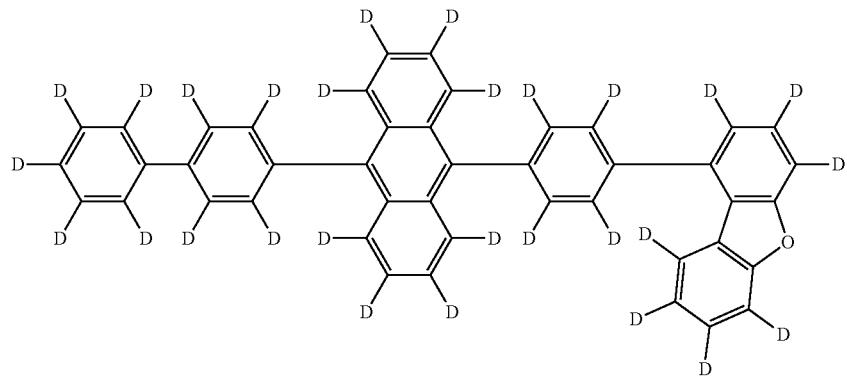

-continued
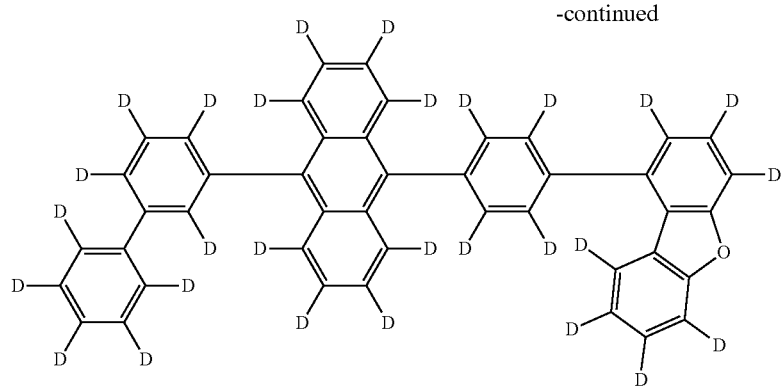
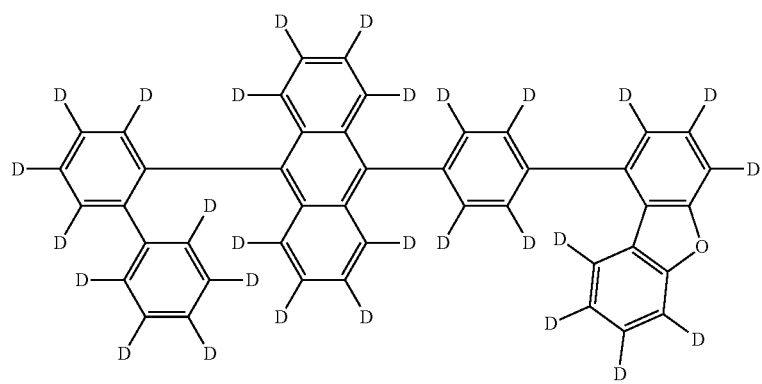
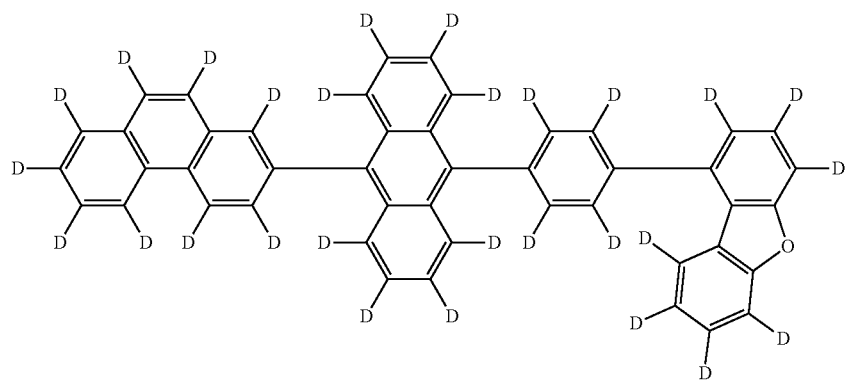
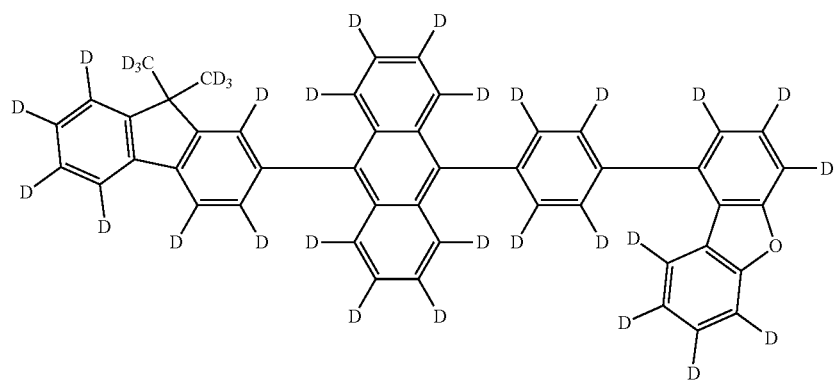

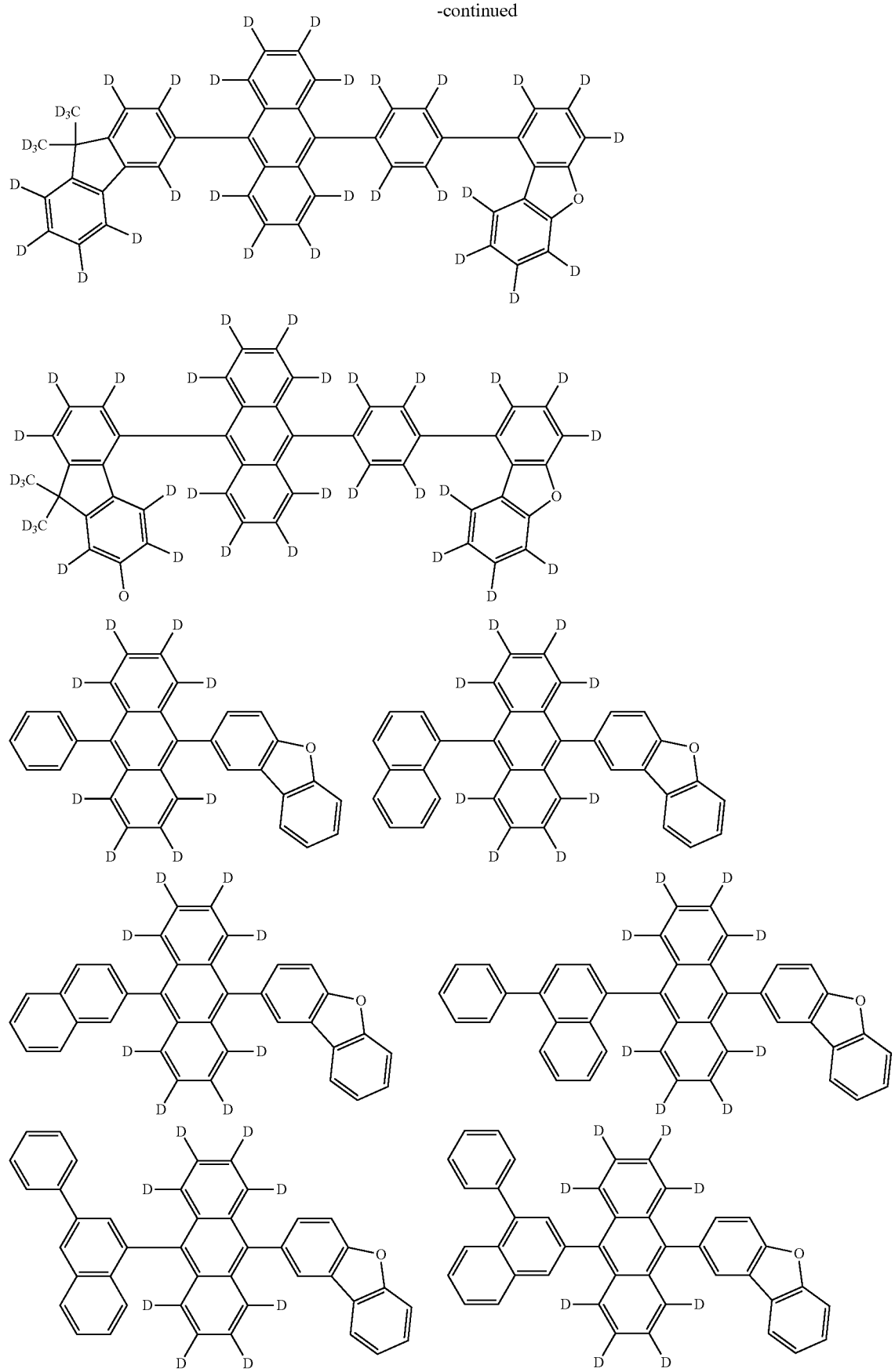

-continued
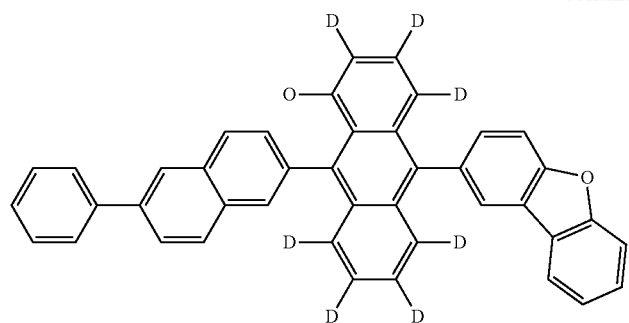
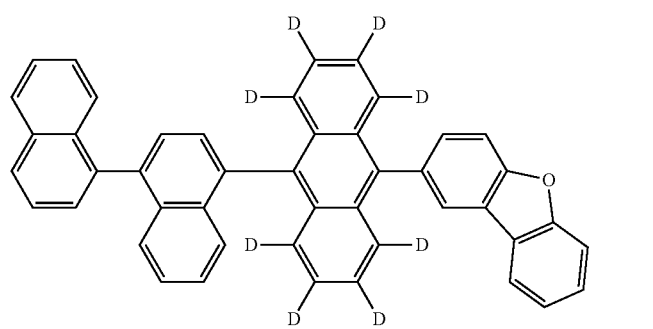
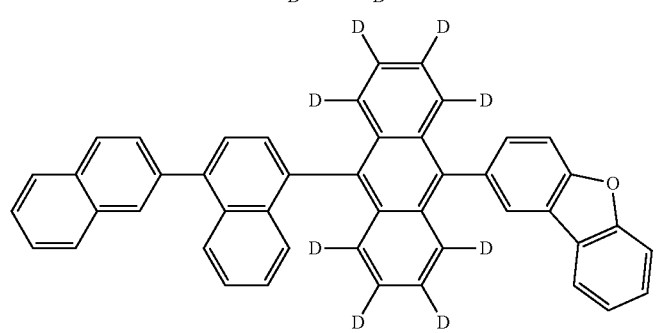
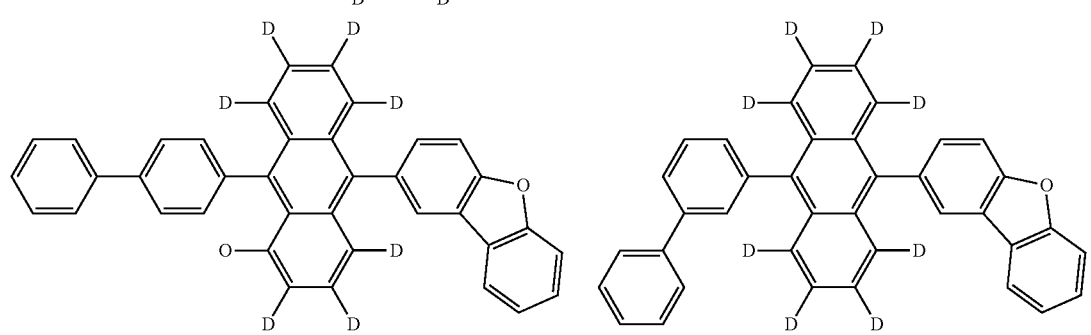
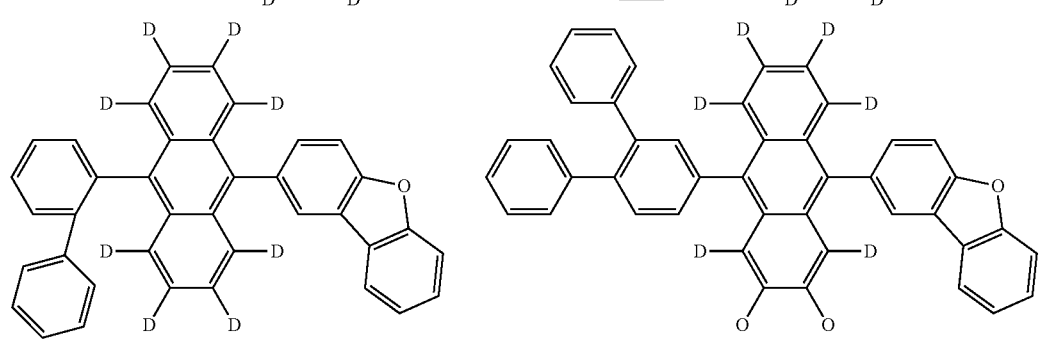

95 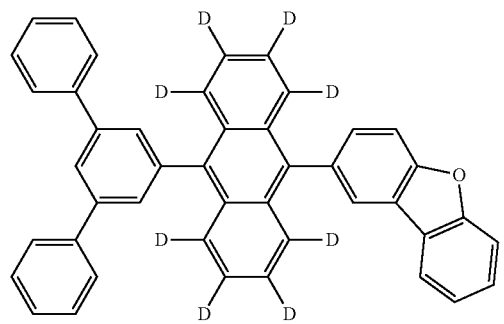
96 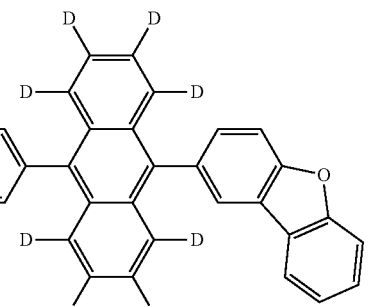
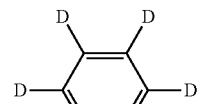
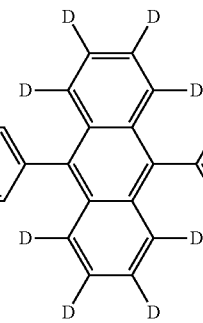
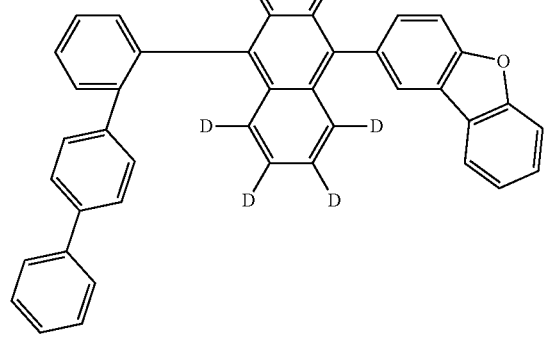
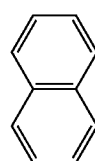
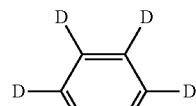
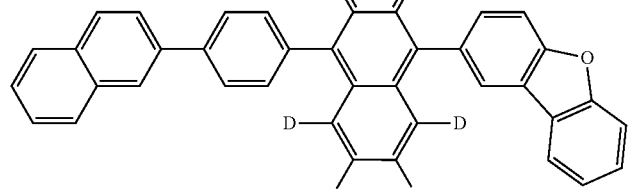
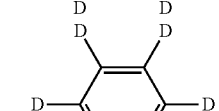
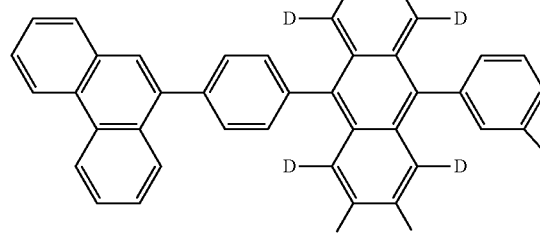
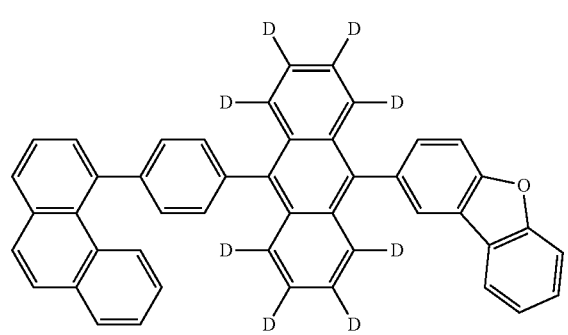
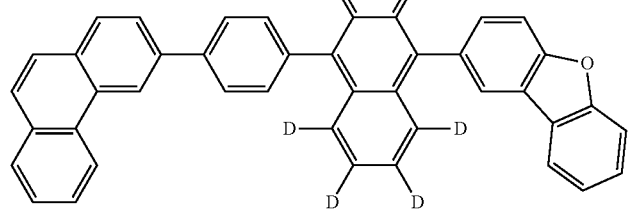

-continued
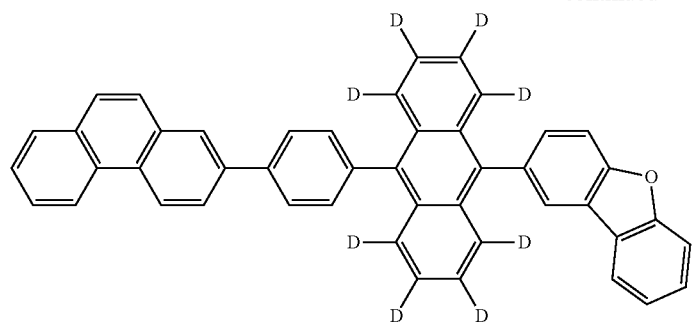

-continued
| 99 | 100 |
|---|---|
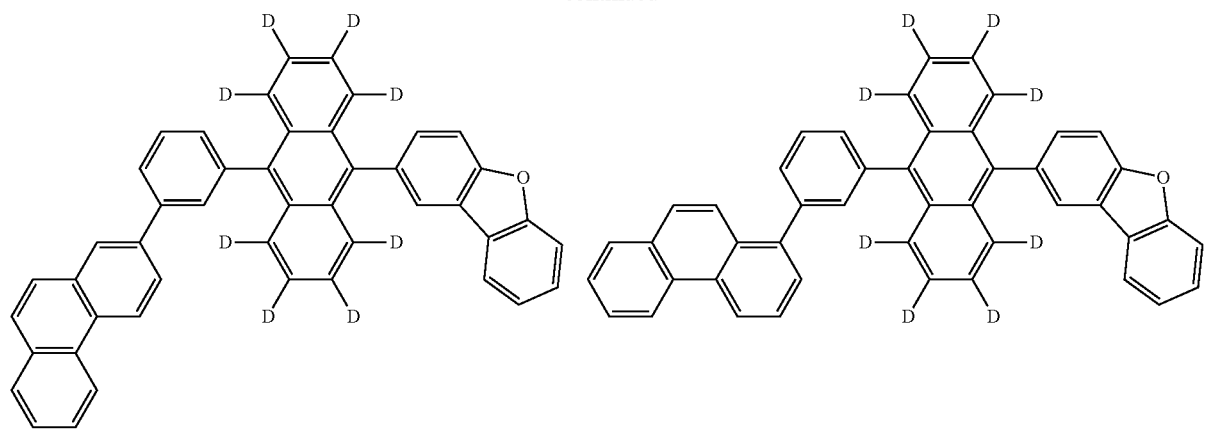
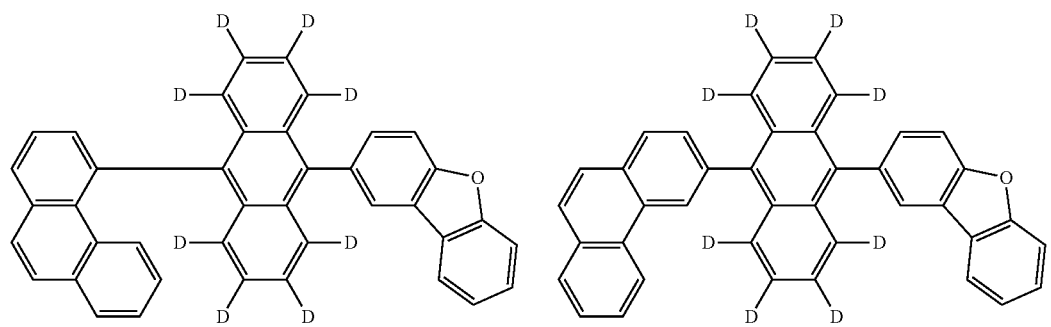
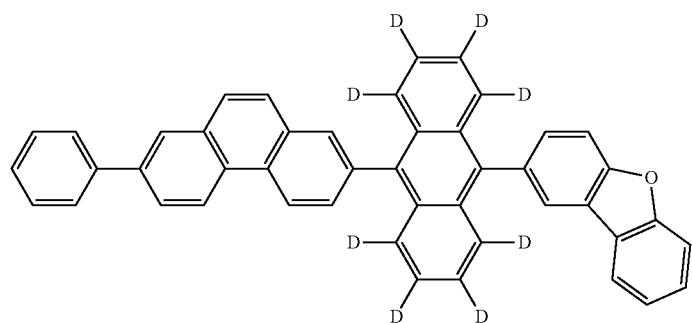
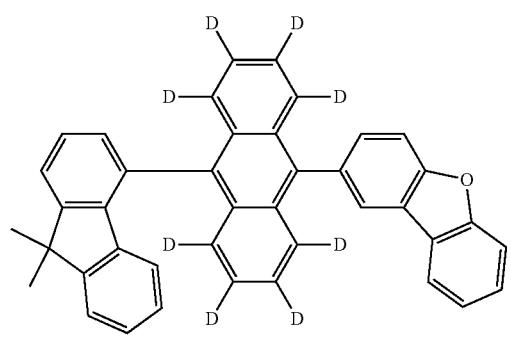

-continued
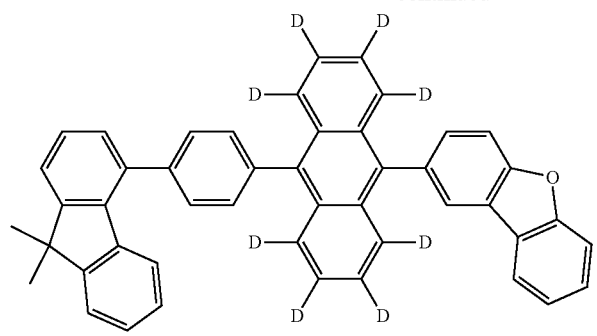
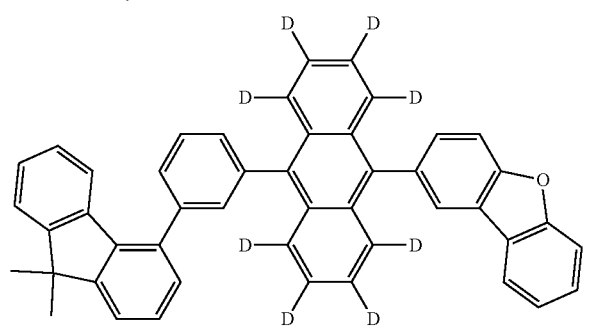
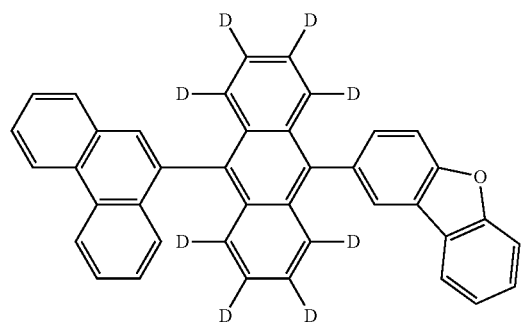
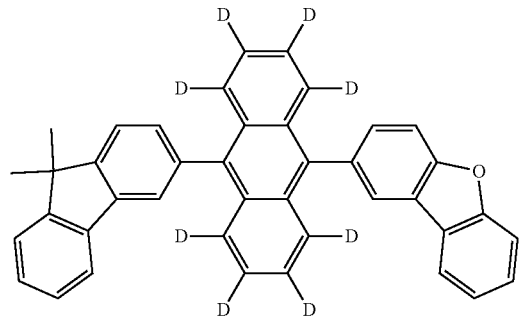
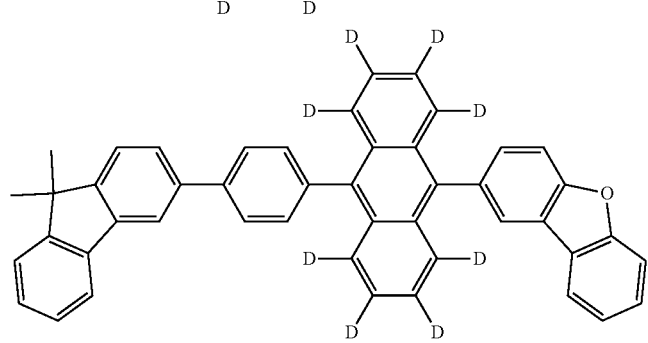

-continued
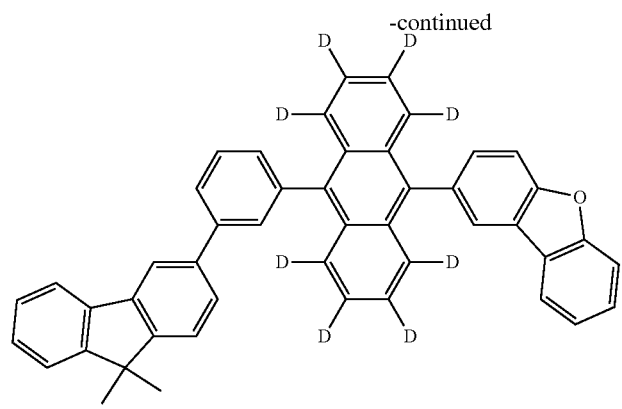
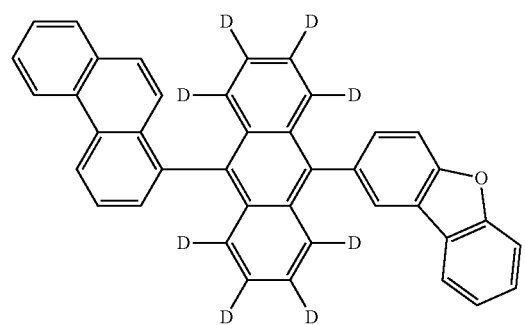
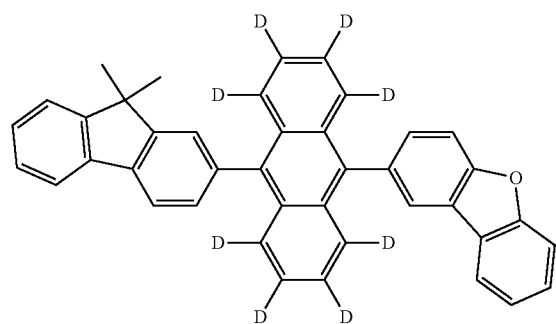
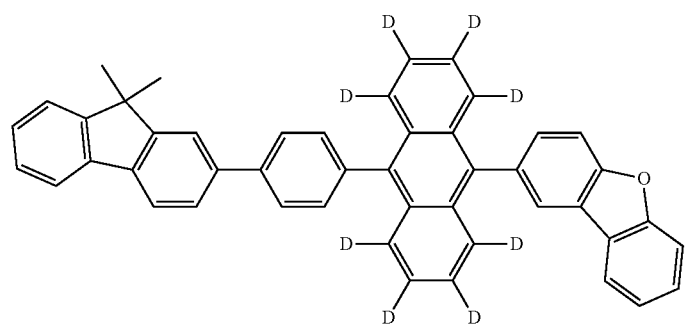

-continued
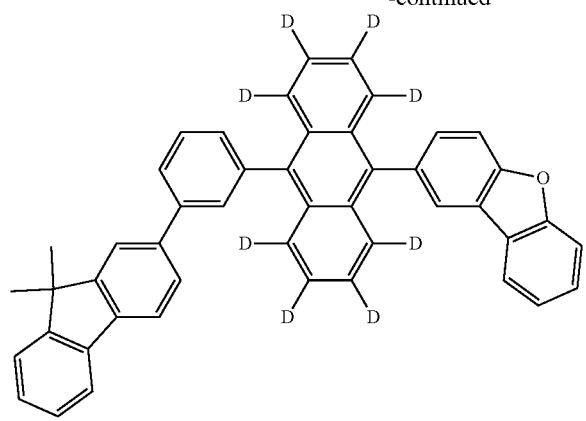
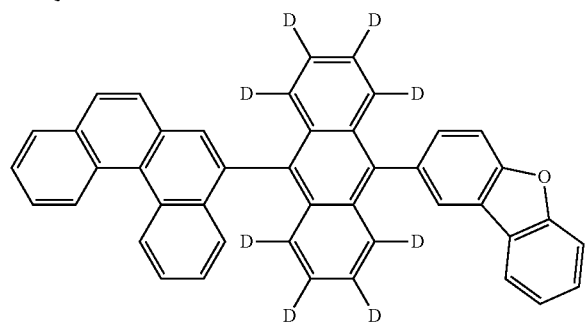
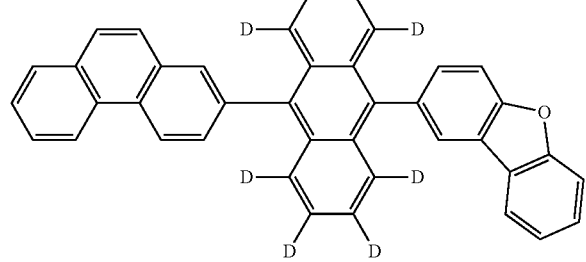
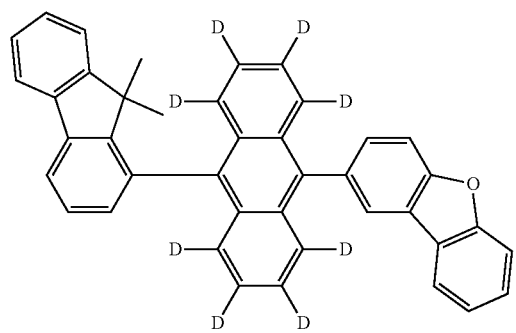
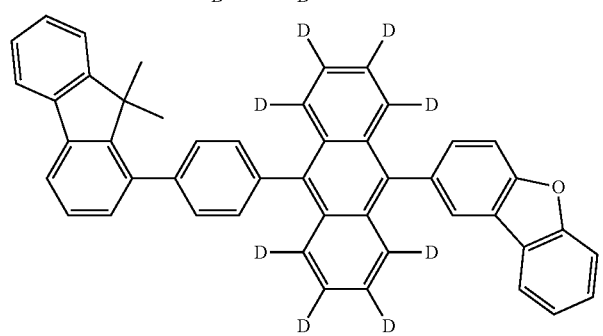

-continued
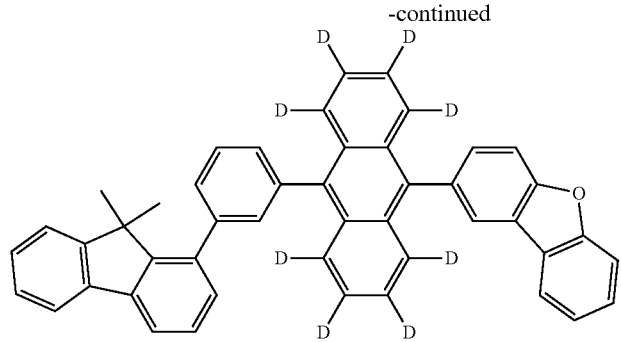
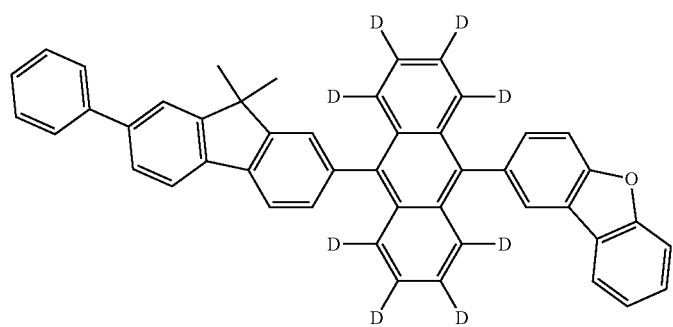
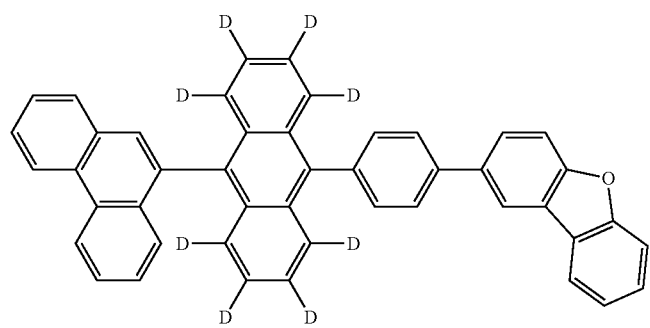
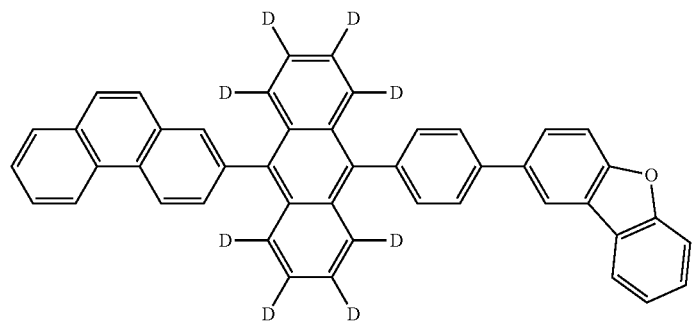
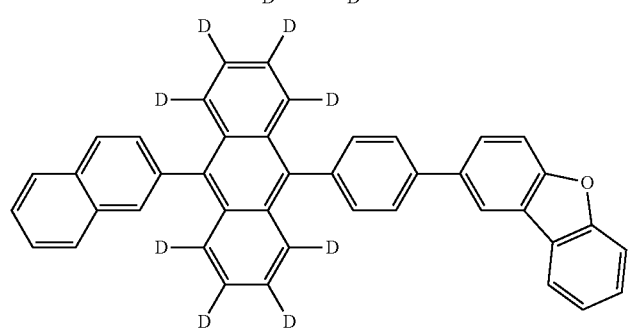

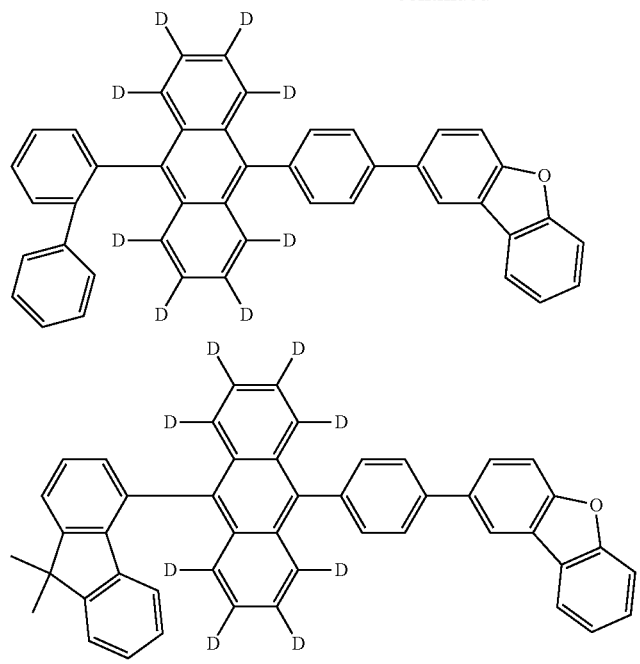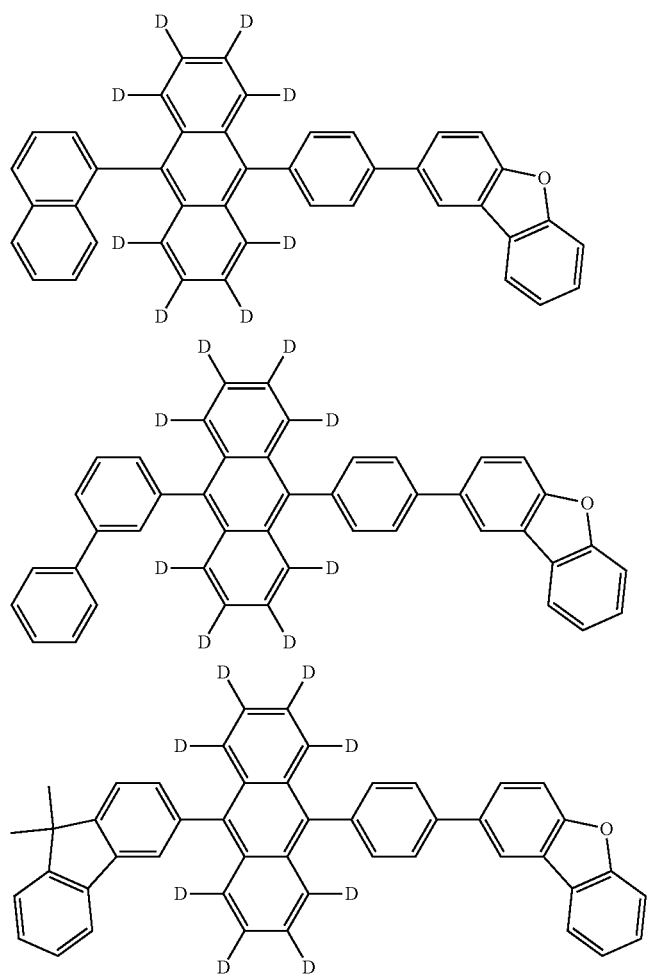

-continued
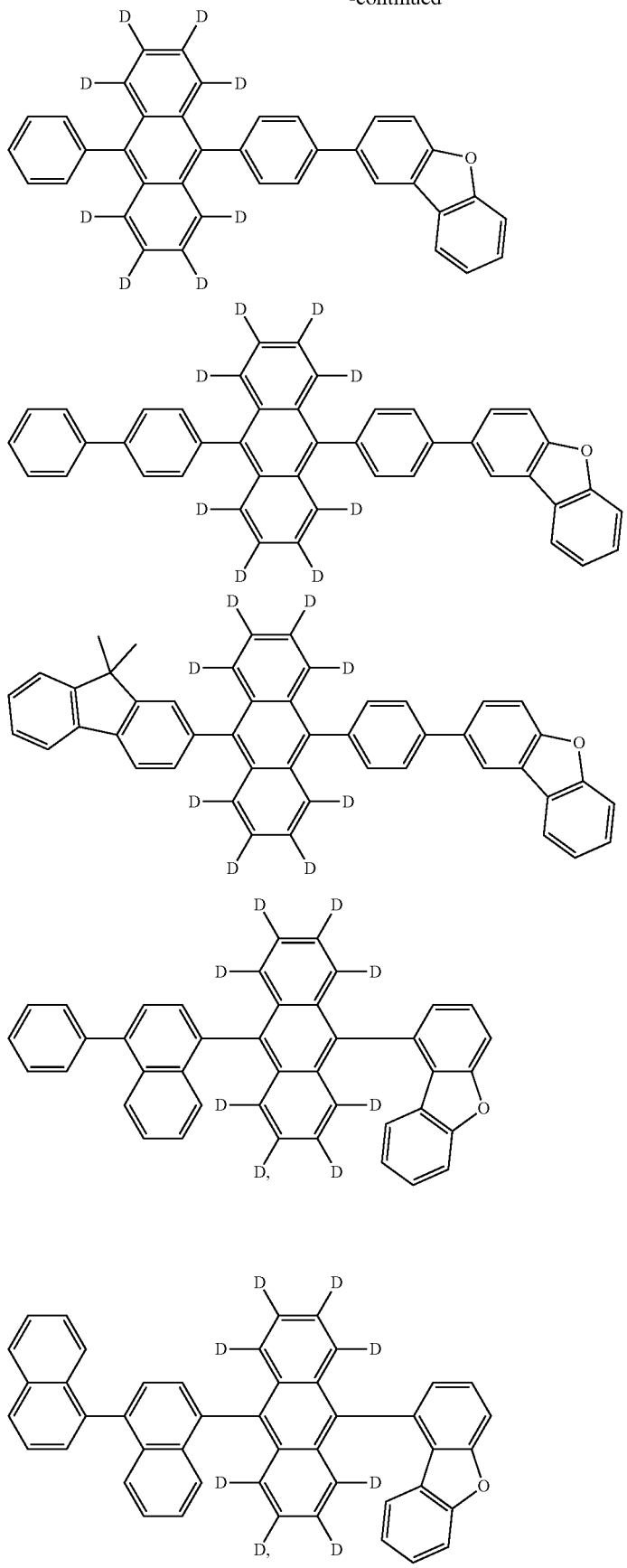

-continued
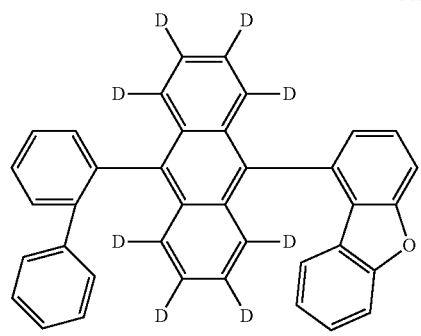
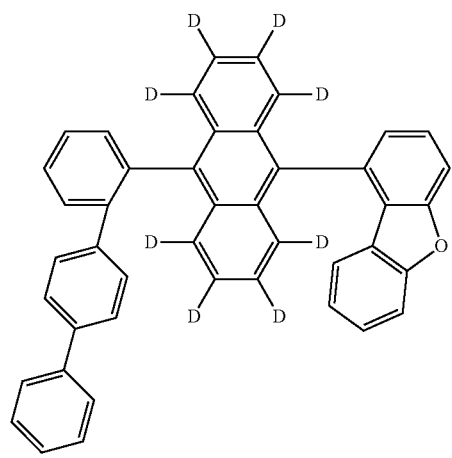
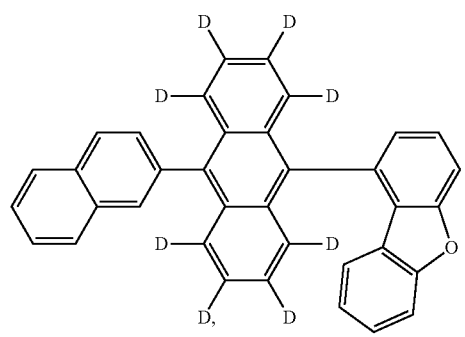
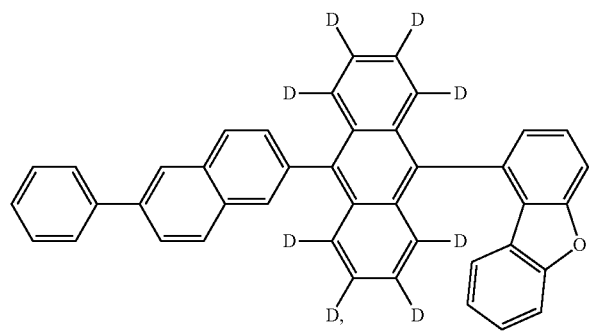

-continued
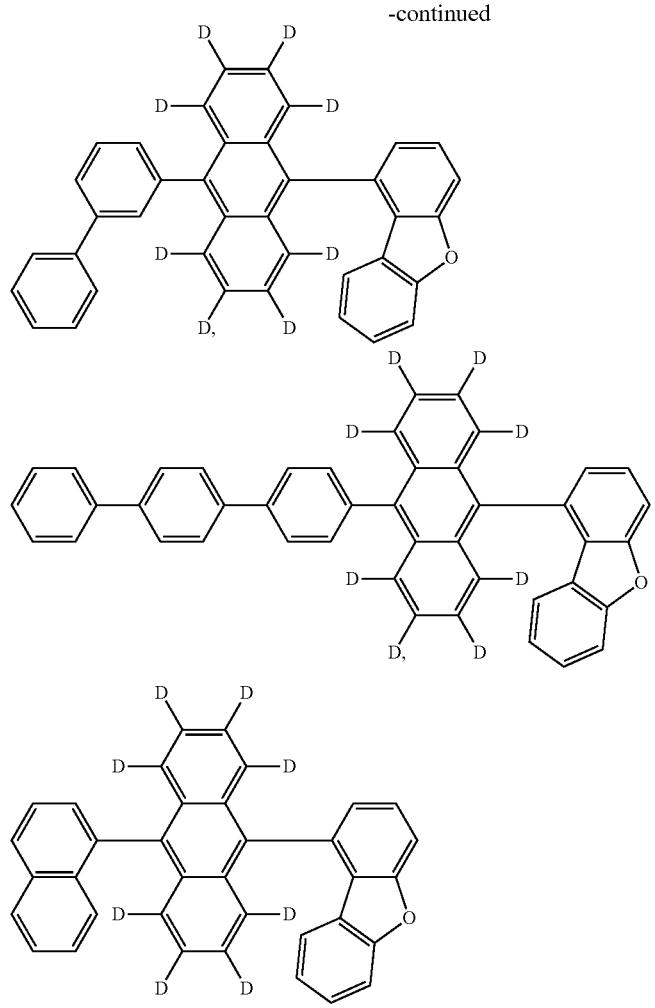
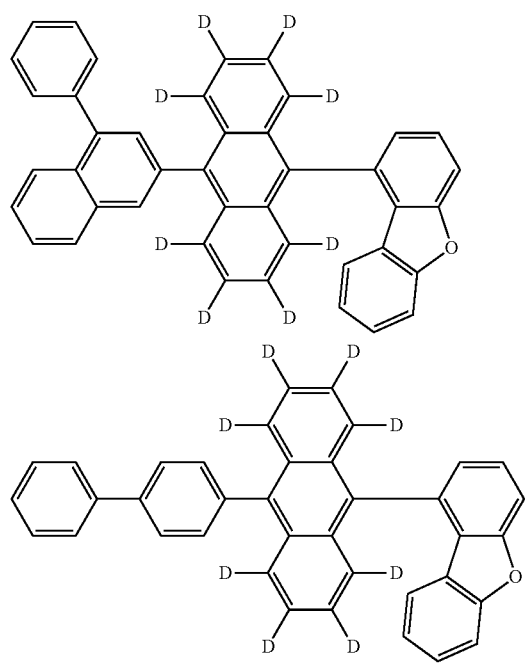

-continued
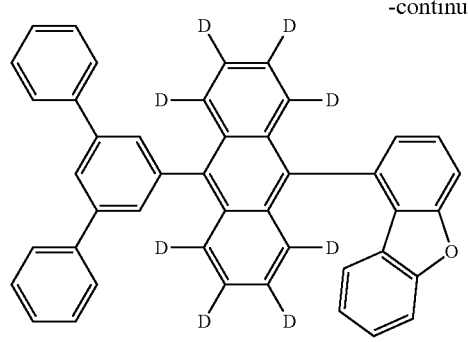
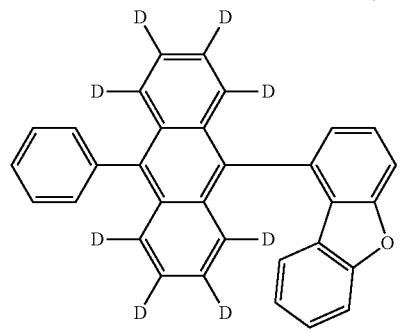
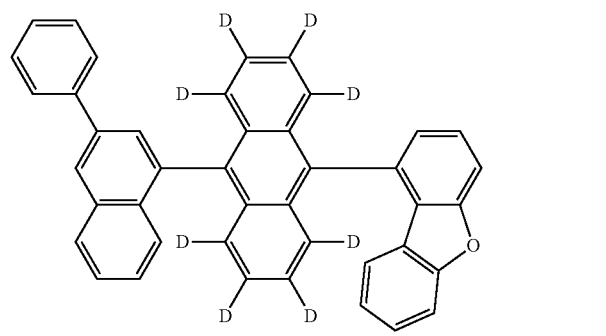
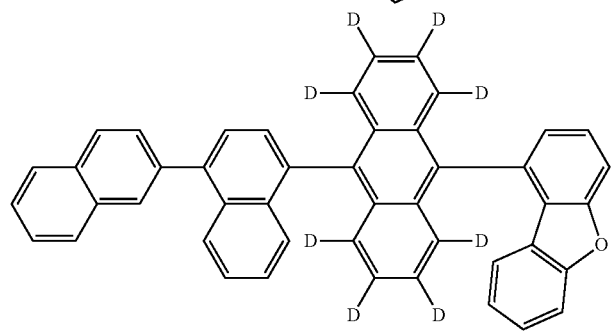
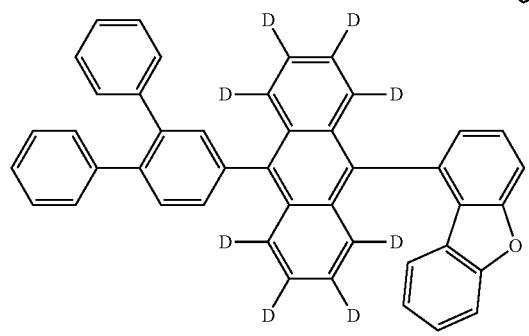

-continued
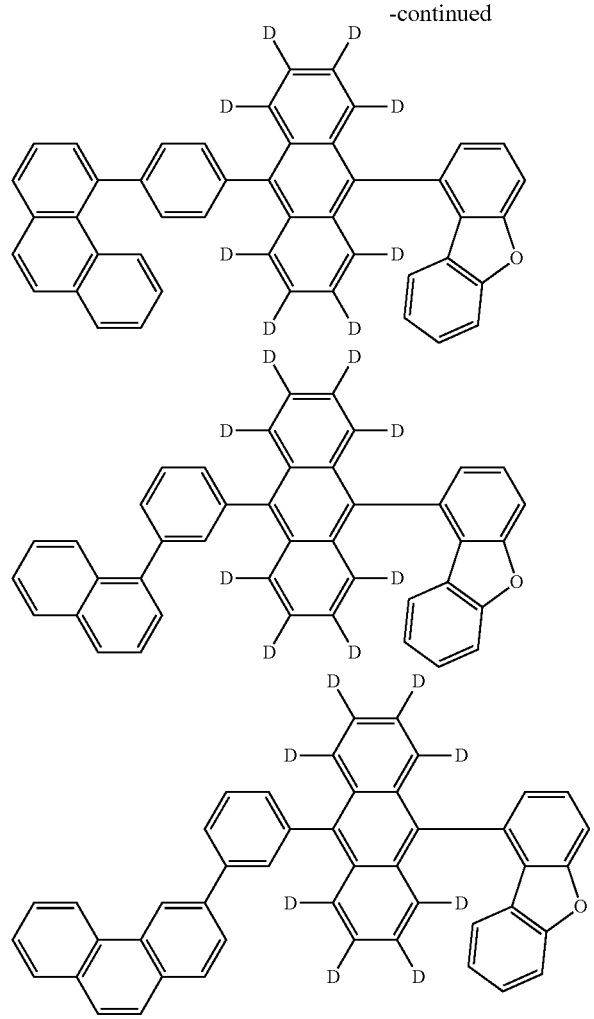
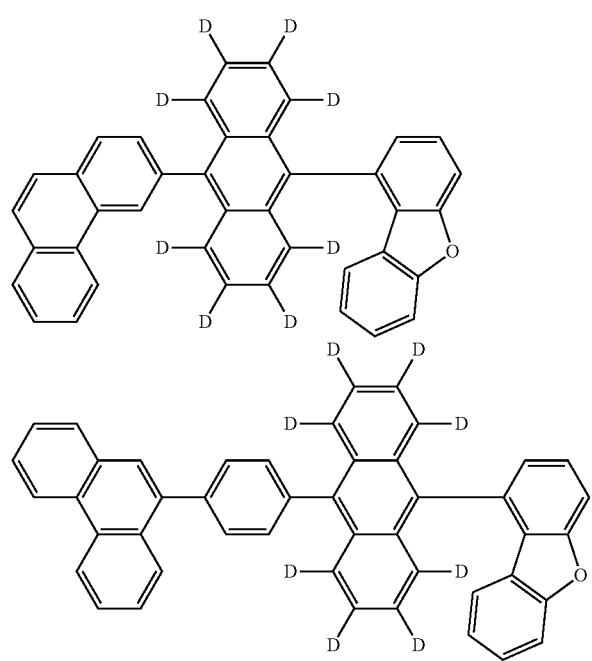

-continued
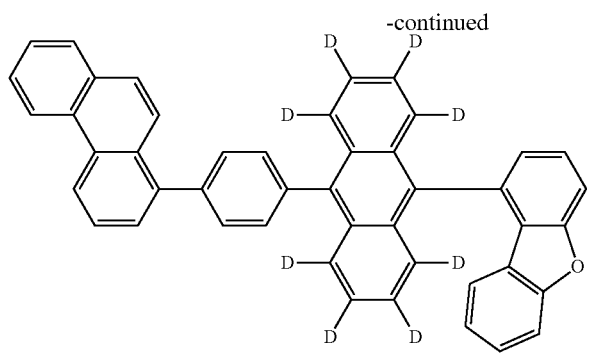
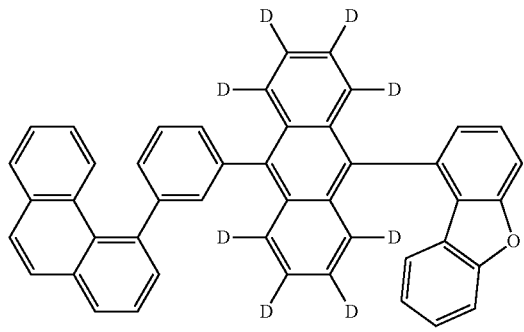
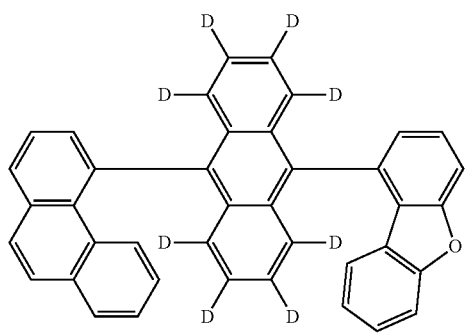
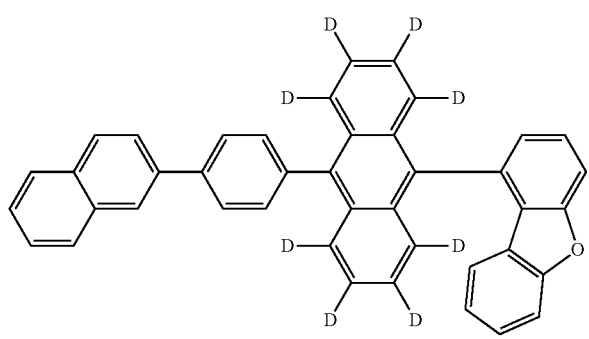
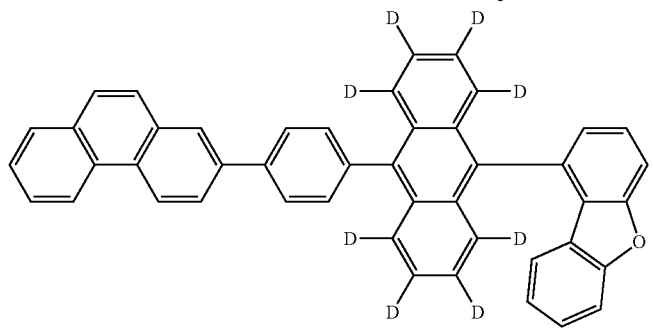

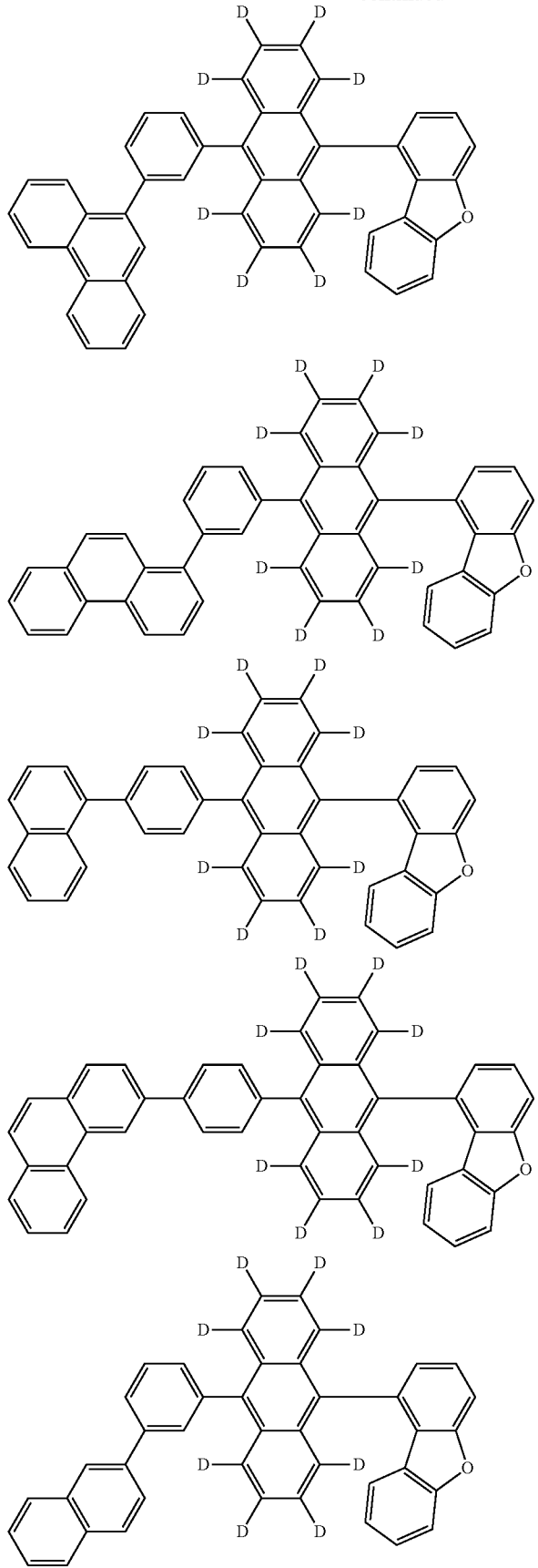

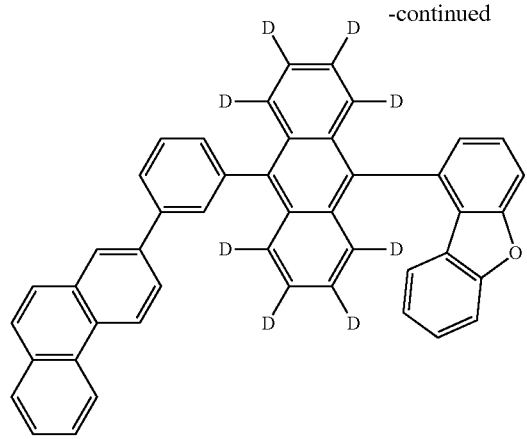
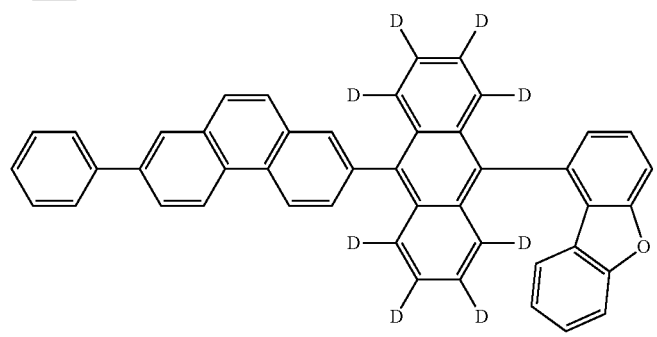
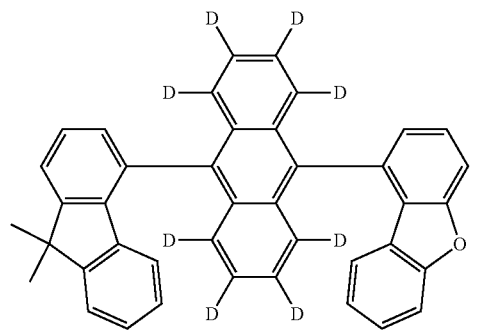
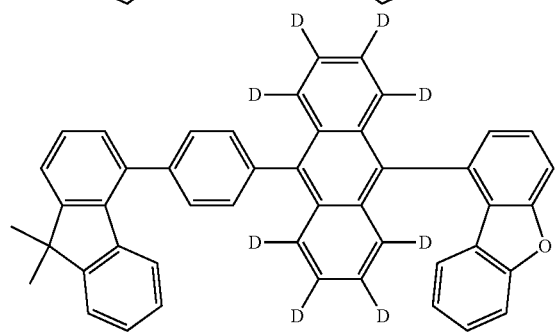
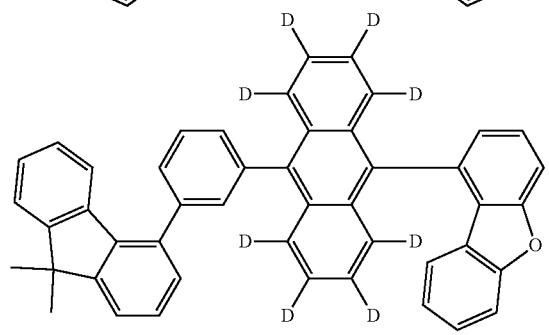

-continued
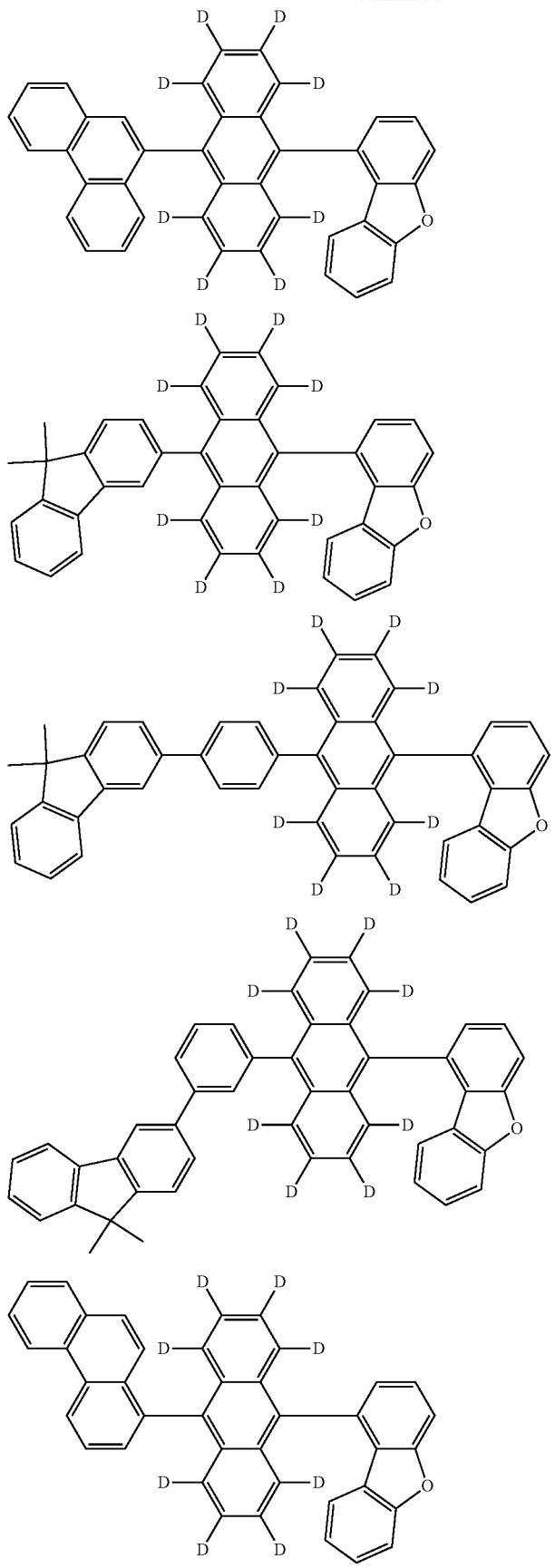

-continued
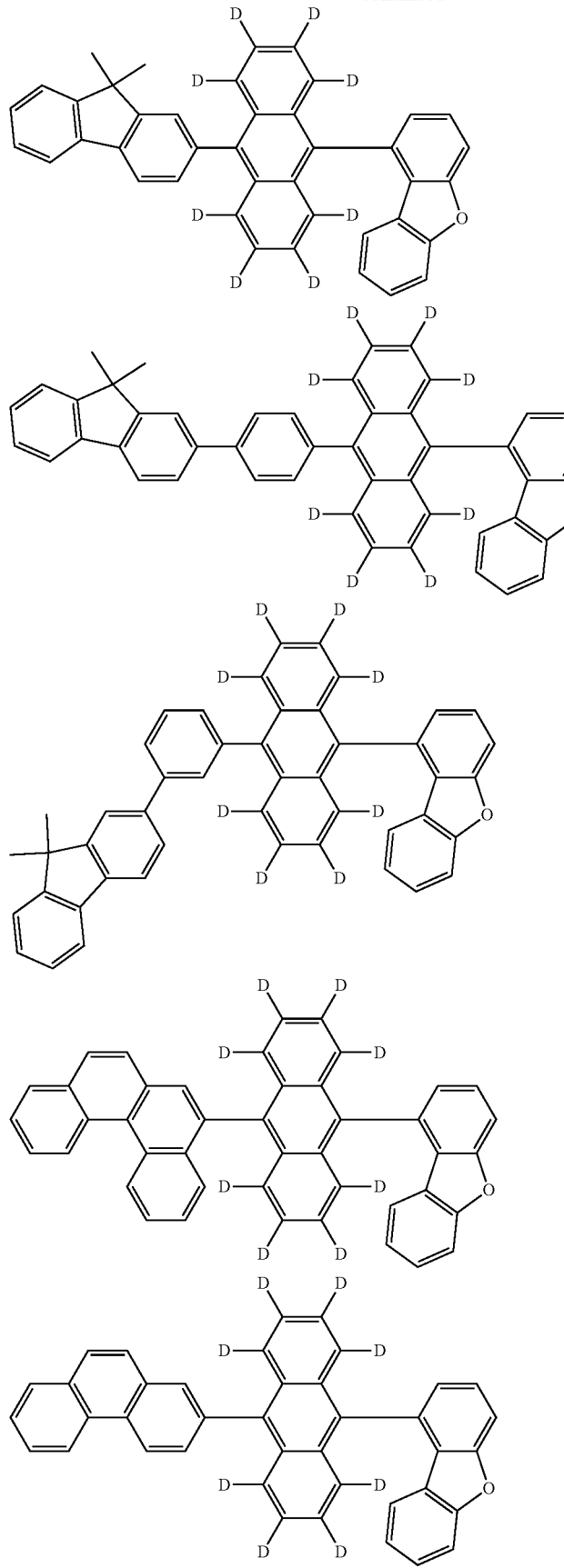

-continued
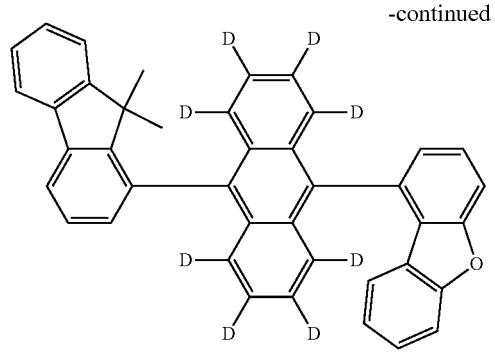
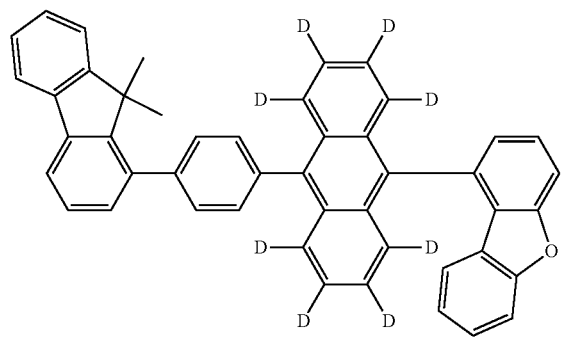
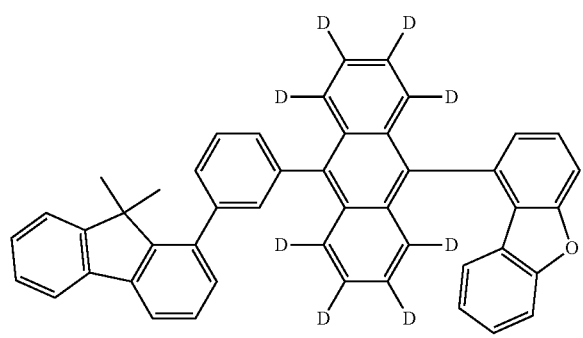
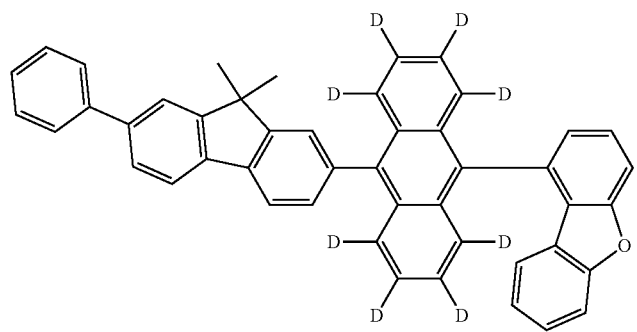

133
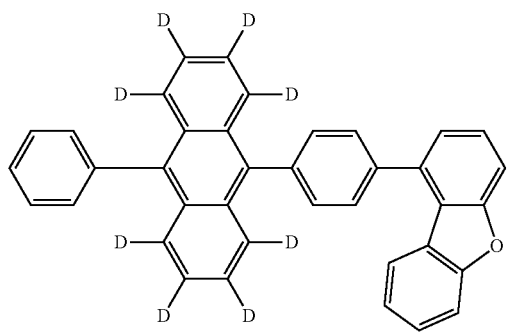
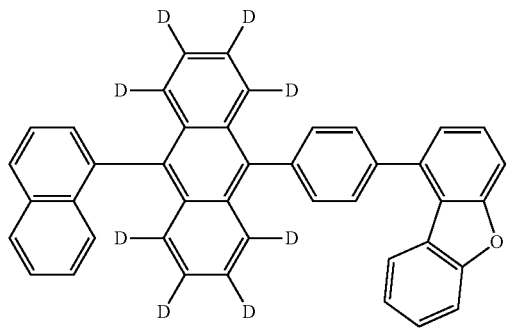
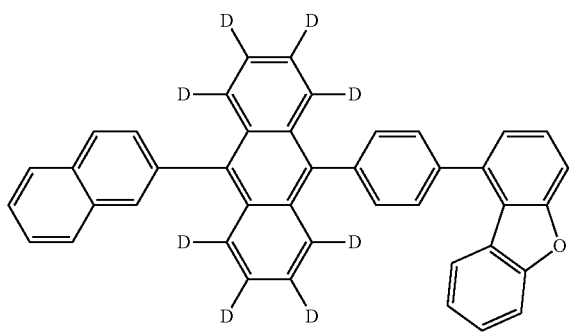
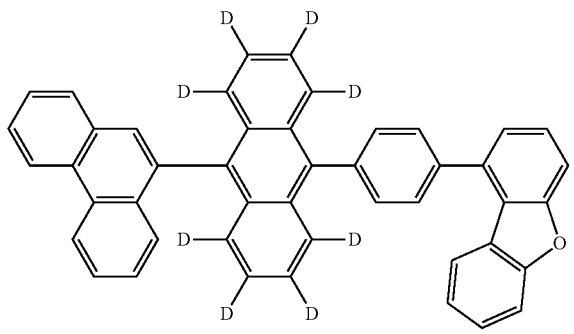
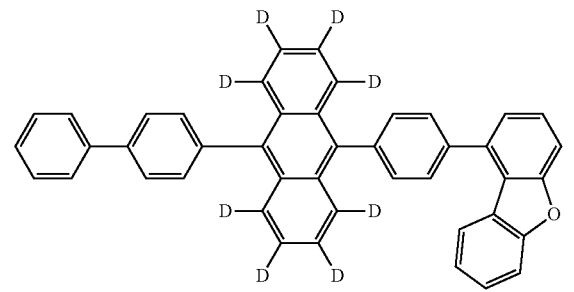
134
-continued
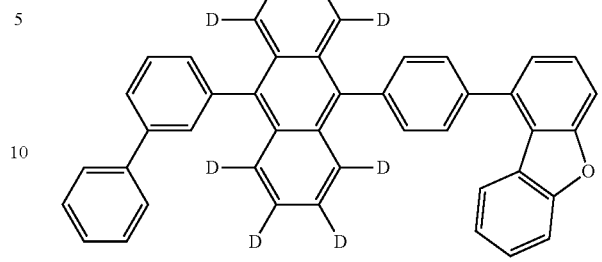
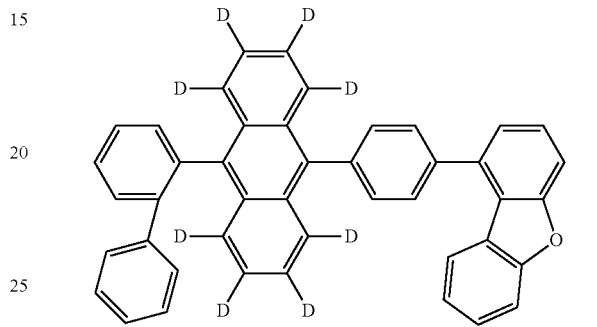
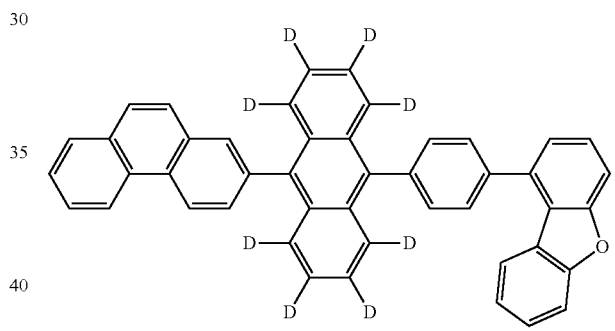
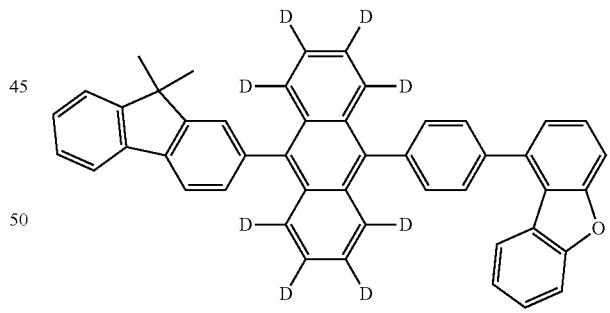
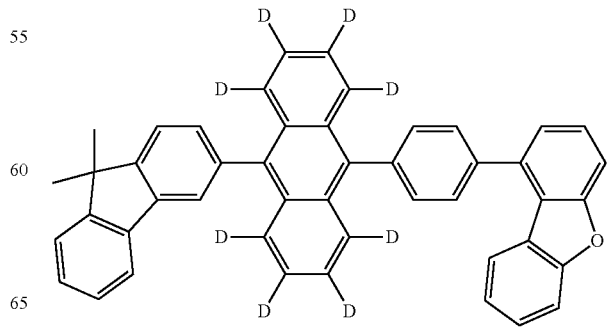

135
-continued
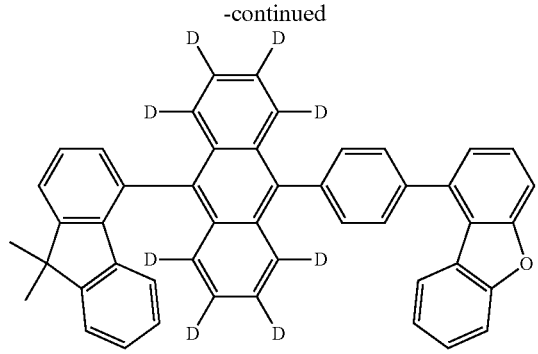
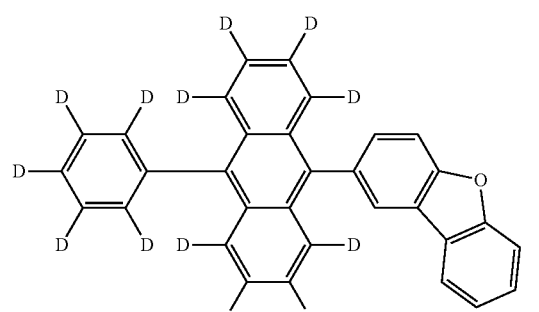
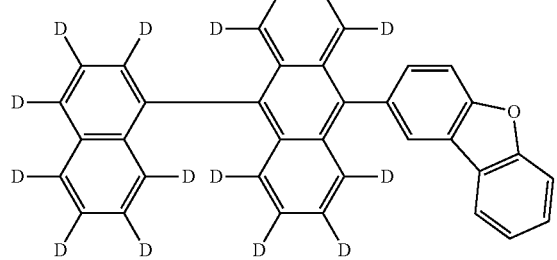
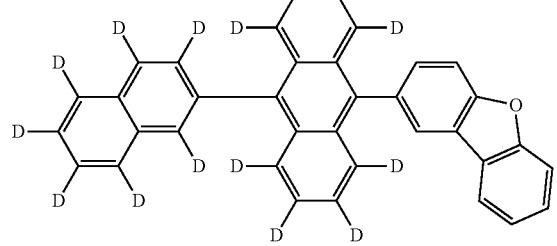
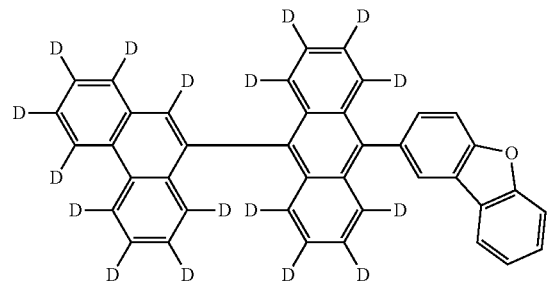
136
-continued
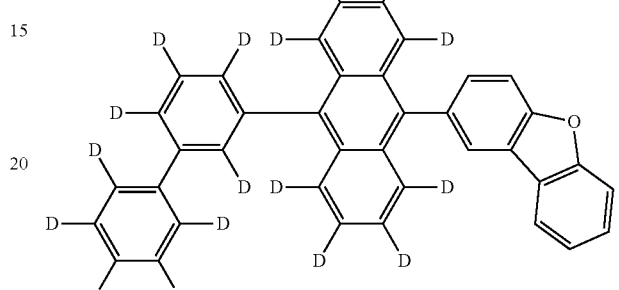
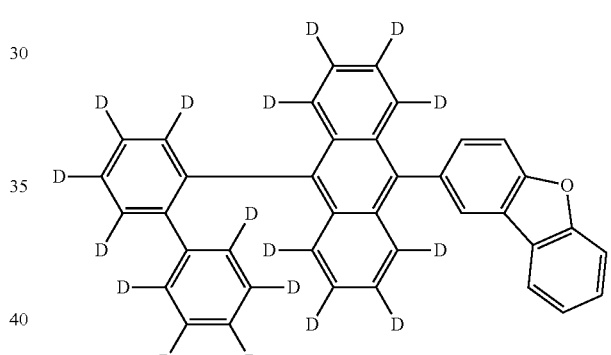
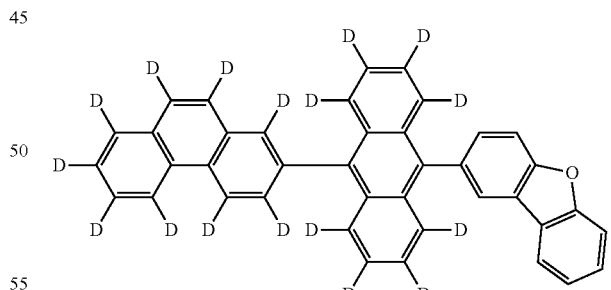
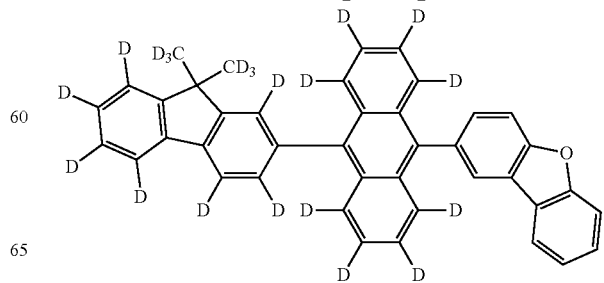

-continued
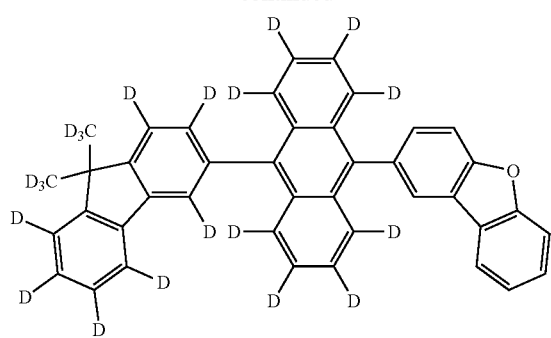
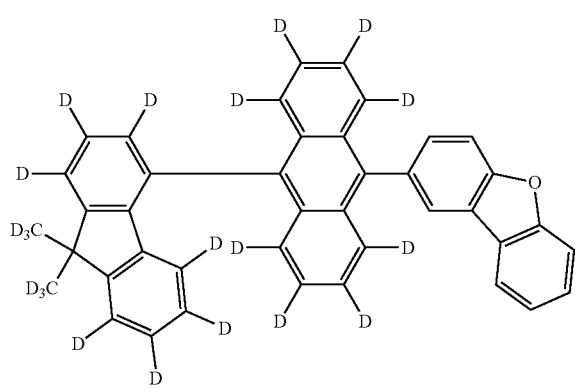
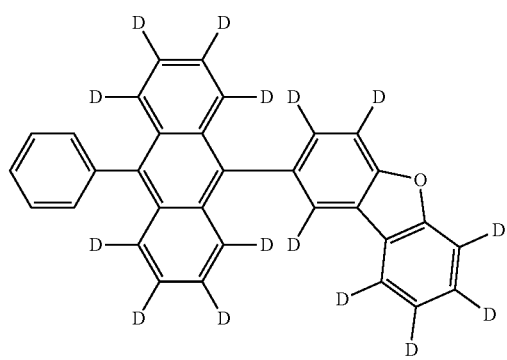
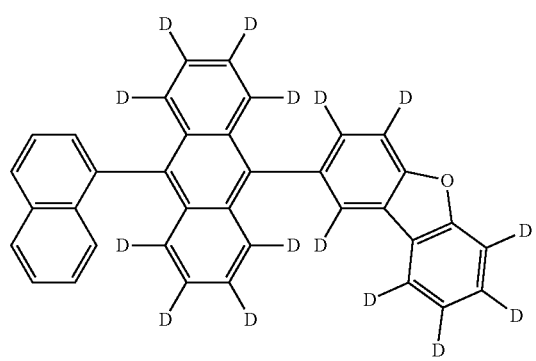
-continued
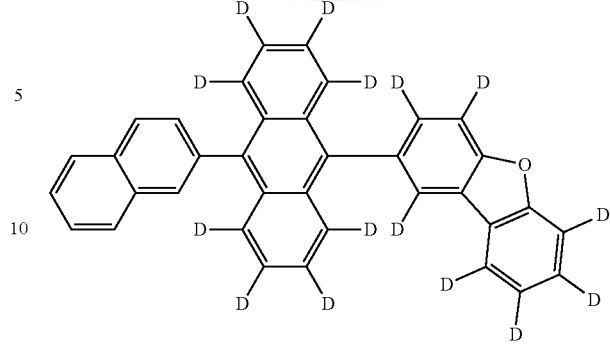
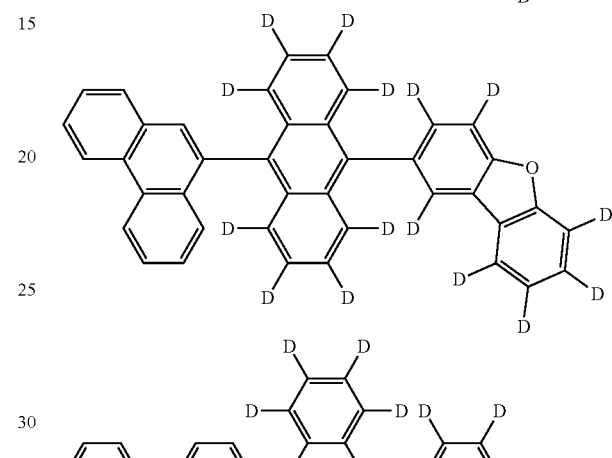
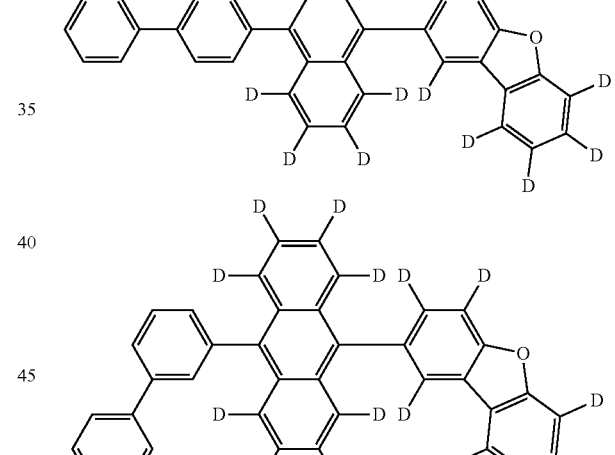
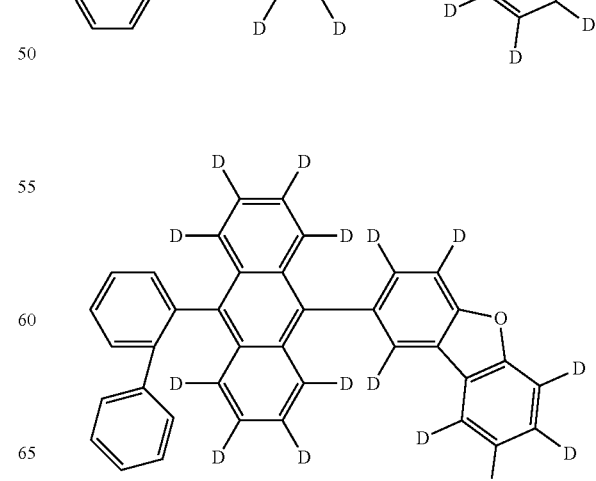

-continued
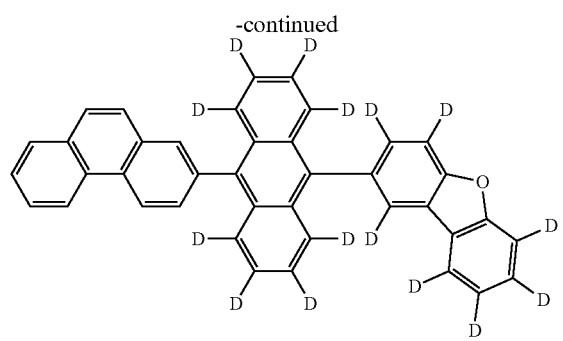
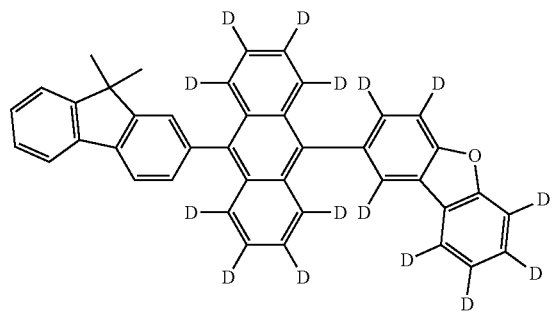
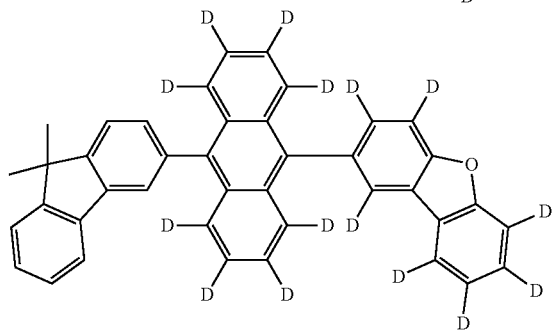
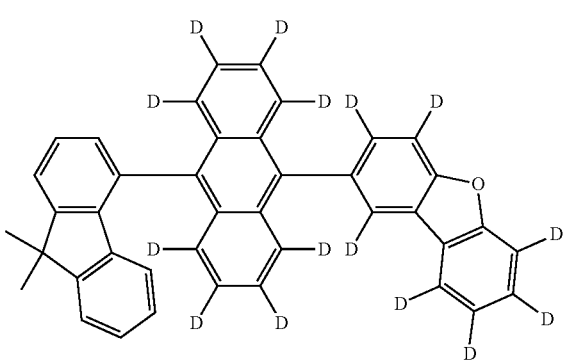
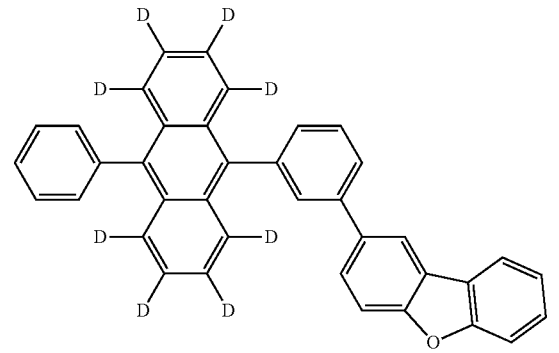
-continued
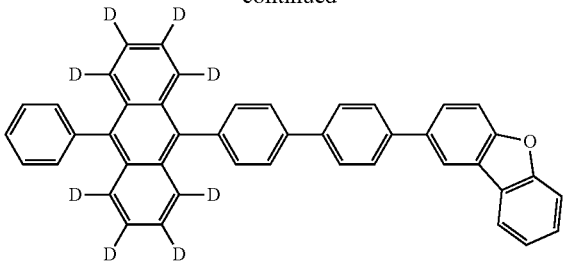
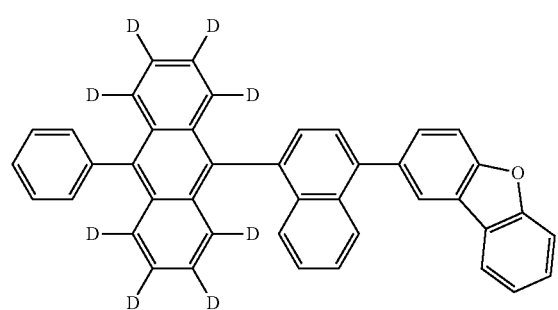
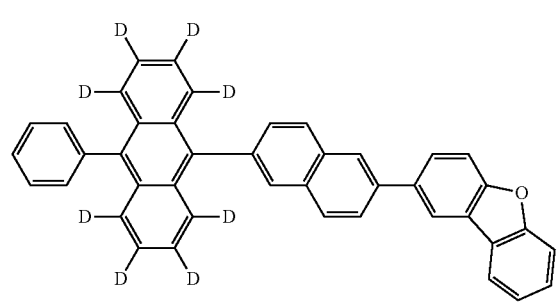
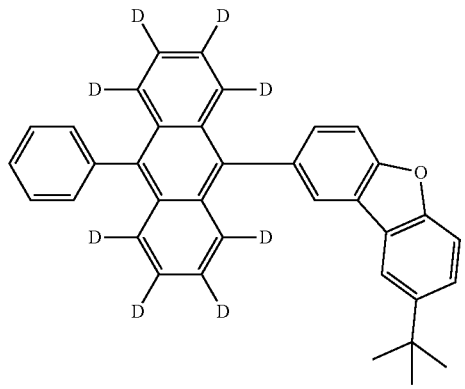
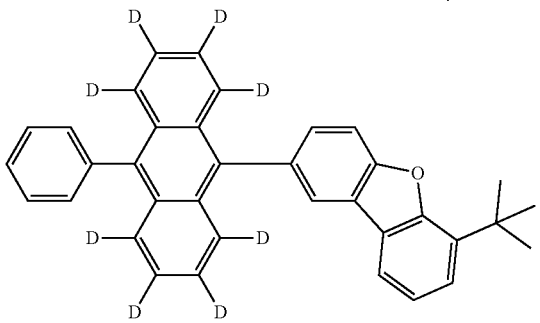

141
-continued
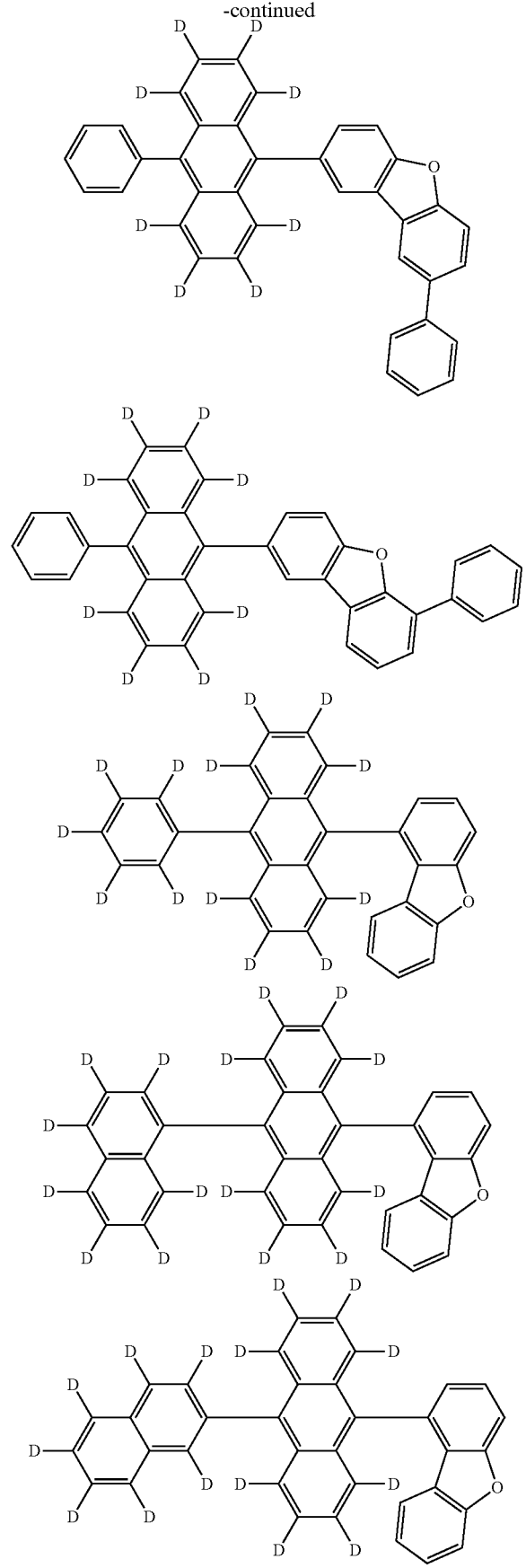
142
-continued
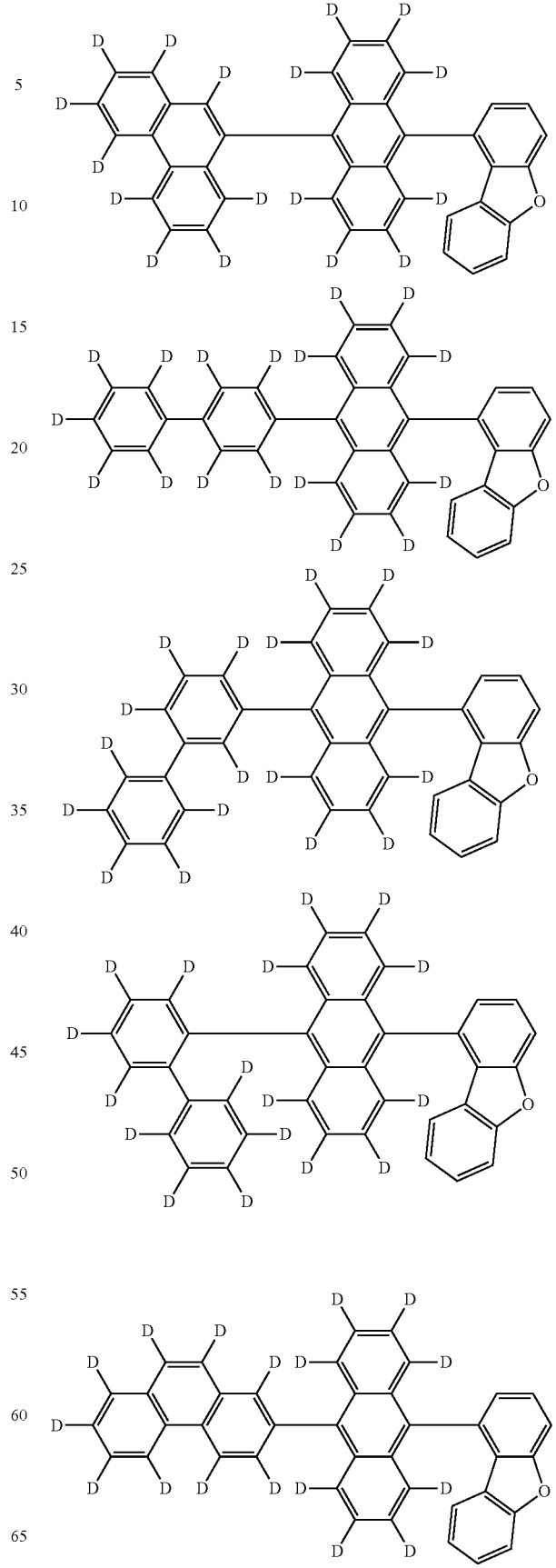

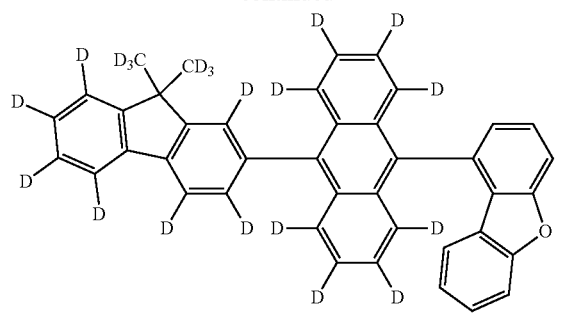
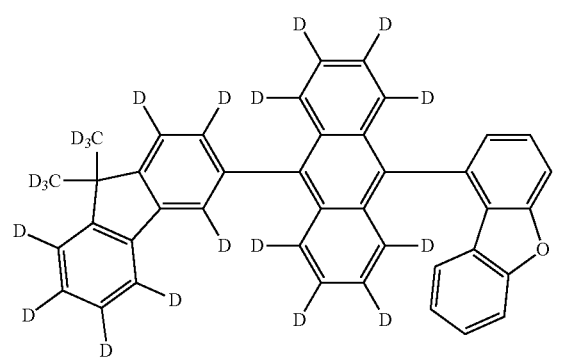
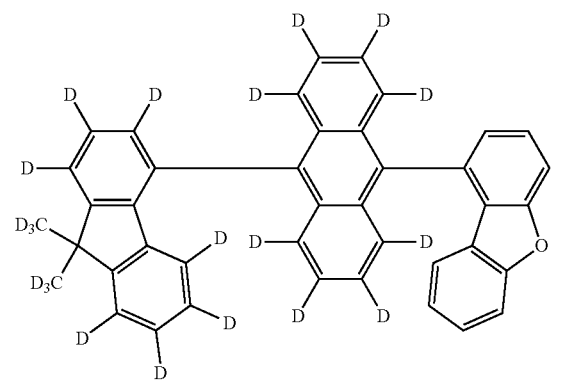

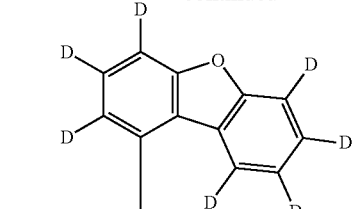

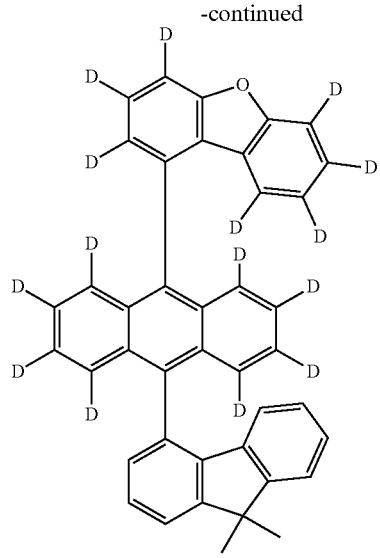
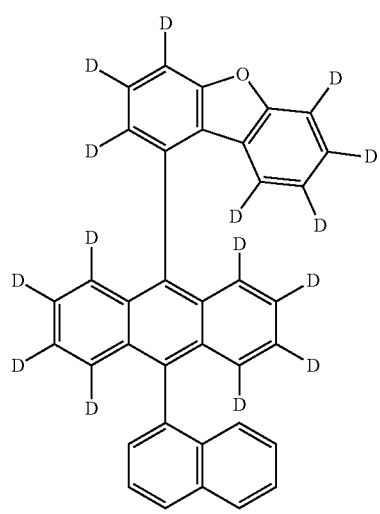
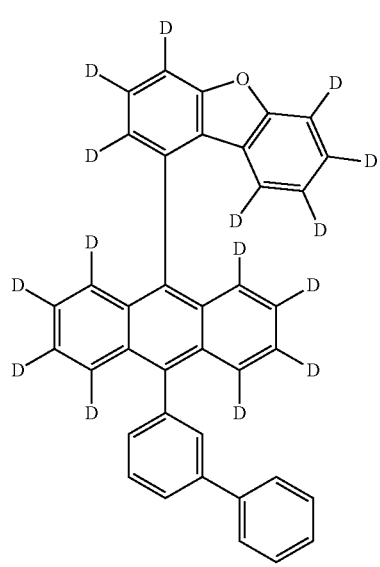
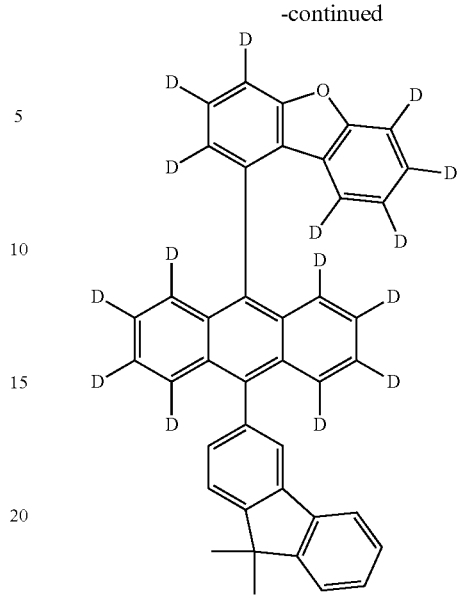
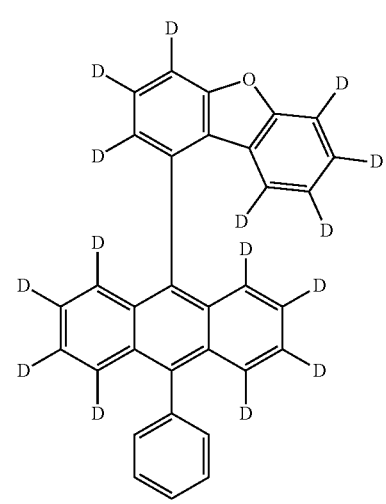
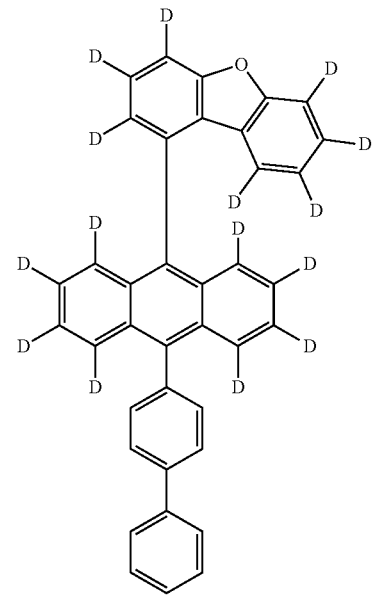

147
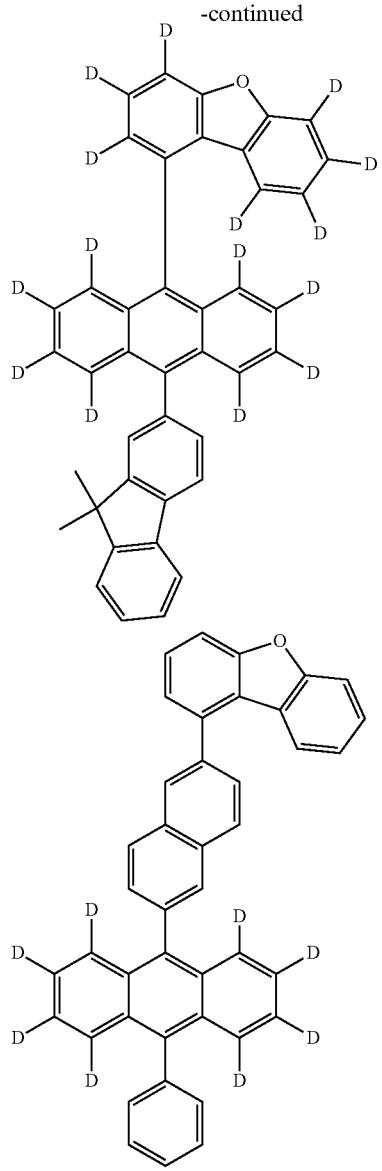
148
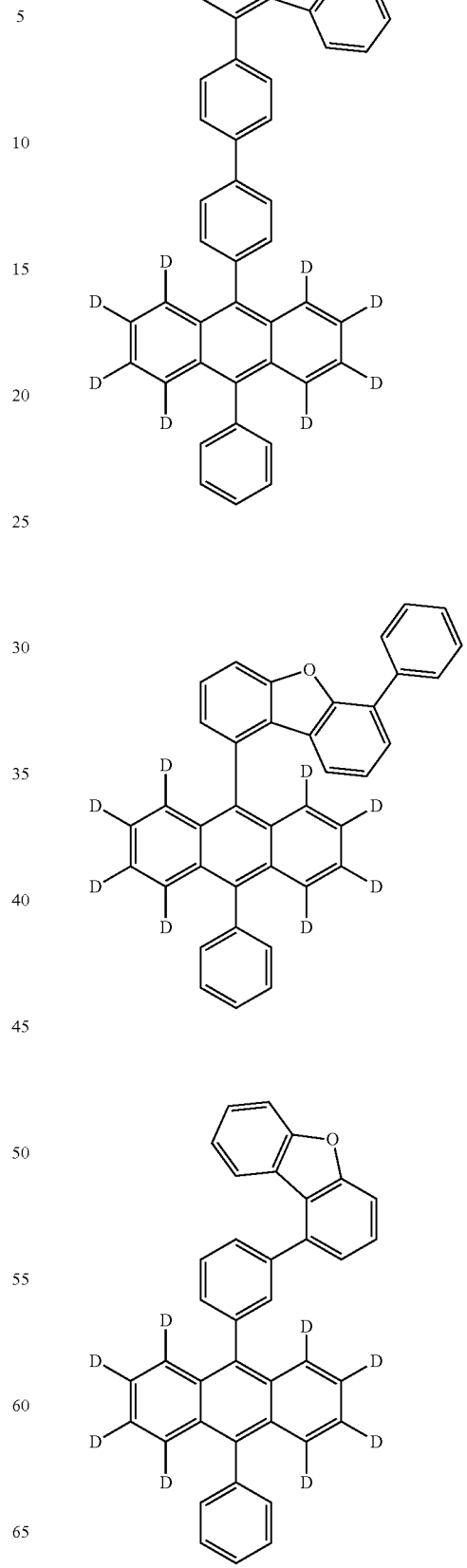

-continued

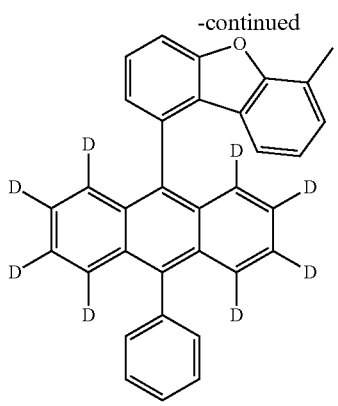

The above compound can be used as a material for organic EL device, preferably a host material for an emitting layer.

[Organic EL Device]

The organic EL device according to one aspect of the invention comprises a cathode, an anode and one or two or more organic layer disposed between the cathode and the anode, and at least one organic layer comprises the compound represented by formula (1) or (2), or the composition of the invention described above. A conventionally known material, device configuration can be applied, except that at least one of organic layer comprises the compound represented by formula (1) or (2), or the composition of the invention described above, as long as the advantageous effect of the Invention is not impaired. In the above organic EL device, one or two or more organic layers preferably comprise emitting layer and the emitting layer comprises the compound represented by formula (1) or (2), or the composition of the invention described above.

In one embodiment, the emitting layer of the organic EL device according to one aspect of the invention contains the compound represented by formula (1) or (2) and the protium compound, and the content ratio of the protium compound to the total of the compound represented by formula (1) or (2) and the protium compound is 99 mol % or less.

In one embodiment, the emitting layer of the organic EL device according to one aspect of the invention contains the compound represented by formula (1) or (2) and the protium compound, and the content ratio of the compound represented by formula (1) or (2) to the total of the compound represented by formula (1) or (2) and the protium compound is 30 mol % or more, 50 mol % or more, 70 mol % or more, 90 mol % or more, 95 mol % or more, 99 mol % or more, or 100 mol %.

One embodiment of the organic EL device preferably has the hole-transporting layer between the anode and the emitting layer.

One embodiment of the organic EL device preferably has the electron-transporting layer between the cathode and the emitting layer.

Specific examples of a typified device configuration of the organic EL device of the invention include structures such as (1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer/a cathode,
(5) an anode/an organic semiconductor layer/an emitting layer/a cathode,
(6) an anode/an organic semiconductor layer/an electron barrier layer/an emitting layer/a cathode,
(7) an anode/an organic semiconductor layer/an emitting layer/an adhesion improving layer/a cathode,
(8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,
(11) an anode/an organic semiconductor layer/an insulating layer/an emitting layer/an insulating layer/a cathode,
(12) an anode/an insulating layer a hole-injecting-transporting layer/an emitting layer/an insulating layer/a cathode, and
(13) an anode/an insulating layer a hole-injecting-transporting layer/an emitting layer an electron-injecting-transporting layer/a cathode.

Among the above-described structures, a configuration of (8) is preferably used, but the configuration is not limited thereto.

In this specification, the term "hole-injecting-transporting layer" herein means "at least one of the hole-injecting layer and the hole-transporting layer", and the term "electron-injecting-transporting layer" herein means "at least one of the electron-injecting layer and the electron-transporting layer".

The emitting layer preferably comprises one or more compounds (dopant material) selected from the group consisting of compounds represented by the following formulas (11), (21), (31), (41), (51), (61), (71) and (81) in addition to the compound (host material) represented by the formula (1) or (2).

(Compound Represented by Formula (11))

The compound represented by the formula (11) is explained below.

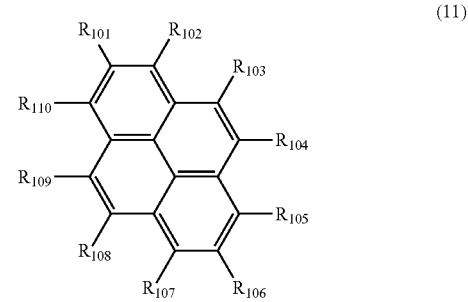

(11)

In the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

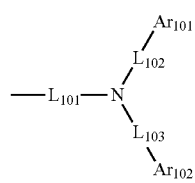

(12)

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms; $L_{101}$ to $L_{103}$ are independently
a single bond,
a substituted or unsubstituted arylene group having 6 to 30 ring carbon atoms, or
a substituted or unsubstituted divalent heterocyclic group having 5 to 30 ring atoms.
In the formula (11), it is preferable that two of $R_{101}$ to $R_{110}$ are the group represented by the formula (12).
In one embodiment, the compound represented by the formula (11) is represented by the following formula (13).

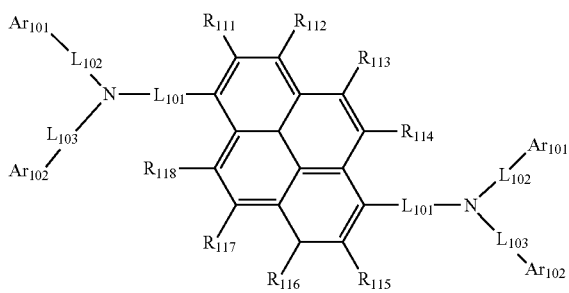

(13)

In the formula (13), $R_{111}$ to $R_{118}$ are the same as $R_{101}$ to $R_{110}$ that is not a monovalent group represented by the formula (12) in the formula (11). $Ar_{901}$, $Ar_{902}$, $L_{101}$, $L_{102}$ and $L_{103}$ are as defined in the formula (12).

In the formula (11), $L_{101}$ is preferably a single bond and $L_{102}$ and $L_{103}$ mare preferably a single bond.

In one embodiment, the compound represented by the formula (11) is represented by the formula (14) or (15).

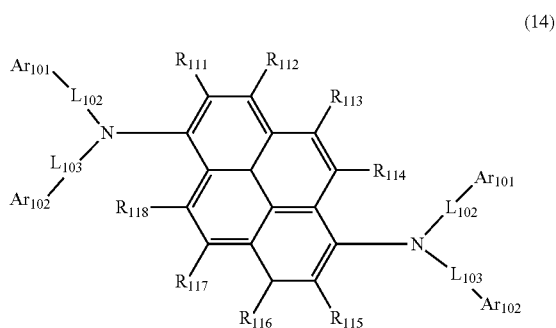

(14)

In the formula (14), $R_{111}$ to $R_{118}$ are as defined in the formula (13). $Ar_{101}$, $Ar_{102}$, $L_{102}$ and $L_{103}$ are as defined in the formula (12).

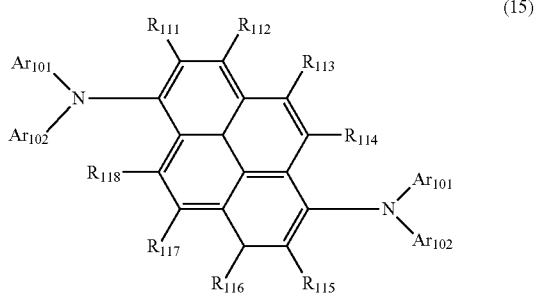

(15)

In the formula (15), $R_{111}$ to $R_{118}$ are as defined in the formula (13). $Ar_{101}$, and $Ar_{102}$ are as defined in the formula (12).

In the formula (11) and formula (12), it is preferable that at least one of $Ar_{101}$ and $Ar_{102}$ is the group represented by the following formula (16).

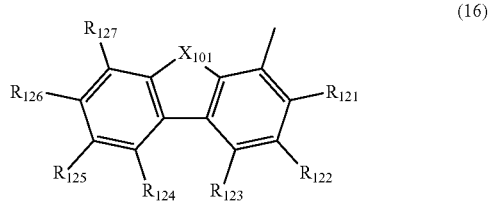

(16)

In the formula (16),
$X_{101}$ is an oxygen atom or a sulfur atom;
one or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:
$R_{121}$ to $R_{12}$ that do not form the substituted or unsubstituted, saturated or unsaturated ring are independently
a hydrogen atom, a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

It is preferable that $X_{101}$ is an oxygen atom.

It is preferable that at least one of $R_{121}$ to $R_{127}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

It is preferable that in the formula (11) and formula (12), $Ar_{101}$ is a group represented by the formula (16) and $Ar_{102}$ is a substituted or unsubstituted aryl group having 6 to 50 ring carbon atoms.

In one embodiment, the compound represented by the formula (11) is represented by the following formula (17).

In the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

As the compound represented by the formula (11), the following compounds can be given as specific examples, for example. In the following example compounds, Me represents methyl group.

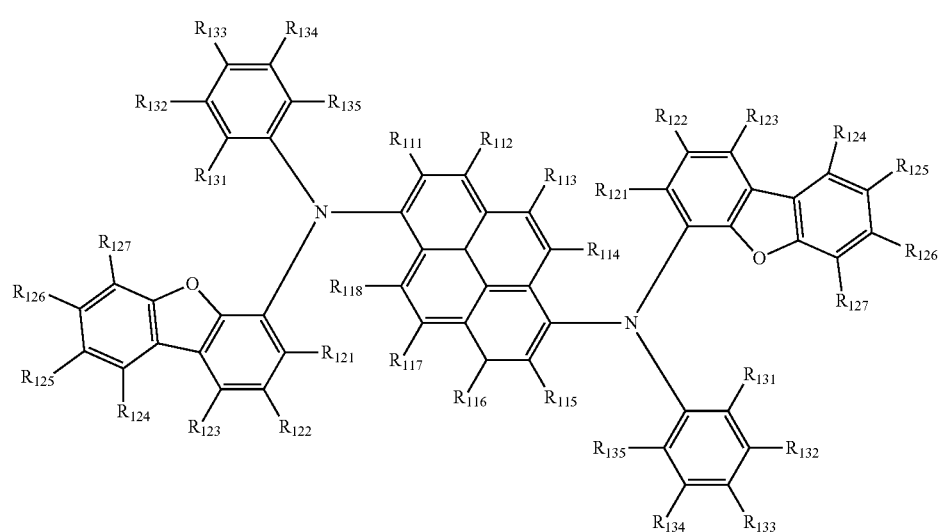

(17)

155
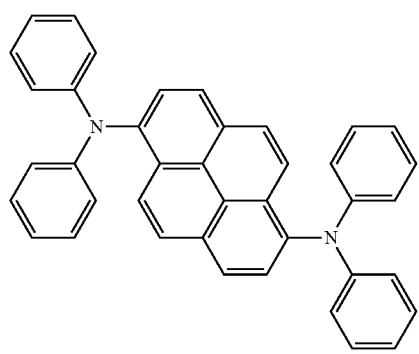
156
-continued
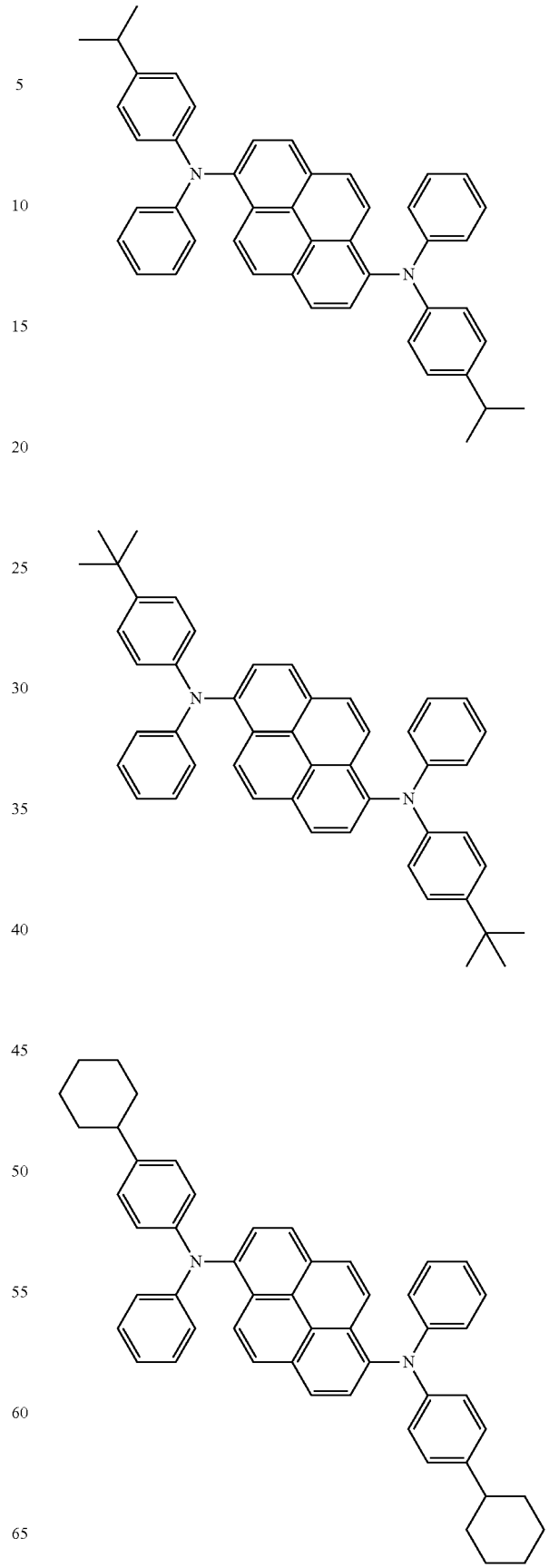

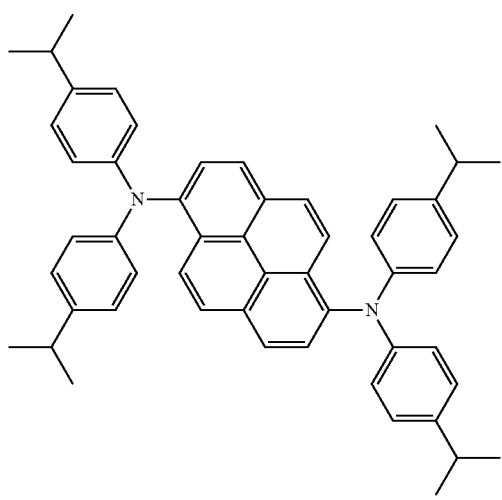
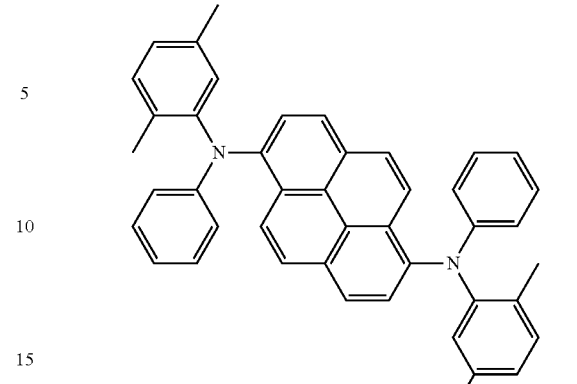
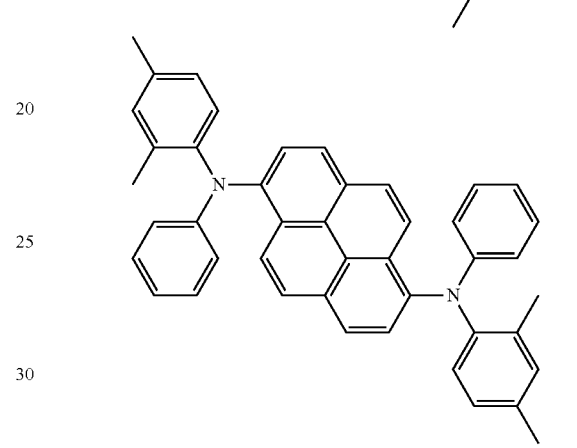
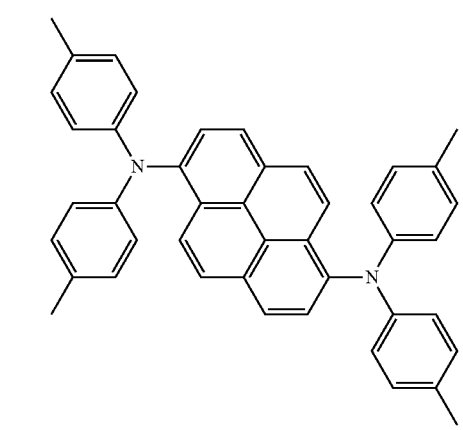
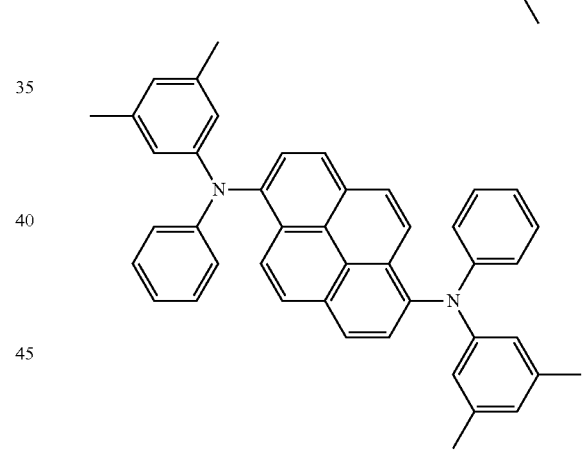
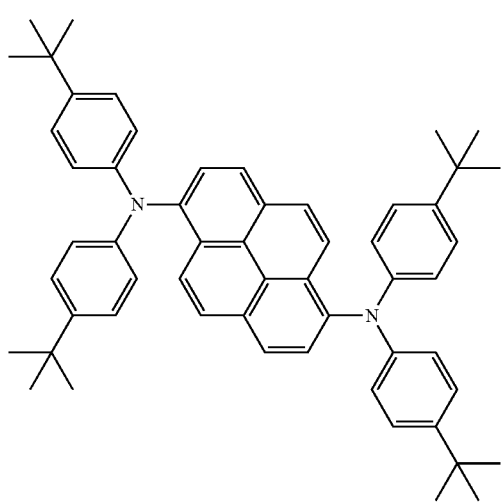
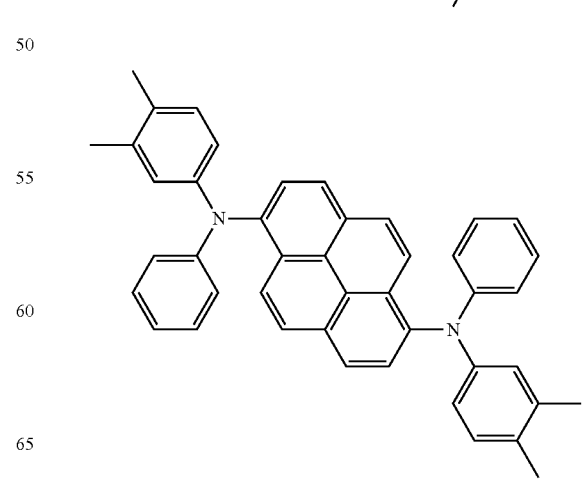

159
-continued
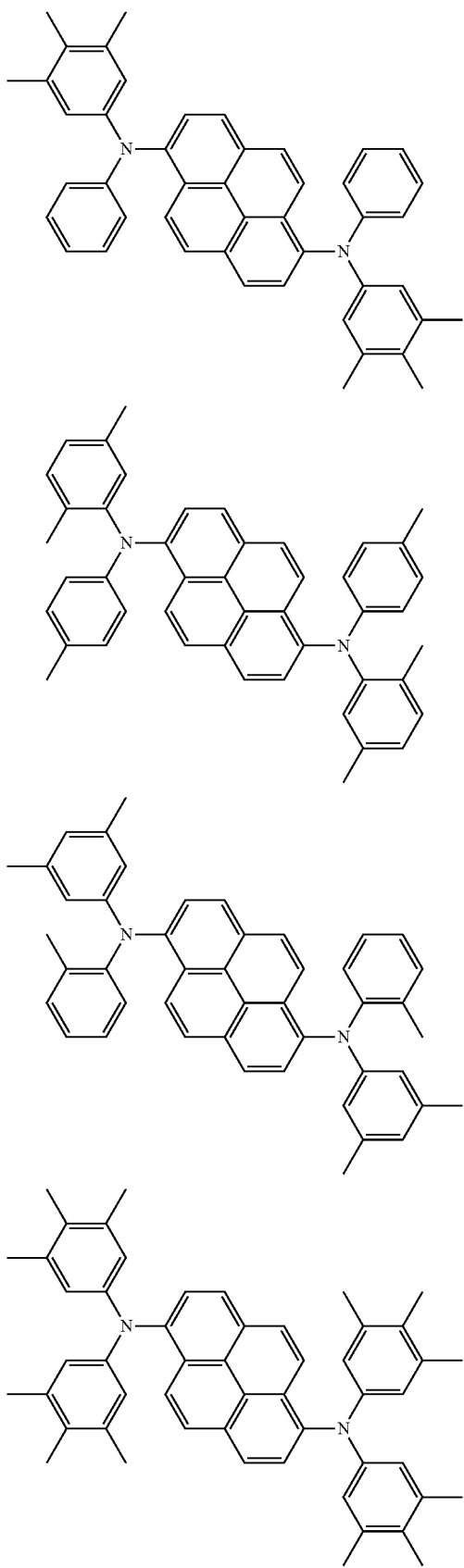
160
-continued
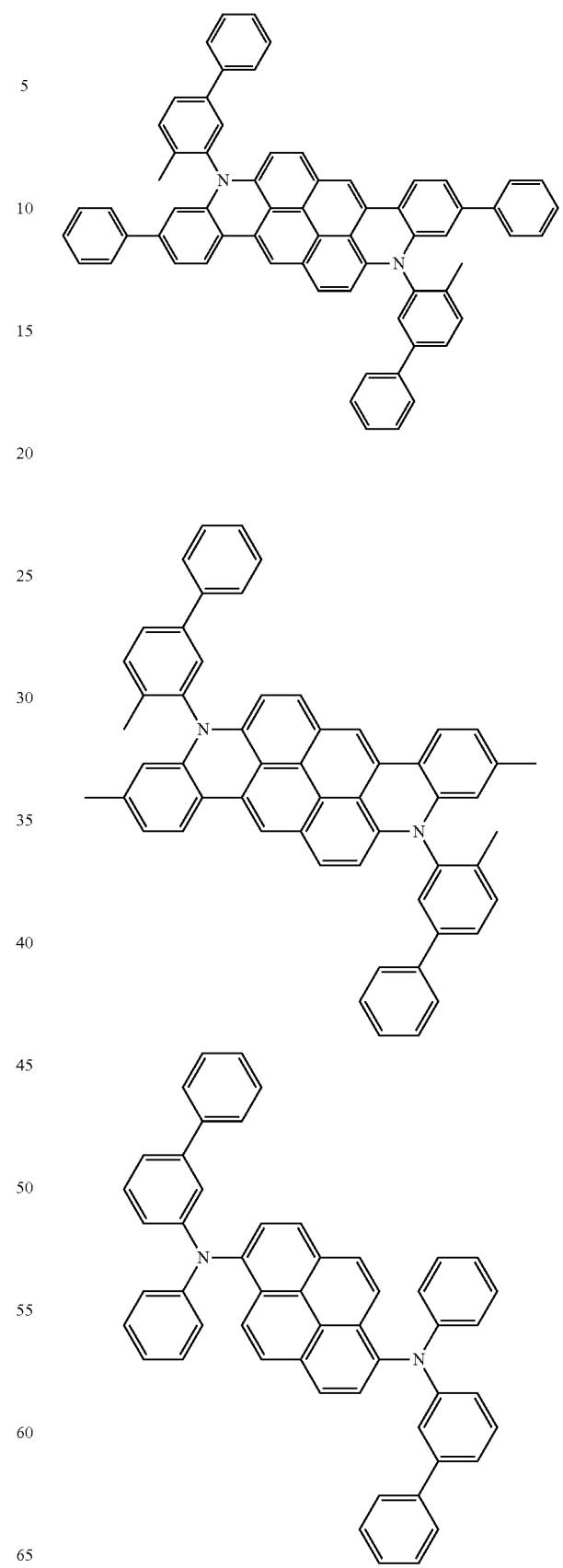

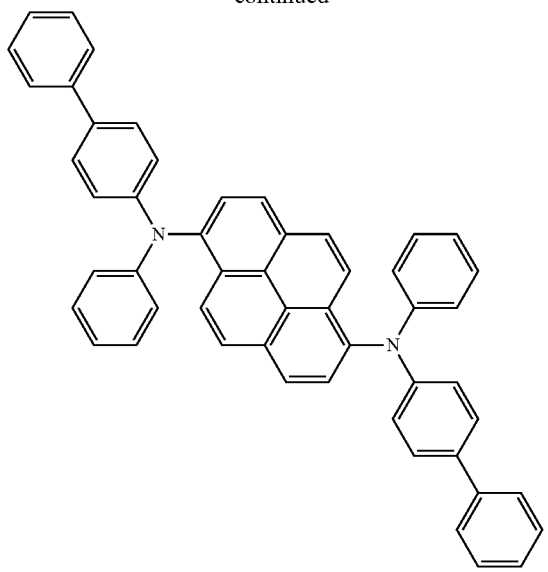
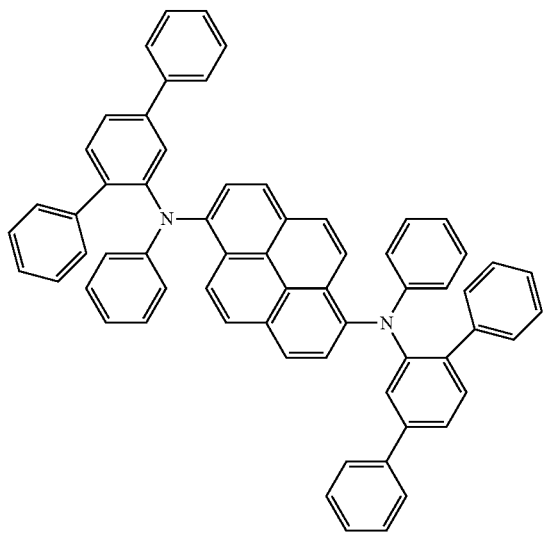
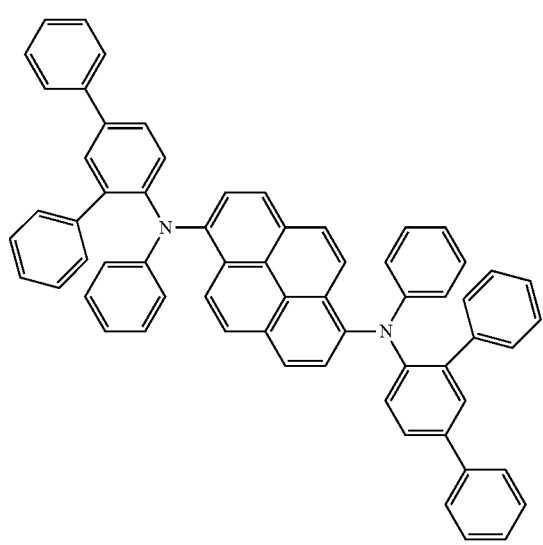
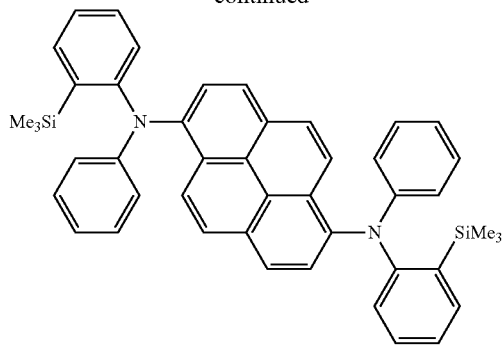
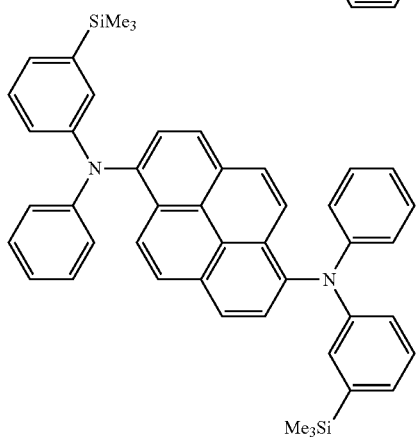
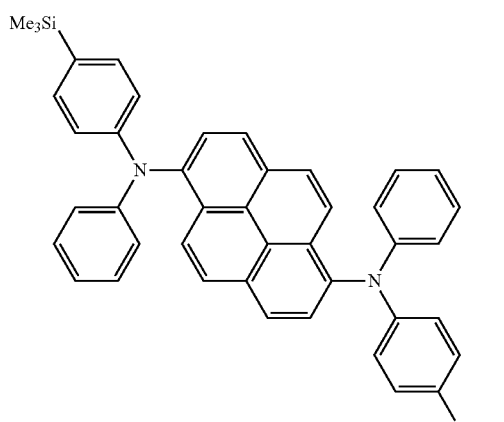
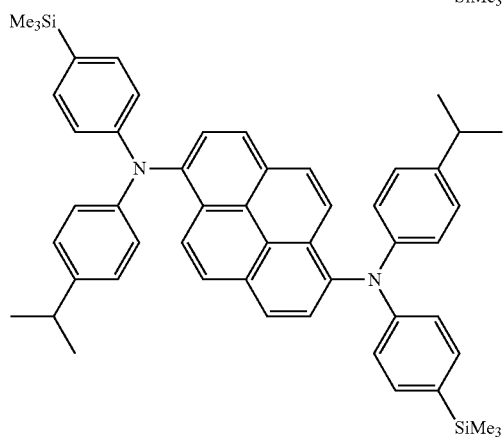

163
-continued
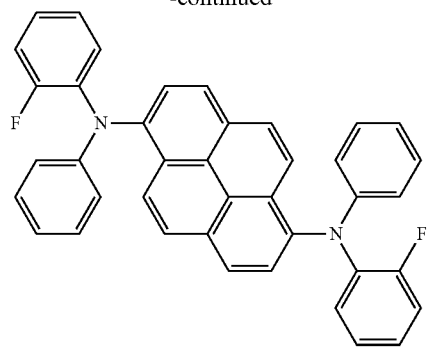
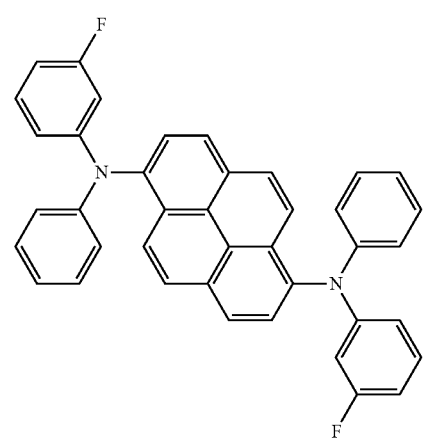
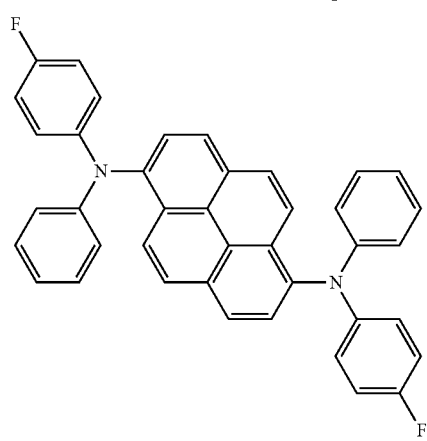
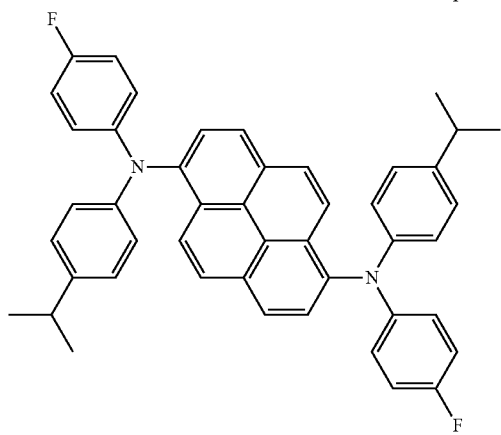
164
-continued
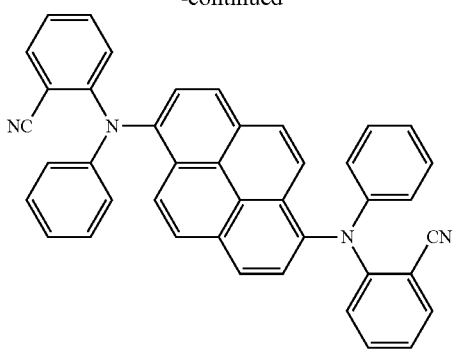
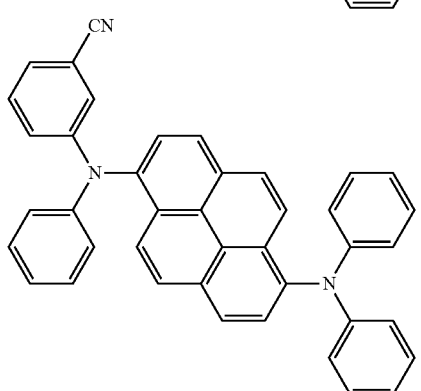
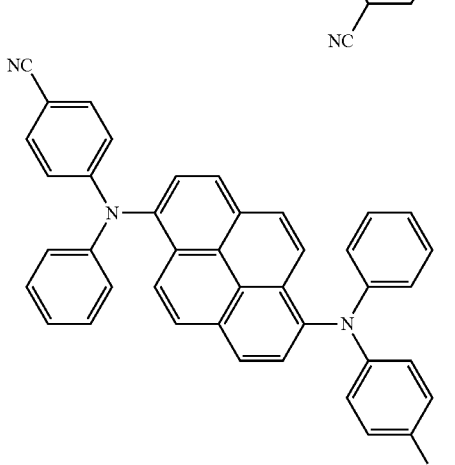

165
-continued
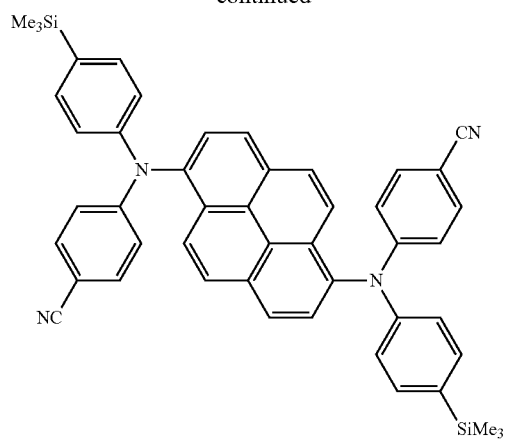
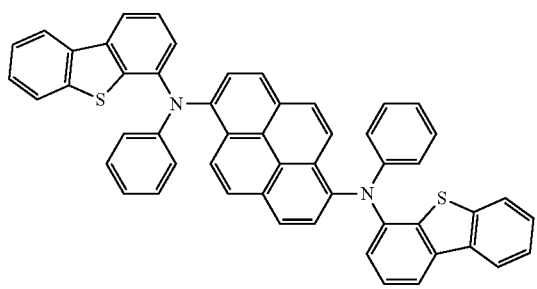
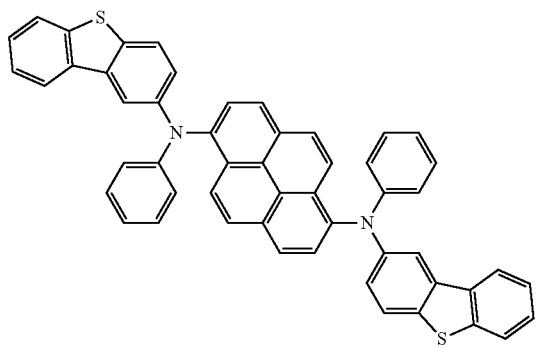
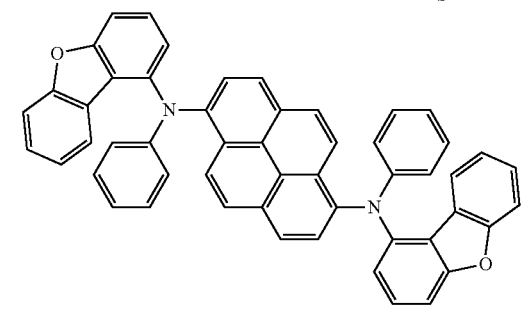
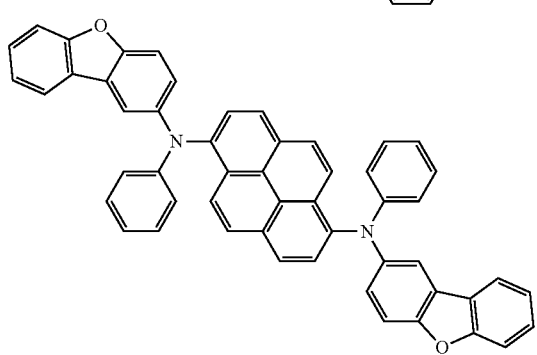
166
-continued
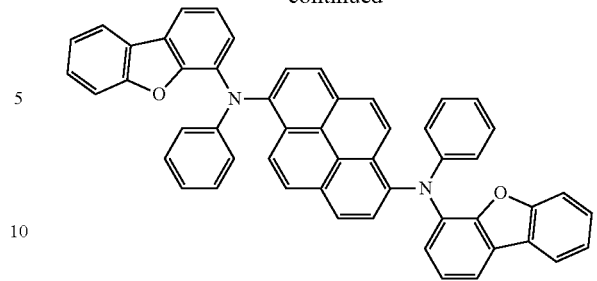
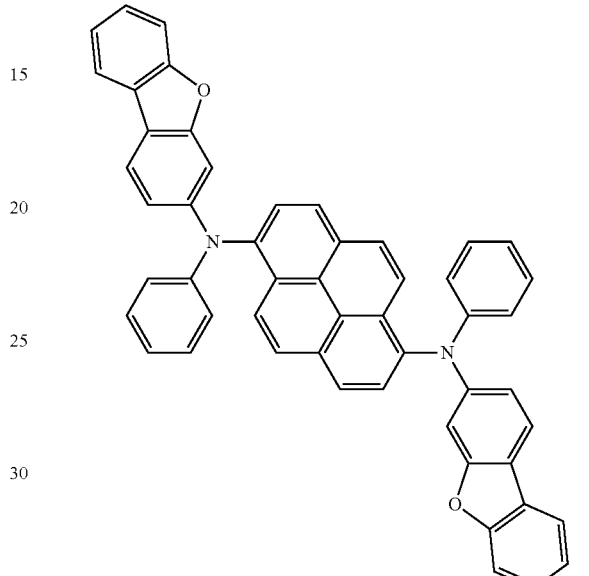
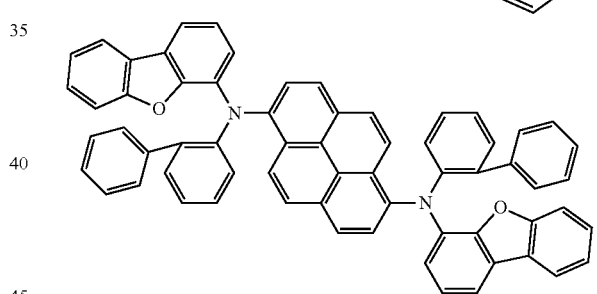
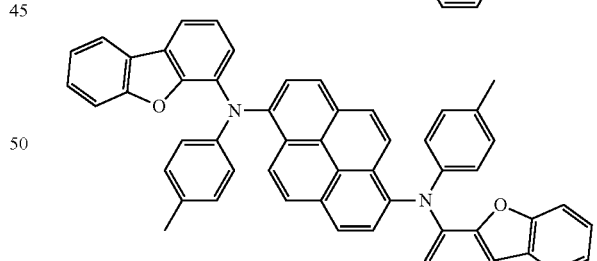
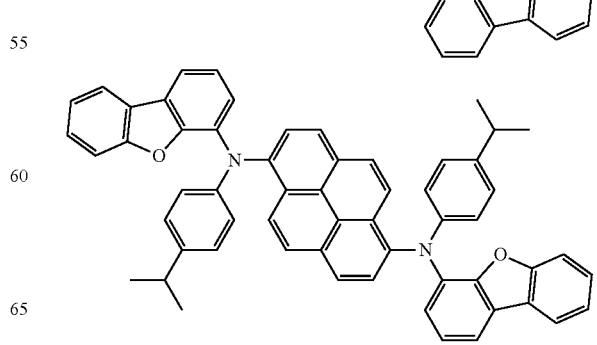

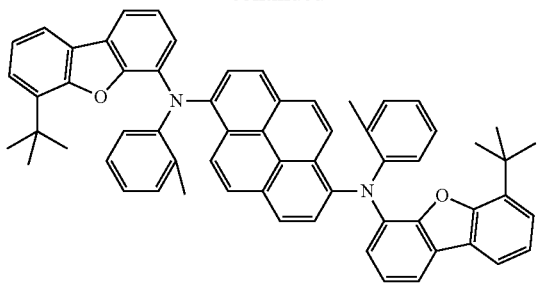
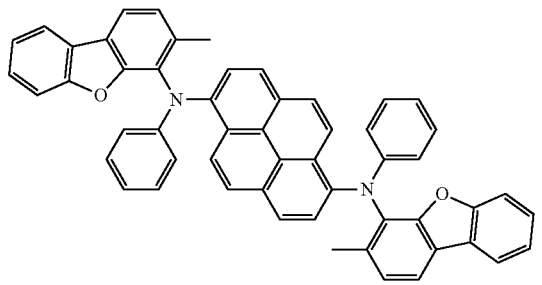
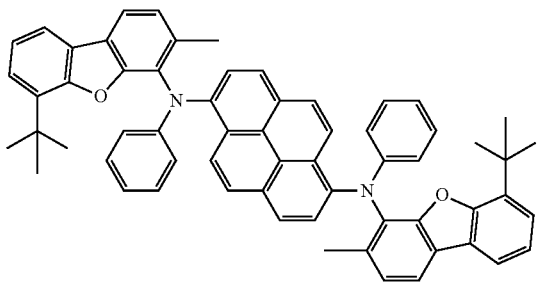
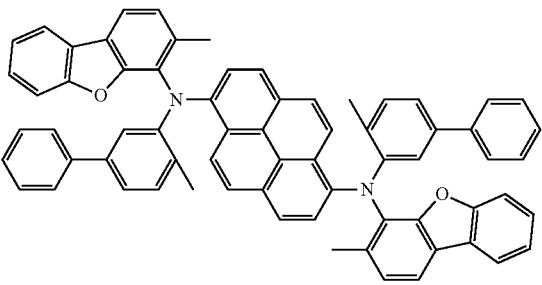
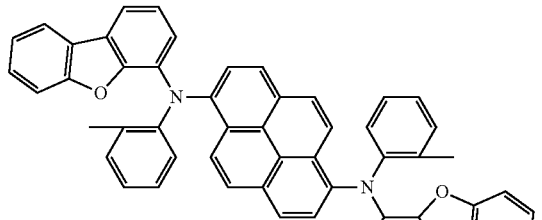
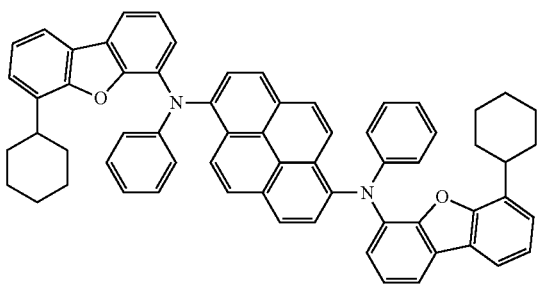
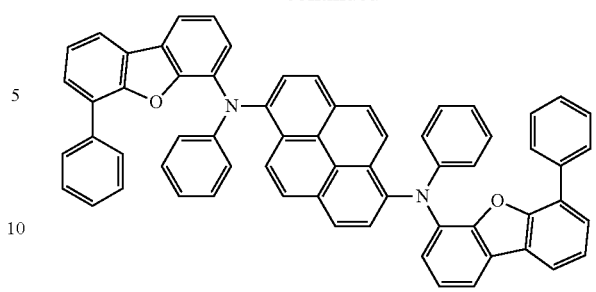
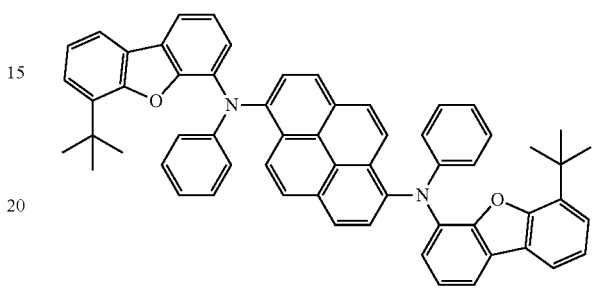
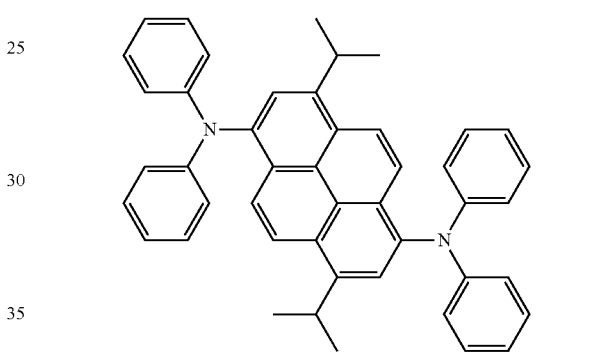
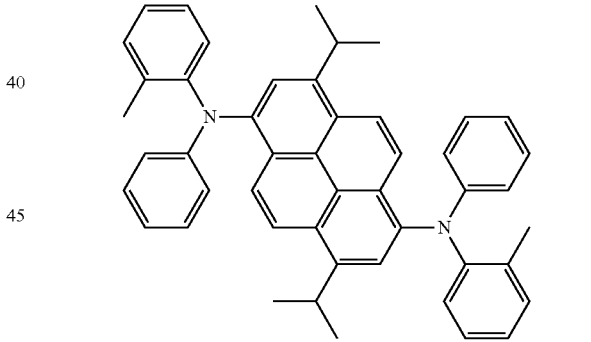
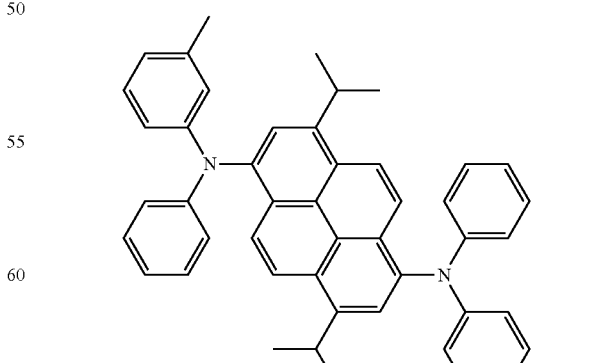
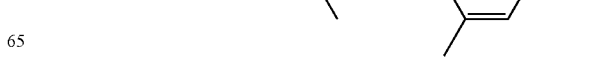

169
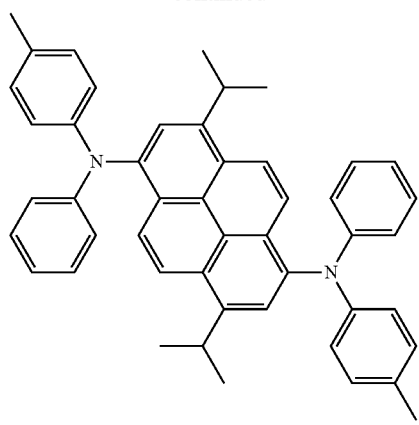
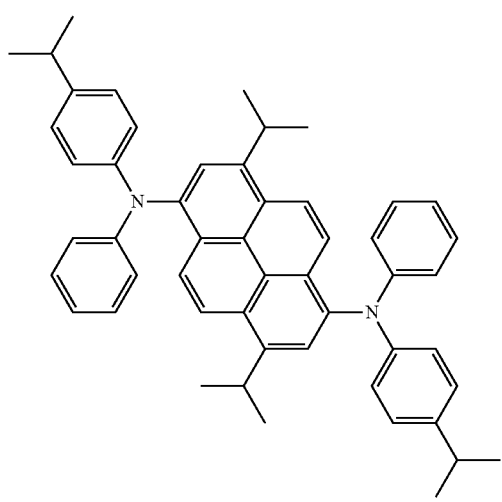
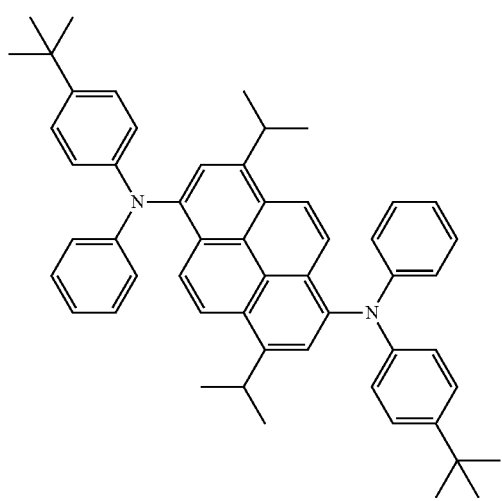
170
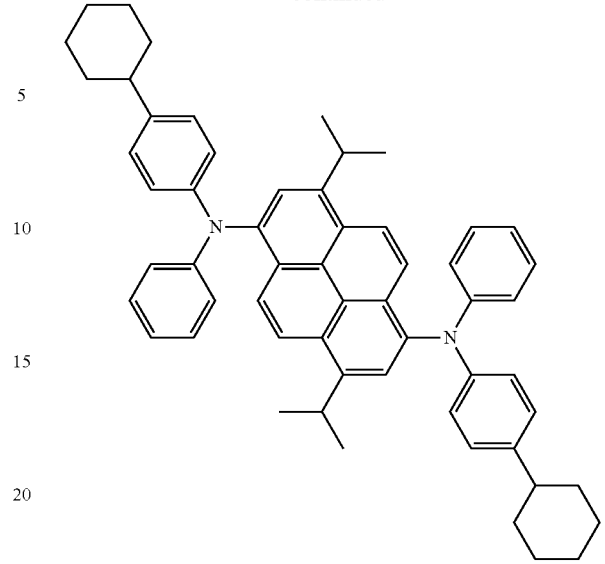
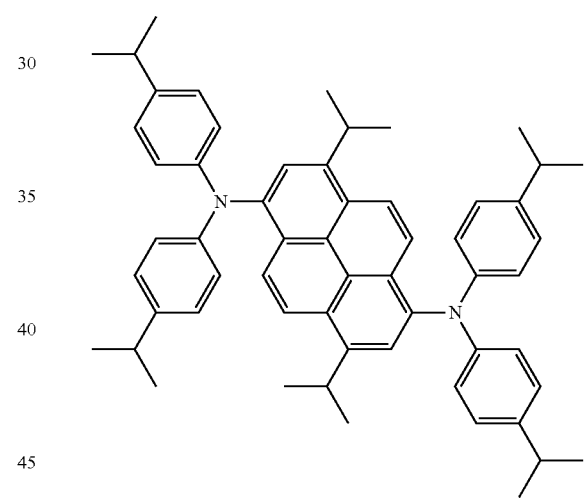
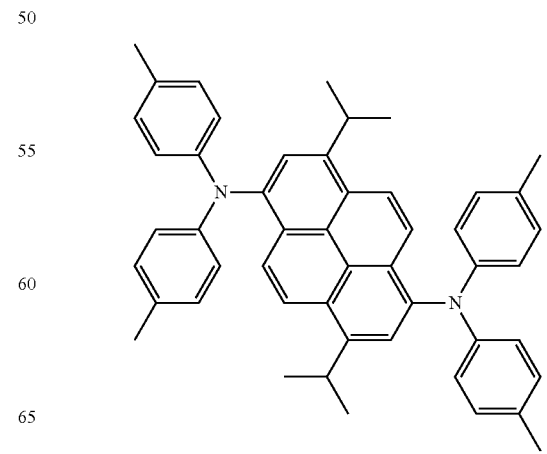

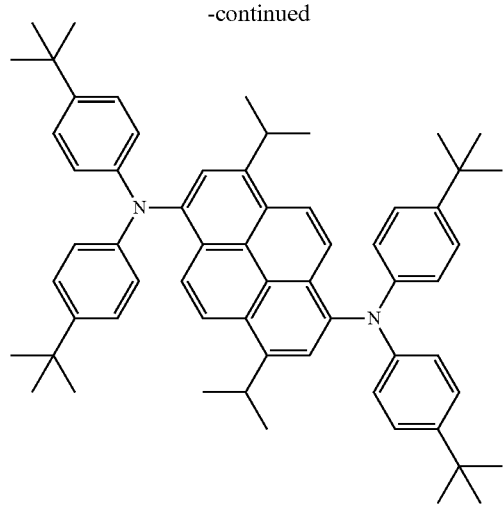
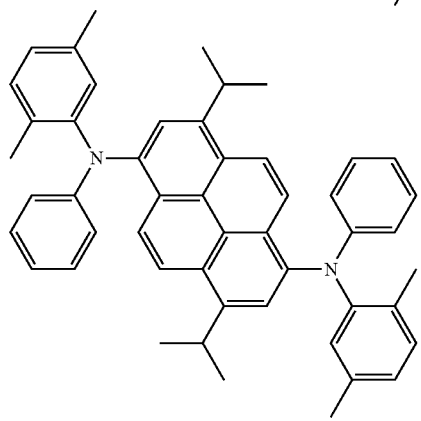
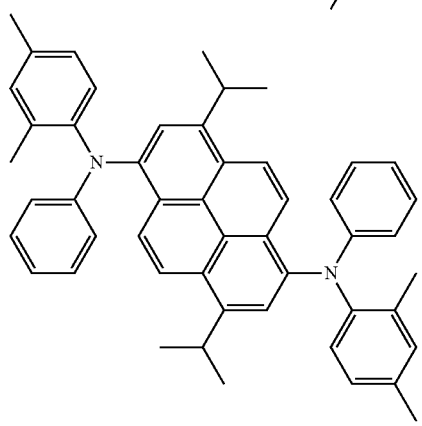
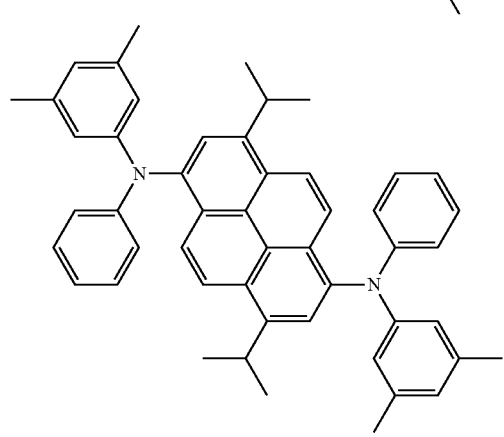
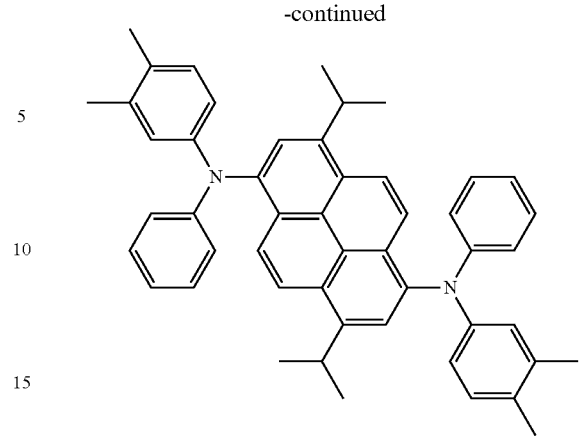
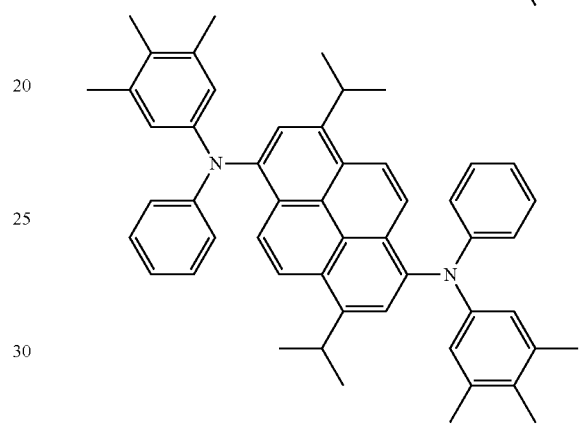
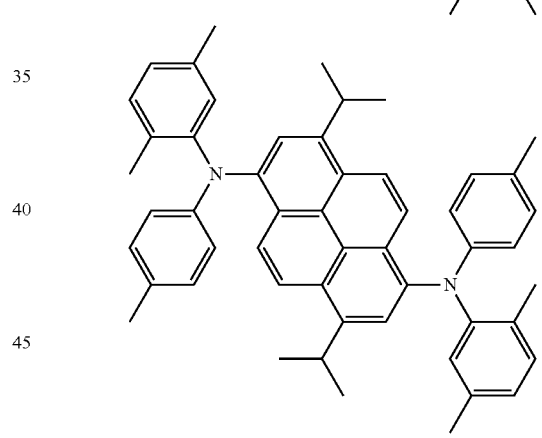
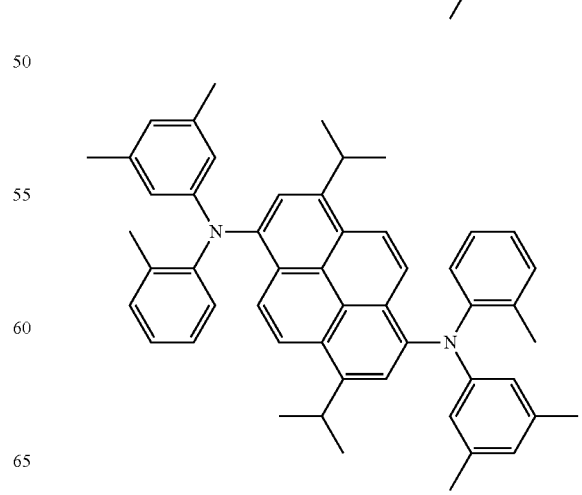

173
-continued
174
-continued
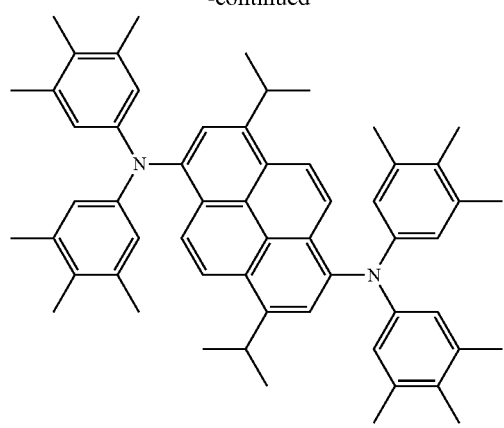
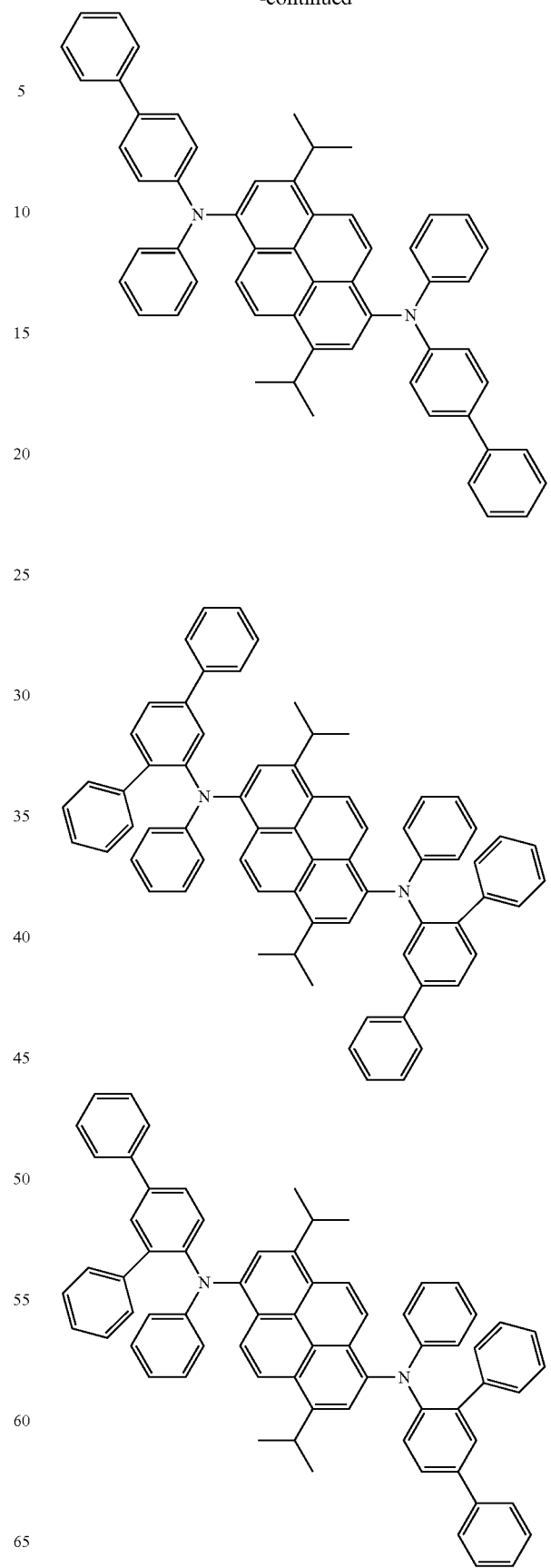

175
-continued
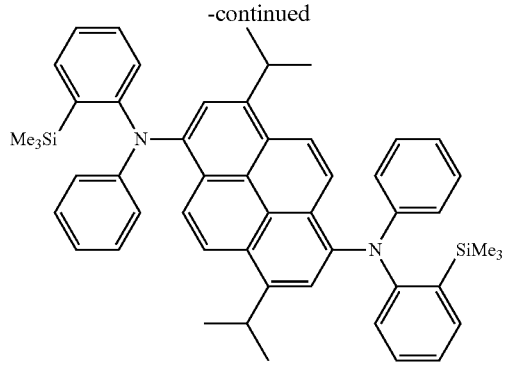
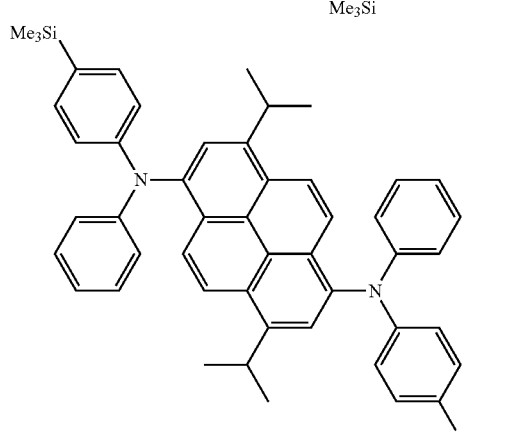
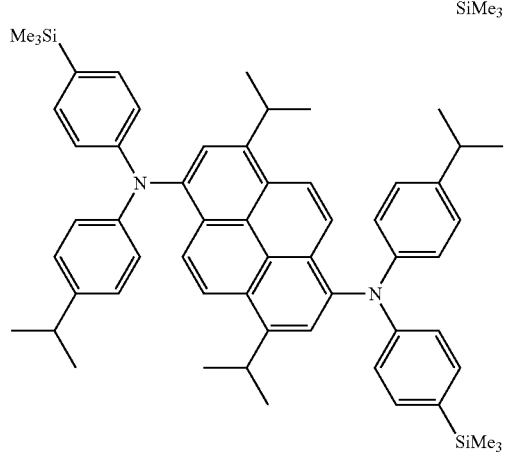
176
-continued
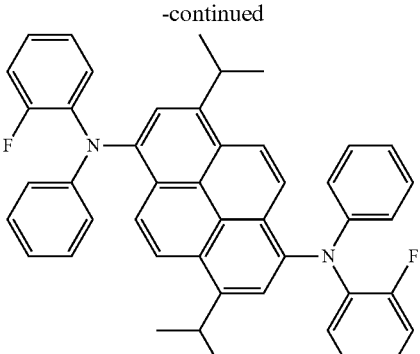
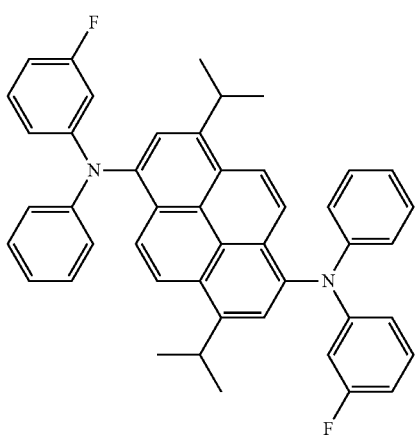
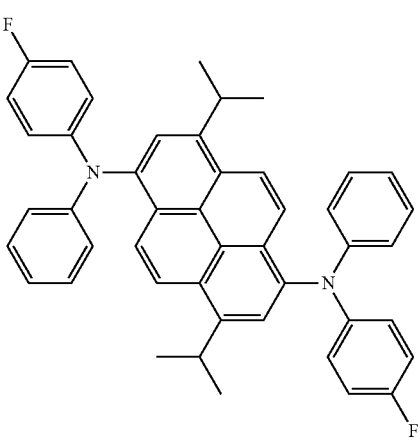

177
-continued
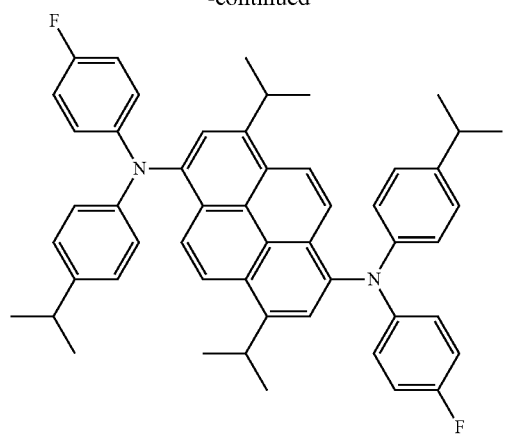
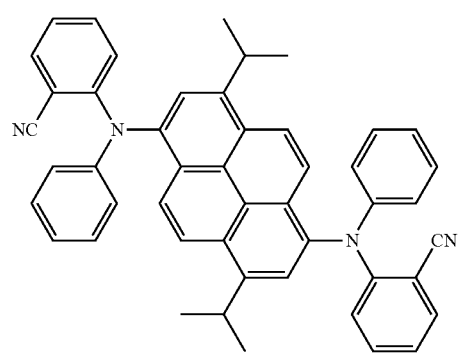
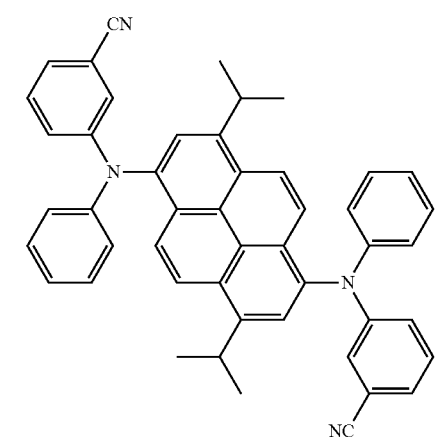
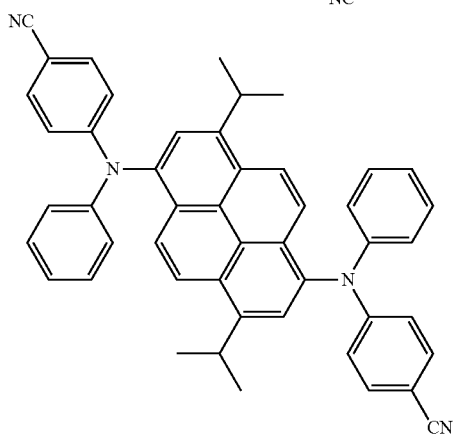
178
-continued
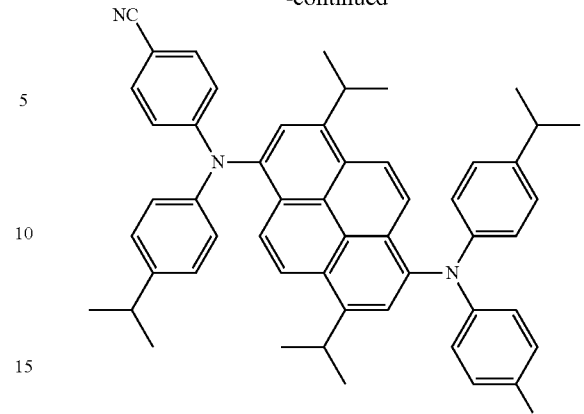
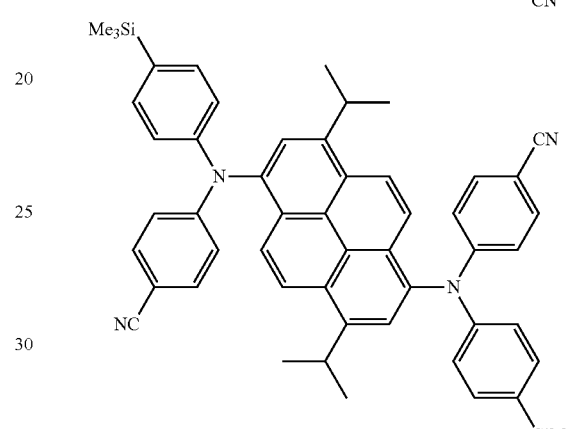
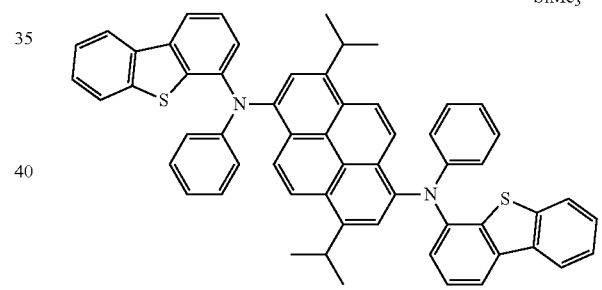
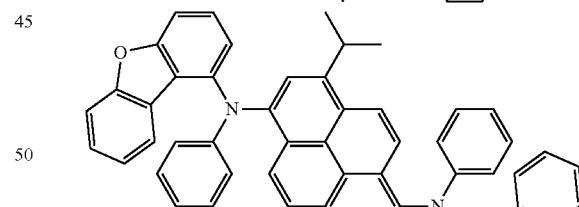
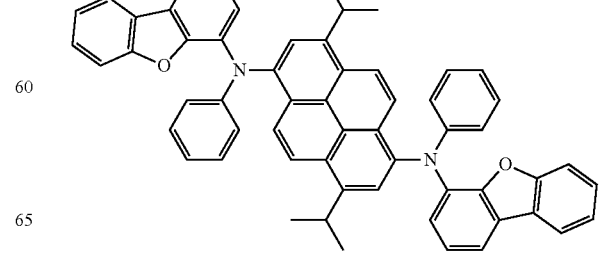

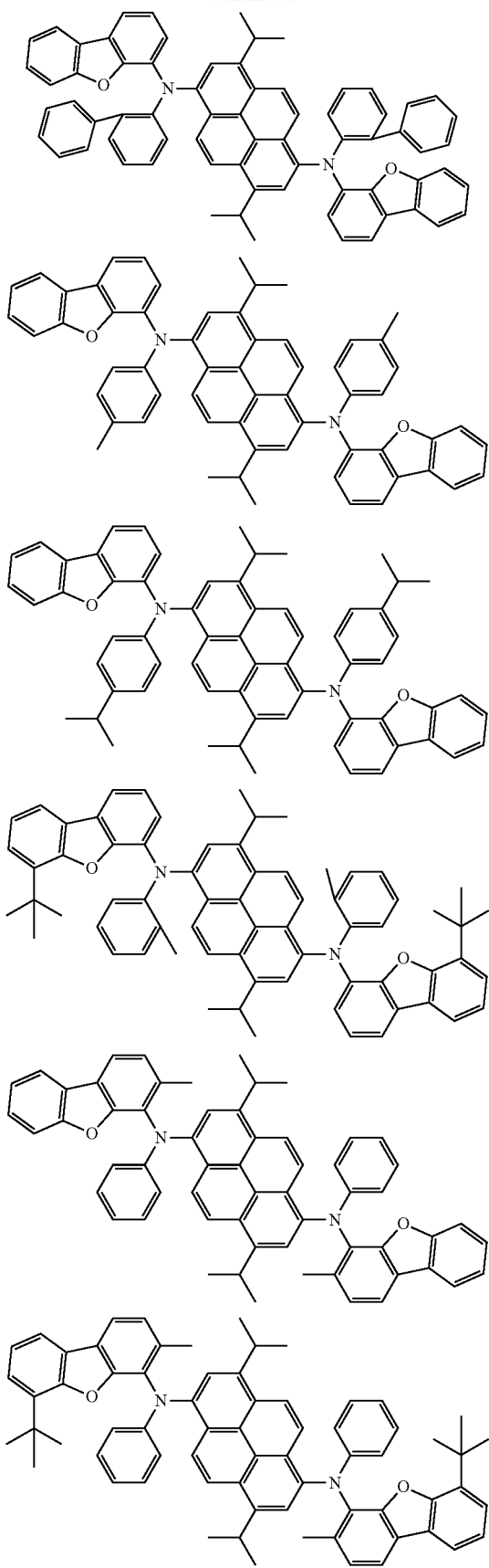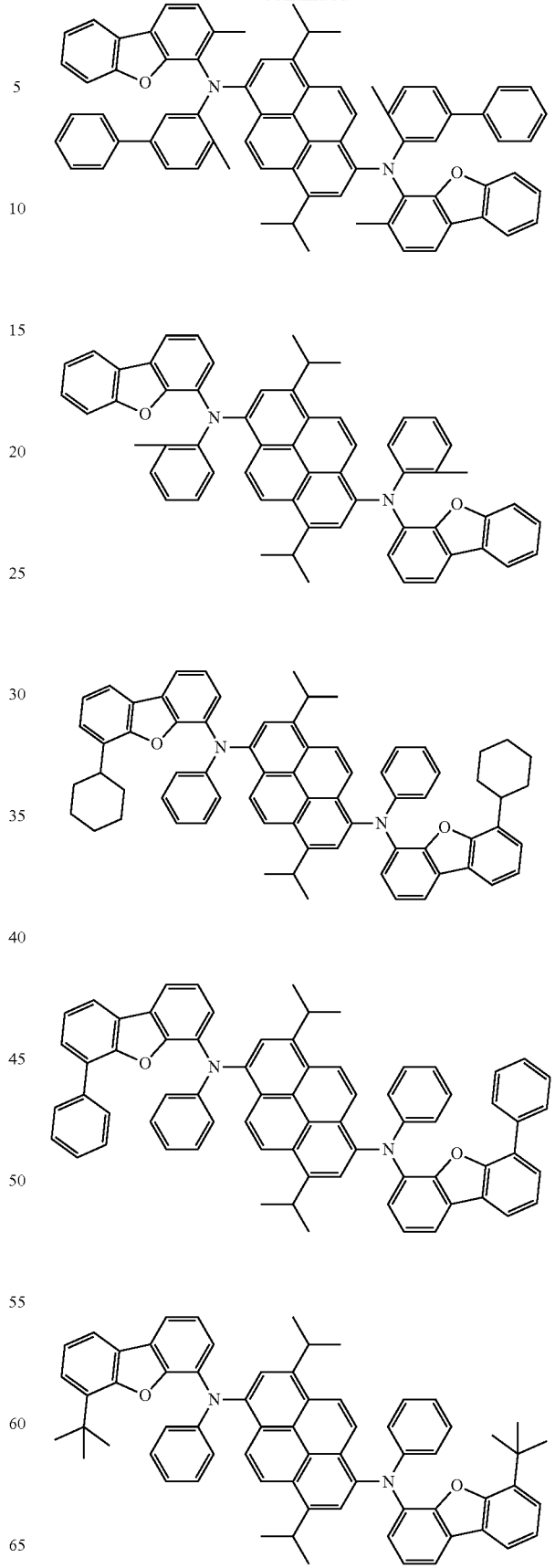

181
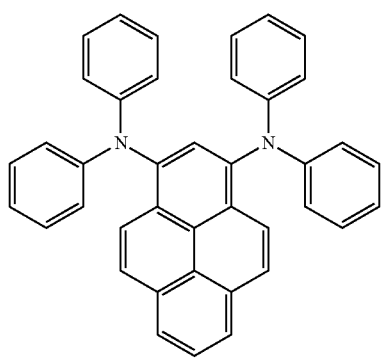
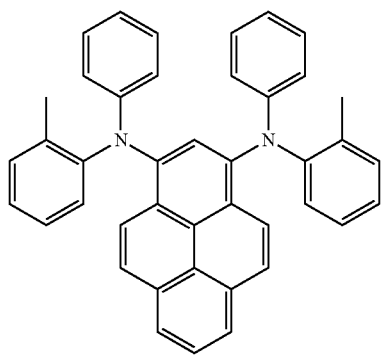
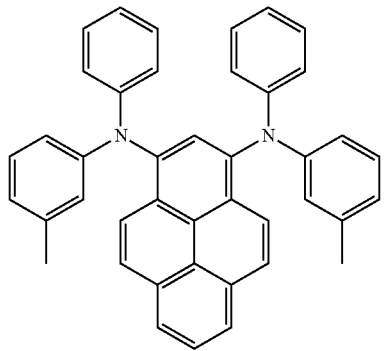
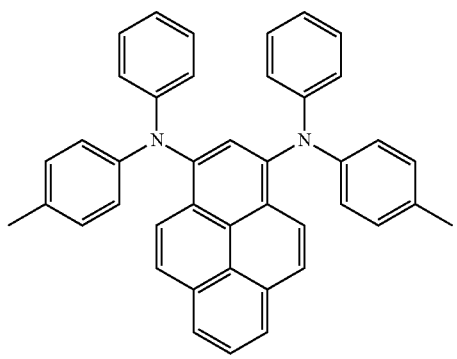
182
-continued
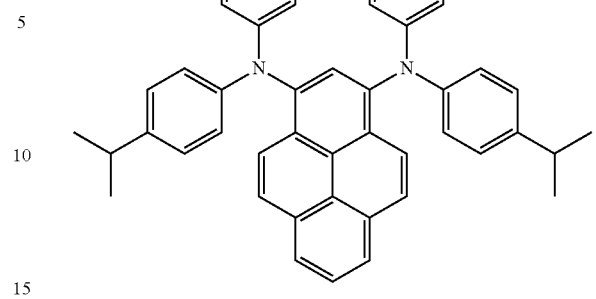
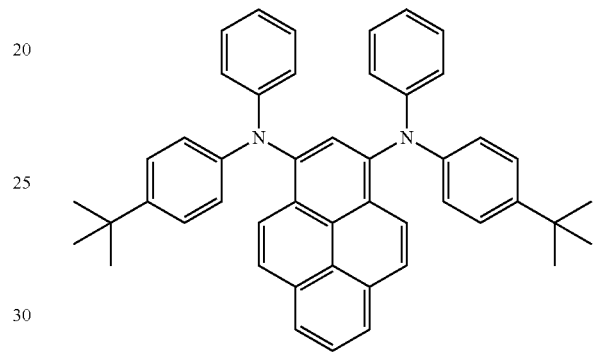
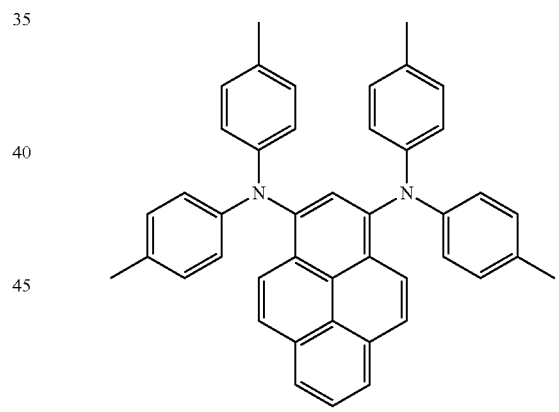
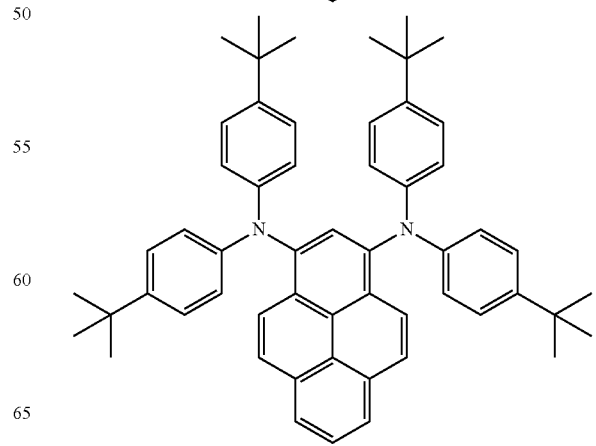

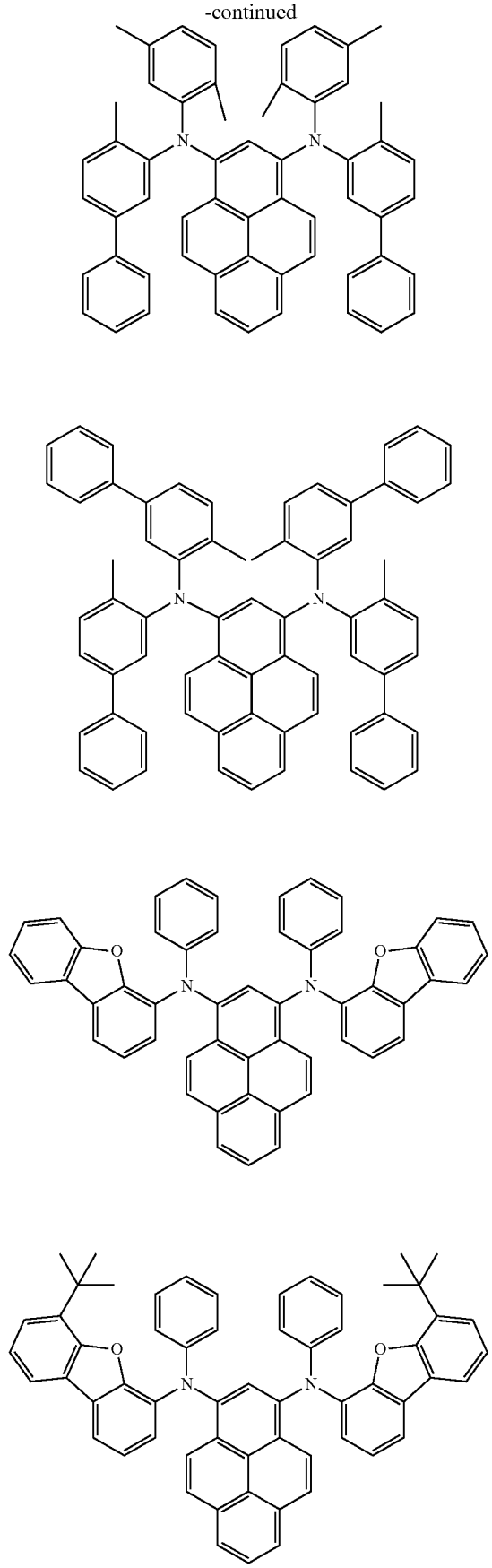

185
-continued
186
-continued
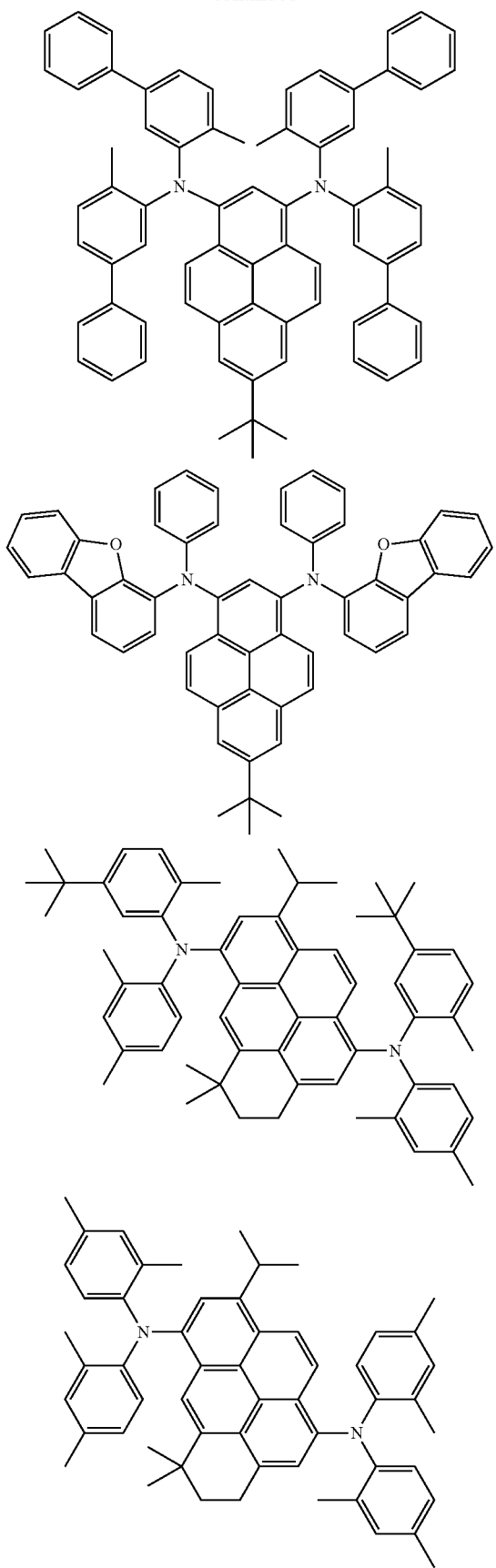
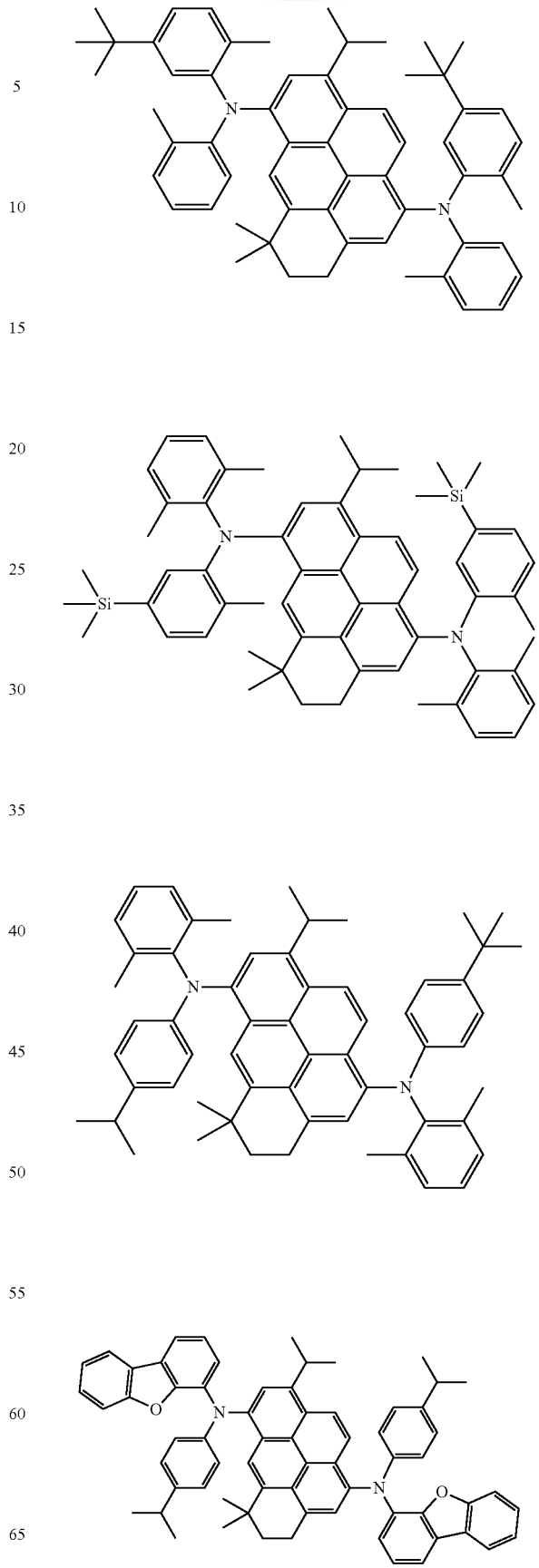

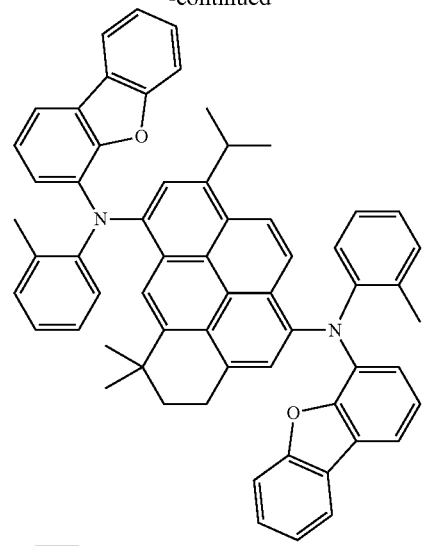
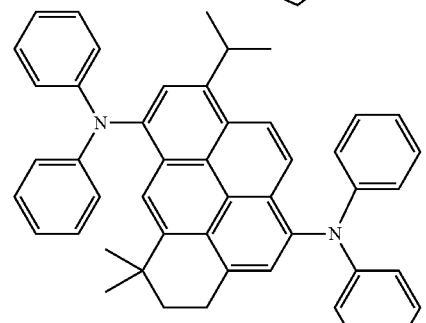
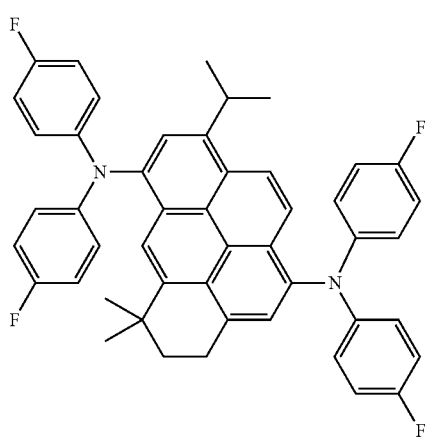
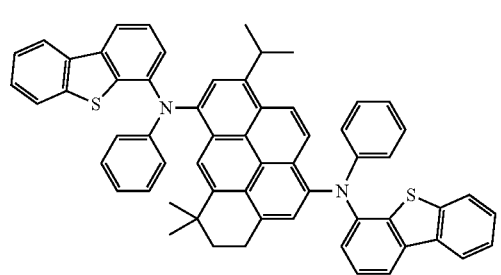
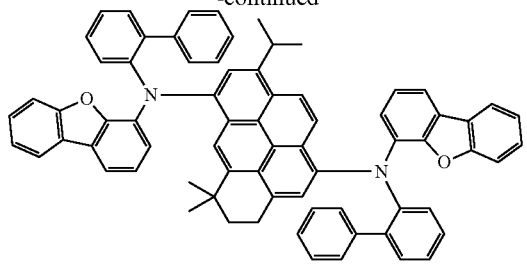
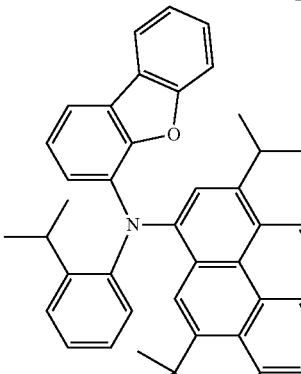
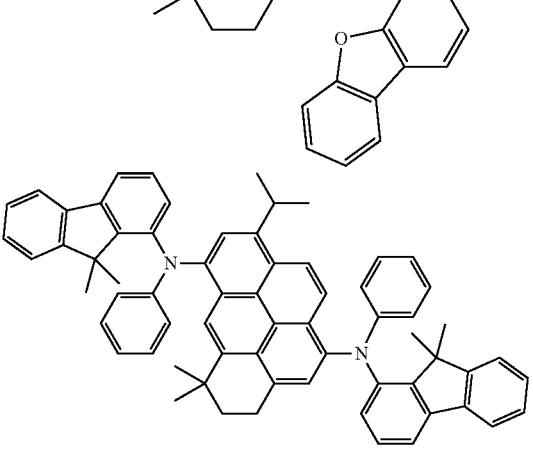
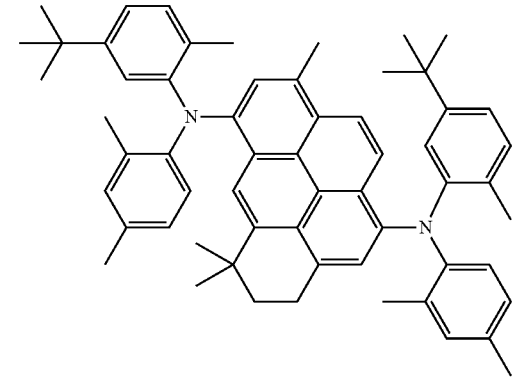
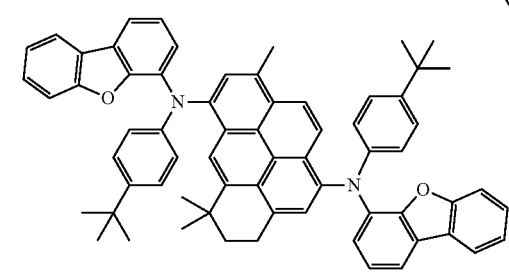

-continued

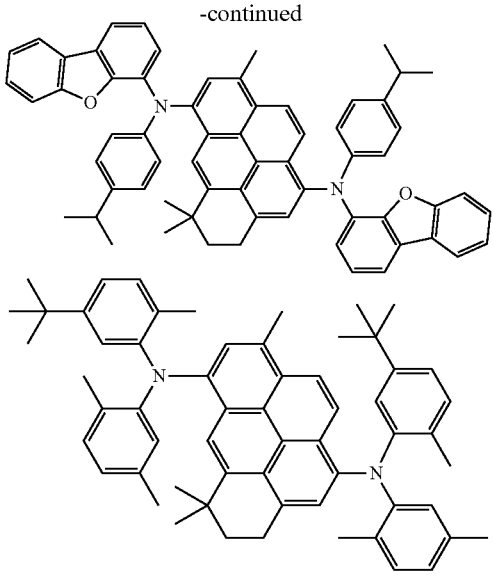

(Compound Represented by Formula (21))

The compound represented by the formula (21) is explained below.

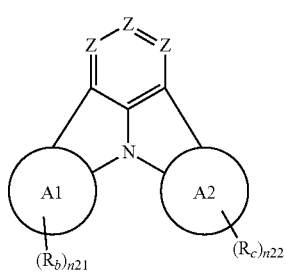

(21)

In the formula (21),

Zs are independently $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;

when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;

when plural $R_c$s exist, one or more pairs of two or more adjacent groups of $R_a$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1).

The "aromatic hydrocarbon ring" of A1 ring and A2 ring has the same structure as the compound obtained by introducing a hydrogen atom into the "aryl group" described above.

The "aromatic hydrocarbon ring" of the A1 ring and the A2 ring contains to carbon atoms in the fused bicyclic structure at the center of the formula (21) as ring atoms. Examples of "substituted or unsubstituted aromatic hydrocarbon ring having 6 to 50 ring carbon atoms" include compounds in which a hydrogen atom is introduced into the "aryl group" described in the example group G1.

The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring having 51 to 50 ring atoms" include compounds in which a hydrogen atom is introduced into the "heterocyclic group" described in the example group G2.

$R_b$ is bonded to one of carbon atoms which form the aromatic hydrocarbon ring of A1 ring, or one of atoms which form the heterocycle of A1 ring.

$R_c$ is bonded to one of carbon atoms which form the aromatic hydrocarbon ring of A2 ring, or one of atoms which form the heterocycle of A2 ring.

It is preferable that at least one (preferably two) of $R_a$ to $R_c$ is a group represented by the following formula (21a).

-$L_{201}$-$Ar_{201}$ (21a)

In the formula (21a), $L_{201}$ is a single bond, a substituted or unsubstituted arylene group having 6 to 30 ring carbon atoms, or a substituted or unsubstituted bivalent heterocyclic group having 5 to 30 ring atoms;

$Ar_{201}$ is a substituted or unsubstituted arylene group having 6 to 50 ring carbon atoms, a substituted or unsubstituted monovalent heterocyclic group having 5 to 50 ring atoms, or a group represented by the following formula (21b):

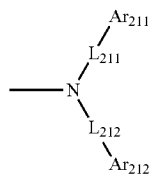

(21b)

wherein in the formula (21b),
$L_{211}$ and $L_{212}$ are independently
a single bond,
a substituted or unsubstituted arylene group having 6 to 30 ring carbon atoms, or
a substituted or unsubstituted divalent heterocyclic group having 5 to 30 ring atoms;
$Ar_{212}$ and $Ar_{22}$ are bonded with each other to form a substituted or unsubstituted, saturated or unsaturated ring, or do not form a substituted or unsubstituted, saturated or unsaturated ring; and
$Ar_{212}$ and $Ar_{22}$ that do not form a substituted or unsubstituted, saturated or unsaturated ring are independently
a substituted or unsubstituted aryl group having 6 to 50 ring carbon atoms or
a substituted or unsubstituted monovalent heterocyclic group having 5 to 50 ring atoms.

In one embodiment, the compound represented by the formula (21) is represented by the following formula (22).

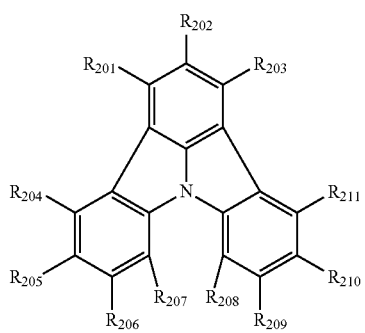

(22)

In the formula (22),
one or more pairs of two or more adjacent groups of $R_{201}$ to $R_{211}$ are bonded with each other to form a substituted or unsubstituted, saturated or unsaturated ring, or do not form a substituted or unsubstituted saturated or unsaturated ring;
$R_{201}$ to $R_{211}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

It is preferable that at least one (preferably two) of $R_{201}$ to $R_{211}$ is the group represented by the formula (21a). It is preferable that $R_{204}$ and $R_{211}$ are the group represented by the formula (21a).

In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which $R_{204}$ to $R_{207}$ bonds to.

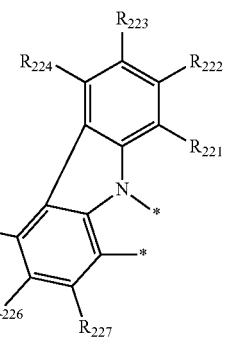

21-1

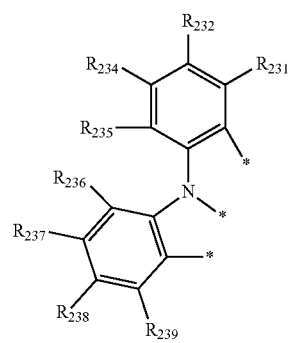

21-2

In the formula (21-1), two bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);
wherein in the formula (21-2), three bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);
One or more pairs of two or more adjacent groups of $R_{221}$ to $R_{227}$ and $R_{232}$ to $R_{239}$ are bonded with each other to form a substituted or unsubstituted, saturated or unsaturated ring, or do not form a substituted or unsubstituted, saturated or unsaturated ring;
$R_{221}$ to $R_{227}$ and $R_{231}$ to $R_{239}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (21) is a compound represented by the following formula (21-3), (21-4), or (21-5).

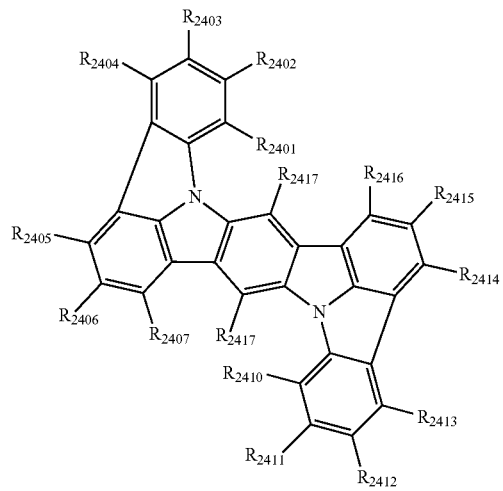

(21-3)

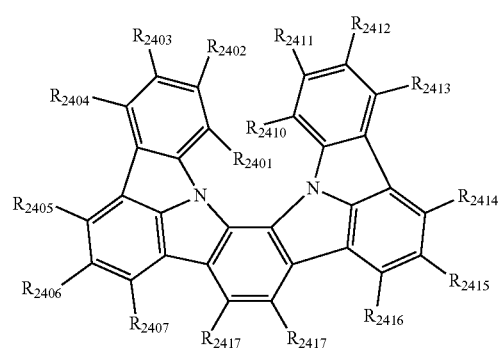

(21-4)

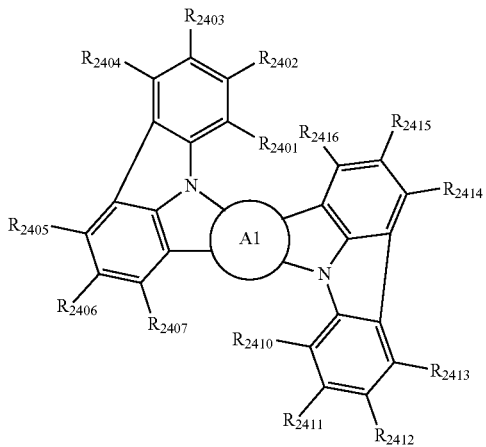

(21-5)

In the formulas (21-3), (21-4) and (21-5),

A1 ring is as defined in the formula (21);

$R_{2401}$ to $R_{2407}$ are the same as $R_{221}$ to $R_{277}$ in the formulas (21-1) and (21-2);

$R_{2410}$ to $R_{2417}$ are the same as $R_{201}$ to $R_{211}$ in the formula (22); and two $R_{2417}$ may be the same with or different from each other.

In one embodiment, the substituted or unsubstituted aromatic hydrocarbon ring having 6 to 50 ring carbon atoms of A1 ring in the formula (21-5) is a substituted or unsubstituted napthalene ring, or a substituted or unsubstituted fluorene ring.

In one embodiment, the substituted or unsubstituted heterocyle having 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7).

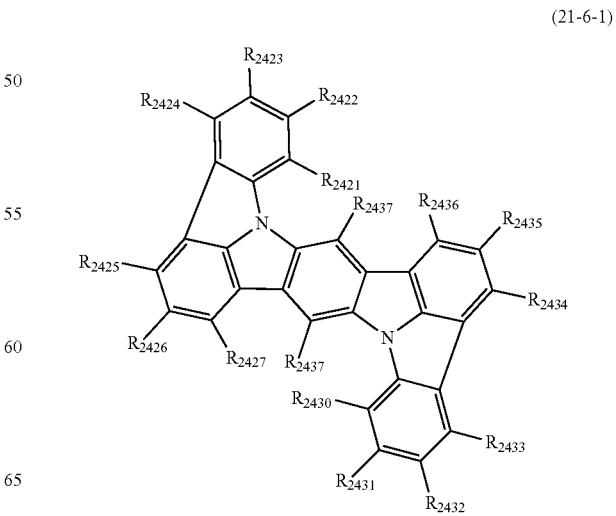

(21-6-1)

(21-6-2)

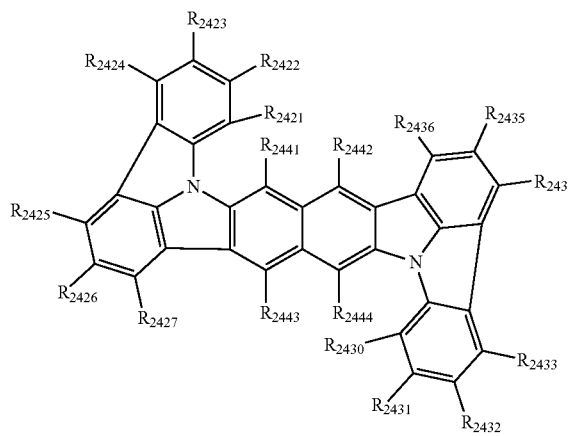

(21-6-3)

(21-6-4)

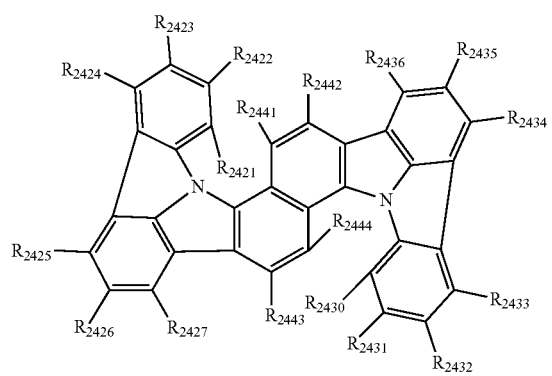

(21-6-5)

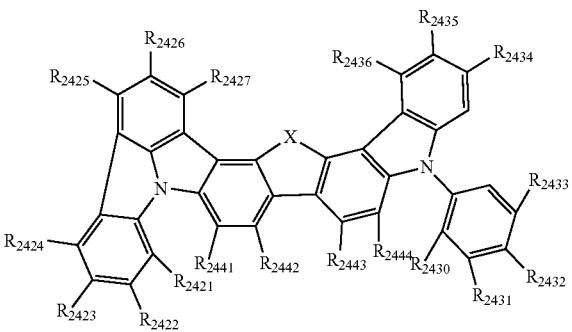

(21-6-6)

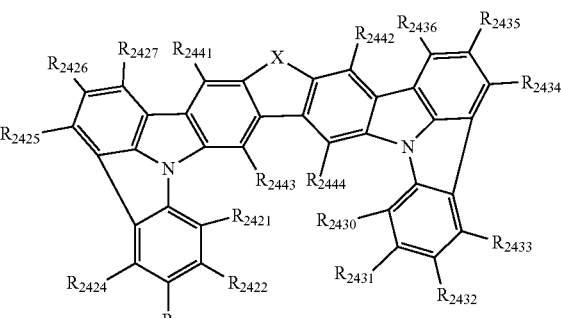

(21-6-7)

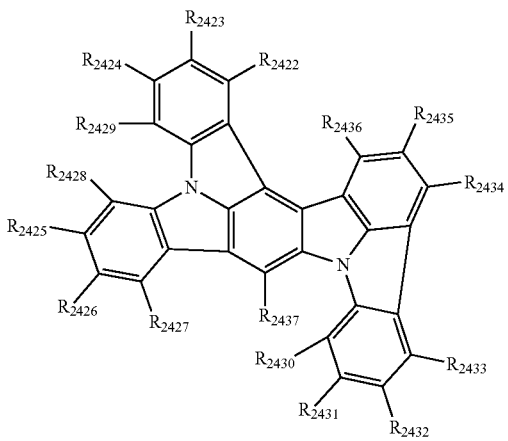

In the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound Represented by Formula (25))

The compound represented by the formula (25) is explained below.

(25)

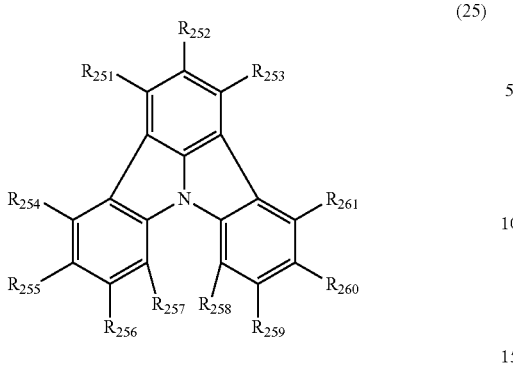

In the formula (25), two or more pairs selected from a group consisting of $R_{251}$ and $R_{252}$, $R_{252}$ and $R_{254}$, $R_{254}$ and $R_{255}$, $R_{255}$ and $R_{256}$, $R_{256}$ and $R_{257}$, $R_{258}$ and $R_{259}$, $R_{259}$ and $R_{260}$, and $R_{260}$ and $R_{261}$ bond with each other to form a substituted or unsubstituted, saturated or unsaturated ring;

Provided that the pair of $R_{251}$ and $R_{252}$ and the pair of $R_{252}$ and $R_{253}$ do not form a ring simultaneously; the pair of $R_{254}$ and $R_{256}$ and the pair of $R_{255}$ and $R_{256}$ do not form a ring simultaneously; the pair of $R_{255}$ and $R_{256}$ and the pair of $R_{256}$ and $R_{257}$ do not form a ring simultaneously; the pair of $R_{258}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

When two or more rings are formed by $R_{251}$ to $R_{261}$, the rings may be the same or different;

$R_2$, to $R_2$, that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or —Si($R_{901}$)($R_{902}$)($R_{903}$),
—O—($R_{904}$),
—S—($R_{905}$),
—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

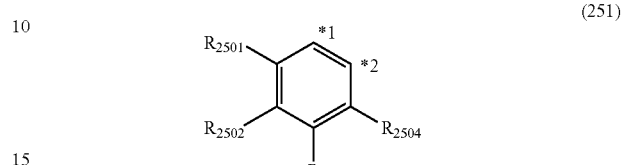
(251)

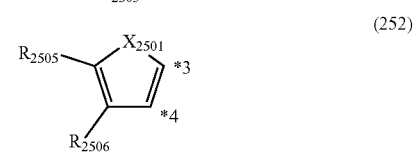
(252)

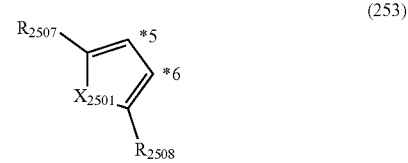
(253)

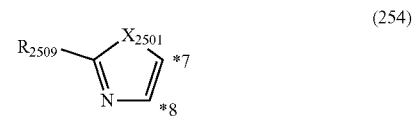
(254)

(255)

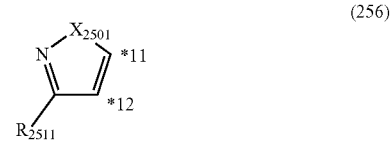
(256)

(257)

In the formulas (251) to (257), each of *1 and *2, *3 and *4, *5 and *6, *7 and *8, *9 and *10, *11 and *12, and *13 and

*14 represents two ring carbon atoms to which $R_n$ and $R_{n+1}$ bond, and $R_n$ may bond to ether one of the two ring carbon atoms of *1 and *2, *3 and *4, *5 and *6, *7 and *8, *9 and *10, *11 and *12, and *13 and *14;

$X_{2501}$ is C($R_{2512}$) ($R_{2513}$), $NR_{2514}$, O or S;

One or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{261}$.

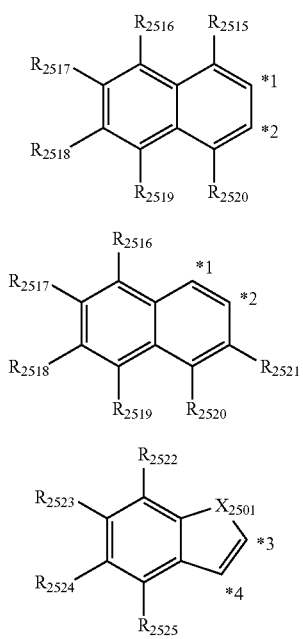

(258)

(259)

(260)

In the formulas (258) to (260),
each of *1 and *2, and *3 and *4 represents two ring carbon atoms to which $R_n$ and $R_{n+1}$ bond, and $R_n$ may bond to either one of the two ring carbon atoms of *1 and *2, or *3 and*4;
$X_{2501}$ is $C(R_{2512})(R_{2513})$, $NR_{2514}$, O or S;
One or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{256}$, and $R_{260}$, more preferably $R_{252}$) is a group which does not form a ring.

(i) Substituent in the case where the ring structure formed by $R_n$ and $R_{n+1}$ has a substituent in the formula (25),
(ii) $R_{251}$ to $R_{261}$ that do not form a ring structure in the formula (25), and
(iii) $R_{2501}$ to $R_{2514}$ and $R_{2515}$ to $R_{2525}$ in the formulas (251) to (260) are preferably independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$N(R_{901})(R_{907})$,
a substituted or unsubstituted aryl group having 6 to 50 ring carbon atoms,
a substituted or unsubstituted monovalent heterocyclic group having 5 to 50 ring atoms, or
a group selected from the following groups.

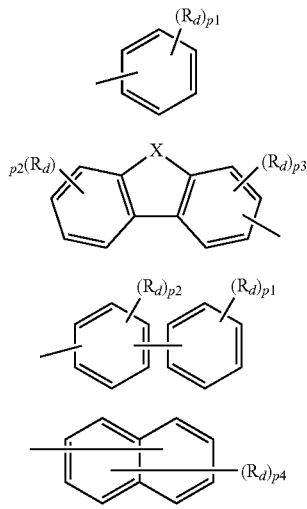

(261)

(262)

(263)

(264)

In the formulas (261) to (264),
$R_d$s are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
—$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
X is $C(R_{901})(R_{902})$, $NR_{903}$, O, or S;
$R_{901}$ to $R_{907}$ are as defined in the formula (1); and
p1 is independently an integer of 0 to 5, p2 is independently an integer of 0 to 4, p3 is an integer of 0 to 3, and p4 is an integer of 0 to 7.

In one embodiment, the compound represented by the formula (25) is represented by the following formulas (25-1) to (25-6).

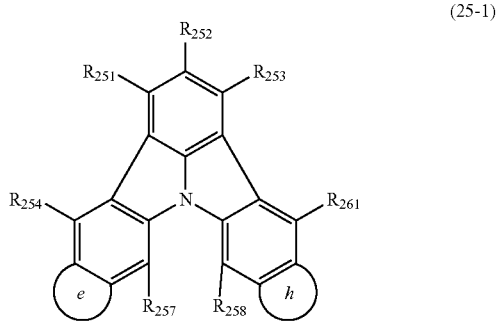

(25-1)

-continued
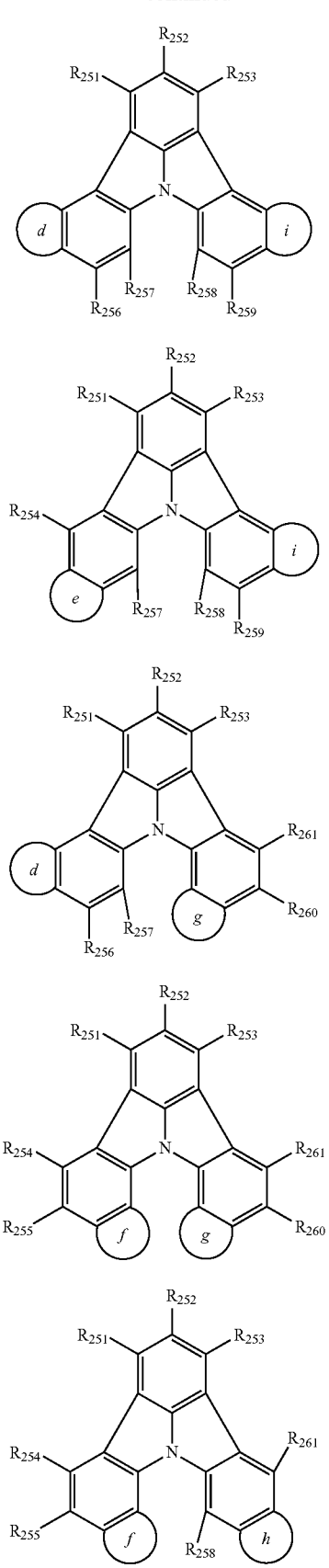
(25-2)
(25-3)
(25-4)
(25-5)
(25-6)
In the formulas (25-1) to (25-6), ring d to ring i are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-7) to (25-12).
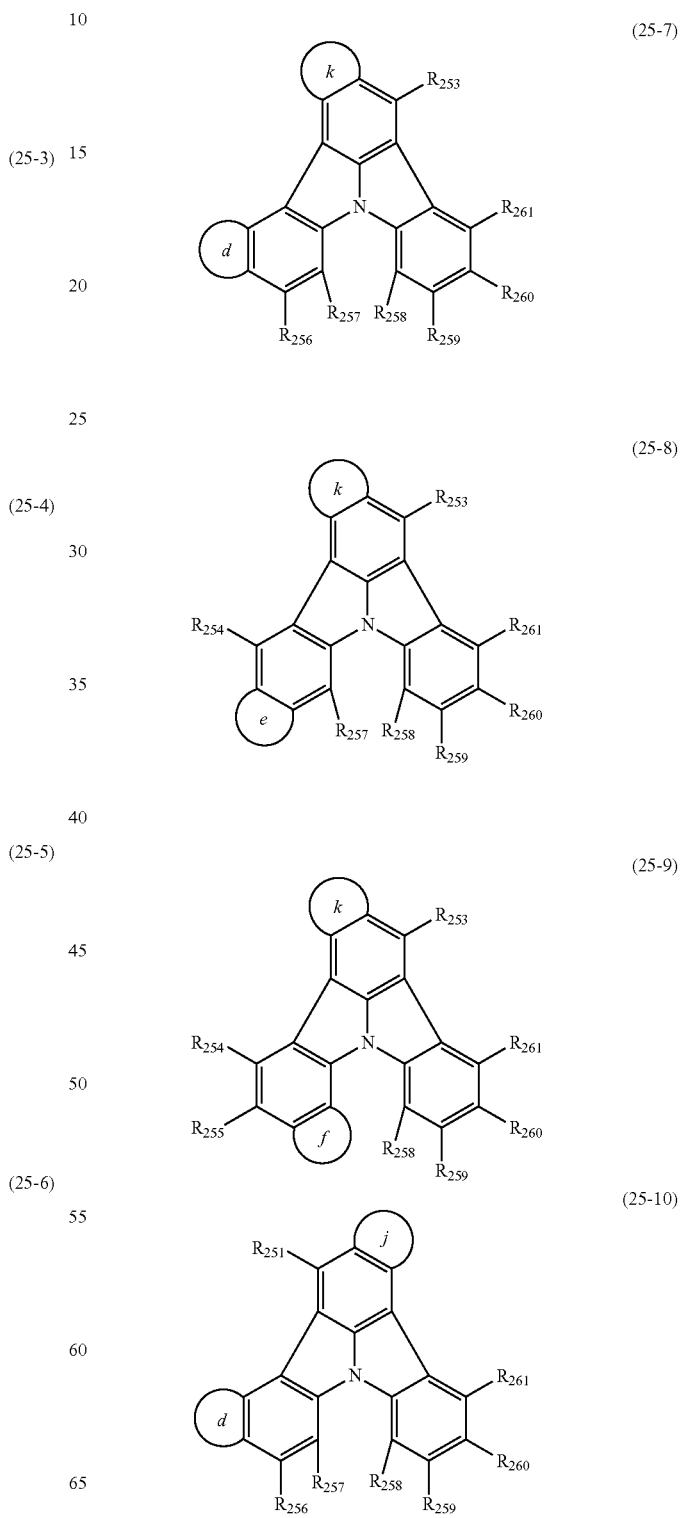
(25-7)
(25-8)
(25-9)
(25-10)

(25-11)
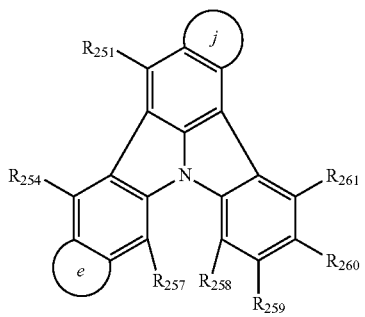
(25-12)
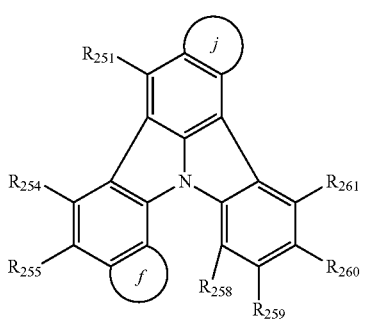
In the formulas (25-7) to (25-12), ring d to ring f, ring k, and ring j are independently a substituted or unsubstituted, saturated or unsaturated ring; and $R_{251}$ to $R_{261}$ are the same as defined in the formula (25).
In one embodiment, the compound represented by the formula (25) is represented by the following formulas (25-13) to (25-21).
(25-13)
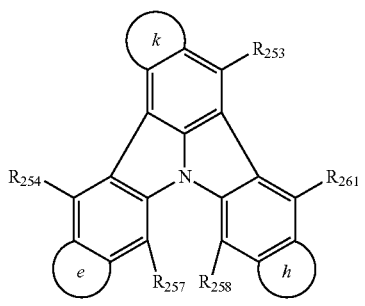
(25-14)
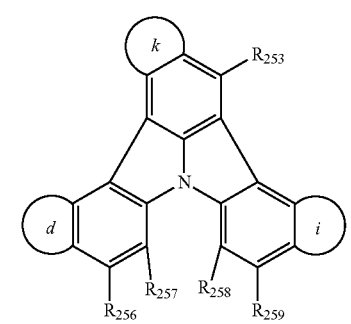
(25-15)
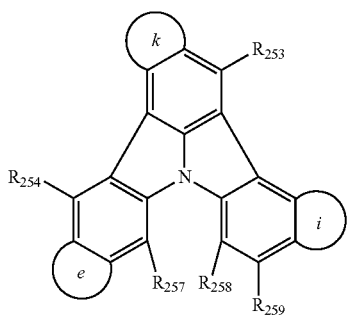
(25-16)
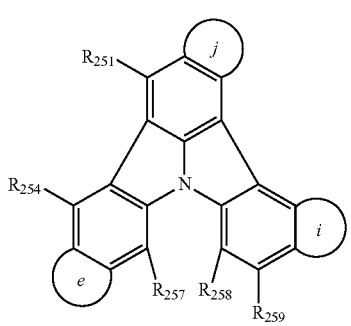
(25-17)
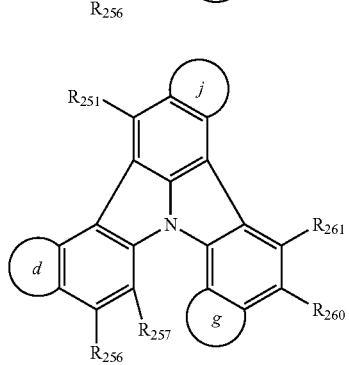
(25-18)
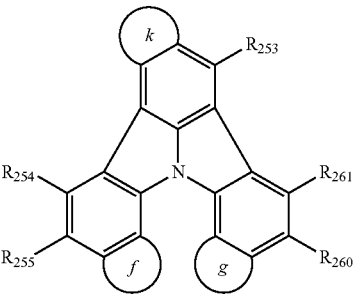
(25-19)

(25-20)

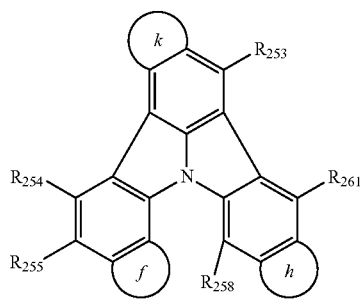

(25-21)

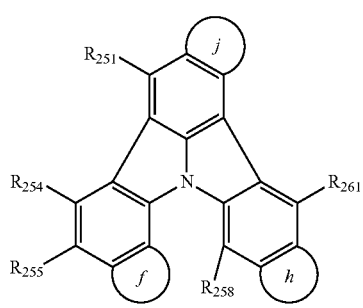

In the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent,

- a substituted or unsubstituted alkyl group having 1 to 50 carbon atoms,
- a substituted or unsubstituted aryl group having 6 to 50 ring carbon atoms, or
- a group represented by the formula (261), (263) or (264)

can be given for example.

In one embodiment, the compound represented by the formula (25) is represented by one of the following formulas (25-22) to (25-25).

(25-22)

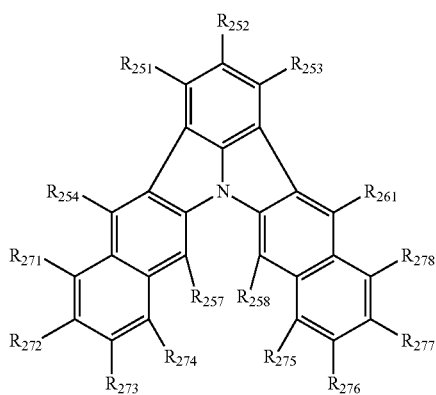

(25-23)

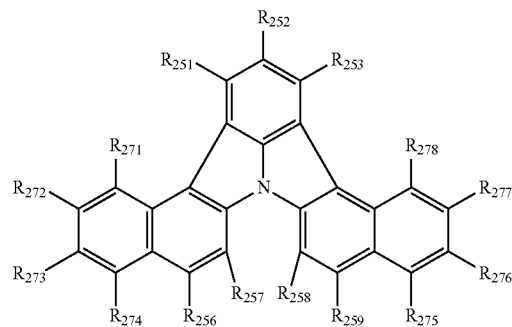

(25-24)

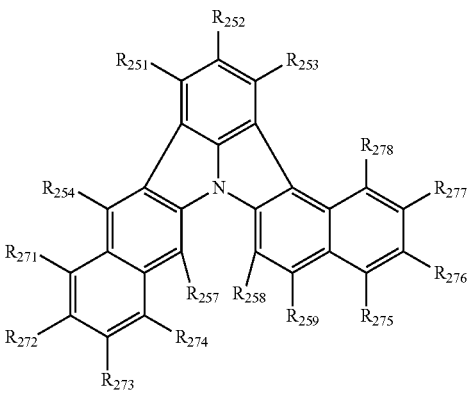

(25-25)

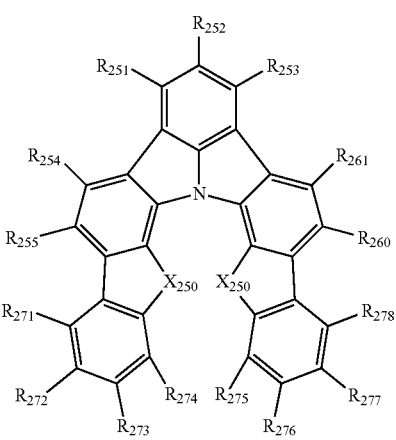

In the formulas (25-22) to (25-25), $X_{250}$ is independently $C(R_{901})(R_{902})$, $NR_{903}$, O or S; $R_{251}$ to $R_{261}$, and $R_{271}$ to $R_{278}$ are the same as $R_{251}$ to $R_{261}$ in the formula (25); and $R_{901}$ to $R_{903}$ are as defined in the formula (1).

In one embodiment, the compound represented by the formula (25) is represented by the following formula (25-26).

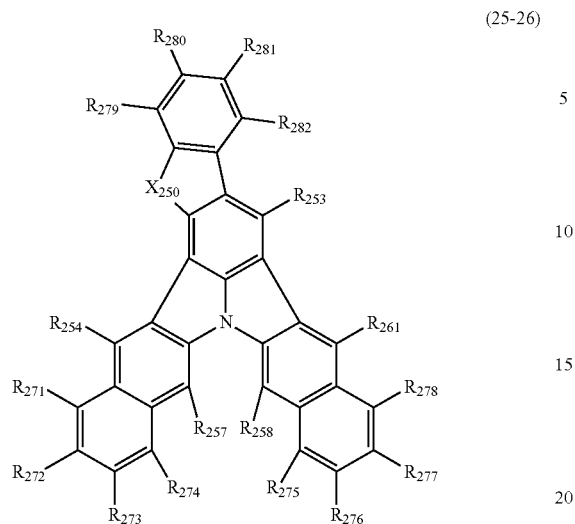
(25-26)
In the formula (25-26), $X_{250}$ is $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).
As the compound represented by the formula (21), the following compounds can be shown for example. In the following example compounds, Me represents methyl group.
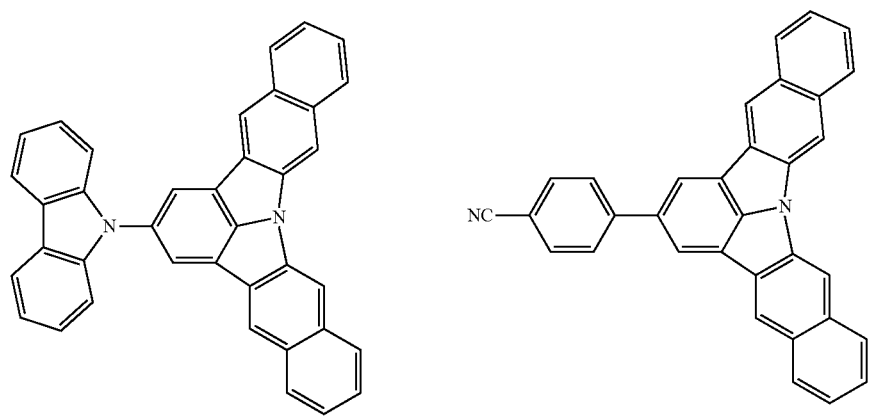
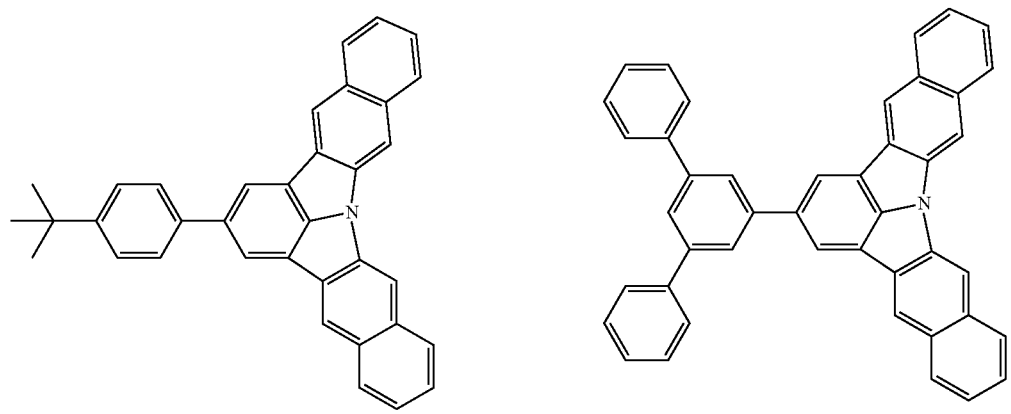

-continued
| 209 | 210 |
|---|---|
| 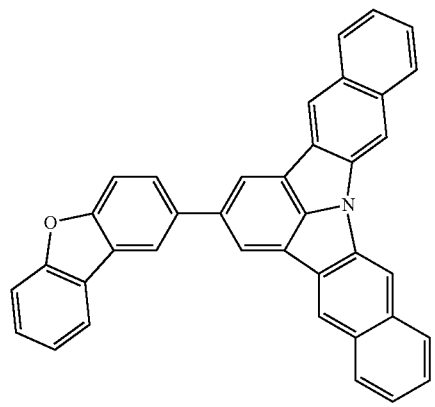 | 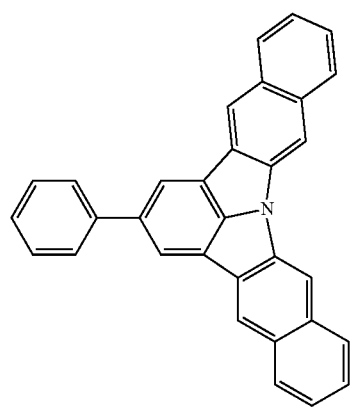 |
| 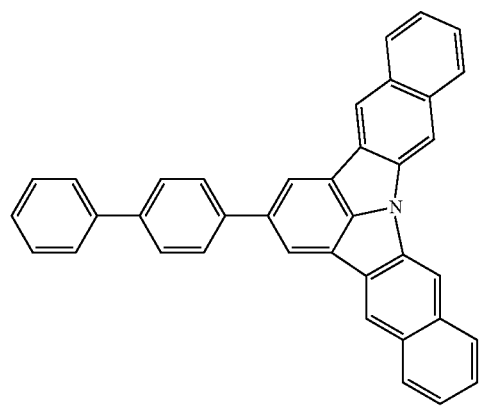 | 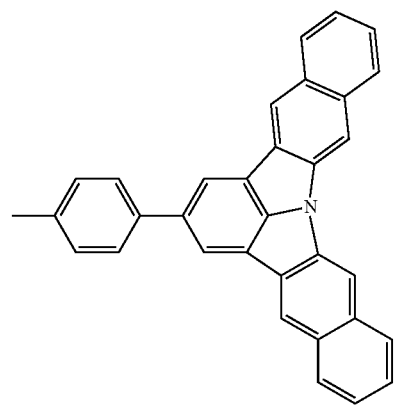 |
| 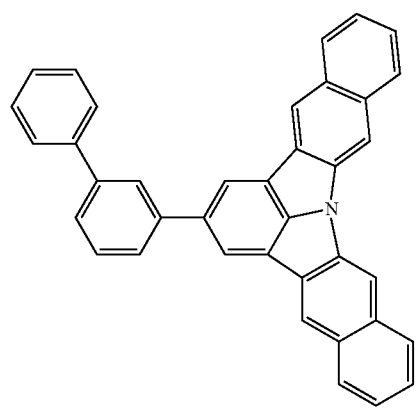 | 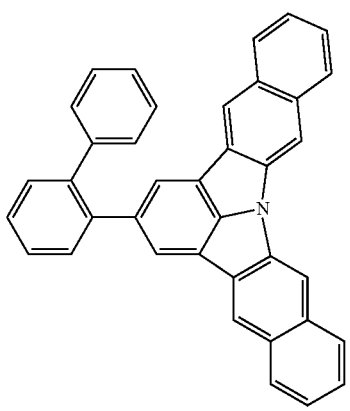 |

-continued
| 211 | 212 |
|---|---|
| 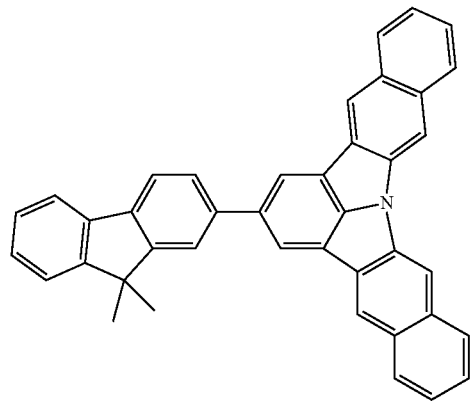 | 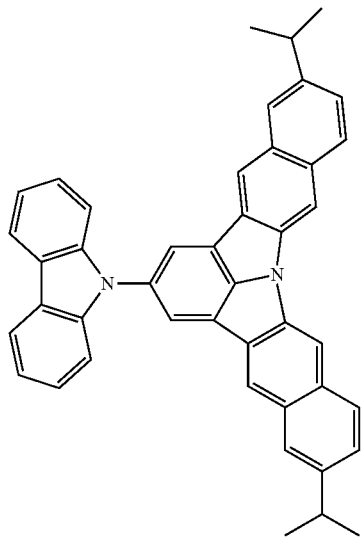 |
| 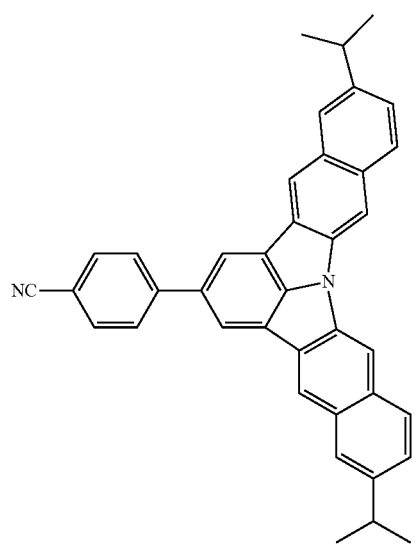 | 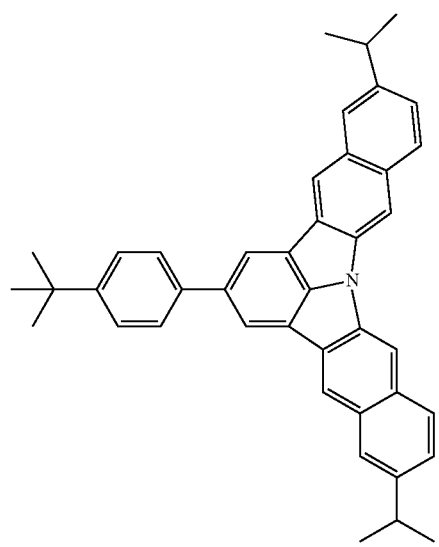 |
| 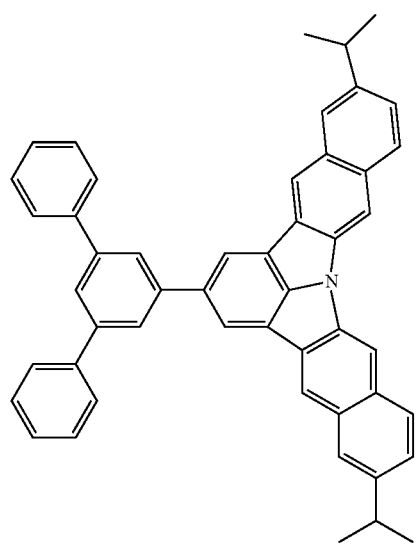 | 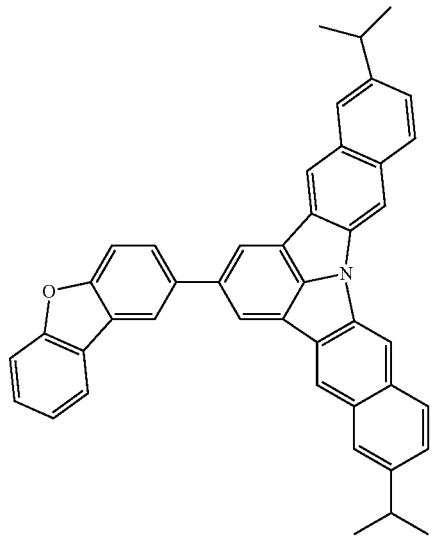 |

213
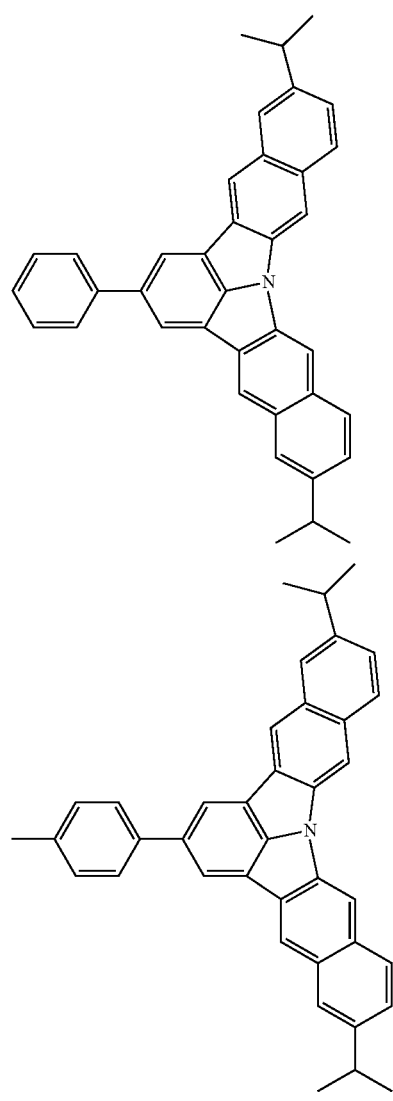
214
-continued
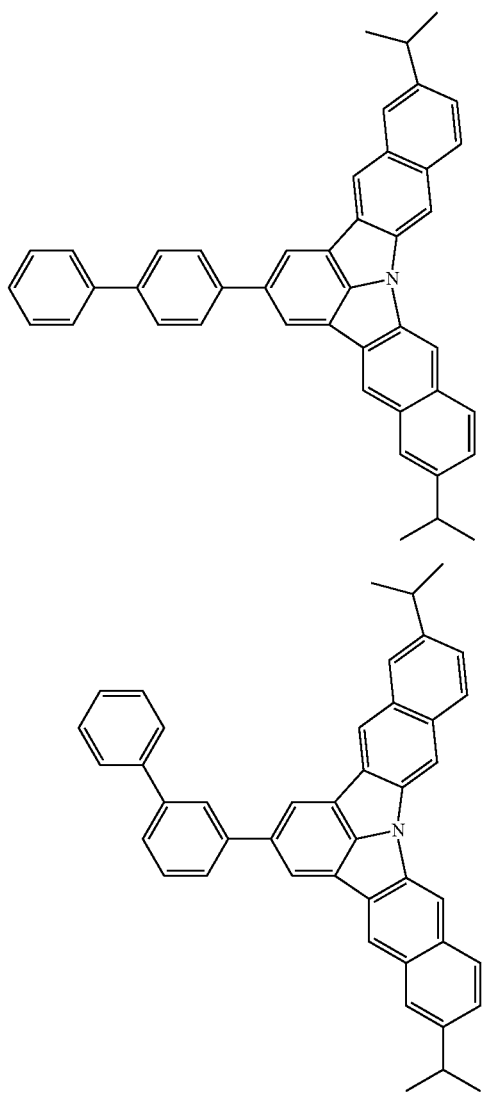
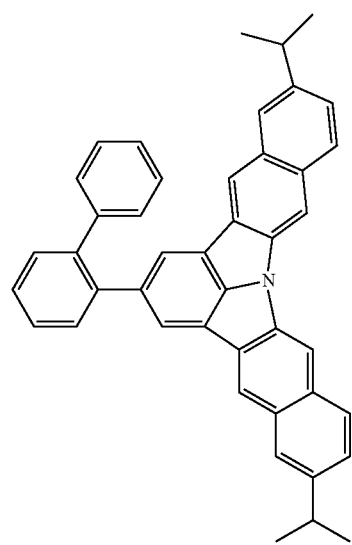
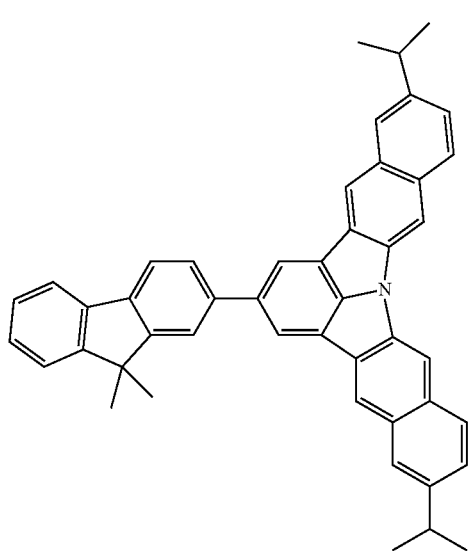

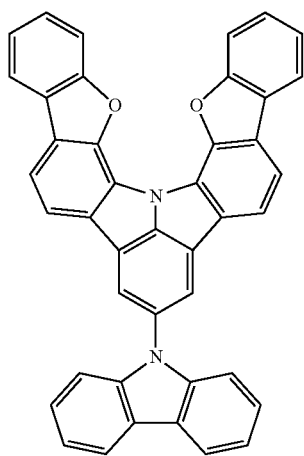
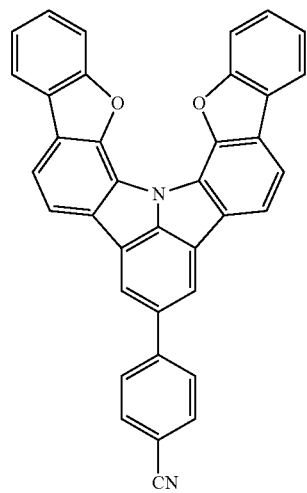
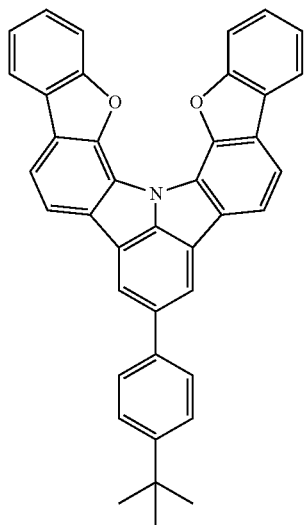
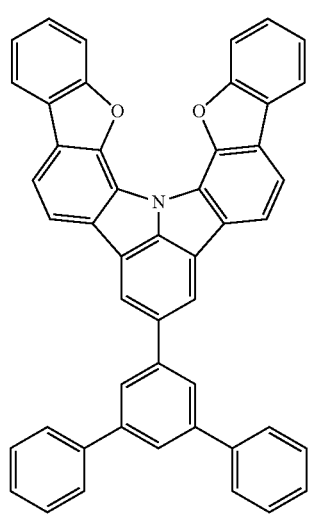
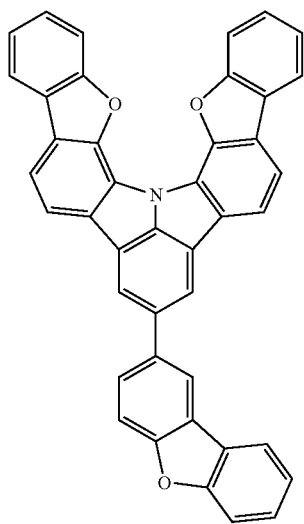
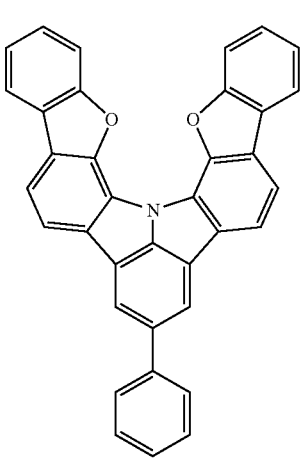

-continued
217
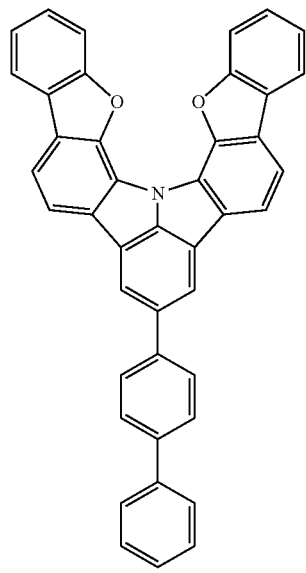
218
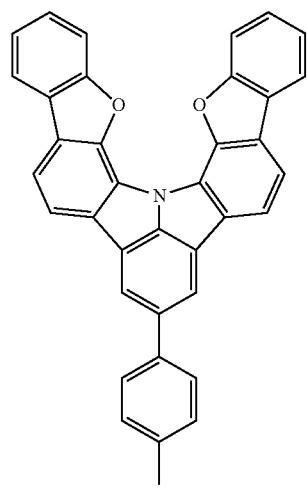
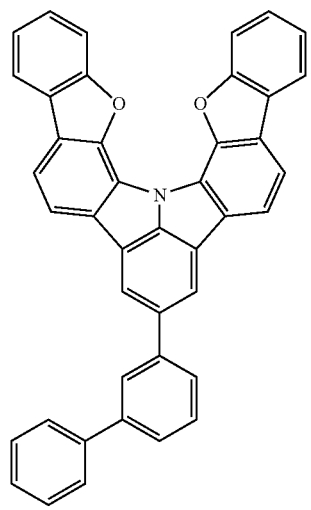
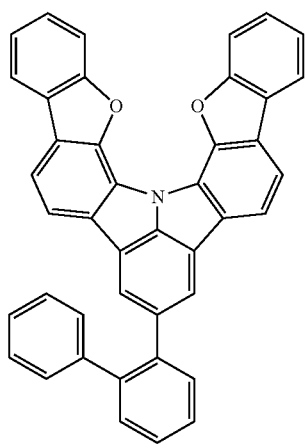
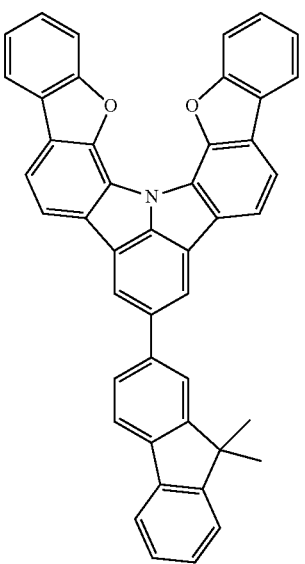
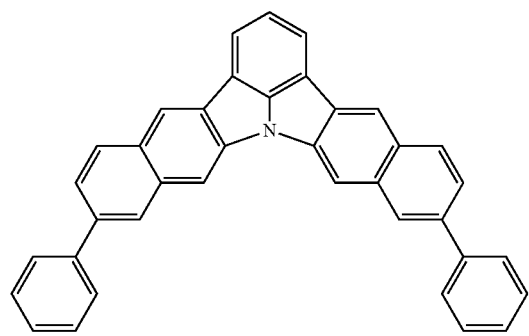
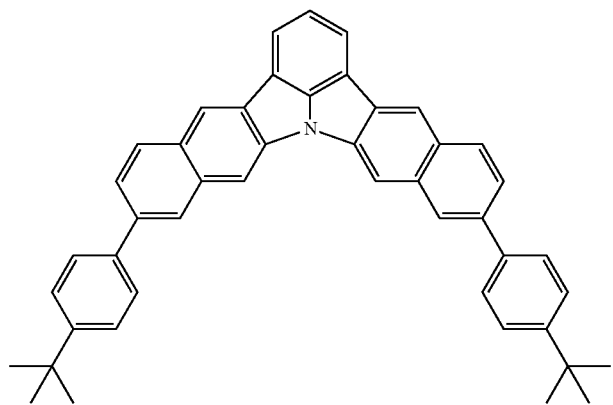

-continued
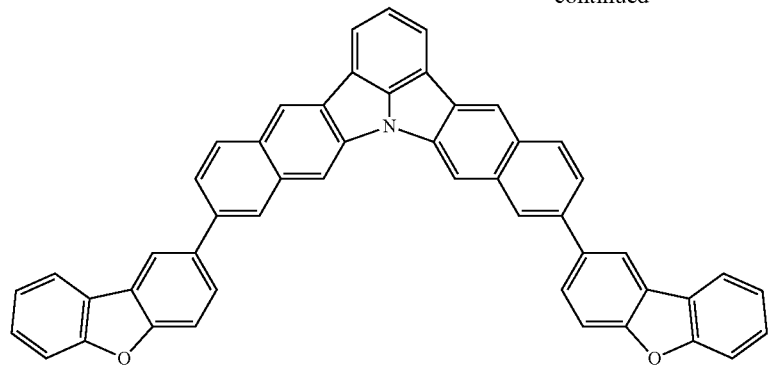
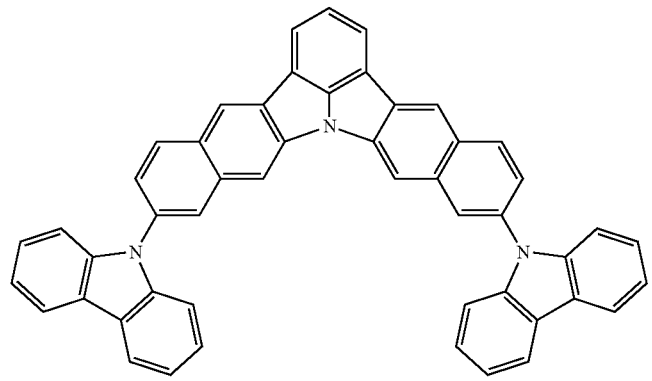
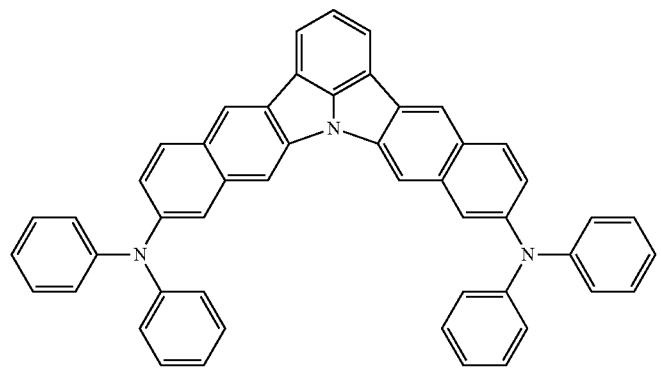
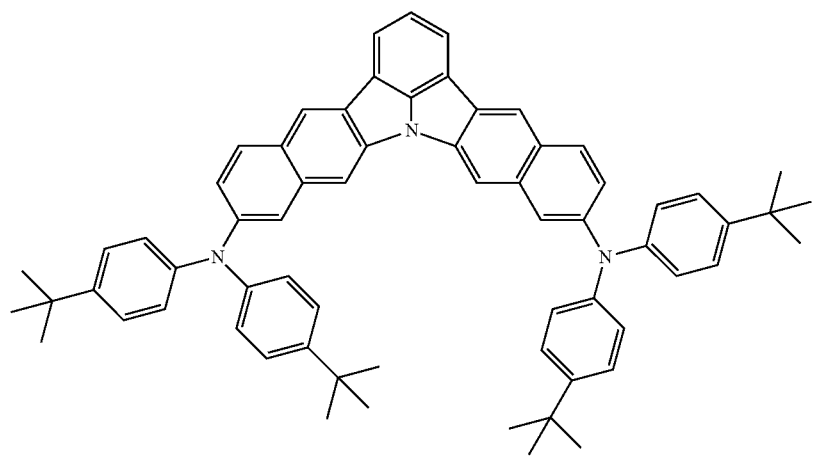

221 222
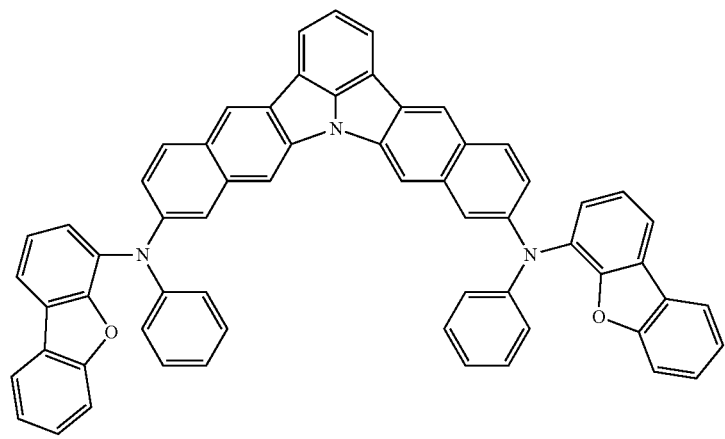
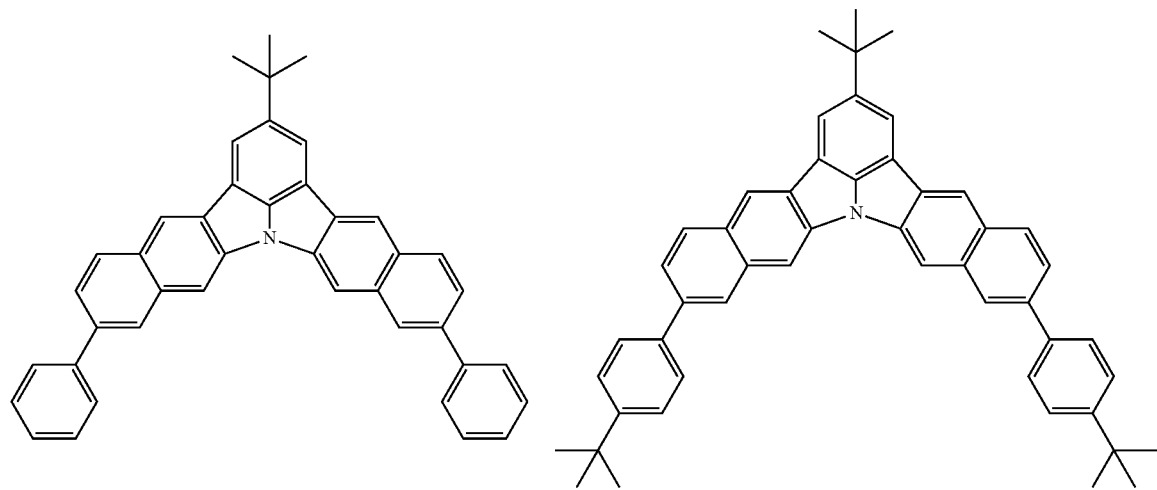
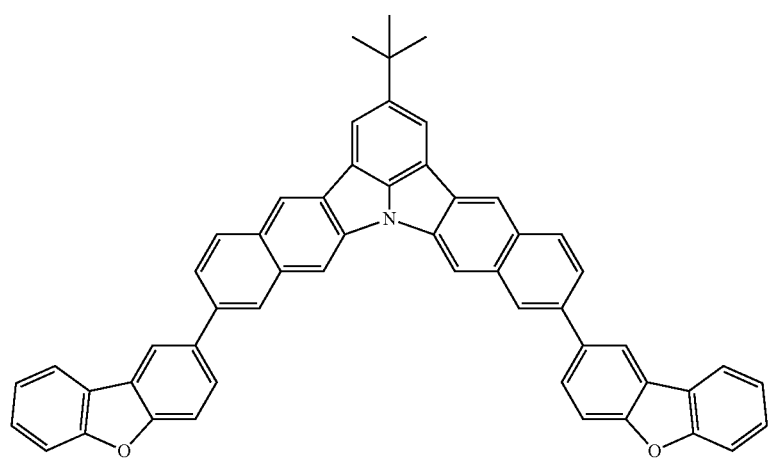

-continued
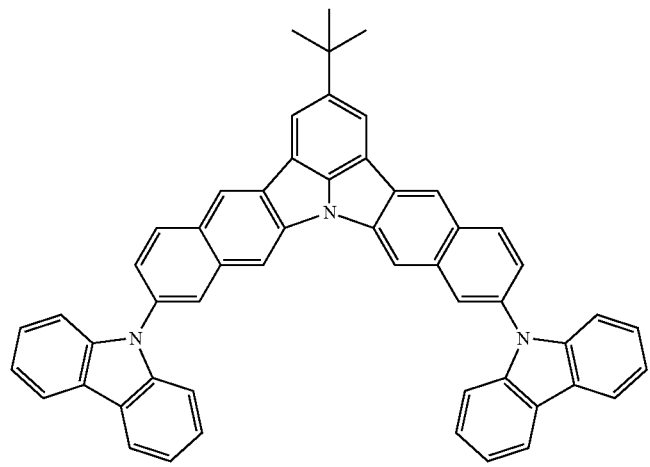
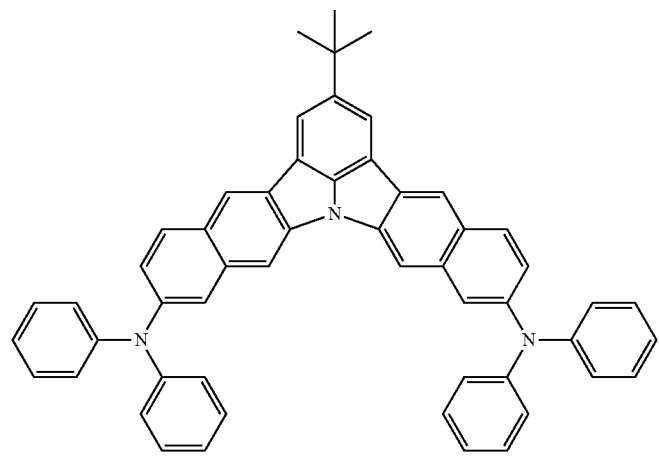
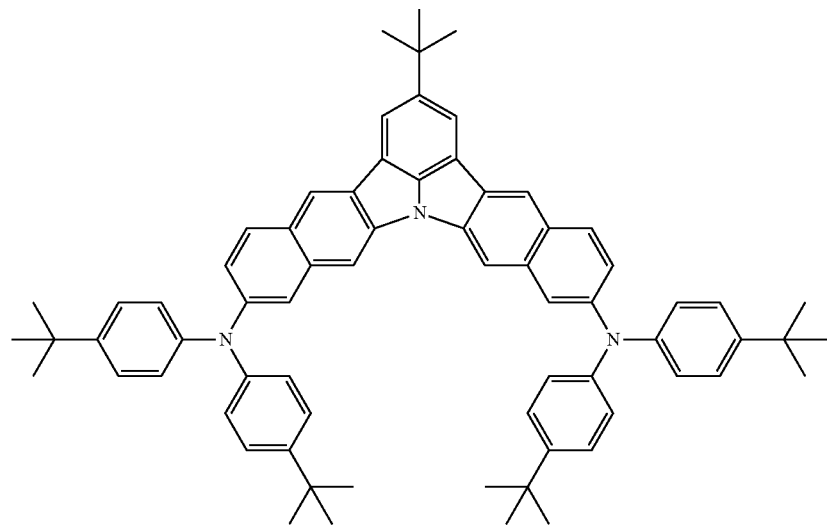

225
-continued
226
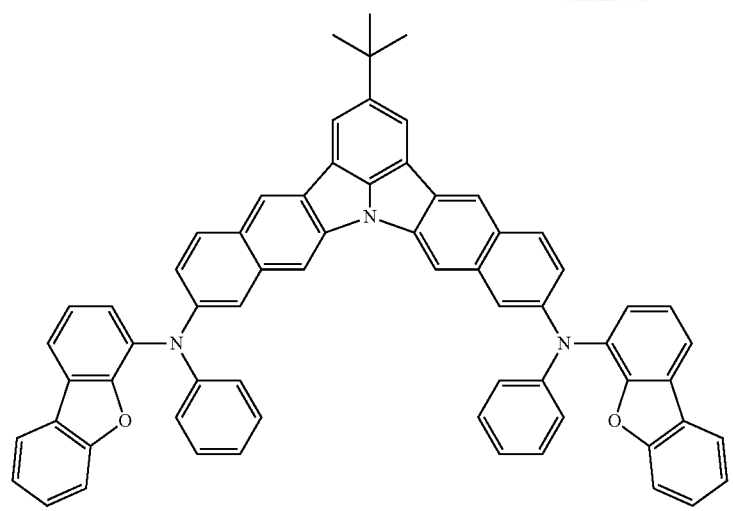
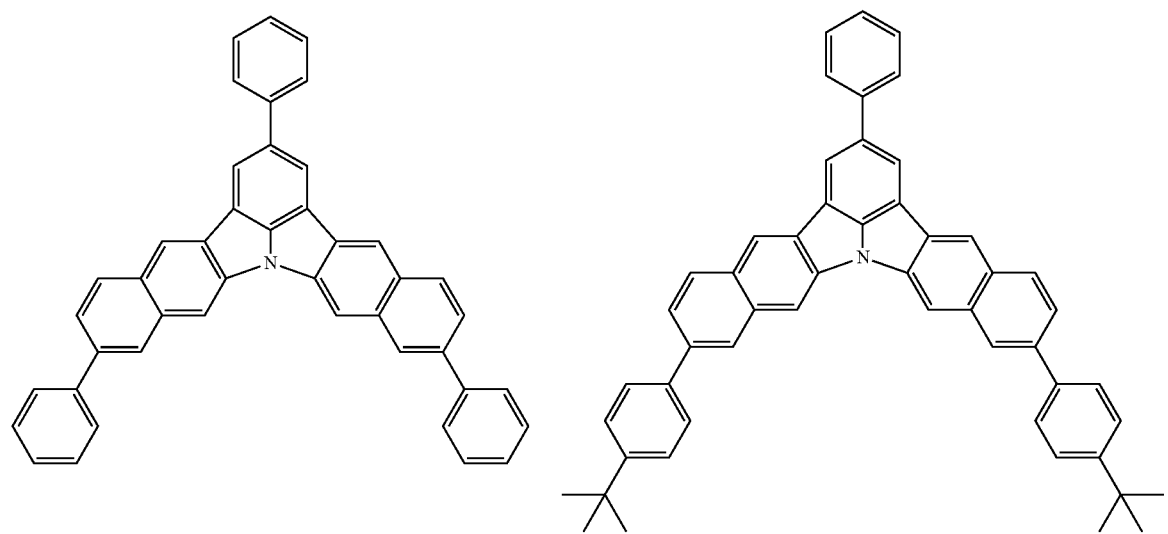
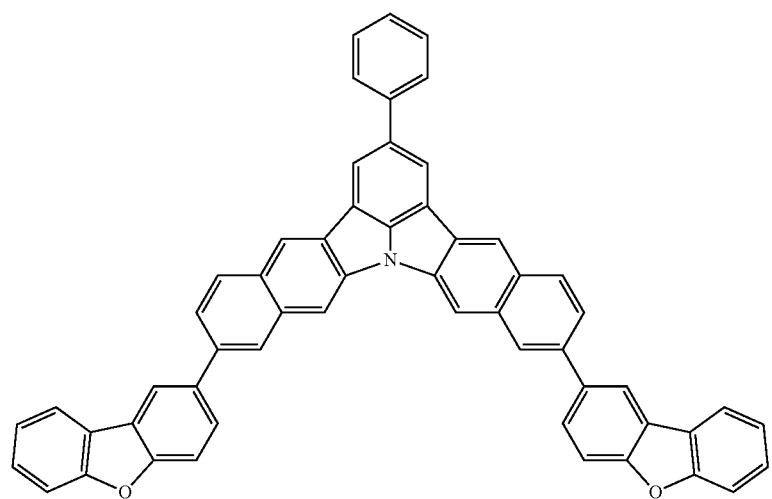

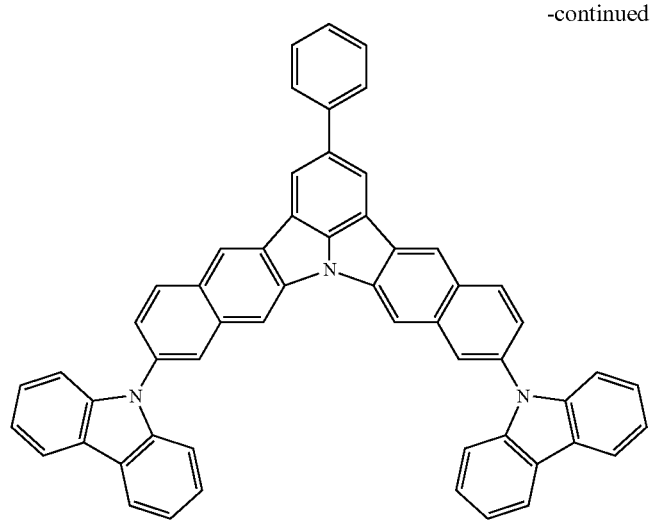
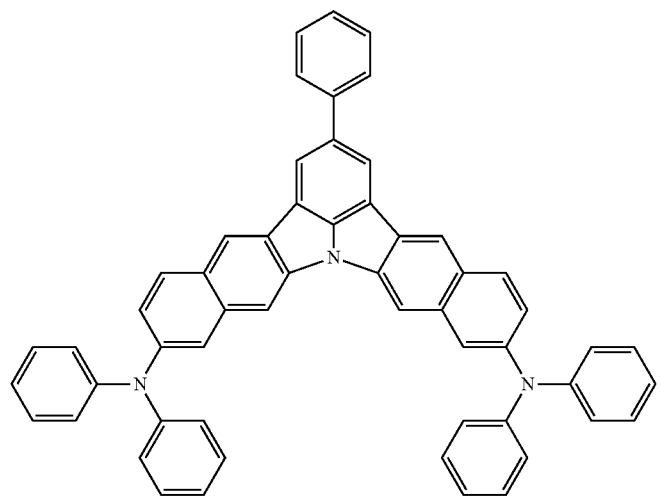
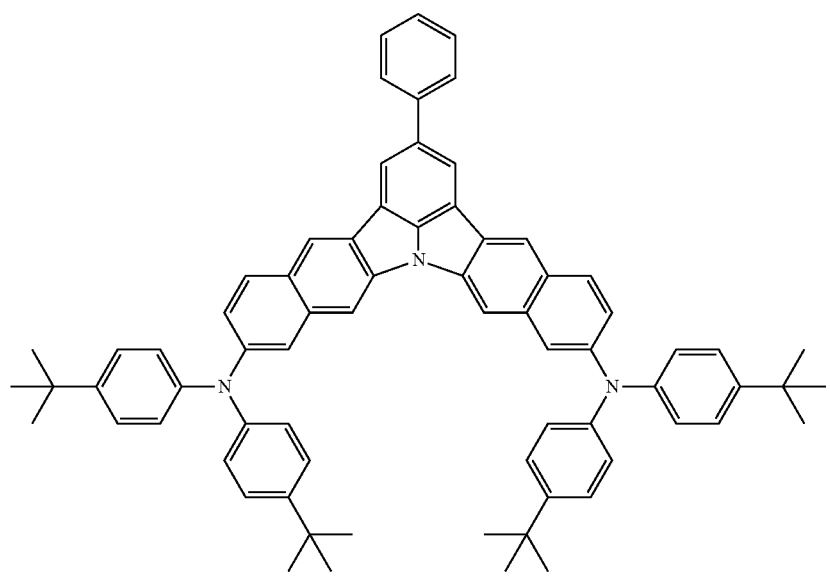

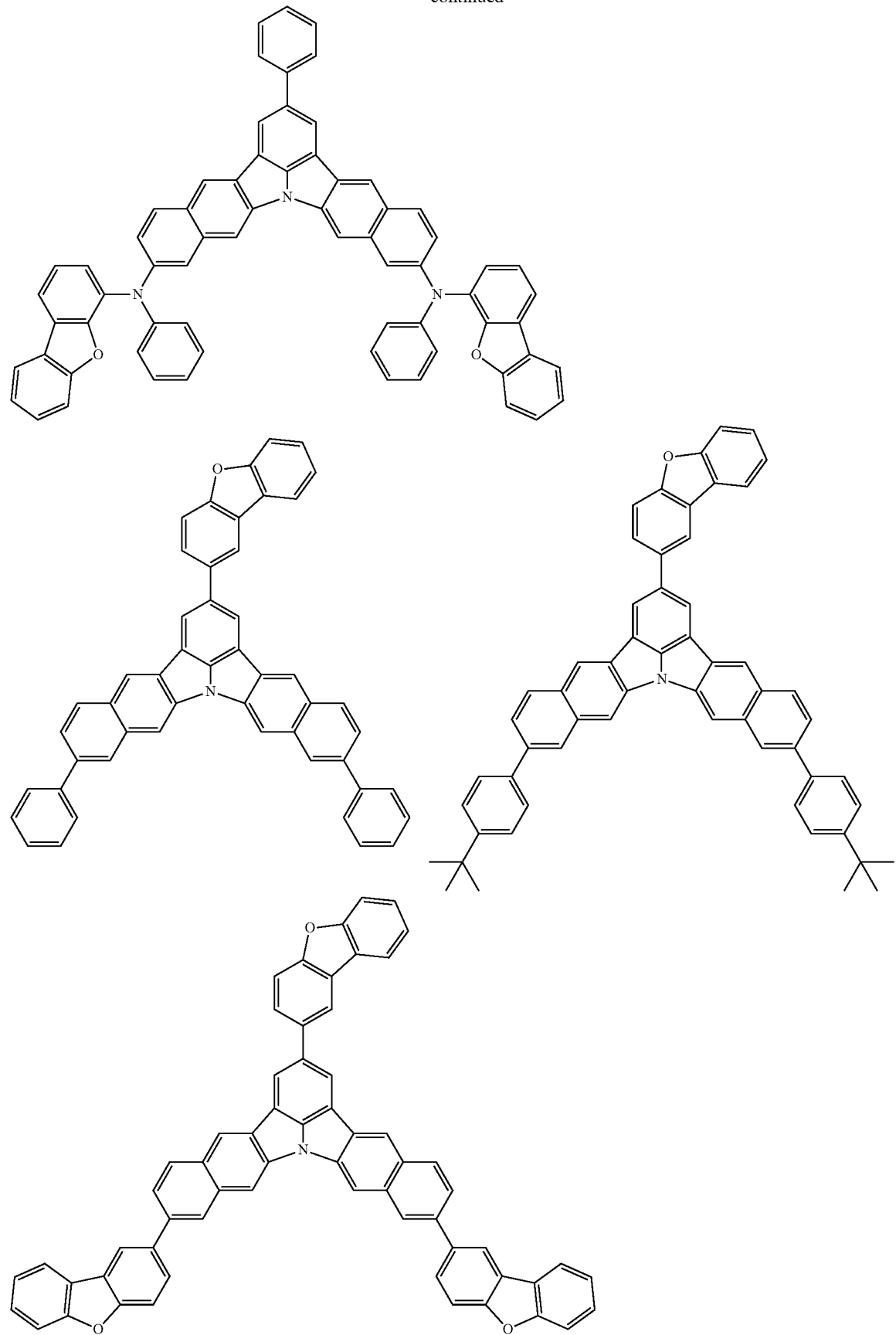

-continued
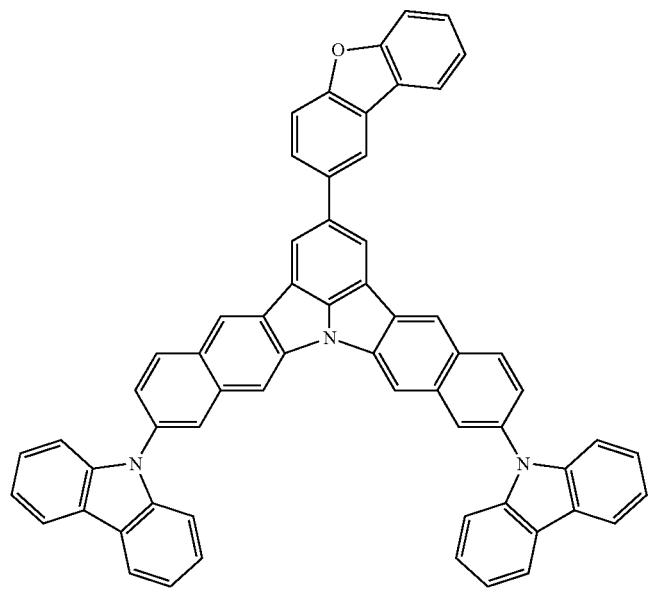
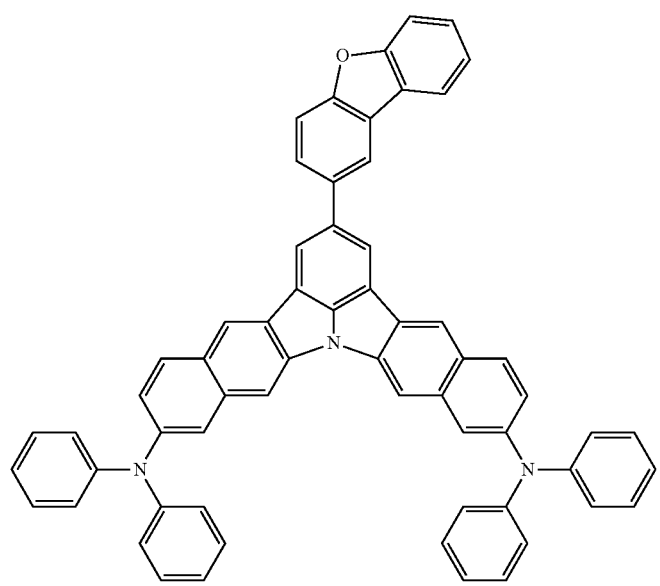

-continued
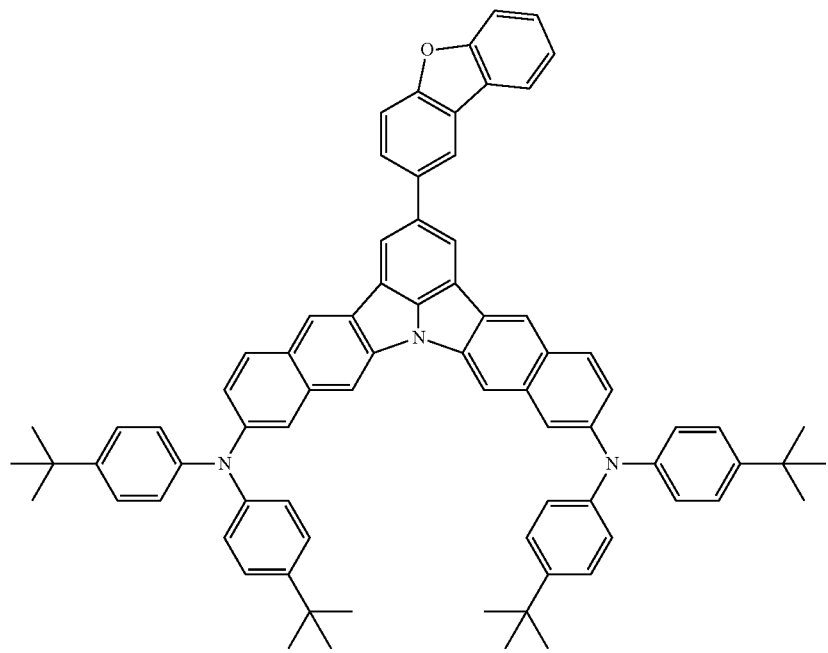
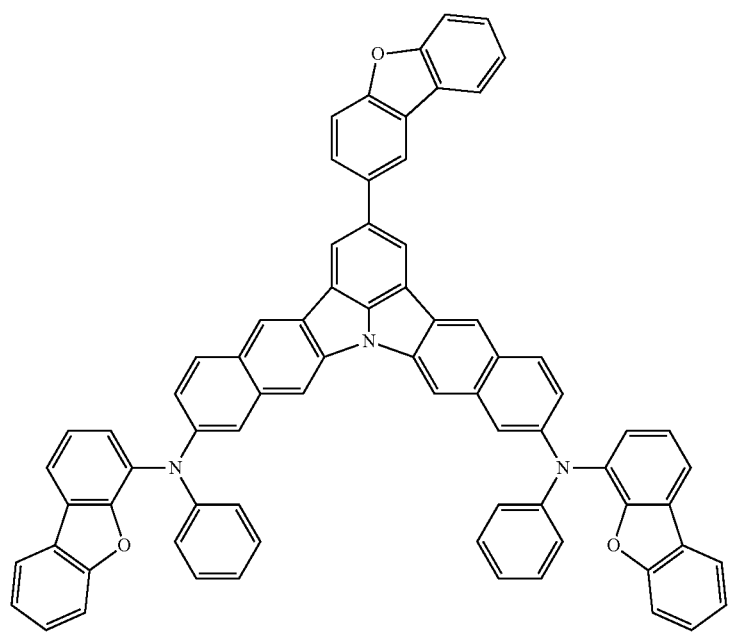

235
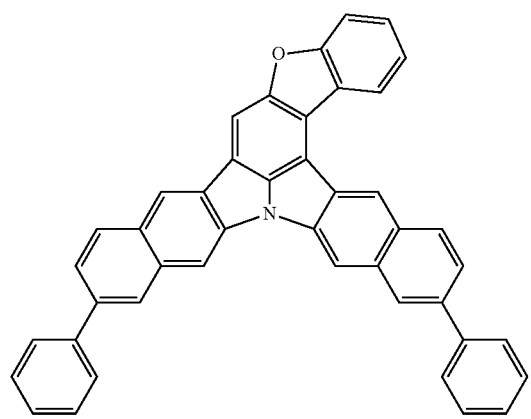
236
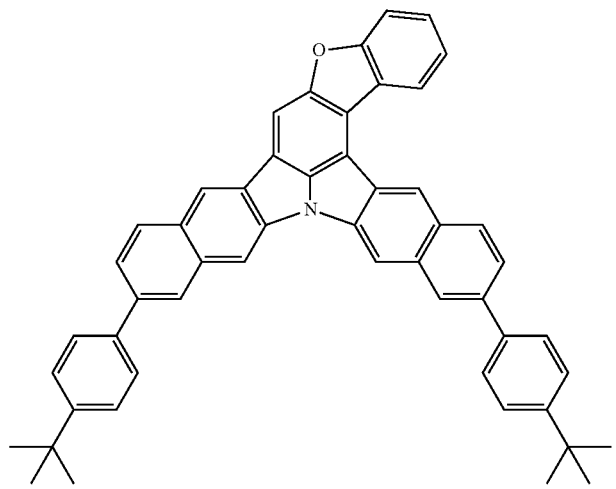
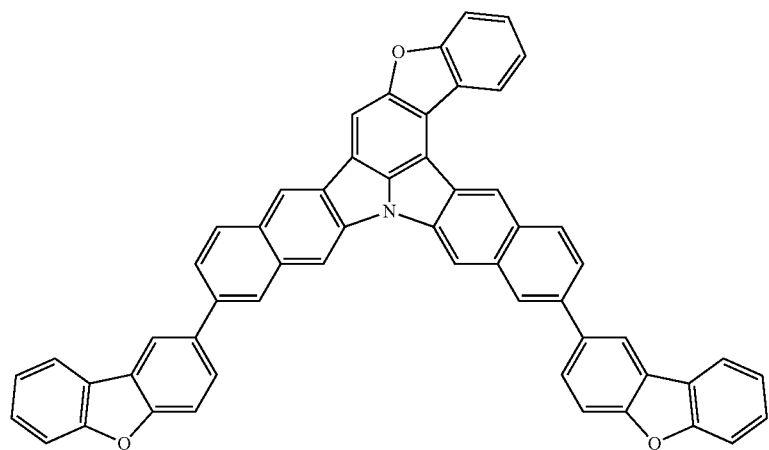
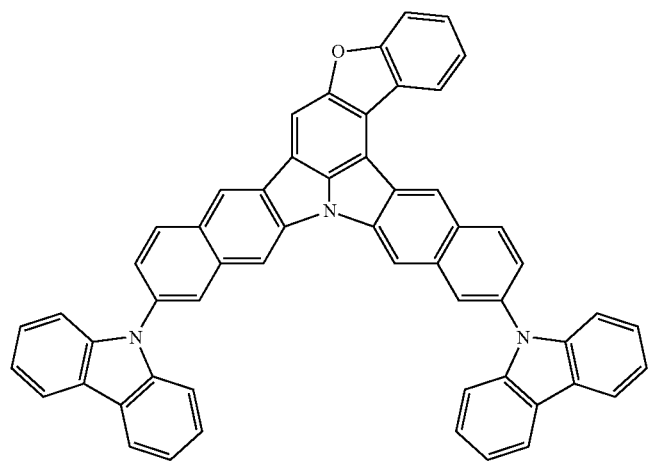

-continued
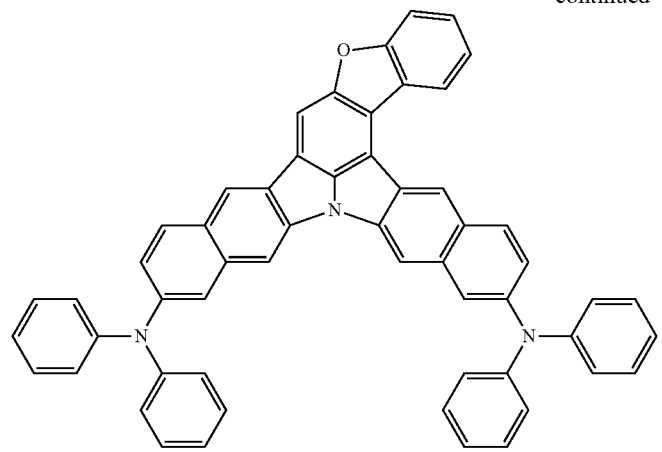
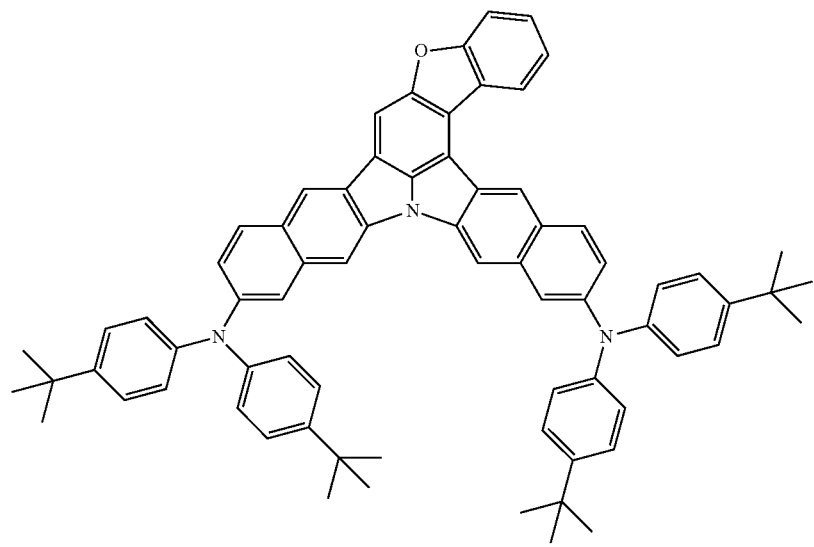
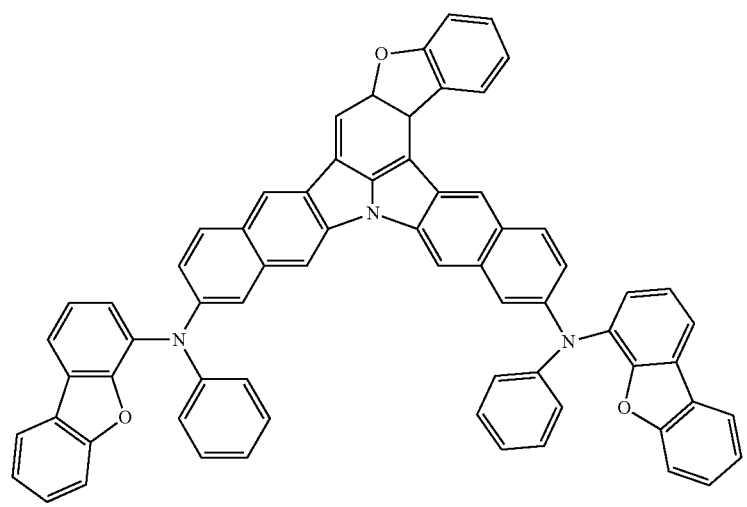

239 240
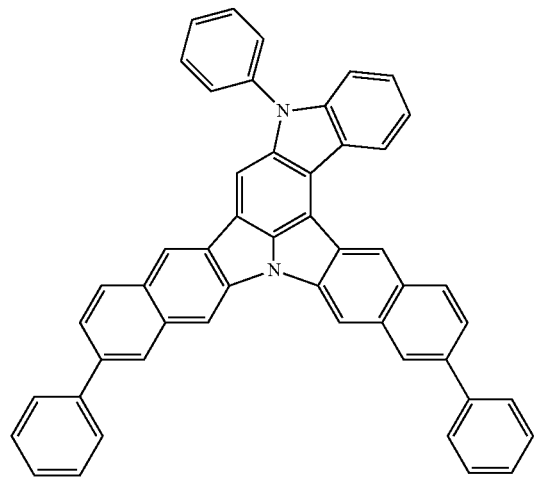
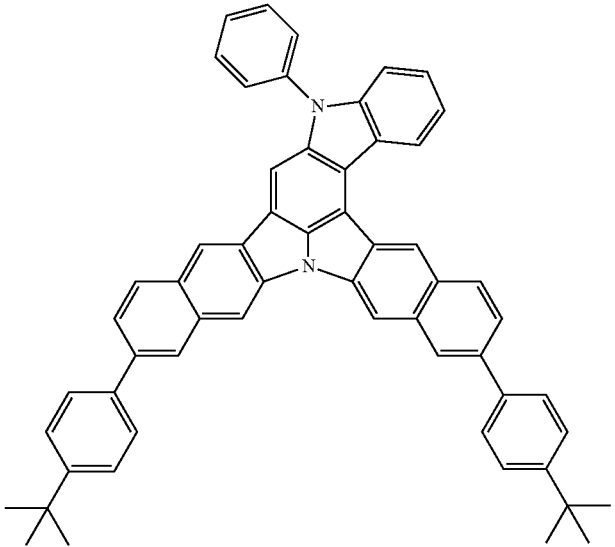
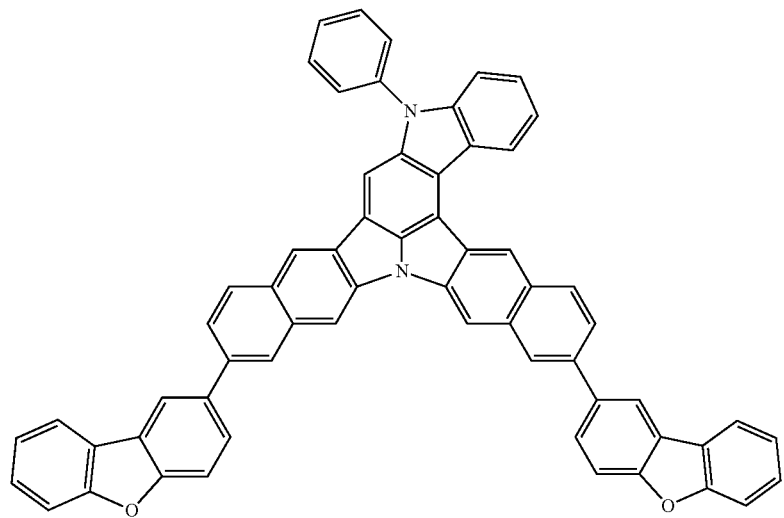
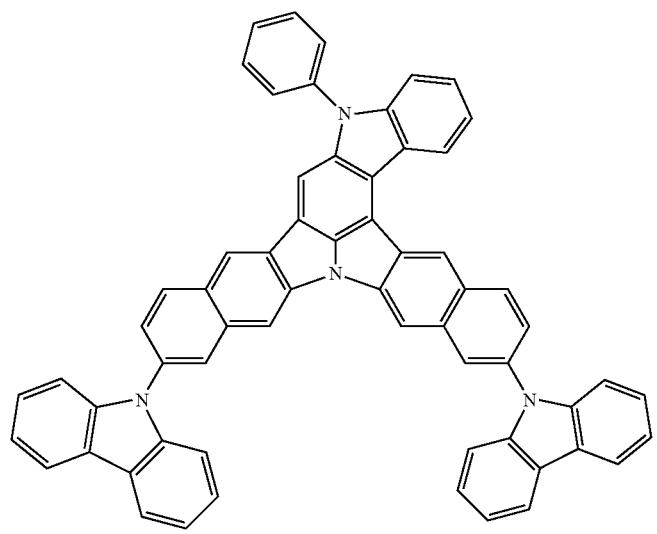

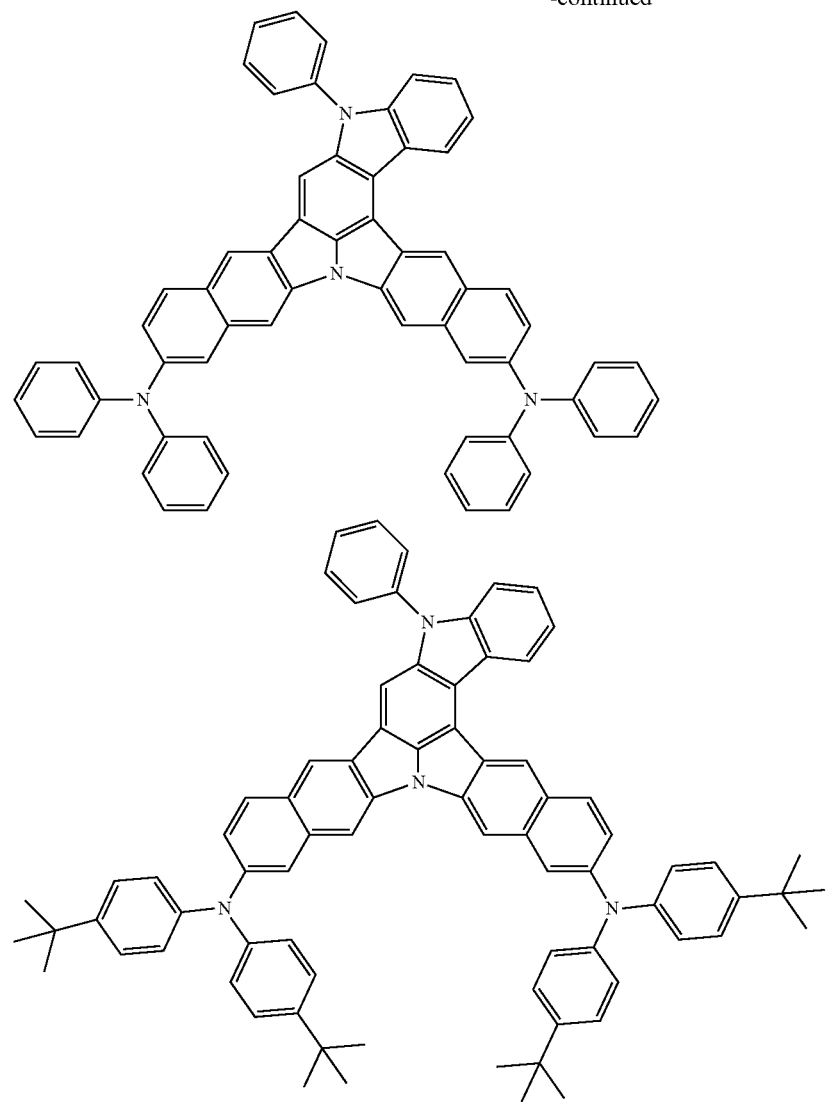
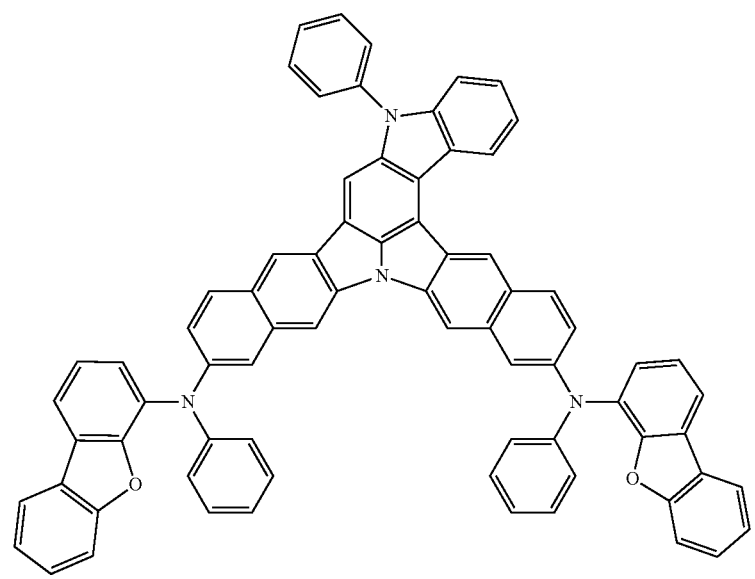

-continued
243
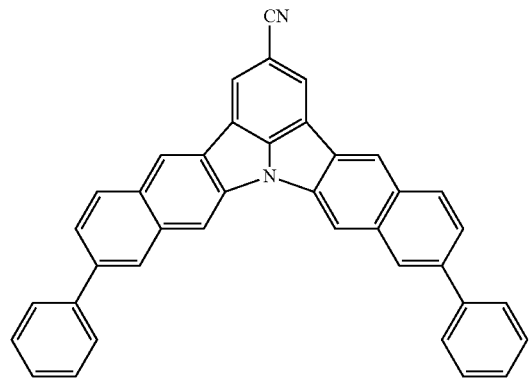
244
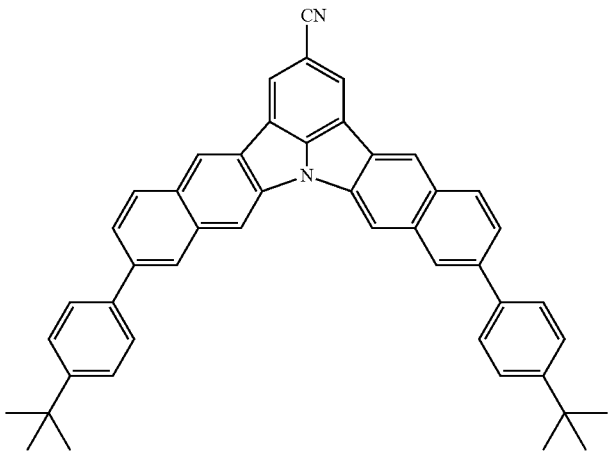
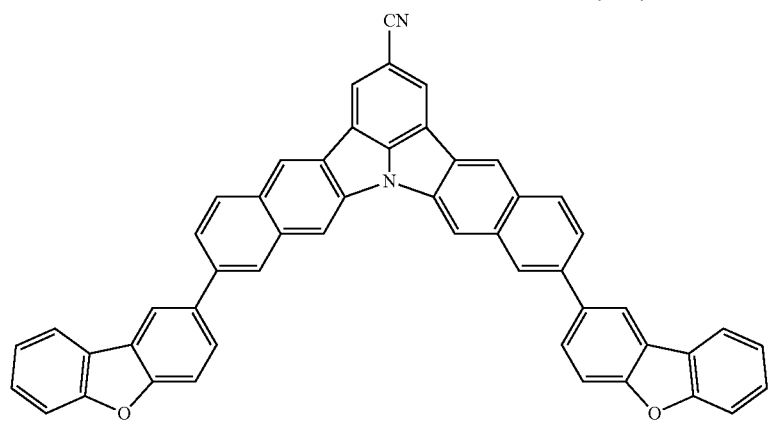
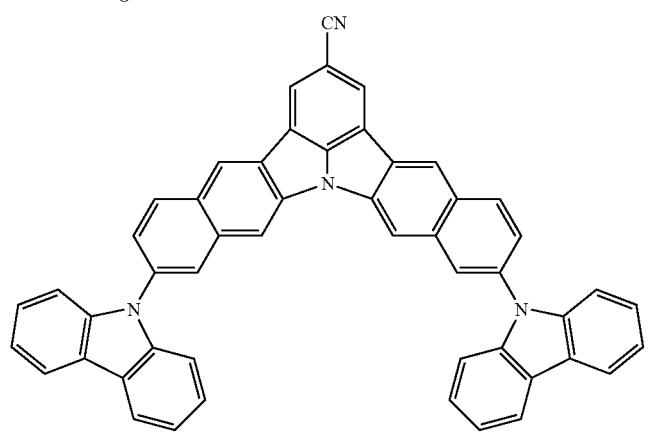
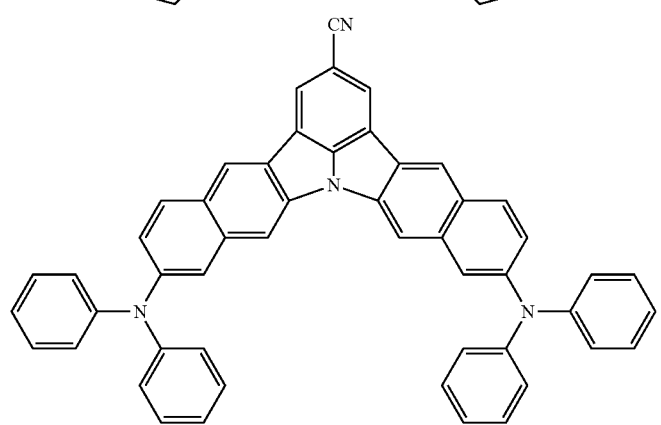

-continued
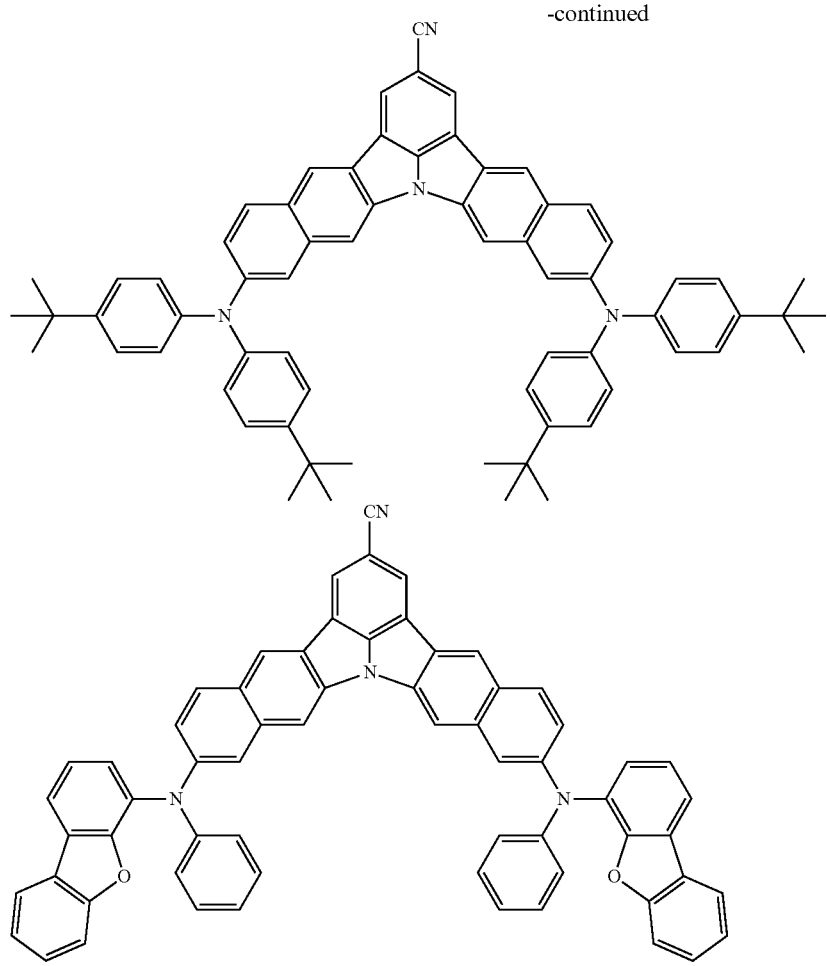
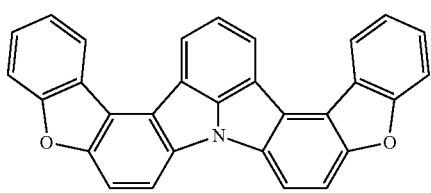
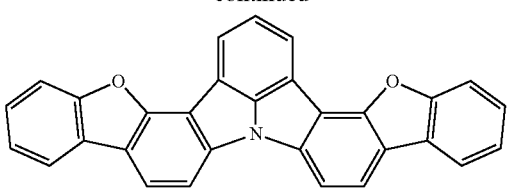
-continued
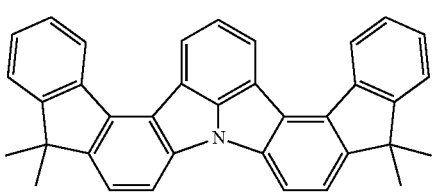
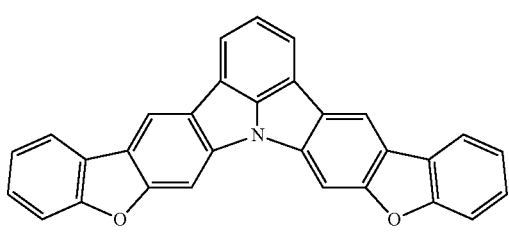
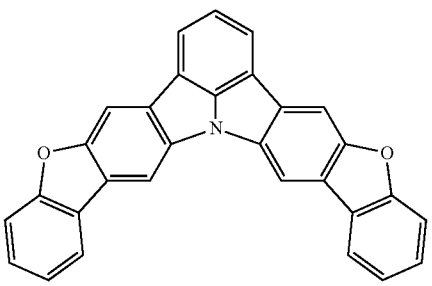

247
-continued
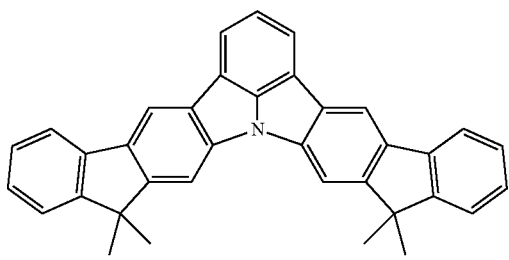
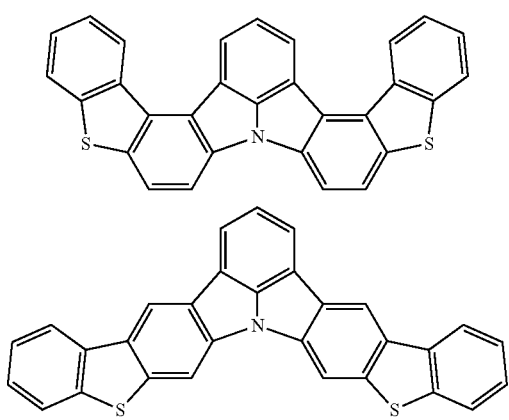
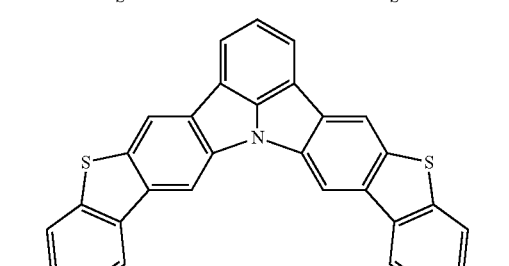
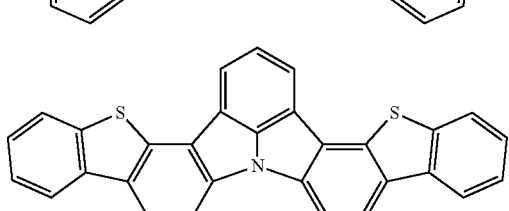
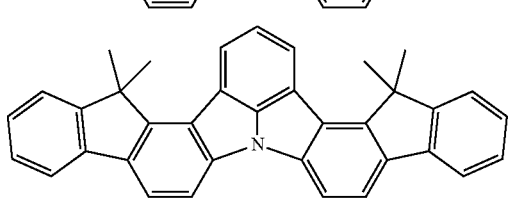
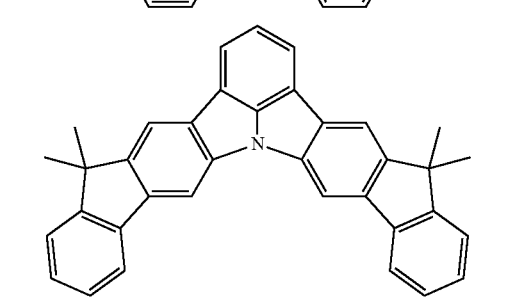
248
-continued
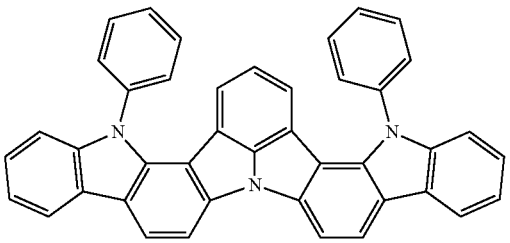
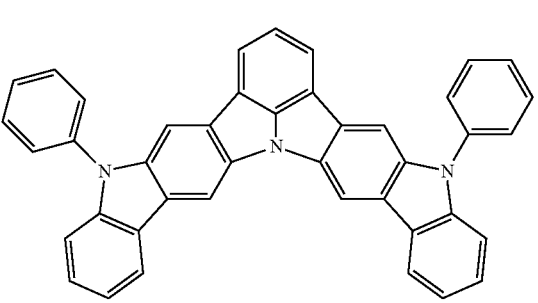
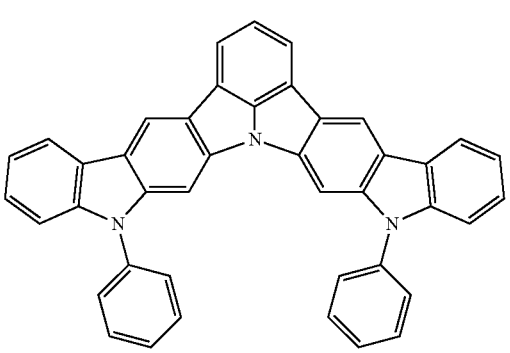
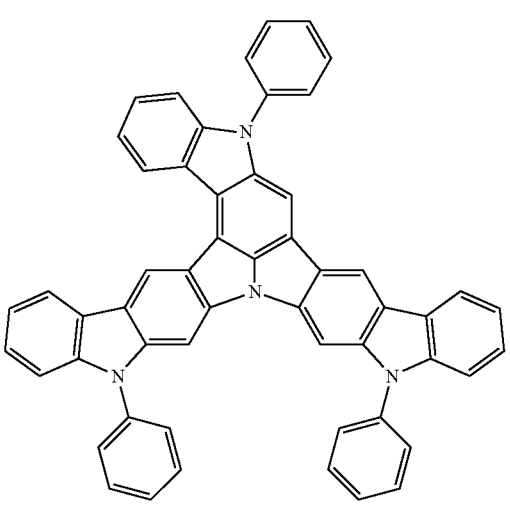

249
-continued
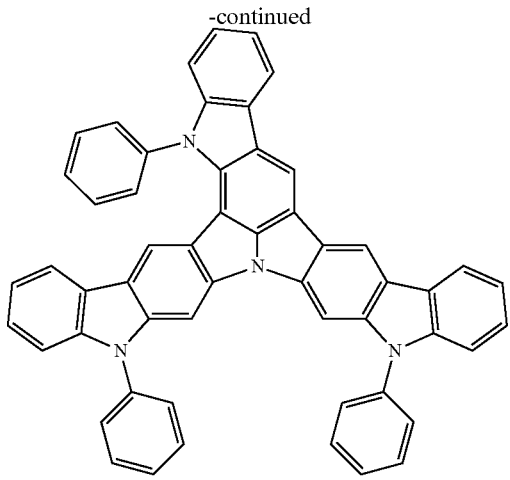
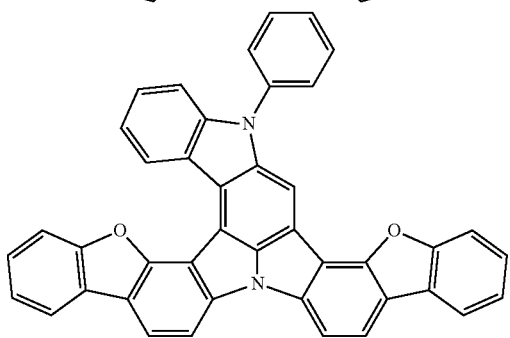
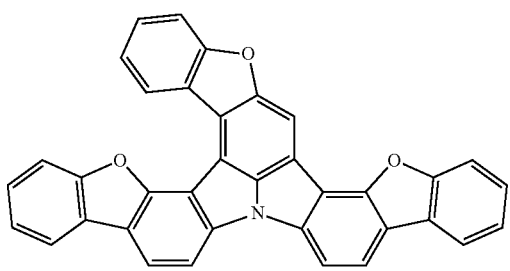
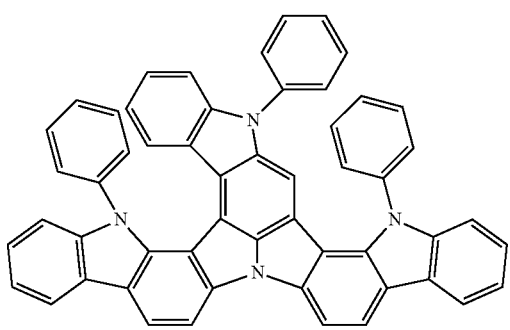
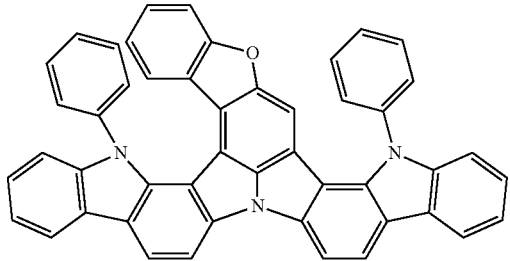
250
-continued
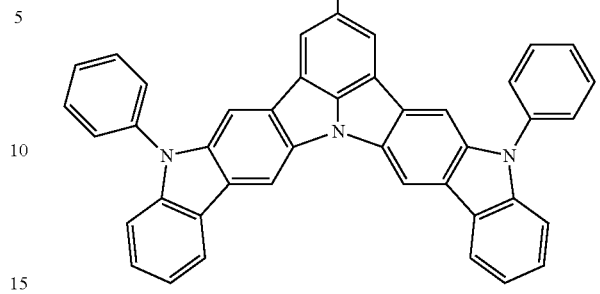
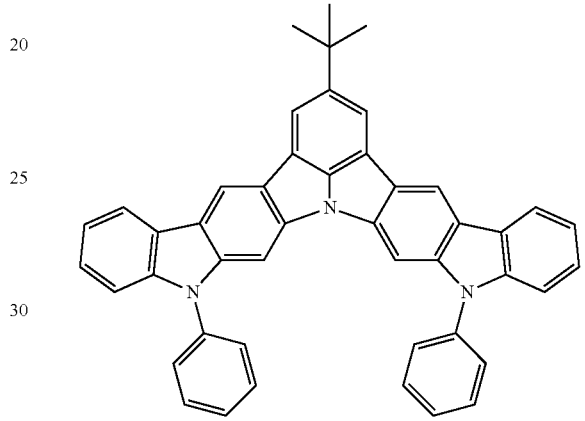
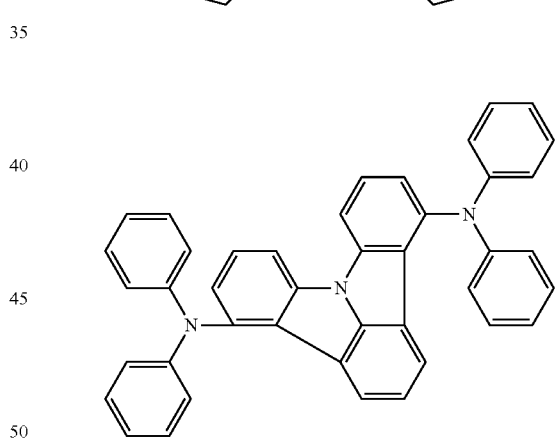
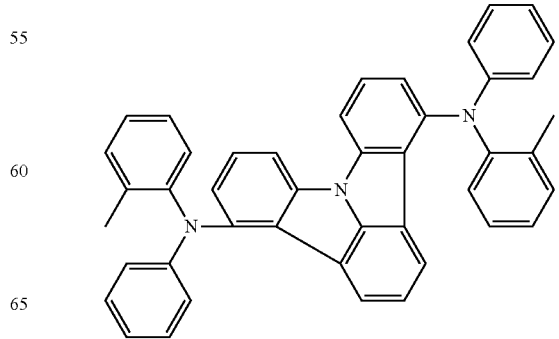

251
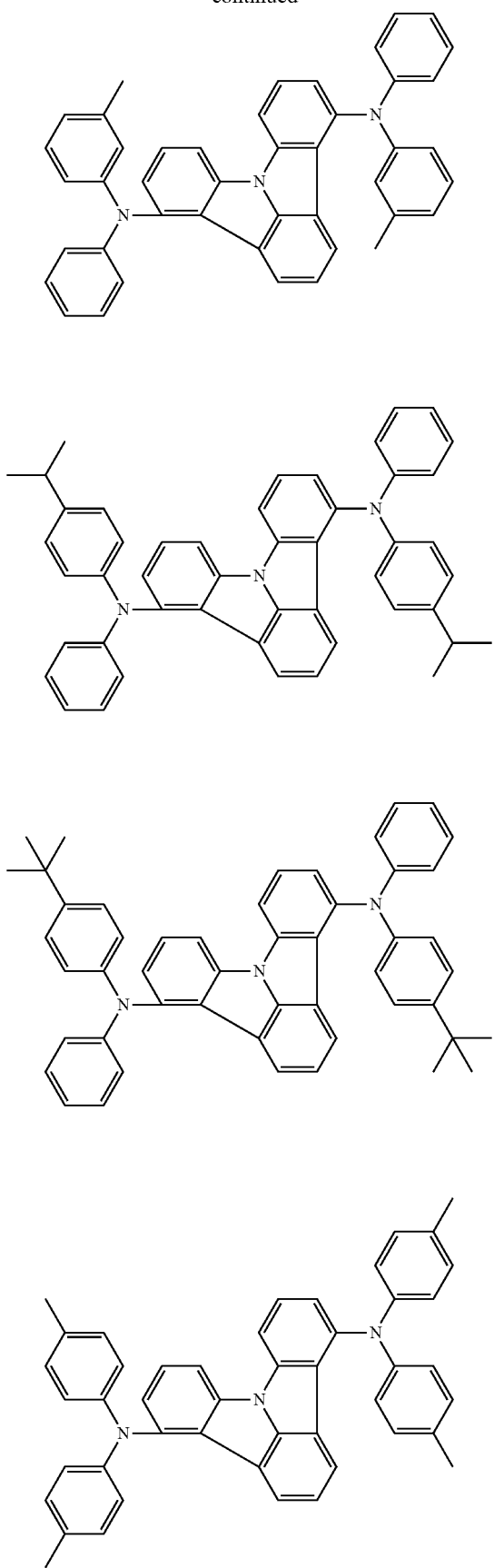
252
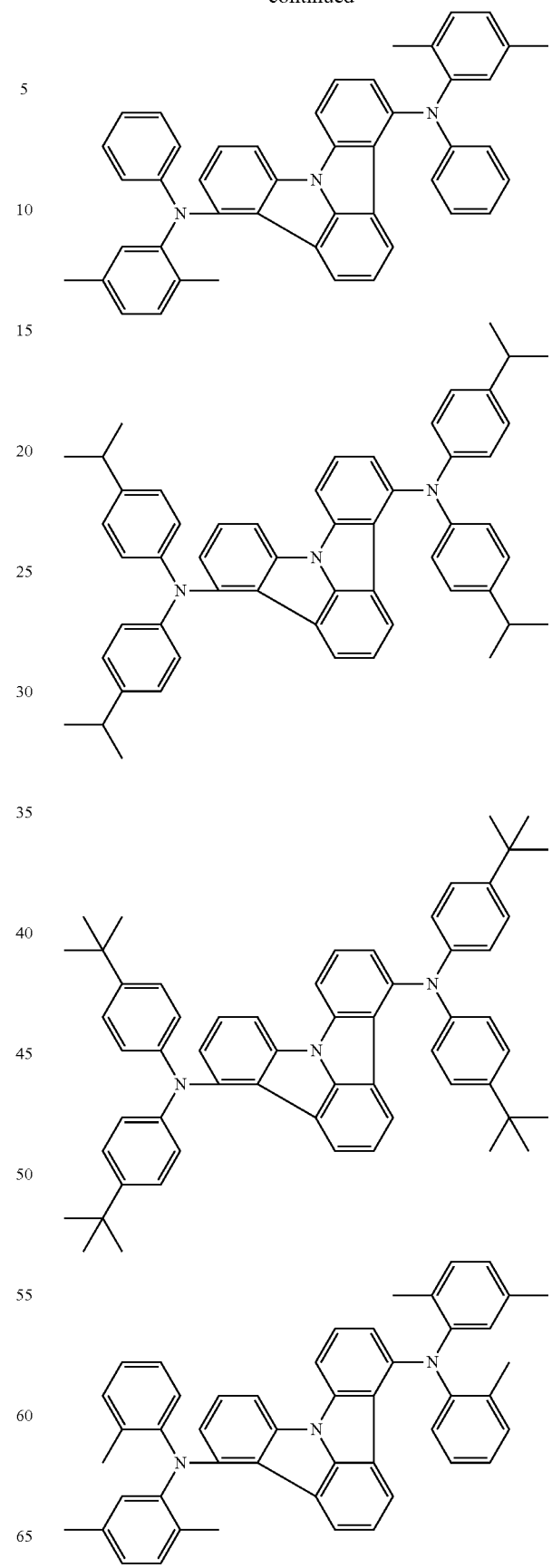

253
-continued
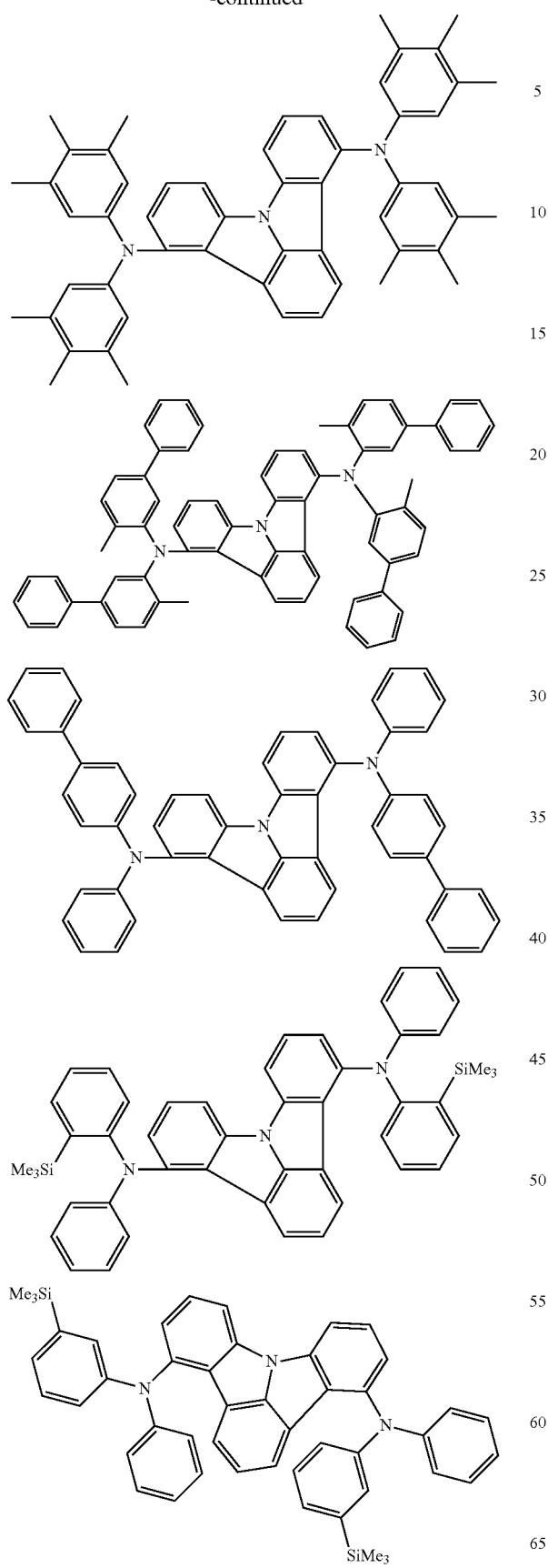
254
-continued
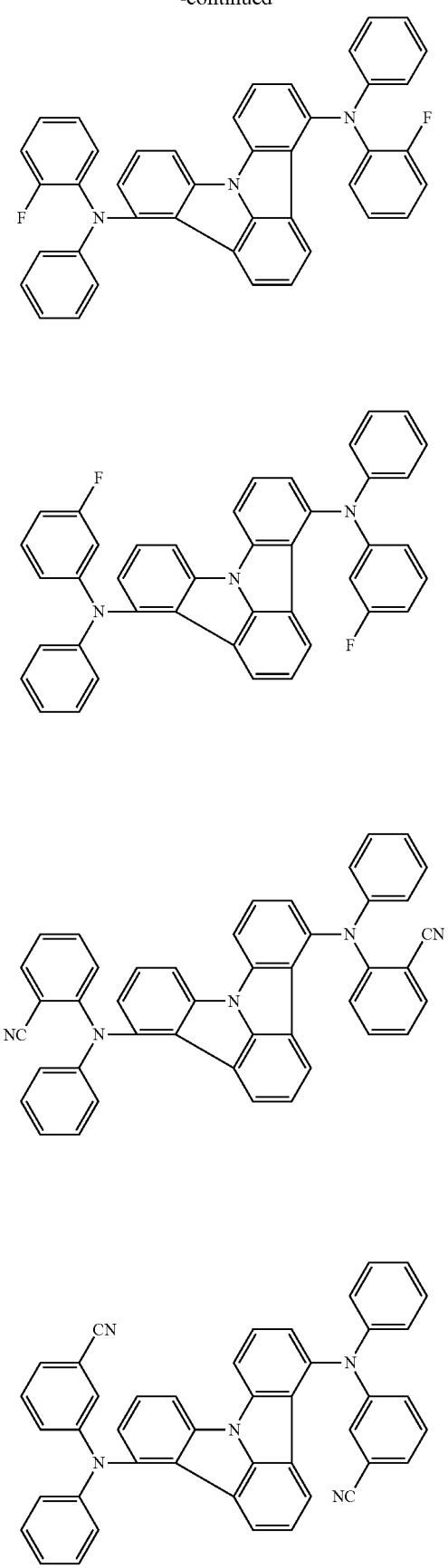

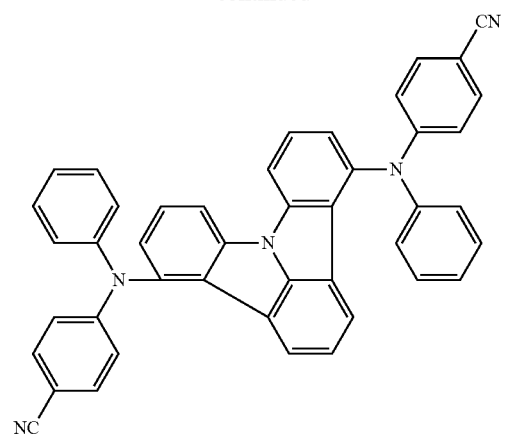
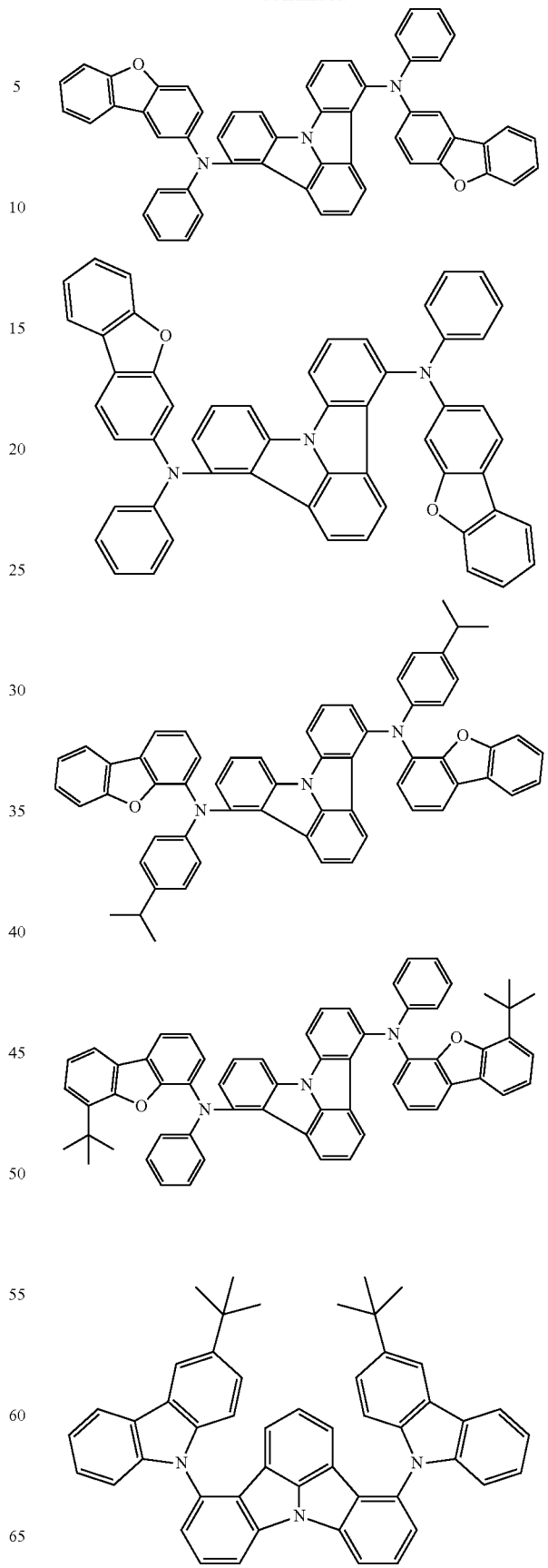

257
-continued
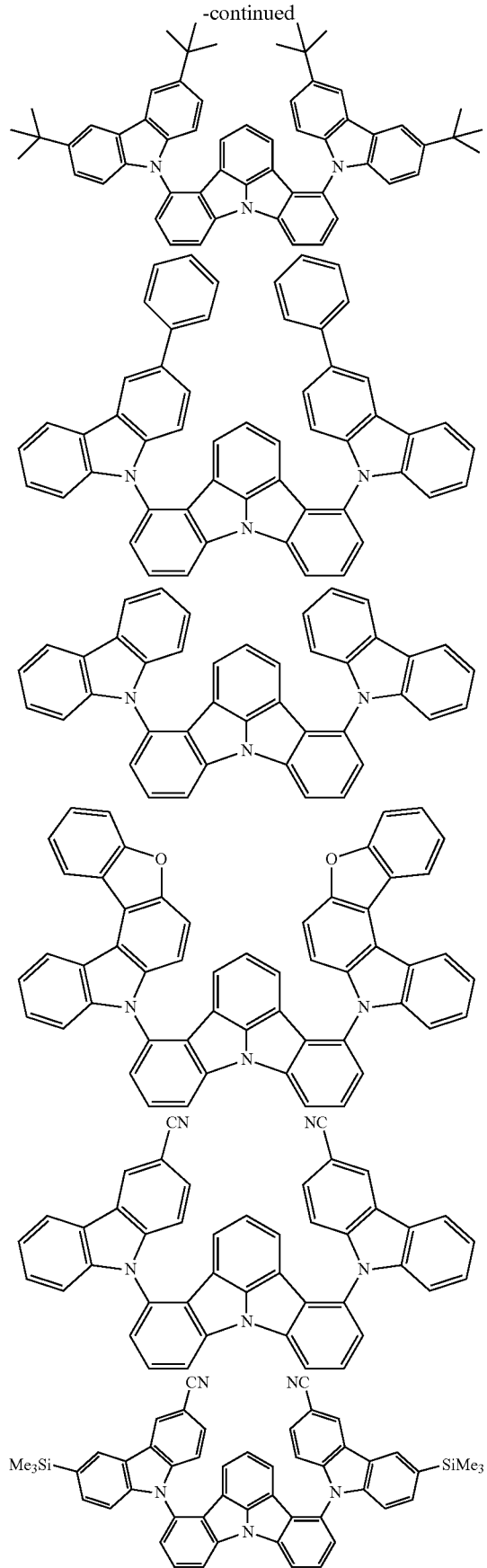
258
-continued
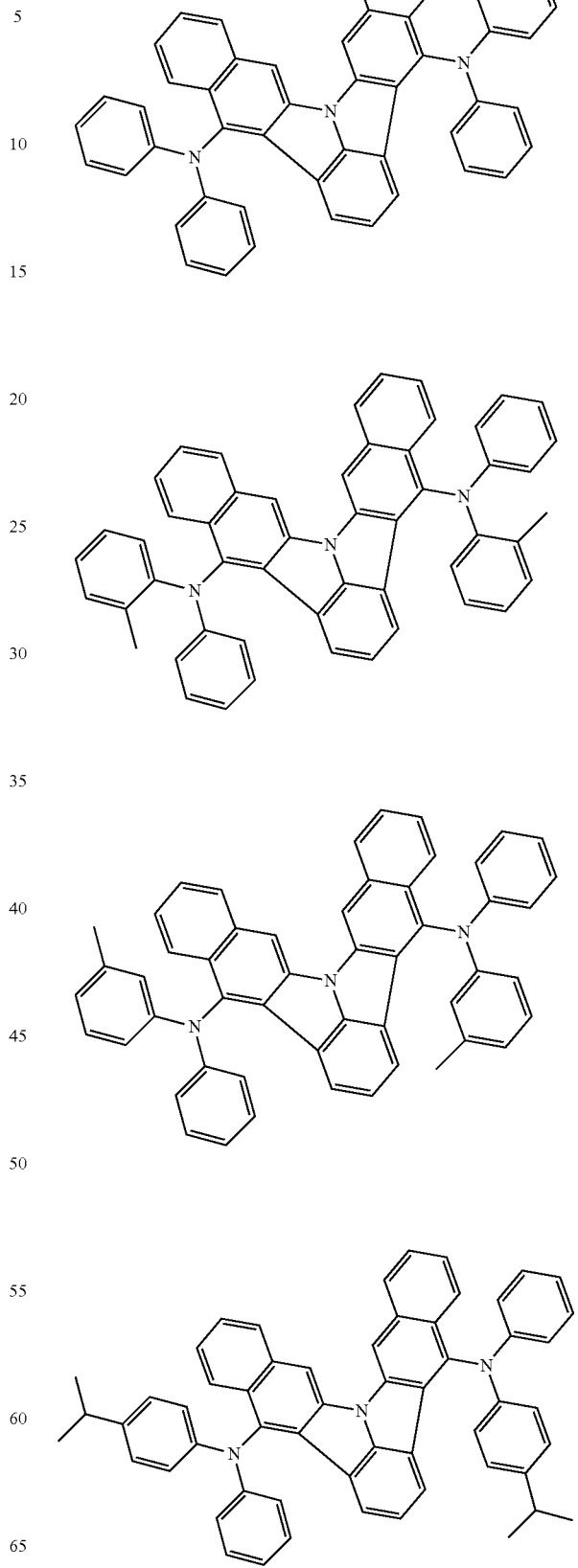

259
-continued
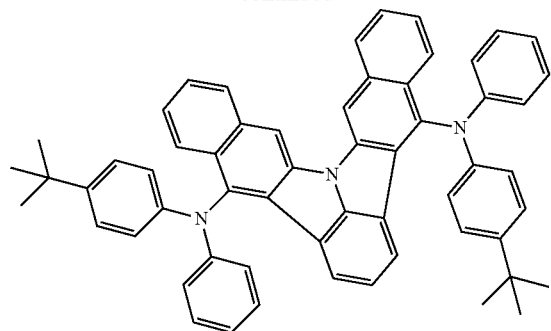
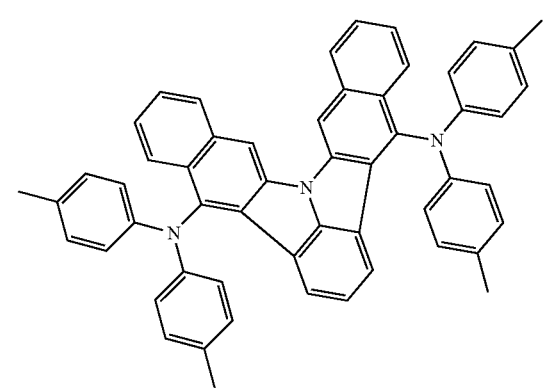
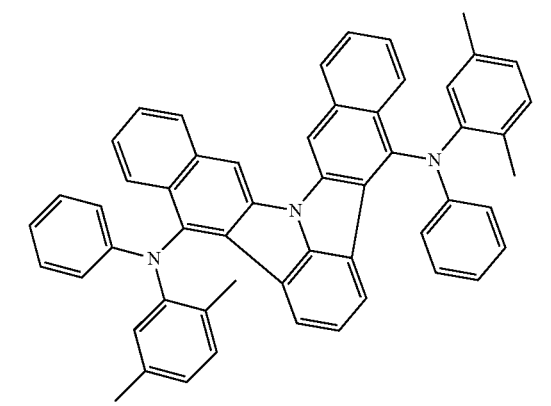
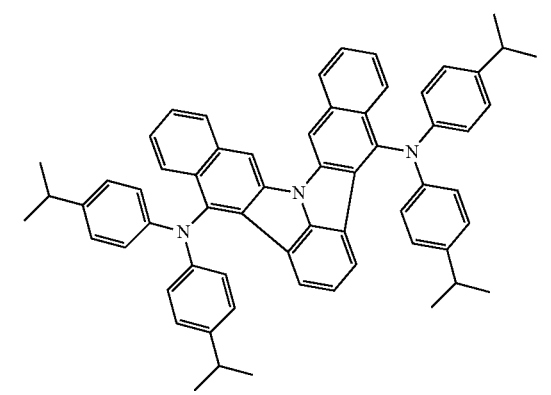
260
-continued
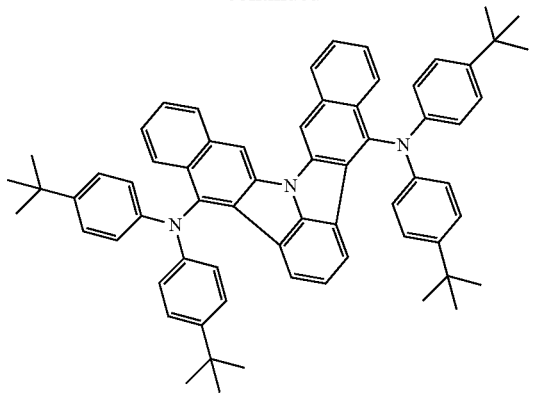
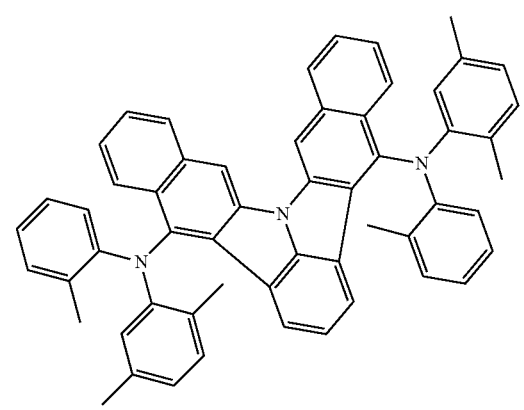
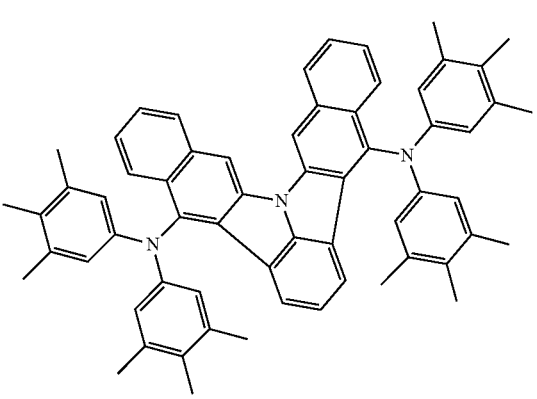
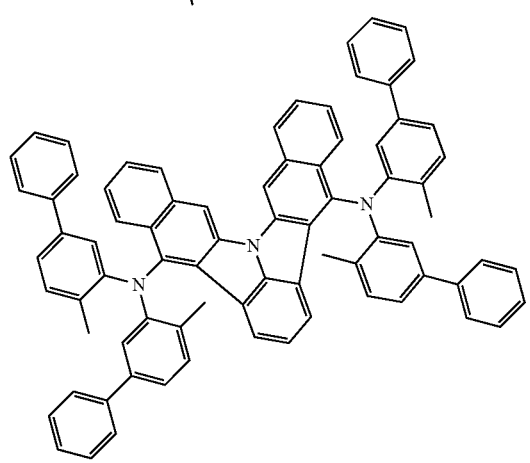

261
-continued
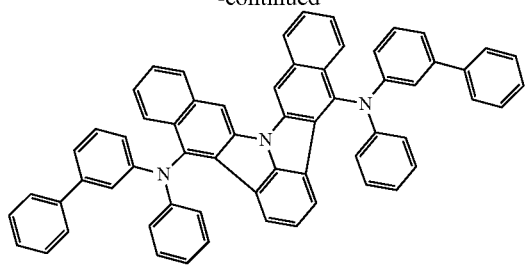
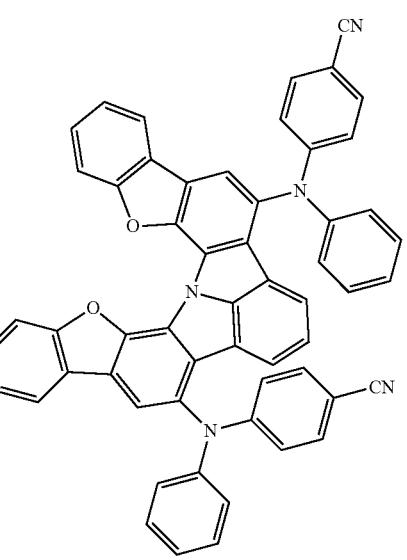
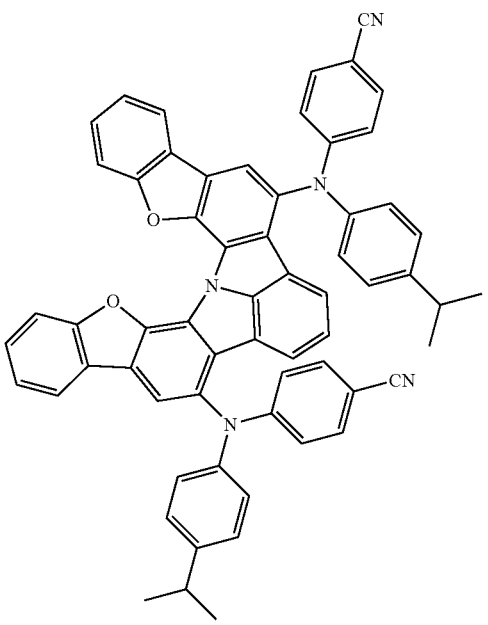
262
-continued
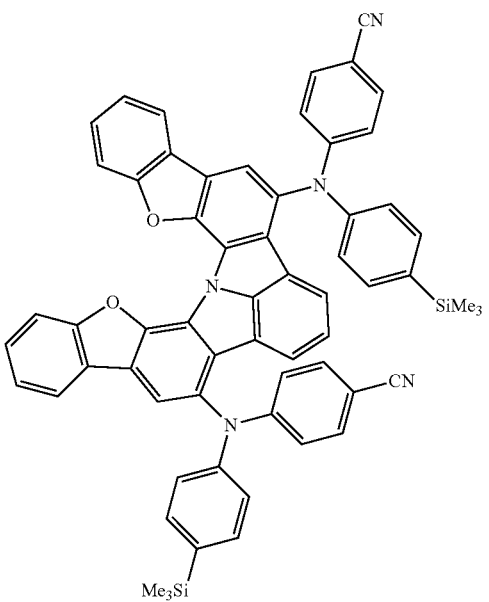
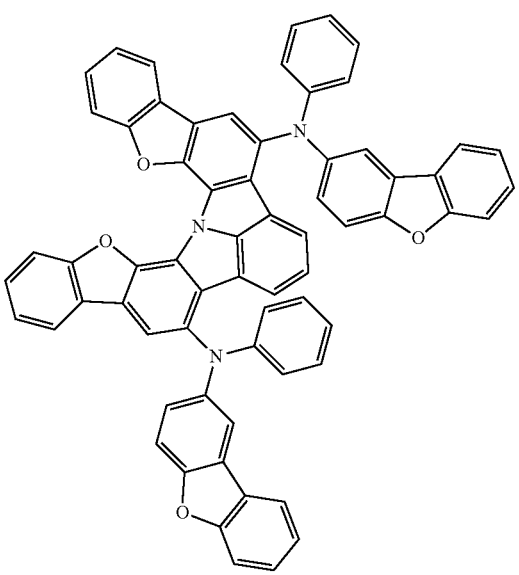
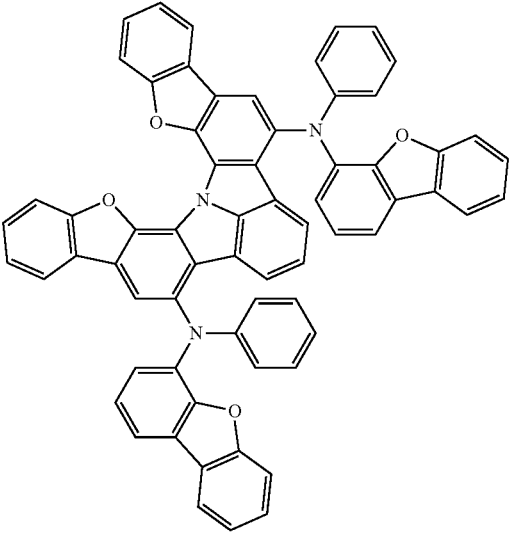

263
-continued
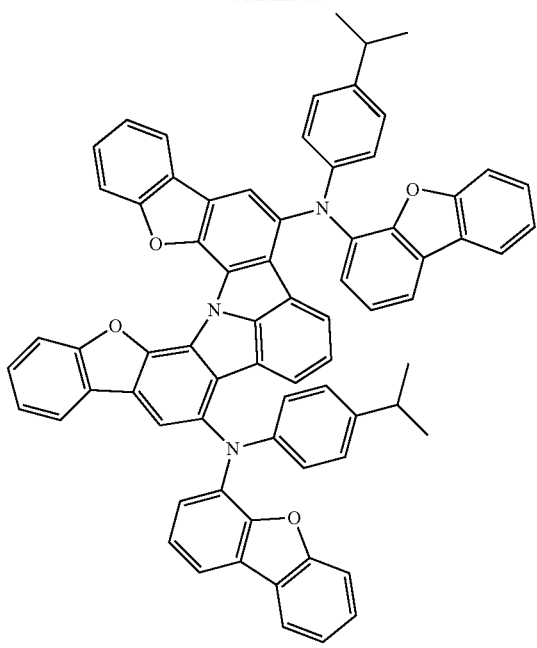
264
-continued
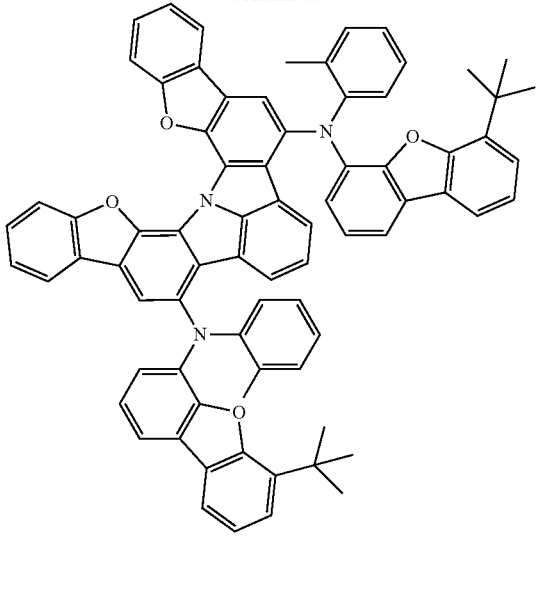
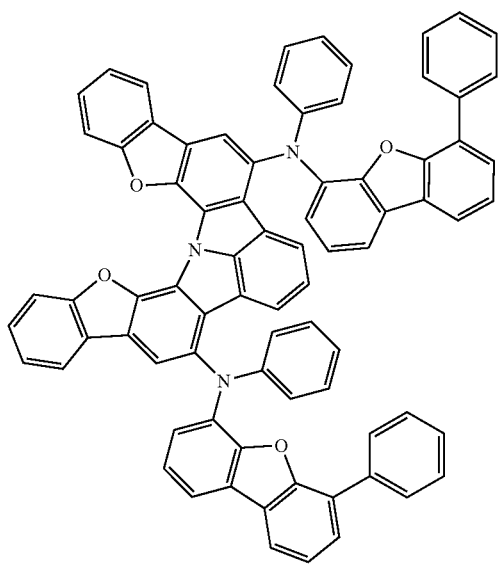
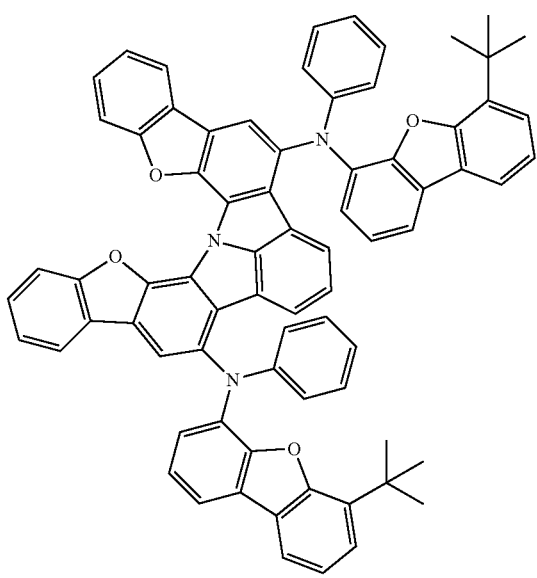
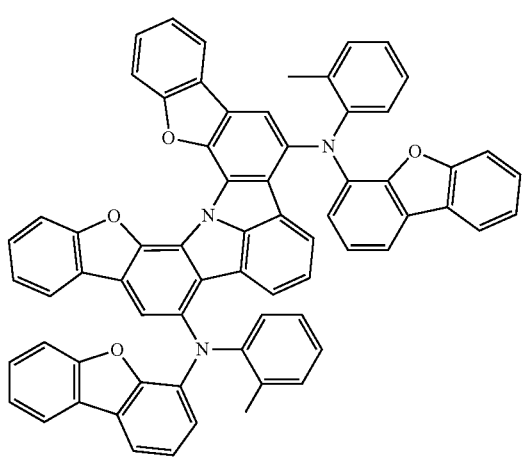

265
-continued
266
-continued
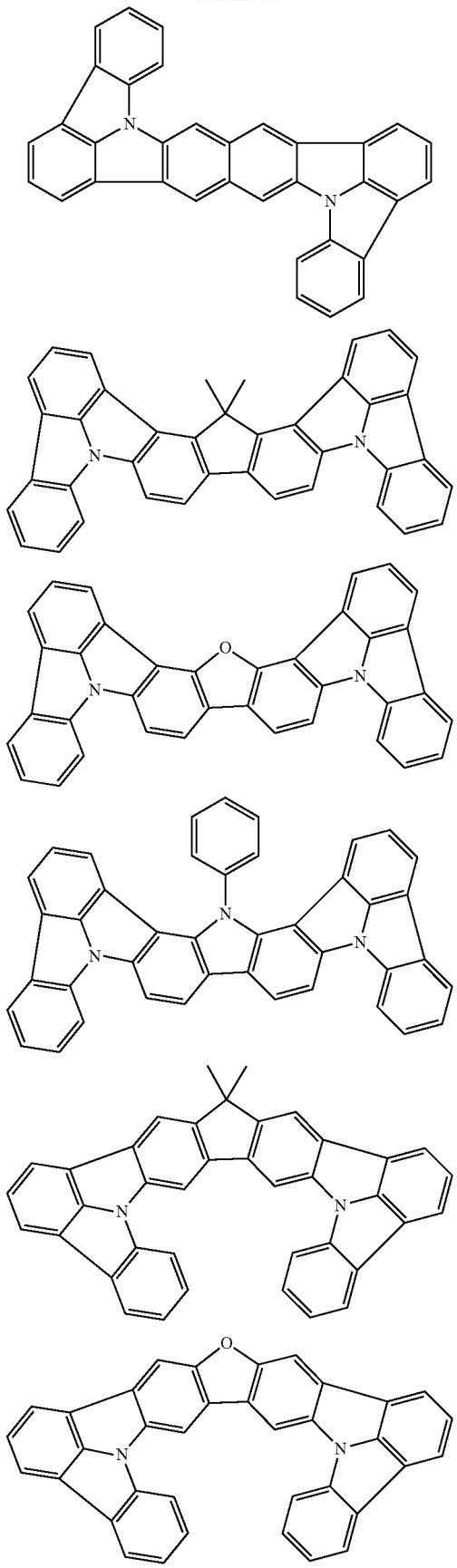
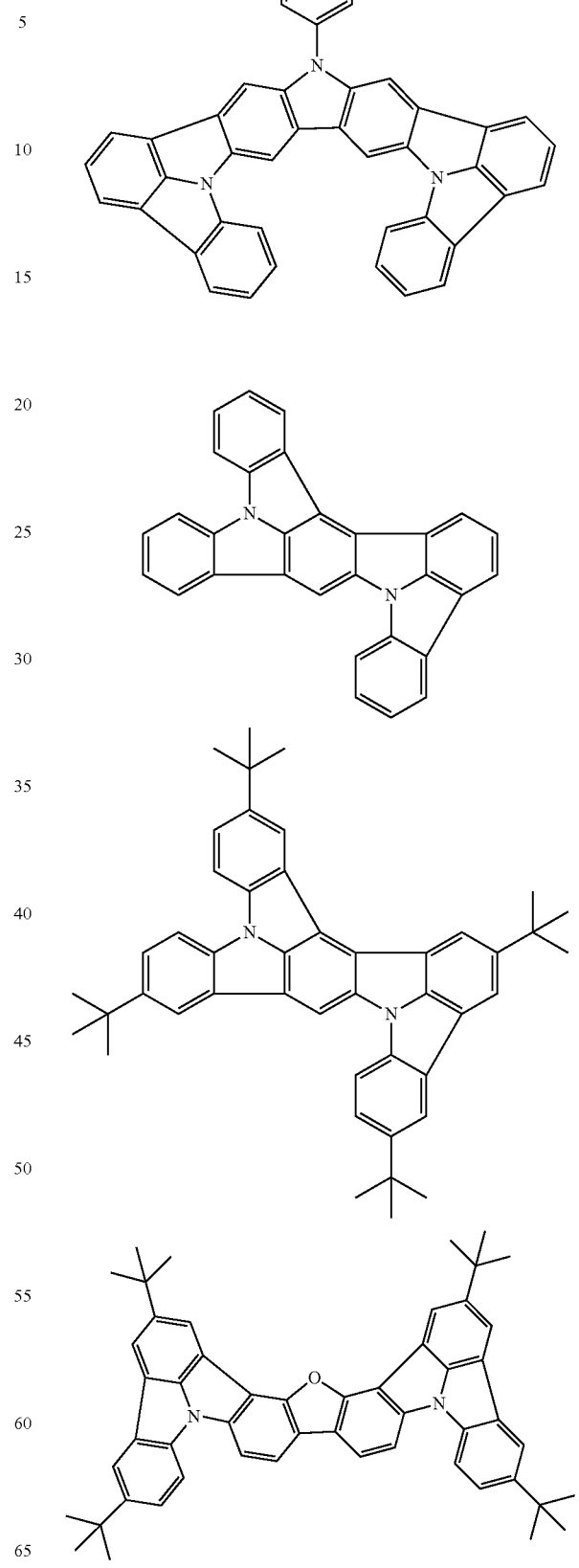

(Compound Represented by Formula (31))

The compound represented by the formula (31) is explained below.

The compound represented by formula (31) is a compound corresponding to the compound represented by the formula (21-3).

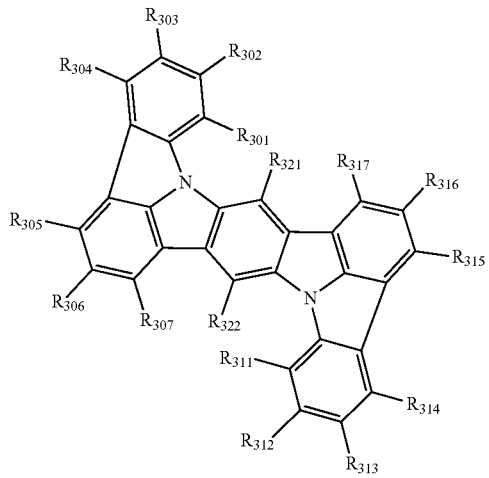

(31)

In the formula (31),
one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{321}$ and $R_{322}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

Example of "One pair of two or more adjacent groups of $R_{301}$ to $R_{307}$ and $R_{311}$ to $R_{317}$" is pairs of $R_{301}$ and $R_{302}$, $R_{302}$ and $R_{303}$, $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{307}$ and $R_{311}$ to $R_{317}$ is a group represented by —N($R_{906}$)($R_{907}$).

In one embodiment, $R_{301}$ to $R_{307}$ and $R_{311}$ to $R_{317}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the following formula (32):

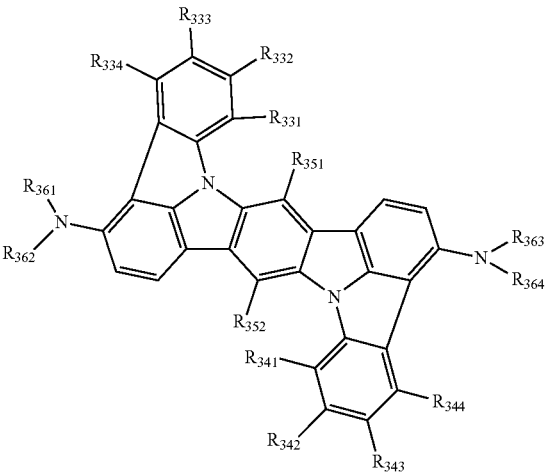

(32)

wherein in the formula (32),
one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;

$R_{331}$ to $R_{334}$ and $R_{341}$ to $R_{344}$ that do not form the substituted or unsubstituted, saturated or unsaturated ring and $R_{351}$ and $R_{352}$ are independently
a hydrogen atom,
a substituted or unsubstituted aryl group having 6 to 50 ring carbon atoms, or
a substituted or unsubstituted monovalent heterocyclic group having 5 to 50 ring atoms; and $R_{361}$ to $R_{364}$ are independently
a substituted or unsubstituted aryl group having 6 to 50 ring carbon atoms, or
a substituted or unsubstituted monovalent heterocyclic group having 5 to 50 ring atoms.

In one embodiment, the compound represented by the formula (31) is a compound represented by the formula (33):

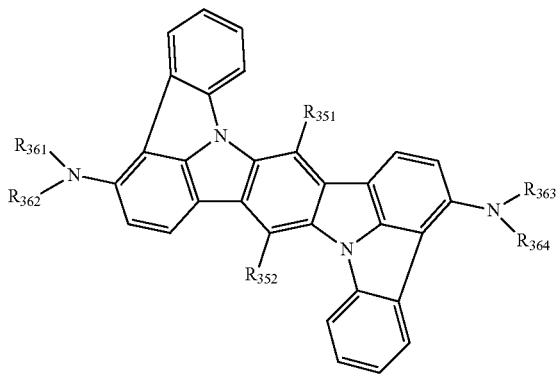
(33)

wherein in the formula (33), $R_{351}$, $R_{352}$, and $R_{361}$ to $R_{364}$ are as defined in the formula (32).

In one embodiment, the compound represented by the formula (31) is a compound represented by the formula (34) or (35):

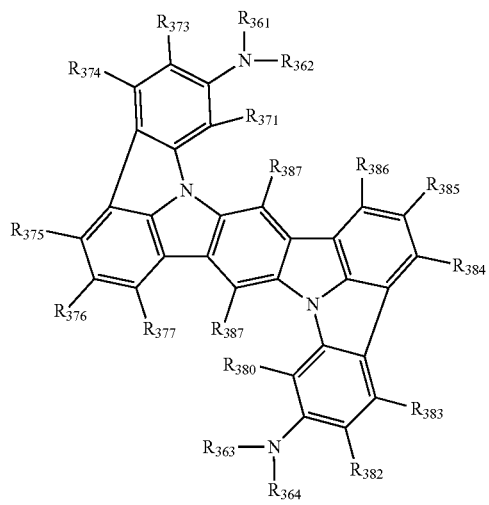
(34)

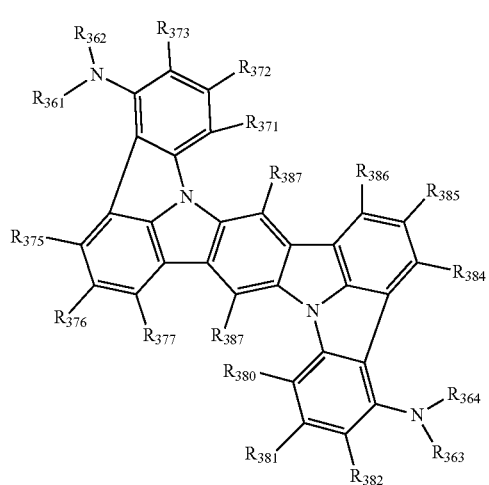
(35)

wherein in the formulas (34) and (35),
$R_{361}$ to $R_{364}$ are as defined in the formula (32);
one or more pairs of two or more adjacent groups of $R_{371}$ to $R_{377}$ and $R_{380}$ to $R_{386}$ form a substituted or unsubstituted, saturated or unsaturated ring, or do not form a substituted or unsubstituted saturated or unsaturated ring; and
$R_{371}$ to $R_{377}$ and $R_{380}$ to $R_{386}$ that do not form the substituted or unsubstituted, saturated or unsaturated ring and $R_{387}$ are independently
a hydrogen atom,
a substituted or unsubstituted aryl group having 6 to 50 ring carbon atoms, or
a substituted or unsubstituted monovalent heterocyclic group having 5 to 50 ring atoms, two $R_{387}$ or may be the same with or different from each other.

In one embodiment, the compound represented by the formula (31) is a compound represented by the formula (34-2) or (35-2):

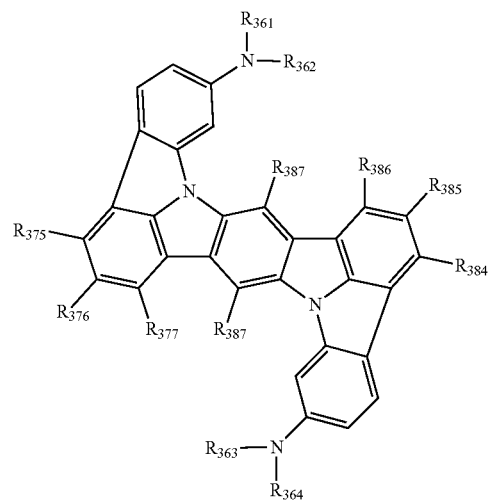
(34-2)

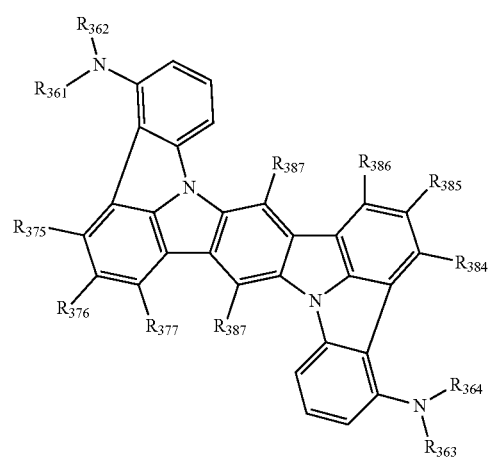
(35-2)

wherein in the formulas (34-2) and (35-2), $R_{361}$ to $R_{364}$, $R_{375}$ to $R_{377}$ and $R_{384}$ to $R_{387}$ are as defined in the formulas (34) and (35).

In one embodiment, $R_{361}$ to $R_{364}$ the formulas (32), (33), (34), (35), (34-2) and (35-2) are independently a substituted or unsubstituted aryl group having 6 to 50 ring carbon atoms (preferably a phenyl group).

In one embodiment, $R_{321}$ and $R_{322}$ in the formula (31), and $R_{351}$ and $R_{352}$ the formulas (32), (33), (34), (35), (34-2) and (35-2) are independently a hydrogen atom or a substituted or unsubstituted aryl group having 6 to 50 ring carbon atoms (preferably a phenyl group).

In one embodiment, the compound represented by the formula (31) is the compound represented by the following formula (36).

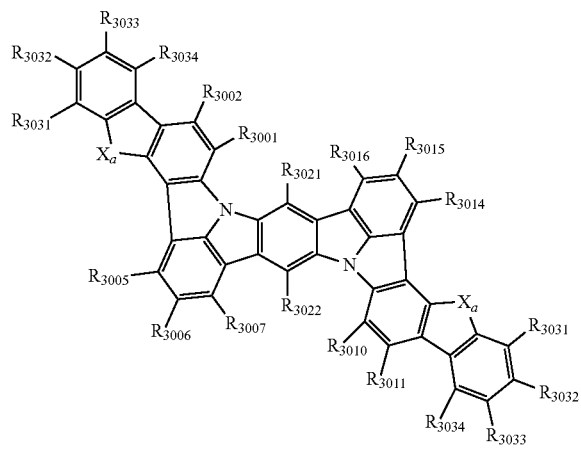

(36)

In the formula (36), one or more pairs of two or more adjacent groups of $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3034}$ bond with each other to form a substituted or unsubstituted, saturated or unsaturated ring or do not form the ring;

$X_a$s are independently selected from O, S and $N(R_{35})$;

$R_{35}$ and $R_{3031}$ bond with each other to form a substituted or unsubstituted, saturated or unsaturated ring or do not form the ring; and $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3035}$ that do not form the ring and $R_{3021}$ and $R_{3022}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, a substituent in the case of "substituted" in the formulas (31) to (36) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

As the compound represented by the formula (31), the following compounds can be given for example. In the following example compounds, Me represents methyl group.

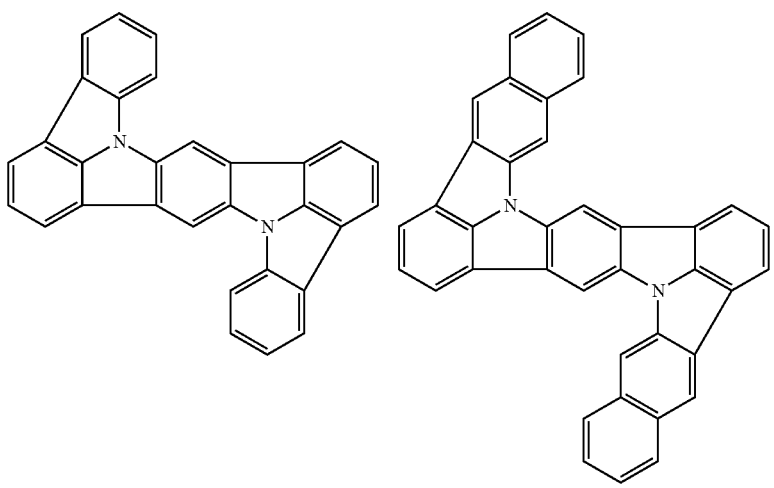

-continued
273 274
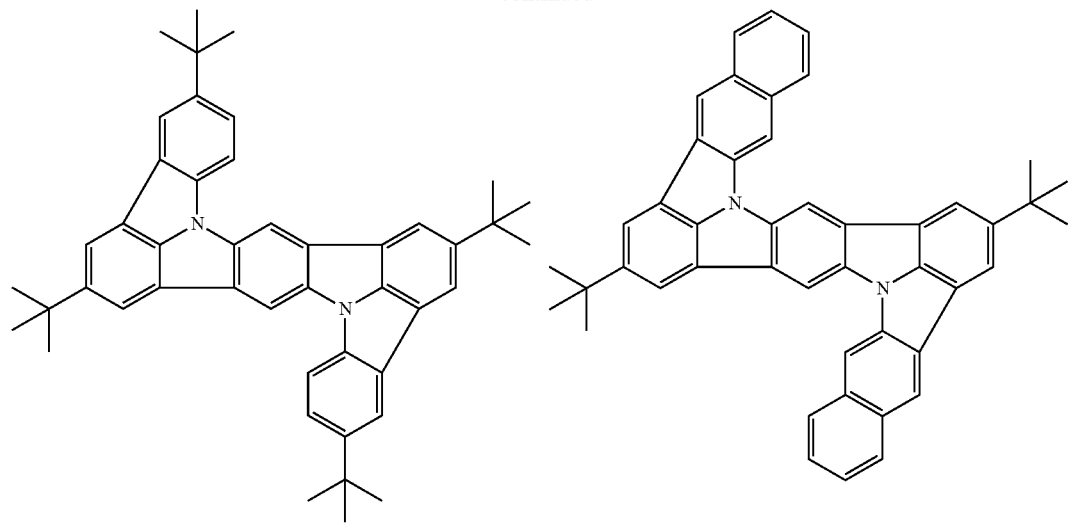
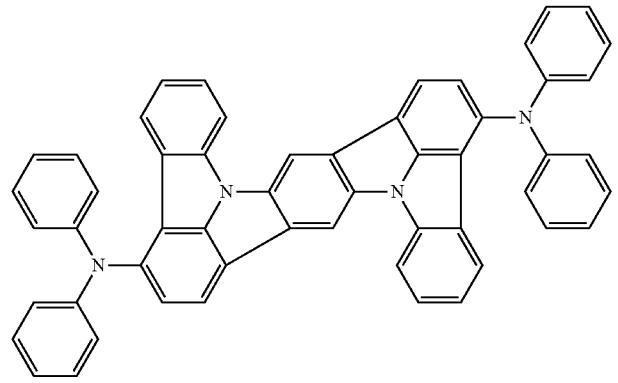
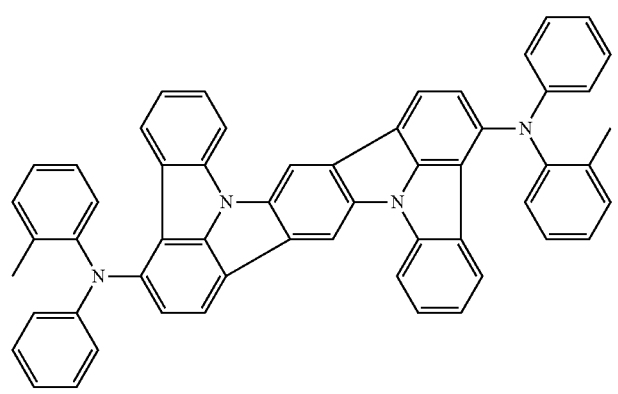
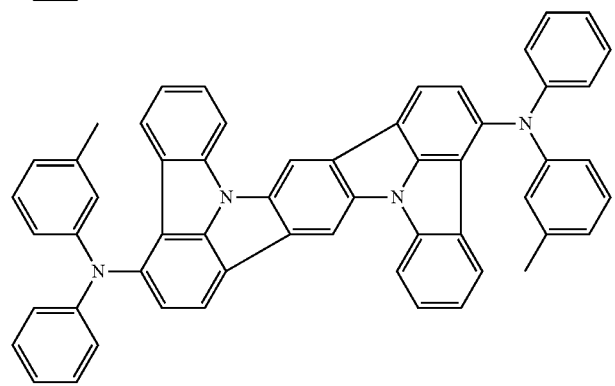

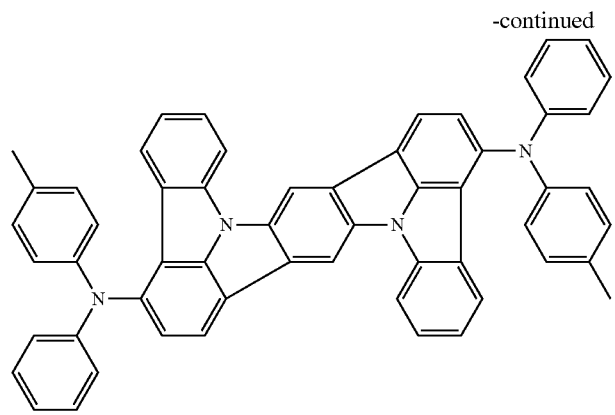
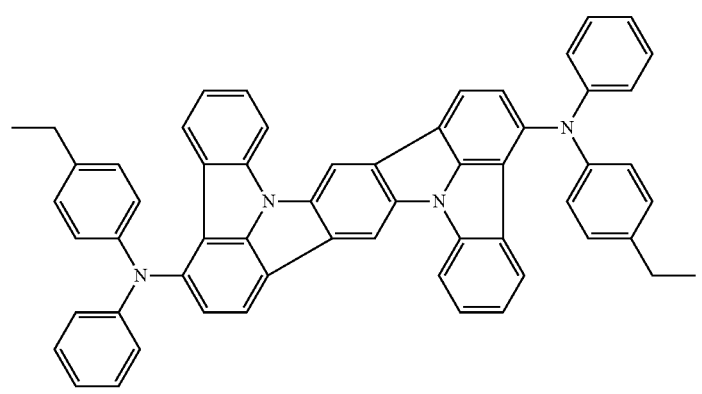
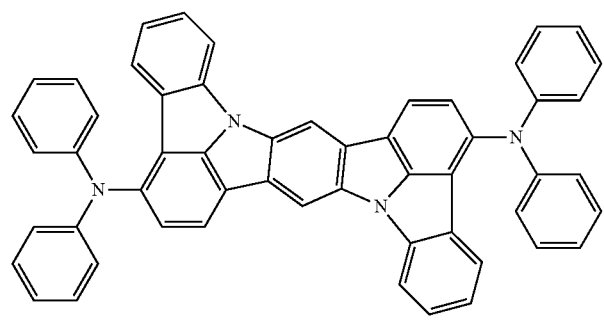

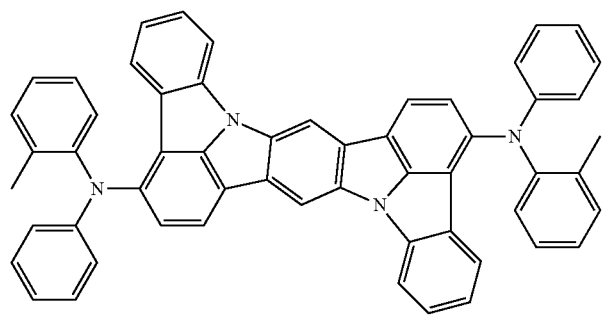
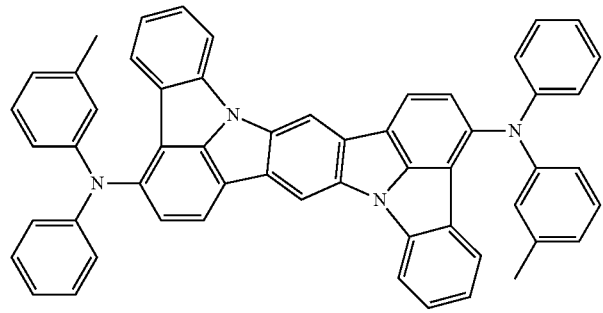
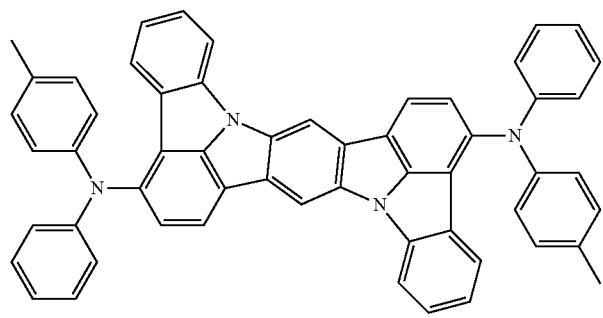
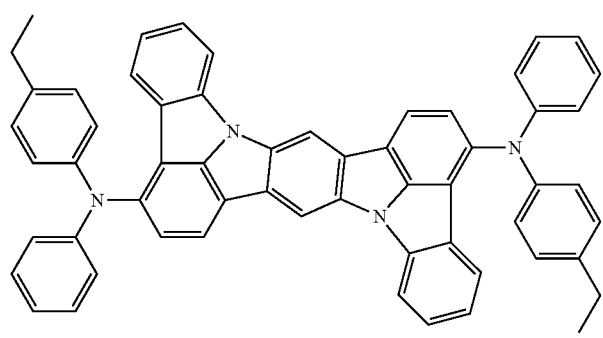
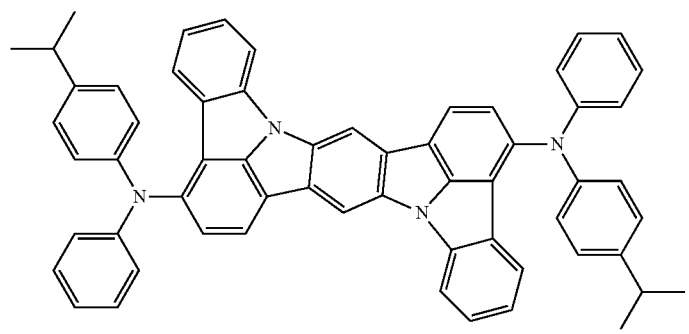

-continued
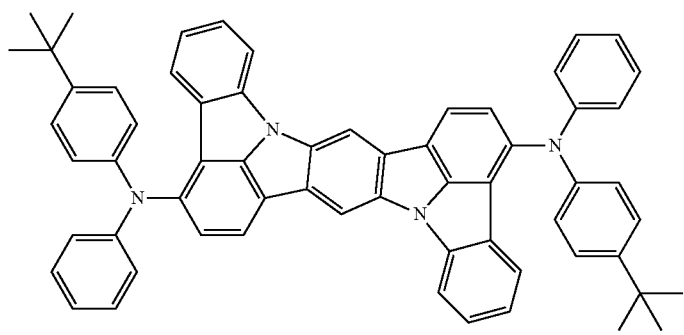
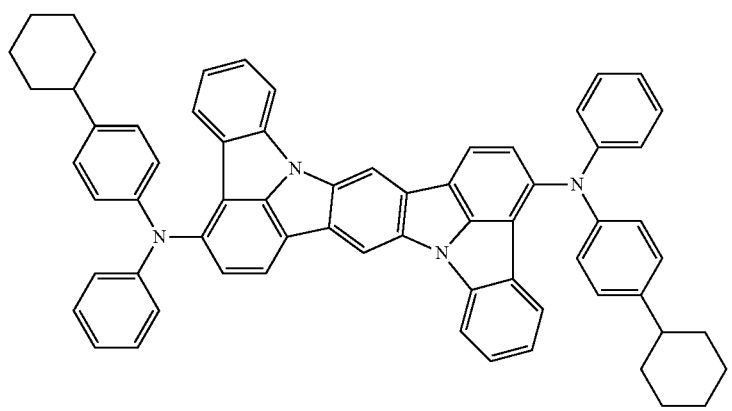
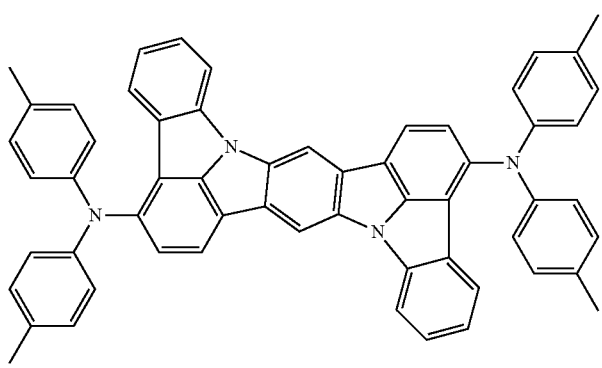
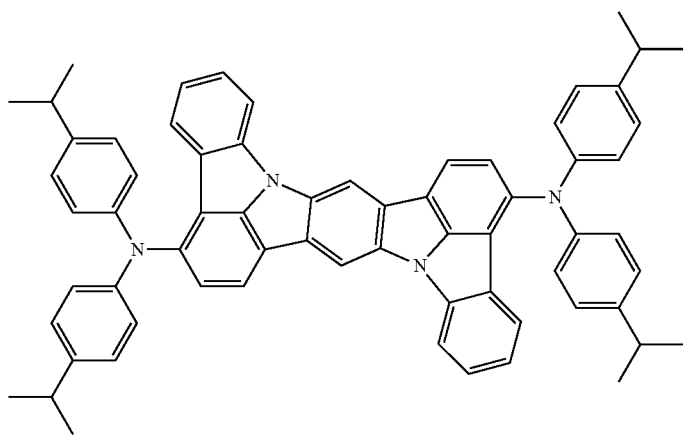

-continued

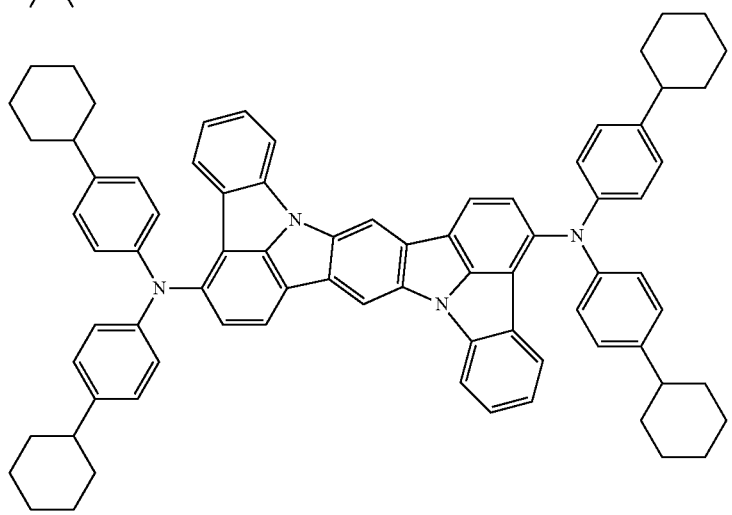
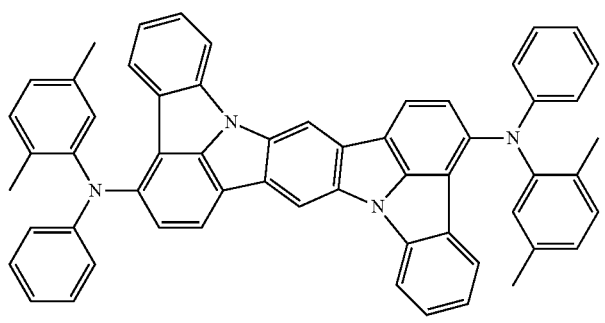
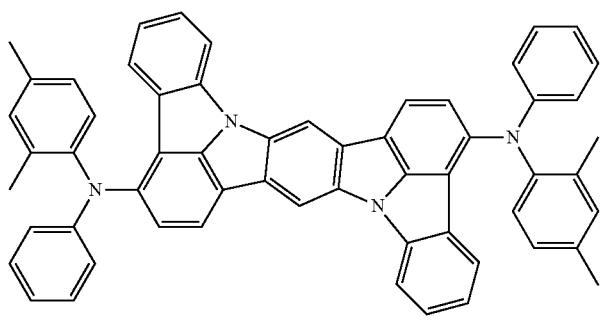

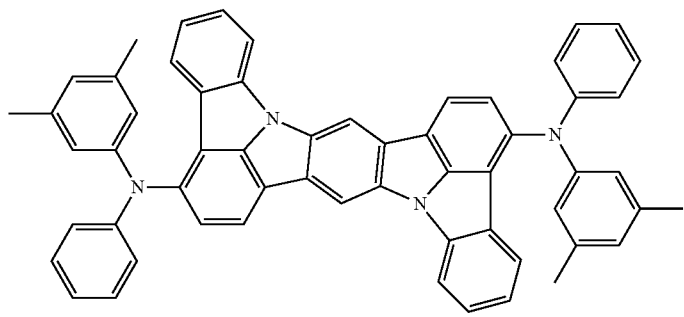
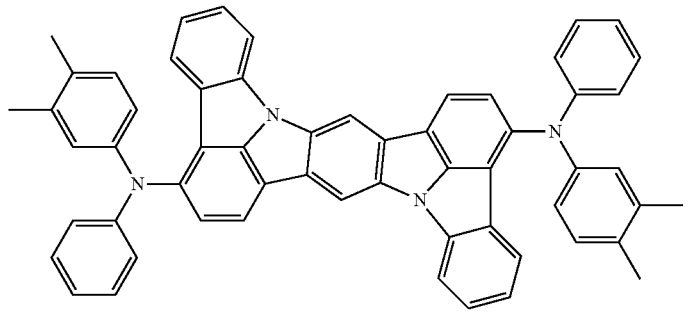
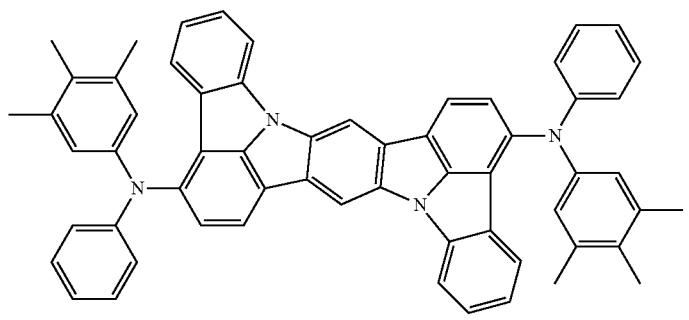
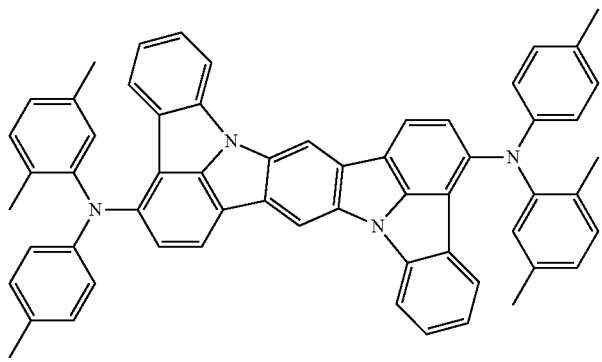
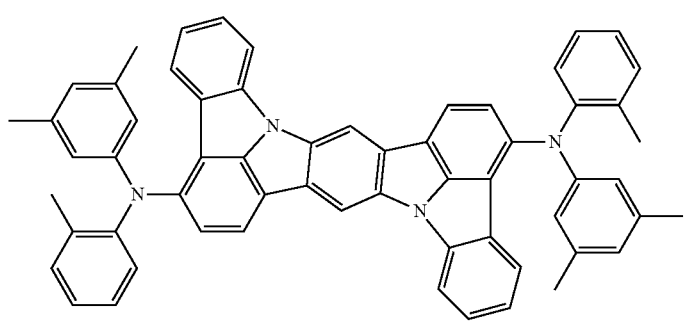

-continued
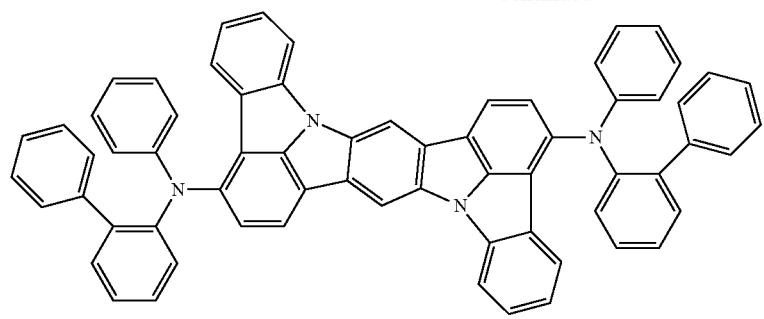
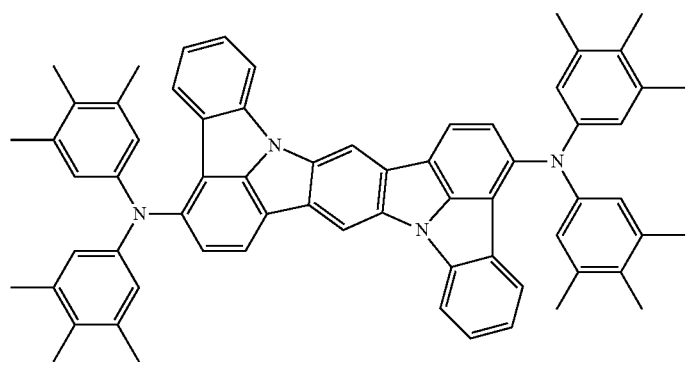
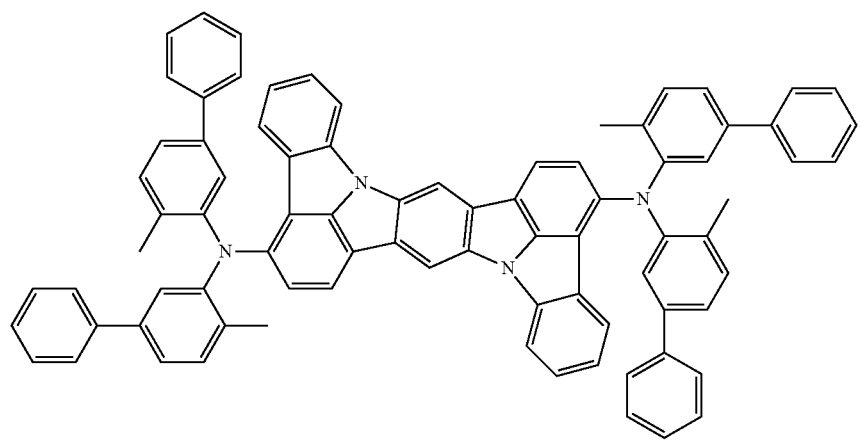
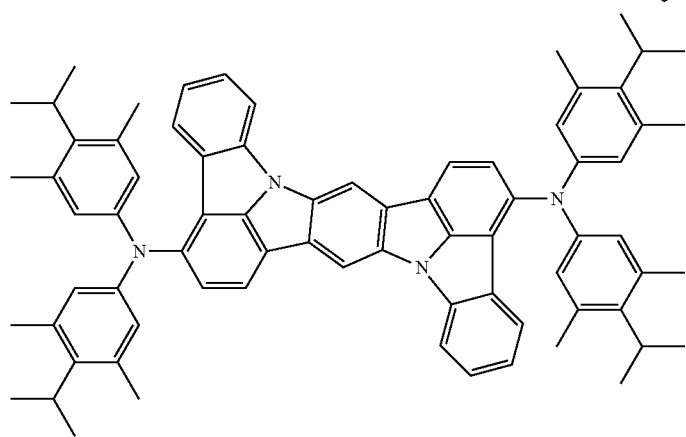

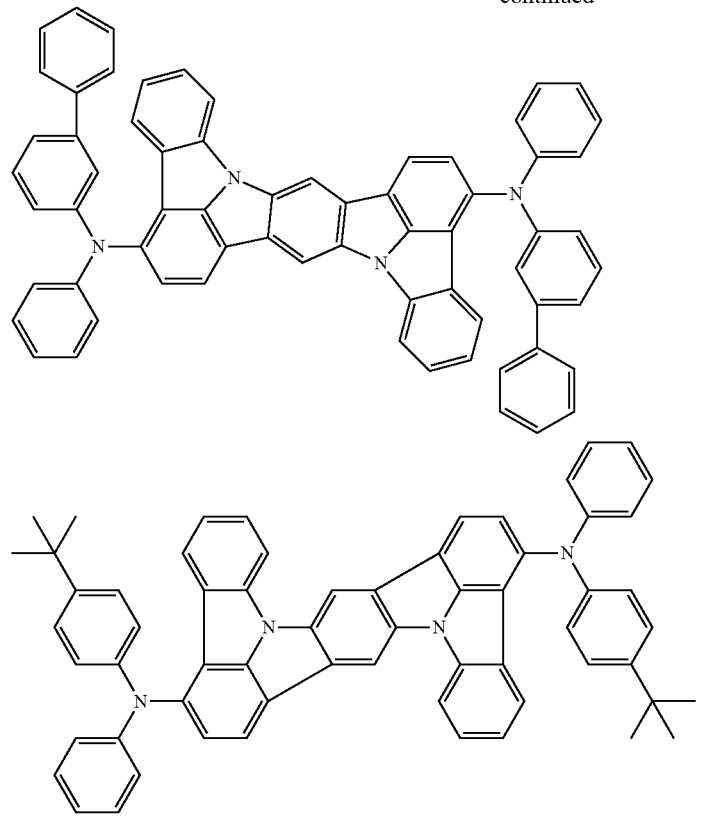
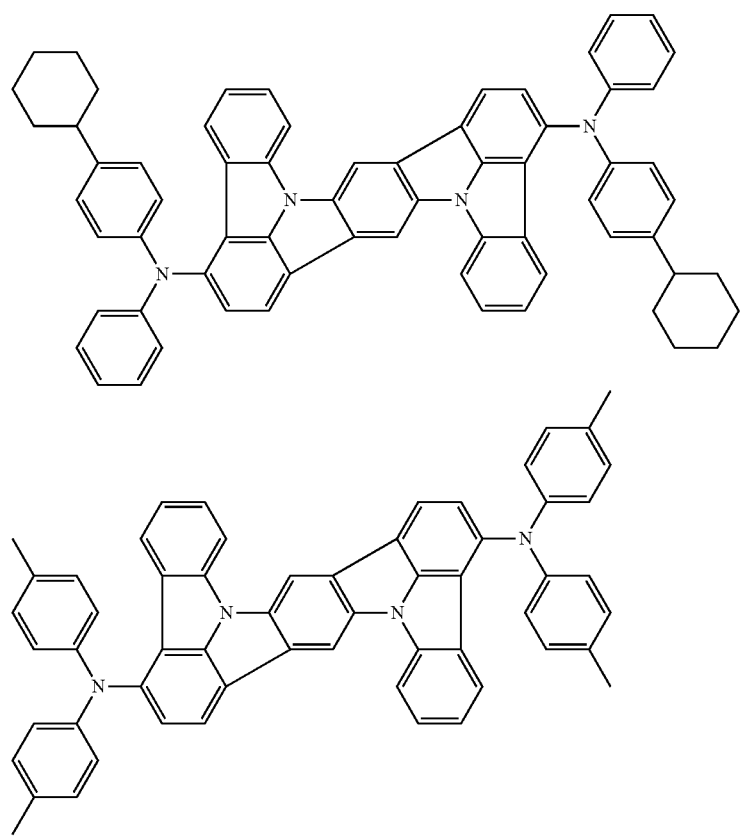

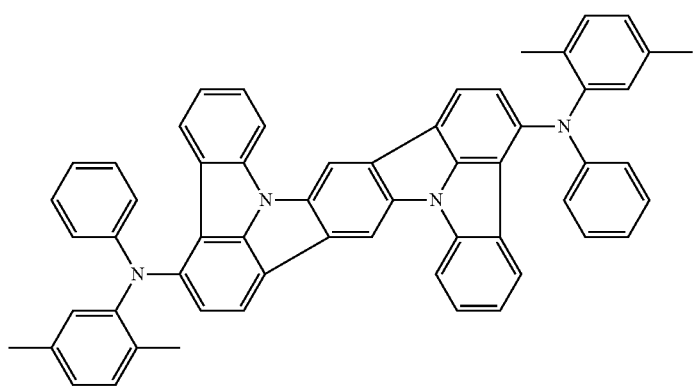
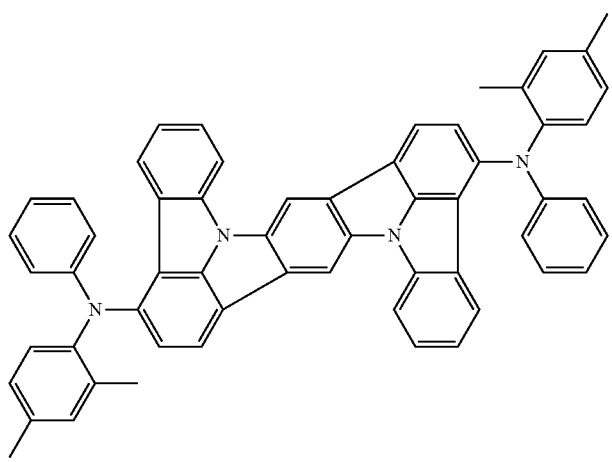
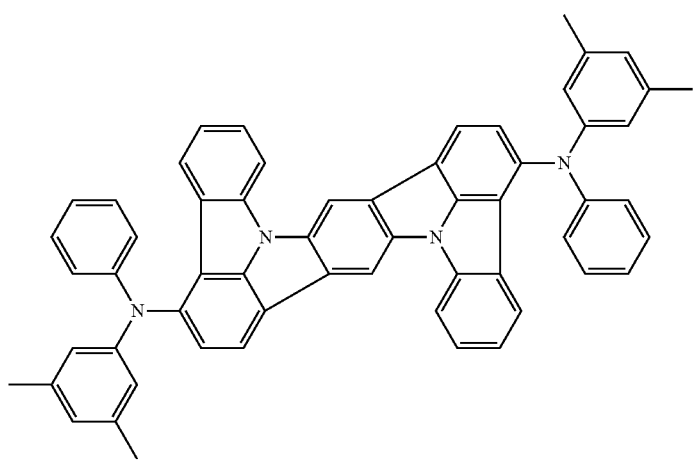

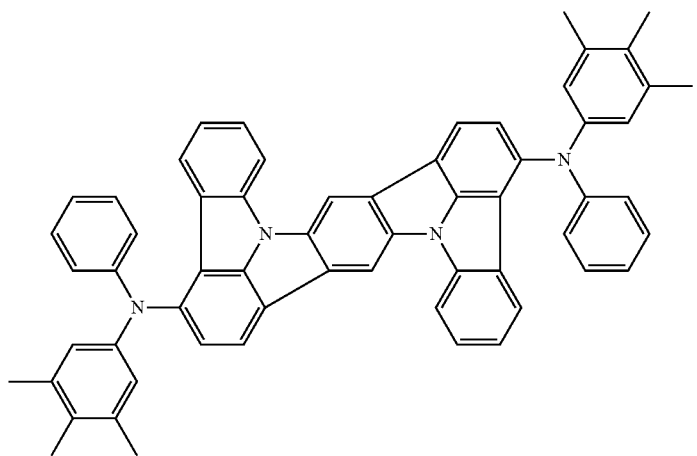
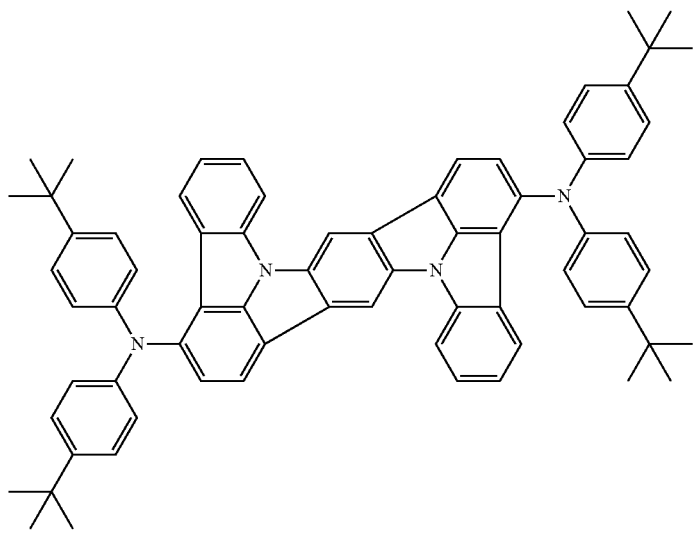

-continued
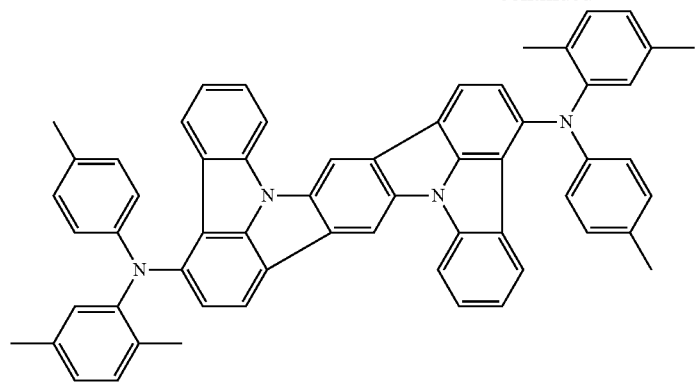
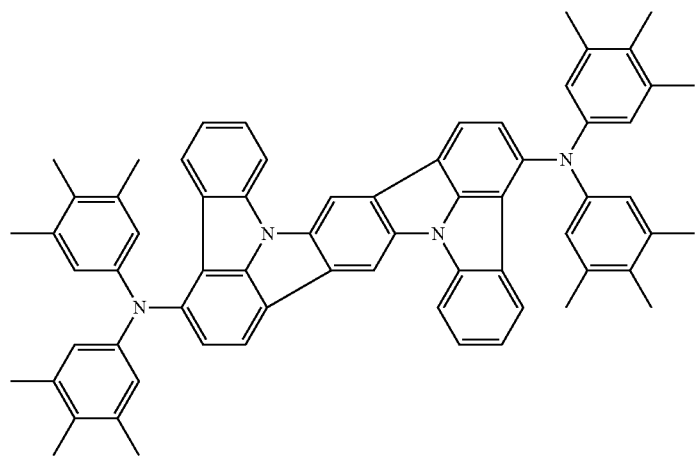
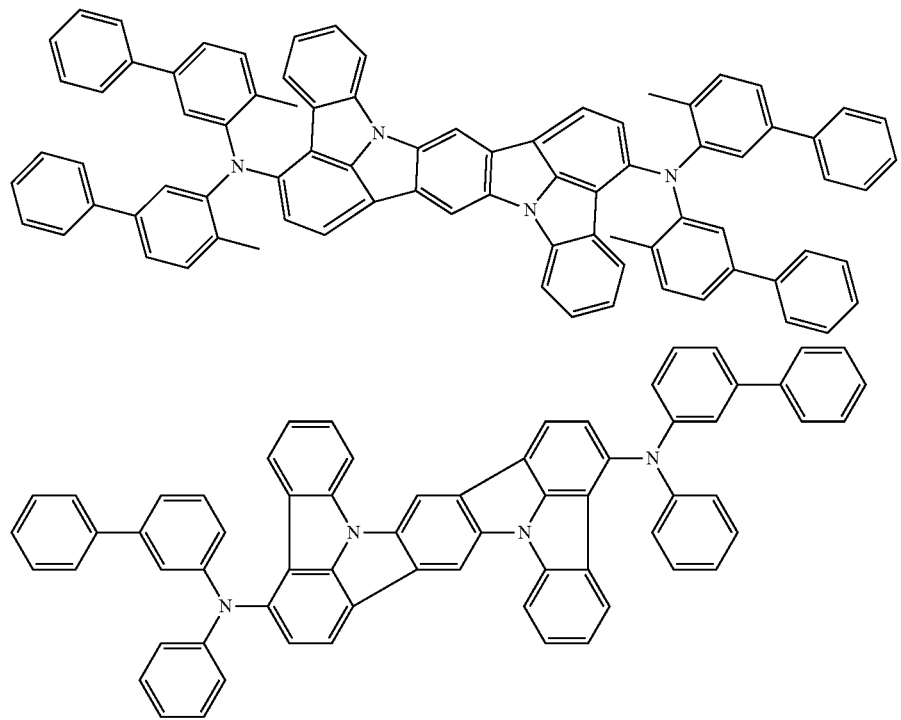

-continued
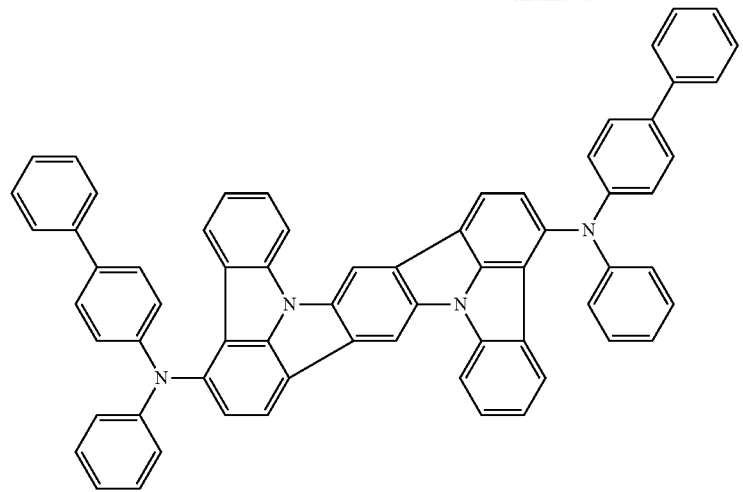
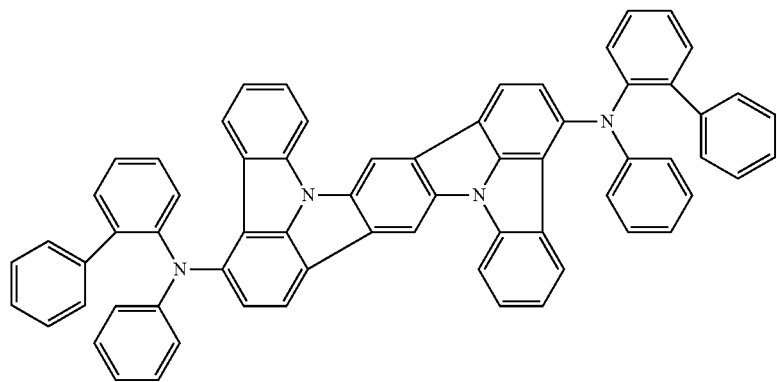
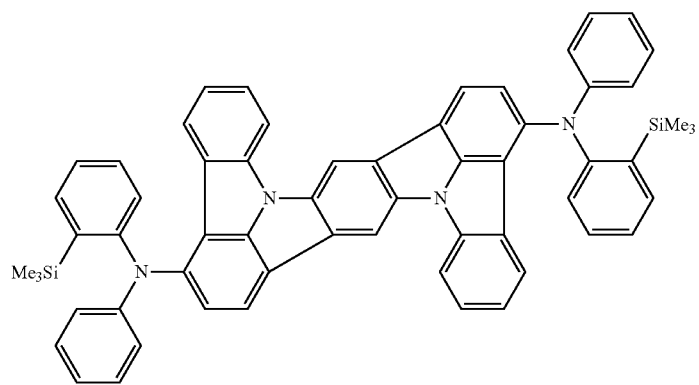
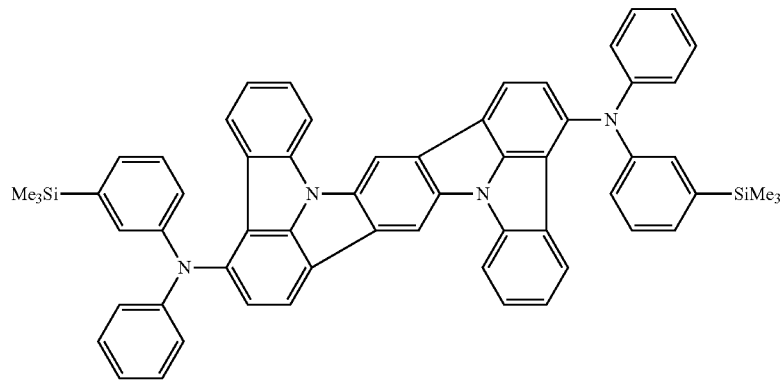

-continued
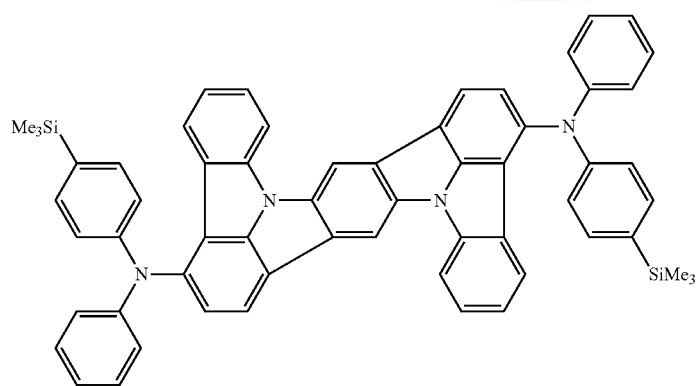
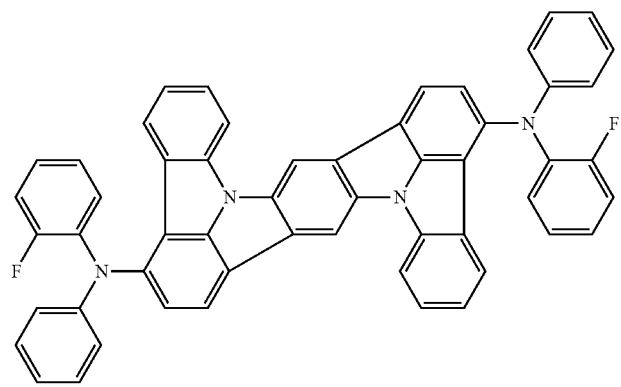
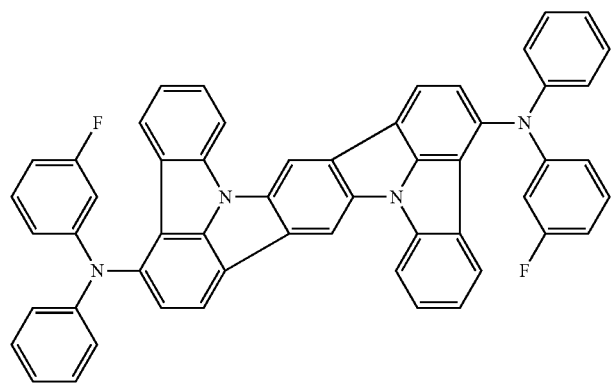
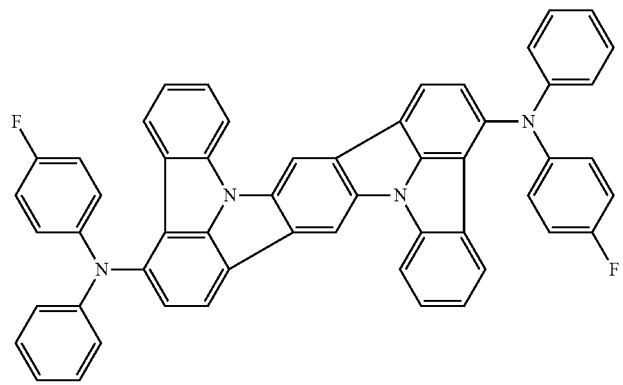

-continued
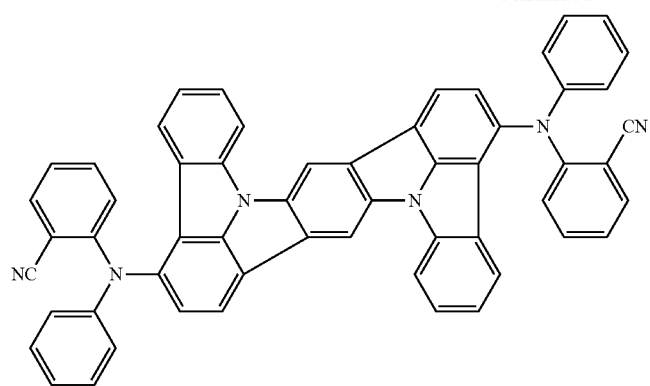
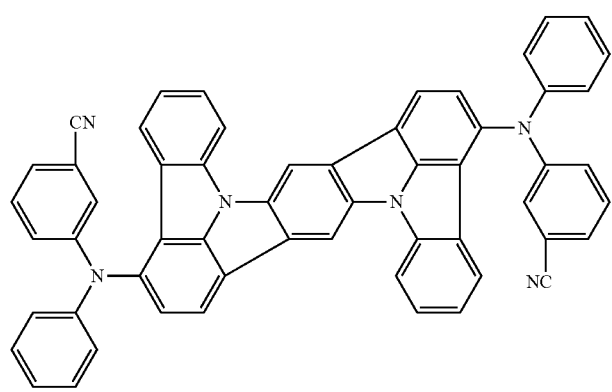
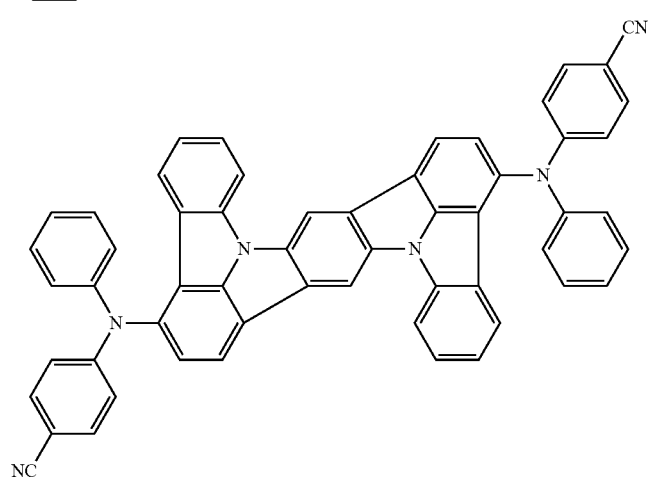
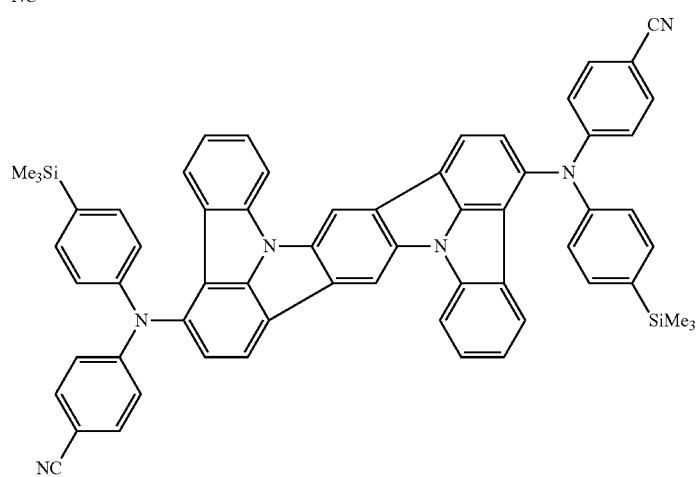

-continued
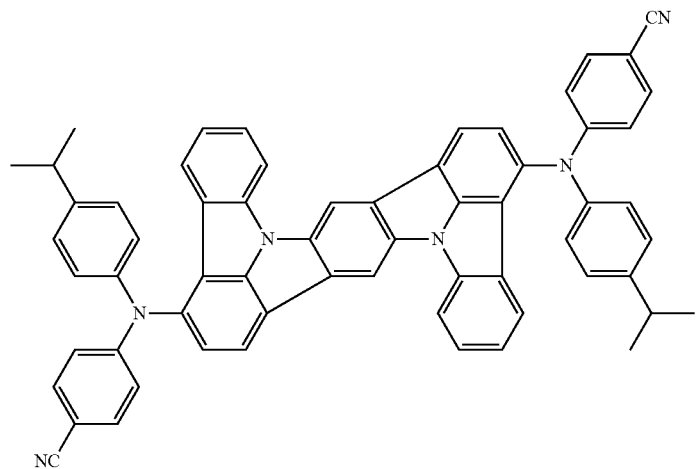
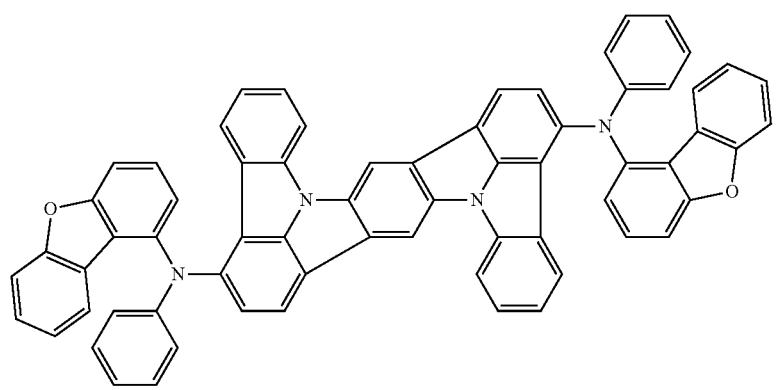
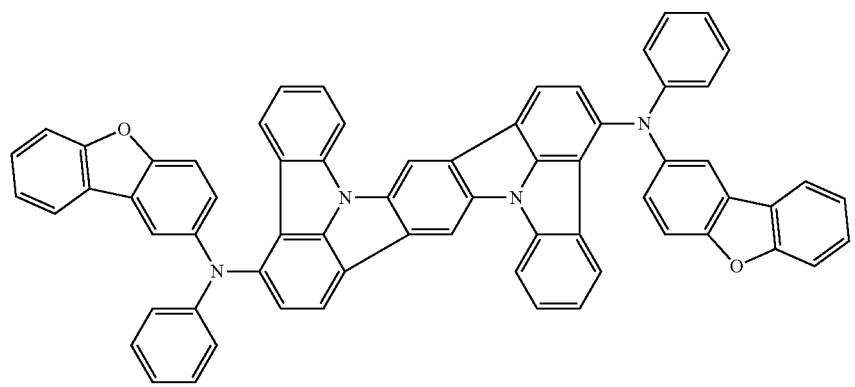
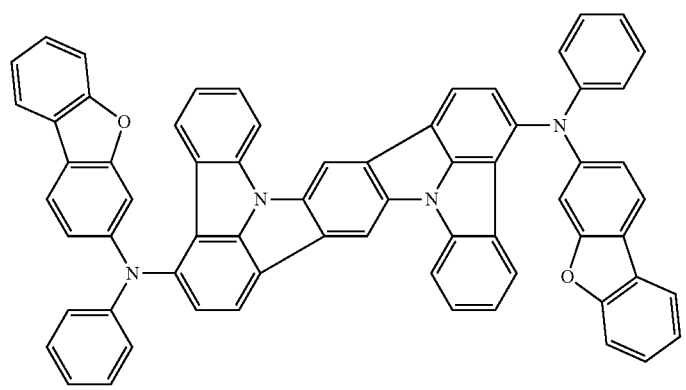

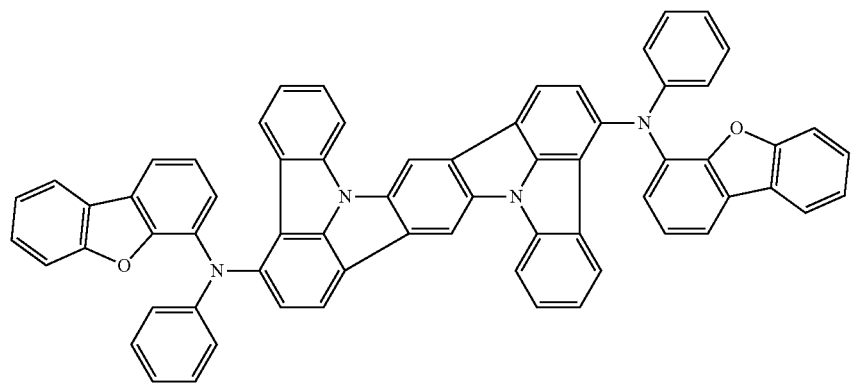
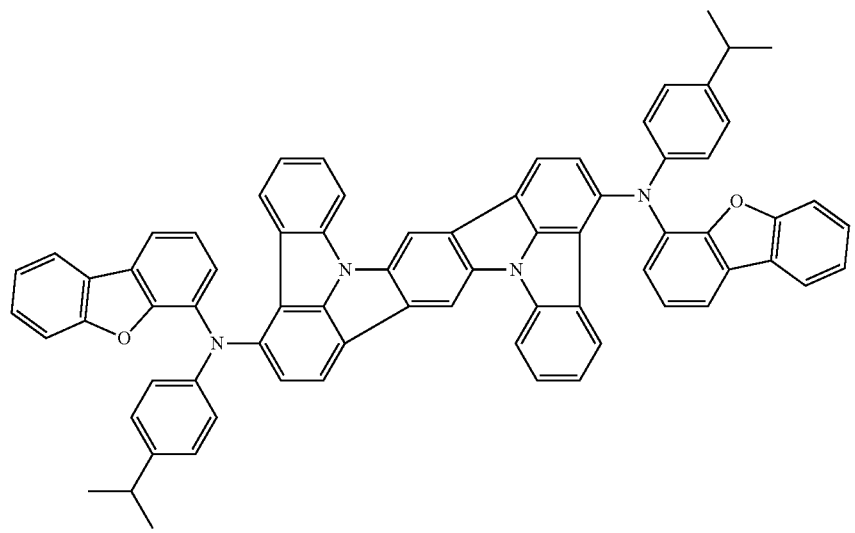
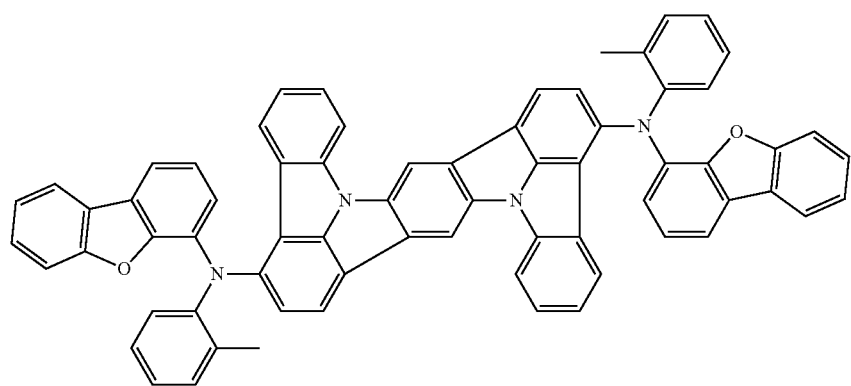

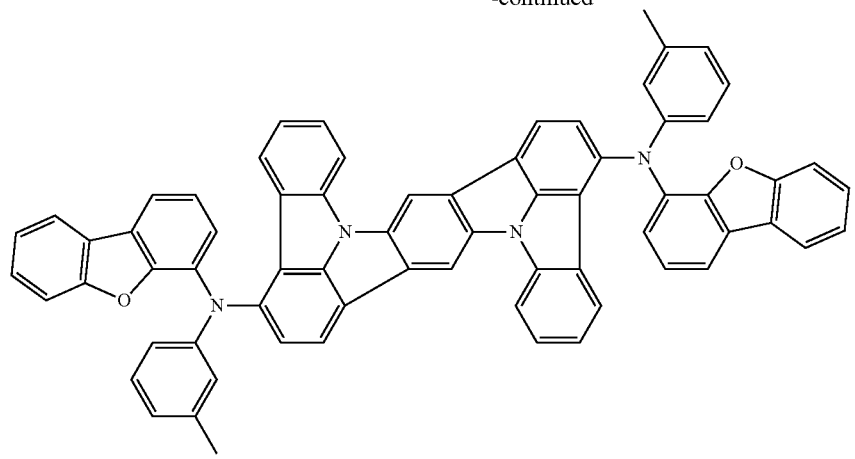
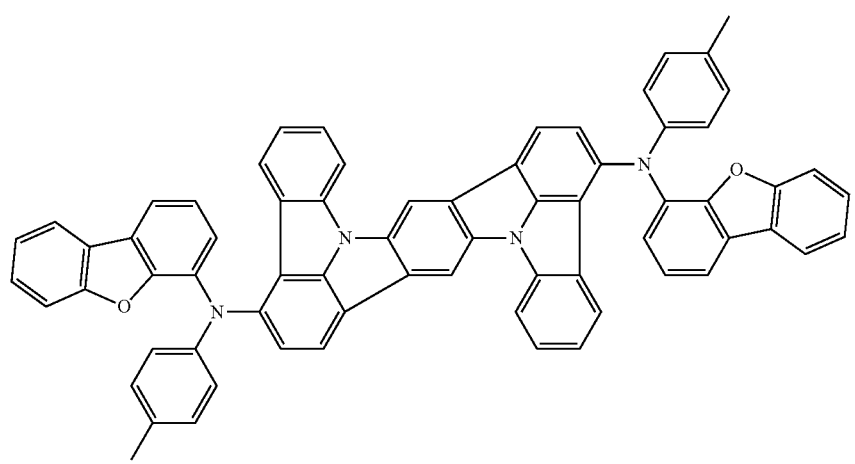
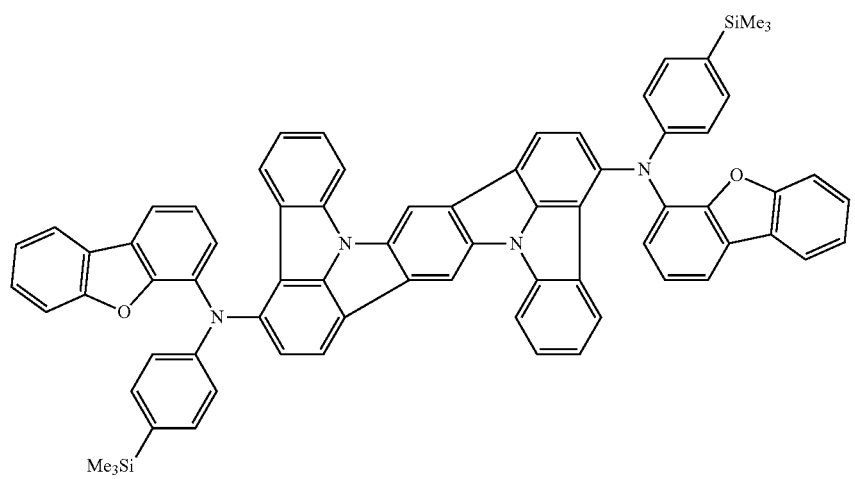

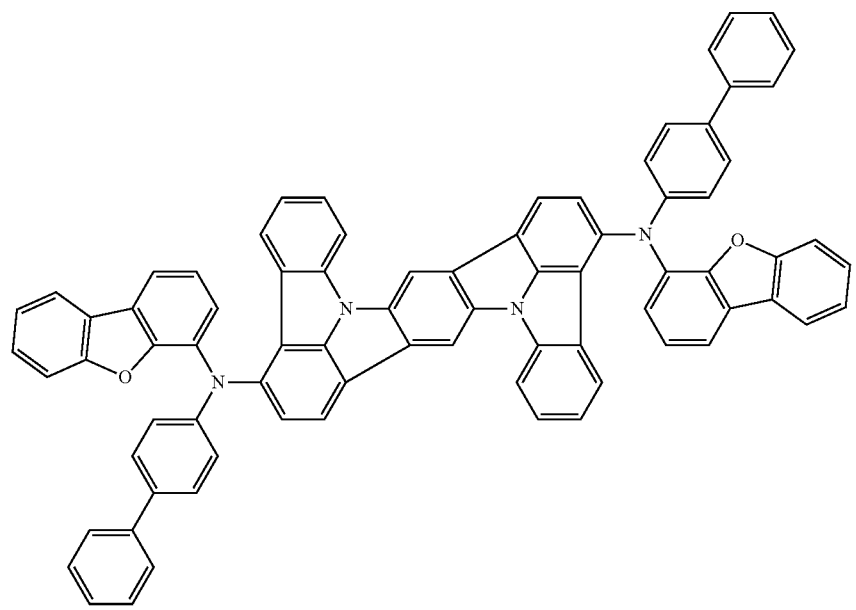
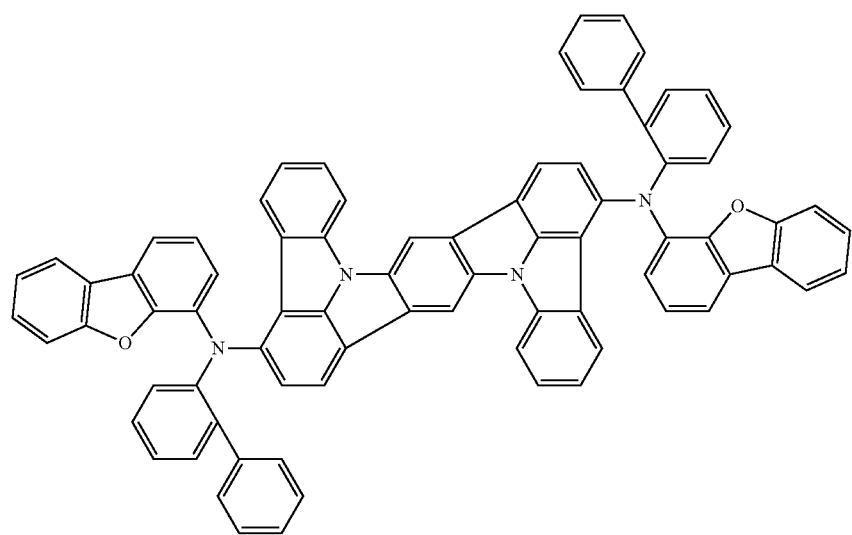
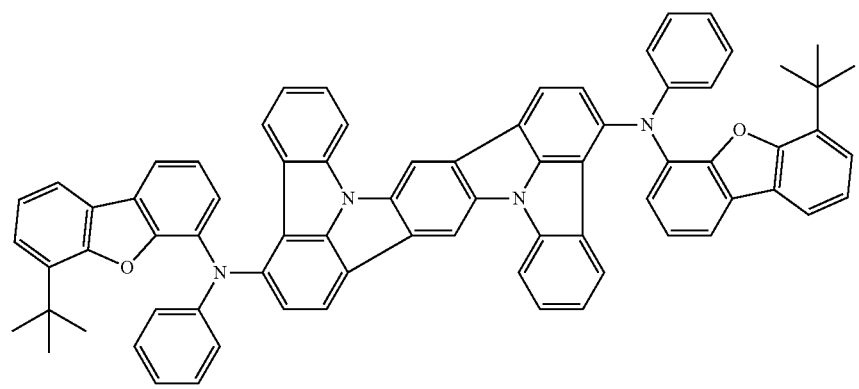

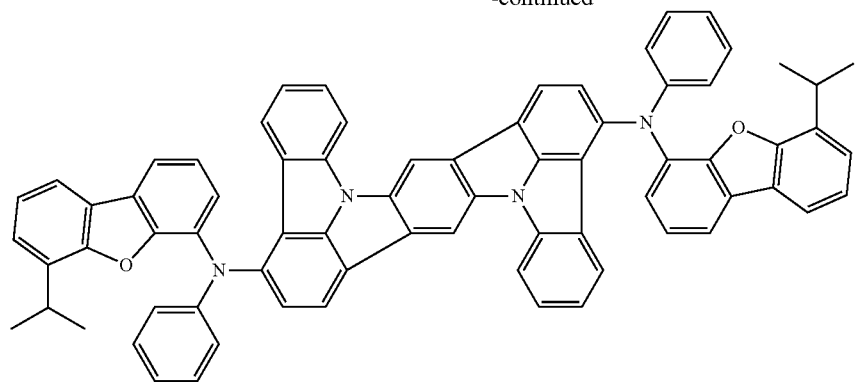
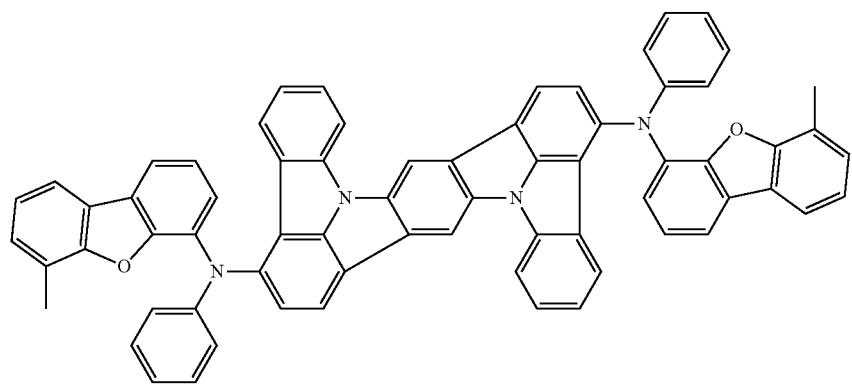
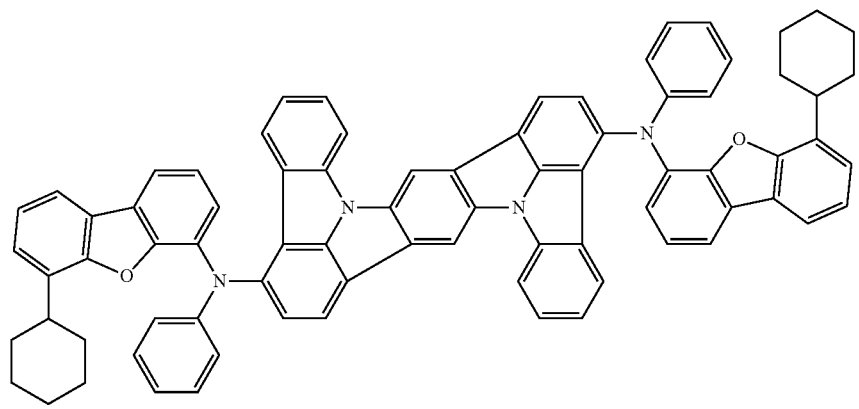
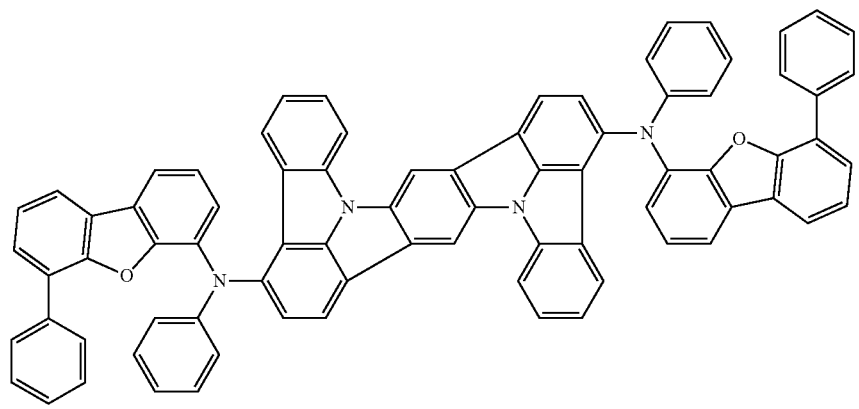

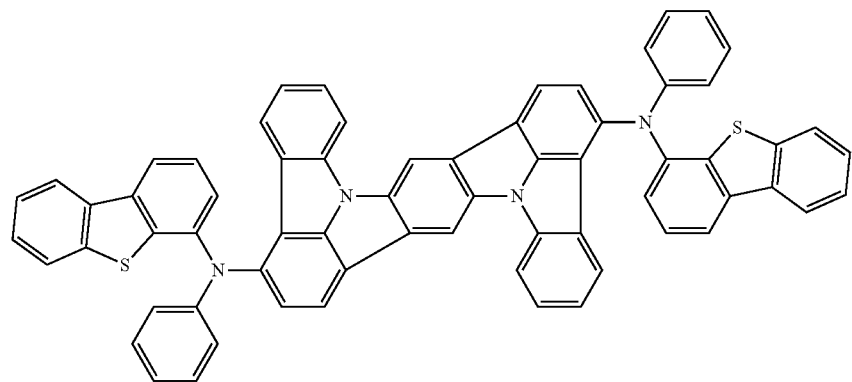
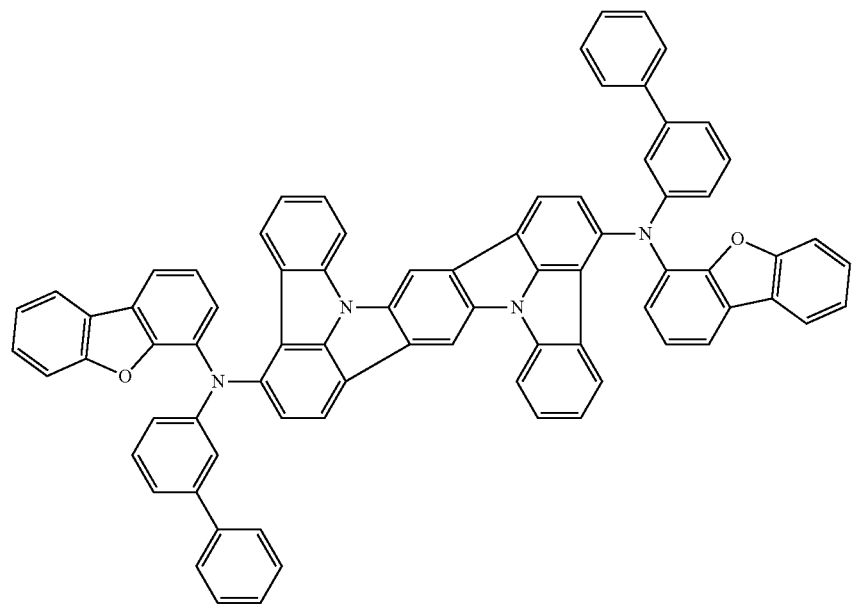
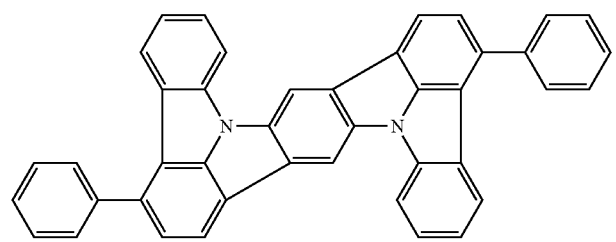
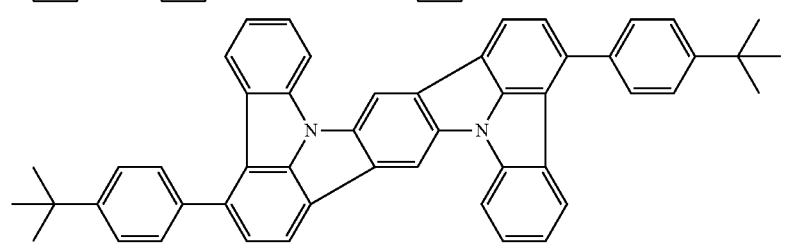
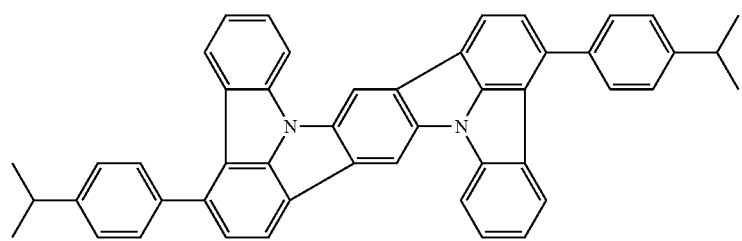

-continued
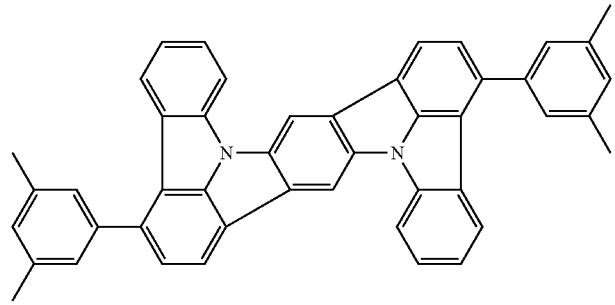
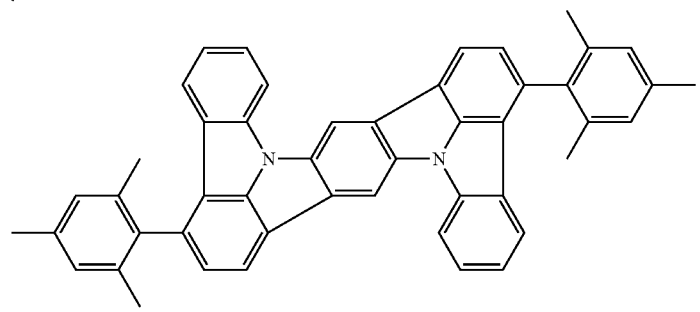
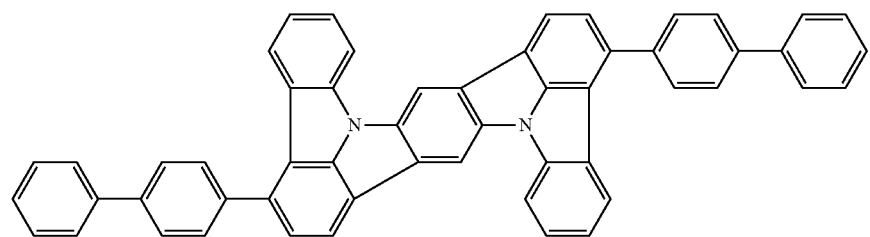
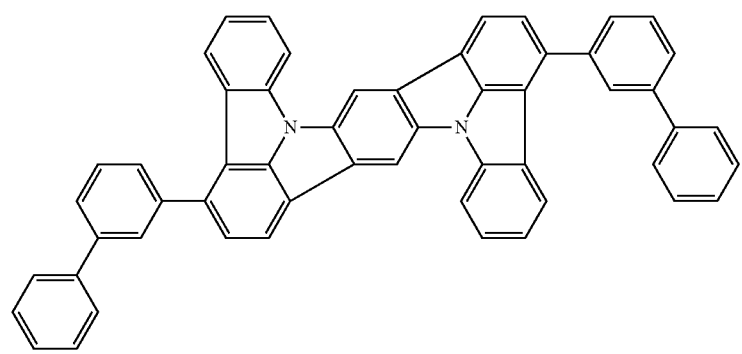
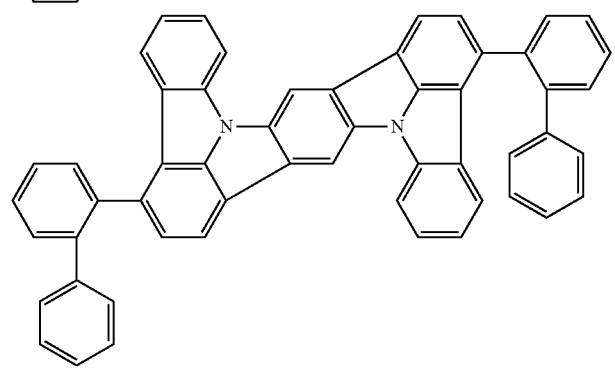

-continued
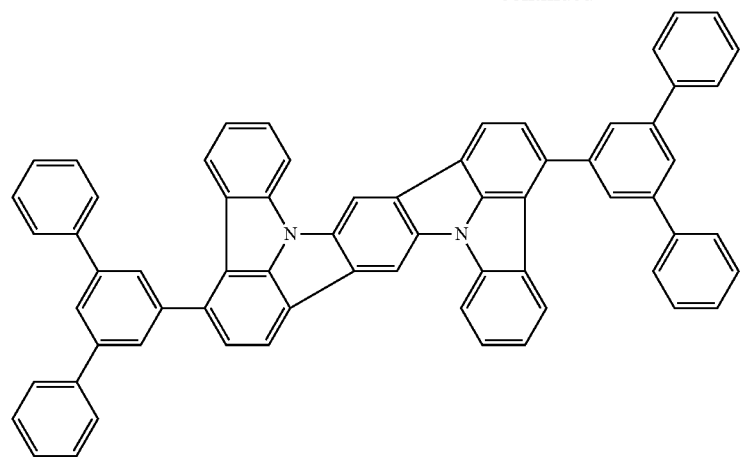
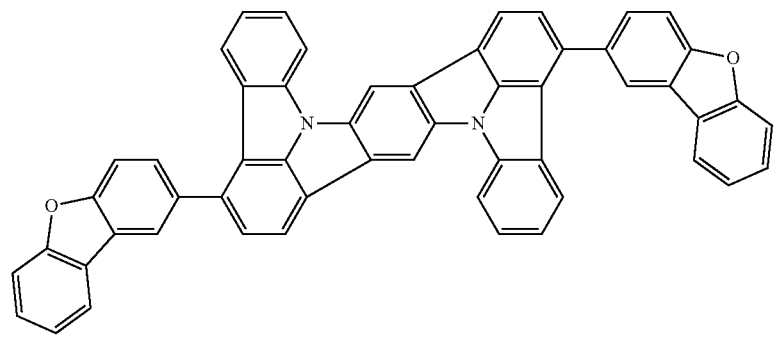
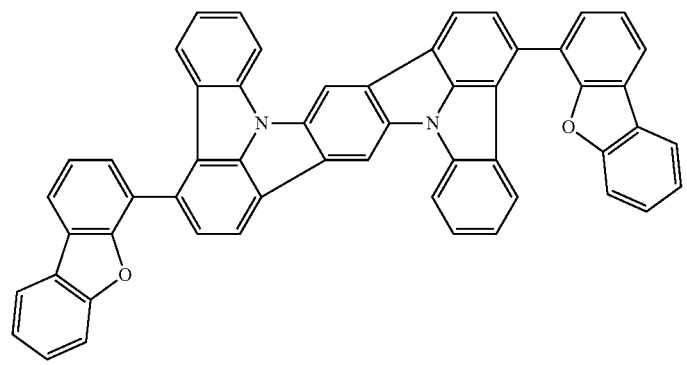
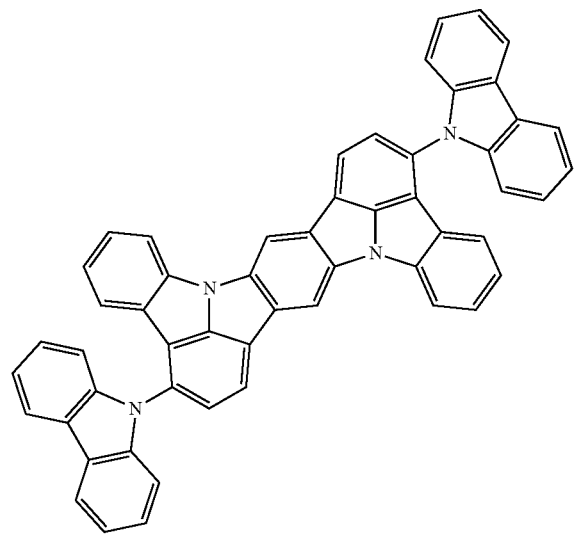

317
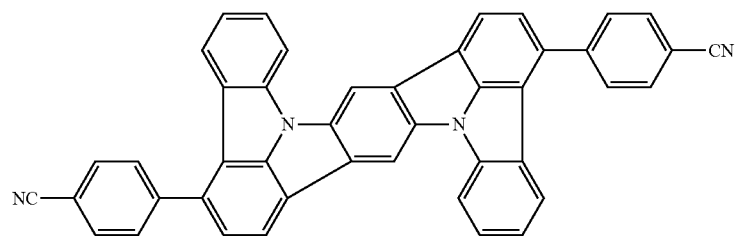
318
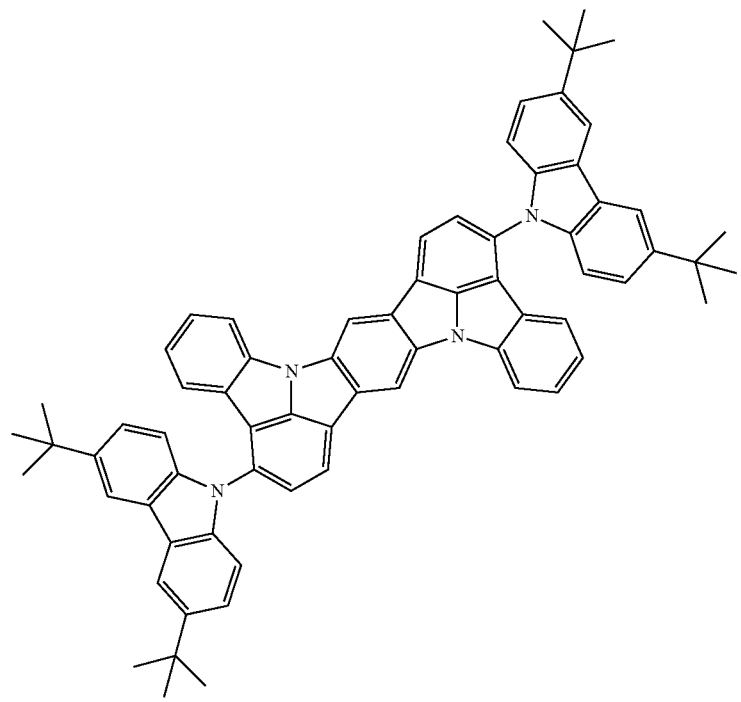
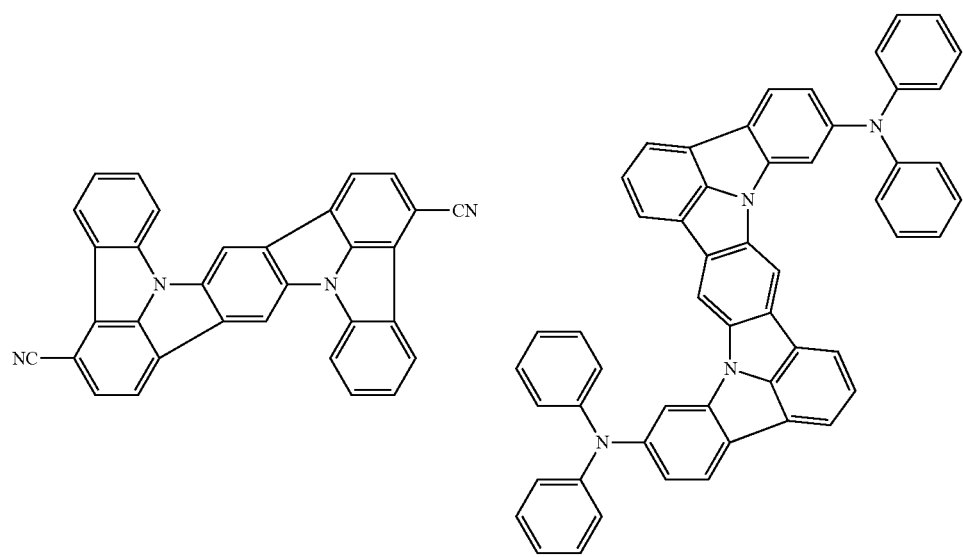

-continued
| 319 | 320 |
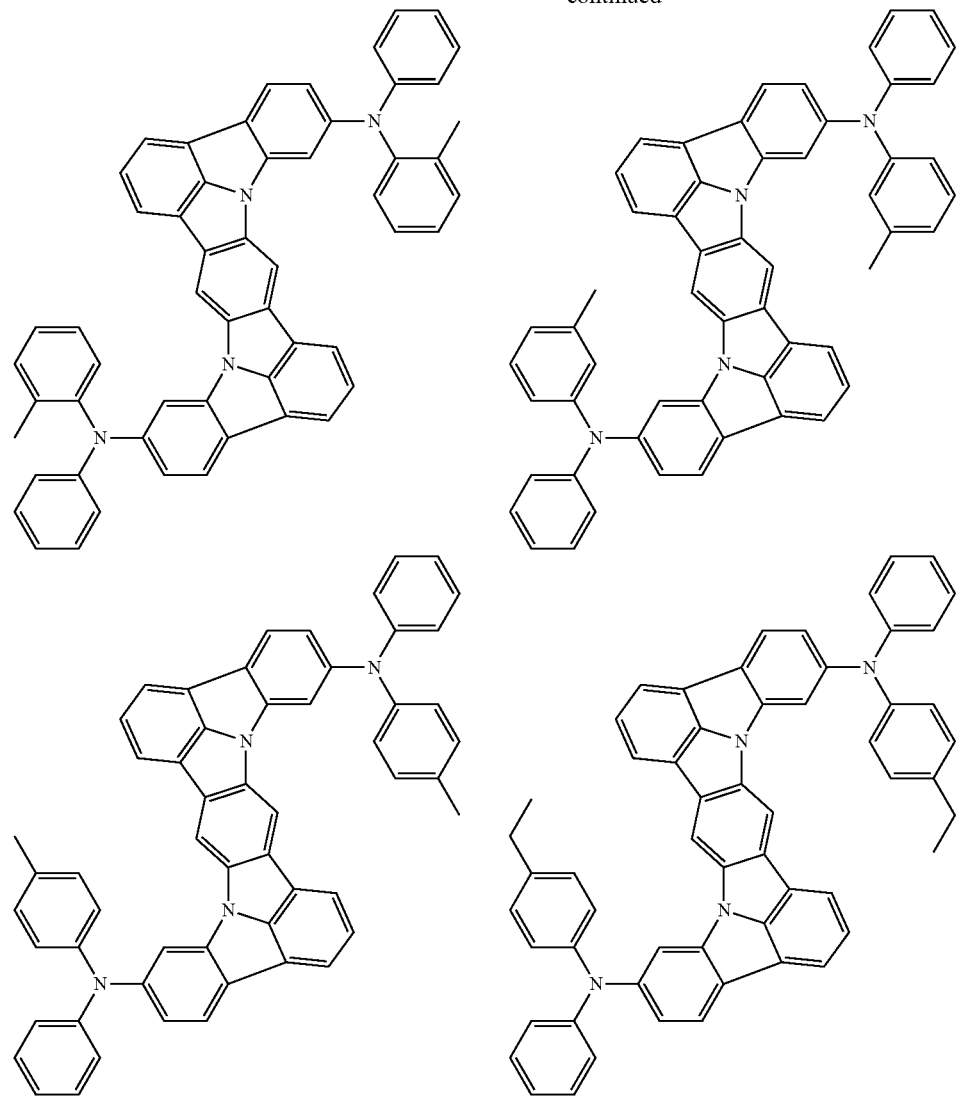
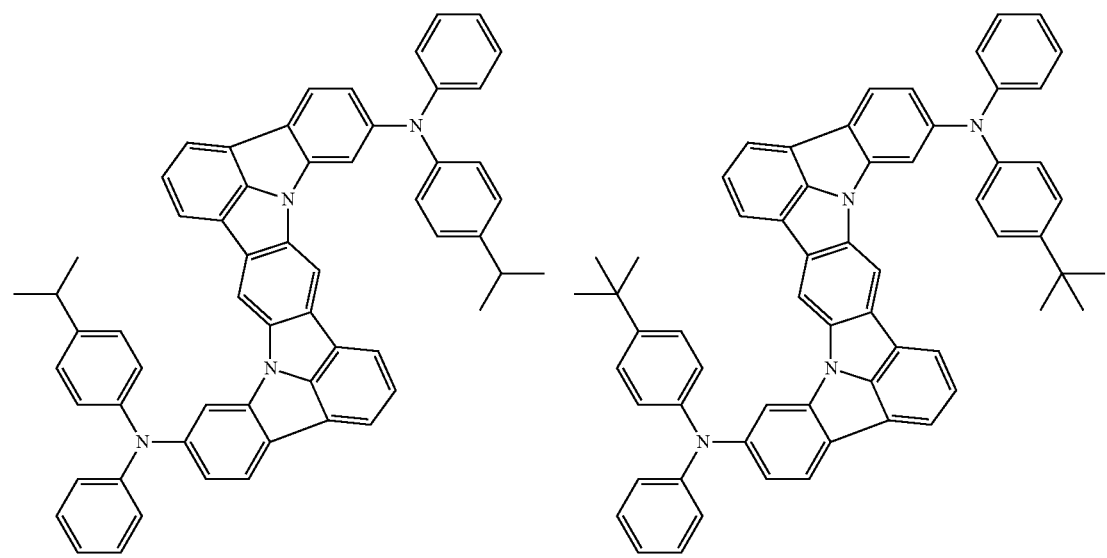

321 322
-continued
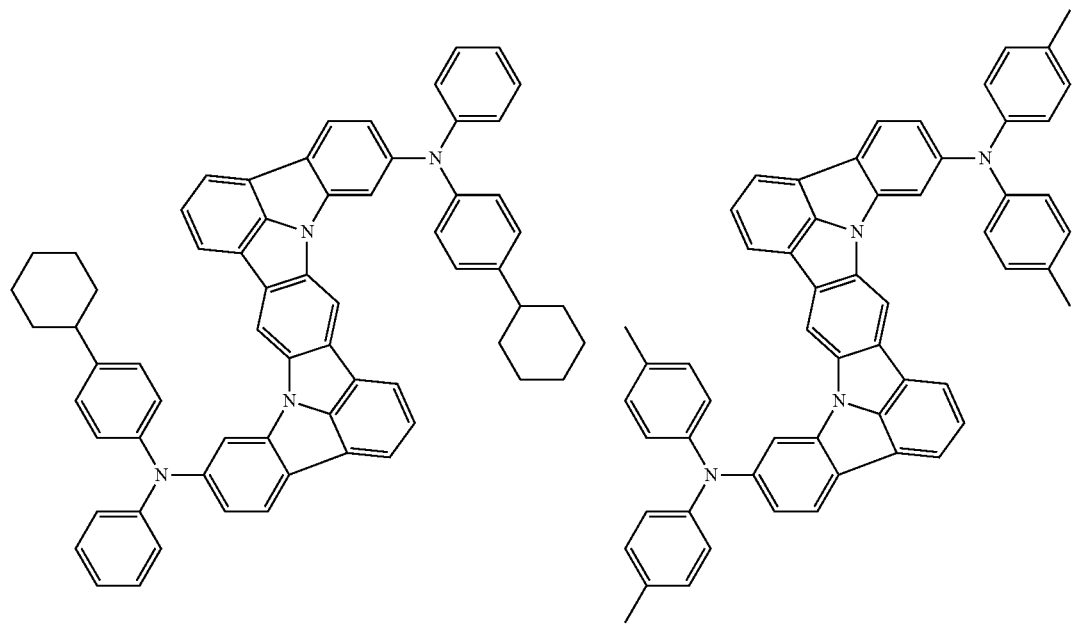
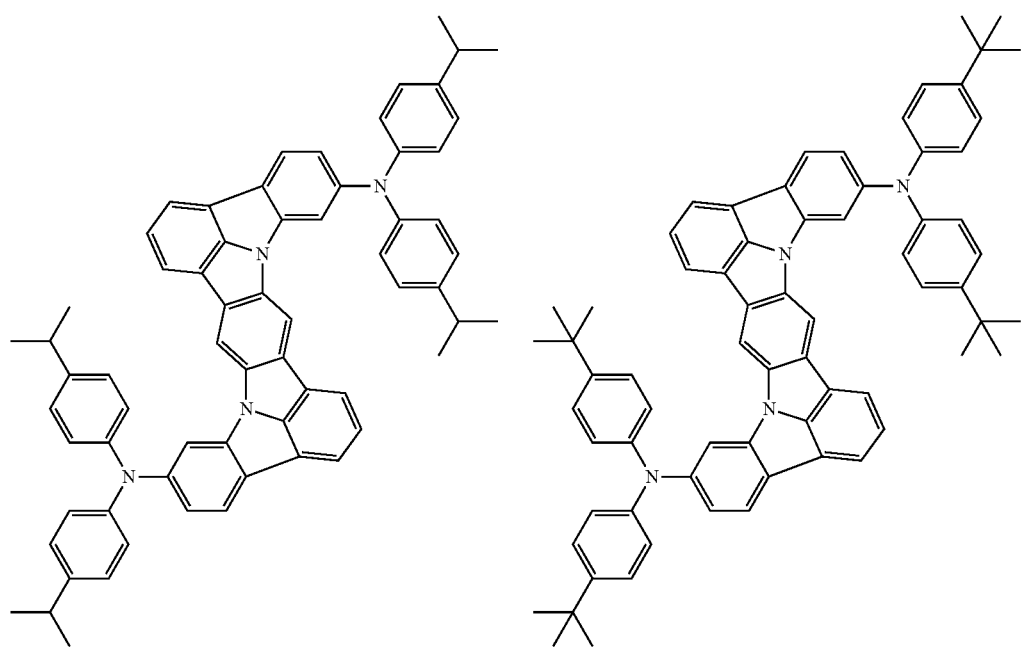

-continued
323
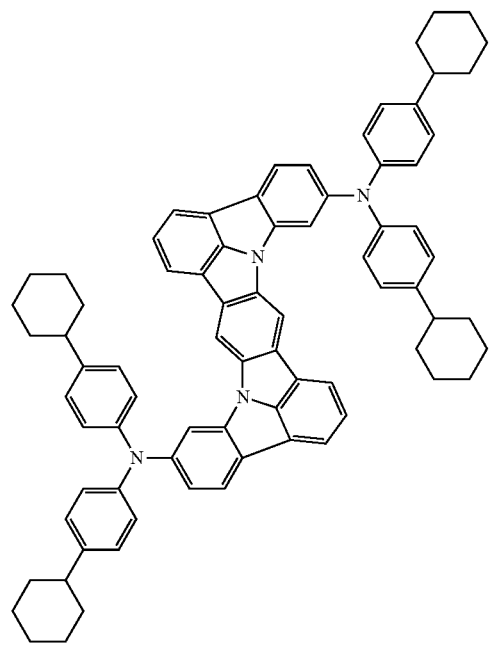
324
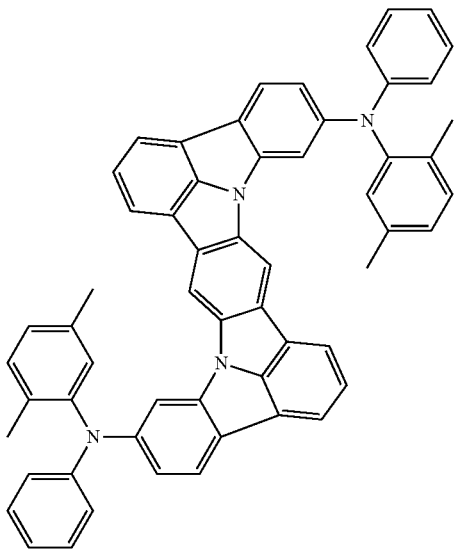
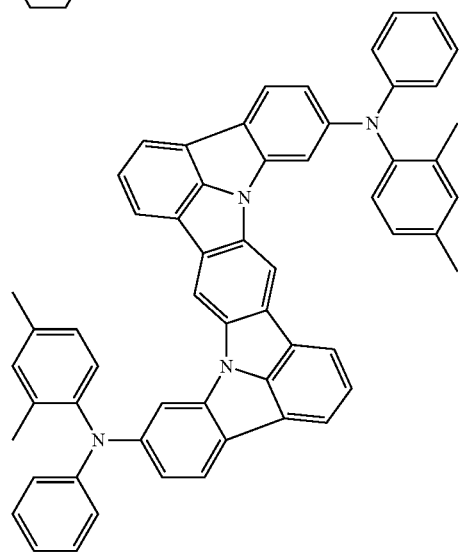
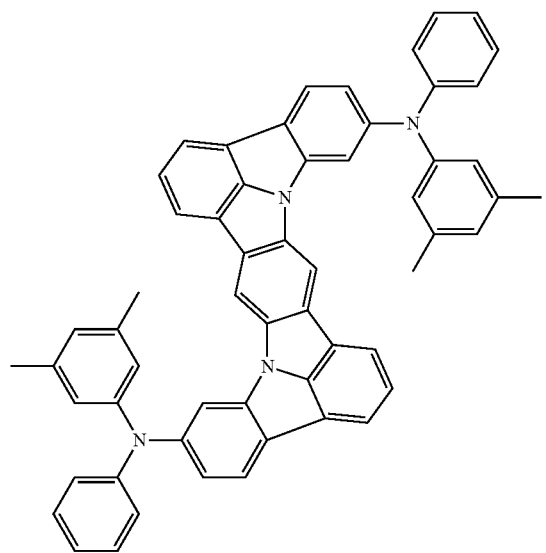
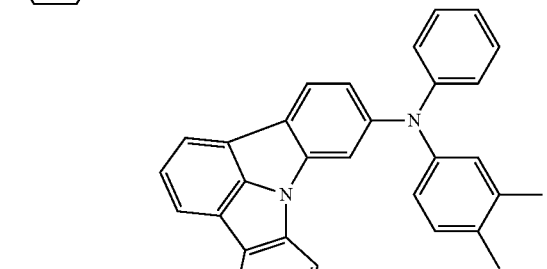
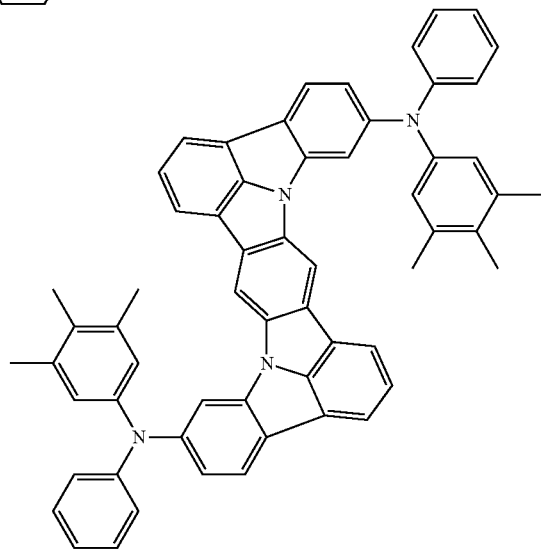
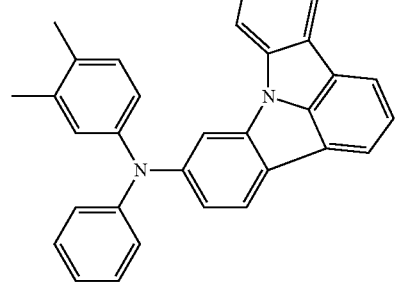

325
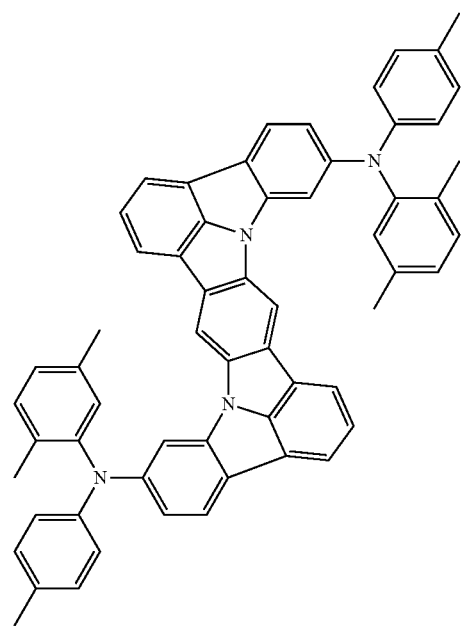
326
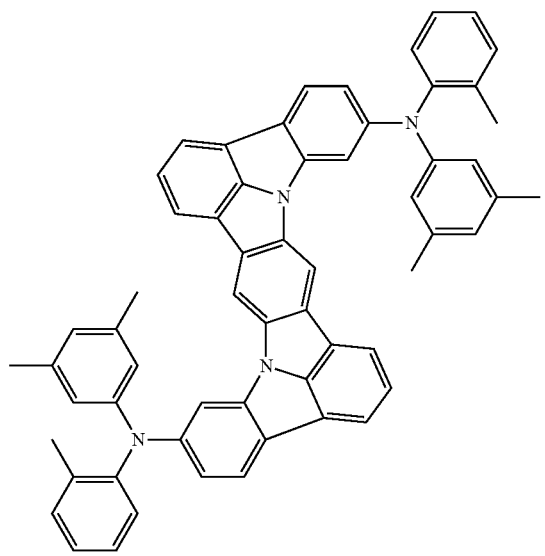
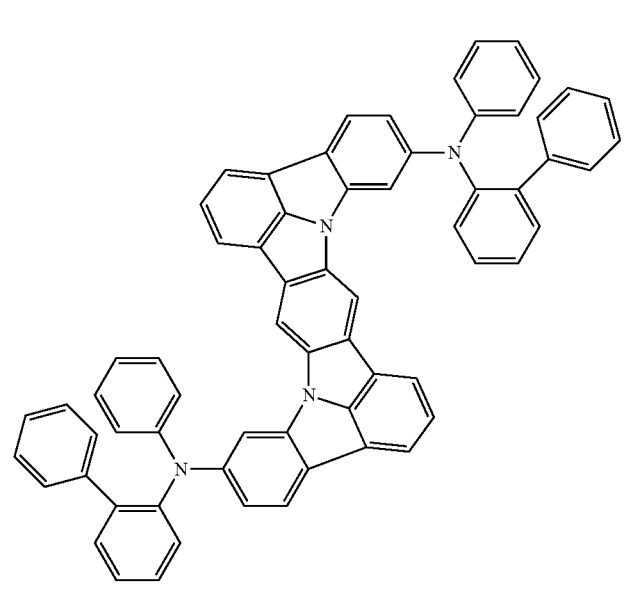
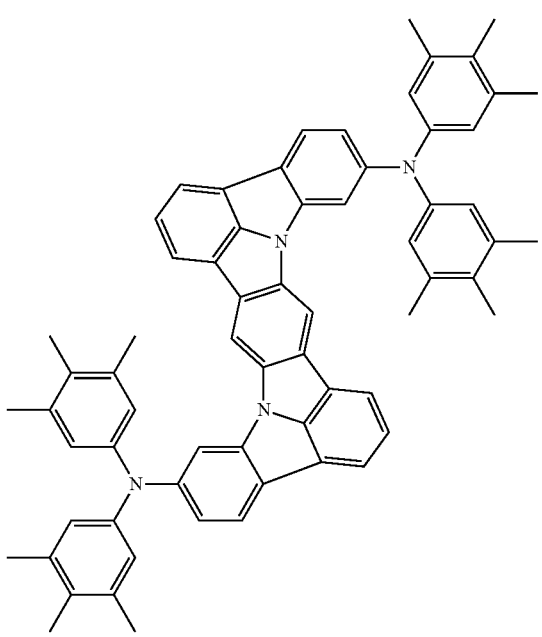

-continued
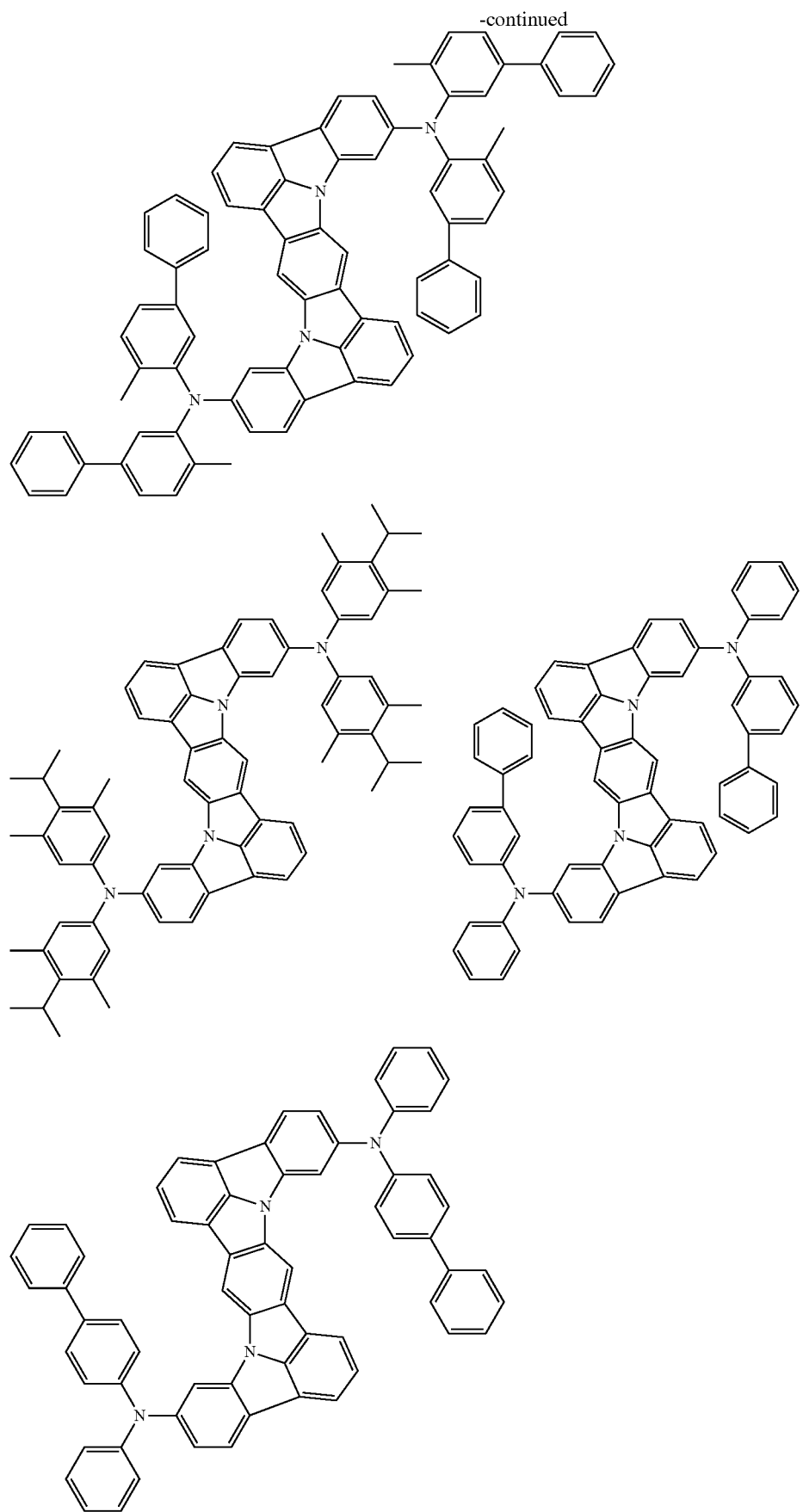

-continued
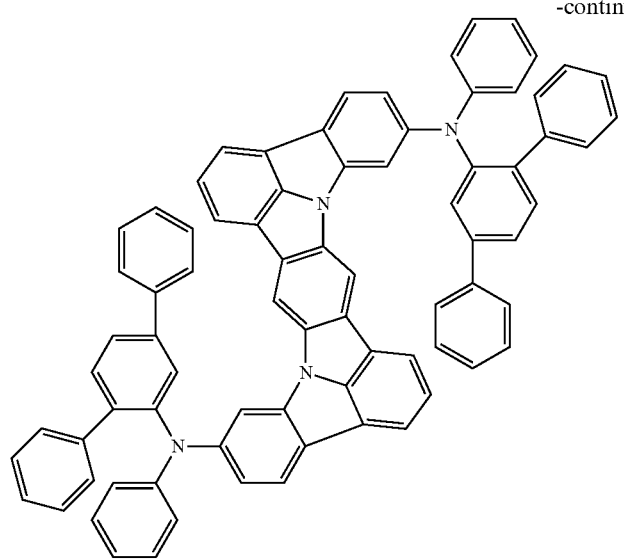
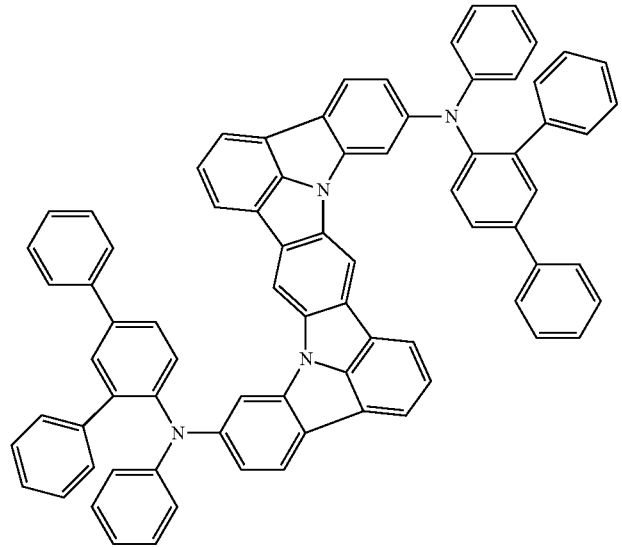
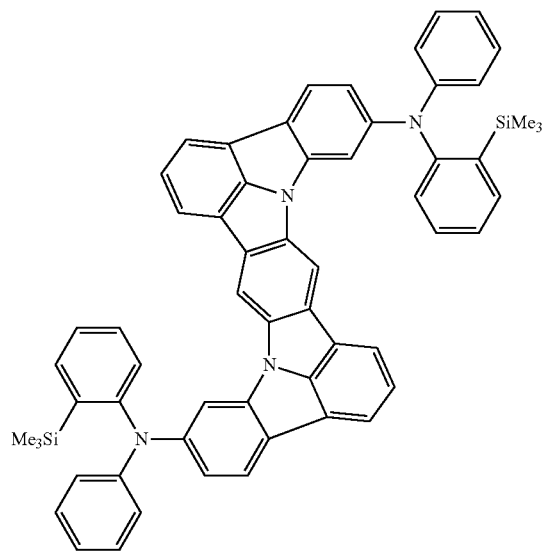 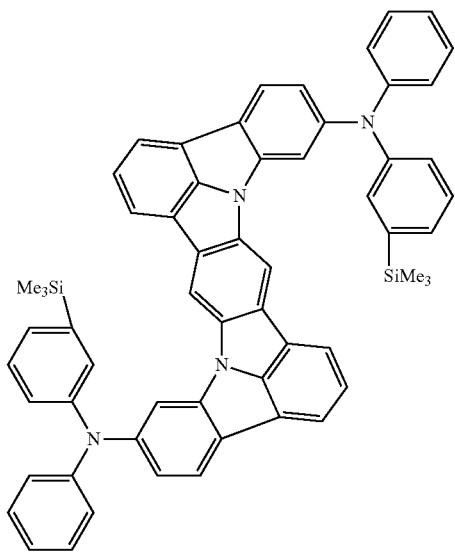

331 332
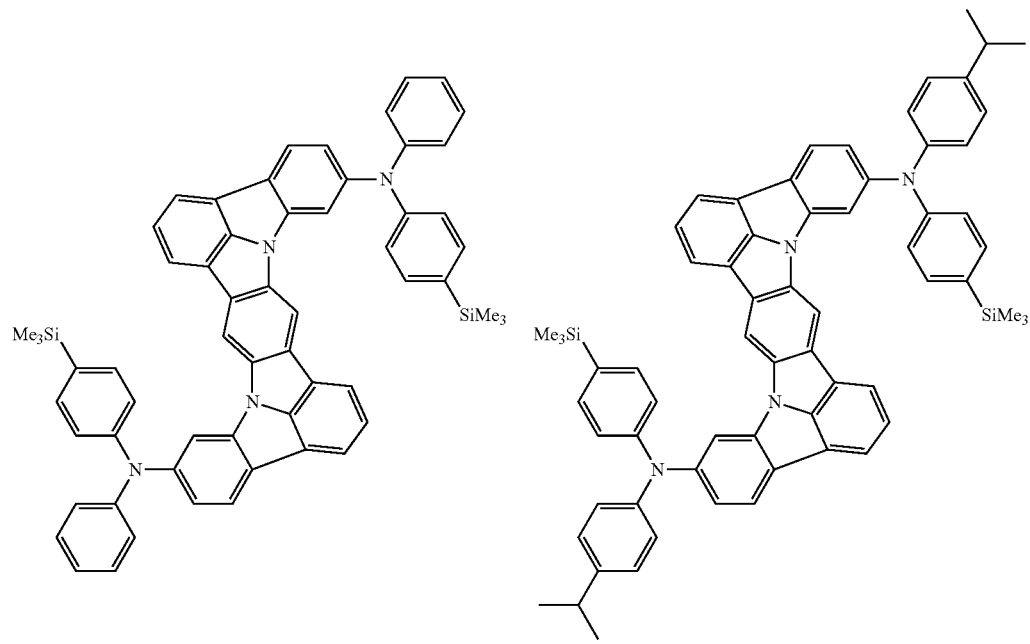
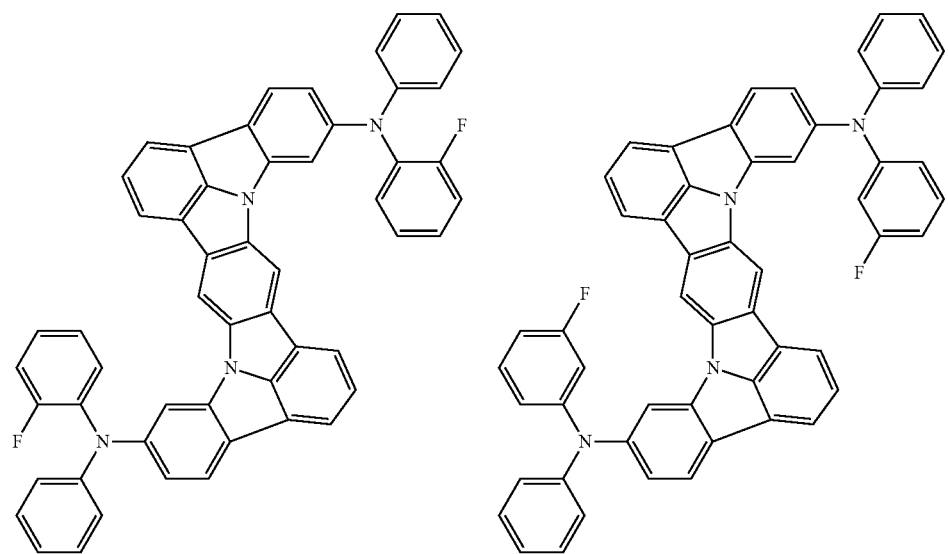

-continued
333
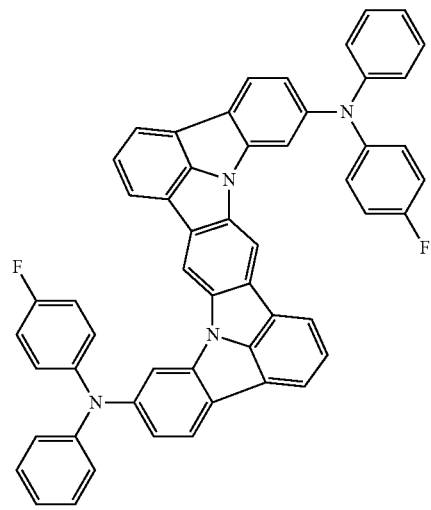
334
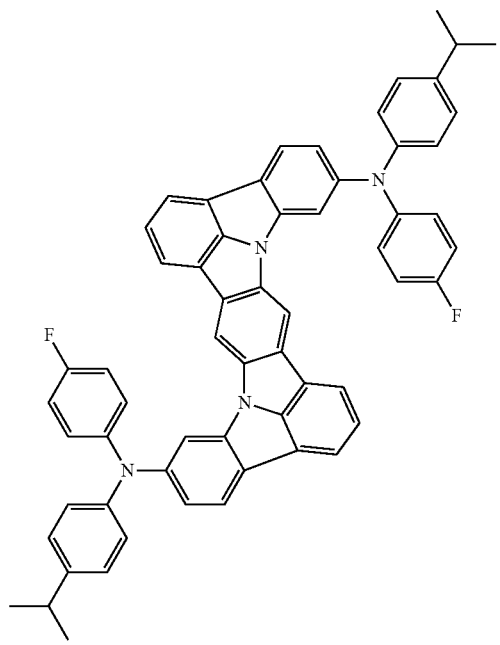
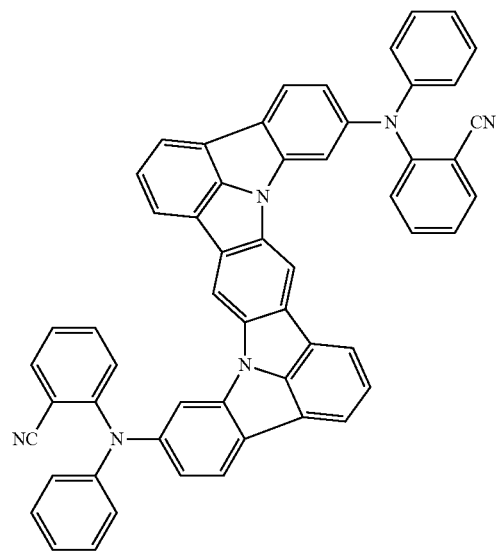
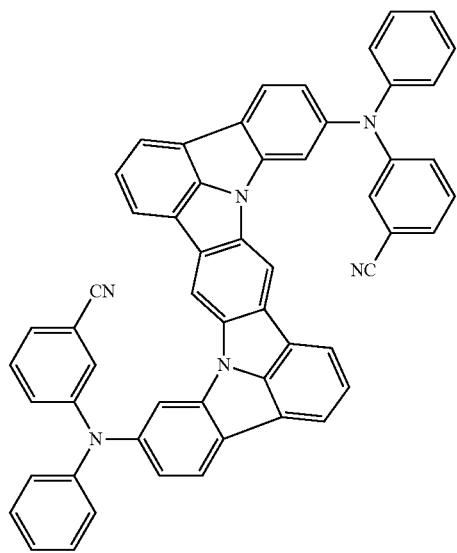

-continued
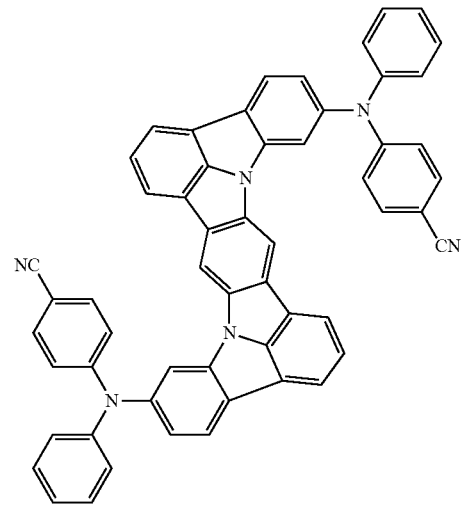 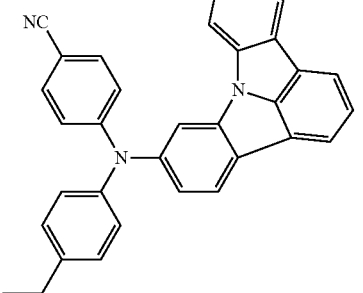
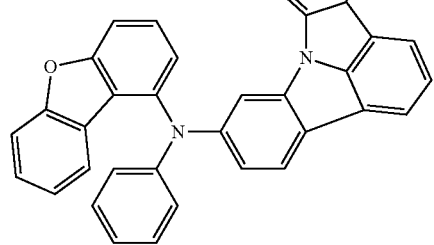 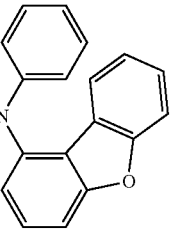
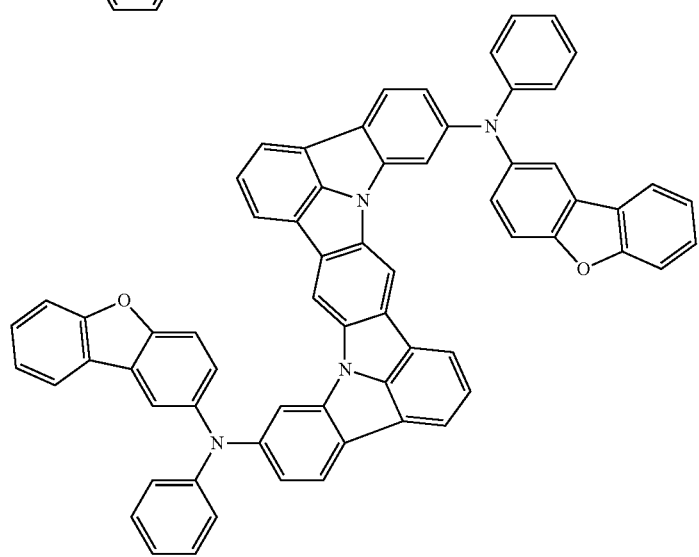

-continued
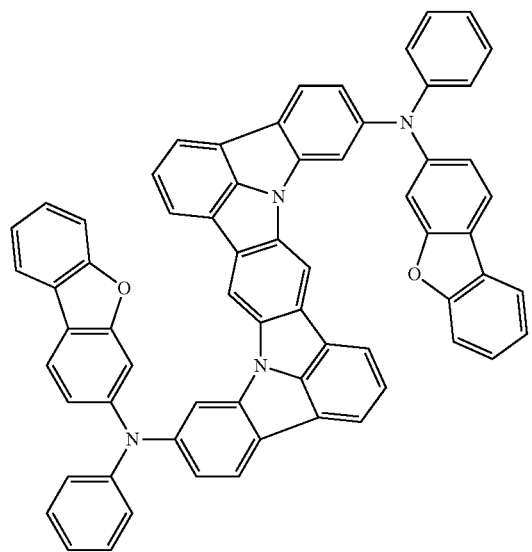
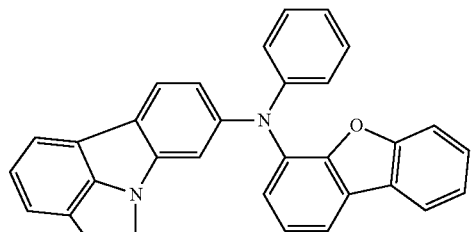
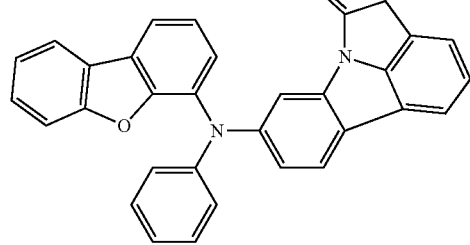
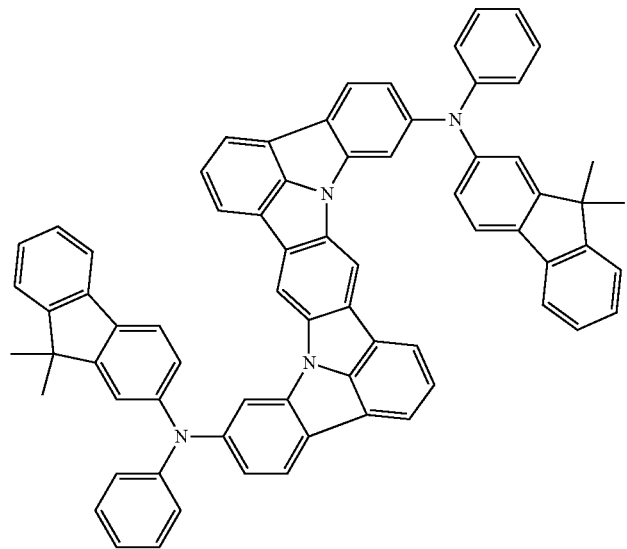

-continued
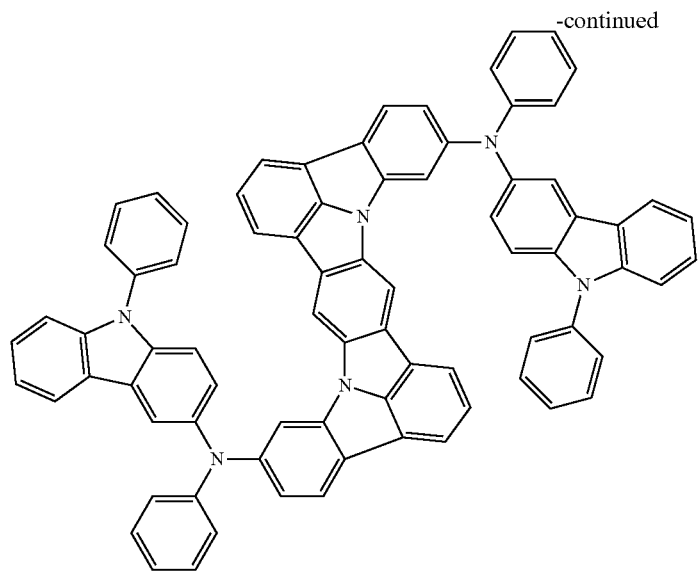
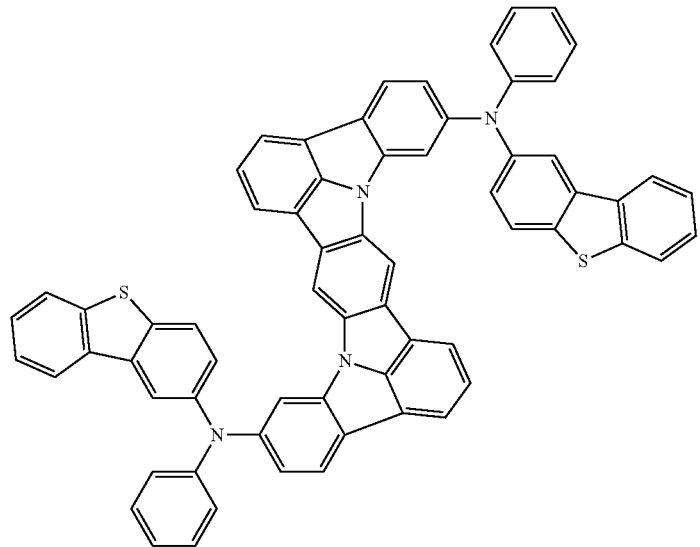
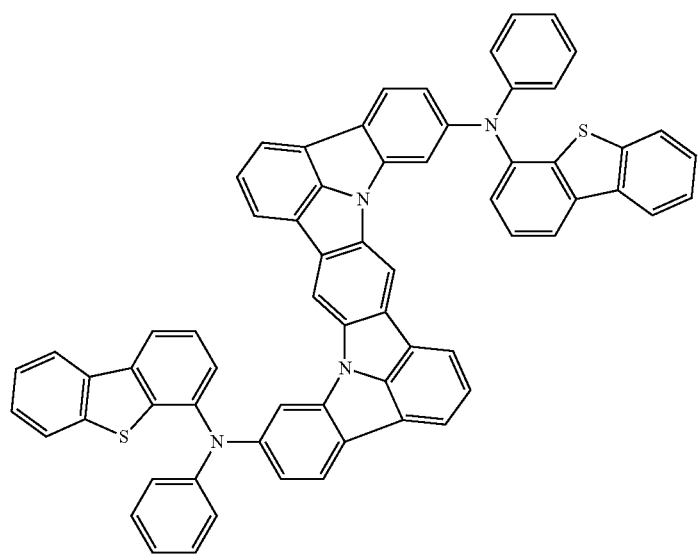

-continued
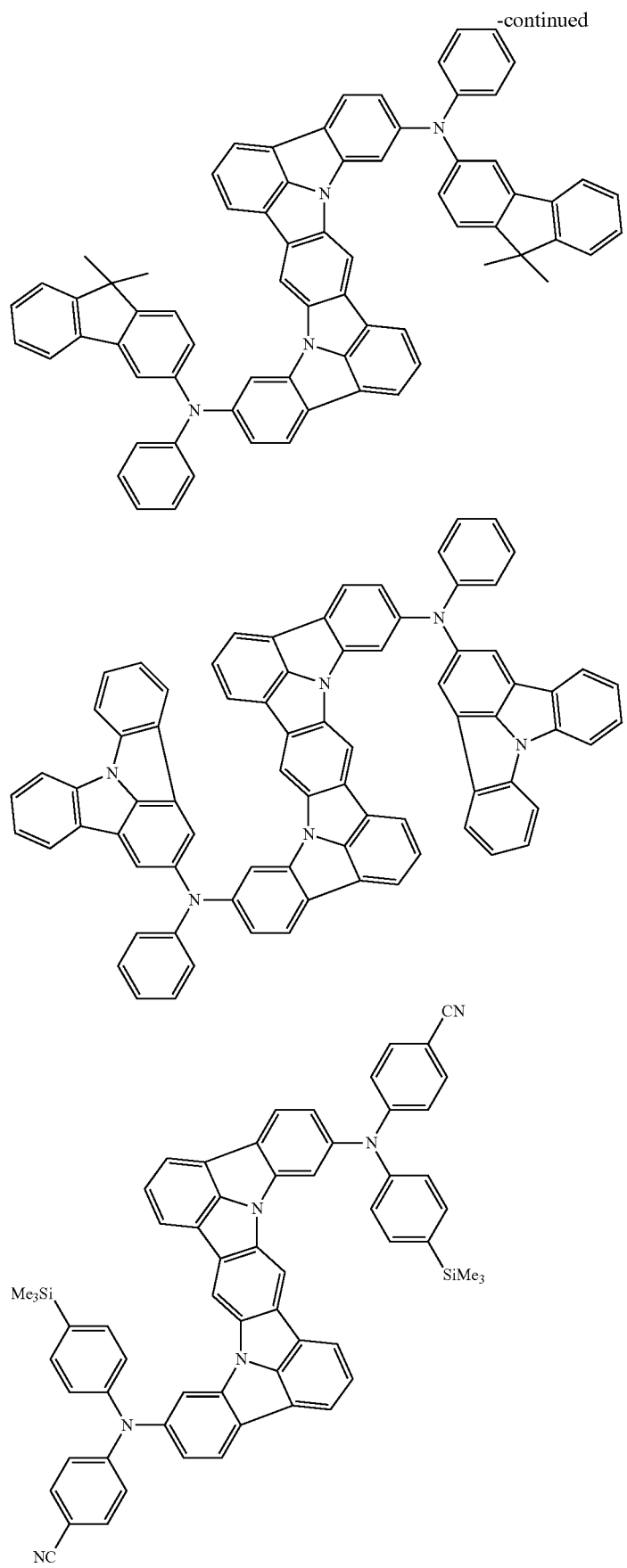

-continued
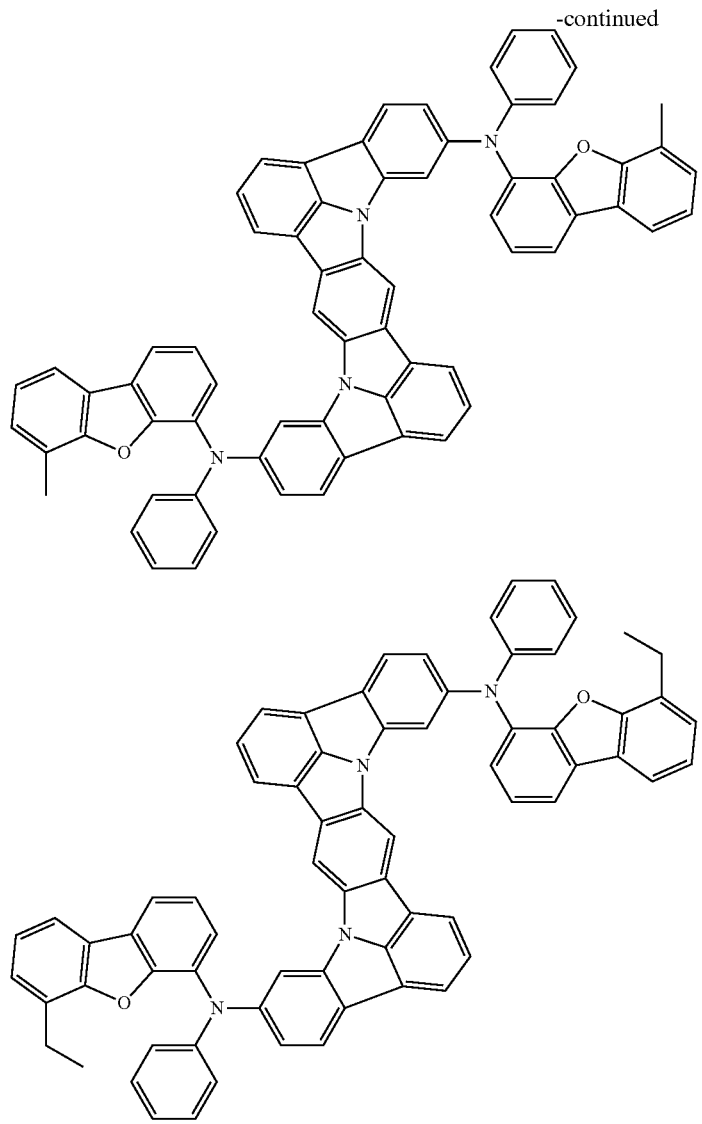
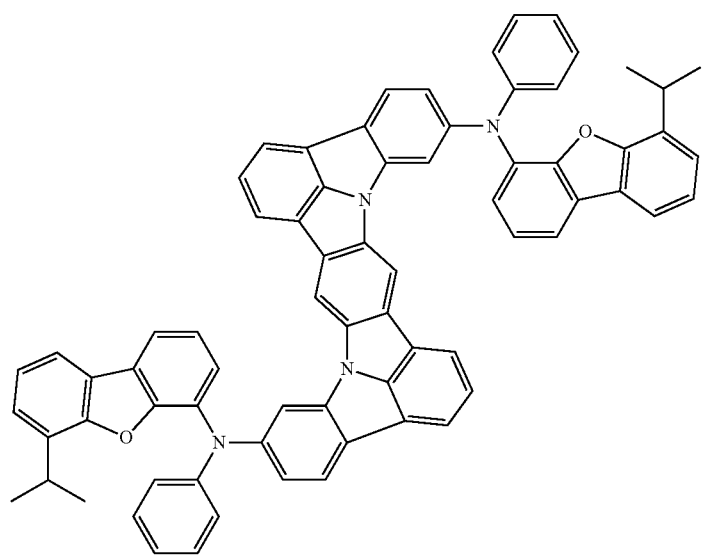

-continued
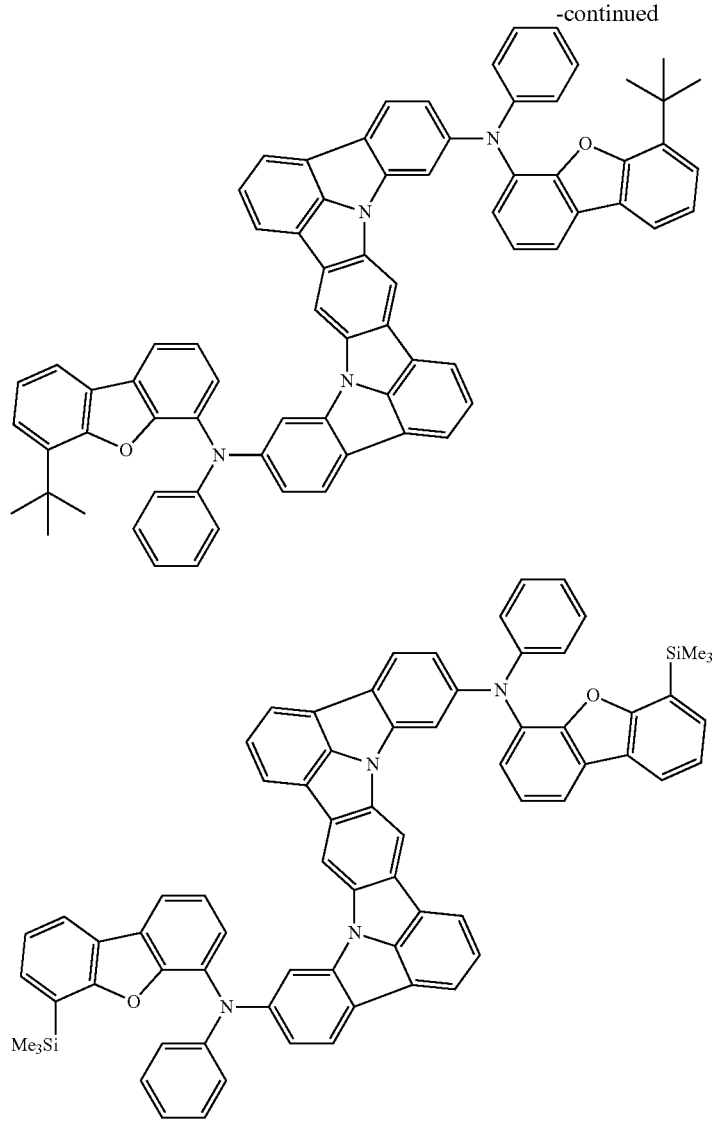
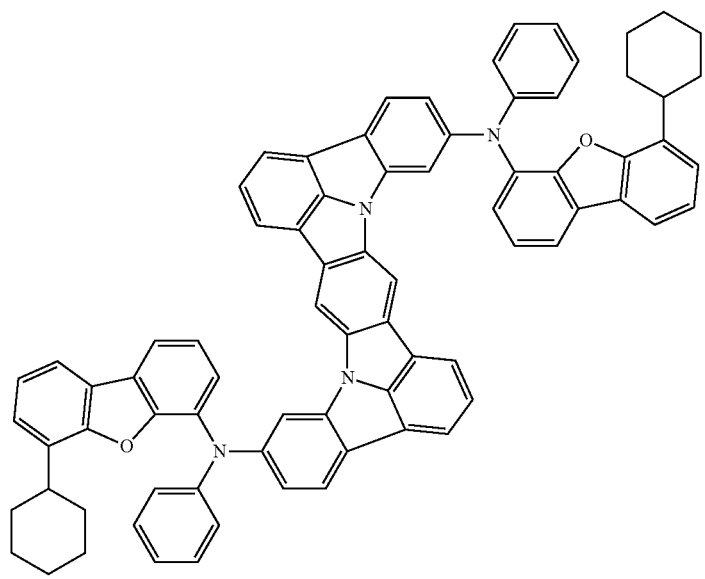

-continued
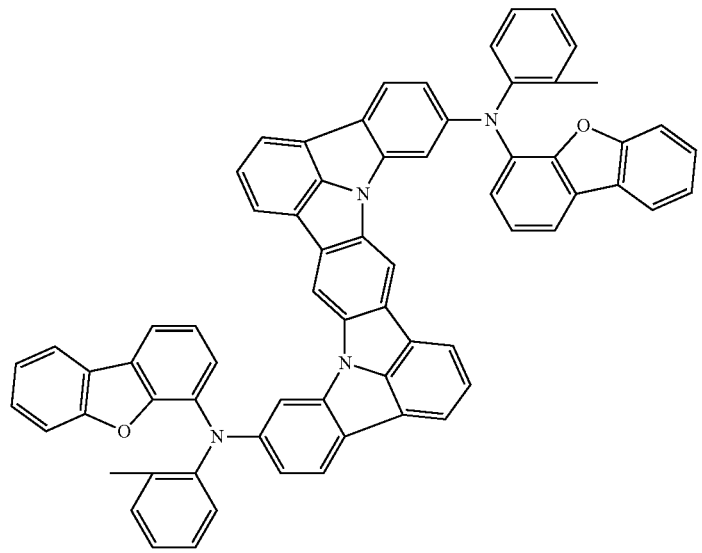
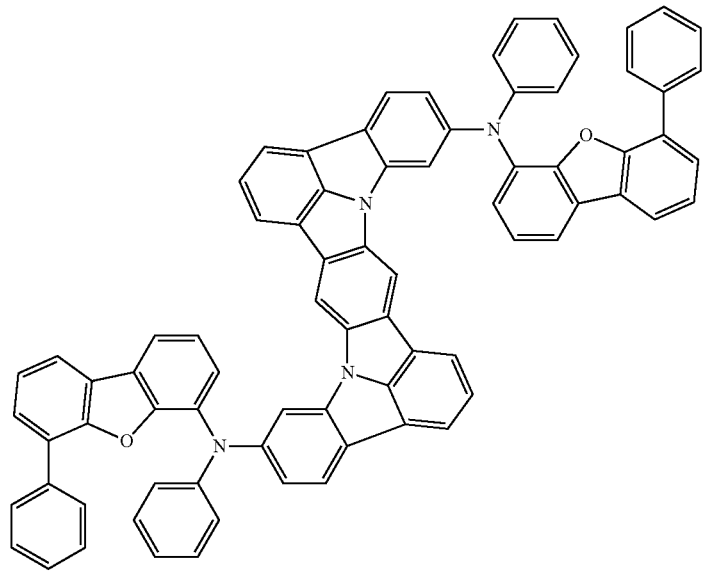
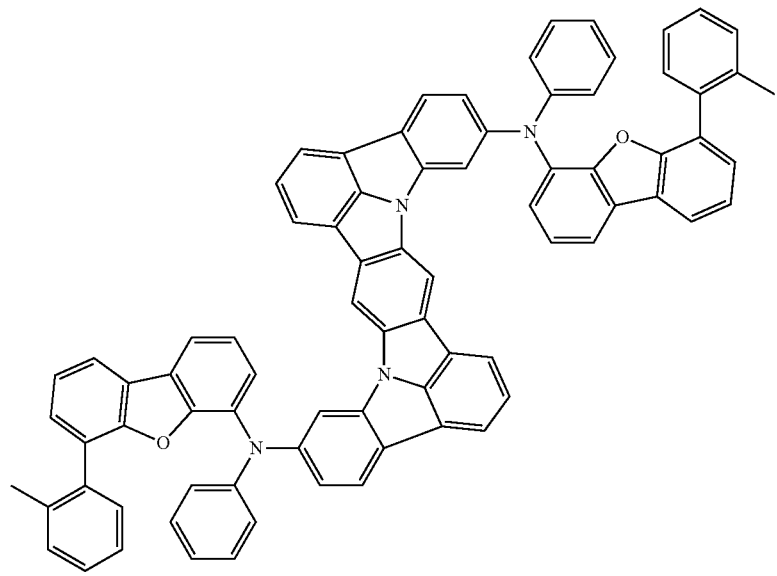

-continued
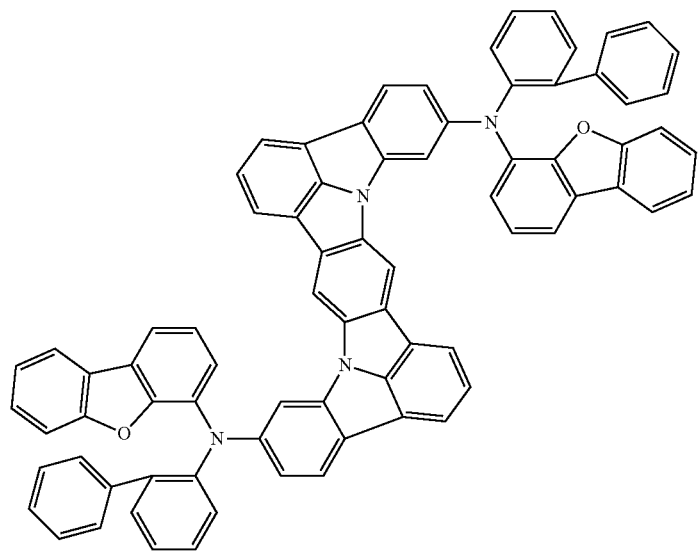
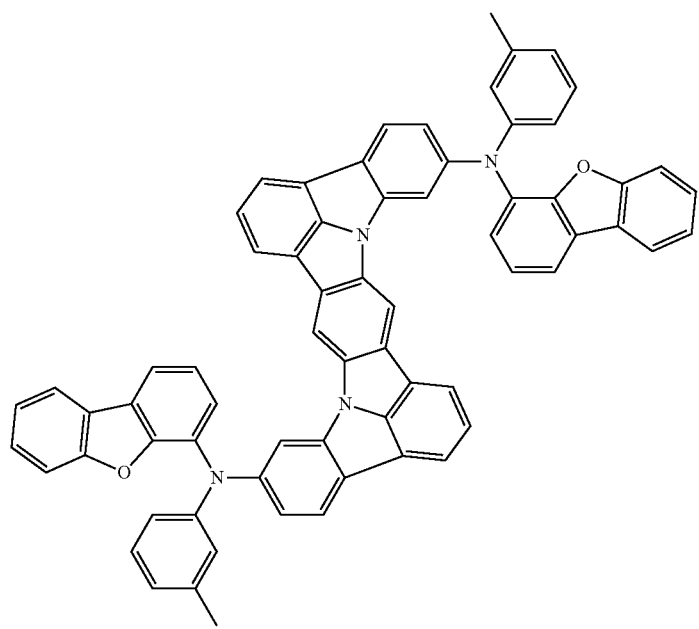

-continued
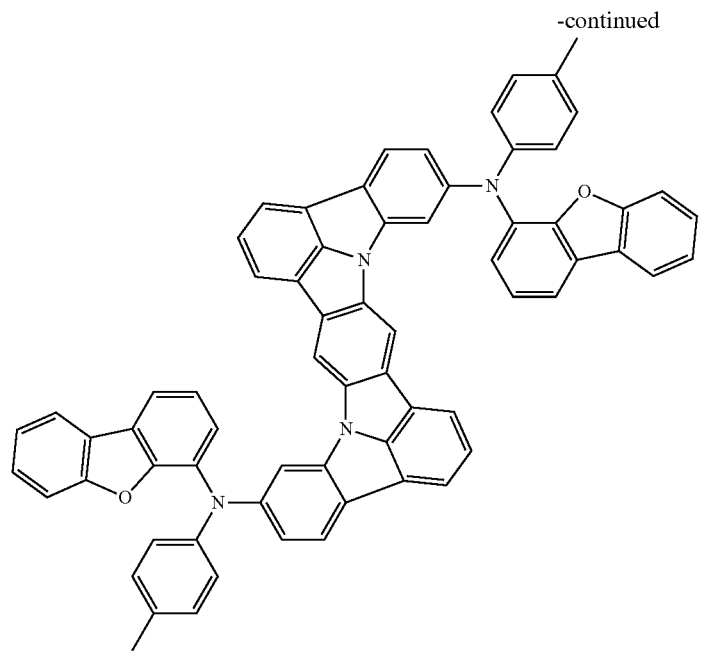
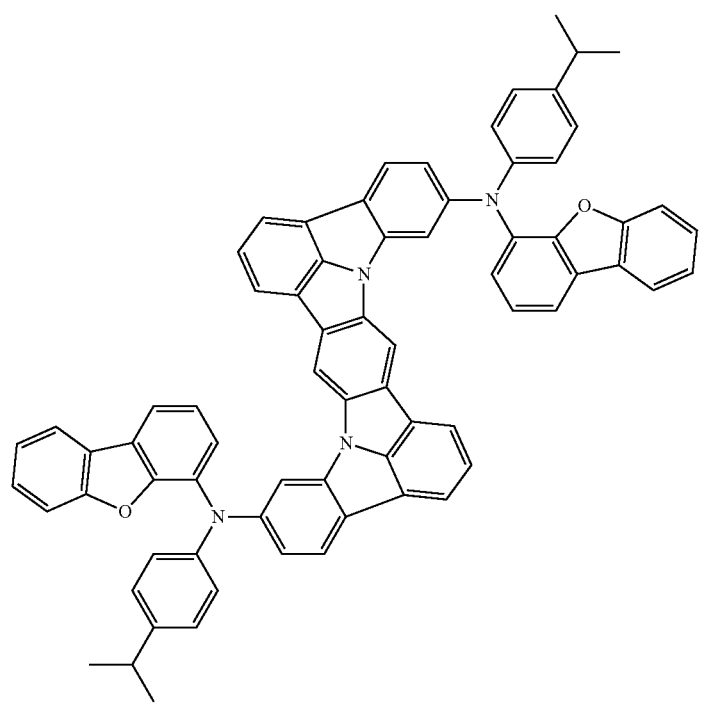

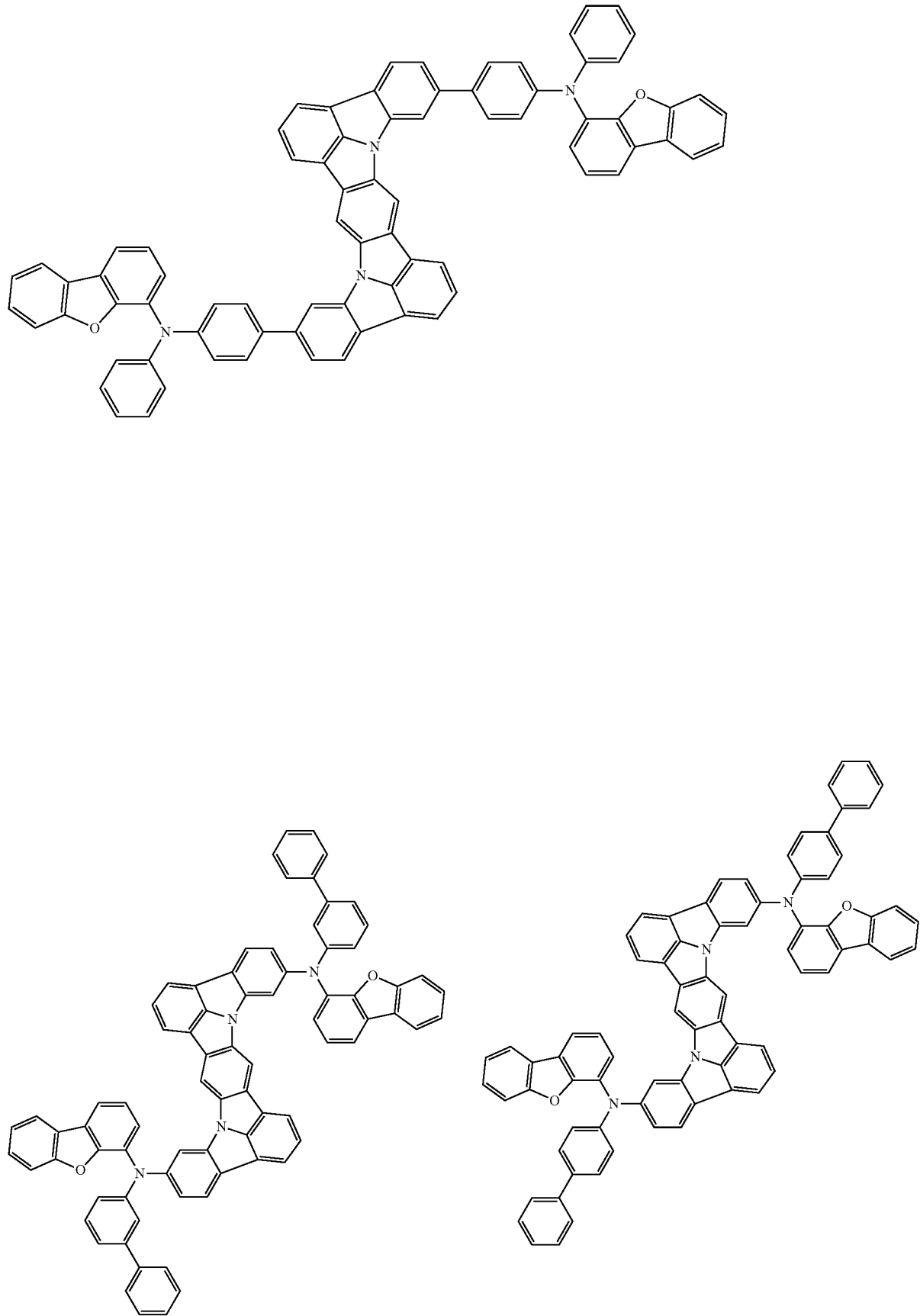

-continued
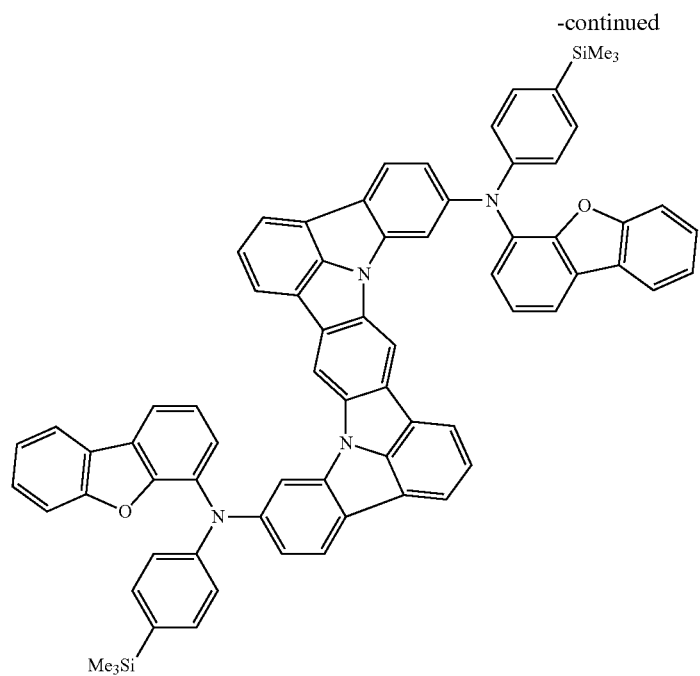
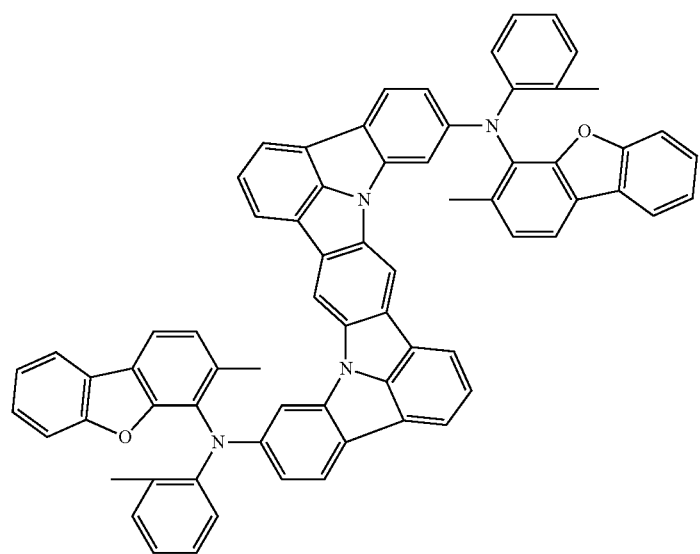

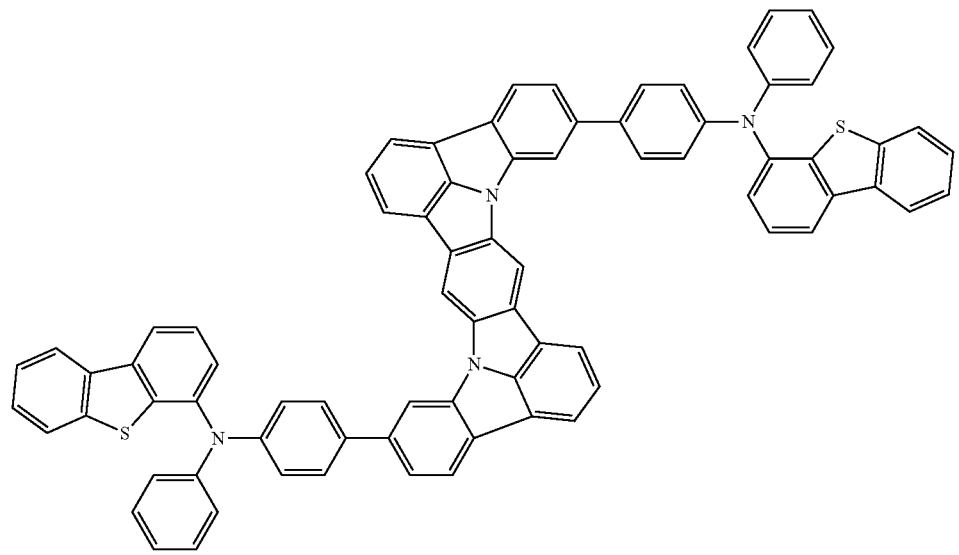
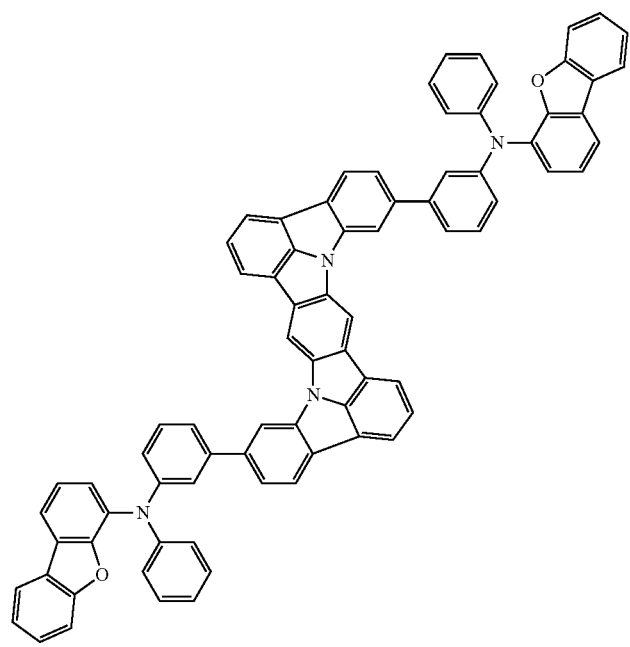

-continued
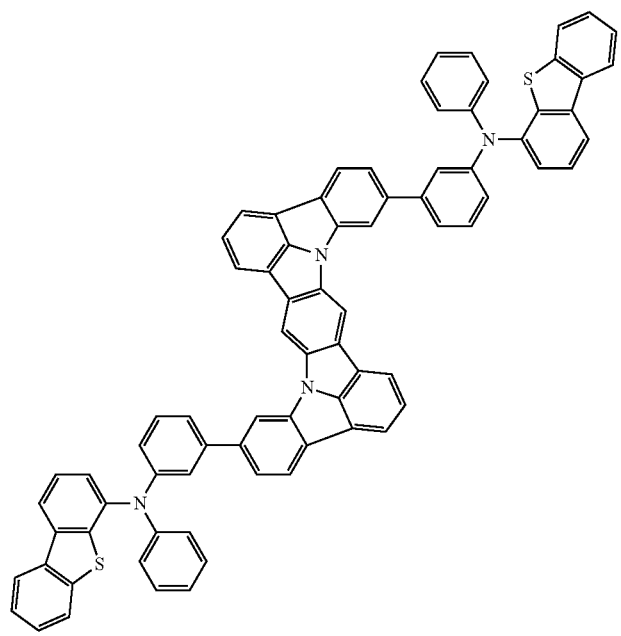
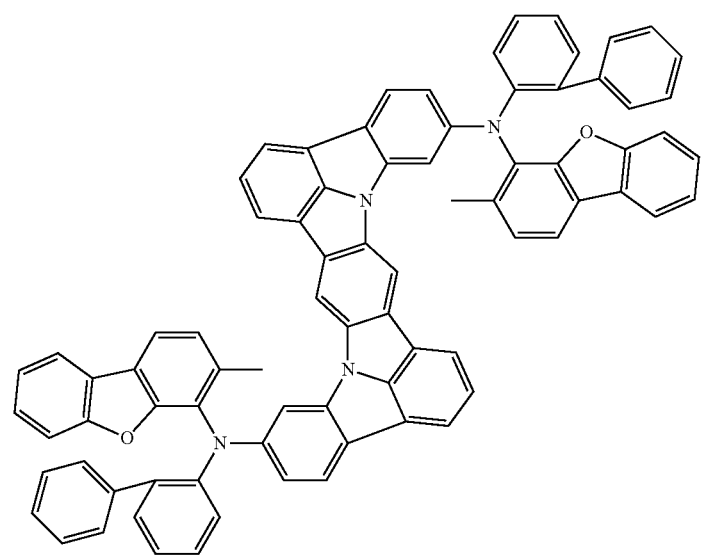

-continued
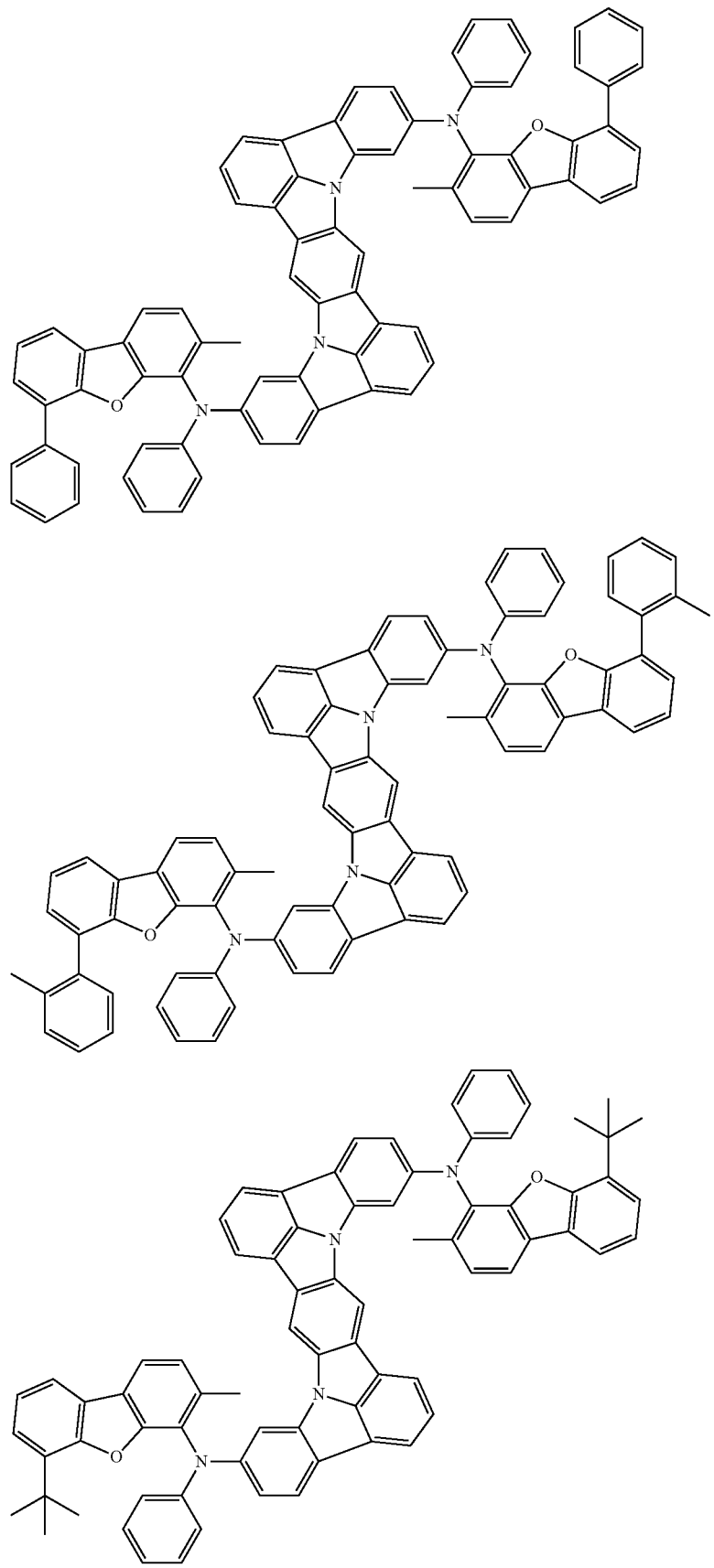

-continued
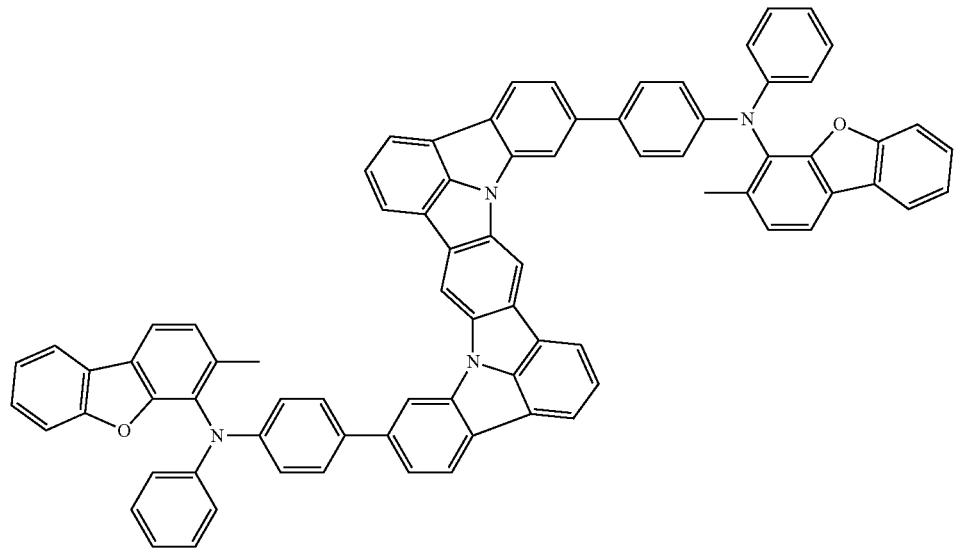
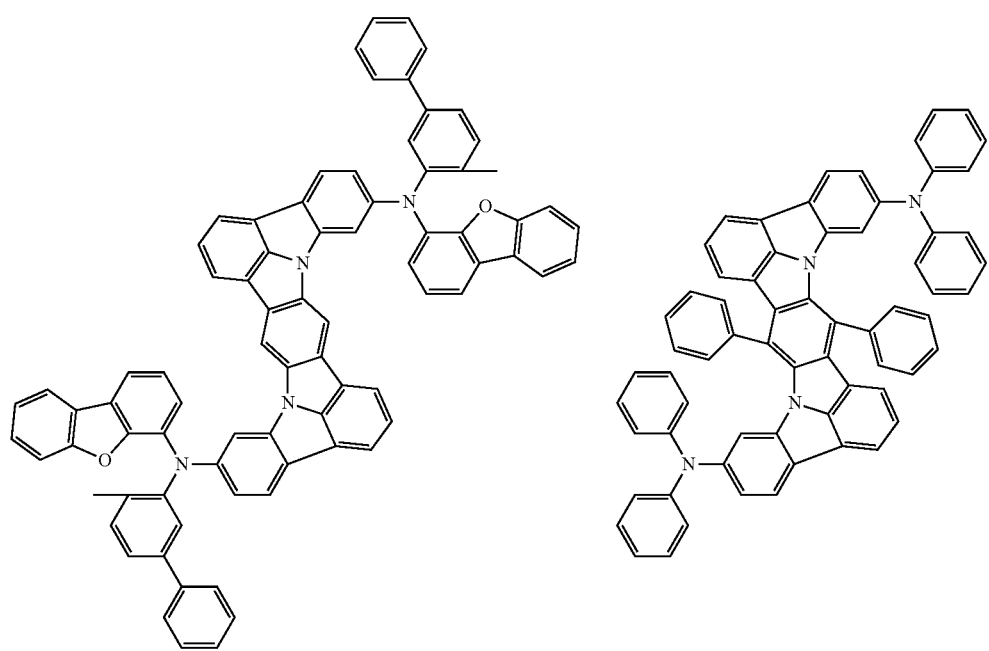

365
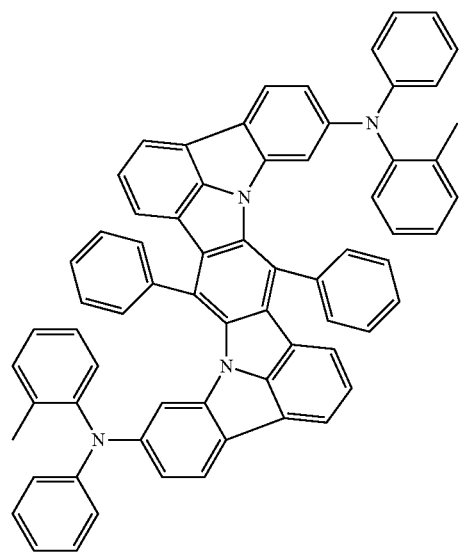
366
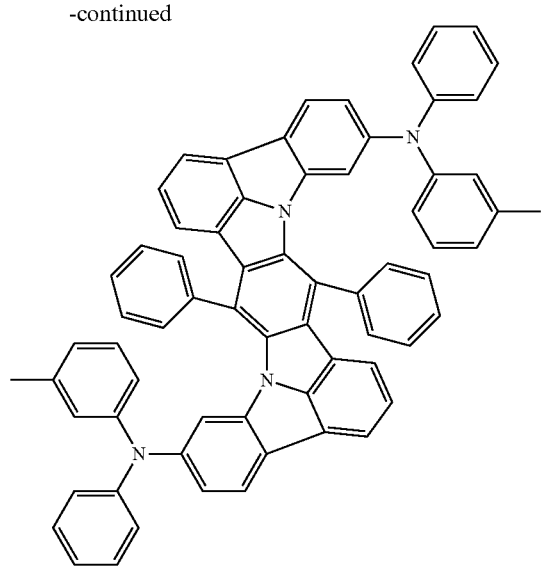
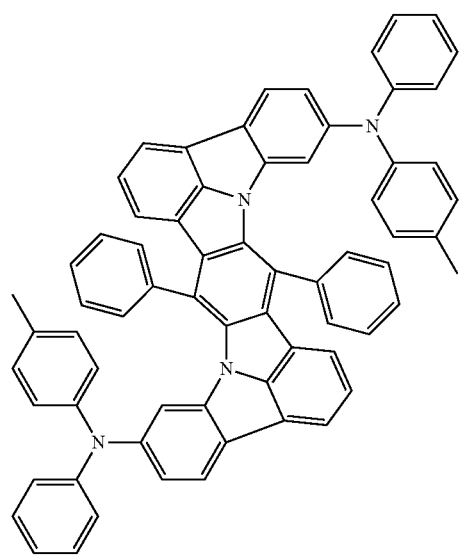
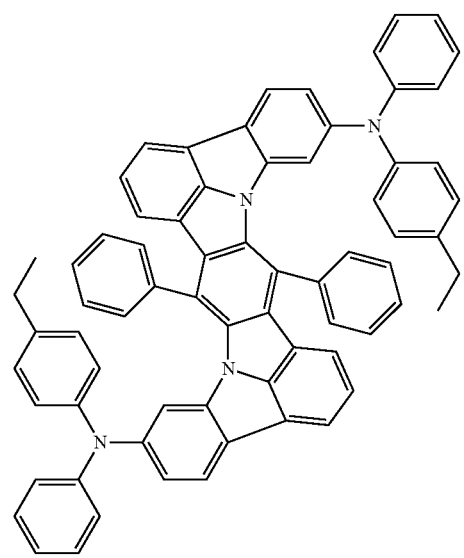
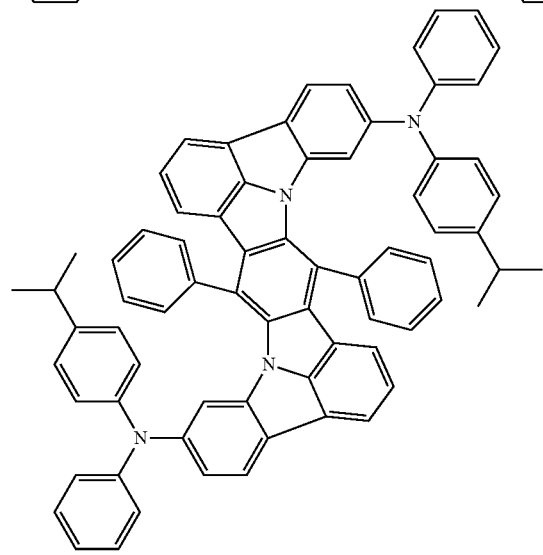
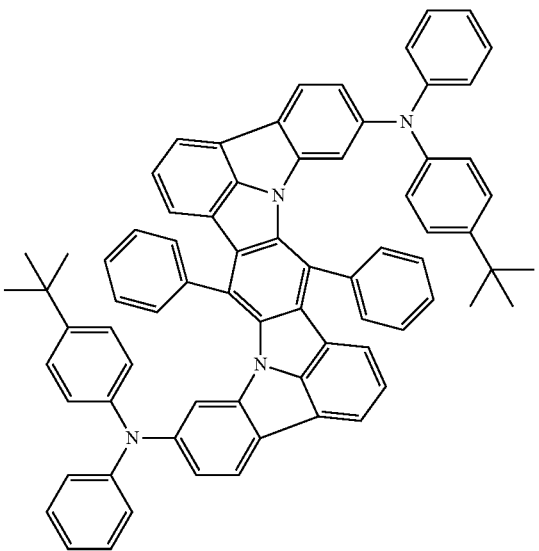

367 368
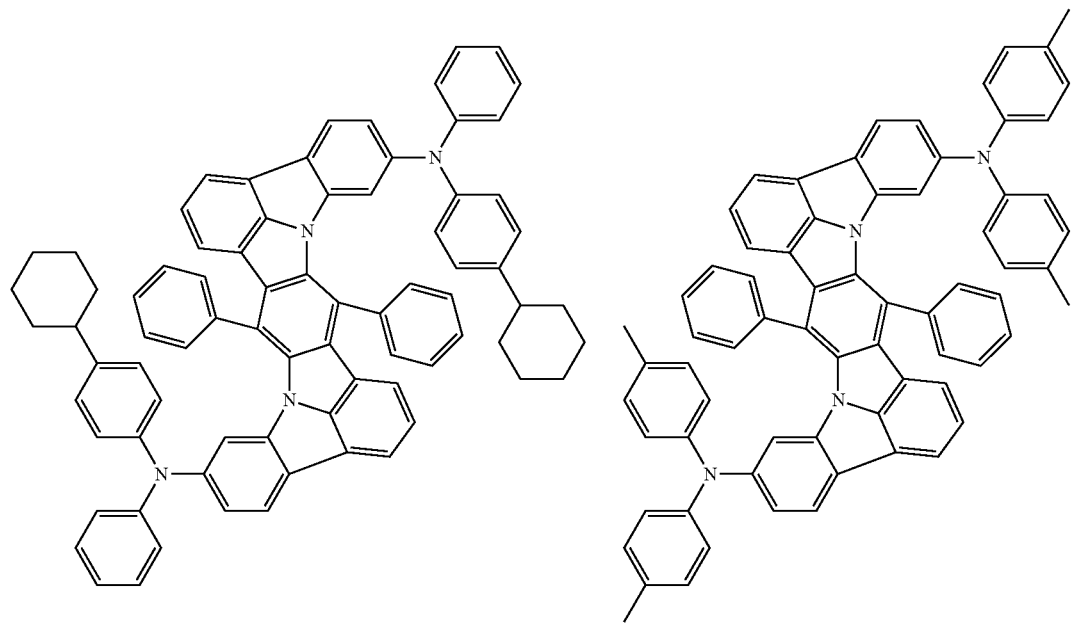
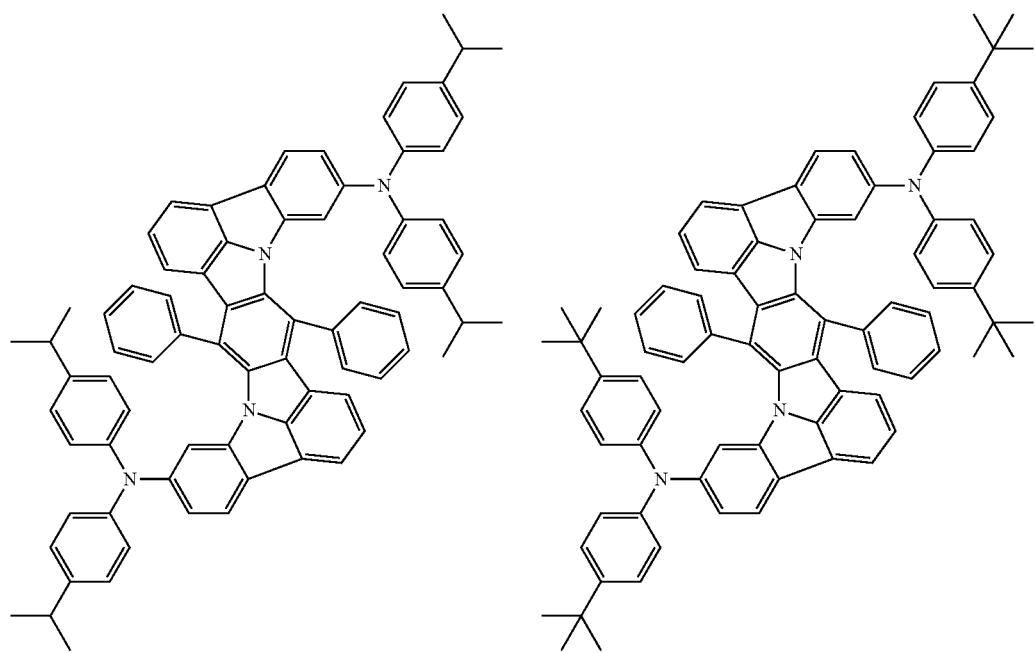

369
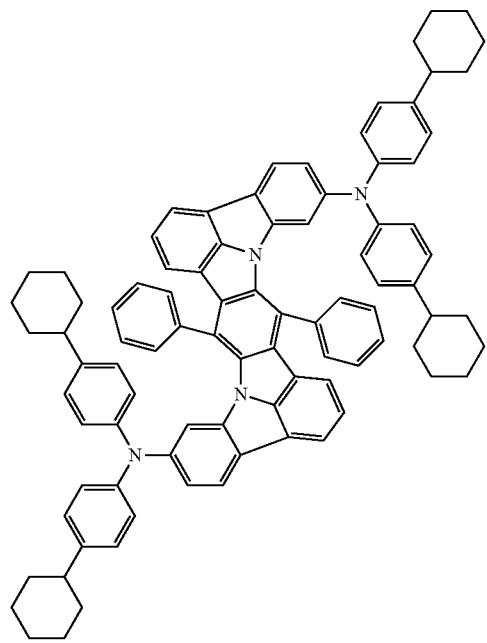
370
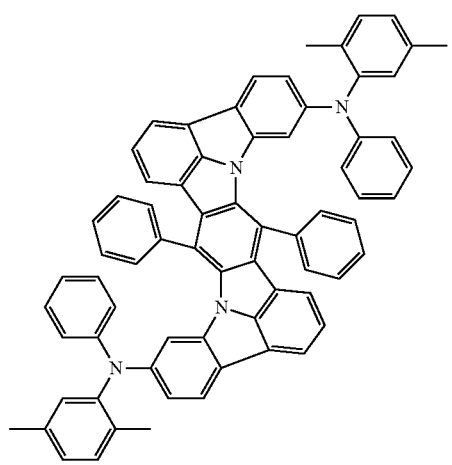
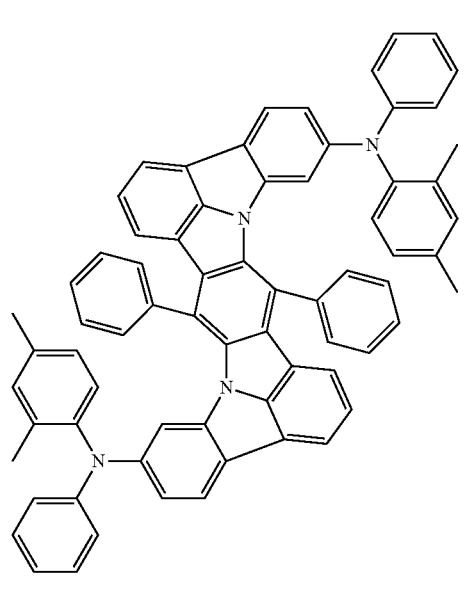
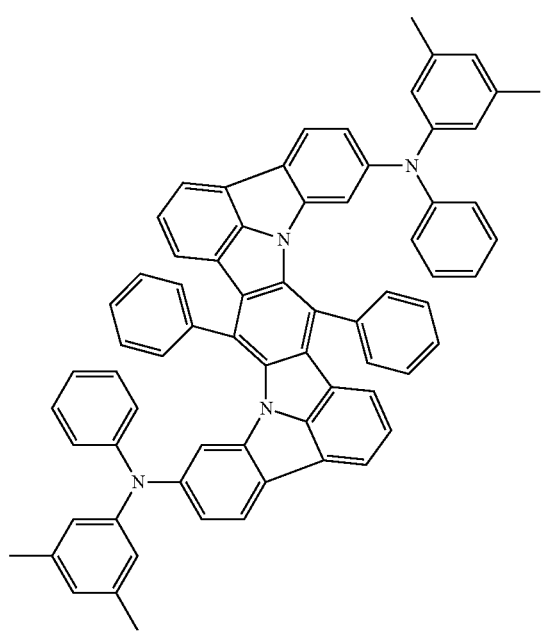

-continued
371
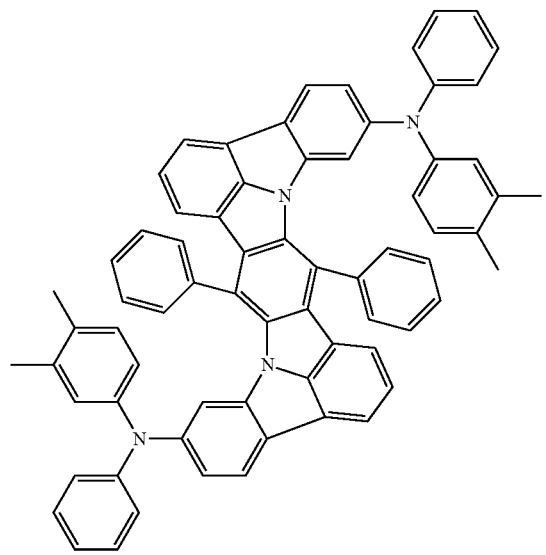
372
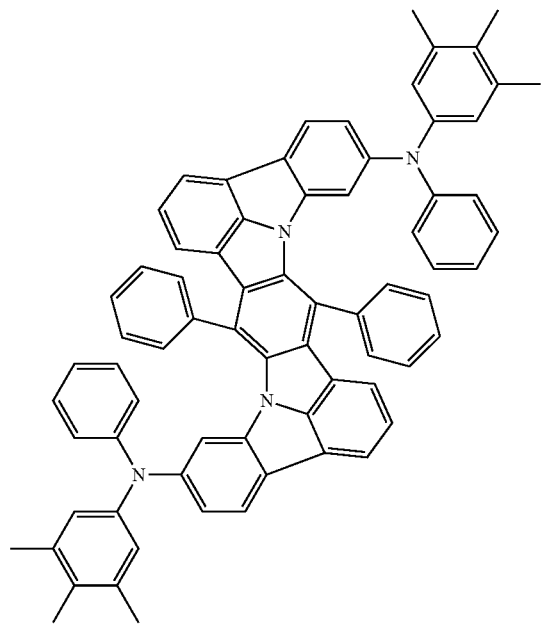
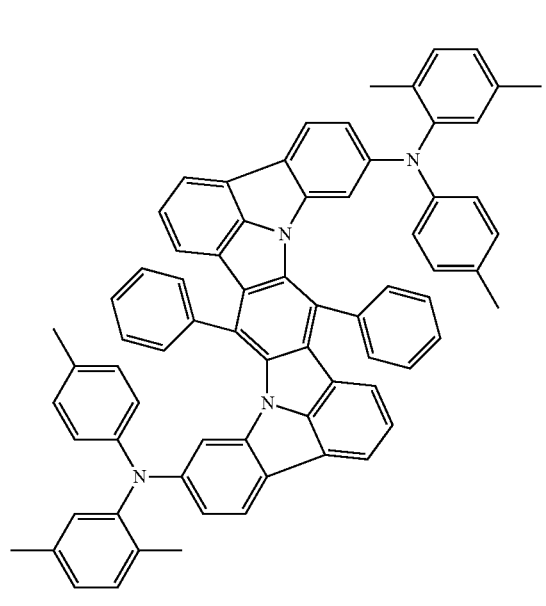
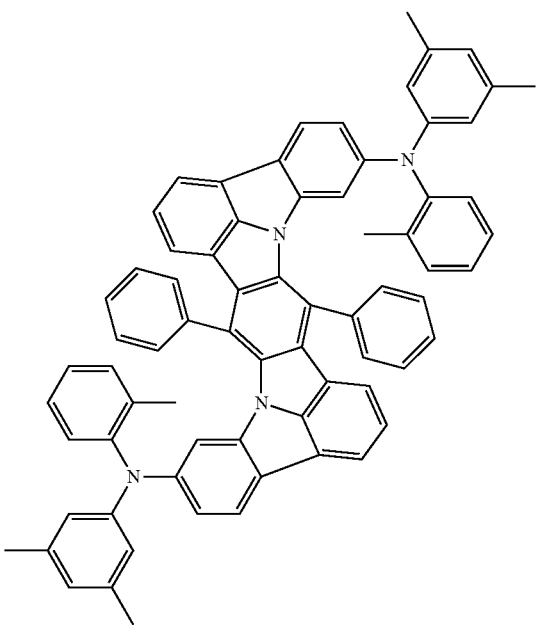

-continued
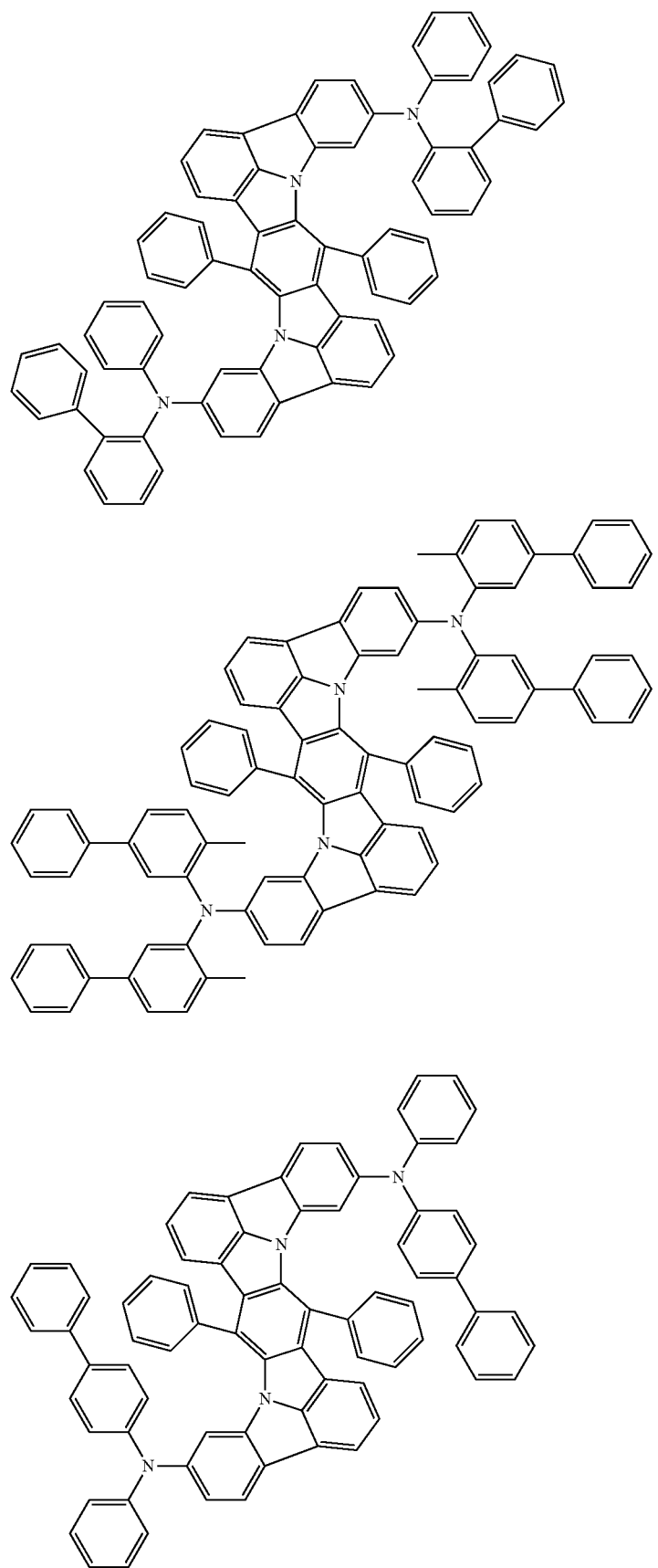

-continued
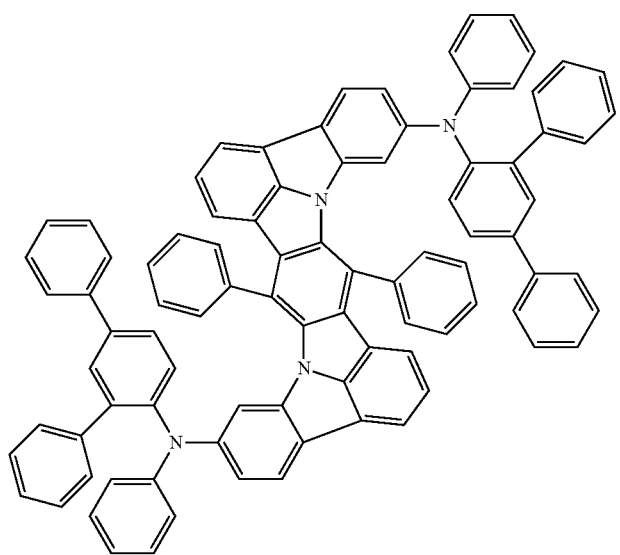 [SMILES: c1ccc(-c2ccc(N(c3ccccc3)c3ccc4c5cccc6c7c(-c8ccccc8)c8c(c(-c9ccccc9)c7n(c4c3)c56)c3cccc4c5ccc(N(c6ccccc6)c6ccc(-c7ccccc7)cc6-c6ccccc6)cc5n8c43)c(-c3ccccc3)c2)cc1]
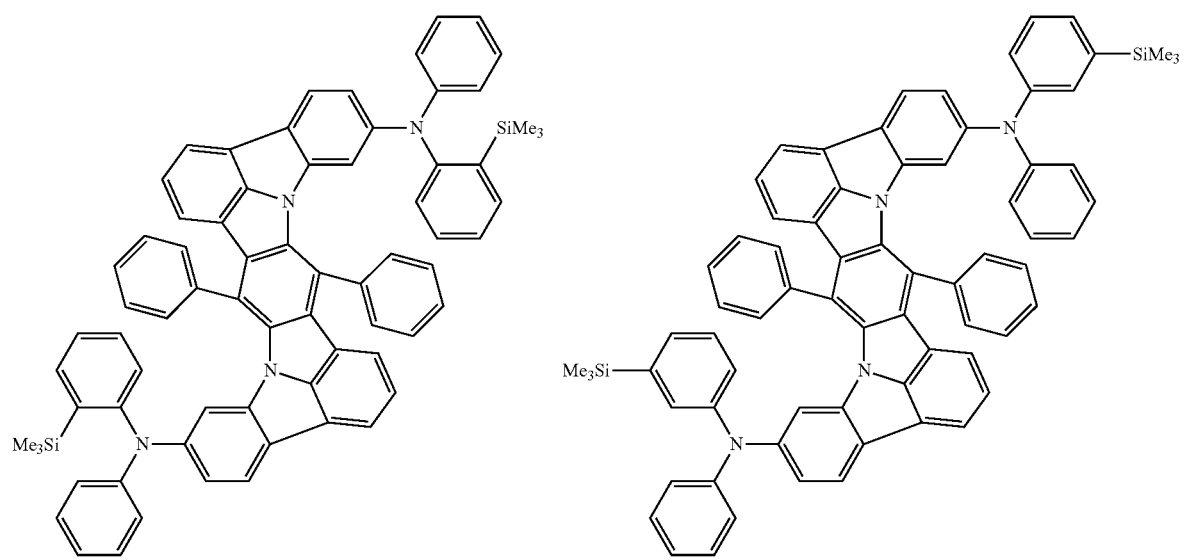

-continued
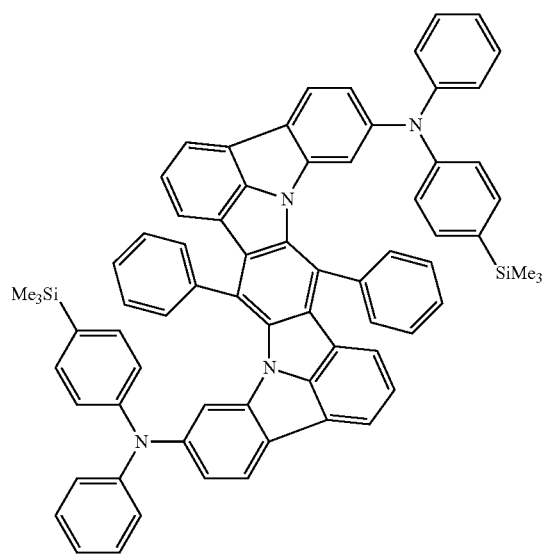
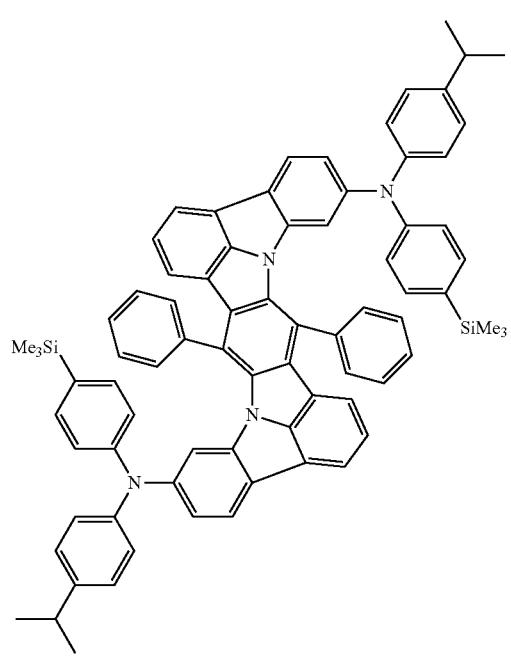

-continued
379
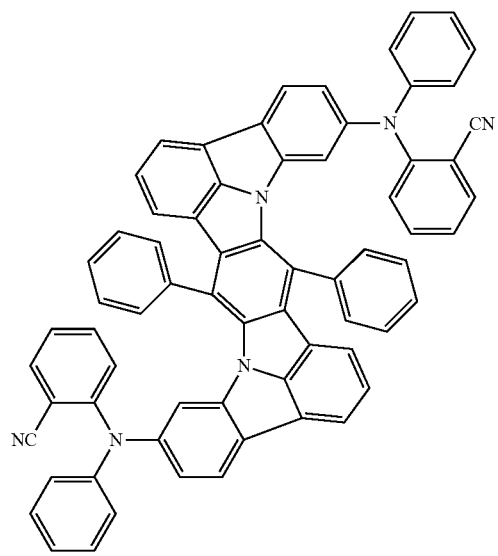
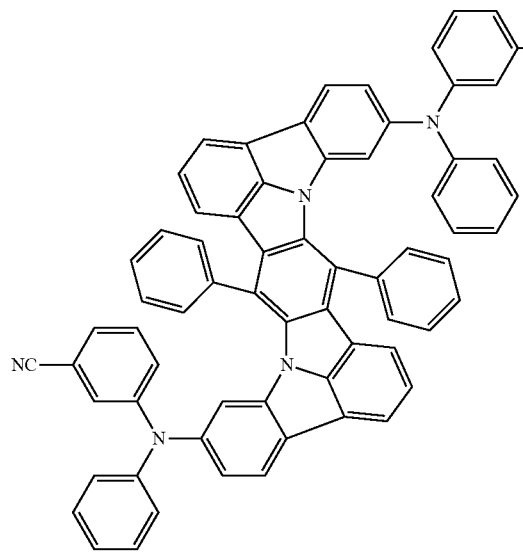
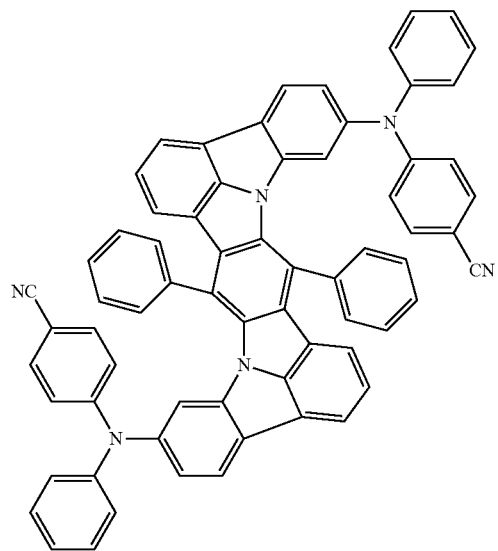
380
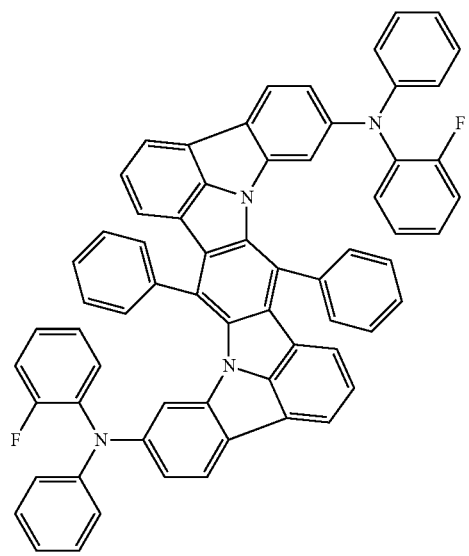
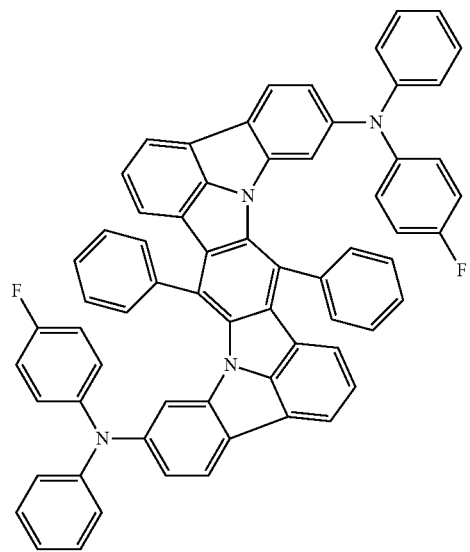
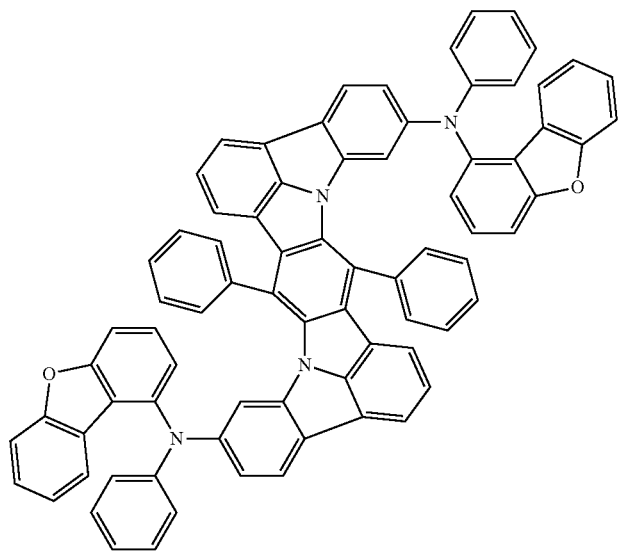

-continued
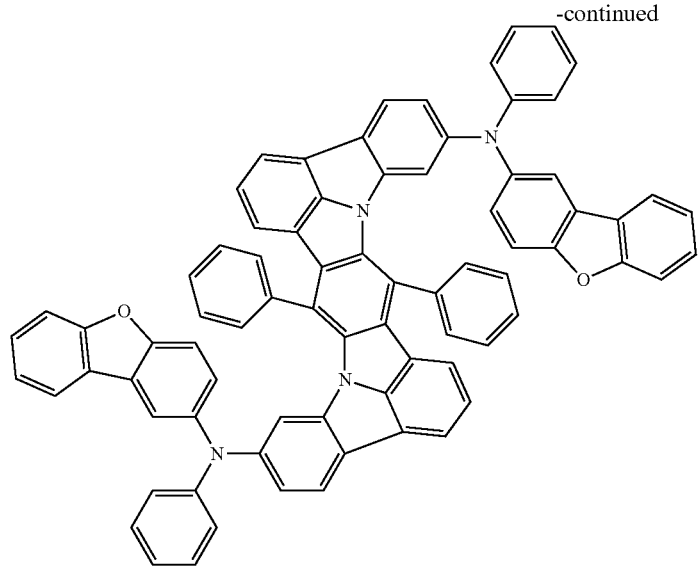
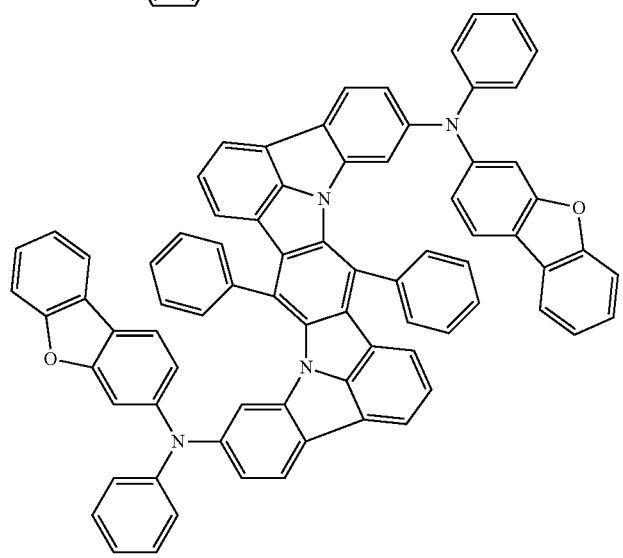
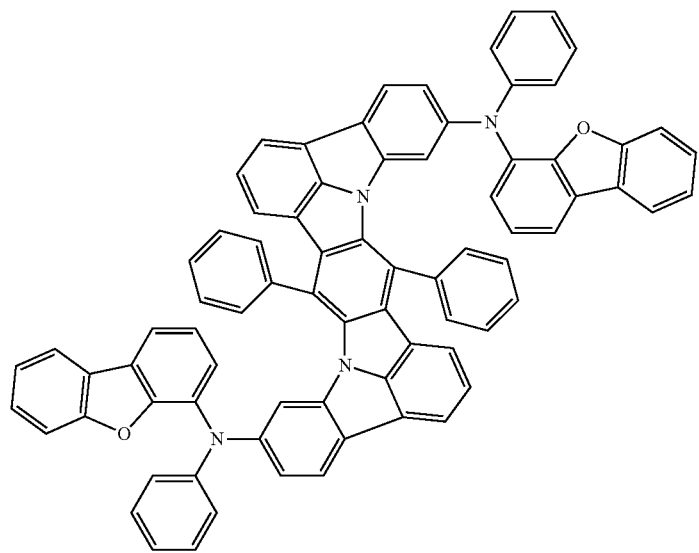

-continued
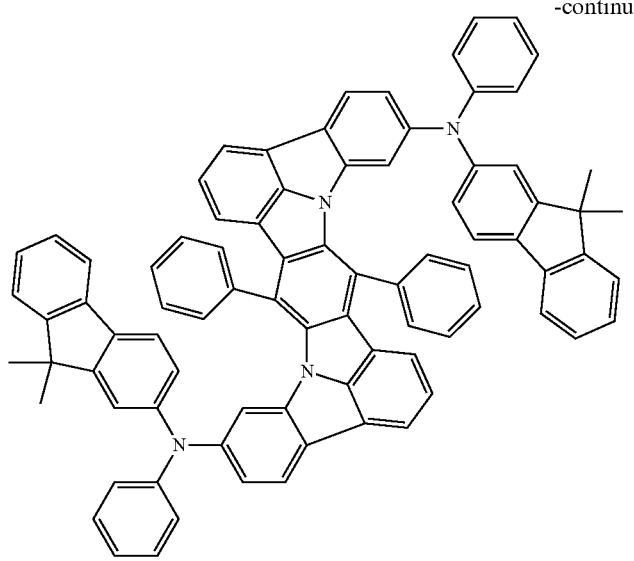
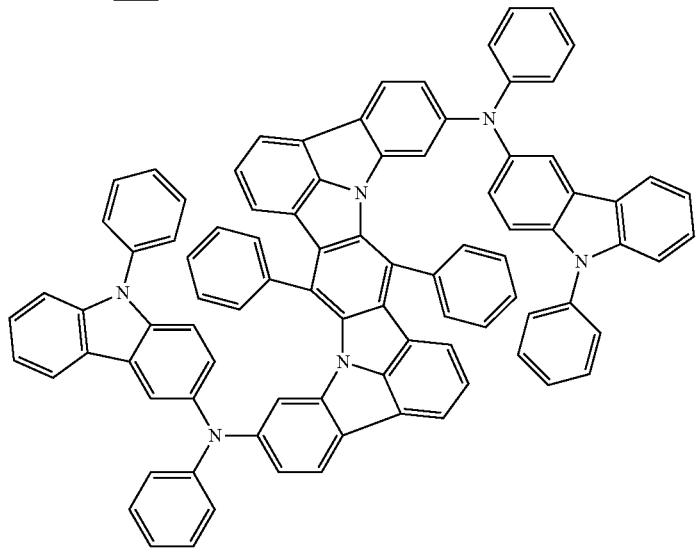
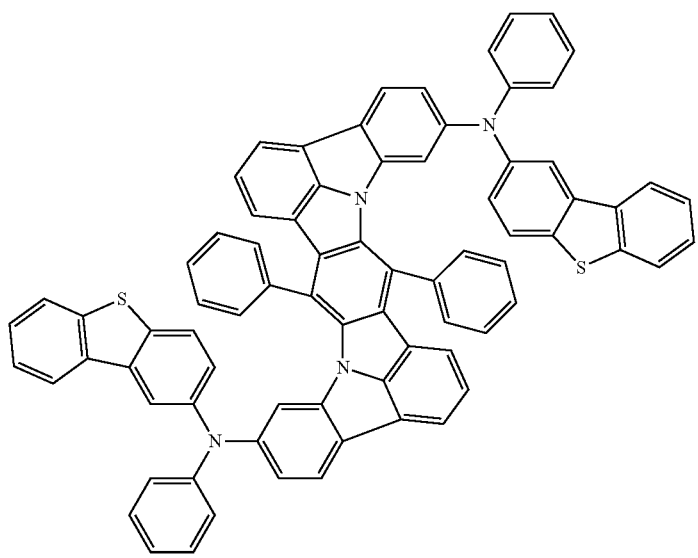

-continued
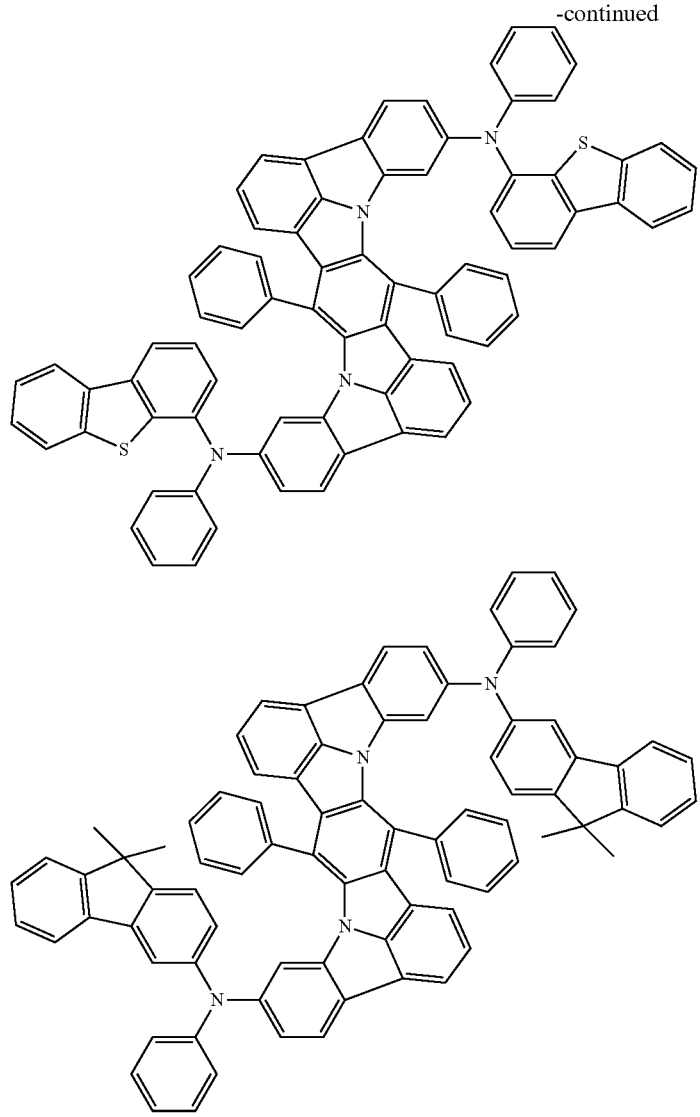
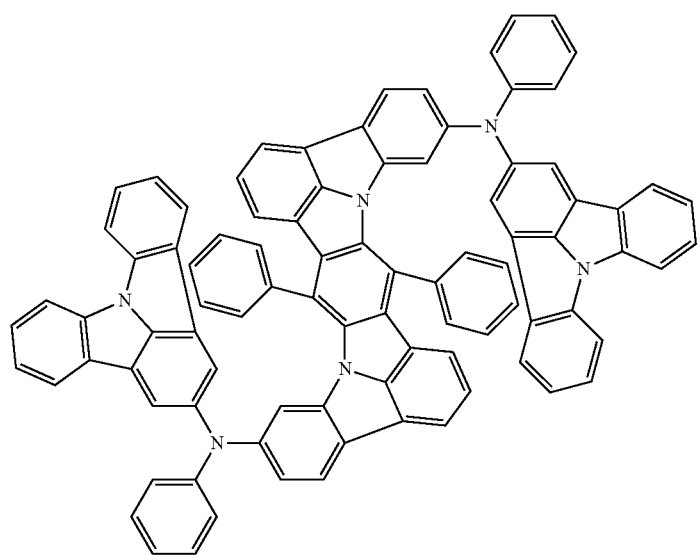

-continued
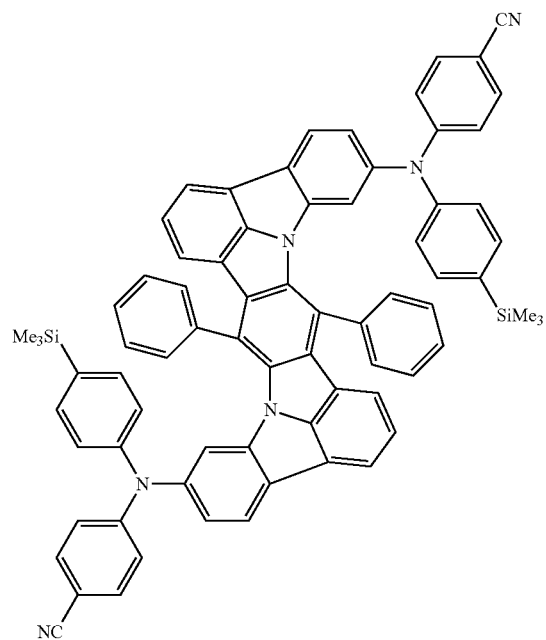
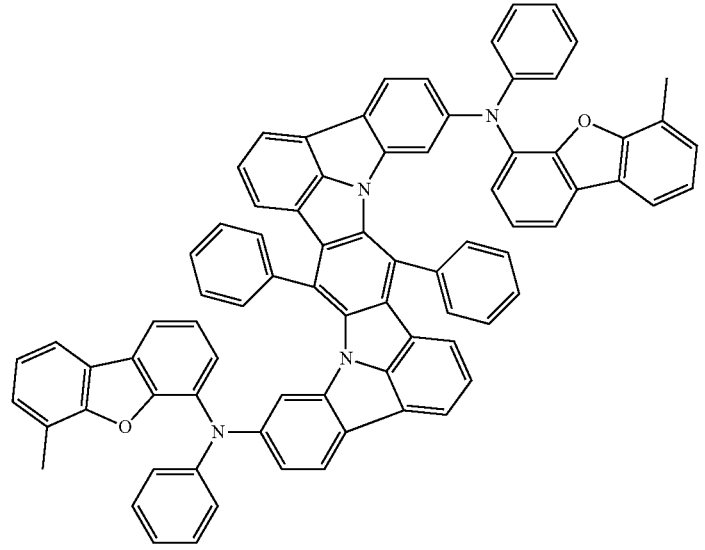
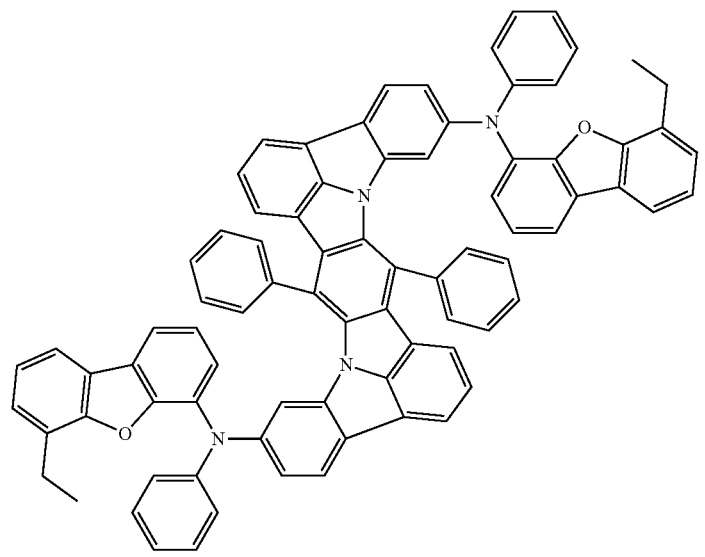

-continued
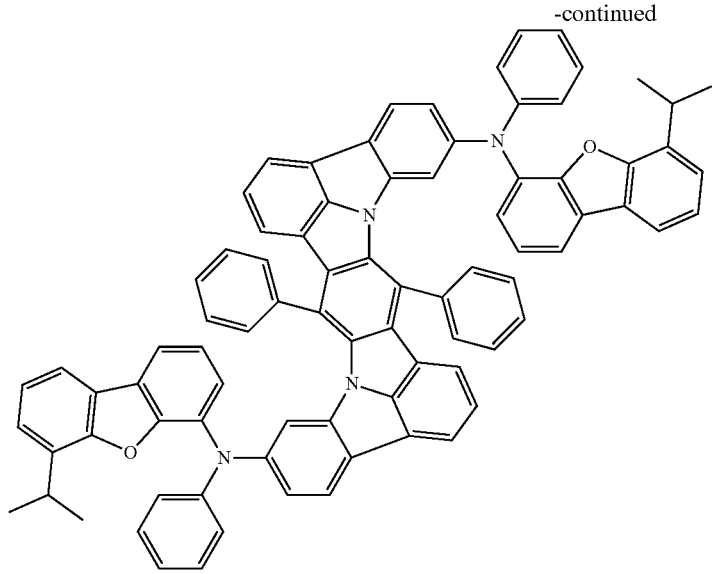
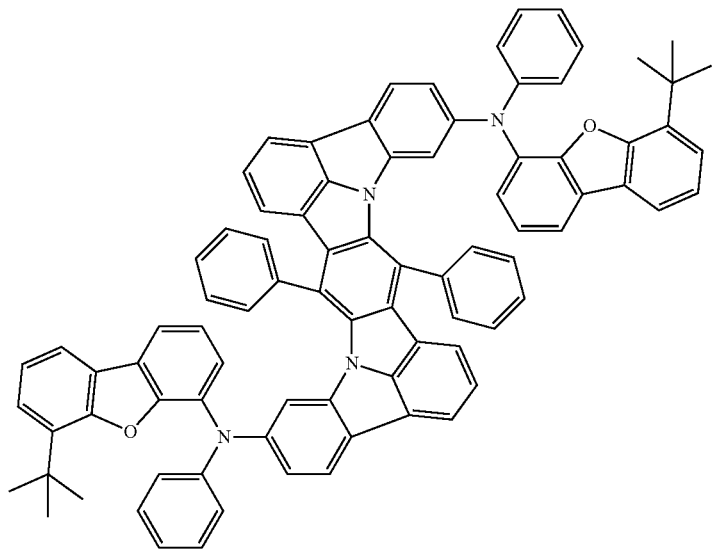
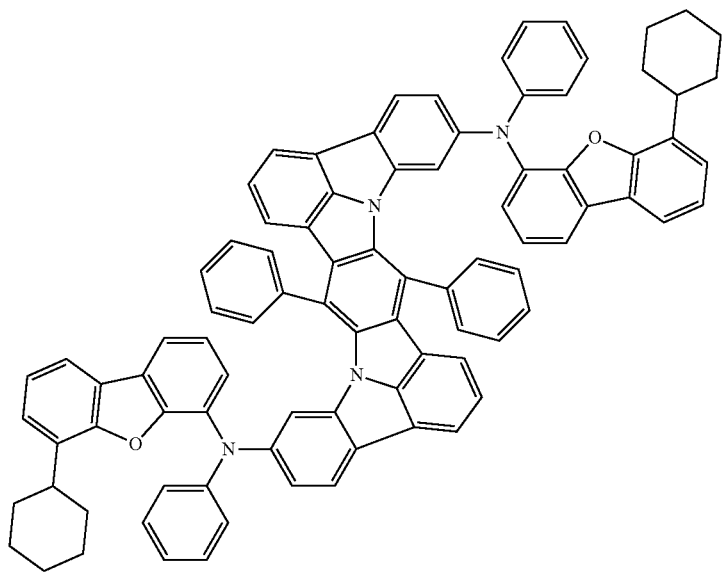

-continued
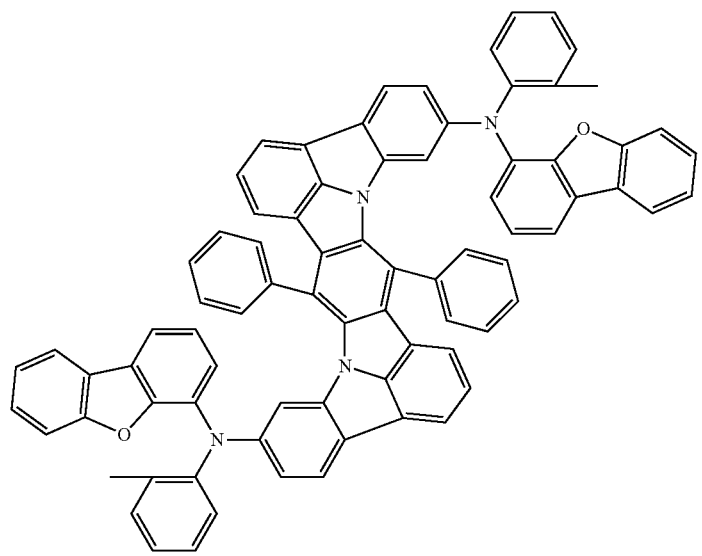
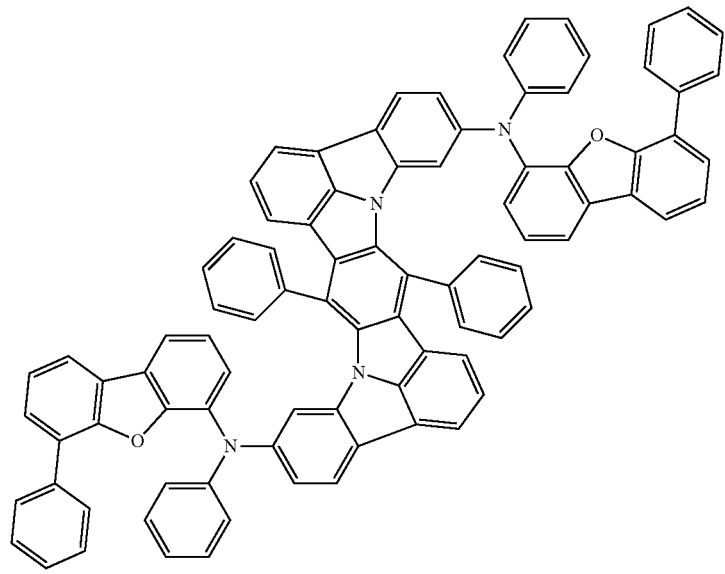
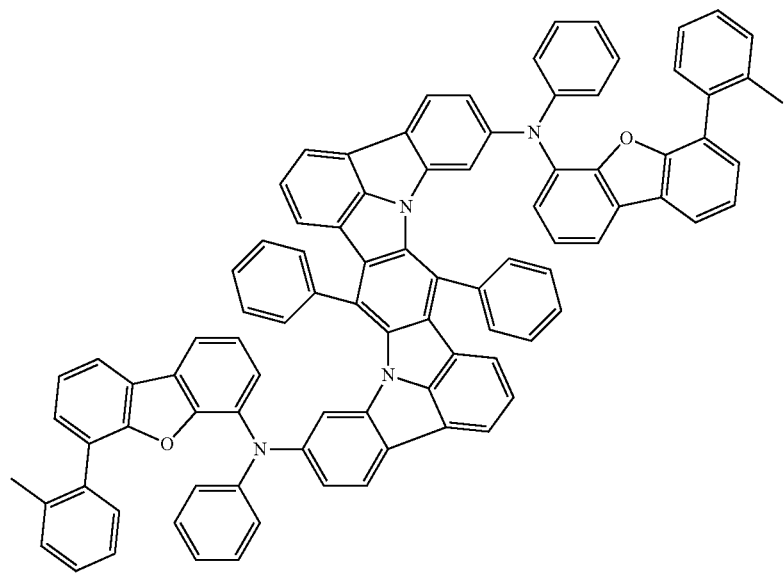

-continued
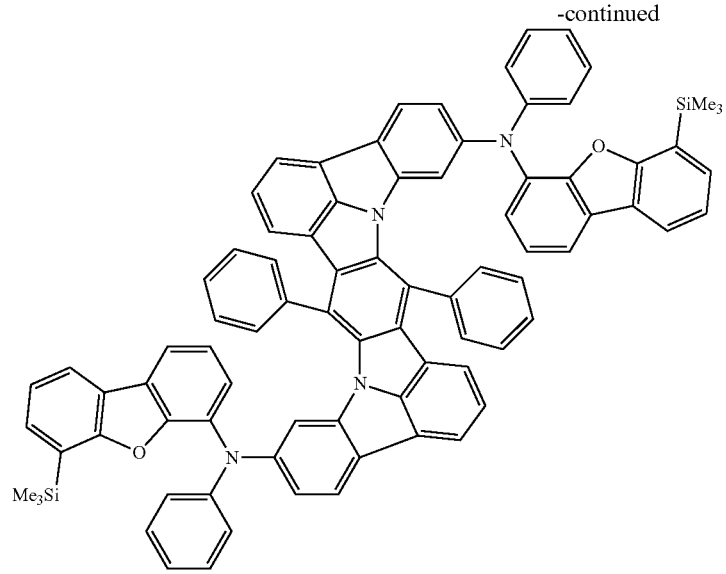
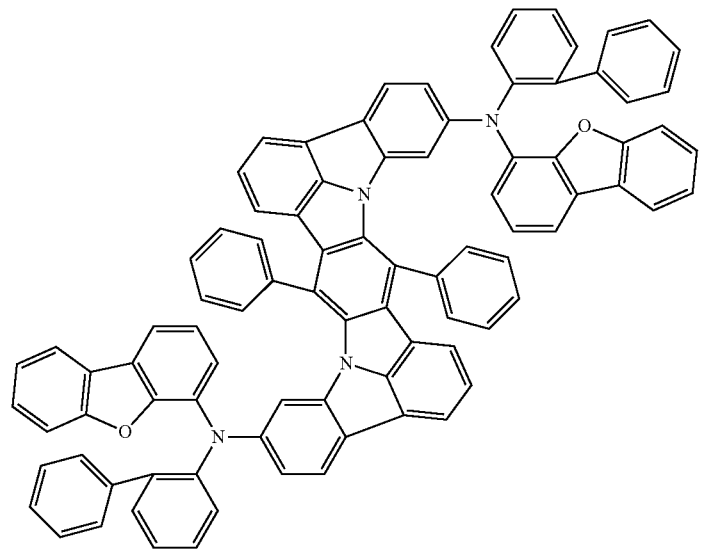
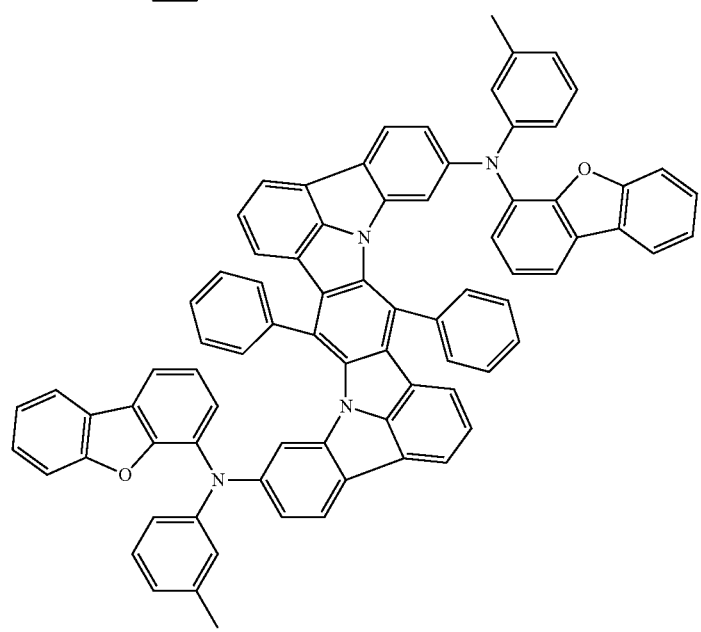

-continued
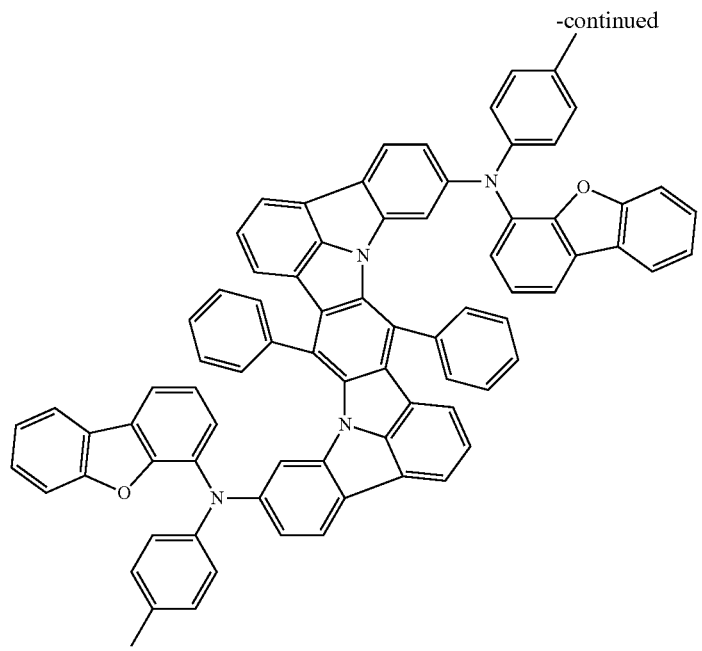
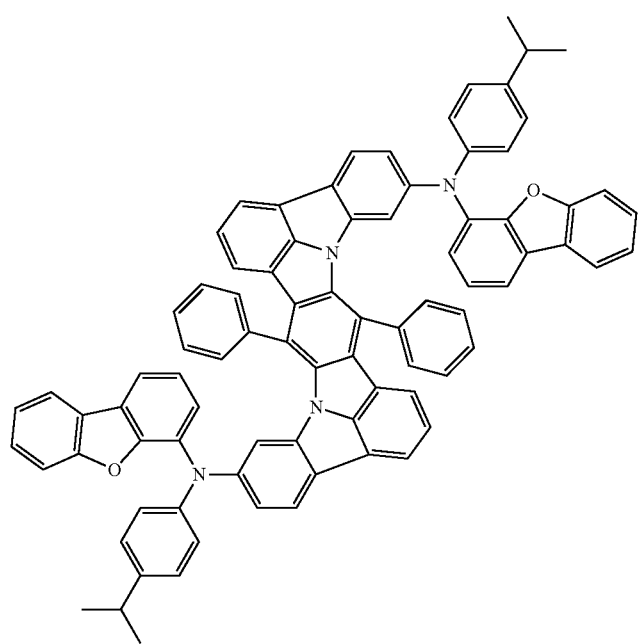

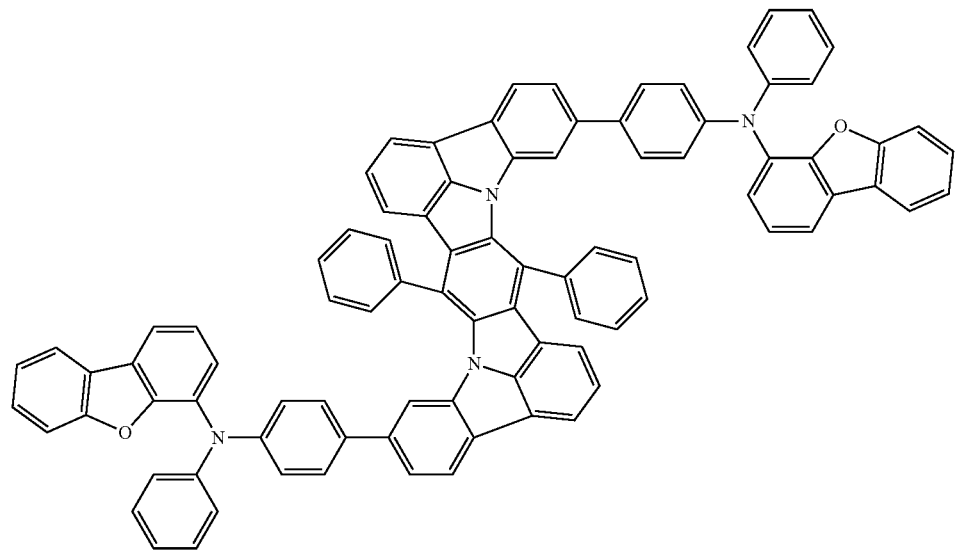
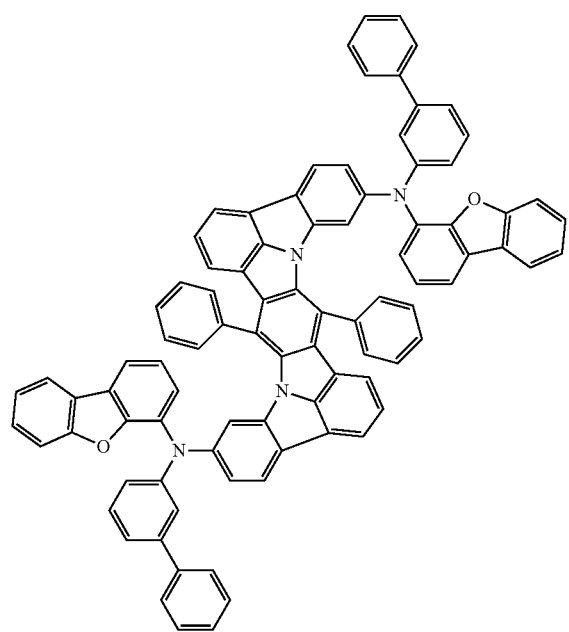

-continued
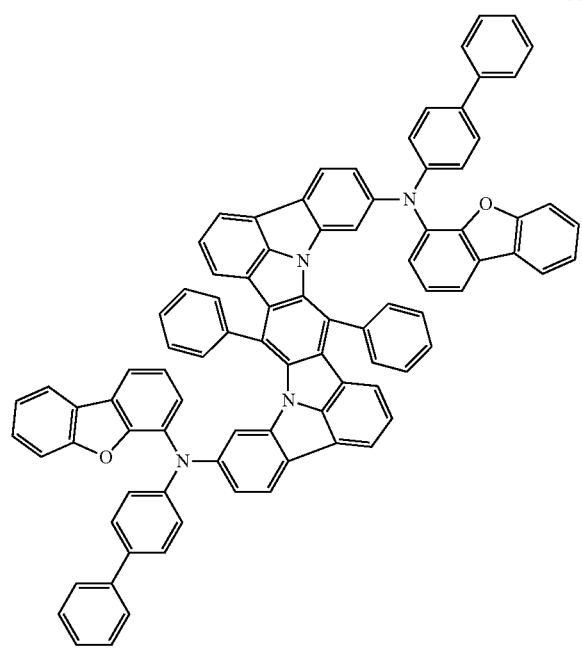
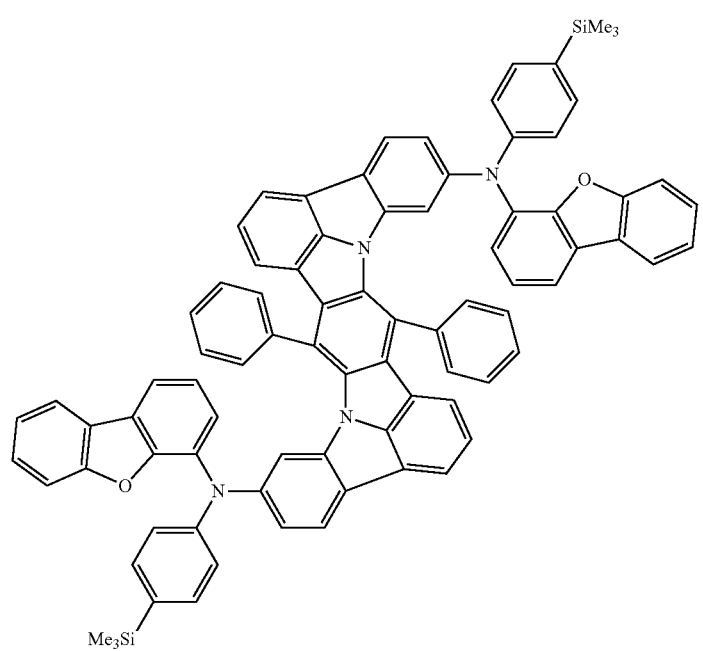

-continued
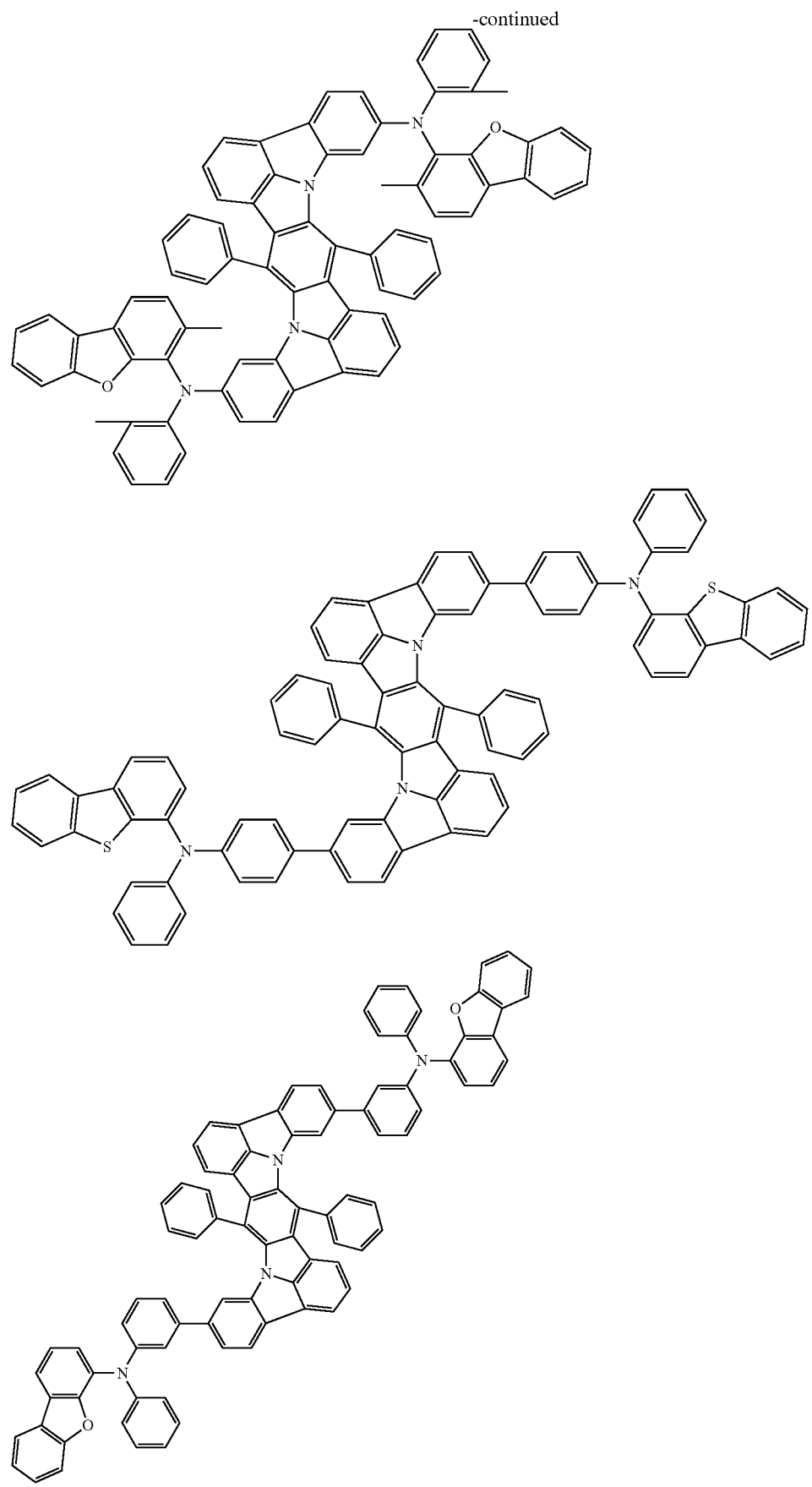

-continued
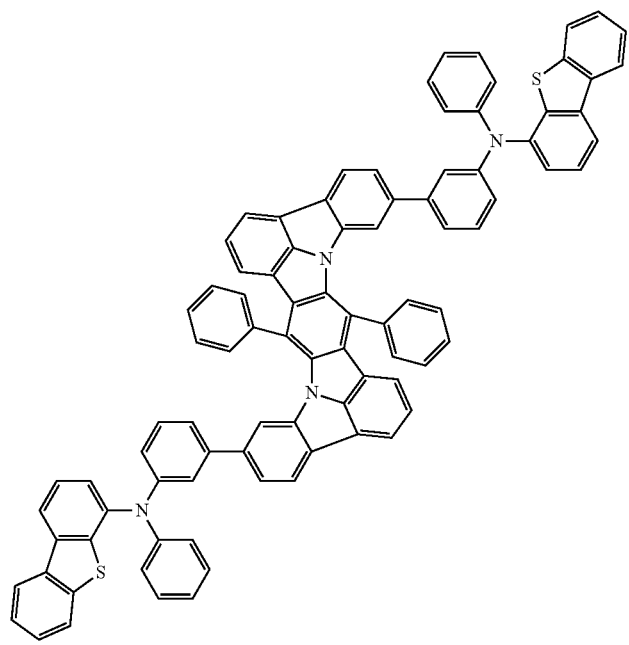
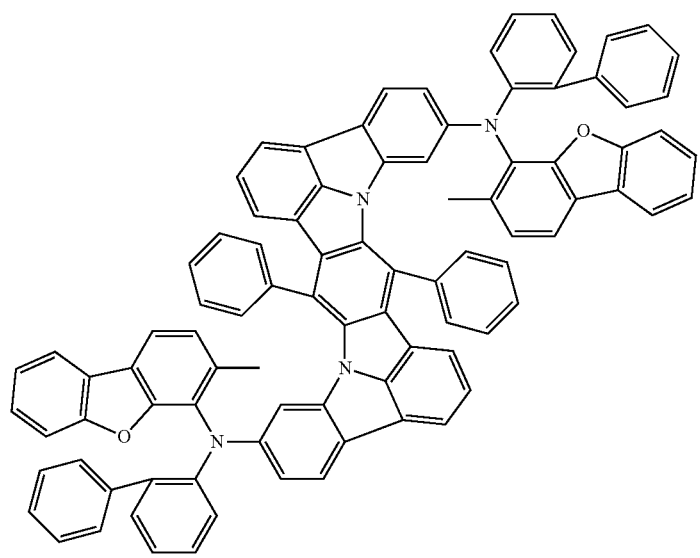

-continued
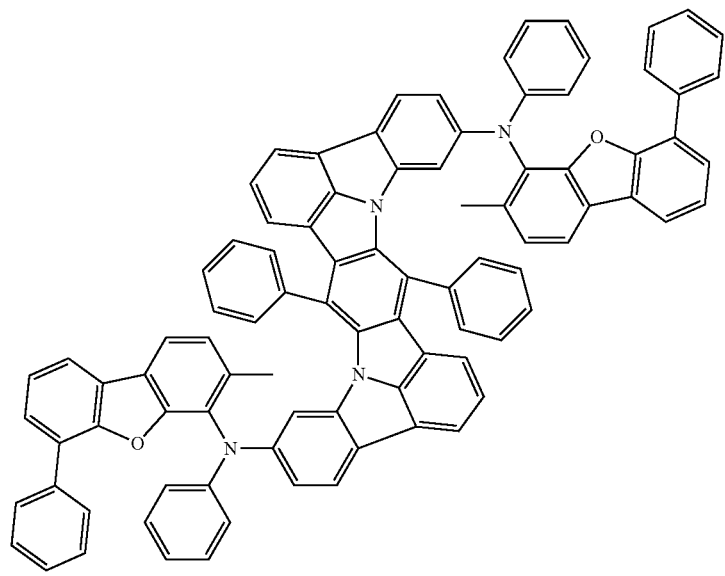
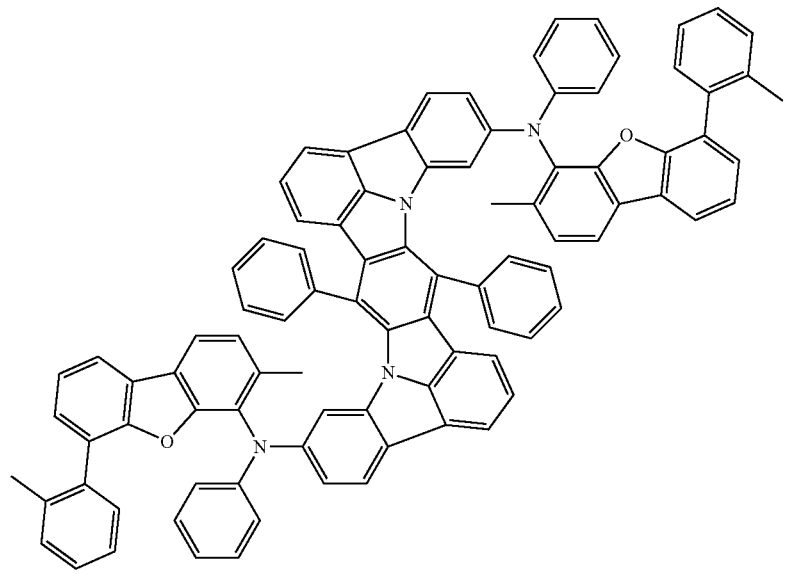
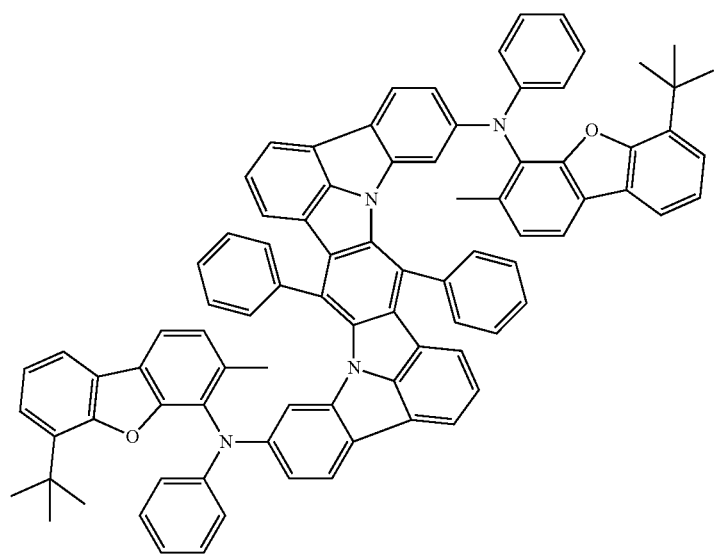

-continued
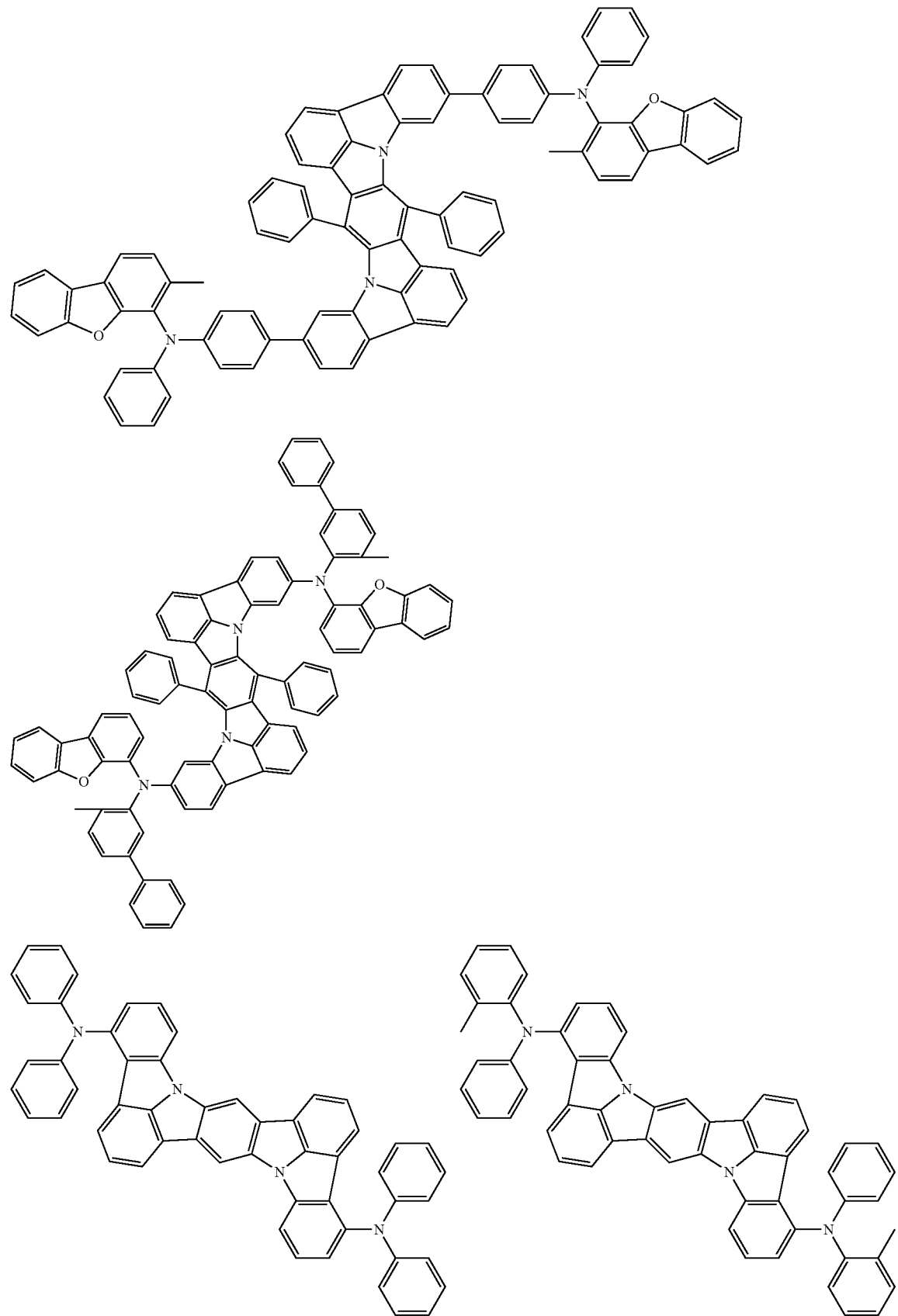

409
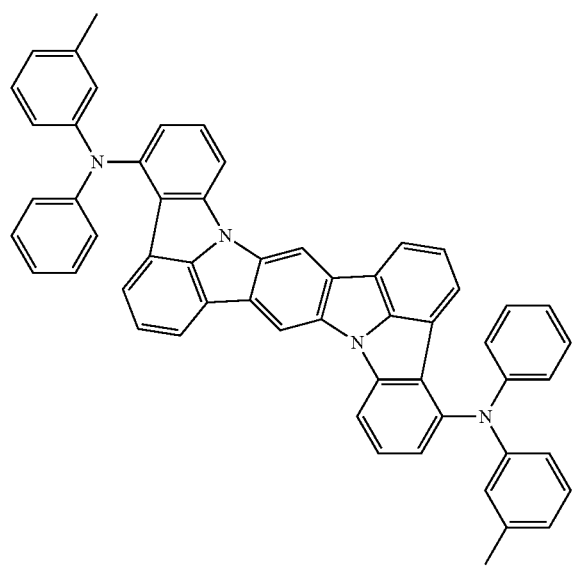
410
-continued
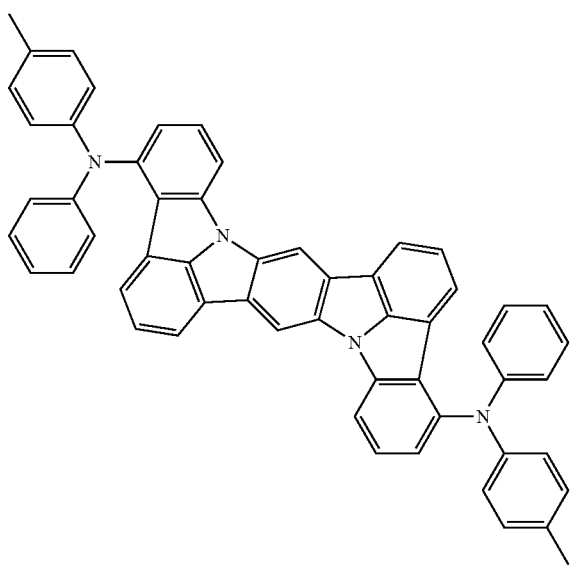
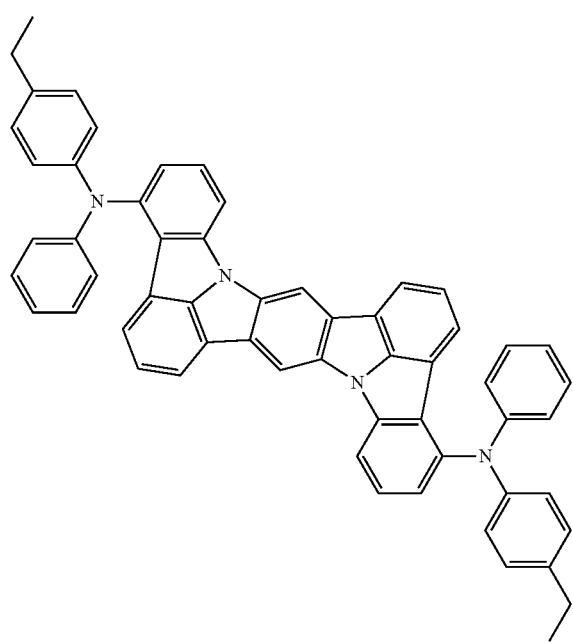

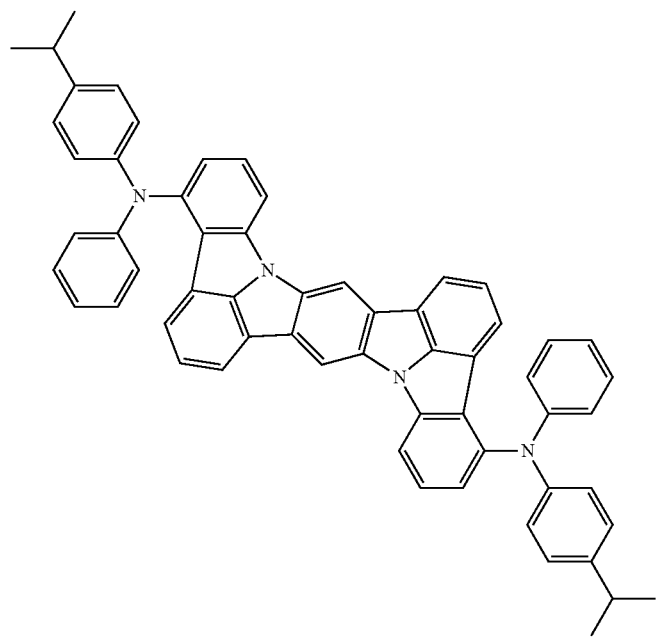
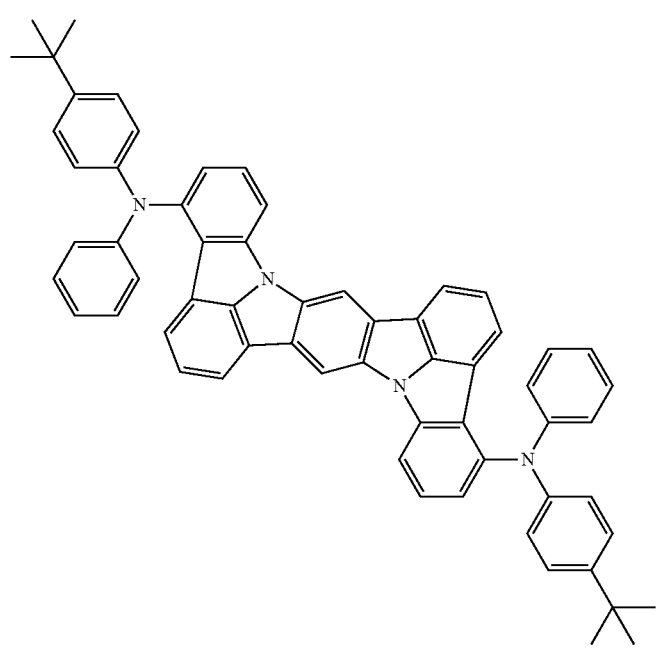

-continued
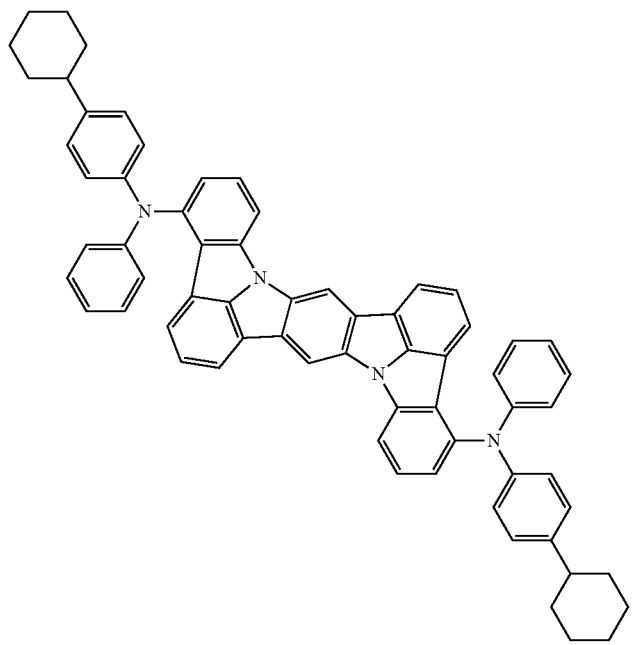
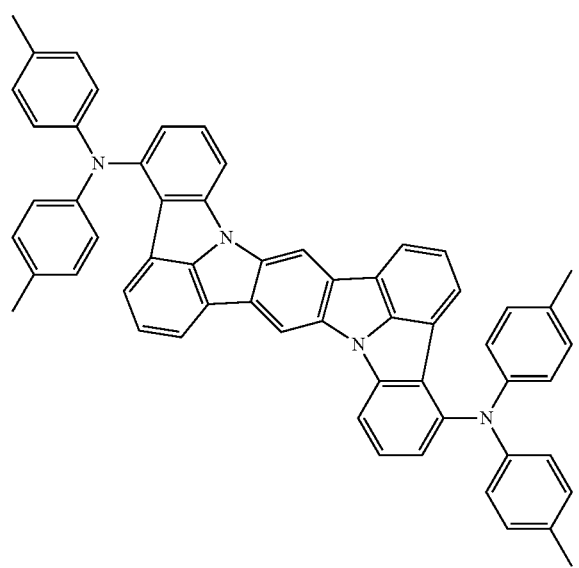

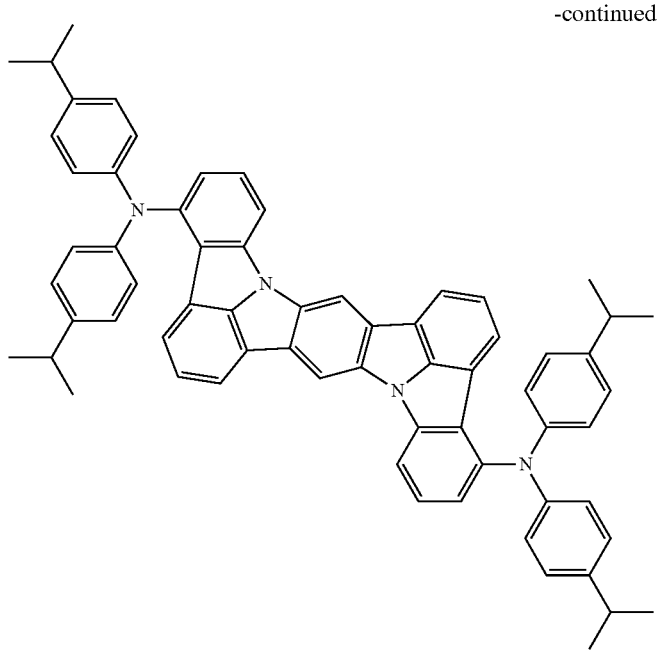
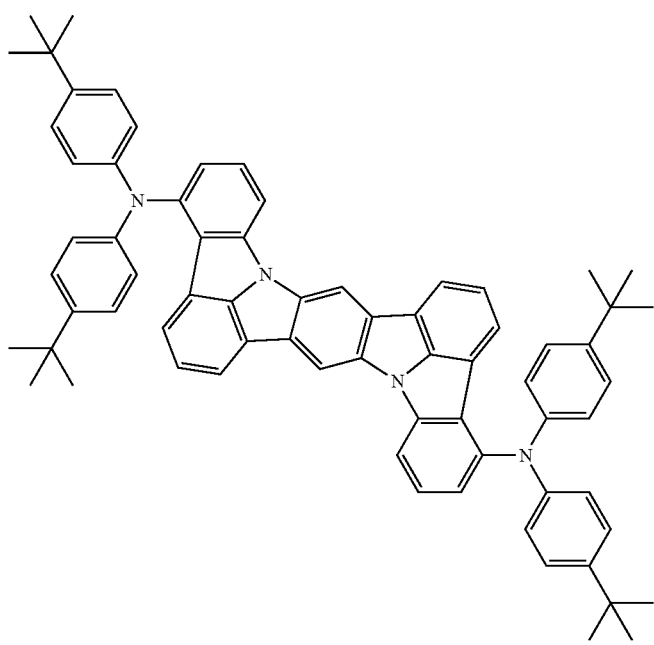

417 418
-continued
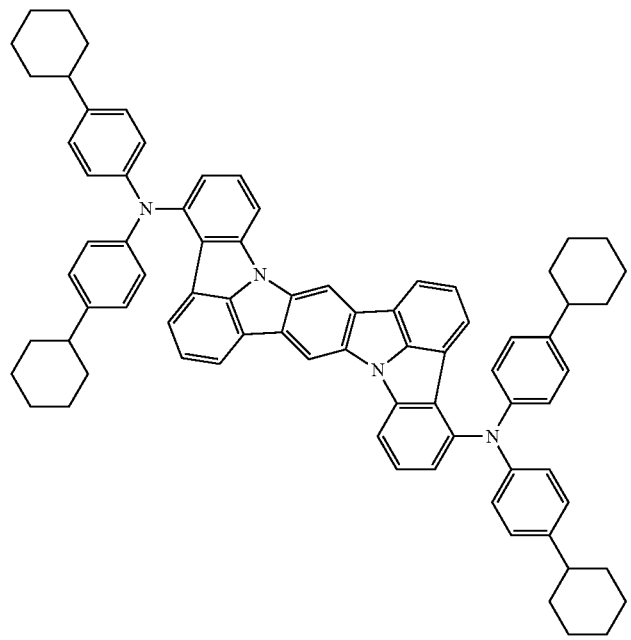
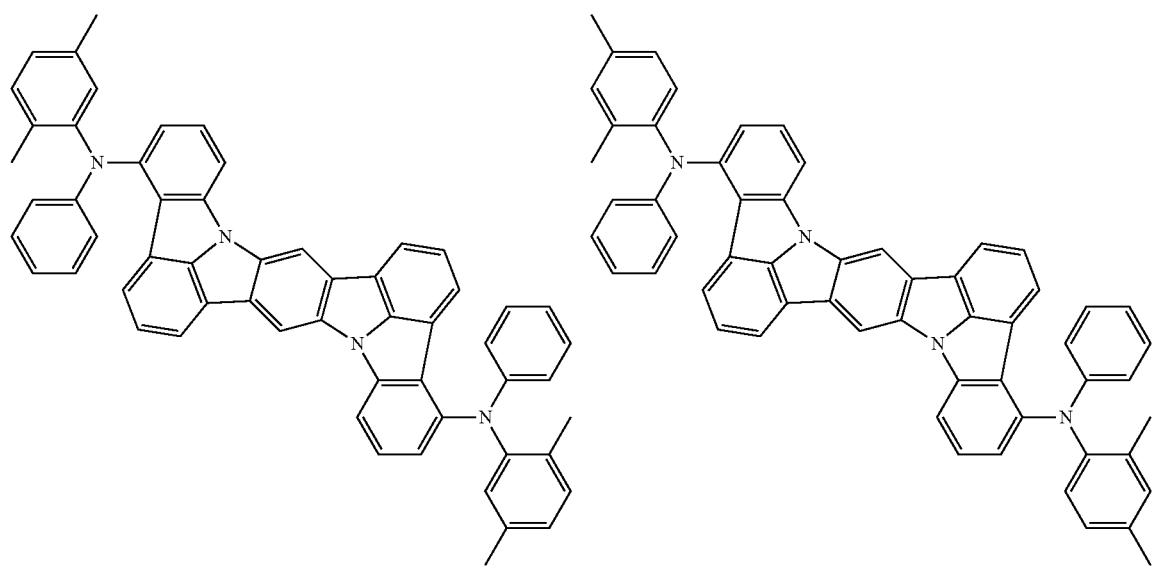

-continued
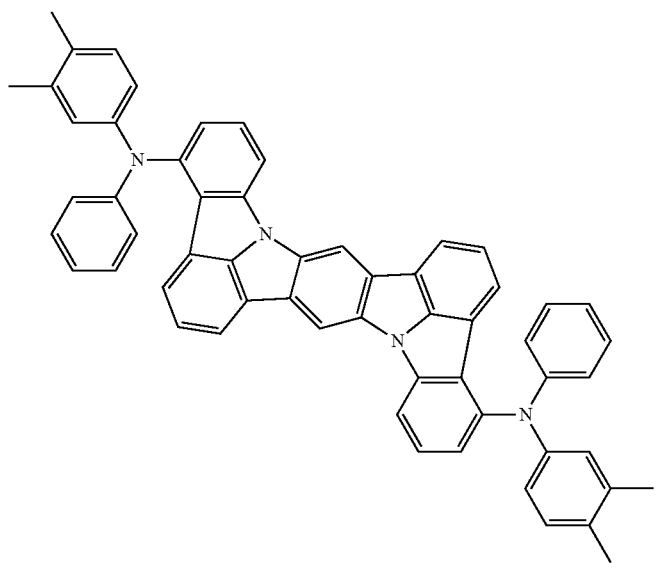
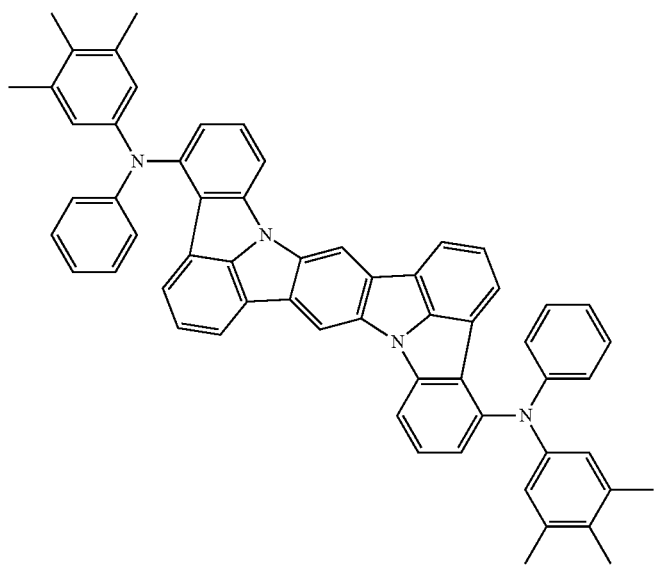

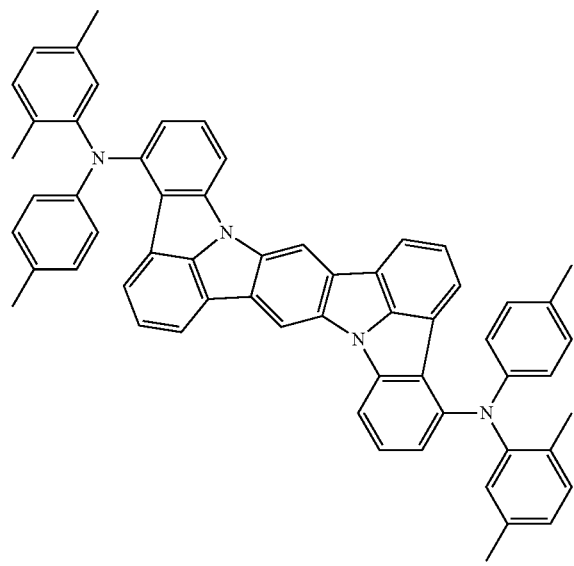
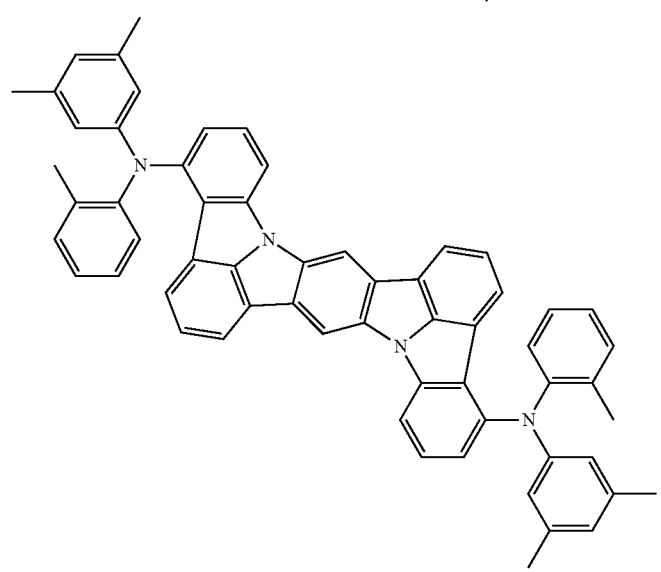
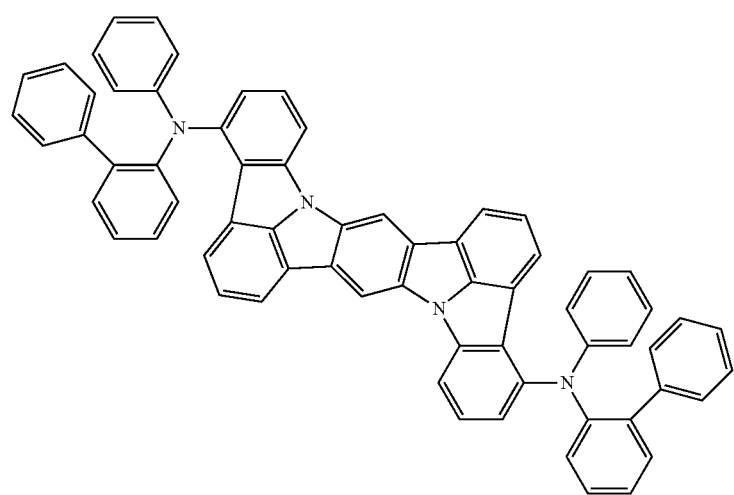

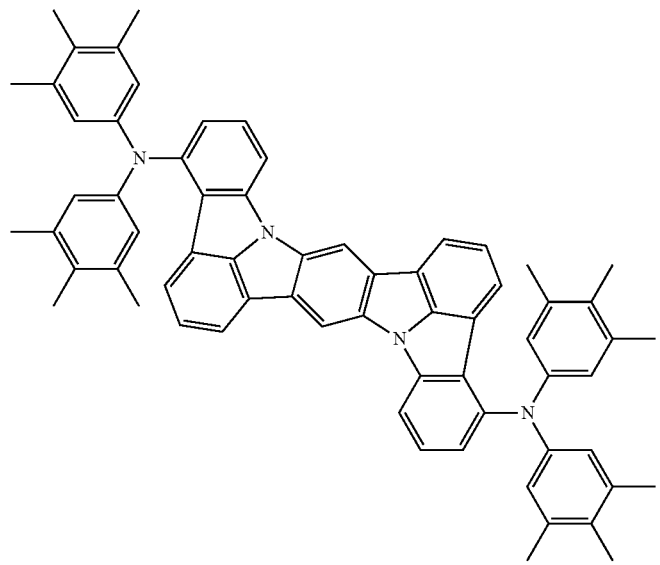
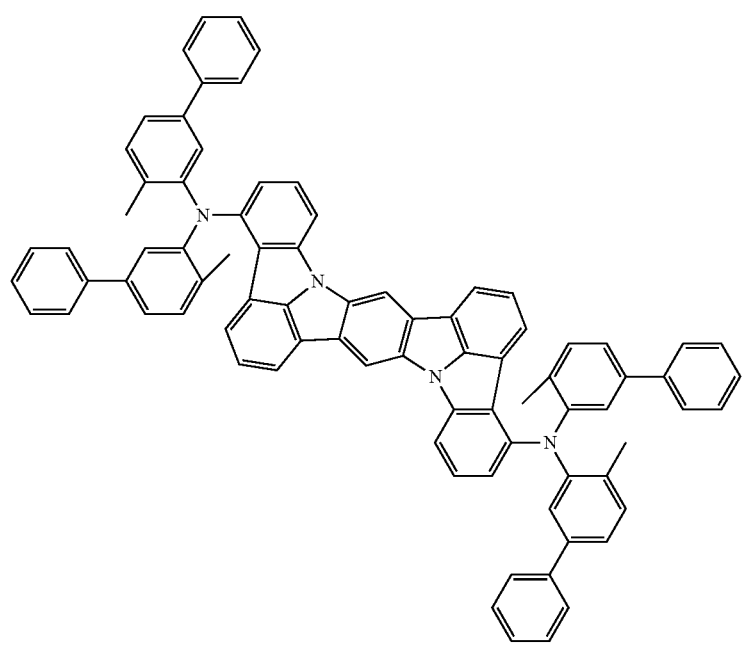

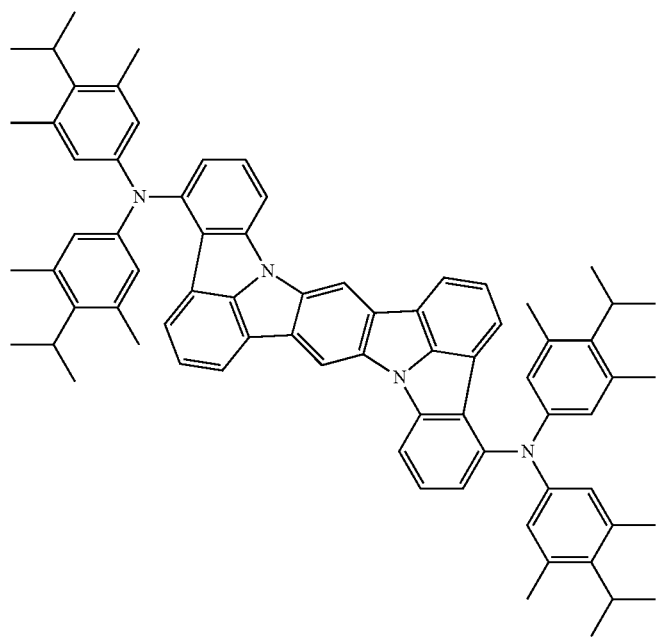
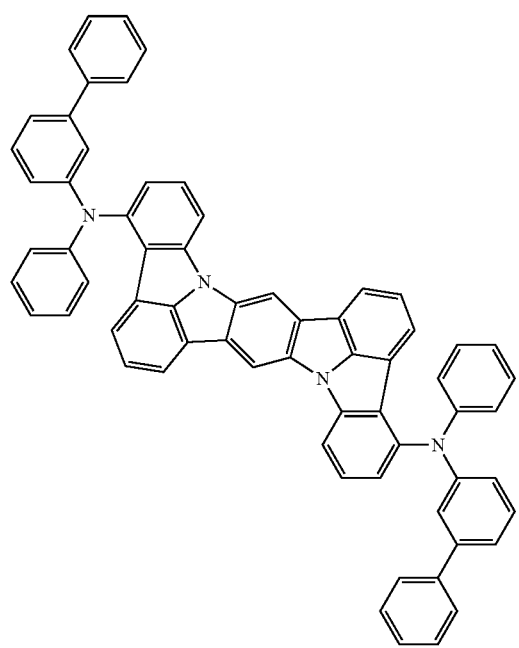

-continued
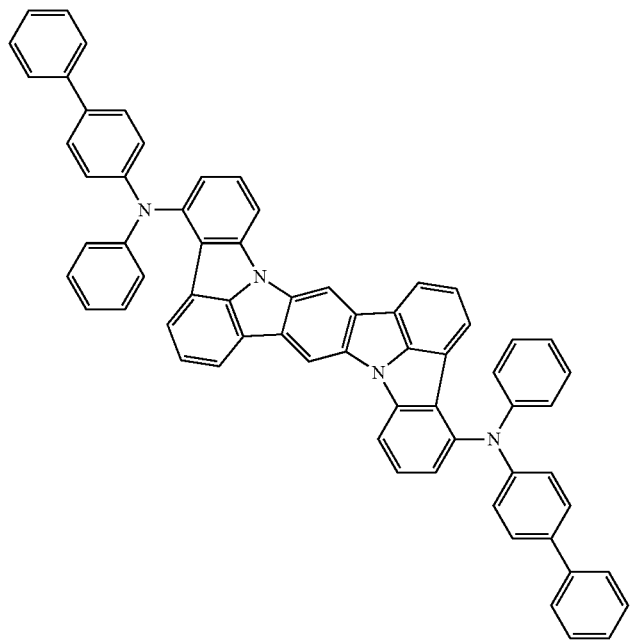
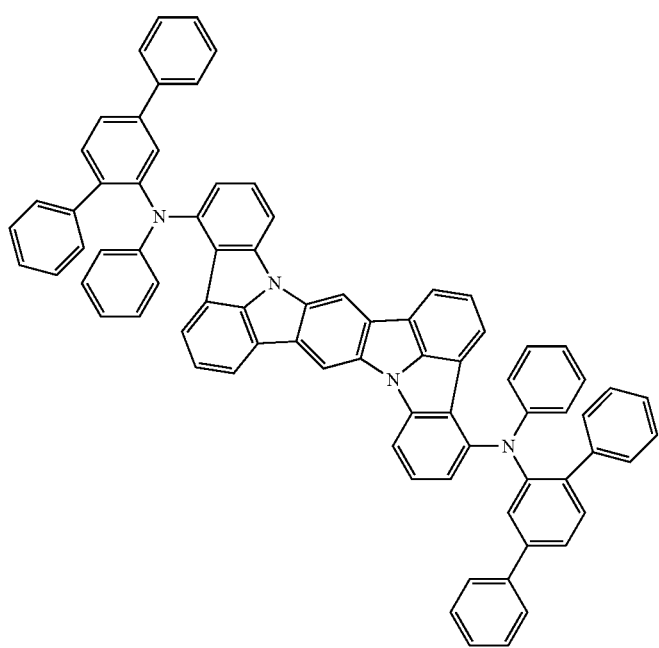

-continued
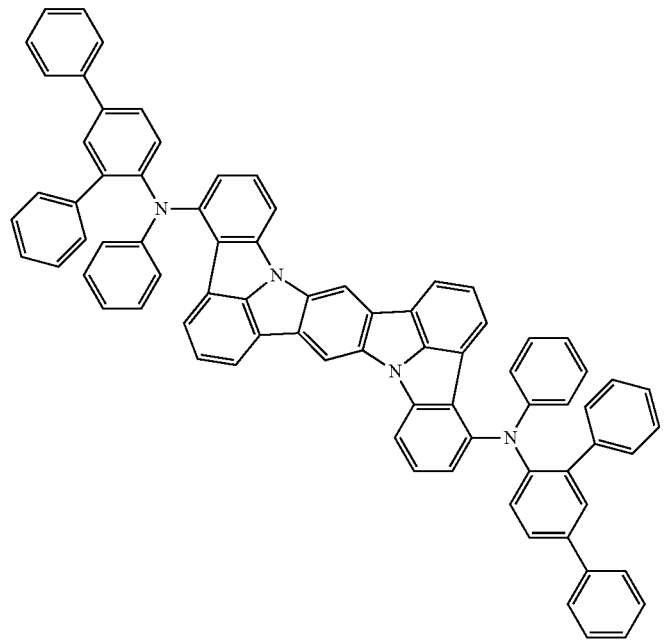
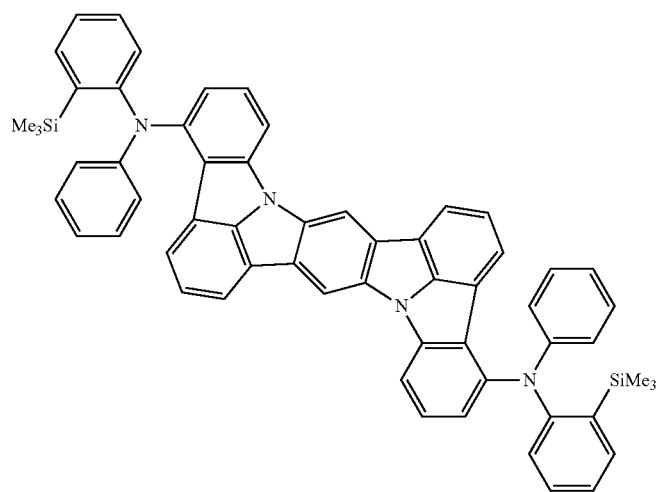
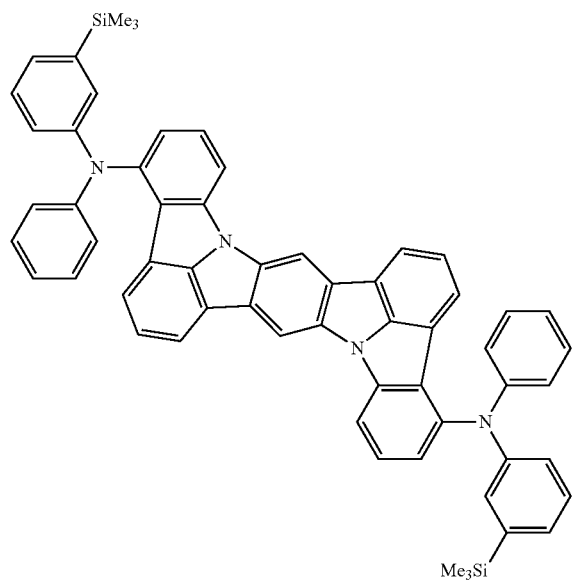

431
432
-continued
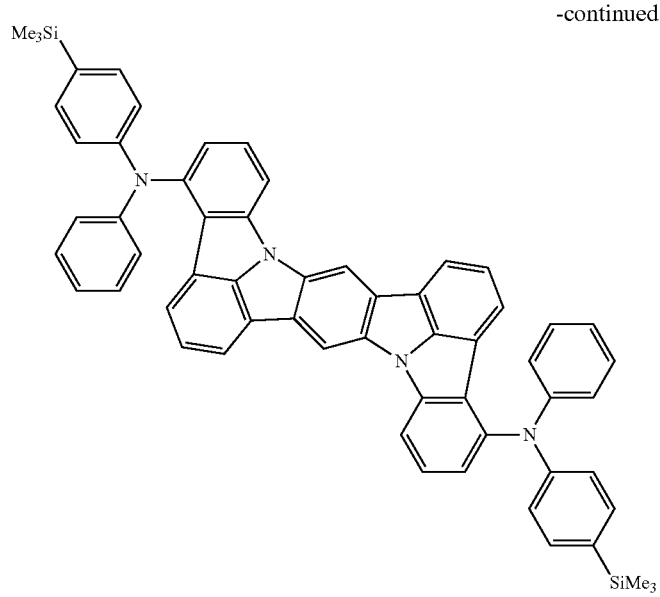
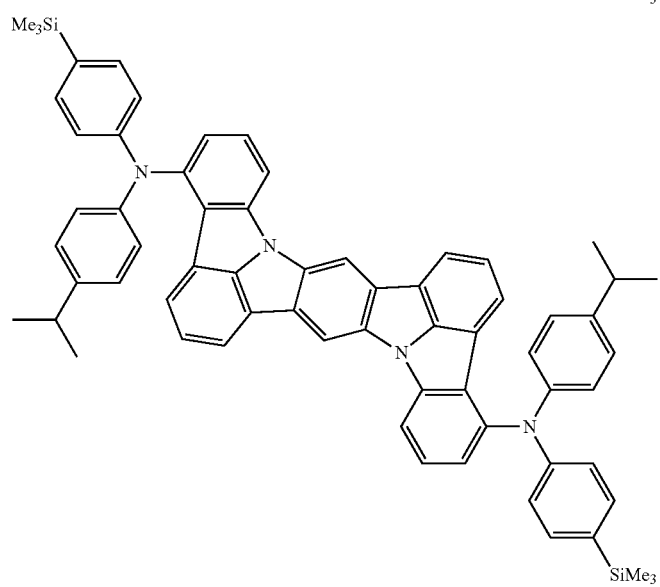
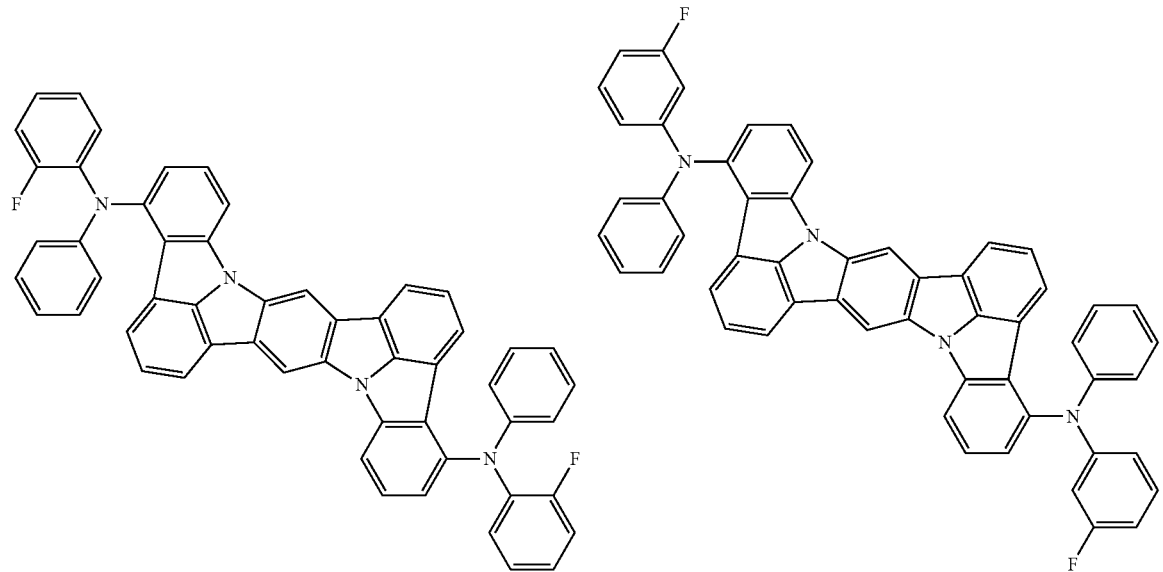

433 434
-continued
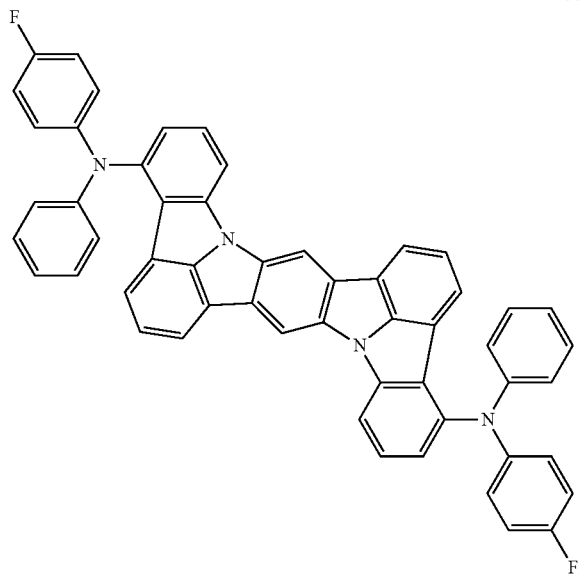
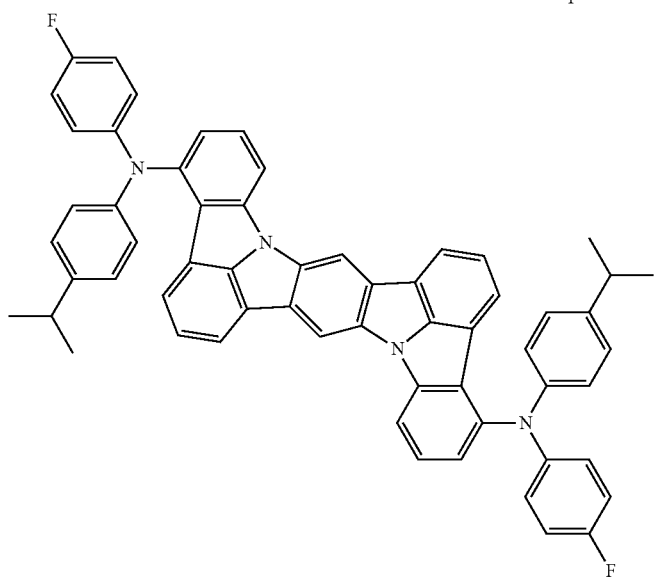
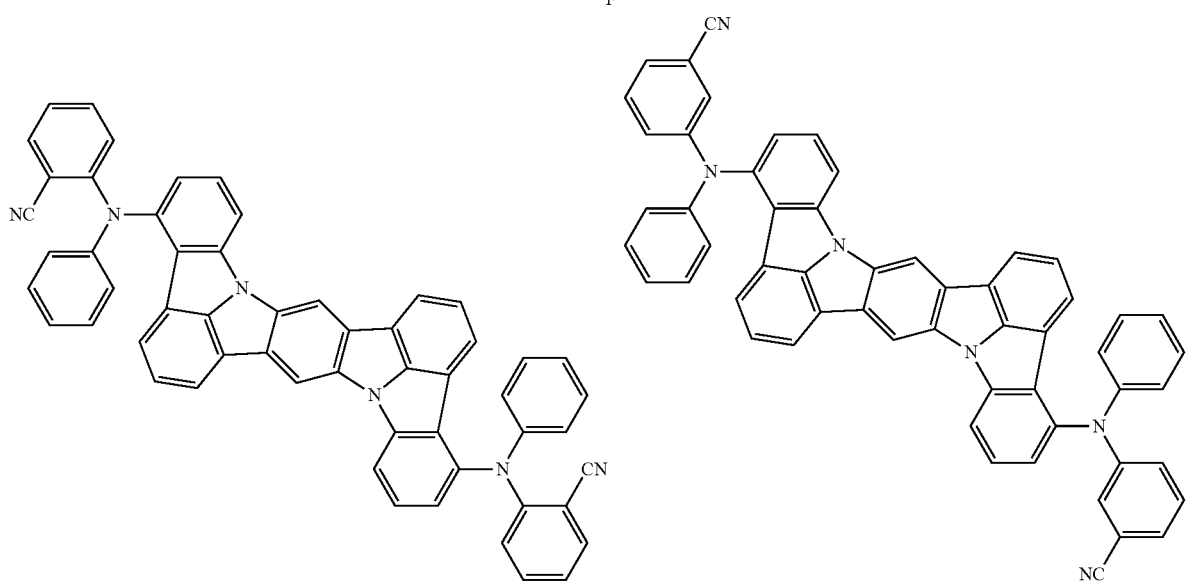

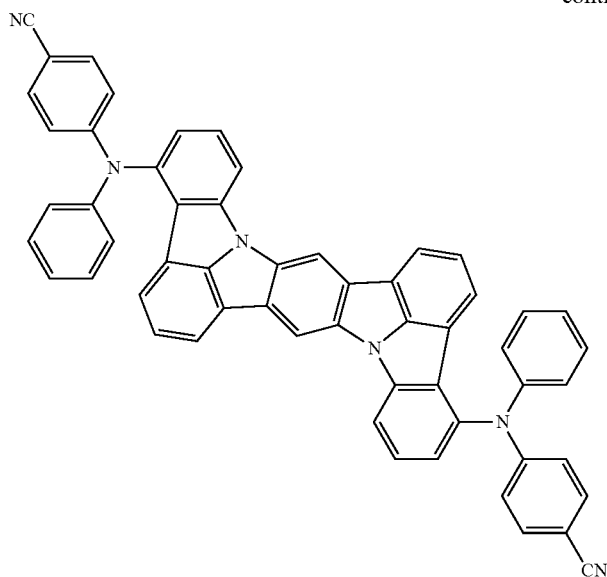
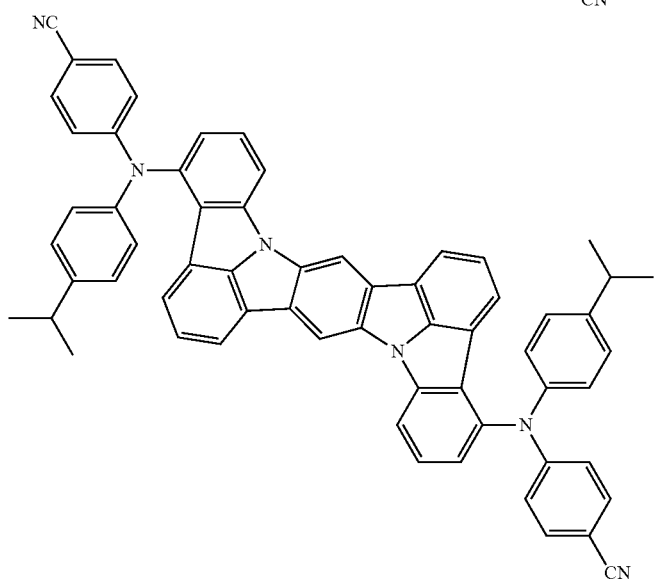
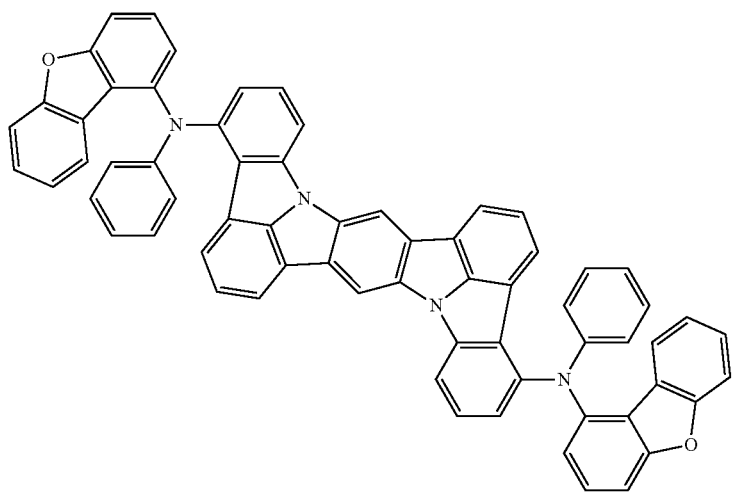

-continued
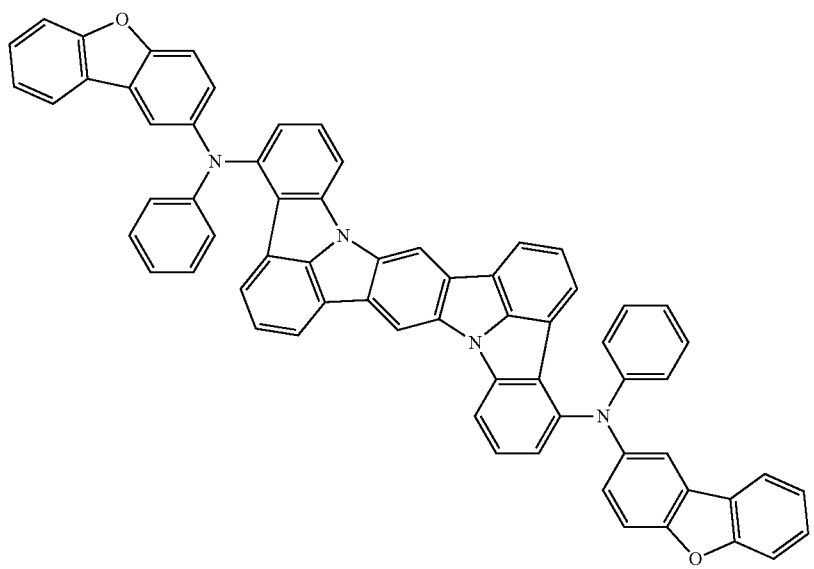
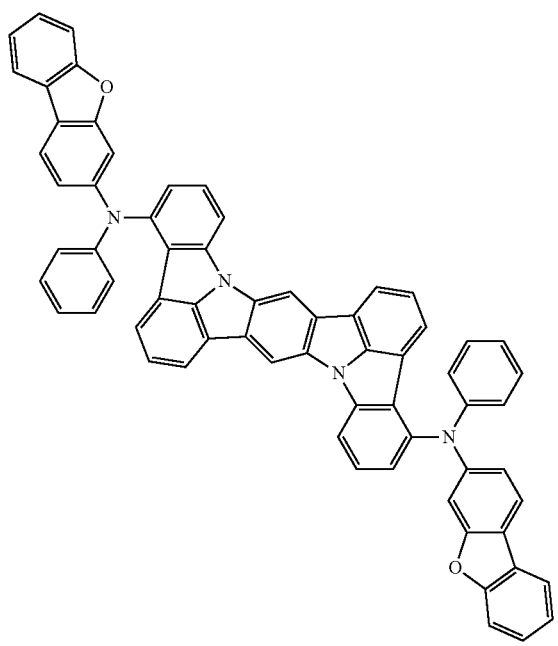
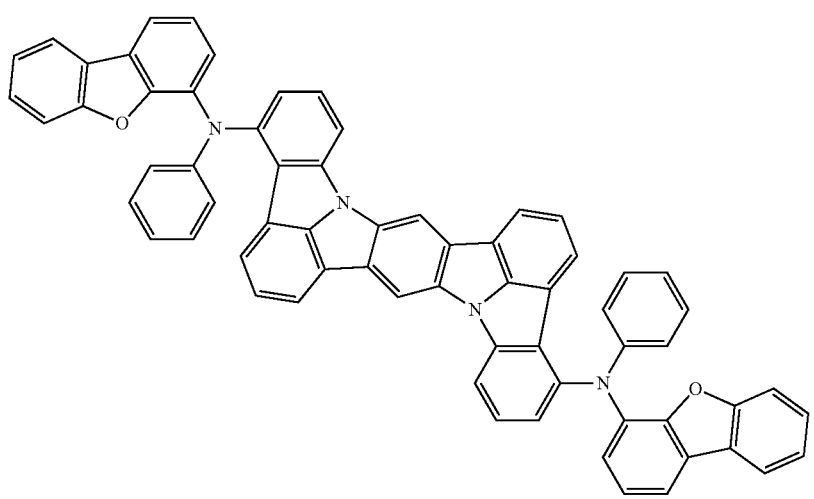

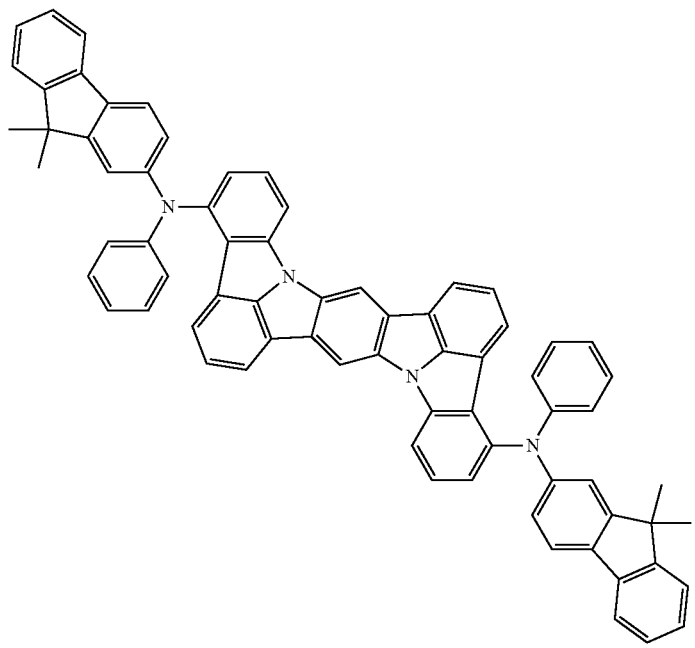
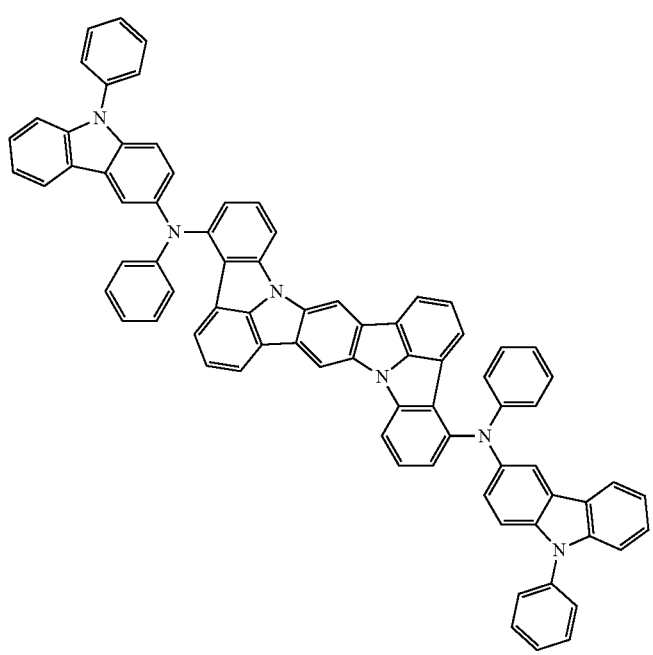

-continued
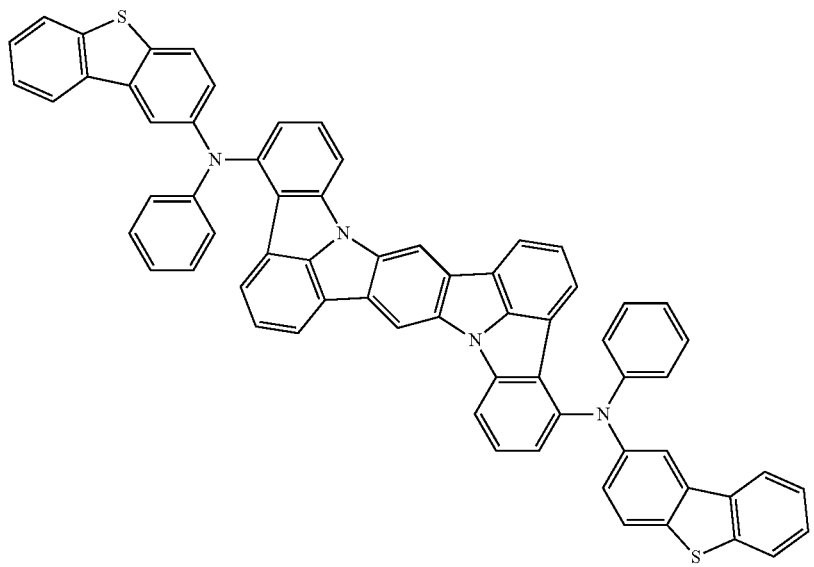
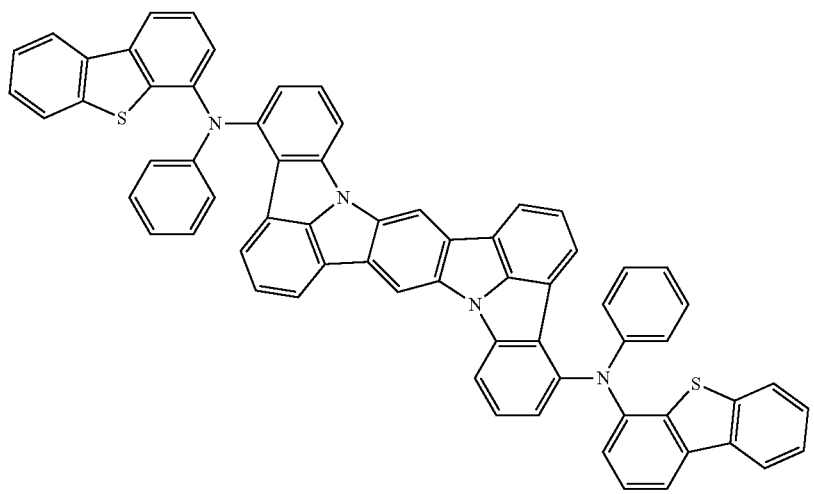
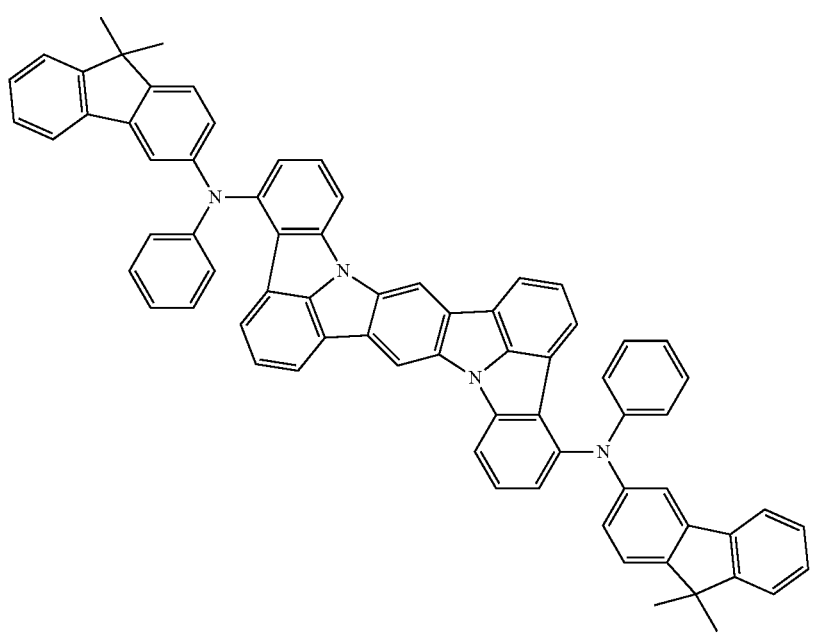

-continued
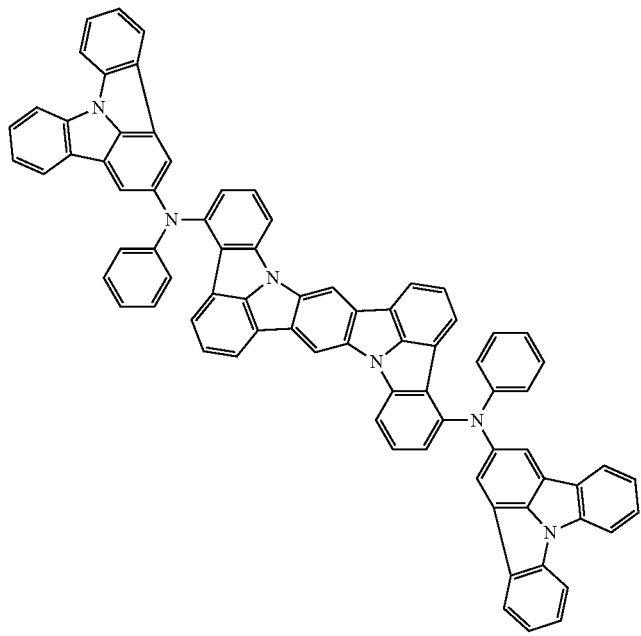
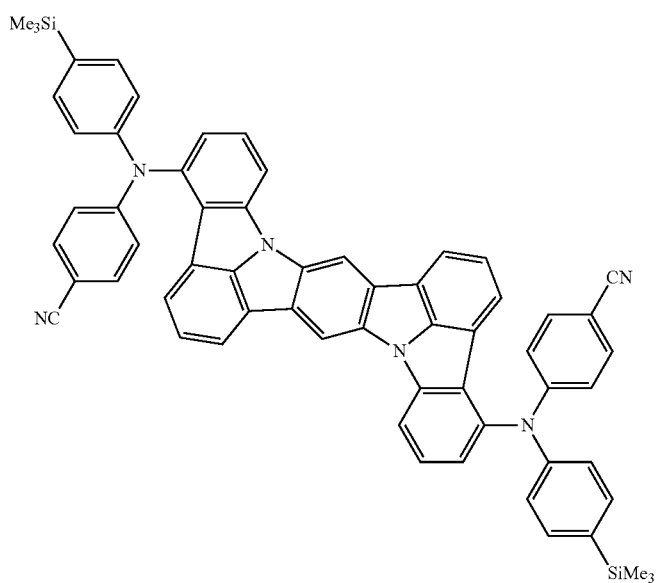
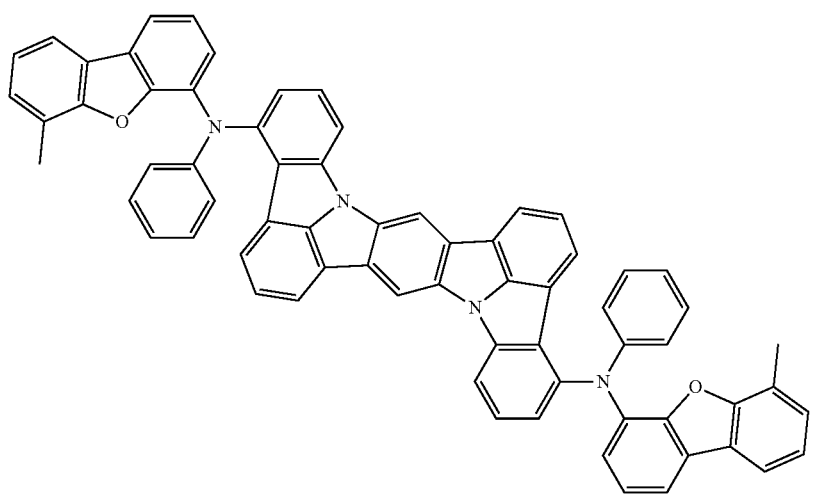

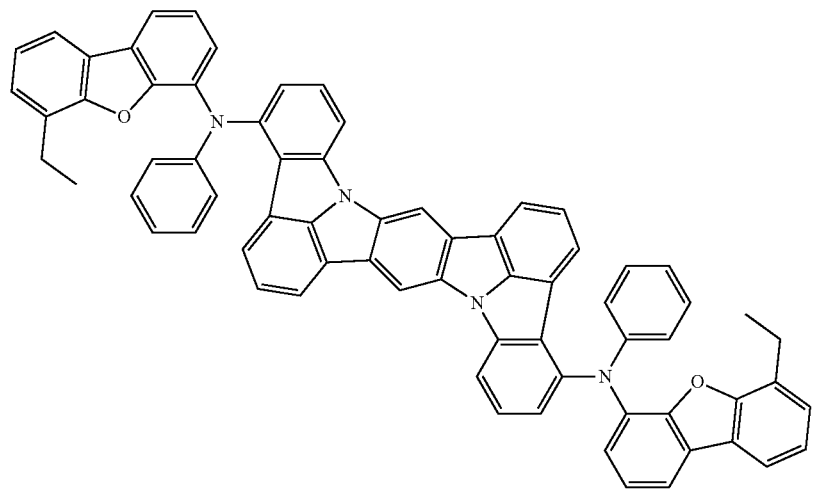
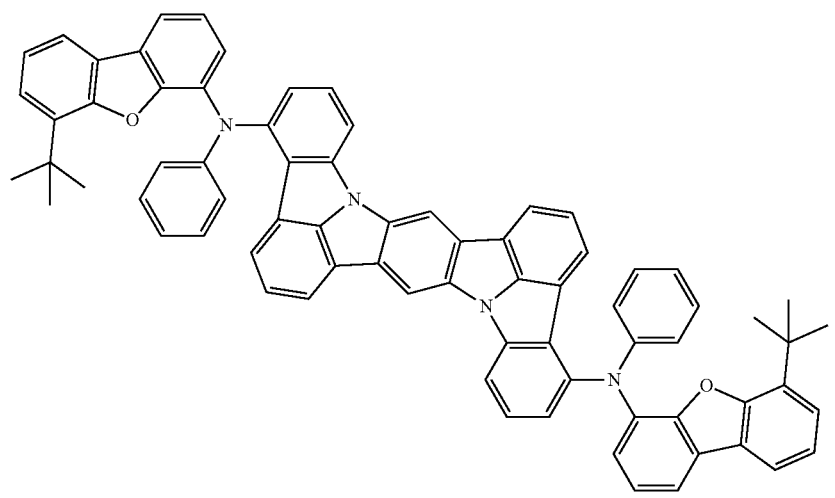

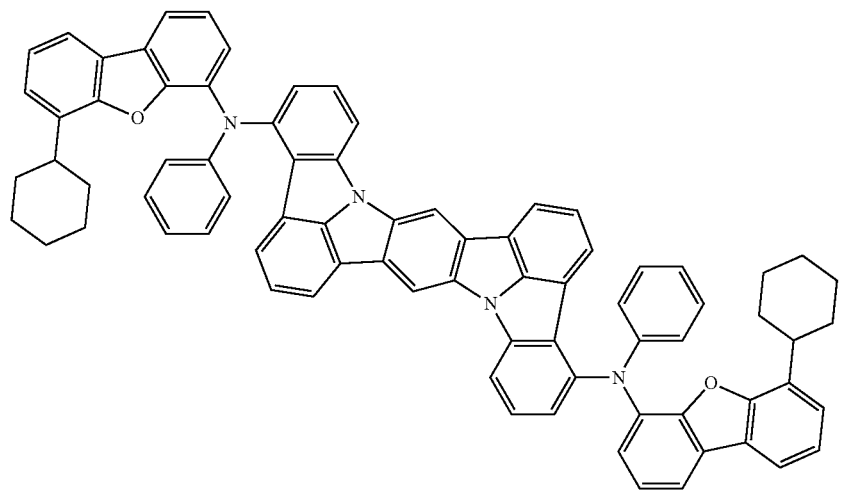
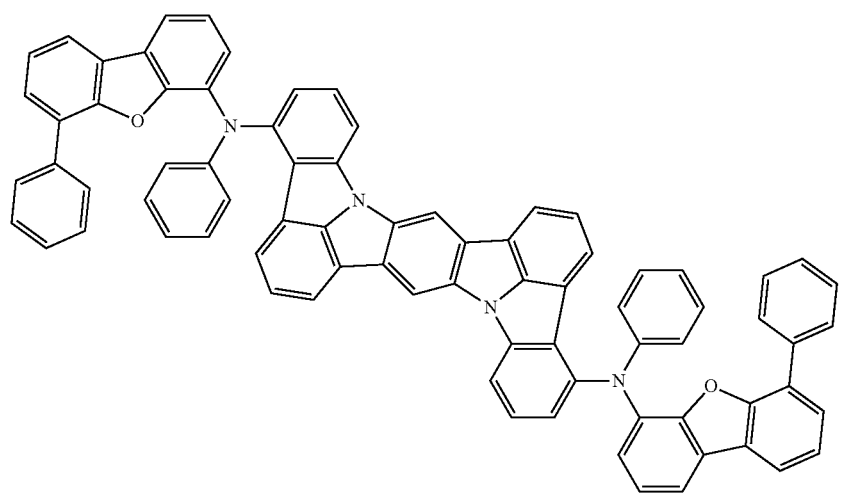
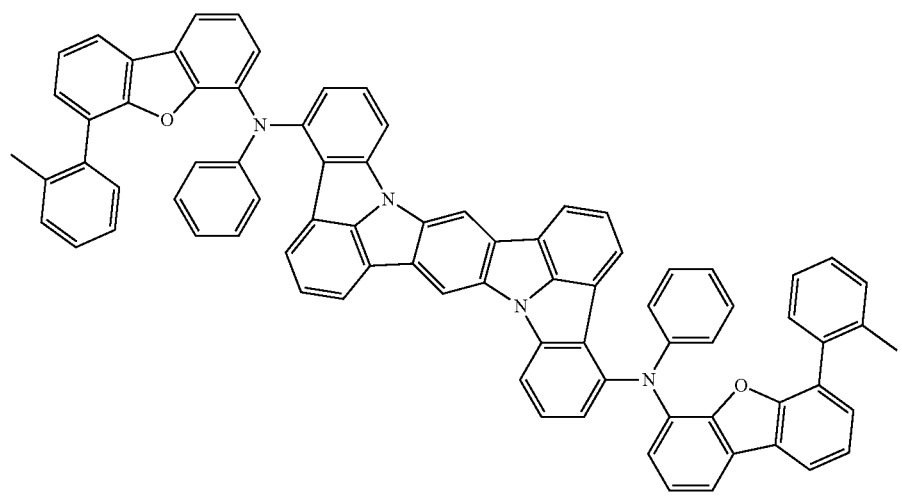

-continued
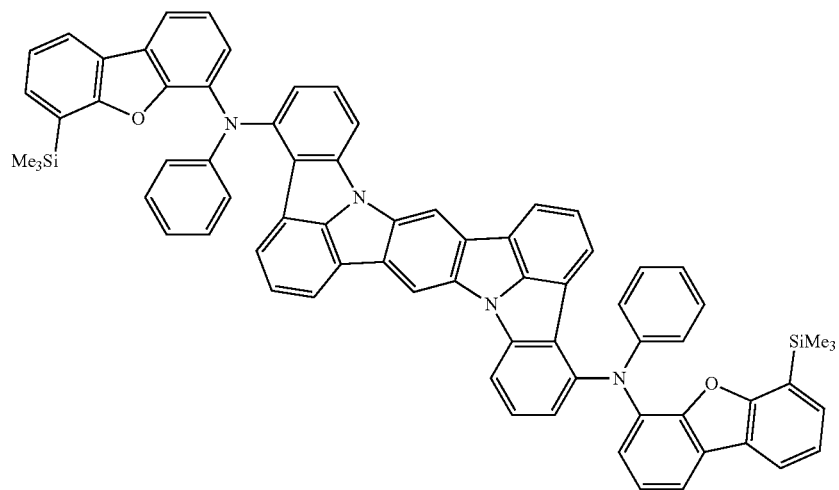
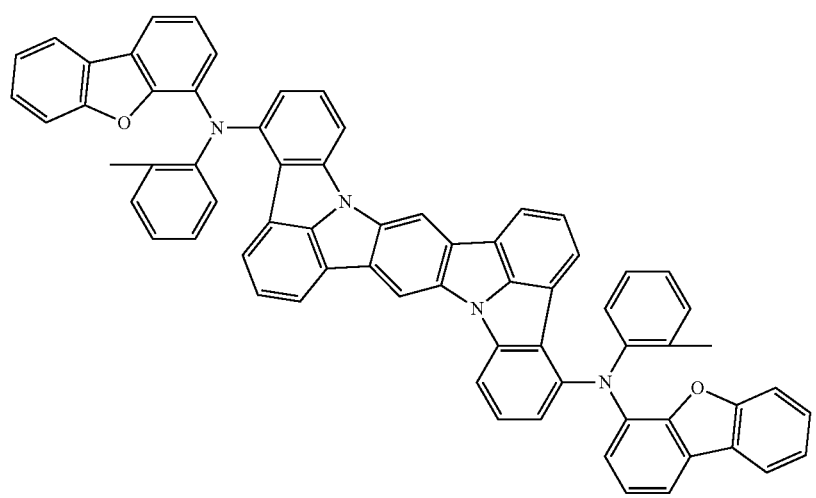
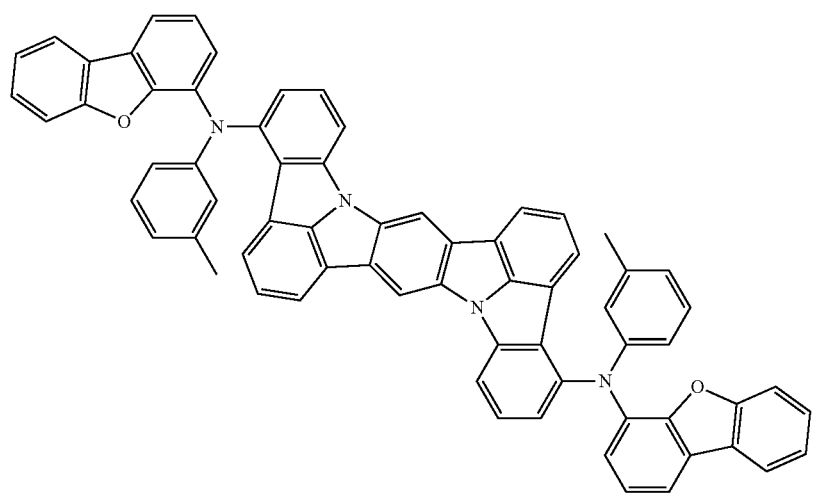

-continued
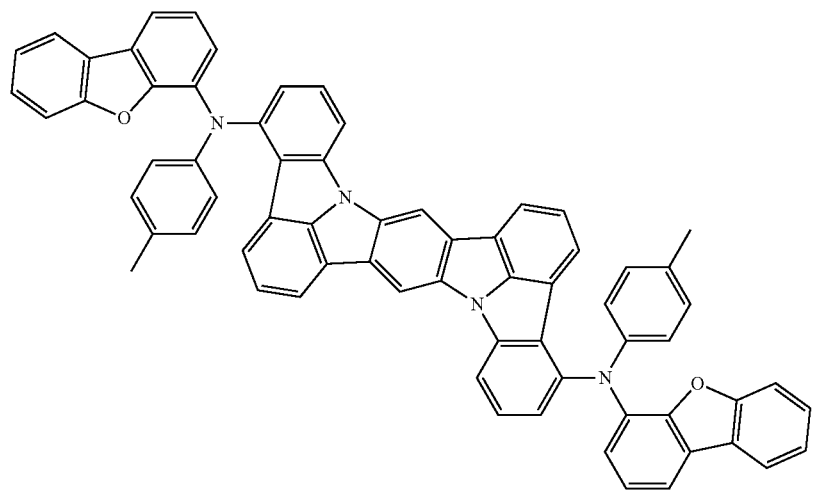
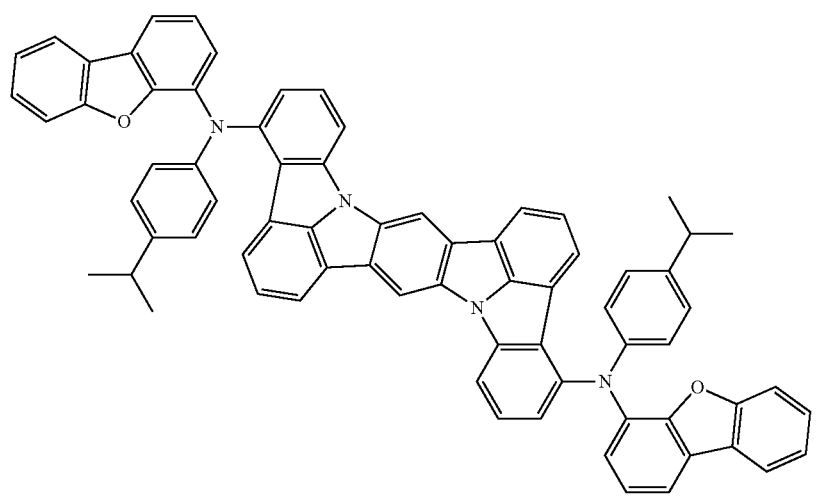
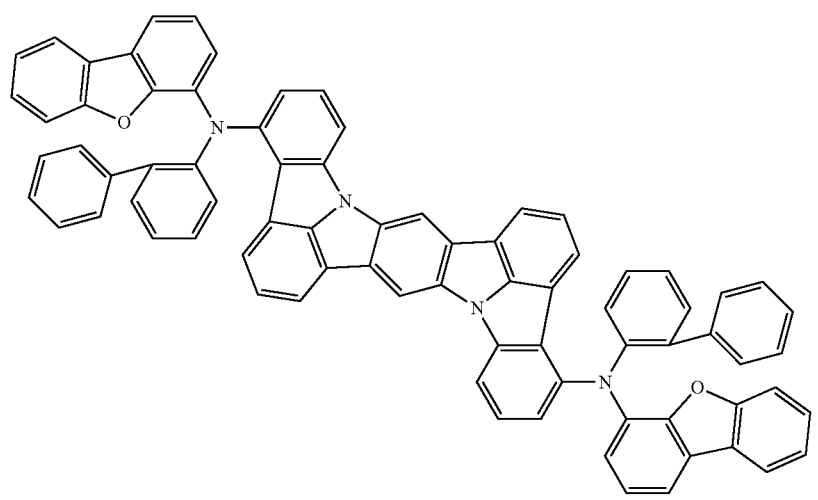

-continued
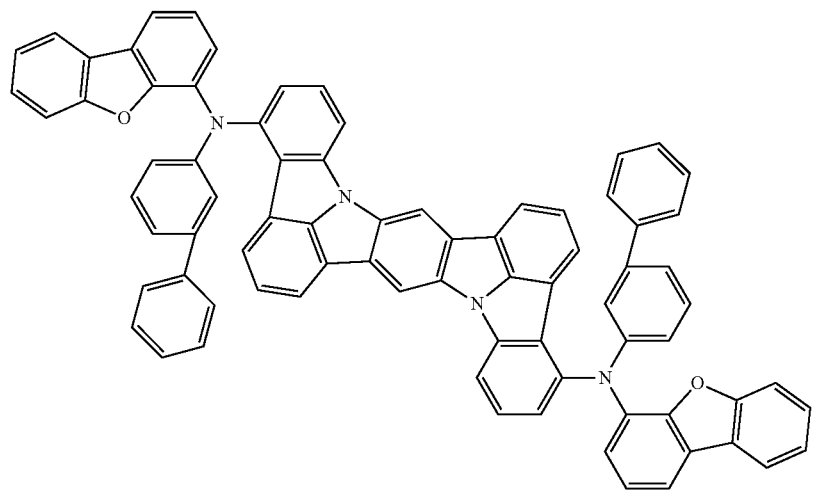
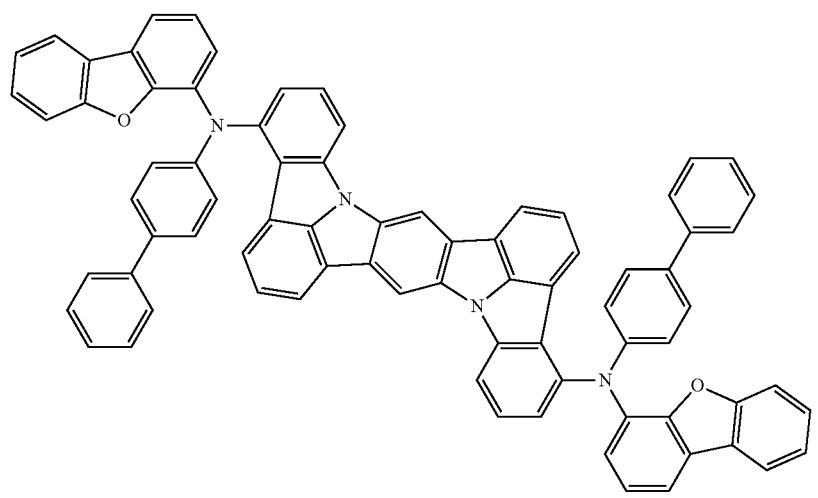
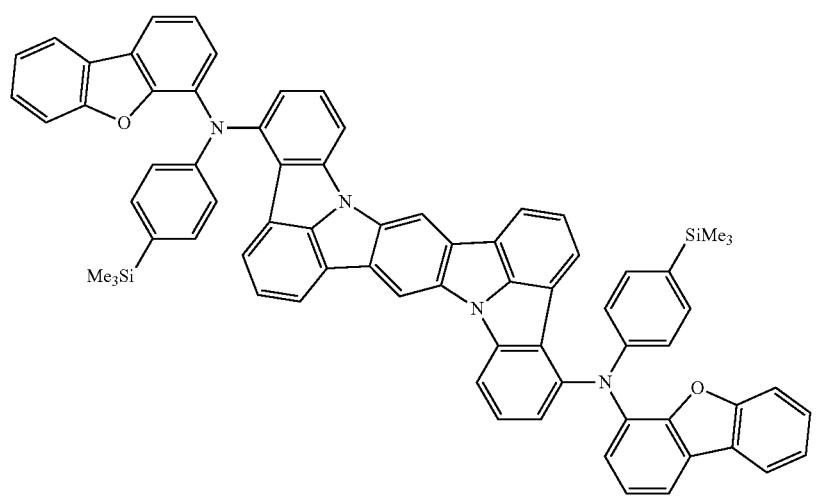

-continued
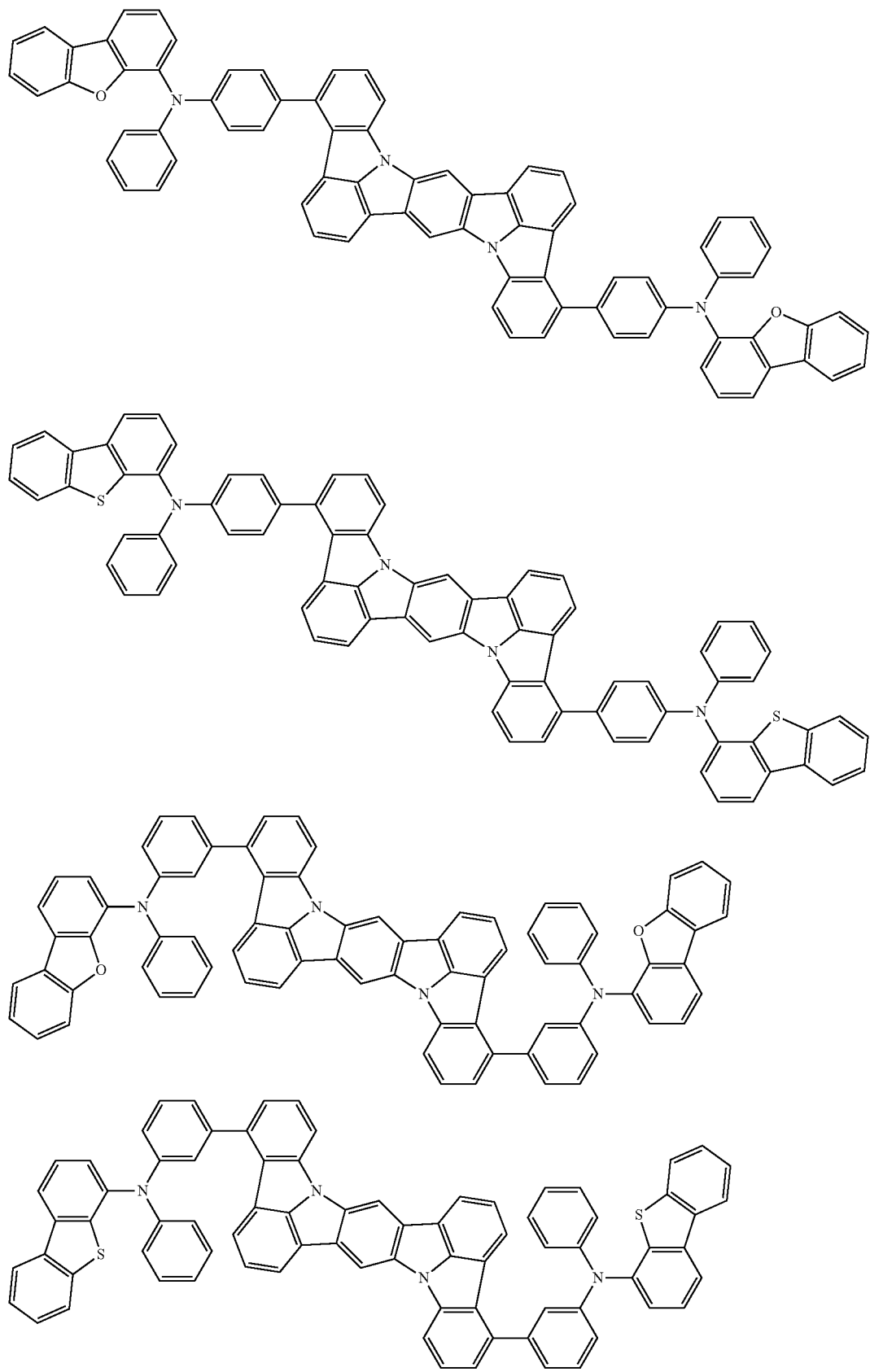

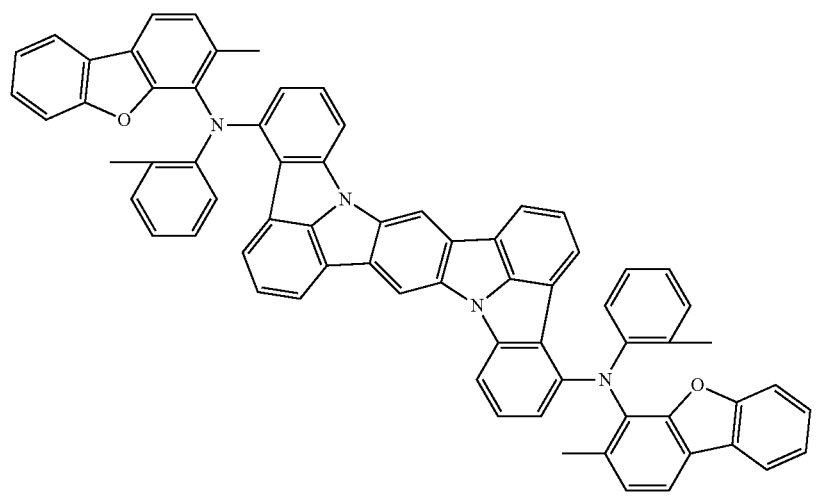
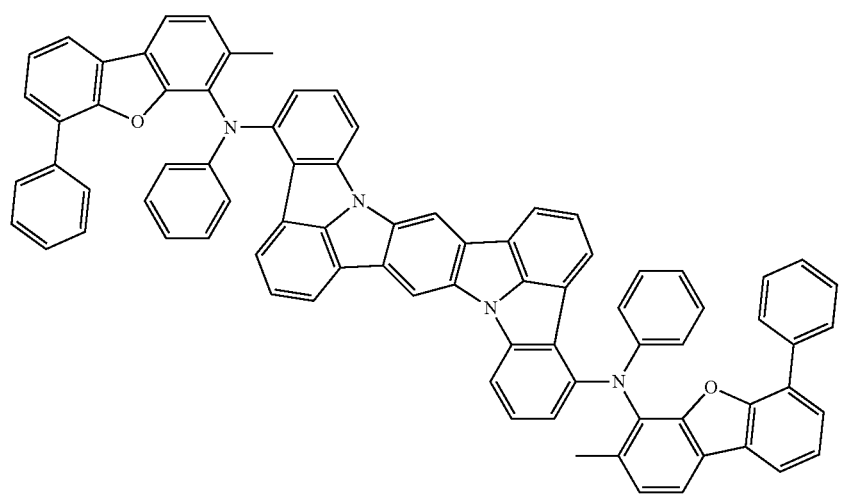
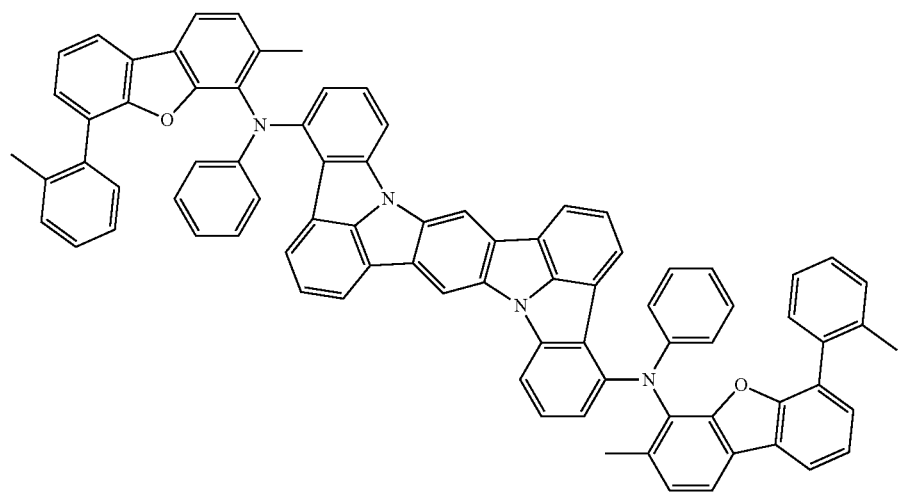

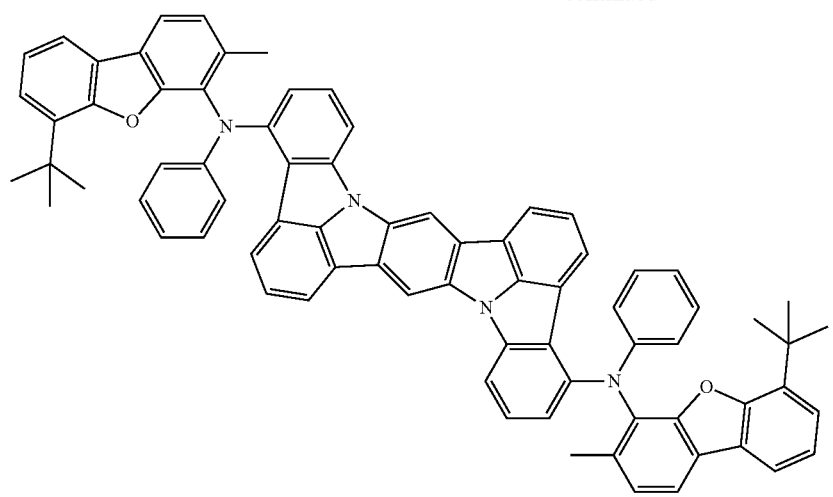
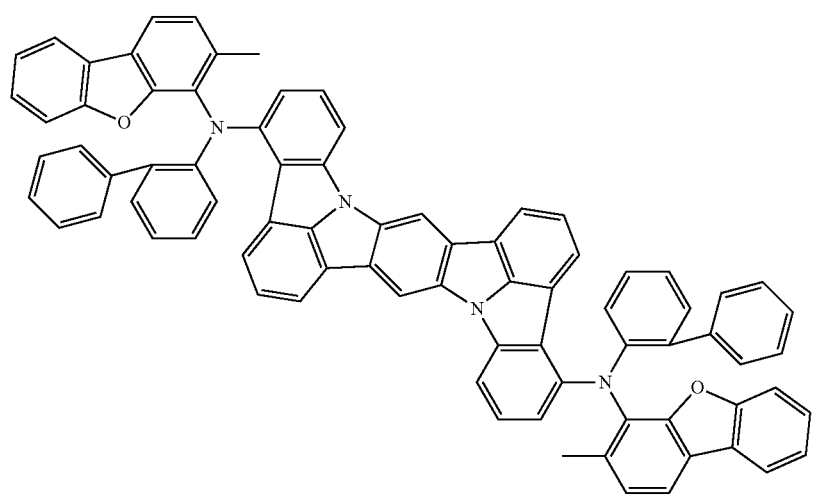
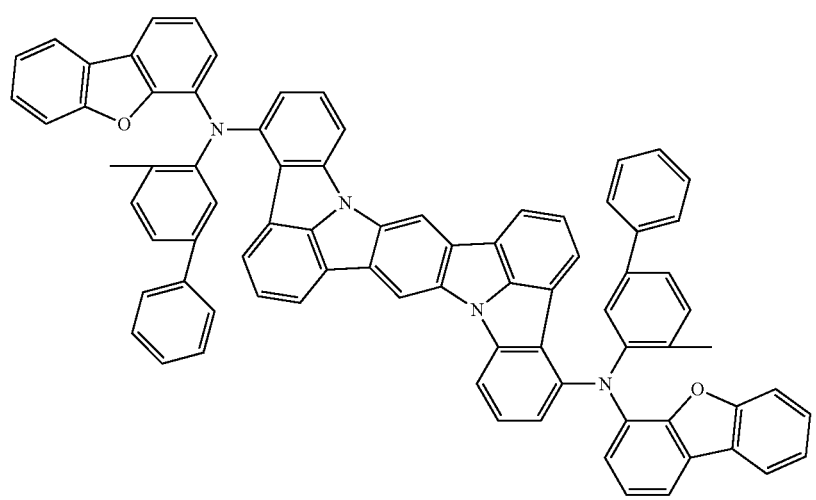

-continued
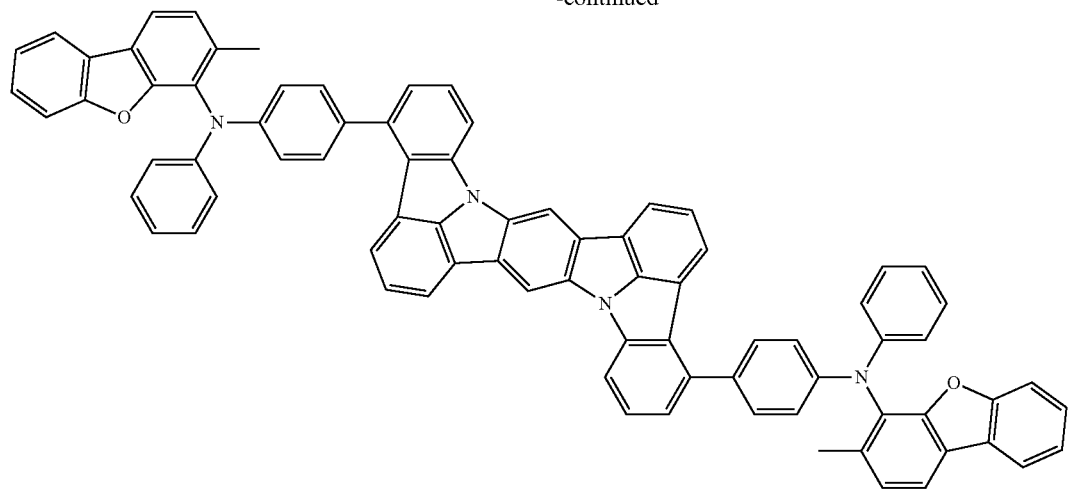
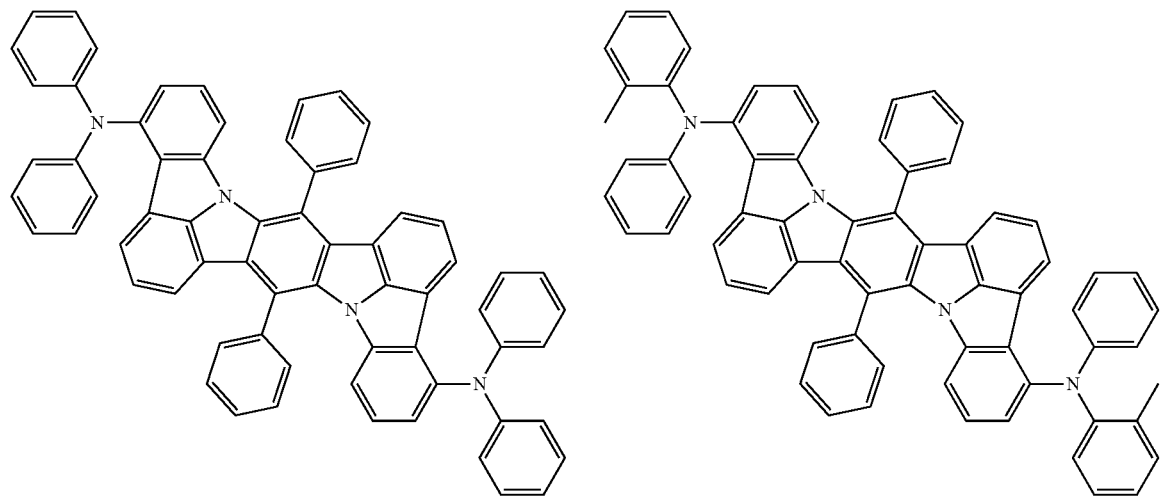
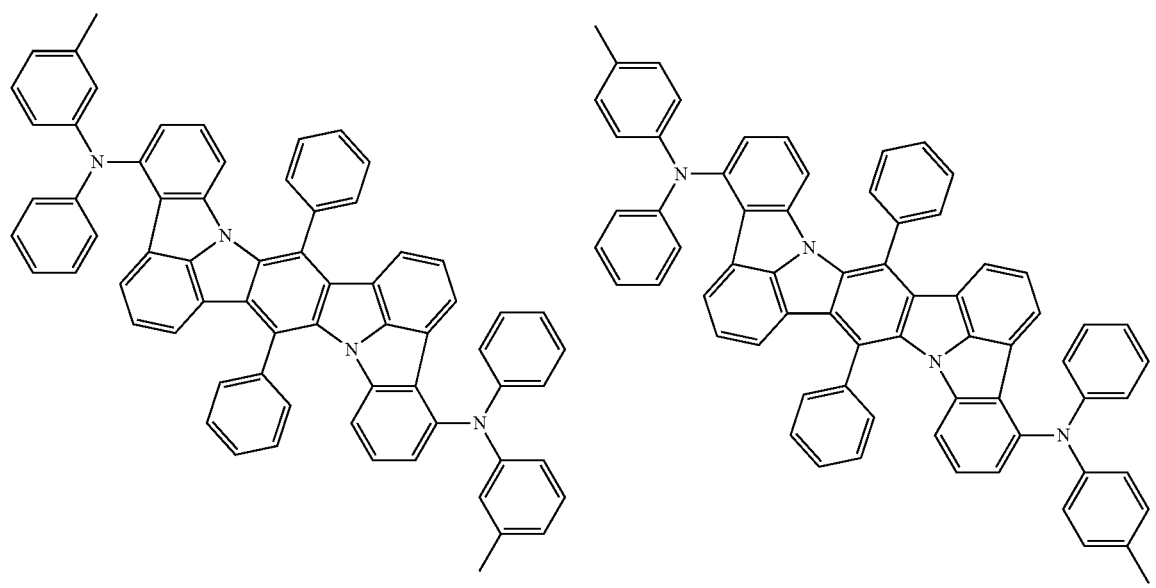

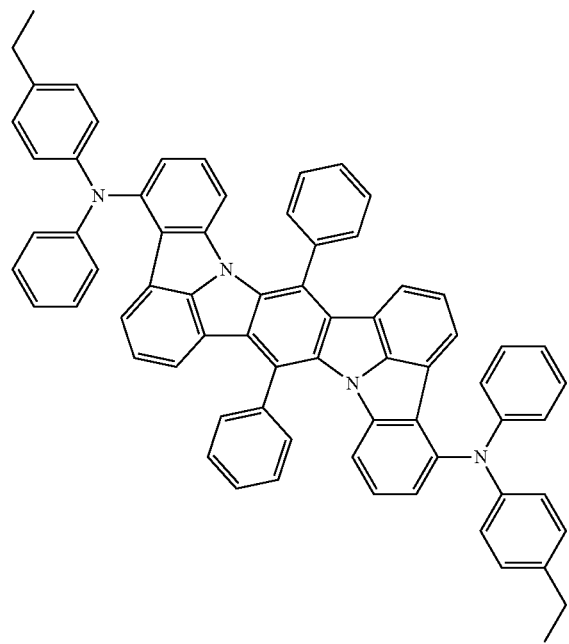
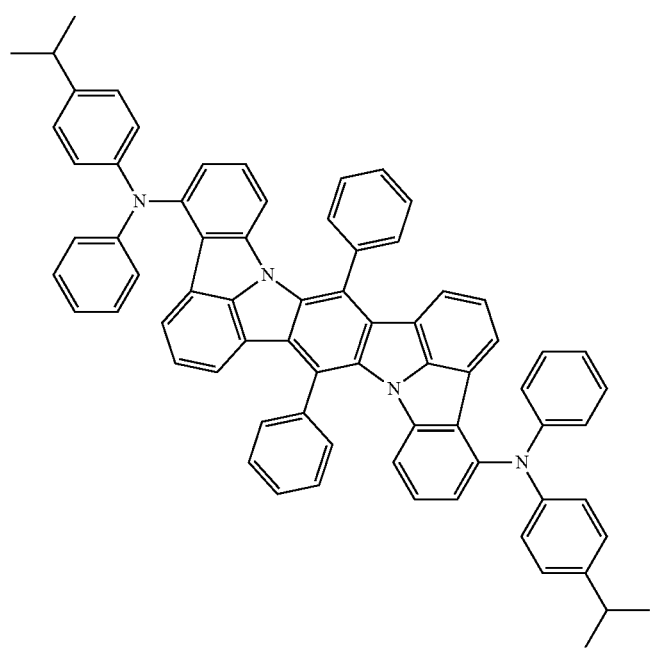

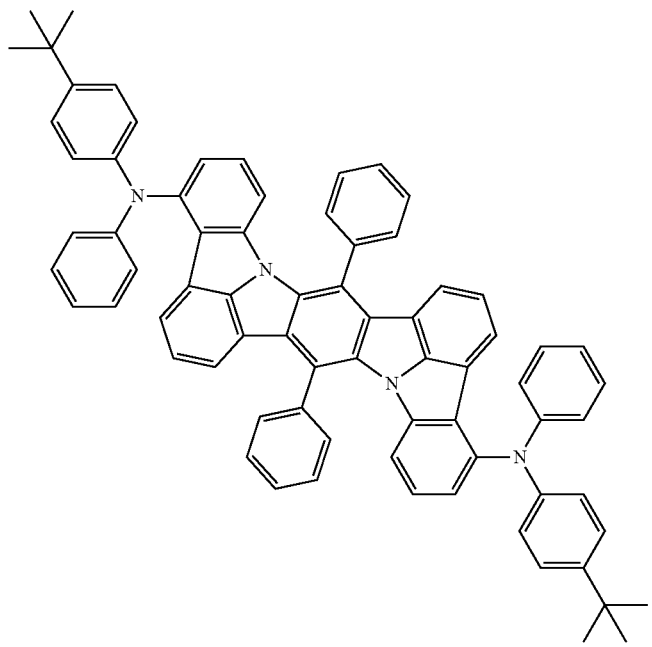
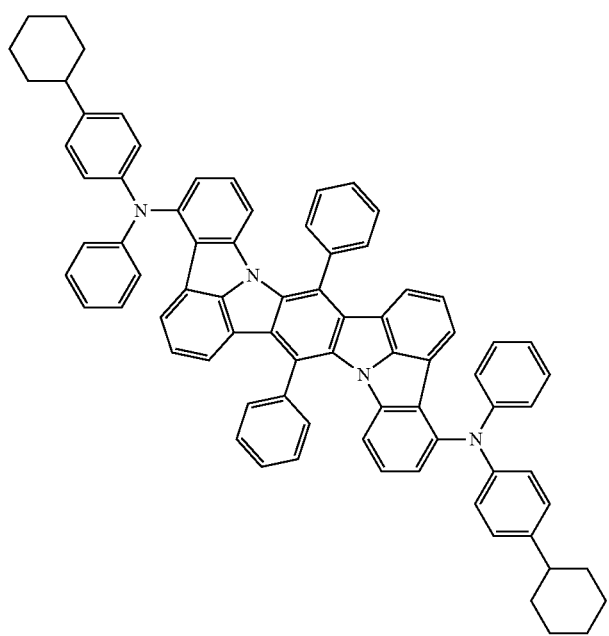

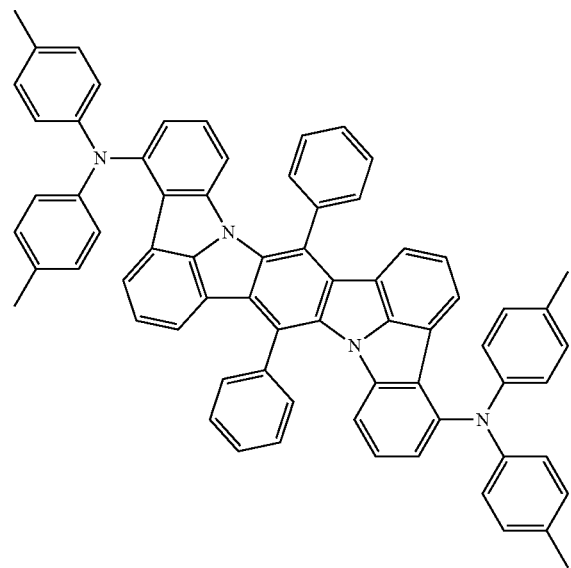
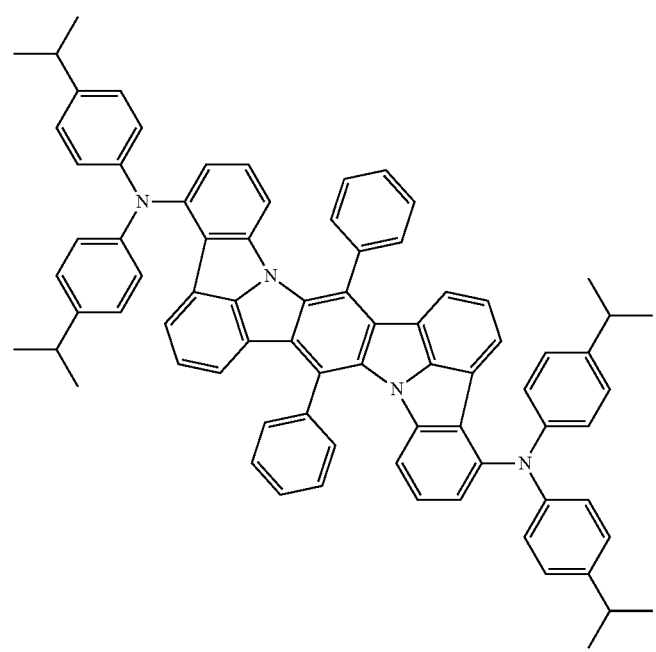

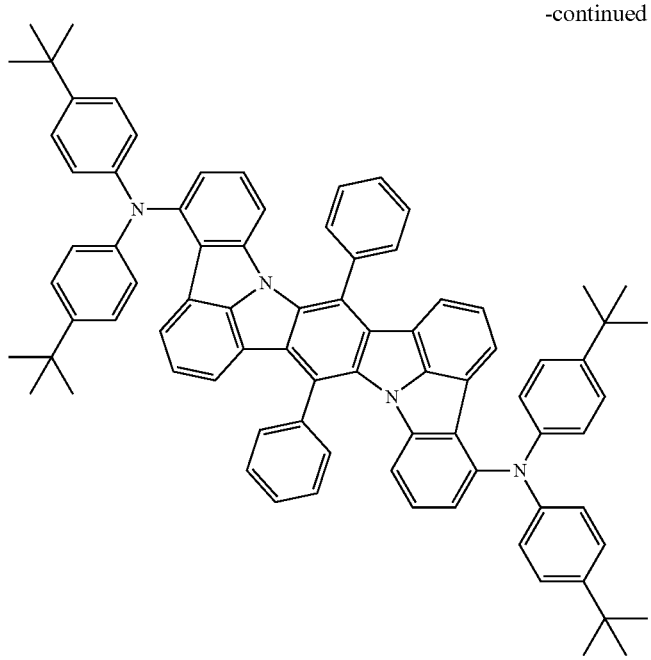
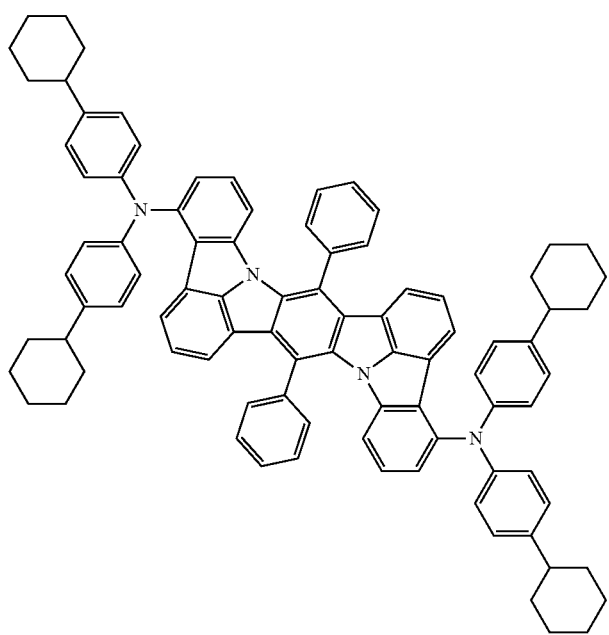

-continued
471
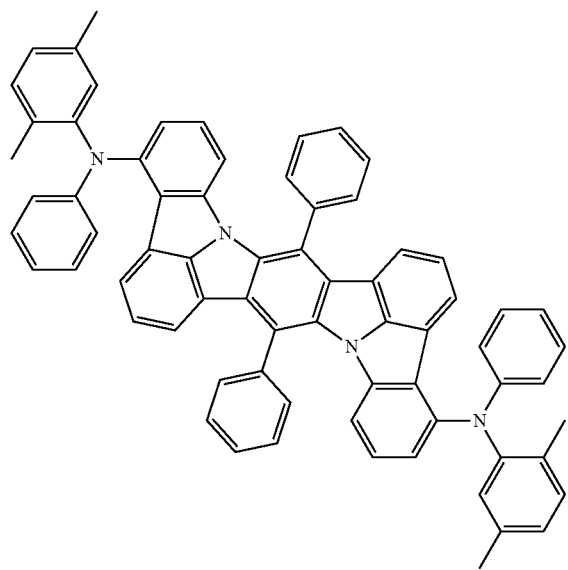
472
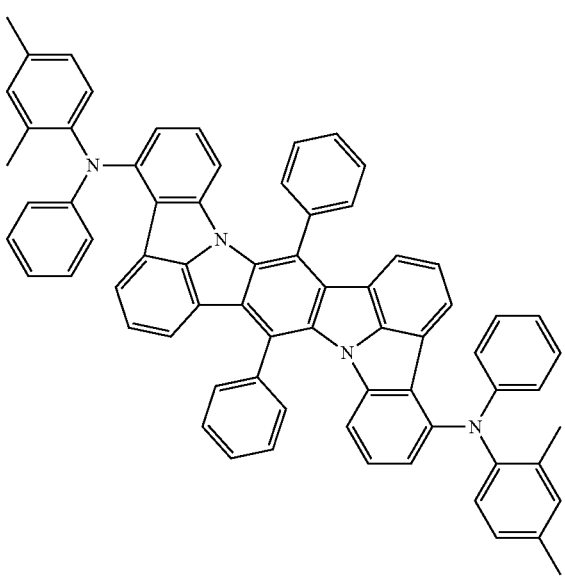
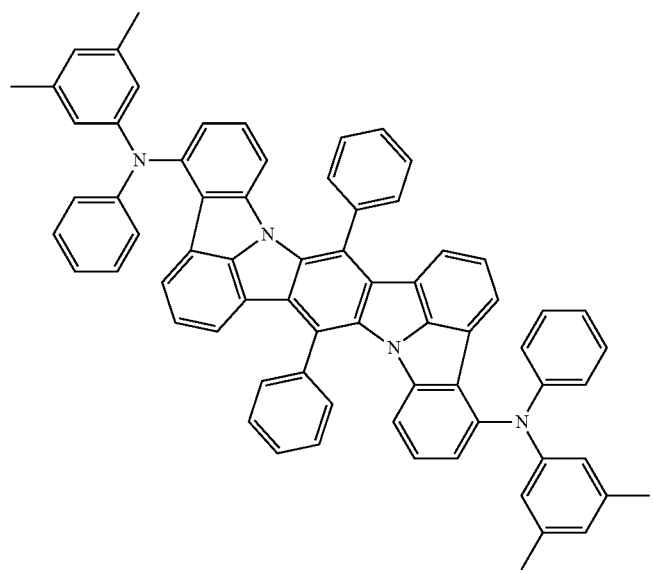
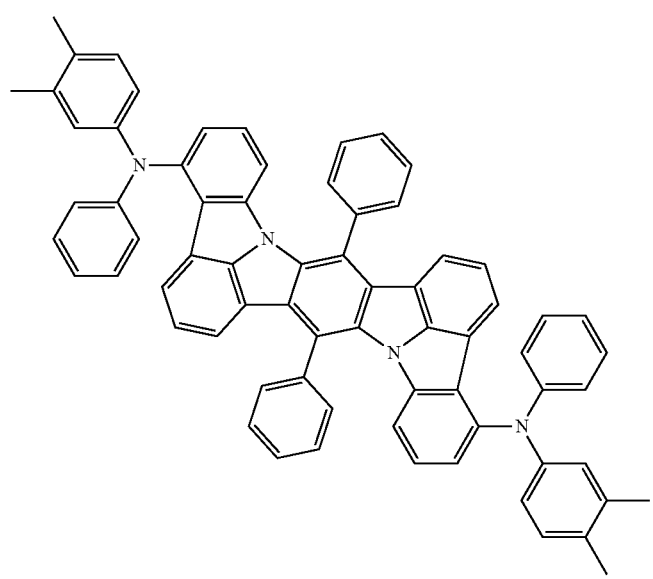

-continued
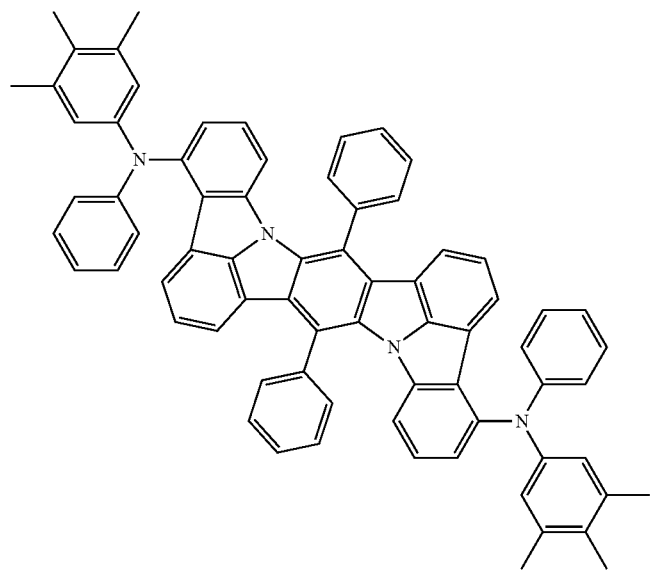
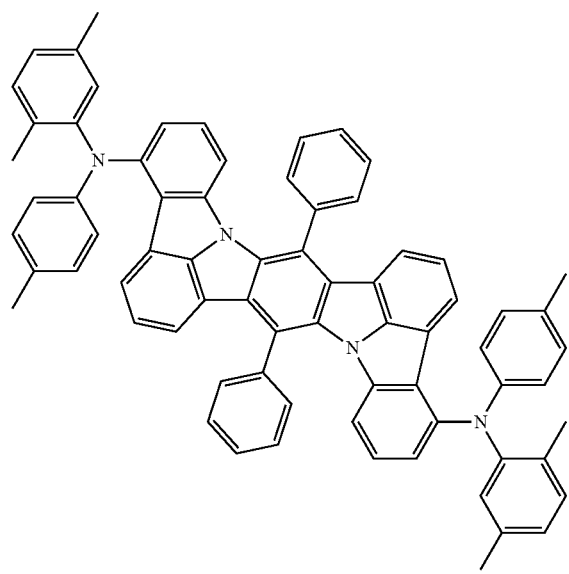
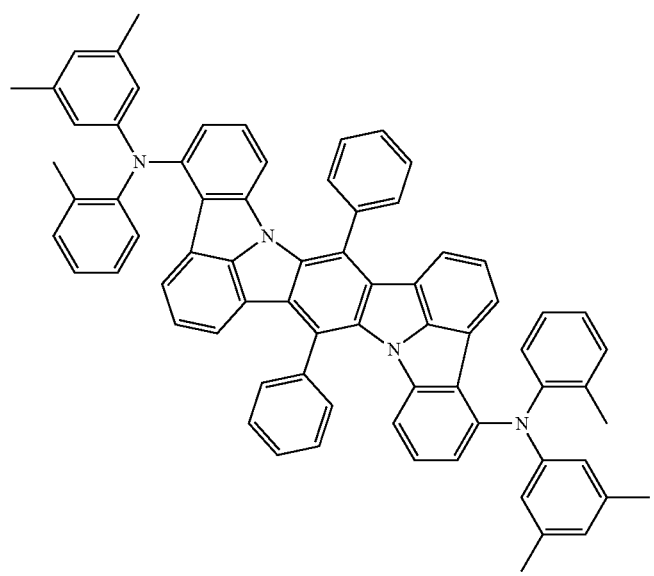

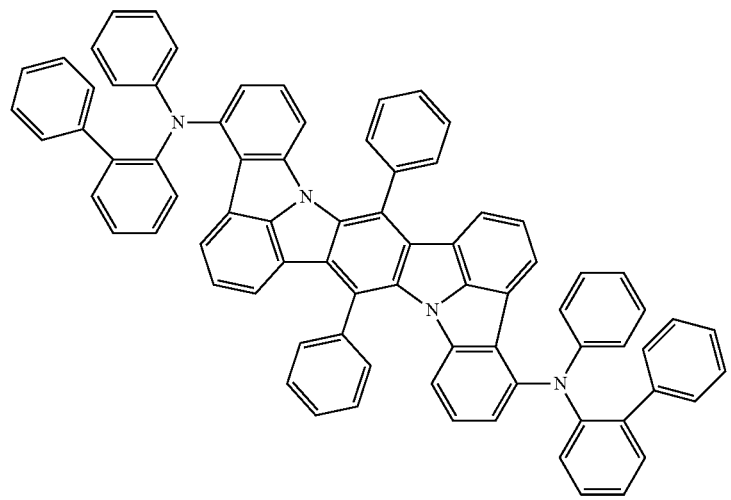
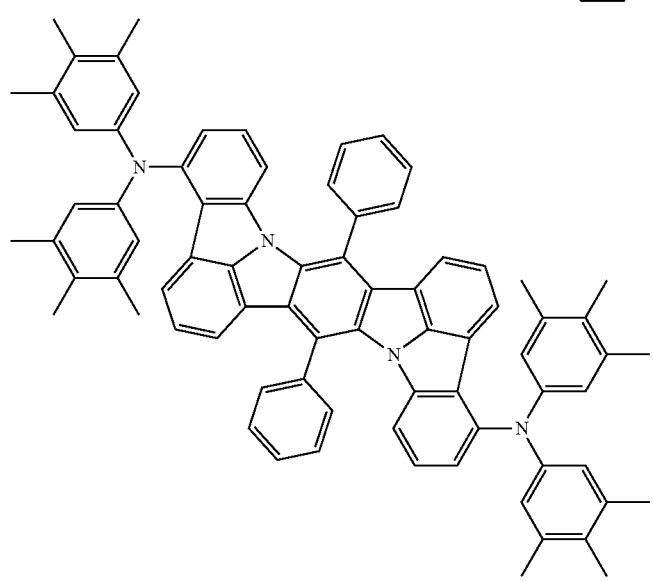
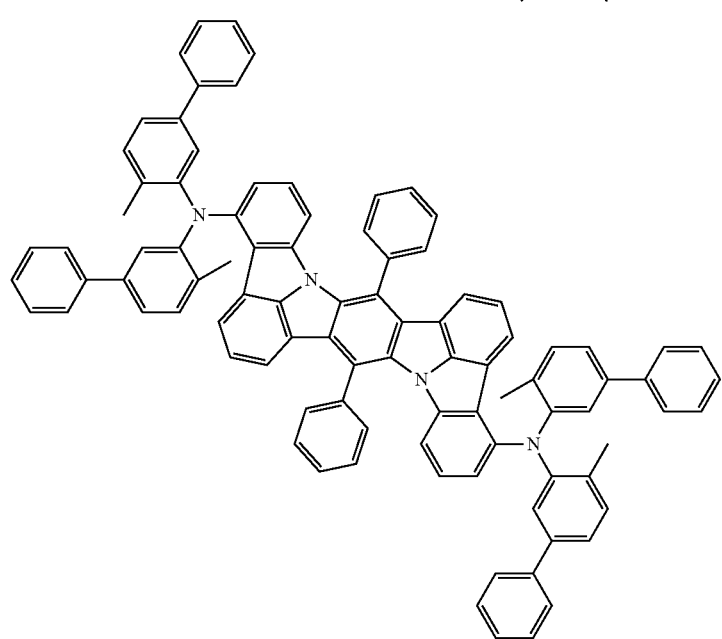

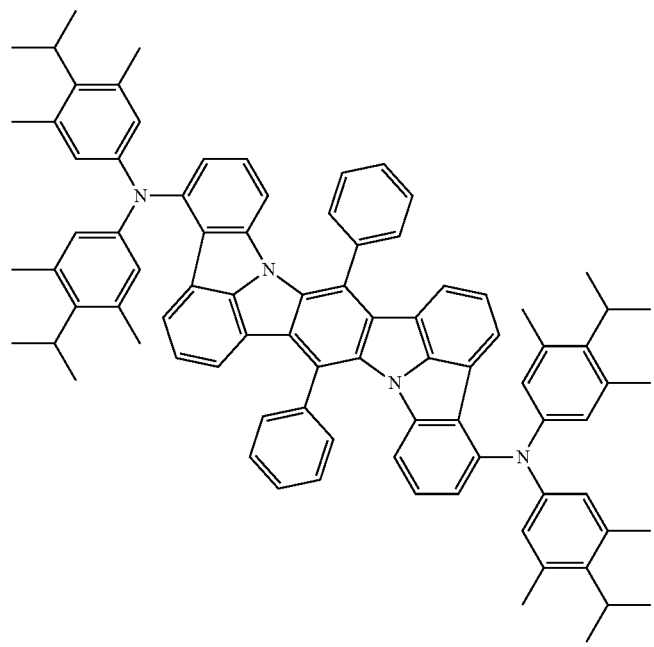
477
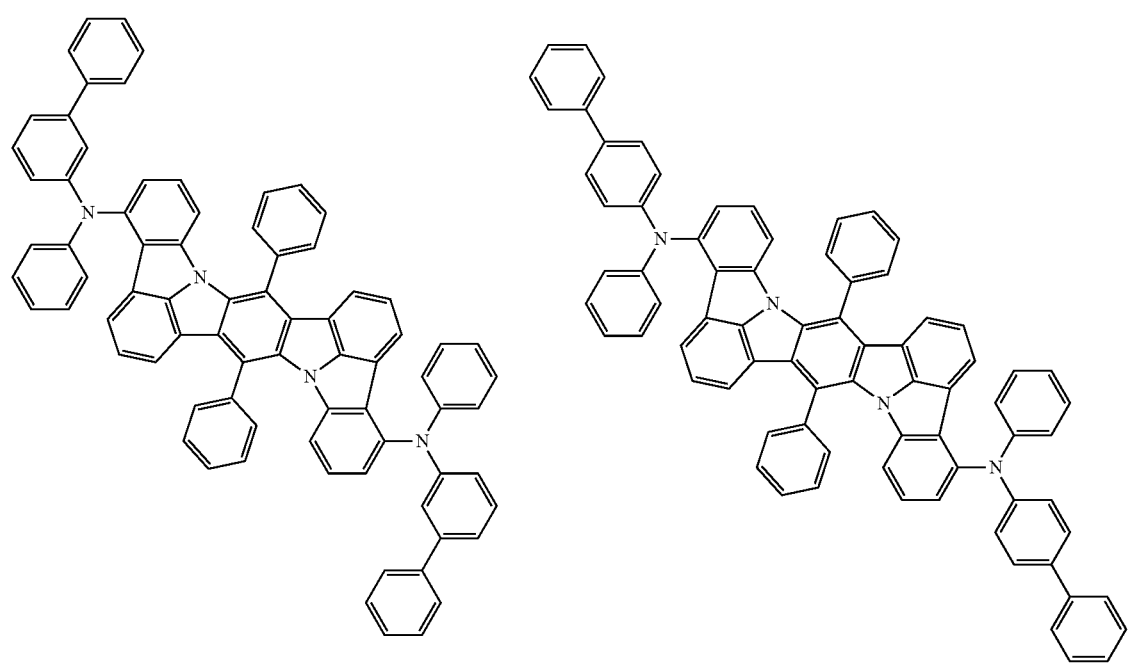 [SMILES: c1ccc(-c2cccc(N(c3ccccc3)c3cccc4c3c3cccc5c6c(-c7ccccc7)c7c(c(-c8ccccc8)c6n4c35)c3cccc4c5c(N(c6ccccc6)c6cccc(-c8ccccc8)c6)cccc5n7c43)c2)cc1 ; c1ccc(-c2ccc(N(c3ccccc3)c3cccc4c3c3cccc5c6c(-c7ccccc7)c7c(c(-c8ccccc8)c6n4c35)c3cccc4c5c(N(c6ccccc6)c6ccc(-c8ccccc8)cc6)cccc5n7c43)cc2)cc1]
478

-continued
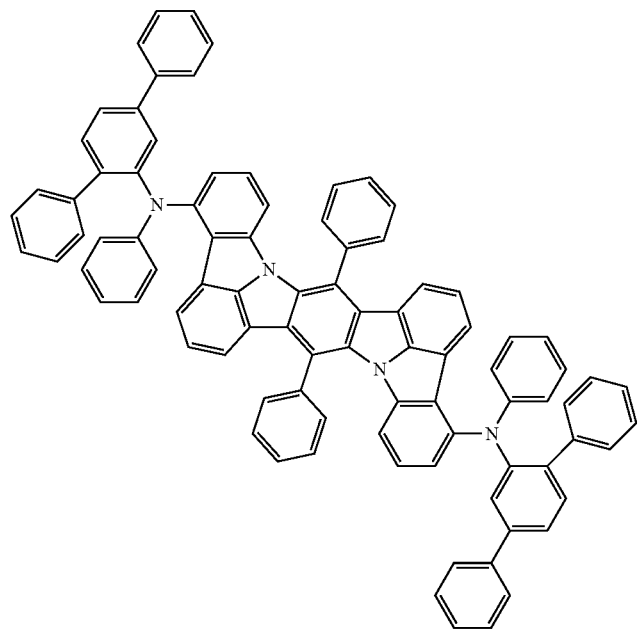
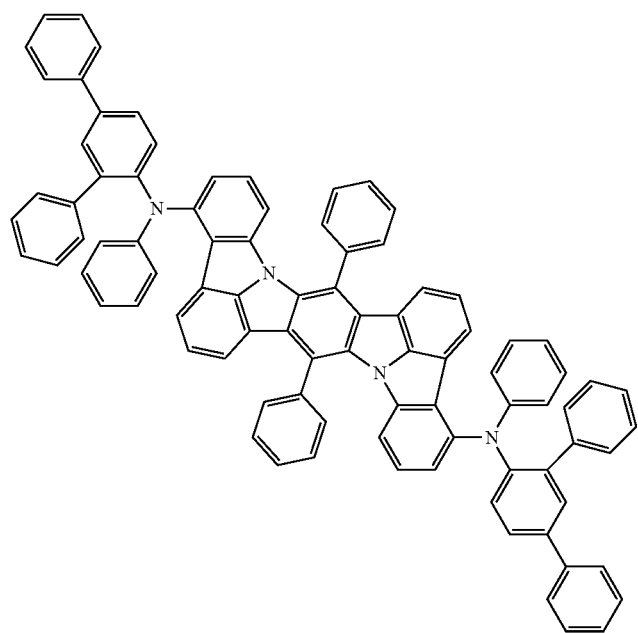

-continued
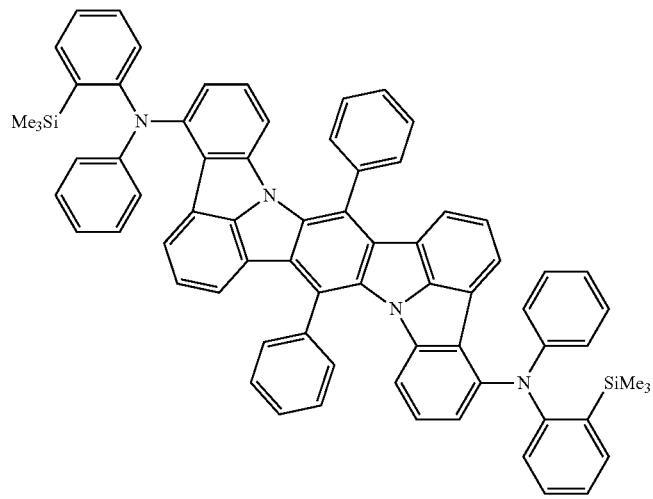
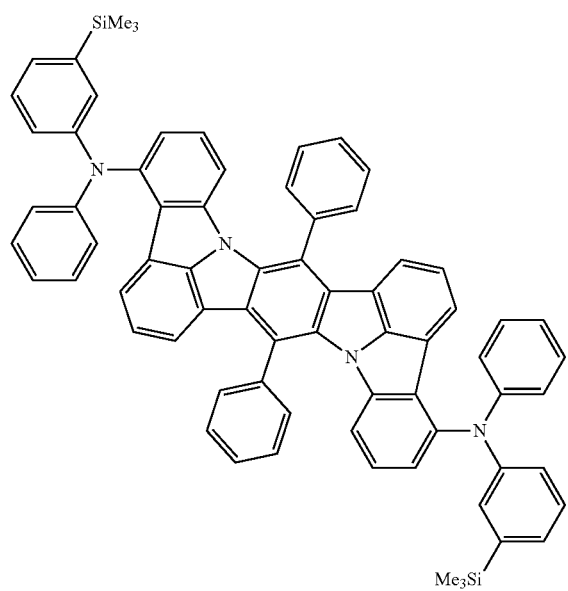
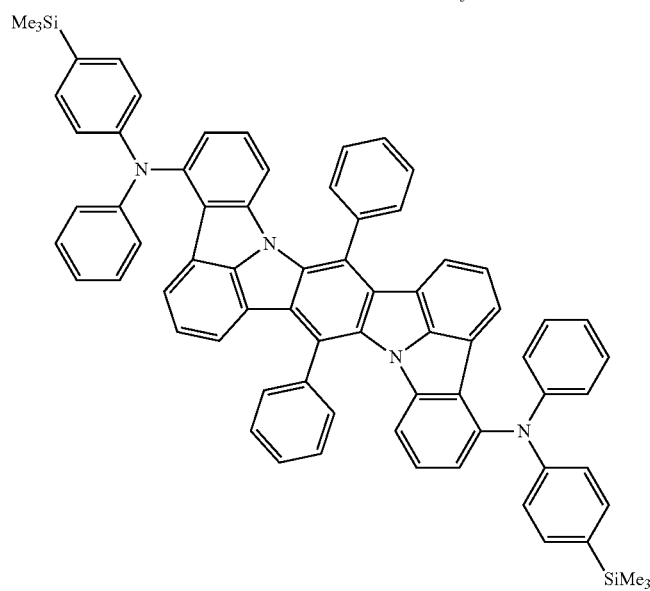

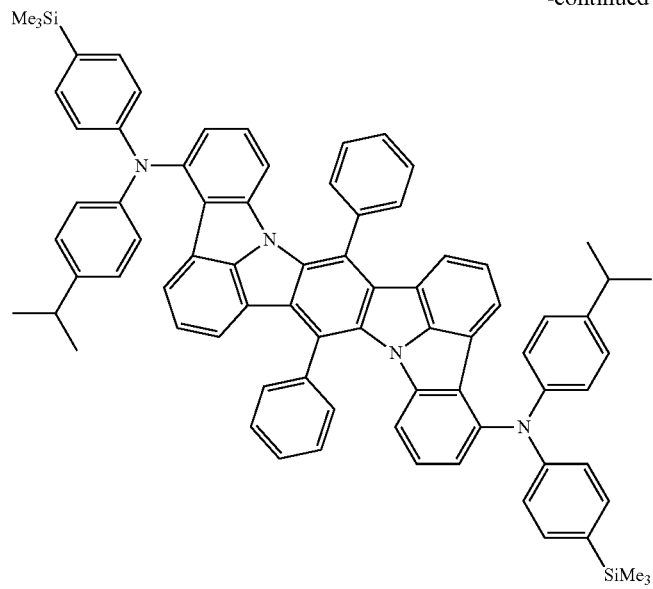
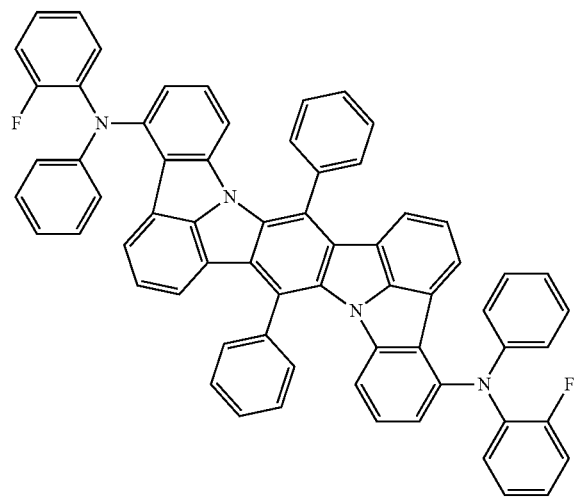
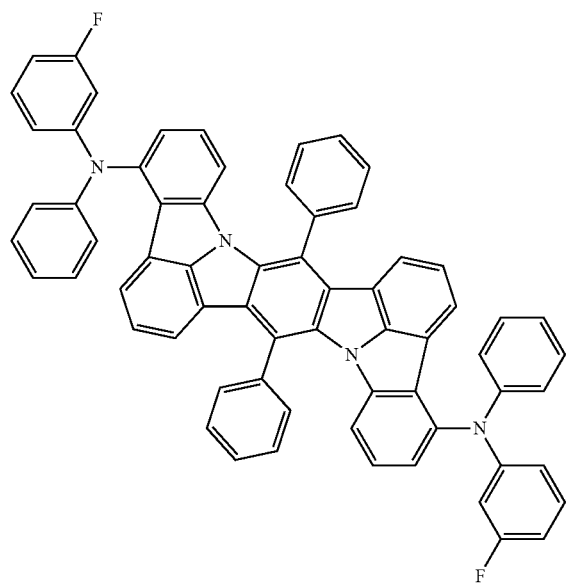

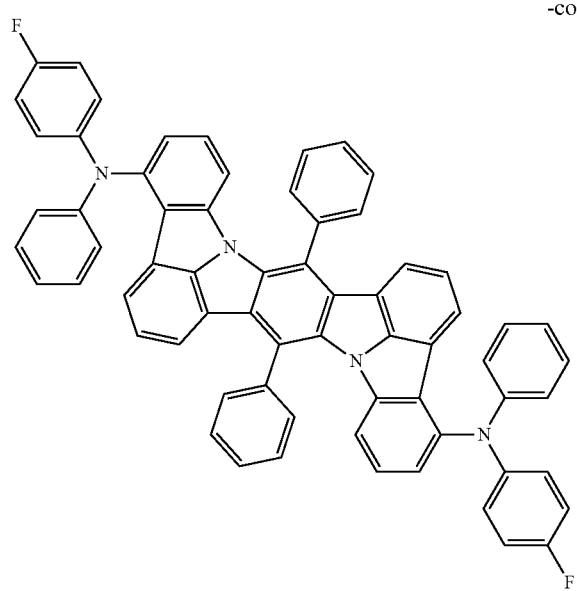
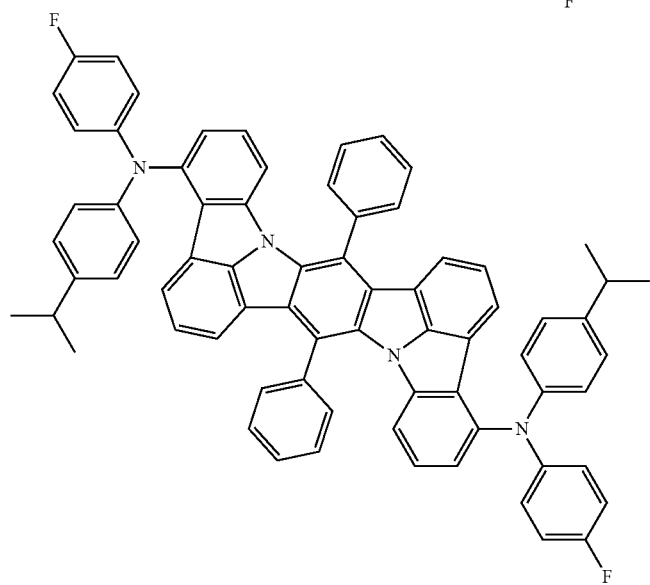
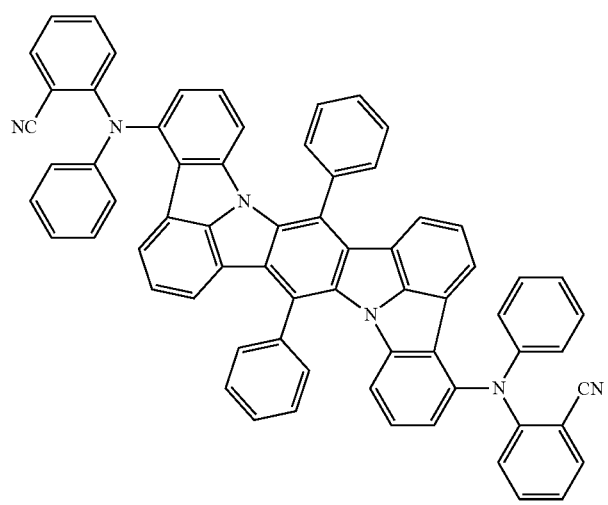

487
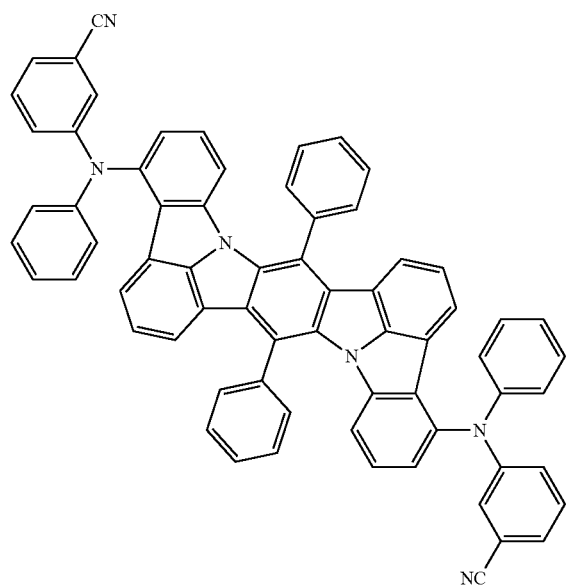
488
-continued
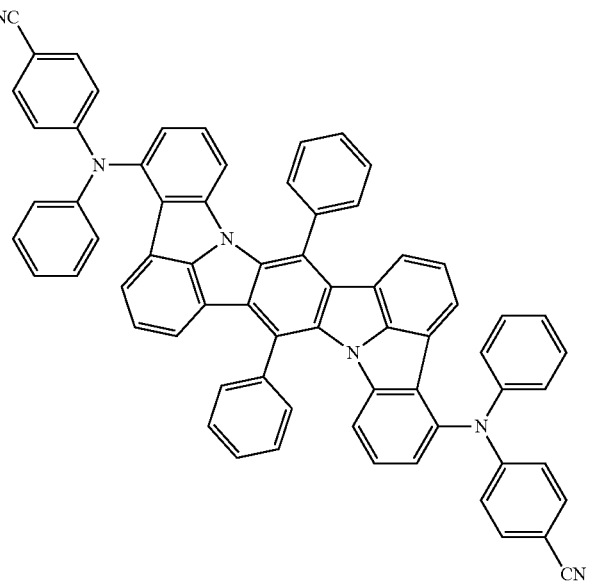
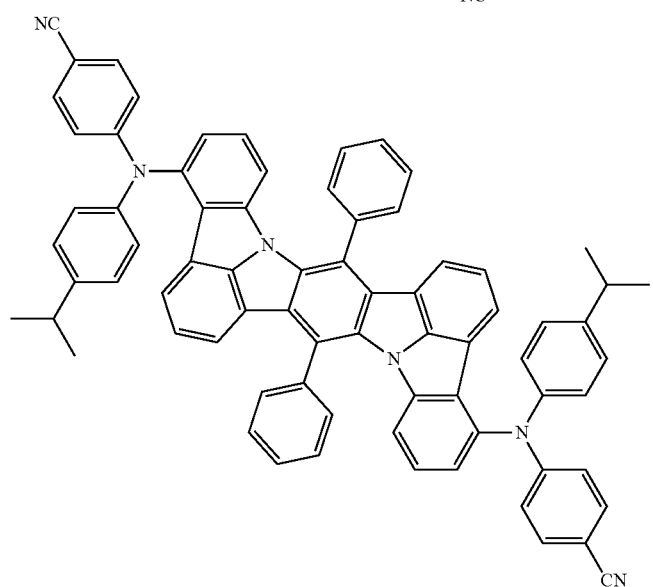
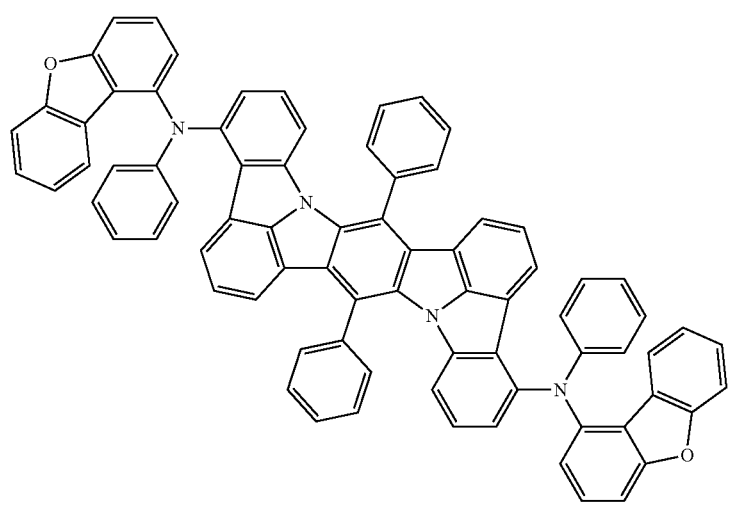

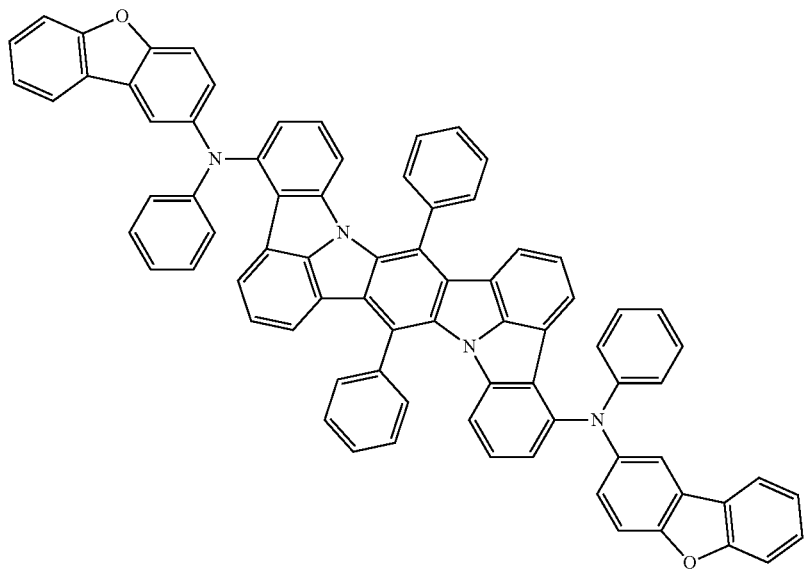
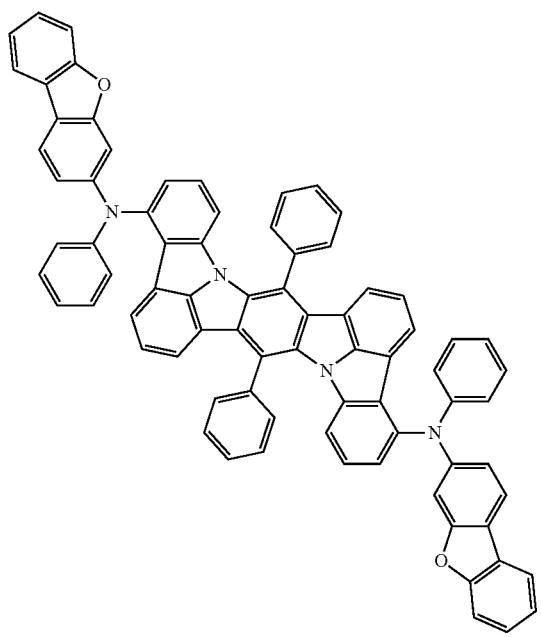
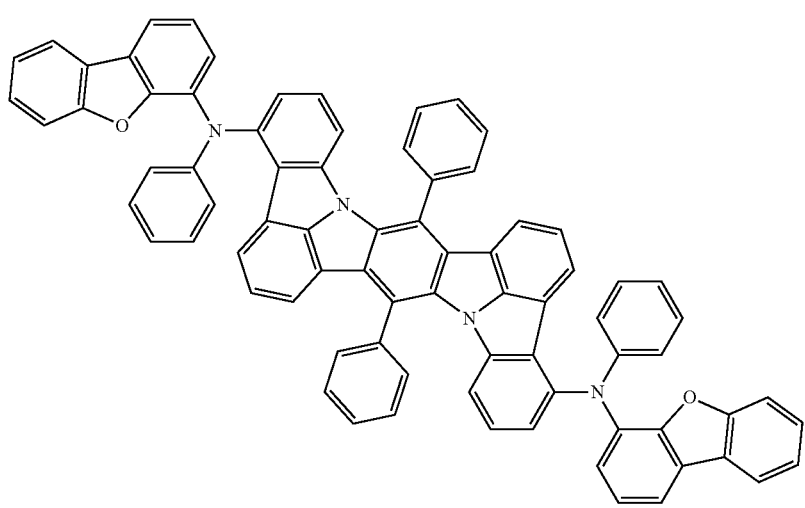

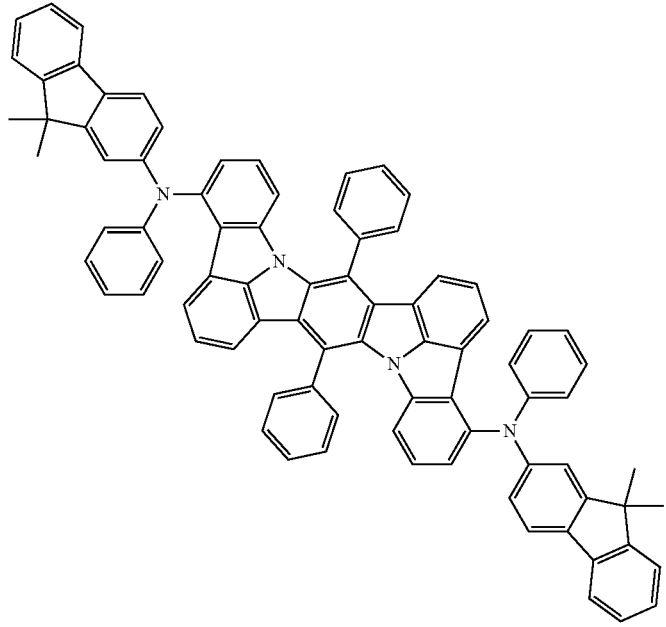
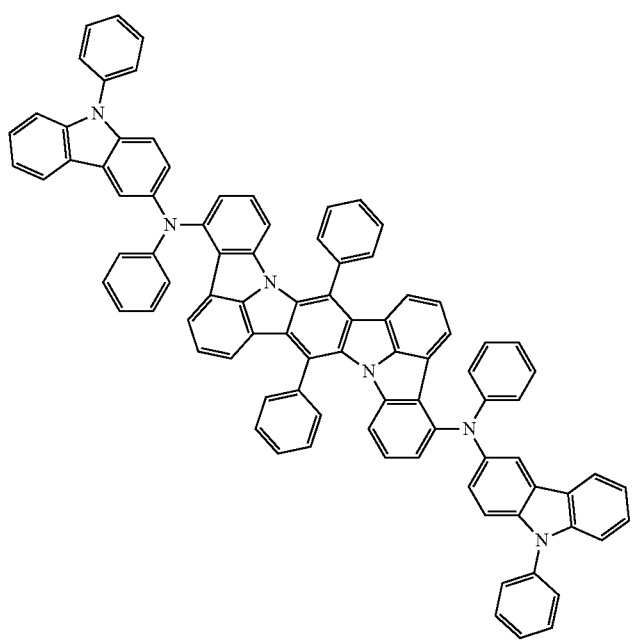

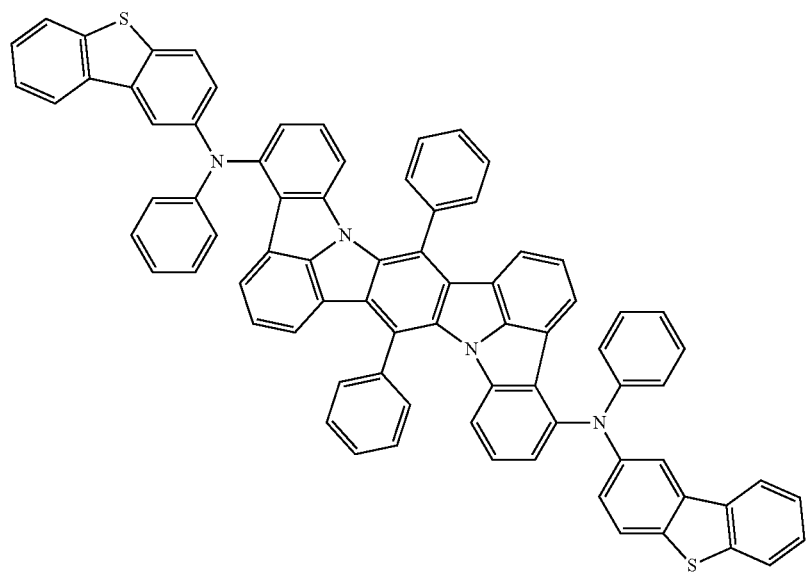
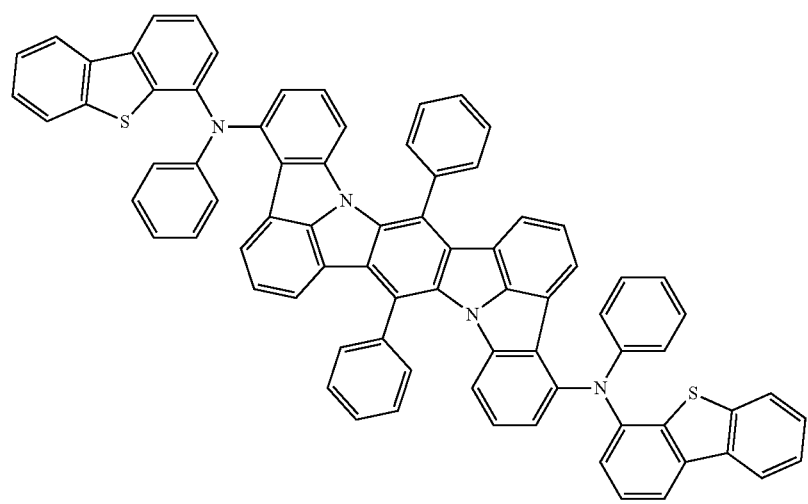
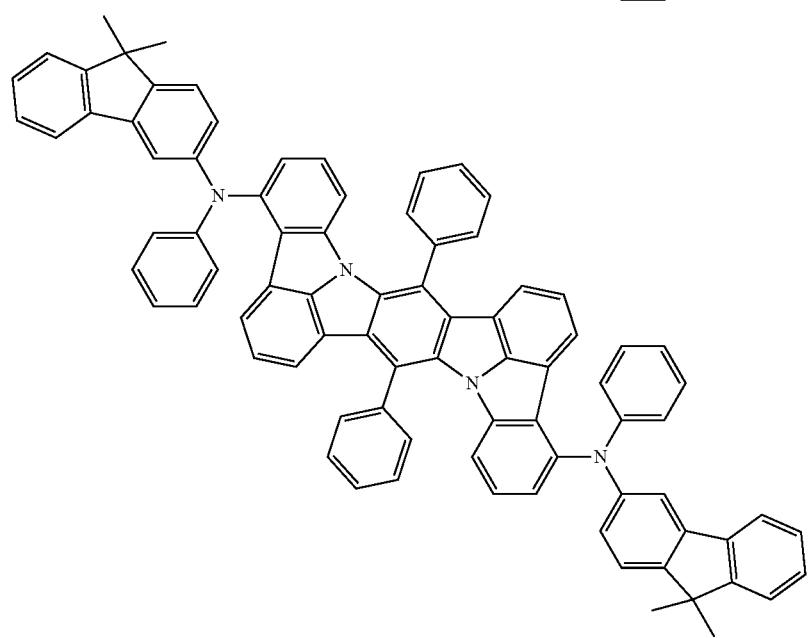

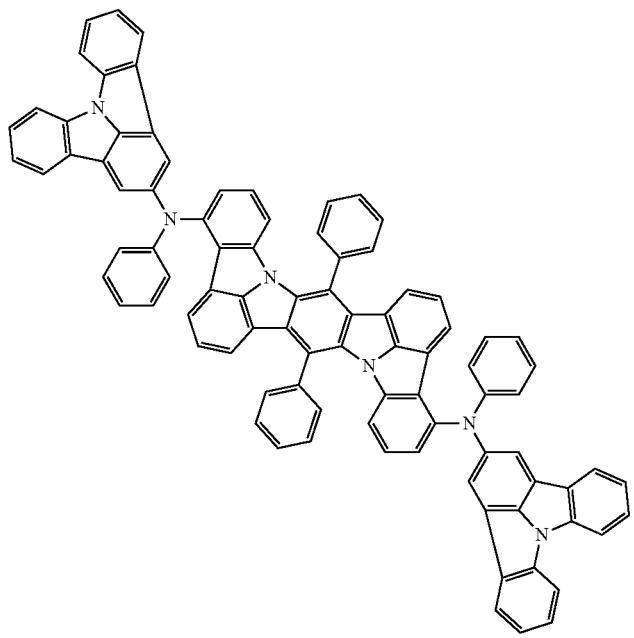
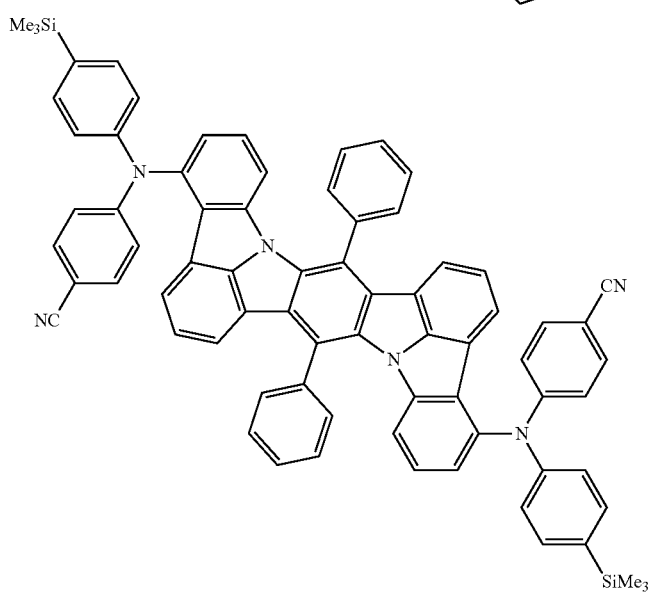
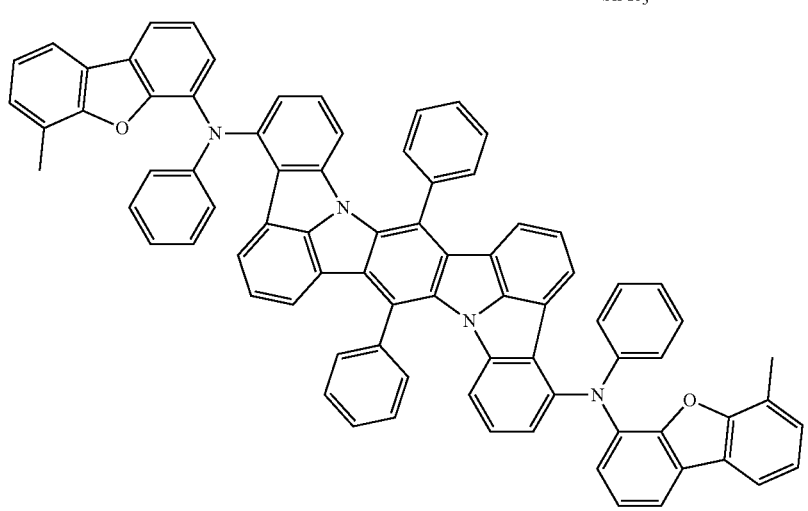

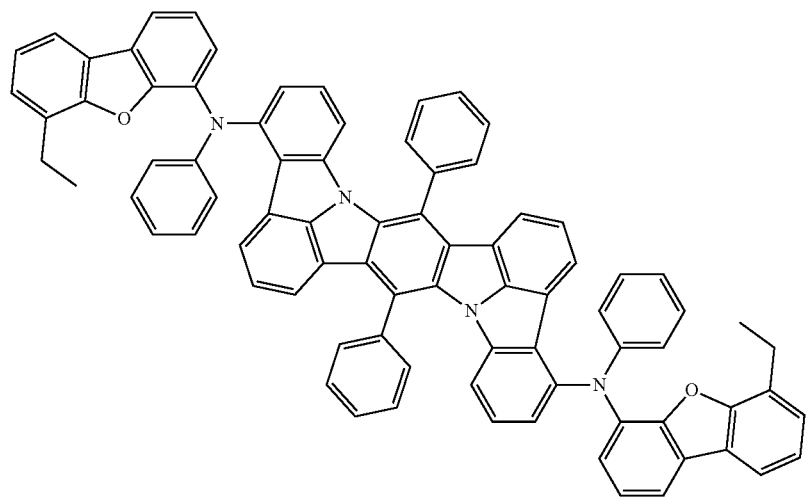
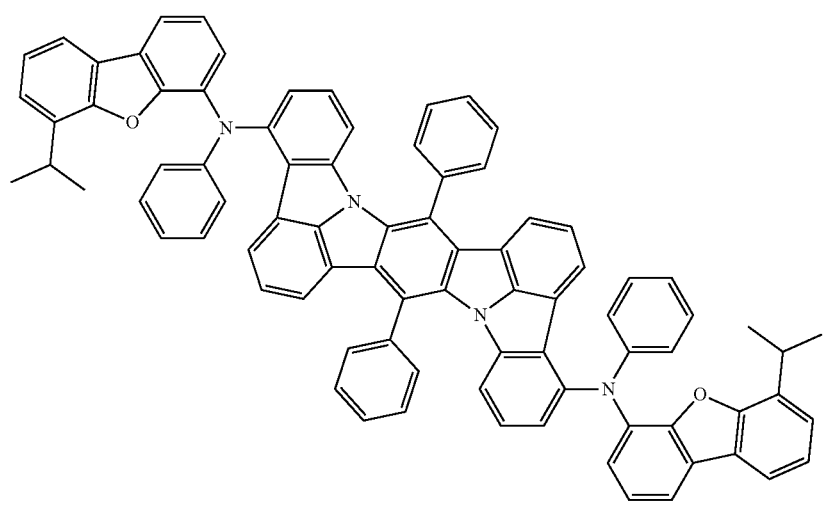

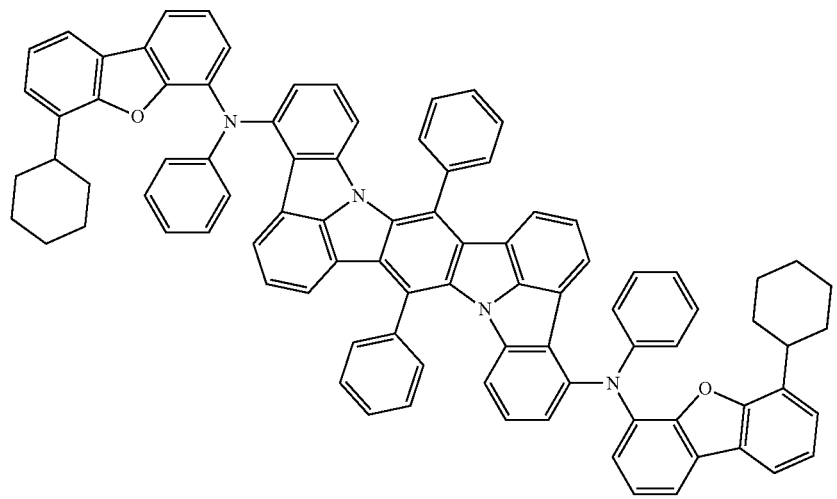
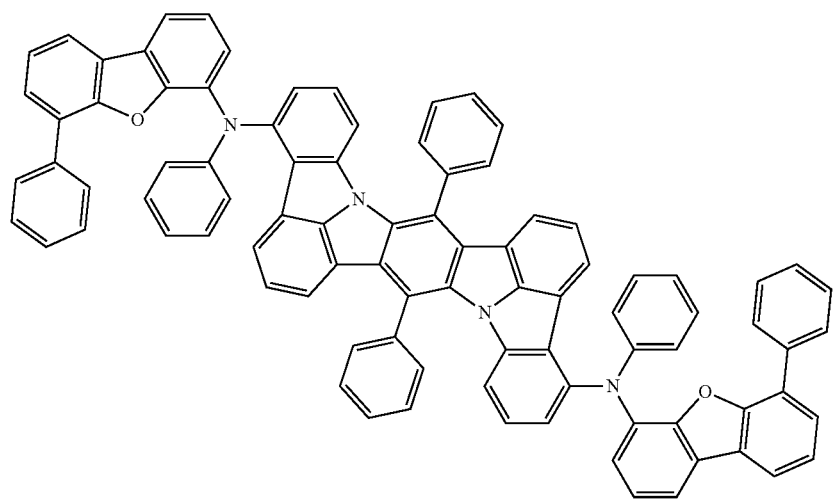
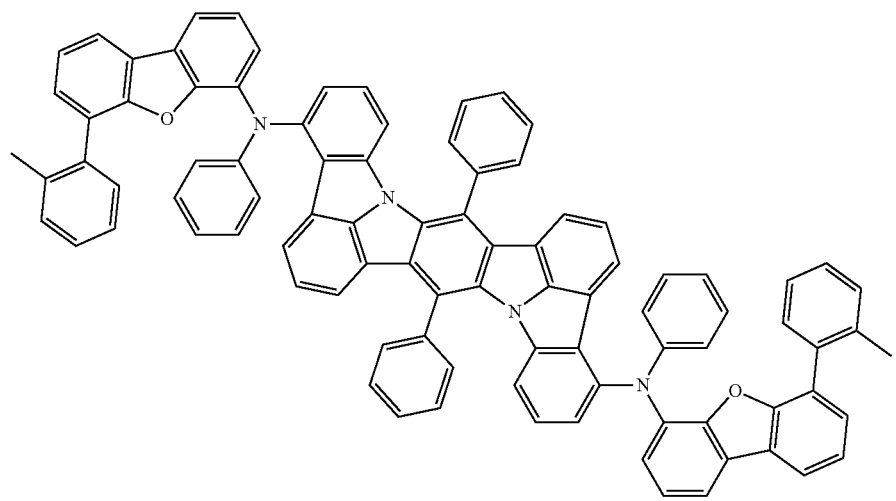

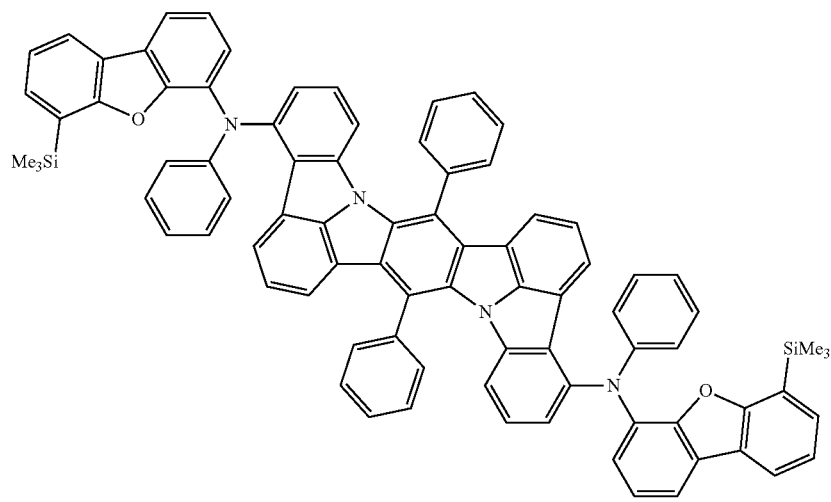
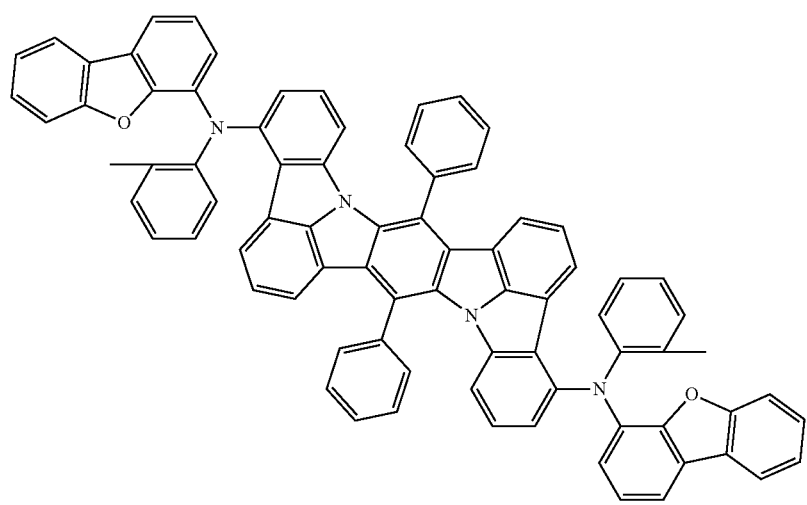
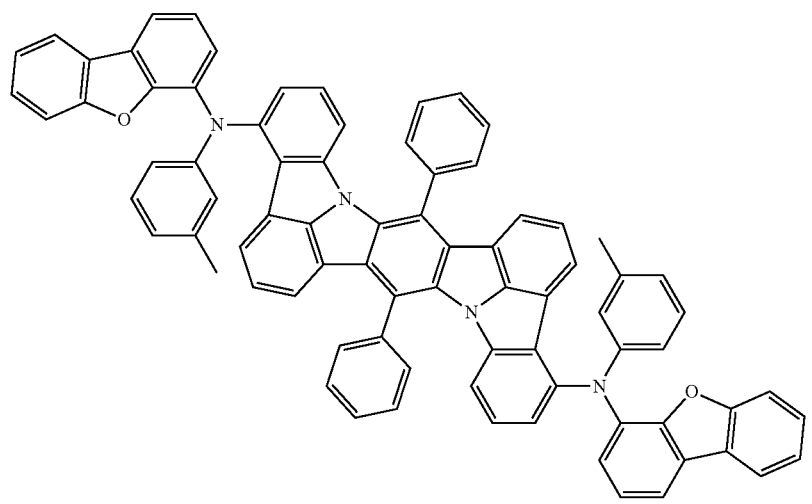

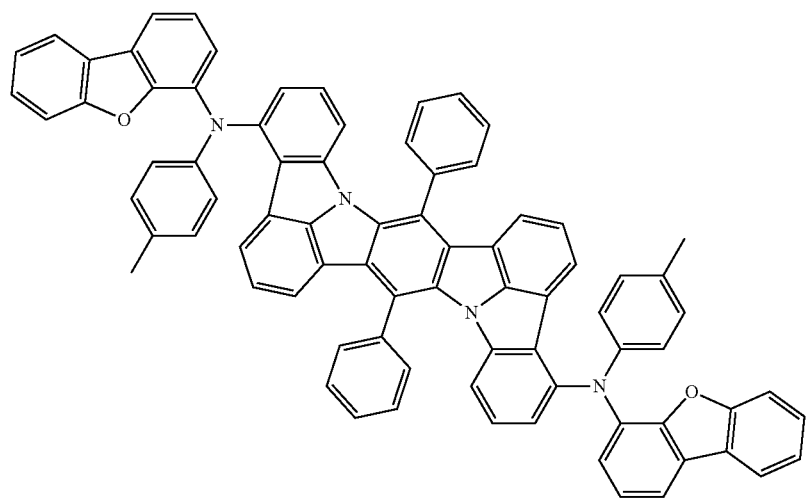
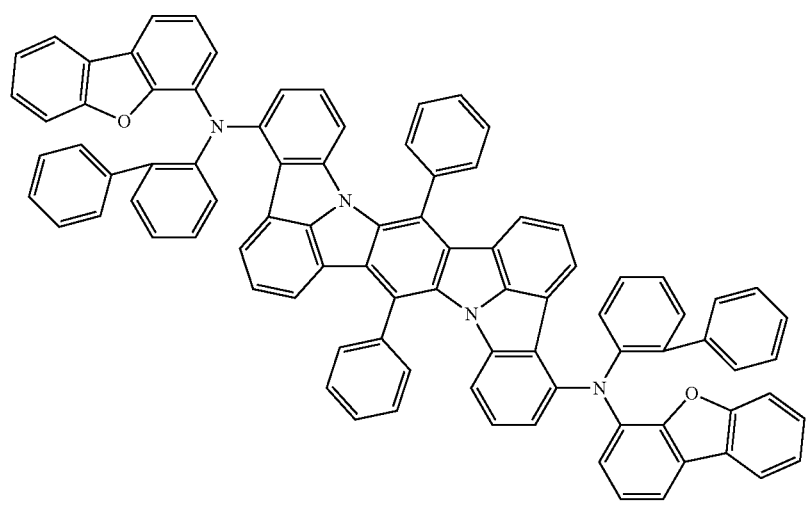

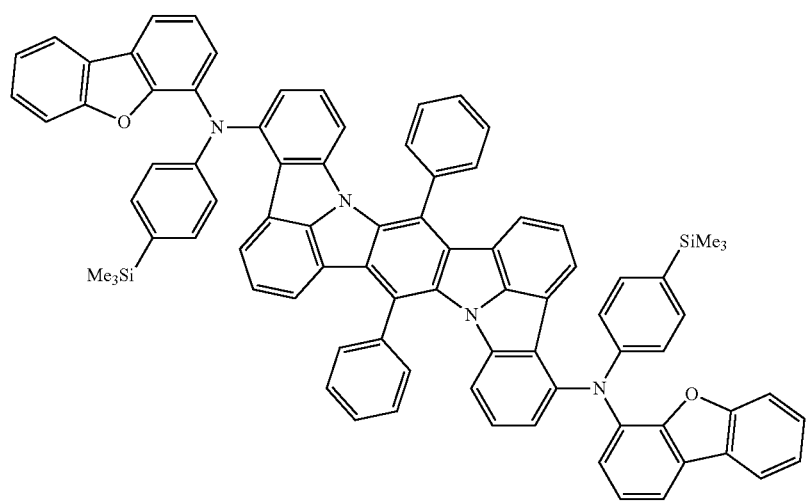

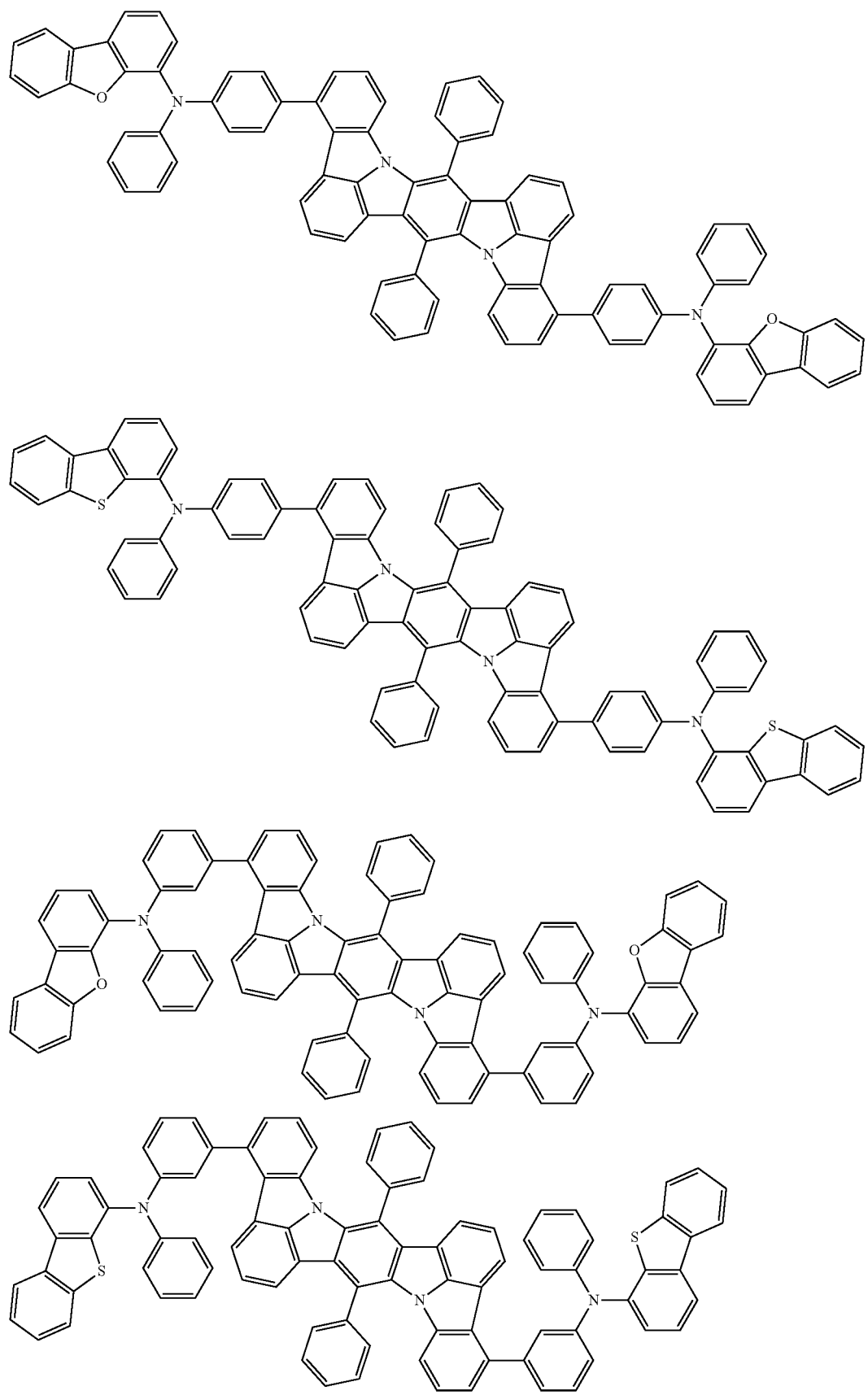

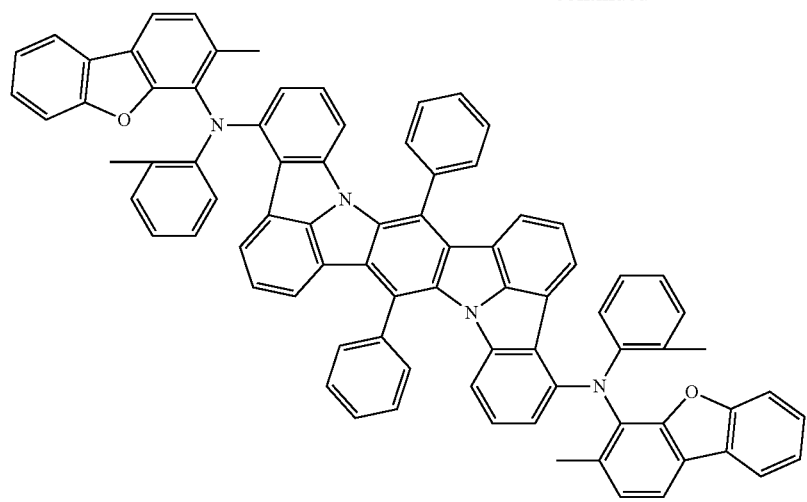
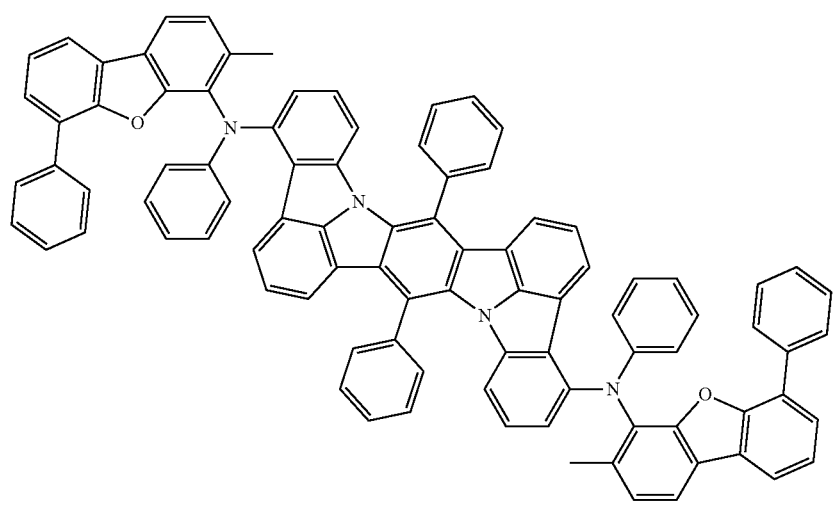
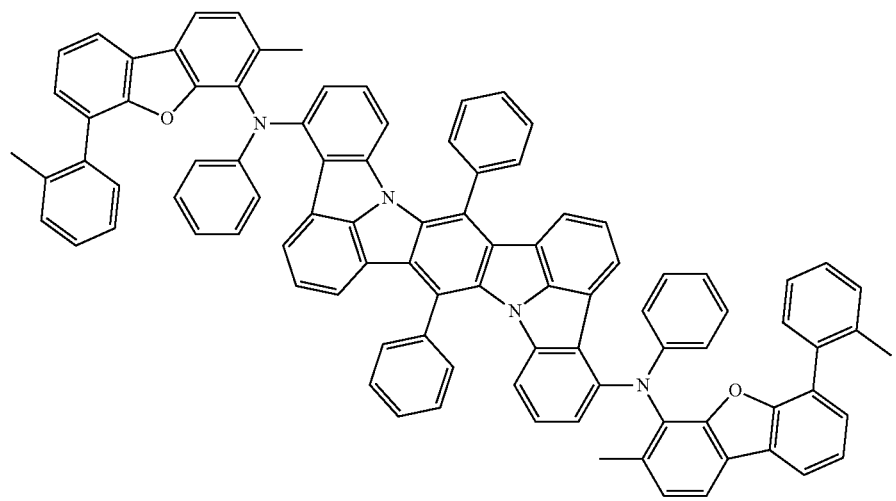

-continued
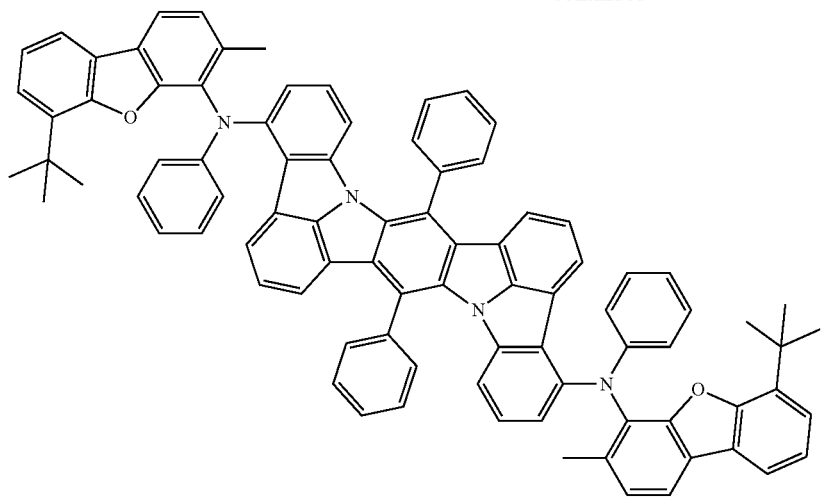
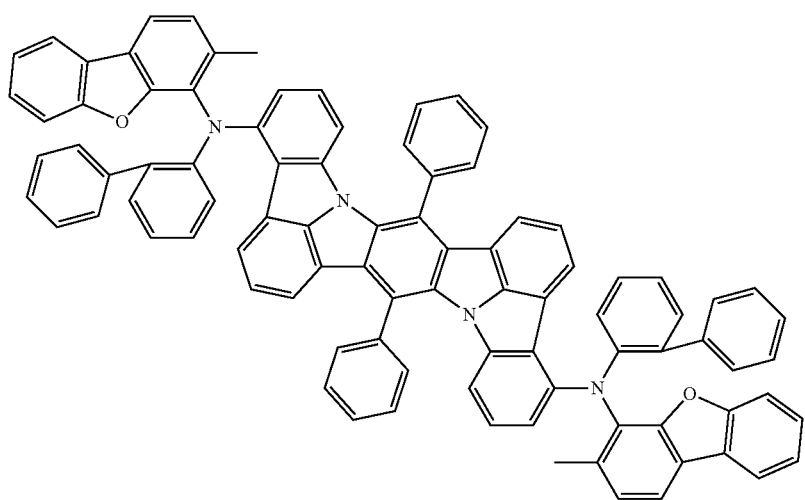
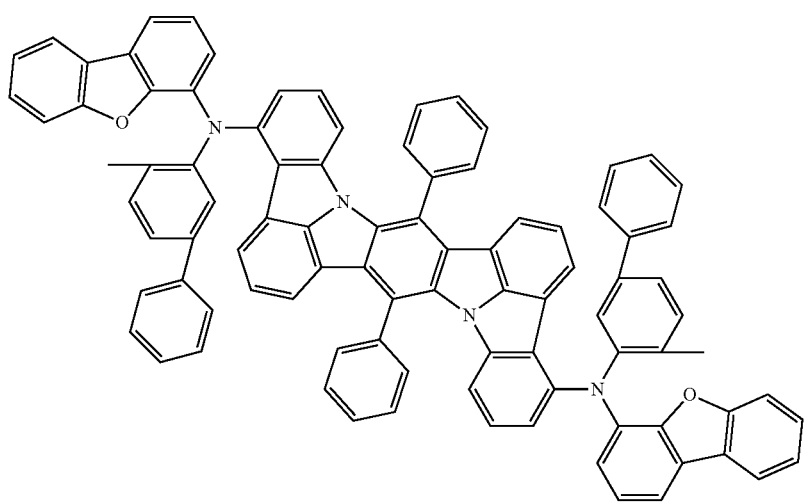

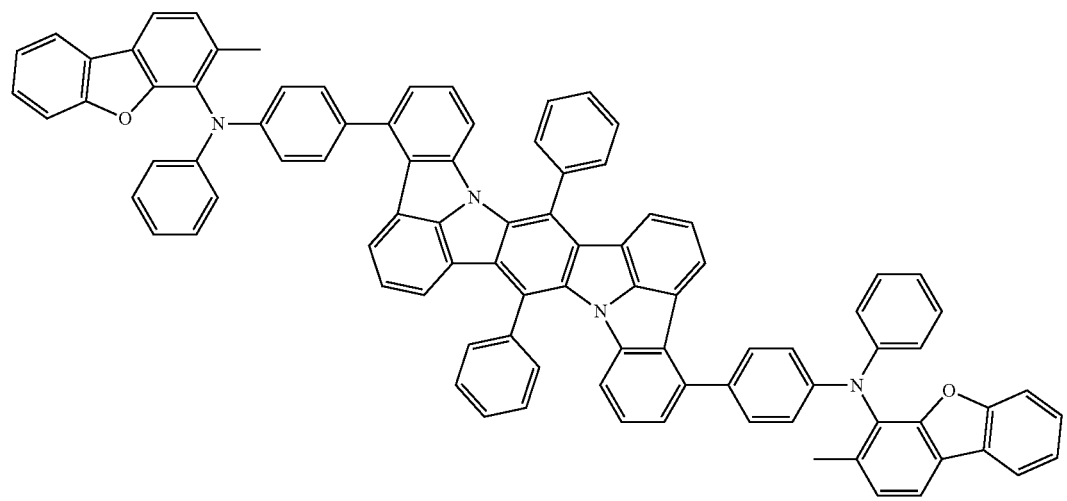
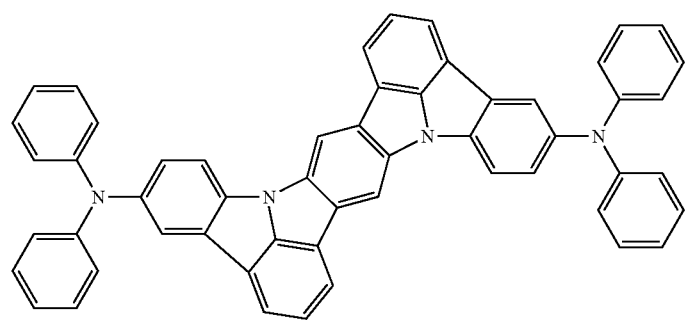
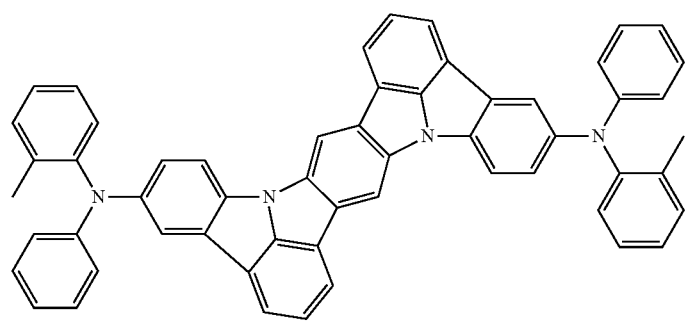
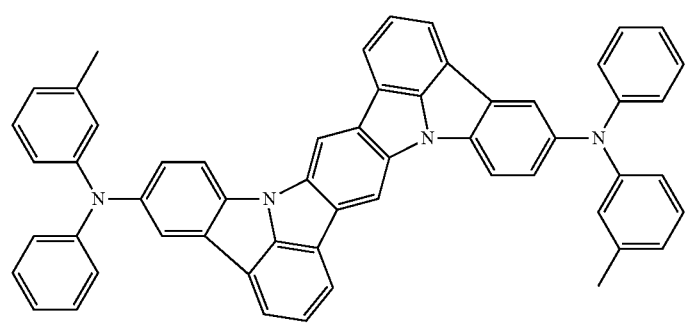

-continued
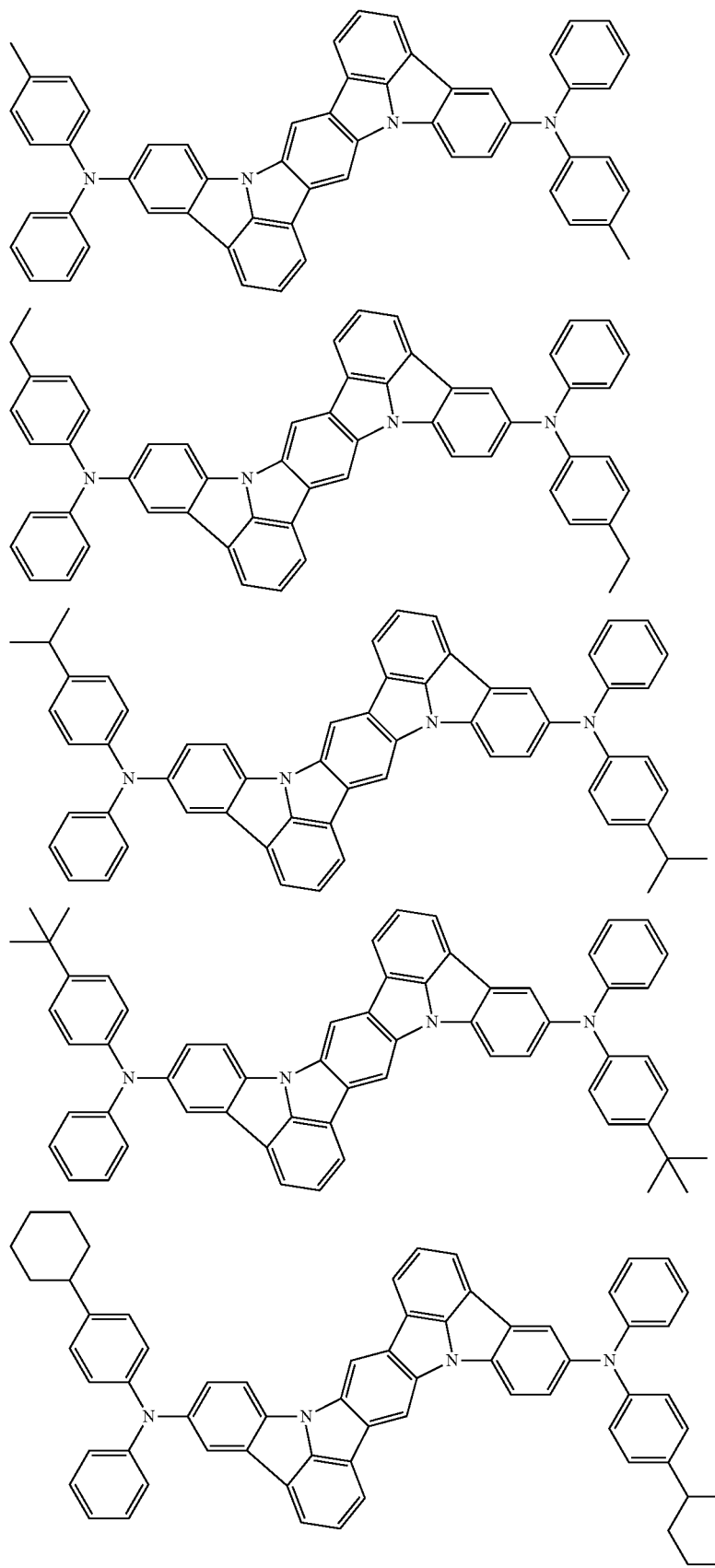

-continued
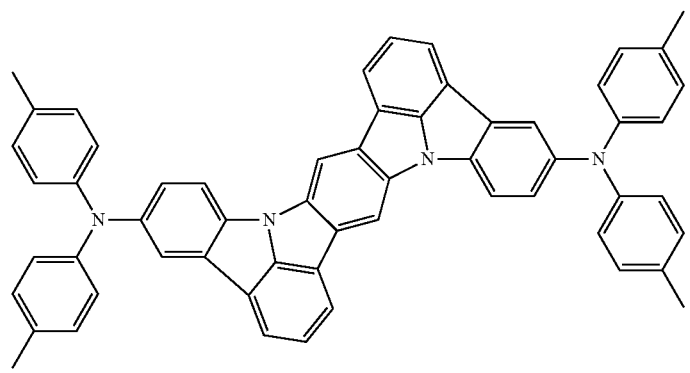
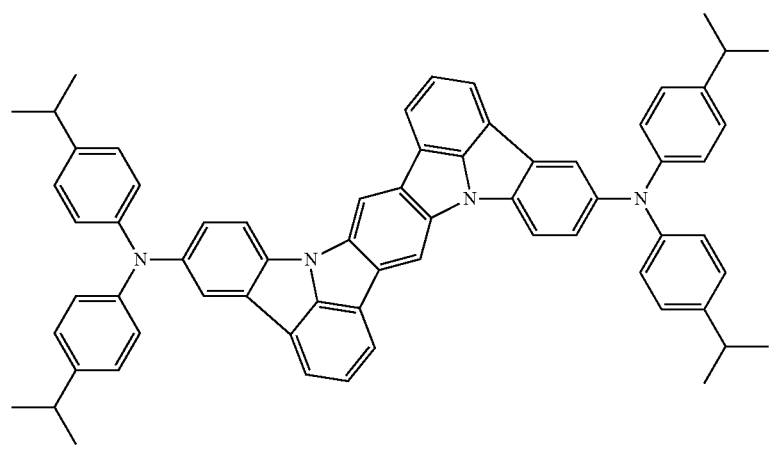
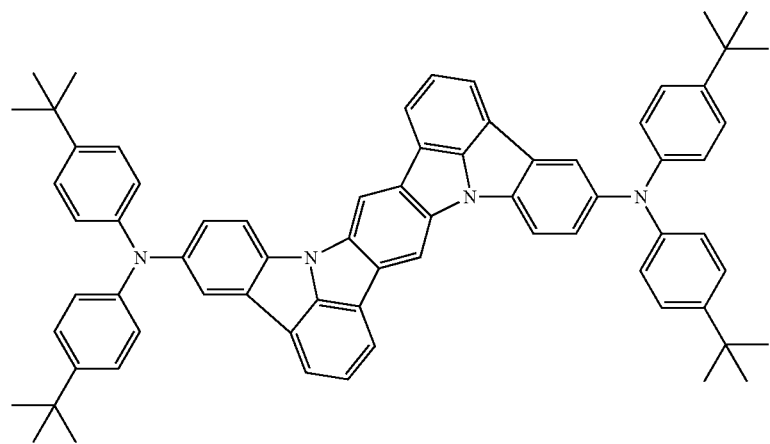

-continued
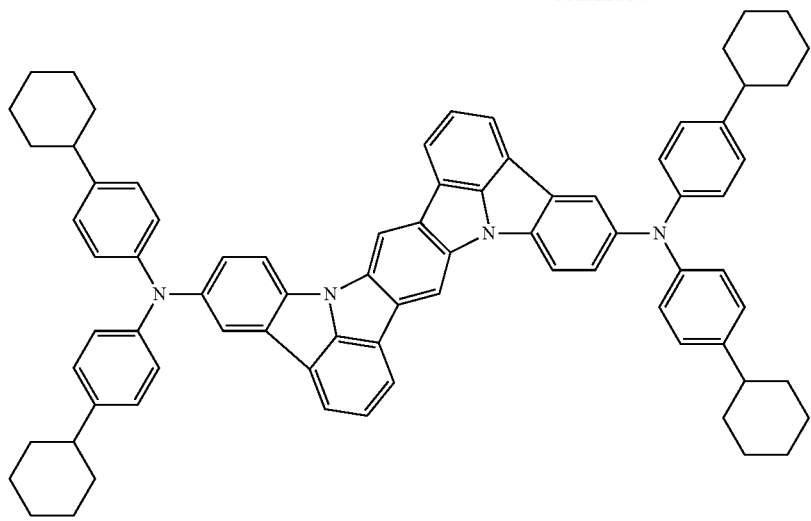
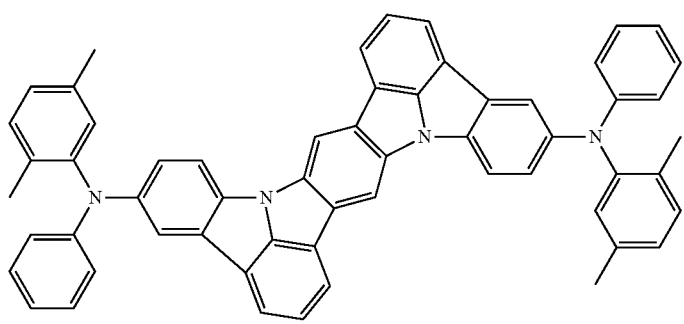
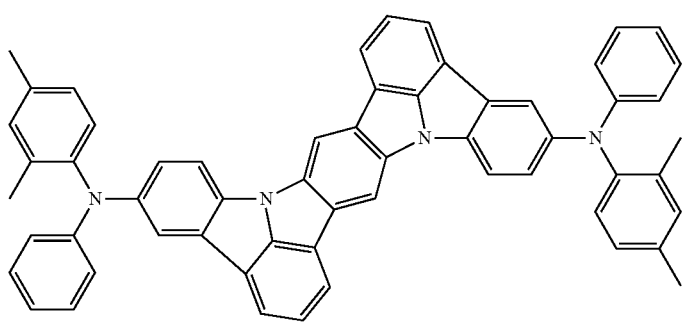
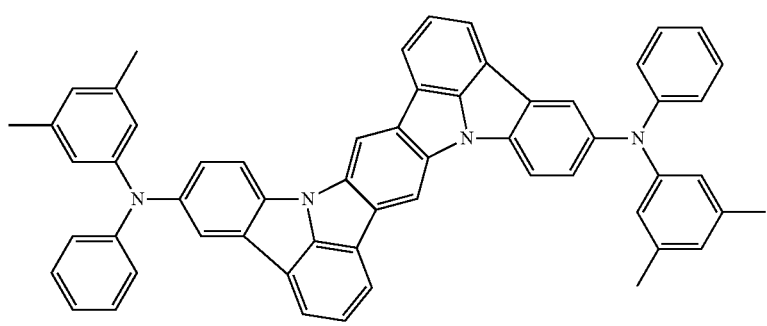

-continued
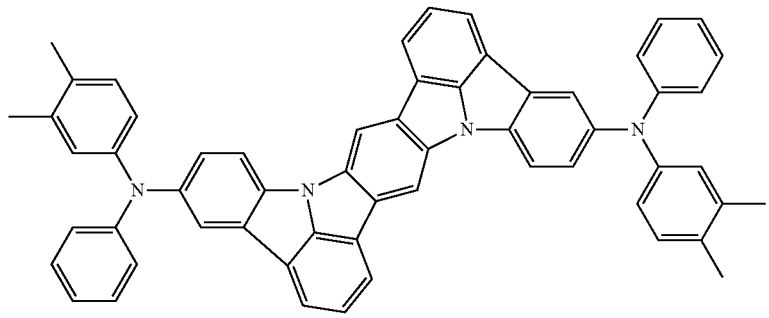
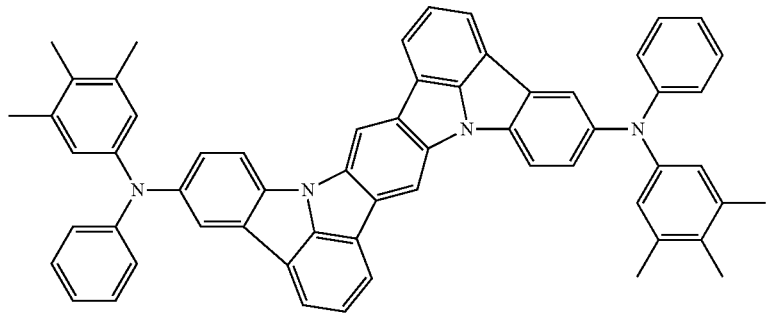
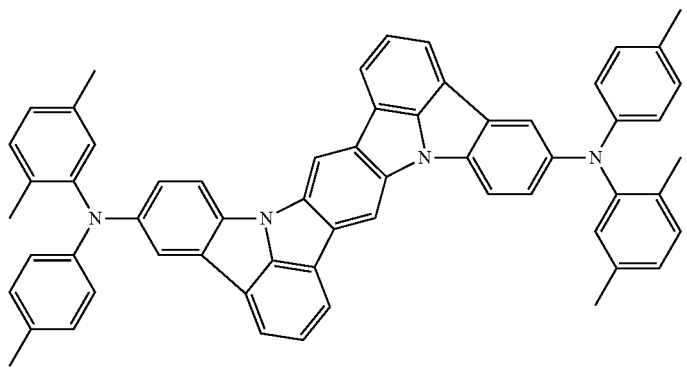
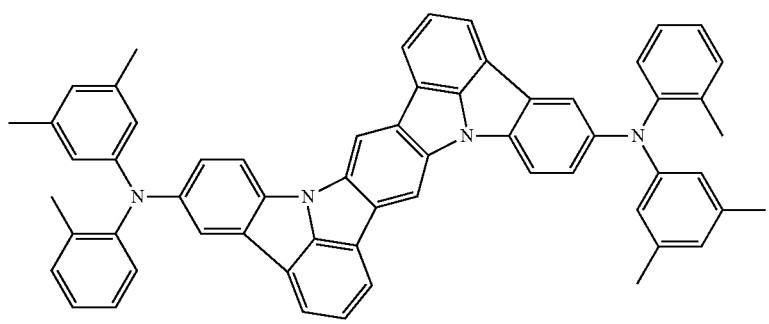
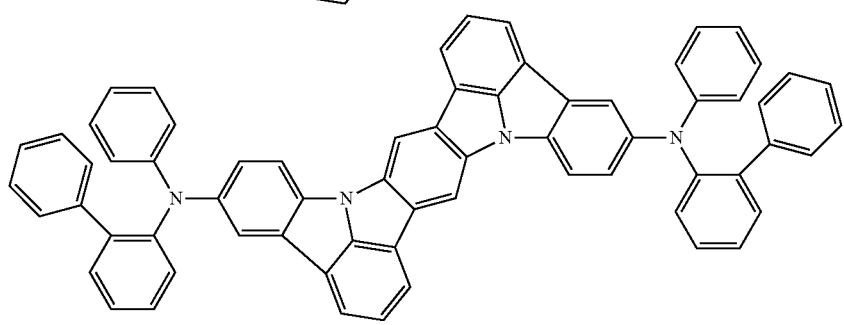

-continued
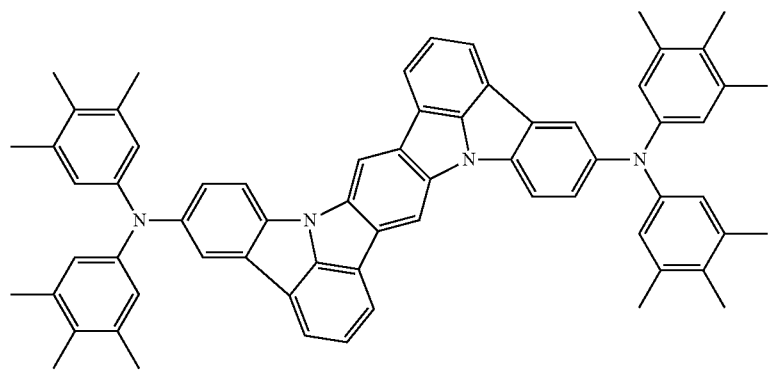
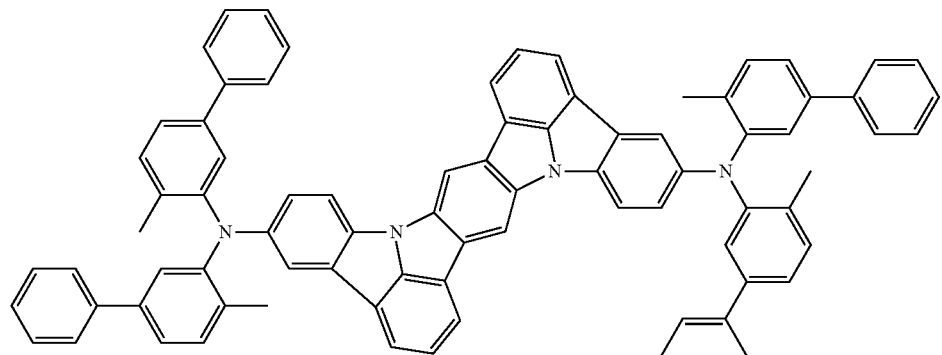
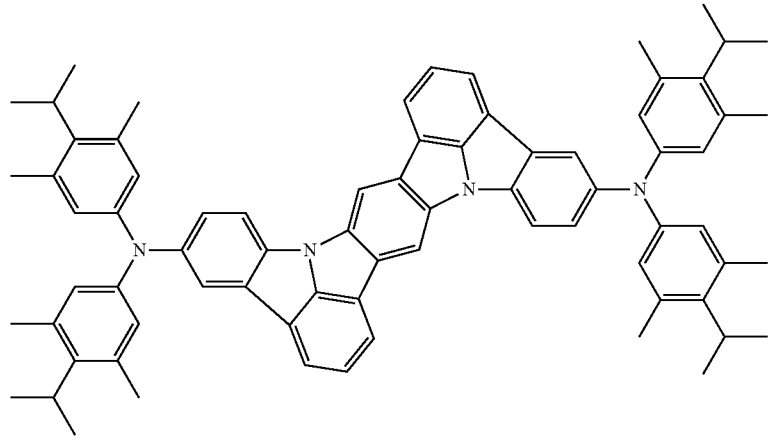
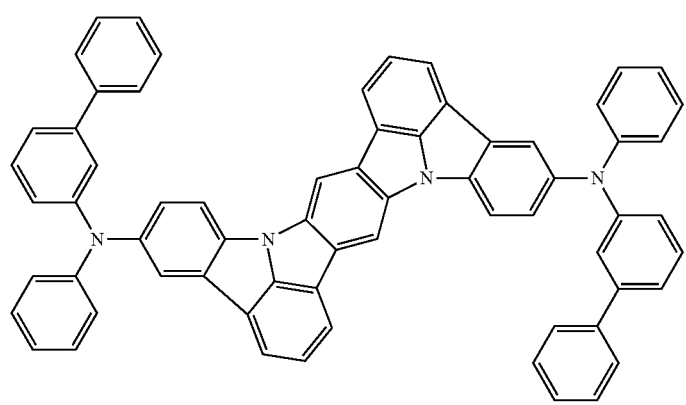

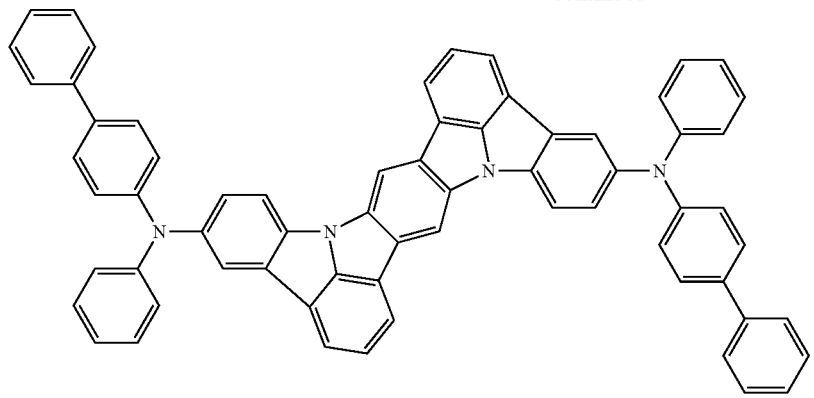
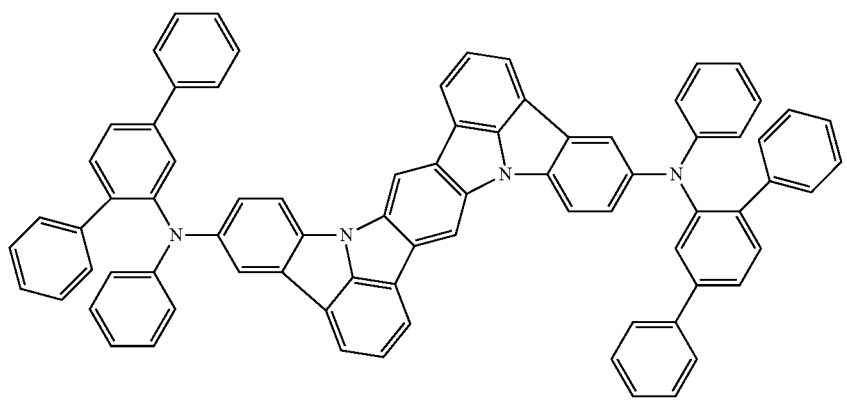
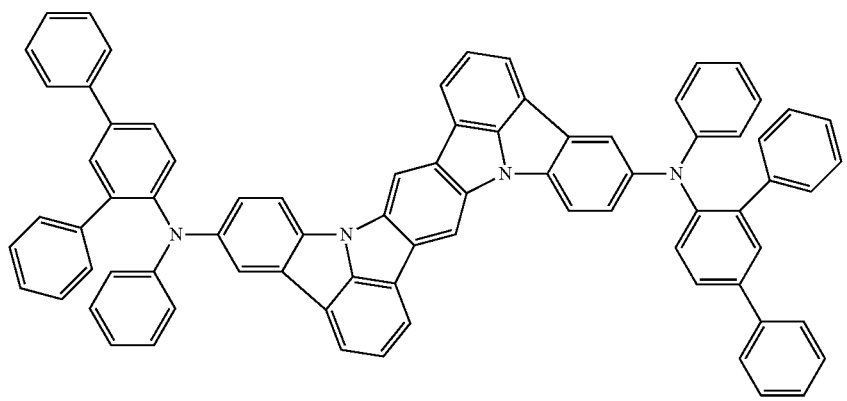
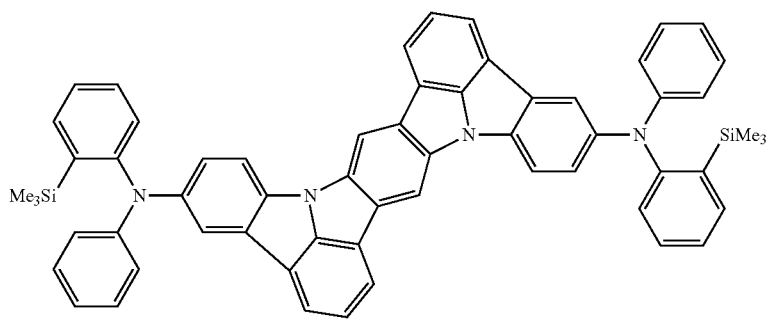

-continued
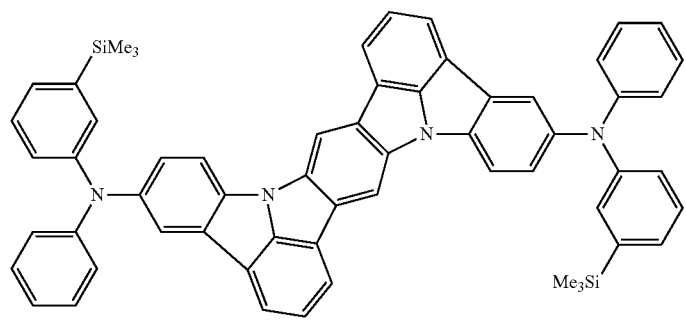
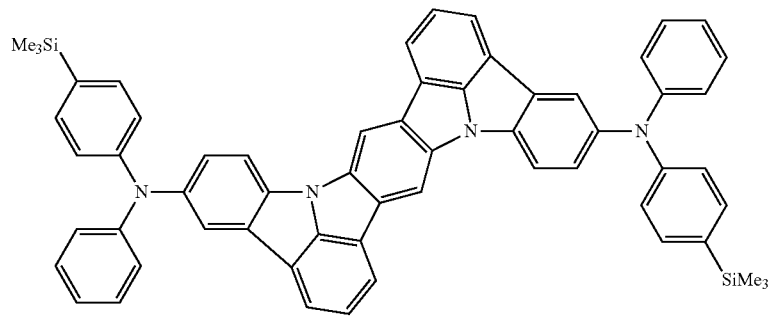
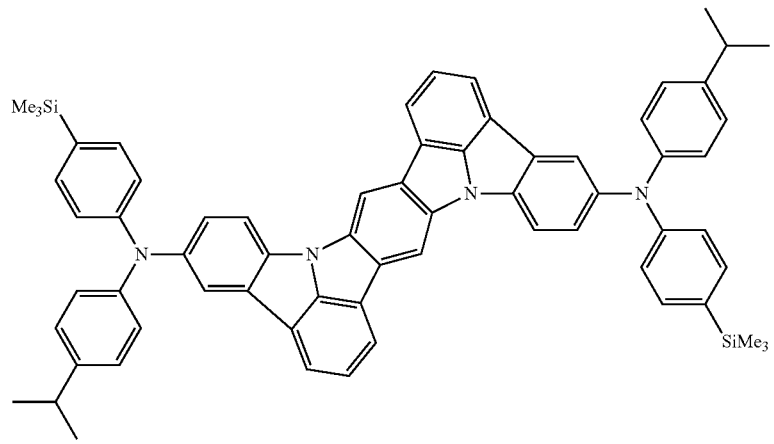
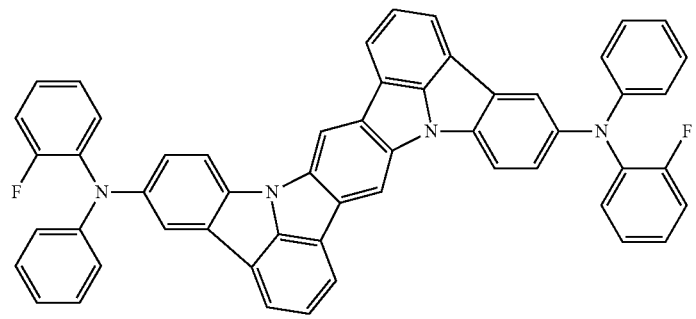
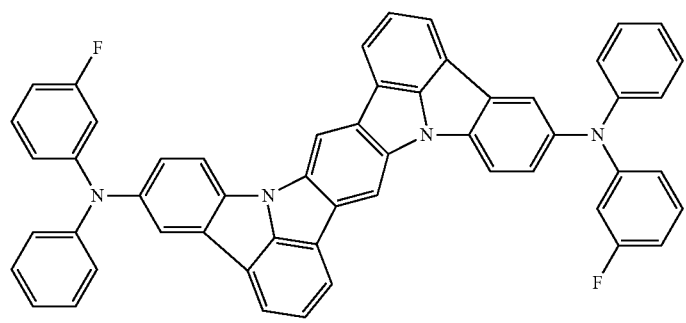

-continued
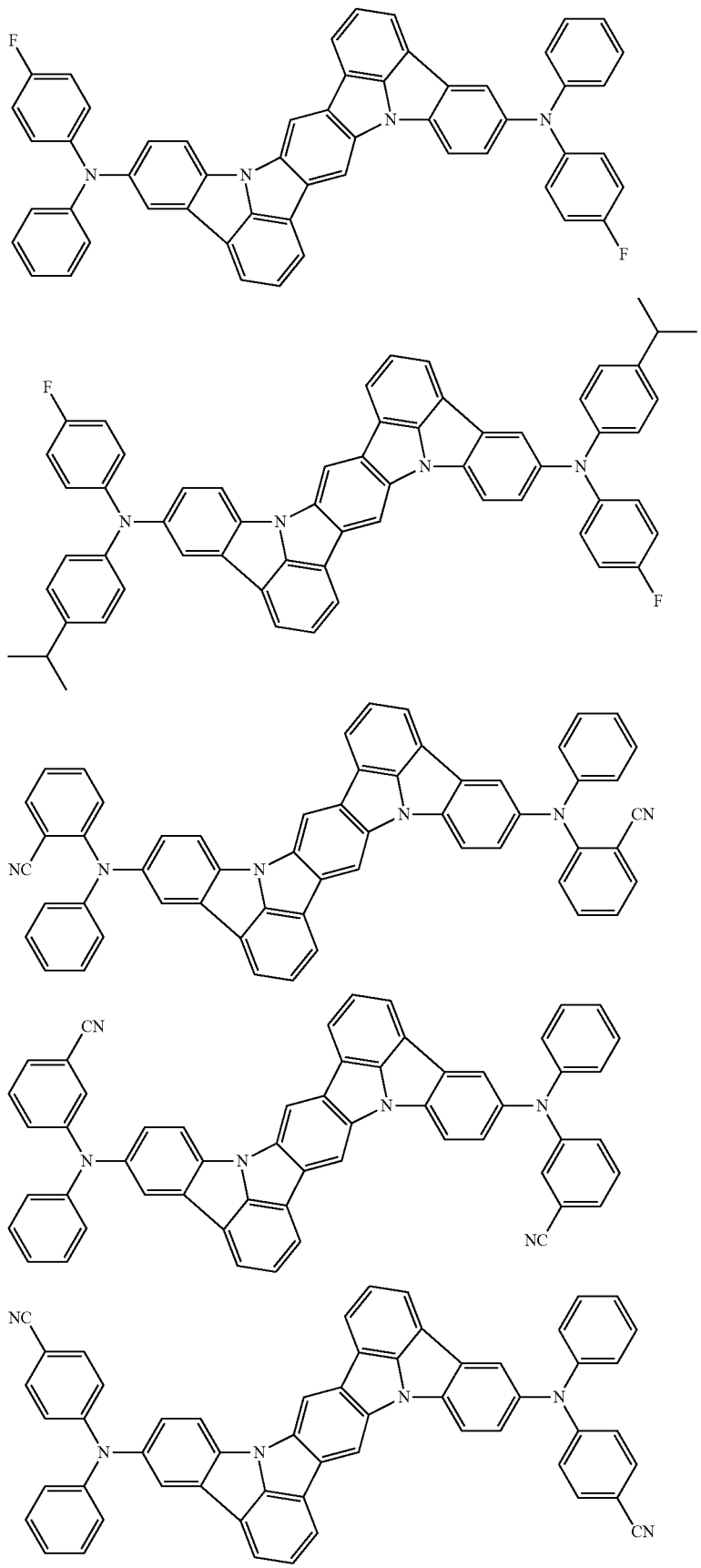

-continued
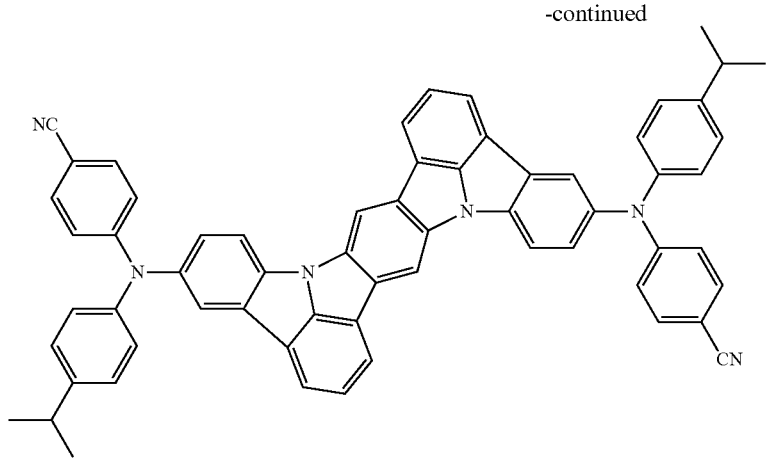
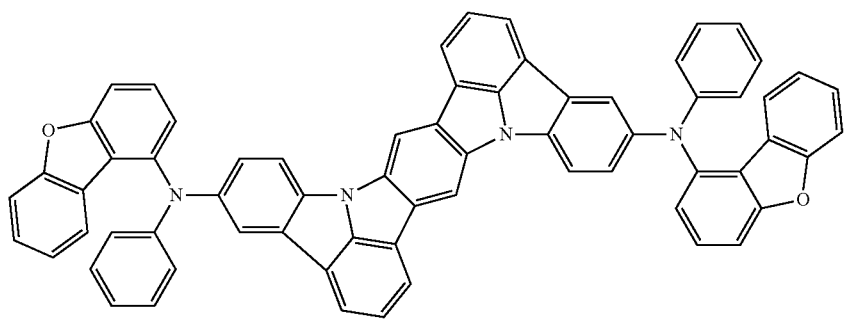
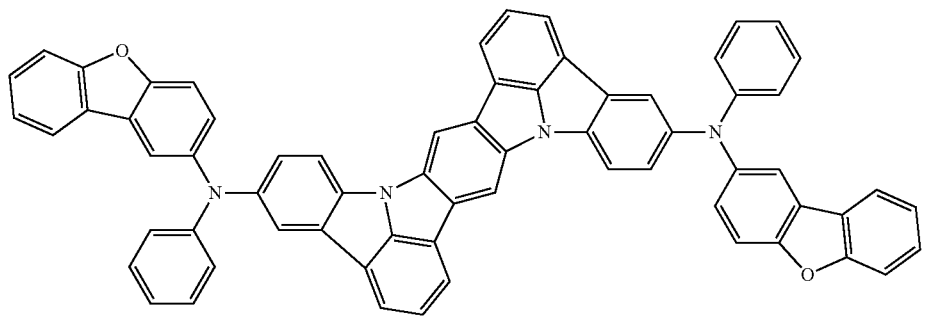
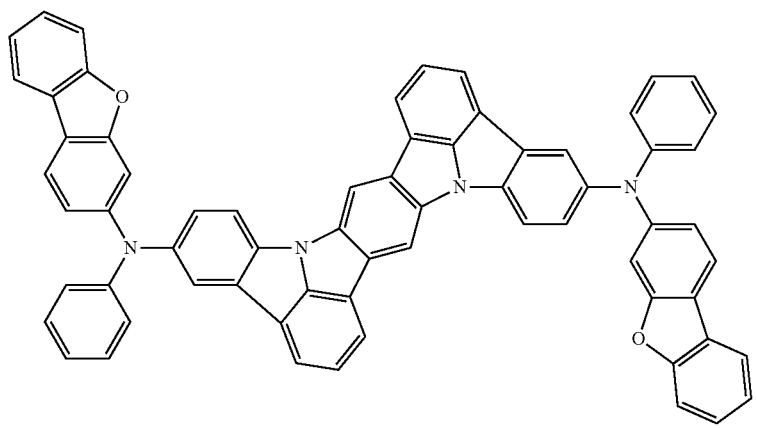

-continued
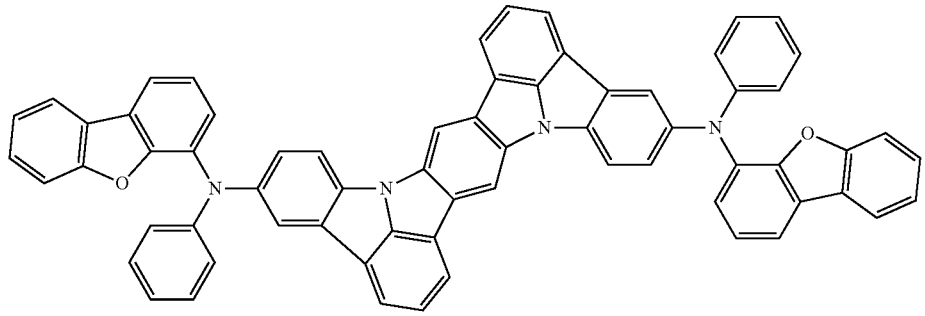
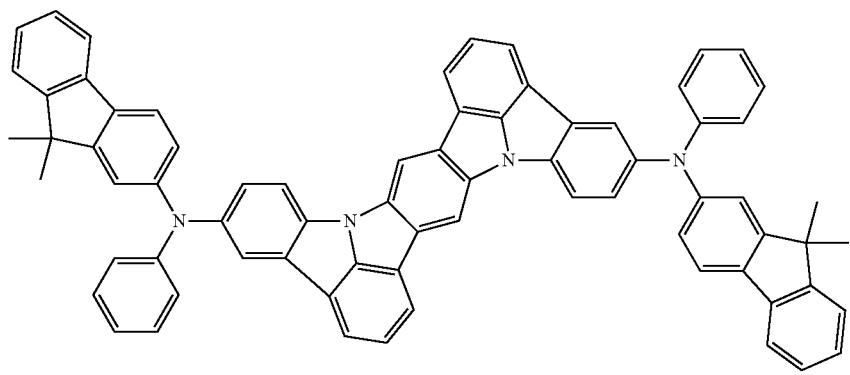
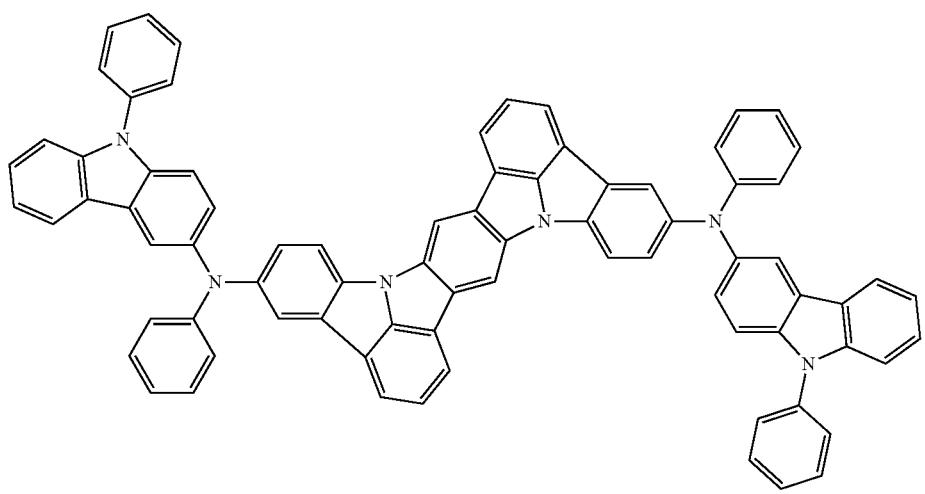
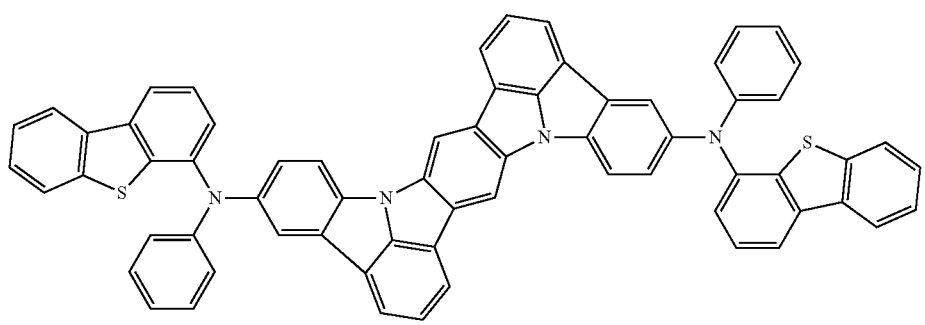

-continued
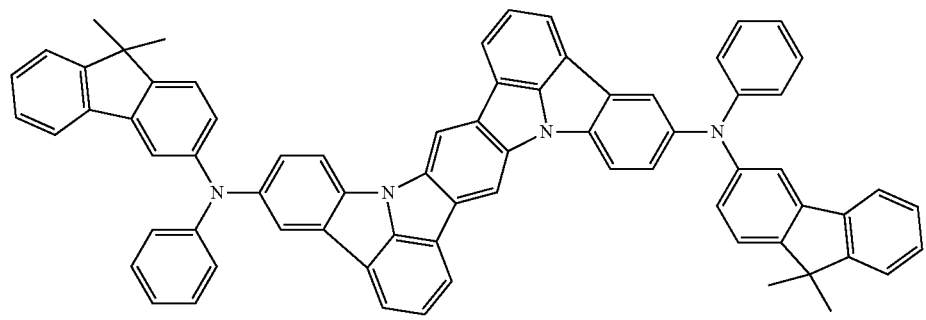
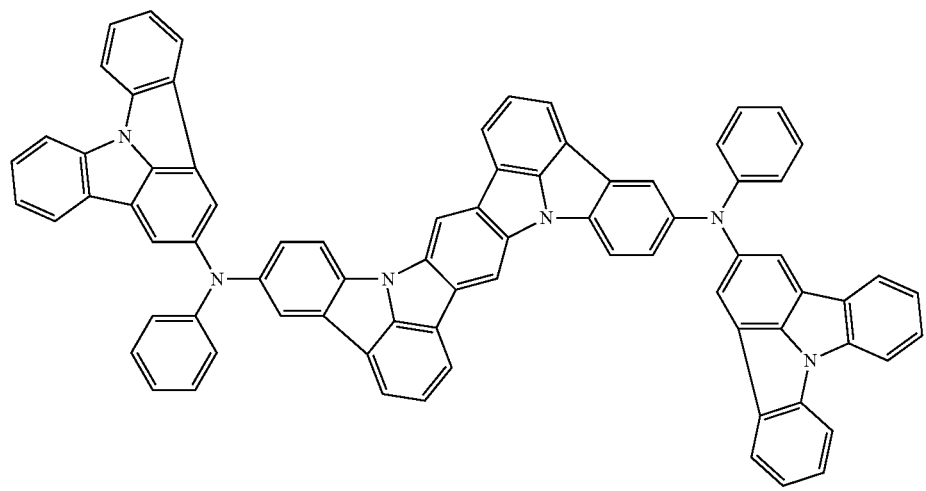
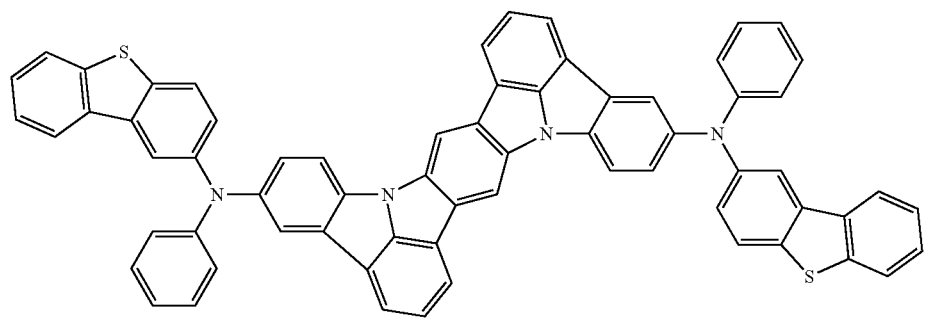
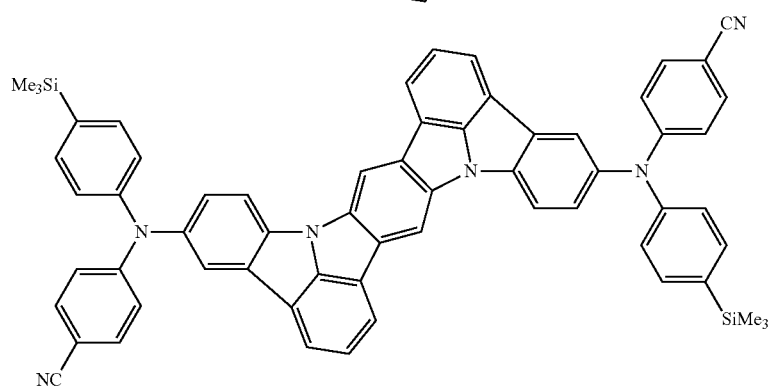

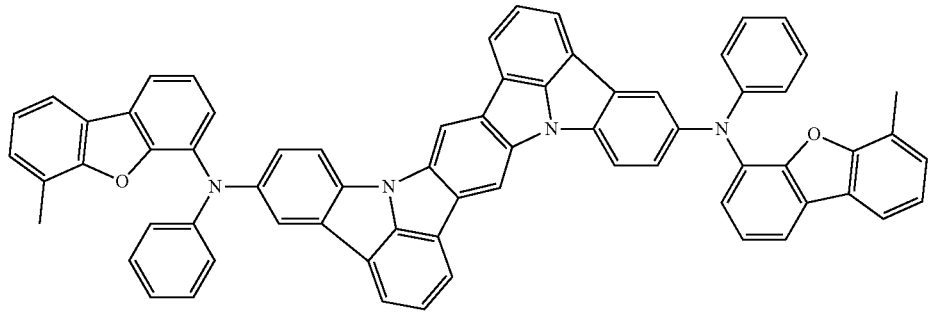
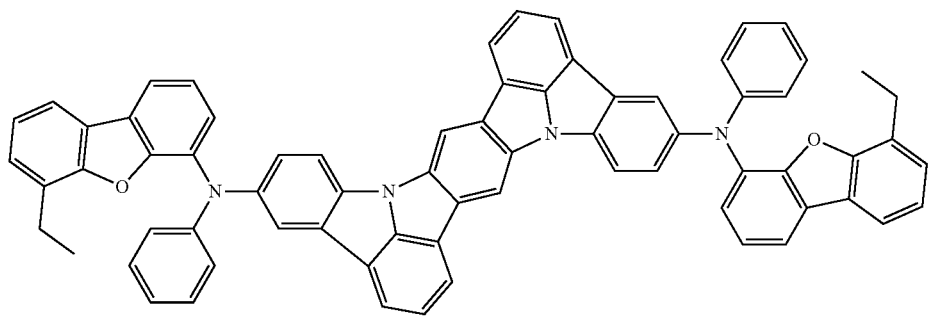
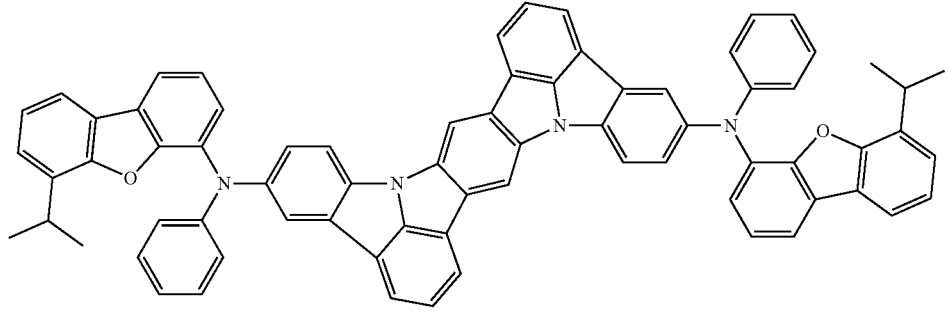
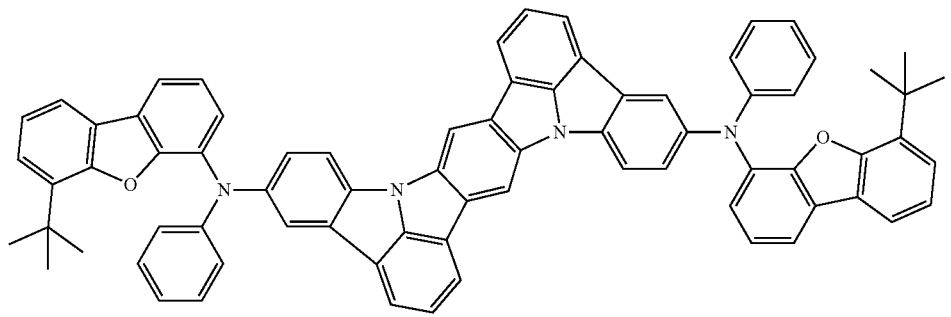
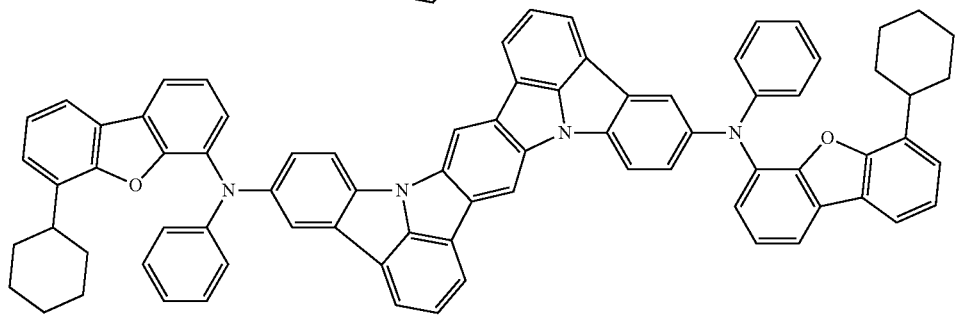

-continued
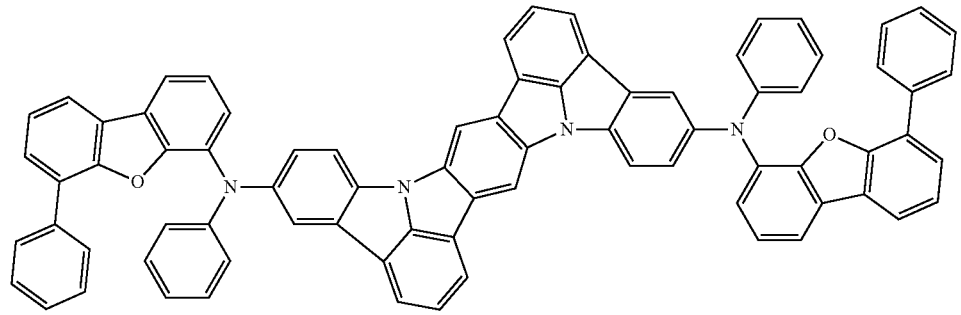
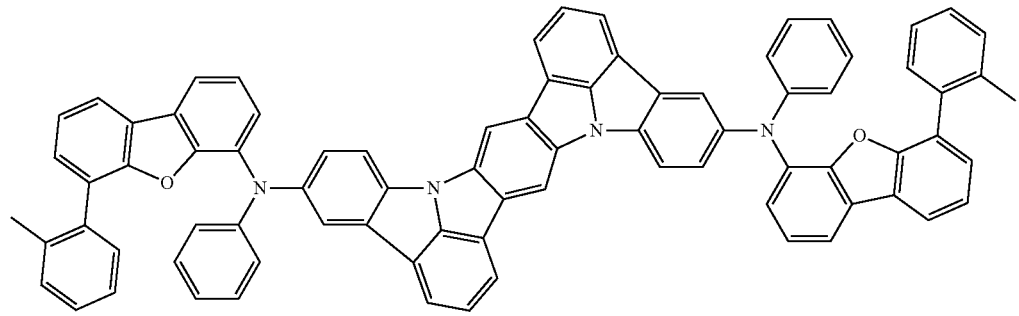
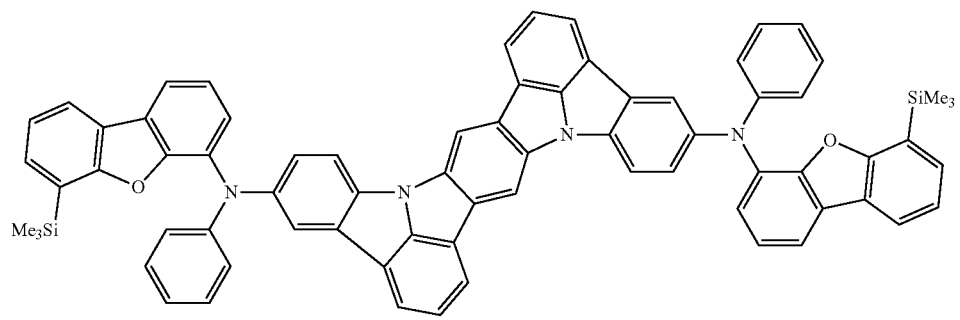
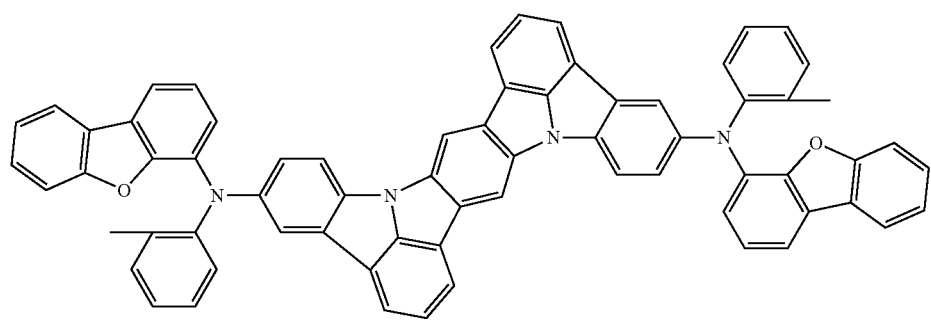
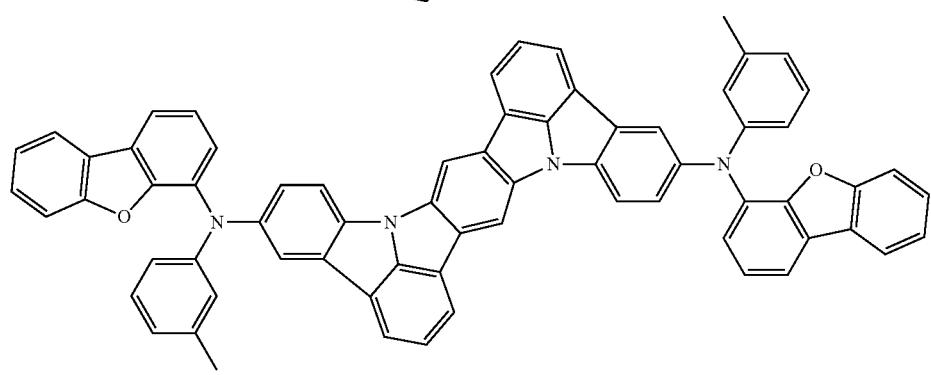

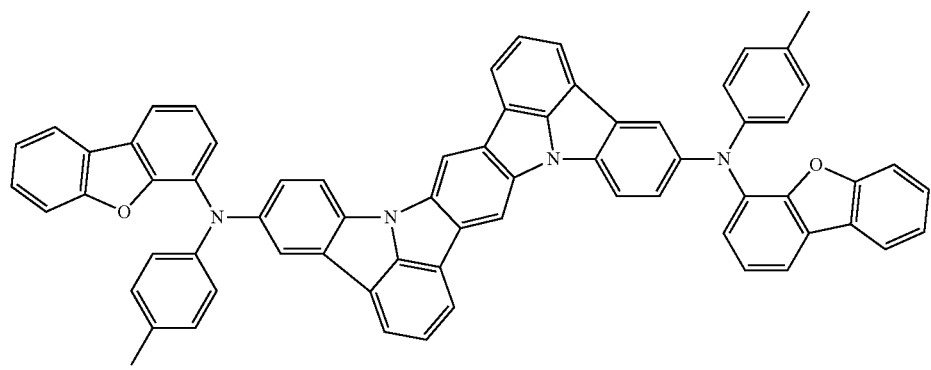
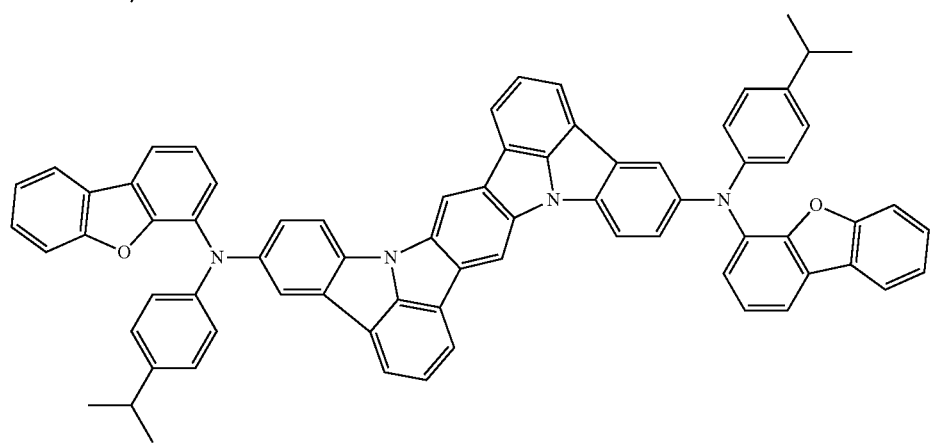
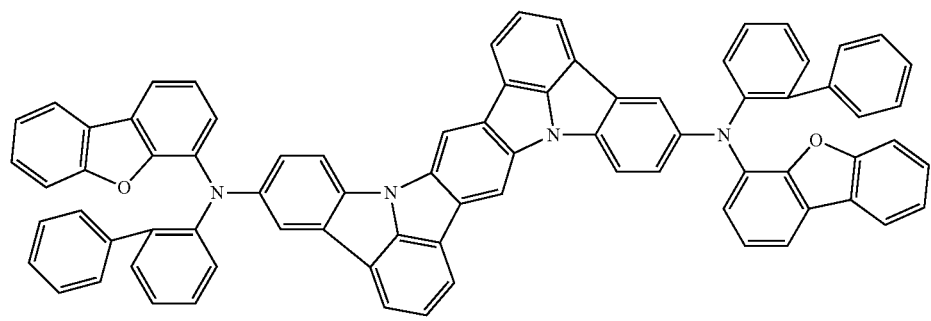
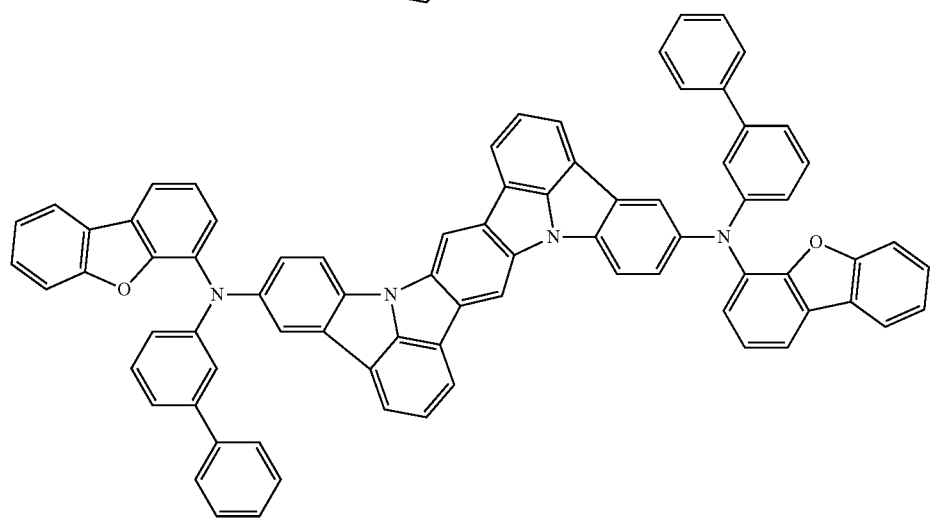

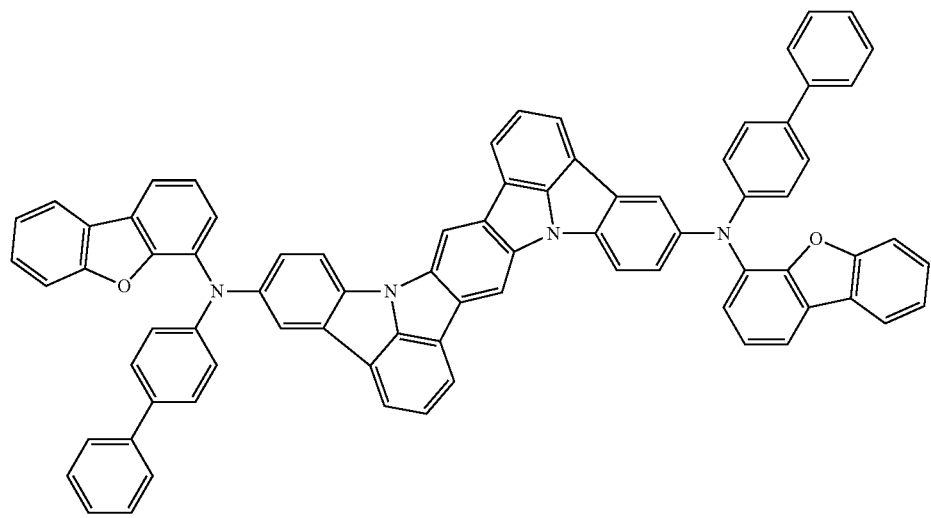
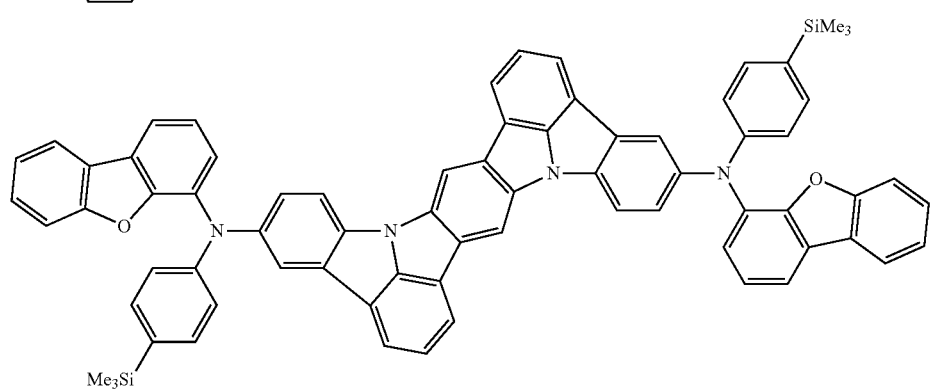
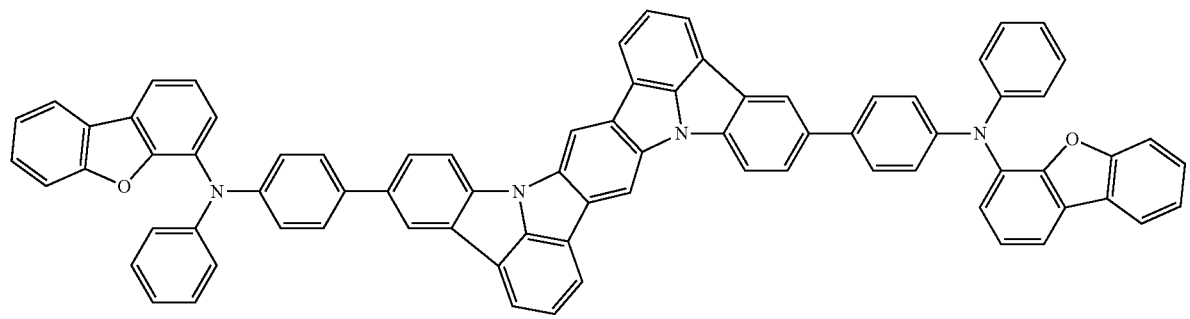
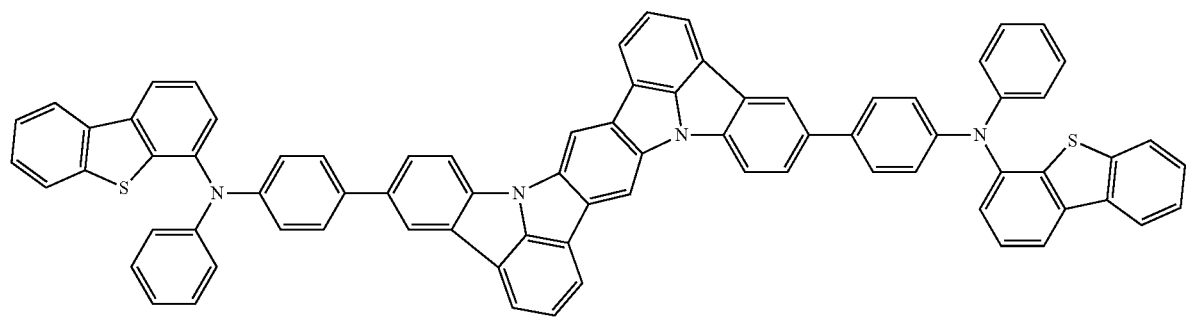

-continued
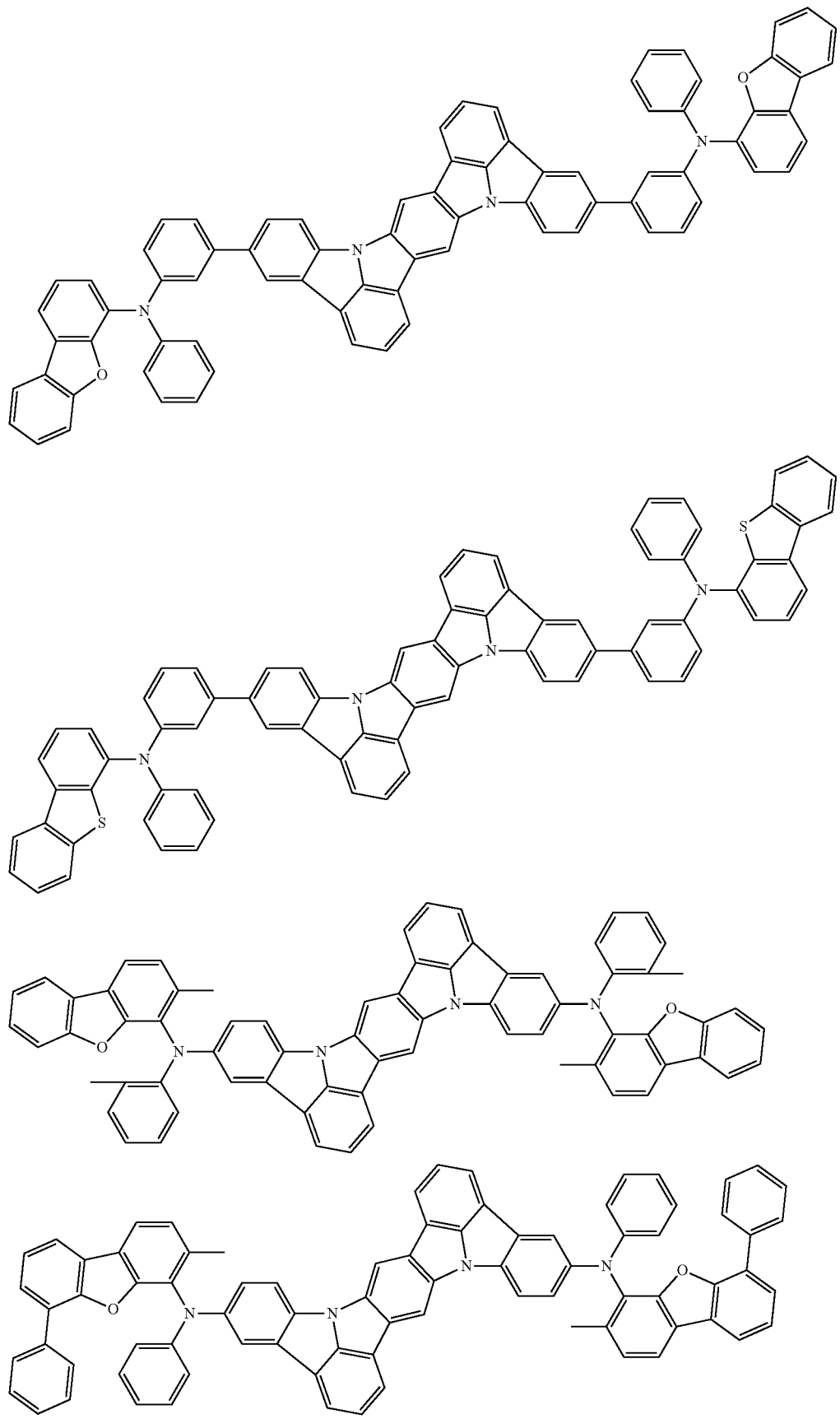

-continued
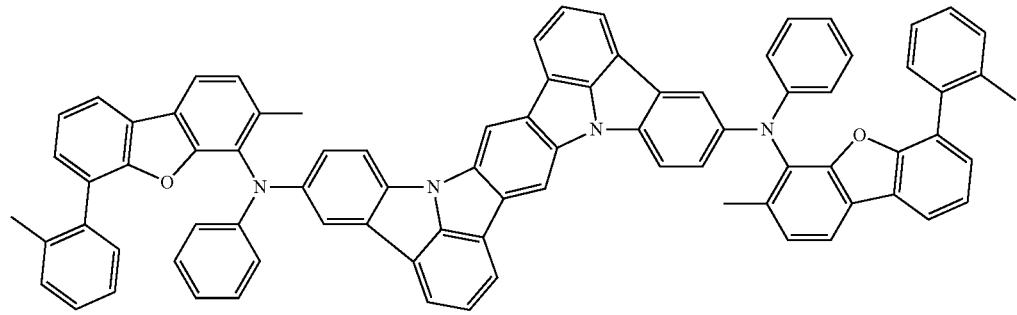
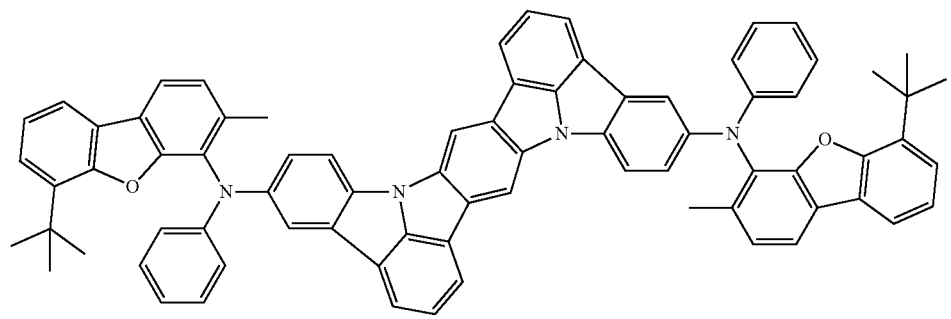
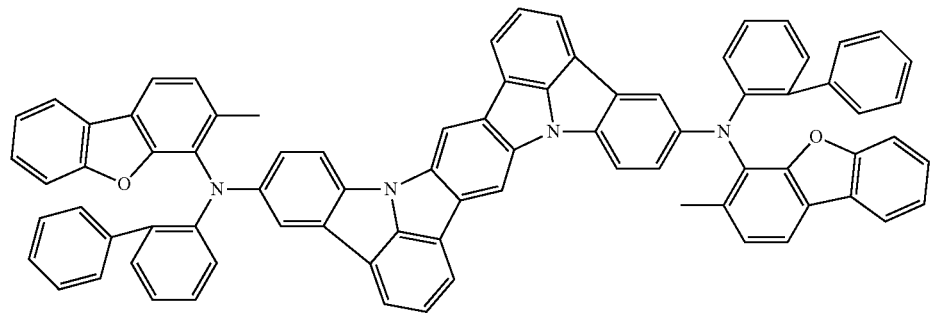
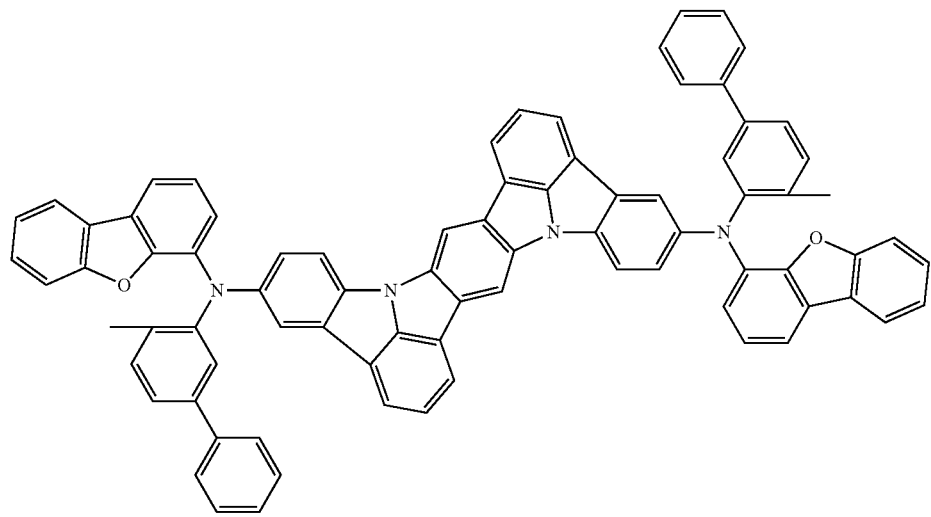

-continued
549 550
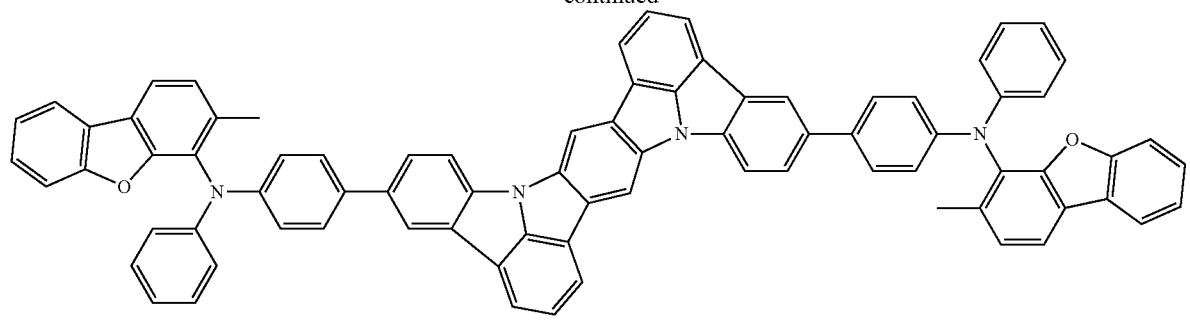
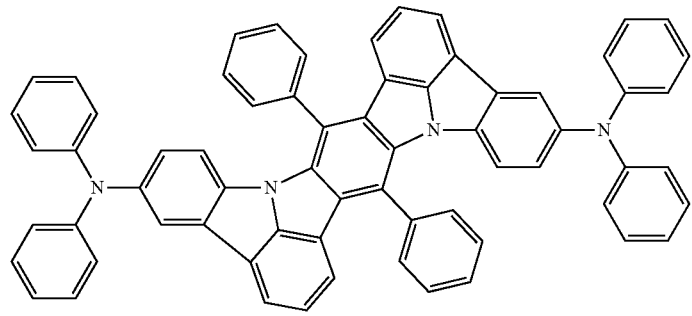
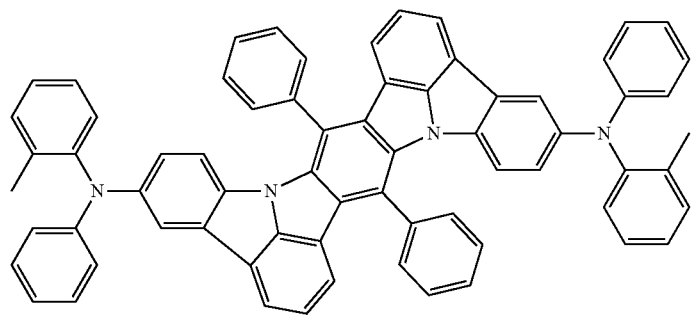
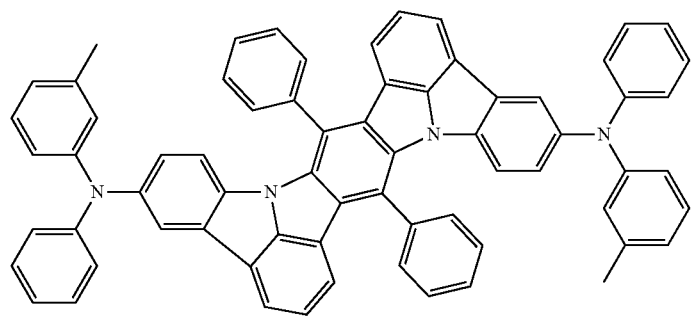
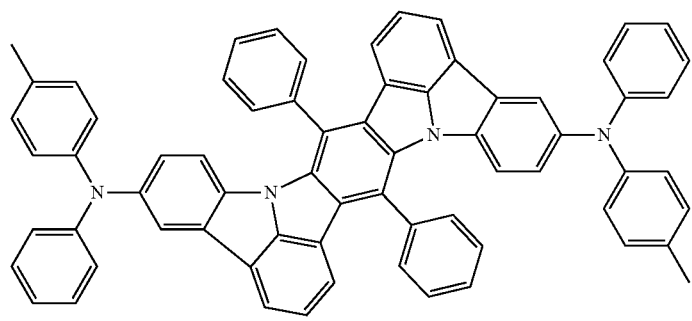

-continued
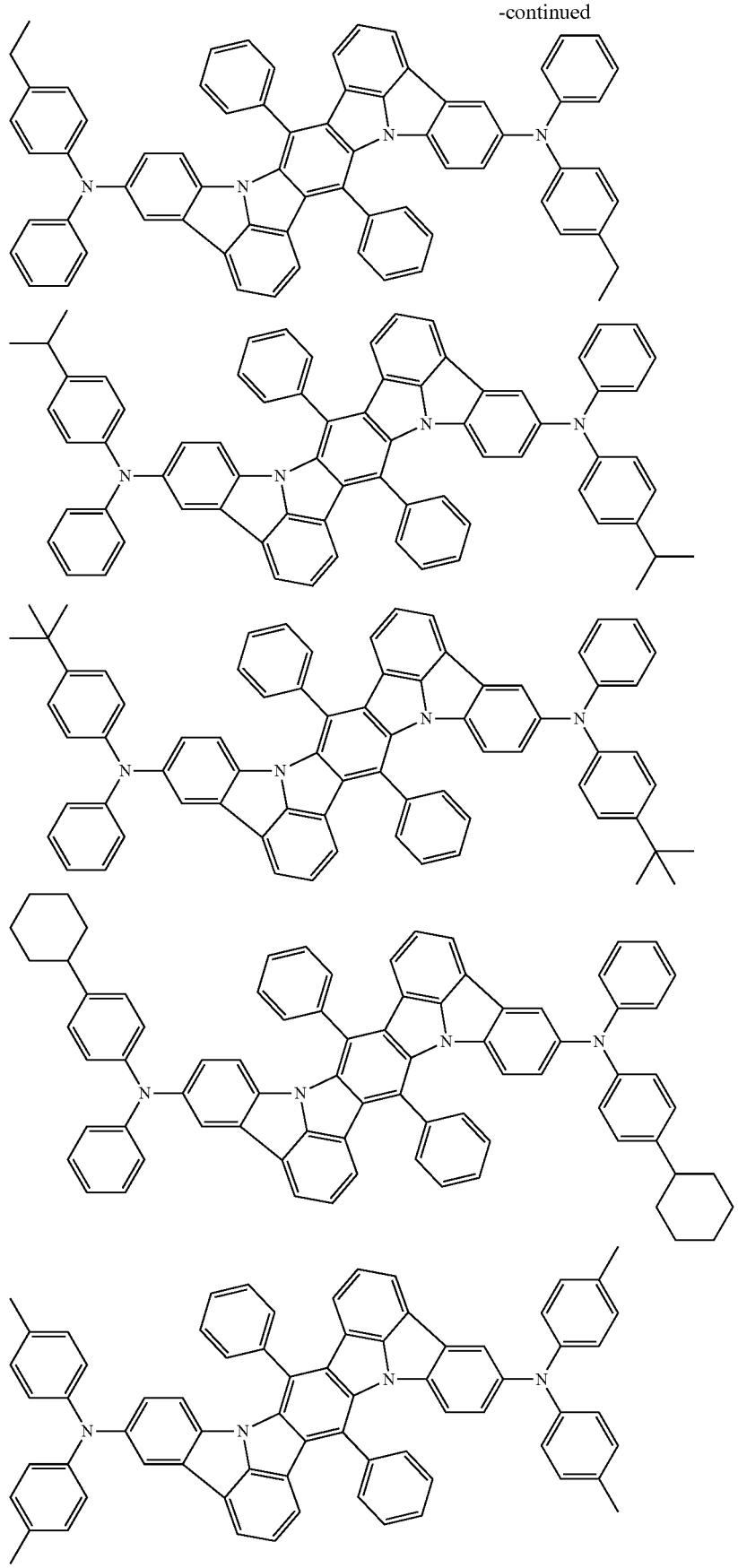

-continued
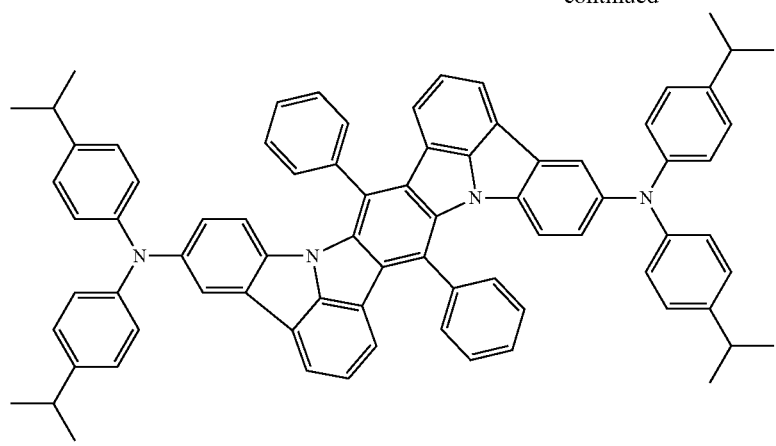
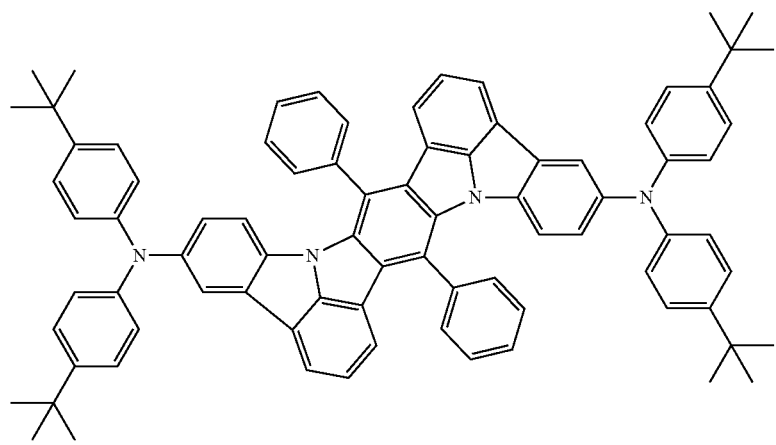
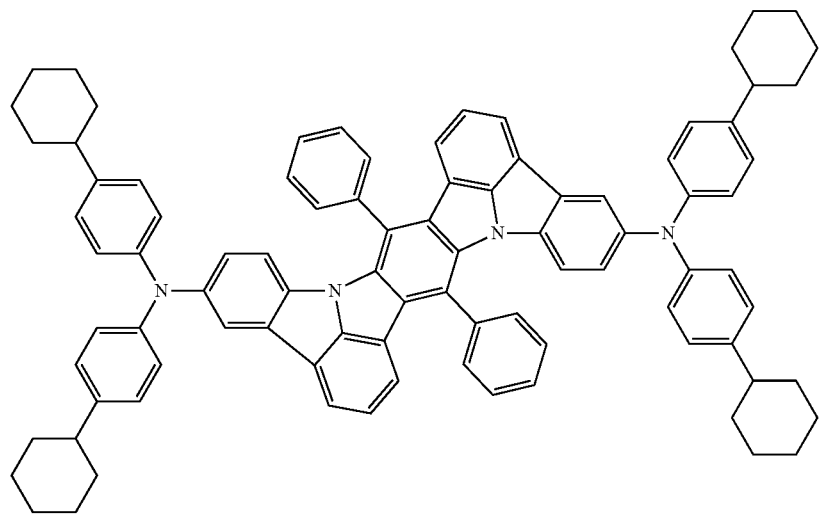
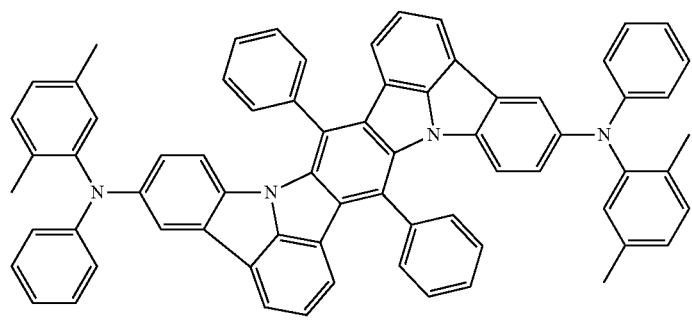

-continued
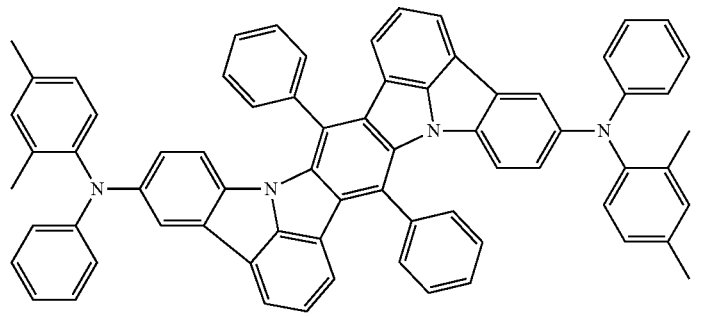
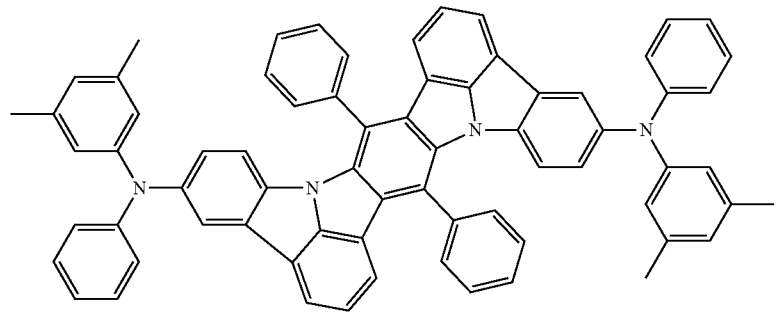
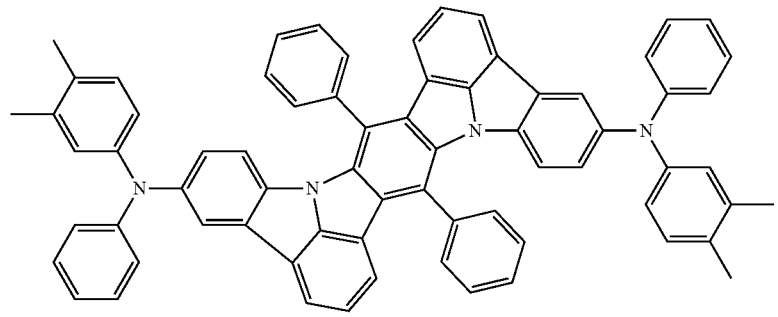
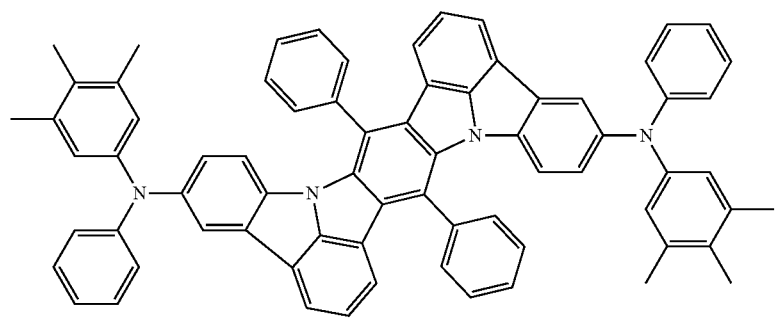
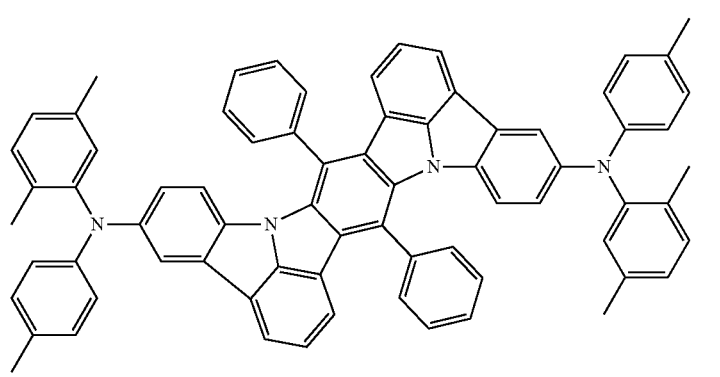

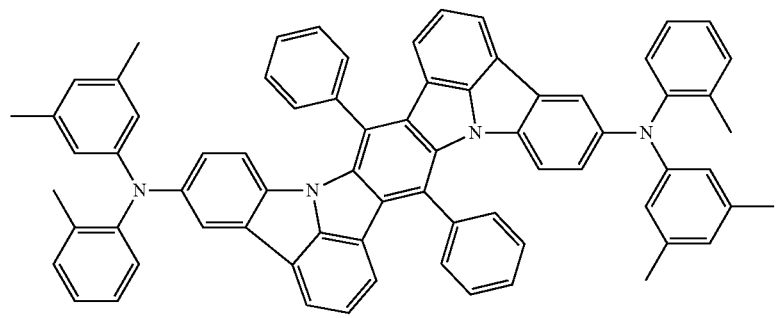
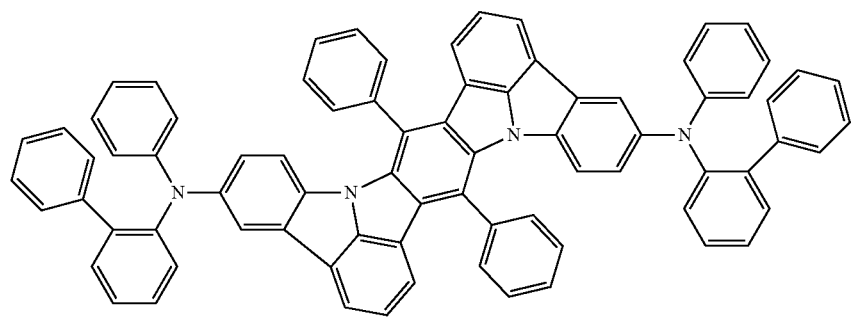
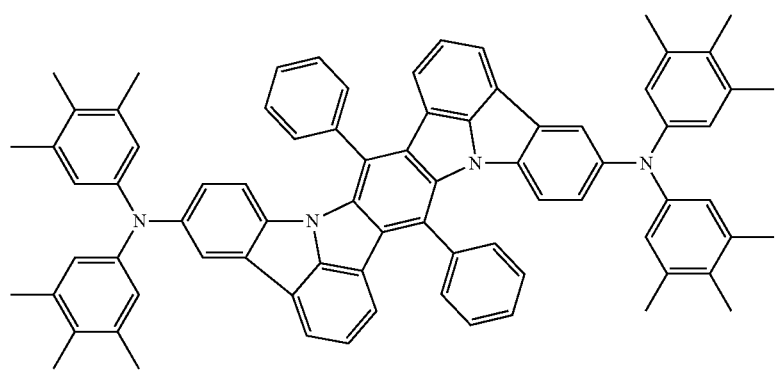
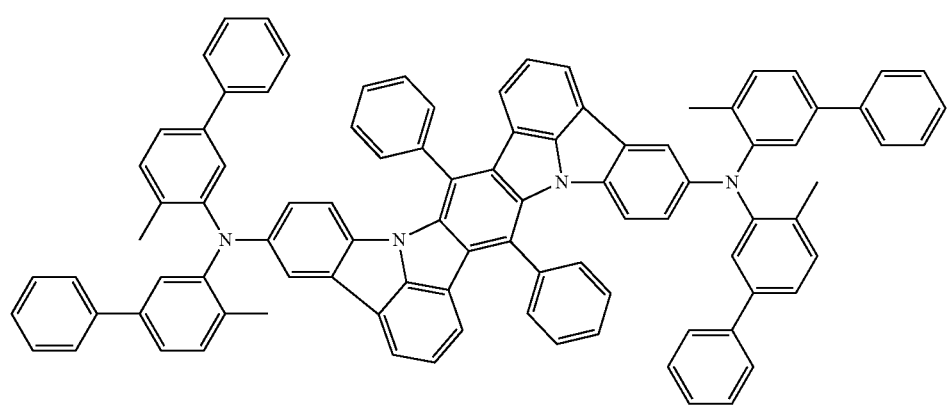

-continued
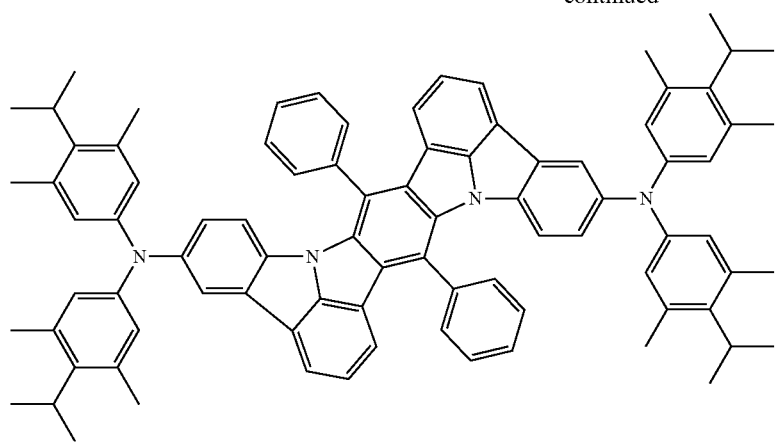
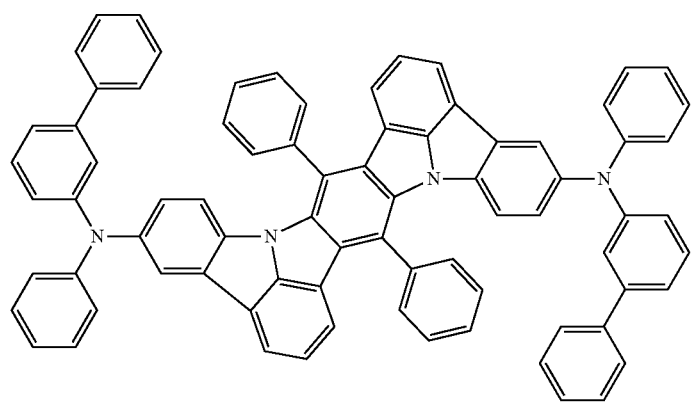
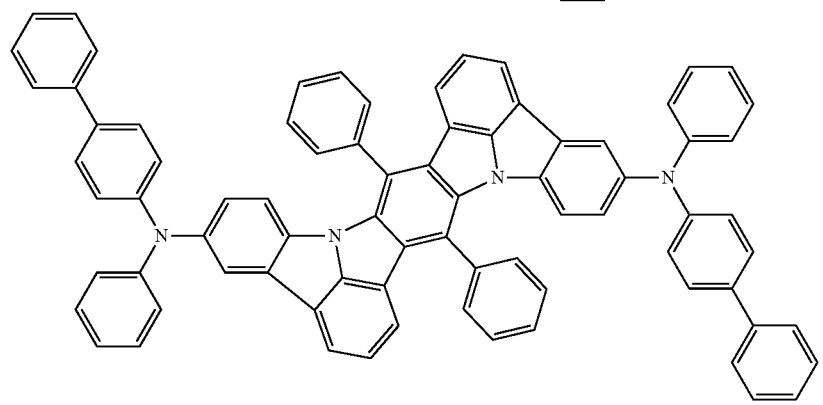
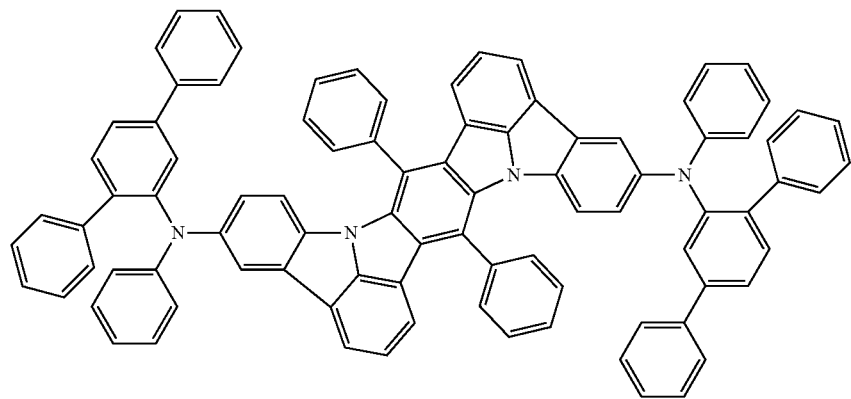

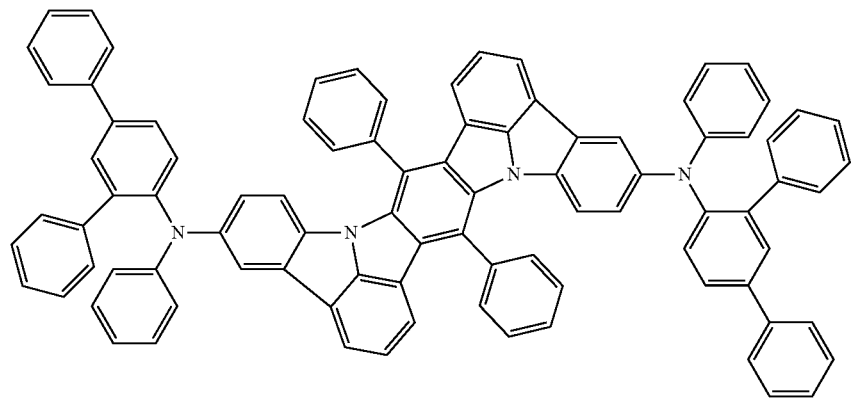
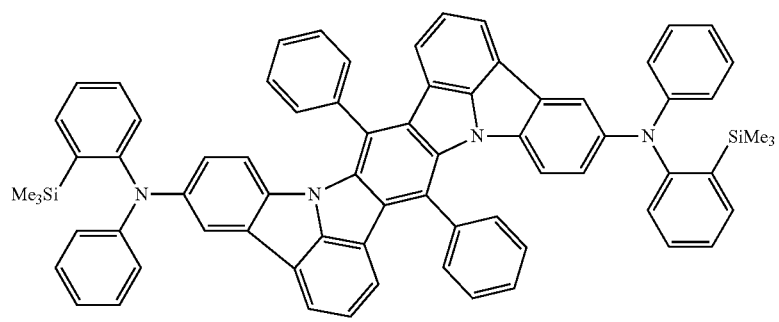
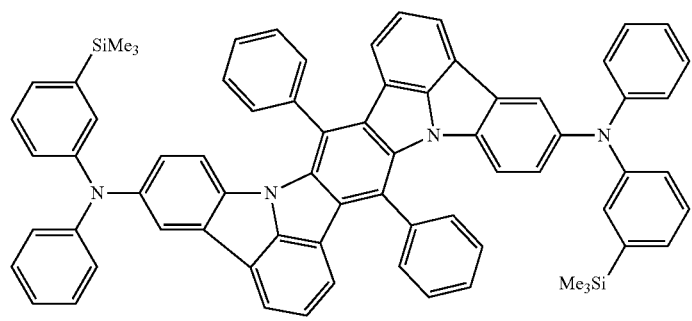
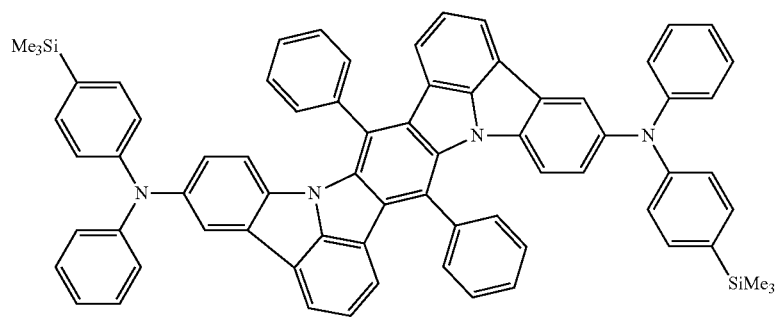

-continued
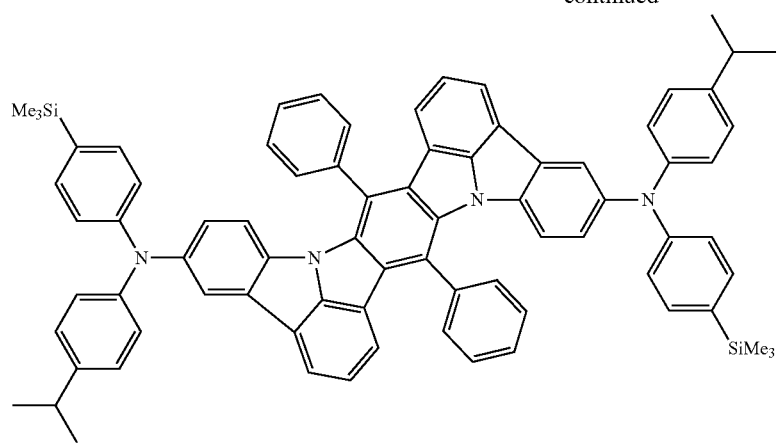
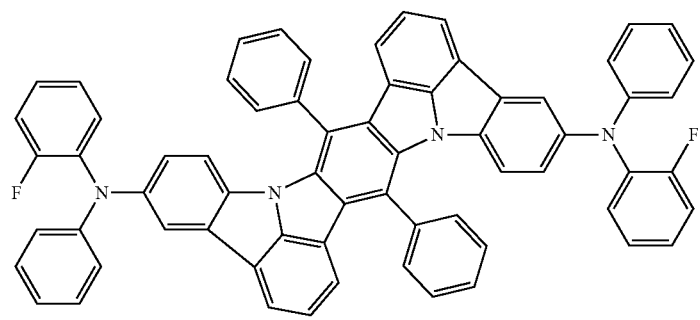
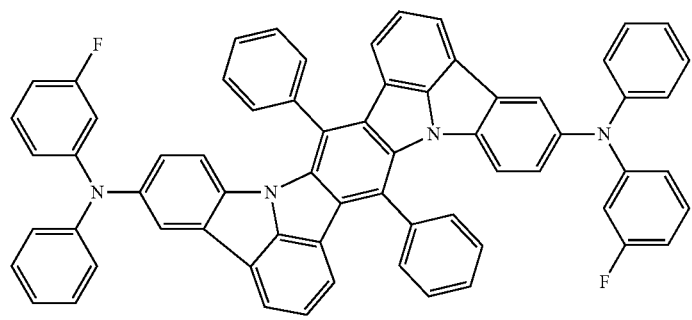
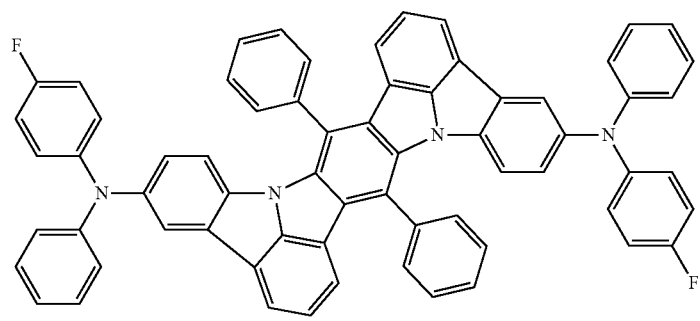

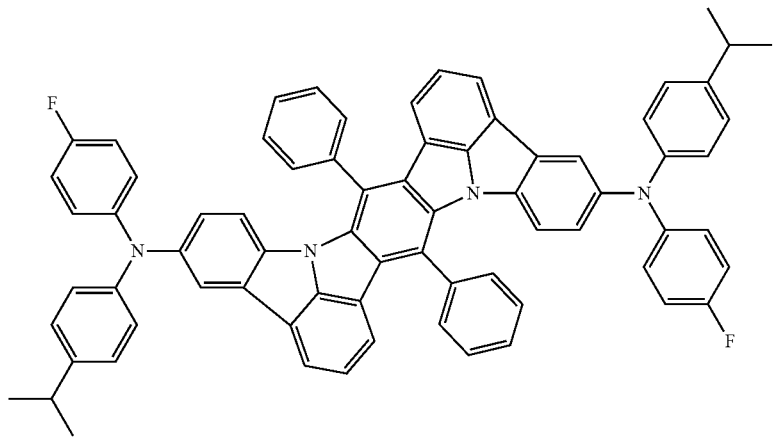
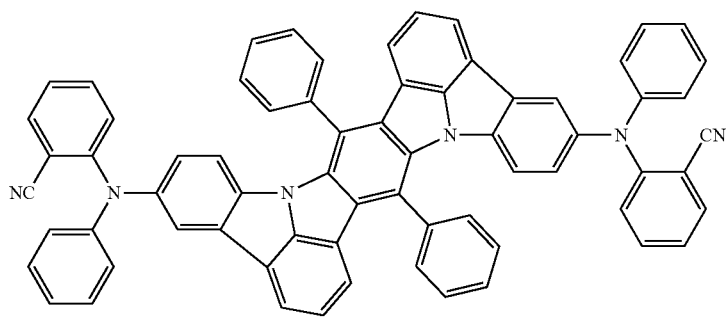
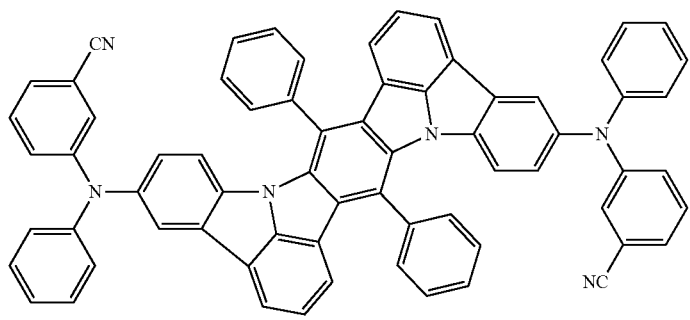
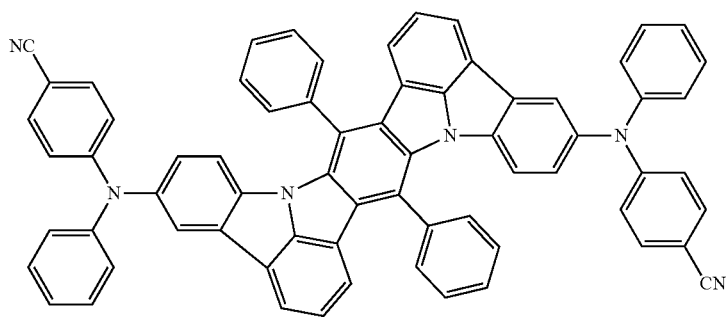

-continued
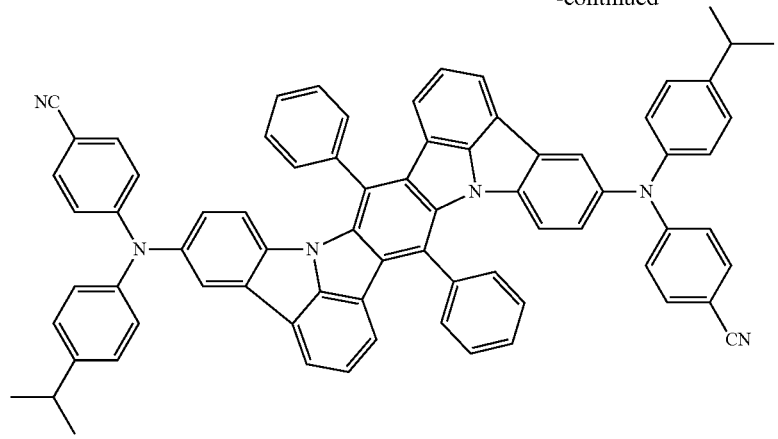
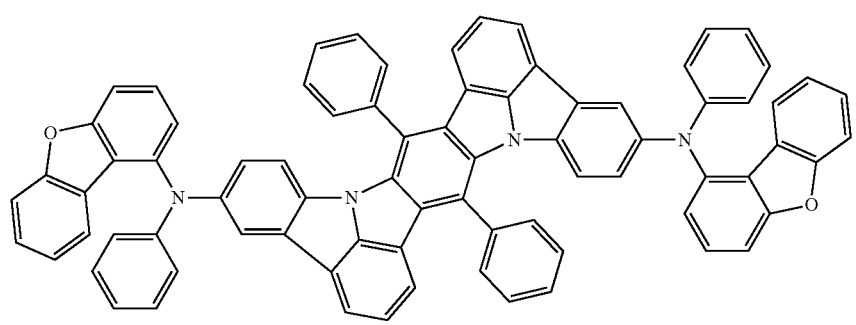
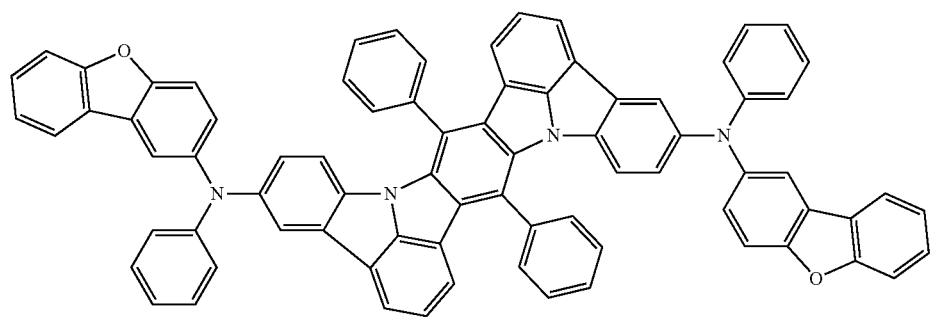
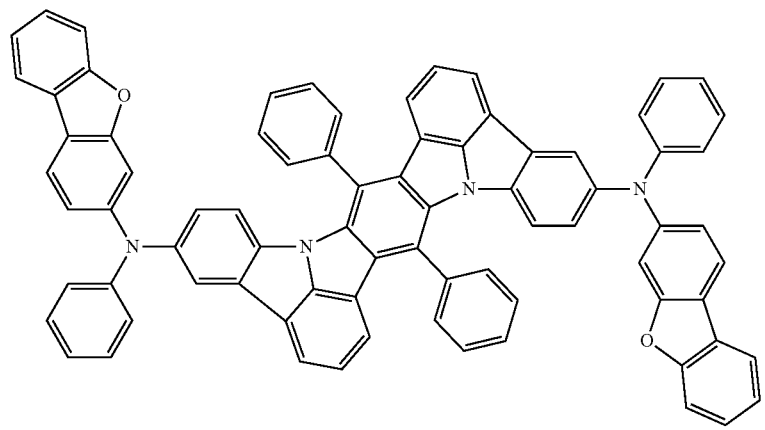

-continued
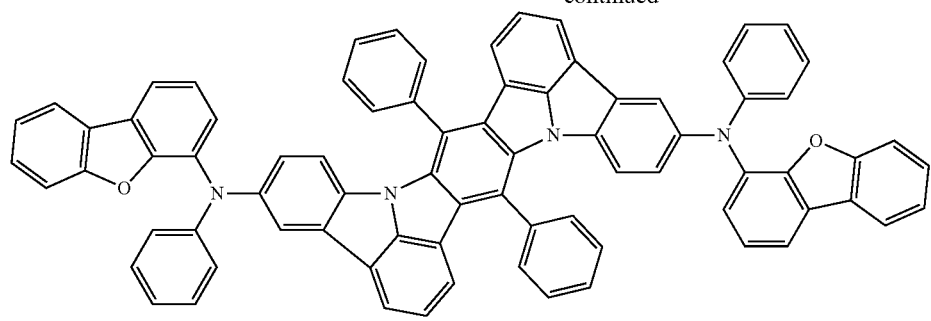
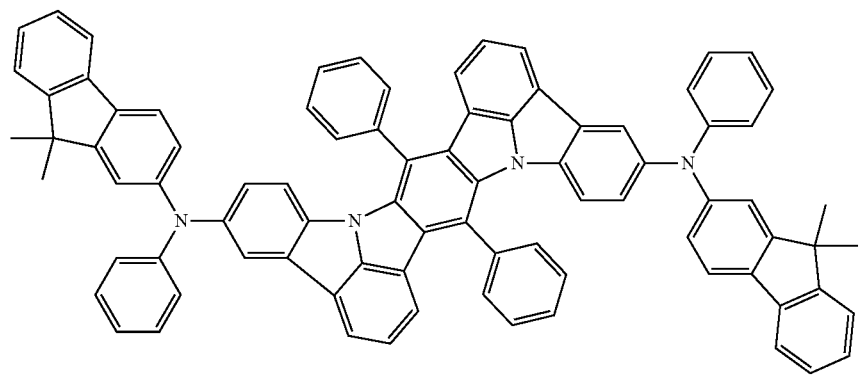
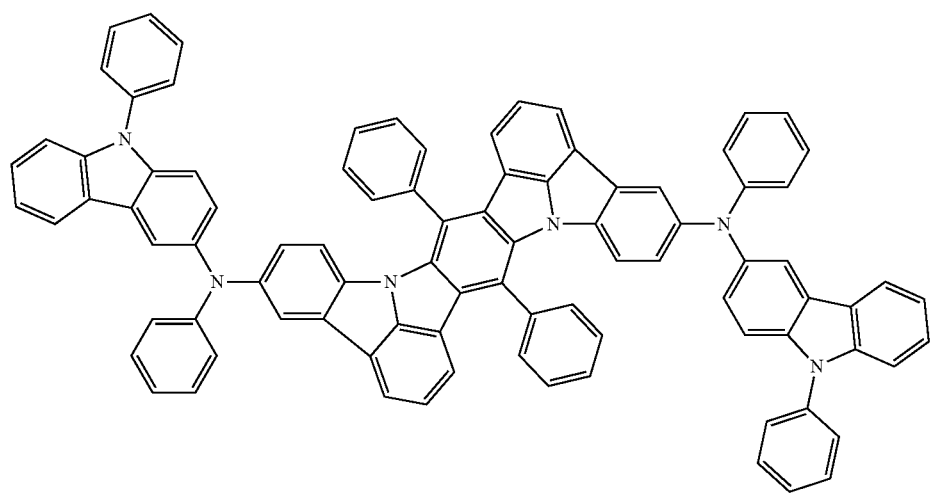
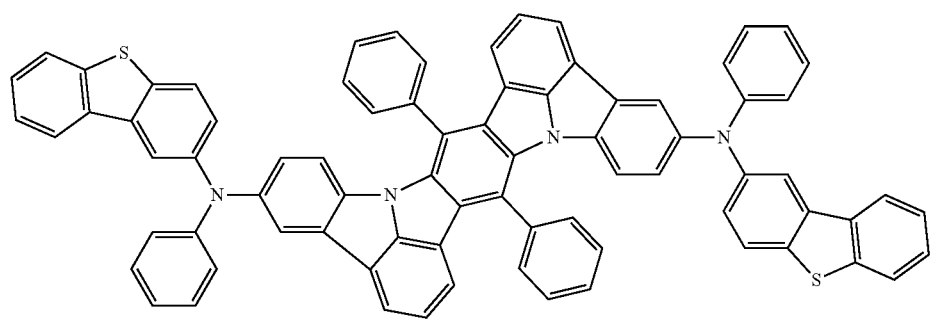

-continued
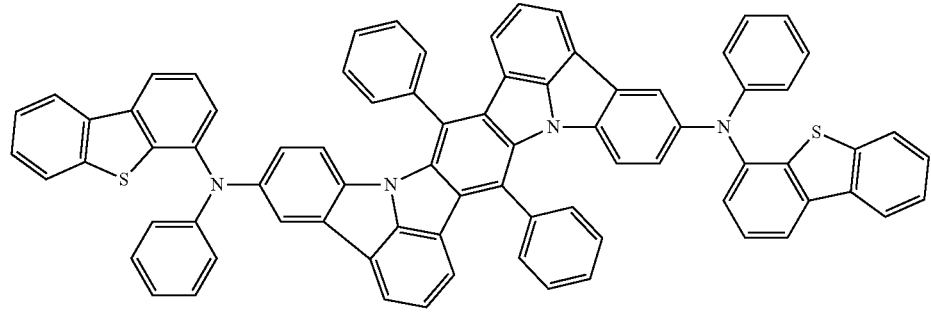
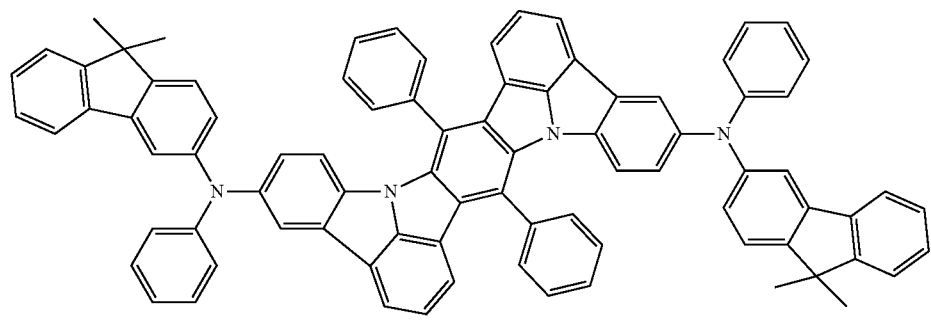
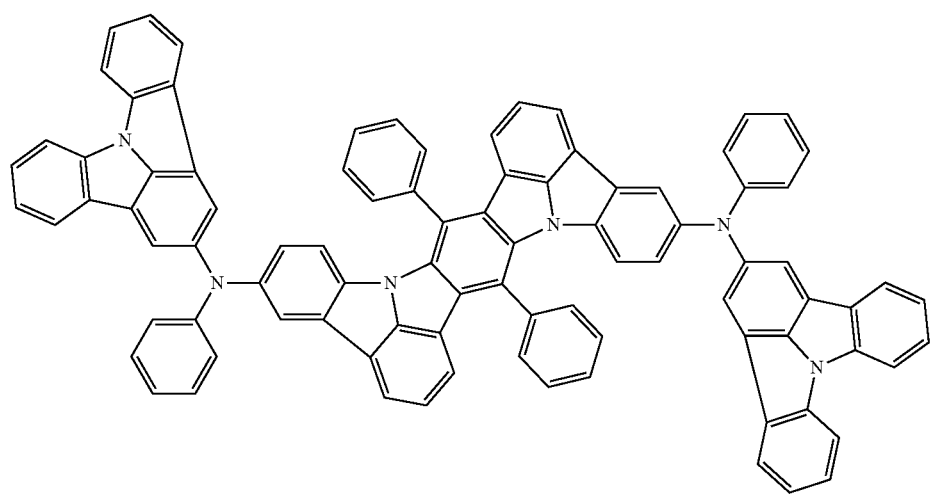
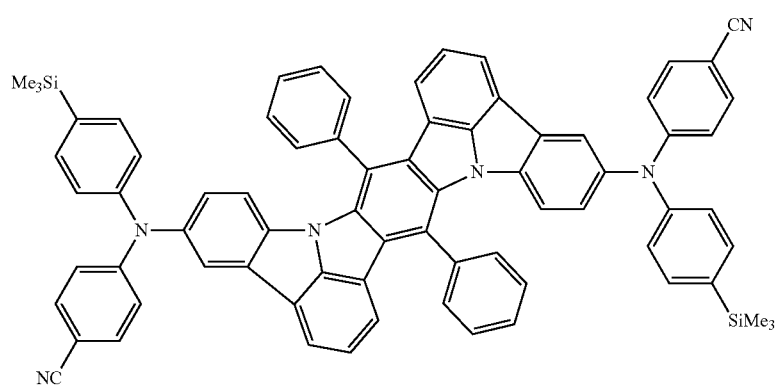

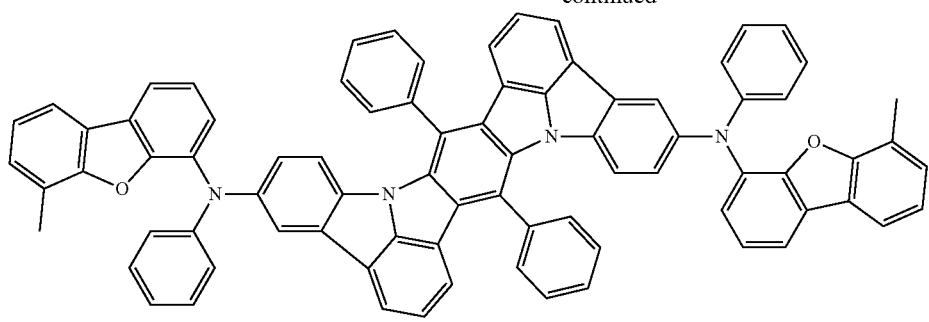
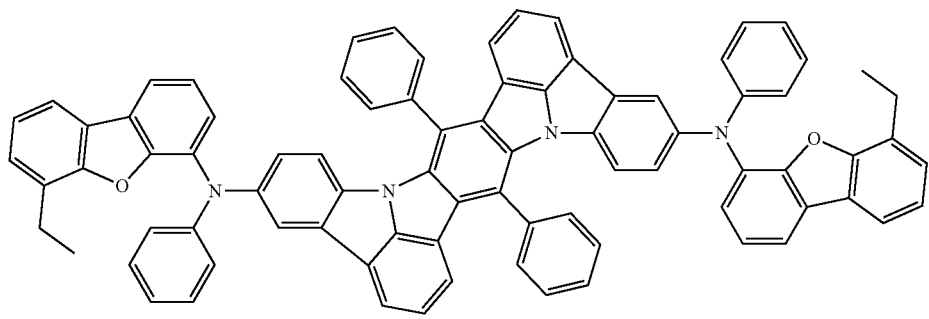
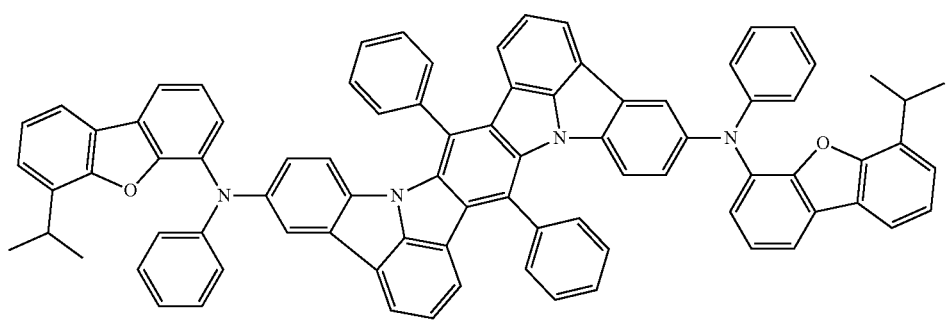
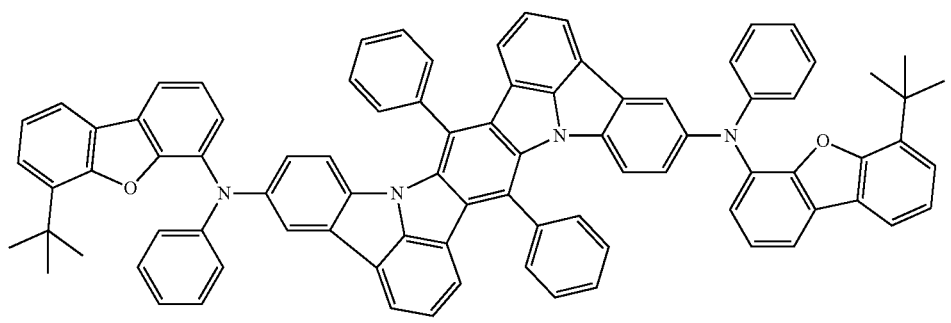
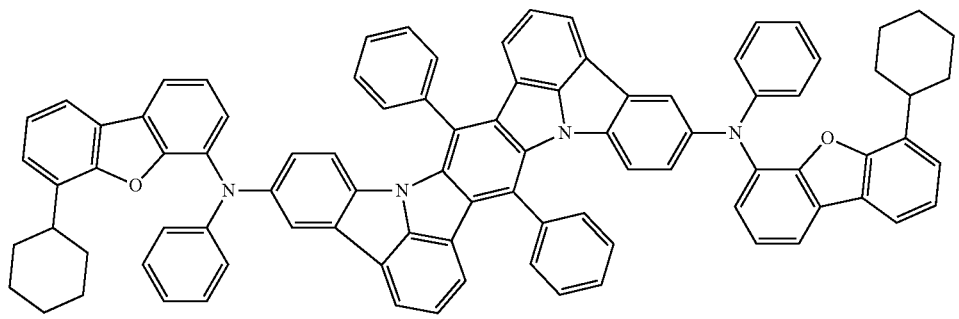

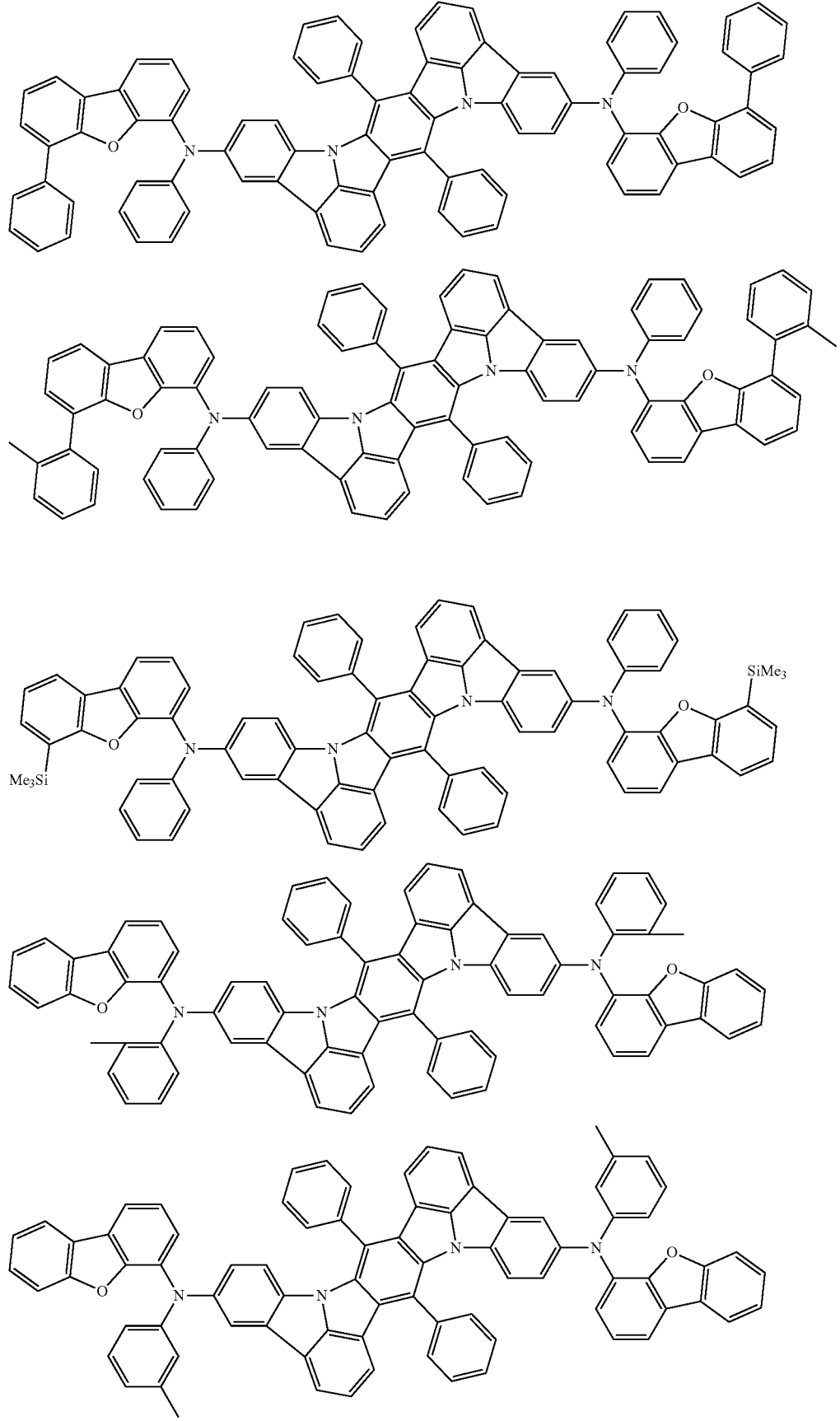

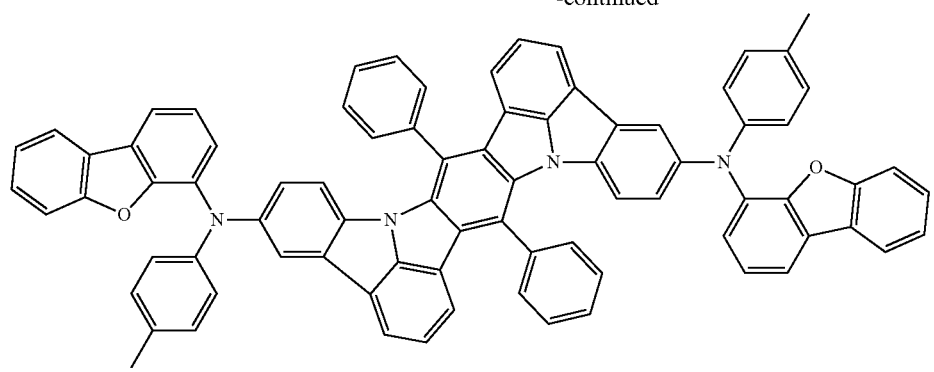
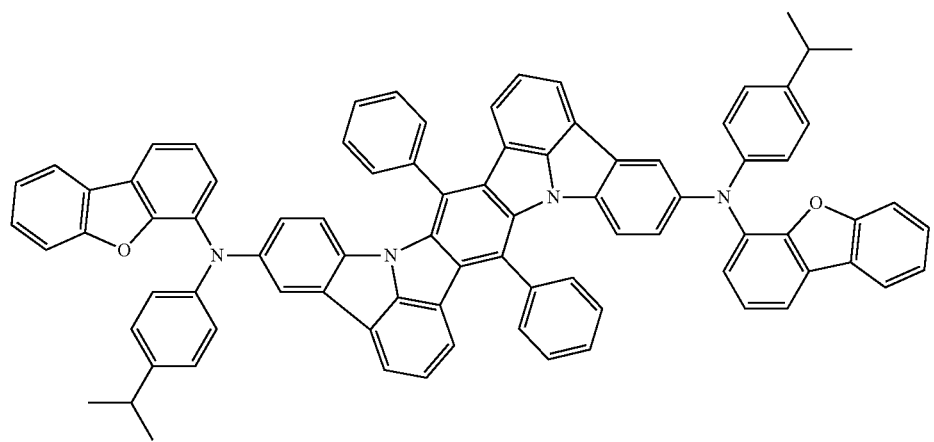
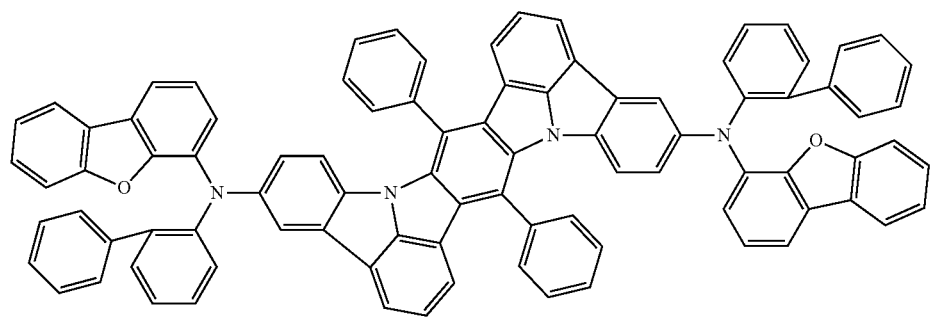
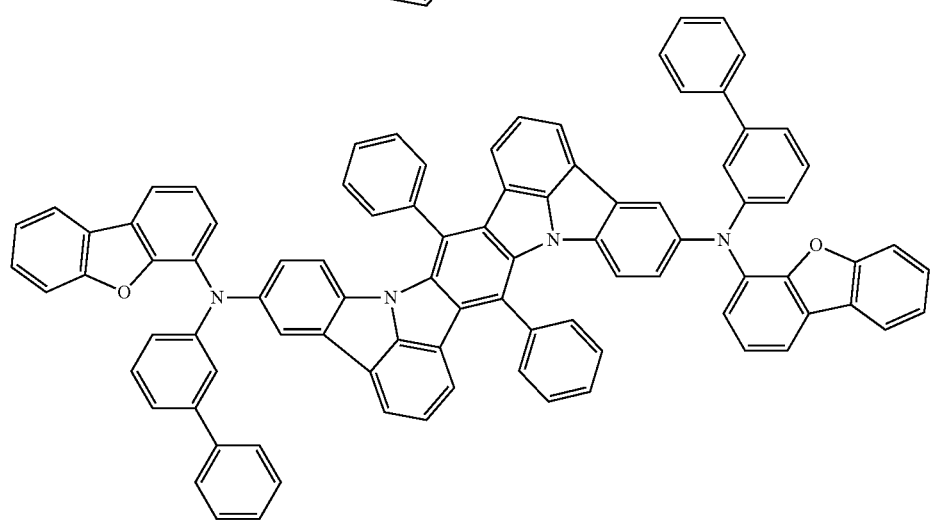

-continued
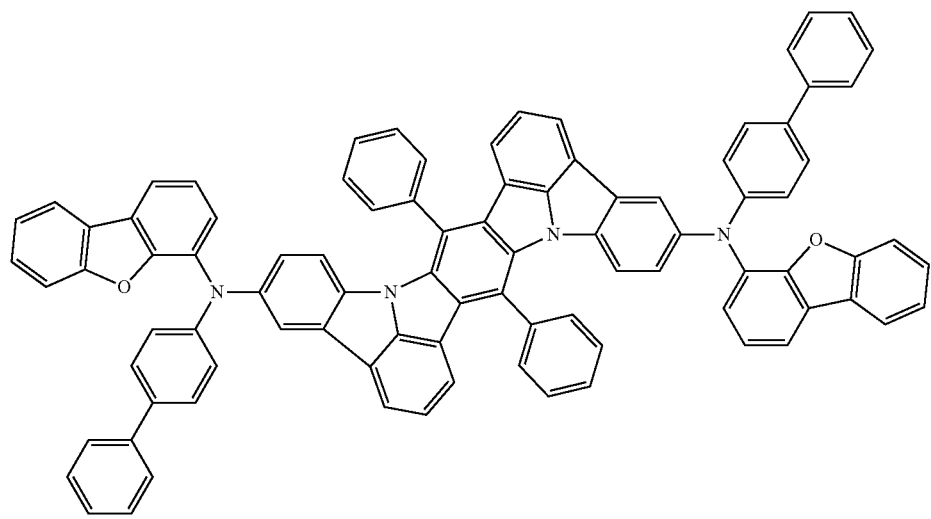
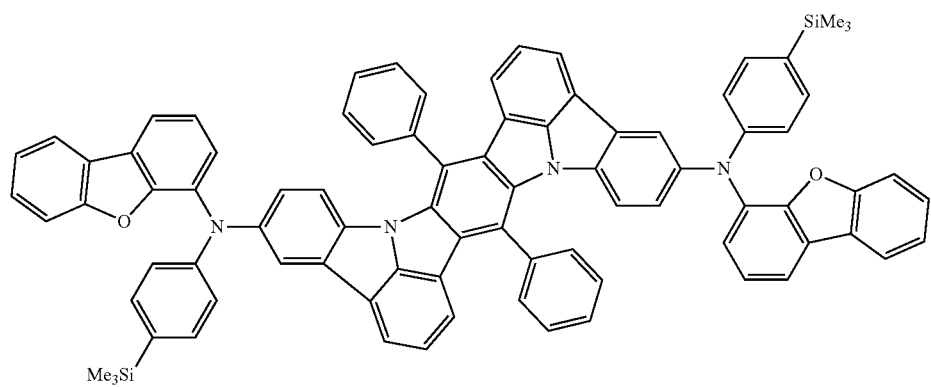
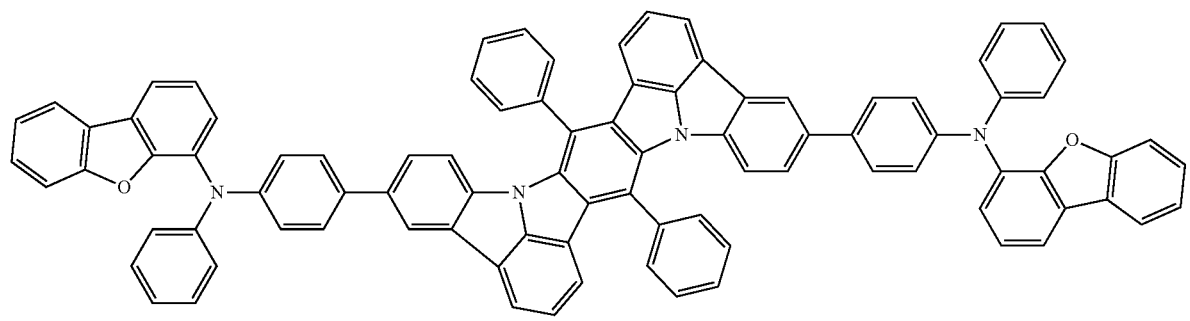
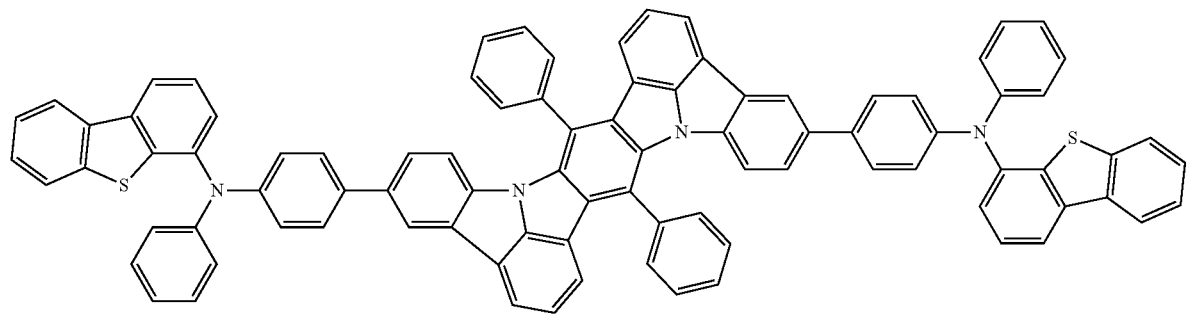

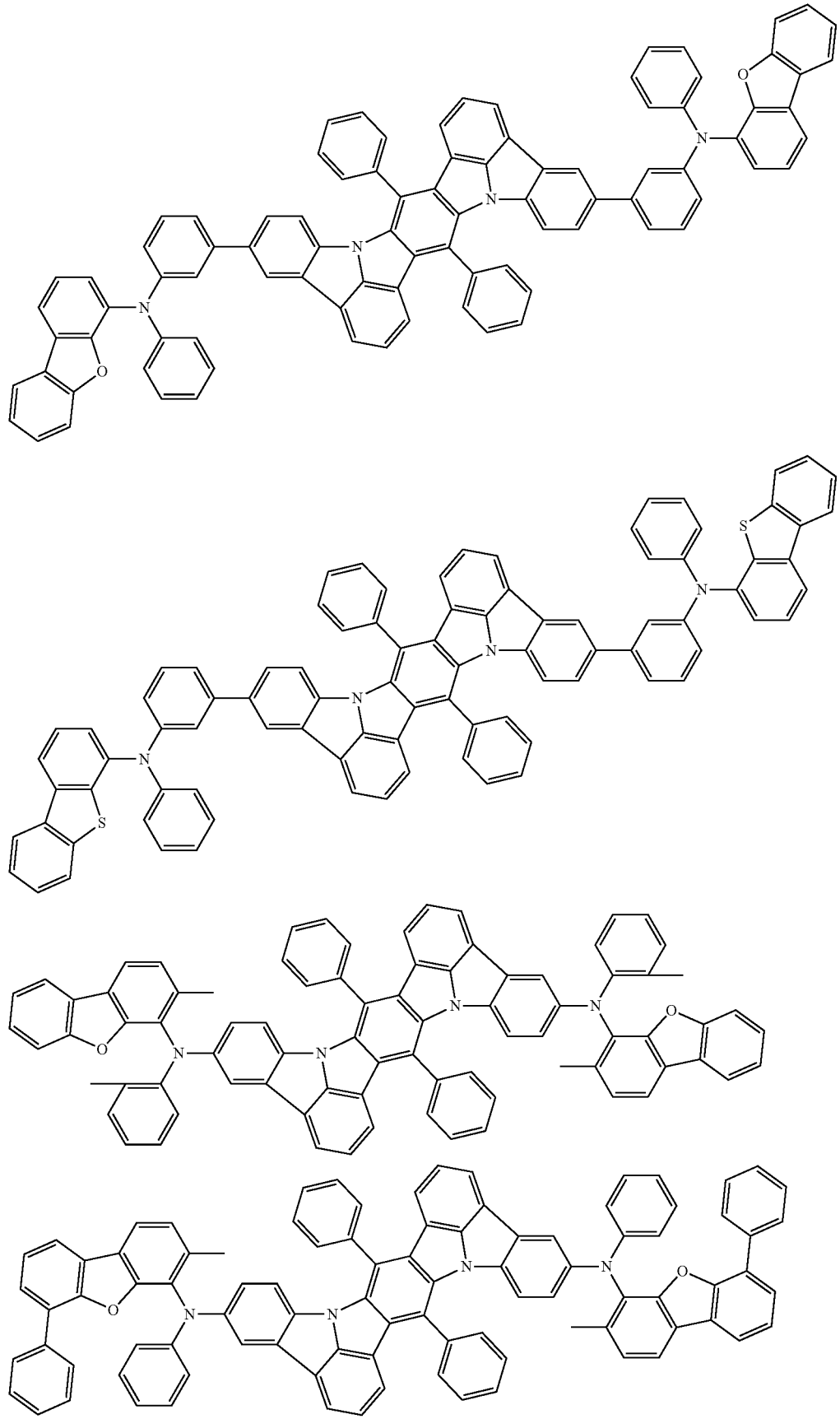

-continued
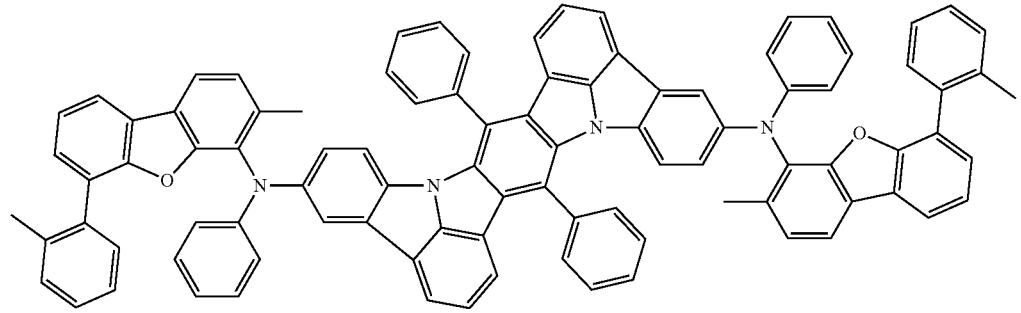
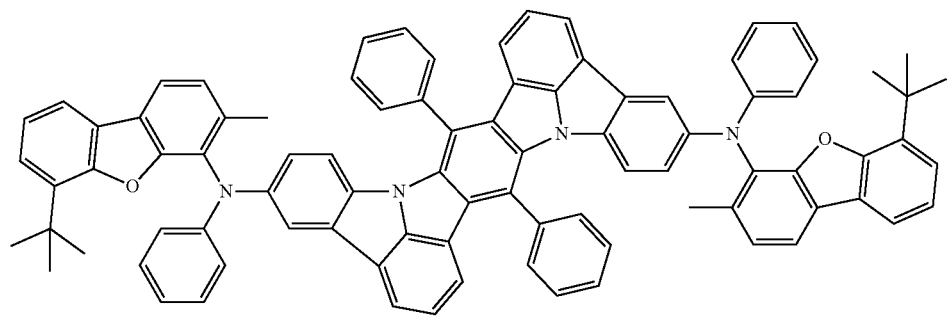
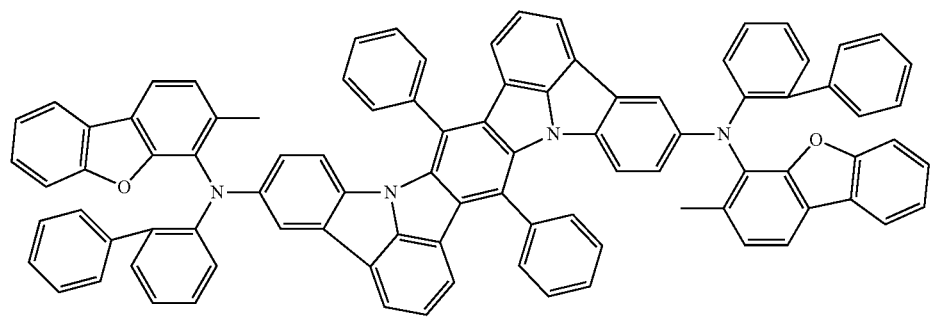
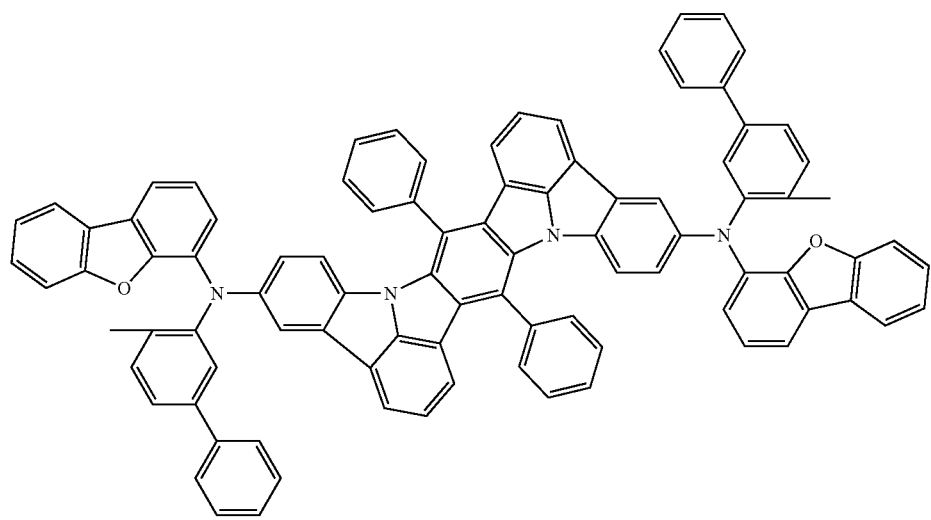

585 586
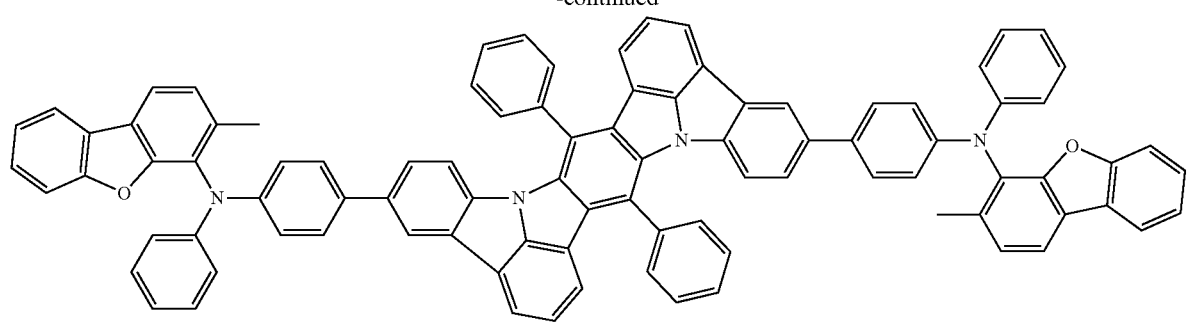
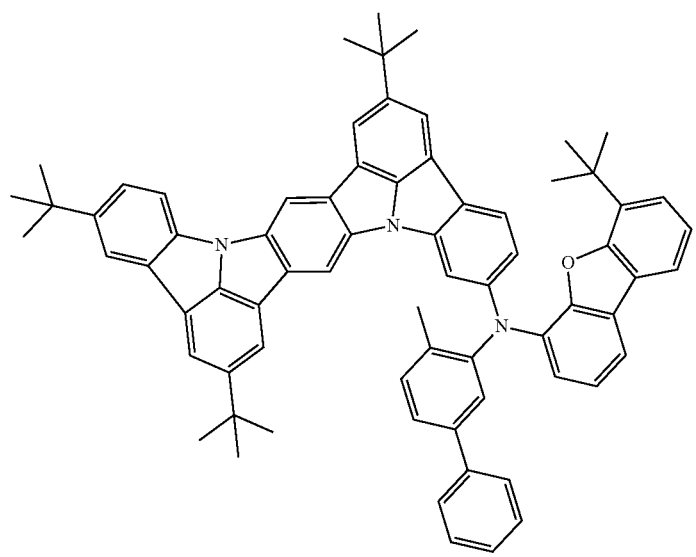
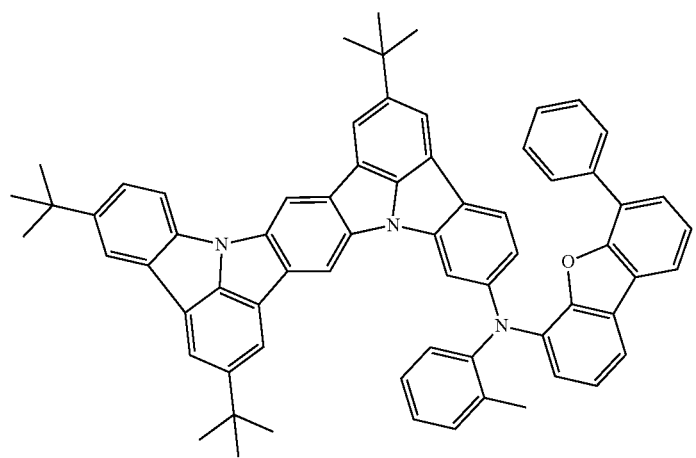

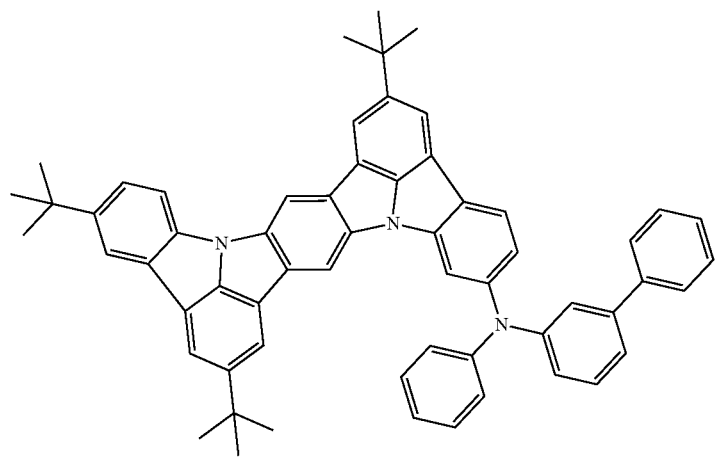
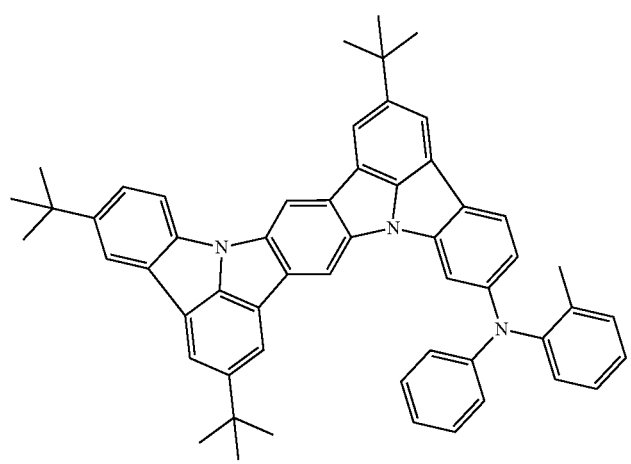
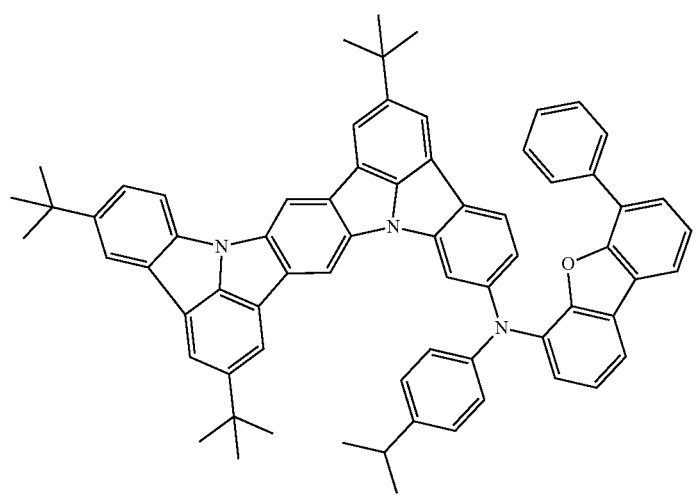

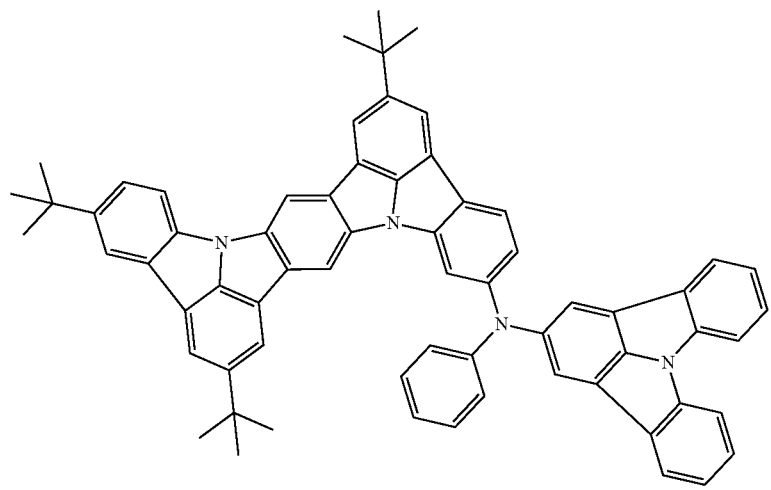
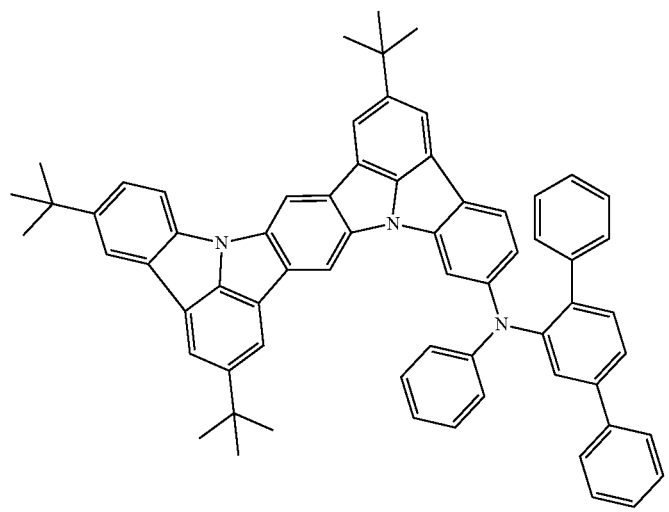
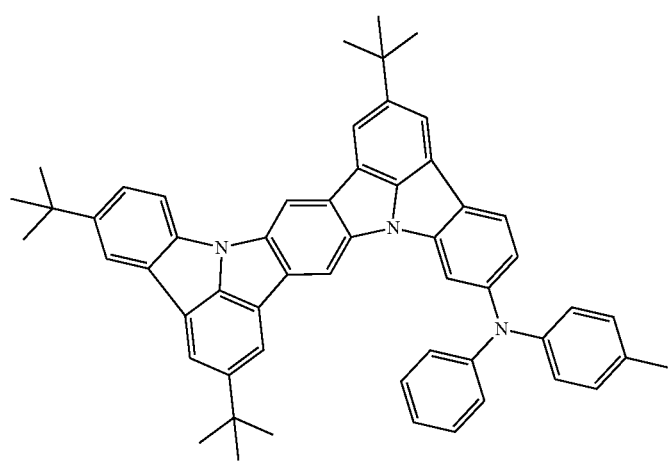

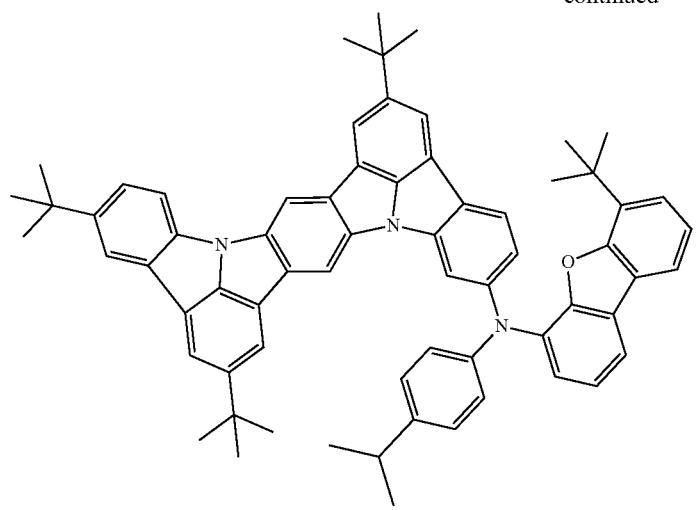
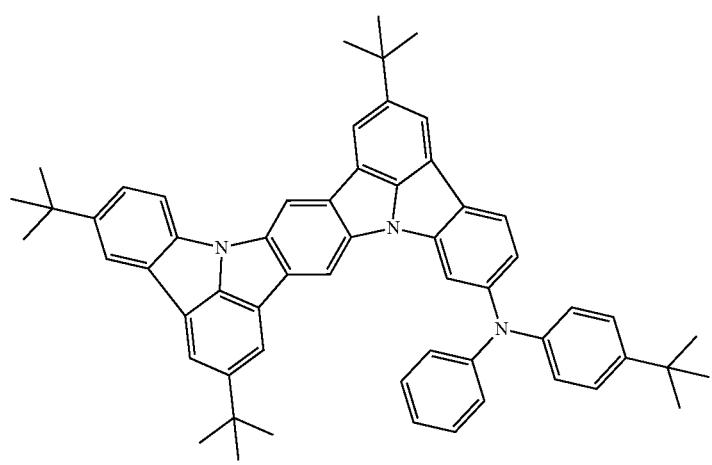
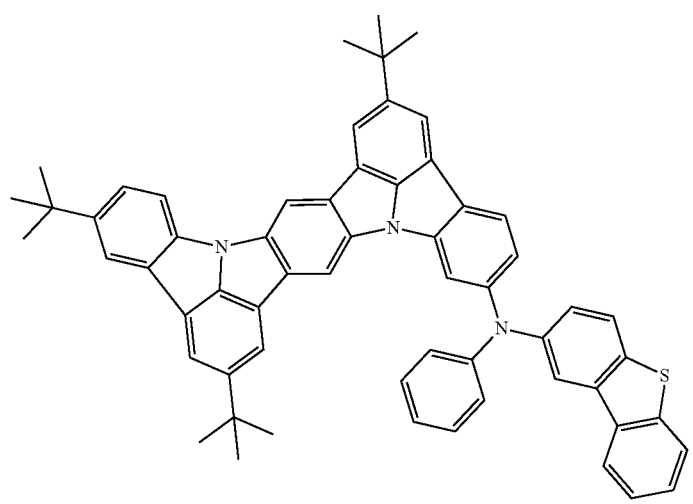

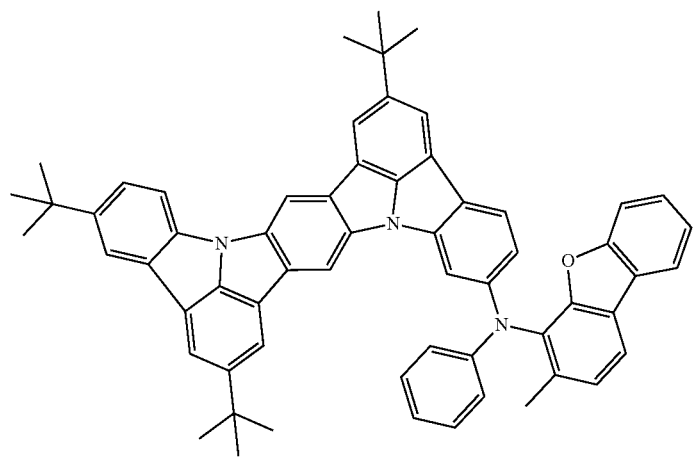
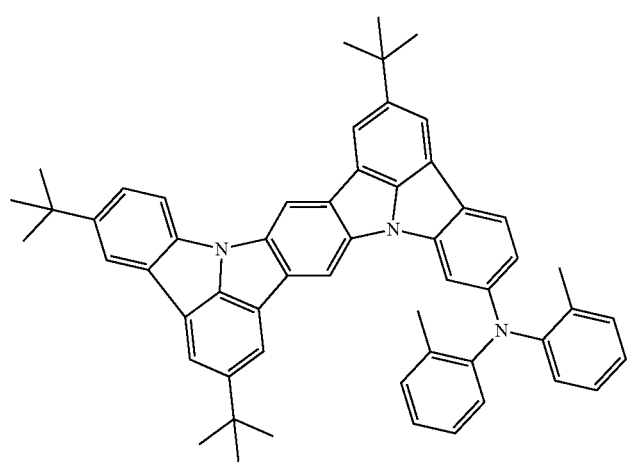
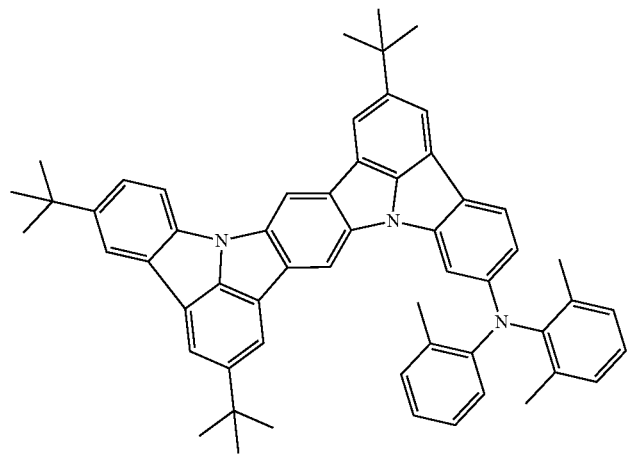

-continued
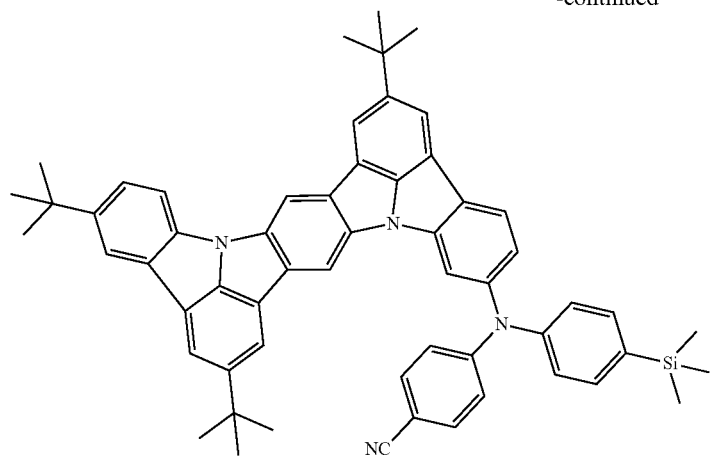
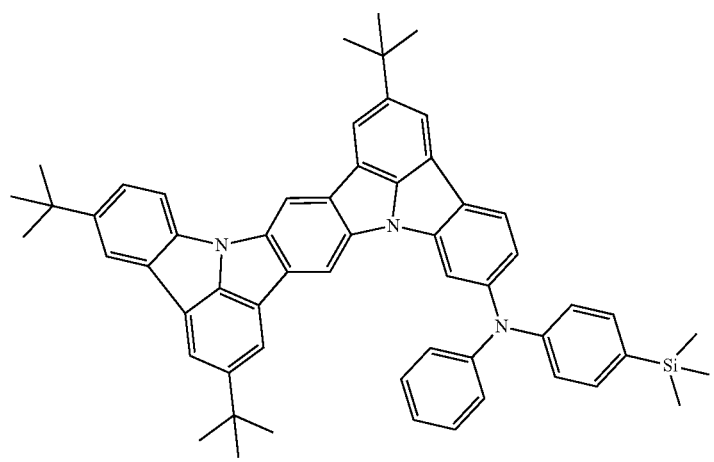
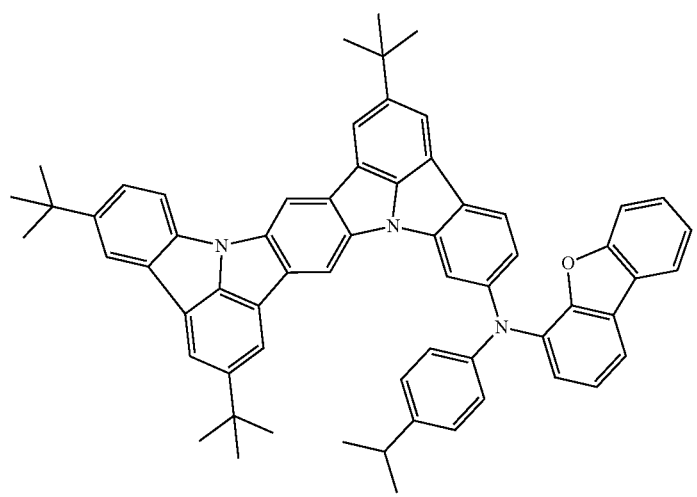

-continued
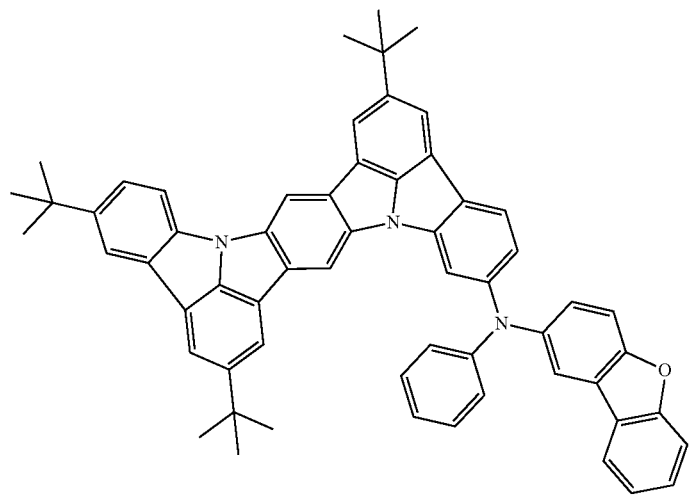
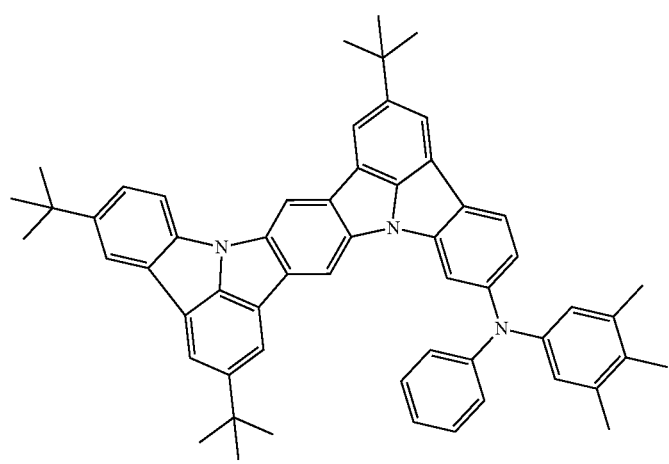
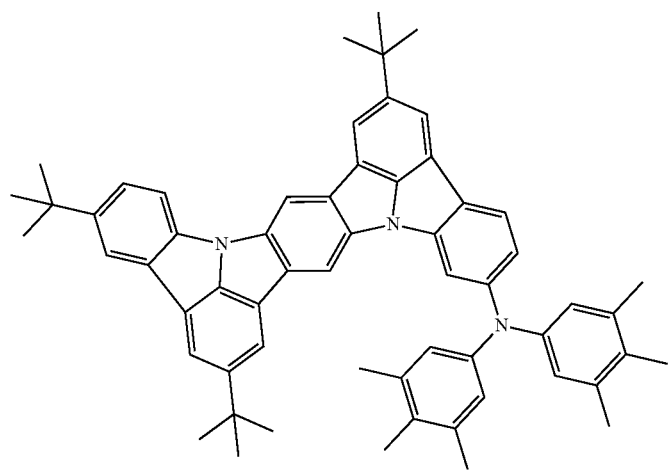

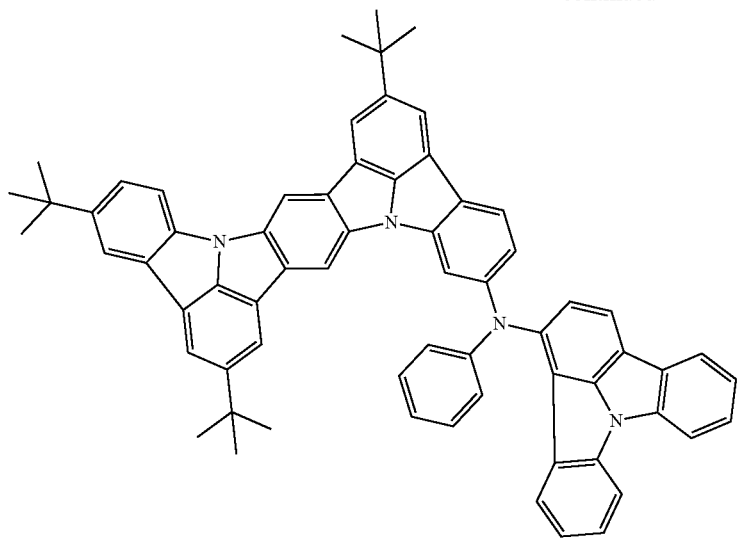
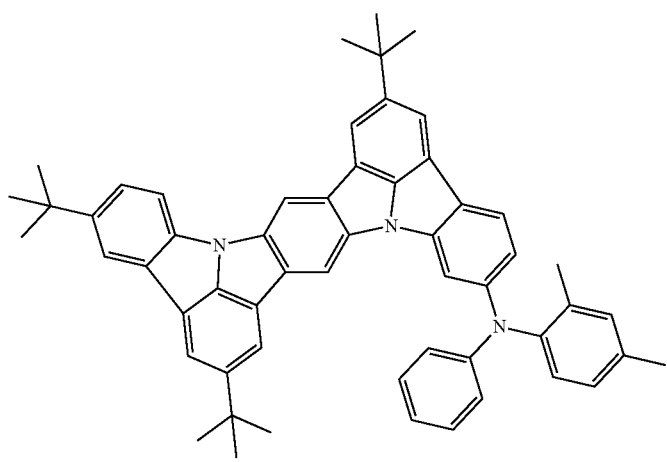
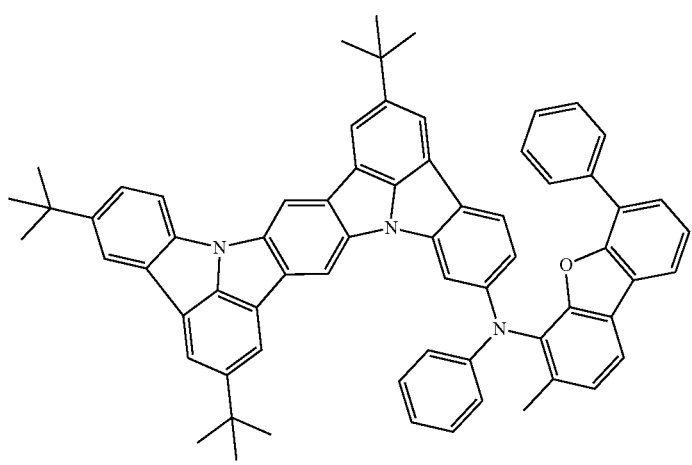

-continued
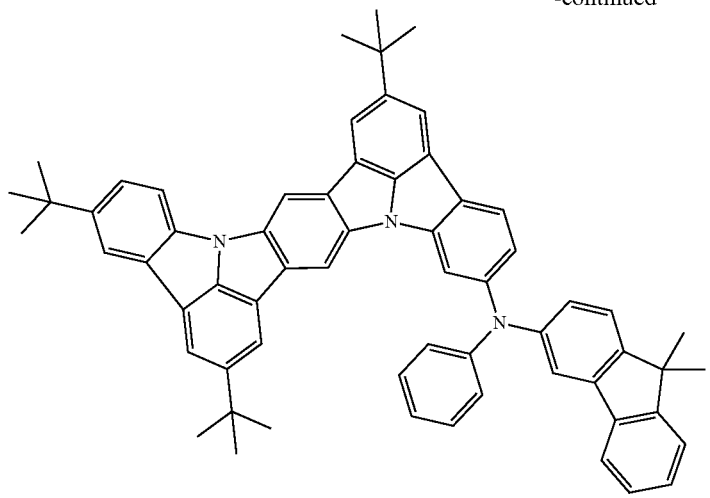
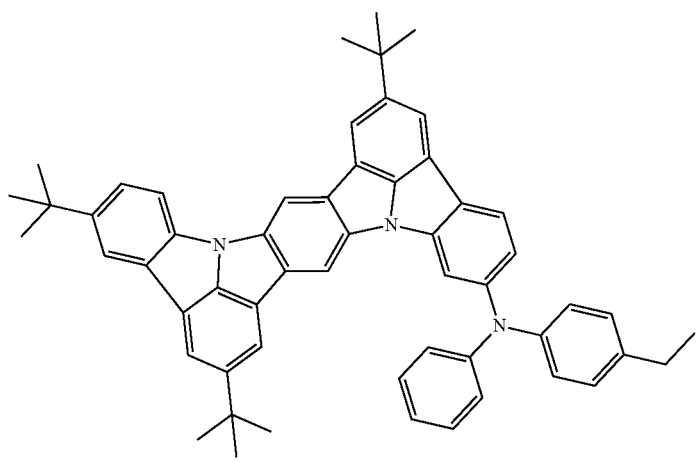
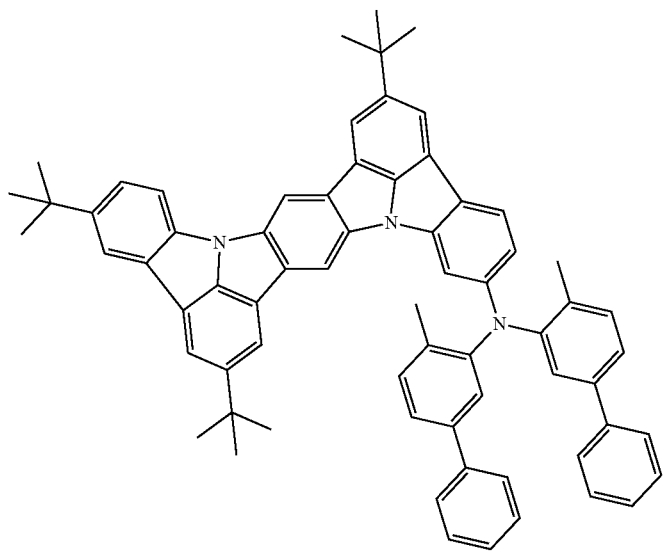

-continued
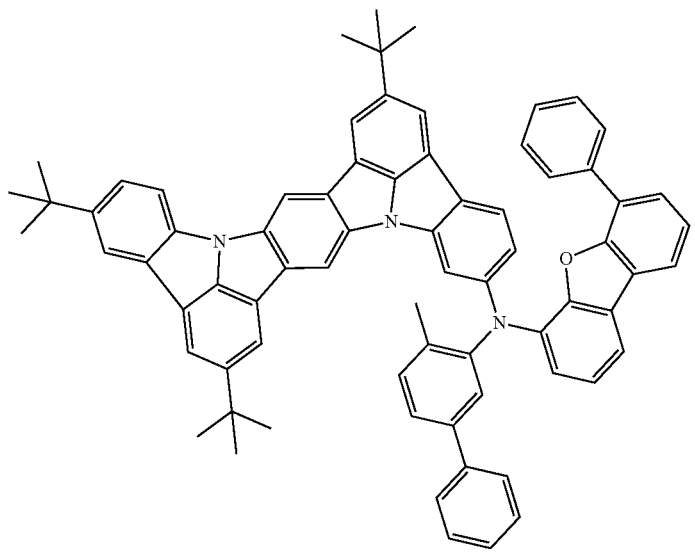
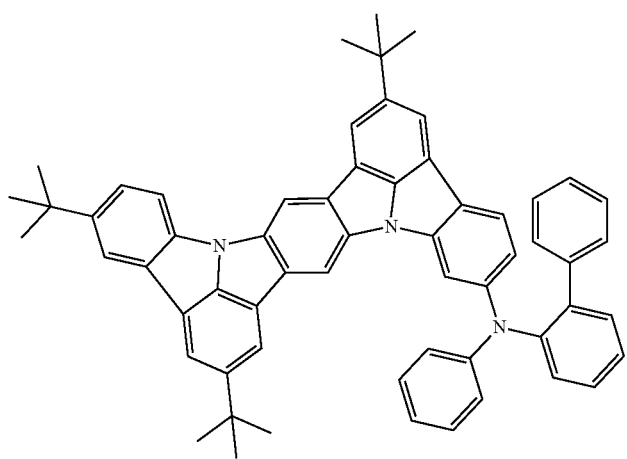
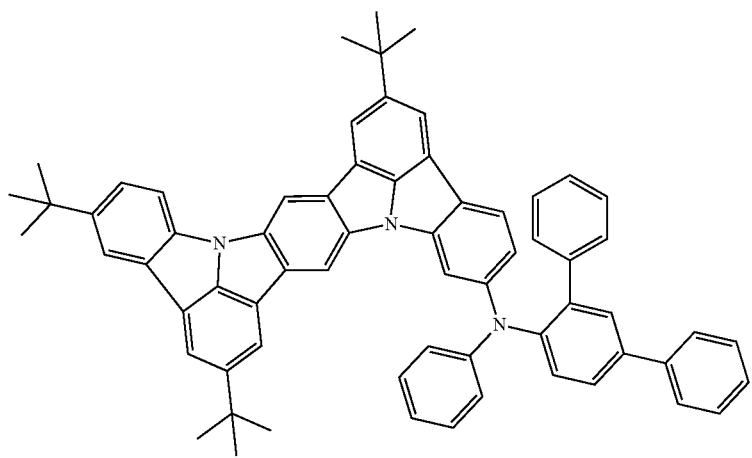

-continued
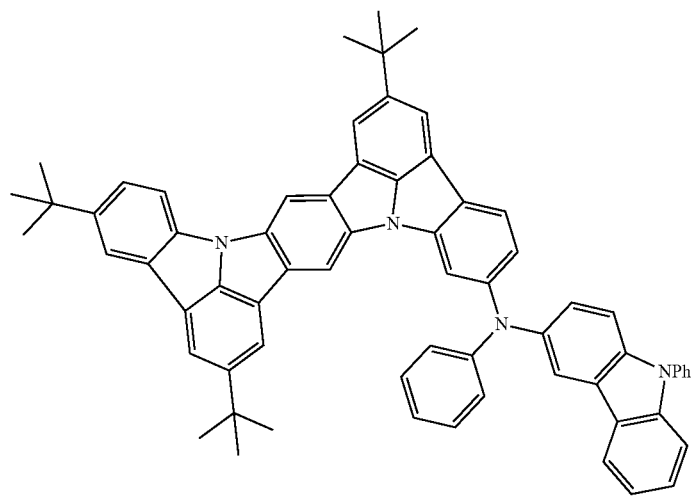
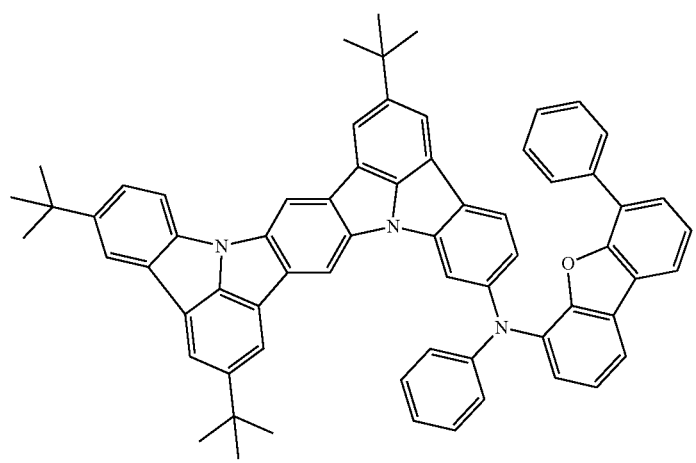
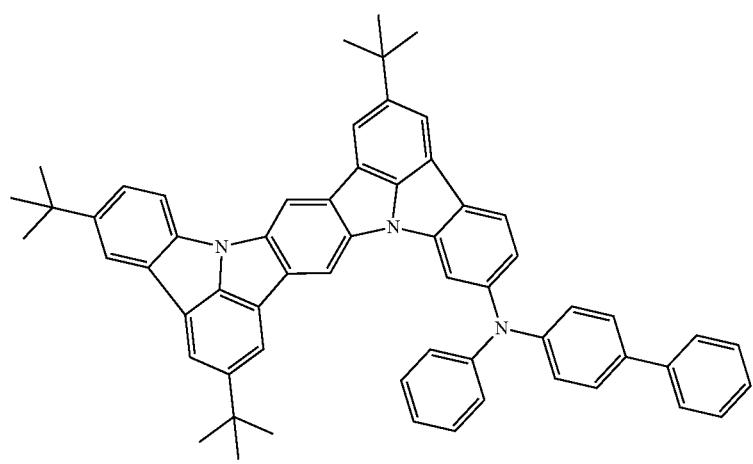

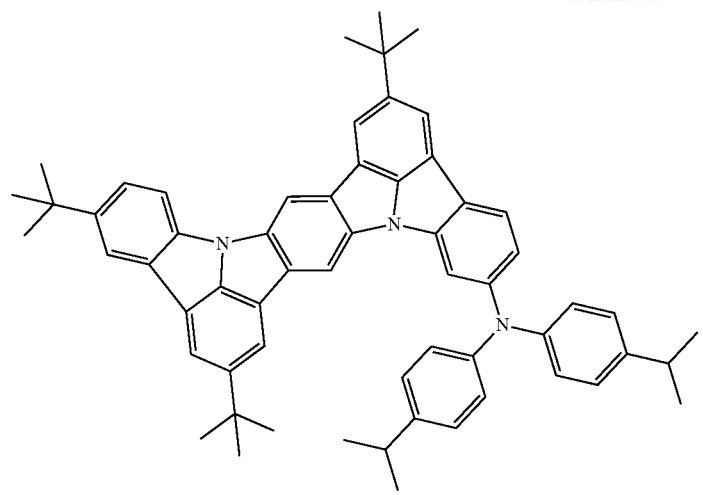
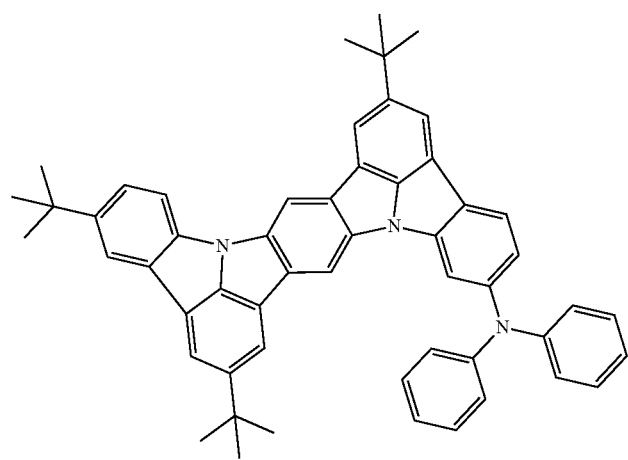
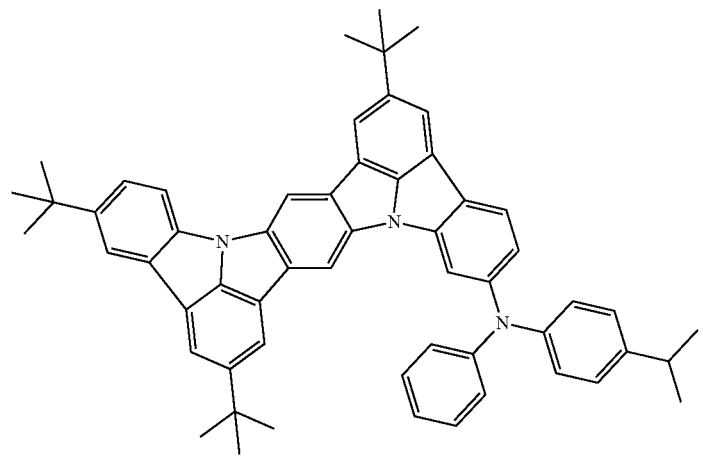

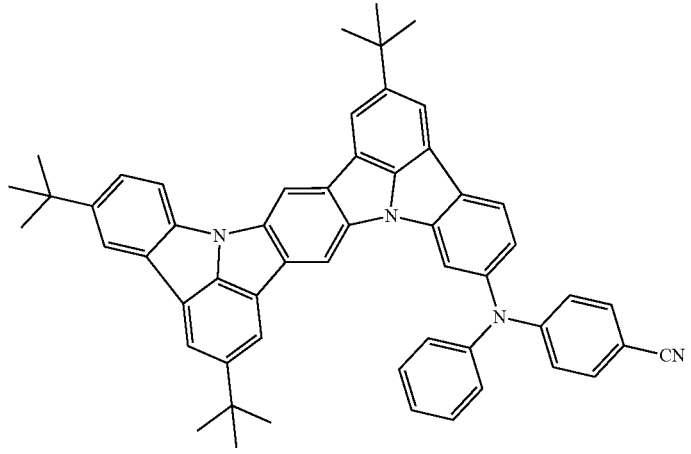
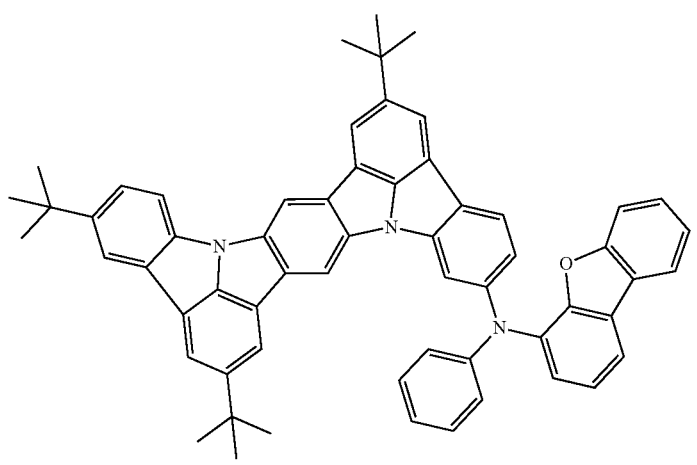
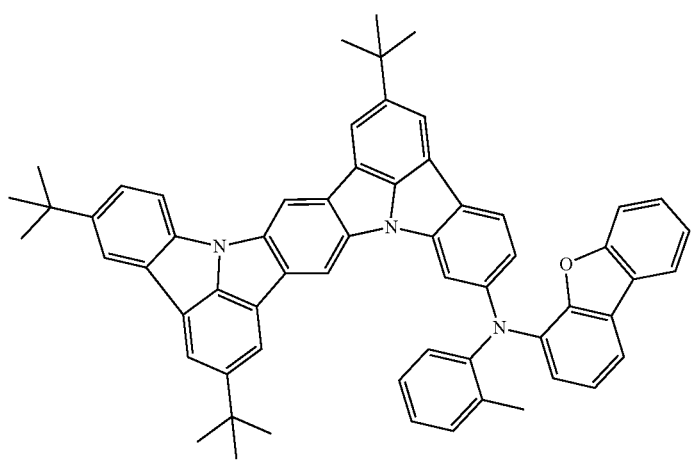

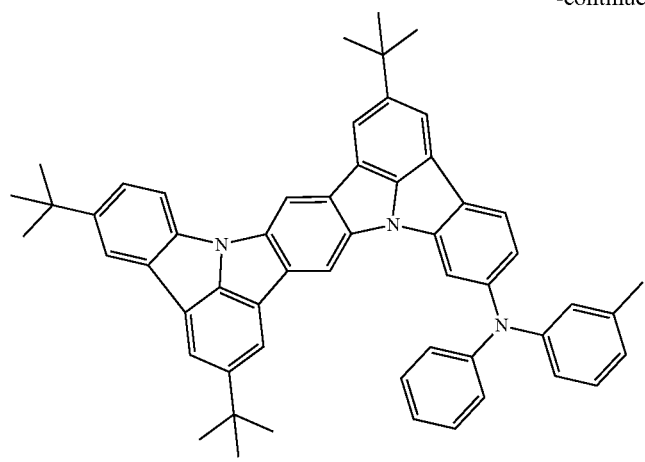
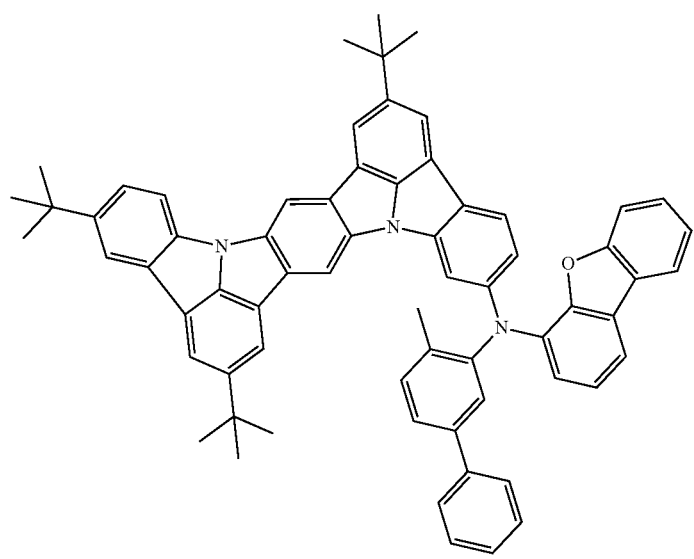
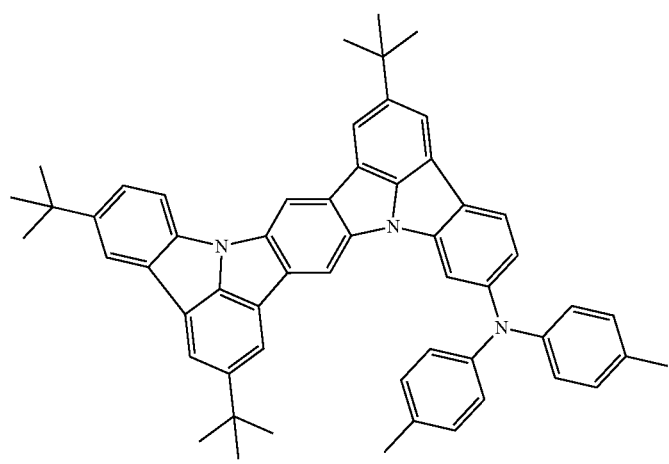

-continued
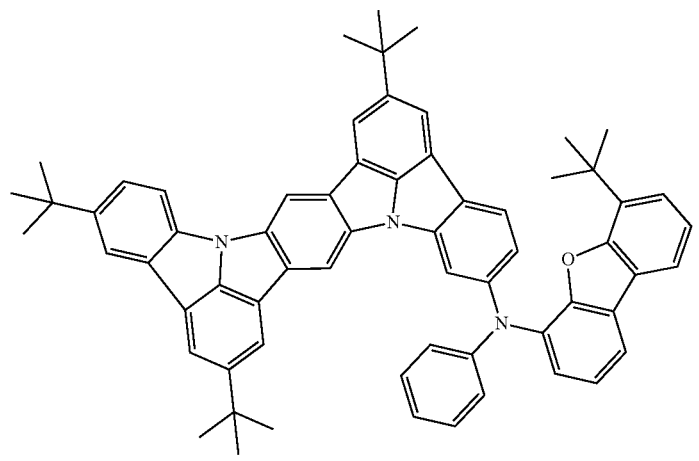
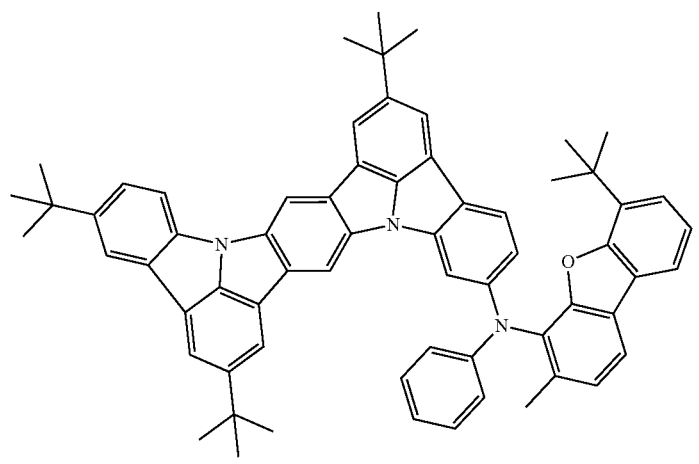
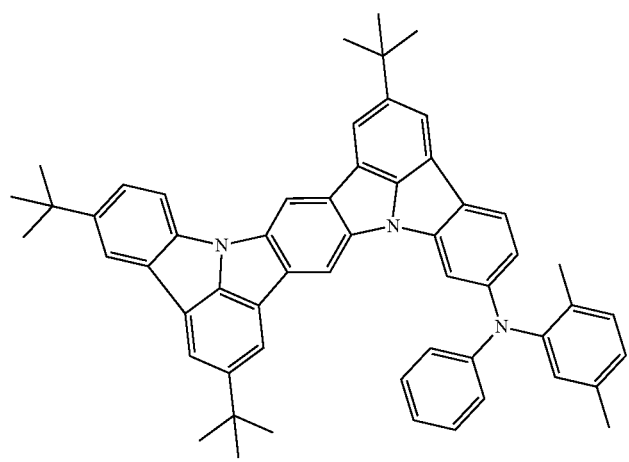

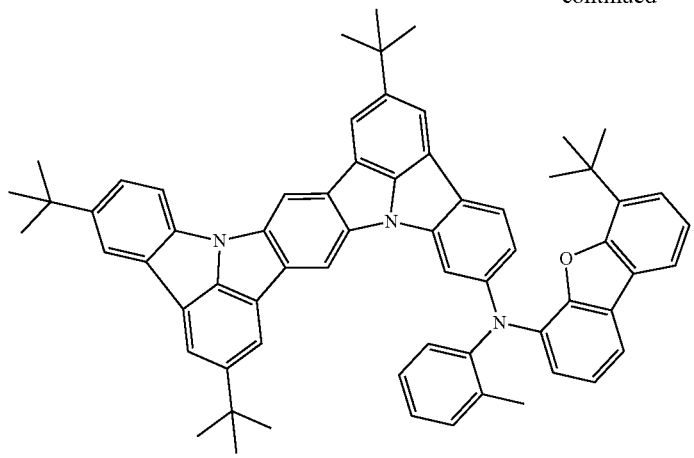
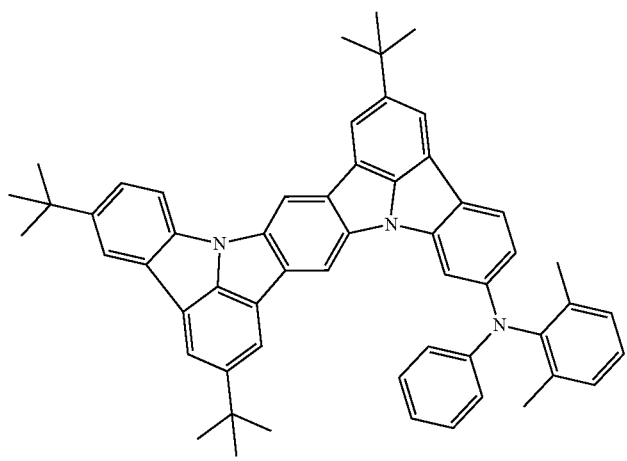
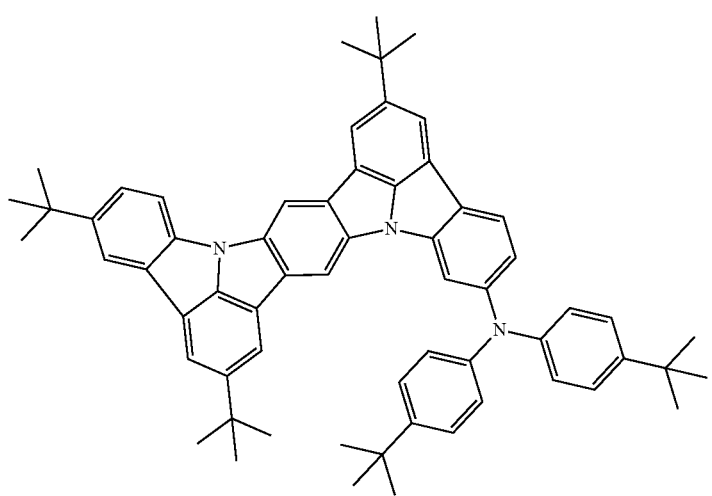

617
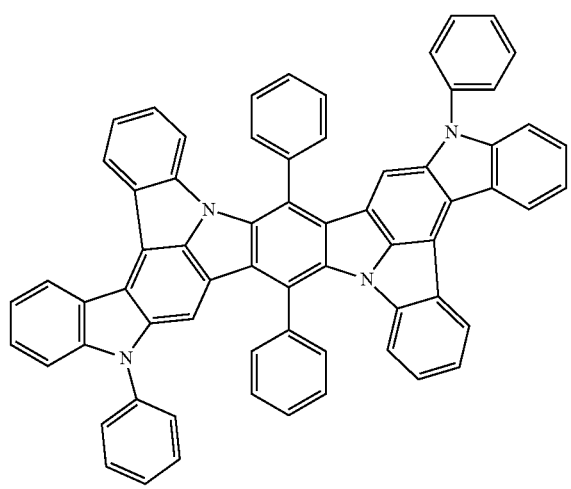
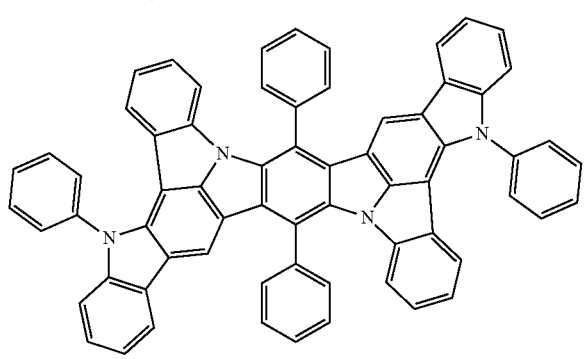
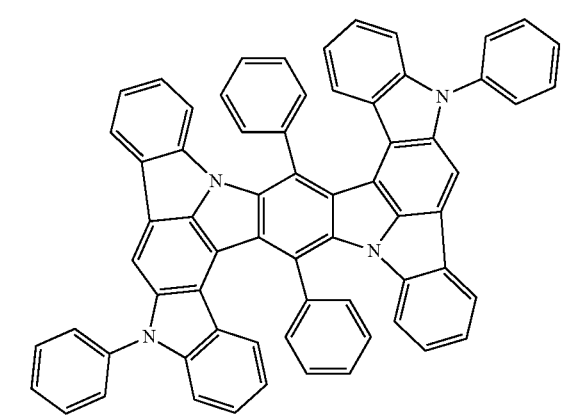
618
-continued
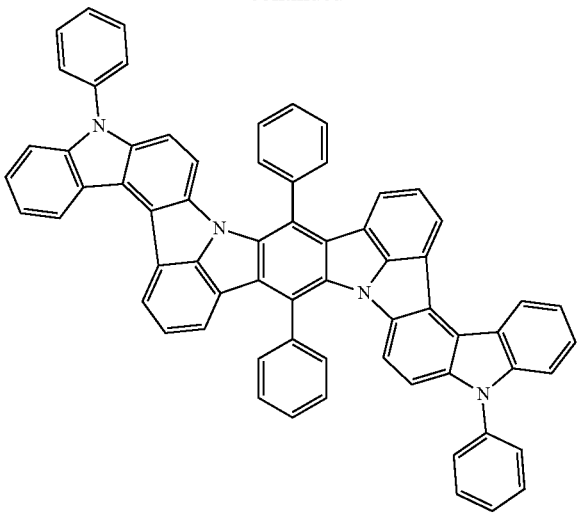
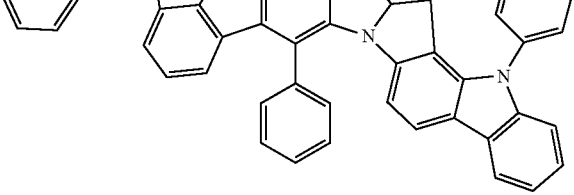
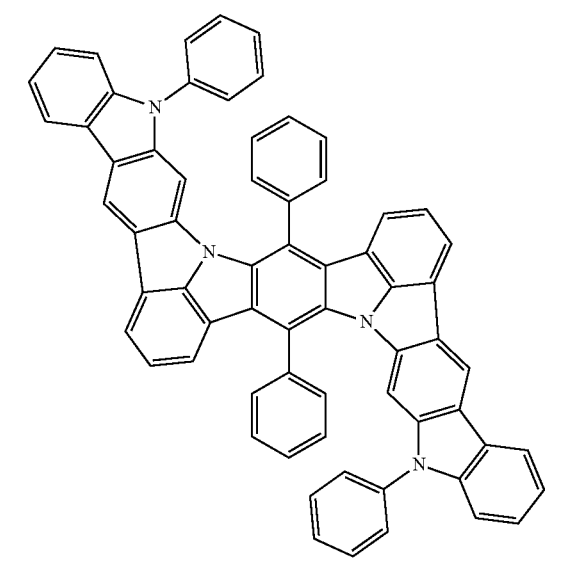

619
-continued
620
-continued
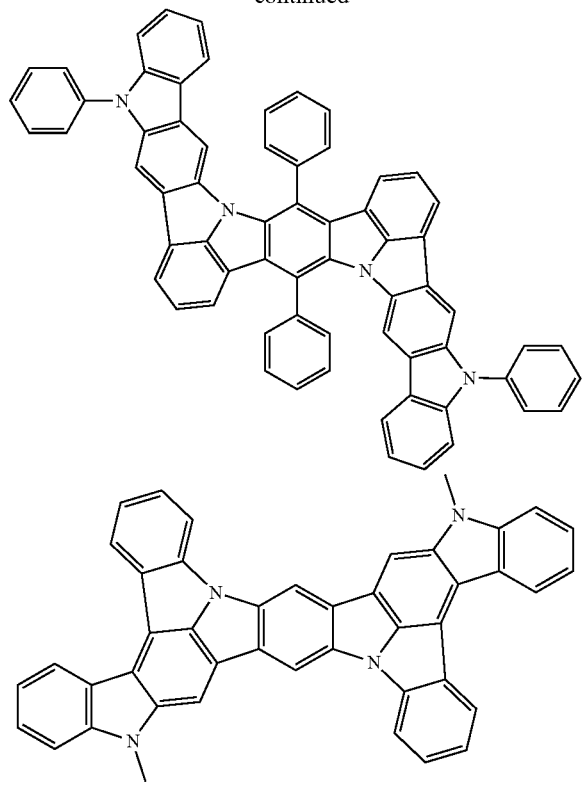
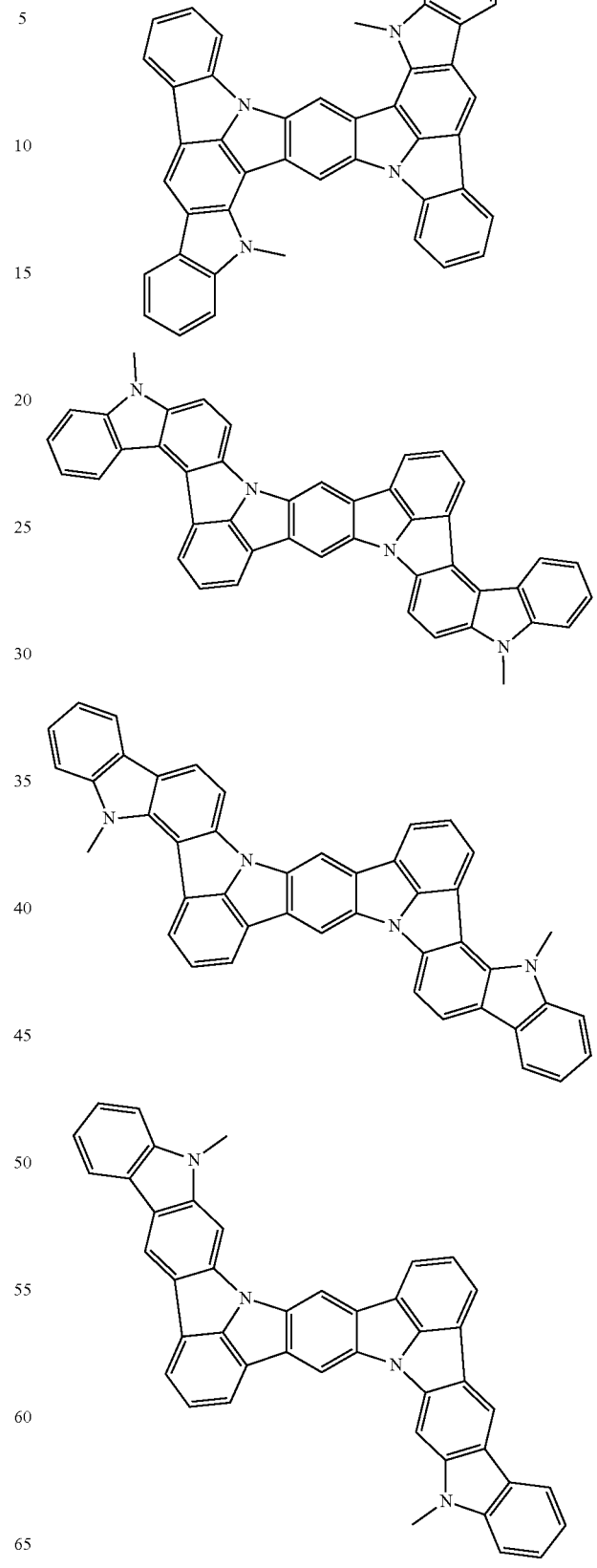

621
-continued
622
-continued
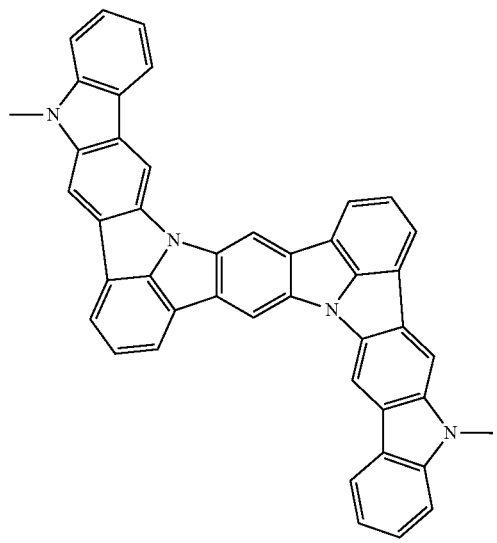
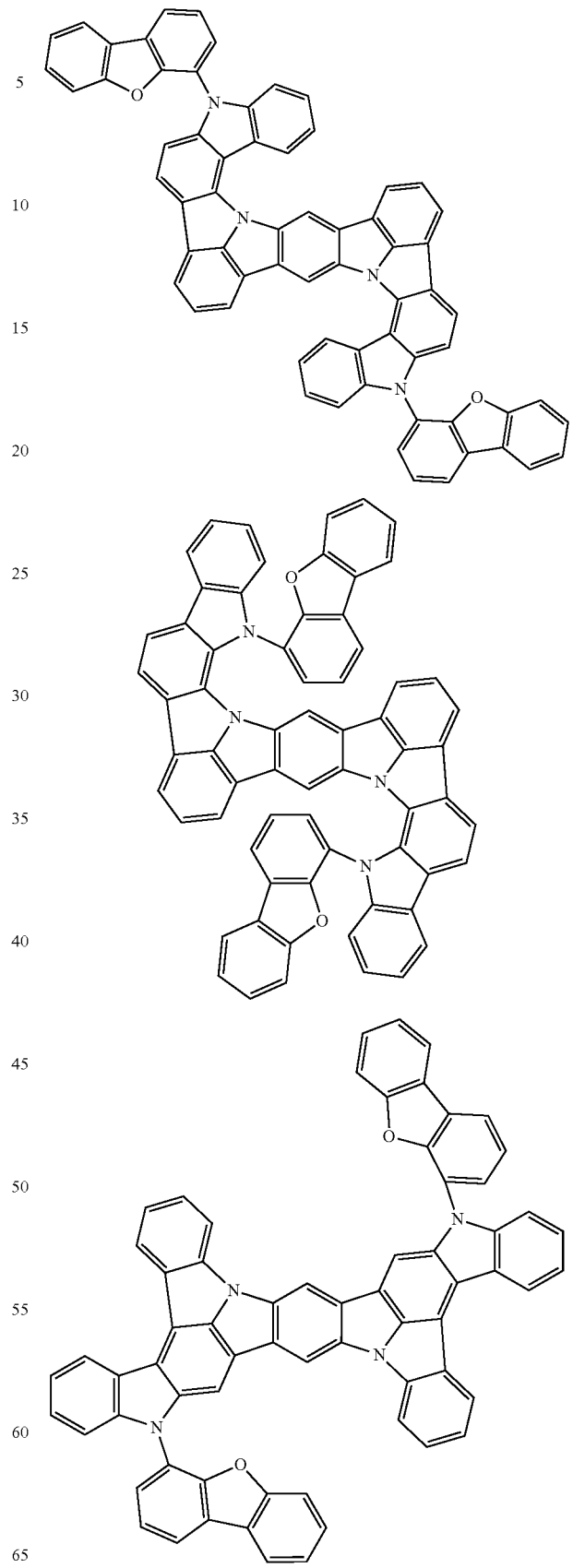

623
-continued
624
-continued
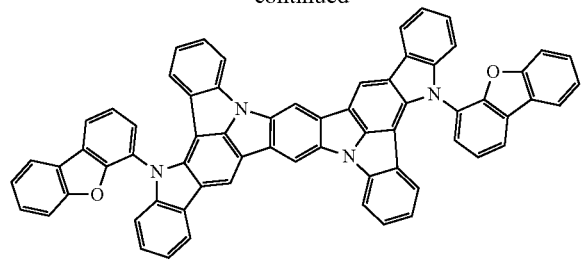
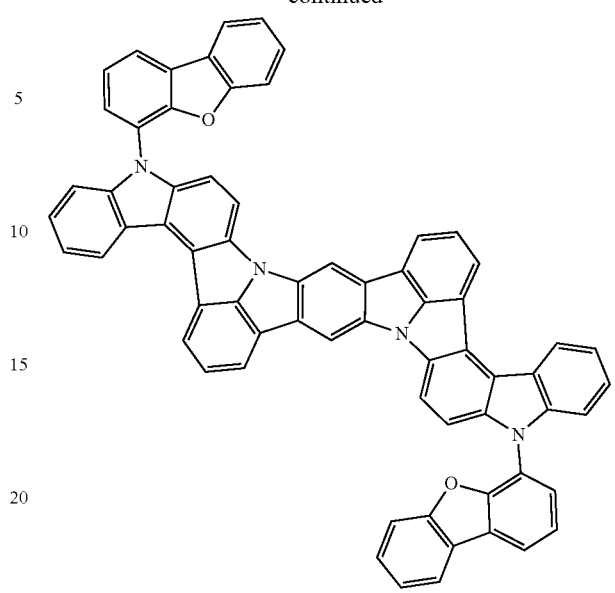
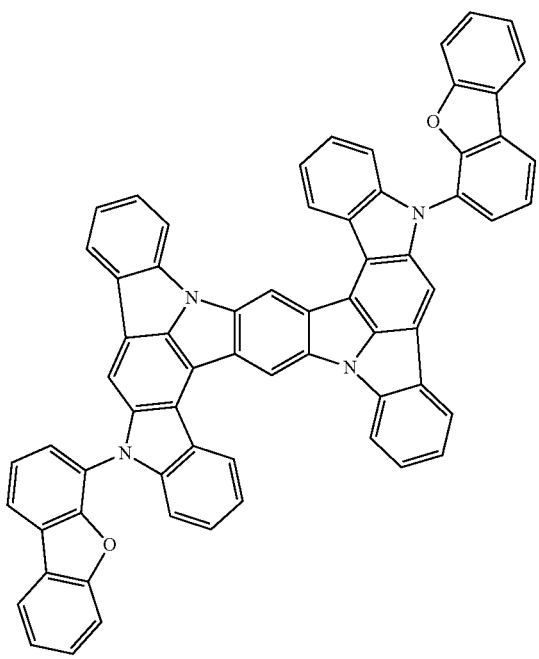
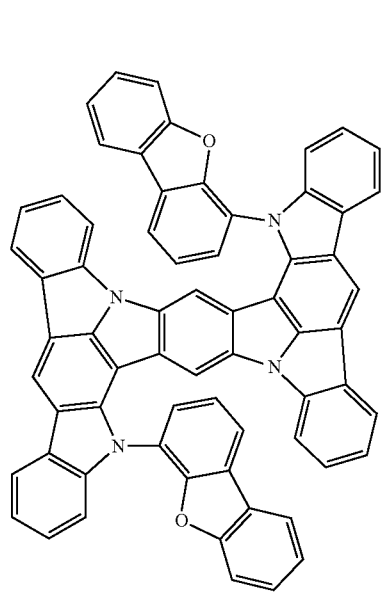
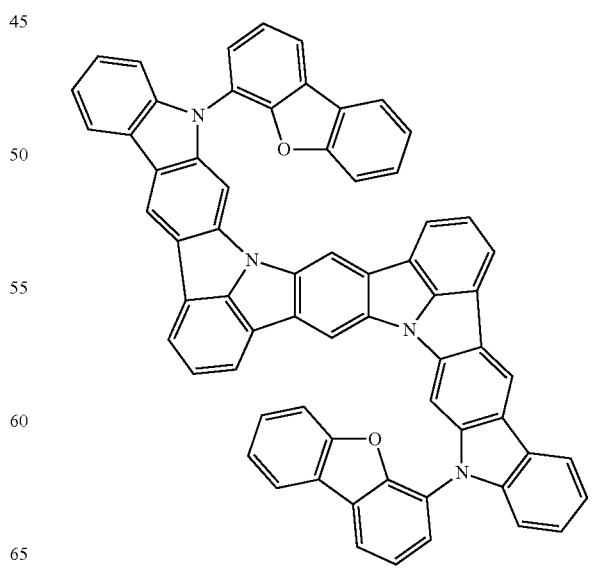

625
-continued
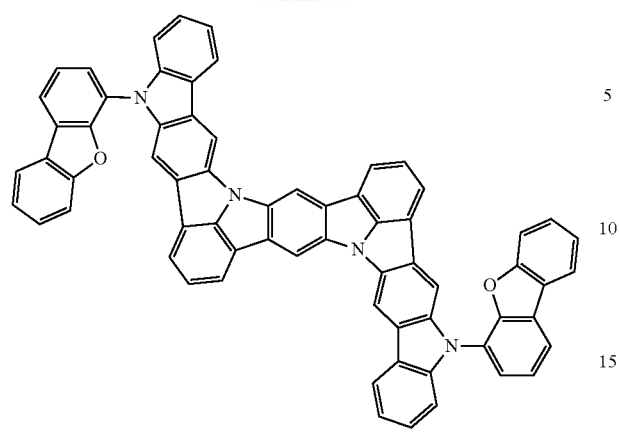
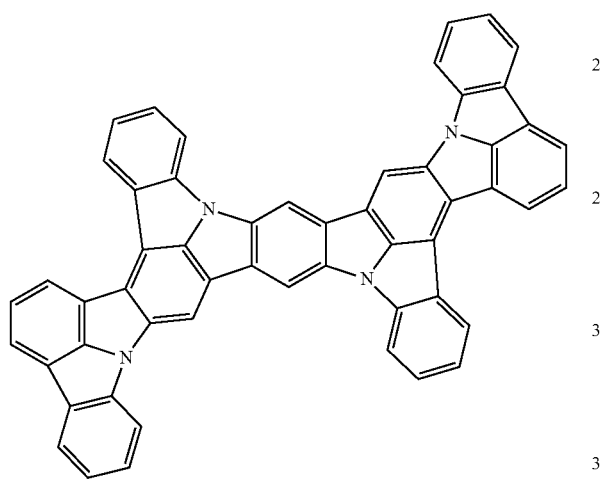
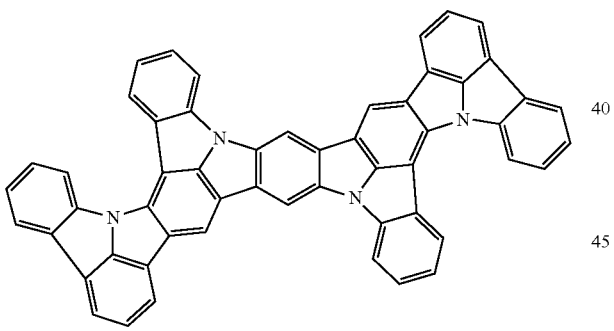
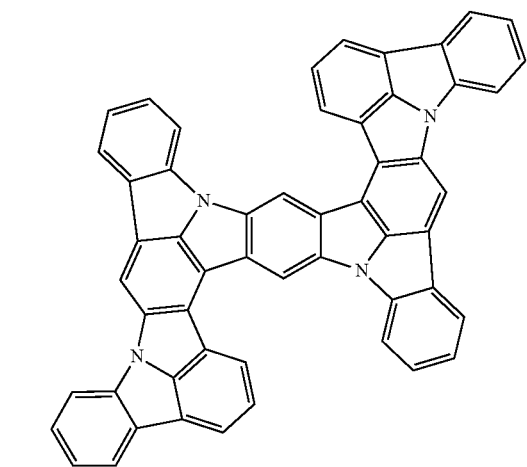
626
-continued
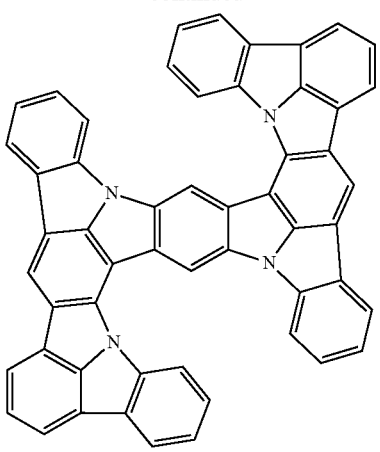
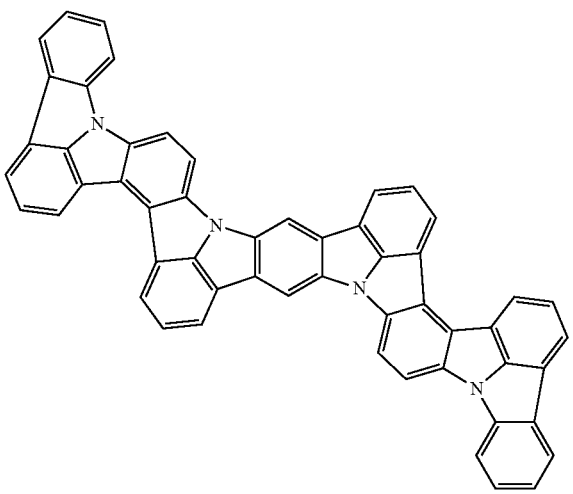
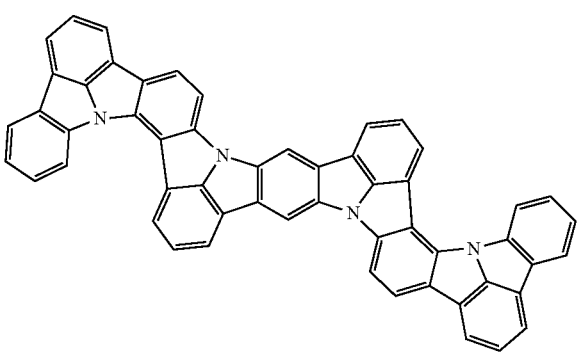

627
-continued
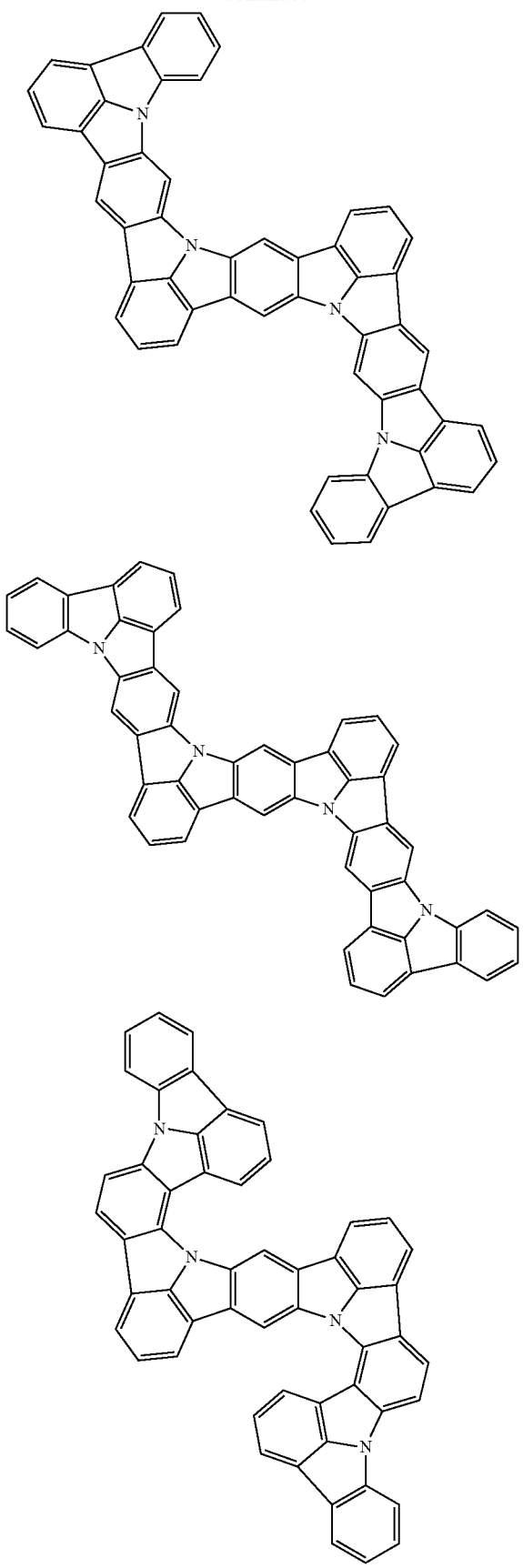
628
-continued
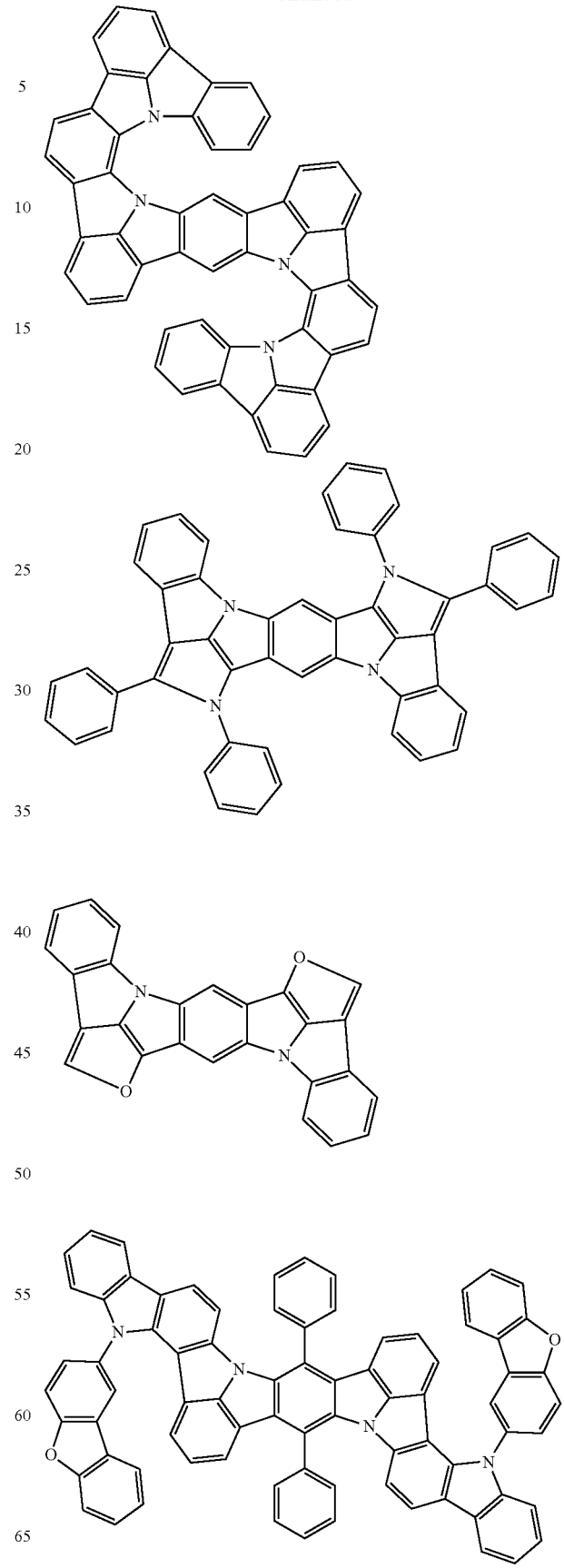

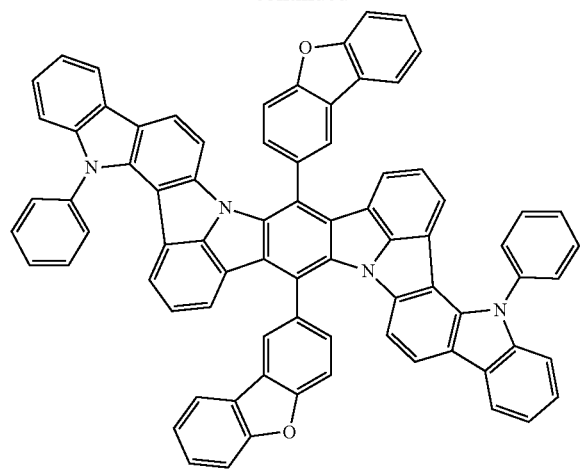

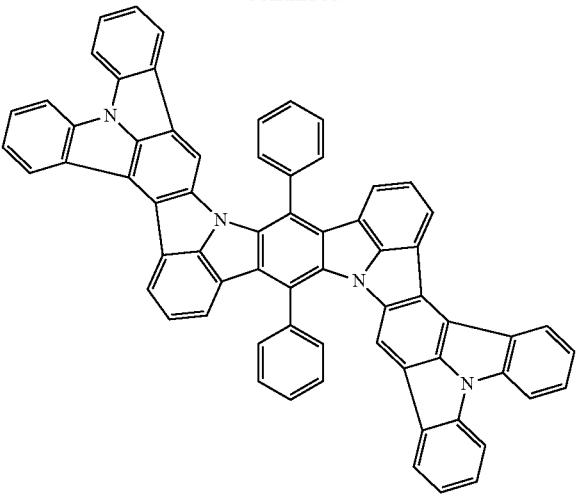 [SMILES: c1ccc(-c2c3c4cccc5c6c7c8ccccc8n8c9ccccc9c(cc6n(c3c(-c3ccccc3)c3c6cccc9c%10c%11c%12ccccc%12n%12c%13ccccc%13c(cc%10n(c23)c69)c%11%12)c45)c78)cc1]

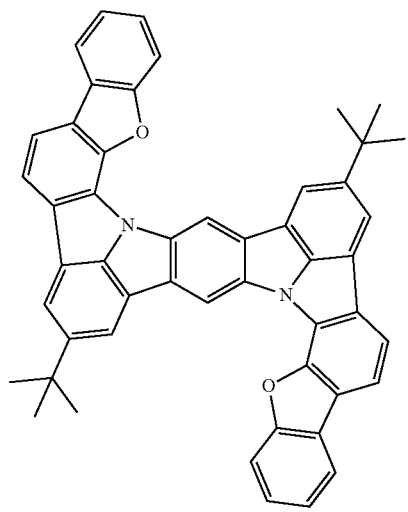

(Compound Represented by Formula (41))

The compound represented by the formula (41) is explained below.

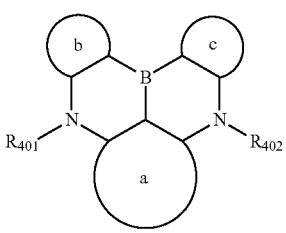

(41)

In the formula (41), a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

The a ring, b ring and c ring are rings (a substituted or unsubstituted aromatic hydrocarbon ring having 6 to 50 ring carbon atoms or a substituted or unsubstituted heterocyclic ring having 5 to 50 ring atoms) fuse to the fused bicyclic structure composed of B atom and two N atoms in the center of the formula (41).

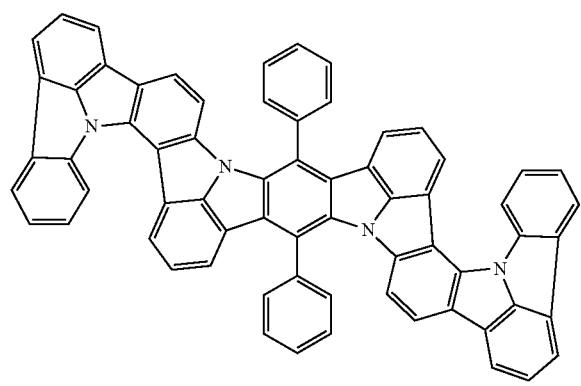

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring having 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocyclic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring having 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ mare bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring having a two-ring fused structure (or three or more rings fused structure) in which a ring containing $R_{401}$ and the a ring are fused. Specific examples of the nitrogen-containing heterocyclic ring include compound and the like corresponding to a heterocyclic group of 2 ring condensation or more containing nitrogen among specific example groups G2.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring having 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group having 6 to 50 ring carbon atoms, or a substituted or unsubstituted monovalent heterocyclic group having 5 to 50 ring atoms, and preferably a substituted or unsubstituted aryl group having 6 to 50 ring carbon atoms.

In one embodiment, the compound represented by the formula (41) is a compound represented by the following formula (42):

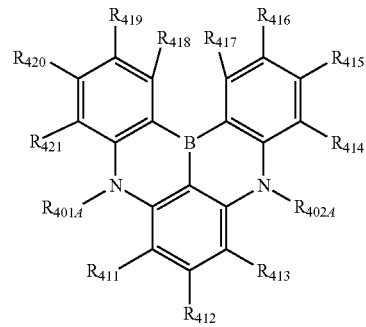

(42)

wherein in the formula (42), $R_{401A}$ is bonded with one or more groups selected from $R_{411}$ or $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form a substituted or unsubstituted heterocyclic ring, or does not form a substituted or unsubstituted heterocyclic ring;

$R_{401A}$ and $R_{402A}$ that do not form a substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

$R_{401A}$ and $R_{402A}$ in the formula (42) correspond to $R_{401}$ and $R_{402}$ in the formula (41).

$R_{401A}$ and $R_{411}$ may be bonded with each other to form a nitrogen-containing heterocyclic ring having two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group having two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to form abenzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom or a substituted or unsubstituted alkyl group having 1 to 50 carbon atoms.

In one embodiment, $R_{411}$ to $R_{421}$ that do not contribute to form a ring are independently a hydrogen atom, a substituted or unsubstituted alkyl group having 1 to 50 carbon atoms, and at least one of $R_{411}$ to $R_{421}$ is a substituted or unsubstituted alkyl group having 1 to 50 carbon atoms.

In one embodiment, the compound represented by the formula (42) is a compound represented by the following formula (43):

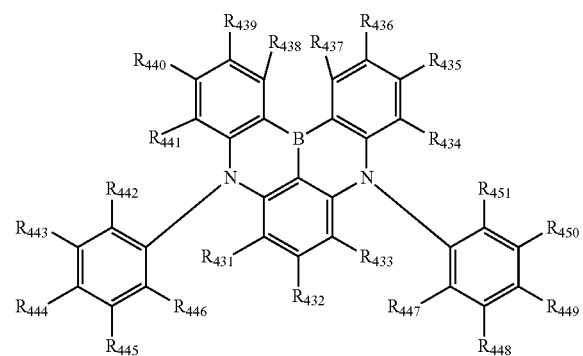

(43)

wherein in the formula (43),
$R_{431}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

One or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

$R_{431}$ may bond to $R_{446}$ to form a substituted or unsubstituted heterocyclic ring. For example, $R_{431}$ may bonds with $R_{446}$ to form a nitrogen-containing heterocyclic ring with three or more fused rings of the benzene ring to which $R_{46}$ bond, a nitrogen-containing ring and the benzene ring of the a ring. As examples of the nitrogen-containing heterocyclic ring, compounds correspond to nitrogen-containing heterocyclic group having three or more ring fused structure in the group G2 can be given. The same applies to the cases where $R_{433}$ and $R_{447}$ are bonded, $R_{434}$ and $R_{451}$ are bonded, and $R_{441}$ and $R_{442}$ are bonded.

In one embodiment, $R_{431}$ to $R_{451}$ that do not contribute to form a ring are independently, a hydrogen atom, a substituted or unsubstituted alkyl group having 1 to 50 carbon atoms, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently, a hydrogen atom, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently a hydrogen atom or a substituted or unsubstituted alkyl group having 1 to 50 carbon atoms.

In one embodiment, $R_{431}$ to $R_{451}$ that do not contribute to form a ring are independently a hydrogen atom, a substituted or unsubstituted alkyl group having 1 to 50 carbon atoms, and at least one of $R_{431}$ to $R_{451}$ is a substituted or unsubstituted alkyl group having 1 to 50 carbon atoms.

In one embodiment, the compound represented by the formula (43) is a compound represented by the following formula (43A):

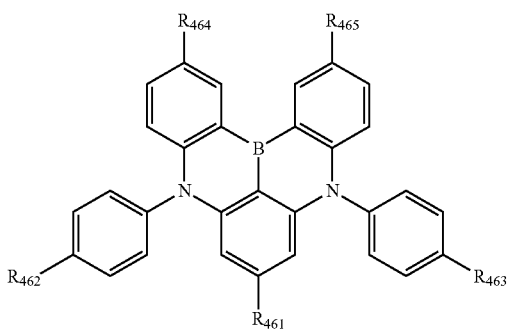

(43A)

wherein in the formula (43A),
$R_{461}$ is
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and
$R_{462}$ to $R_{465}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, $R_{461}$ to $R_{465}$ are independently a substituted or unsubstituted alkyl group having 1 to 50 carbon atoms or a substituted or unsubstituted aryl group having 6 to 50 ring carbon atoms.

In one embodiment, $R_{461}$ and $R_{465}$ are independently a substituted or unsubstituted alkyl group having 1 to 50 carbon atoms.

In one embodiment, the compound represented by the formula (43) is a compound represented by the following formula (43B):

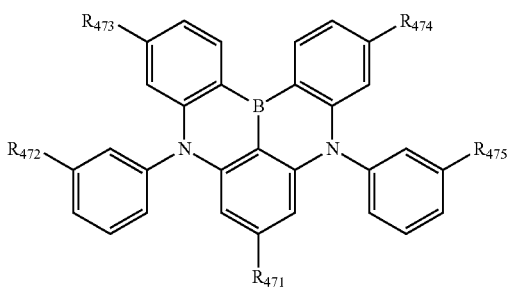

(43B)

wherein in the formula (43B),
$R_{471}$ and $R_{472}$ are independently,
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms;
$R_{473}$ to $R_{475}$ are independently,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms; and
$R_{906}$ and $R_{907}$ are as defined in the formula (1).

In one embodiment, the compound represented by the formula (43) is the compound represented by the following formula (43B'):

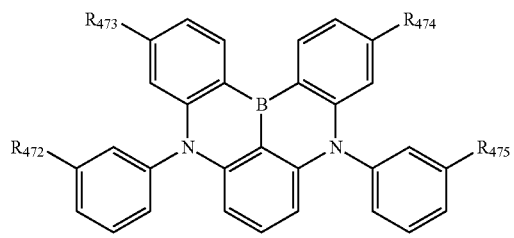

(43B')

wherein in the formula (43B'), $R_{472}$ to $R_{475}$ are as defined in the formula (43B).

In one embodiment, at least one of $R_{471}$ to $R_{475}$ is
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—N($R_{906}$) ($R_{907}$), or
a substituted or unsubstituted aryl group having 6 to 50 ring carbon atoms.

In one embodiment,
$R_{472}$ is
a hydrogen atom,
a substituted or unsubstituted alkyl group having 1 to 50 carbon atoms,
—N($R_{906}$) ($R_{907}$), or
a substituted or unsubstituted aryl group having 6 to 50 ring carbon atoms; and
$R_{471}$ and $R_{473}$ to $R_{475}$ are independently a substituted or unsubstituted alkyl group having 1 to 50 carbon atoms,
—N(R$_{906}$) (R$_{907}$), or
a substituted or unsubstituted aryl group having 6 to 50 ring carbon atoms.

In one embodiment, the compound represented by the formula (43) is a compound represented by the formula (43C):

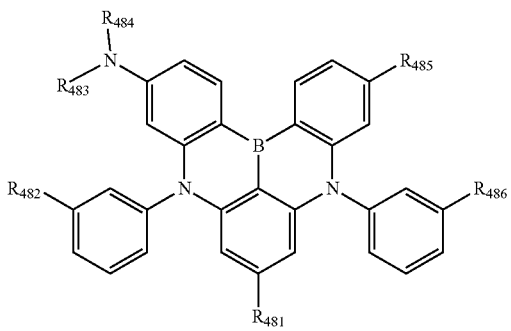

(43C)

wherein in the formula (43C),
R$_{481}$ and R$_{482}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms; and
R$_{483}$ to R$_{486}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms, or
a substituted or unsubstituted aryl group having 6 to 50 ring carbon atoms.

In one embodiment, the compound represented by the formula (43) is the compound represented by the following formula (43C'):

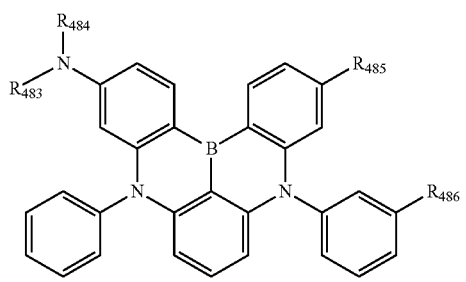

(43C')

wherein in the formula (43C'), R$_{483}$ to R$_{486}$ are as defined in the formula (43C).

In one embodiment, R$_{481}$ to R$_{486}$ are independently a substituted or unsubstituted alkyl group having 1 to 50 carbon atoms or a substituted or unsubstituted aryl group having 6 to 50 ring carbon atoms.

In one embodiment, R$_{481}$ to R$_{486}$ are independently a substituted or unsubstituted aryl group having 6 to 50 ring carbon atoms.

The compound represented by the formula (41) can be synthesized by the following method: An intermediate is obtained by bonding the a ring, the b ring and the c ring with linking groups (a group containing N—R$_1$ and a group containing N—R$_2$) (first reaction), and a final compound is obtained by bonding the a ring, the b ring and the c ring with a linking group (a group containing B) (second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples. In the following example compounds, Me represents methyl group and tBu represents tert-butyl group.

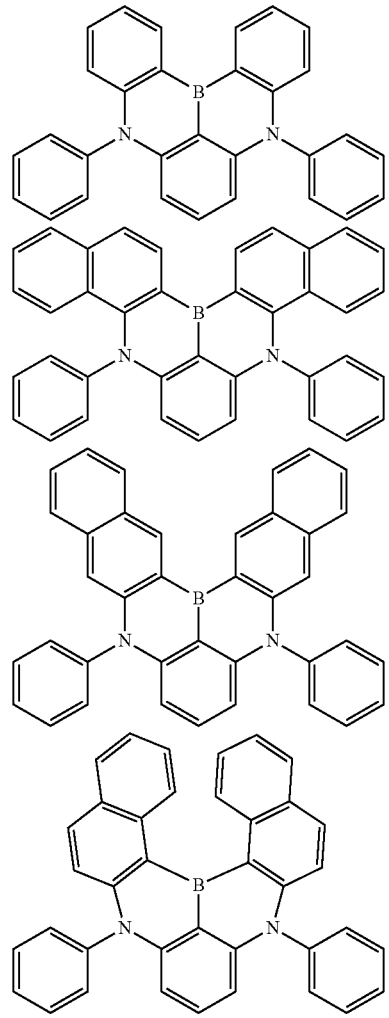

639
-continued
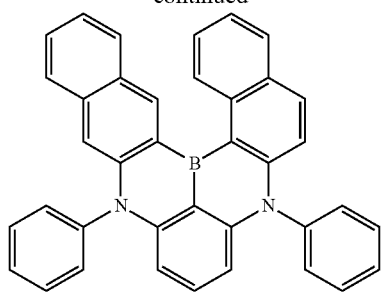
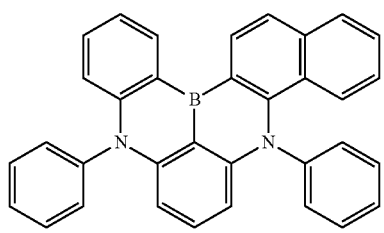
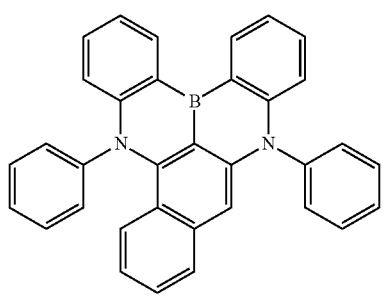
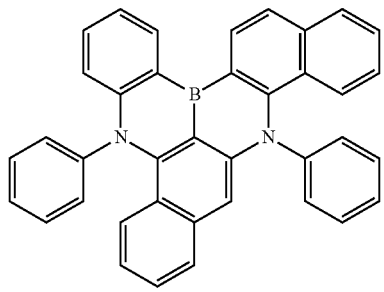
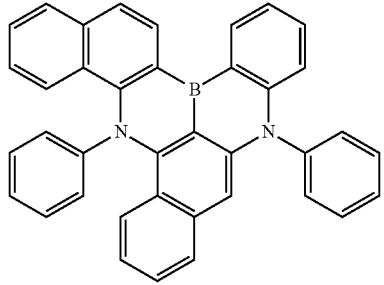
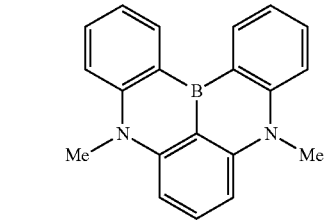
640
-continued
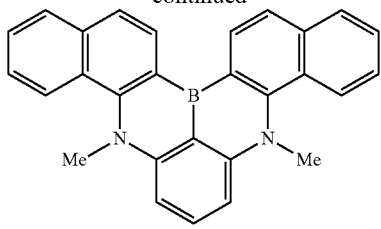
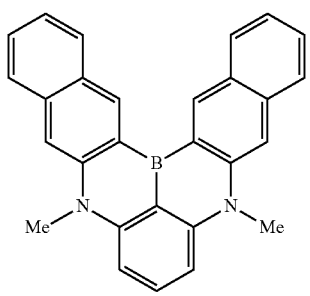
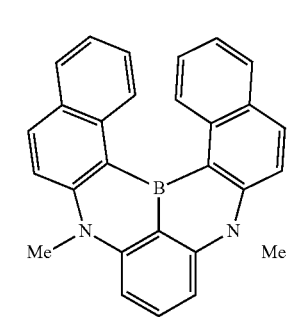
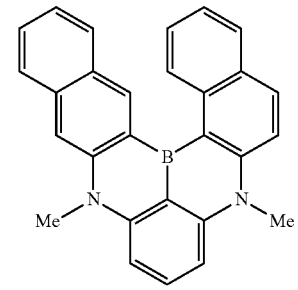
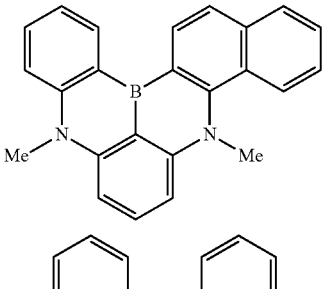
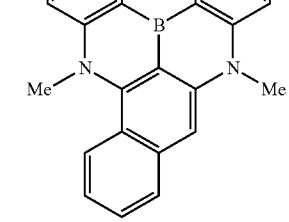

641
-continued
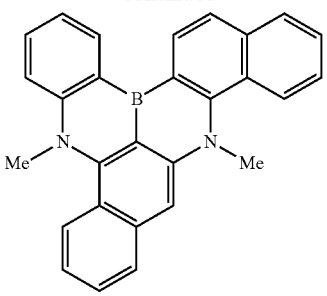
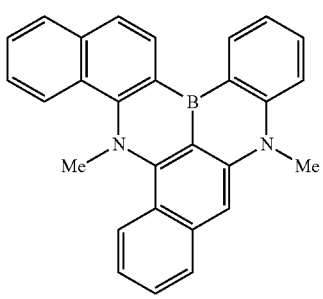
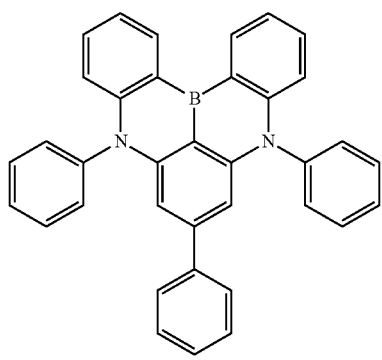
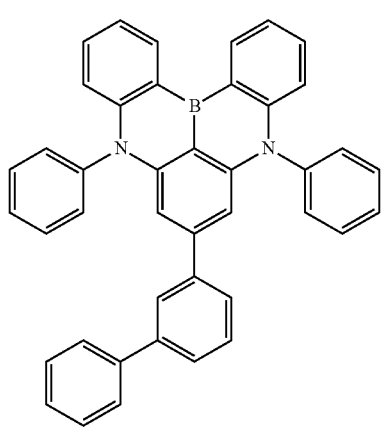
642
-continued
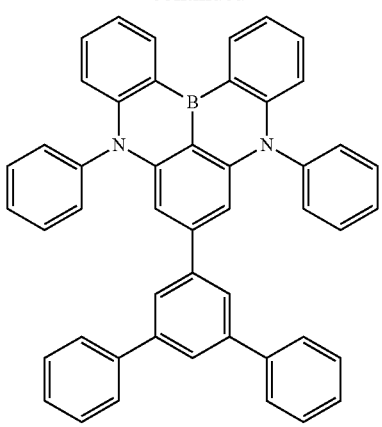
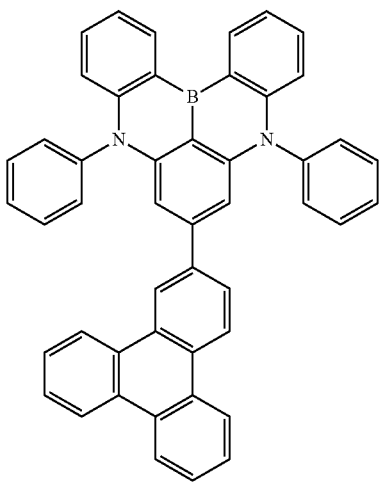
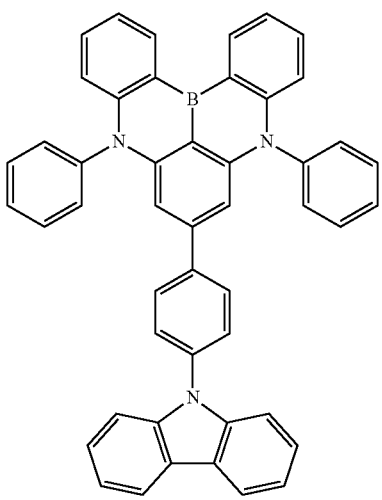

643
-continued
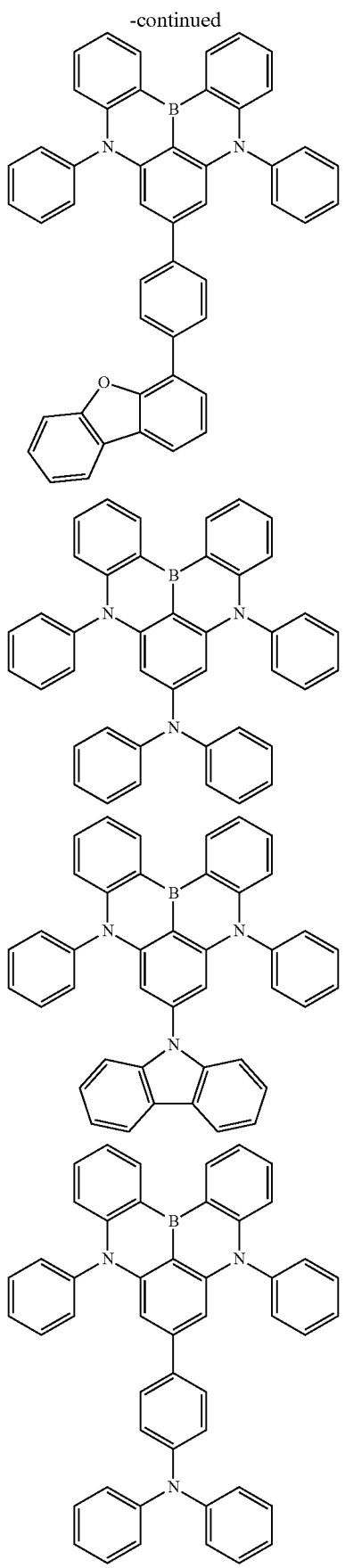
644
-continued
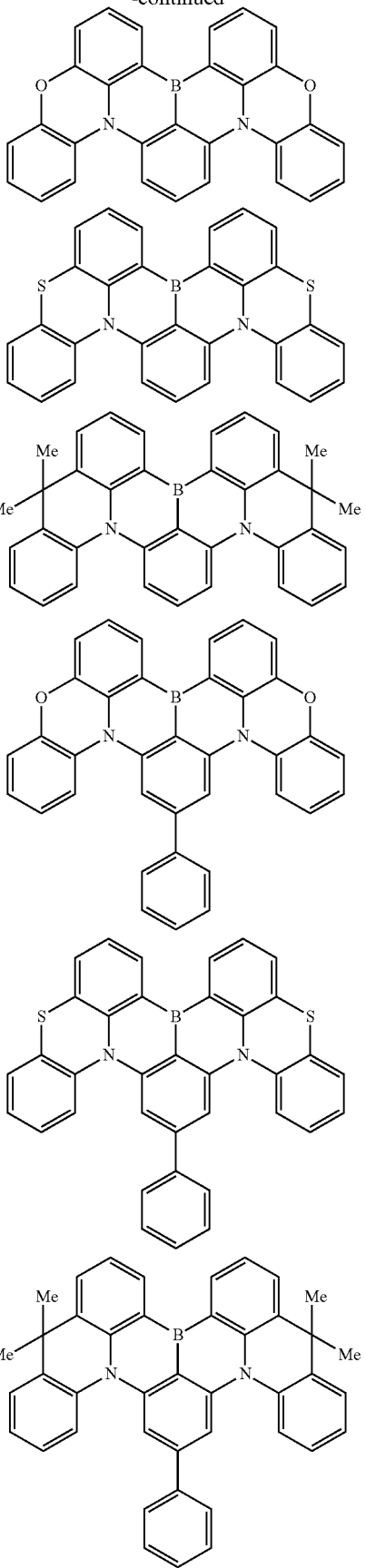

645
-continued
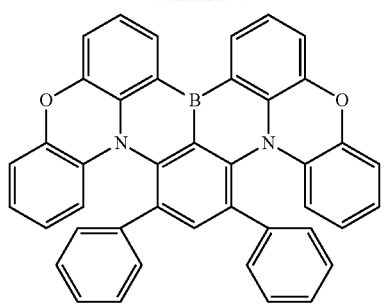
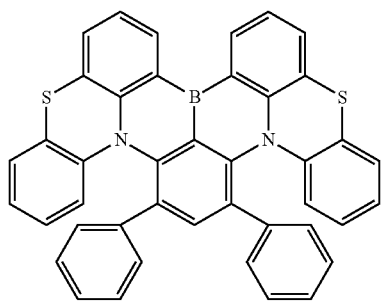
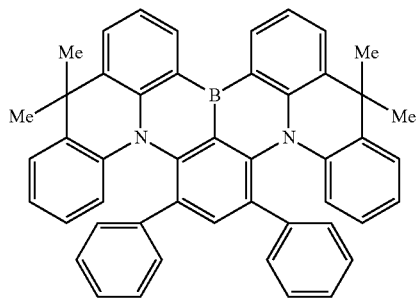
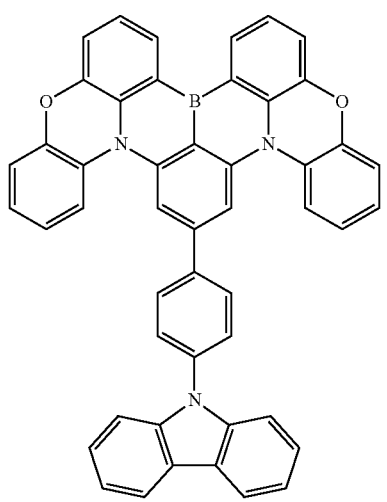
646
-continued
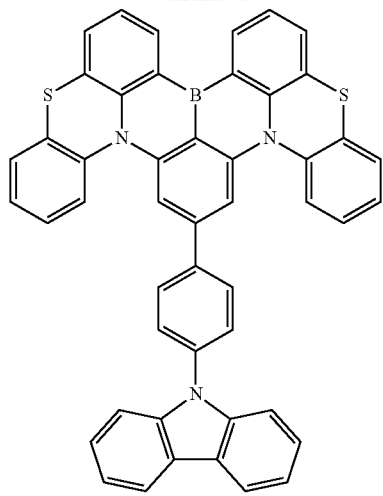
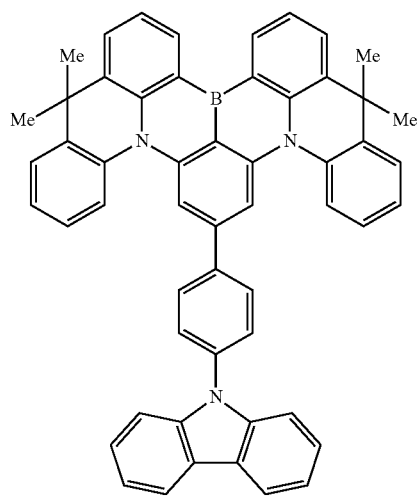
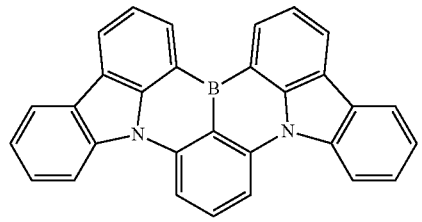
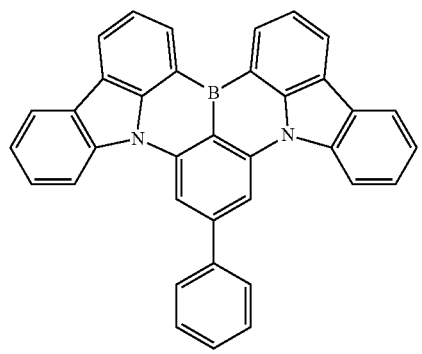

647
-continued
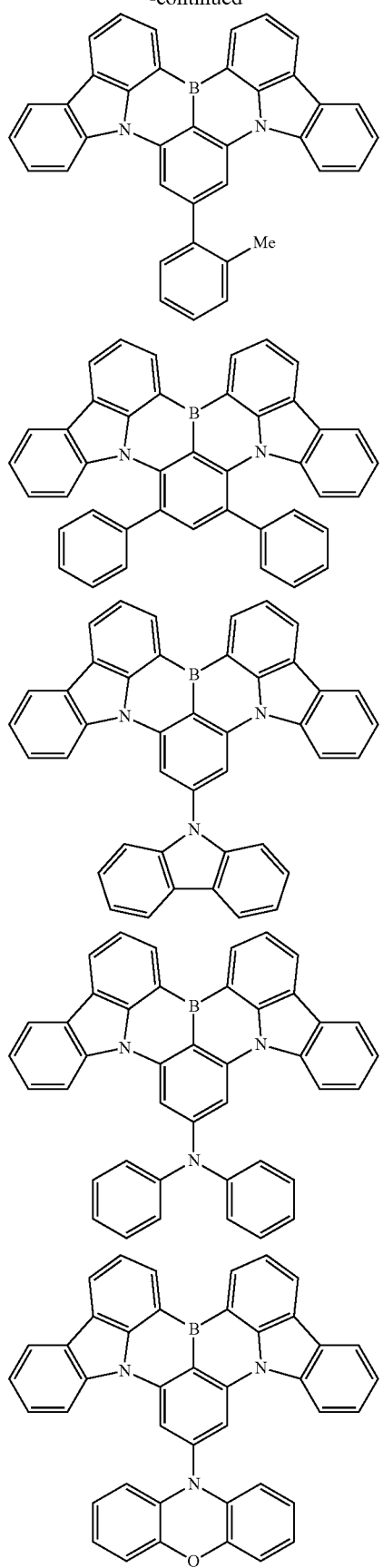
648
-continued
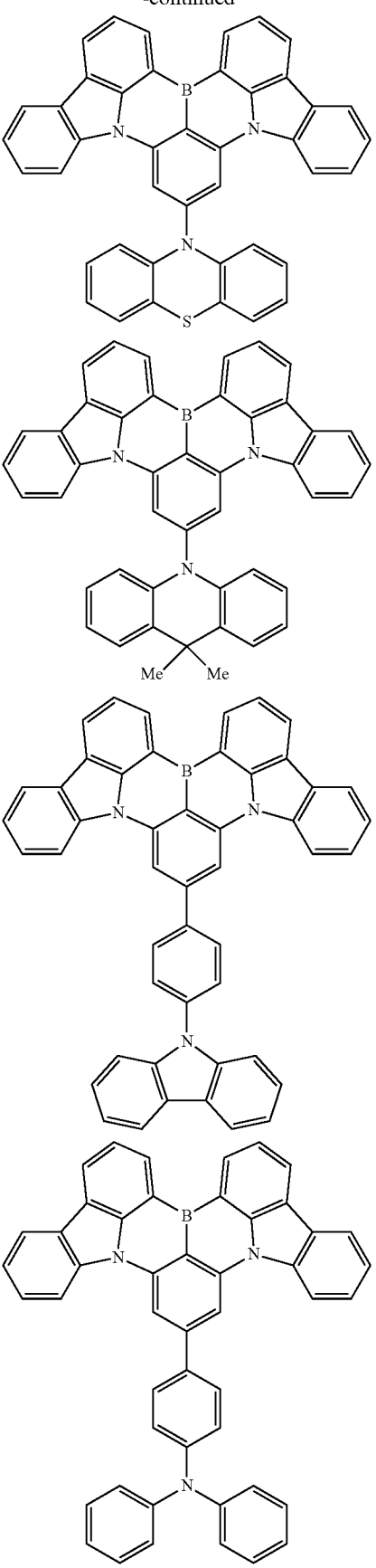

| 649 -continued | 650 -continued |
|---|---|
| 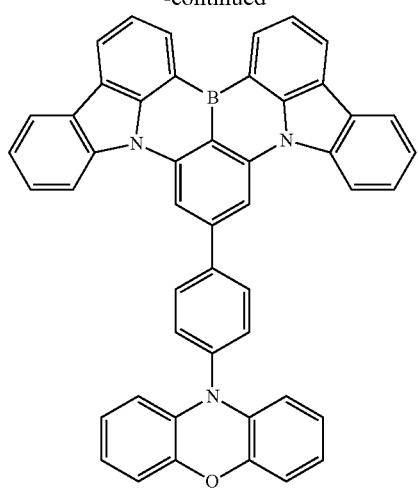 | 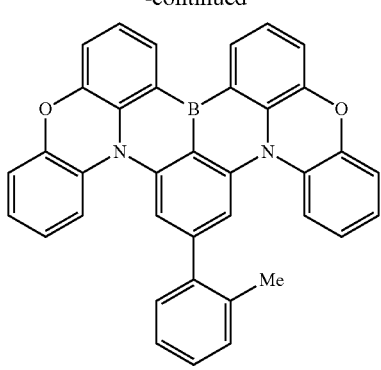 |
| 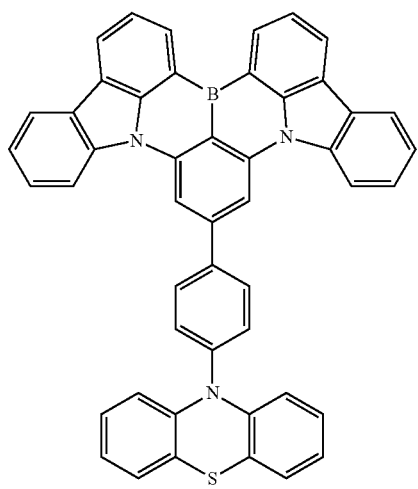 | 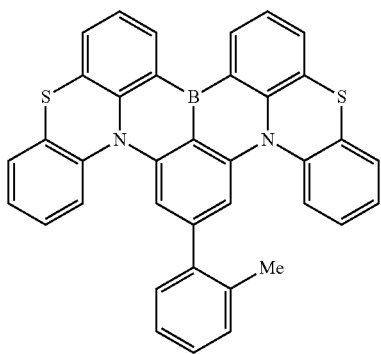 |
| | 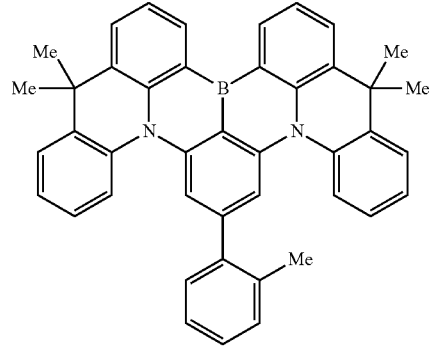 |
| 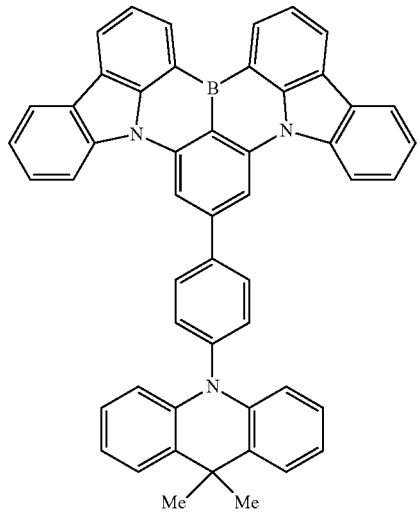 | 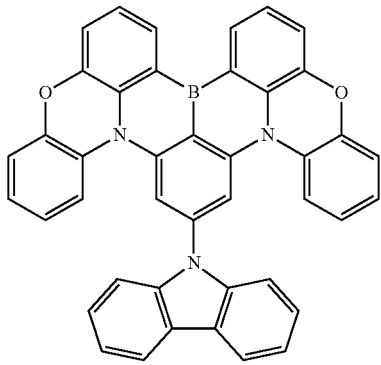 |

651
-continued
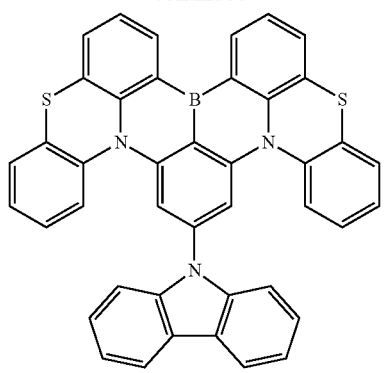
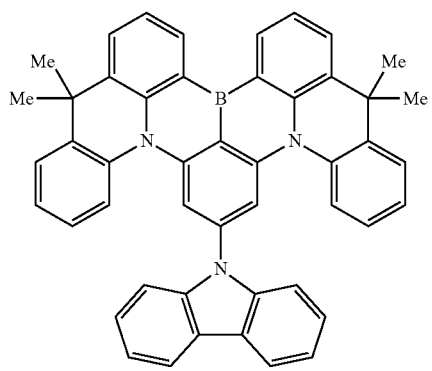
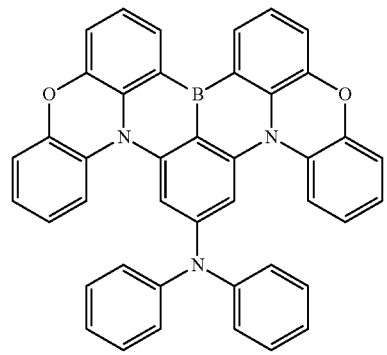
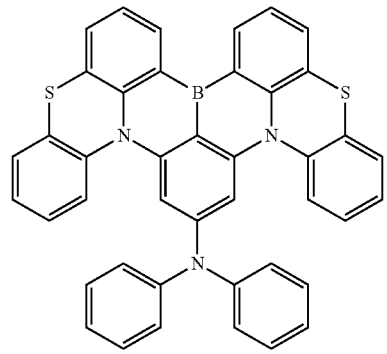
652
-continued
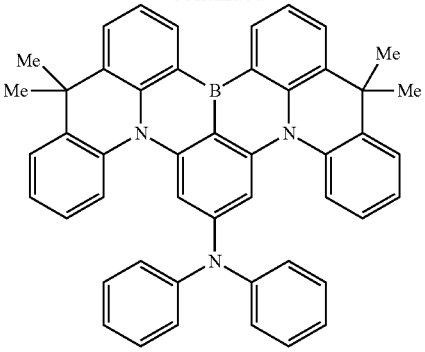
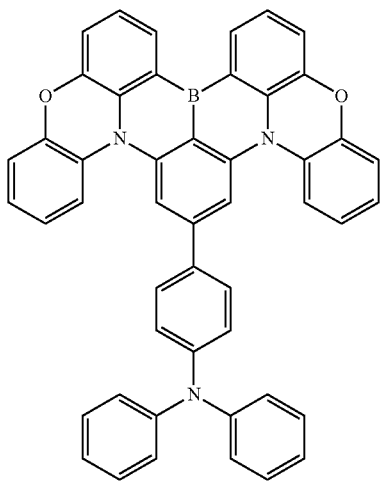
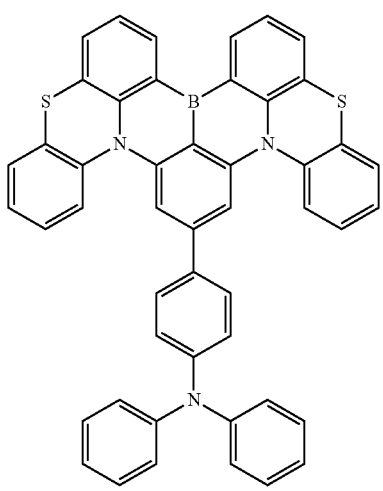

653
-continued
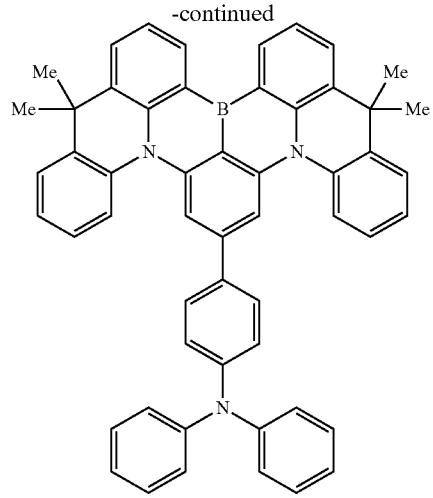
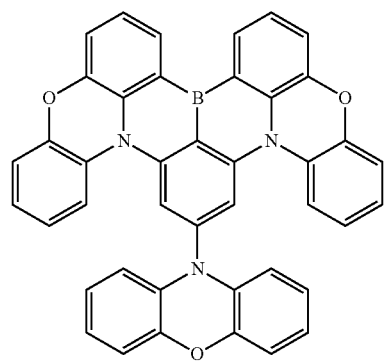
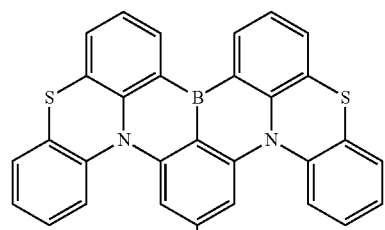
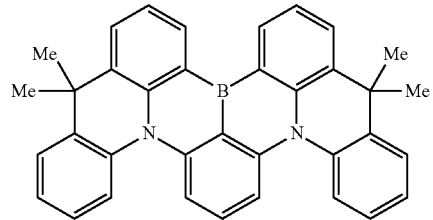
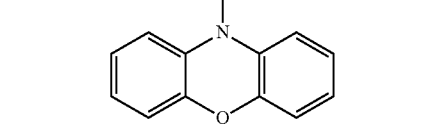
654
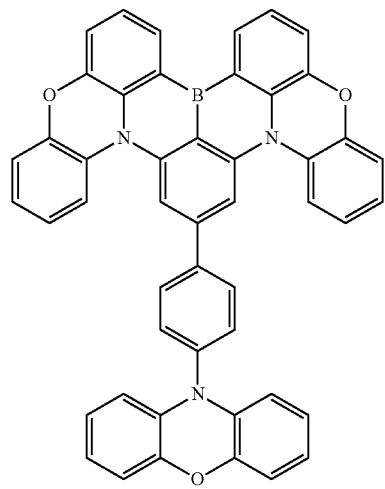
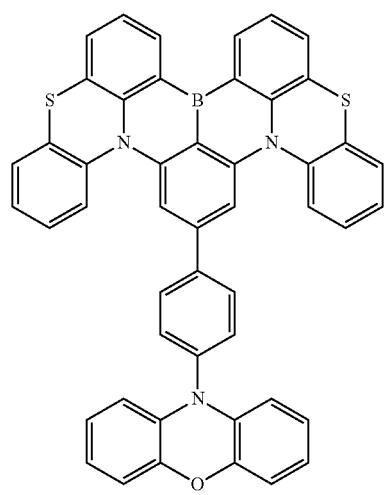
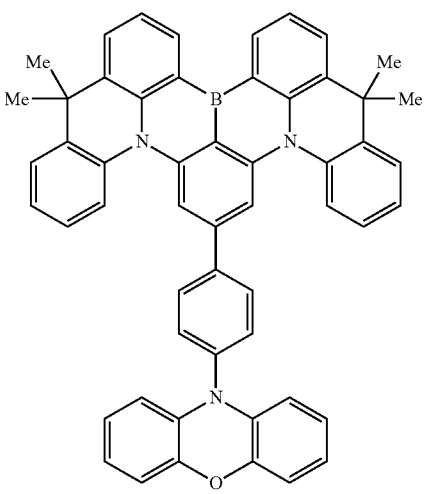

655
-continued
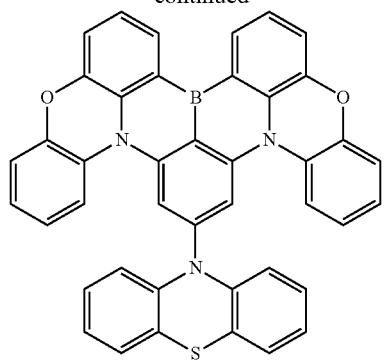
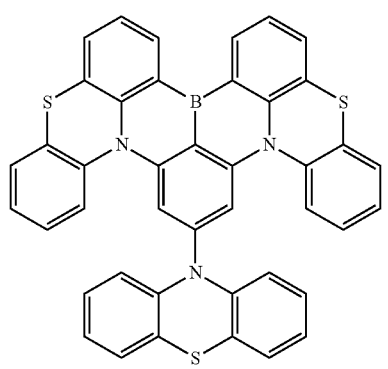
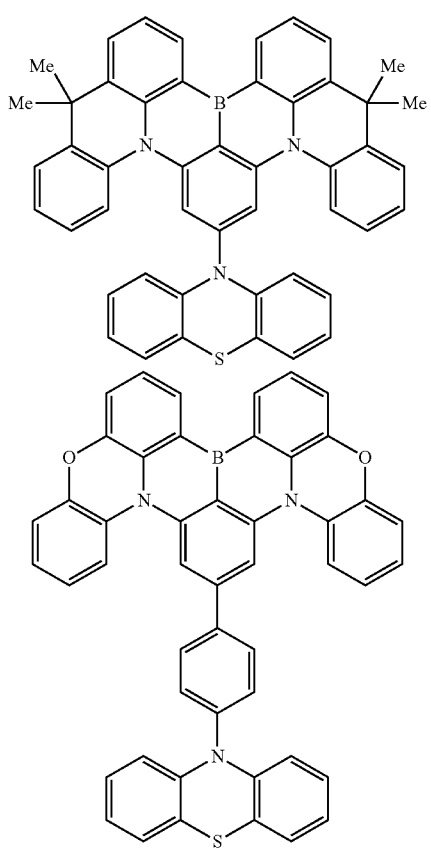
656
-continued
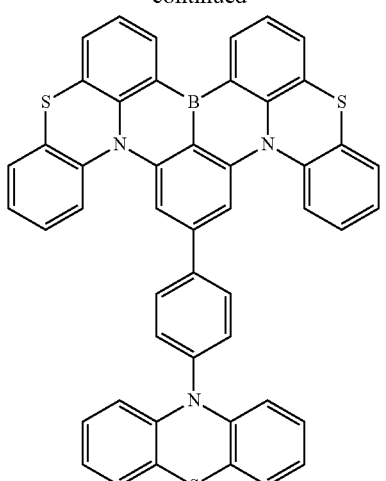
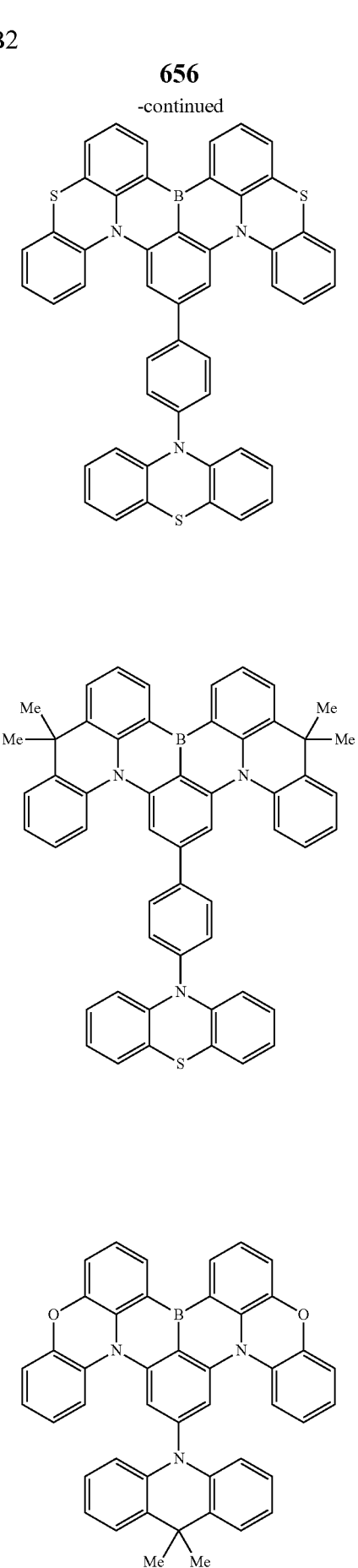

657
-continued
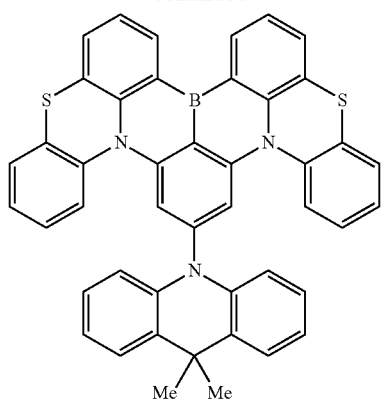
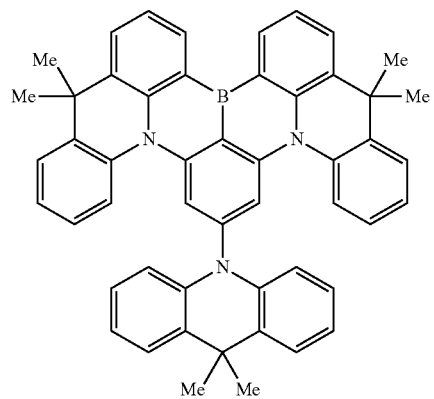
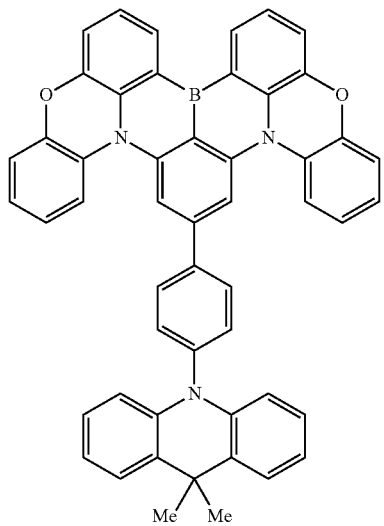
658
-continued
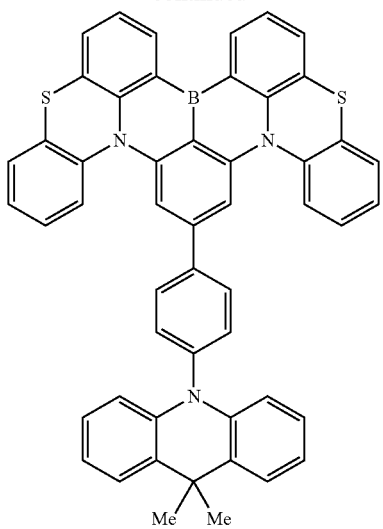
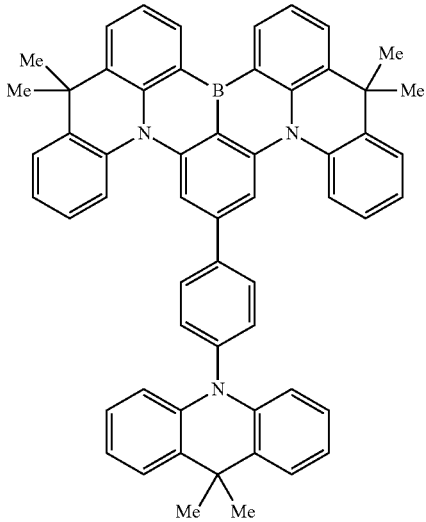
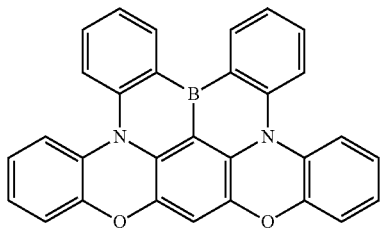
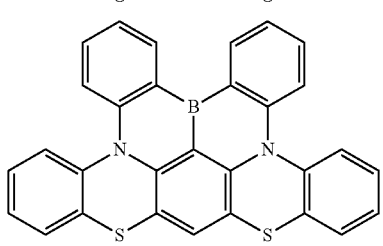

659
-continued
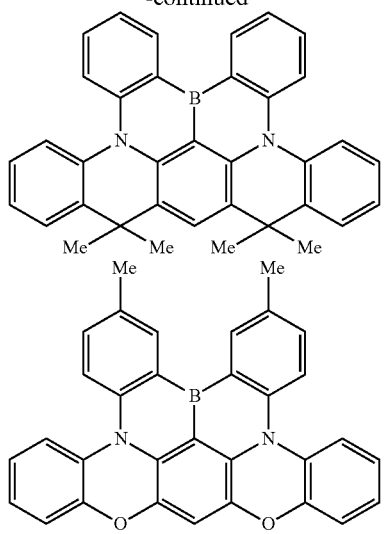
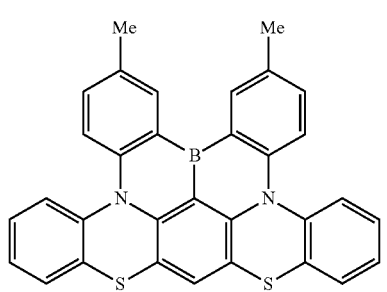
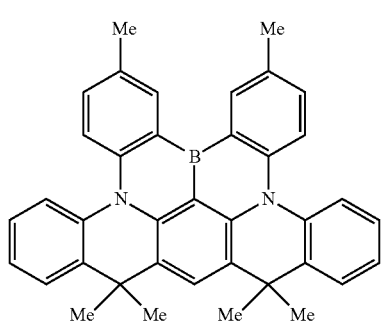
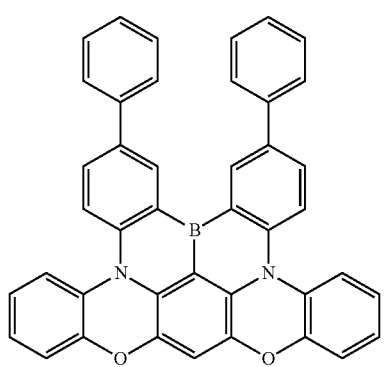
660
-continued
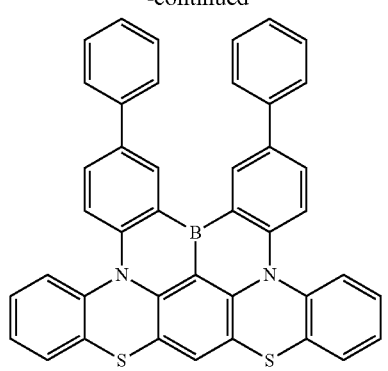
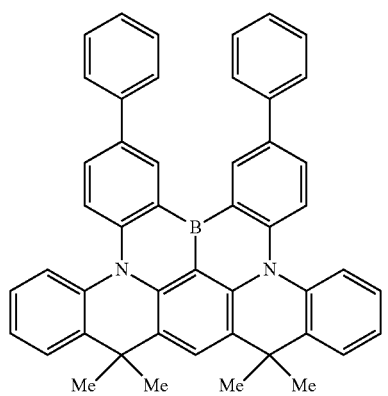
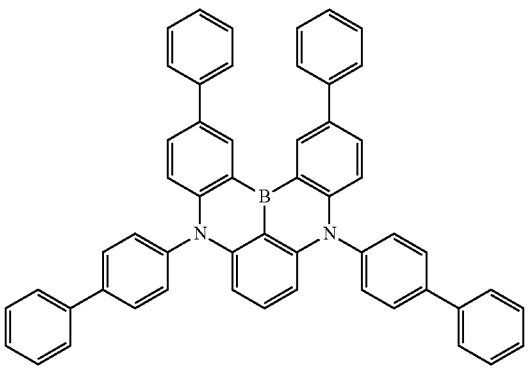
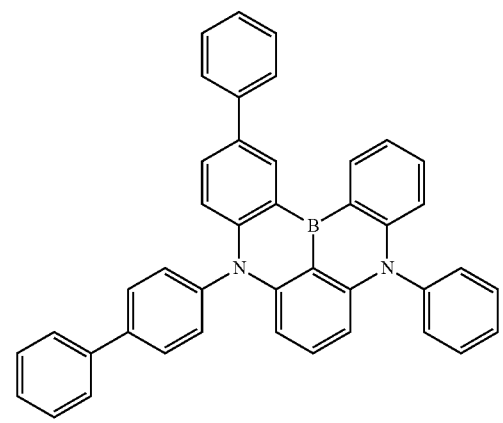

661
-continued
662
-continued
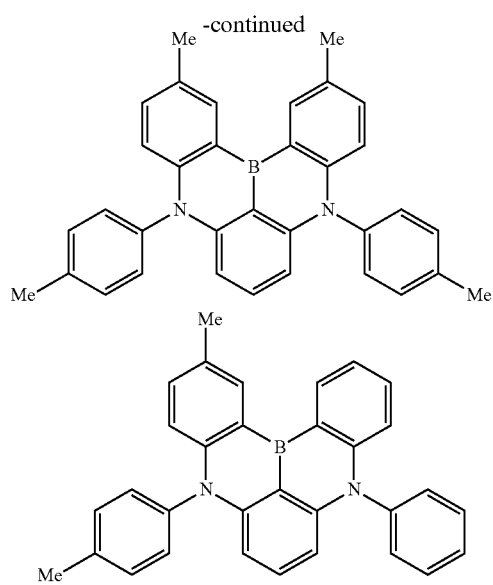
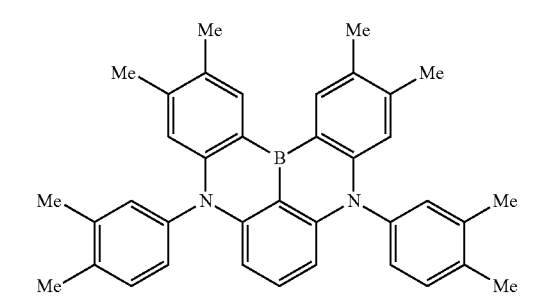
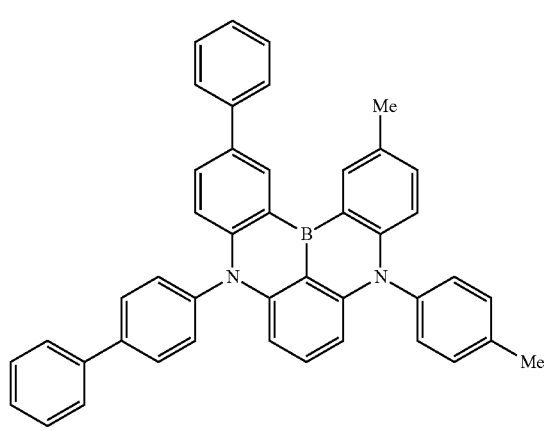
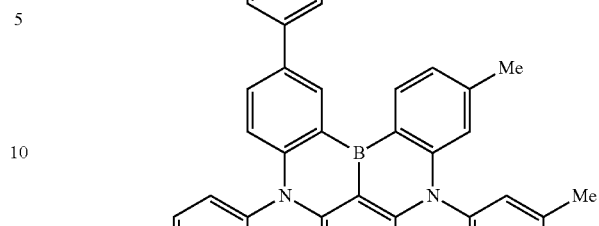
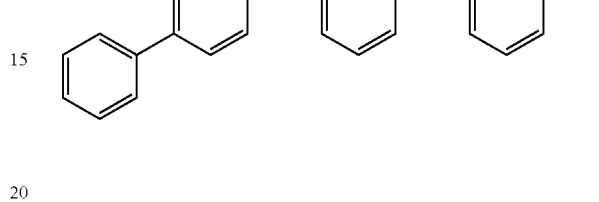

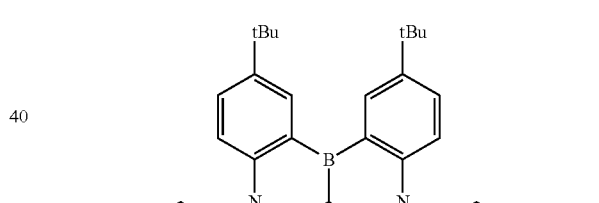
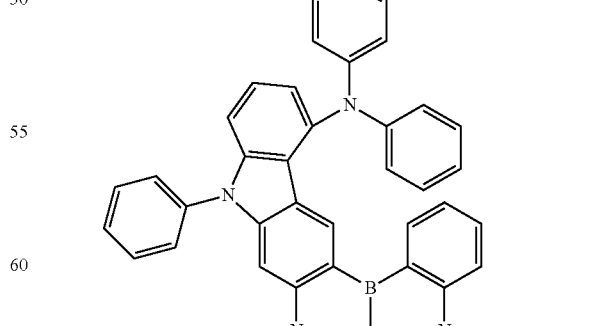
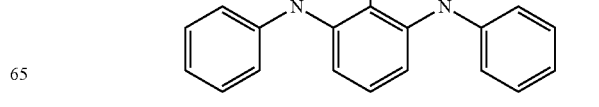

663
-continued
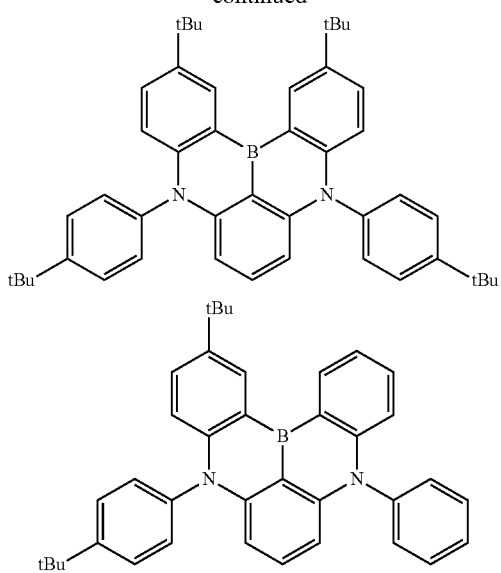
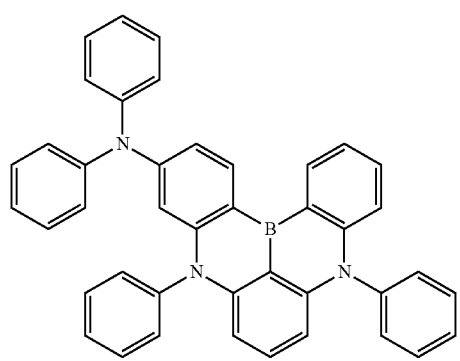
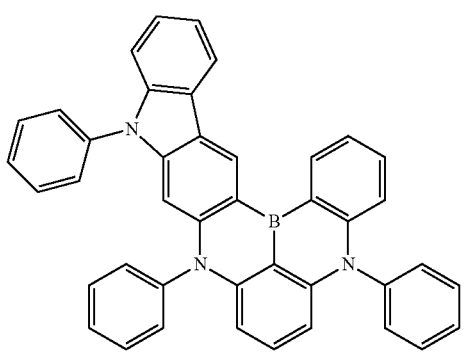
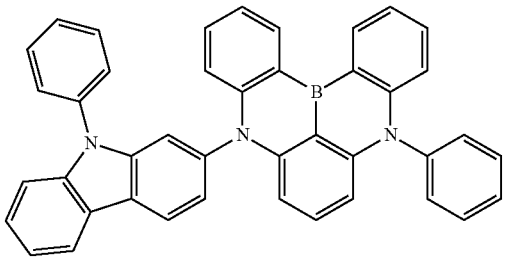
664
-continued
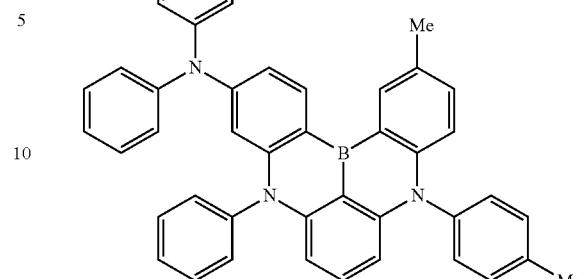
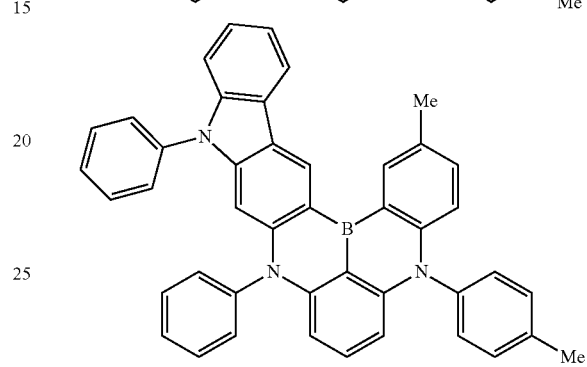
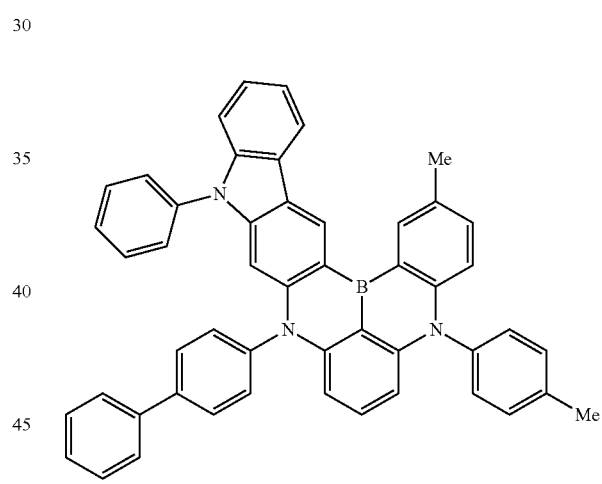
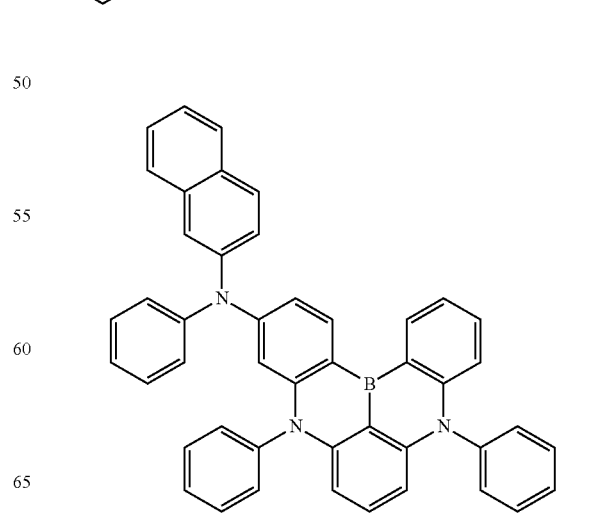

665
-continued
666
-continued
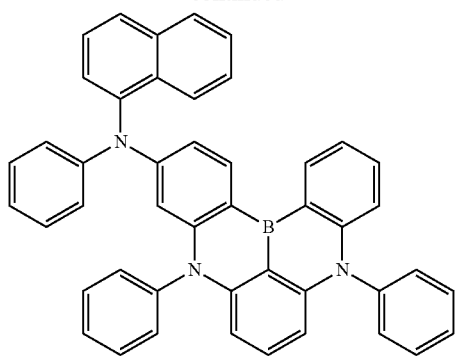
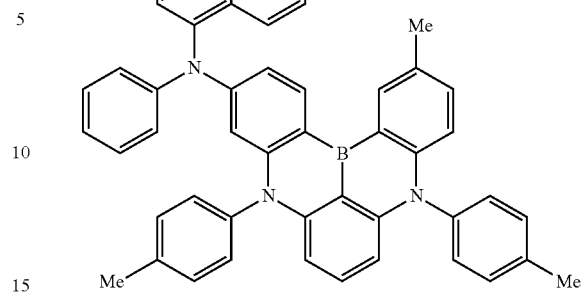
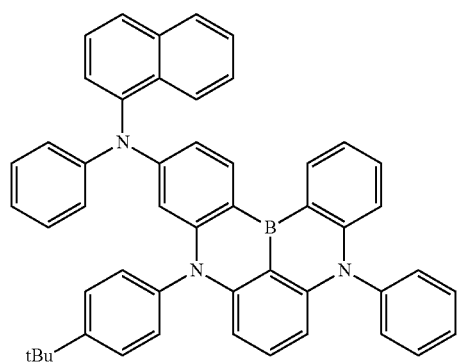
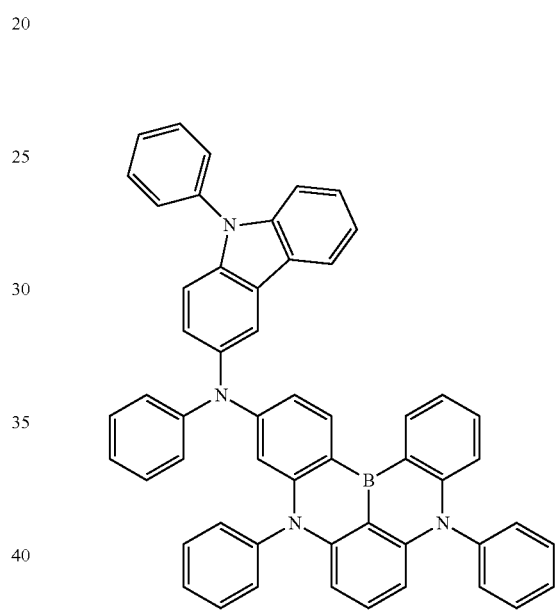
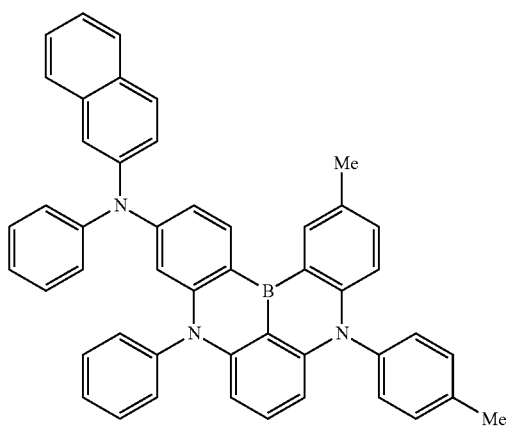
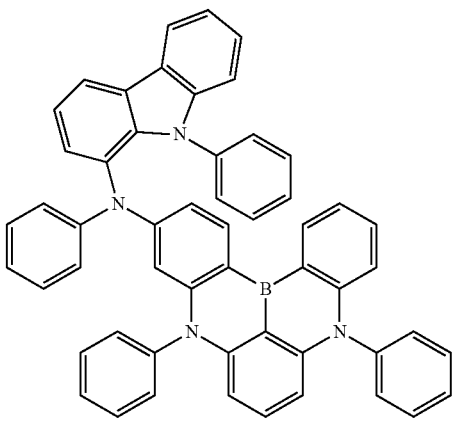

-continued
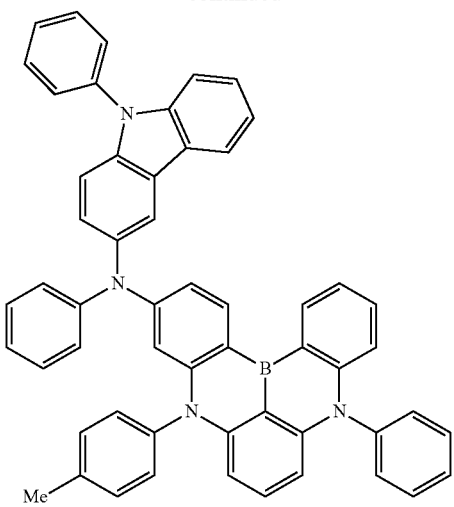
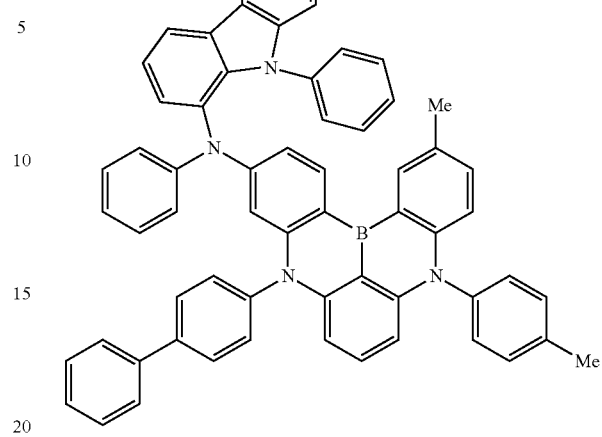
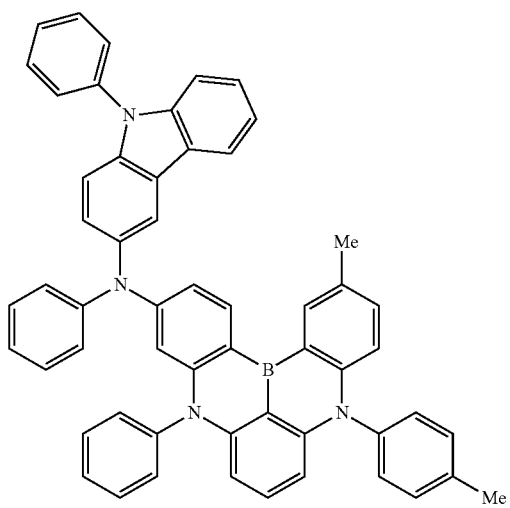
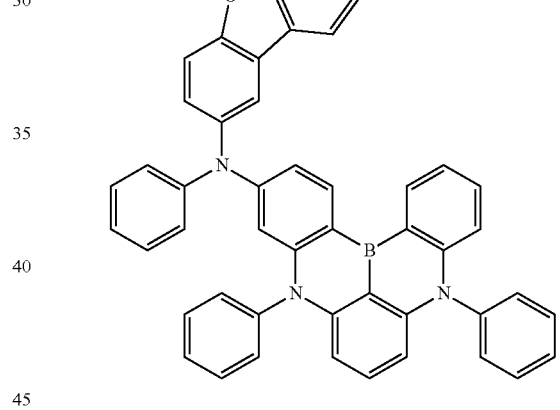
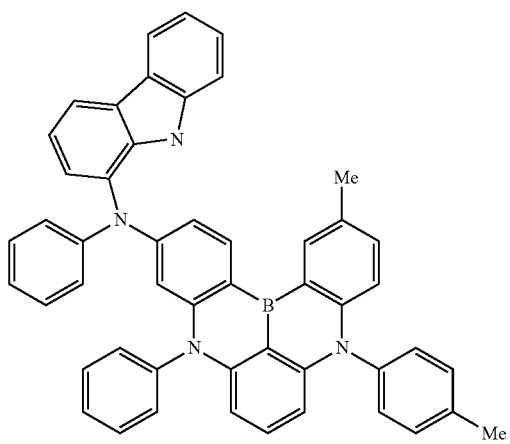
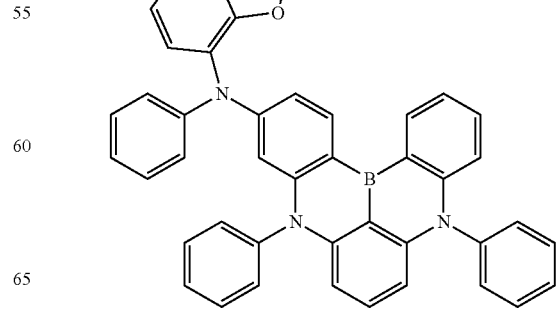

-continued
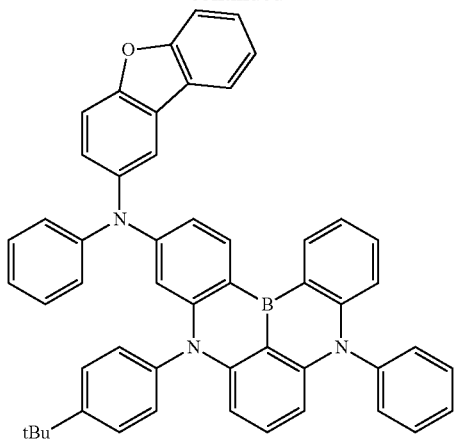
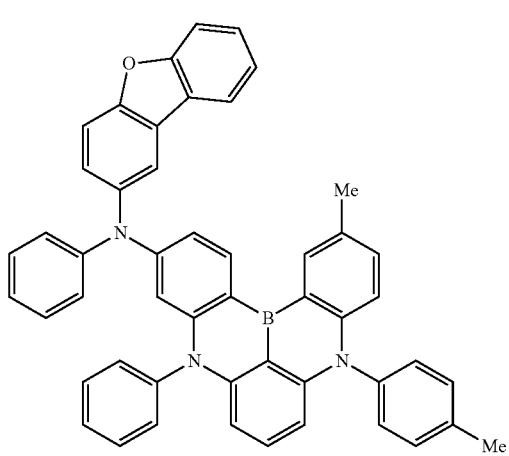
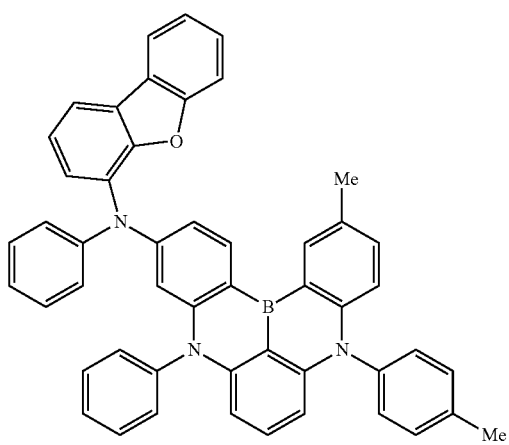
-continued
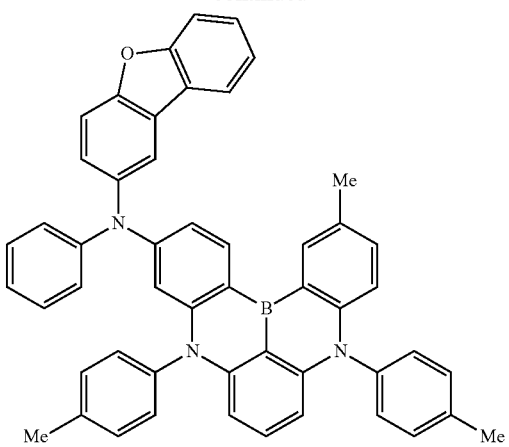
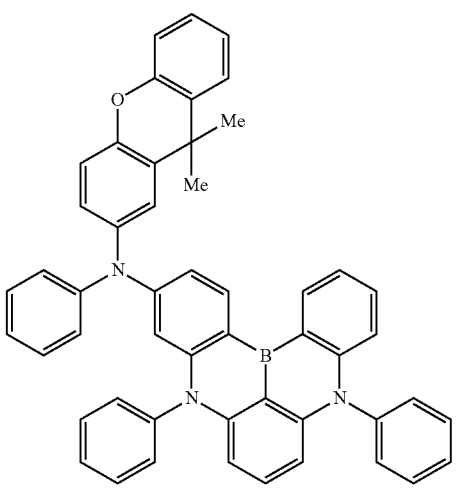
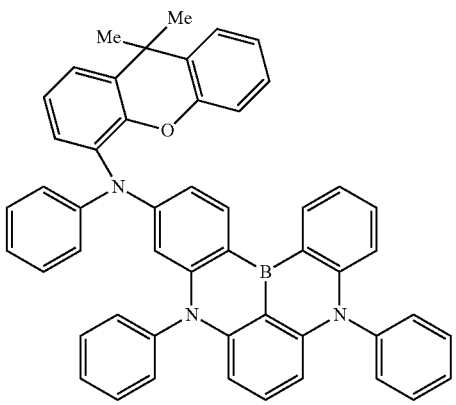

| 671 -continued | 672 -continued |
|---|---|
| 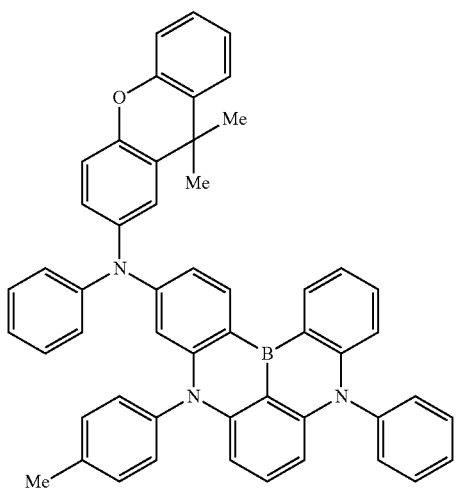 | 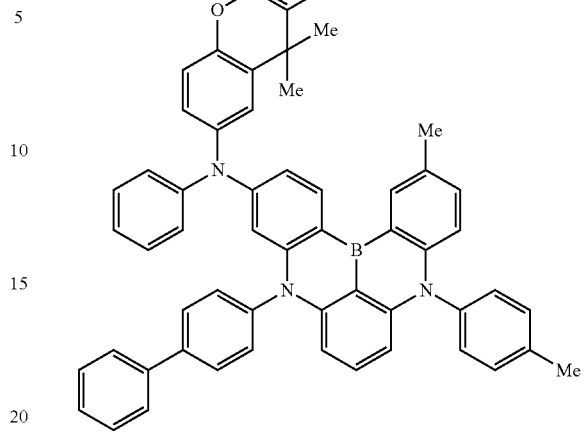 |
| 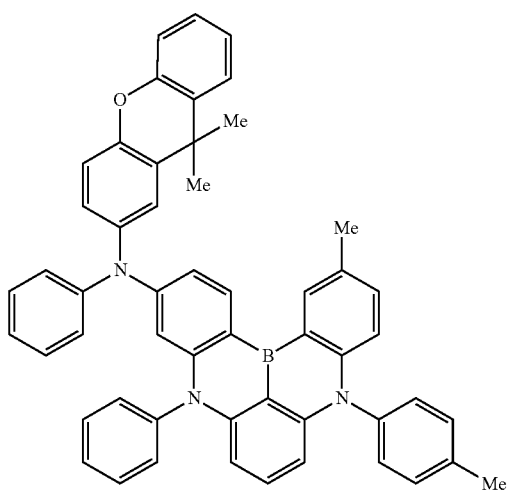 | 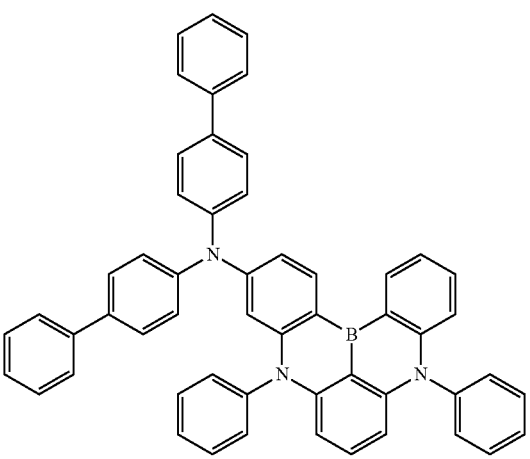 |
| 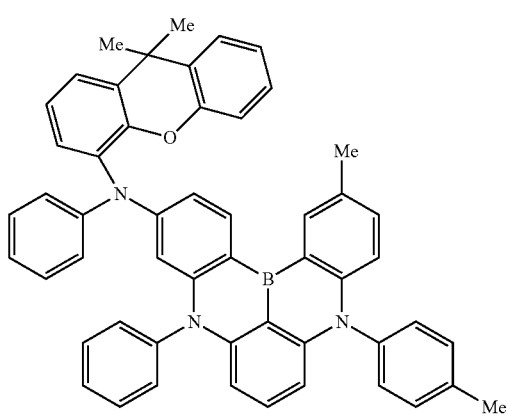 | 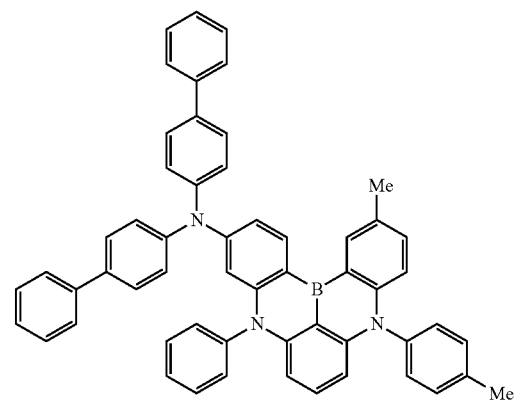 |

673
-continued
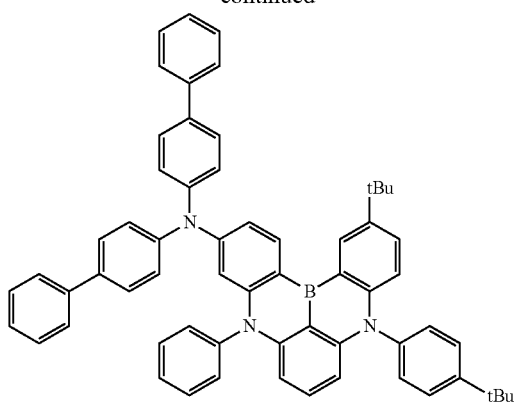
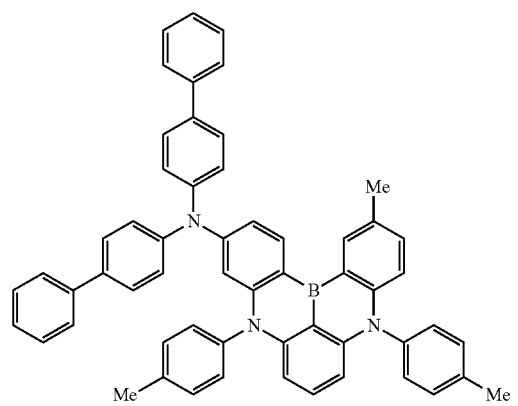
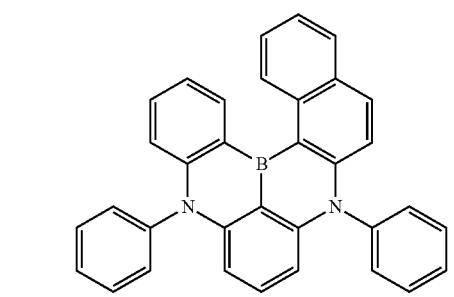
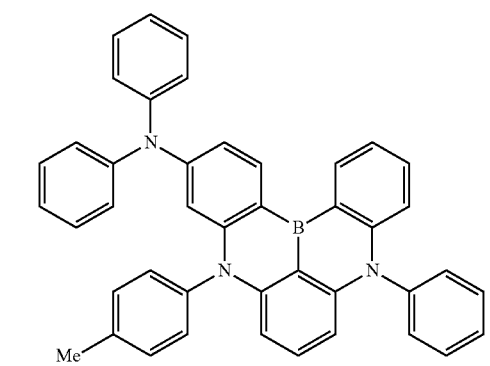
674
-continued
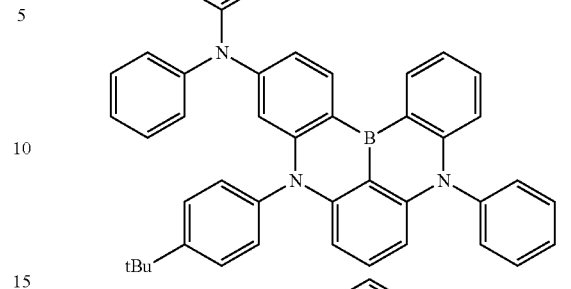
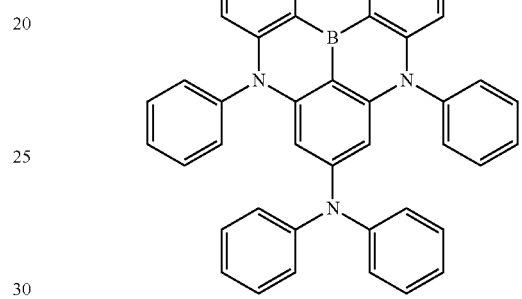
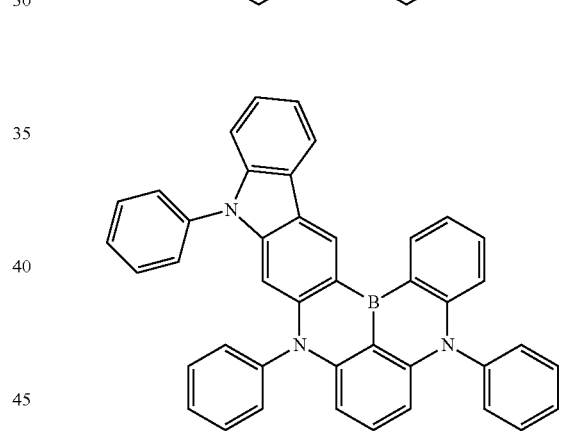
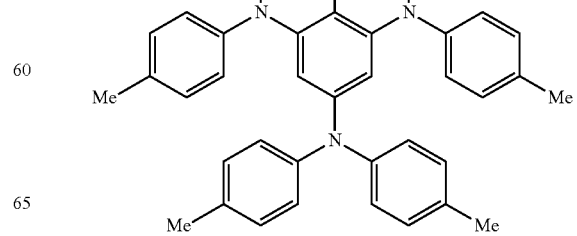

675
-continued
676
-continued
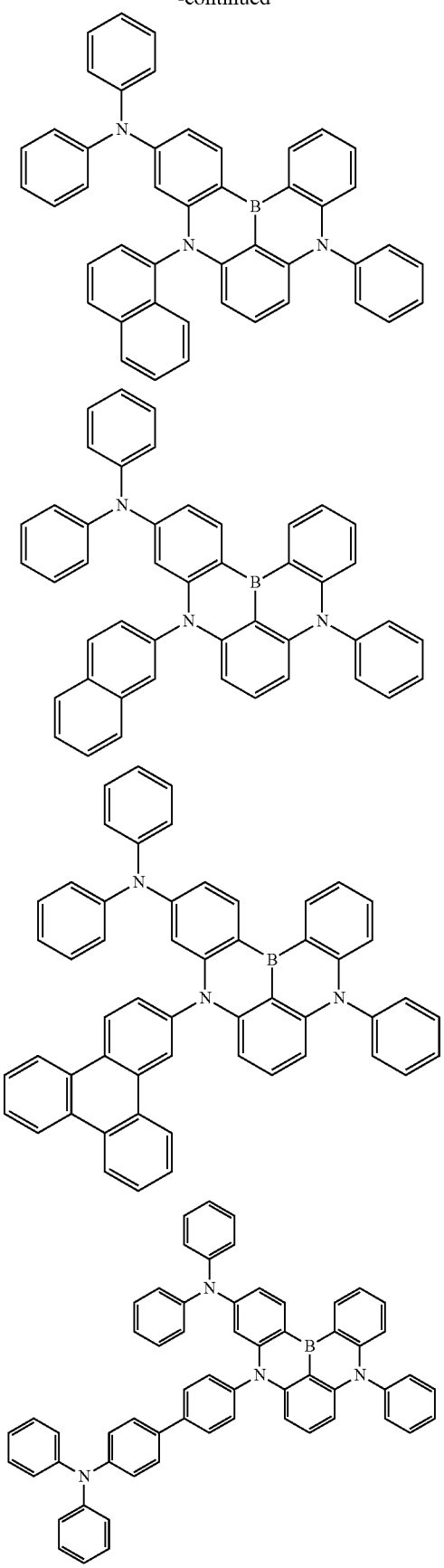
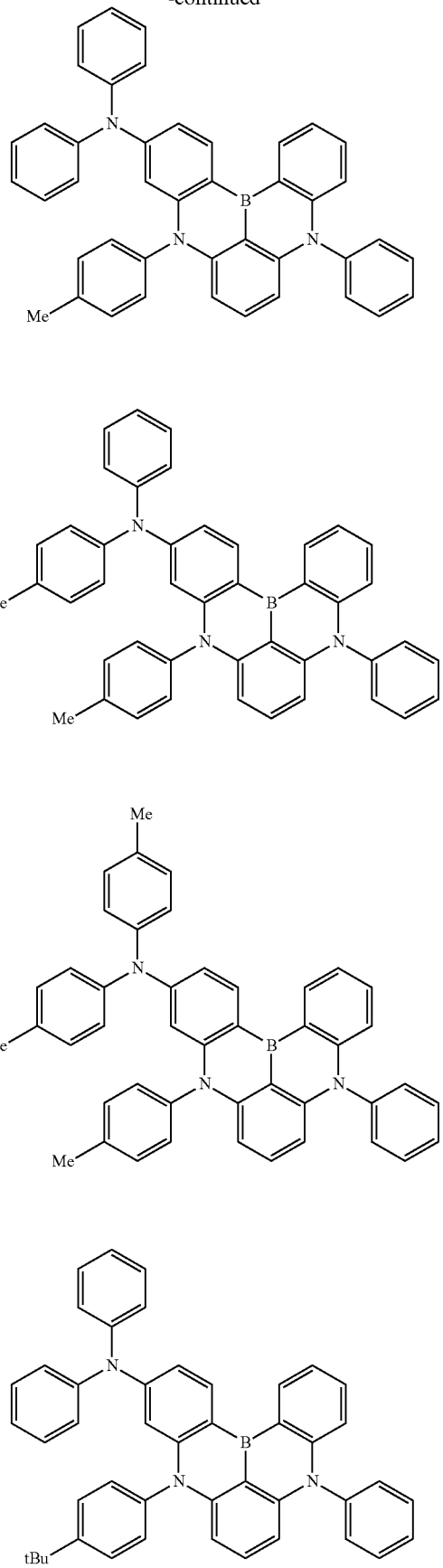

677
-continued
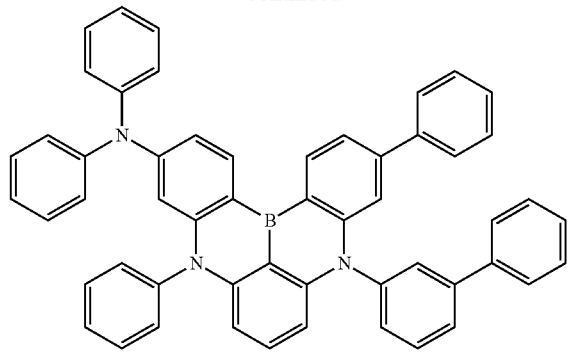
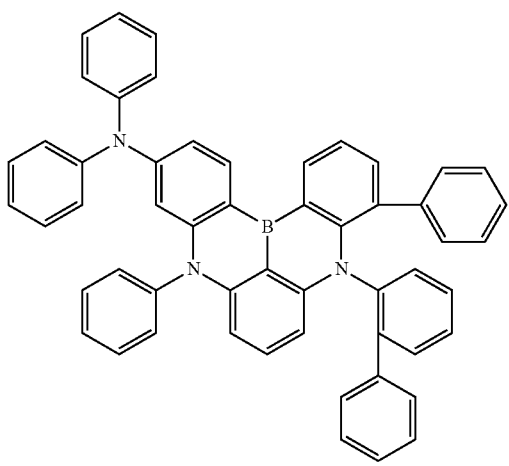
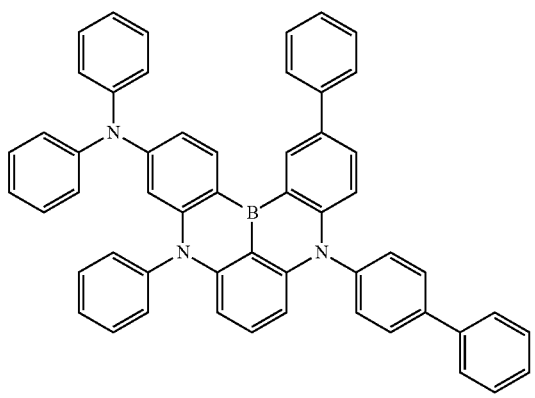
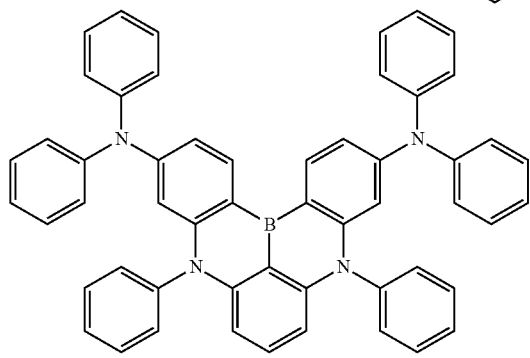
678
-continued
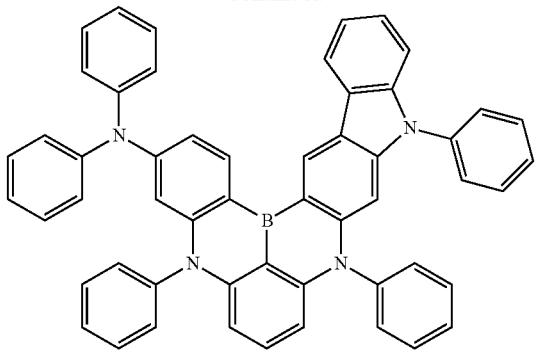
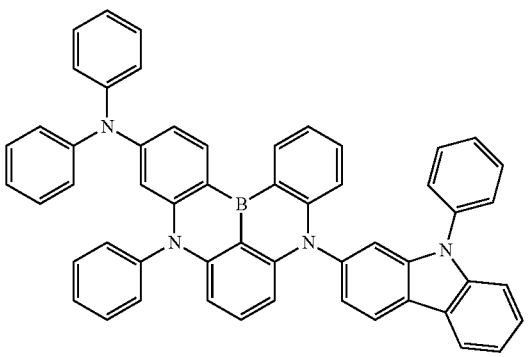
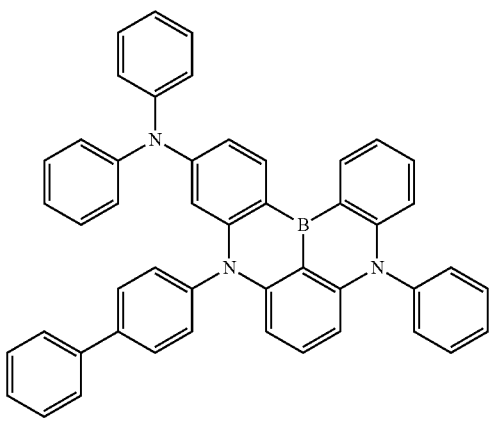
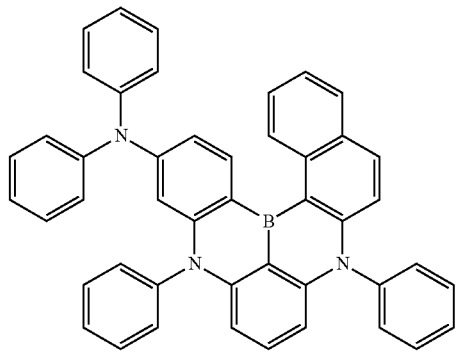

679
-continued
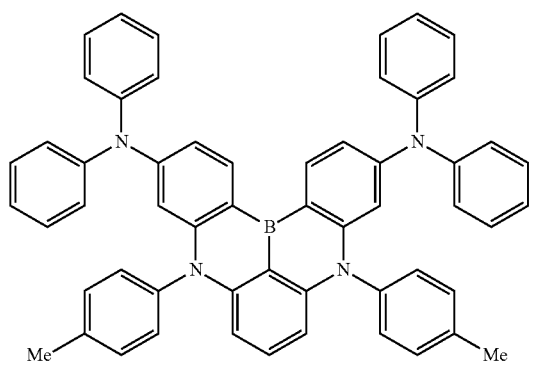
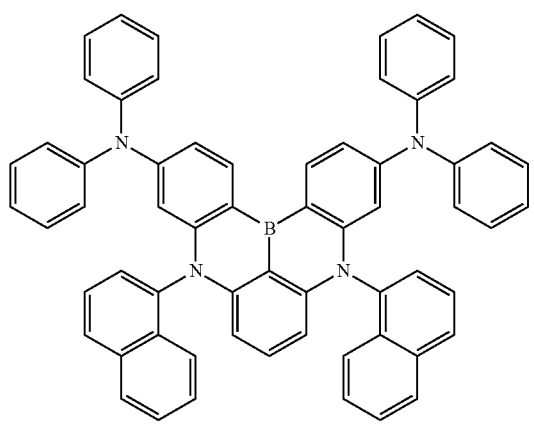
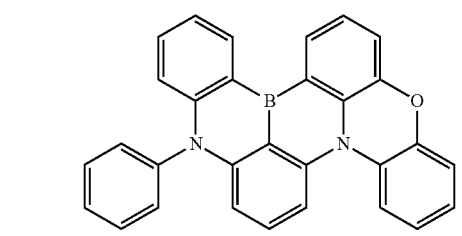
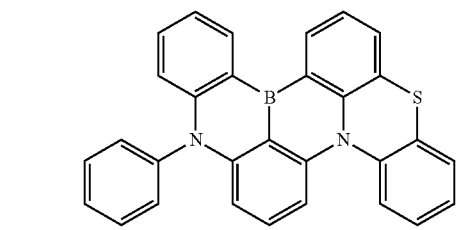
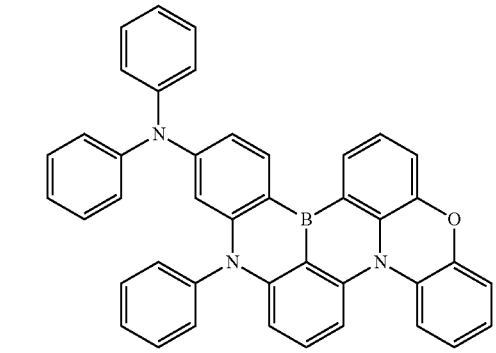
680
-continued
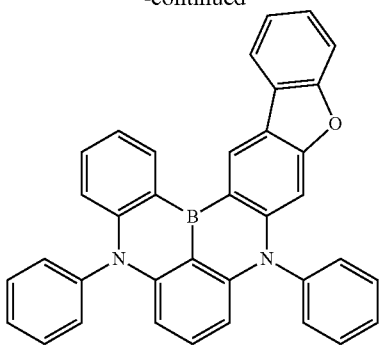
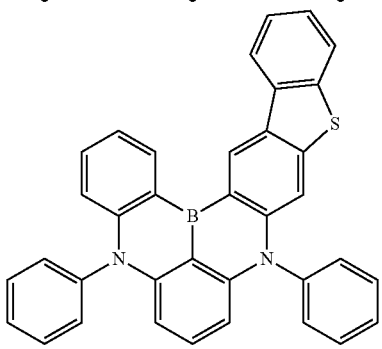
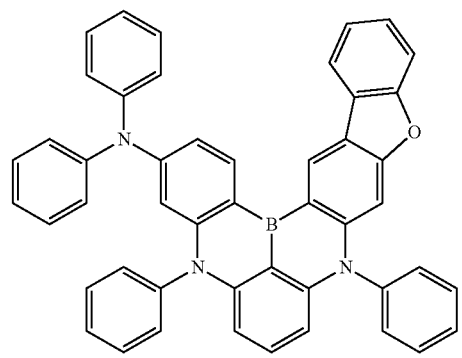
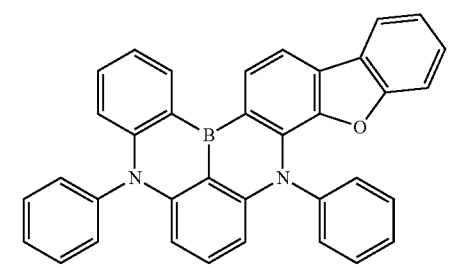
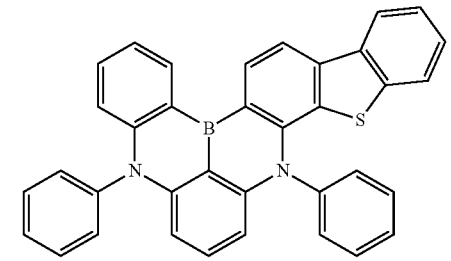

(Compound Represented by Formula (51))

The compound represented by the formula (51) is explained below $$p\text{-}q\text{-}r\text{-}s\text{-}t \quad (51)$$

(52) — phenyl ring with $(R_{501})_{m1}$

(53) — naphthyl ring with $(R_{501})_{m2}$

(54) — five-membered ring with $X_{501}$

(55) —
$$\begin{array}{c} Ar_{501} \\ | \\ L_{501}\text{—}N\text{—}Ar_{502} \end{array}$$
with $(R_{501})_{m3}$

(56) —
$$\begin{array}{c} Ar_{501} \\ | \\ L_{501}\text{—}N\text{—}Ar_{502} \end{array}$$
with $(R_{501})_{m4}$ (naphthyl)

In the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{901}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;
$R_{901}$ to $R_{907}$ are as defined in the formula (1);
$Ar_{501}$ and $Ar_{502}$ are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
$L_{501}$ is
a substituted or unsubstituted alkylene group having 1 to 50 carbon atoms,
a substituted or unsubstituted alkenylene group having 2 to 50 carbon atoms,
a substituted or unsubstituted alkynylene group having 2 to 50 carbon atoms,
a substituted or unsubstituted cycloalkylene group having 3 to 50 ring carbon atoms,
a substituted or unsubstituted arylene group having 6 to 50 ring carbon atoms, or
a substituted or unsubstituted divalent heterocyclic group having 5 to 50 ring atoms;
m1 is independently an integer of 0 to 2, m2 is independently an integer of 0 to 4, m3 is independently an integer of 0 to 3, and m4 is independently an integer of 0 to 5; when plural $R_{501}$s exist, the plural $R_{501}$s may be the same or different;

In the formula (51), each of the p ring to the t ring is fused to an adjacent ring by sharing two carbon atoms. The position and direction of fusing are not limited, and condensation is possible at any position and direction.

In one embodiment, in the formula (52) or (53) of the r ring, $R_{501}$ is a hydrogen atom.

In one embodiment, the compound represented by the formula (51) is represented by any one of the following formulas (51-1) to (51-6):

(51-1)

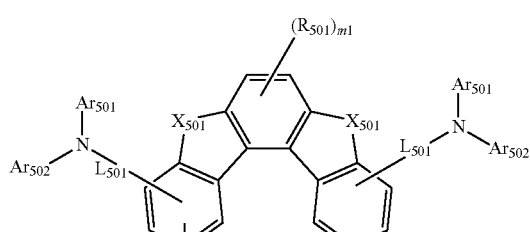

(51-2)

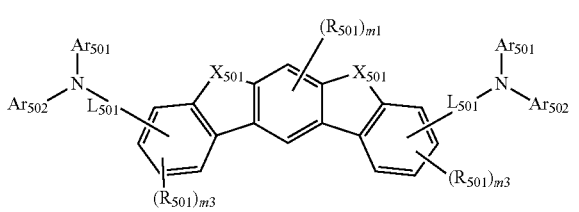

(51-3)

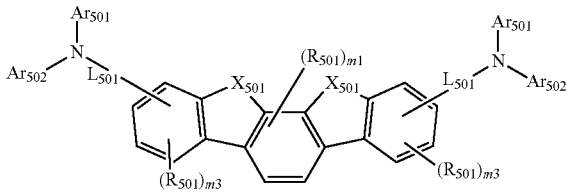

(51-4)

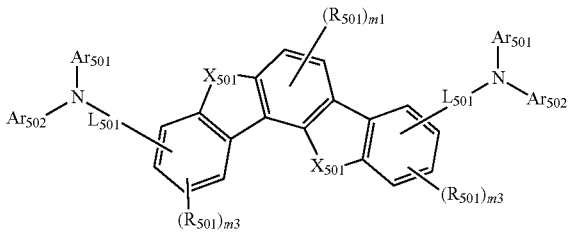

(51-5)

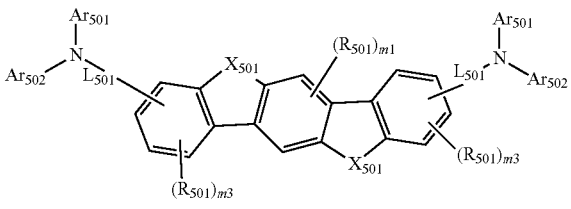

(51-6)

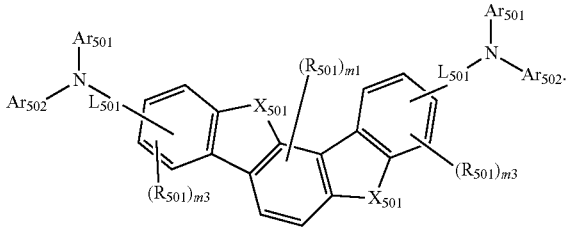

wherein in the formulas (51-1) to (51-6), $R_{501}$, $X_{501}$, $Ar_{502}$, $Ar_{502}$, $L_{501}$, m1 and m3 are as defined in the formula (51).

In one embodiment, the compound represented by the formula (51) is represented by any one of the following formulas (51-11) to (51-13):

(51-11)

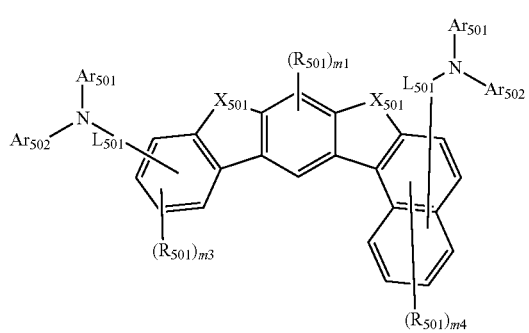

(51-12)
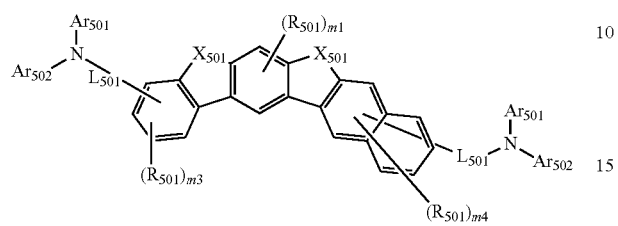
(51-13)
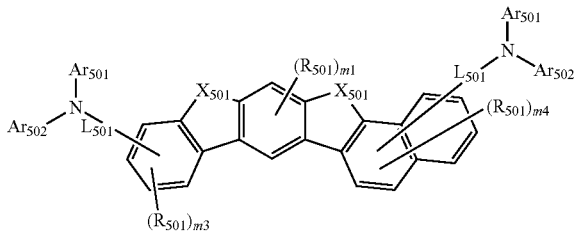
wherein in the formulas (51-11) to (51-13), $R_{501}$, $X_{501}$, $Ar_{501}$, $Ar_{502}$, $L_{501}$, m1, m3 and m4 are as defined in the formula (51).
In one embodiment, the compound represented by the formula (51) is represented by any one of the following formulas (51-21) to (51-25):
(51-21)
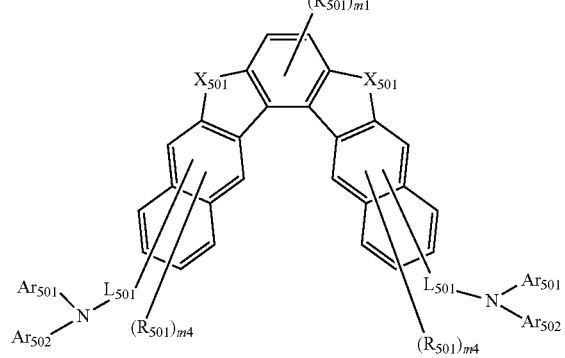
(51-22)
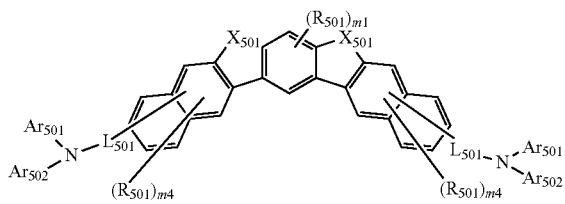
(51-23)
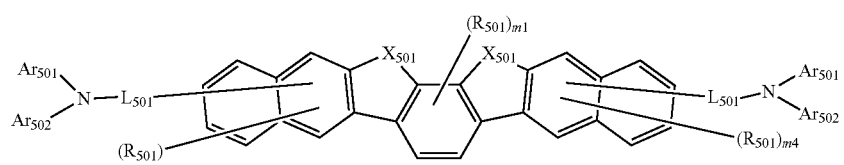
(51-24)
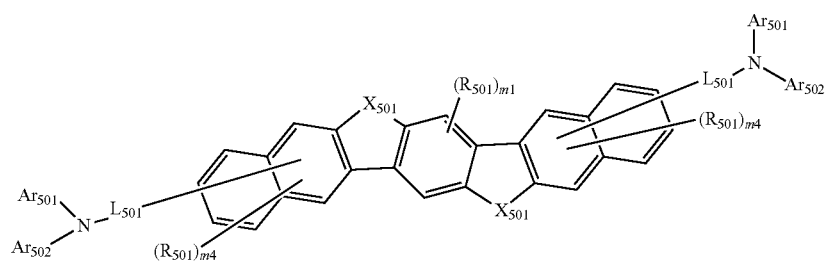
(51-25)
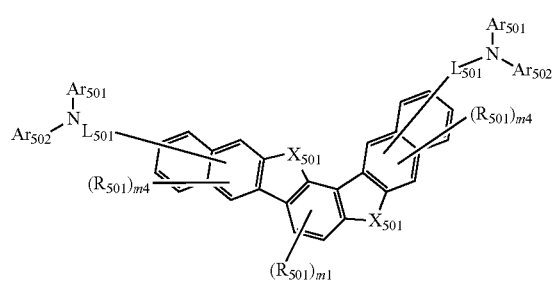

wherein in the formulas (51-21) to (51-25), $R_{501}$, $X_{501}$, $Ar_{501}$, $Ar_{502}$, $L_{501}$, m1 and m4 are as defined in the formula (51).

In one embodiment, the compound represented by the formula (51) is represented by anyone of the following formulas (51-31) to (51-33):

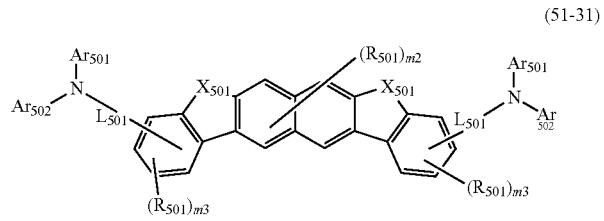

(51-31)

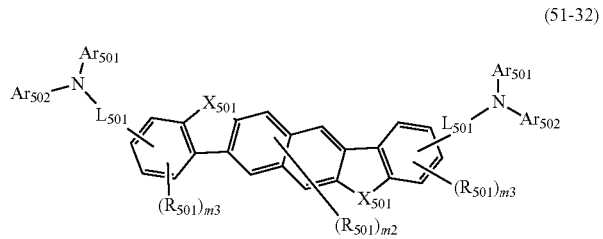

(51-32)

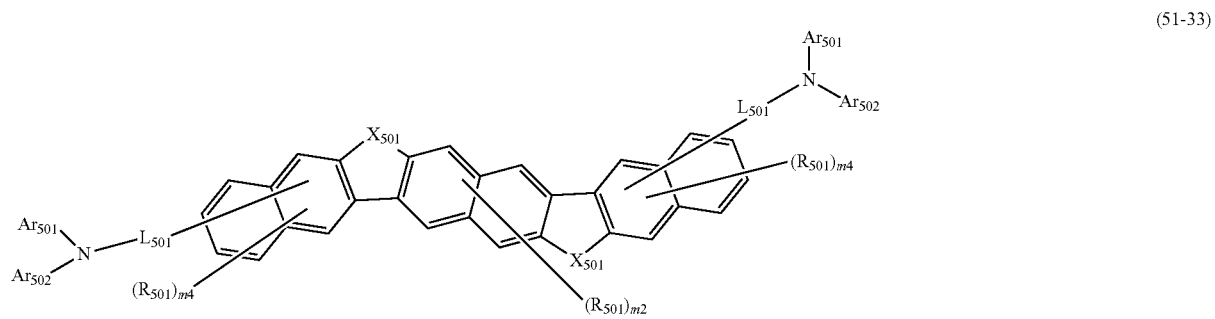

(51-33)

wherein in the formulas (51-31) to (51-33), $R_{501}$, $X_{501}$, $Ar_{501}$, $Ar_{502}$, $L_{501}$, m2 to m4 are as defined in the formula (51).

In one embodiment, $Ar_{501}$ and $Ar_{502}$ are independently a substituted or unsubstituted aryl group having 6 to 50 ring carbon atoms.

In one embodiment, one of $Ar_{501}$ and $Ar_{502}$ is a substituted or unsubstituted aryl group having 6 to 50 ring carbon atoms and the other is a substituted or unsubstituted monovalent heterocyclic ring having 5 to 50 ring atoms.

As examples of the compound represented by the formula (51), the following compounds can be given, for example. In the following example compounds, Me represents methyl group.

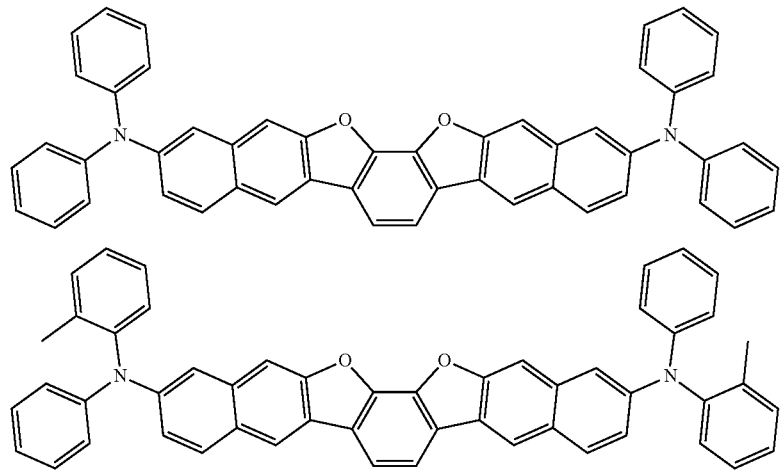

-continued
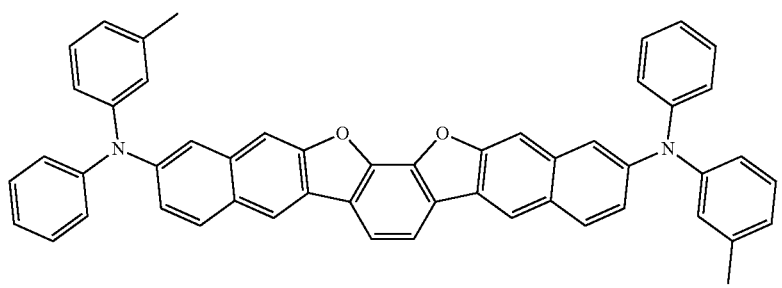
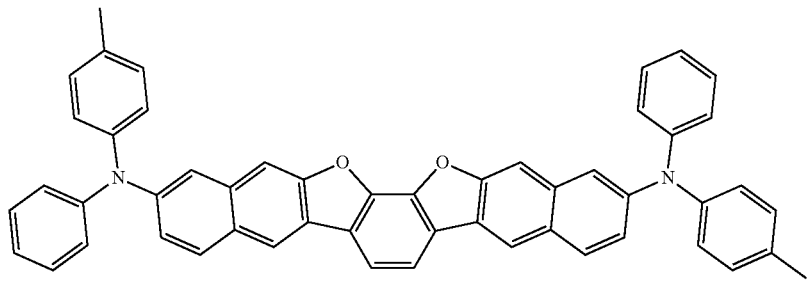
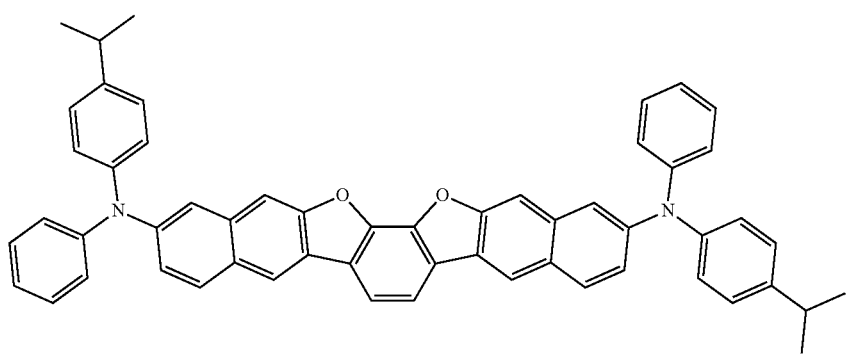
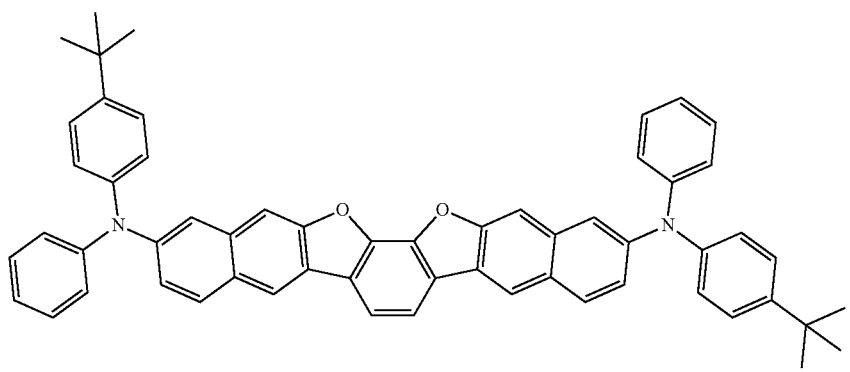
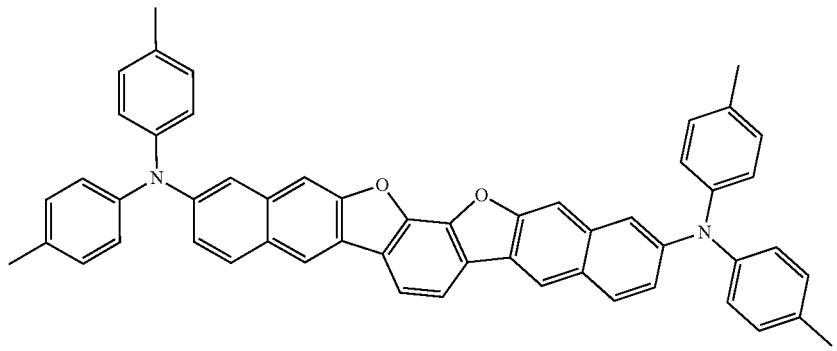

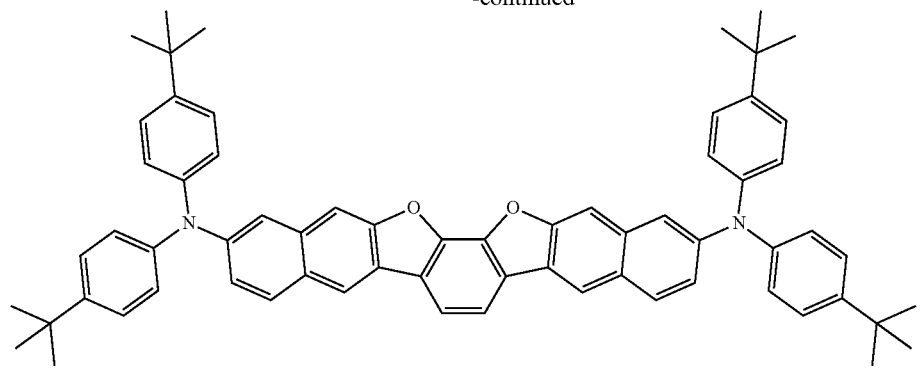
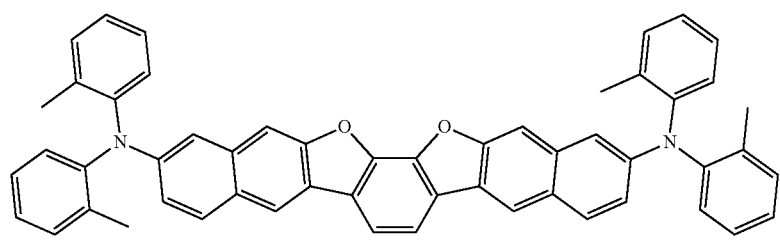
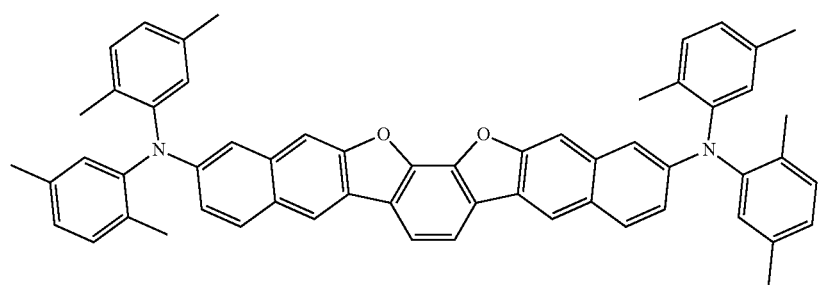
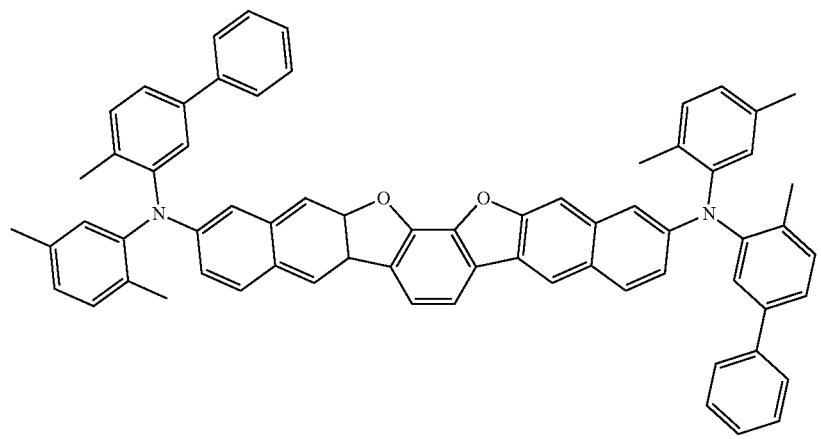

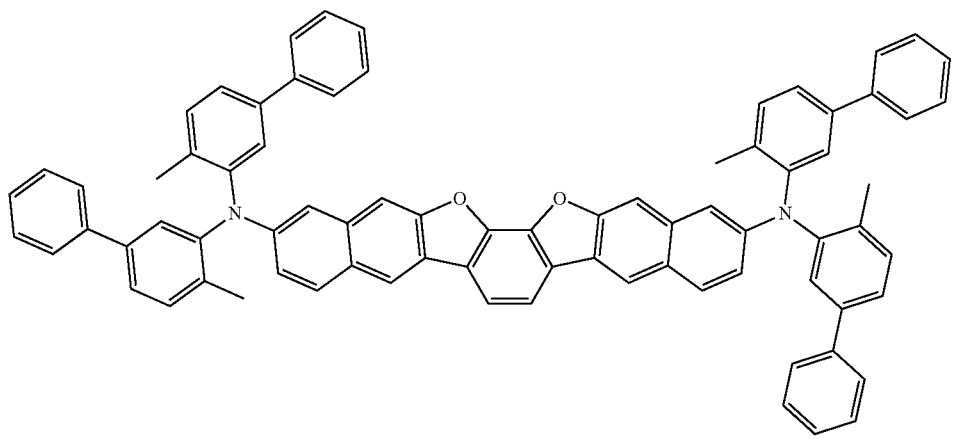
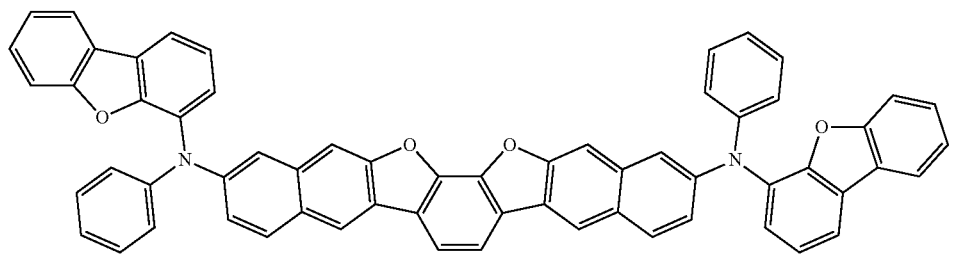
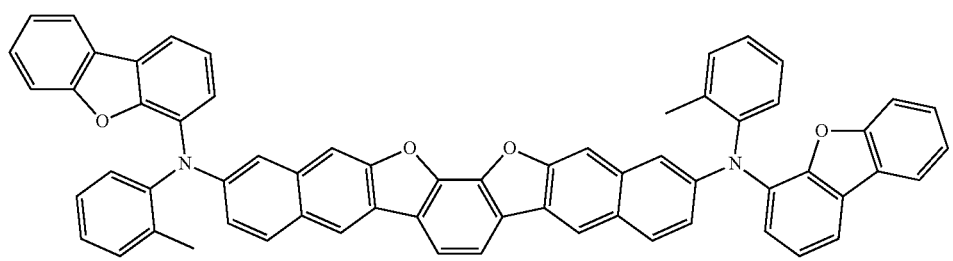
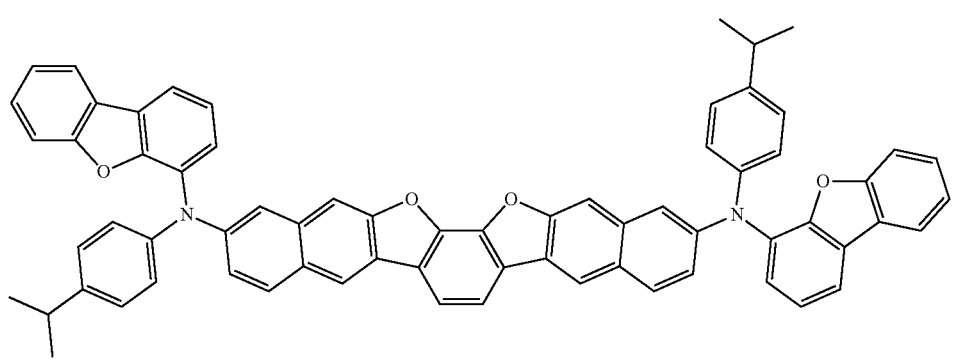
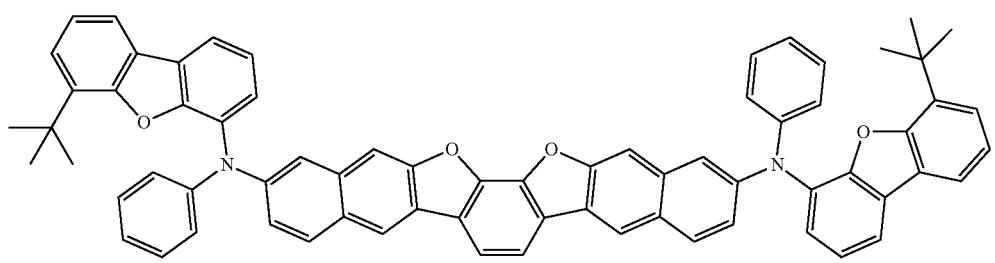

-continued
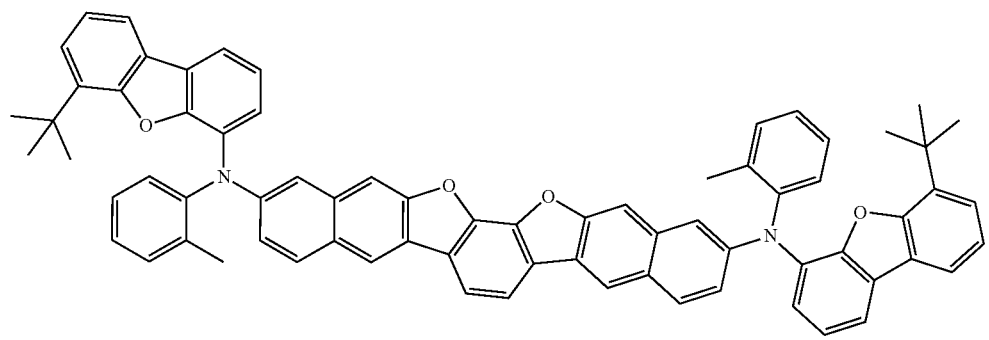
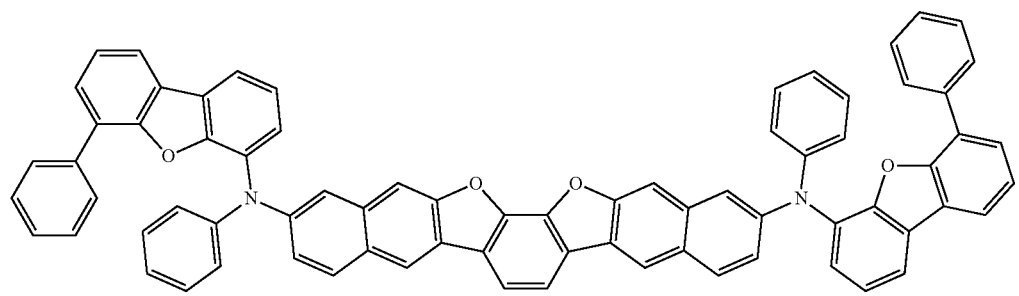
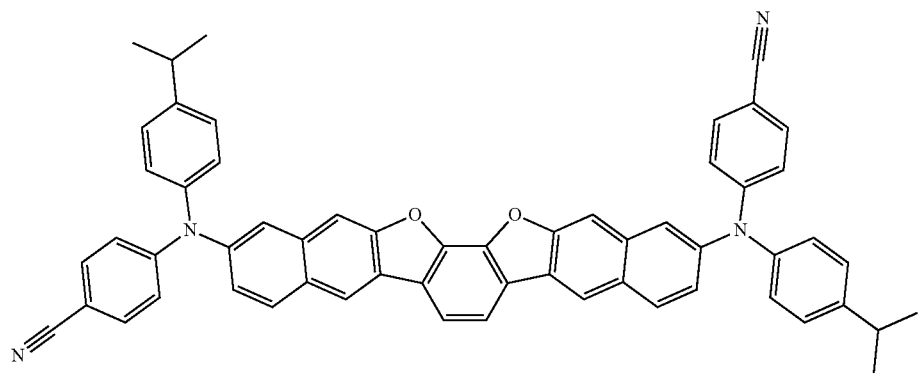
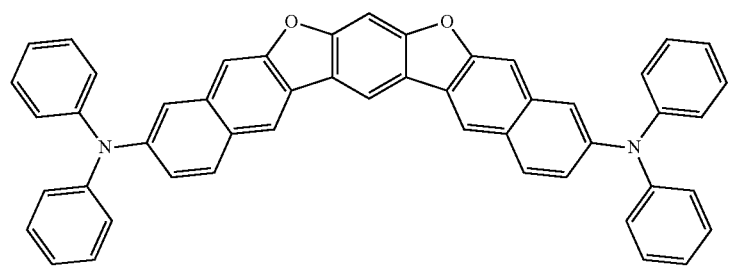
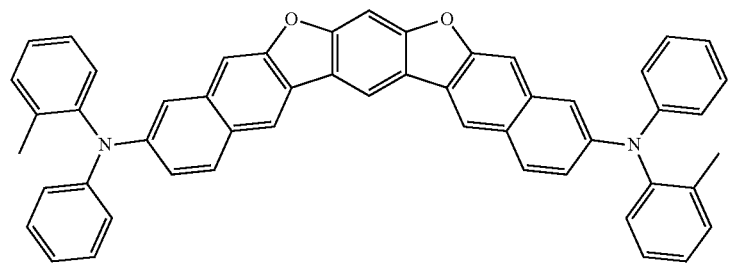

-continued
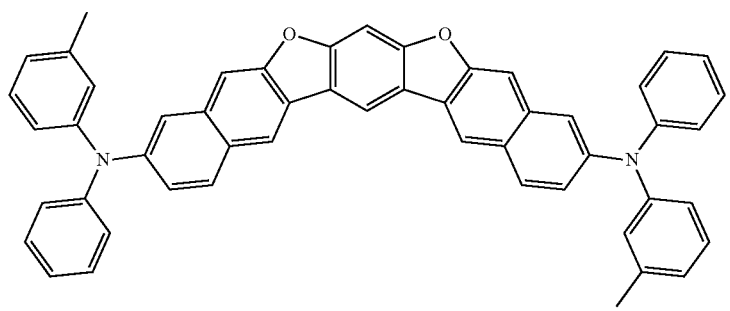
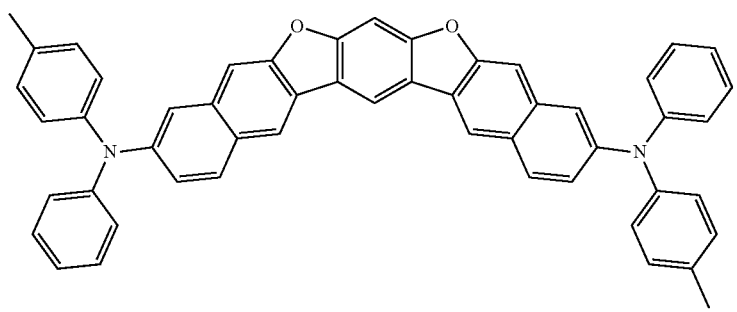
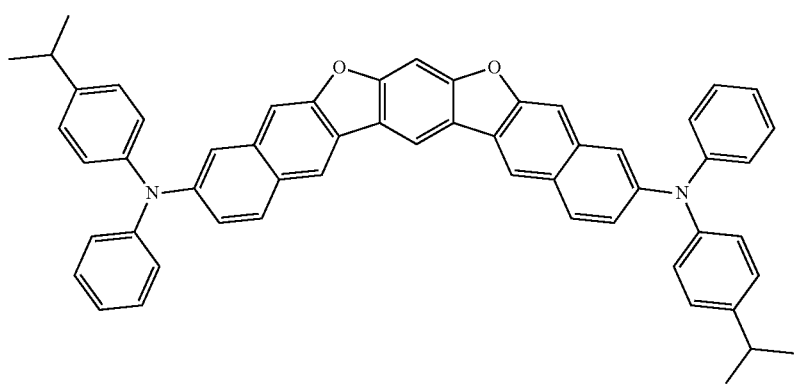
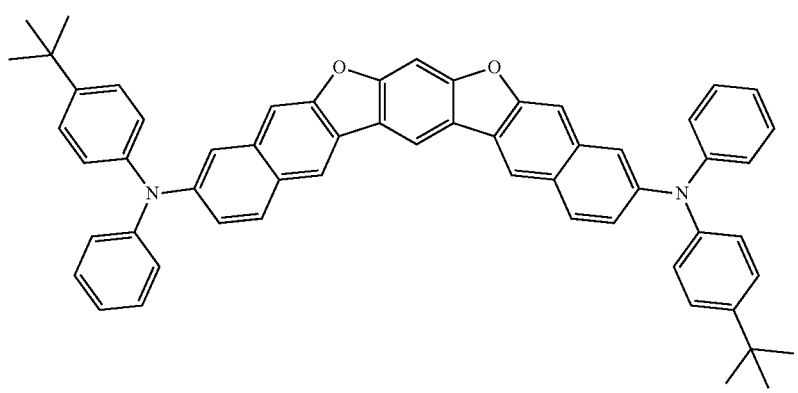
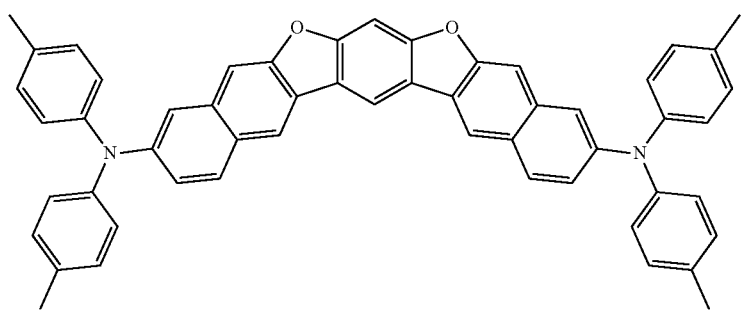

-continued
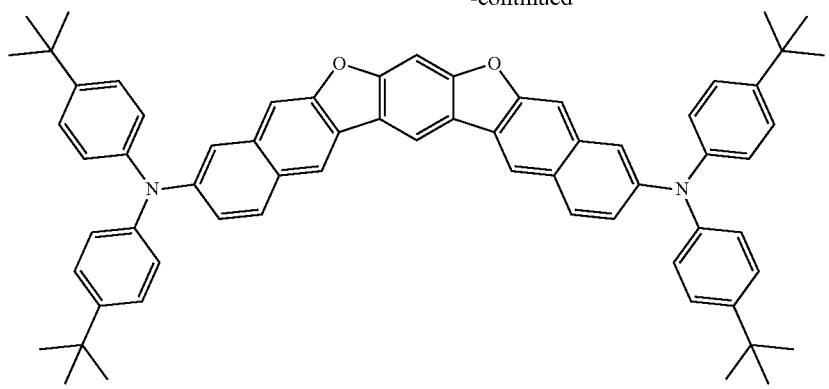
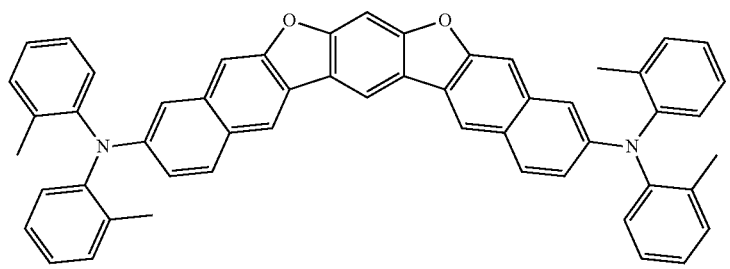
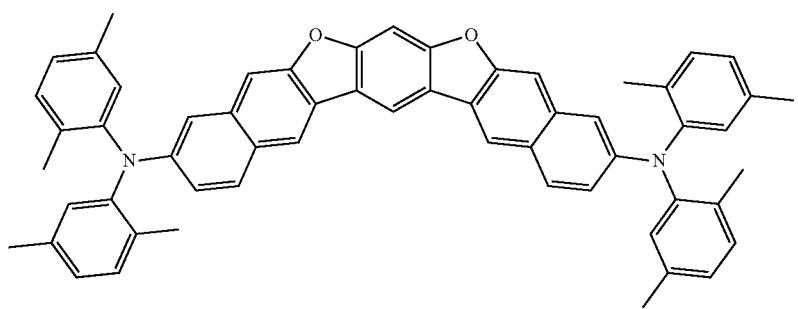
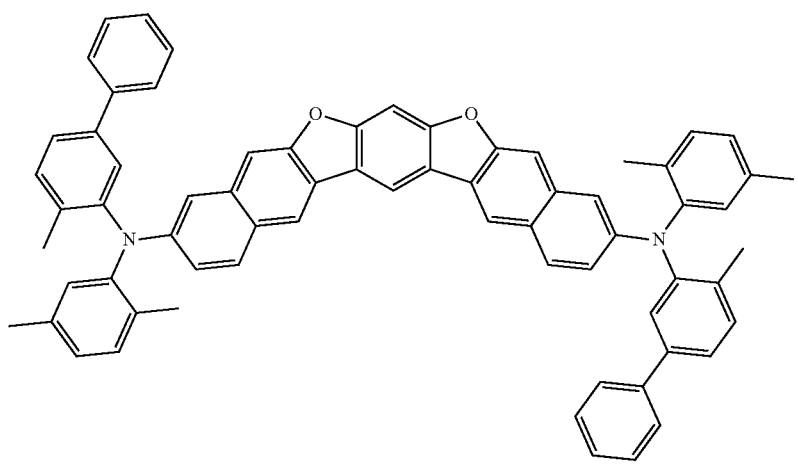

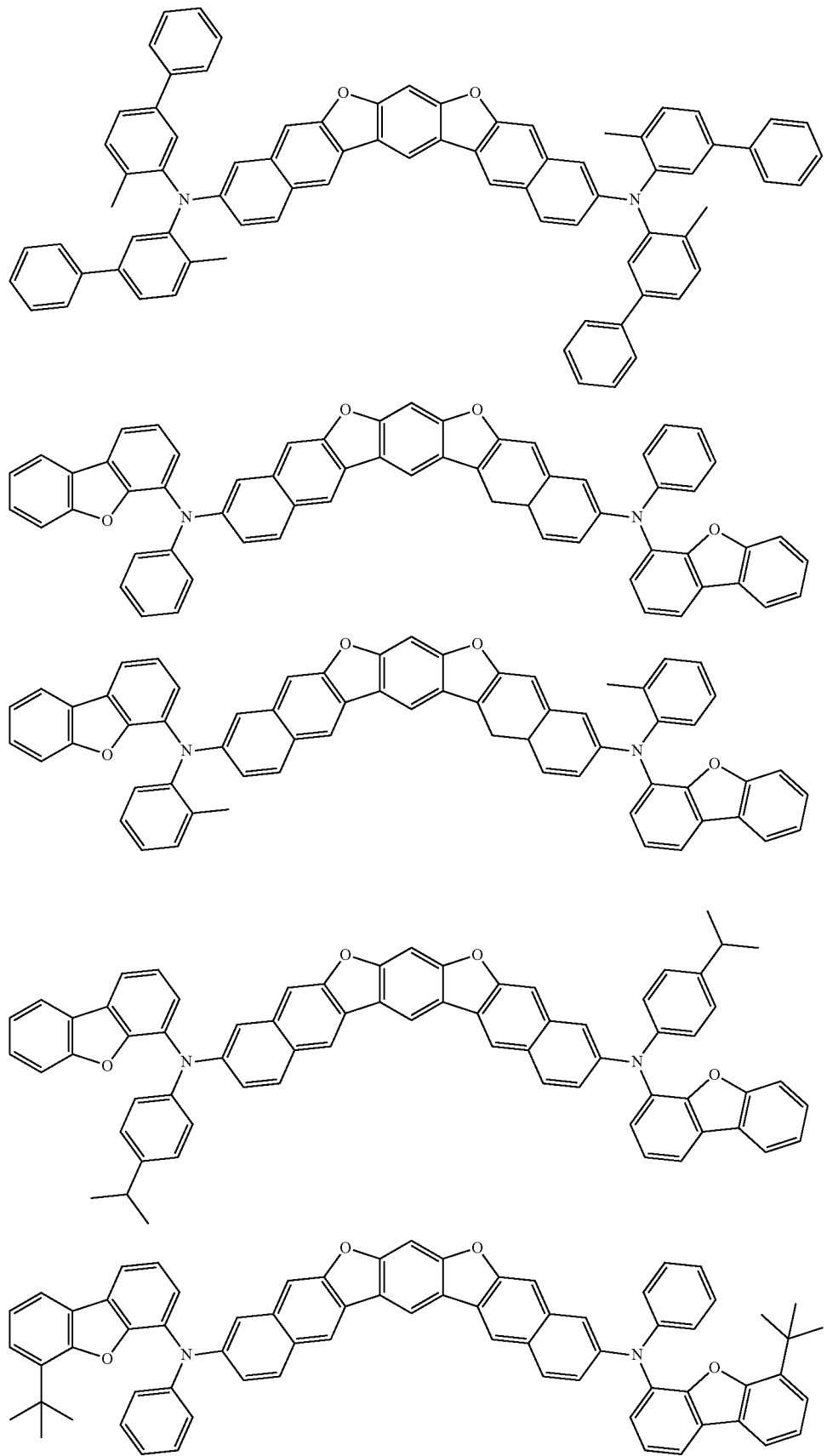

-continued
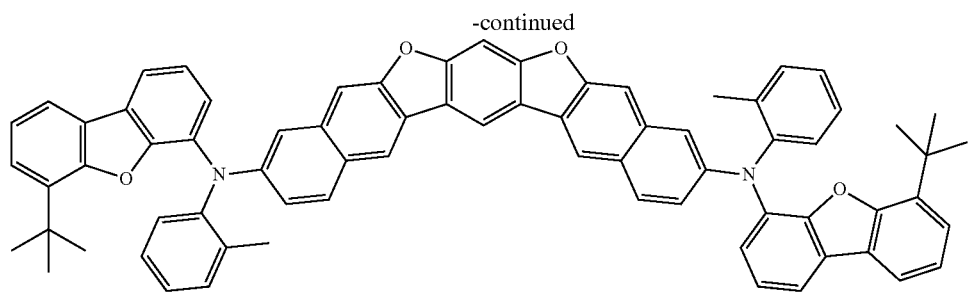
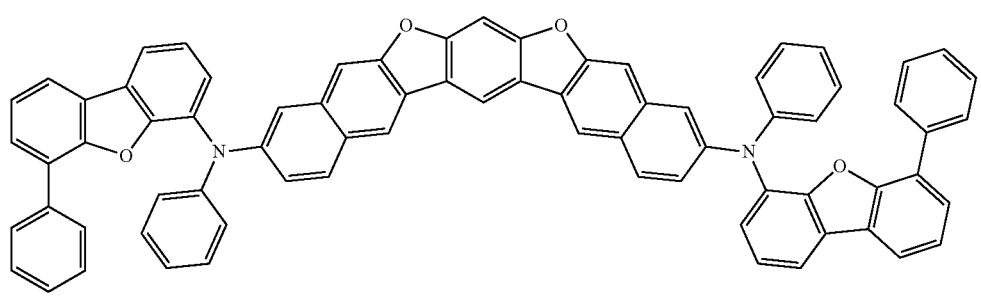
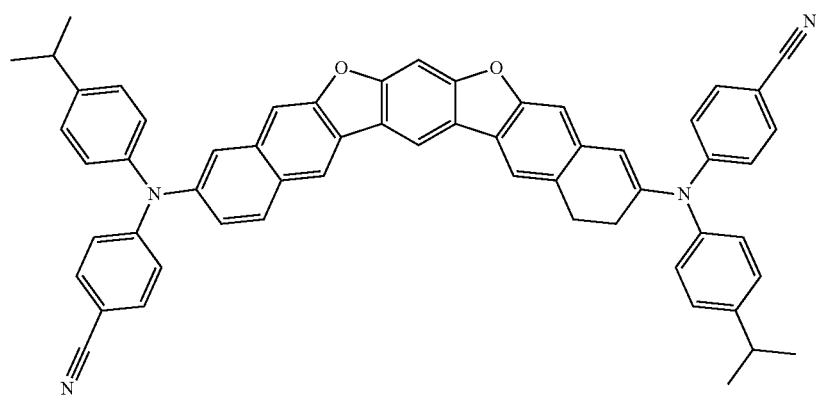
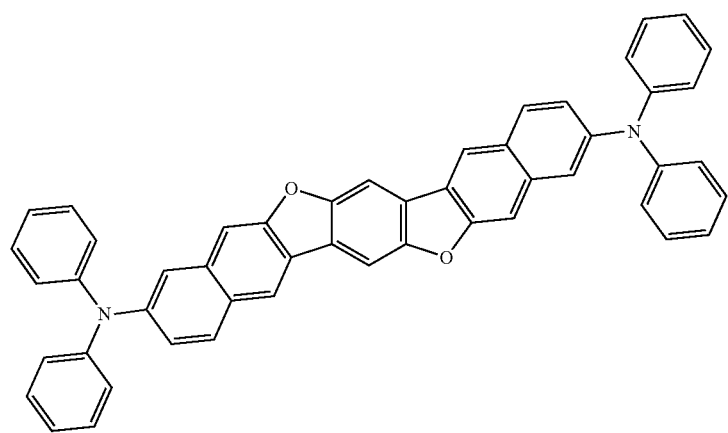

-continued
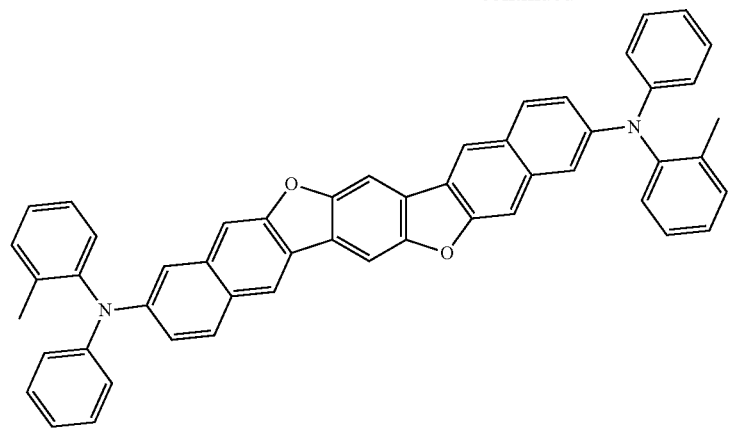
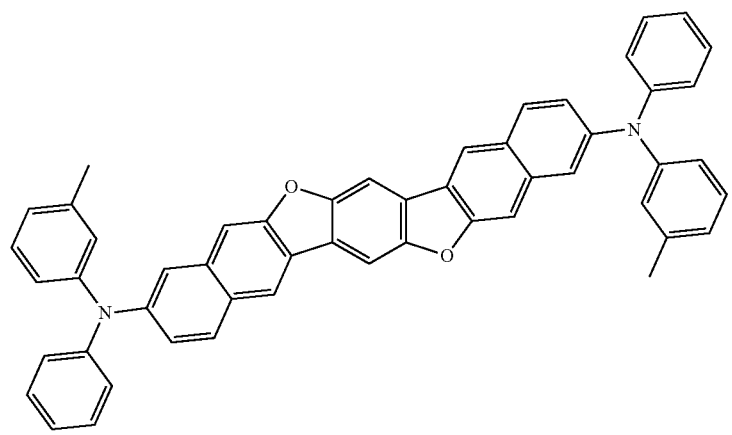
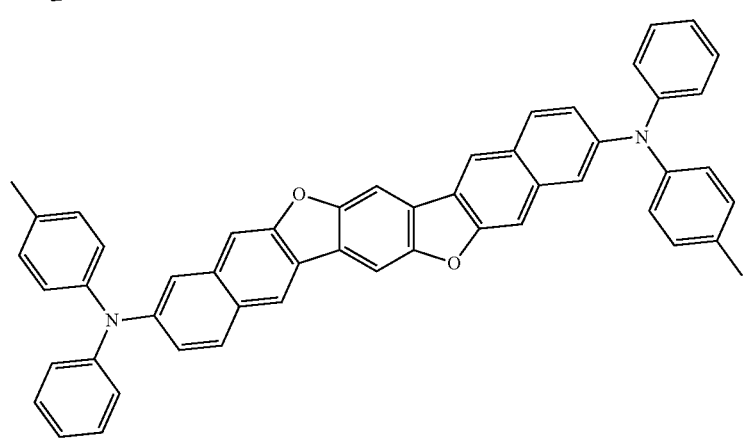
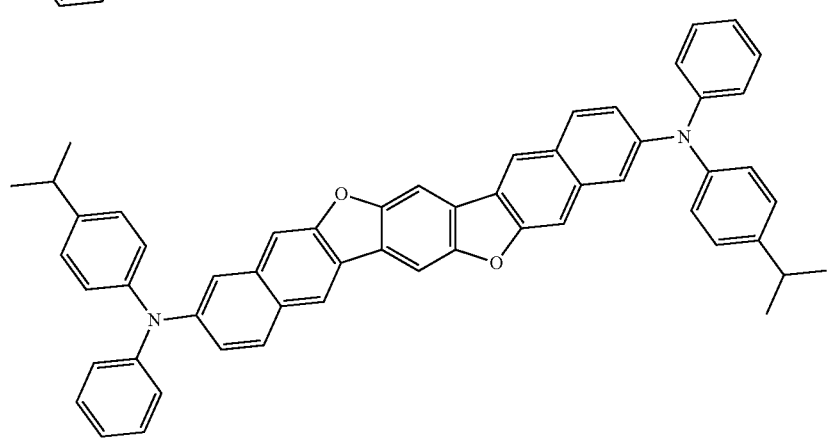

-continued
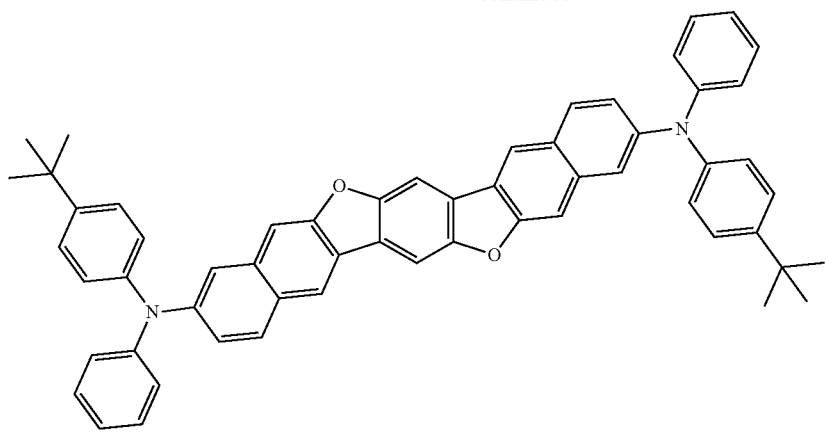
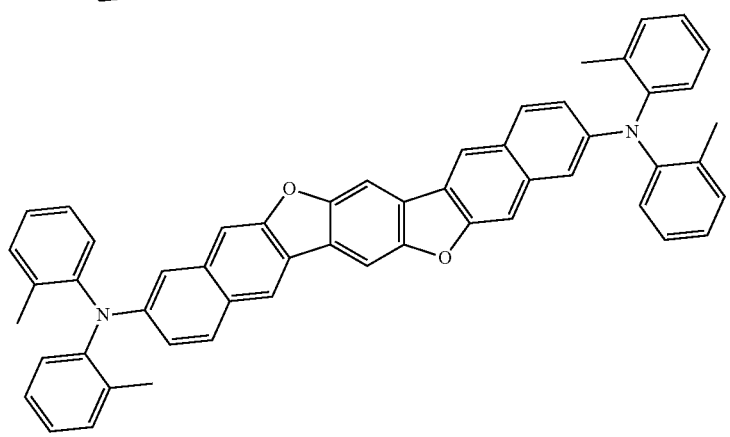
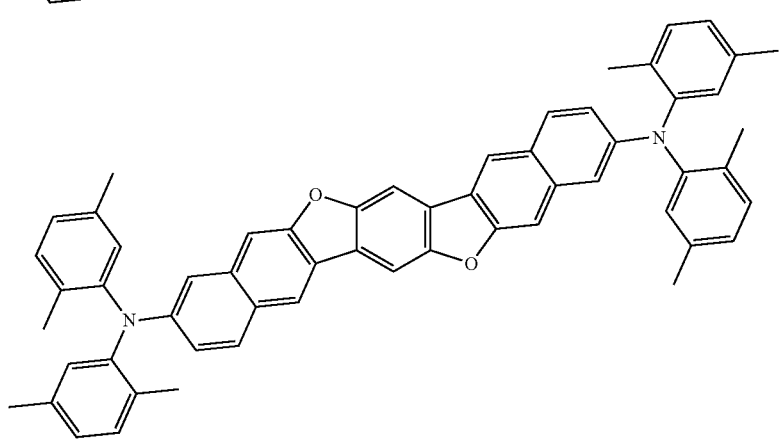
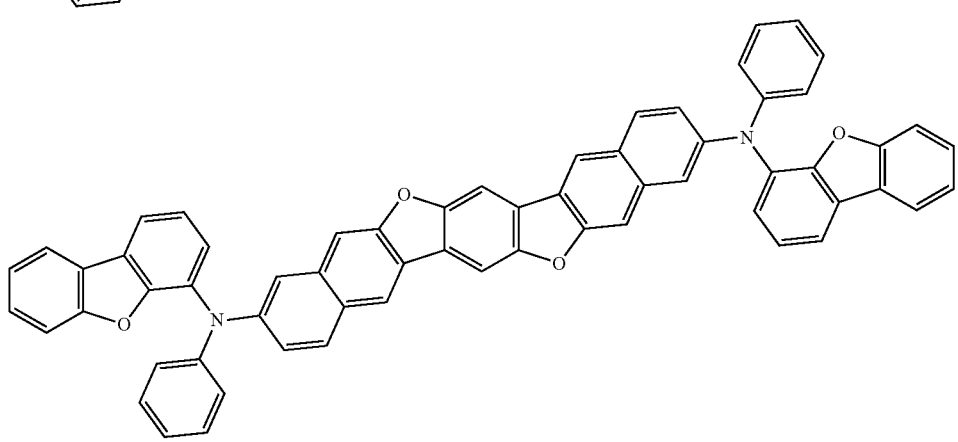

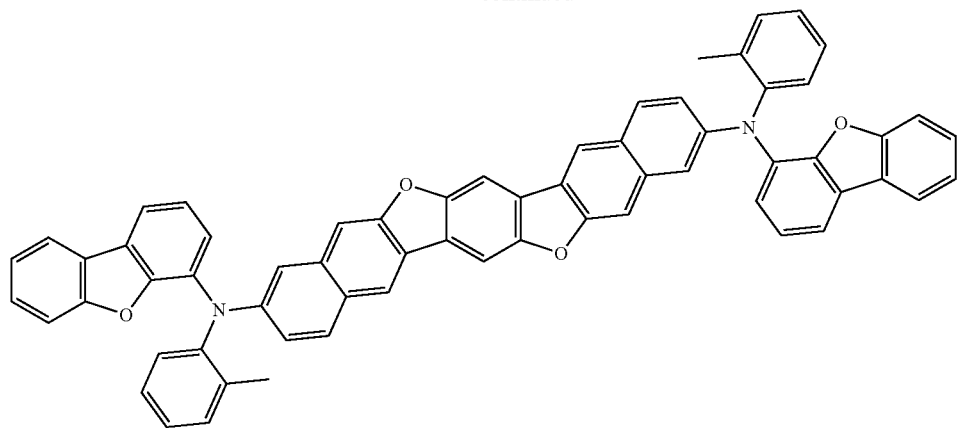
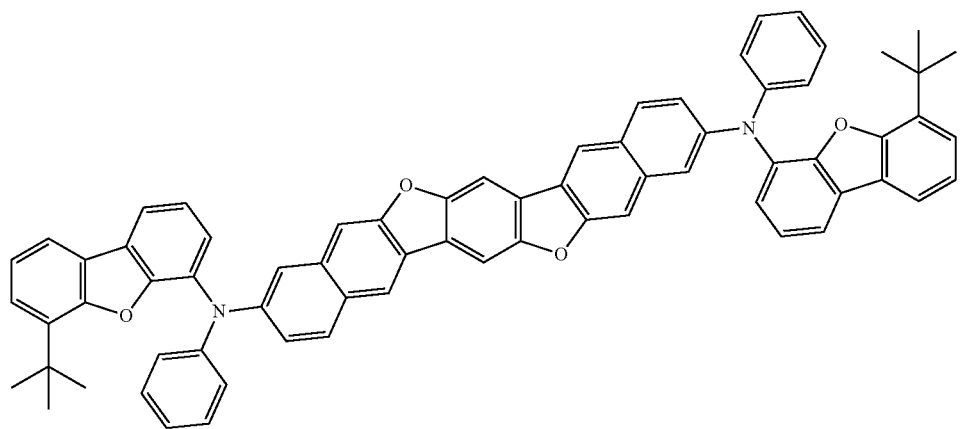
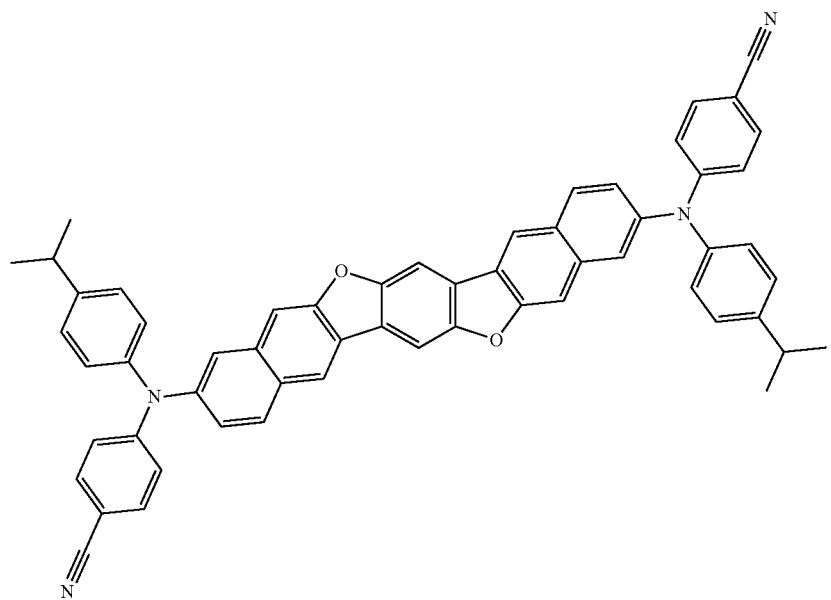

-continued
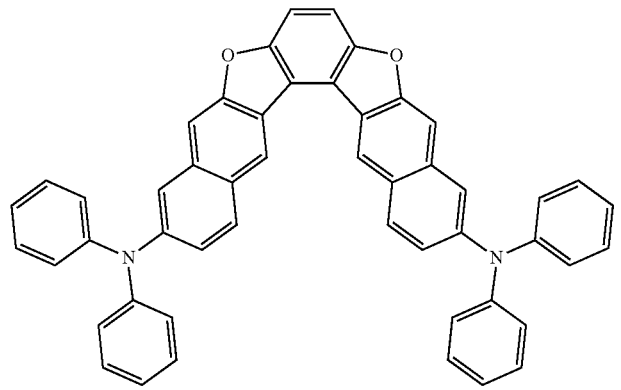
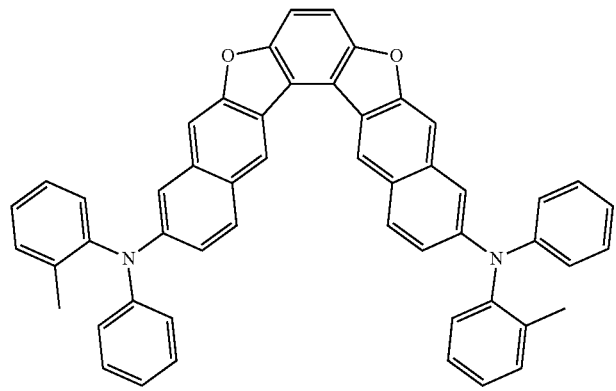
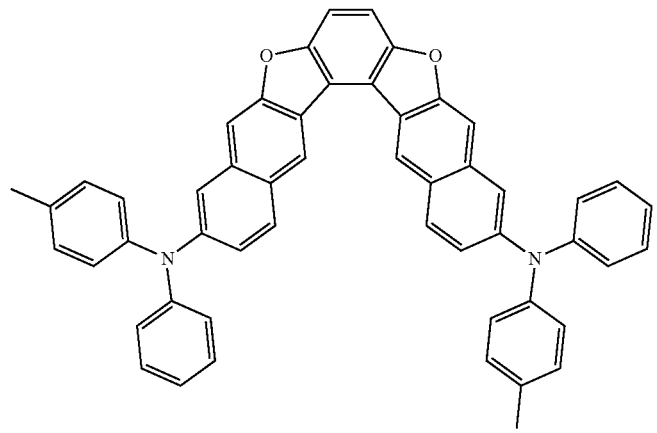
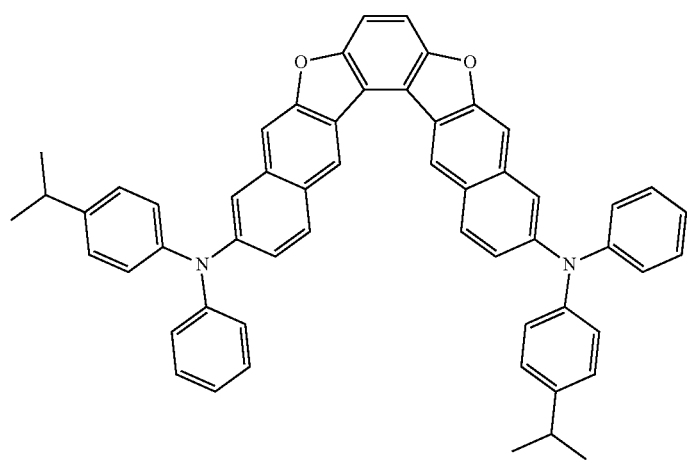

713 714
-continued
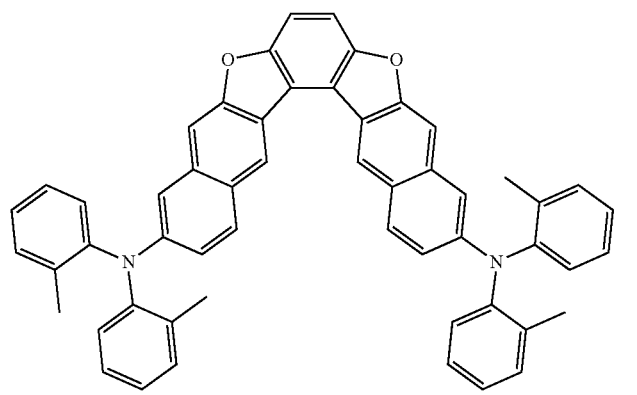
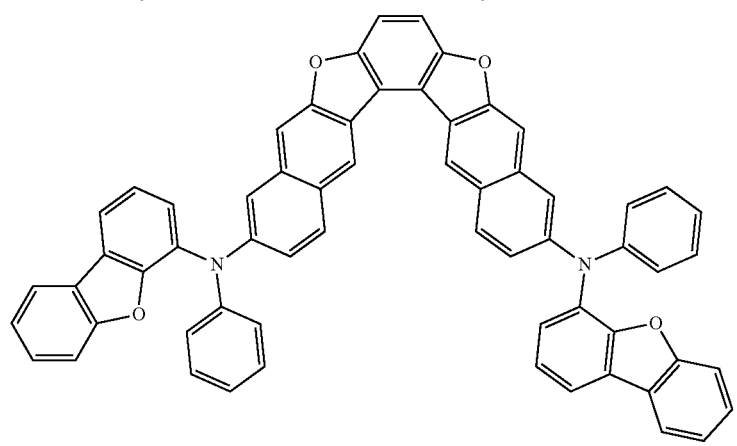
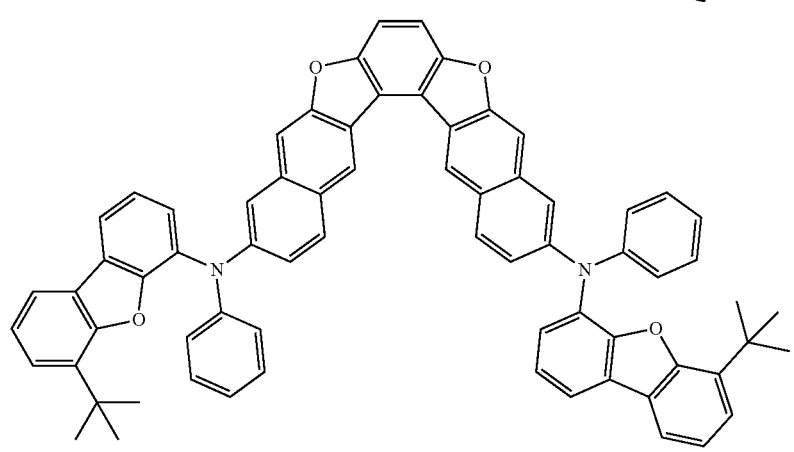
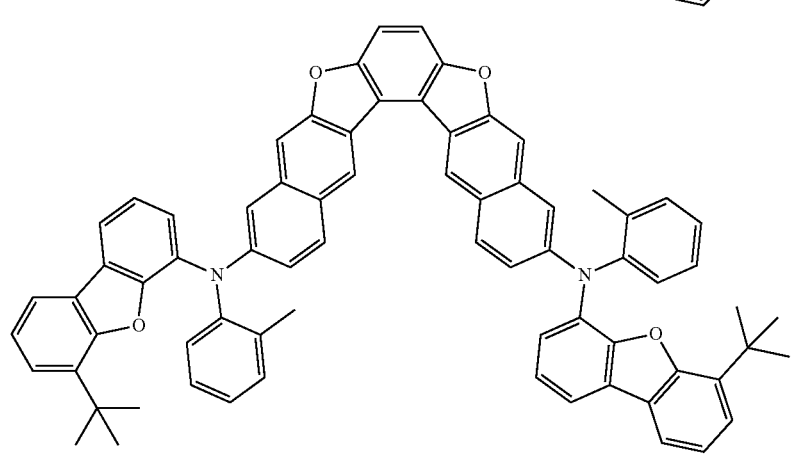

715
-continued
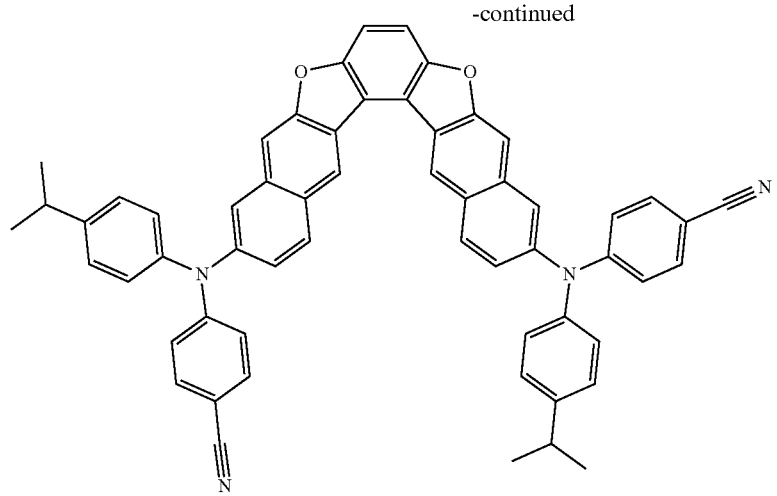
716
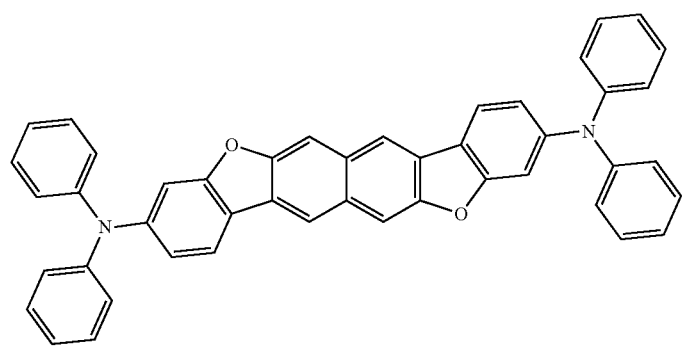
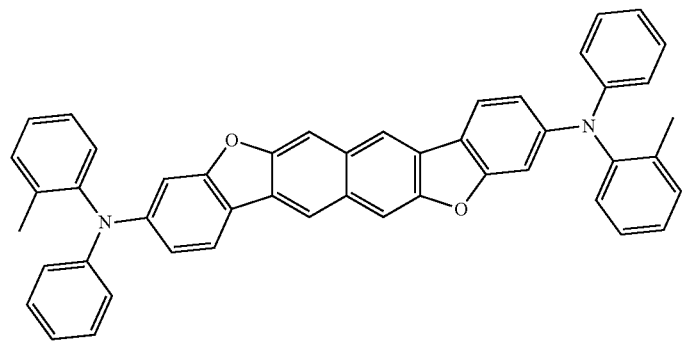
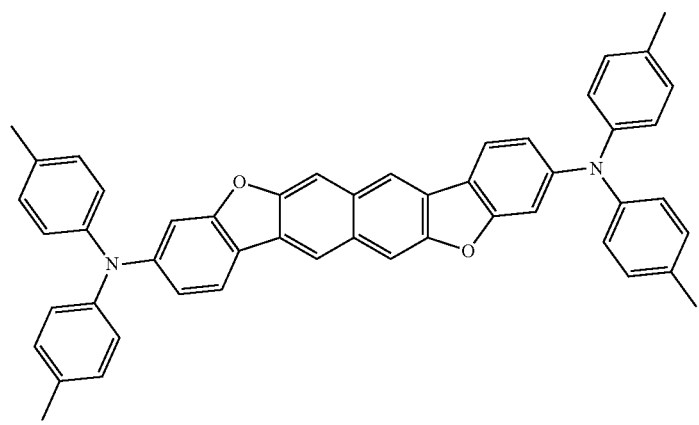

-continued
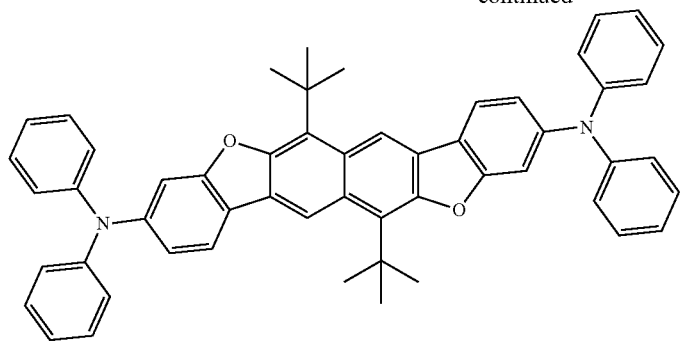
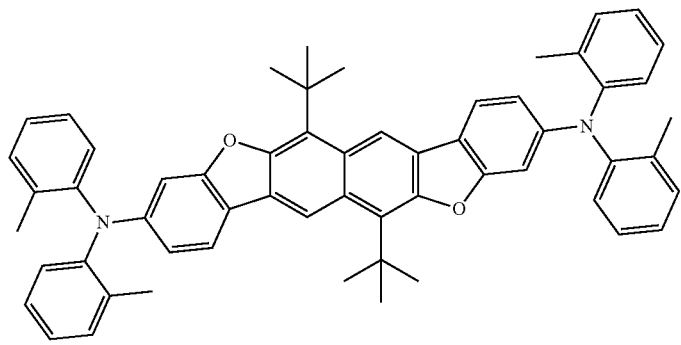
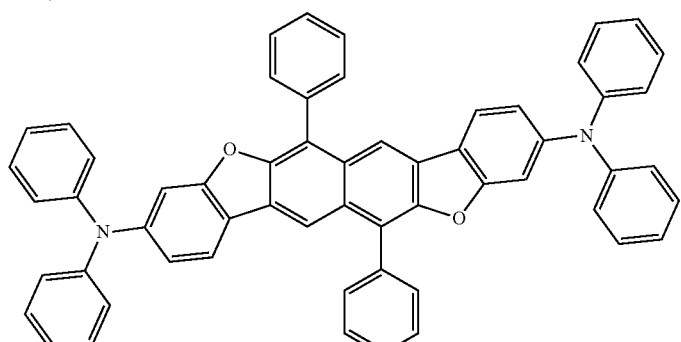
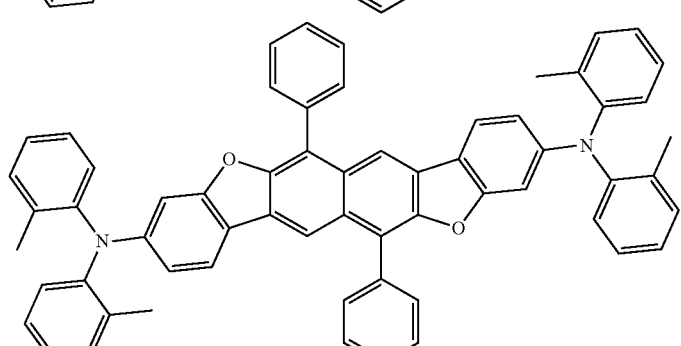
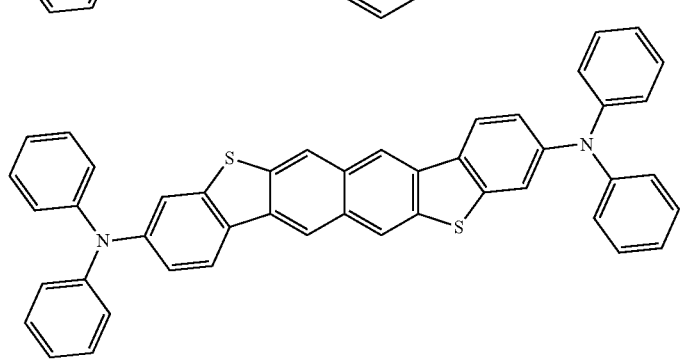

-continued
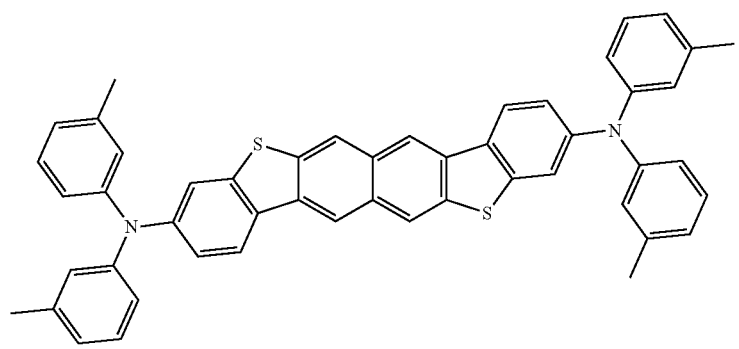
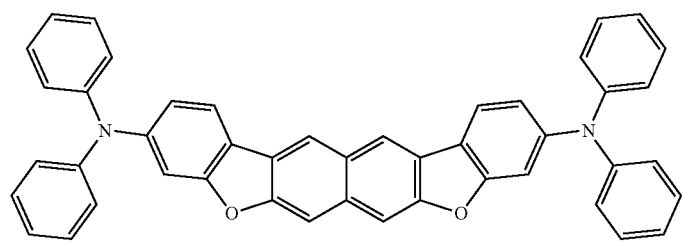
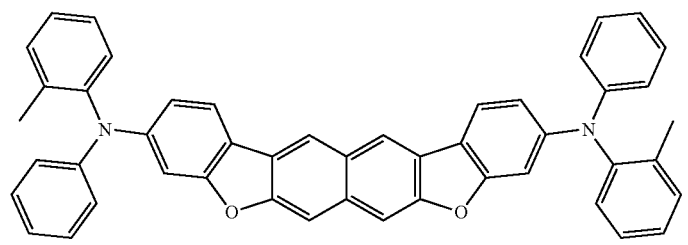
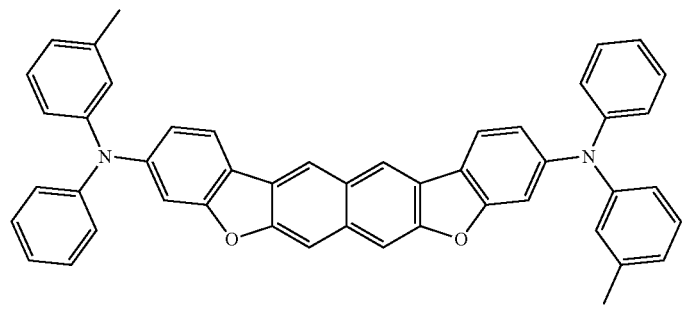
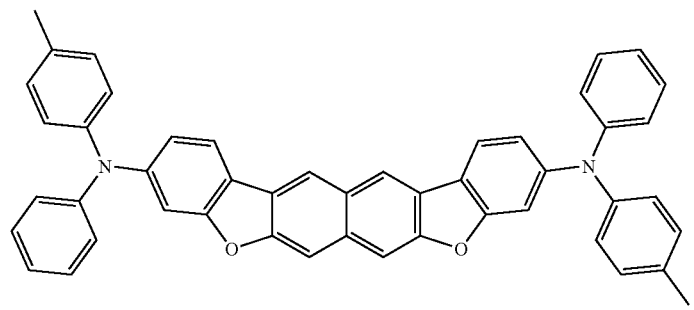

-continued
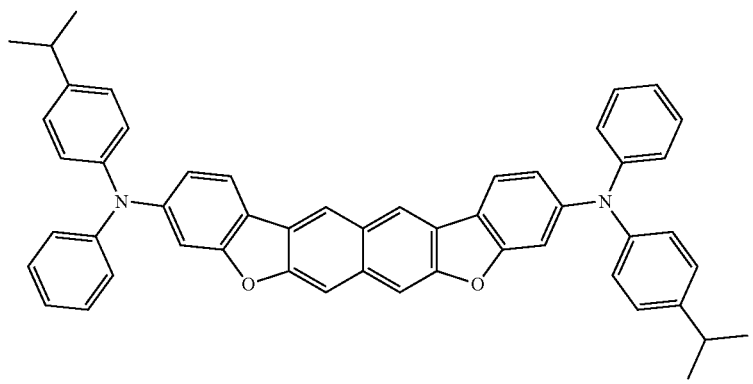
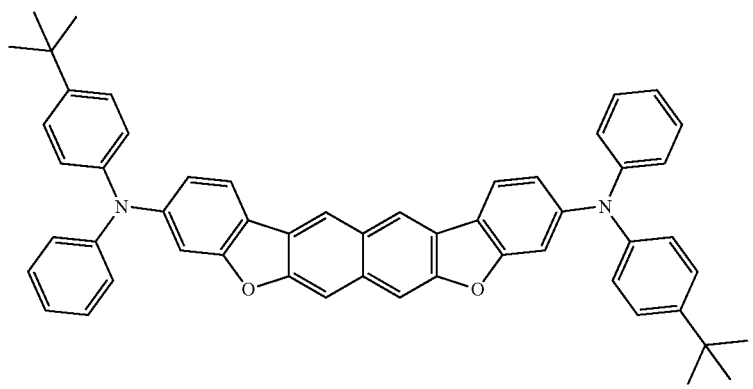
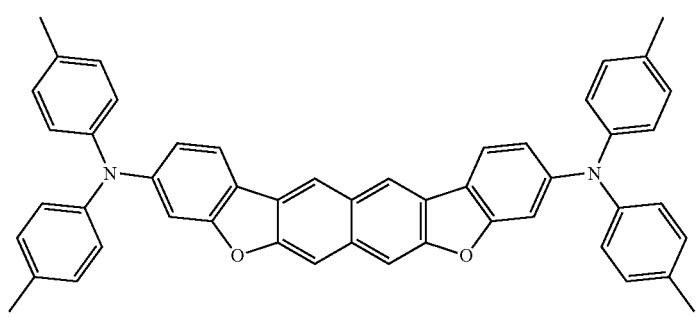
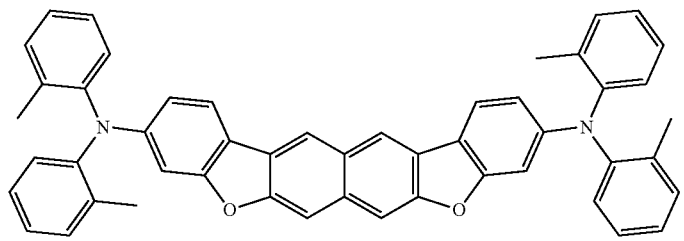
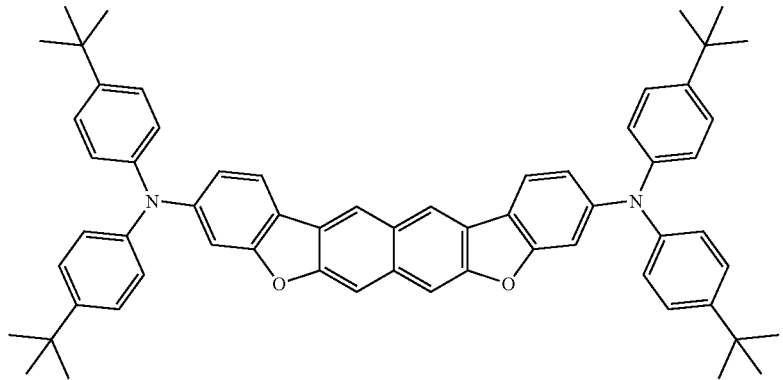

-continued
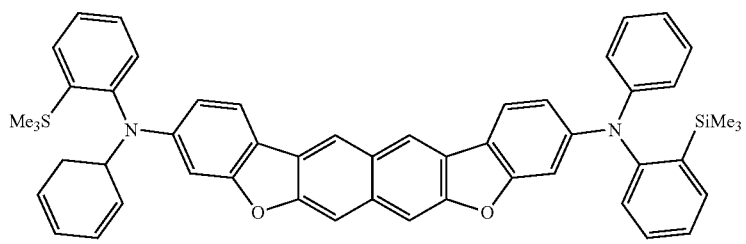
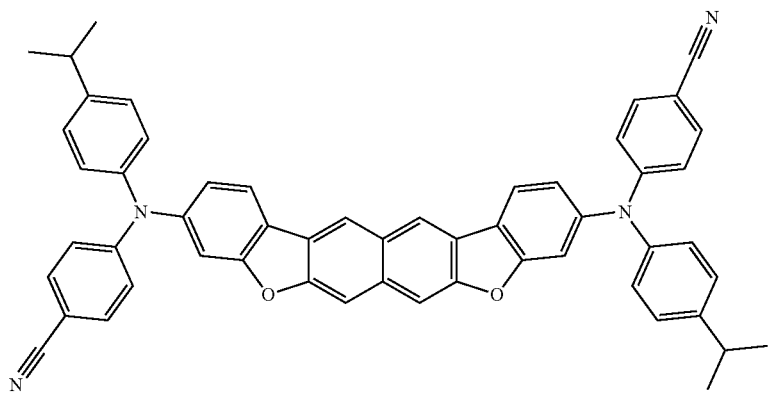
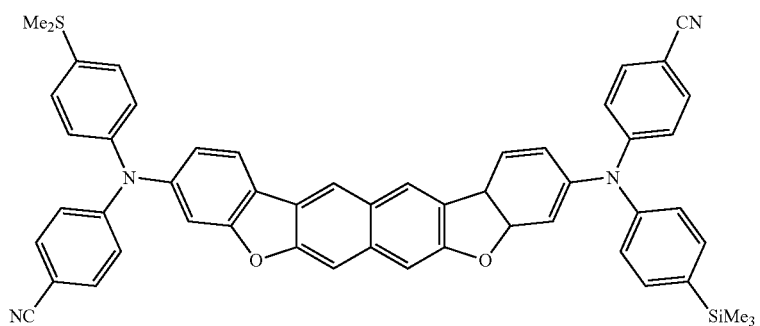
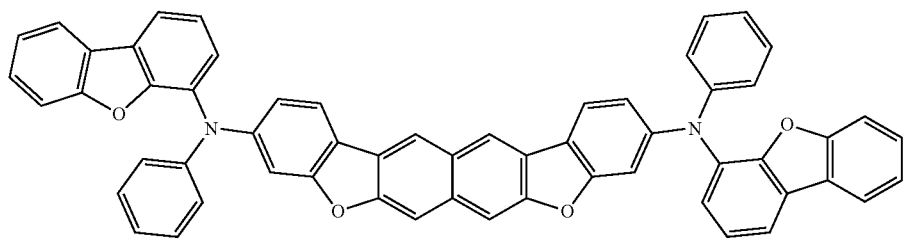
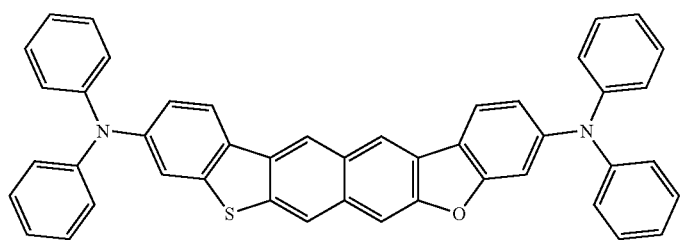

-continued
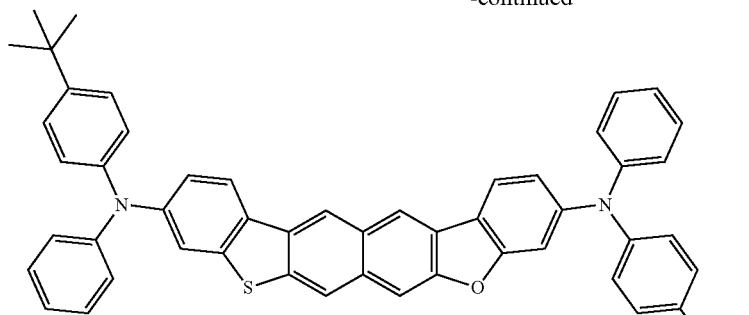
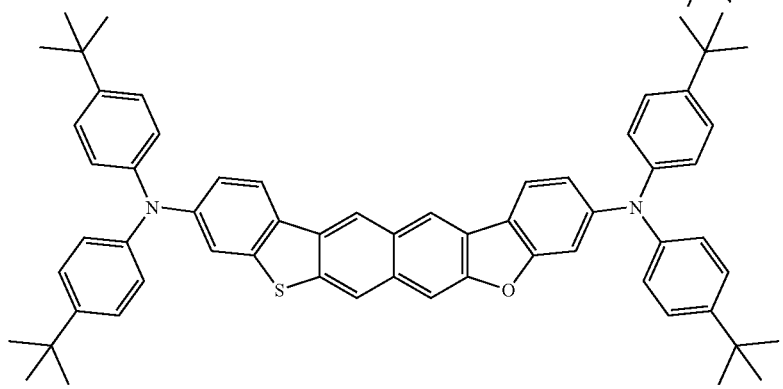
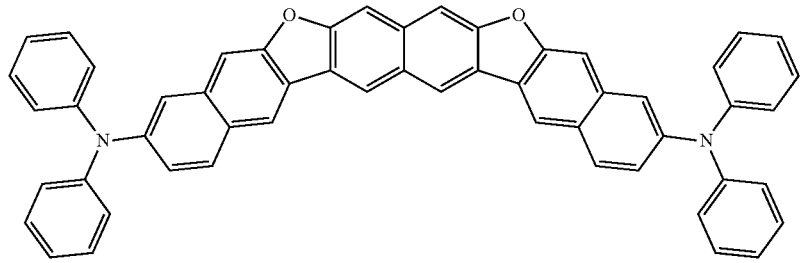
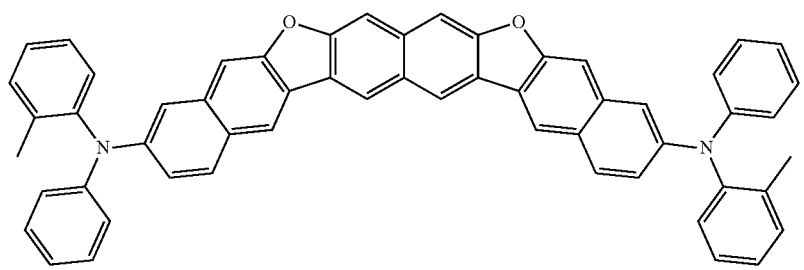
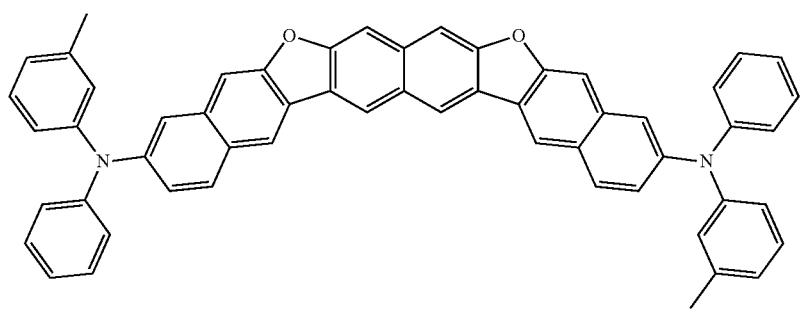

-continued
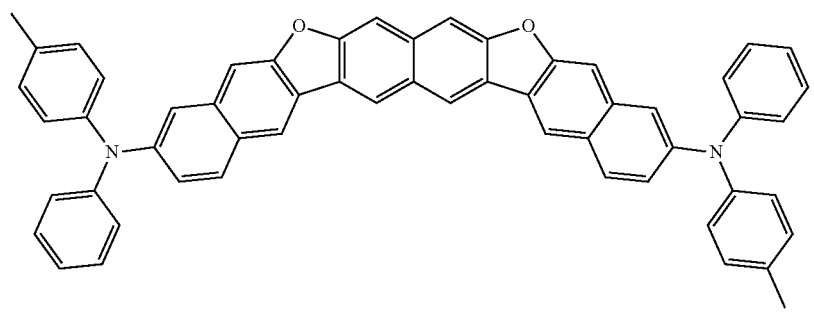
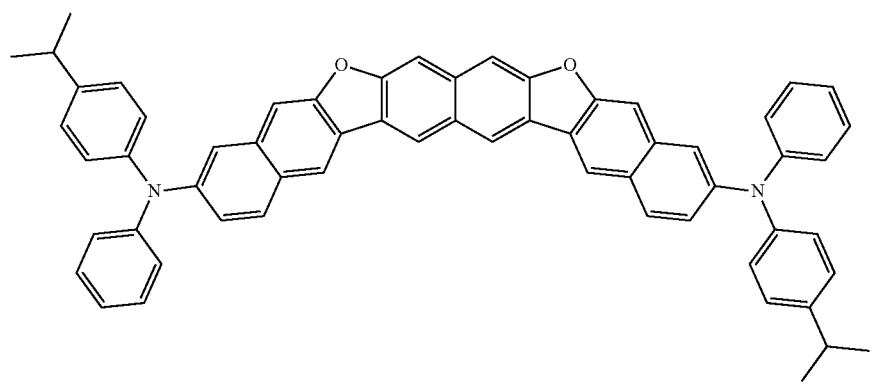
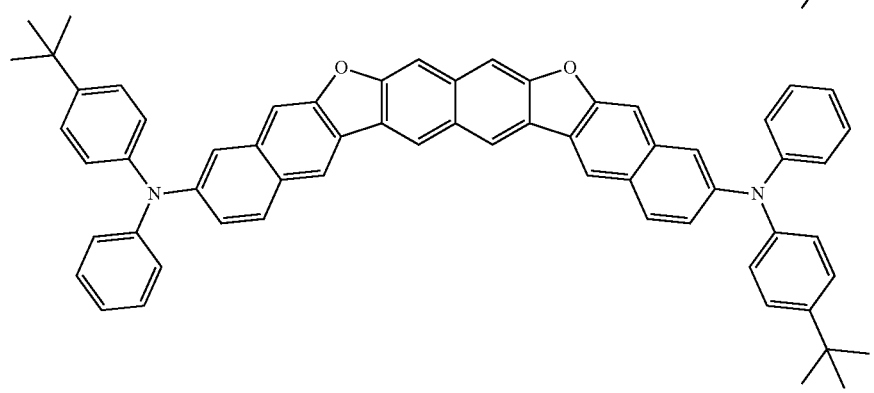
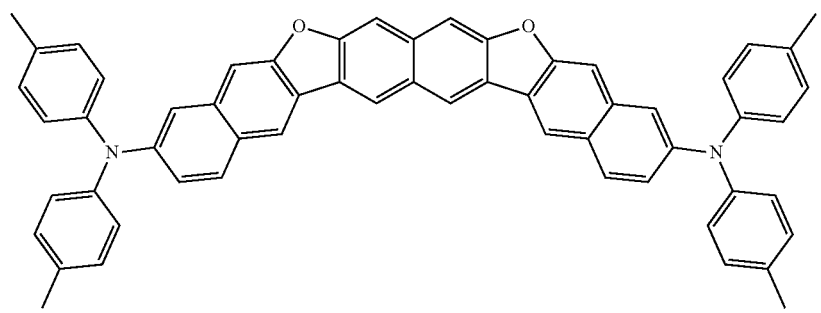
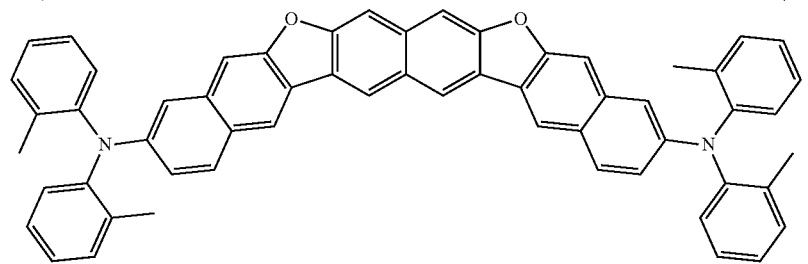

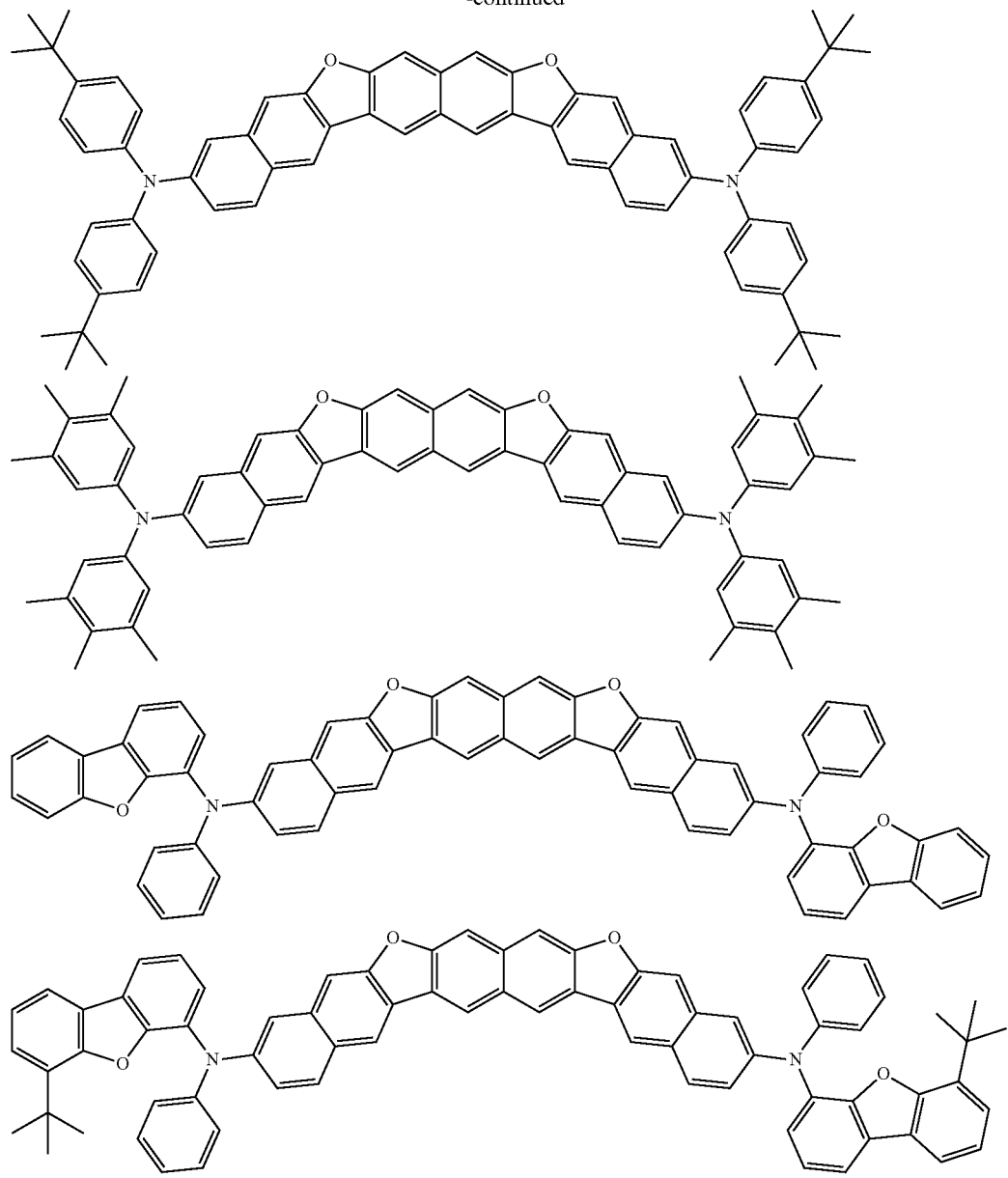

(Compound Represented by Formula (61))

The compound represented by the formula (61) is explained below.

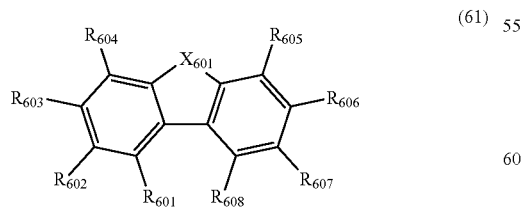

In the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

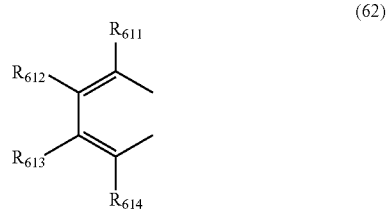

-continued (63)

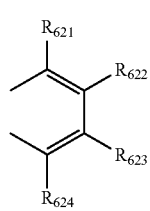

at least one of $R_{601}$ to $R_{604}$ that does not form the divalent group represented by the formula (62), and $R_{611}$ to $R_{614}$ is a monovalent group represented by the following formula (64);
at least one of $R_{605}$ to $R_{608}$ that do not form the divalent group represented by the formula (63), and $R_{621}$ to $R_{624}$ is a monovalent group represented by the following formula (64);
$X_{601}$ is an oxygen atom, a sulfur atom, or $NR_{609}$;
$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (1);

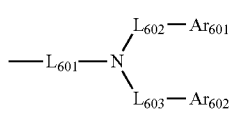

(64)

wherein, in the formula (64), $Ar_{601}$ and $Ar_{602}$ are independently a substituted or unsubstituted aryl group having 6 to 50 ring carbon atoms, or
a substituted or unsubstituted monovalent heterocyclic group having 5 to 50 ring atoms;
$L_{601}$ to $L_{603}$ are independently
a single bond,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

In the formula (61), positions at which the divalent group represented by the formula (62) and the divalent group represented by the formula (63) are formed are not limited, and said groups can be formed at possible positions in $R_{601}$ to $R_{608}$.

In one embodiment, the compound represented by the formula (61) is represented by any one of the following formulas (61-1) to (61-6):

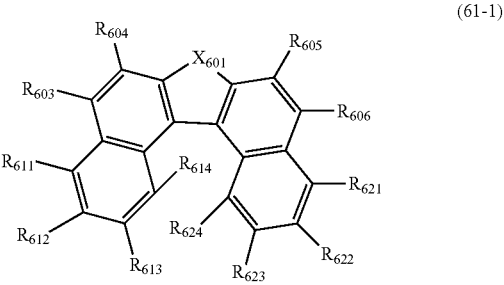
(61-1)

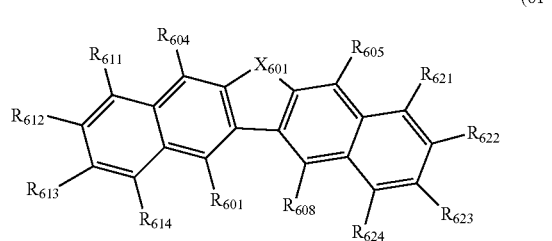
(61-2)

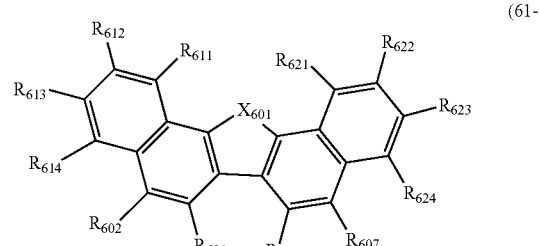
(61-3)

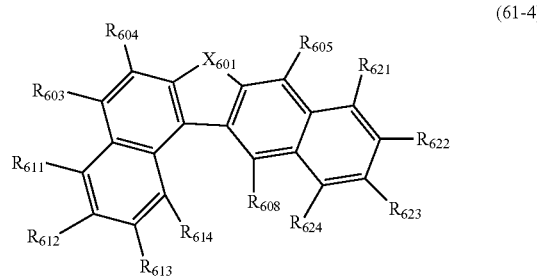
(61-4)

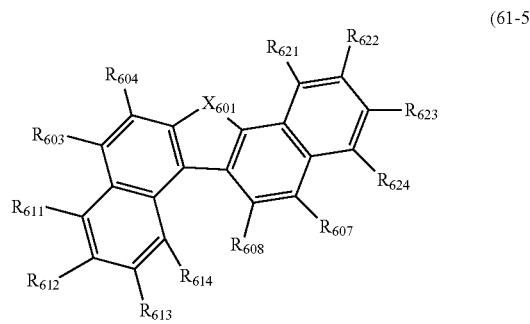
(61-5)

(61-6)

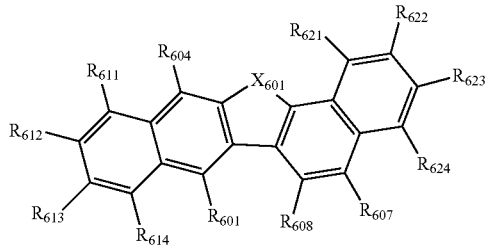

wherein in the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (61) is represented by any one of the following formulas (61-7) to (61-18):

(61-7)

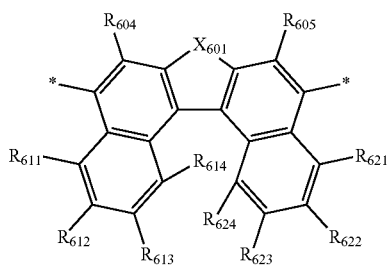

(61-8)

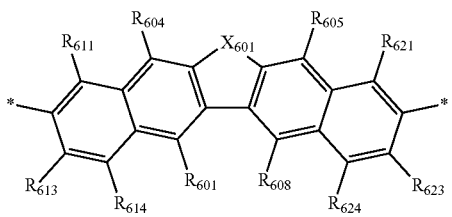

(61-9)

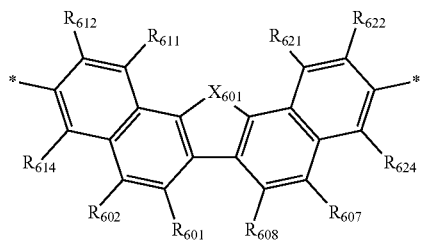

(61-10)

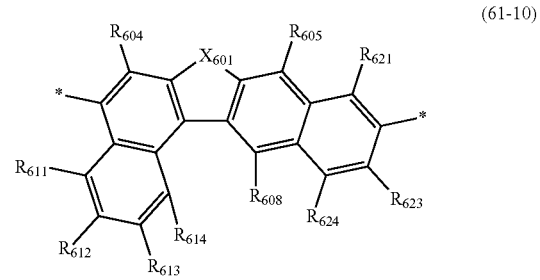

(61-11)

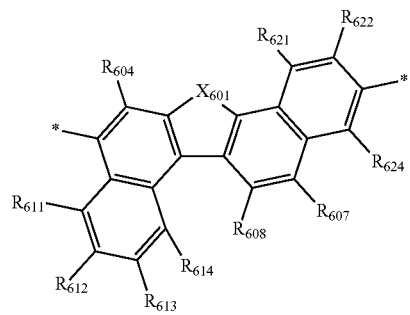

(61-12)

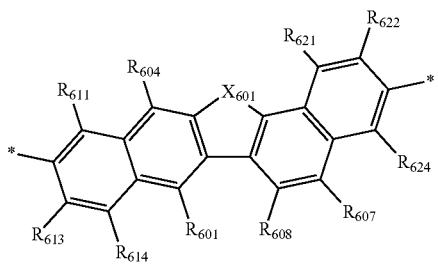

(61-13)

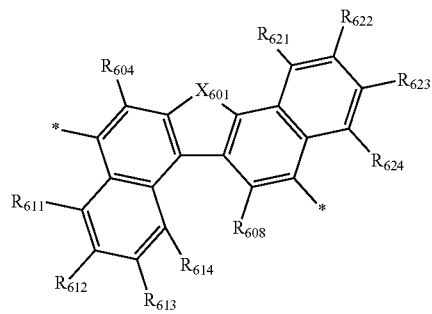

(61-14)
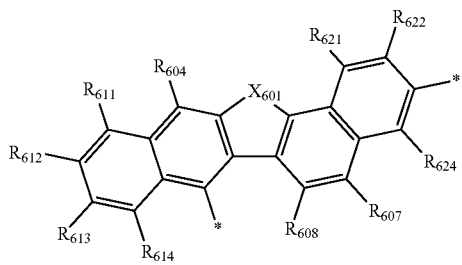

(61-15)
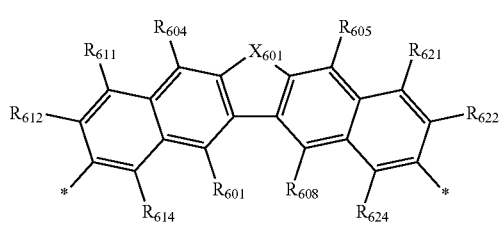

(61-16)
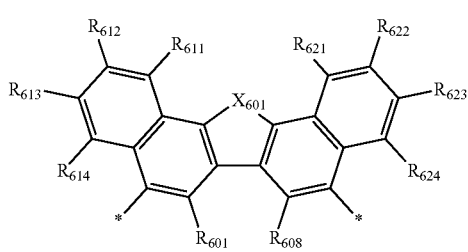

(61-17)
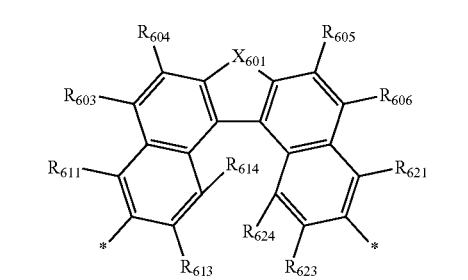

(61-18)
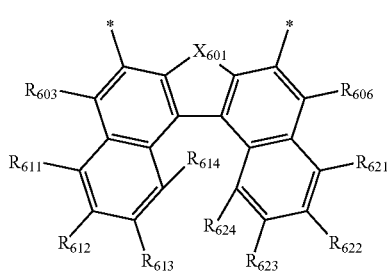

wherein in the formulas (61-7) to (61-18), $X_{601}$ is as defined in the formula (61); * is a single bond bonding to the monovalent group represented by the formula (64); and $R_{601}$ to $R_{624}$ are the same as $R_{601}$ to $R_{624}$ that are not monovalent groups represented by the formula (64).

$R_{601}$ to $R_{608}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms.

The monovalent group represented by the formula (64) is preferably represented by the following formulas (65) or (66):

(65)
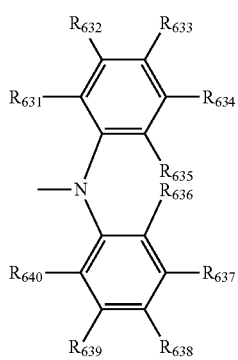

wherein in the formula (65), $R_{631}$ to $R_{640}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1);

(66)
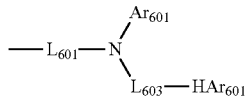

wherein in the formula (66), $Ar_{601}$, $L_{601}$ and $L_{603}$ are as defined in the formula (64); and $HAr_{601}$ is a structure represented by the following formula (67);

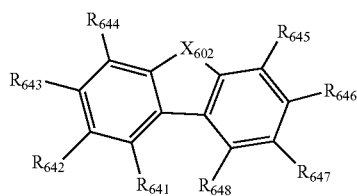

(67)

wherein in the formula (67) $X_{602}$ is an oxygen atom or a sulfur atom;

any one of $R_{641}$ to $R_{648}$ is a single bond bonding to $L_{603}$;

$R_{641}$ to $R_{648}$ which are not single bonds are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{907}$, to $R_{907}$ are as defined in the formula (1).

As specific example of the compound represented by the formula (61), in addition to the compounds described in WO2014/104144, the following compounds can be given, for example. In the following example compounds, Me represents methyl group.

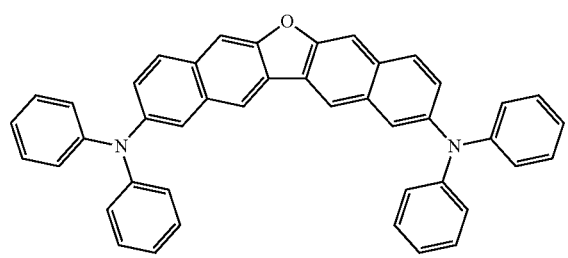

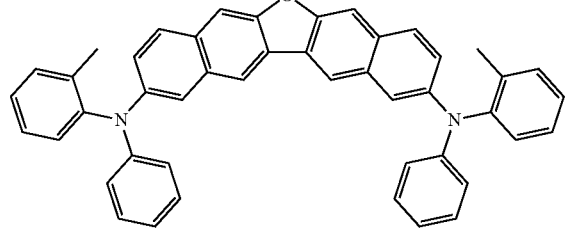

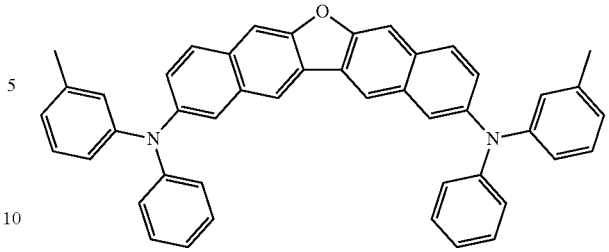

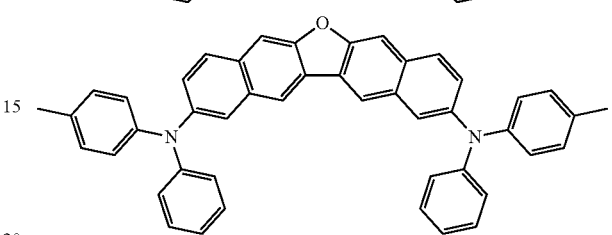

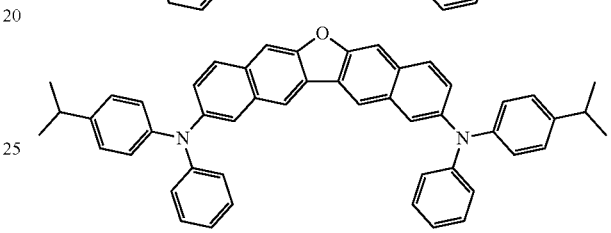

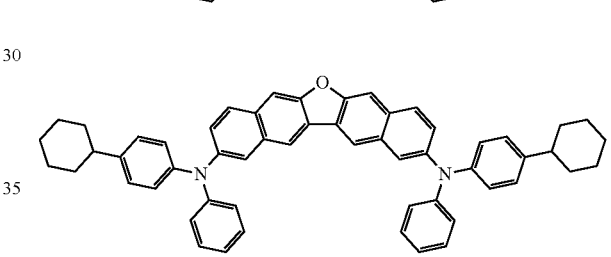

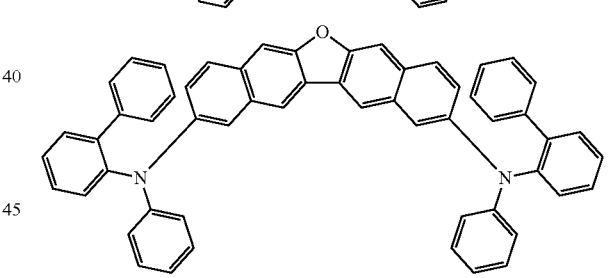

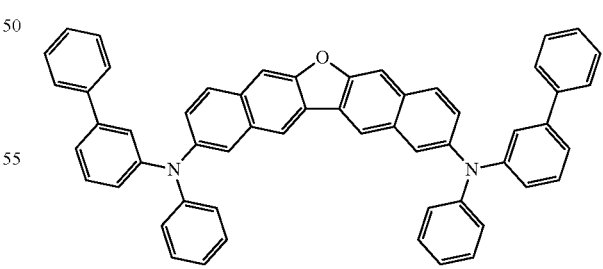

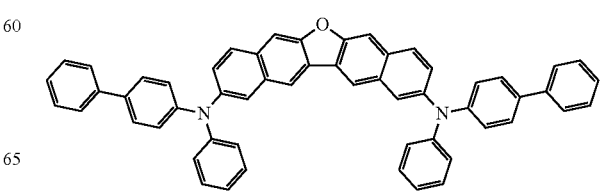

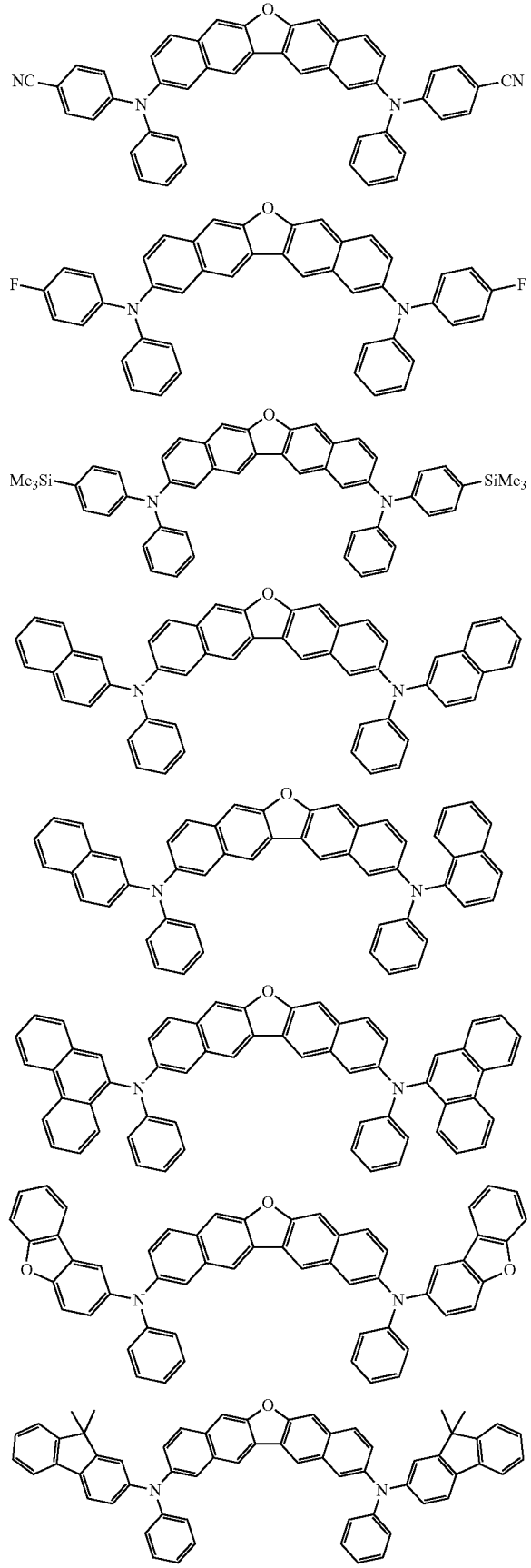
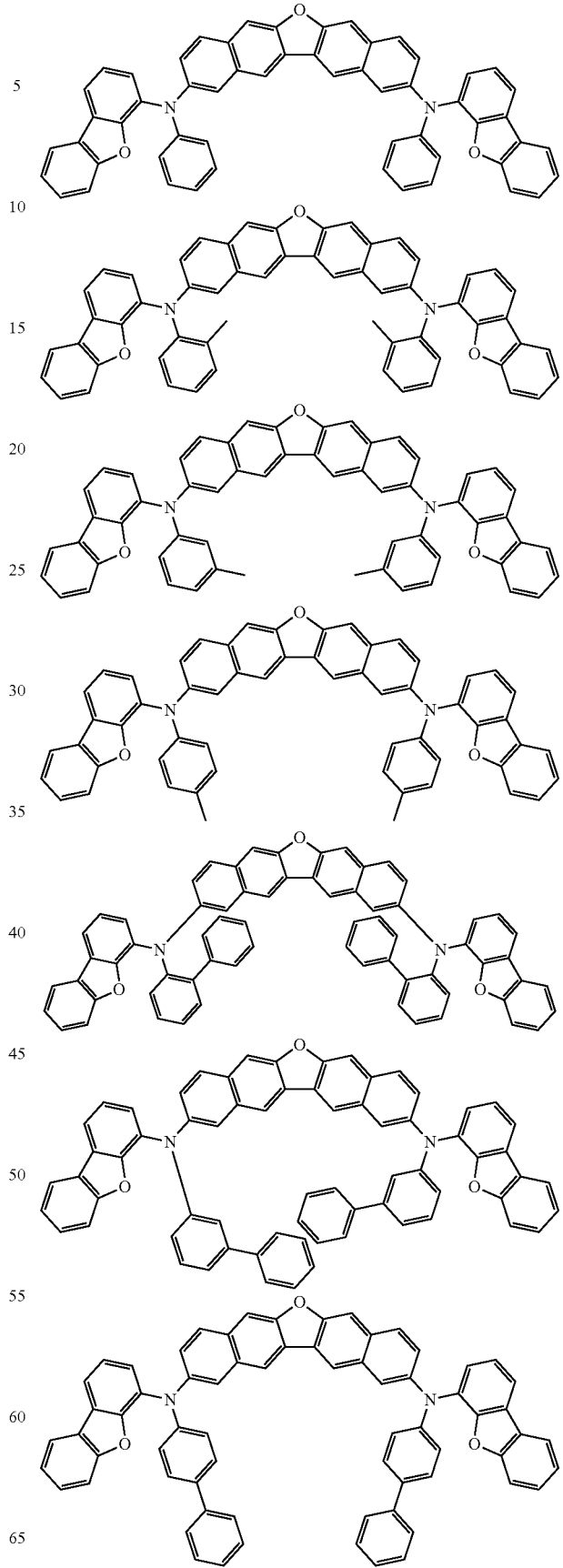

741
-continued
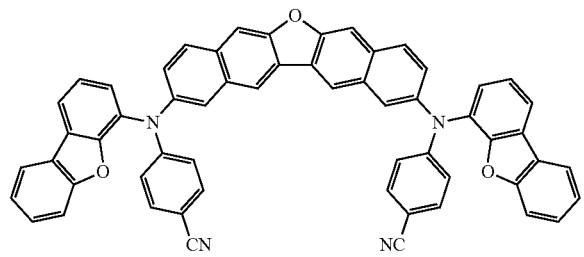
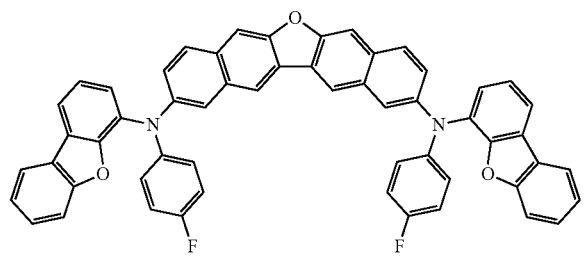
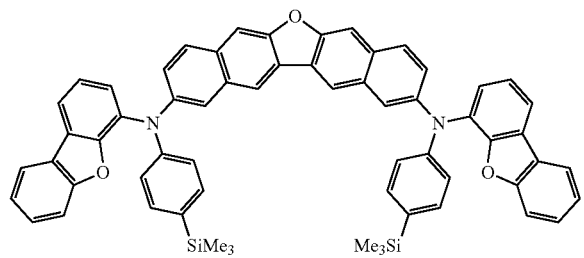
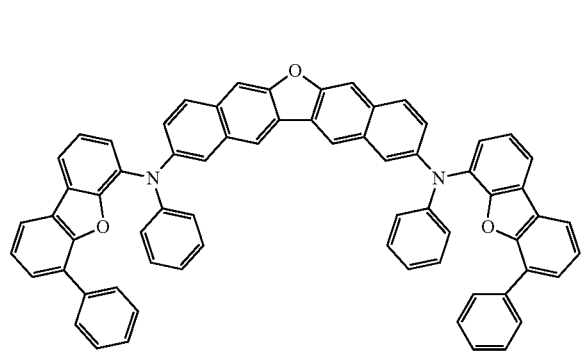
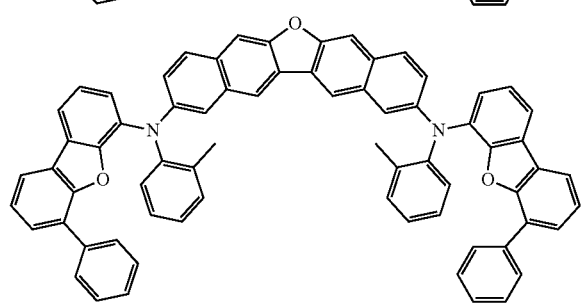
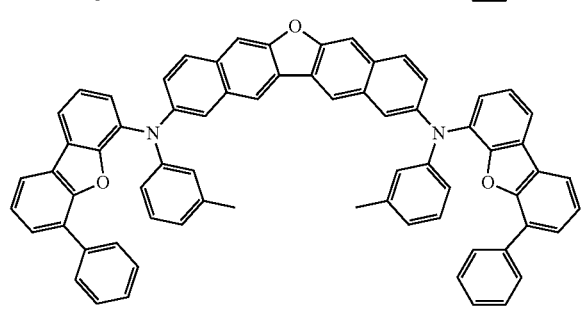
742
-continued
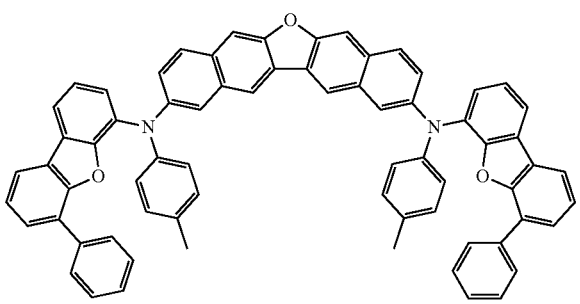
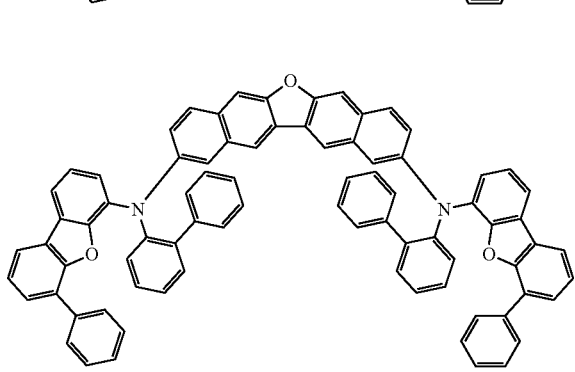
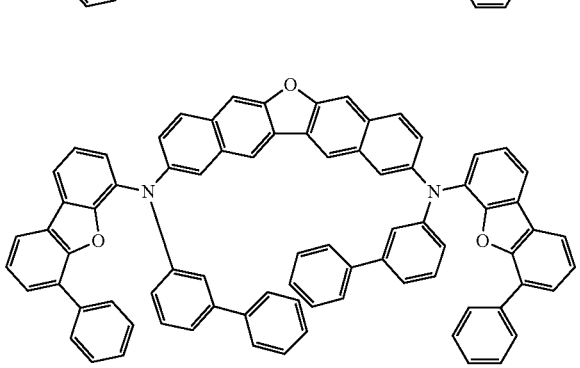
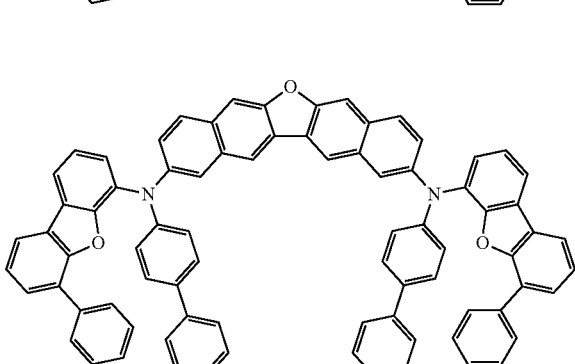
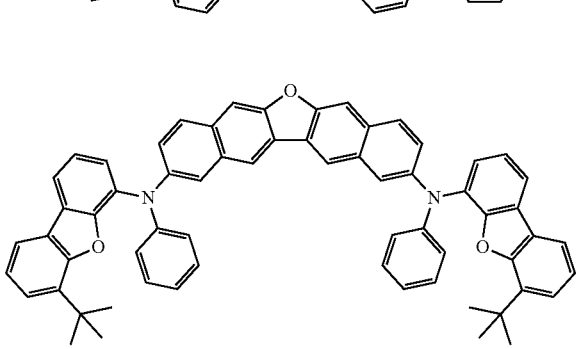

743
-continued
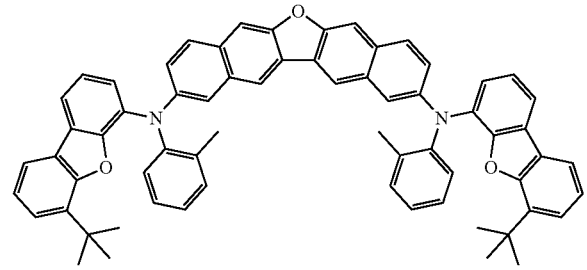
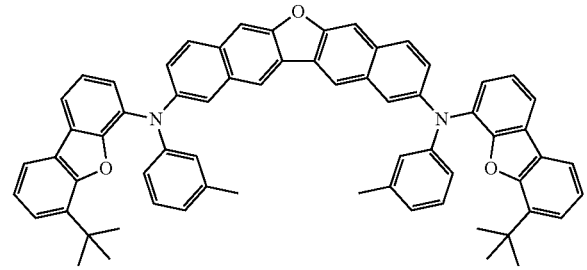
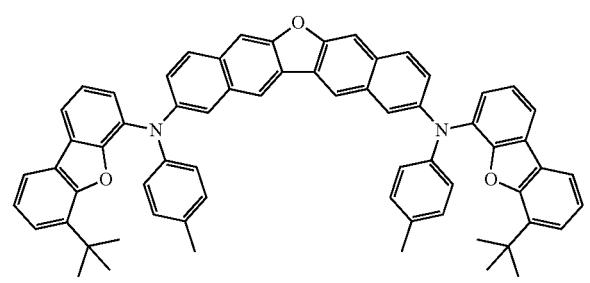
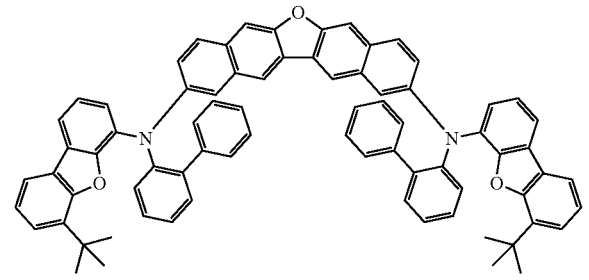
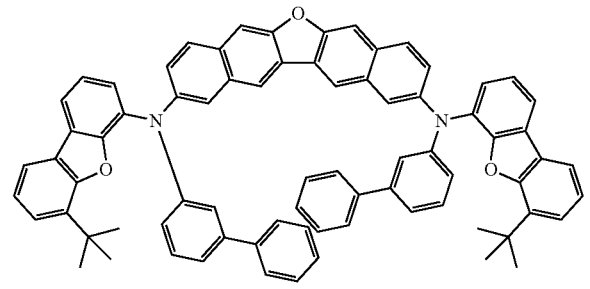
744
-continued
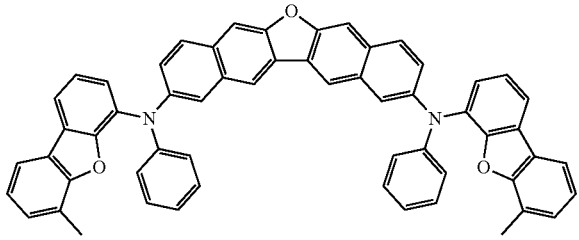
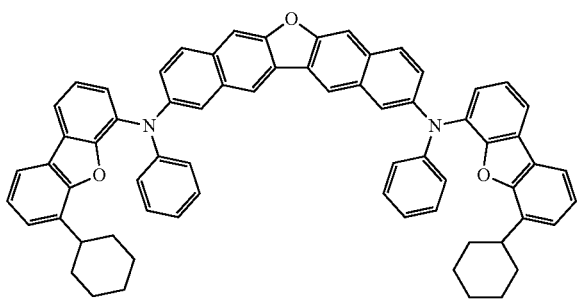
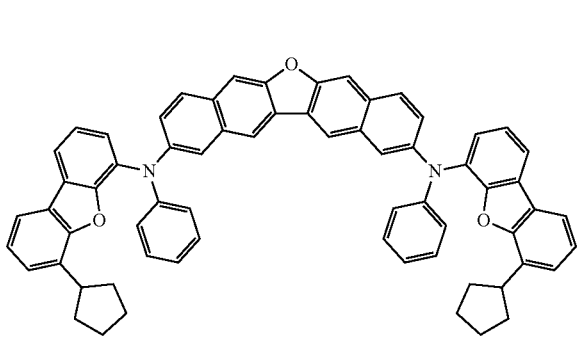
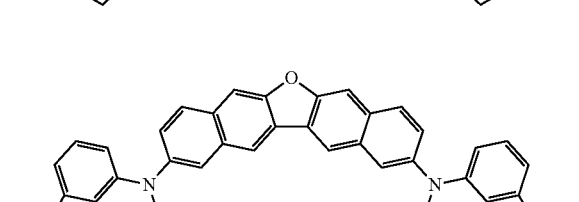
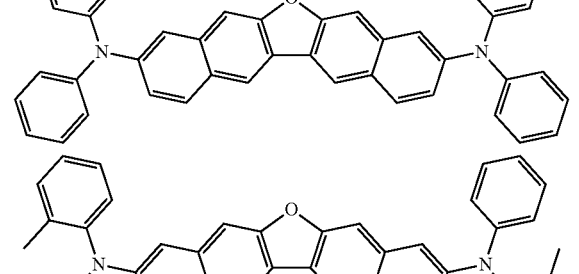

745
-continued
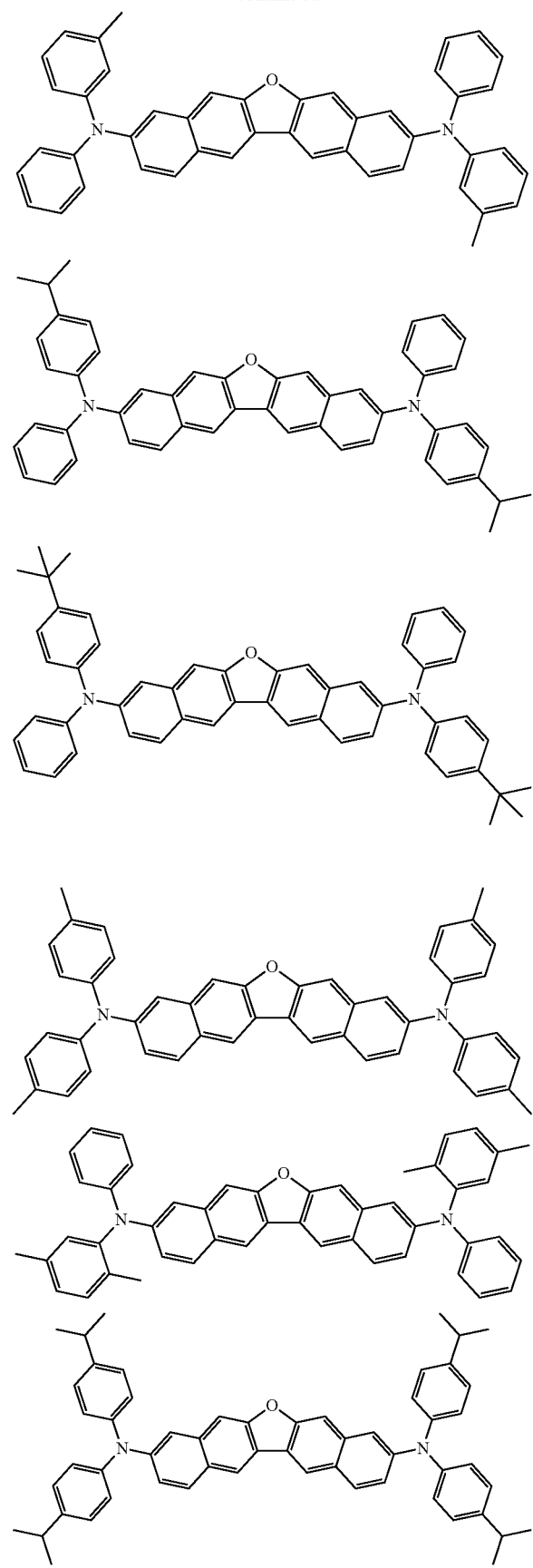
746
-continued
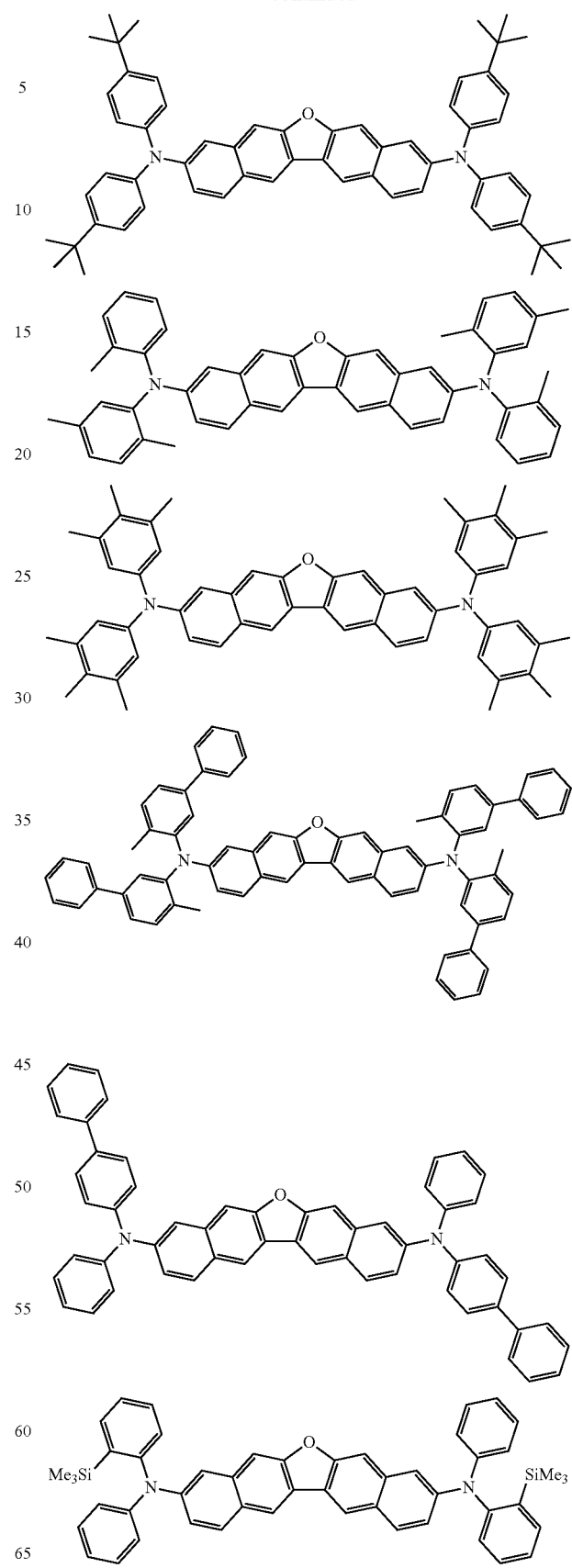

747
-continued
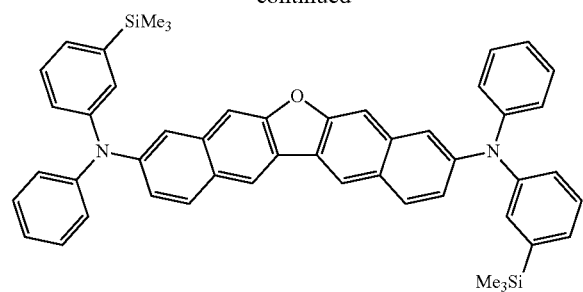
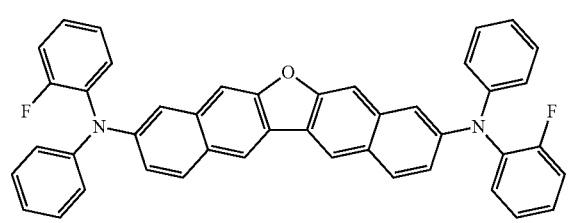
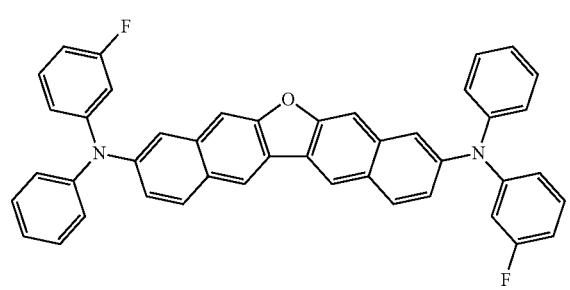
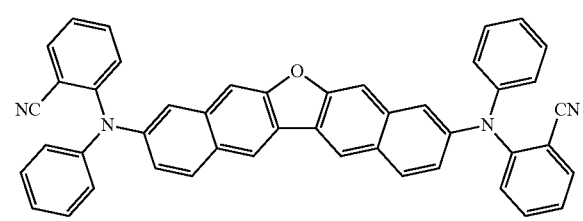
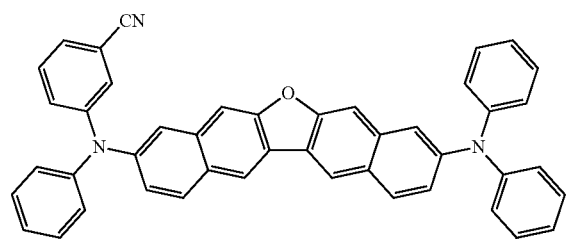
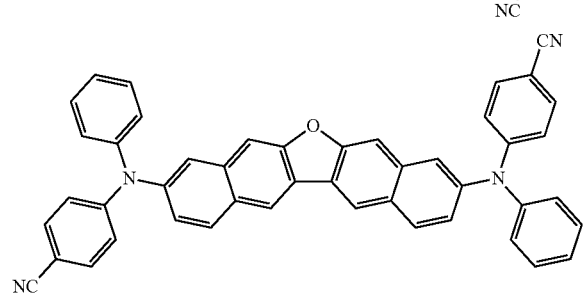
748
-continued
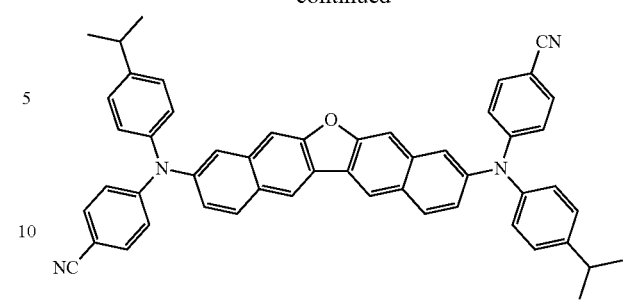
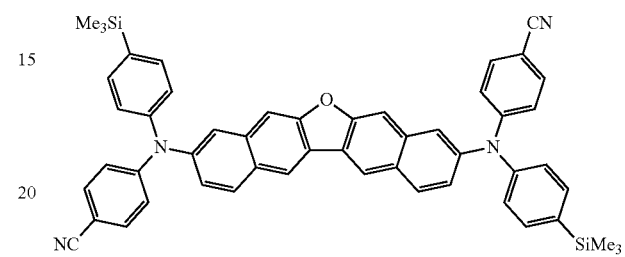

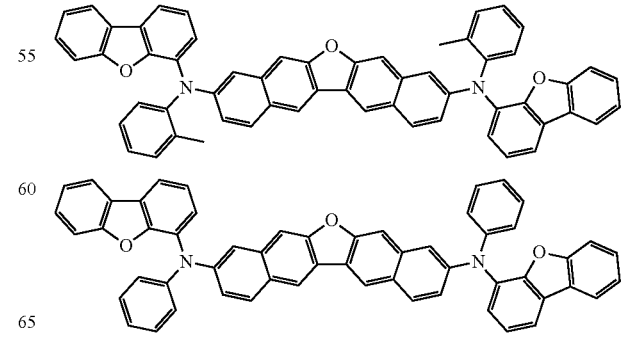

749
-continued
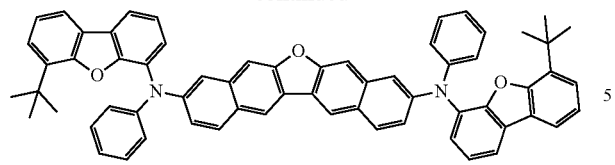
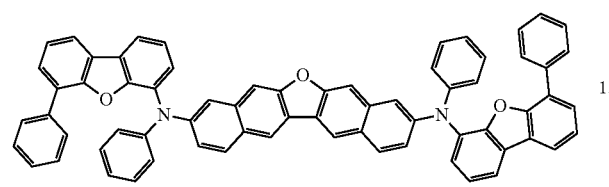
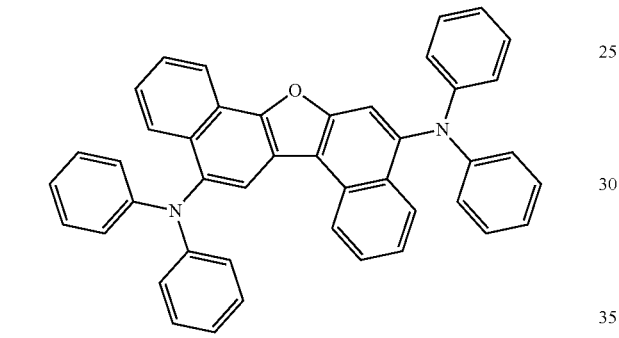
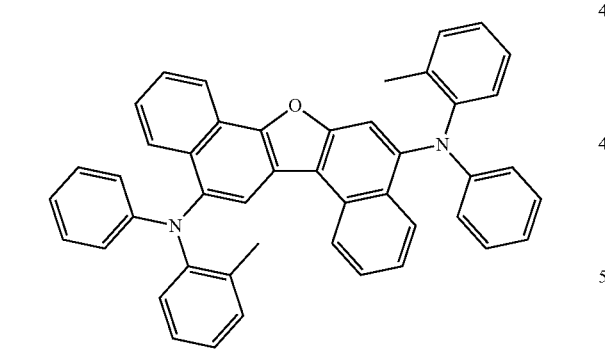
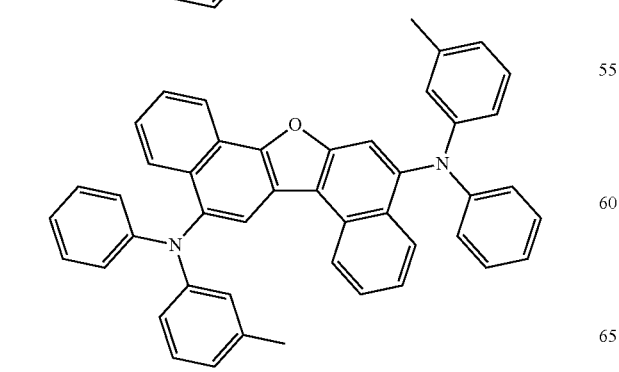
750
-continued
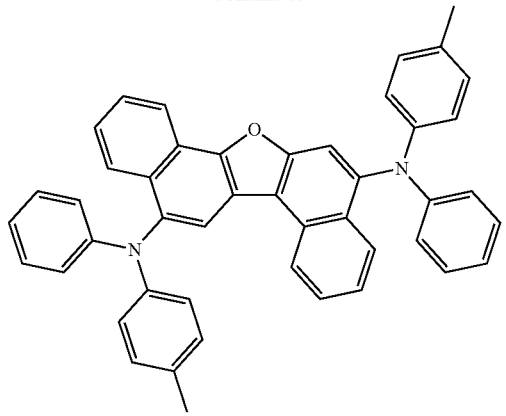
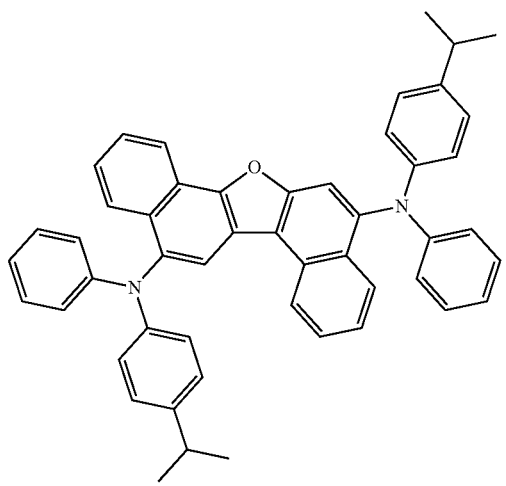
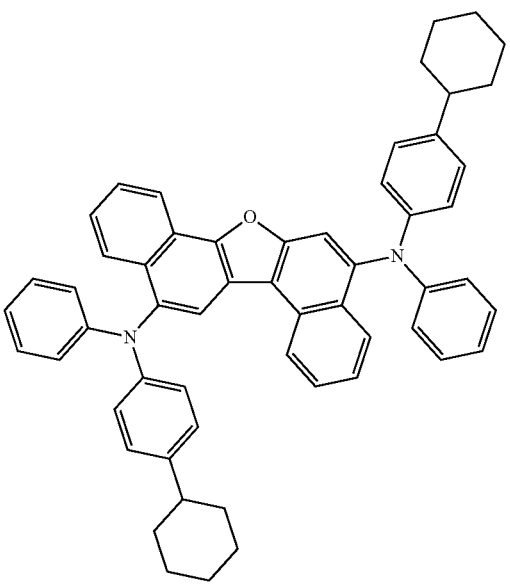

751
-continued
752
-continued
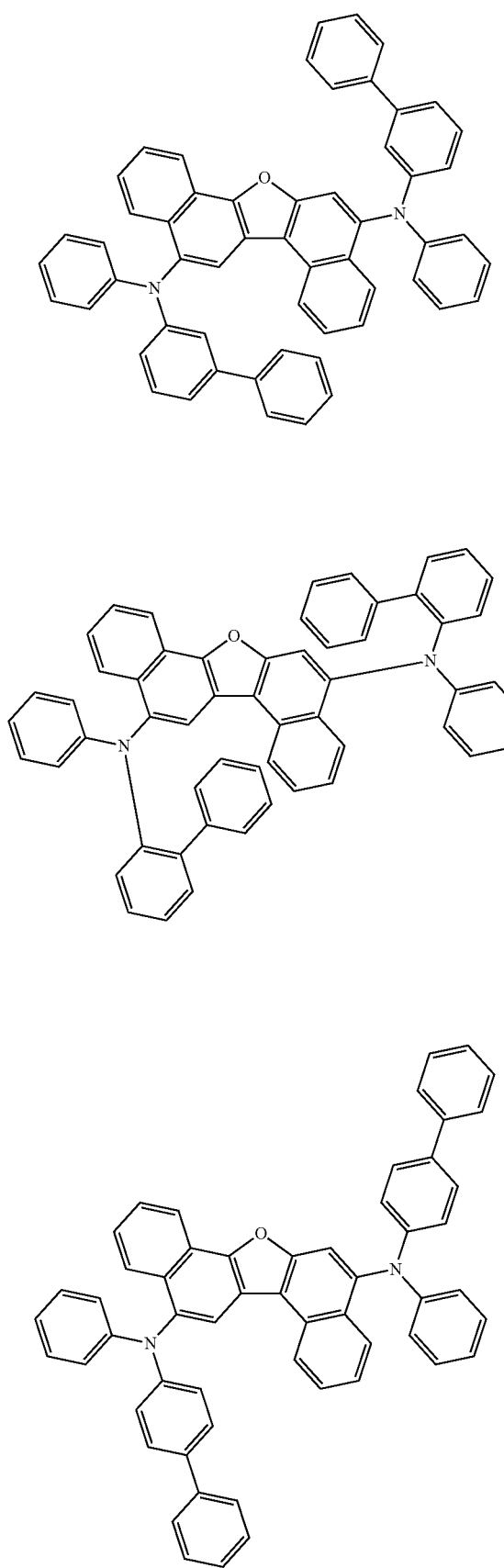
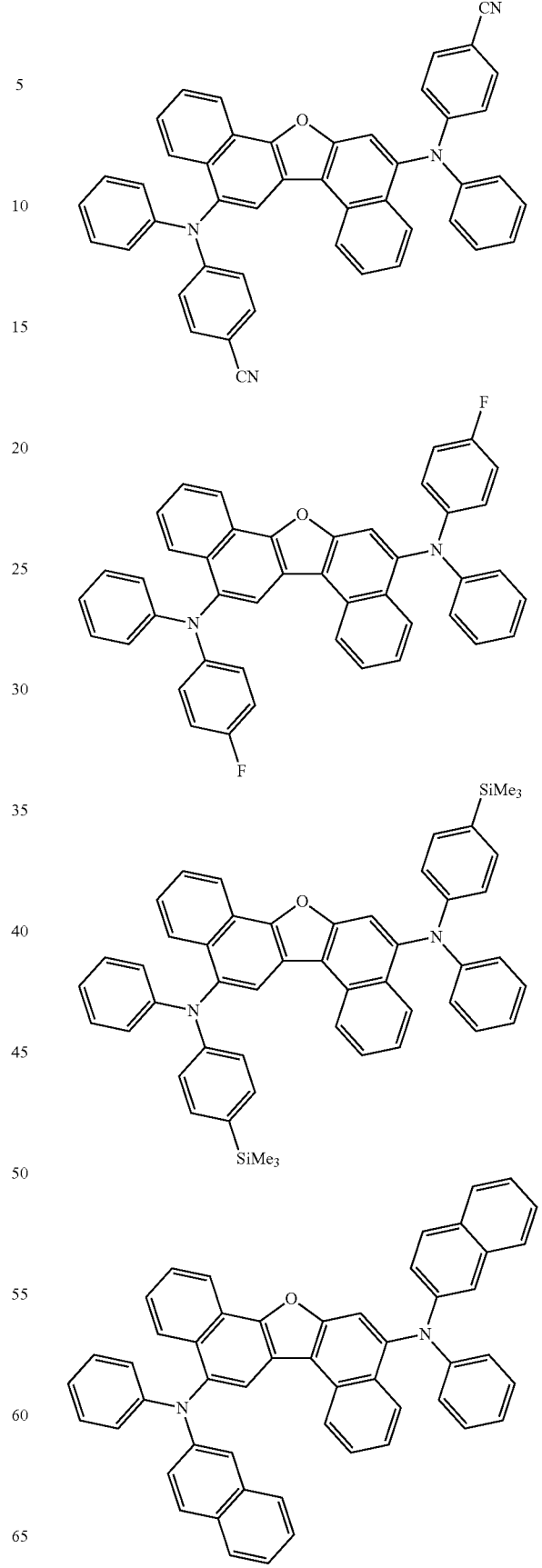

753
-continued
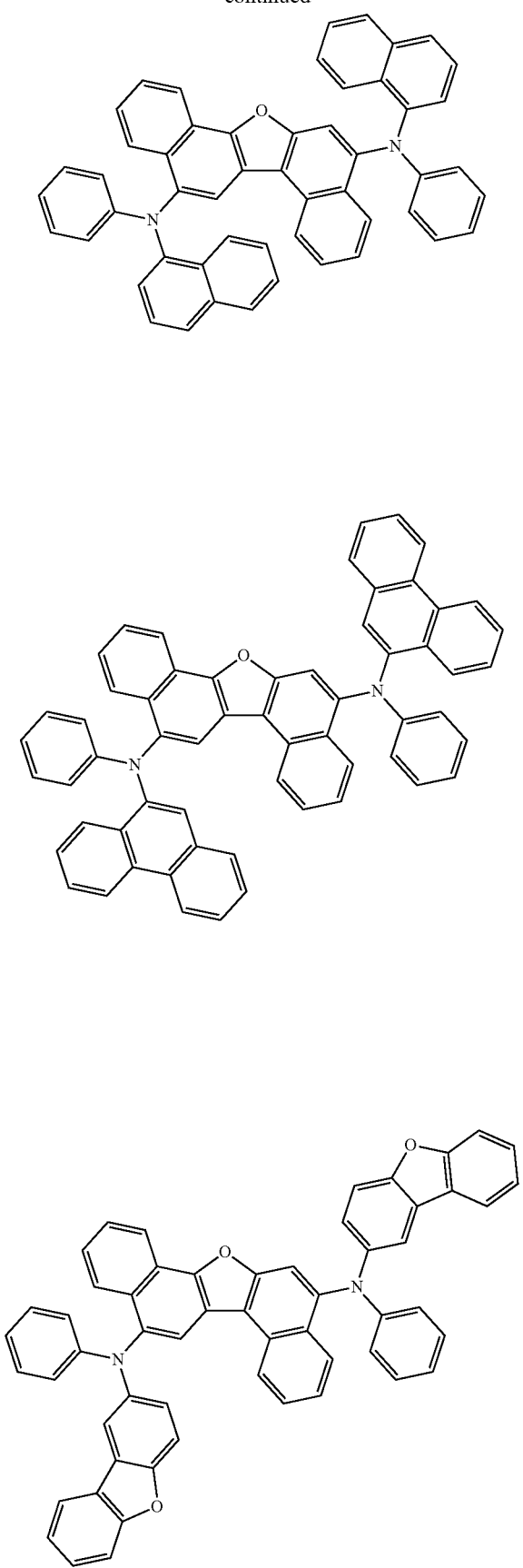
754
-continued
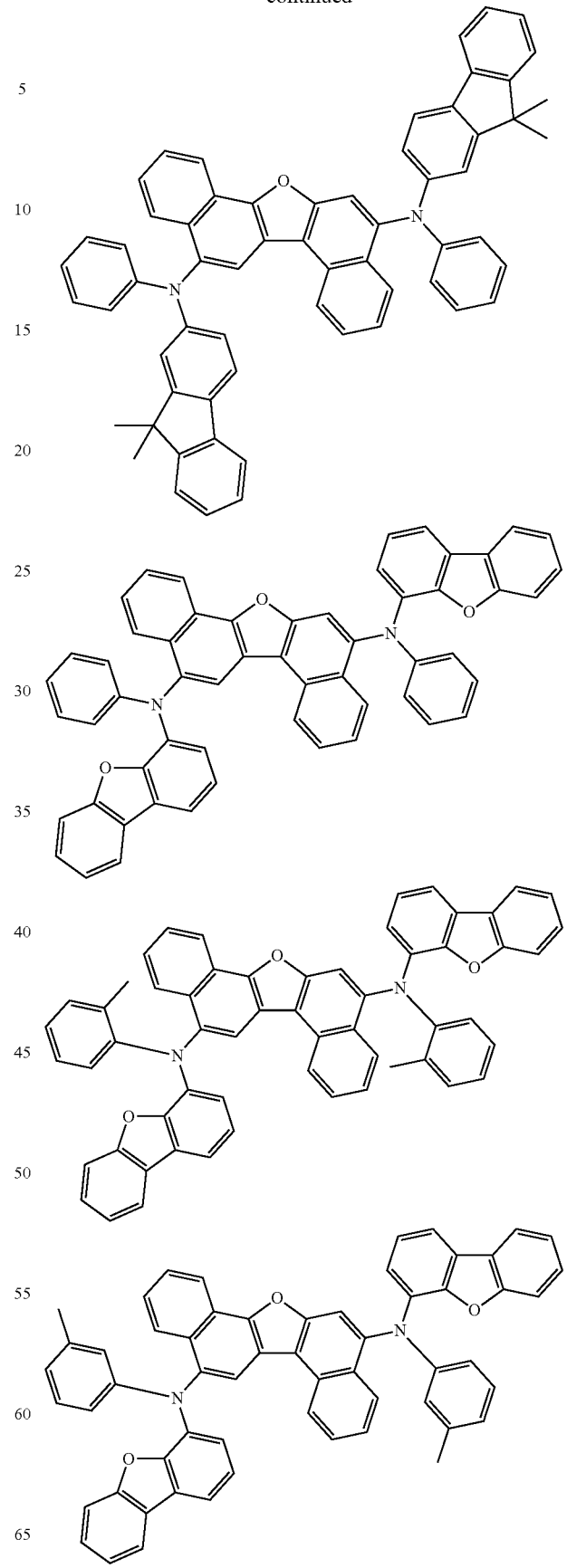

755
-continued
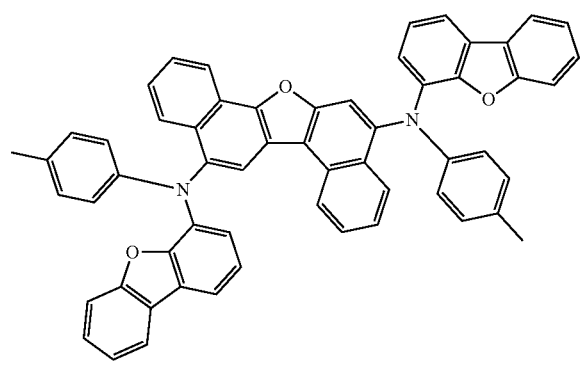
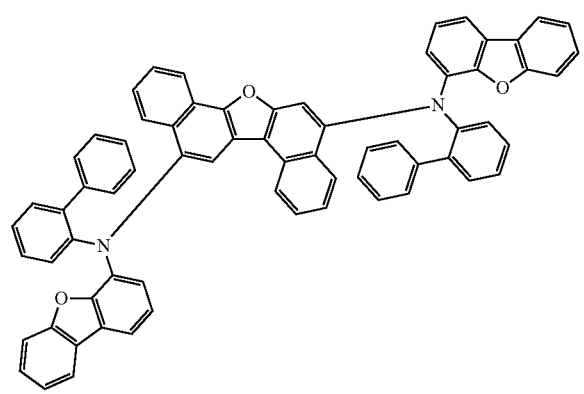
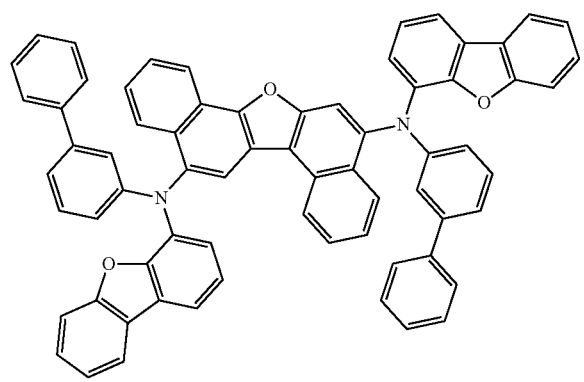
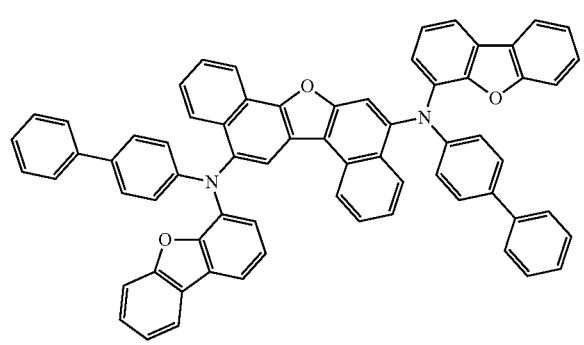
756
-continued
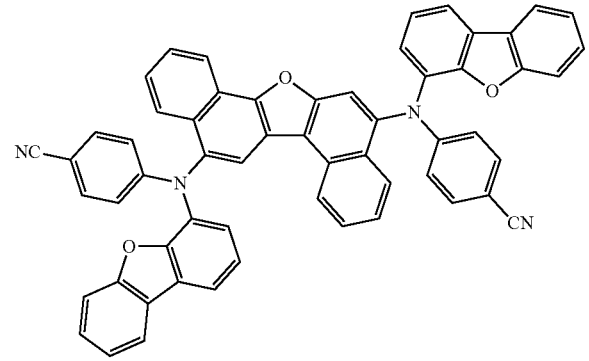
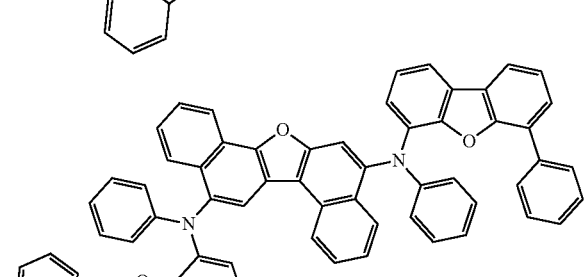
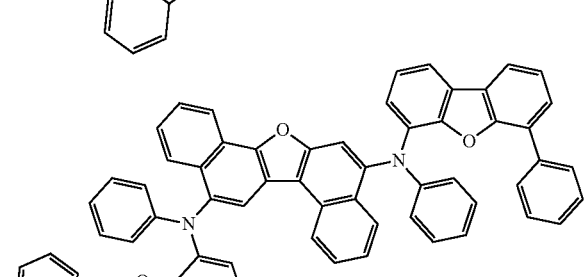
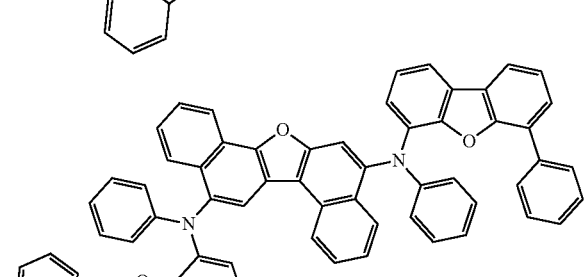

757
-continued
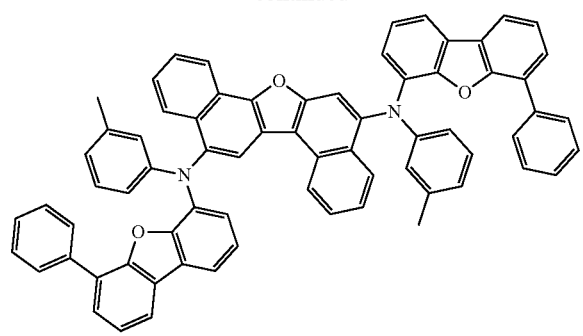
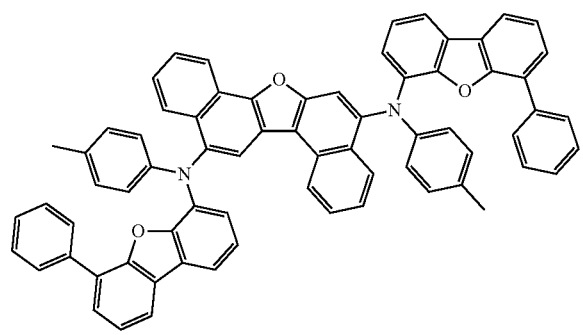
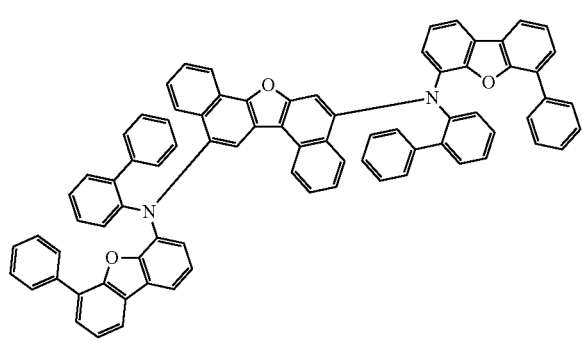
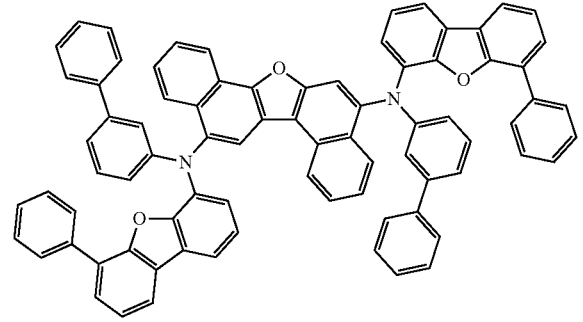
758
-continued
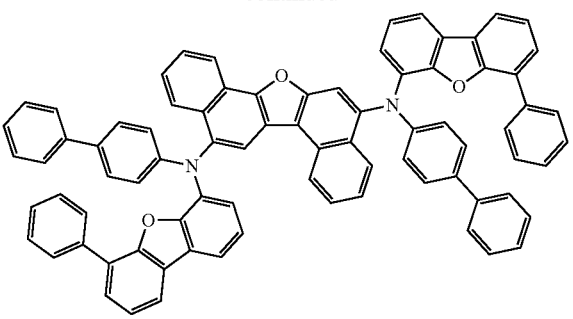
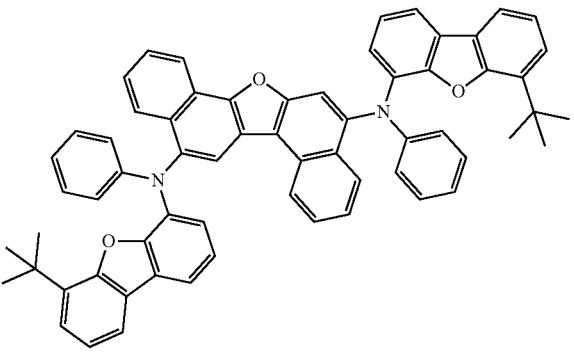
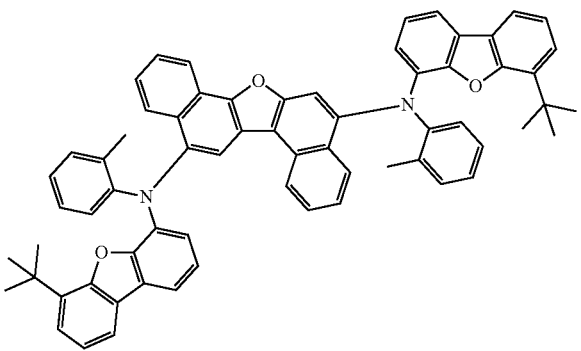

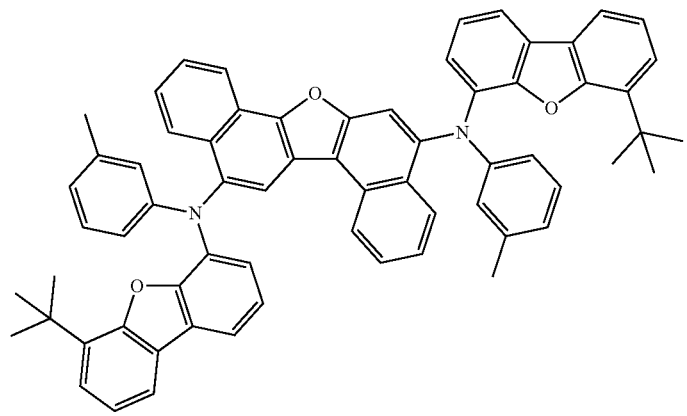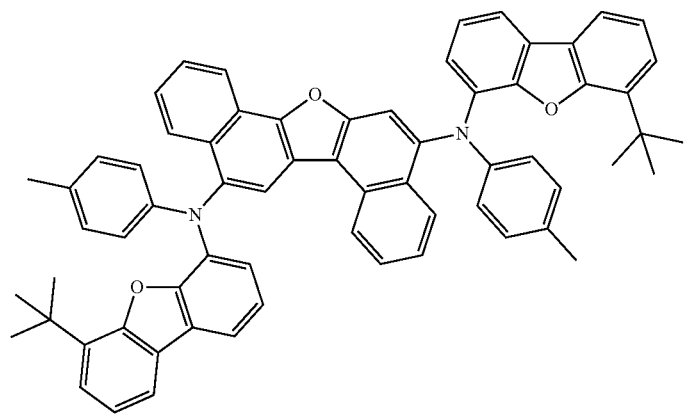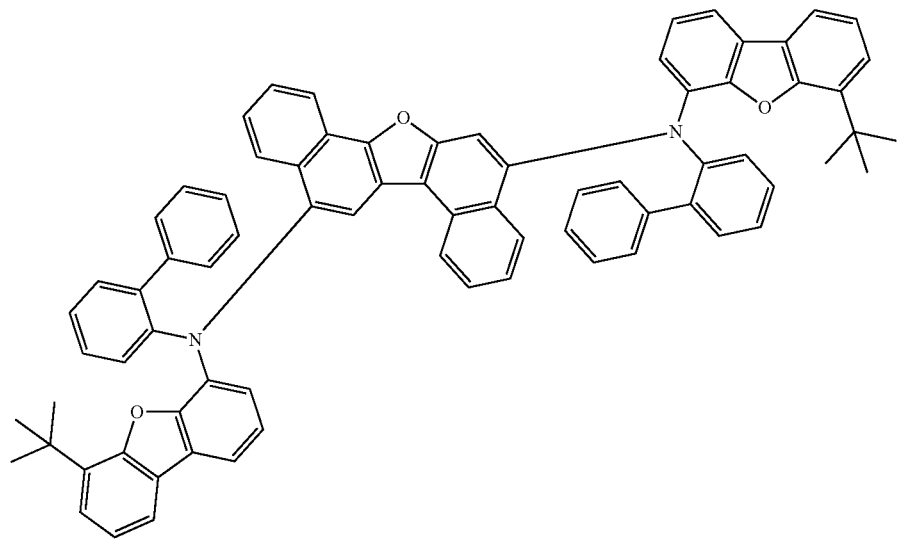

-continued
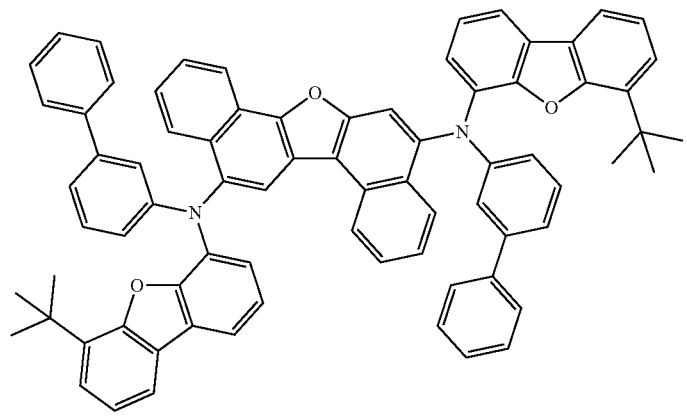
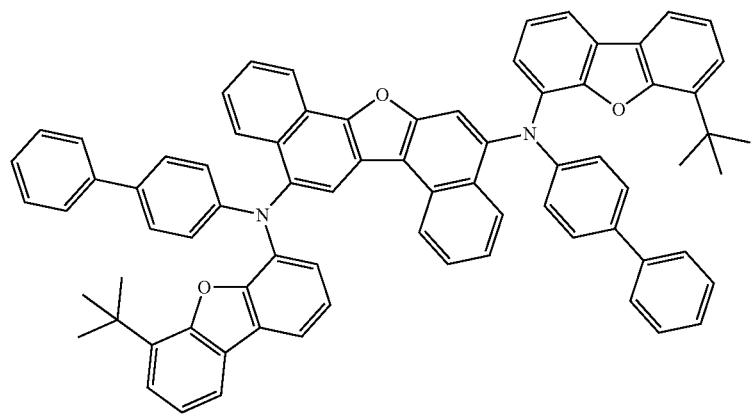
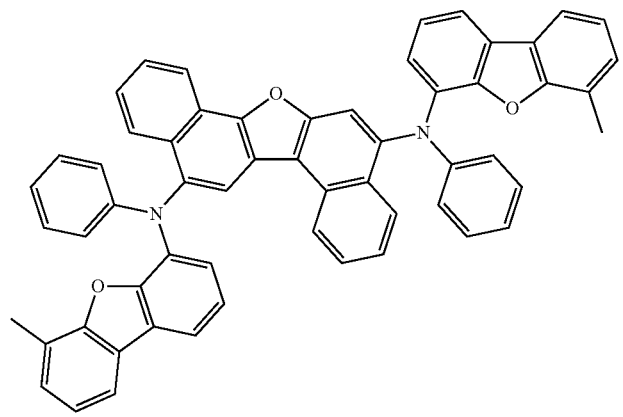
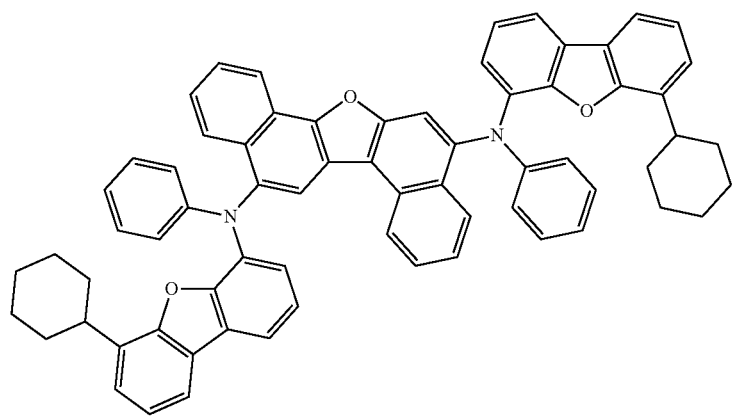

-continued
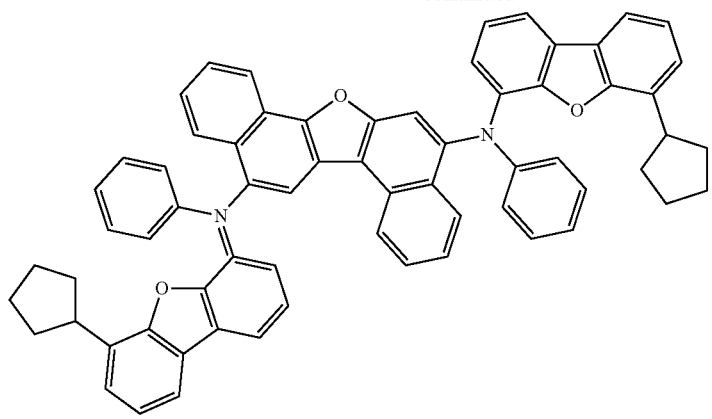
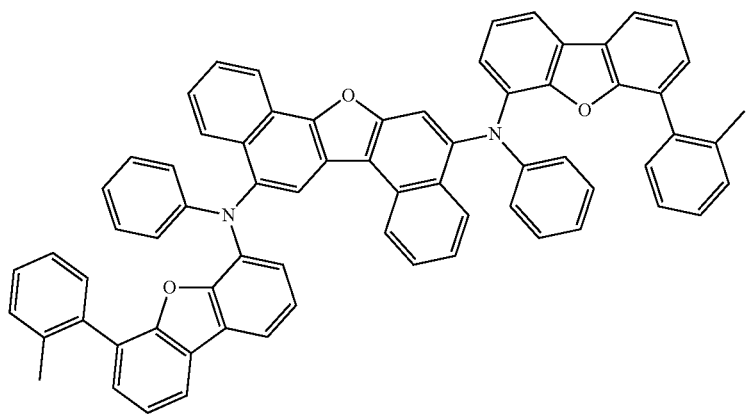
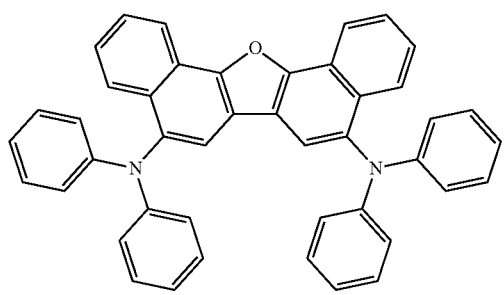
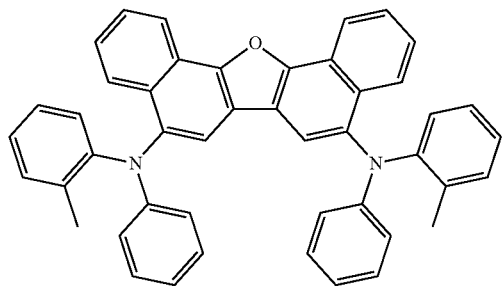
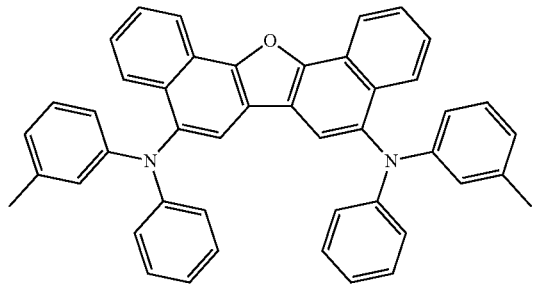

765
-continued
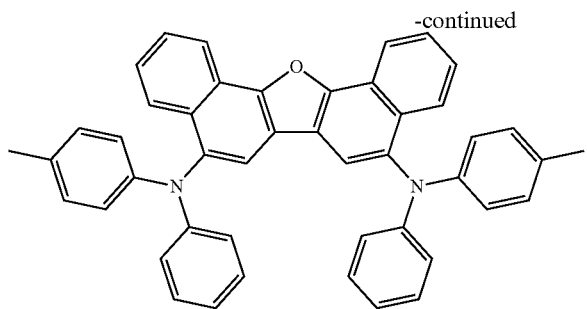
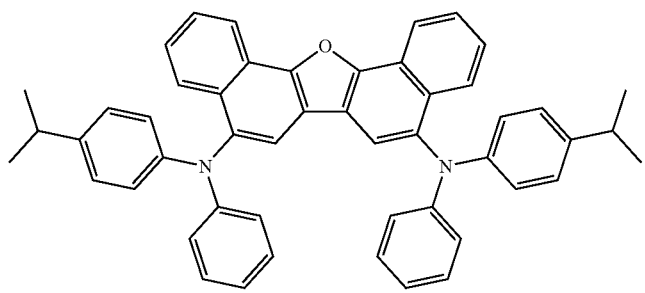
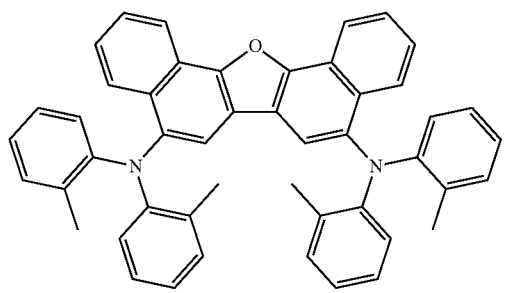
766
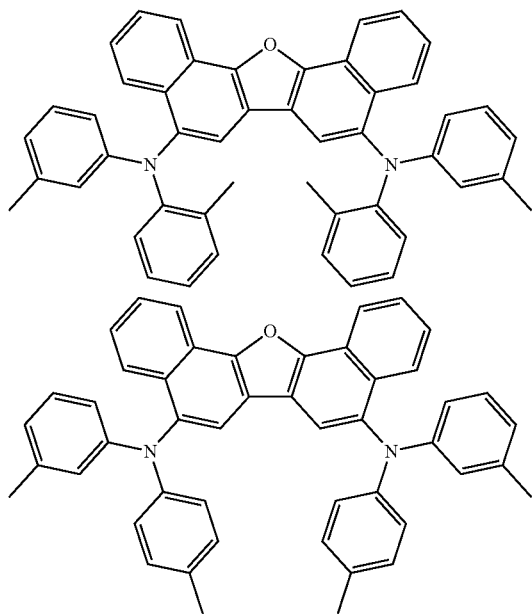

-continued
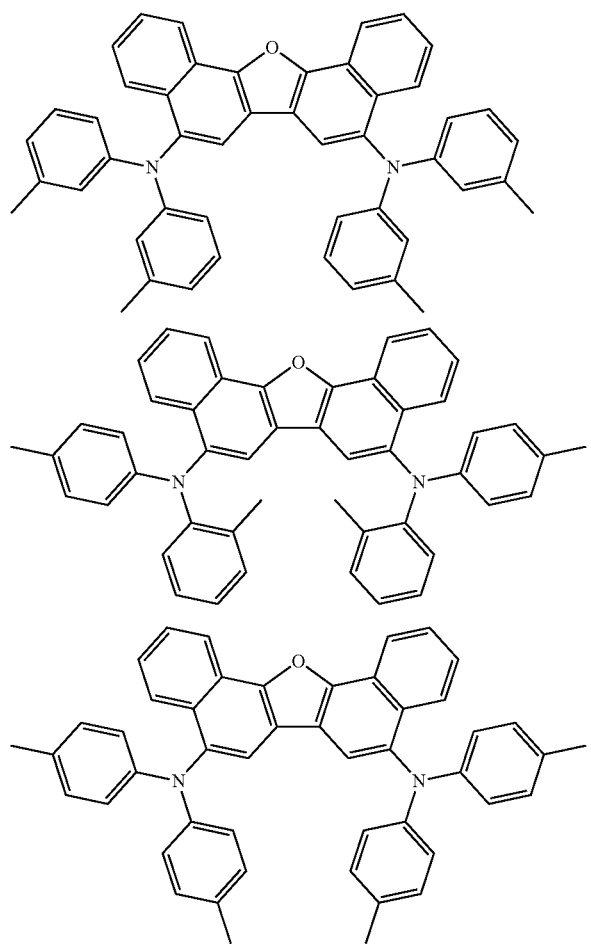
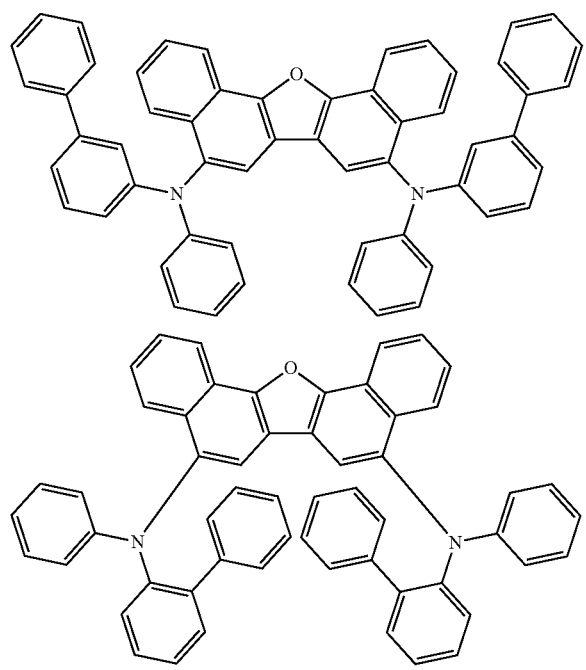

-continued
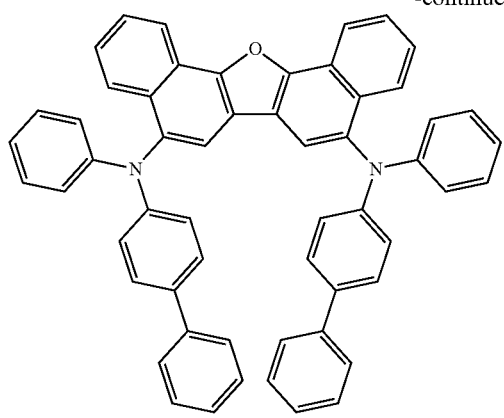
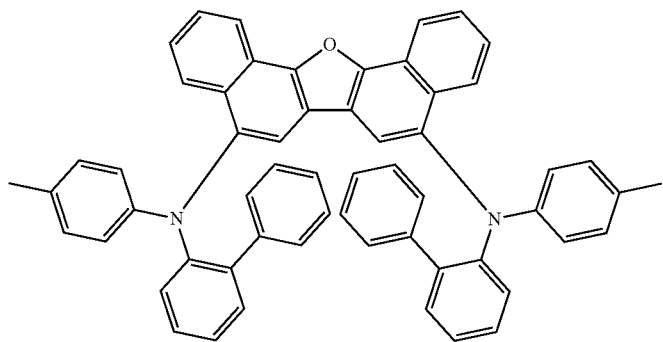
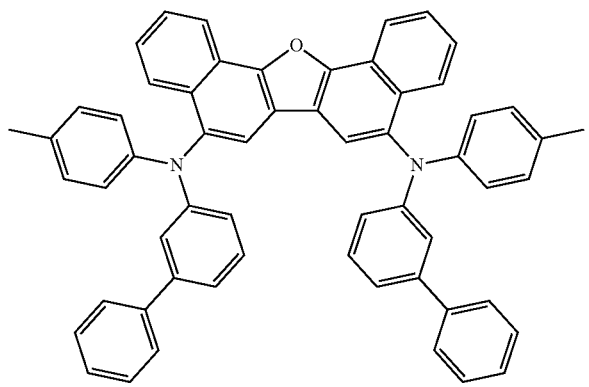
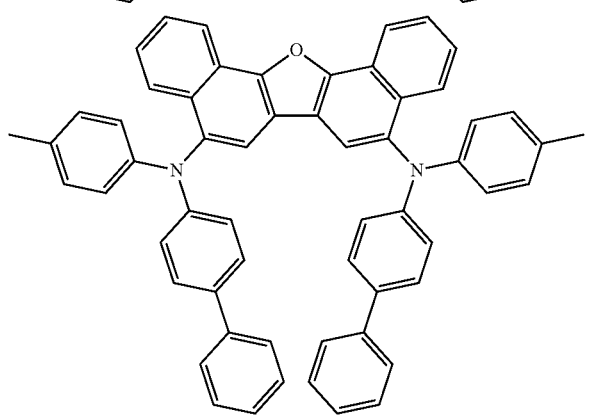

771
-continued
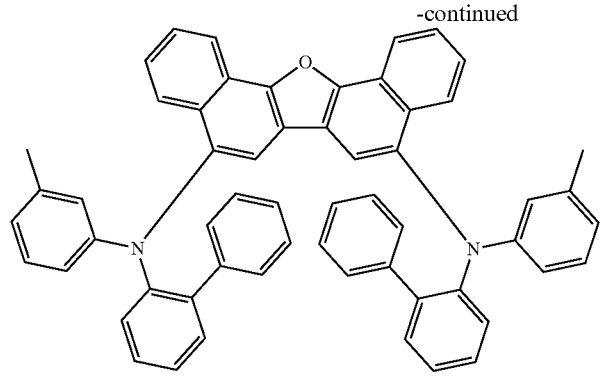
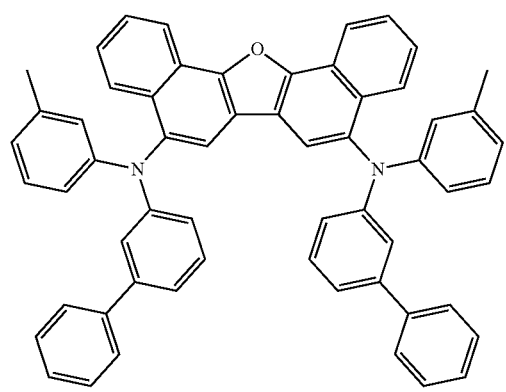
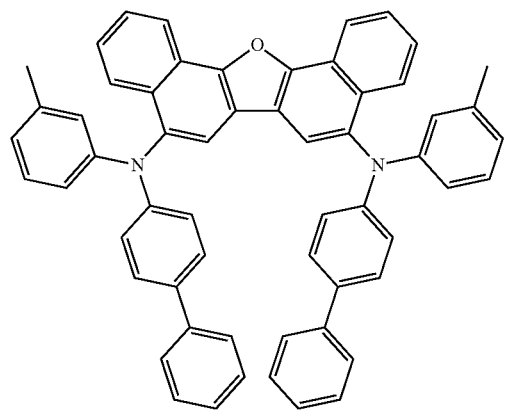
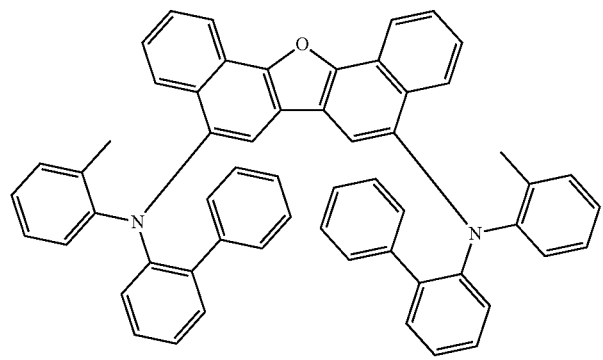
772

-continued
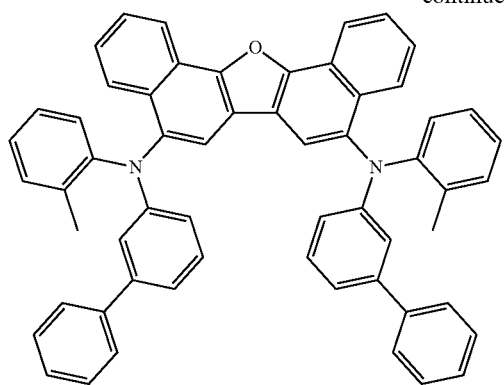
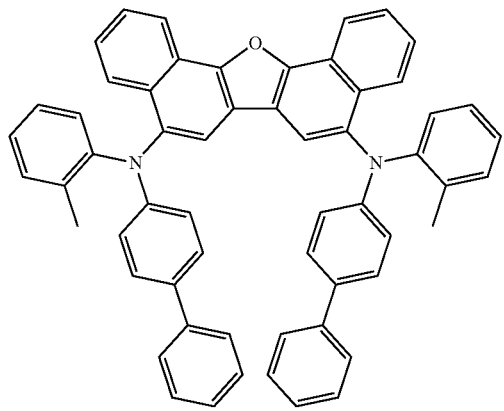
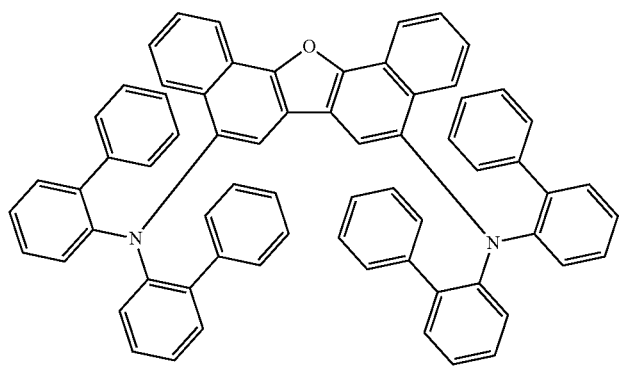
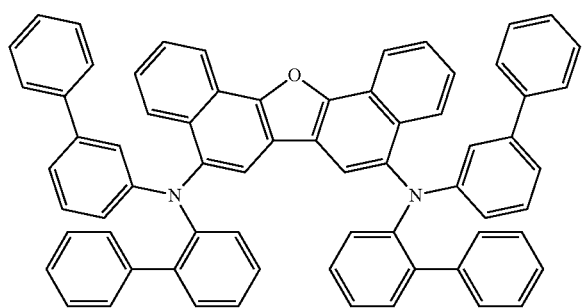

-continued
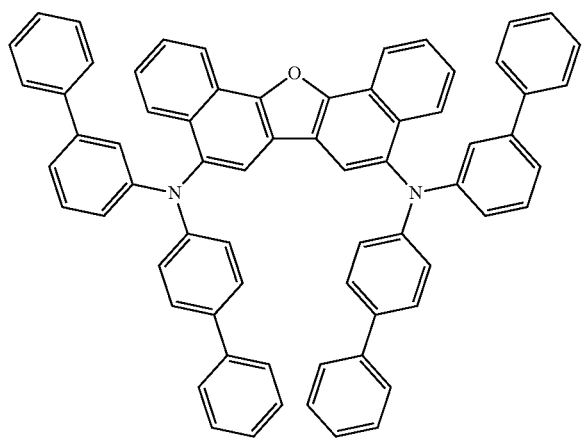
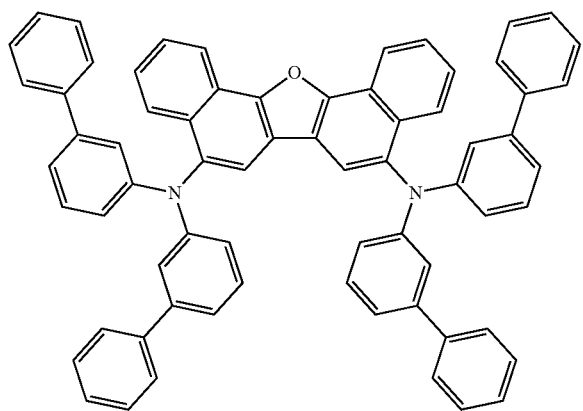
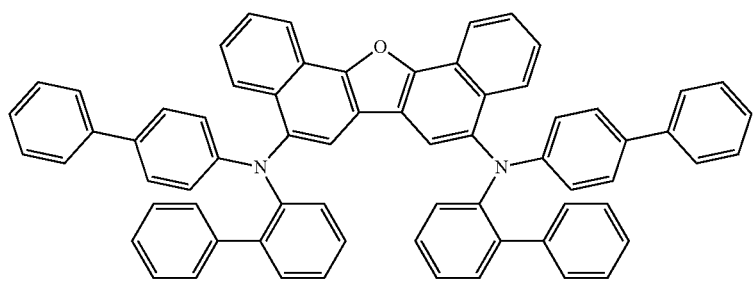
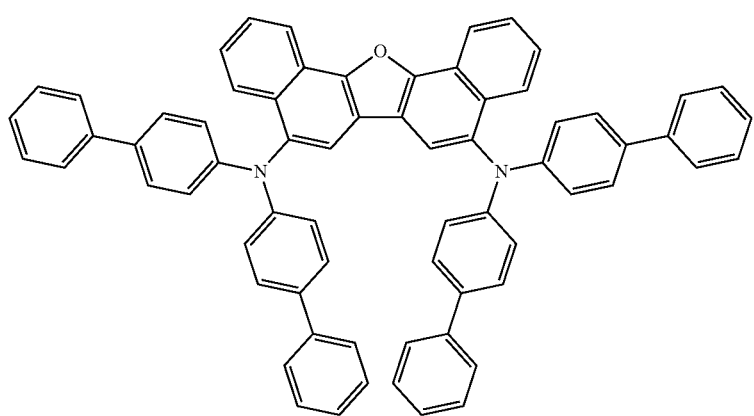

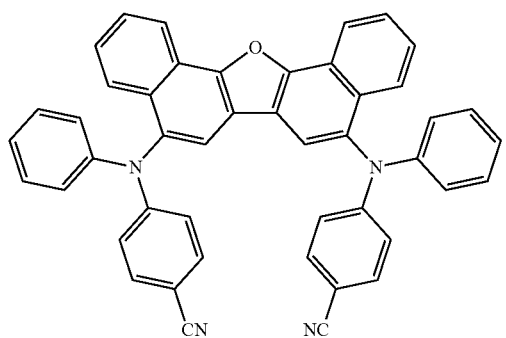
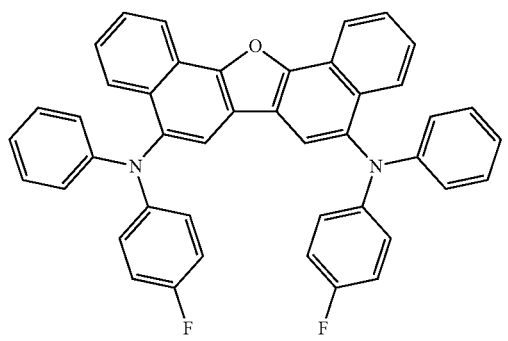
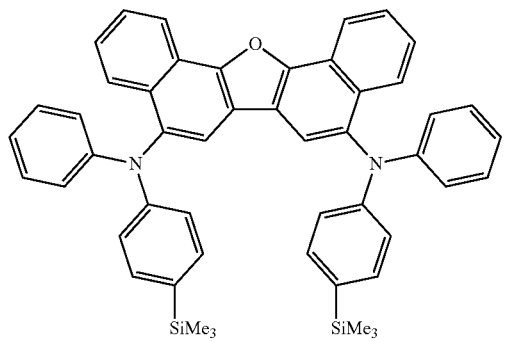
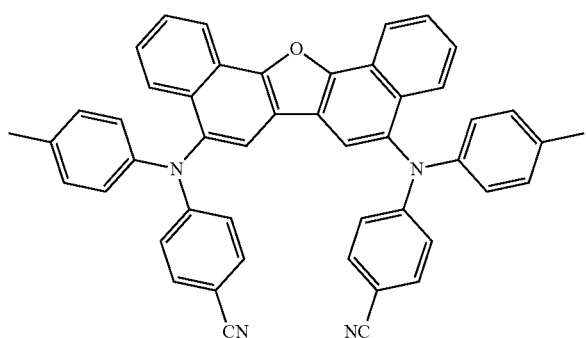
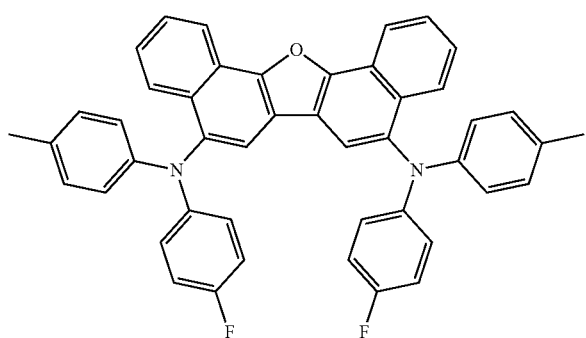

-continued
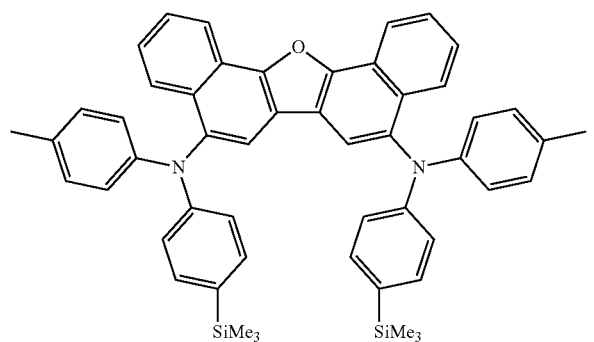
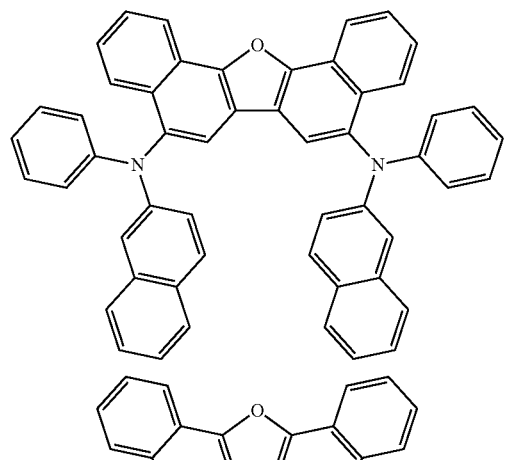
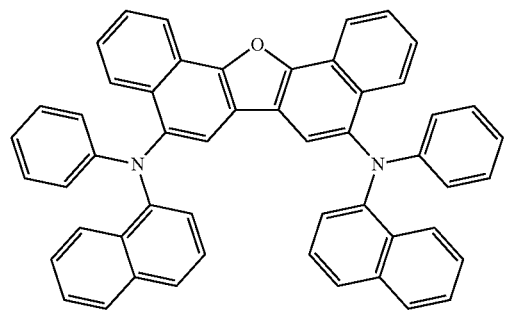
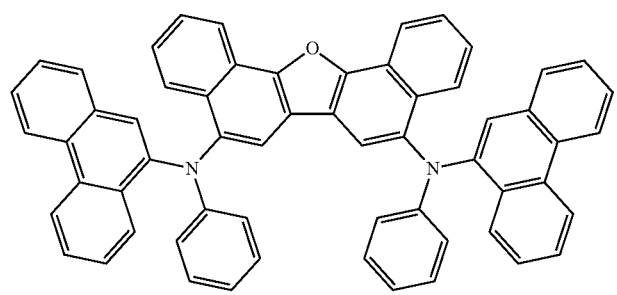
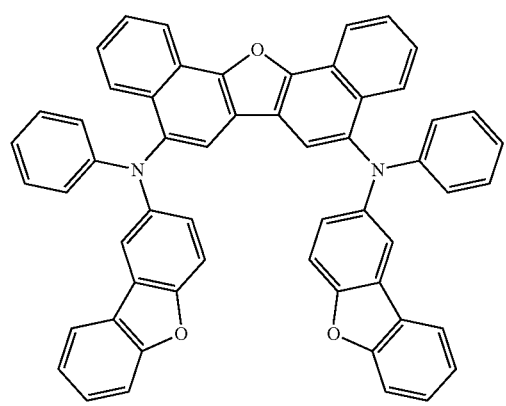

-continued
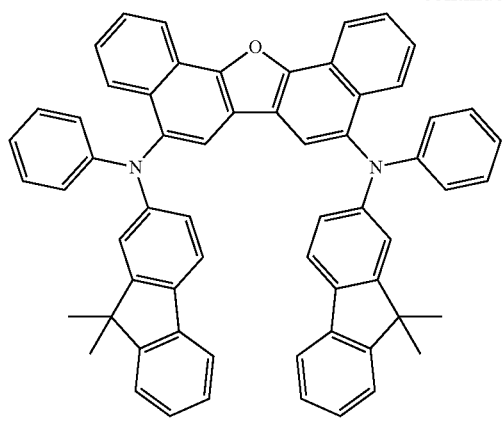
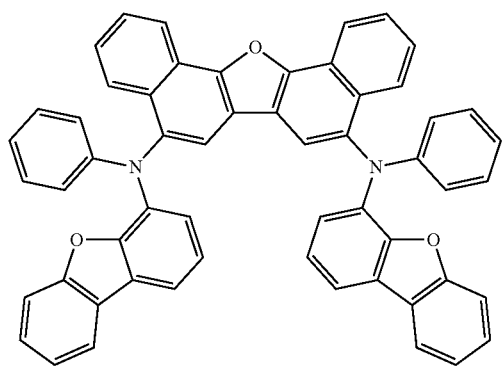
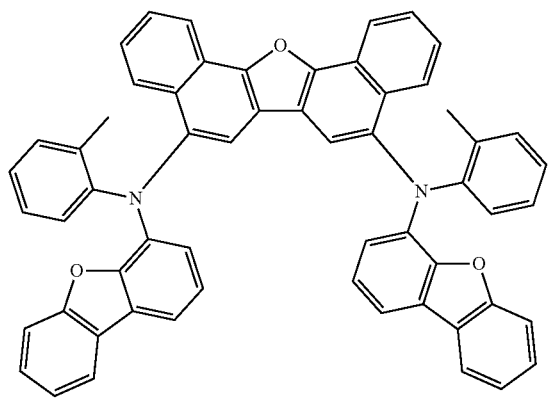
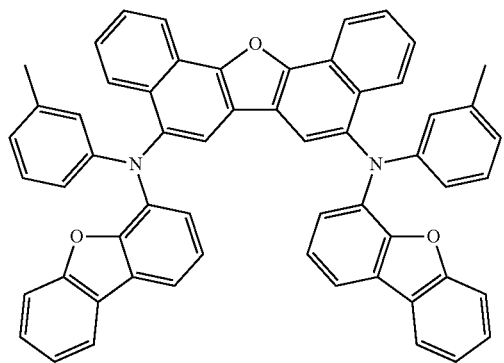

783
-continued
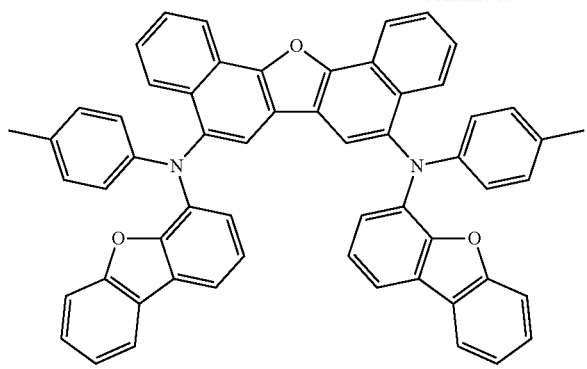
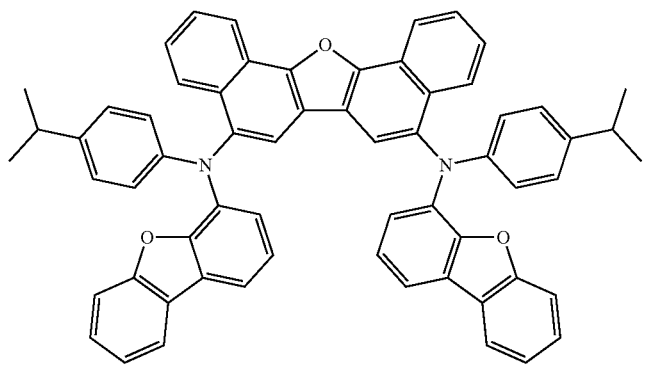
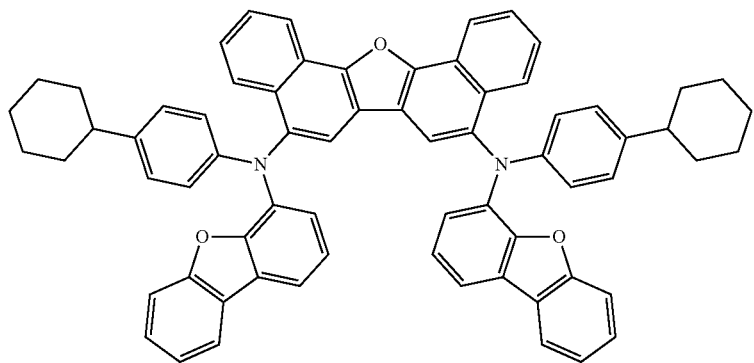
784
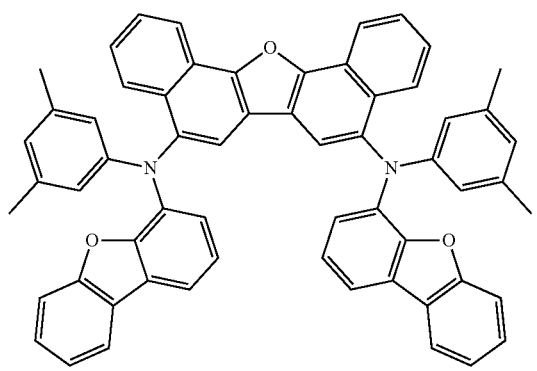

-continued
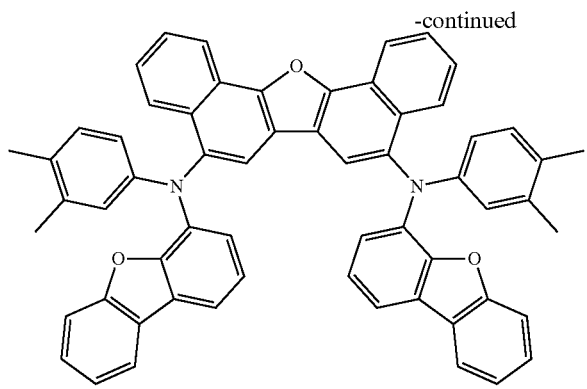
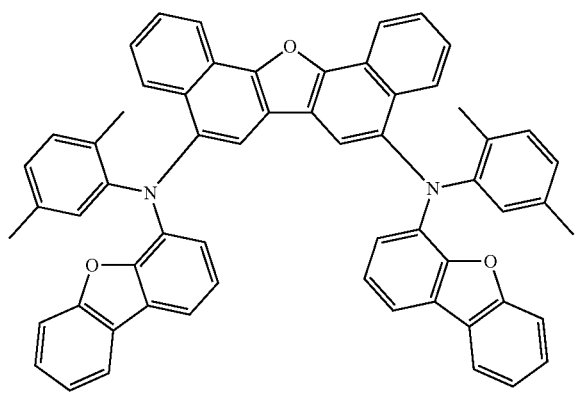
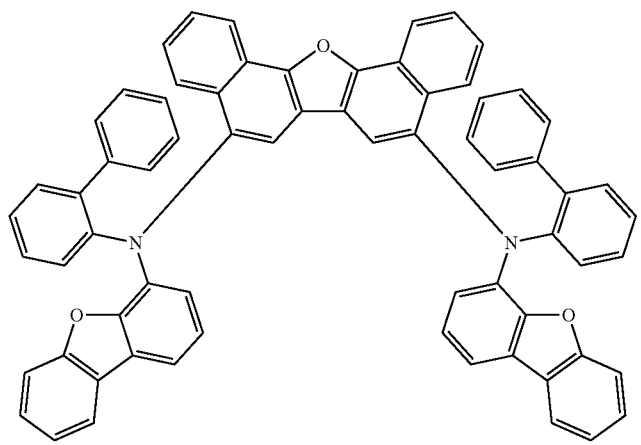
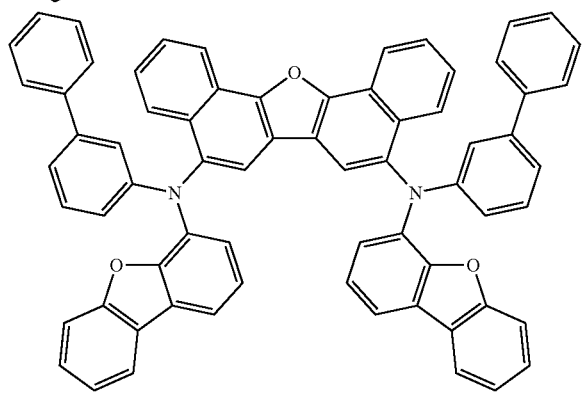

-continued
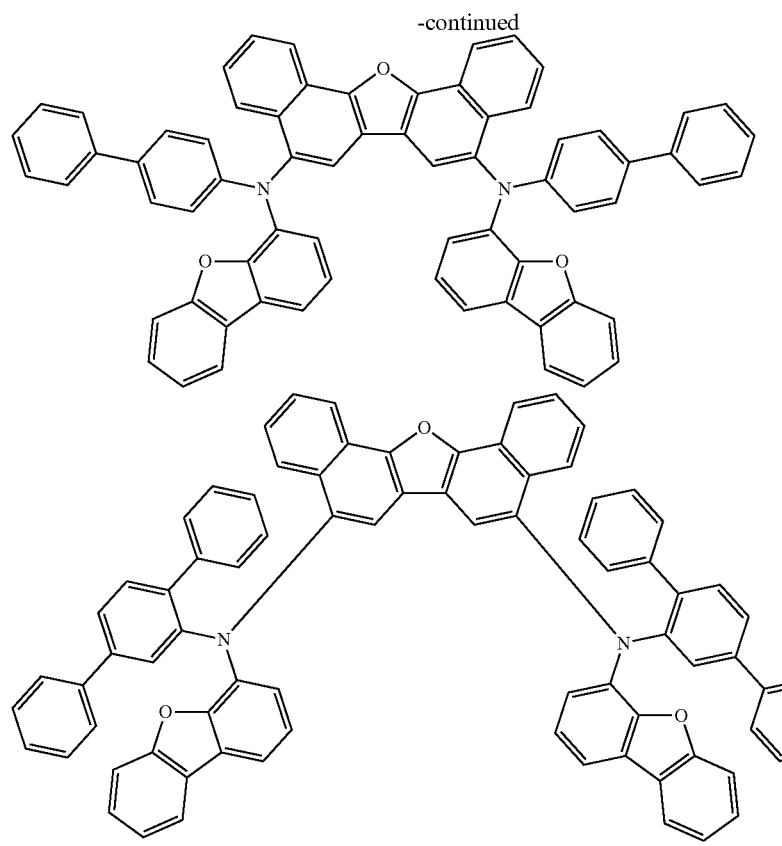
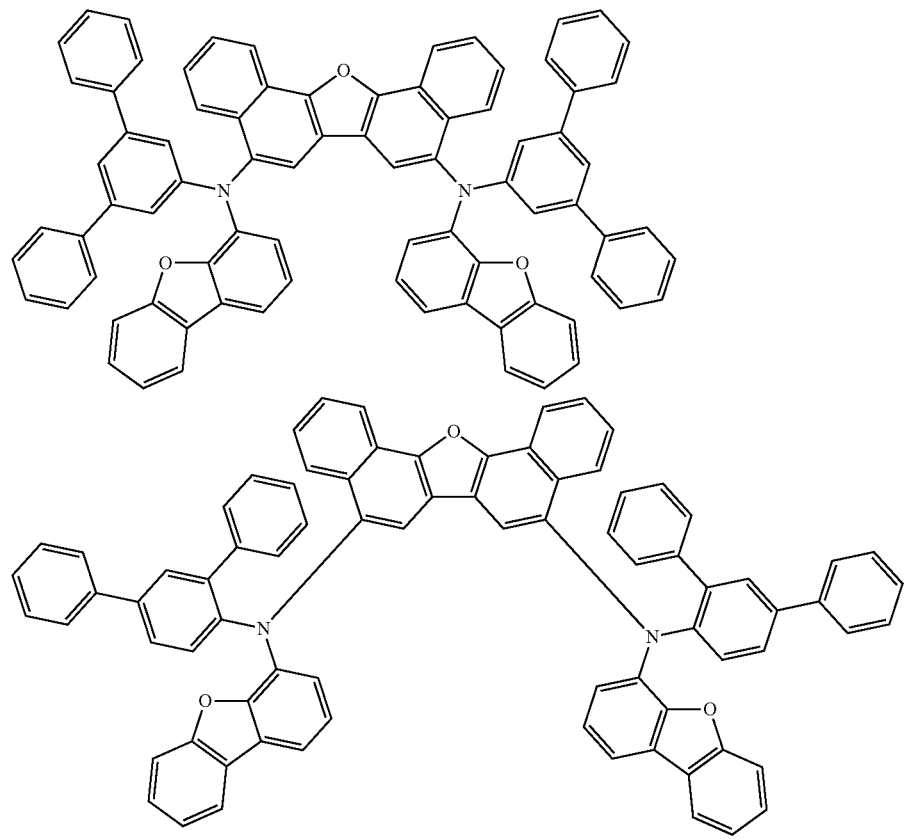

-continued
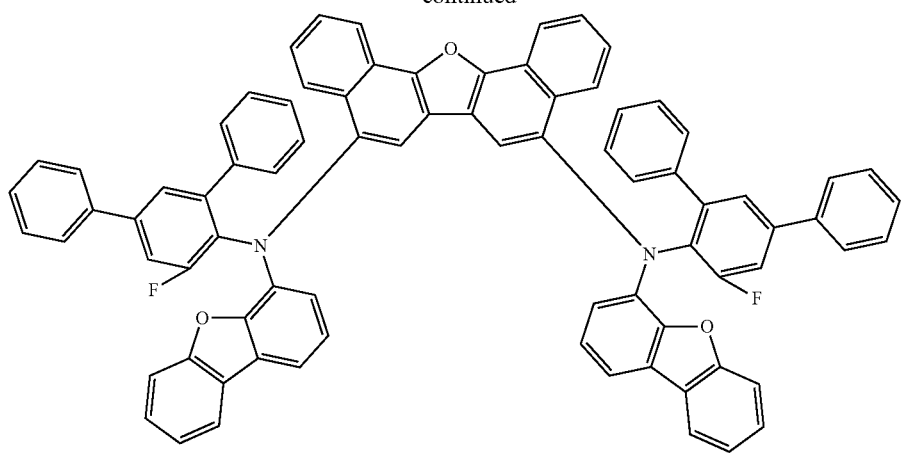
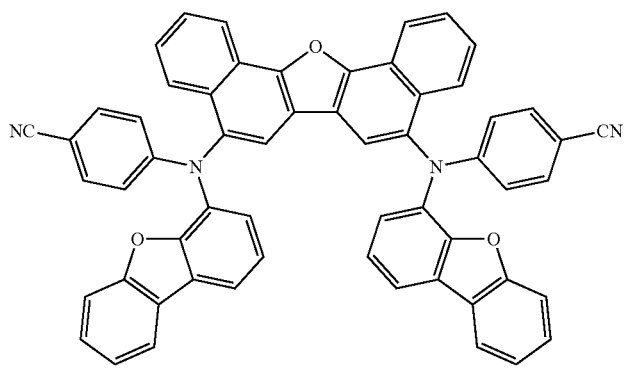
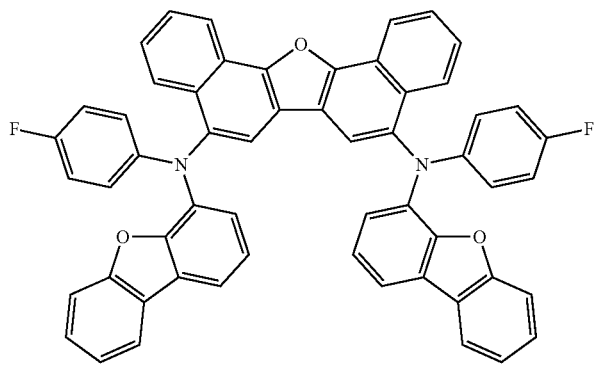
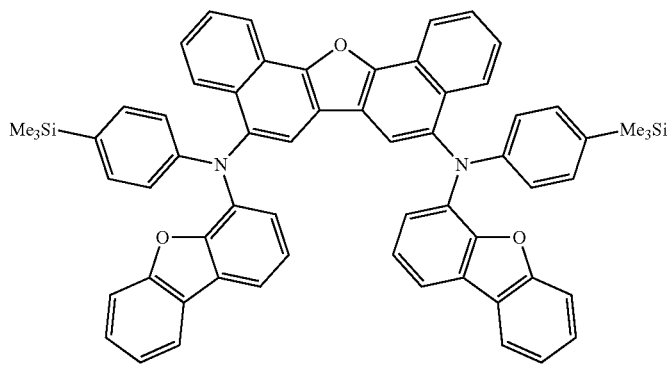

-continued
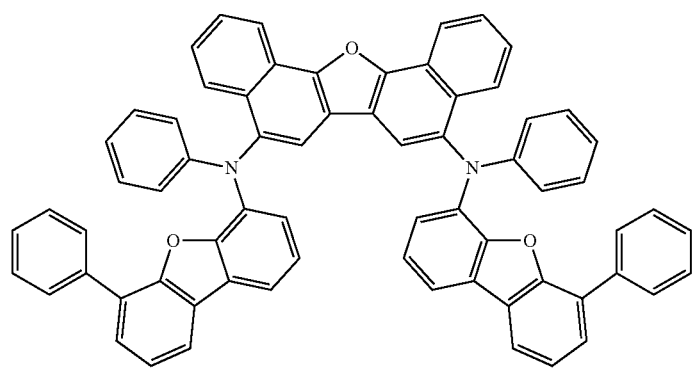
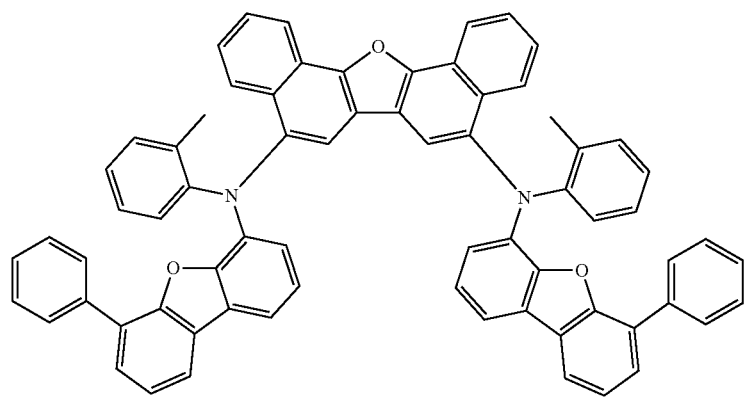
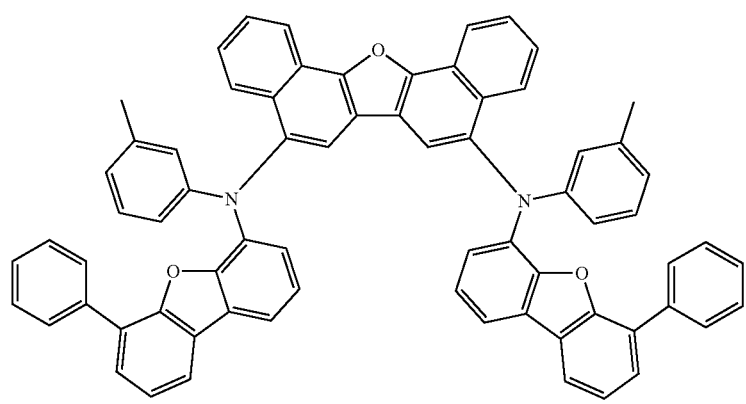
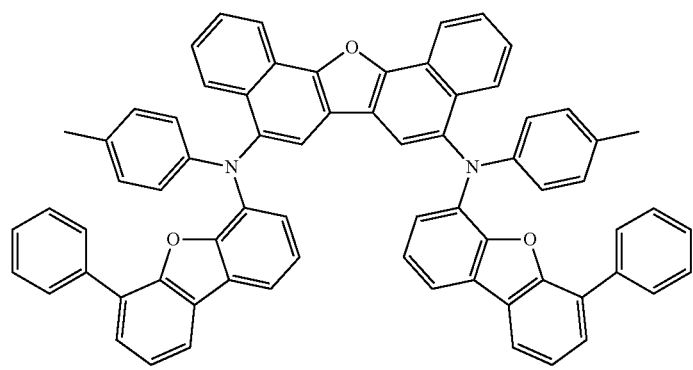

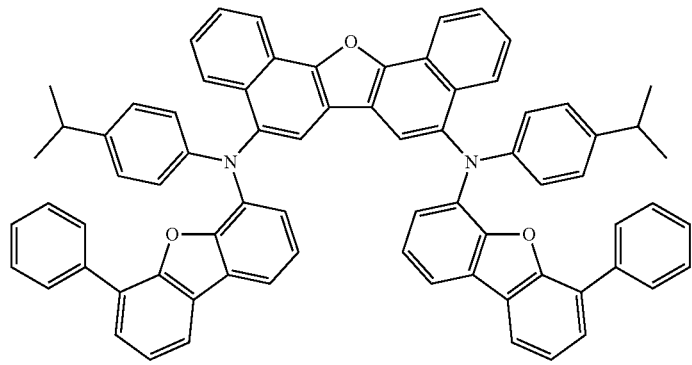
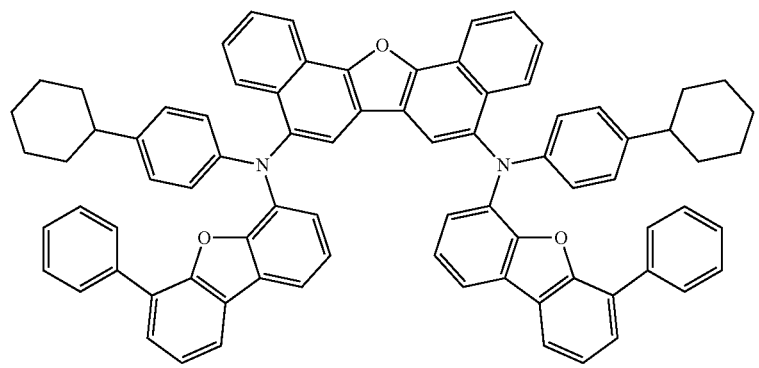
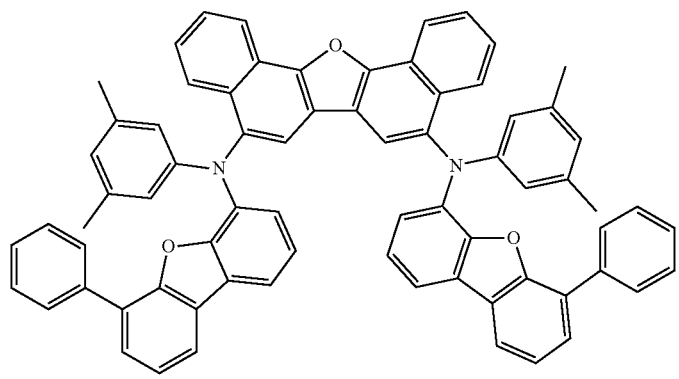
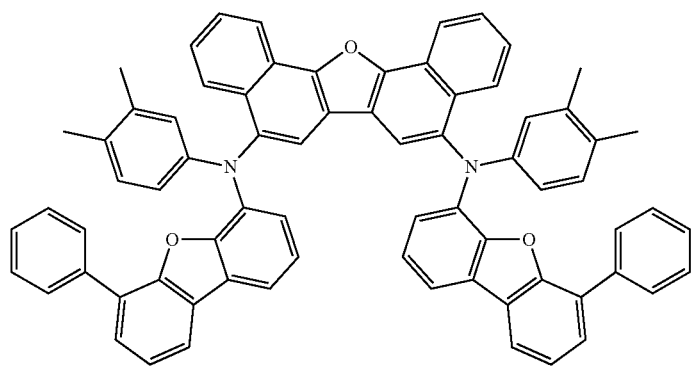

-continued
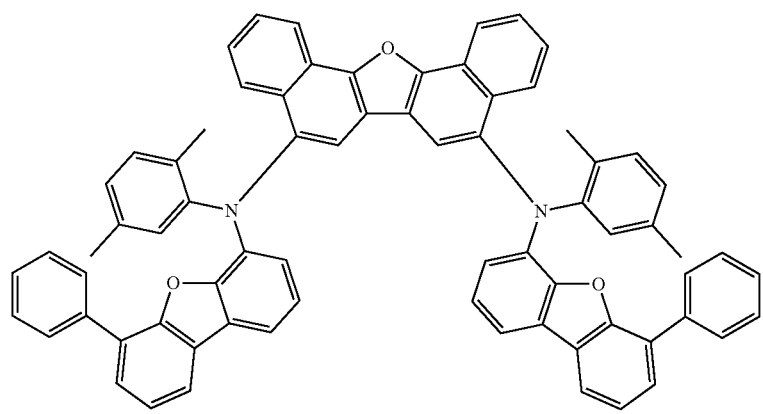
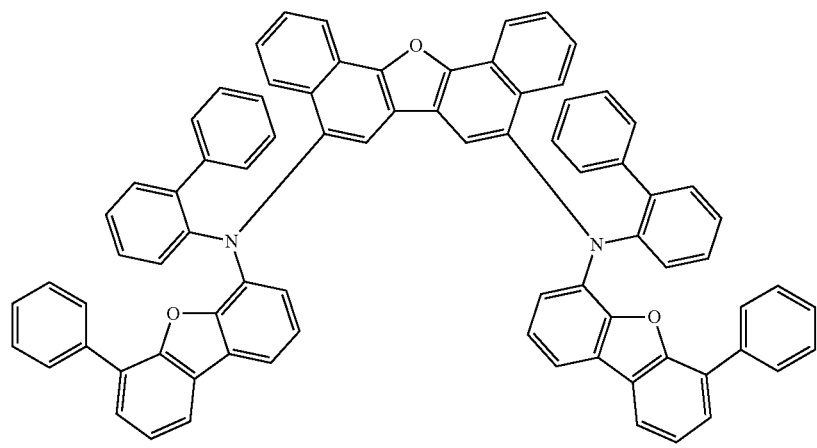
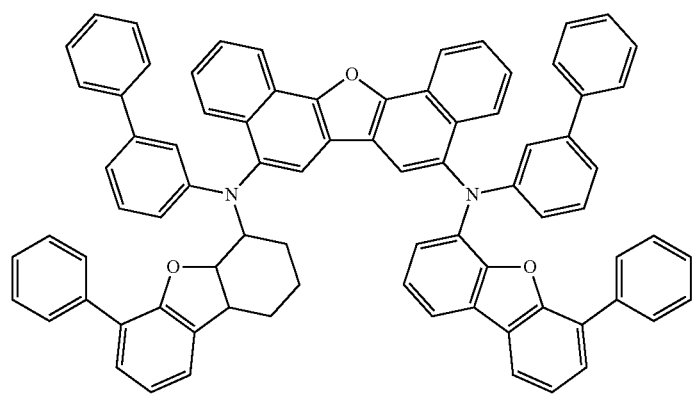
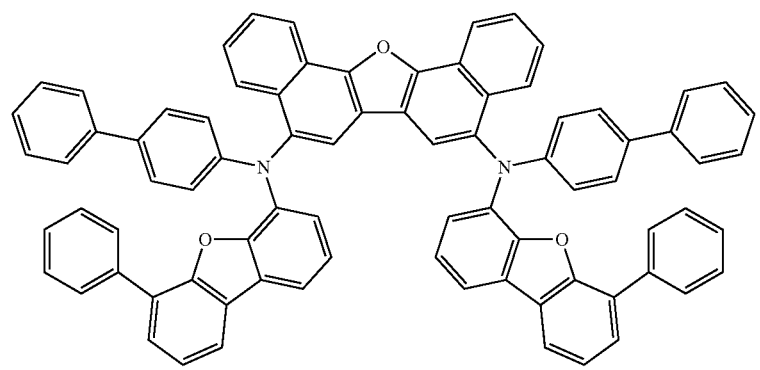

-continued
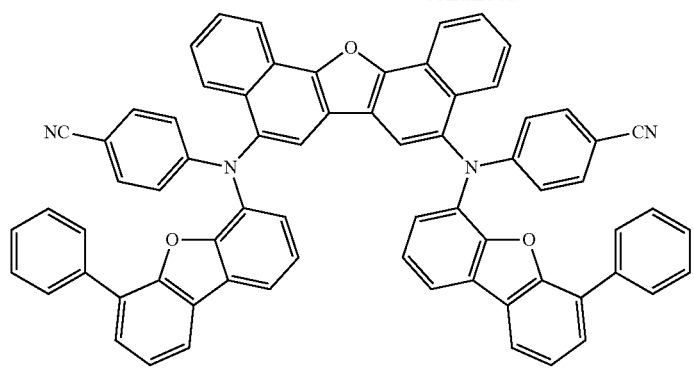
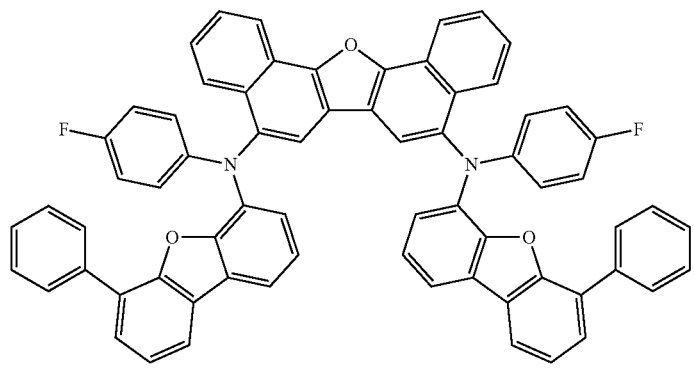
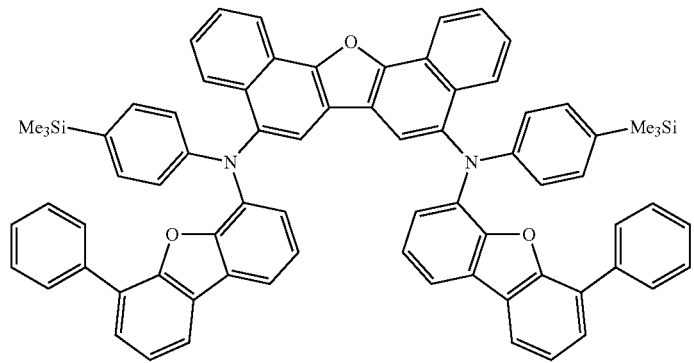
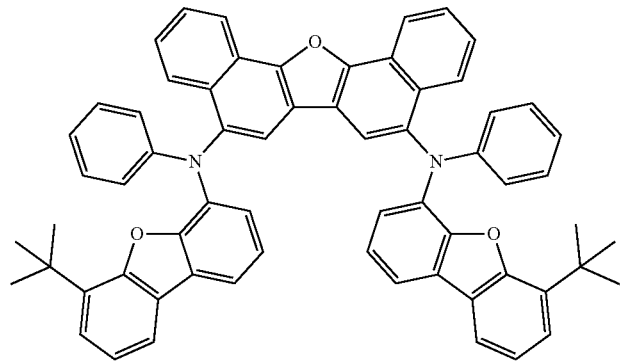

-continued
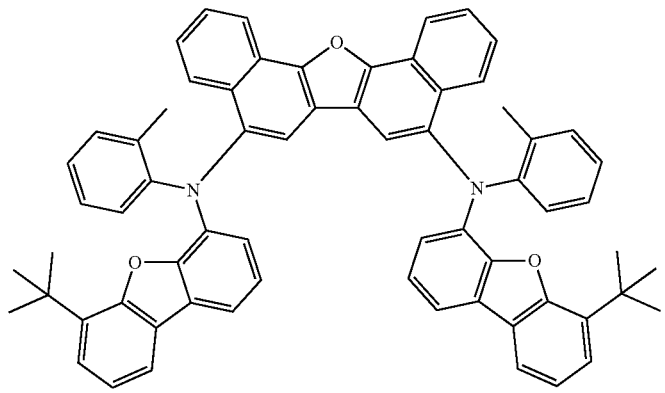
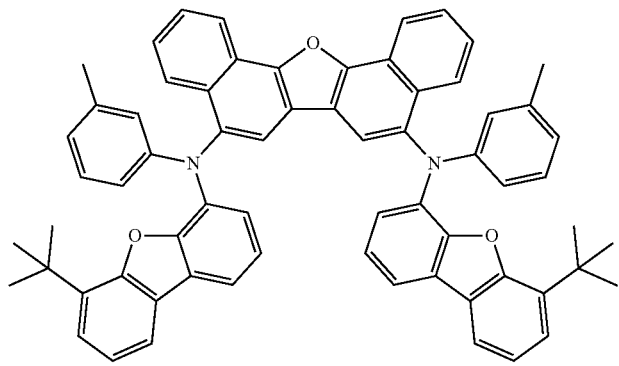
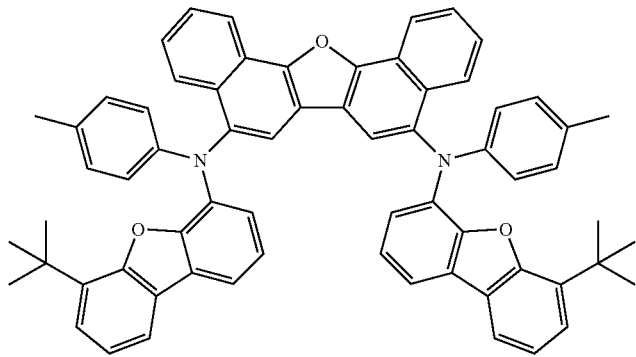
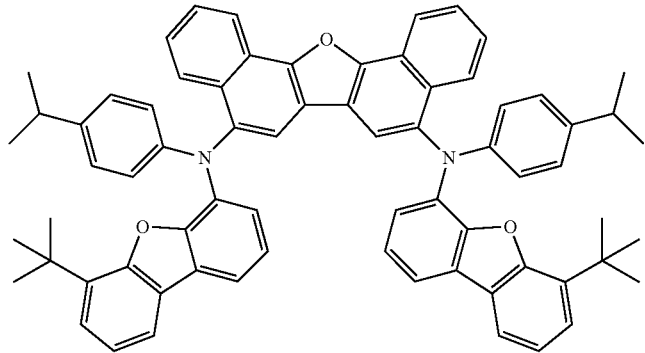

801
-continued
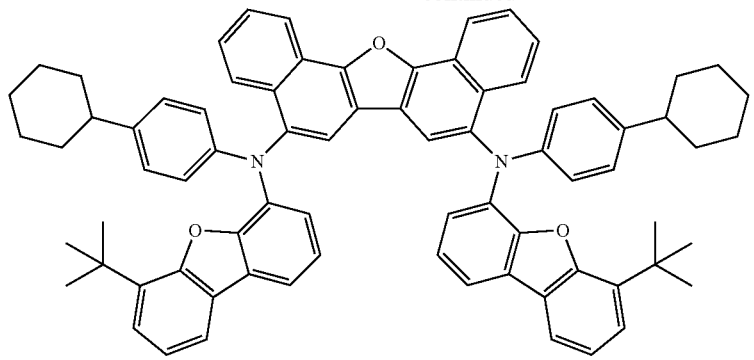
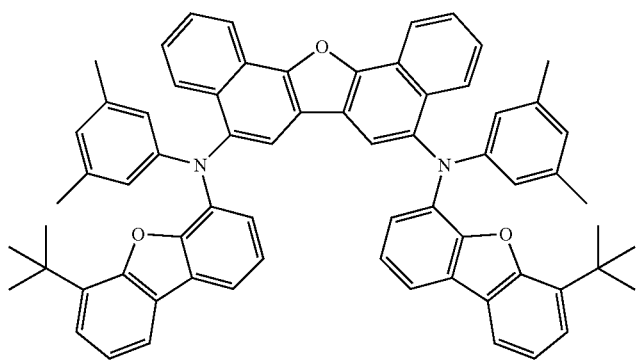
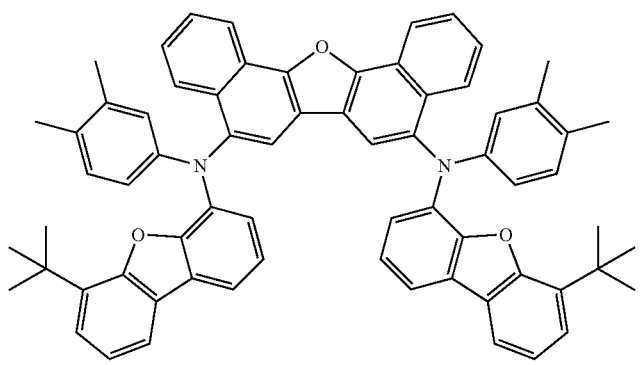
802
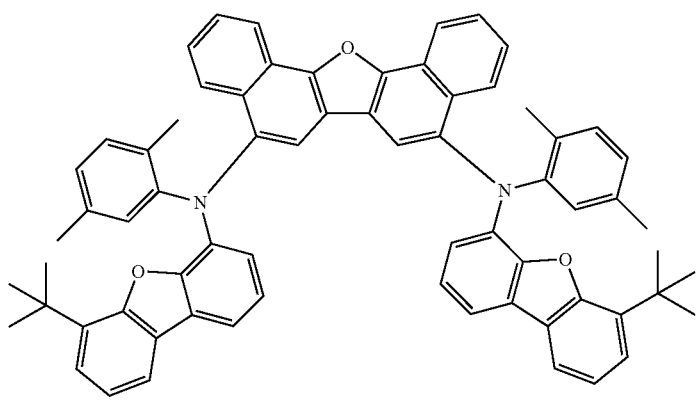

803
-continued
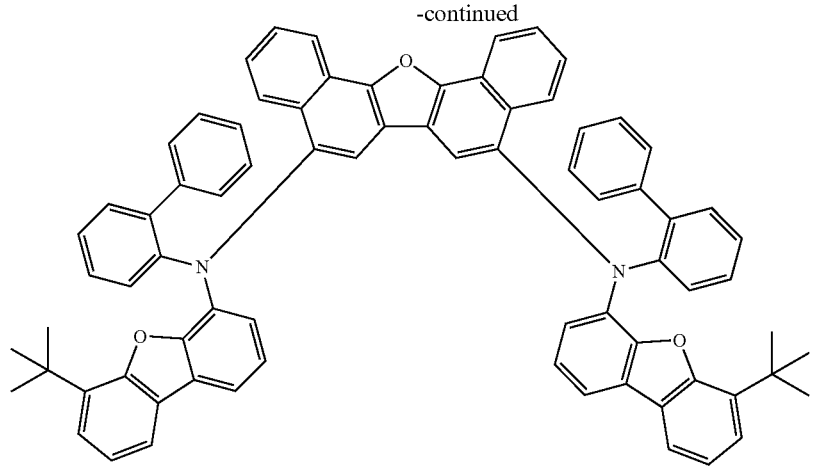
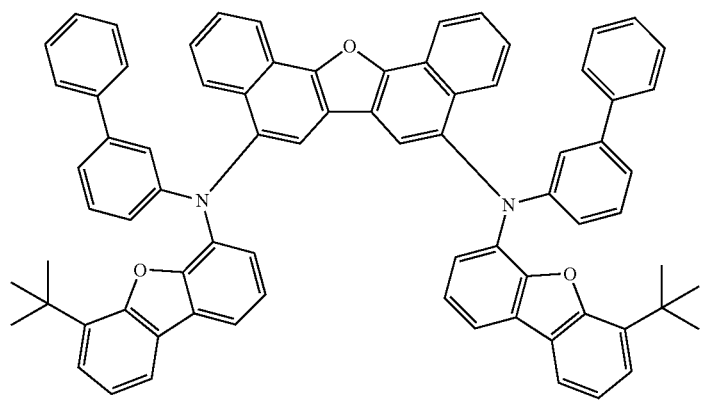
804
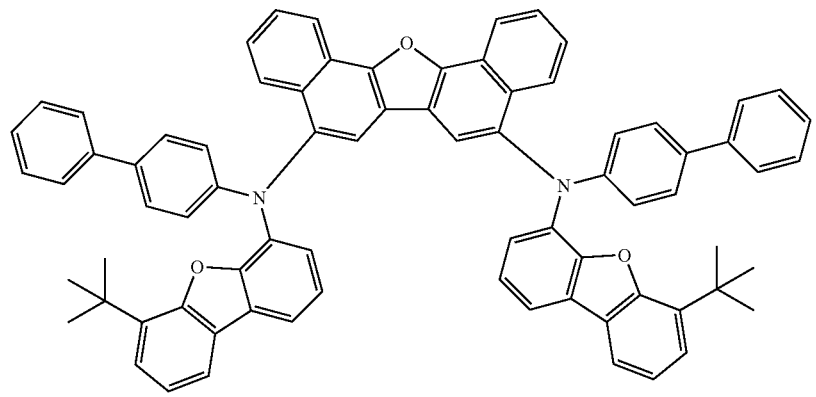
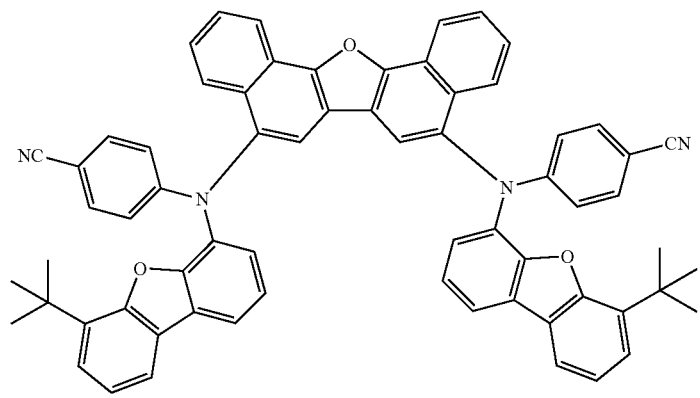

805
-continued
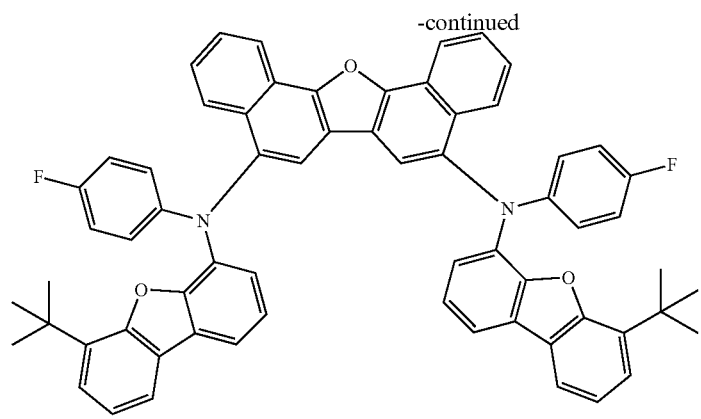
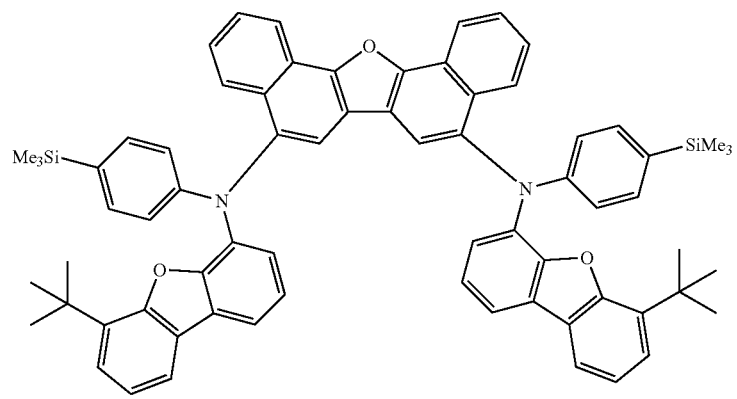
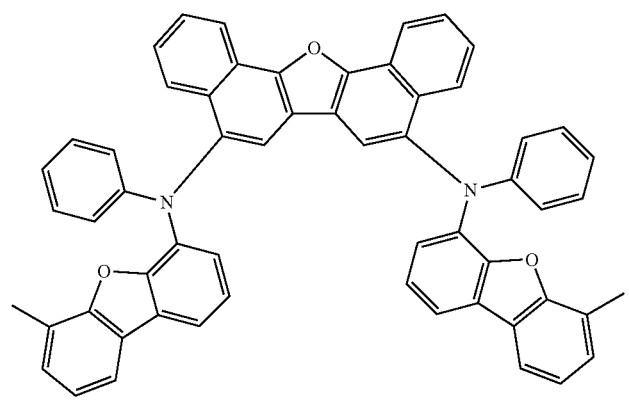
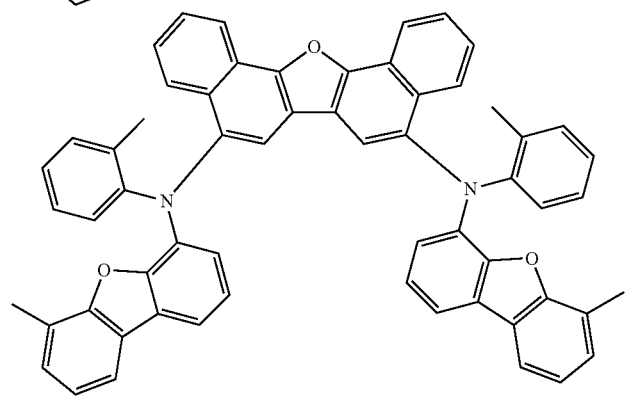
806

807 808
-continued
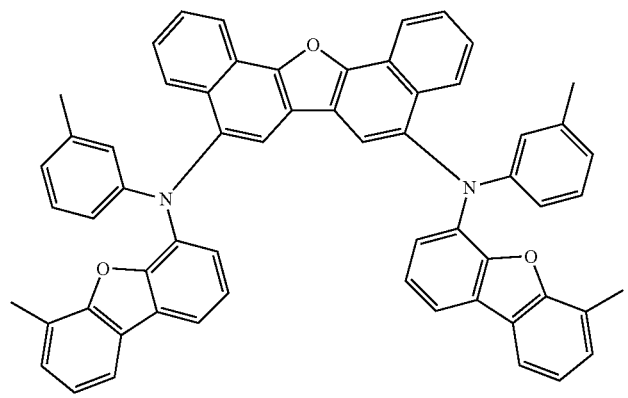
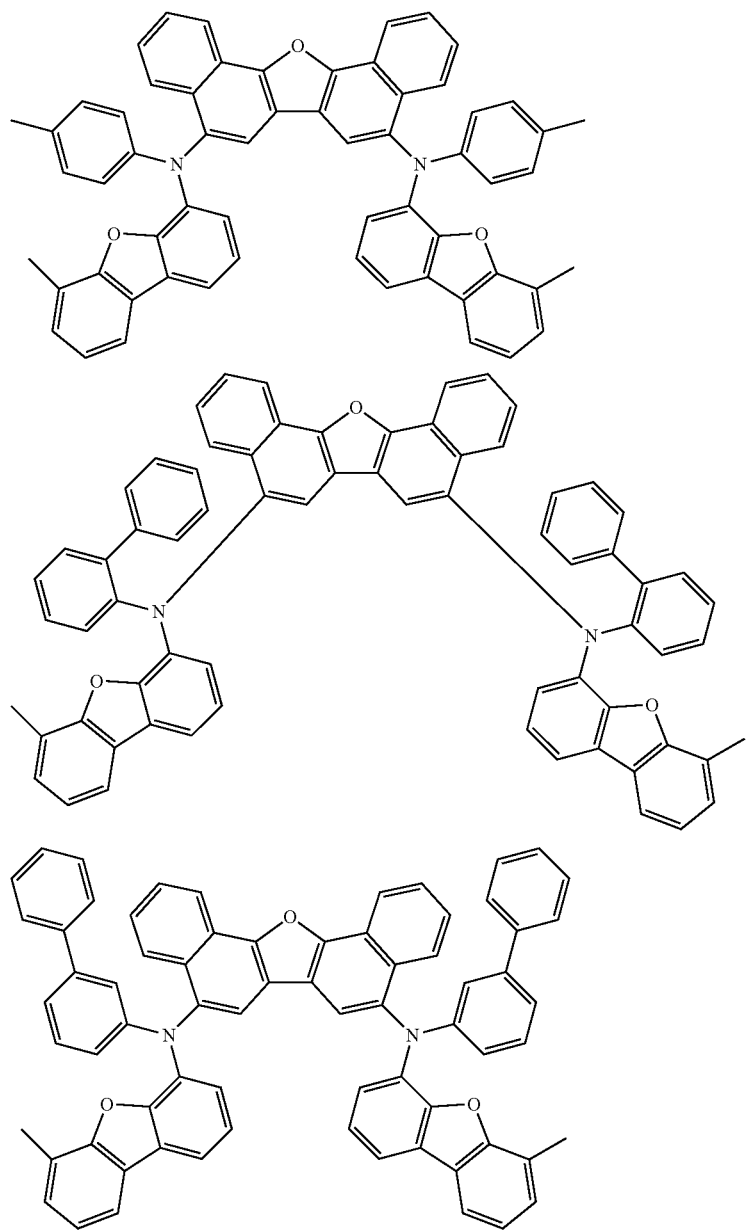

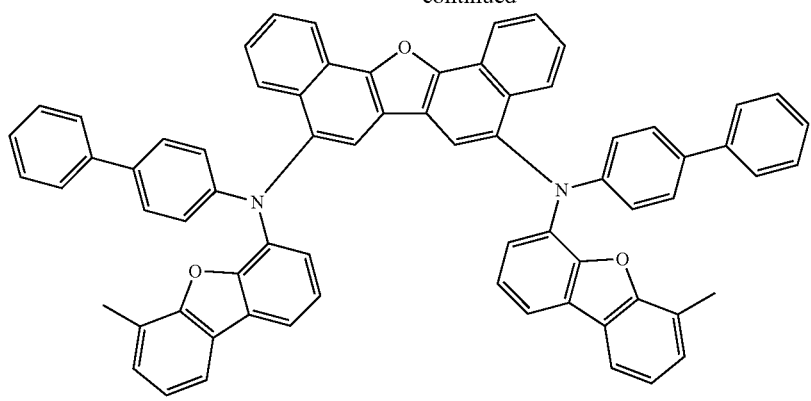
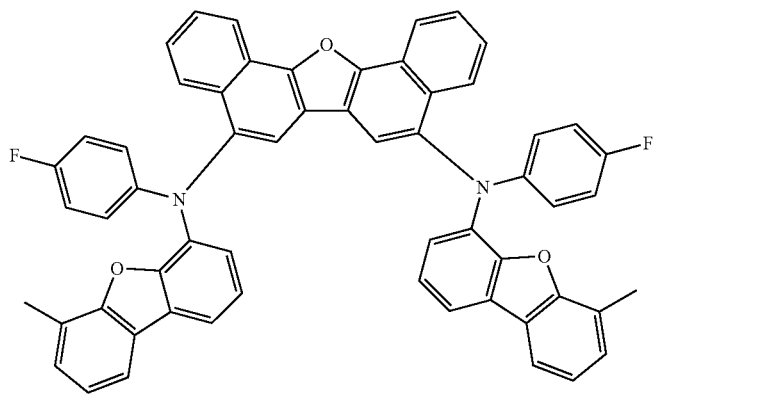
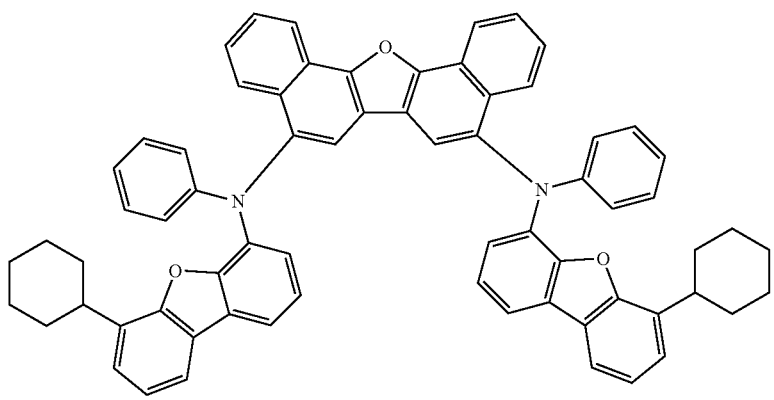
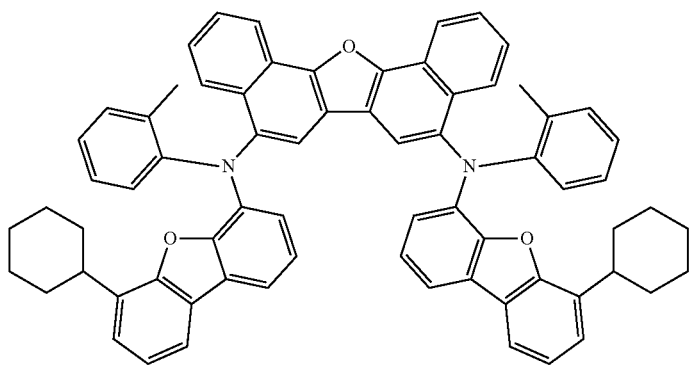

-continued
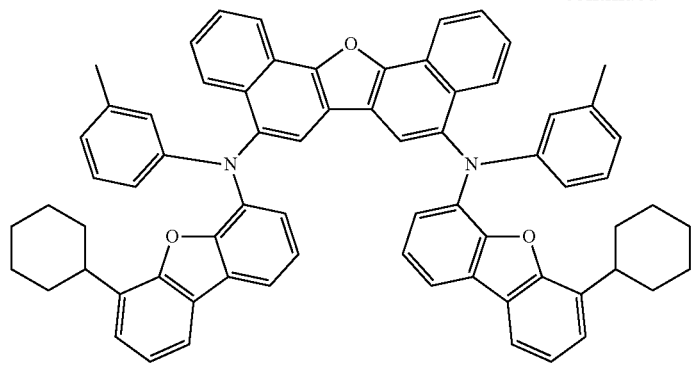
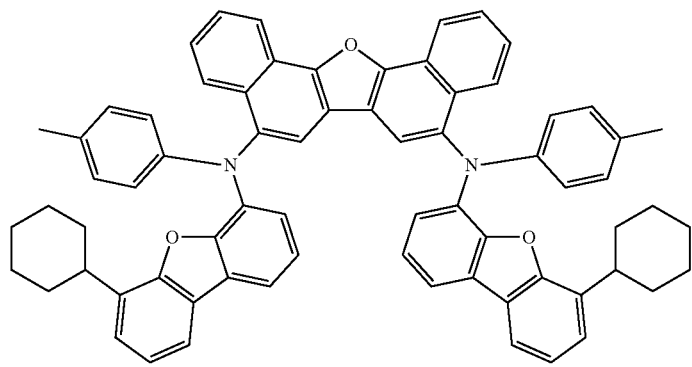
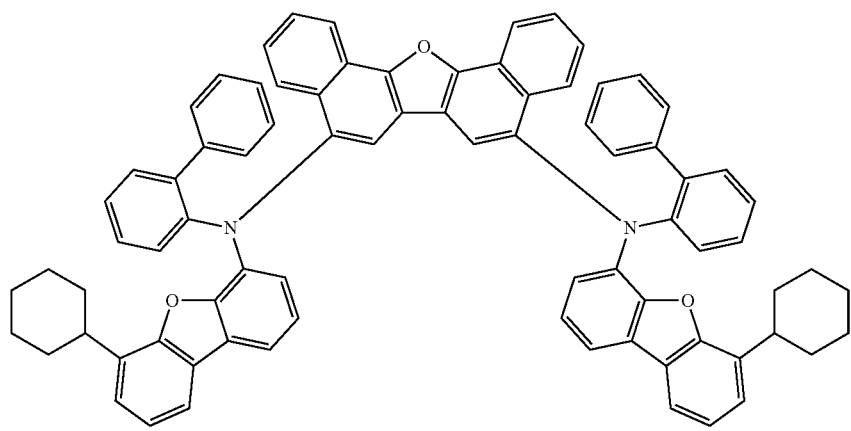
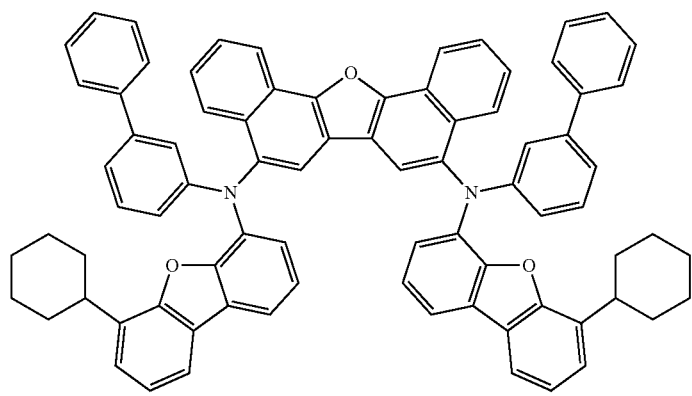

813    -continued    814
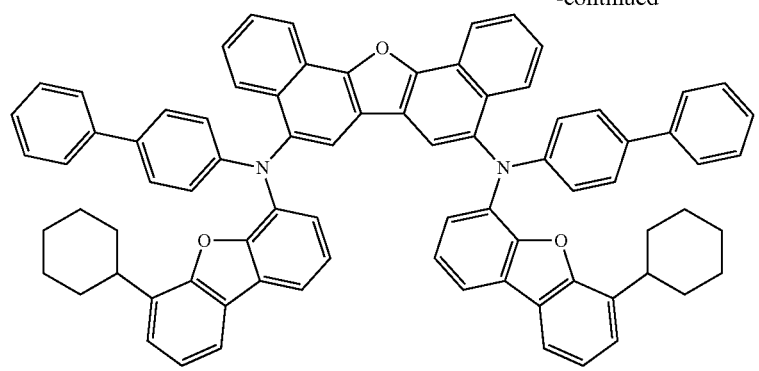
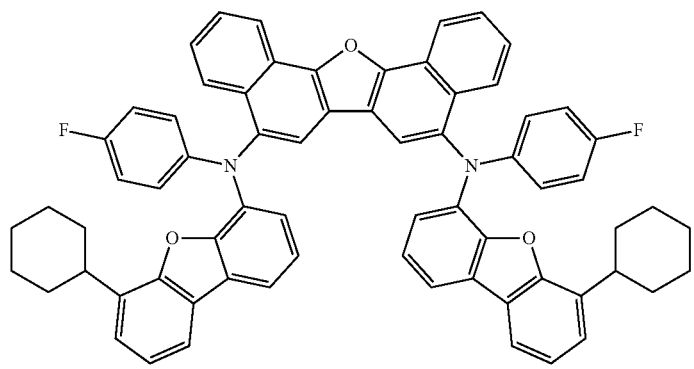
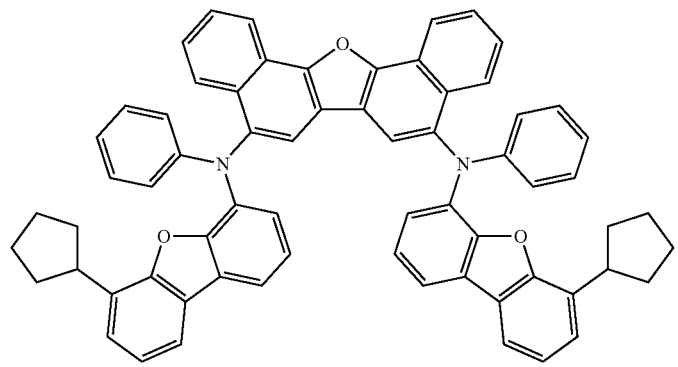
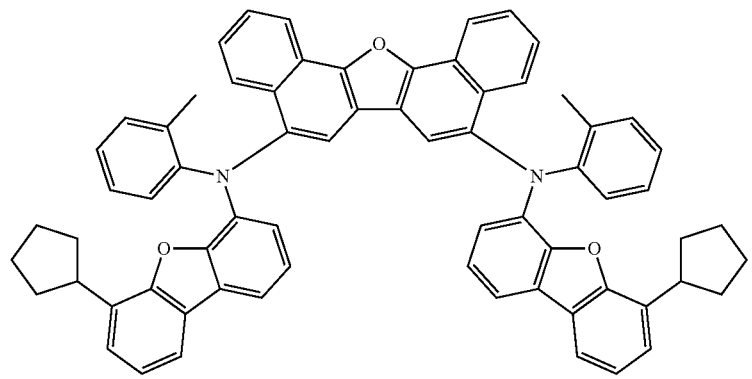

815
816
-continued
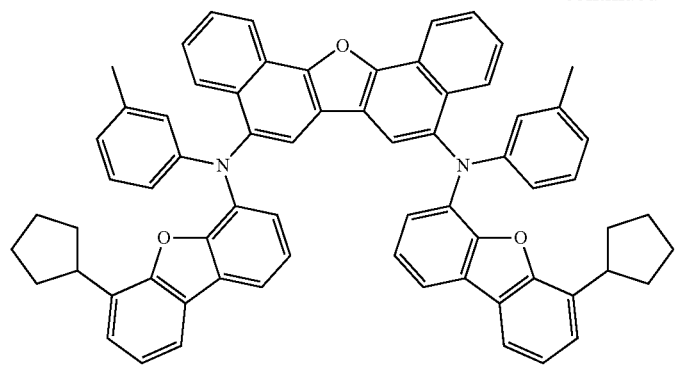
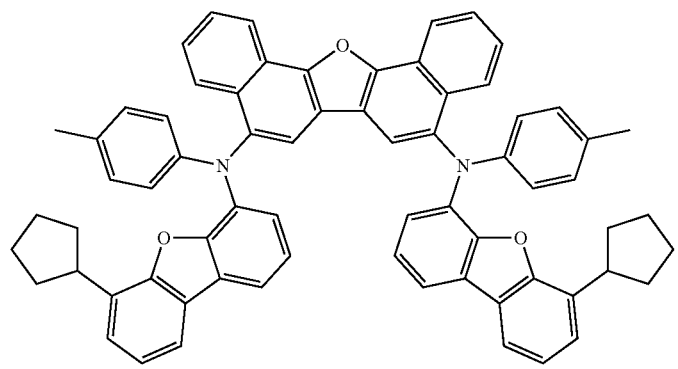
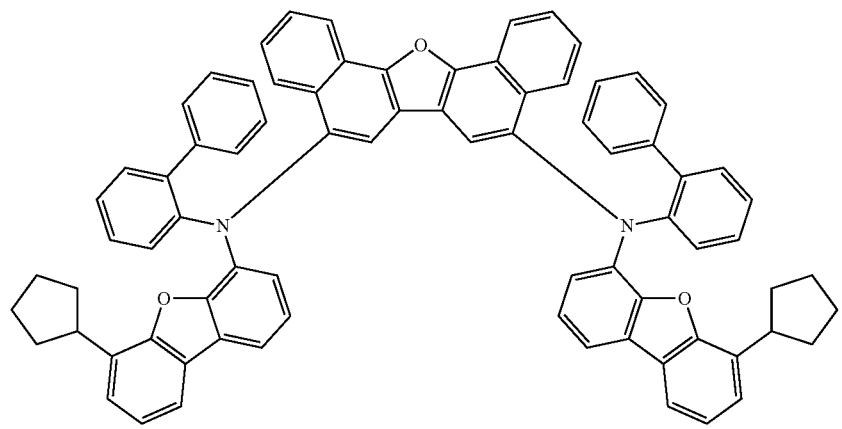
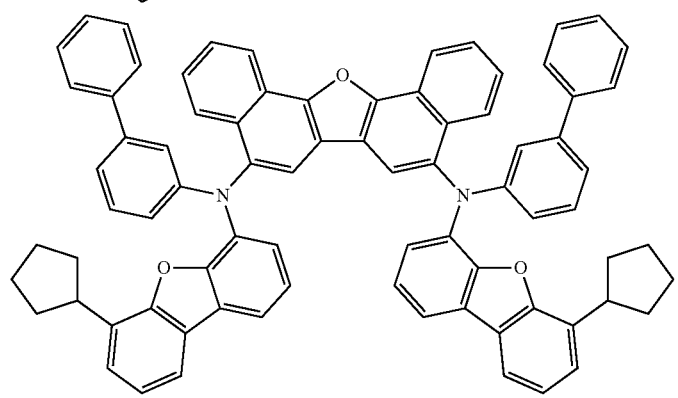

817
-continued
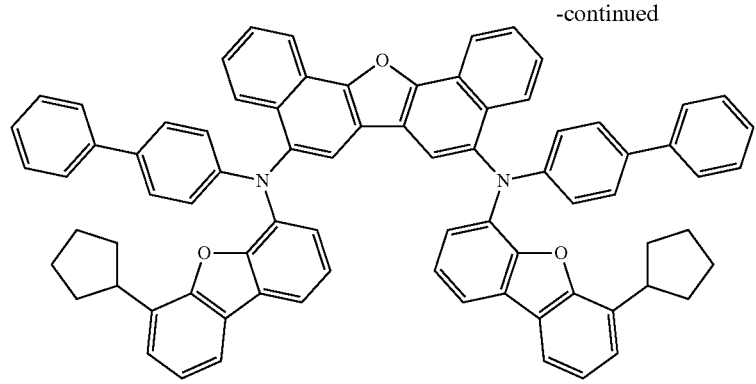
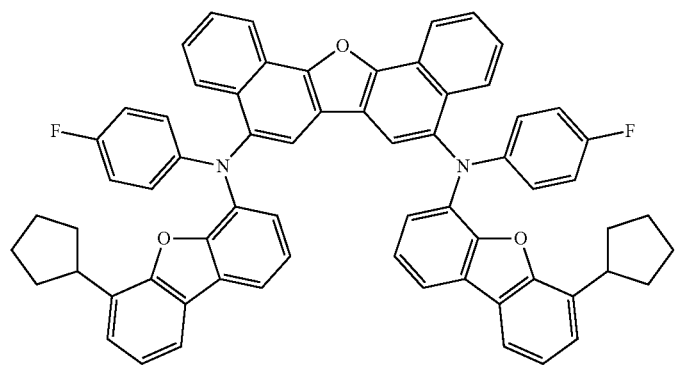
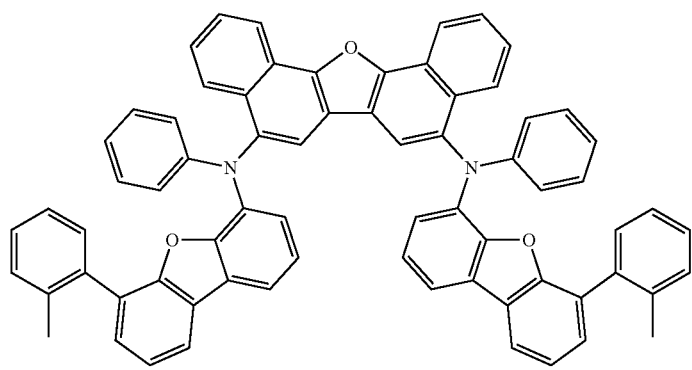
818
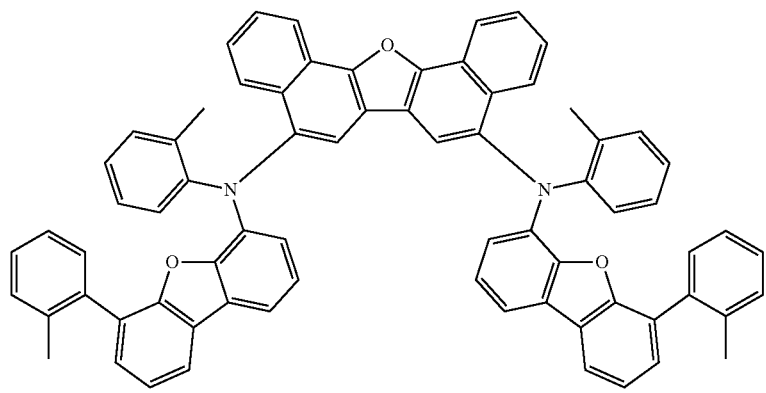

819                    820
-continued
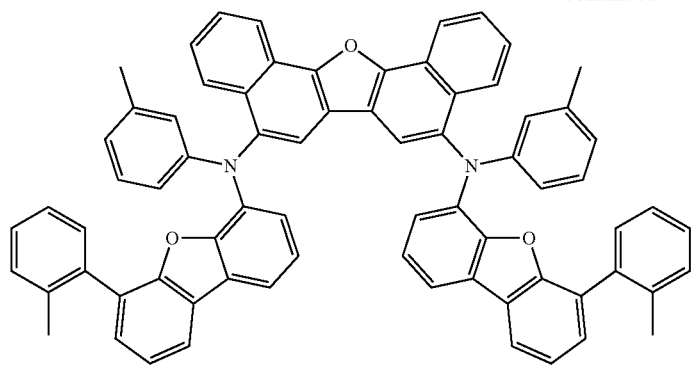
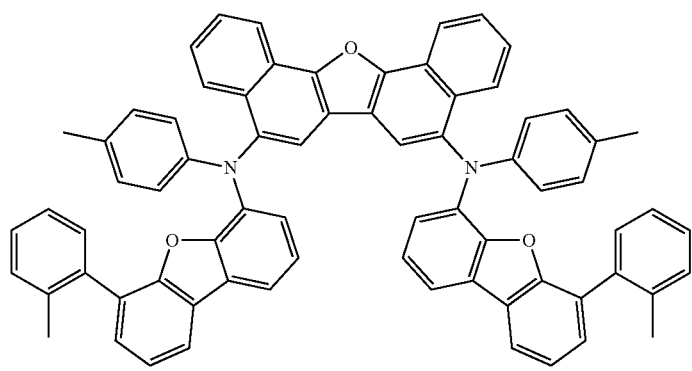
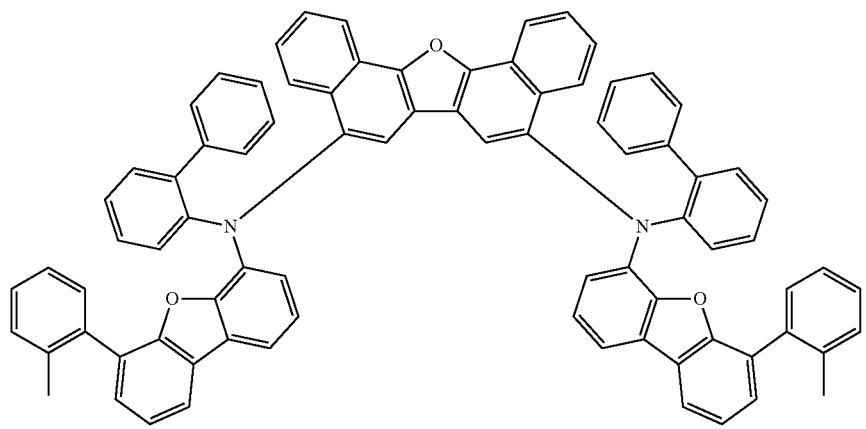
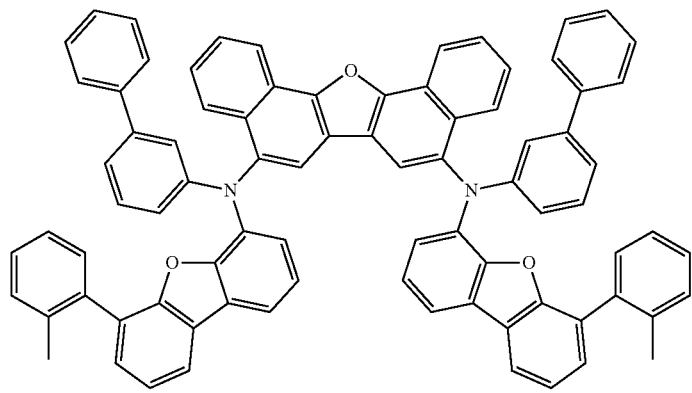

821
822
-continued
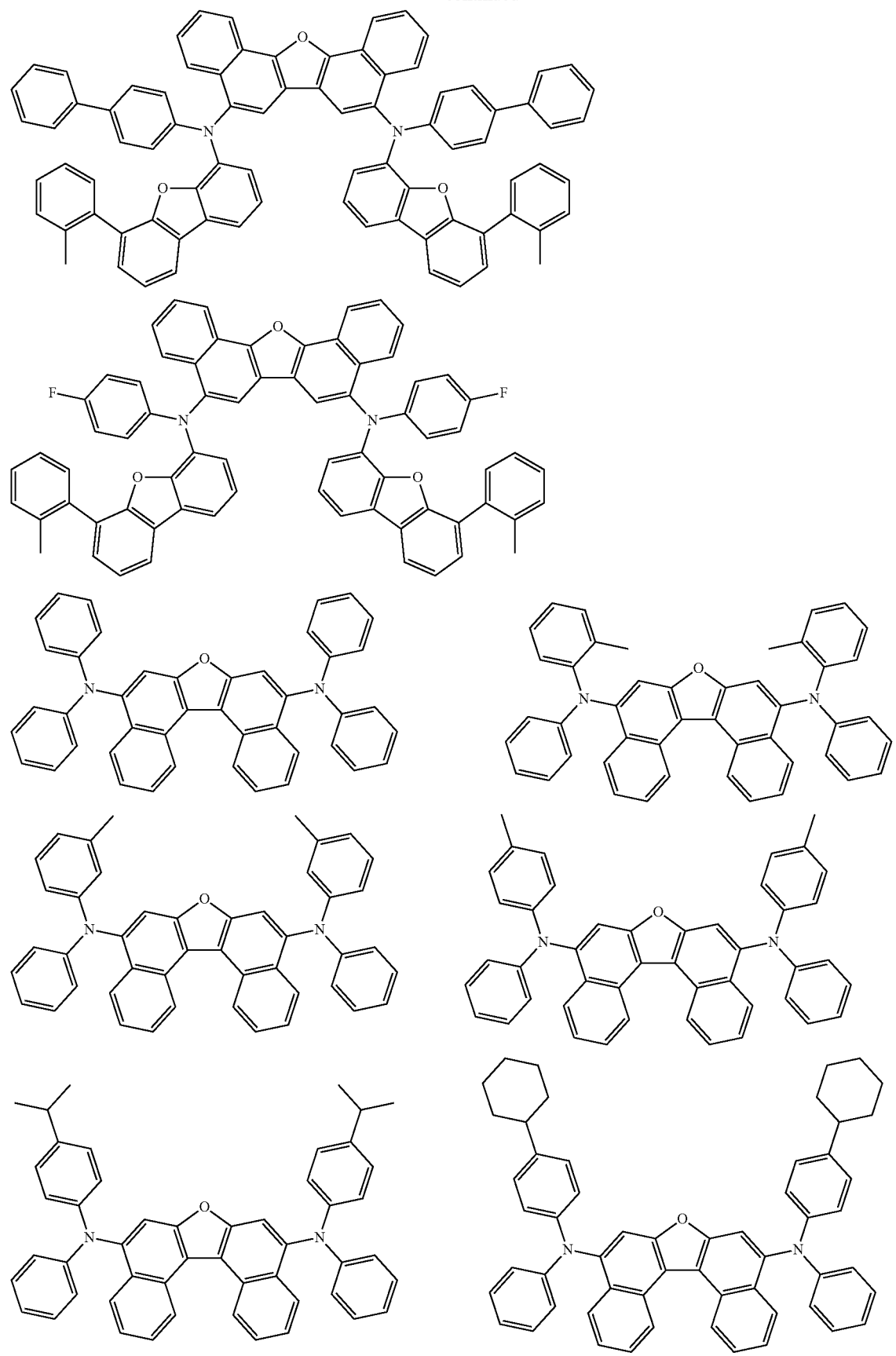

-continued
| 823 | 824 |
|---|---|
| 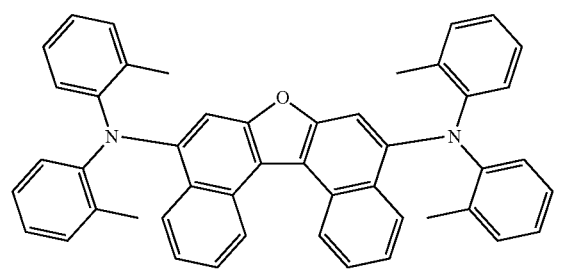 | 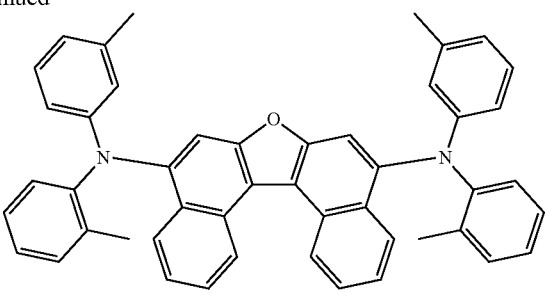 |
| 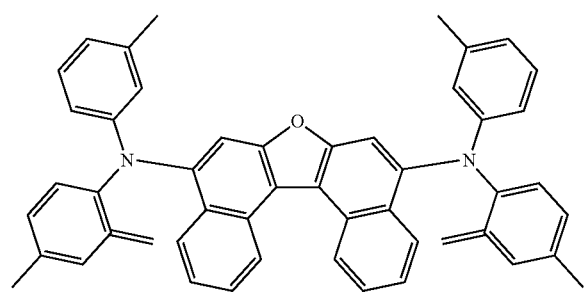 | 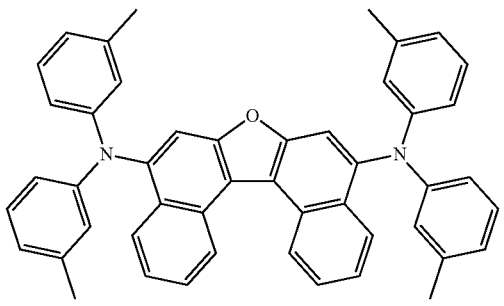 |
| 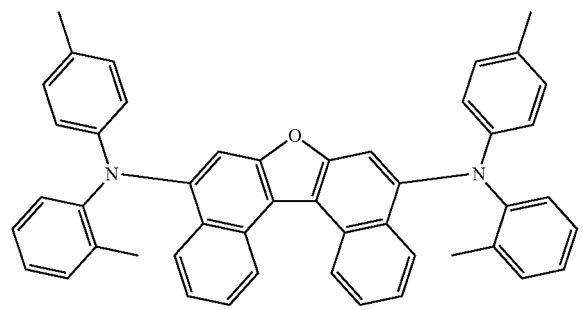 | 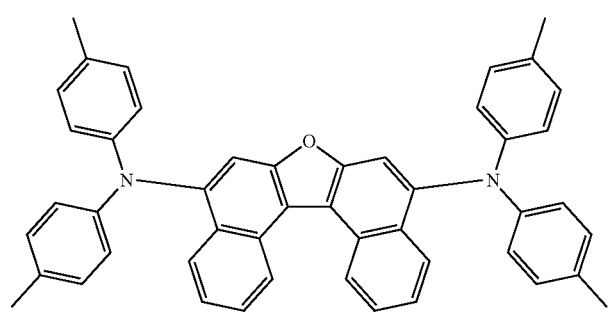 |
| 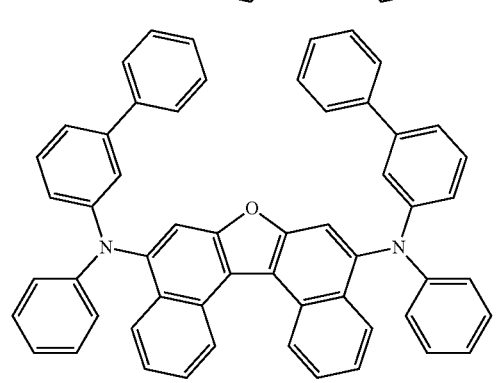 | 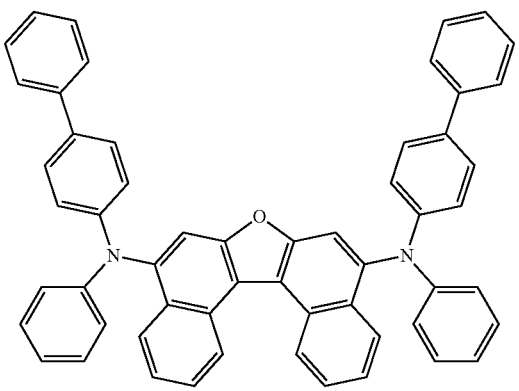 |
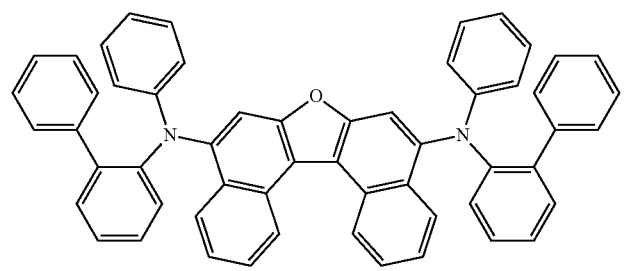

-continued
825 826
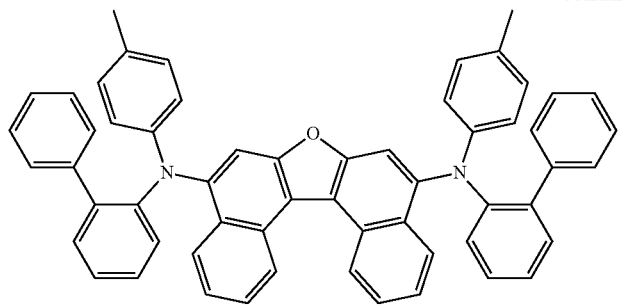 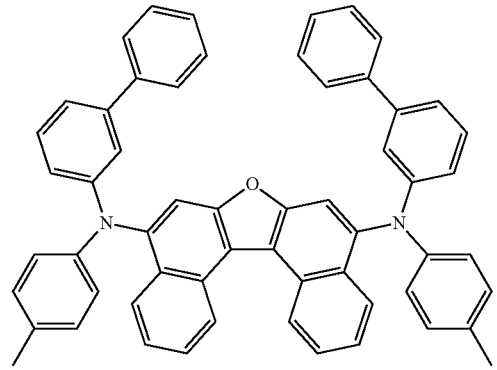
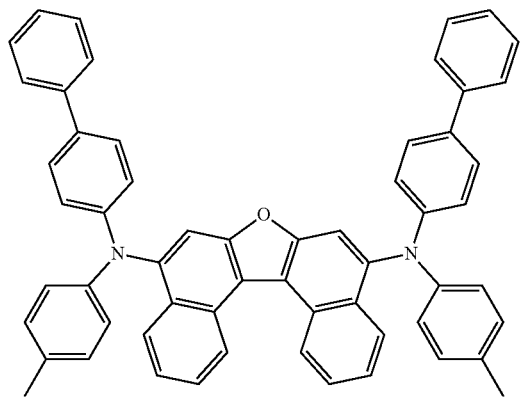 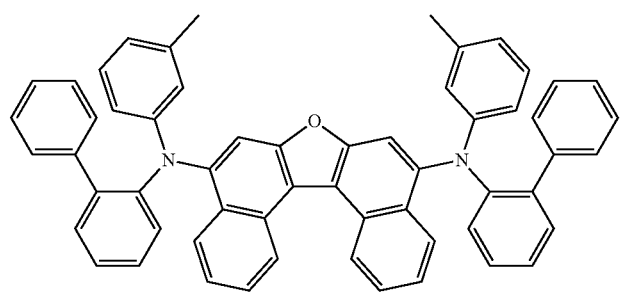
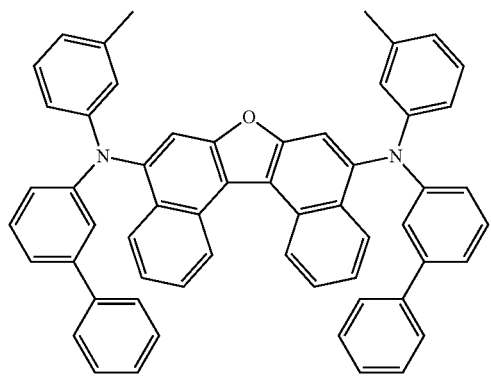 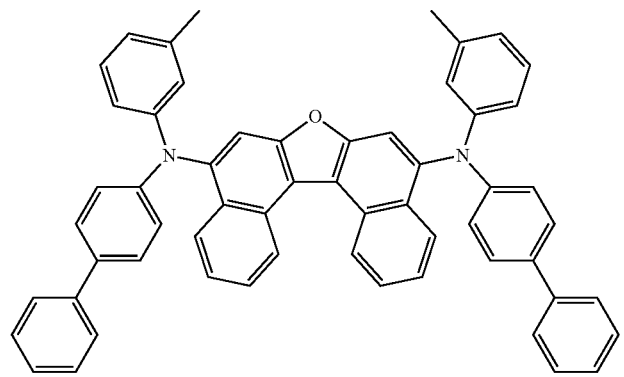
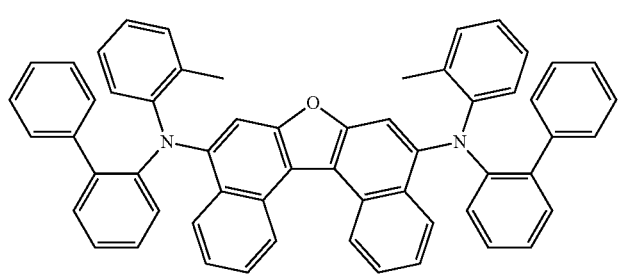 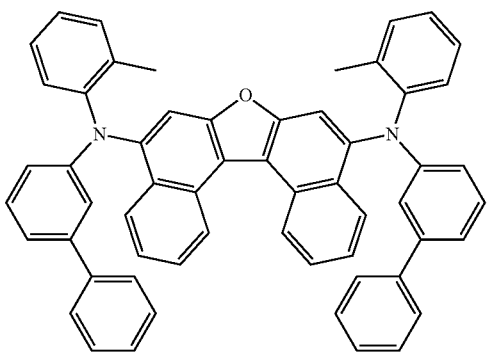

827
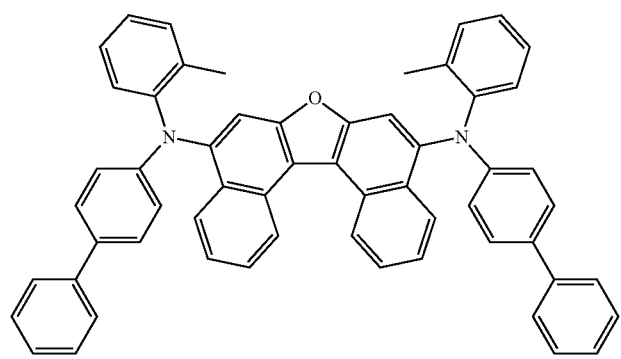
-continued
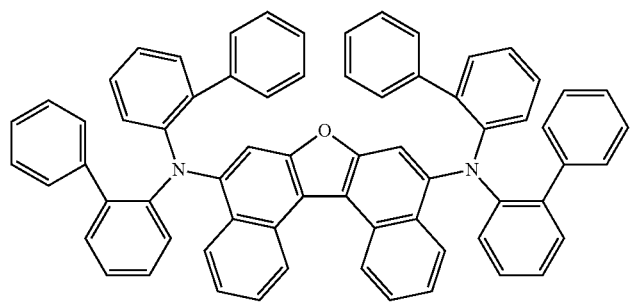
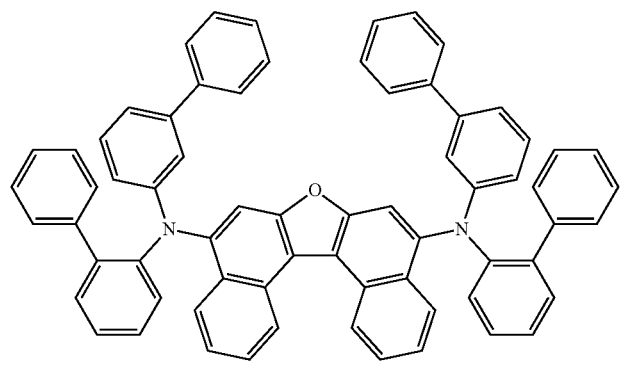
828
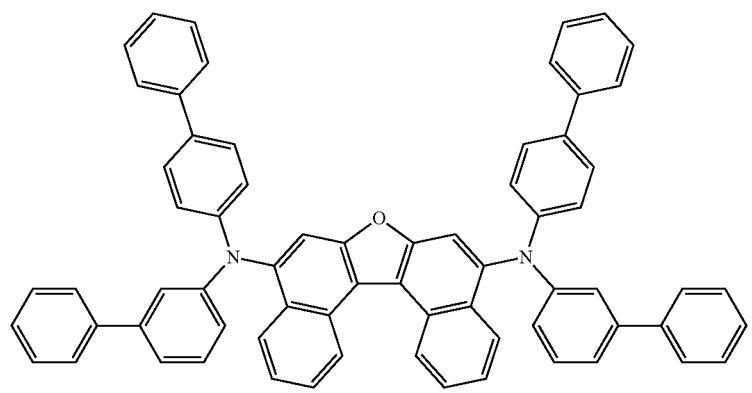

-continued
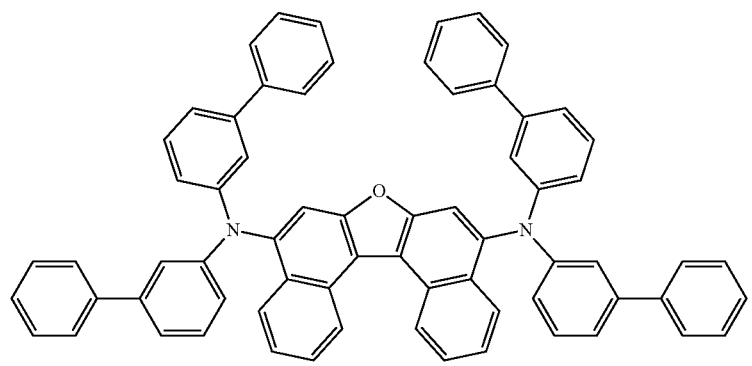
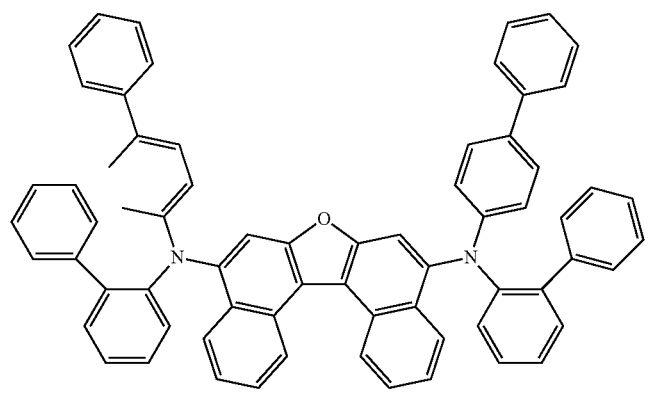
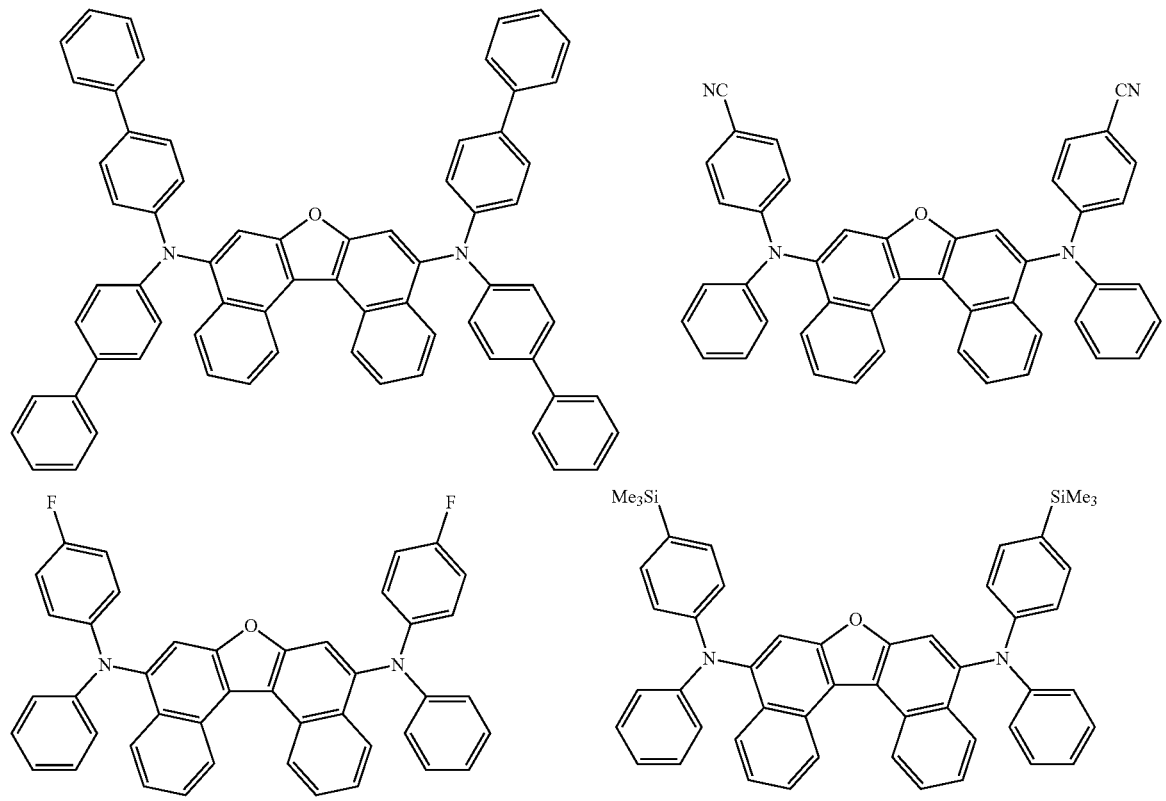

831
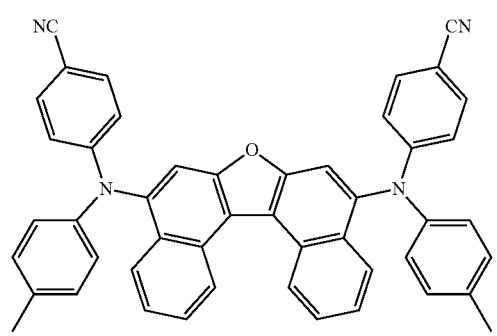
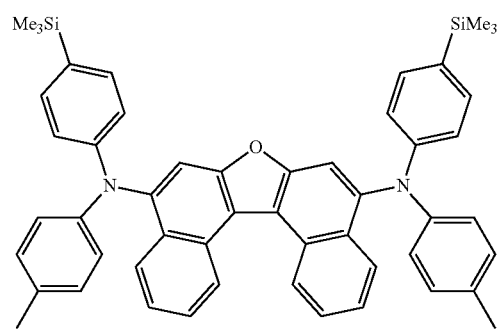
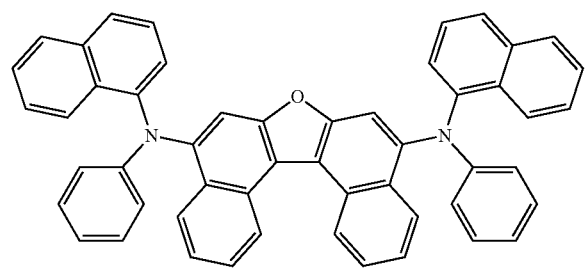
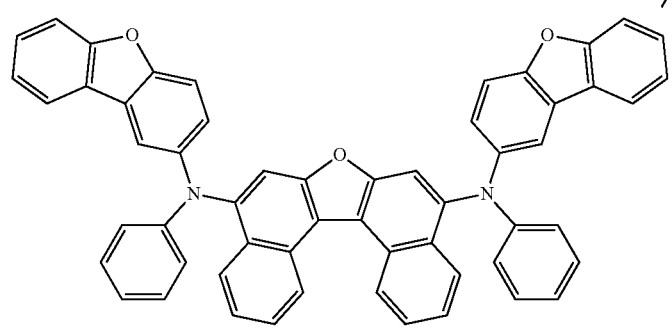
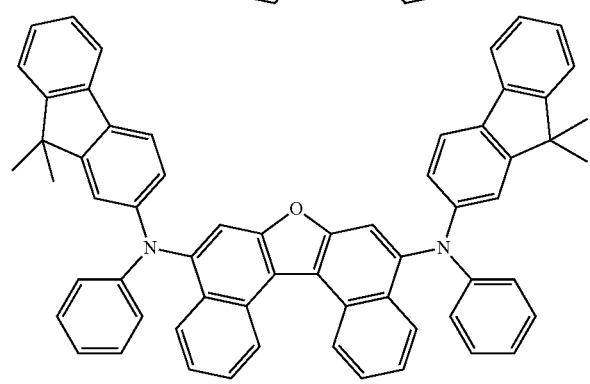
832
-continued
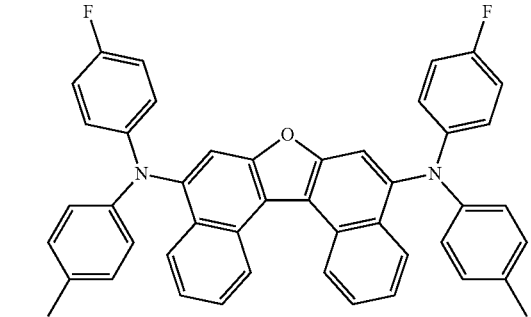
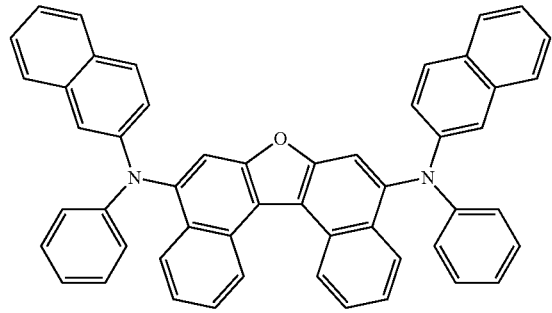
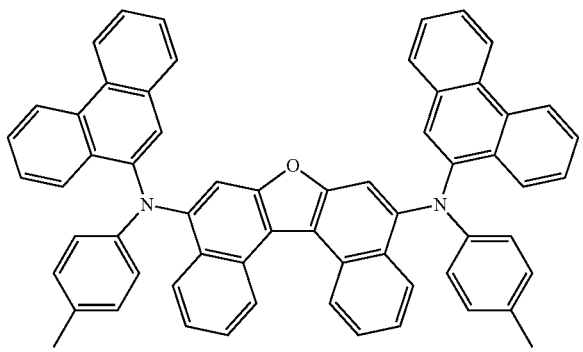

-continued
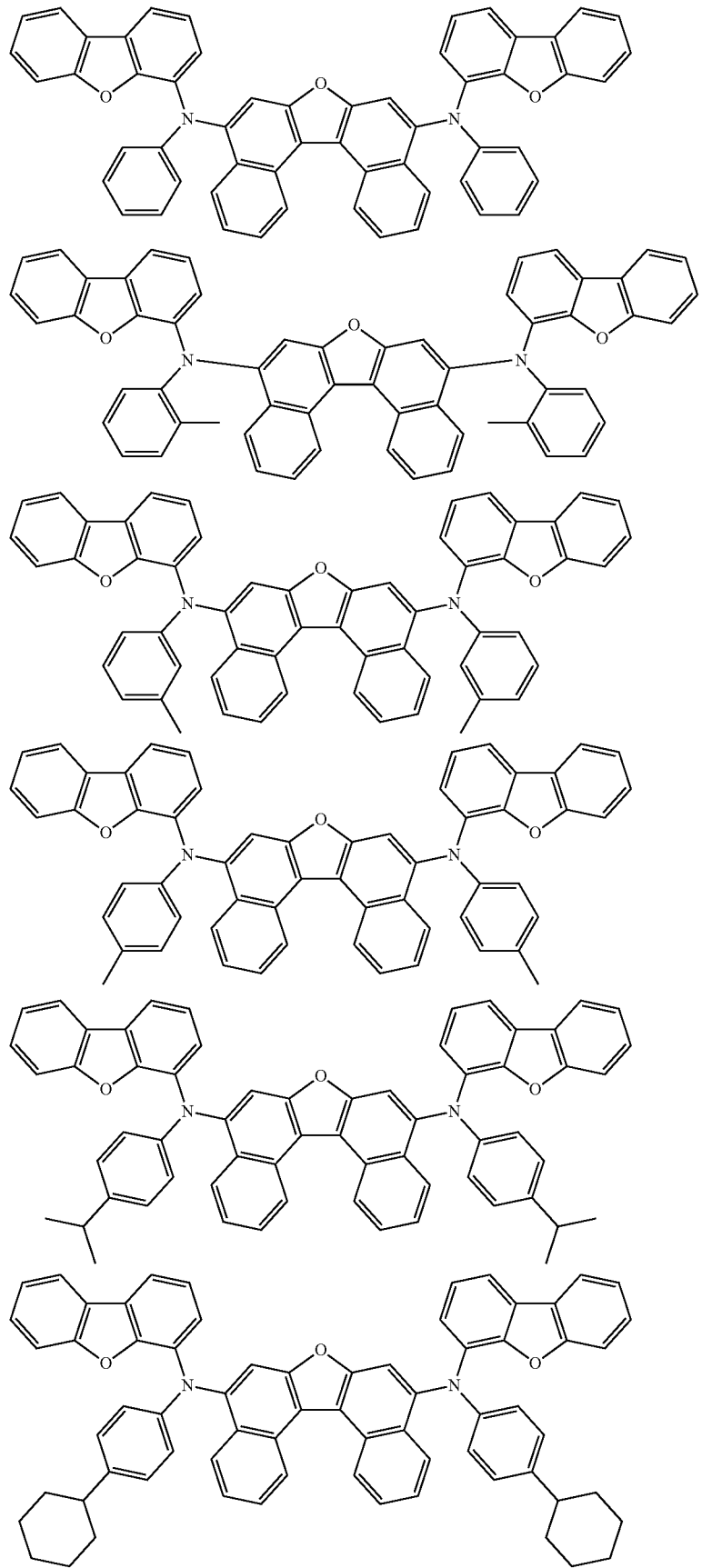

835
-continued
836
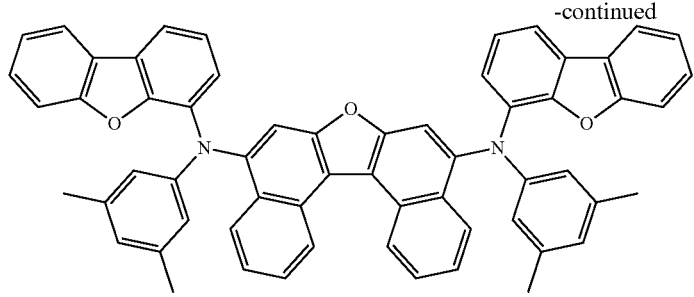
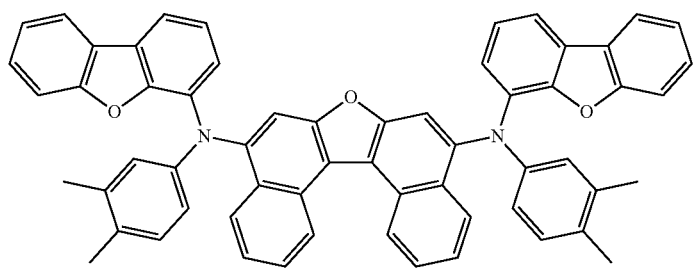
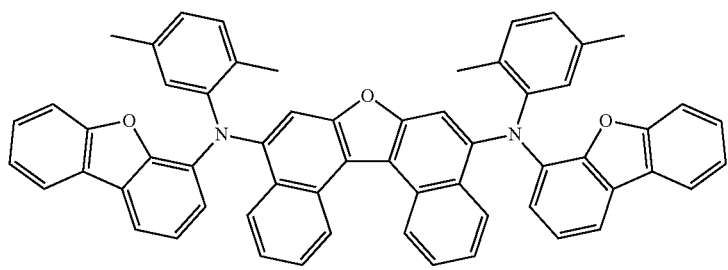
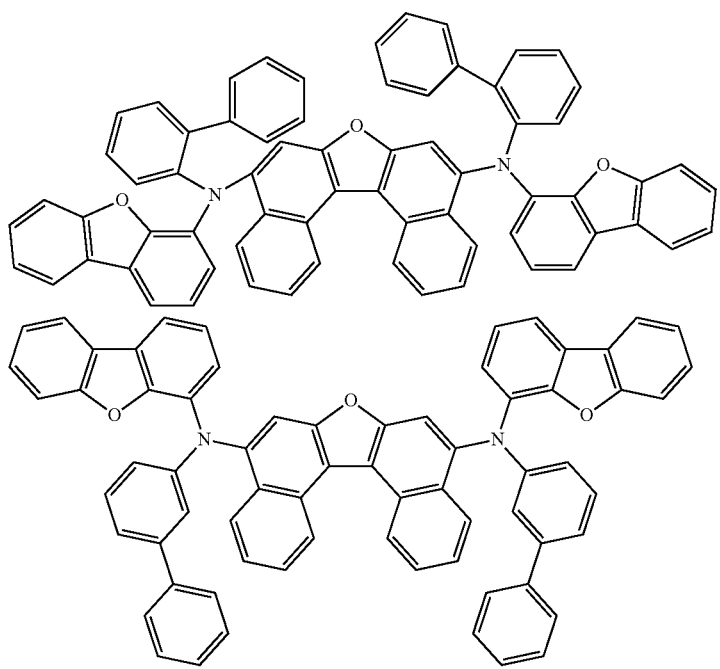

-continued
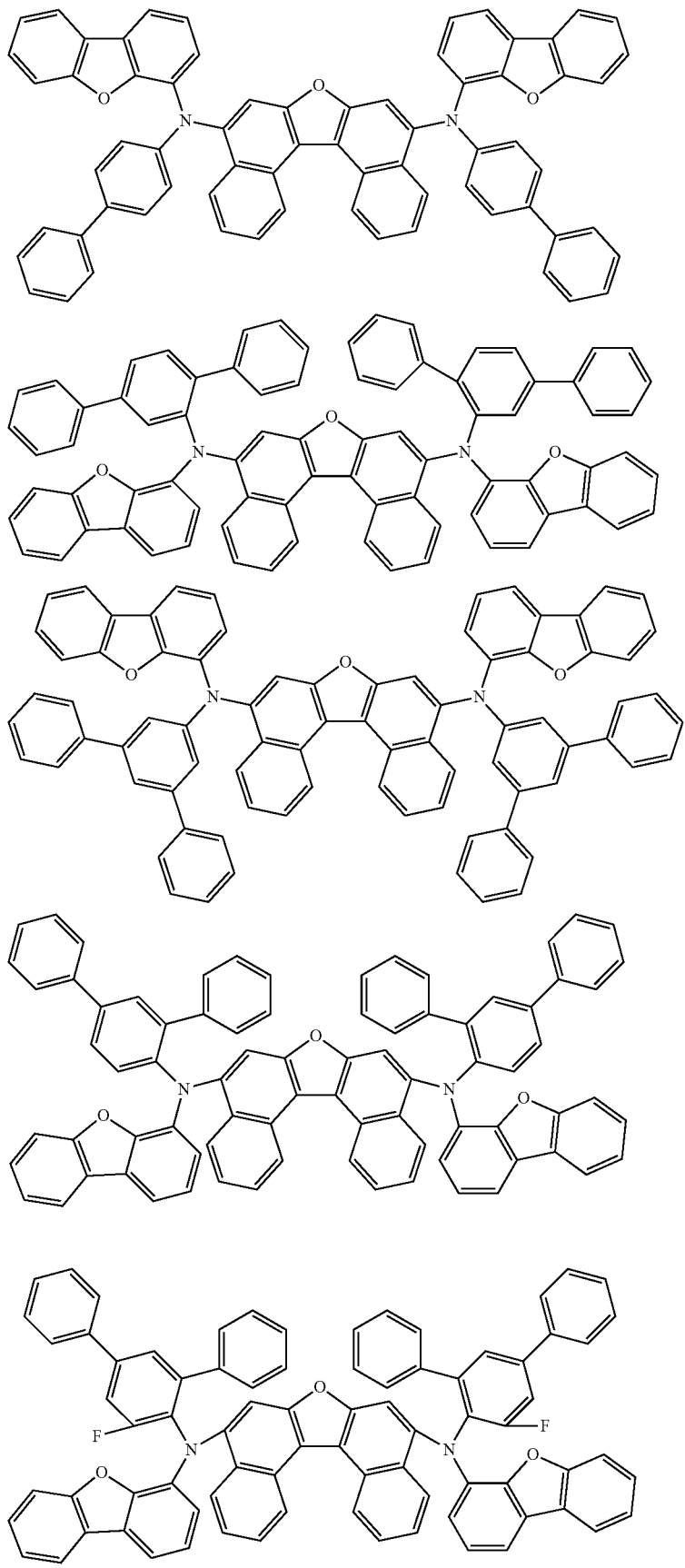

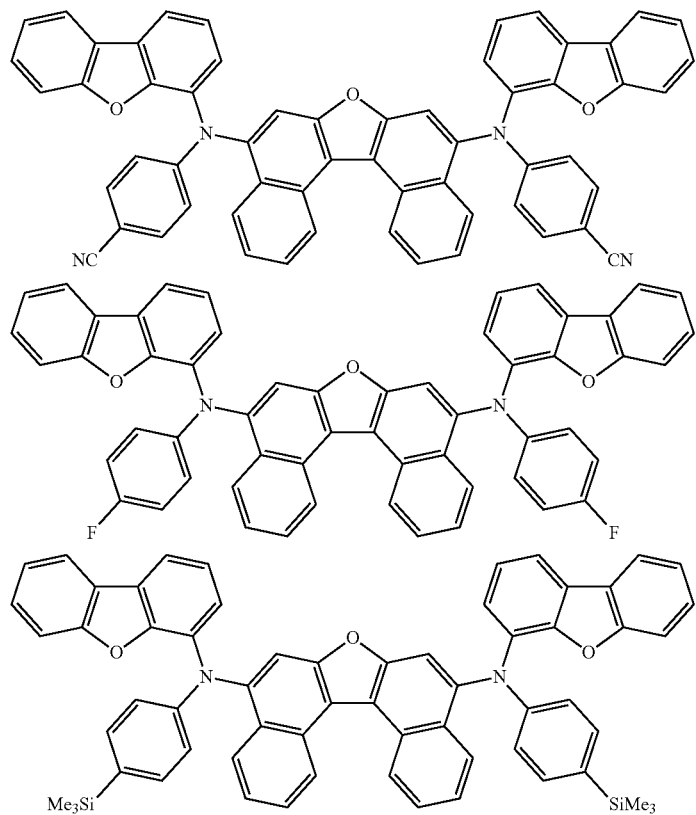
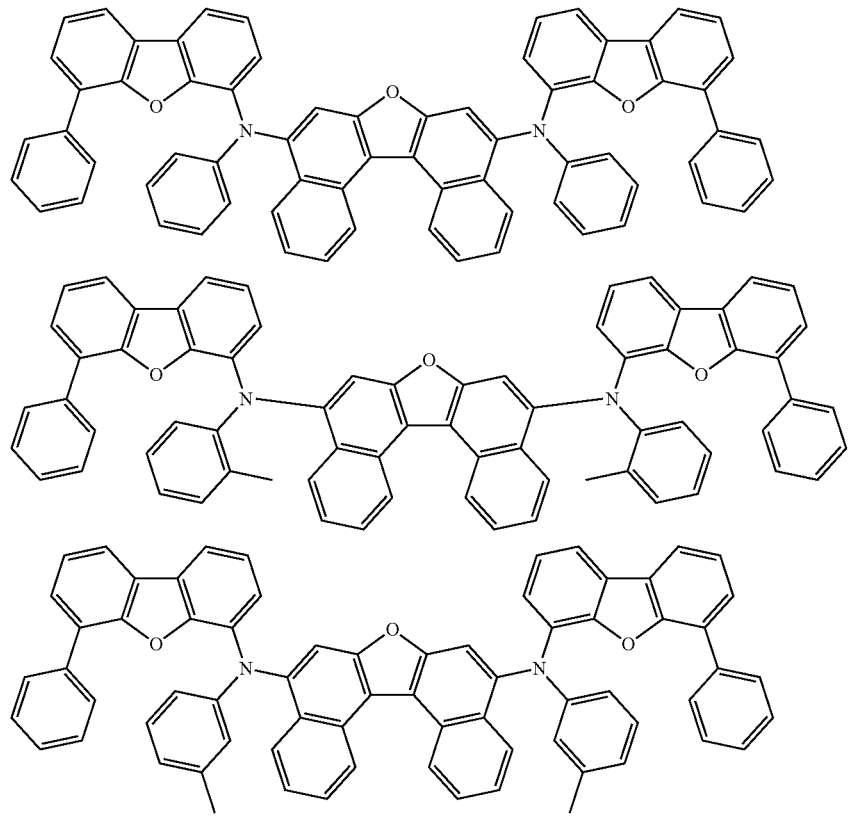

-continued
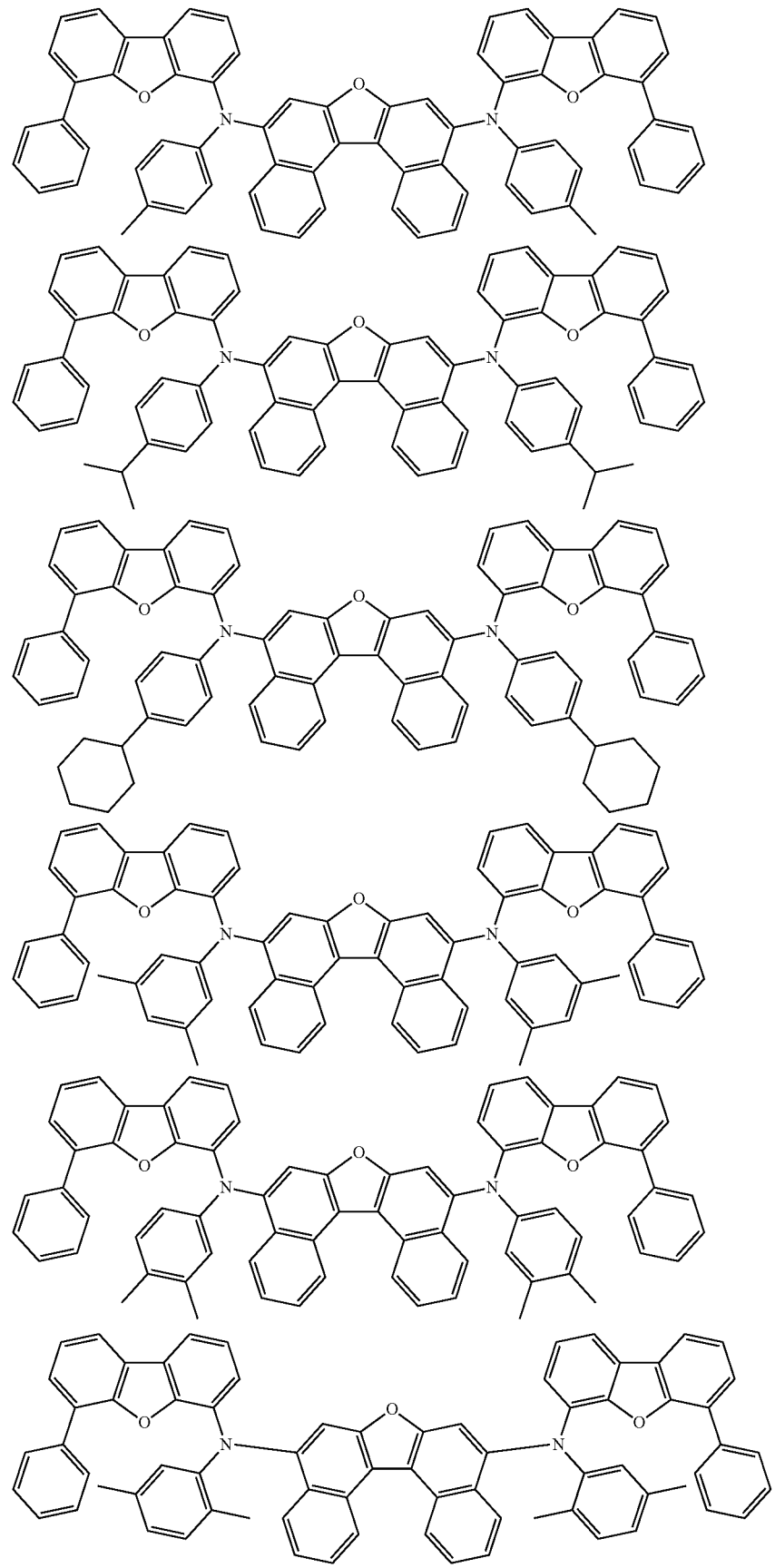

-continued
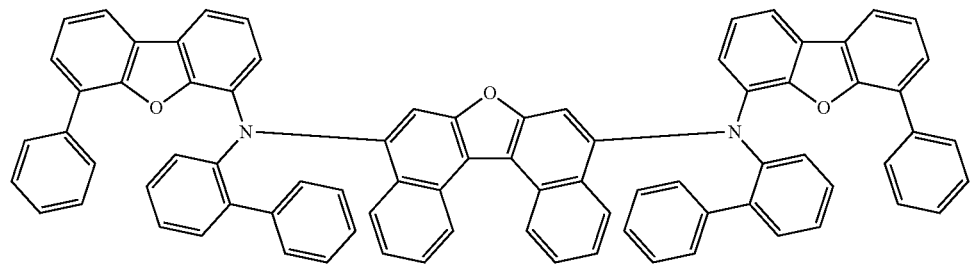
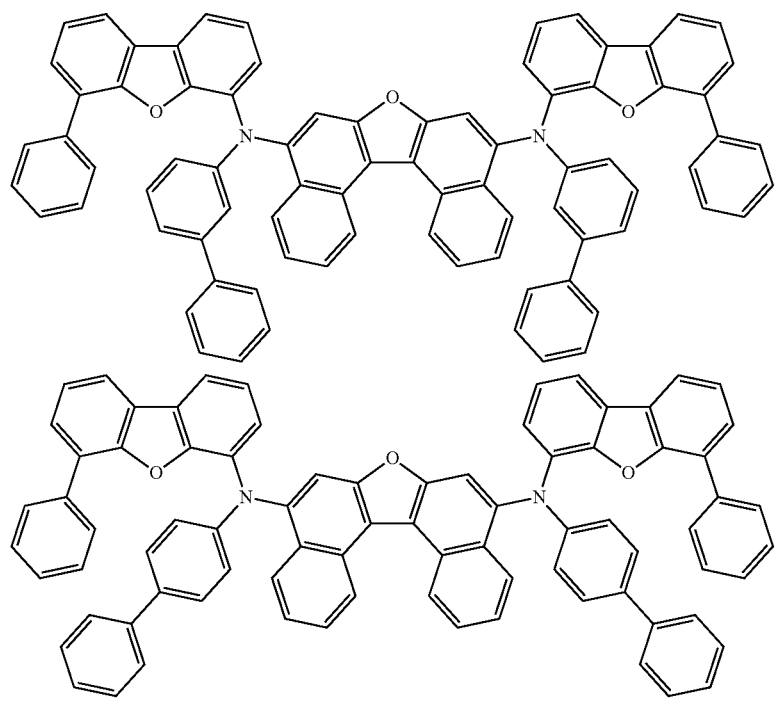
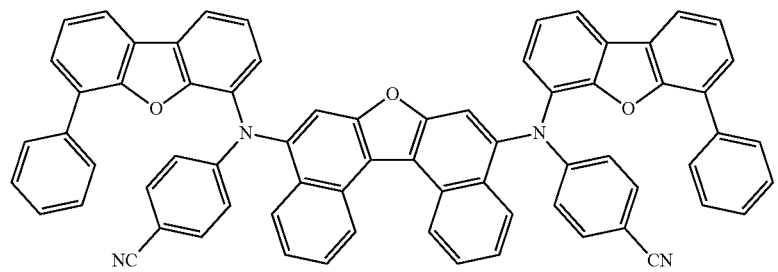
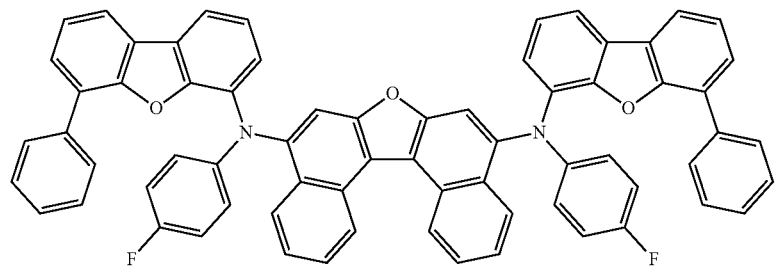

-continued
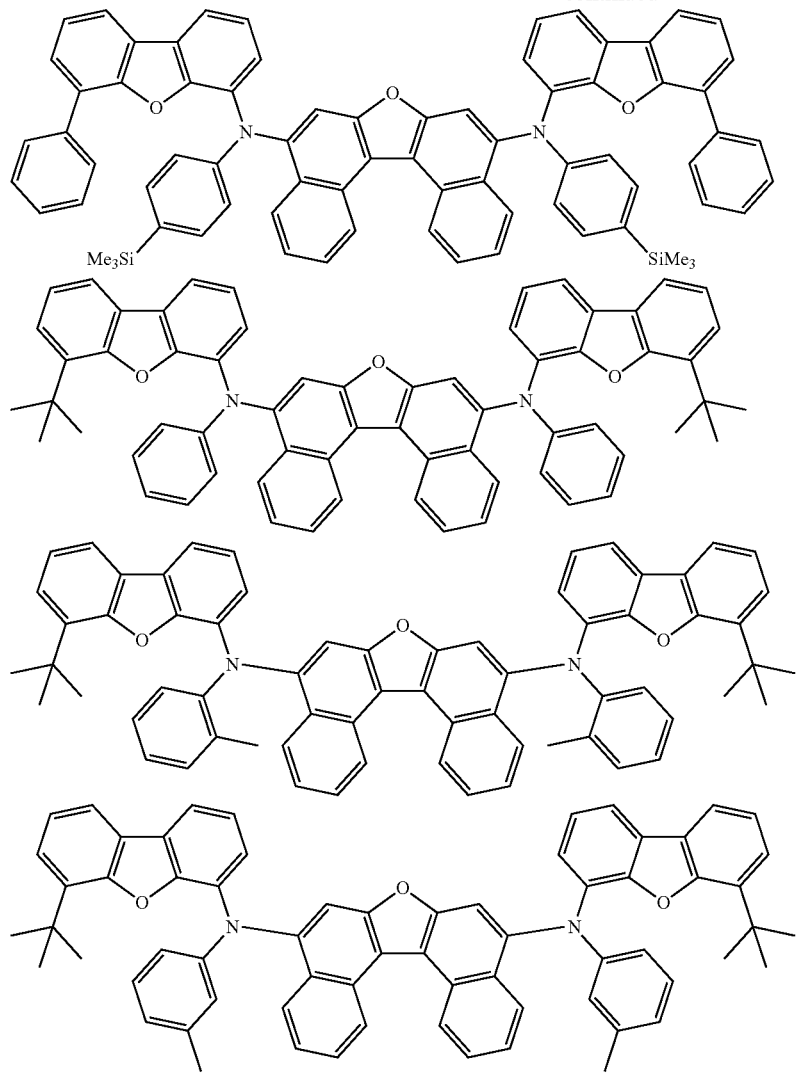
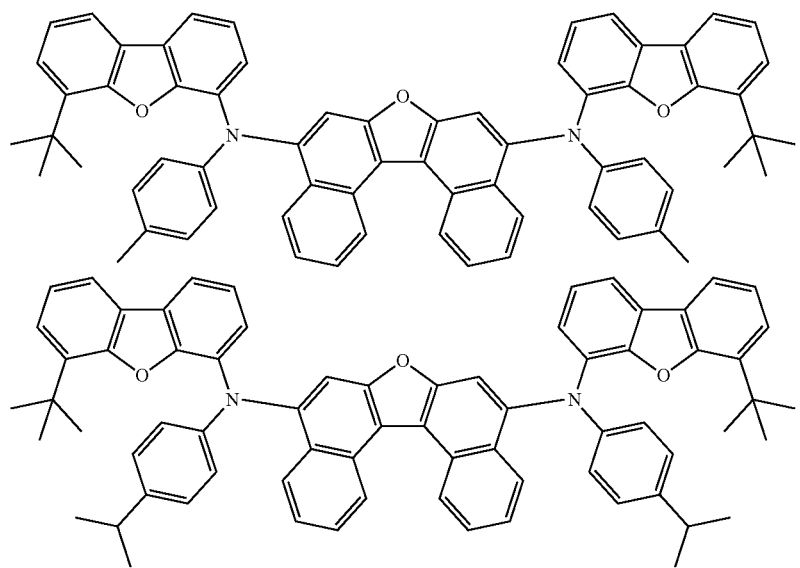

-continued
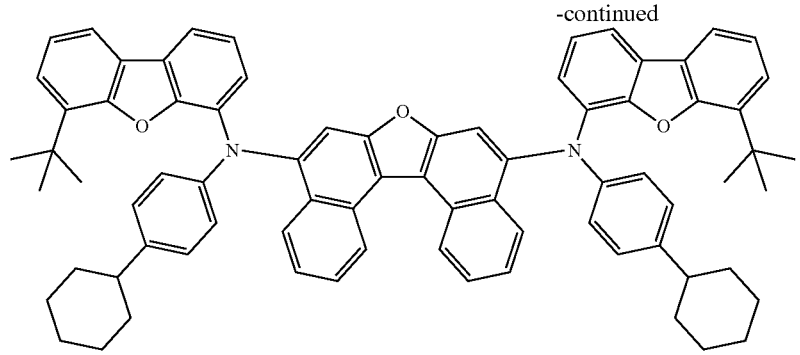
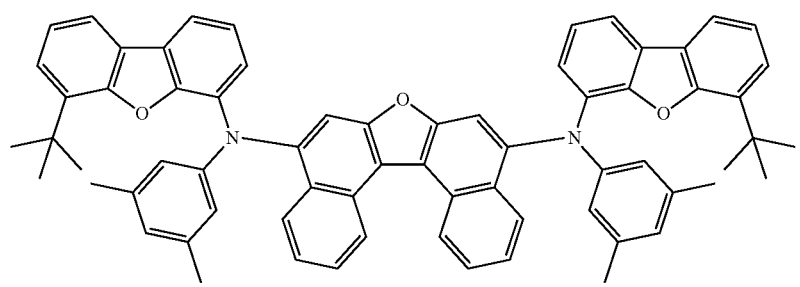
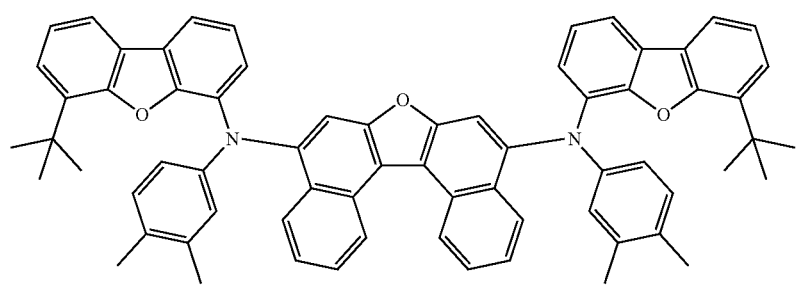
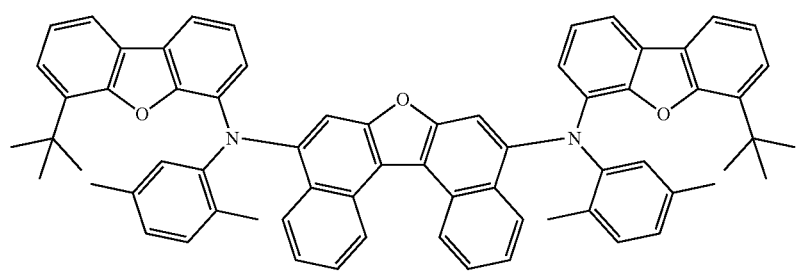
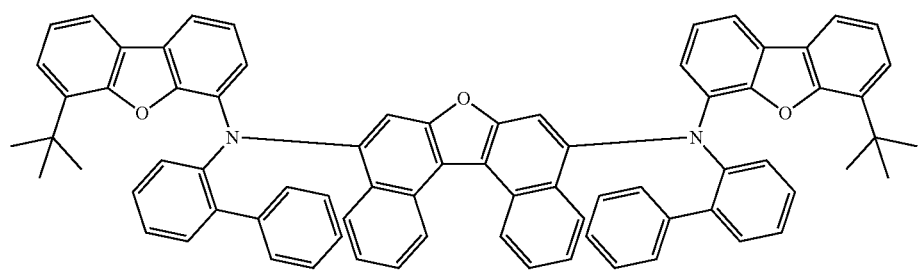

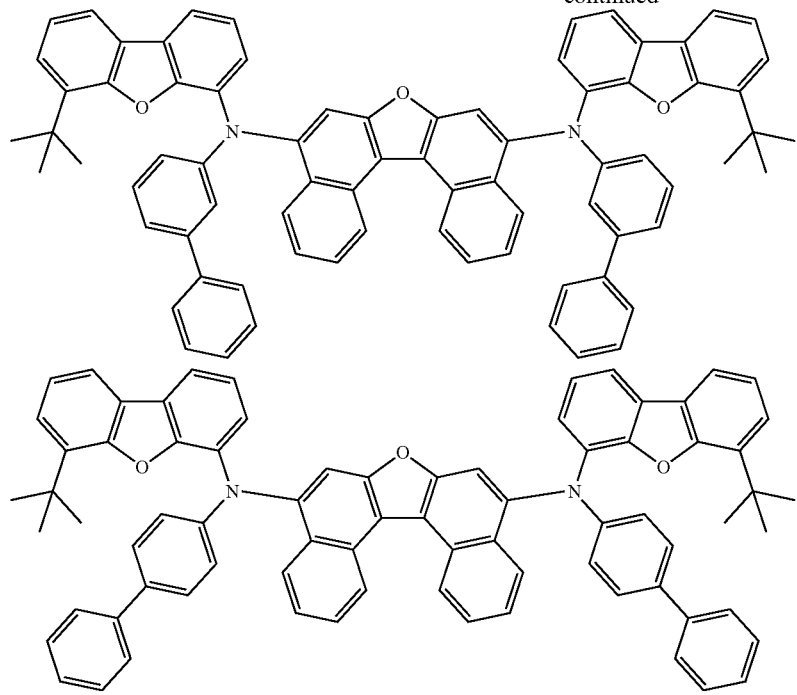
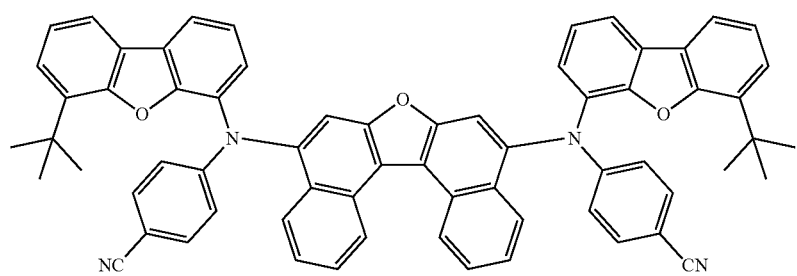
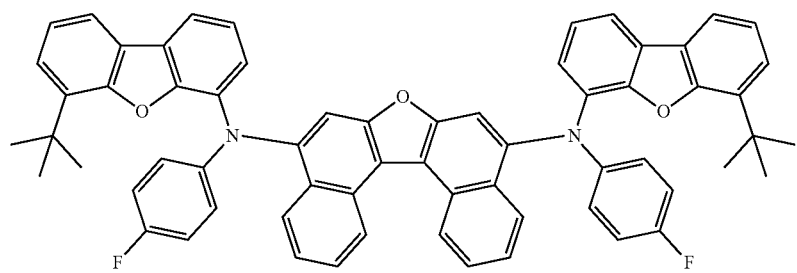 [SMILES: CC(C)(C)c1cccc2c1oc1c(N(c3ccc(F)cc3)c3cc4oc5cc(N(c6ccc(F)cc6)c6cccc7c6oc6c(C(C)(C)C)cccc67)c6ccccc6c5c4c4ccccc34)cccc12]
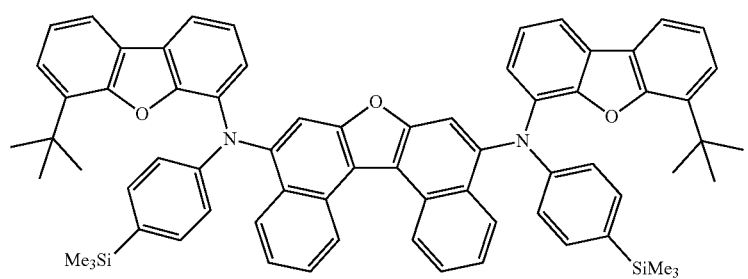

-continued
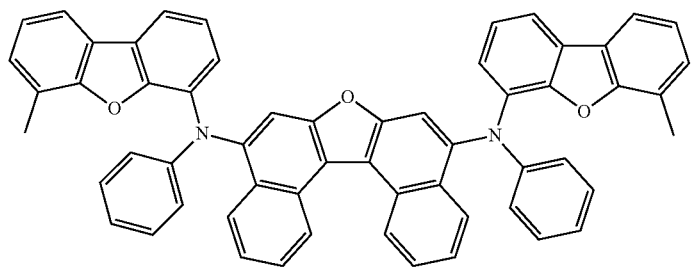
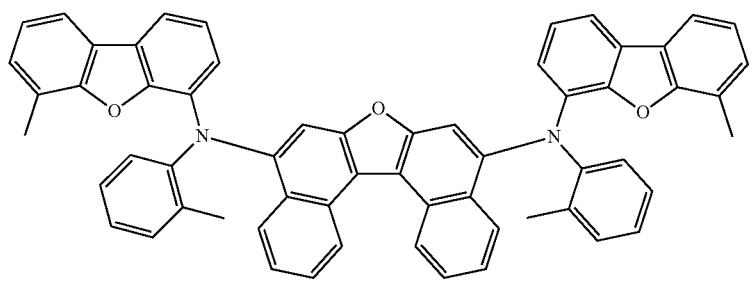
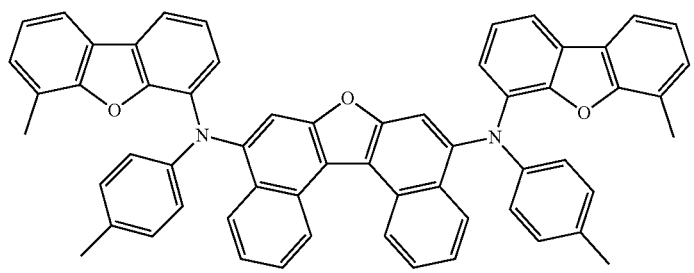
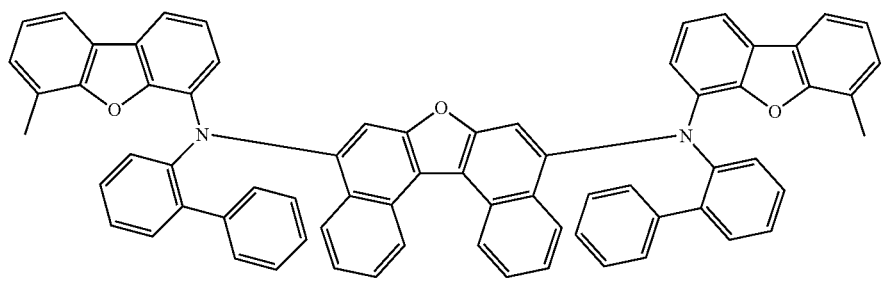
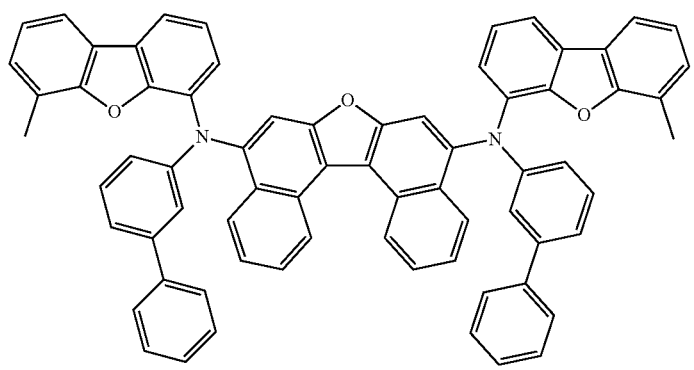

-continued
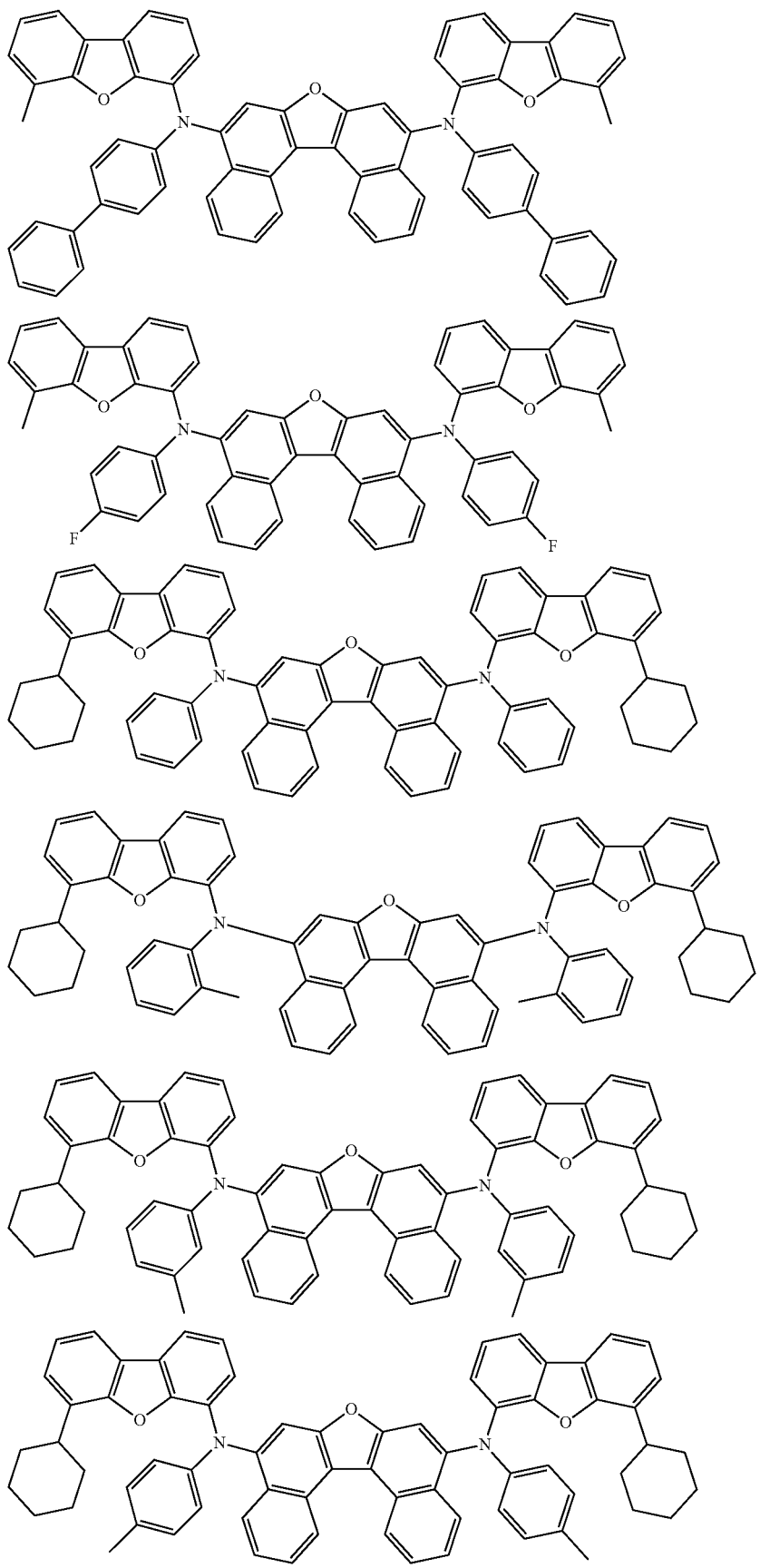

855 856
-continued
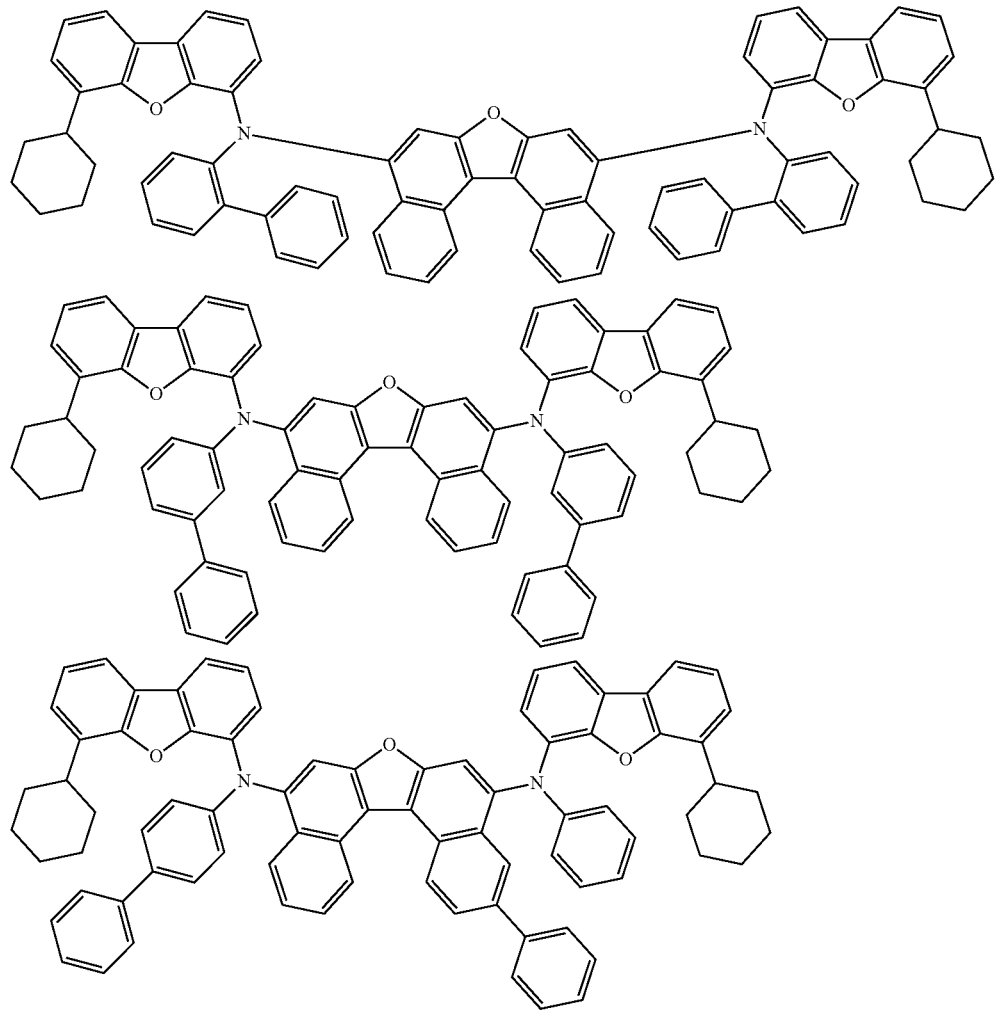
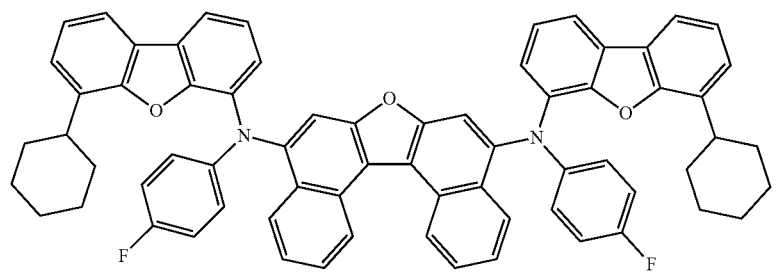
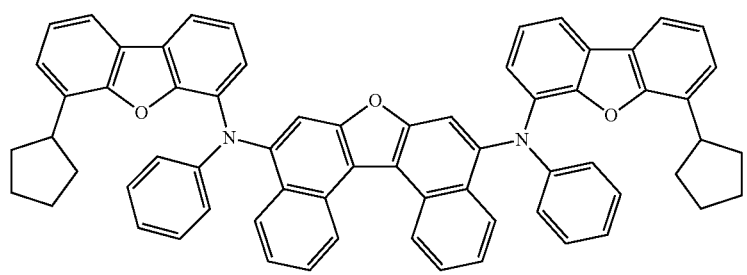

-continued
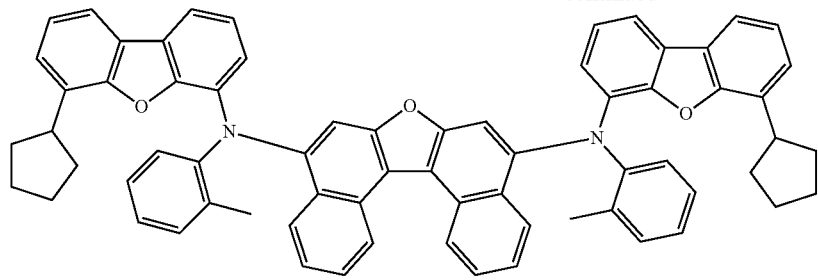
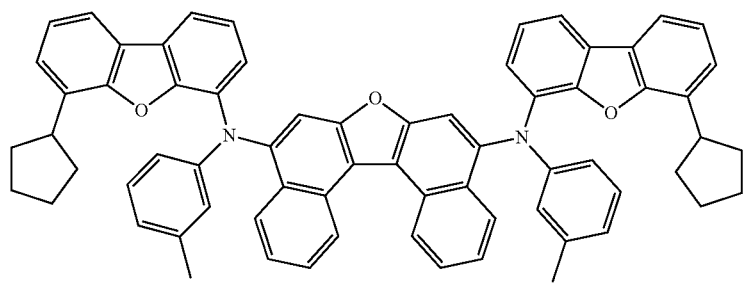
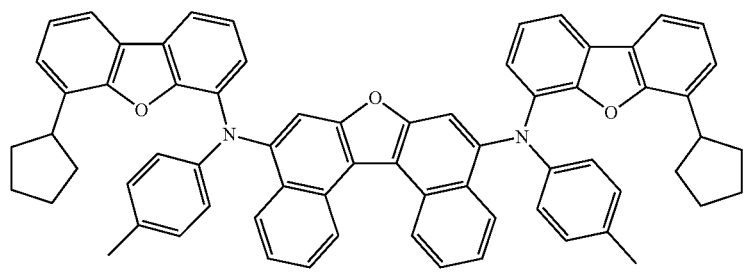
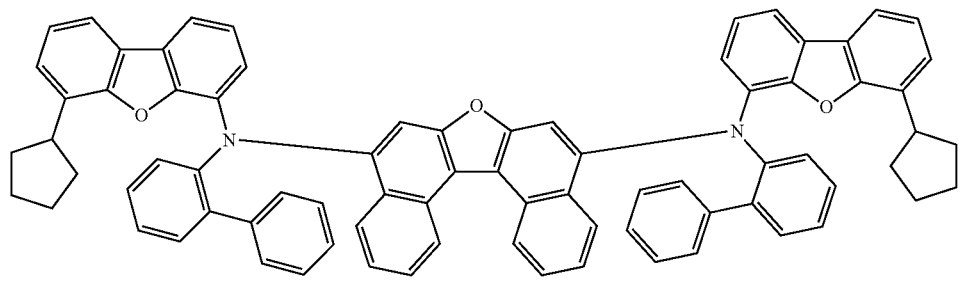
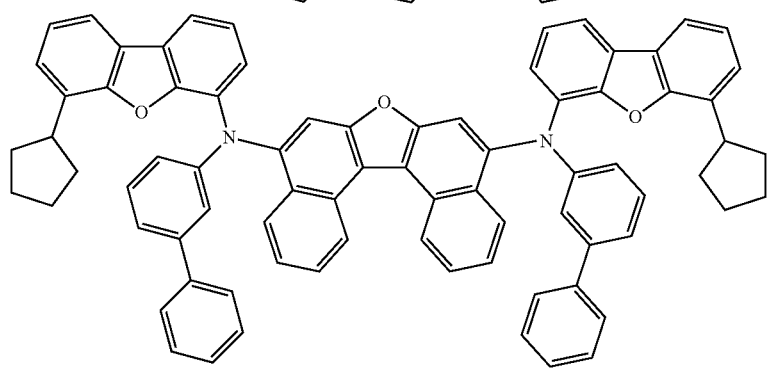

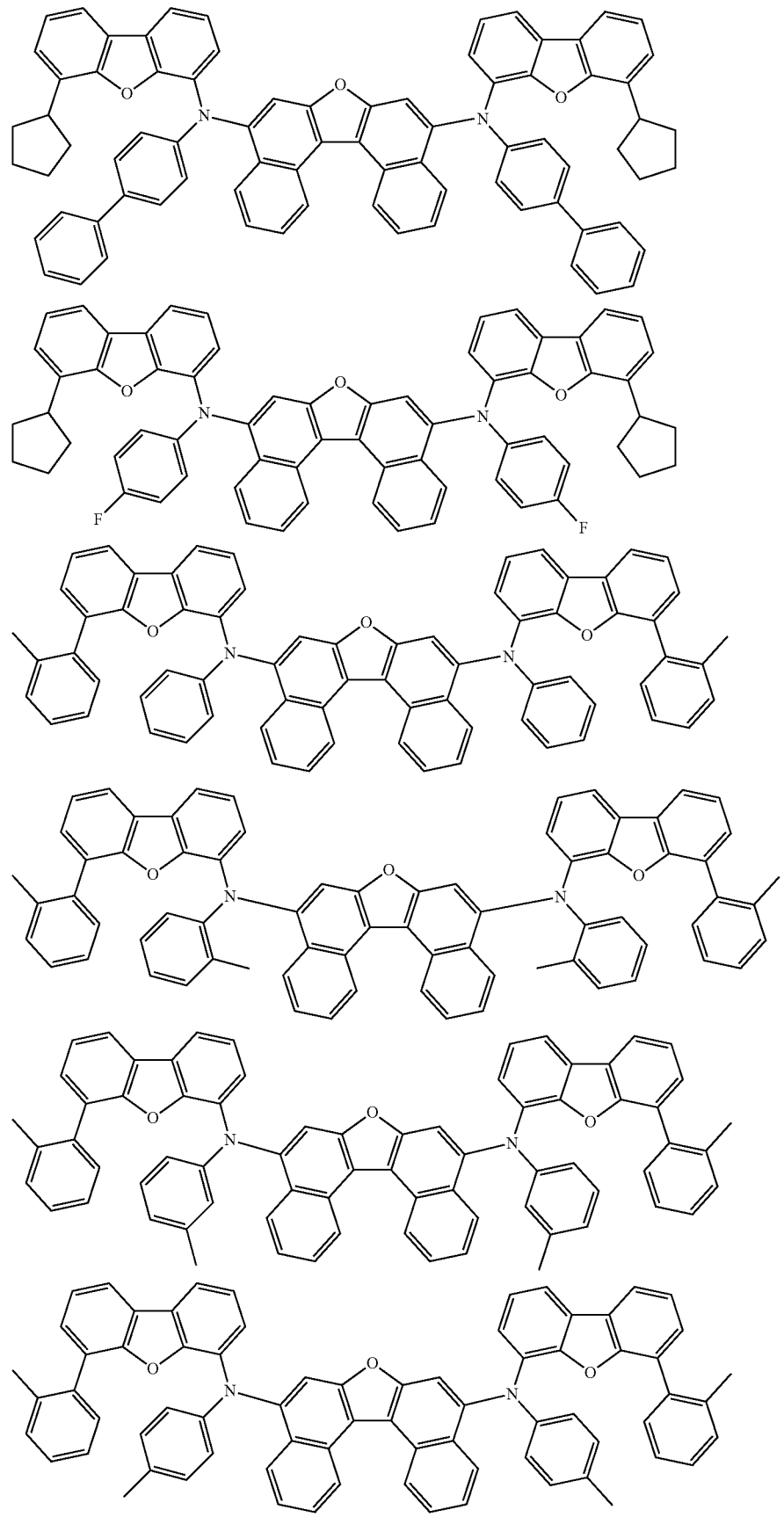

-continued
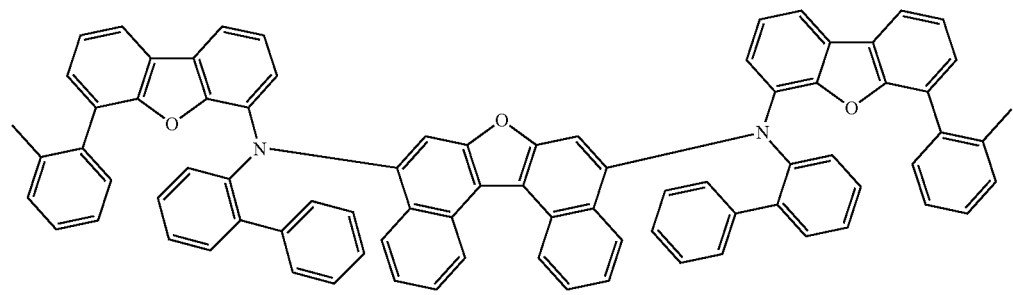
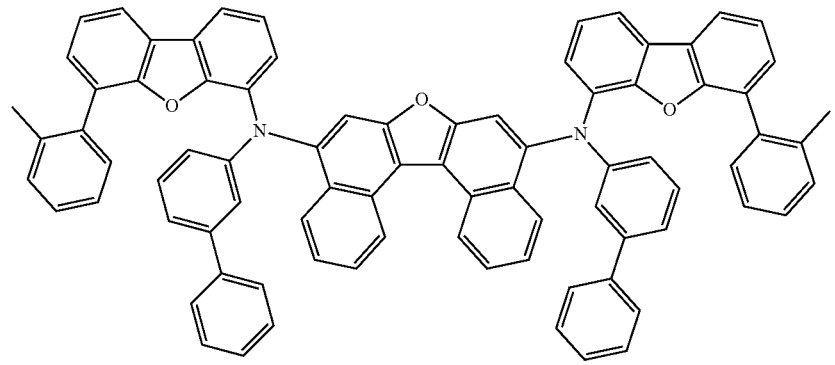
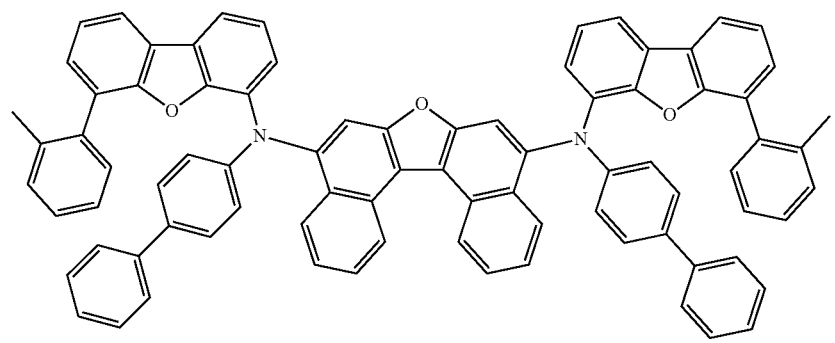
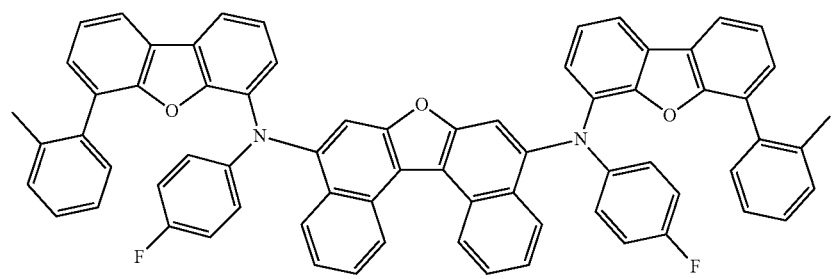
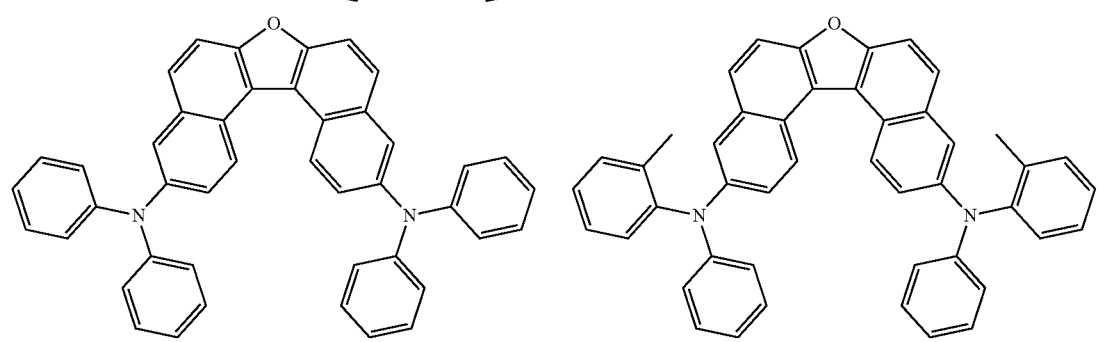
| 861 | 862 |

-continued
| 863 | 864 |
|---|---|
| 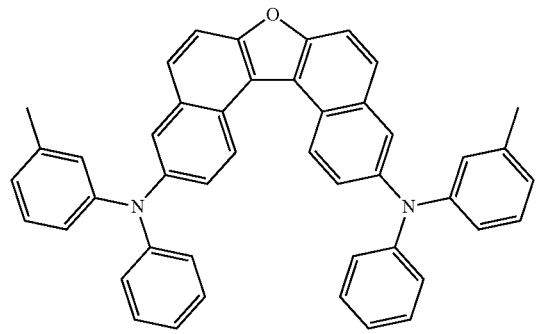 | 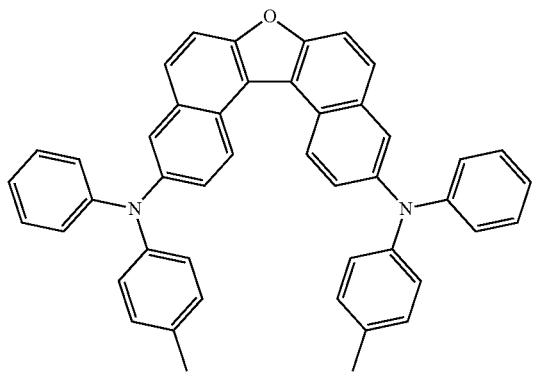 |
| 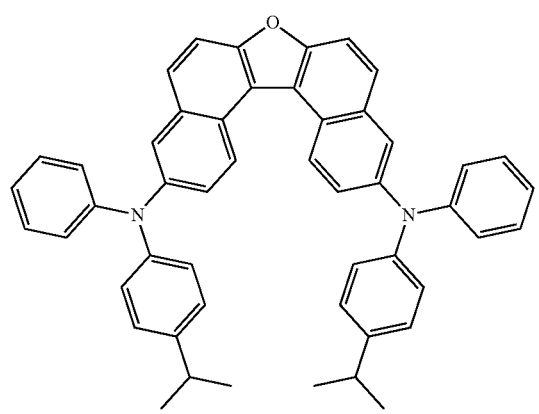 | 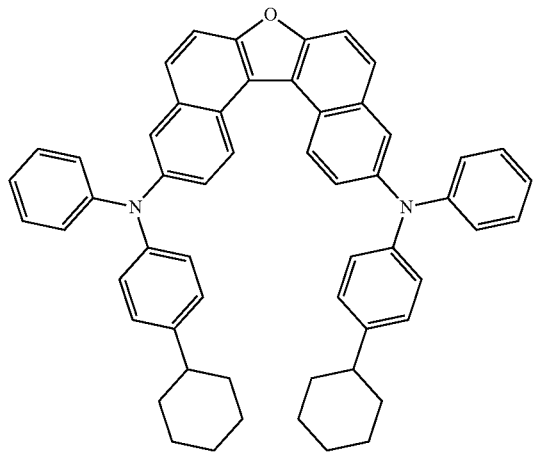 |
| 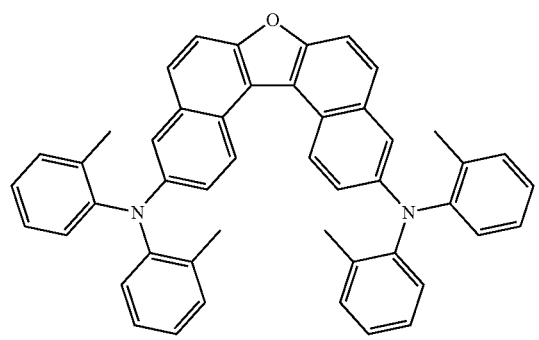 | 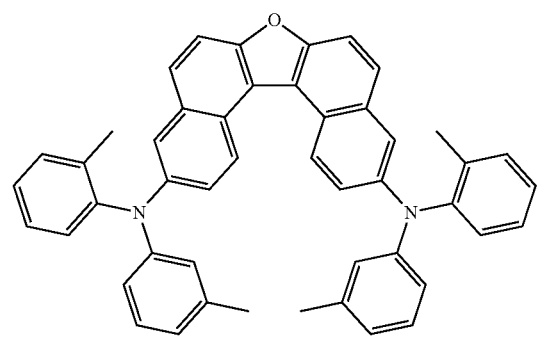 |
| 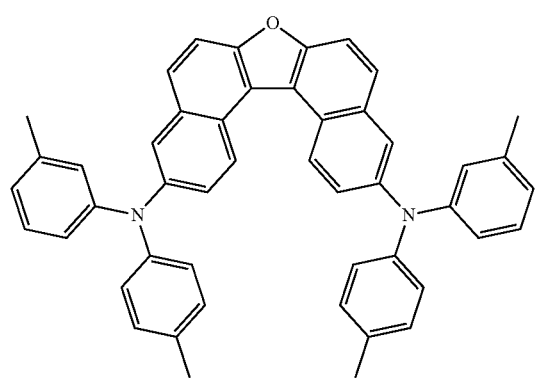 | 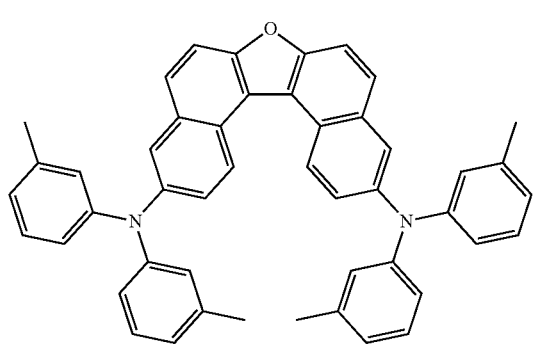 |

| 865 | 866 |
|---|---|
| 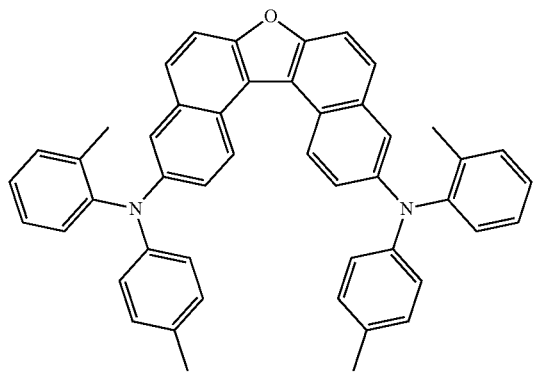 | 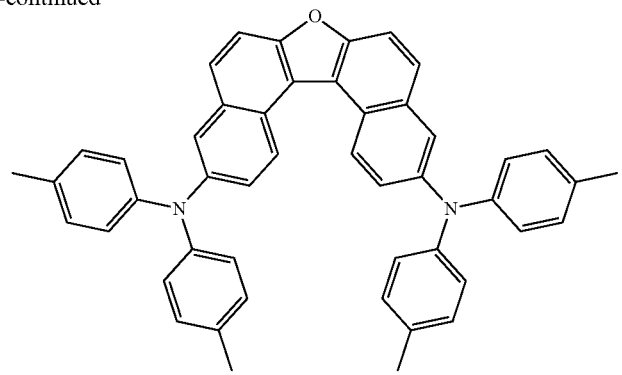 |
| 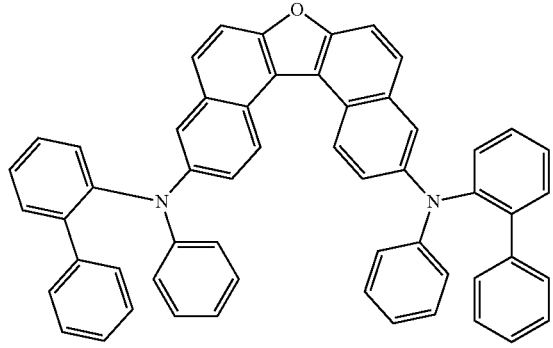 | 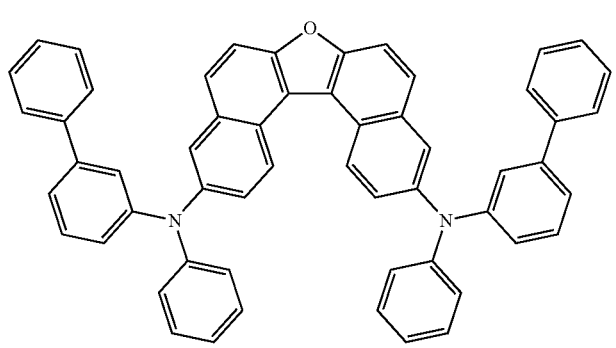 |
| 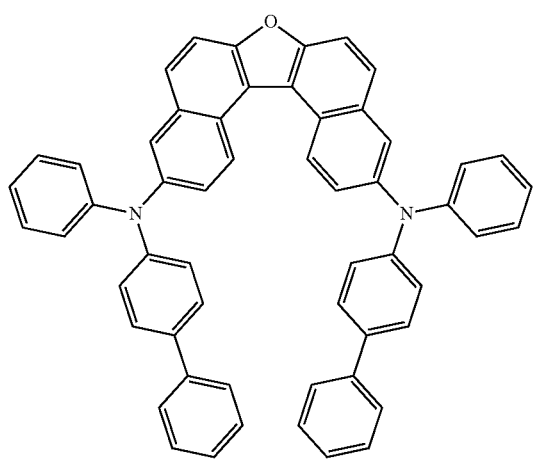 | 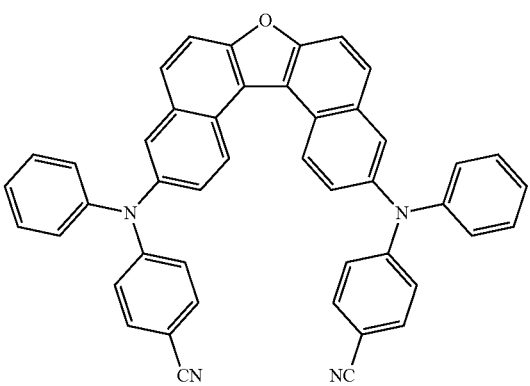 |
| 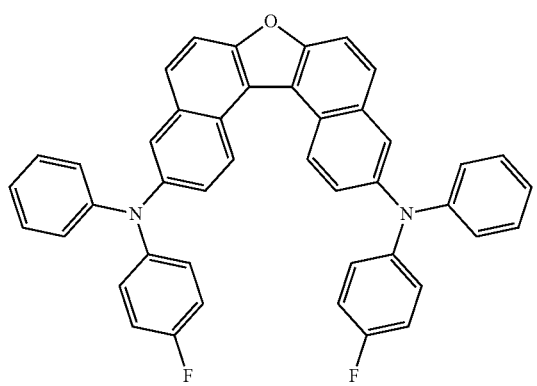 | 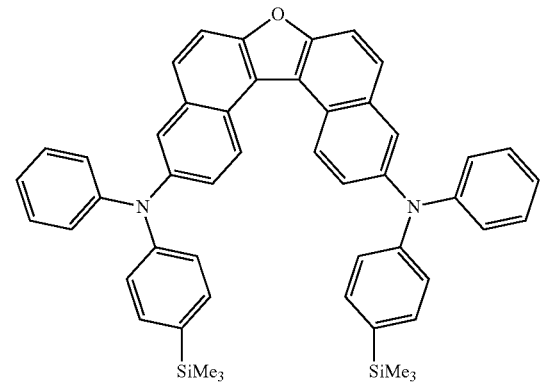 |

867  868
-continued
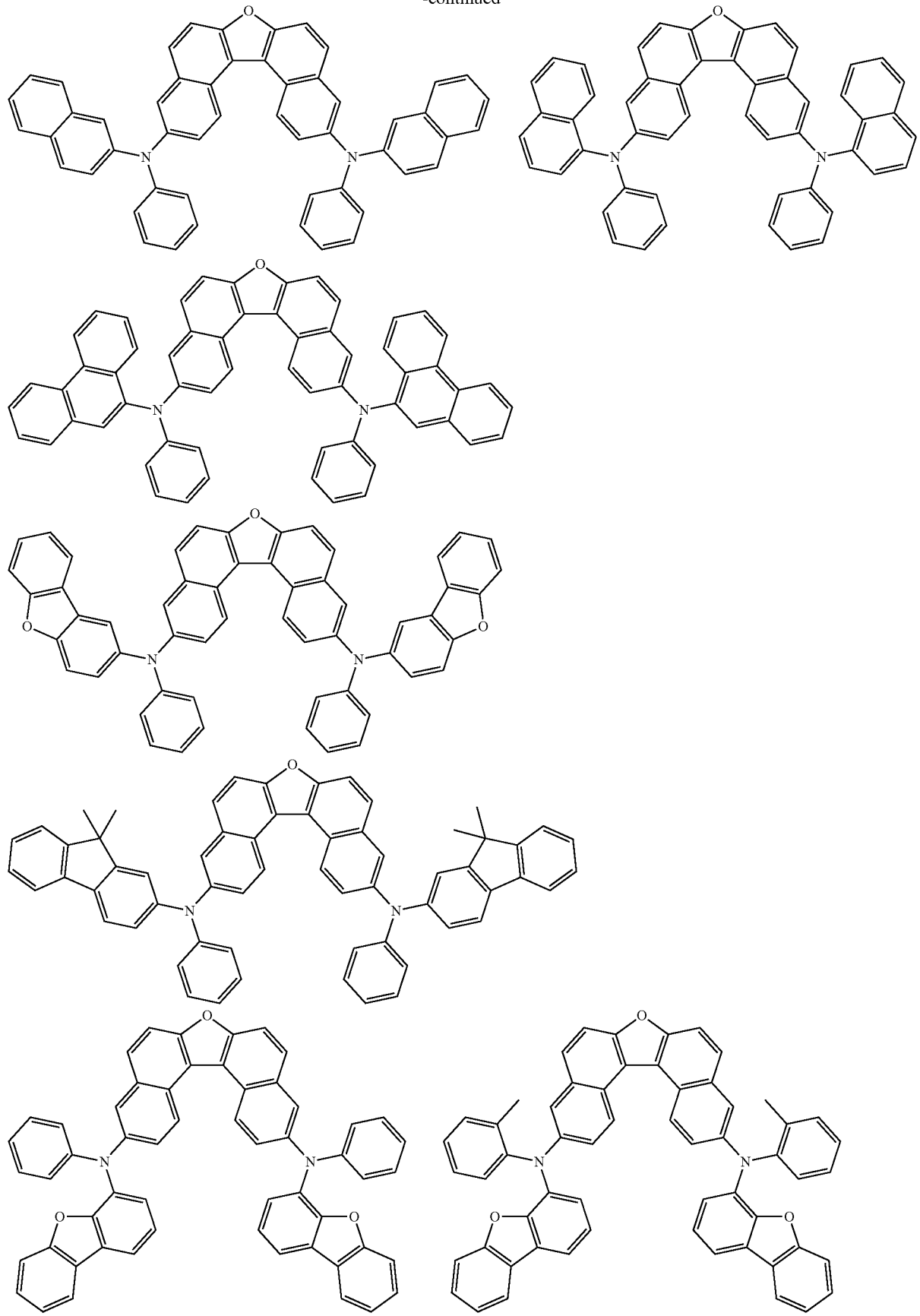

-continued
869 870
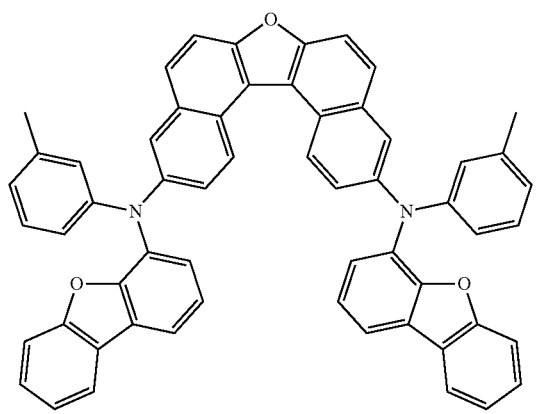 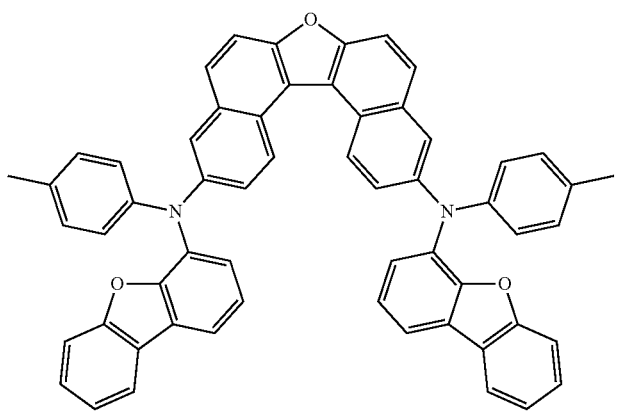
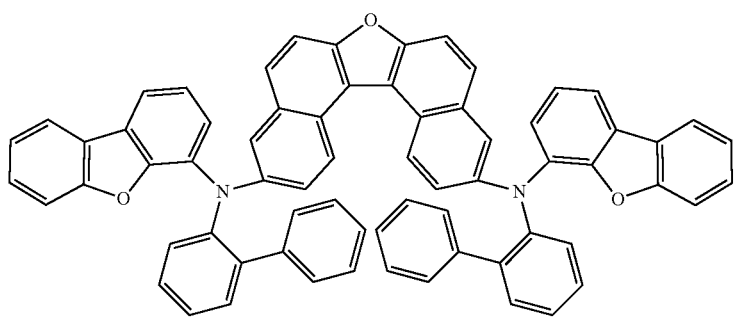
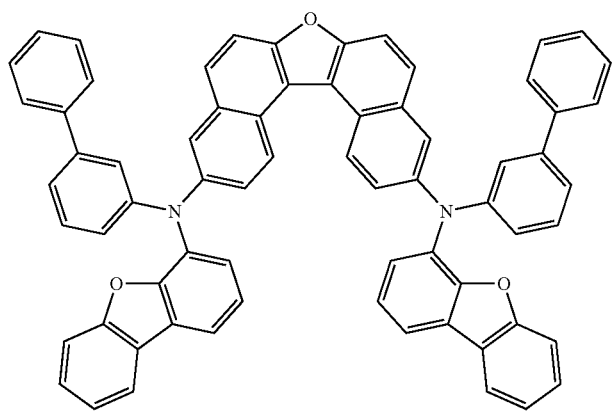
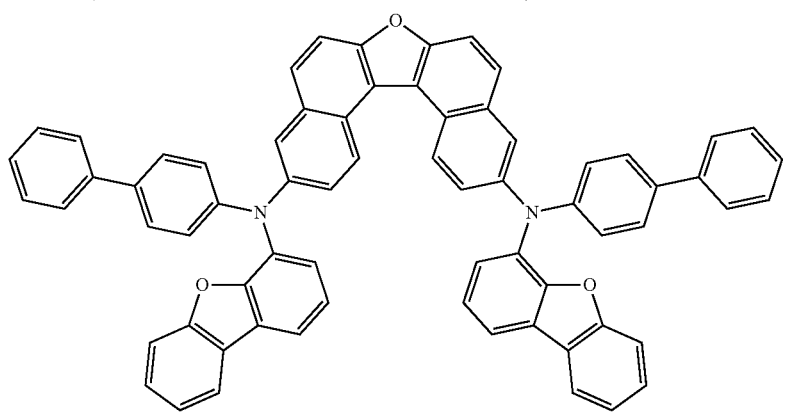

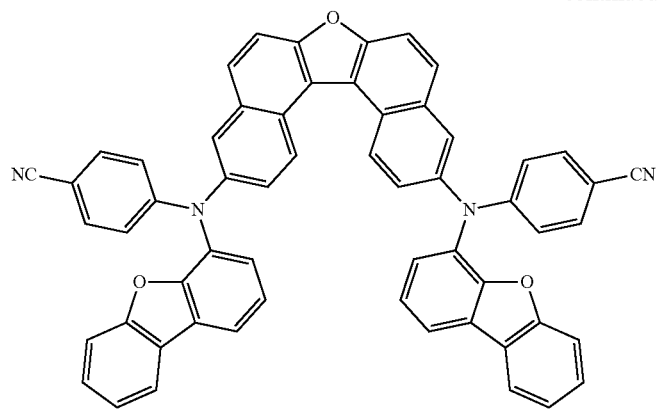
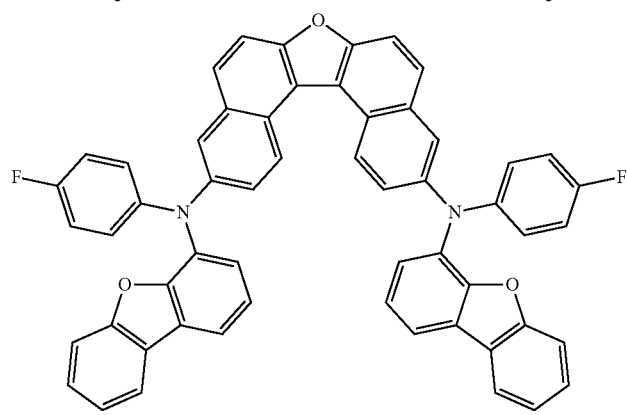
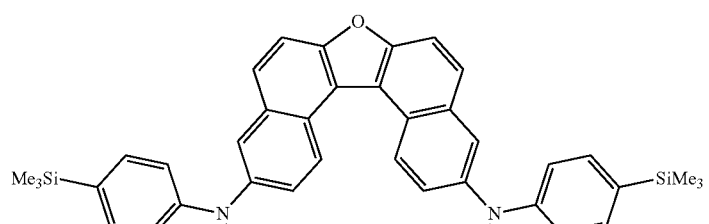
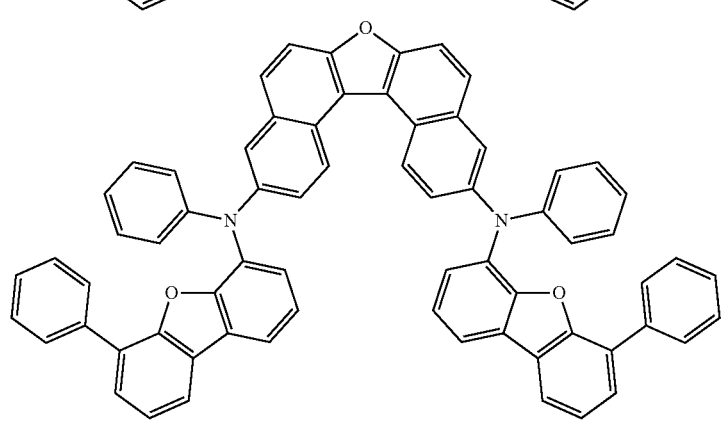

873
874
-continued
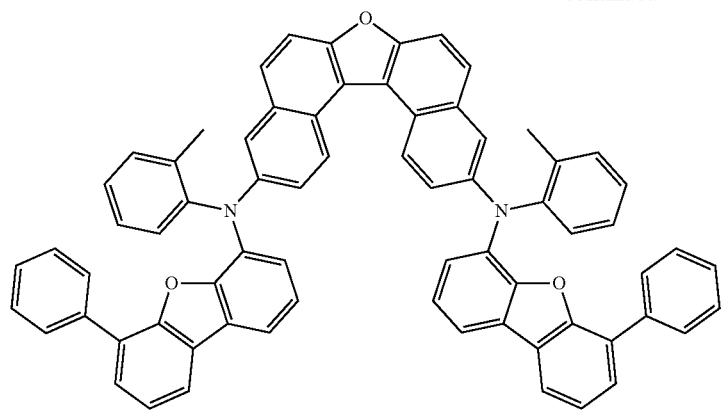
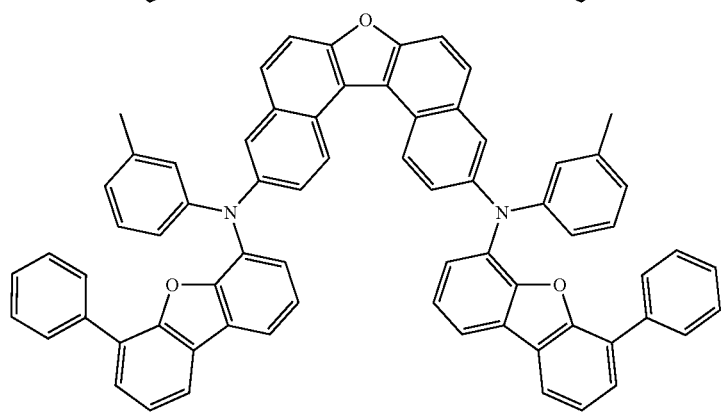
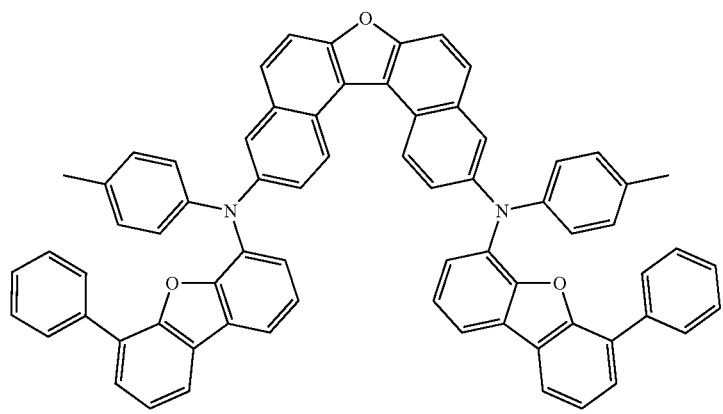
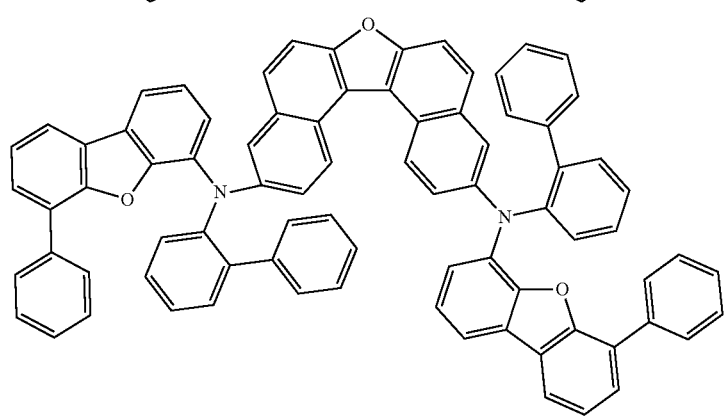

-continued
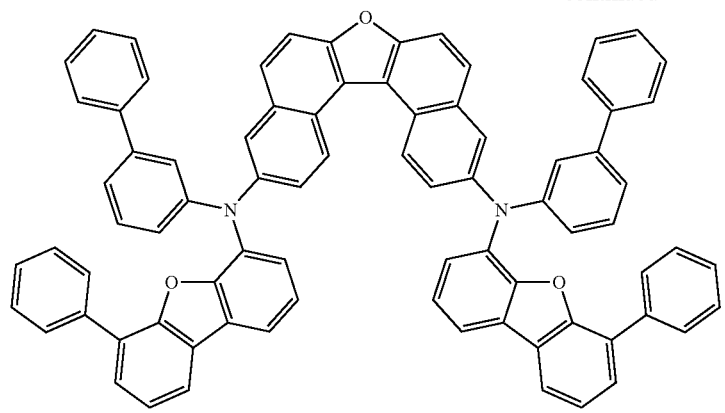
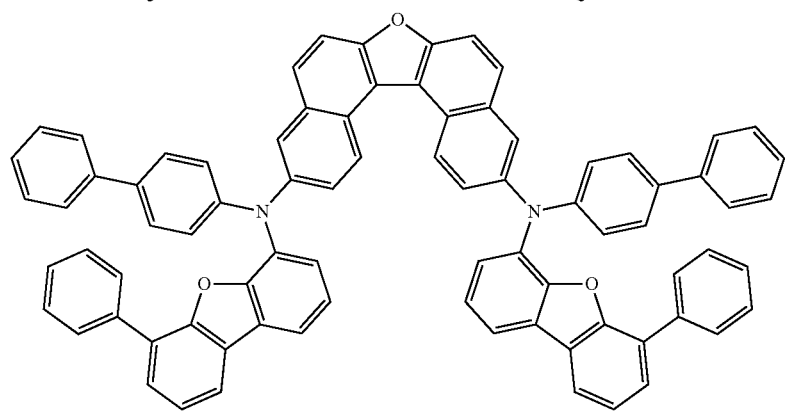
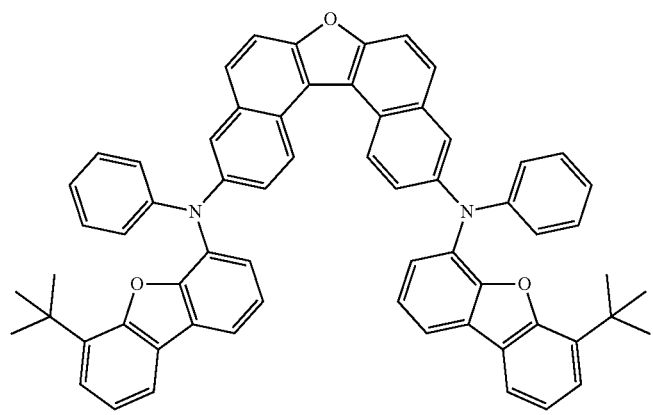
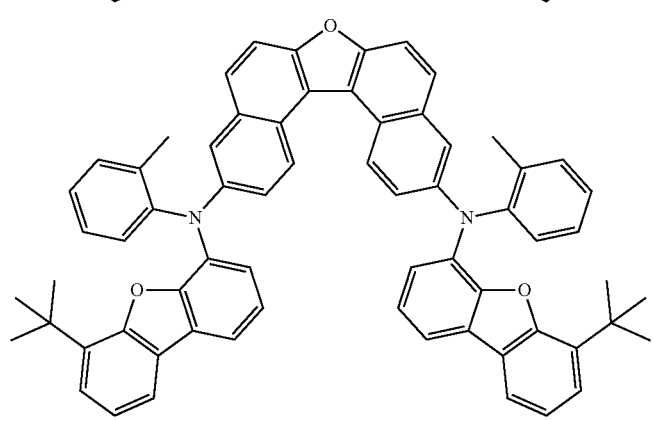

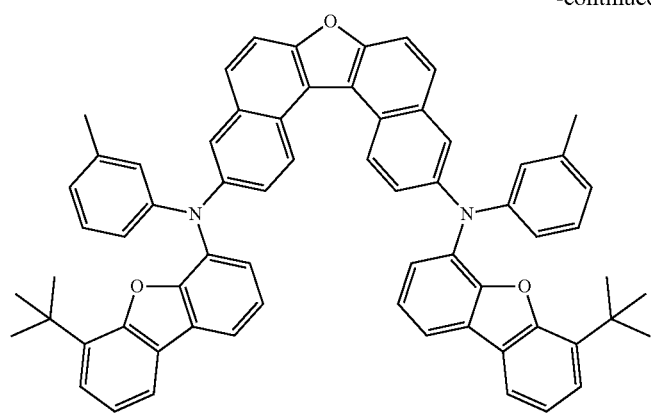
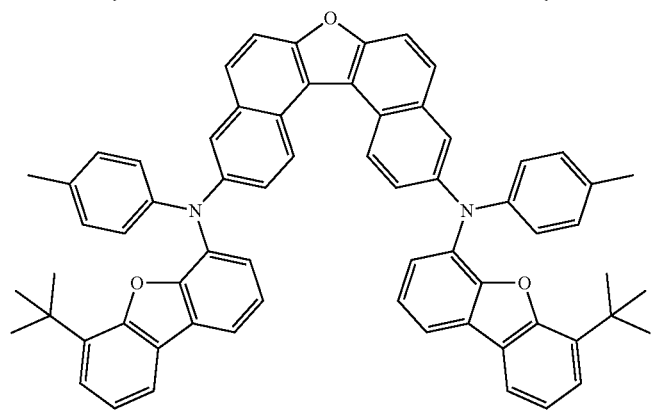
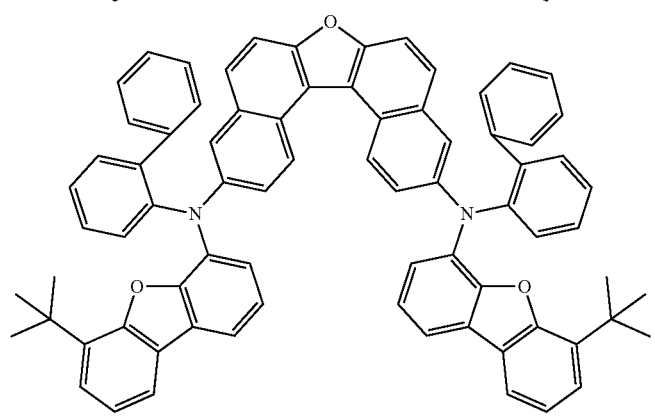
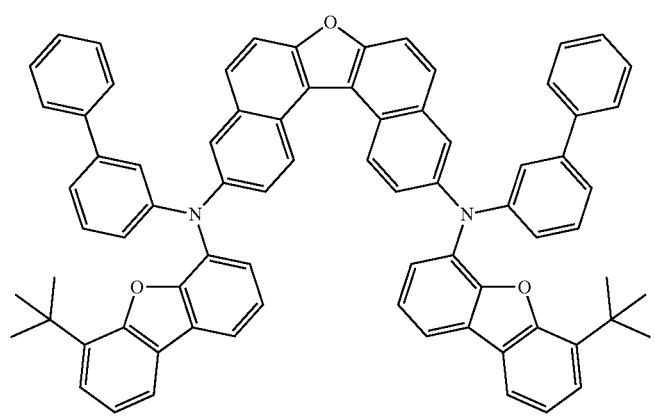

-continued
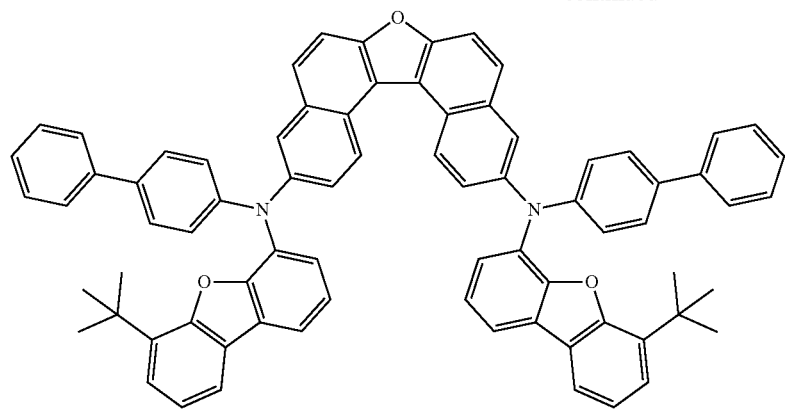
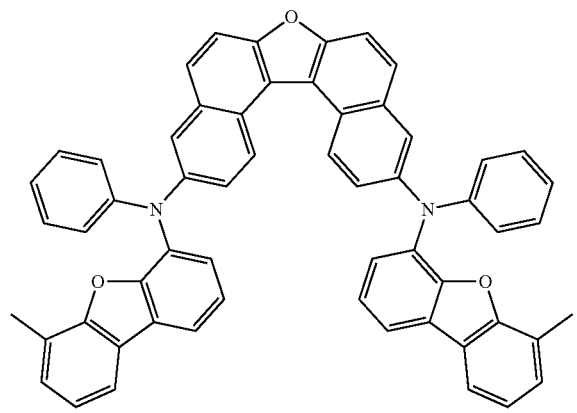
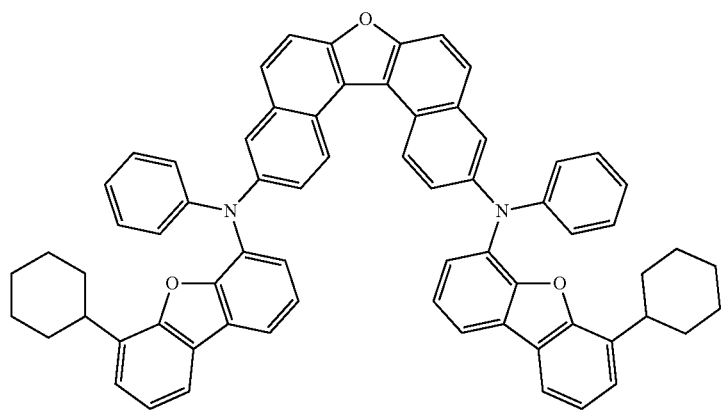
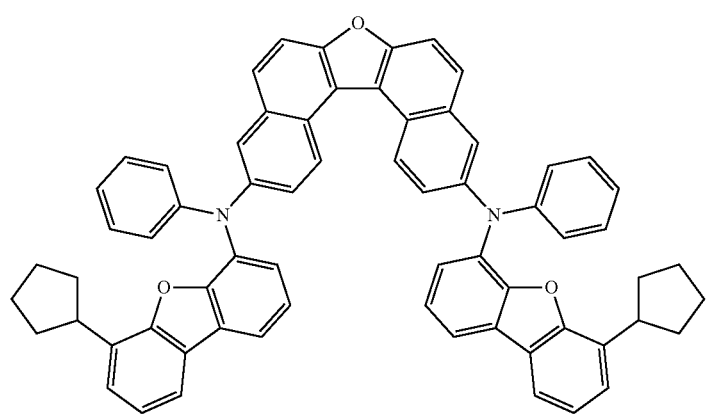

881 882
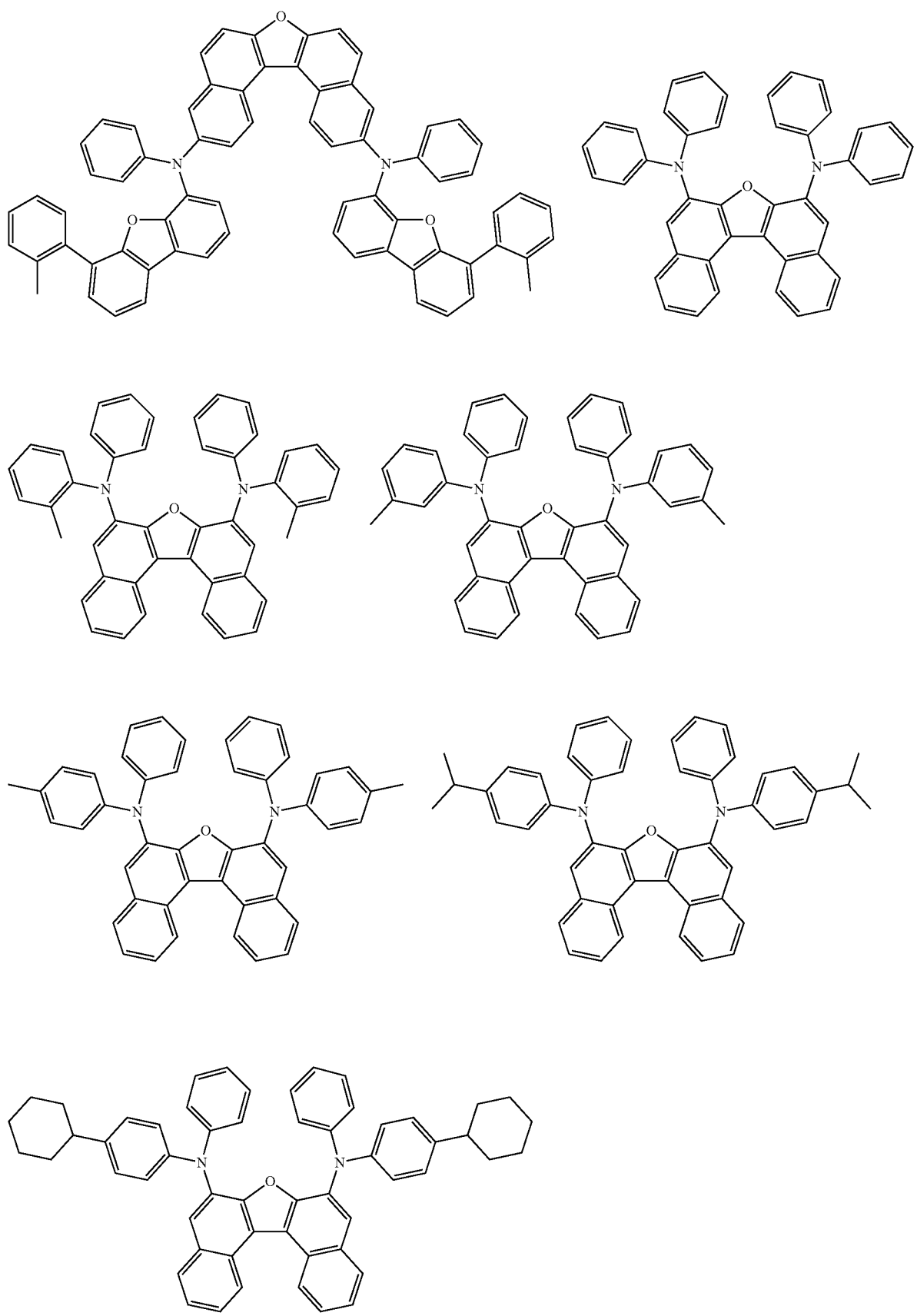
-continued 883
884
-continued
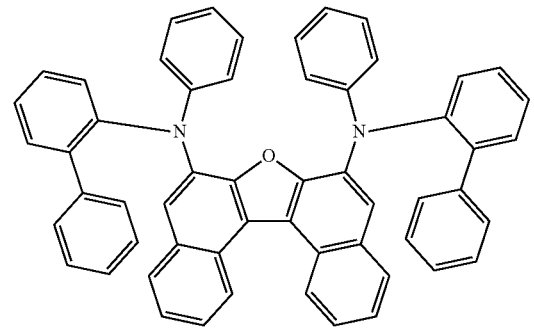
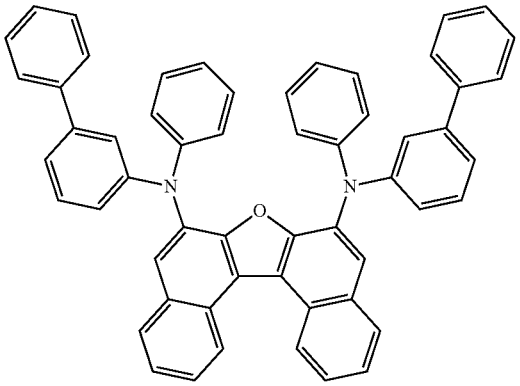
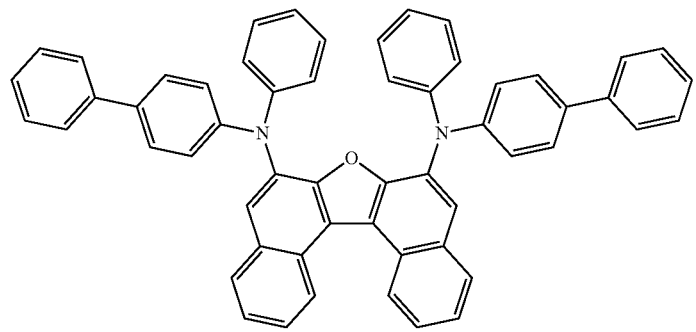
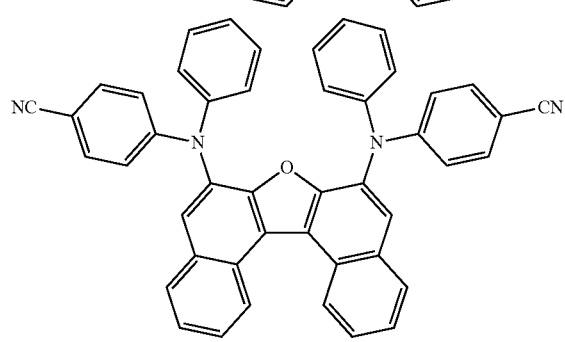
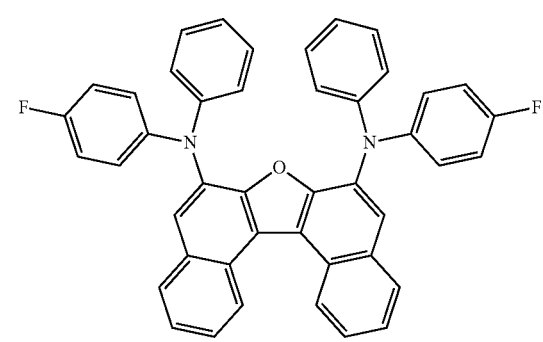
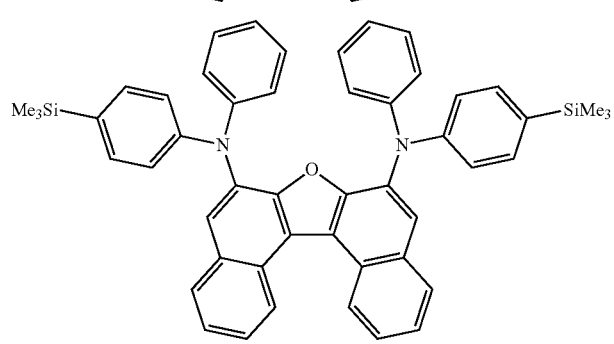
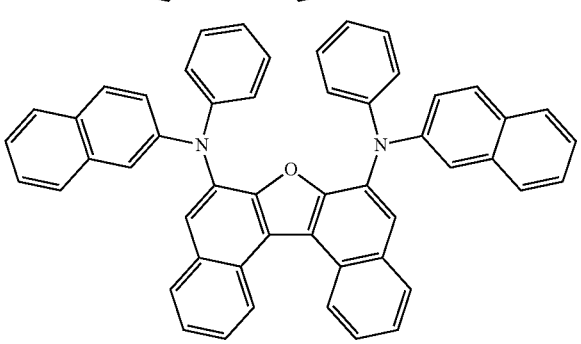
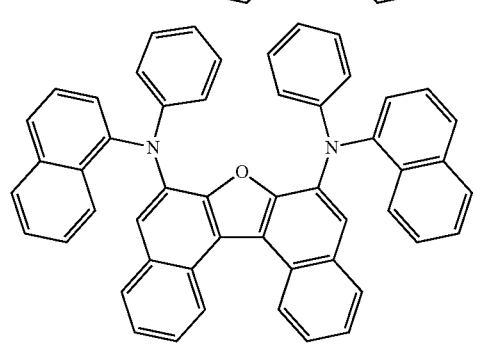
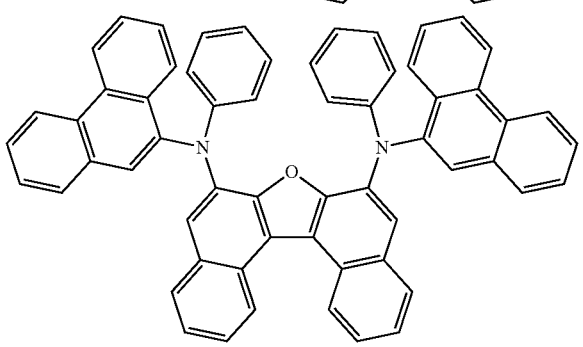

885 886
-continued
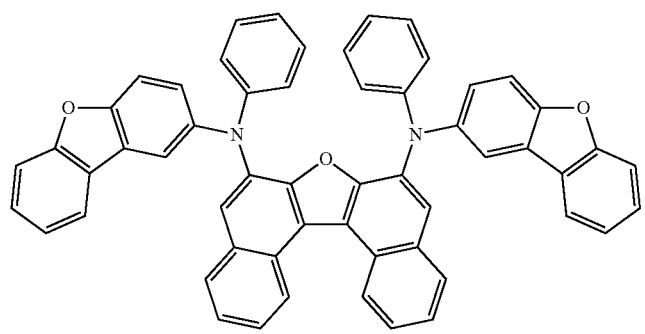
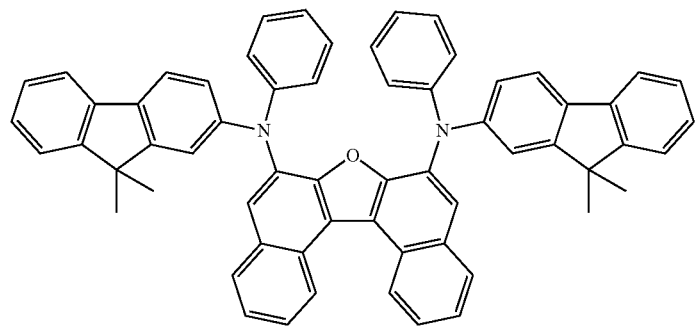
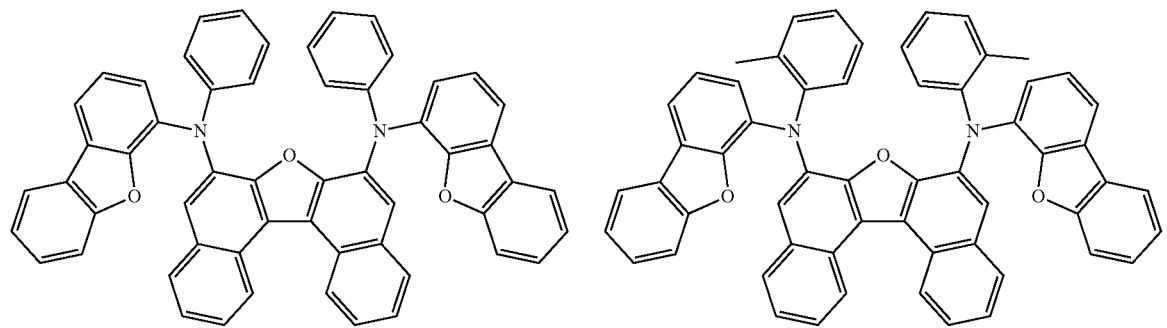
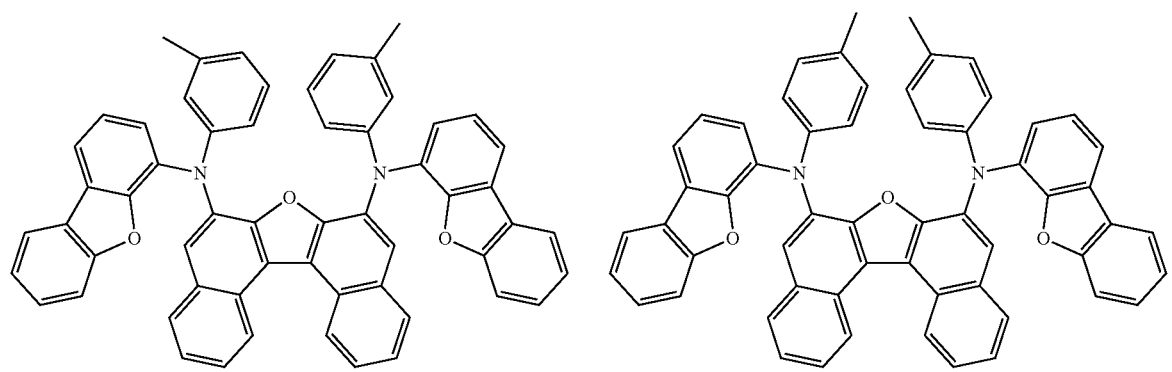

-continued
887 888
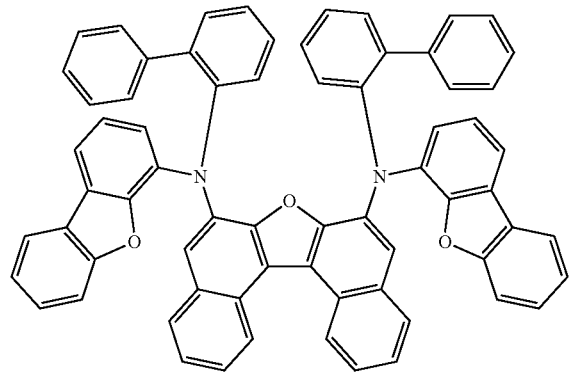
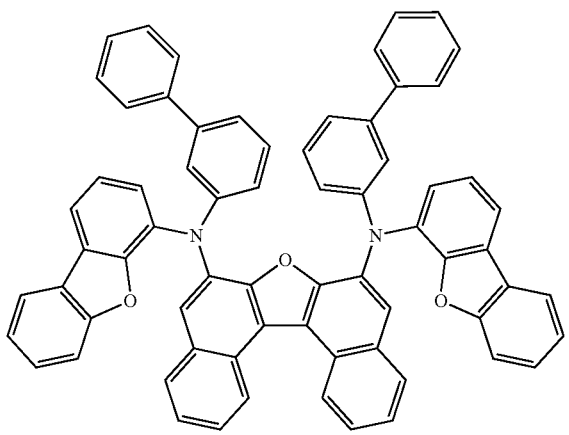
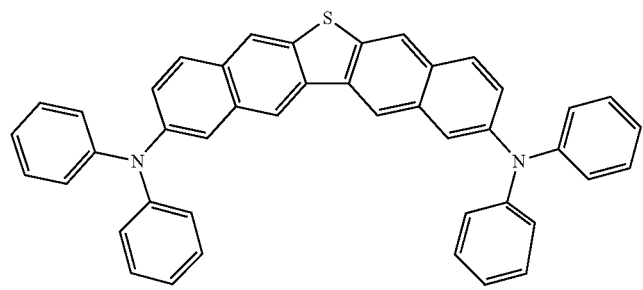
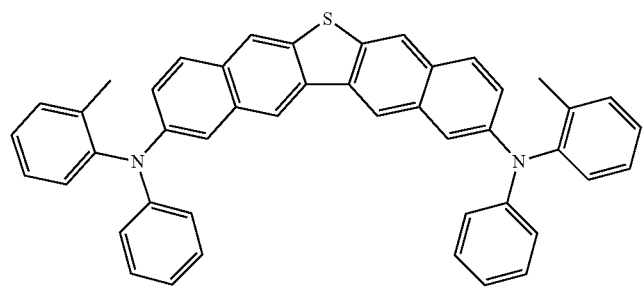
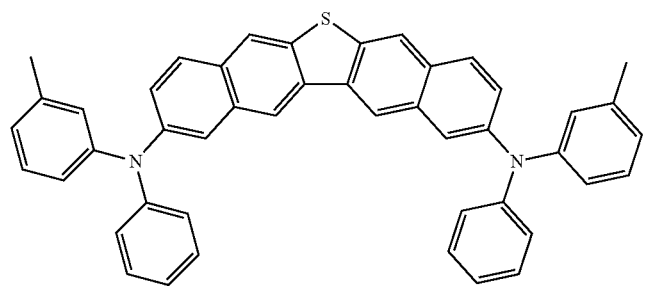
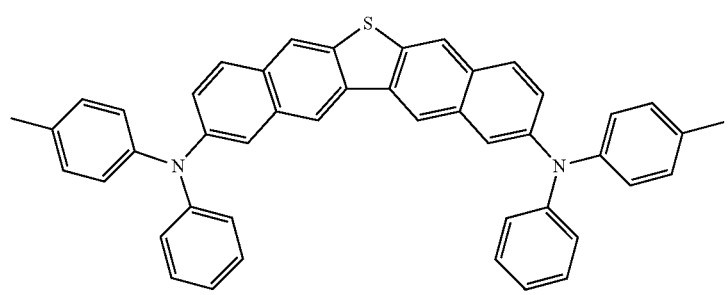

-continued
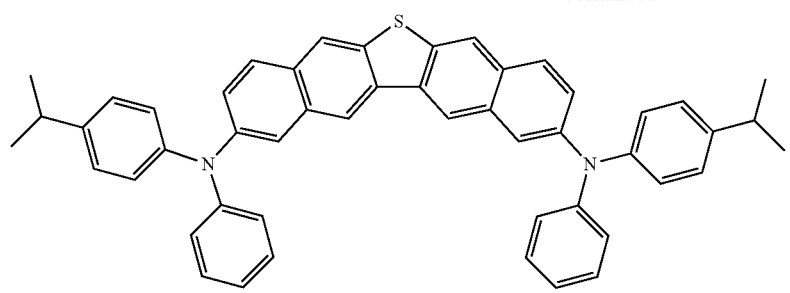
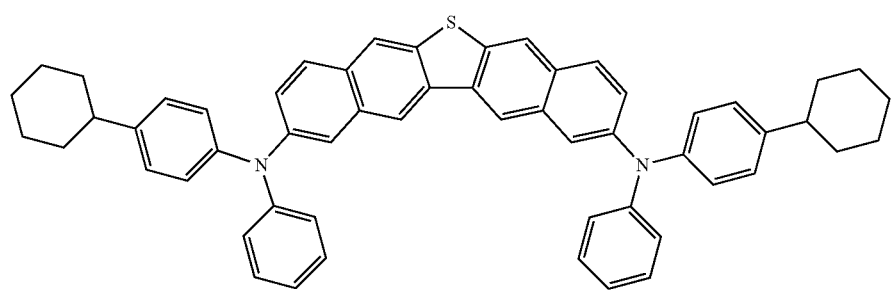
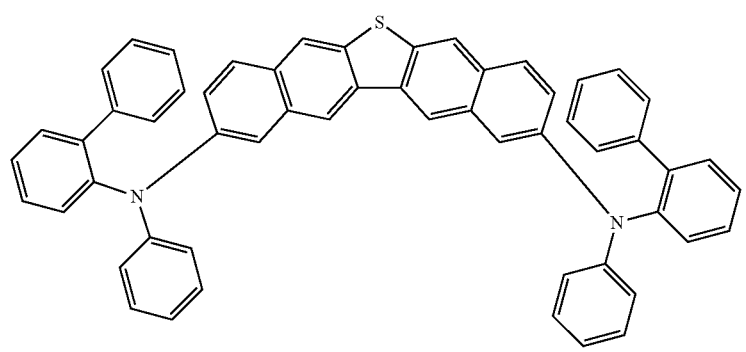
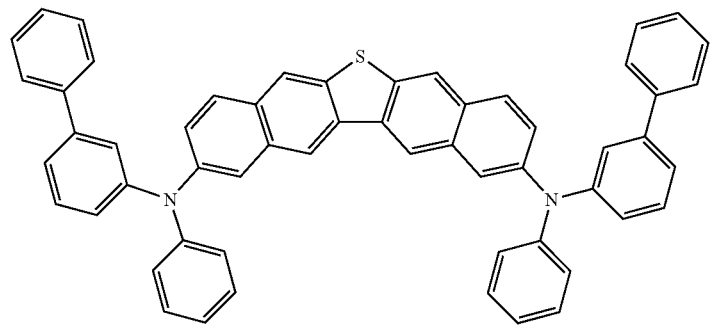
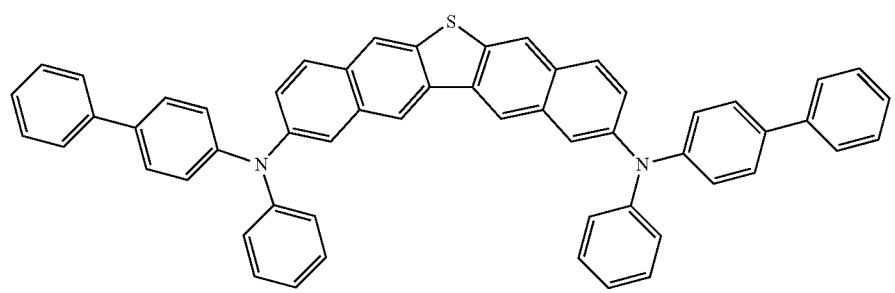

-continued
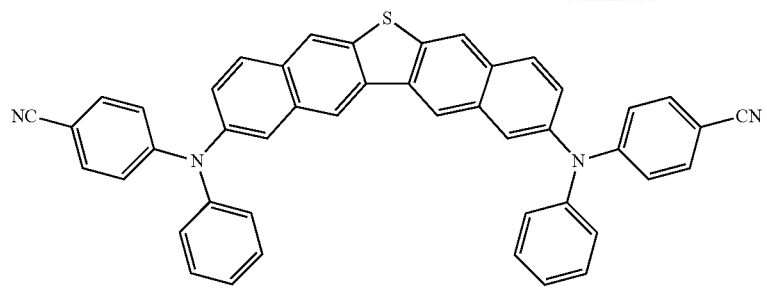
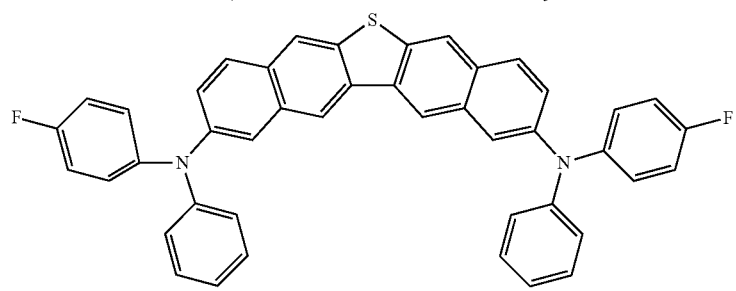
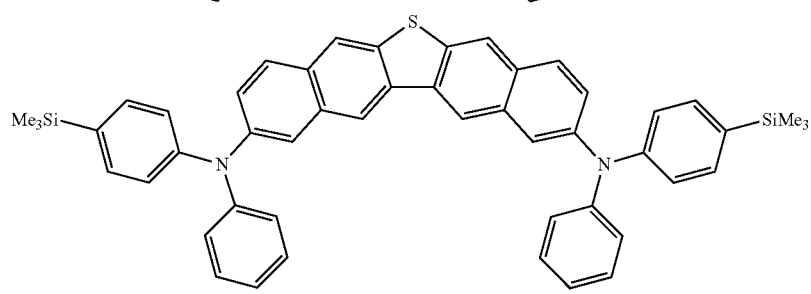
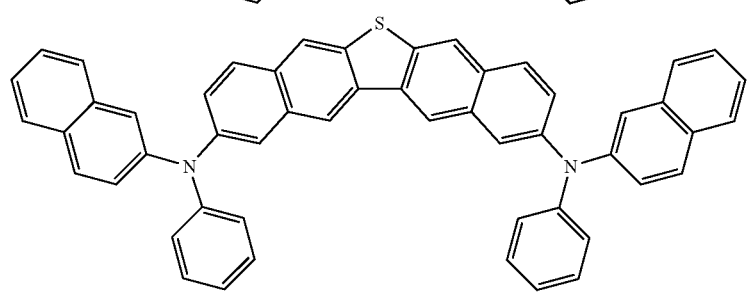
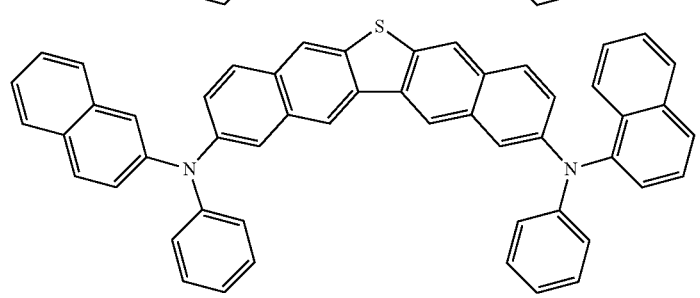
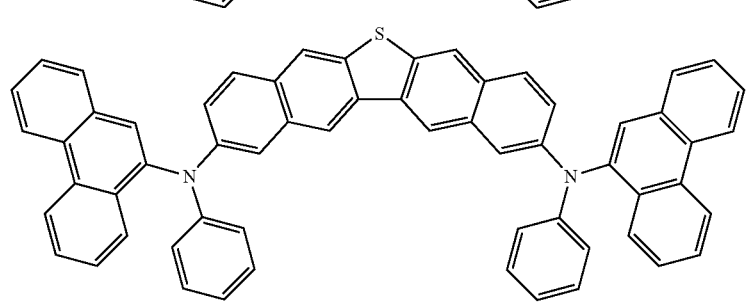

-continued
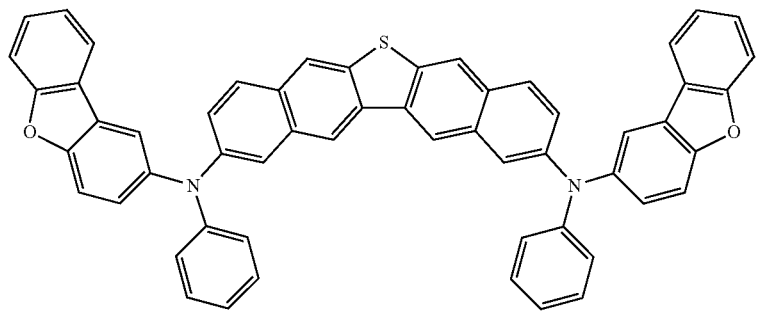
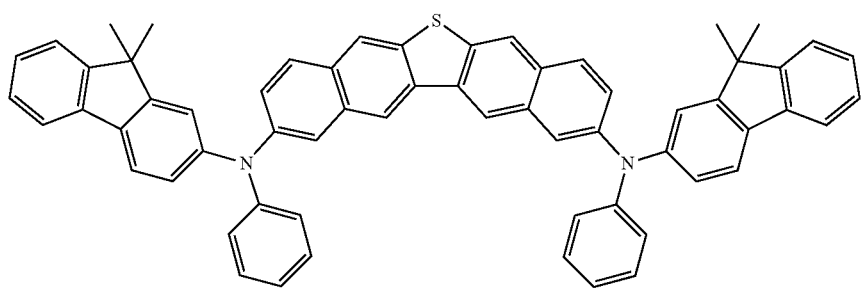
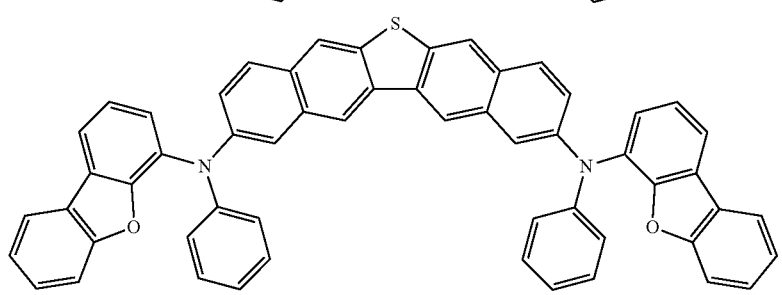
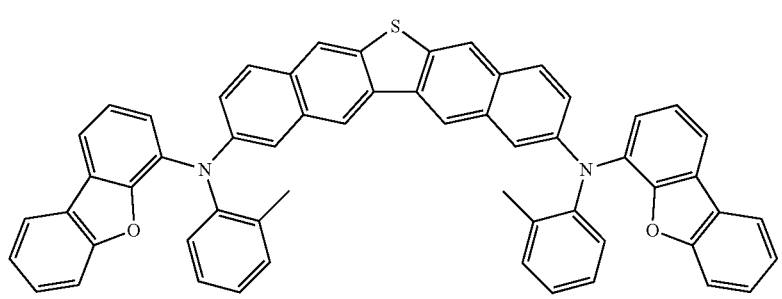
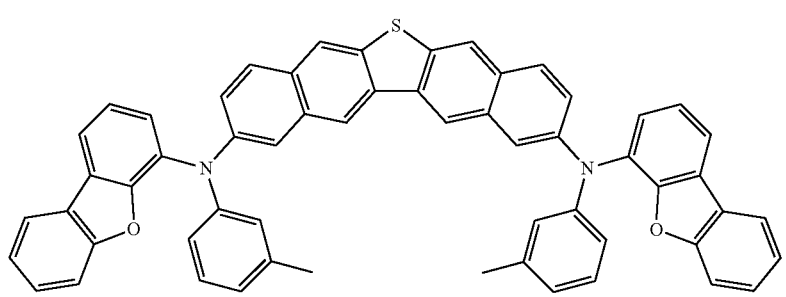

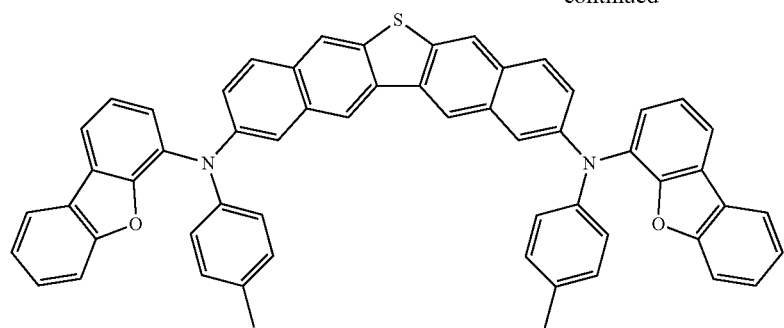
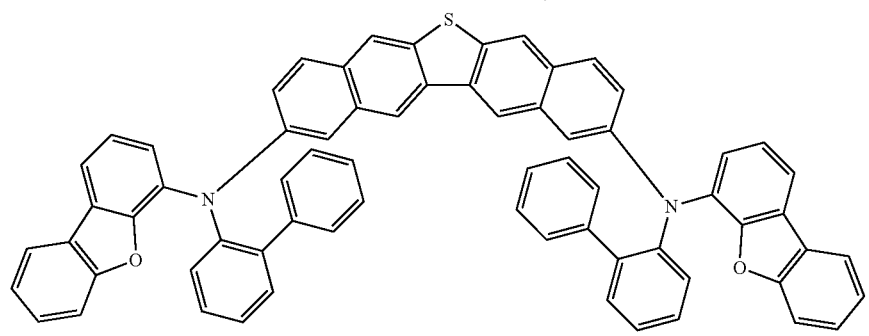
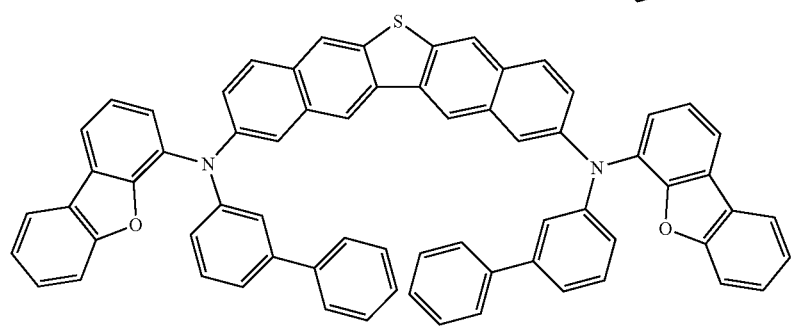
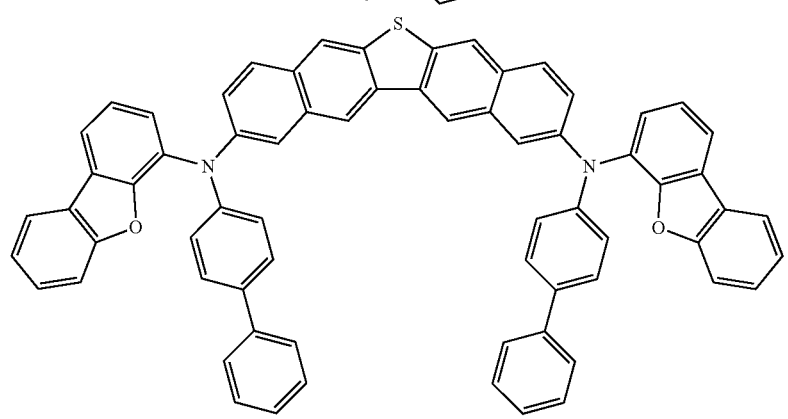
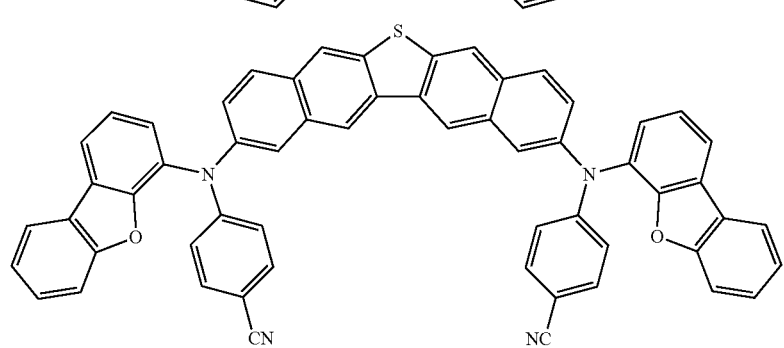

-continued
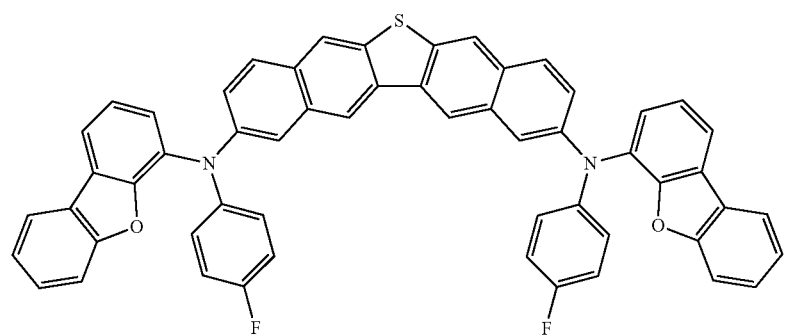
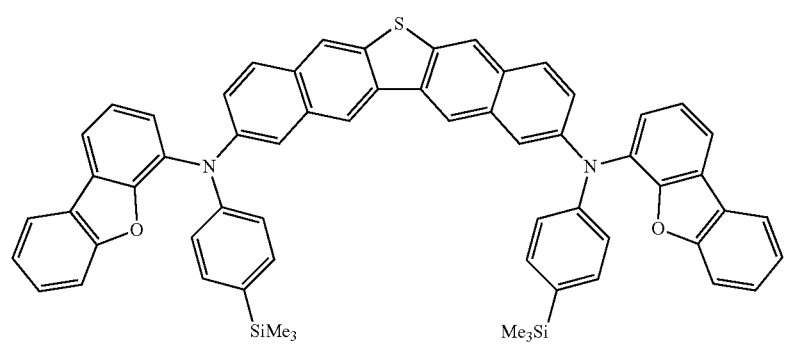
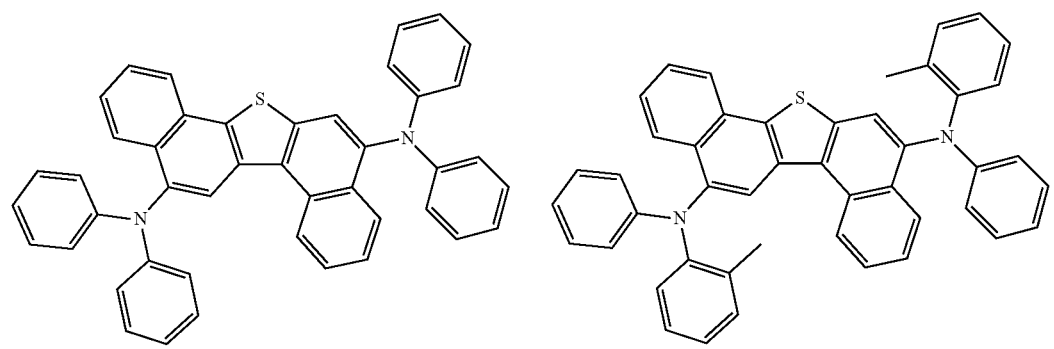
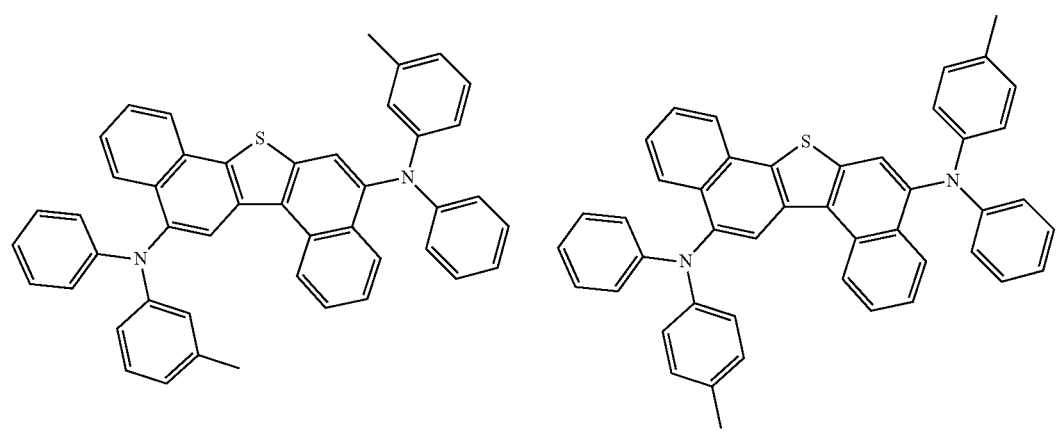

-continued
899
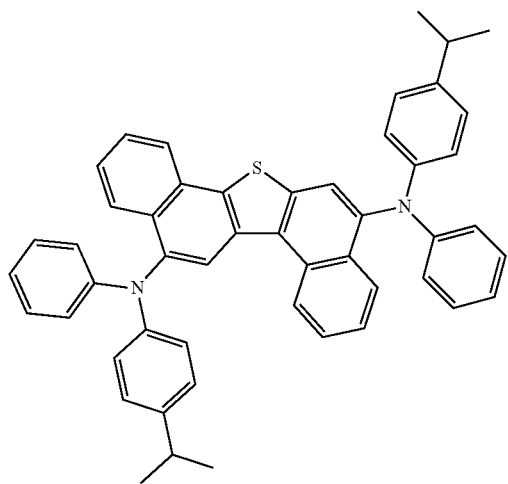
900
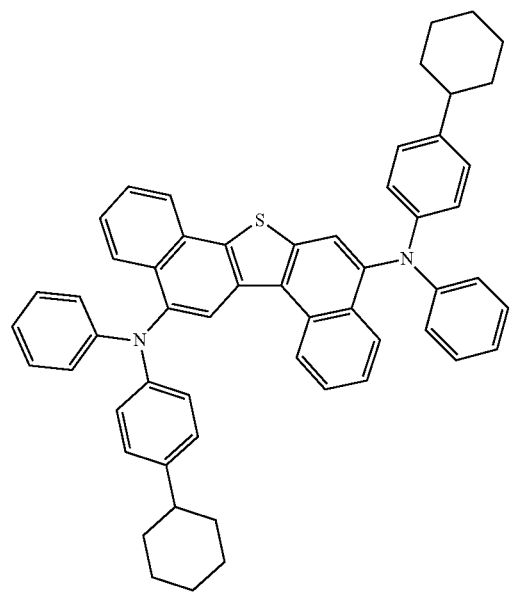
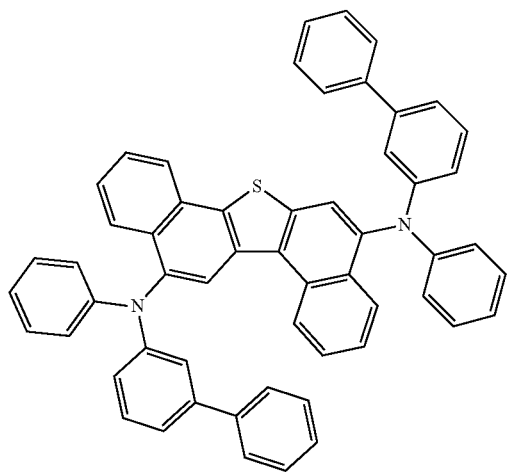
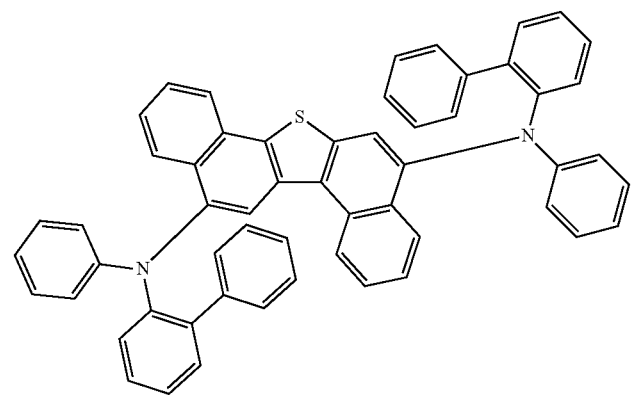
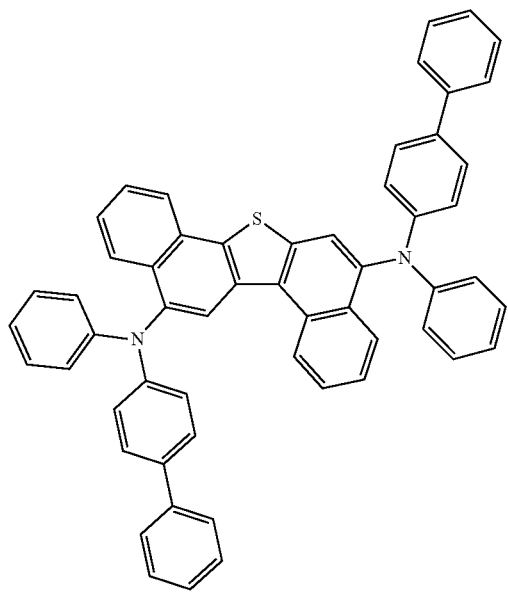
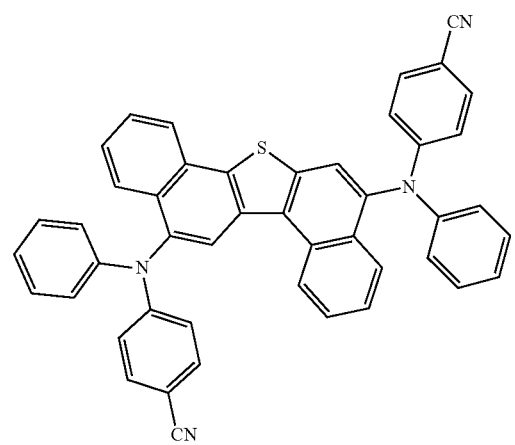

-continued
901
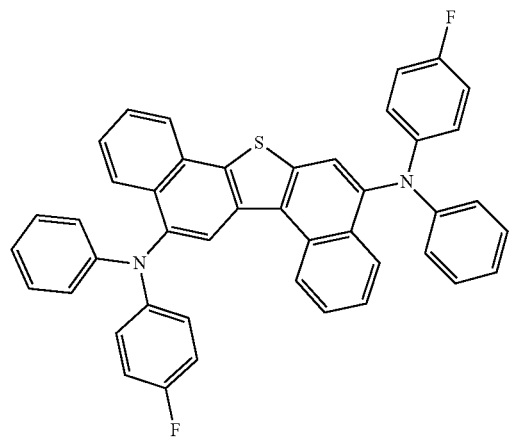
902
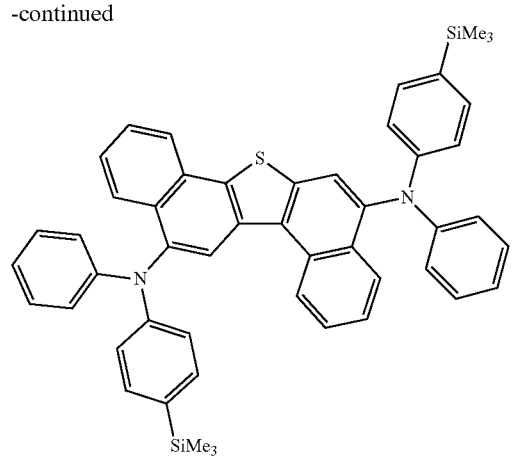
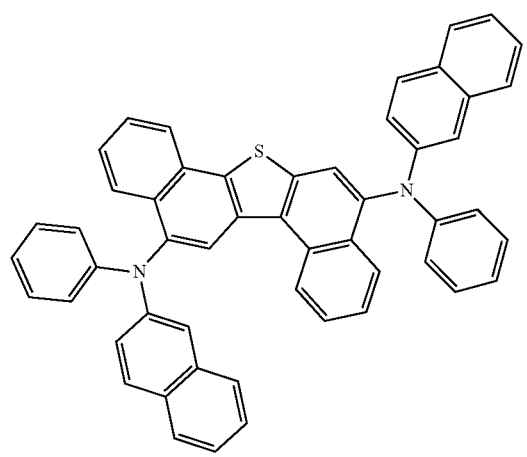
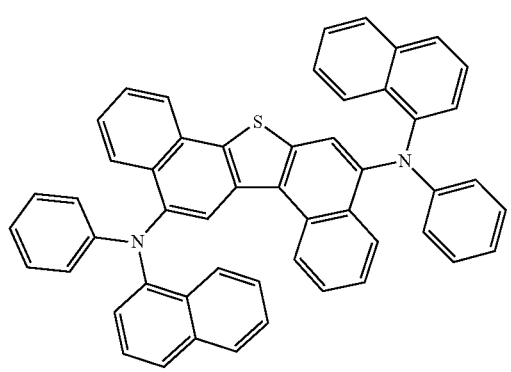
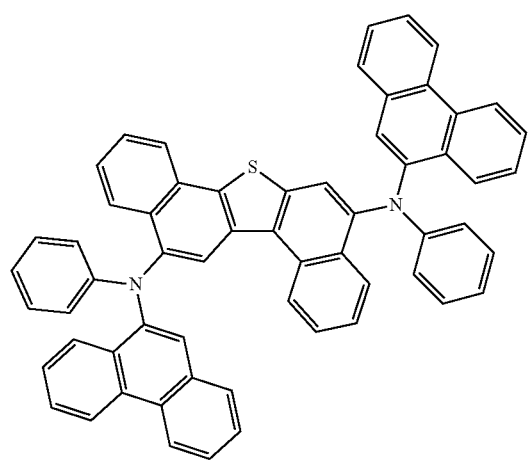

-continued
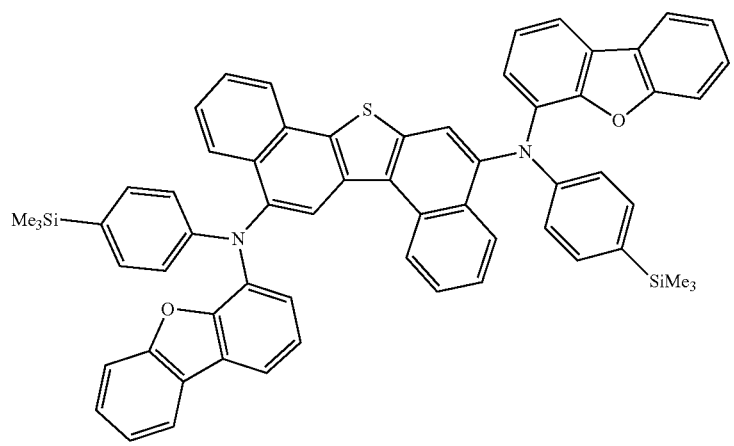
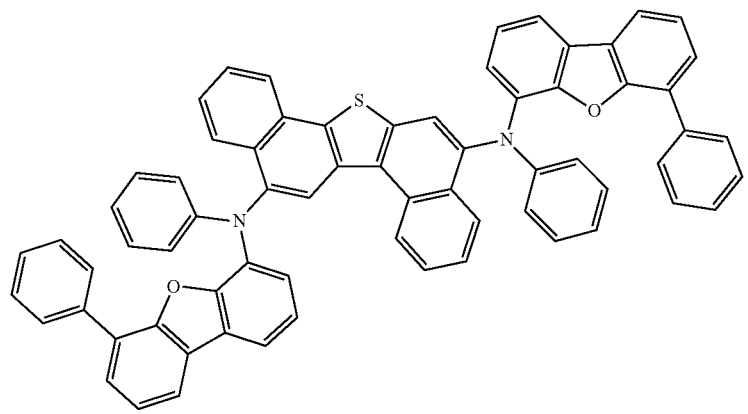
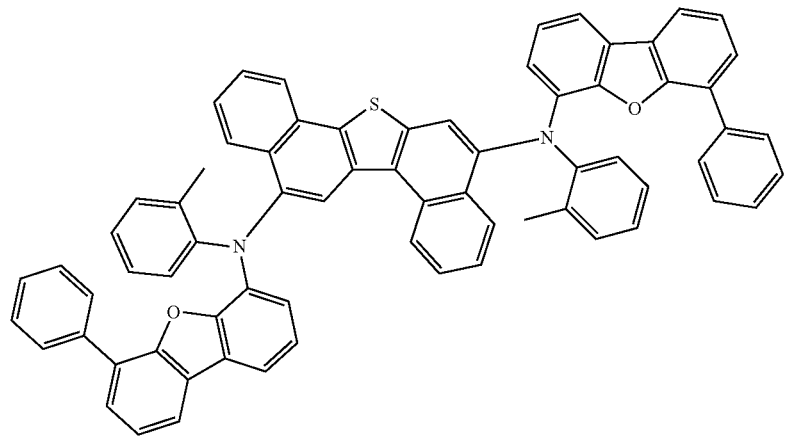
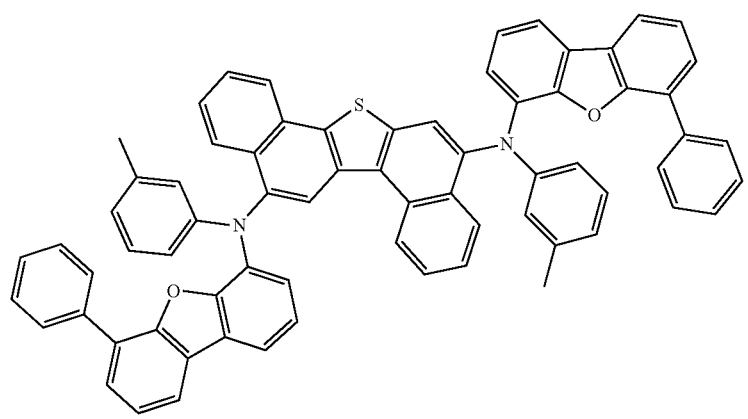

-continued
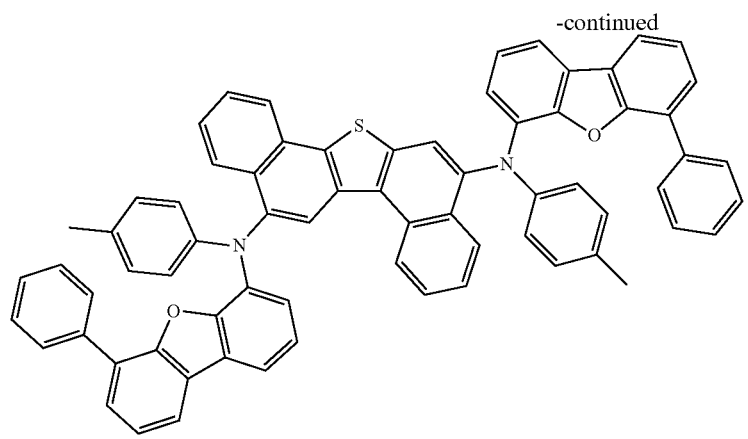
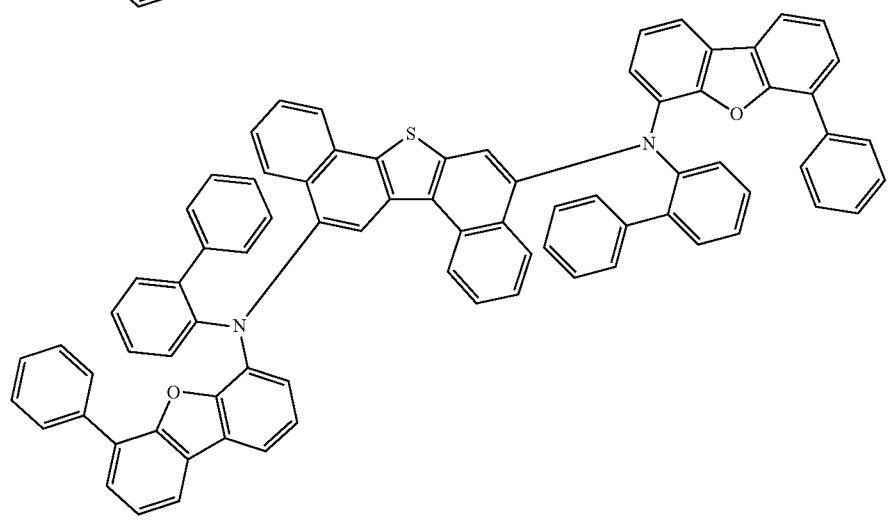
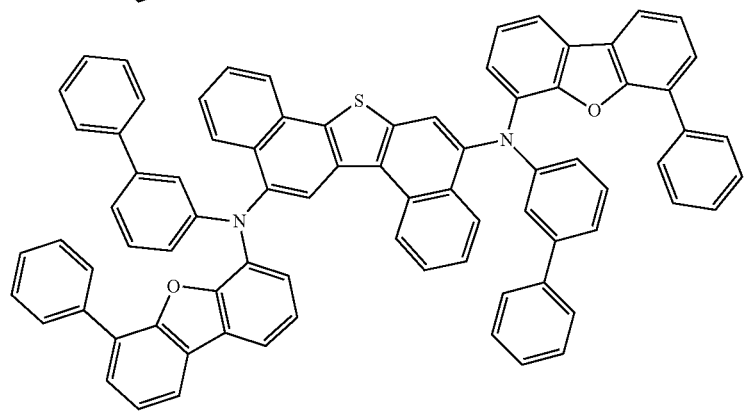
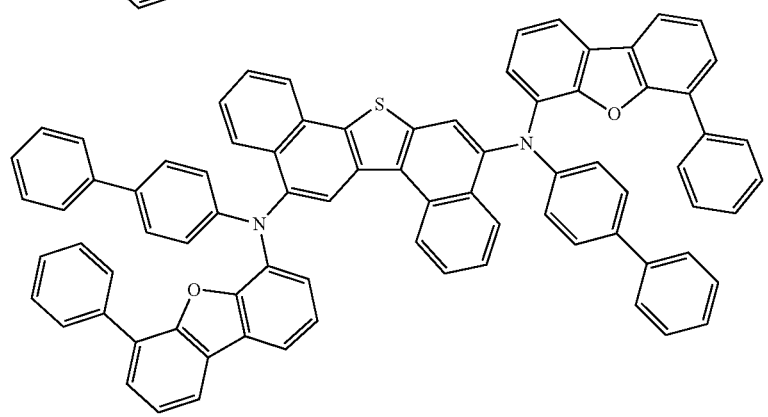

907 908
-continued
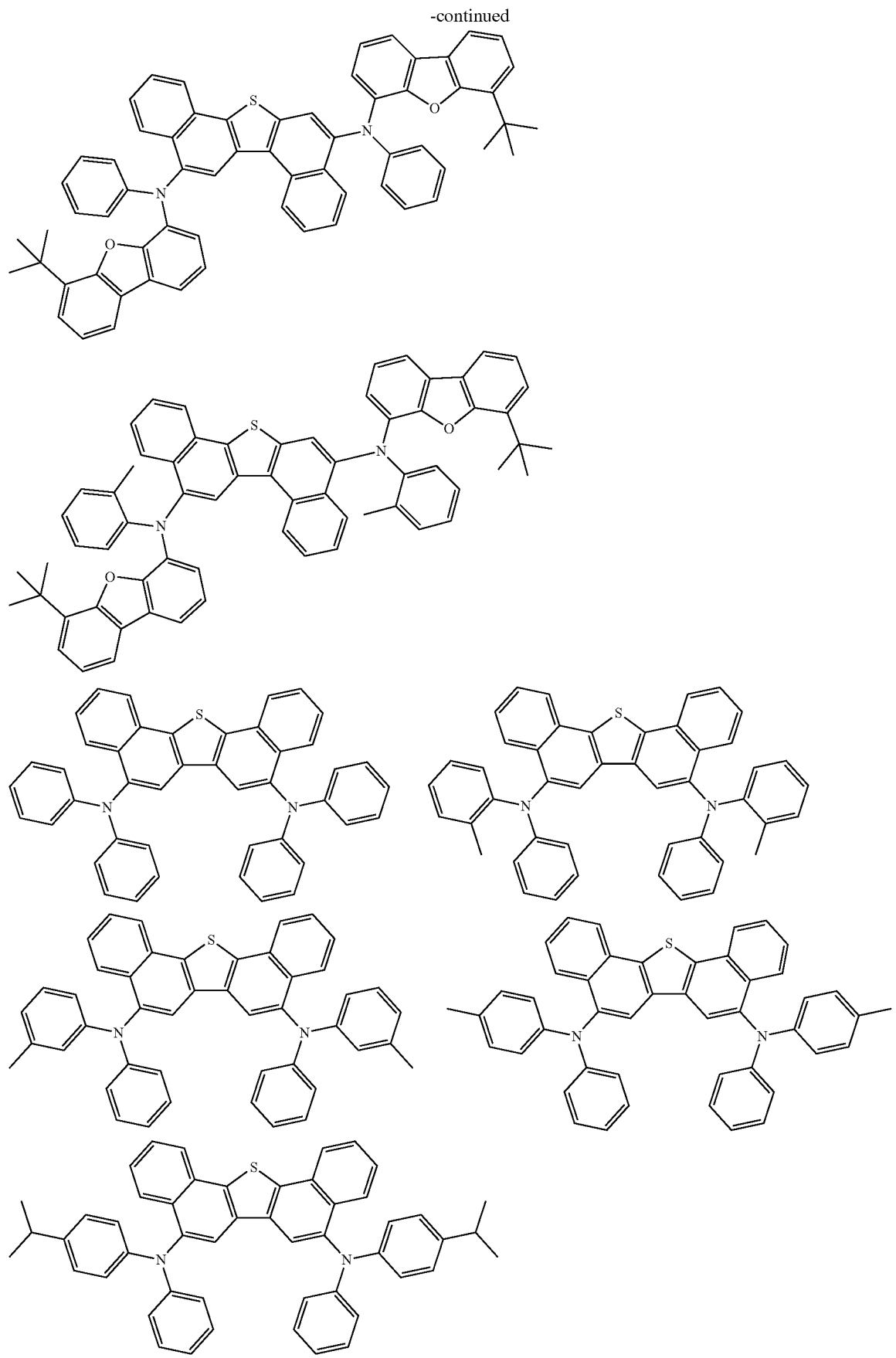

-continued
909 910
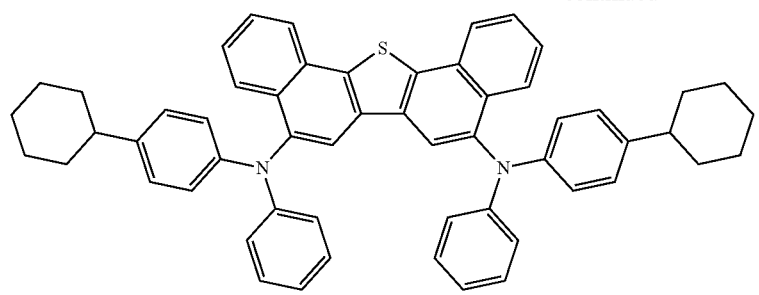
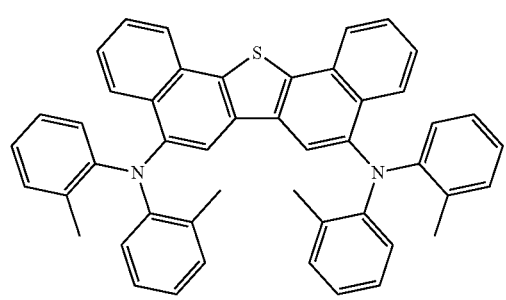
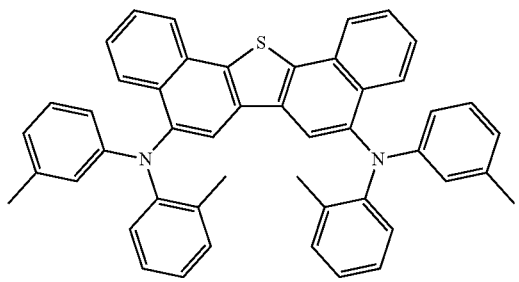
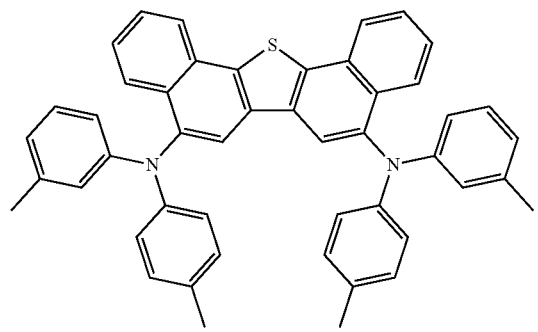
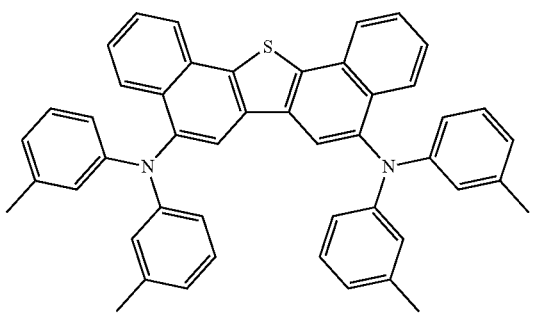
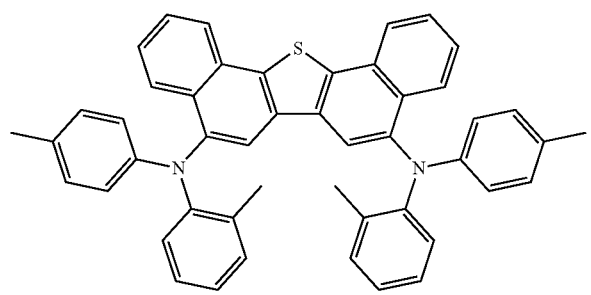
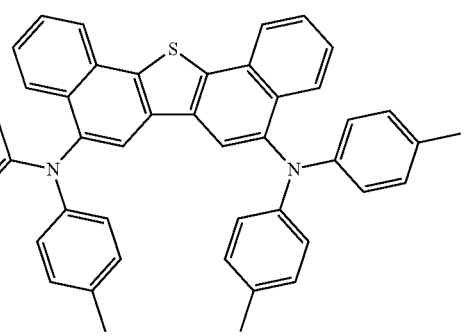
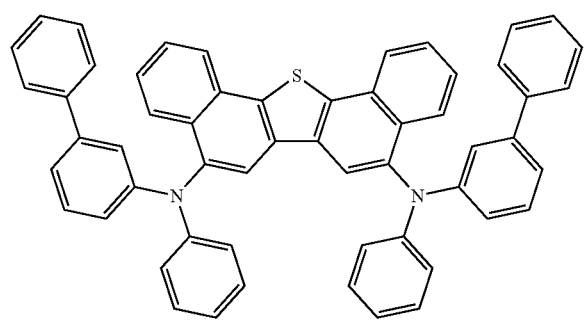
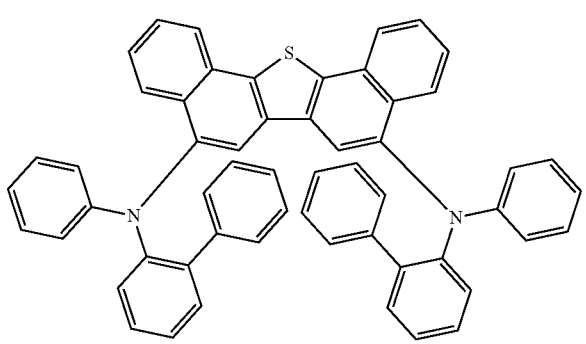

-continued
911
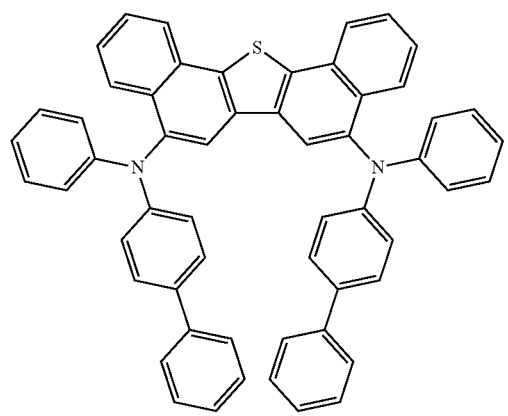
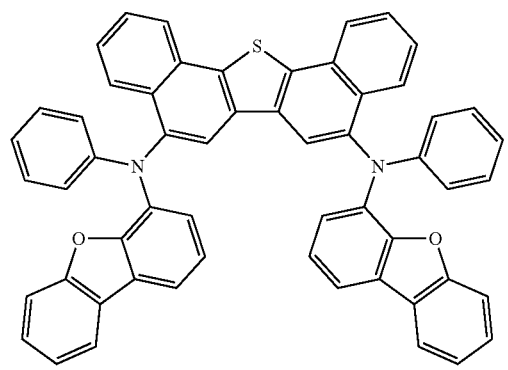
912
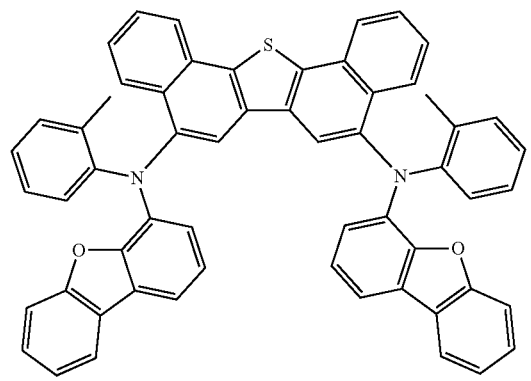
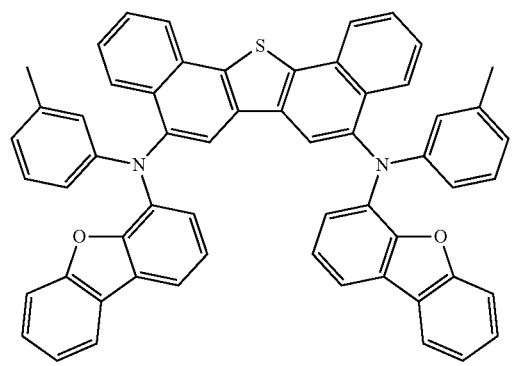
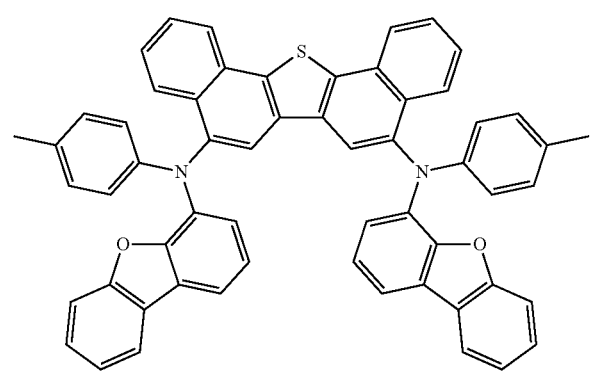
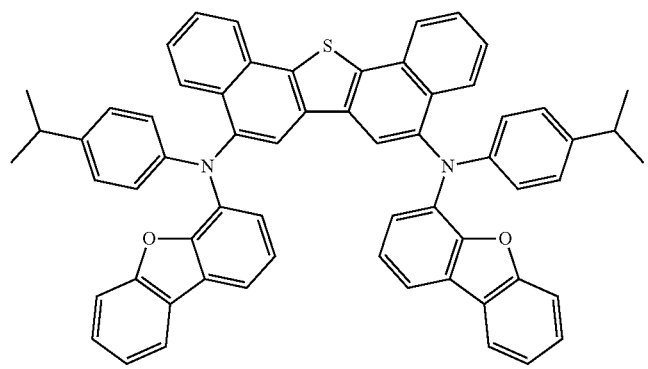

913    914
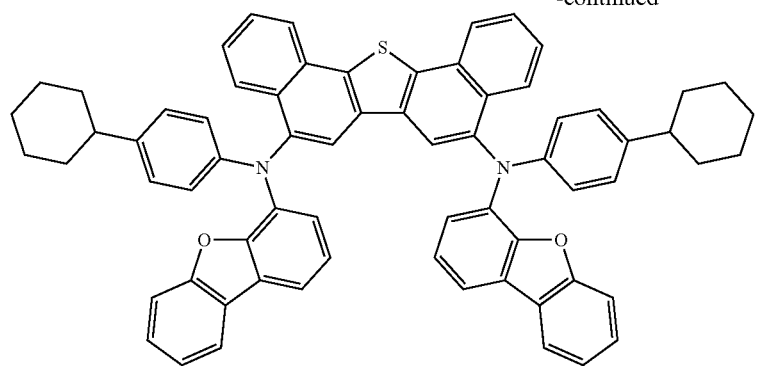
-continued

-continued
915
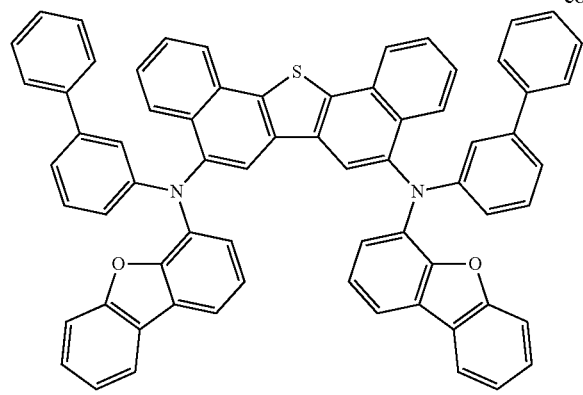
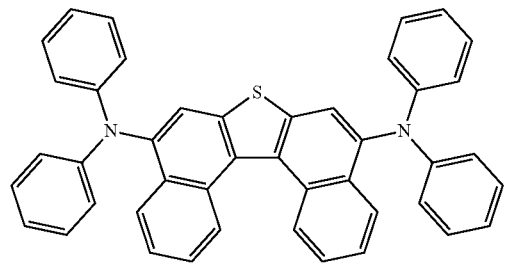
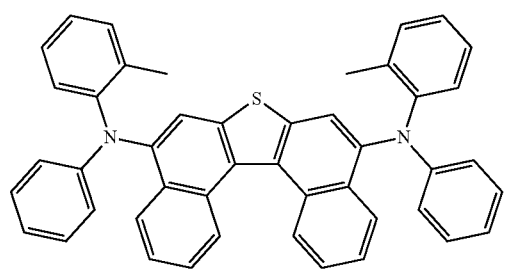
916
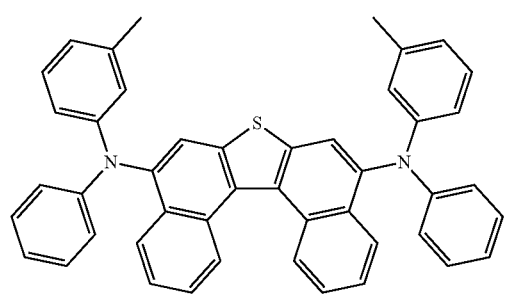
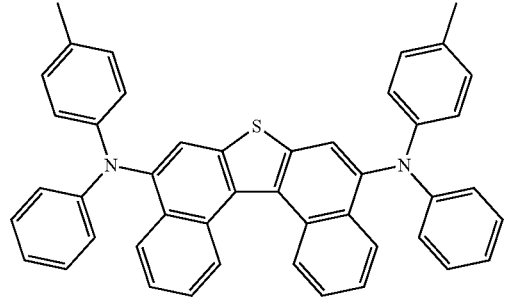
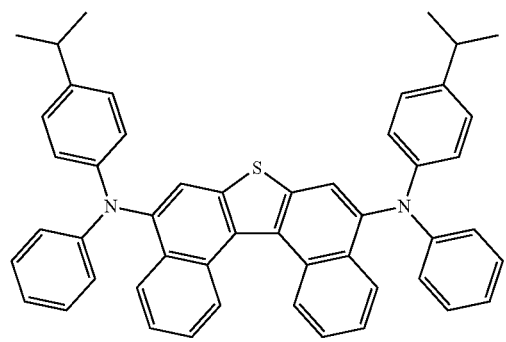
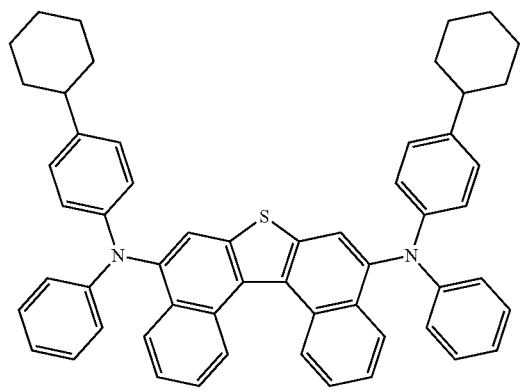
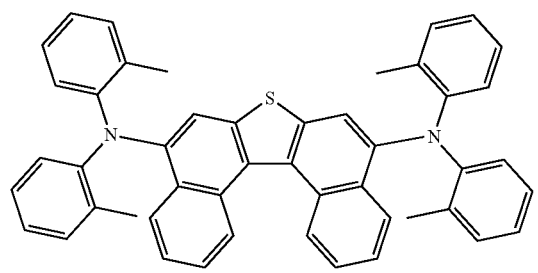
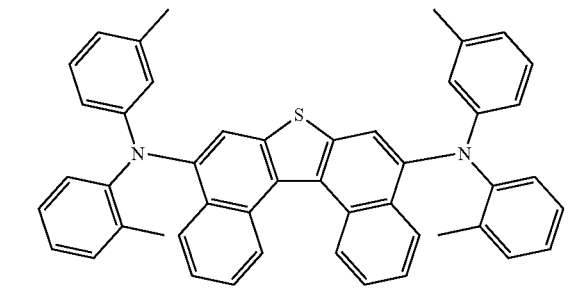

-continued
| 917 | 918 |
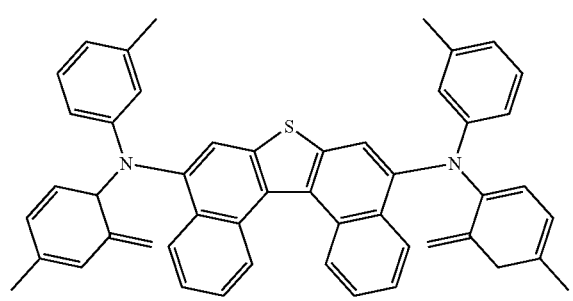
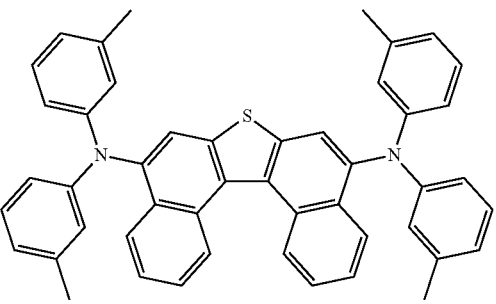
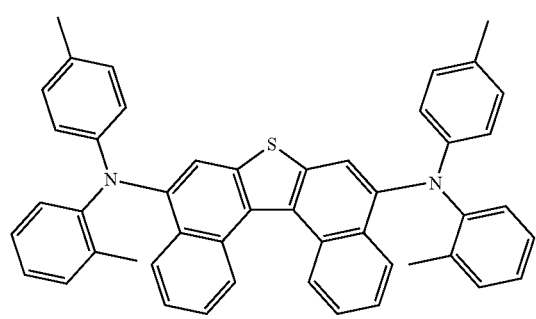
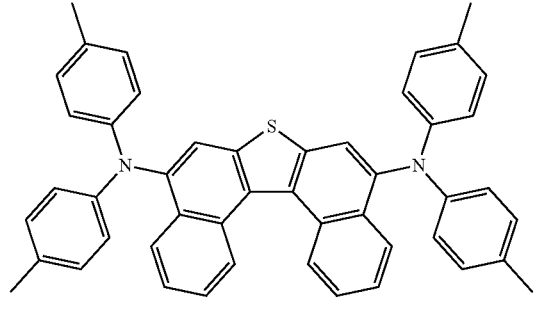
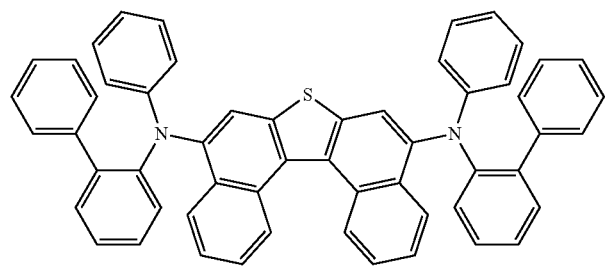
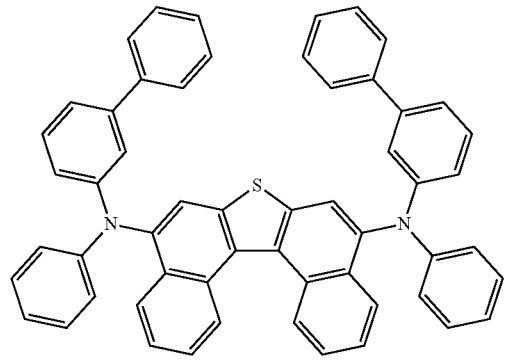
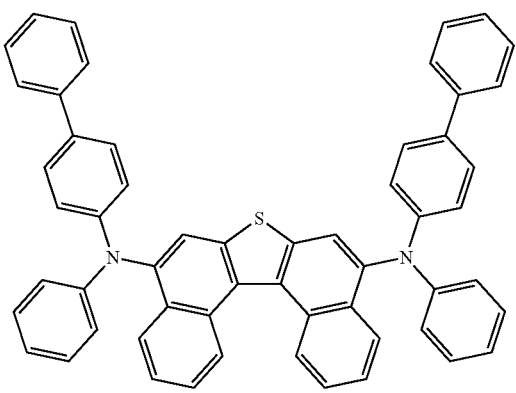
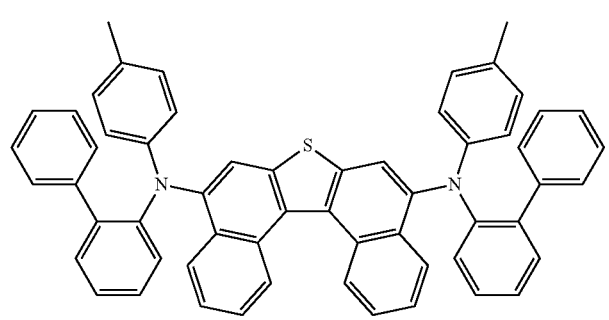

-continued
919 920
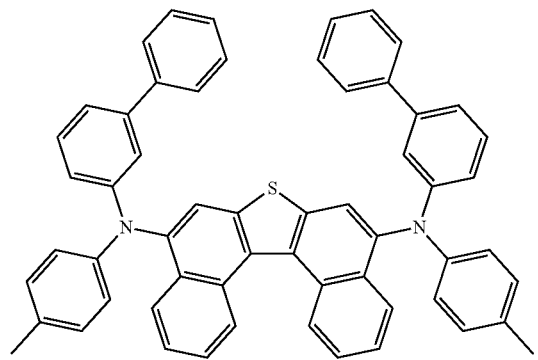
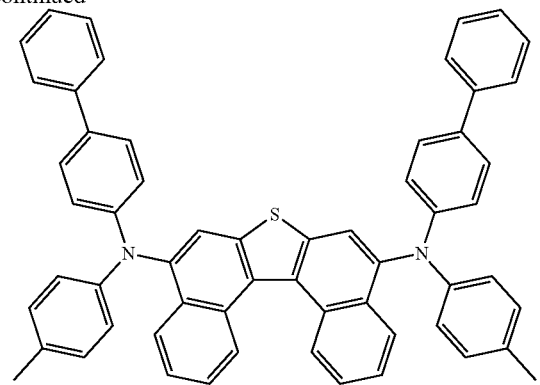
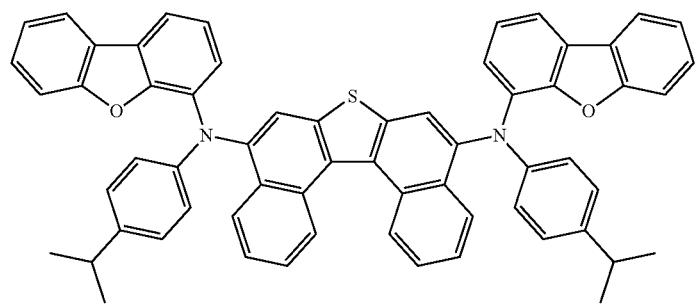
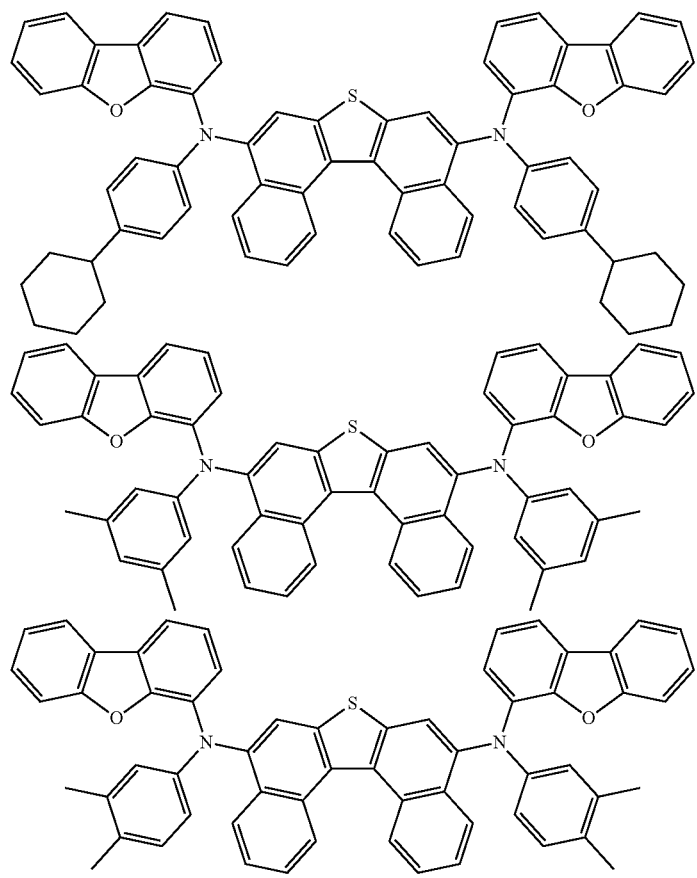

921
-continued
922
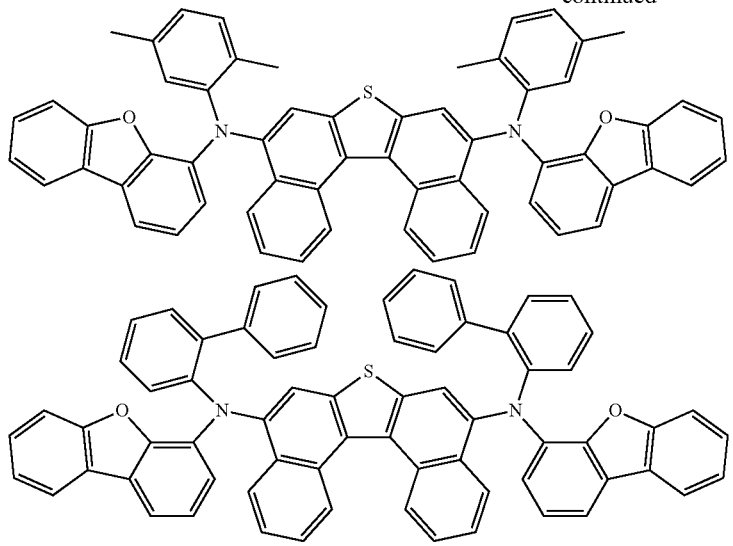
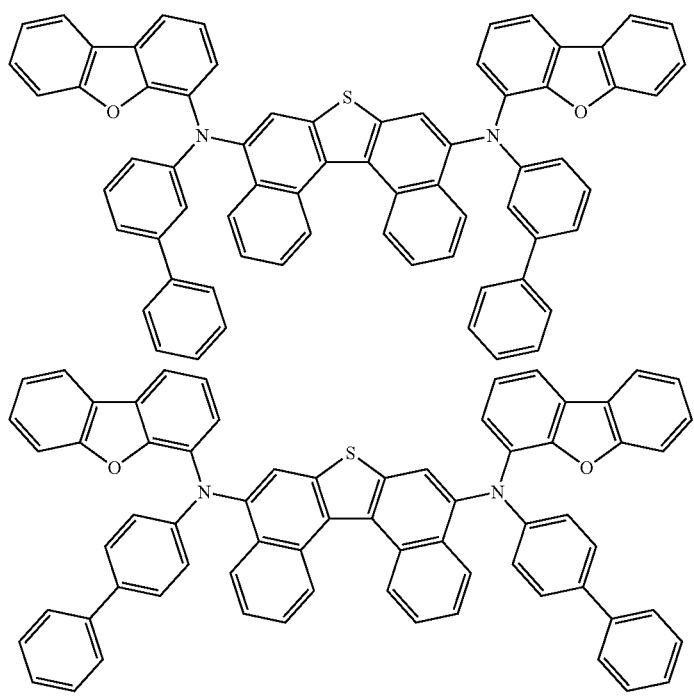
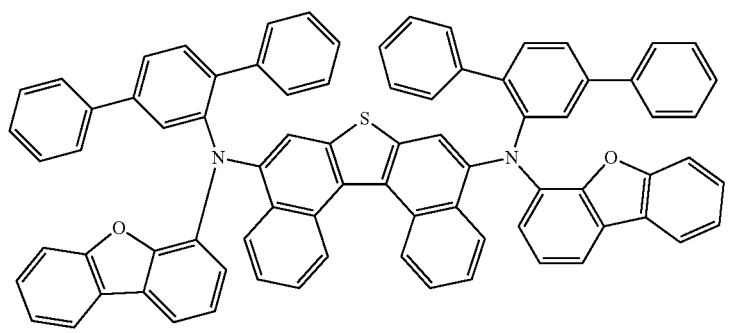

923                                                 924
-continued
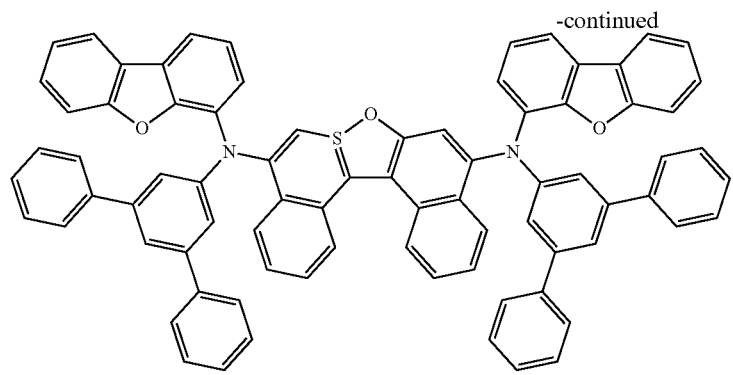
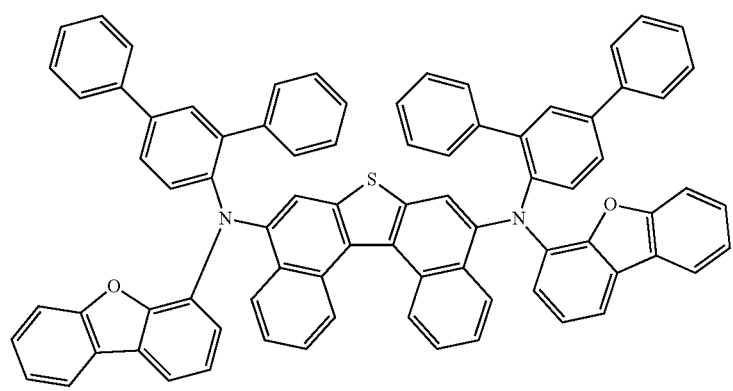
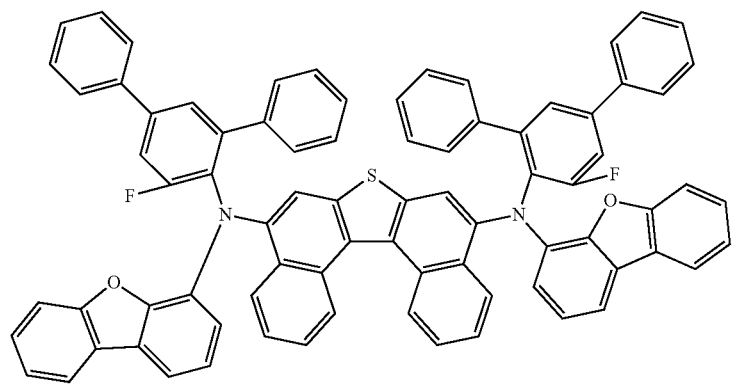
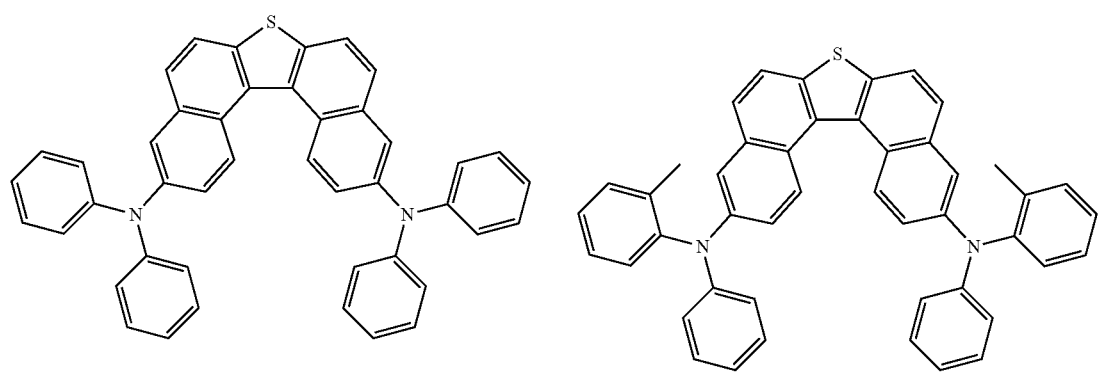

-continued
| 925 | 926 |
|---|---|
| 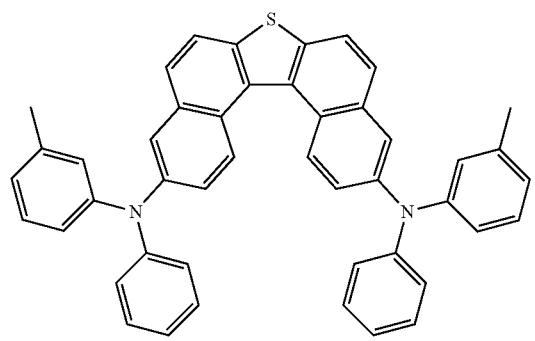 | 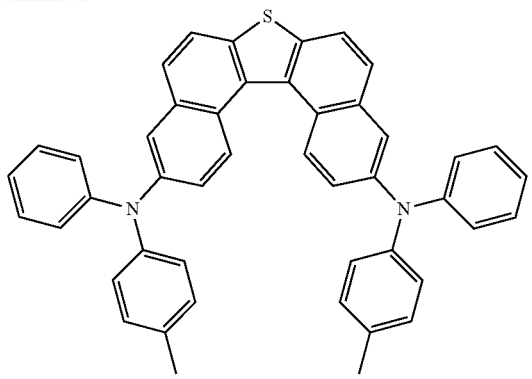 |
| 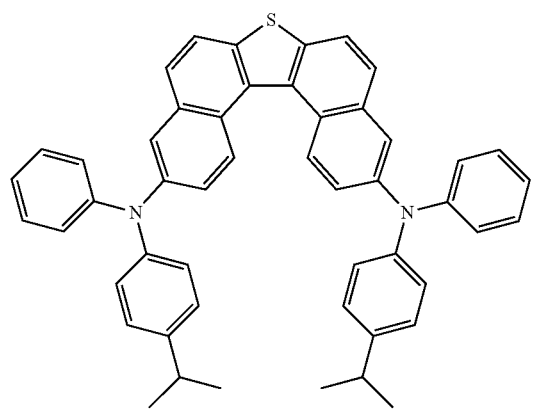 | 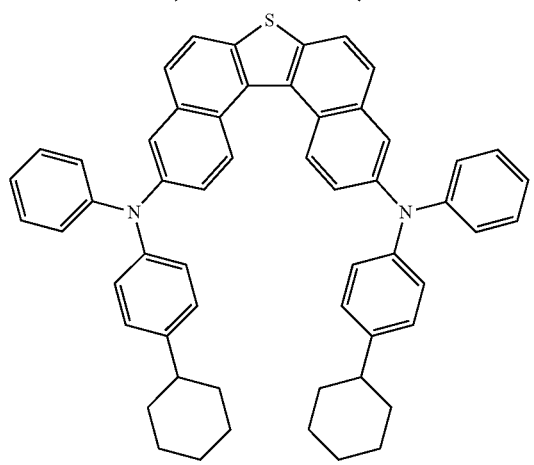 |
| 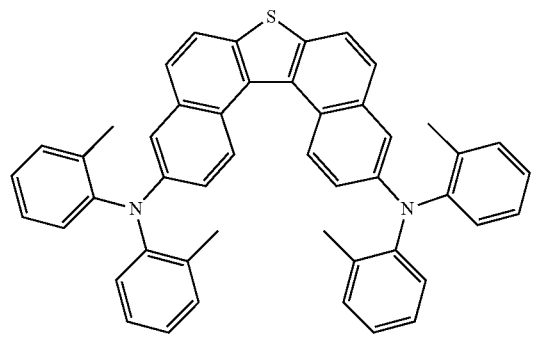 | 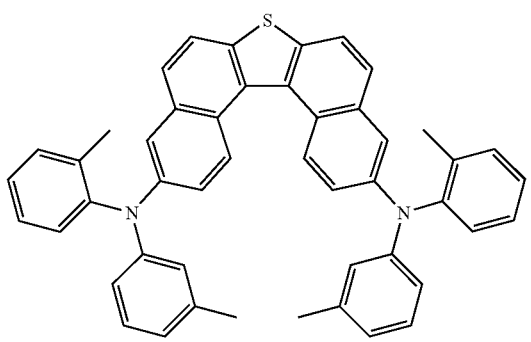 |
| 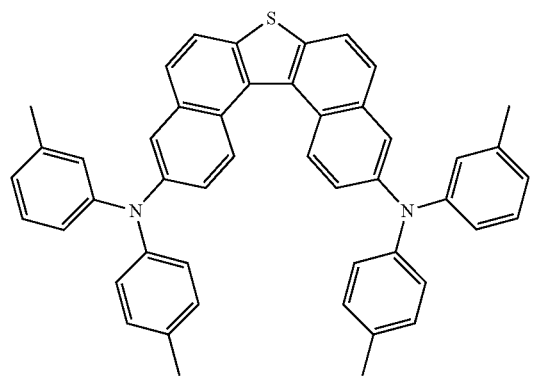 | 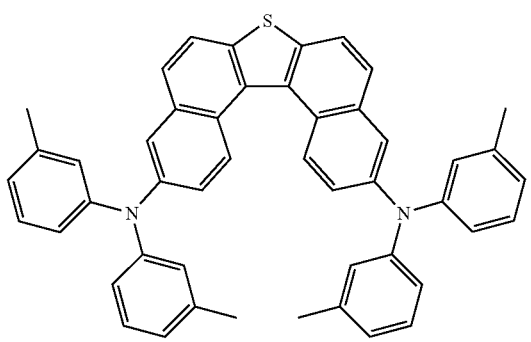 |

-continued
| 927 | 928 |
|---|---|
| 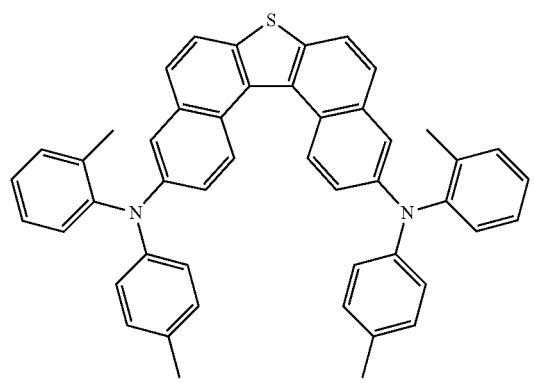 | 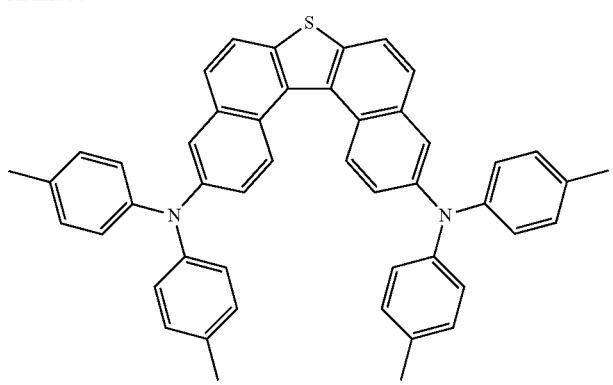 |
| 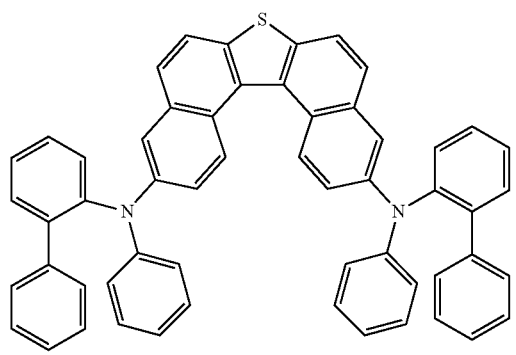 | 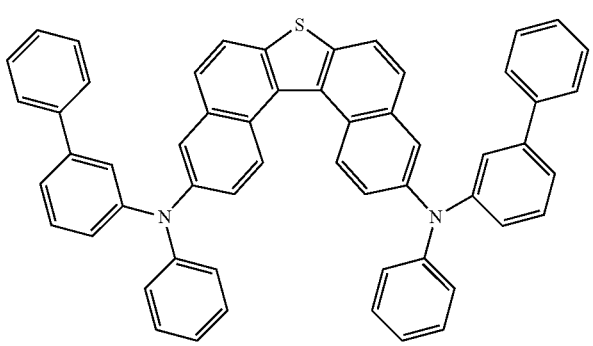 |
| 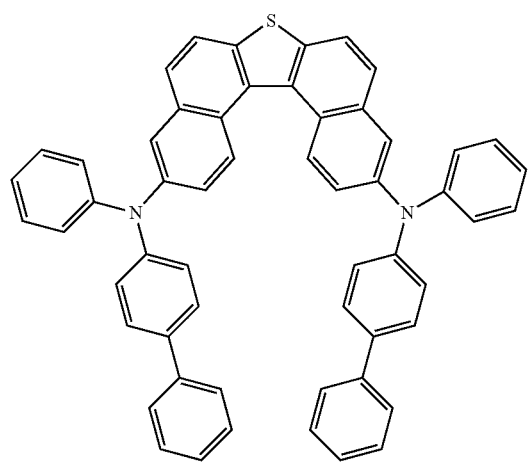 | |
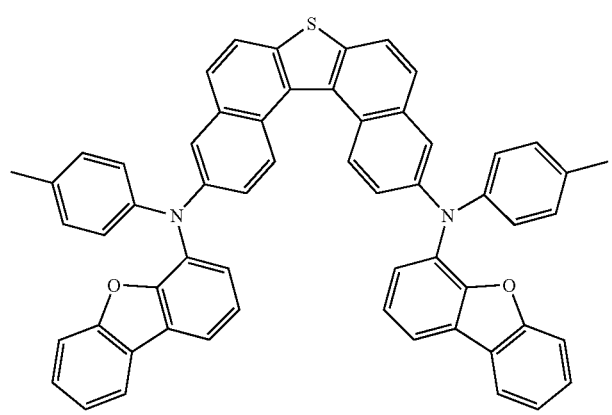

929 930
-continued
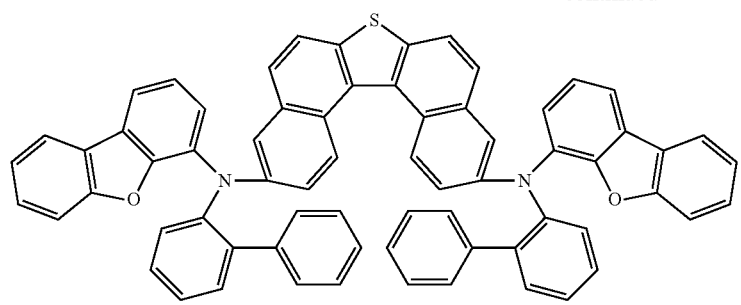
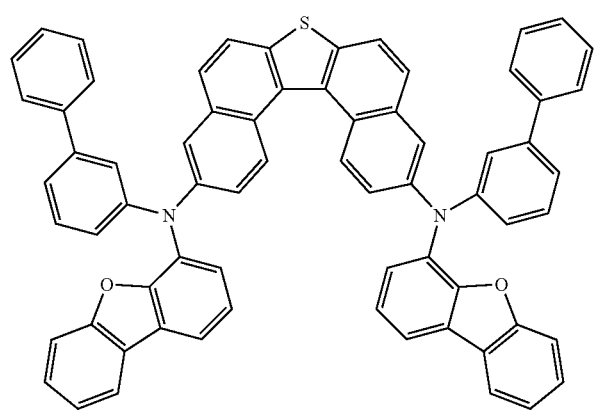
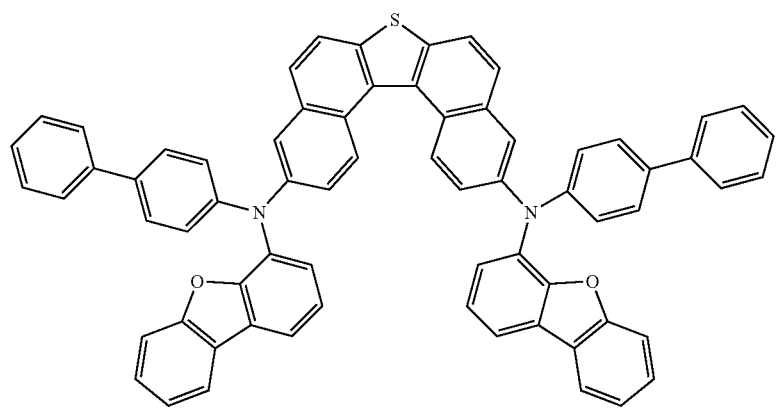
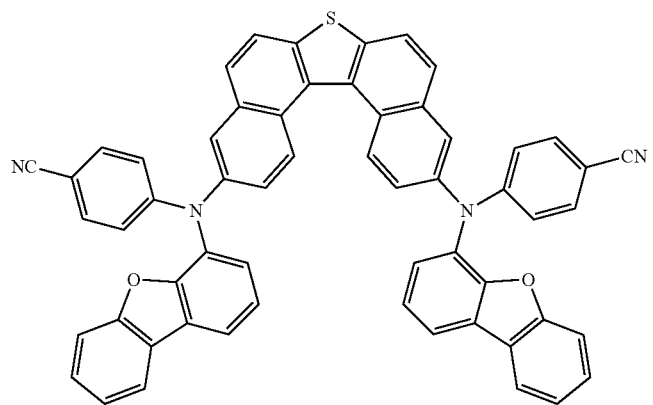

931
-continued
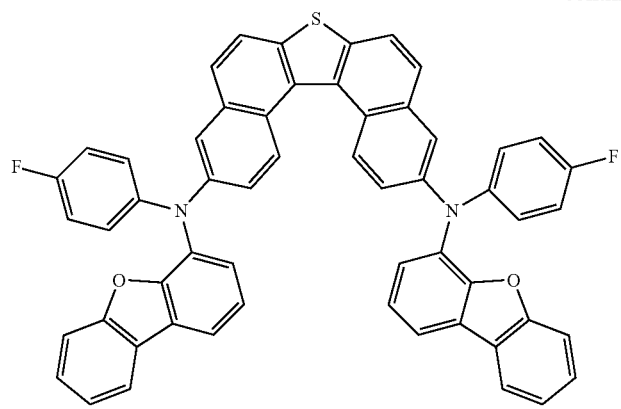
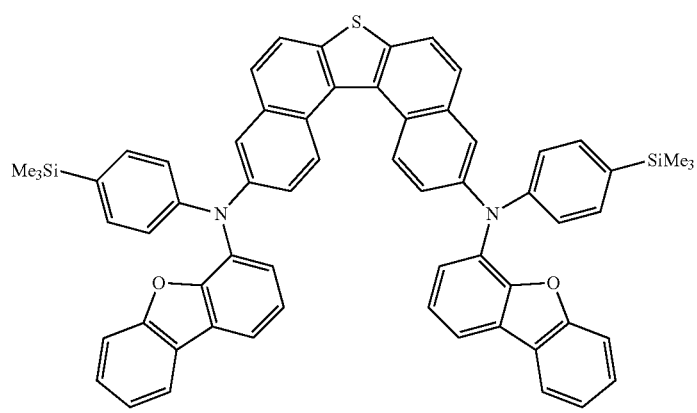
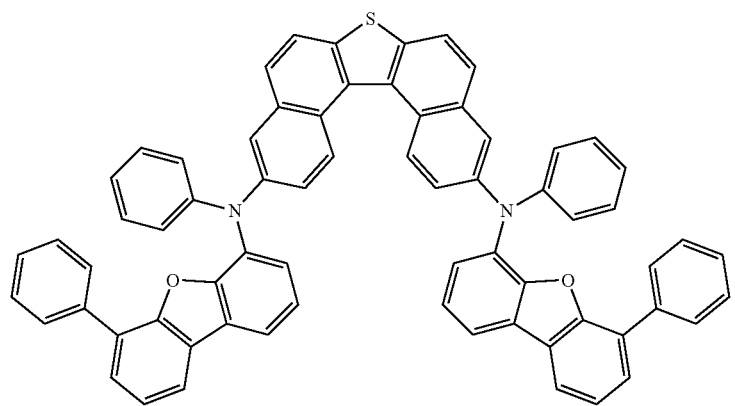
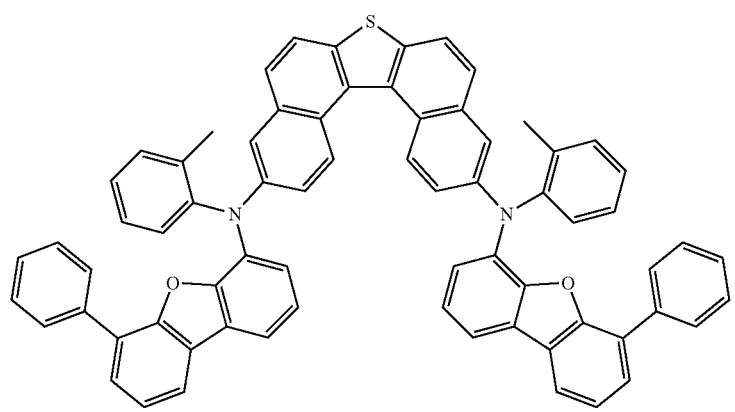
932

-continued
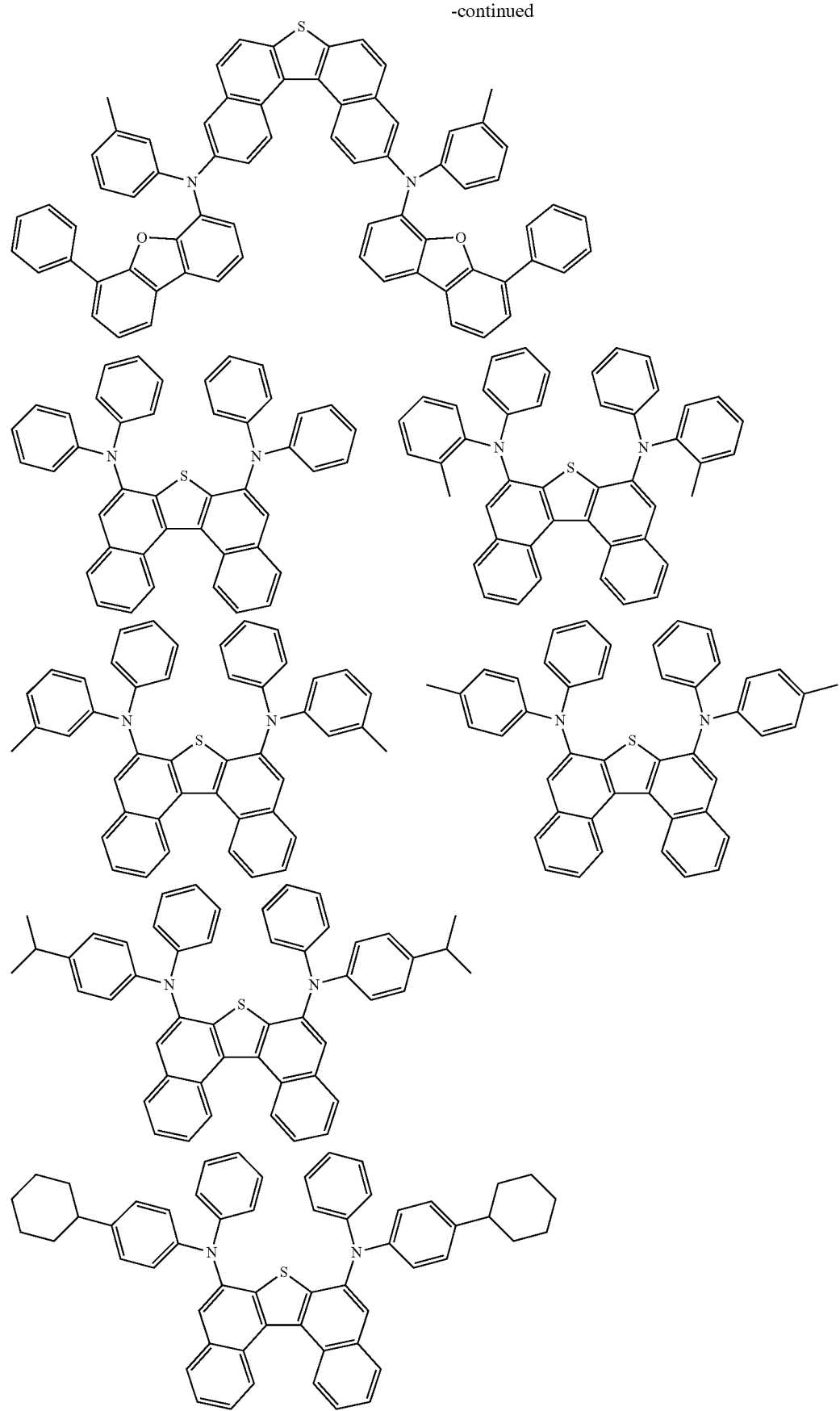

-continued
935
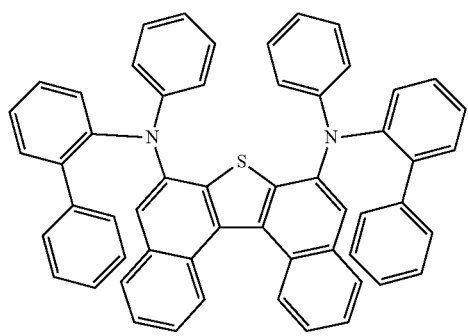
936
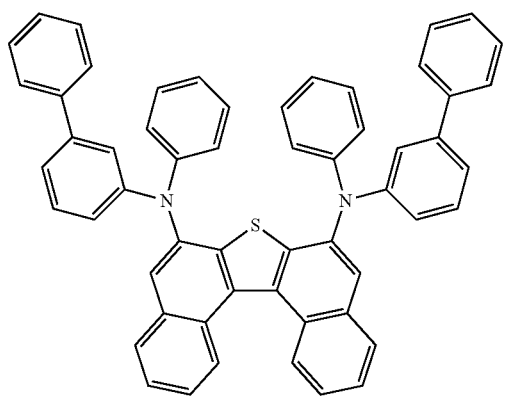
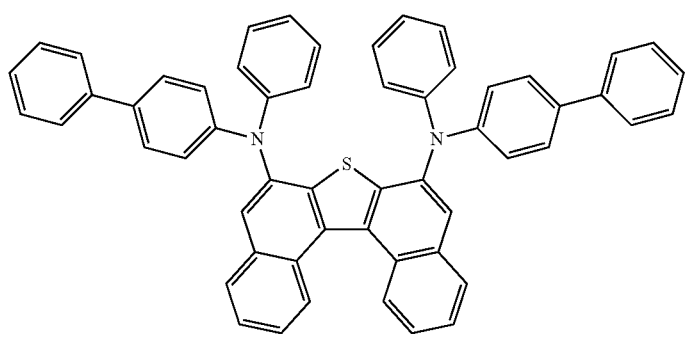
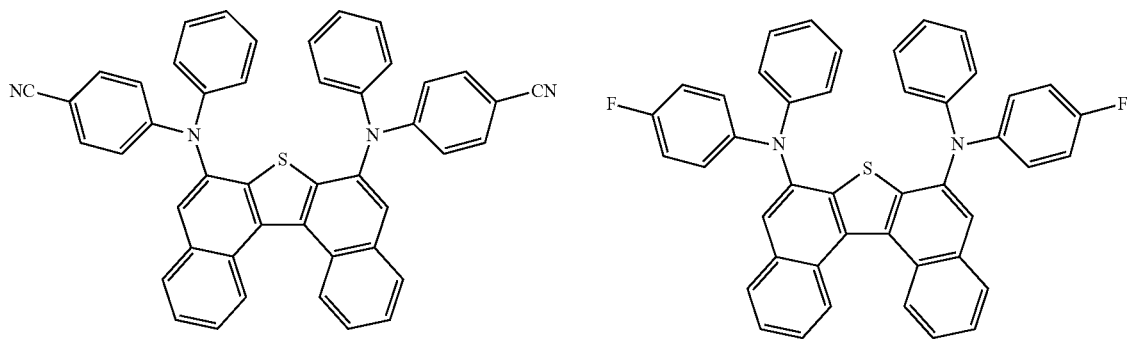
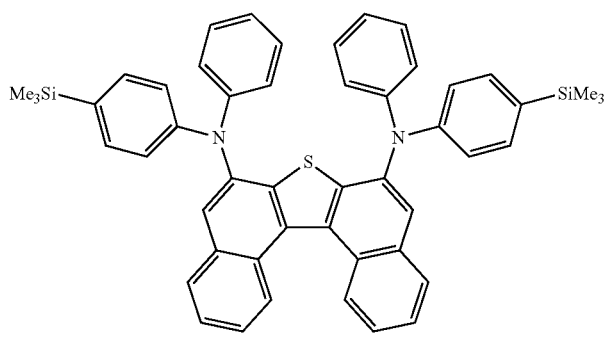

-continued
937 938
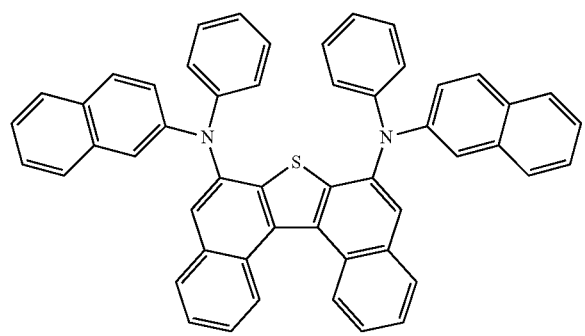
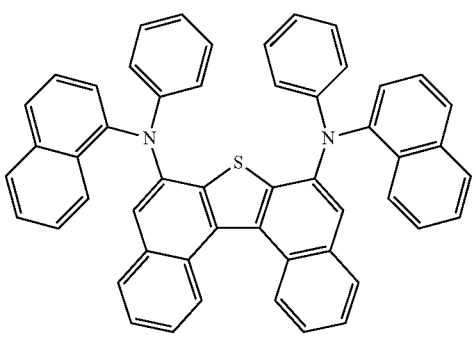
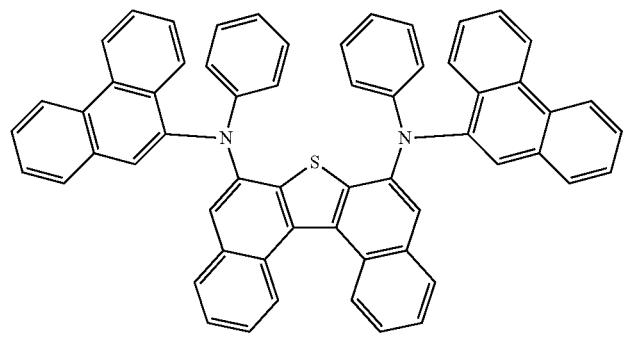
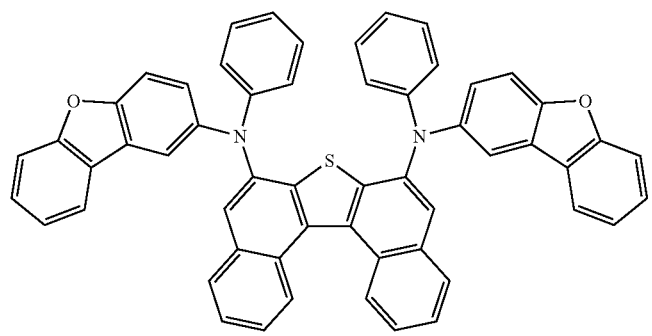
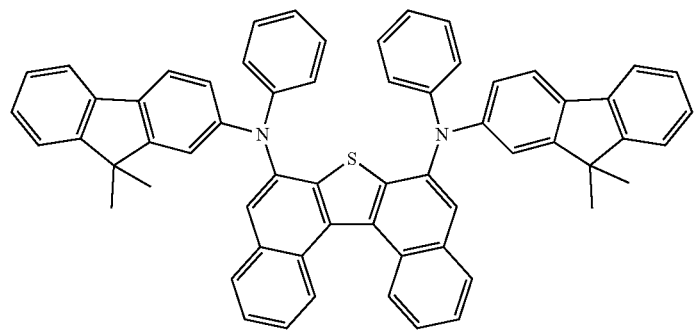
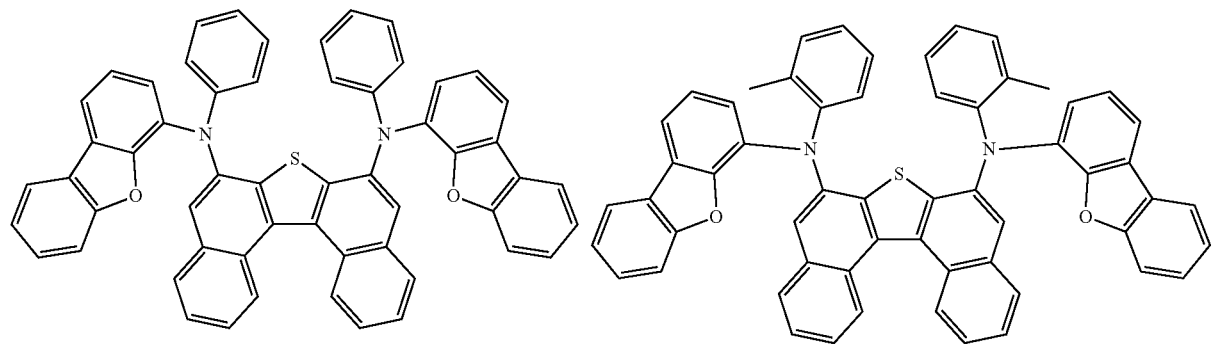

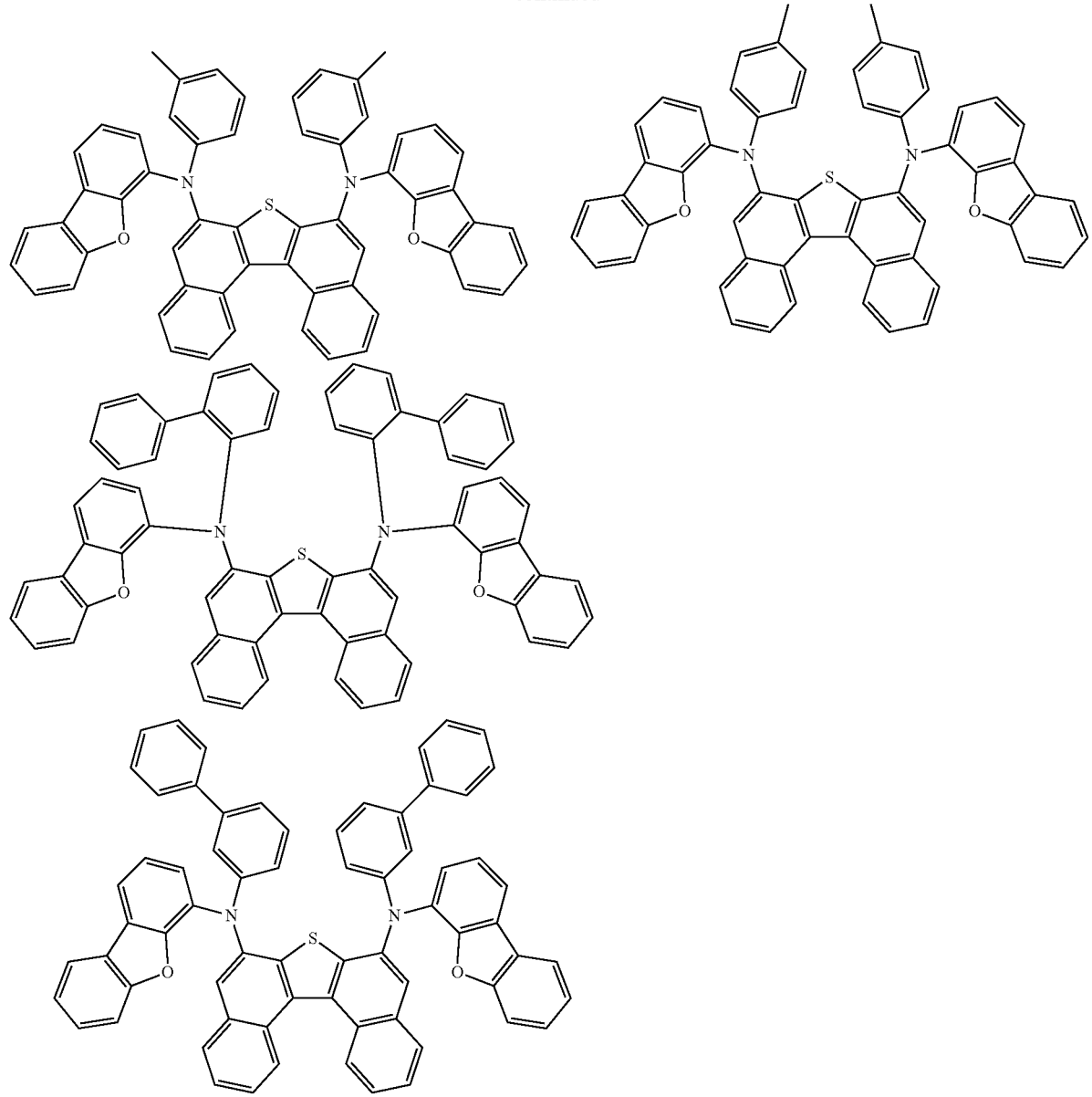

(Compound Represented by Formula (71))

The compound represented by the formula (71) is explained below.

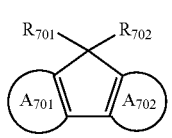

In the formula (71),
A$_{701}$ ring and A$_{702}$ ring a independently
a substituted or unsubstituted aromatic hydrocarbon ring having 6 to 50 ring carbon atoms, or
a substituted or unsubstituted heterocyclic ring having 5 to 50 ring atoms;

One or more rings selected from the group consisting of A$_{701}$ ring and A$_{702}$ ring are bonded to the bond * of the structure represented by the following formula (72);

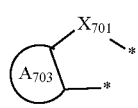

wherein, in the formula (72),
A$_{703}$ rings are independently
a substituted or unsubstituted aromatic hydrocarbon ring having 6 to 50 ring carbon atoms, or
a substituted or unsubstituted heterocyclic ring having 5 to 50 ring atoms;
X$_{701}$ is NR$_{703}$, C(R$_{704}$)(R$_{705}$), Si(R$_{706}$)(R$_{707}$), Ge(R$_{708}$)(R$_{709}$), O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{907}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1).

One or more selected from the group consisting of $A_{701}$ ring and $A_{702}$ ring is bonded to * in the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{701}$ ring is bonded to * in the structure represented by the formula (72).

In one embodiment, the group represented by the formula (73) is bonded to one or both of $A_{701}$ ring and $A_7$m ring:

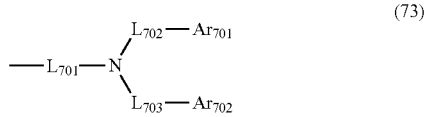
(73)

wherein in the formula (73), $Ar_{701}$ and $Ar_{702}$ are independently a substituted or unsubstituted aryl group having 6 to 50 ring carbon atoms, or a substituted or unsubstituted monovalent heterocyclic group having 5 to 50 ring atoms; and $L_{701}$ to $L_{703}$ are independently a single bond, a substituted or unsubstituted arylene group having 6 to 30 ring carbon atoms, a substituted or unsubstituted divalent heterocyclic group having 5 to 30 ring atoms, or a divalent linking group formed by bonding 2 to 4 above mentioned groups.

In one embodiment, in addition to $A_{701}$ ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group having 6 to 50 ring carbon atoms.

In one embodiment, $R_{701}$ and $R_{702}$ are bonded with each other to form a fluorene structure.

In one embodiment, $Ar_{701}$ ring and $Ar_{702}$ ring are substituted or unsubstituted aromatic hydrocarbon rings having 6 to 50 ring carbon atoms, and they are substituted or unsubstituted benzene rings, for example.

In one embodiment, $Ar_{703}$ ring is a substituted or unsubstituted aromatic hydrocarbon ring having 6 to 50 ring carbon atoms, and it is a substituted or unsubstituted benzene ring, for example.

In one embodiment, $X_{701}$ is O or S.

As specific example of the compound represented by the formula (71), the following compounds can be given, for example. In the following example compounds, Me represents methyl group.

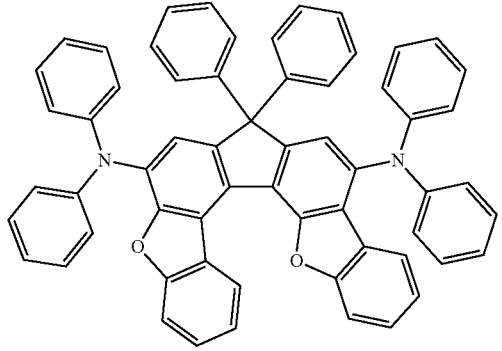

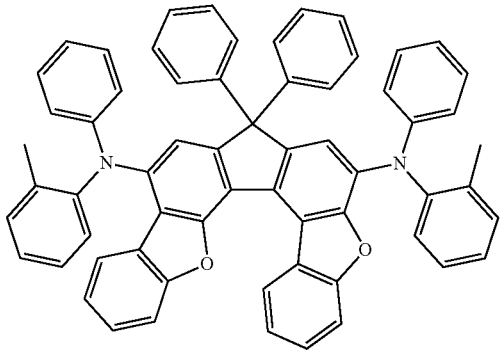

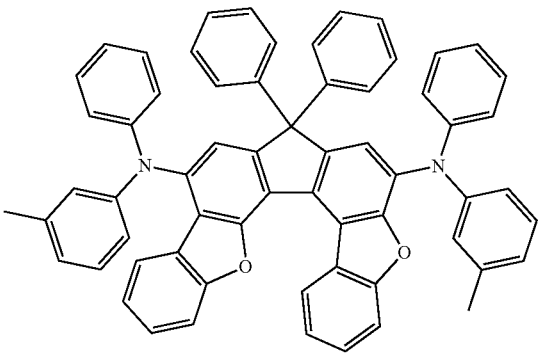

943
-continued
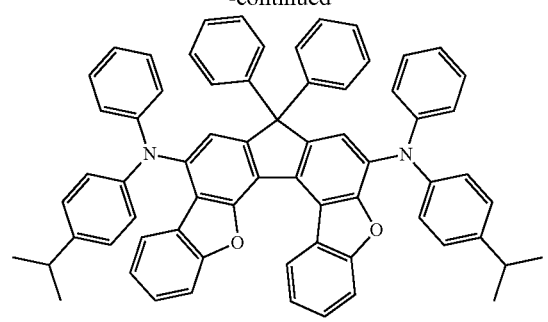
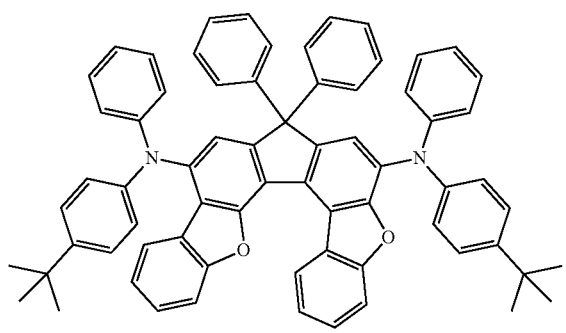
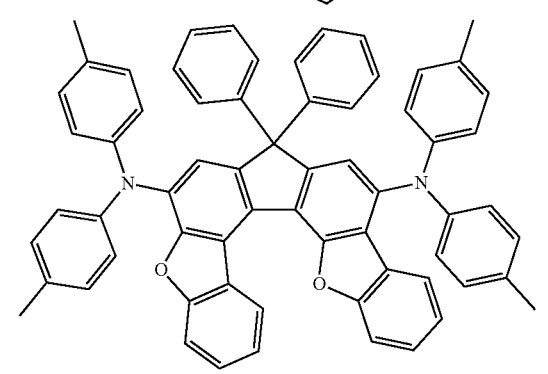
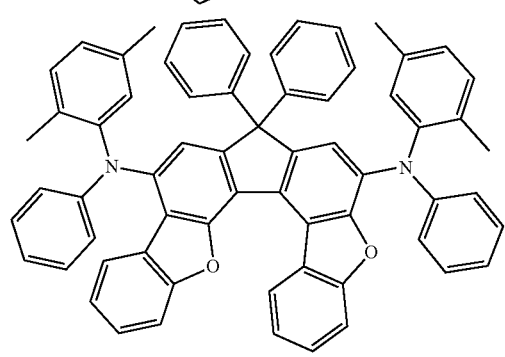
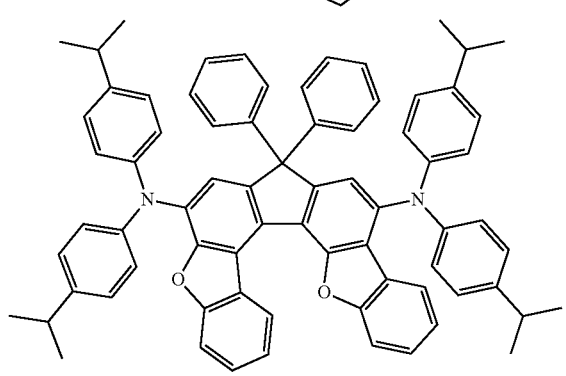
944
-continued
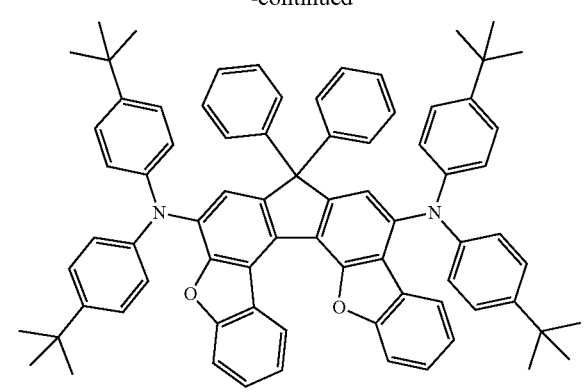
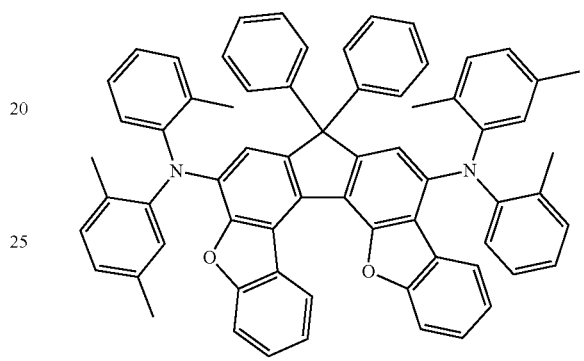
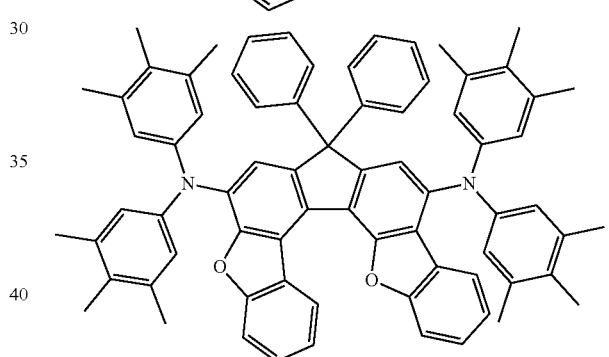
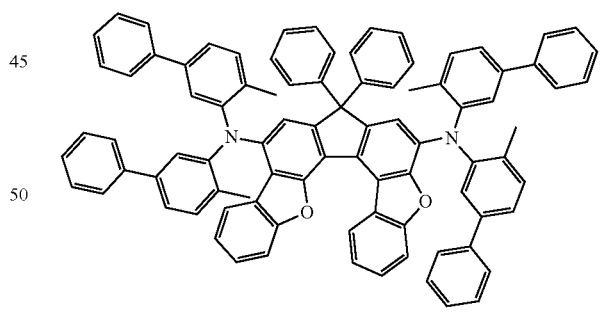
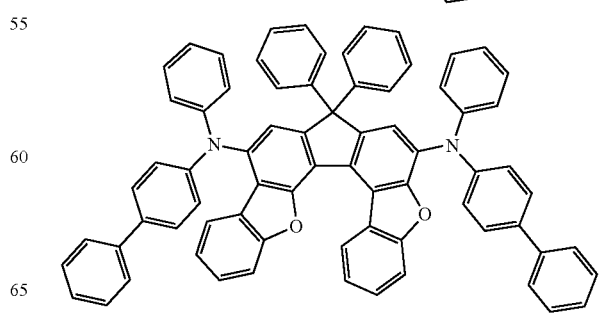

-continued
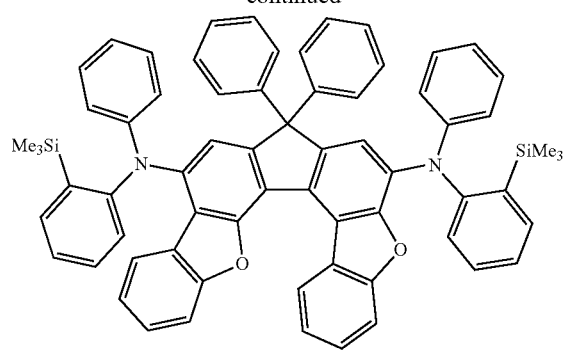
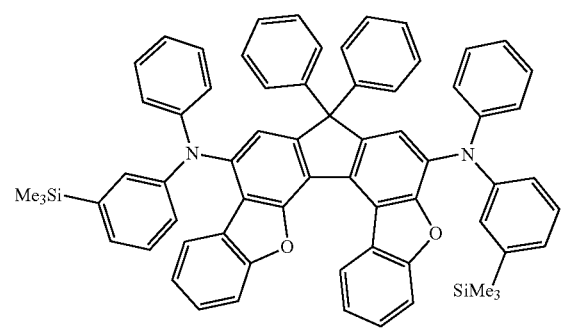
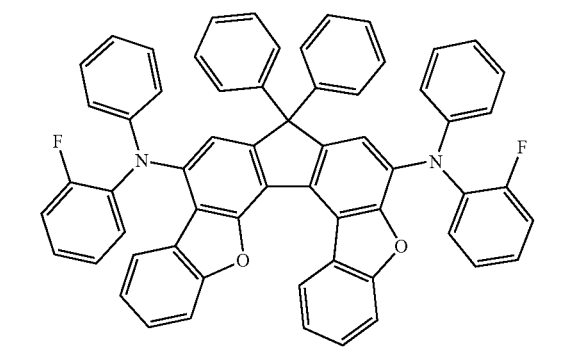
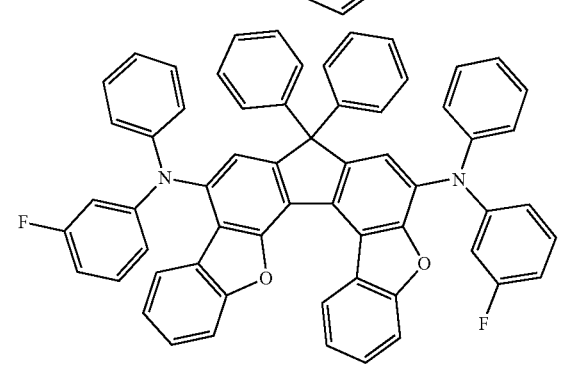
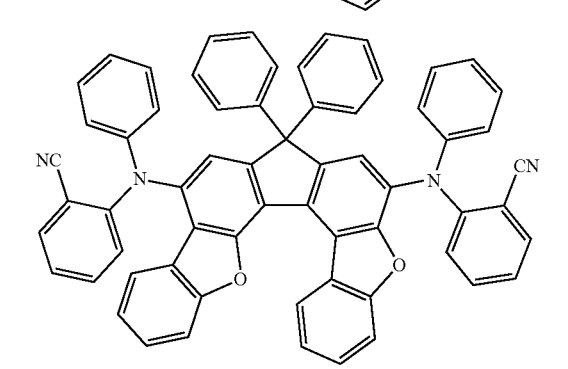
-continued
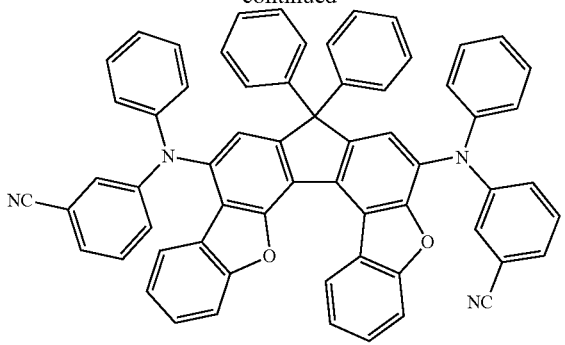
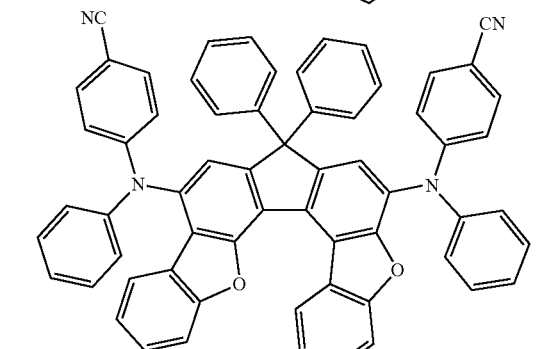
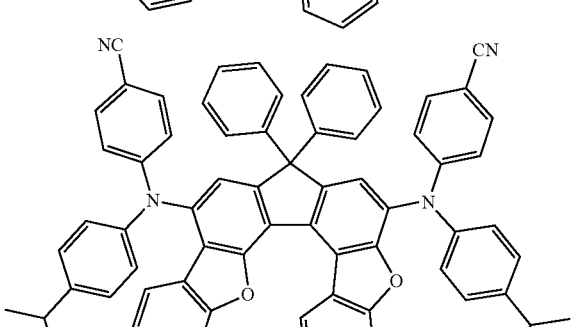
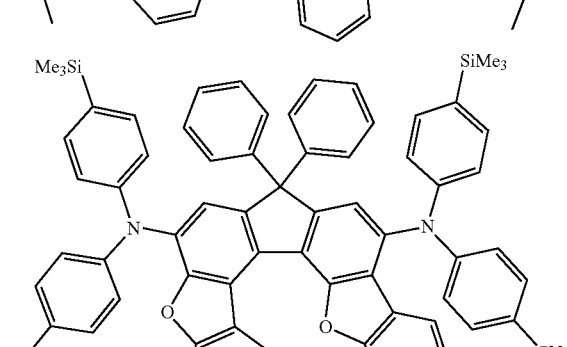
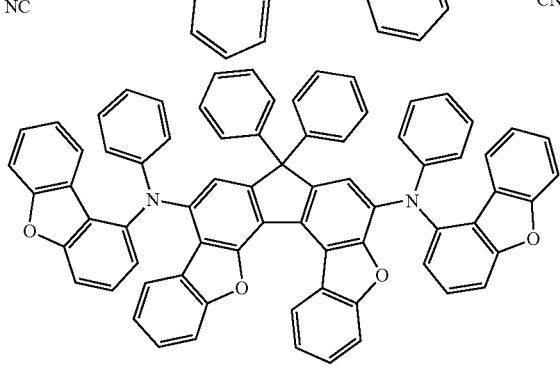

947
-continued
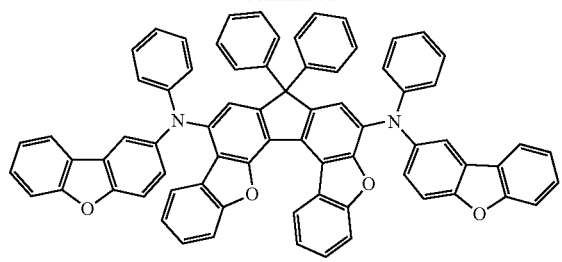
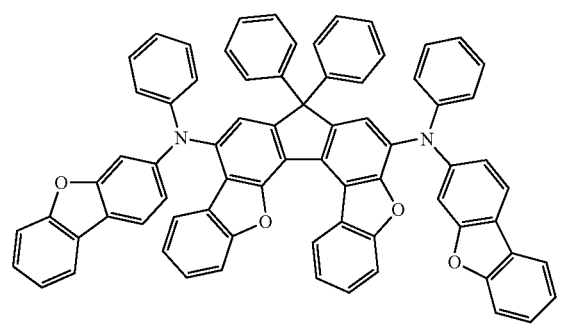
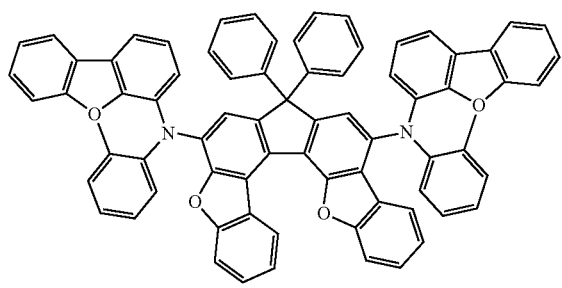
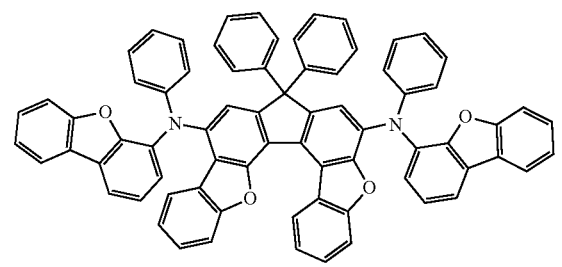
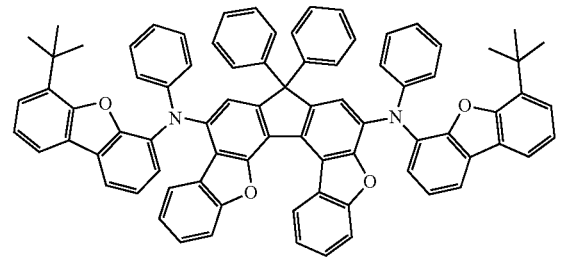
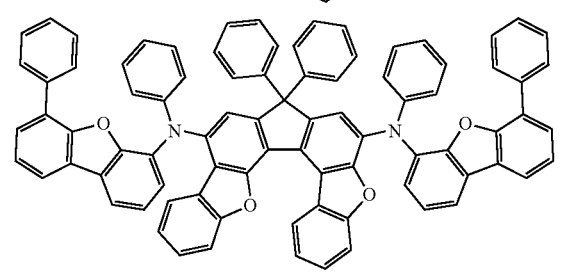
948
-continued
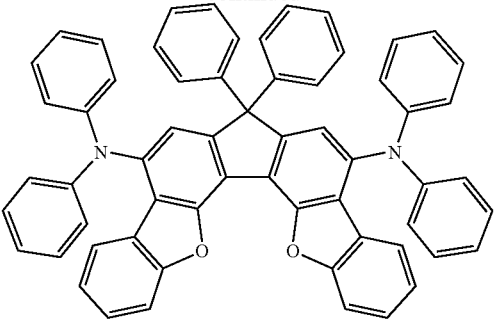
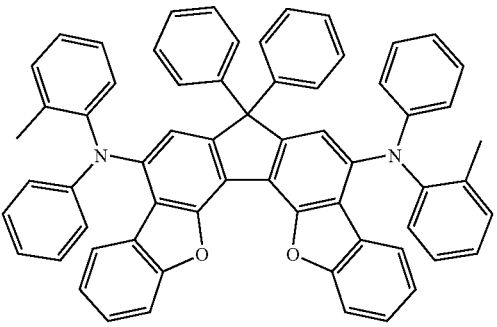
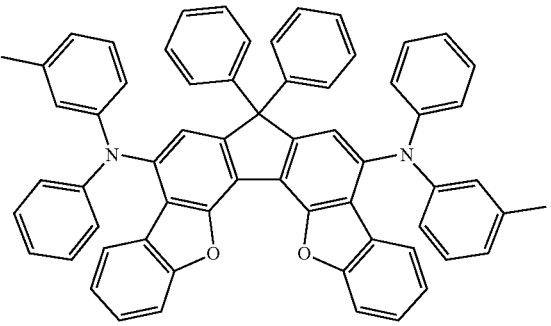
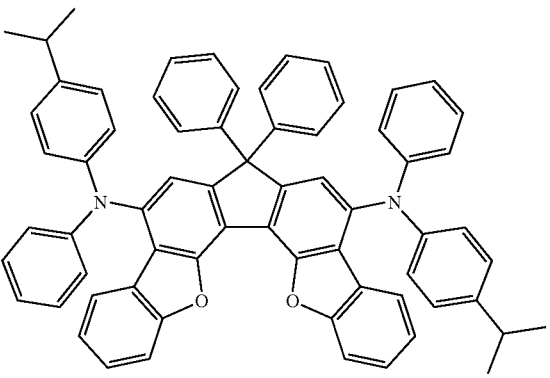
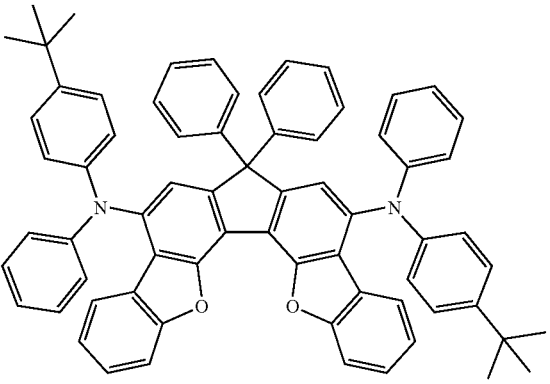

| 949 -continued | 950 -continued |
|---|---|
| 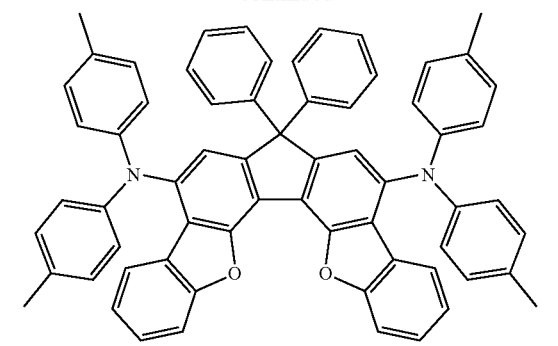 | 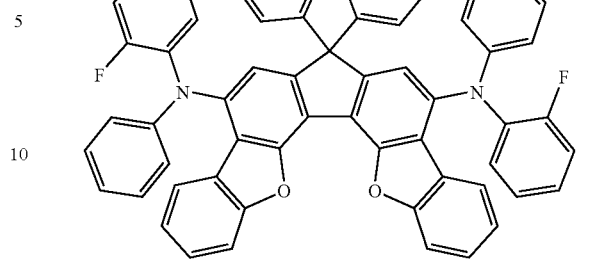 |
| 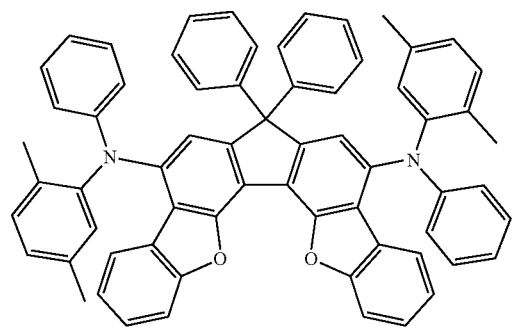 | 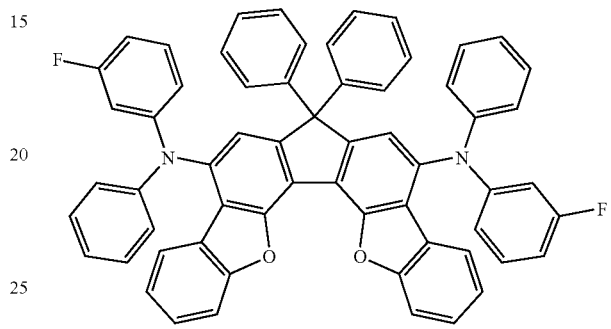 |
| 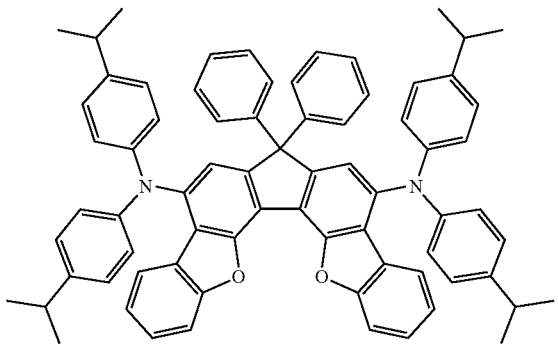 | 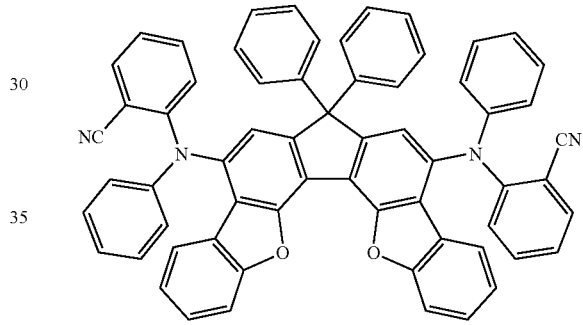 |
| 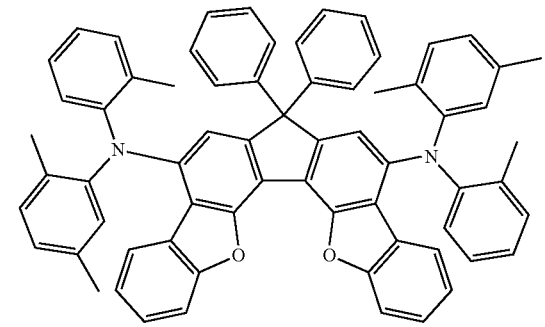 | 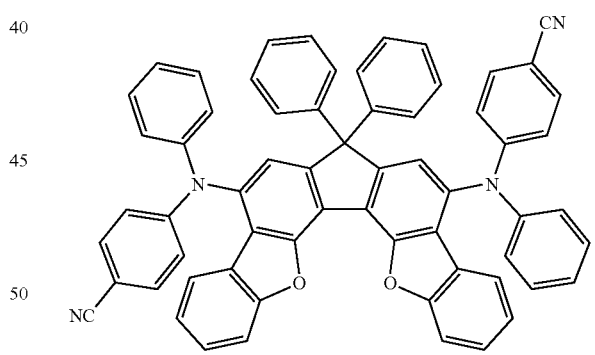 |
| 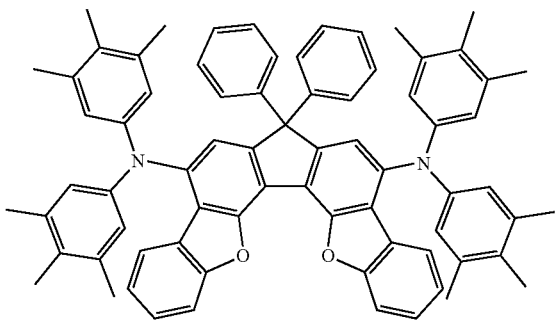 | 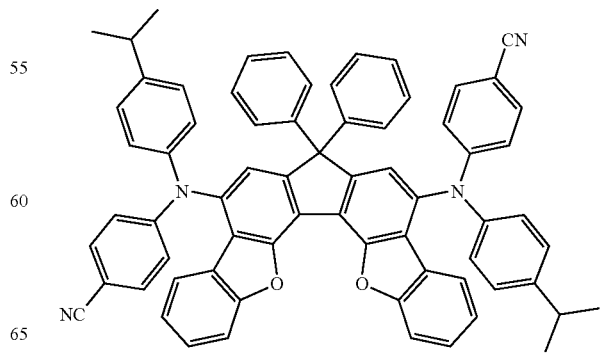 |

951
-continued
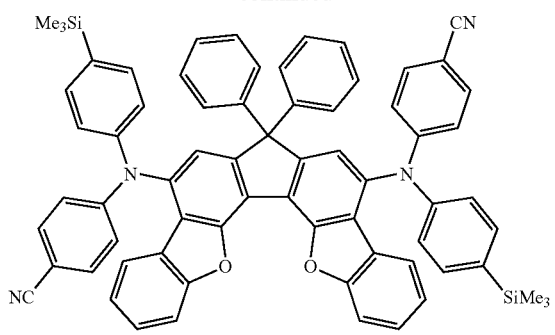
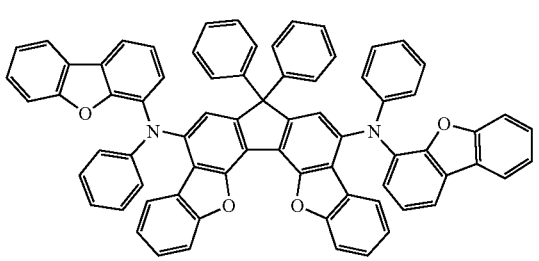
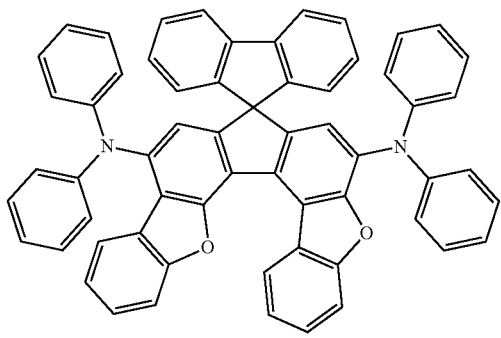
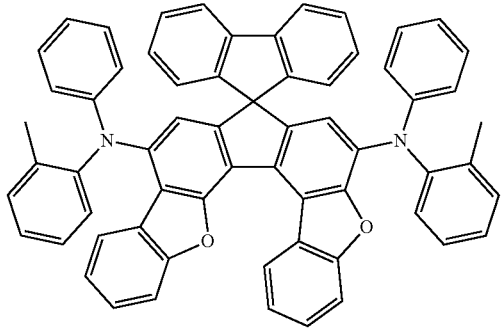
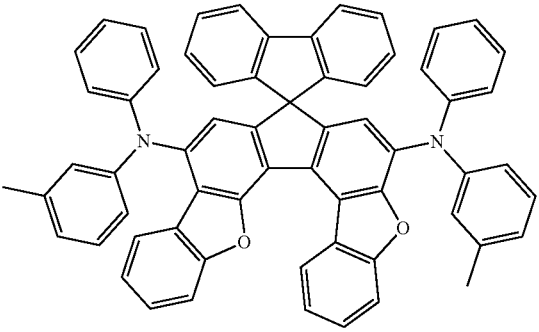
952
-continued
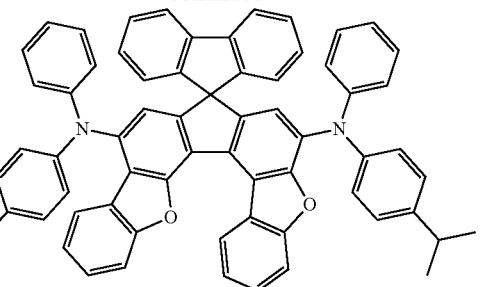
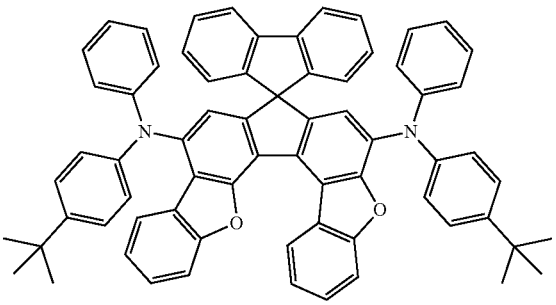
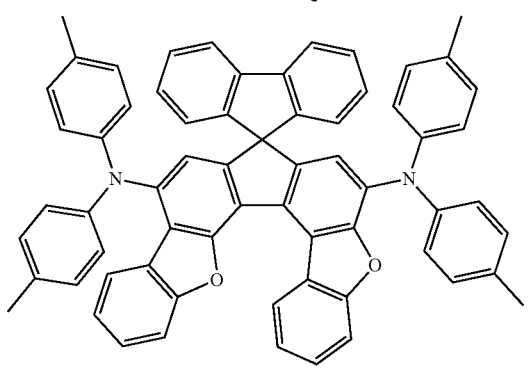
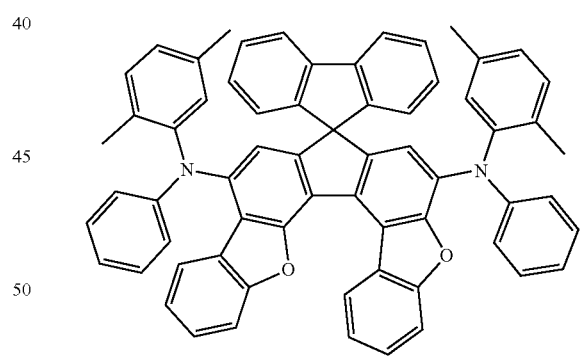
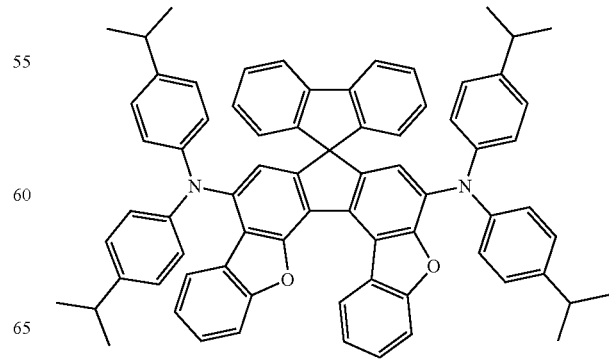

| 953 -continued | 954 -continued |
|---|---|
| 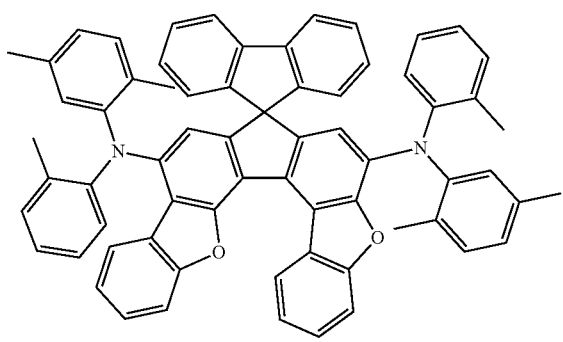 | 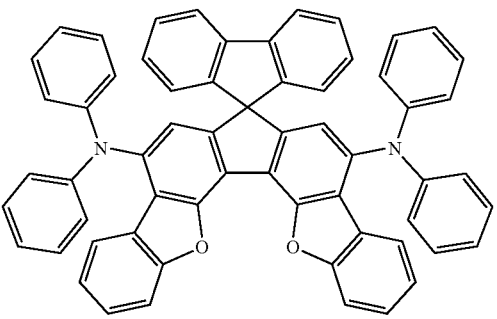 |
| 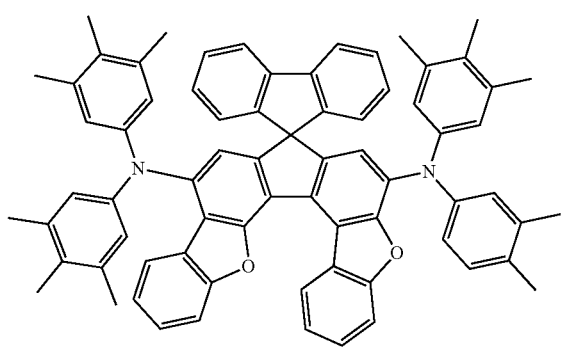 | 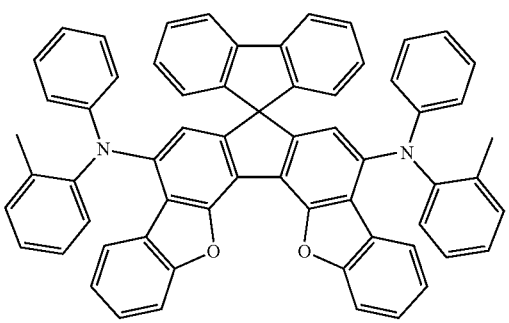 |
| 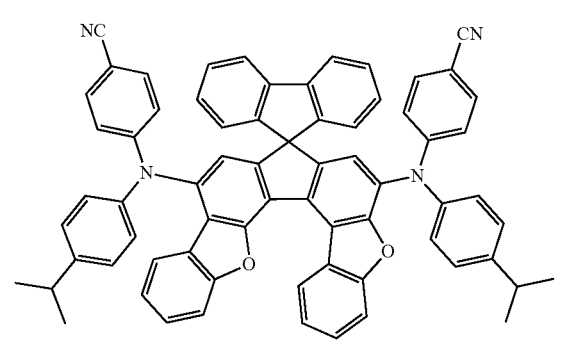 | 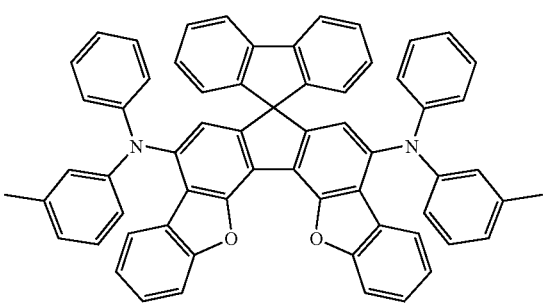 |
| 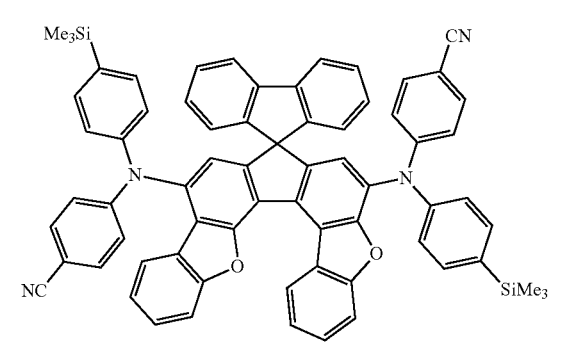 | 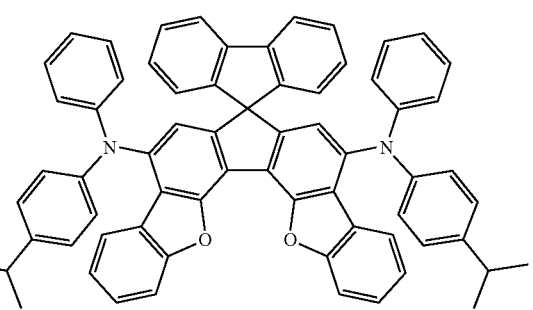 |
| 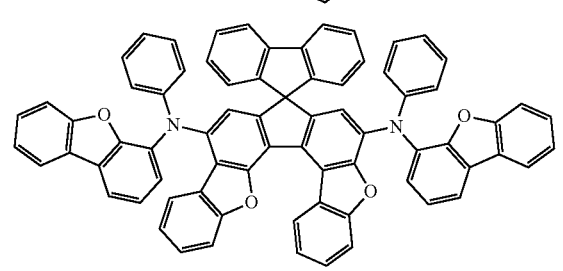 | 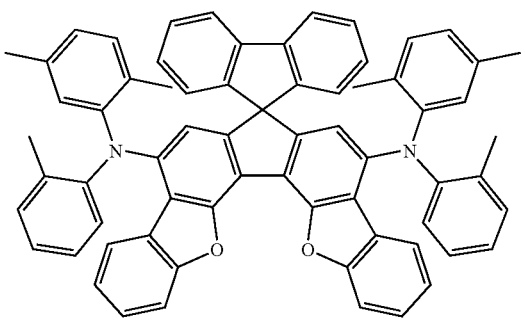 |

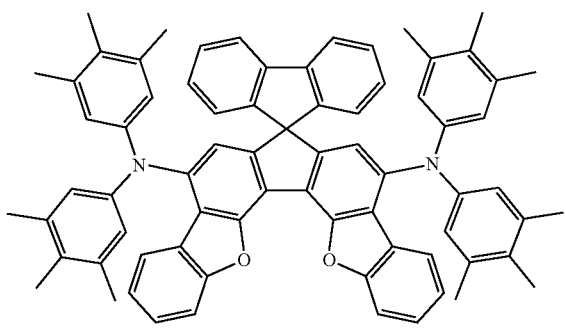

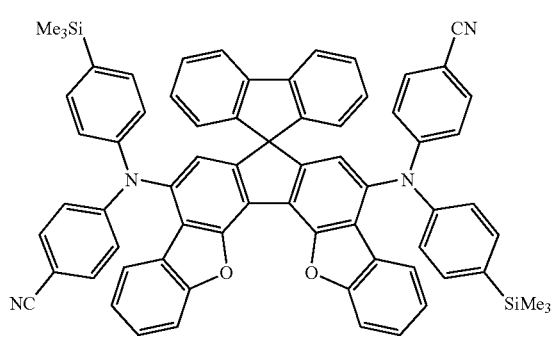

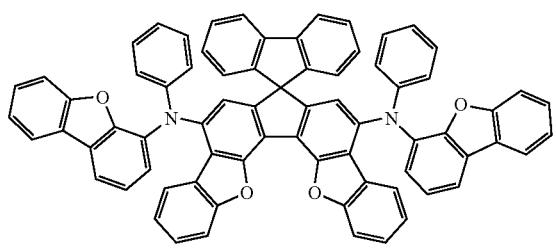

(Compound Represented by Formula (81))

The compound represented by the formula (81) is explained below.

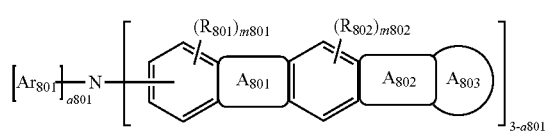
(81)

(82)

(83)

In the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—$O$—$(R_{904})$,

—$S$—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when these are 2, plural $R_{801}$s or $R_{802}$s may be the same or different;

a801 is an integer of 0 to 2; when a801 is 0 or 1, the structure in the parenthese indicated by "3-a801" may be the same or different from each other; when a801 is 2, $Ar_{801}$s may be the same or different from each other.

In one embodiment, $Ar_{801}$ is a substituted or unsubstituted aryl group having 6 to 50 ring carbon atoms.

In one embodiment, $A_{803}$ ring is a substituted or unsubstituted aromatic hydrocarbon ring having 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group having 1 to 50 carbon atoms.

In one embodiment, a801 is 1.

As specific example of the compound represented by the formula (81), the following compounds can be given, for example.

| 957 | 958 |
|---|---|
| 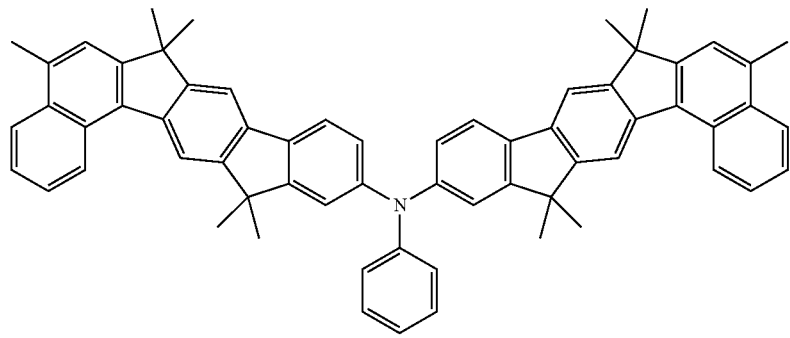 | 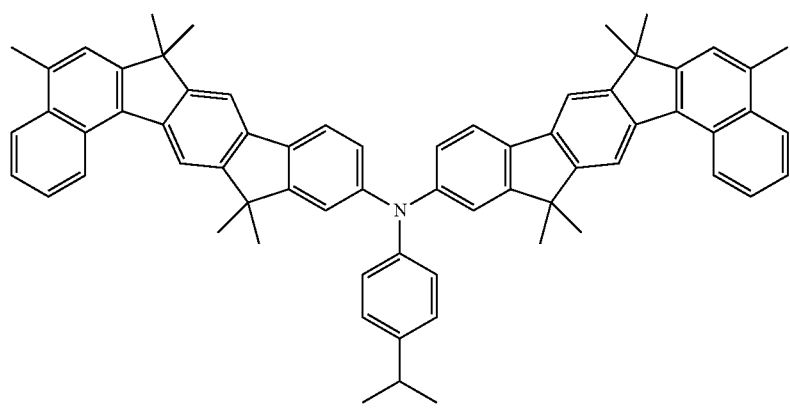 |
| 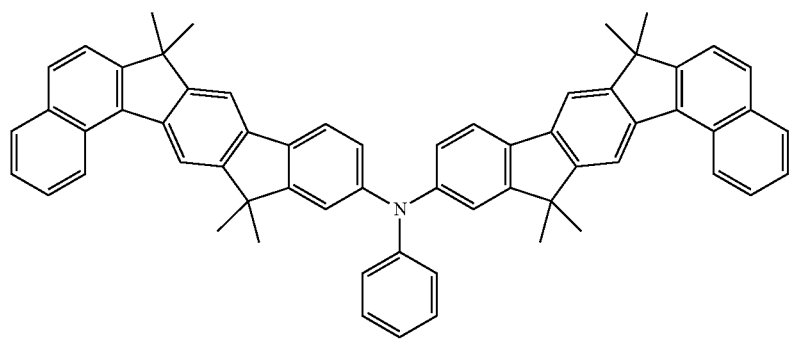 | 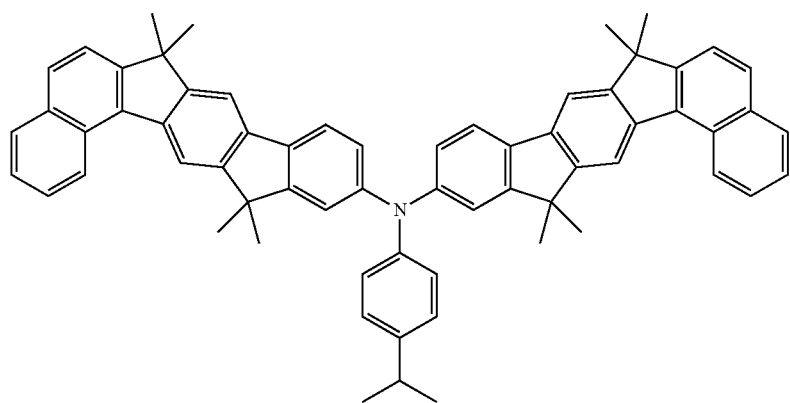 |

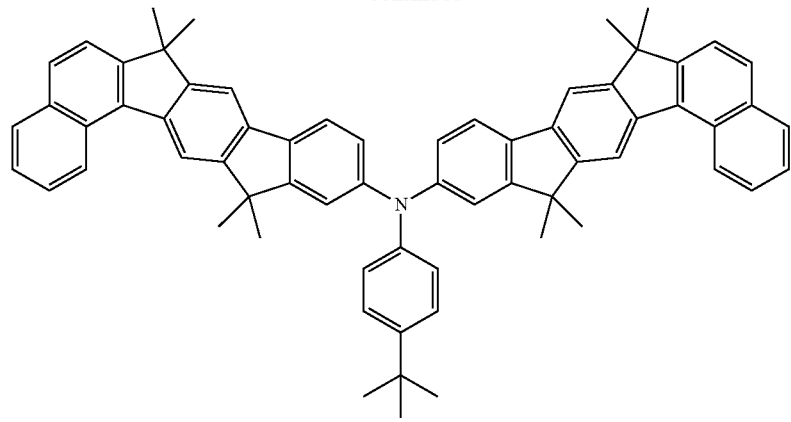
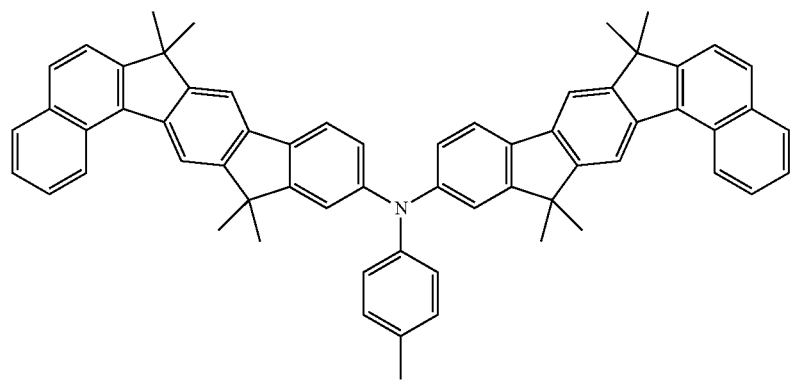
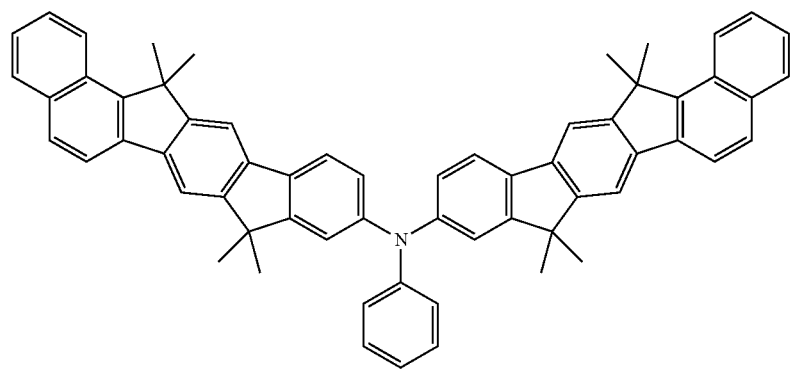
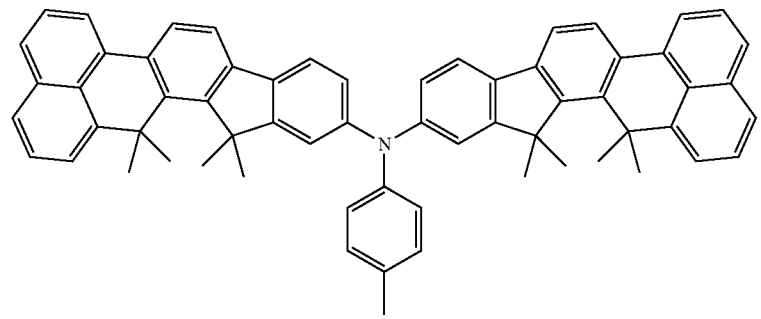

-continued

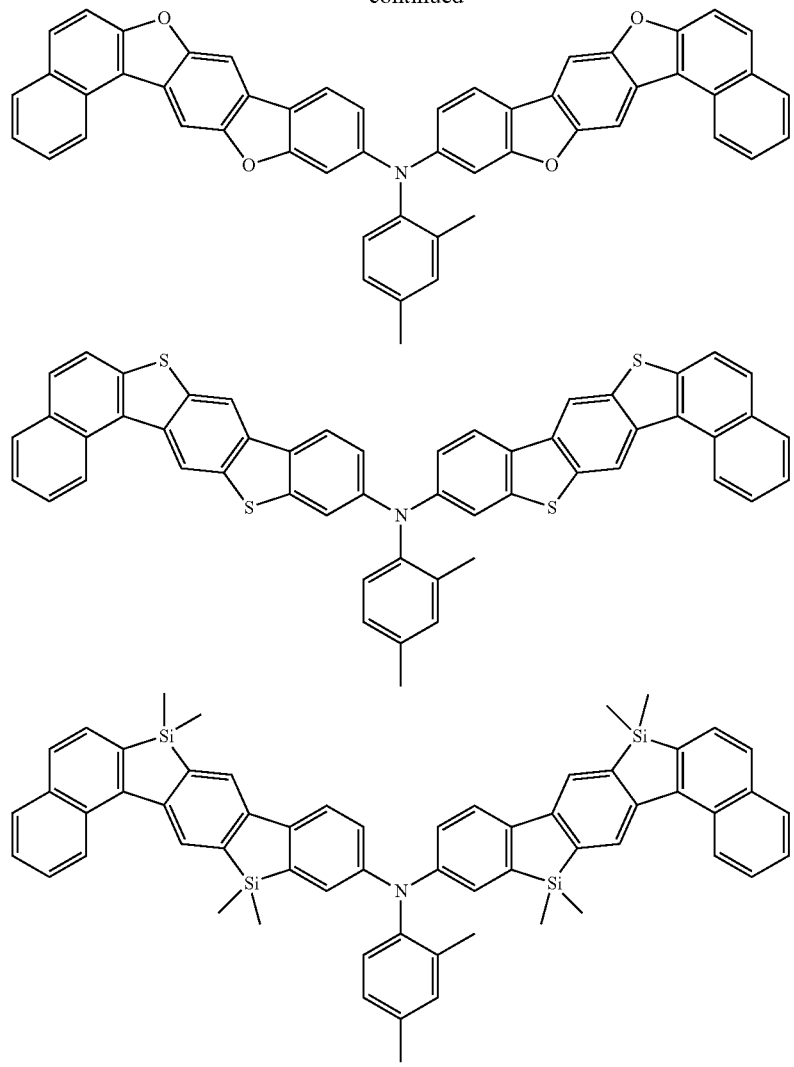

A content of the compound (host material) represented by the formula (1) or (2) in the emitting layer is preferably 80 mass % or more and 99 mass % or less based on the total mass of the emitting layer. A content of the one or more compounds (dopant material) selected from the group consisting of compounds represented by formulas (11), (21), (31), (41), (51), (61), (71) and (81) is preferably 1 mass % or more and 20 mass % or less based on a total mass of the emitting layer.

Hereinbelow, an explanation will be made on elements and materials other than the above-mentioned compound constituting each layer that can be used in the organic EL device according to one aspect of the invention.

(Substrate)

The substrate is used as a supporting body of the emitting device. As the substrate, glass, quarts, plastic or the like can be used. Further, a flexible substrate may be used. The flexible substrate means a substrate that can be bent. For example, aplastic substrate made of polycarbonate or vinyl polychloride or the like can be given.

(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, god (Au), platinum (Pt) or a nitride of a metal material (e.g. titanium nitride) or the like can be given.

(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used (Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.

(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.

(Host Material of Emitting Layer)

The emitting layer may have a structure in which the substance having high luminescent property (guest material) described above is dispersed in another substance (host material). Various materials can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.

(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.

(Electron-Injecting Layer)

The electron-injection layer is a layer containing a substance having a high electron-injection property. For the electron-injection layer, alkali metals, alkaline earth metals or a compound thereof such as lithium (Li), ytterbium (Yb), lithium fluoride (LiF), cesium fluoride (CsF), calcium fluoride ($CaF_2$), metal complex compound such as 8-quinolinolato lithium (Liq), lithium oxide (LiOx) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium (Li) and cesium (Cs), alkaline earth metals such as magnesium (Mg), calcium (Ca), and strontium (Sr), an alloy containing these metals (for example, MgAg and ALi), a rare earth metal such as europium (Eu) and ytterbium (Yb), and an alloy containing a rare earth metal.

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 μm.

[Electronic Device]

The electronic device according to one aspect of the invention is characterized in that it is provided with the organic EL device according to one aspect of the invention.

Specific examples of the electronic device include a display element such as an organic EL panel module; a display such as a TV, a mobile phone or a PC; and emitting devices such as lightings and lights for automobiles or the like.

EXAMPLES

The invention will specifically be explained with the examples and the comparative examples below, and shall not be limited to the contents of the examples in anyway.

Synthesis Example 1 [Synthesis of Compound BH-1]

(Synthesis of Intermediate 1)

To 13.3 g (50.0 mmol) of 9-bromoanthracene-d9, 6.4 g (52.5 mmol) of phenylboronic acid and 1.2 g (1.00 mmol) of Pd[$PPh_3$]4, 75 ml of toluene, 75 ml of dimethoxyethane and 75 ml (150.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 10.9 g of white solid. By conducting FD-MS analysis, the resulting compound was identified as Intermediate 1 as follows (yield: 83%).

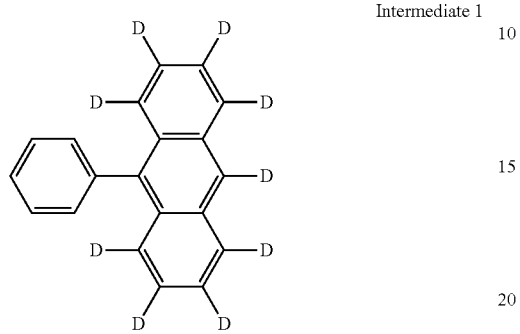

Intermediate 1

(Synthesis of Intermediate 2)

5.3 g (20.0 mmol) of Intermediate 1 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na$_2$CO$_3$, and thereafter with water, and the separated organic phase was dried with MgSO$_4$, followed by being filtered and concentrated.

The concentrated residue was dispersed in methanol (100 mL), and the precipitated crystal was dried to obtain 6.5 g of white solid. By conducting FD-MS analysis, the resulting compound was identified as Intermediate 2 as follows (yield: 95%).

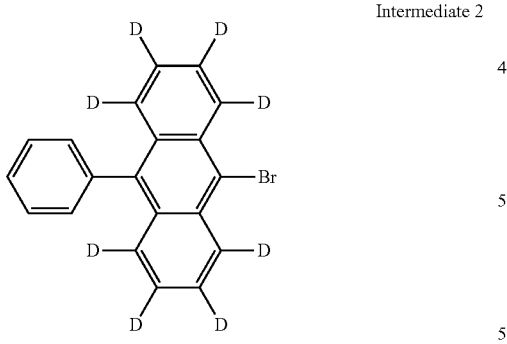

Intermediate 2

(Synthesis of Compound BH-1)

To 1.7 g (5.0 mmol) of Intermediate 2, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.6 g of white solid. By conducting FD-MS analysis, the resulting compound was identified as Compound BH-1 as follows (yield: 75%).

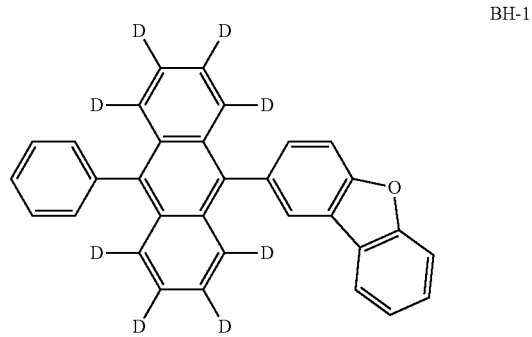 [SMILES: [2H]c1c([2H])c([2H])c2c(-c3ccc4oc5ccccc5c4c3)c3c([2H])c([2H])c([2H])c([2H])c3c(-c3ccccc3)c2c1[2H]]

BH-1

Synthesis Example 2 [Synthesis of Compound BH-2]

(Synthesis of Intermediate 3)

To 13.3 g (50.0 mmol) of 9-bromoanthracene-d9, 9.0 g (52.5 mmol) of 1-naphthalene boronic acid and 1.2 g (1.00 mmol) of Pd[PPh$_3$]4, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 13.3 g of white solid. By conducting FD-MS analysis, the resulting compound was identified as Intermediate 3 as follows (yield: 85%).

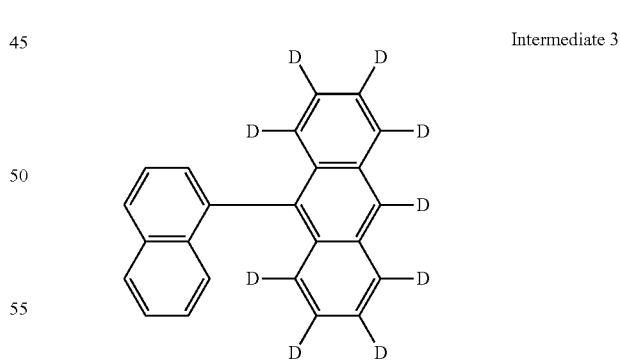

Intermediate 3

(Synthesis of Intermediate 4)

6.3 g (20.0 mmol) of Intermediate 3 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na₂CO₃, and thereafter with water three times. The organic phase was dried with MgSO₄, followed by being filtered and concentrated.

The concentrated residue was dispersed in methanol (100 ml), and the precipitated crystal was died to obtain 7.5 g of white solid. By conducting FD-MS analysis, the resulting compound was identified as Intermediate 4 as follows (yield: 96%).

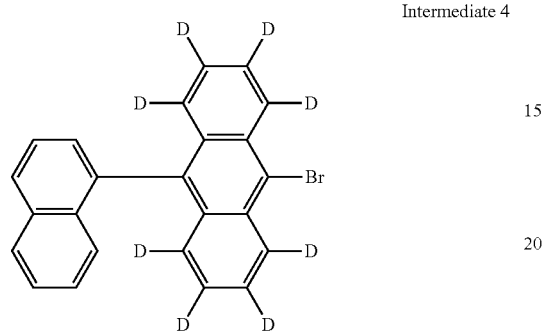

Intermediate 4

(Synthesis of Compound BH-2)

To 2.0 g (5.0 mmol) of Intermediate 4, 1.1 g (5.3 mmol) of dibenzofuran-2-boronic acid and 0.1 g (0.1 mmol) of Pd[PPh₃]₄, 7.5 ml of toluene, 7.5 ml of dimethoxyethane and 7.5 ml (15.0 mmol) of 2M Na₂CO₃ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO₄, followed by being filtered and concentrated. The concentrated residue was purified with silica gel column chromatography to obtain 1.7 g of white solid. By conducting FD-MS analysis, the resulting compound was identified as Compound BH-2 as follows (yield: 70%).

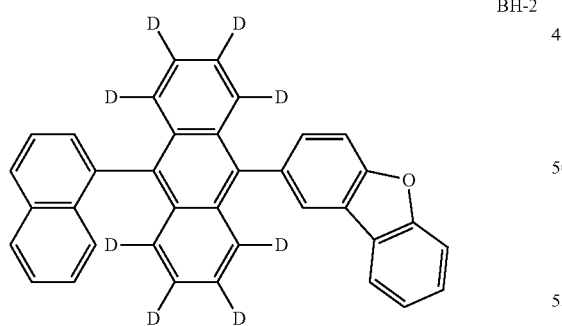

BH-2

Synthesis Example 3 [Synthesis of Compound BH-3]

Except that 1.1 g (5.3 mmol) of dibenzofuran-1-boronic acid was used instead of dibenzofuran-2-boronic acid, the reaction was carried out in the same way as in the synthesis example 1, thereby obtaining 1.3 g of white crystal. By conducting FD-MS analysis, the resulting compound was identified as Compound BH-3 as follows (yield: 62%).

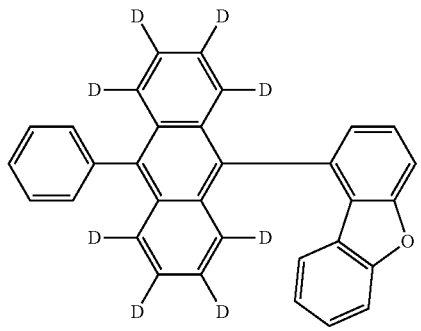

BH-3

Synthesis Example 4 [Synthesis of Compound BH-4]

Except that 1.5 g (5.3 mmol) of 4-(2-dibenzofuranyl) phenyl boronic acid was used instead of dibenzofuran-2-boronic acid, the reaction was carried out in the same way as in the synthesis example 1, thereby obtaining 1.8 g of white crystal. By conducting FD-MS analysis, the resulting compound was identified as Compound BH-4 as follows (yield: 71%).

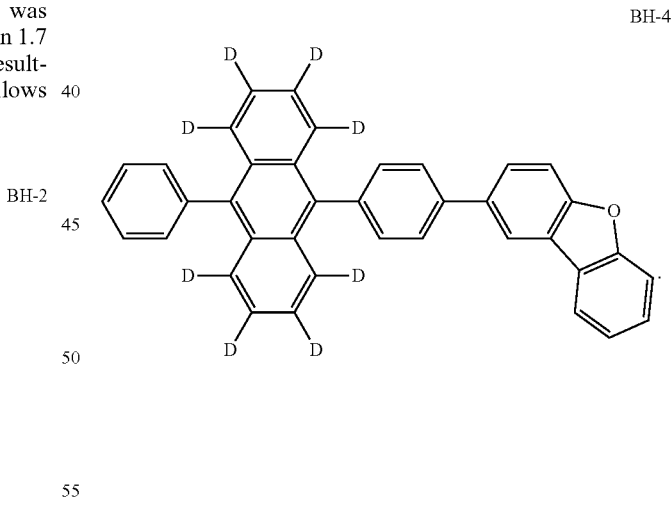

BH-4

Synthesis Example 5 [Synthesis of Compound BH-5]

Except that 1.5 g (5.3 mmol) of 4-(2-dibenzofuranyl) phenyl boronic acid was used instead of dibenzofuran-2-boronic acid, the reaction was carried out in the same way as in the synthesis example 2, thereby obtaining 2.0 g of white crystal. By conducting FD-MS analysis, the resulting compound was identified as Compound BH-5 as follows (yield: 73%).

BH-5

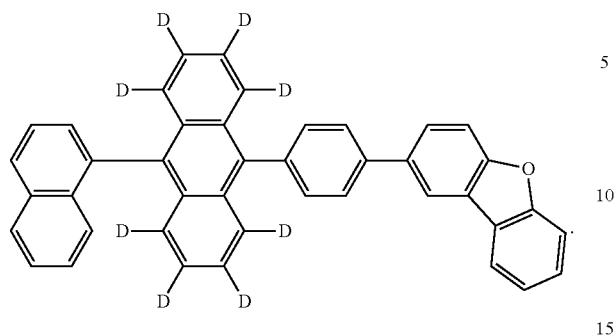

Synthesis Example 6 [Synthesis of Compound BH-6]

(Synthesis of Intermediate 5)

To 13.3 g (50.0 mmol) of 9-bromoanthracene-d9, 10.4 g (52.5 mmol) of 4-biphenylboronic acid and 1.2 g (1.00 mmol) of Pd[PPh$_3$]4, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 14.1 g of white solid. By conducting FD-MS analysis, the resulting compound was identified as Intermediate 5 as follows (yield: 83%).

Intermediate 5 white solid. By conducting FD-MS analysis, the resulting compound was identified as Intermediate 6 as follows (yield: 96%).

Intermediate 6

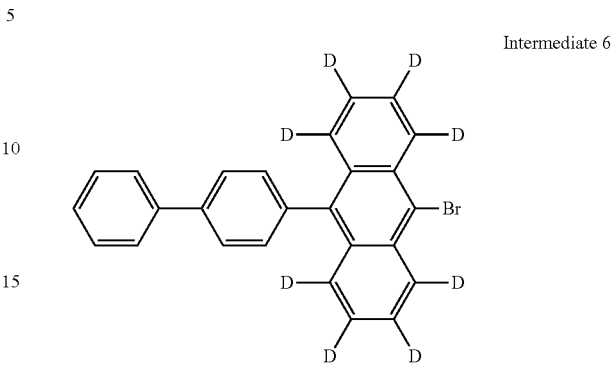

(Synthesis of Compound BH-6)

To 2.1 g (5.0 mmol) of Intermediate 6, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.6 g of white solid. By conducting FD-MS analysis, the resulting compound was identified as Compound BH-6 as follows (yield: 64%).

BH-6

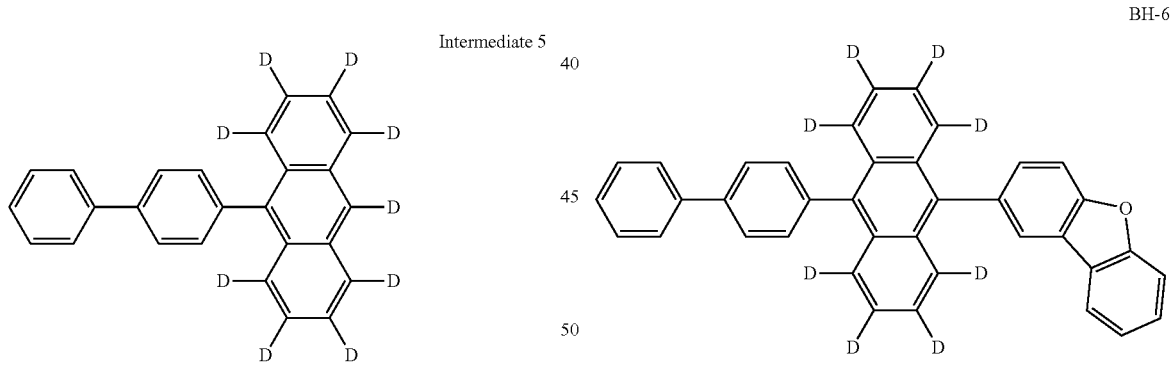

(Synthesis of Intermediate 6)

6.8 g (20.0 mmol) of Intermediate 5 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na$_2$CO$_3$, and thereafter with water three times. The organic phase was dried with MgSO$_4$, followed by being filtered and concentrated.

The concentrated residue was dispersed in methanol (100 mL), and the precipitated crystal was dried to obtain 8.0 g of Synthesis Example 7 [Synthesis of Compound BH-7]

(Synthesis of Intermediate 7)

To 13.3 g (50.0 mmol) of 9-bromoanthracene d9, 10.4 g (52.5 mmol) of 3-biphenylboronic acid and 1.2 g (1.00 mmol) of Pd[PPh$_3$]4, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 13.6 g of white solid. By conducting FD-MS analysis, the resulting compound was identified as Intermediate 7 as follows (yield: 80%).

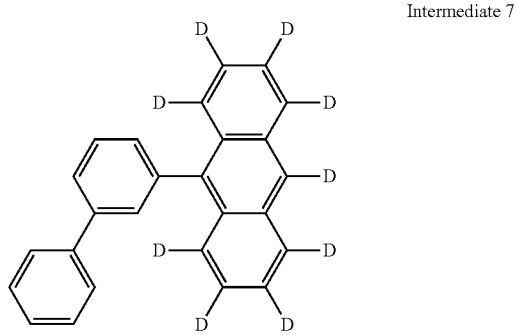 [SMILES: [2H]c1c([2H])c([2H])c2c(-c3cccc(-c4ccccc4)c3)c3c([2H])c([2H])c([2H])c([2H])c3c([2H])c2c1[2H]]

Intermediate 7

(Synthesis of Intermediate 8)

6.8 g (20.0 mmol) of Intermediate 7 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water three times. The organic phase was dried with $MgSO_4$, followed by being filtered and concentrated.

The concentrated residue was dispersed in methanol (100 mL), and the precipitated crystal was dried to obtain 8.0 g of white solid. By conducting FD-MS analysis, the resulting compound was identified as Intermediate 8 as follows (yield: 96%).

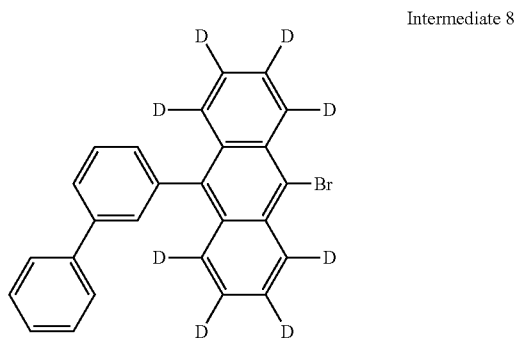 [SMILES: [2H]c1c([2H])c([2H])c2c(-c3cccc(-c4ccccc4)c3)c3c([2H])c([2H])c([2H])c([2H])c3c(Br)c2c1[2H]]

Intermediate 8

(Synthesis of Compound BH-7)

To 2.1 g (5.0 mmol) of Intermediate 8, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 1.5 g of white solid. By conducting FD-MS analysis, the resulting compound was identified as Compound BH-7 as follows (yield: 59%).

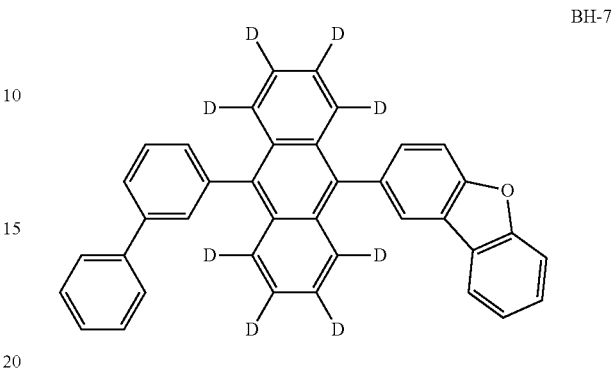

BH-7

Synthesis Example 8 [Synthesis of Compound BH-8]

(Synthesis of Intermediate 9)

To 13.3 g (50.0 mmol) of 9-bromoanthracene d9, 10.4 g (52.5 mmol) of 2-biphenylboronic acid and 1.2 g (1.00 mmol) of Pd[PPh$_3$]4, 75 ml of toluene, 75 ml of dimethoxyethane and 75 ml (150.0 mmol) of 2M $Na_2CO_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with $MgSO_4$, followed by being filtered and concentrated. The concentrated residue was purified with silica gel column chromatography to obtain 10.9 g of white solid. By conducting FD-MS analysis, the resulting compound was identified as Intermediate 9 as follows (yield: 64%).

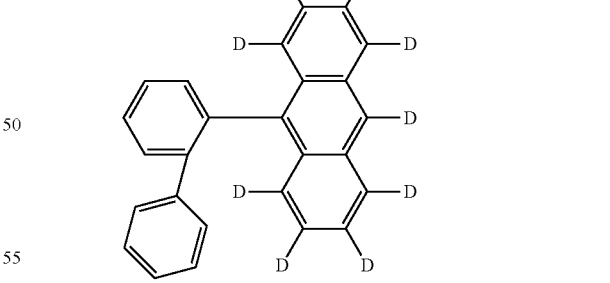

Intermediate 9

(Synthesis of Intermediate 10)

6.8 g (20.0 mmol) of Intermediate 9 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M $Na_2S_2O_3$ aqueous solution. The organic phase was further washed with 10% $Na_2CO_3$, and thereafter with water three times.

The organic phase was dried with MgSO$_4$, followed by being filtered and concentrated.

The concentrated residue was dispersed in methanol (100 mL), and the precipitated crystal was dried to obtain 8.0 g of white solid. By conducting FD-MS analysis, the resulting compound was identified as Intermediate 10 as follows (yield: 96%).

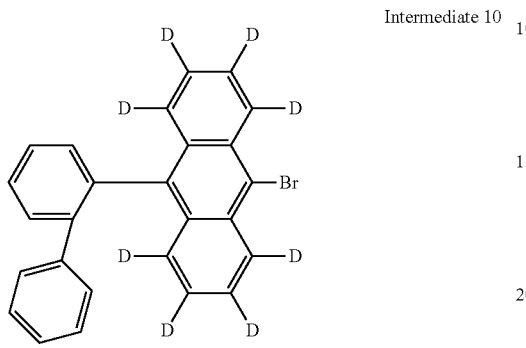

Intermediate 10

(Synthesis of Compound BH-8)

To 2.1 g (5.0 mmol) of Intermediate 10, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.6 g of white solid. By conducting FD-MS analysis, the resulting compound was identified as Compound BH-8 as follows (yield: 63%).

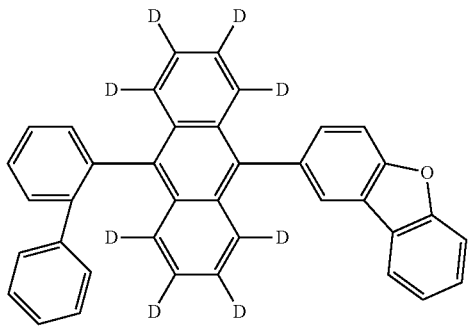

BH-8

Synthesis Example 9 [Synthesis of Compound BH-9]

(Synthesis of Intermediate 11)

To 13.3 g (50.0 mmol) of 9-bromoanthracene d9, 13.0 g (52.5 mmol) of 4-(1-naphthyl) phenylboronic acid and 1.2 g (1.00 mmol) of Pd[PPh$_3$]4, 75 ml of toluene, 75 ml of dimethoxyethane and 75 ml (150.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 15.6 g of white solid. By conducting FD-MS analysis, the resulting compound was identified as Intermediate 11 as follows (yield: 80%).

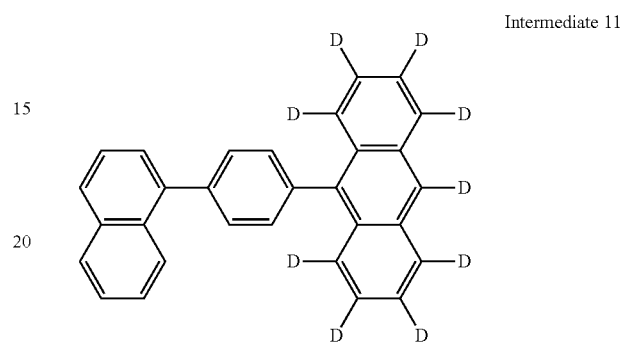

Intermediate 11

(Synthesis of Intermediate 12)

7.8 g (20.0 mmol) of Intermediate 11 was solubilized in 120 ml of dichloromethane, and the resulting solution was dropped into the solution of 3.2 g (20.0 mmol) of bromine in 12 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10%/Na$_2$CO$_3$, and thereafter with water three times. The organic phase was dried with MgSO$_4$, followed by being filtered and concentrated.

The concentrated residue was dispersed in methanol (100 ml), and the precipitated crystal was dried to obtain 8.6 g of white solid. By conducting FD-MS analysis, the resulting compound was identified as Intermediate 12 as follows (yield: 92%).

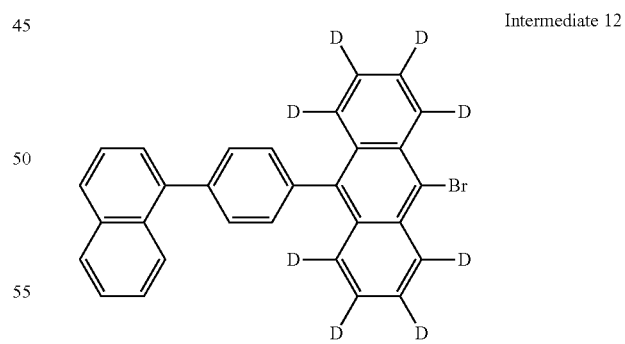

Intermediate 12

(Synthesis of Compound BH-9)

To 2.3 g (5.0 mmol) of Intermediate 12, 1.1 g (5.3 mmol) of dibenzofuran-2-boronic acid and 0.1 g (0.1 mmol) of Pd[PPh$_3$]$_4$, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO₄, followed by being filtered and concentrated. The concentrated residue was purified with silica gel column chromatography to obtain 1.9 g of white solid. By conducting FD-MS analysis, the resulting compound was identified as Compound BH-10 as follows (yield: 68%).

BH-9

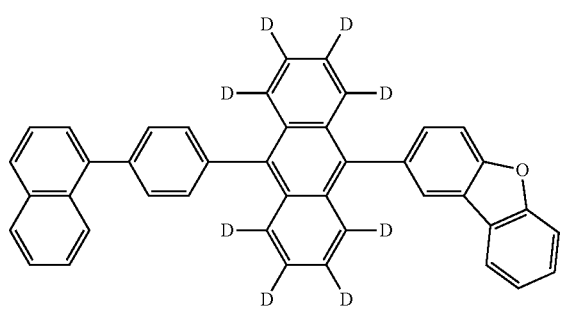

Synthesis Example 10 [Synthesis of Compound BH-10]

Except that 1.8 g (5.3 mmol) of 4-(2-dibenzofuranyl)-1-naphthalenyl-boronic acid was used instead of dibenzofuran-2-boronic acid, the reaction was carried out in the same way as in the synthesis example 1, thereby obtaining 1.7 g of white crystal. By conducting FD-MS analysis, the resulting compound was identified as Compound BH-10 as follows (yield: 60%).

BH-10

Synthesis Example 11 [Synthesis of Compound BH-11]

Except that 1.8 g (5.3 mmol) of 6-(2-dibenzofuranyl)-2-naphthalenyl-boronic acid was used instead of dibenzofuran-2-boronic acid, the reaction was carried out in the same way as in the synthesis example 1, thereby obtaining 1.5 g of white crystal. By conducting FD-MS analysis, the resulting compound was identified as Compound BH-11 as follows (yield: 55%).

BH-11

Synthesis Example 12 [Synthesis of Compound BH-12]

Except that 1.8 g (5.3 mmol) of 6-(2-dibenzofuranyl)-2-naphthalenyl-boronic acid was used instead of dibenzofuran-2-boronic acid, the reaction was carried out in the same way as in the synthesis example 2, thereby obtaining 2.0 g of white crystal. By conducting FD-MS analysis, the resulting compound was identified as Compound BH-12 as follows (yield: 65%).

BH-12

Synthesis Example 13 [Synthesis of Compound BH-13]

Except that 1.5 g (5.3 mmol) of 3-(2-dibenzofuranyl) phenylboronic acid was used instead of dibenzofuran-2-boronic acid, the reaction was carried out in the same way as in the synthesis example 1, thereby obtaining 1.3 g of white crystal. By conducting FD-MS analysis, the resulting compound was identified as Compound BH-13 as follows (yield: 52%).

BH-13

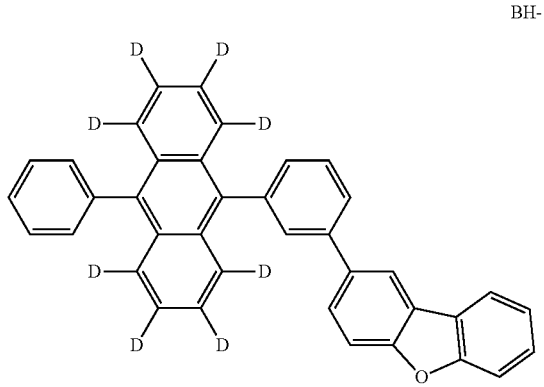

Synthesis Example 14 [Synthesis of Compound BH-14]

Except that 1.5 g (5.3 mmol) of 3-(2-dibenzofuranyl)phenylboronic acid was used instead of dibenzofuran-2-boronic acid, the reaction was carried out in the same way as in the synthesis example 2, thereby obtaining 1.4 g of white crystal. By conducting FD-MS analysis, the resulting compound was identified as Compound BH-14 as follows (yield: 50%).

BH-14

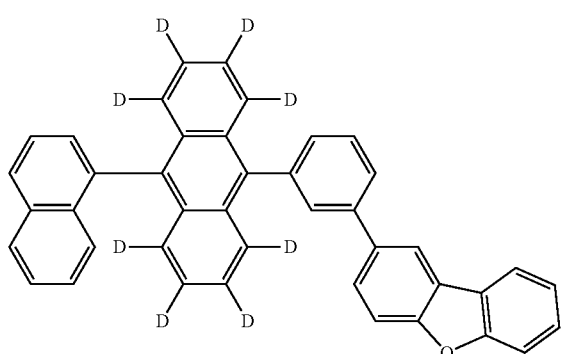

Synthesis Example 15 [Synthesis of Compound BH-15]

Except that 1.5 g (5.3 mmol) of 4-(1-dibenzofuranyl)phenylboronic acid was used instead of dibenzofuran-2-boronic acid, the reaction was carried out in the same way as in the synthesis example 1, thereby obtaining 1.6 g of white crystal. By conducting FD-MS analysis, the resulting compound was identified as Compound BH-15 as follows (yield: 62%).

BH-15

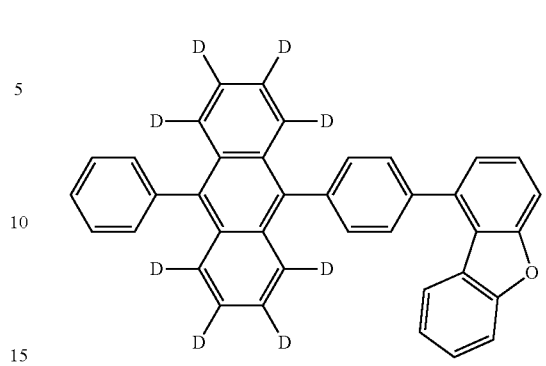

Synthesis Example 16 [Synthesis of Compound BH-16]

(Synthesis of Intermediate 13)

To 1.33 g (5.00 mmol) of 9-bromoanthracene-d9, 0.67 g (5.25 mmol) of phenyl-d5-boronic acid and 0.12 g (0.10 mmol) of Pd[PPh$_3$]4, 7.5 ml of toluene, 7.5 ml of dimethoxyethane and 7.5 ml (15.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 1.07 g of white solid. By conducting FD-MS analysis, the resulting compound was identified as Intermediate 13 as follows (yield: 80%).

Intermediate 13

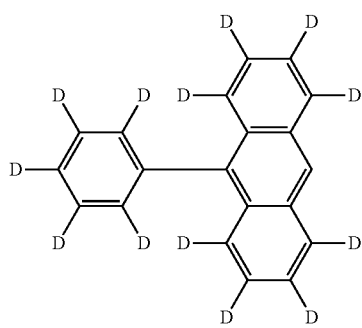

(Synthesis of Intermediate 14)

1.07 g (4.0 mmol) of Intermediate 13 was solubilized in 25 ml of dichloromethane, and the resulting solution was dropped into the solution of 0.64 g (4.0 mmol) of bromine in 3 ml of dichloromethane at room temperature, followed by being stirred for one hour.

After completion of the reaction, the sample was transferred to a separating funnel and washed with 2M Na$_2$S$_2$O$_3$ aqueous solution. The organic phase was further washed with 10% Na$_2$CO$_3$, and thereafter with water. The organic phase was dried with MgSO$_4$, followed by being filtered and concentrated.

The concentrated residue was dispersed in methanol (100 ml), and the precipitated crystal was dried to obtain 1.3 g of white solid. By conducting FD-MS analysis, the resulting compound was identified as Intermediate 14 as follows (yield: 95%).

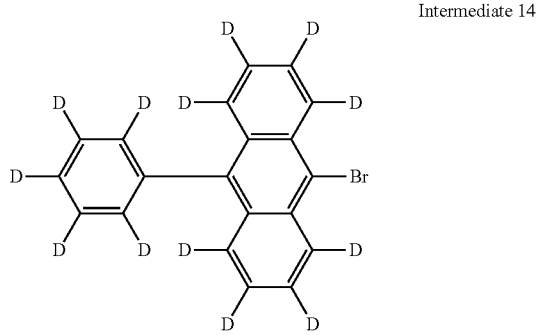 [SMILES: [2H]c1c([2H])c([2H])c(-c2c3c([2H])c([2H])c([2H])c([2H])c3c(Br)c3c([2H])c([2H])c([2H])c([2H])c23)c([2H])c1[2H]]

Intermediate 14

(Synthesis of Compound BH-16)

To 0.87 g (2.5 mmol) of Intermediate 14, 0.58 g (2.65 mmol) of dibenzofuran d7-2-boronic acid and 0.06 g (0.05 mmol) of Pd[PPh$_3$]4, 5 ml of toluene, 5 ml of dimethoxyethane and 5 ml (10.0 mmol) of 2M Na$_2$CO$_3$ aqueous solution were added under an atmosphere of argon, followed by being heated to reflux while stirring for 10 hours.

After completion of the reaction, having been cooled to room temperature, the sample was transferred to a separating funnel and extracted with dichloromethane. The resulting organic phase was dried with MgSO$_4$, followed by being filtered and concentrated. The concentrated residue was purified with silica gel column chromatography to obtain 0.77 g of white solid. By conducting FD-MS analysis, the resulting compound was identified as Compound BH-16 as follows (yield: 70%).

BH-16

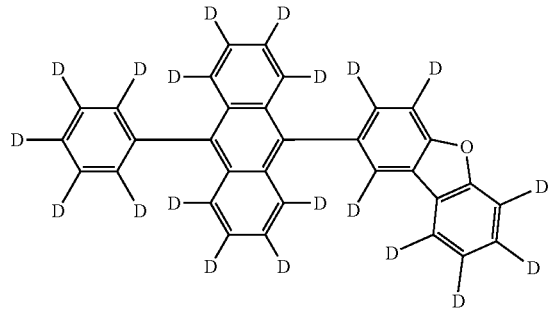

Example 1 [Fabrication and Evaluation of Organic EL Device]

(Fabrication of Organic EL Device)

A glass substrate of 25 mm by 75 mm by 1.1 mm thick with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of ITO was 130 nm.

The cleaned glass substrate with a transparent electrode was mounted in a substrate holder of a vacuum vapor deposition apparatus. First, compound HI was deposited on the surface where the transparent electrode was formed so as to cover the transparent electrode, thereby forming an HI film having a thickness of 5 nm. This HI film functioned as a hole-injecting layer.

Subsequent to the formation of the HI film, compound HT-1 was deposited to form an HT-1 film in a thickness of 80 nm on the HI film. This HT-1 film functioned as a hole-transporting layer (a first hole-transporting layer). Subsequent to the formation of the HT-1 film, compound HT-2 was deposited to form an HT-2 film in a thickness of 10 nm on the HT-1 film. This HT-2 film functioned as an electron-blocking layer (a second hole-transporting layer).

Compound BH-1 (host material) and compound BD-1 (dopant material) were co-deposited on the HT-2 film so that the ratio of compound BD-1 was 4 mass % to form a BH-1:BD-1 film in a thickness of 25 nm. This BH-1:BD-1 film functioned as an emitting layer.

Compound ET-1 was deposited on the emitting layer to form an ET-1 film in a thickness of 10 nm. This ET-1 film functioned as a hole-barrier layer.

Compound ET-2 was deposited on the ET-1 layer to form an ET-2 layer in a thickness of 15 nm. This ET-2 layer functioned as an electron-transporting layer. UF was deposited on the ET-2 layer to form a UF film in a thickness of 1 nm. Al metal was deposited on the UF film to form a metal cathode in a thickness of 80 nm. An organic EL device was thus fabricated.

The layer construction of the fabricated organic EL device was as follows.

ITO (130)/HI (5)/HT-1 (80)/HT-2 (10)/BH-1:BD-1 (25:4 mass %)/ET-1 (10)/ET-2 (15)/LiF (1)/Al (80)

The numbers in the parenthesis denote the thickness of each layer (unit: nm).

The compounds used in Example 1 as well as the subsequent examples and comparative examples are shown below.

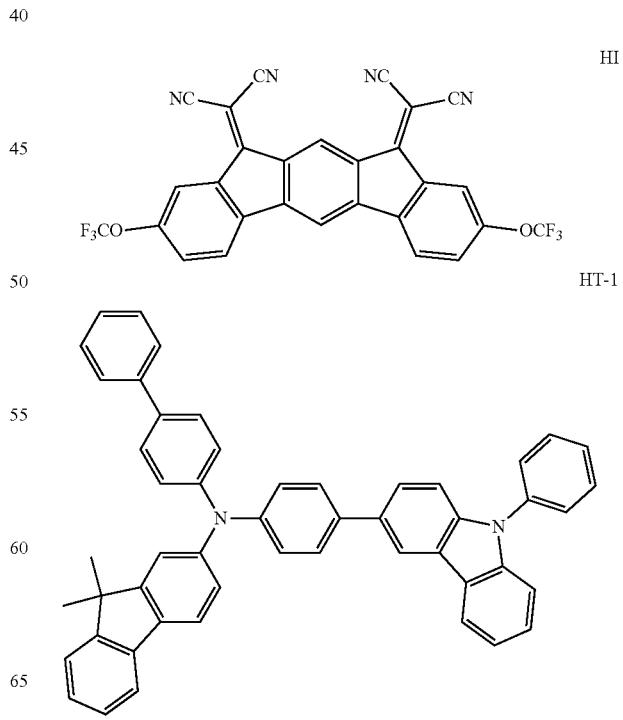

HT-2
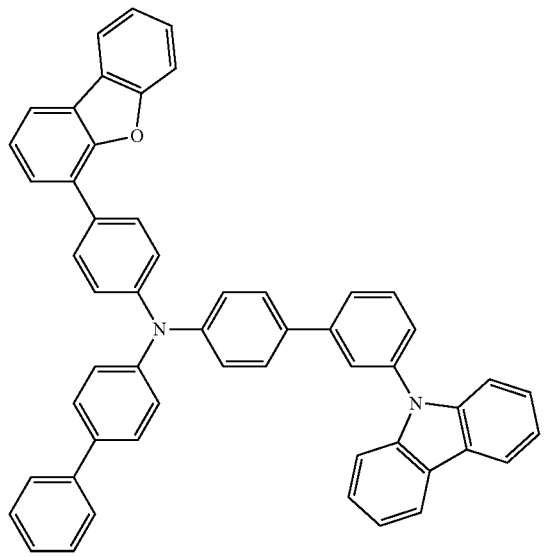
ET-1
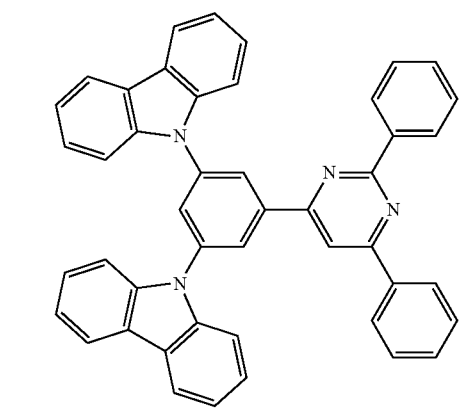
ET-2
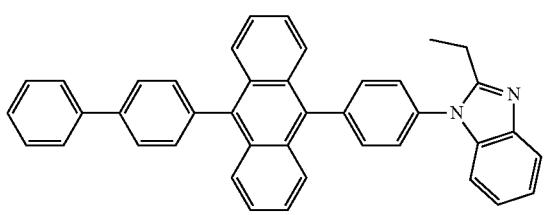
BH-1
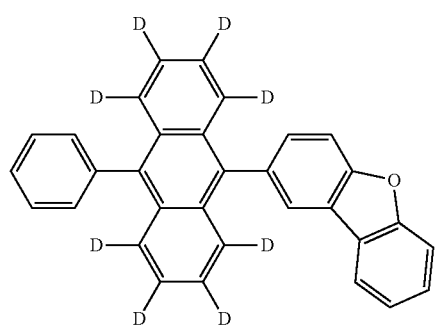
BH-1-a
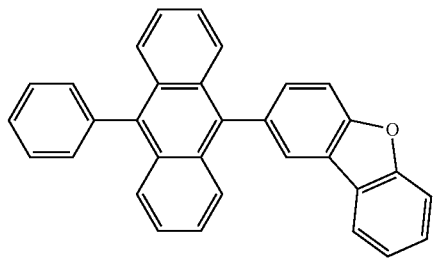
BH-1-b
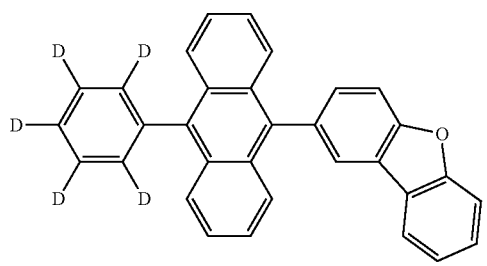
BH-2
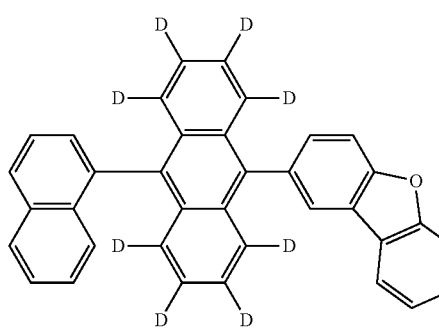
BH-2-a
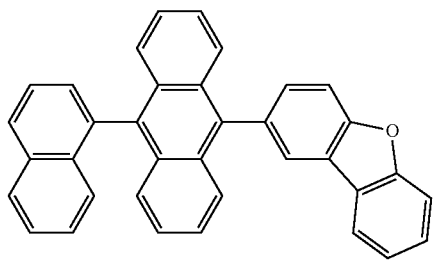
BH-3
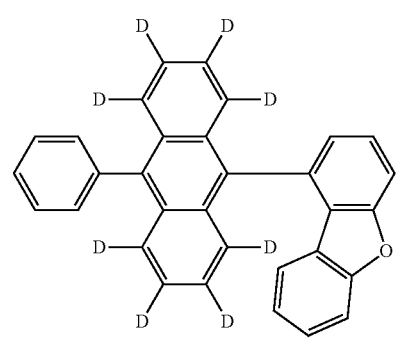

BH-3-a
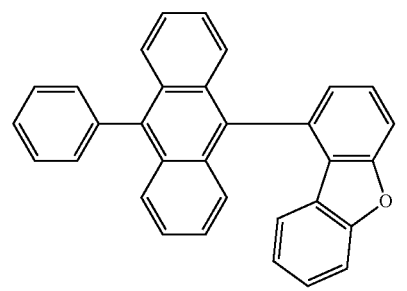
BH-4
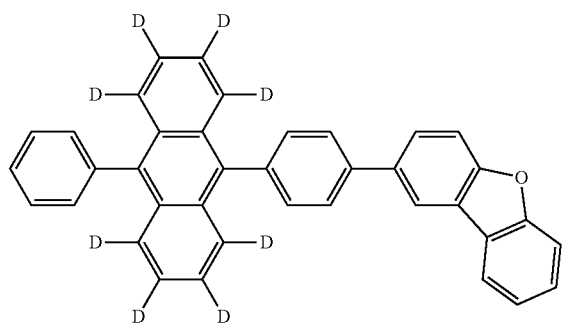
BH-4-a
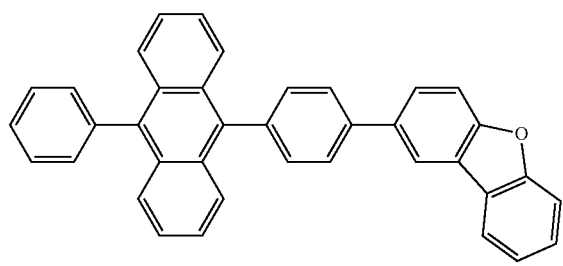
BH-4-b
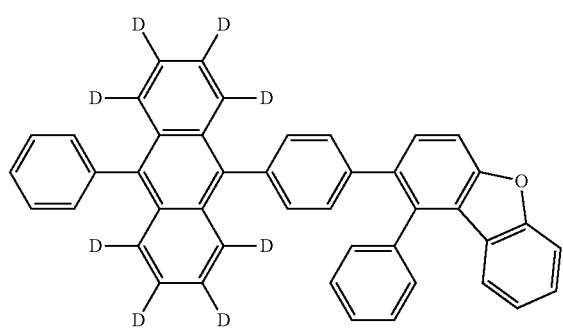
BH-5
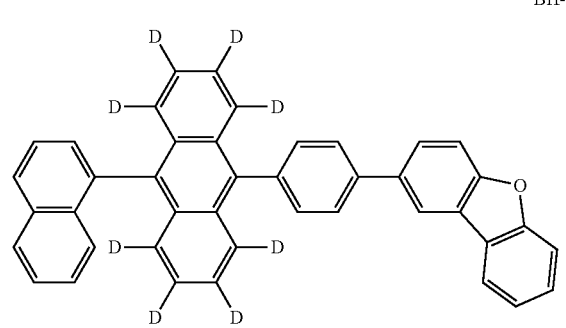
BH-5-a
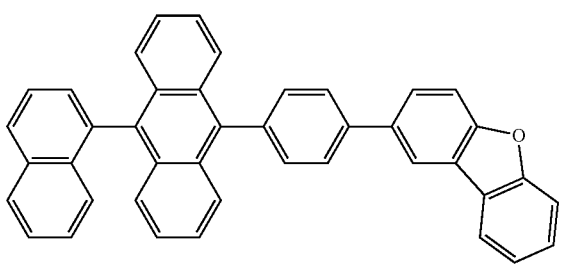
BH-5-b
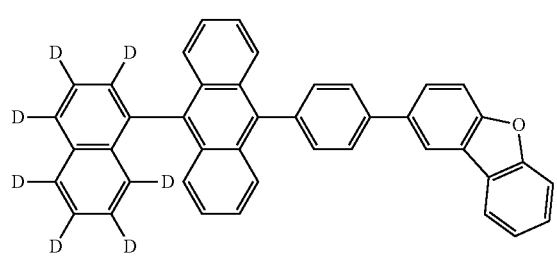
BH-6
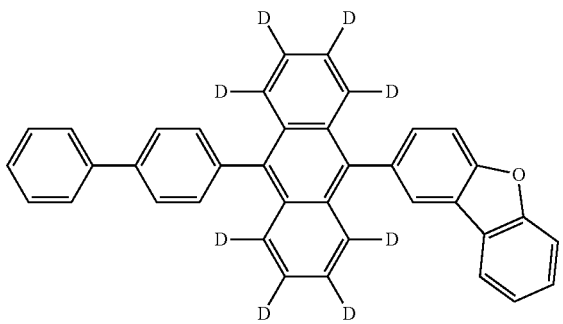
BH-6-a
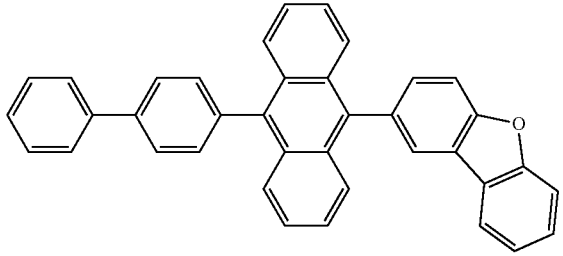
BH-7
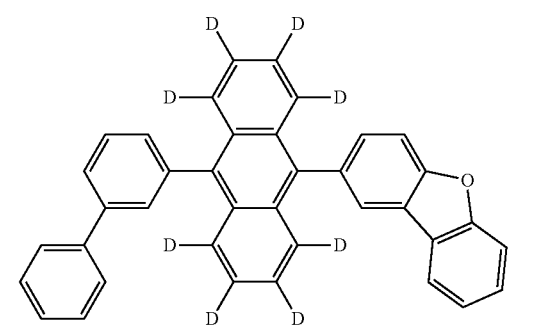

BH-7-a
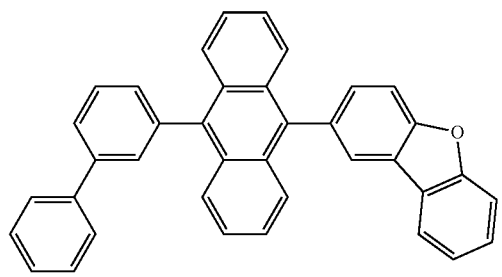
BH-8
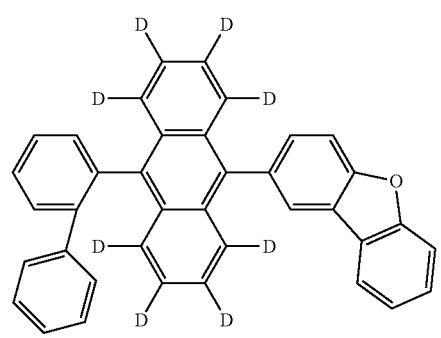
BH-8-a
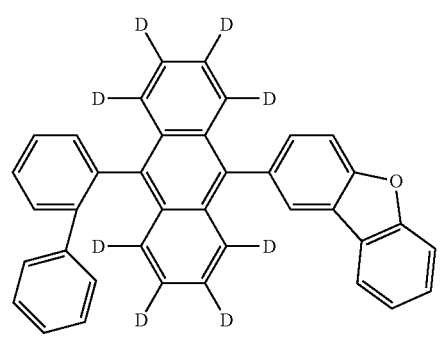
BH-9
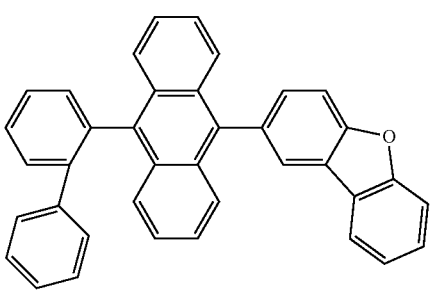
BH-9-a
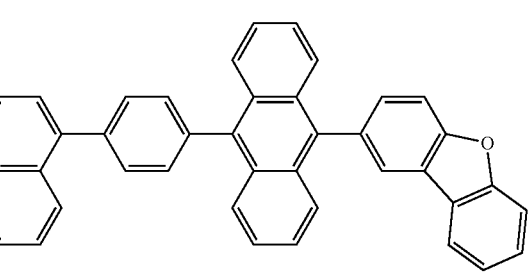
BH-10
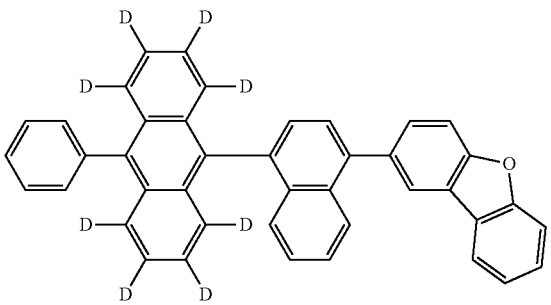
BH-10-a
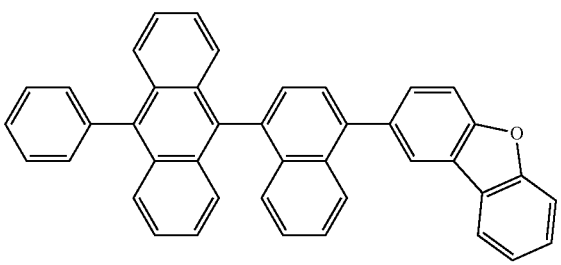
BH-11
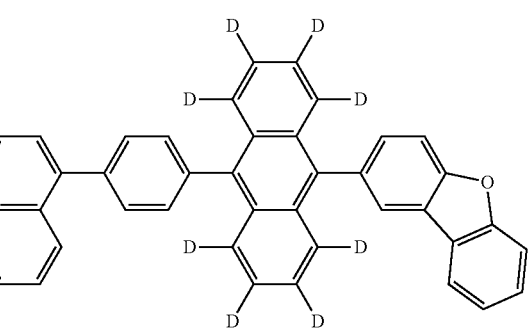
BH-11-a
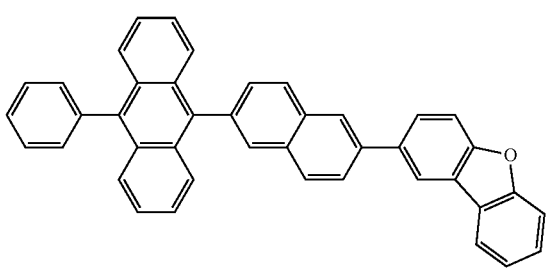
BH-12
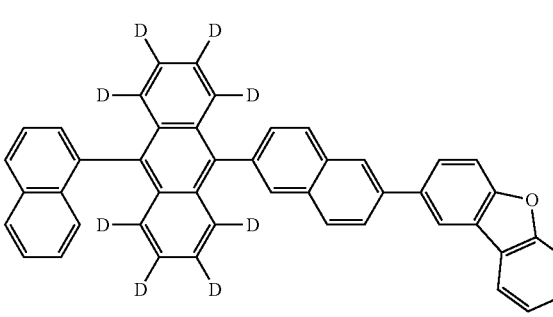

-continued
BH-12-a
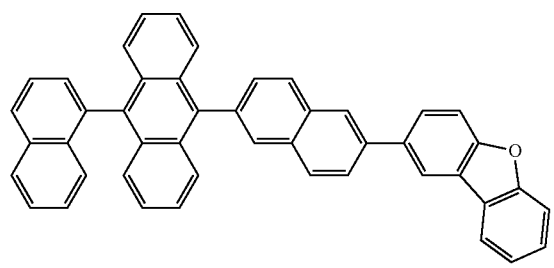
BH-13
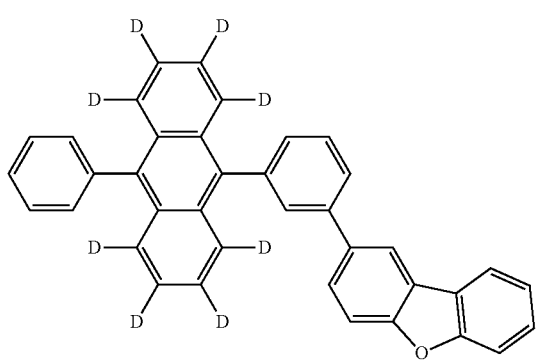
BH-13-a
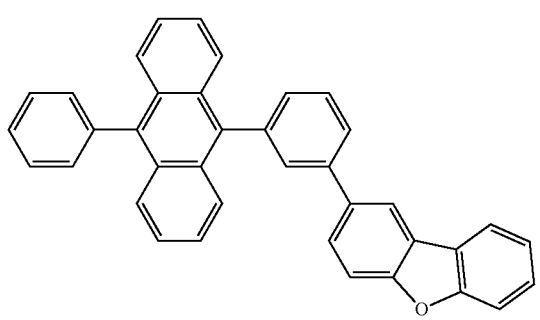
BH-14
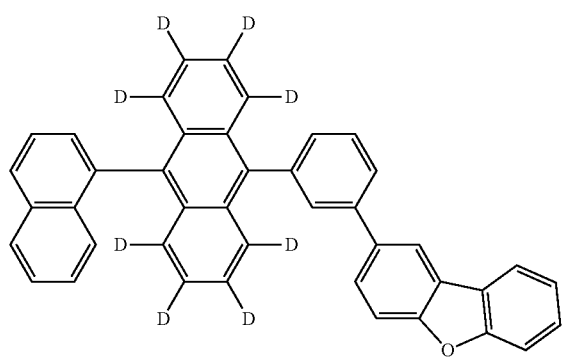
-continued
BH-14-a
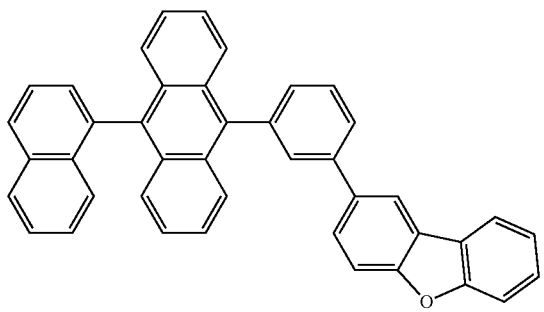
BH-15
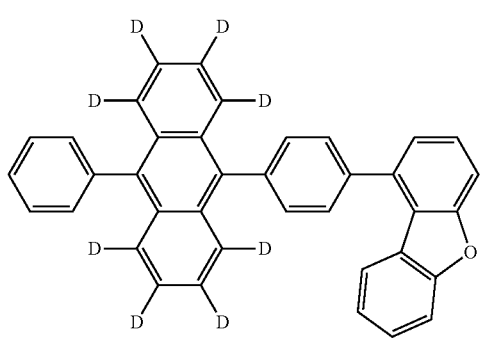
BH-15-a
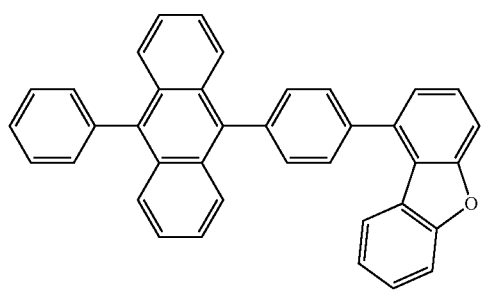
BH-16
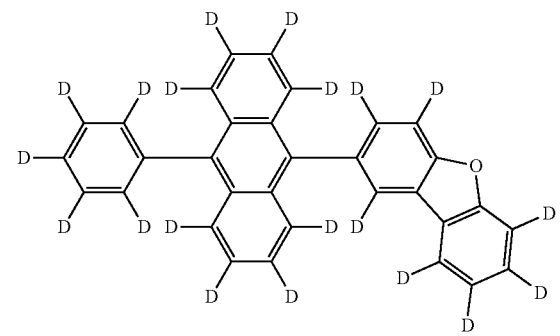

BH-1-c
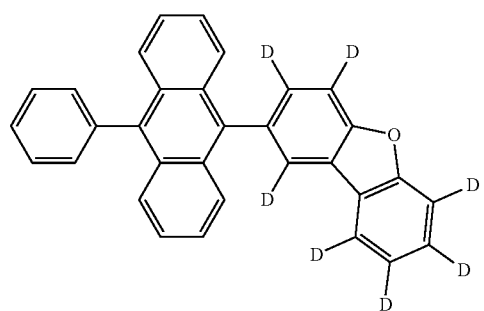
BD-1
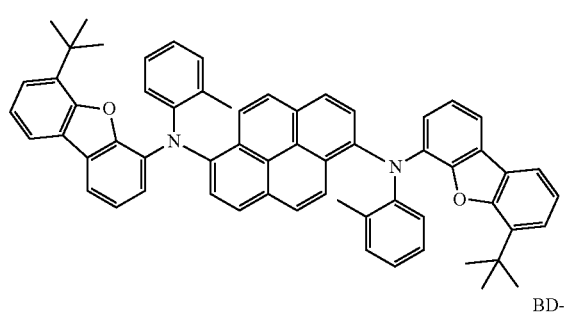
BD-2
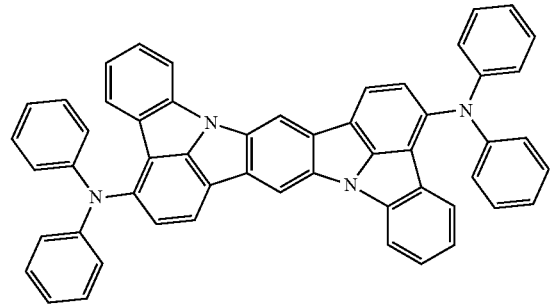
BD-3
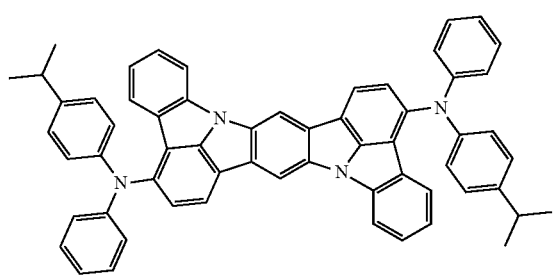
BD-4
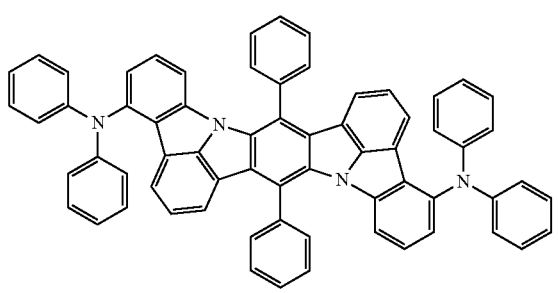
BD-5
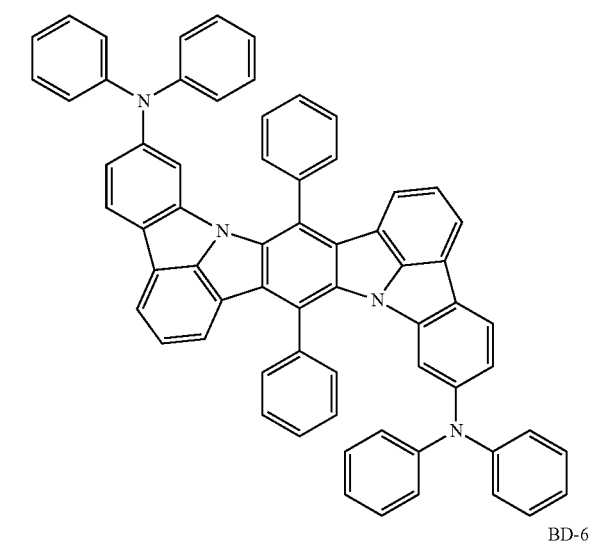
BD-6
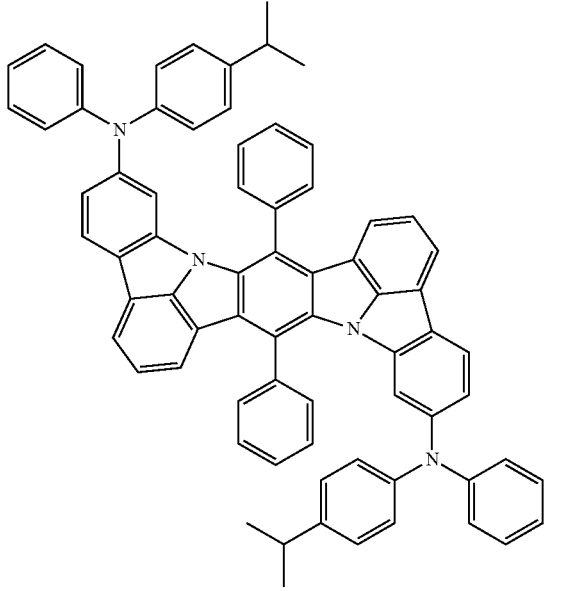
BD-7
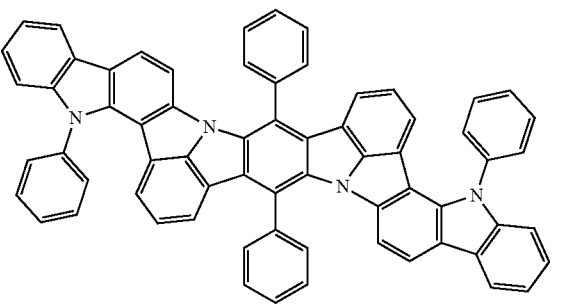
(Evaluation of Organic EL Device)
A voltage was applied to the obtained organic EL device so that the current density was 50 mA/cm$^2$, and the time until the luminance reached 95% with respect to the initial luminance (LT95) was measured. The results are shown in Table 1.

Further, a voltage was applied to the obtained organic EL device so that the current density was 10 mA/cm², and spectral radiance spectrum was measured using a spectroradiometer "CS-1000" (manufactured by Konica Minolta, Inc.) to determine CIE1931 chromaticity coordinate (CIEx, CIEy). The results are shown in Table 1.

Comparative Examples 1-1 and 1-2

Except that the compound shown in the following table was used as the host material of the emitting layer, the organic EL device was fabricated and evaluated in the same manner as in Example 1. The results are shown in Table 1.

TABLE 1

| | Emitting layer | | | | |
|---|---|---|---|---|---|
| | Host | Dopant | | Chromaticity | |
| | material | material | LT95(h) | CIEx | CIEy |
| Example 1 | BH-1 | BD-1 | 155 | 0.139 | 0.090 |
| Comp. Ex. 1-1 | BH-1-a | BD-1 | 94 | 0.139 | 0.090 |
| Comp. Ex. 1-2 | BH-1-b | BD-1 | 95 | 0.139 | 0.090 |

Example 2, Comparative Example 2

Except that the compounds shown in the following table were used as the material of the emitting layer, the organic EL devices were fabricated and evaluated in the same manner as in Example 1. The results are shown in Table 2.

TABLE 2

| | Emitting layer | | | | |
|---|---|---|---|---|---|
| | Host | Dopant | | Chromaticity | |
| | material | material | LT95(h) | CIEx | CIEy |
| Example 2 | BH-2 | BD-1 | 80 | 0.139 | 0.090 |
| Comp. Ex. 2 | BH-2-a | BD-1 | 49 | 0.139 | 0.090 |

Example 3, Comparative Example 3

Except that the compounds shown in the following the were used as the host material of the emitting layer, the organic EL devices were fabricated and evaluated in the same manner as in Example 1. The results are shown in Table 3.

TABLE 3

| | Emitting layer | | | | |
|---|---|---|---|---|---|
| | Host | Dopant | | Chromaticity | |
| | material | material | LT95(h) | CIEx | CIEy |
| Example 3 | BH-3 | BD-1 | 70 | 0.139 | 0.090 |
| Comp. Ex. 3 | BH-3-a | BD-1 | 40 | 0.139 | 0.090 |

Example 4, Comparative Examples 4-1 and 4-2

Except that the compounds shown in the following table were used as the host material of the emitting layer, the organic EL devices were fabricated and evaluated in the same manner as in Example 1. For organic EL device obtained in Example 4 and Comparative Example 4-2, the driving voltages at the time of driving were measured at room temperature 10 mA/cm²a DC (direct current) constant current. The results are shown in Table 4.

TABLE 4

| | Emitting layer | | | | | |
|---|---|---|---|---|---|---|
| | Host | Dopant | | Chromaticity | | |
| | material | material | LT95(h) | CIEx | CIEy | Voltage(V) |
| Example 4 | BH-4 | BD-1 | 170 | 0.139 | 0.091 | 3.7 |
| Comp. Ex. 4-1 | BH-4-a | BD-1 | 101 | 0.139 | 0.091 | — |
| Comp. Ex. 4-2 | BH-4-b | BD-1 | 120 | 0.139 | 0.090 | 4.1 |

Example 5, Comparative Examples 5-1 and 5-2

Except that the compound shown in the following table was used as the host material of the emitting layer, the organic EL device was fabricated and evaluated in the same manner as in Example 1. The results are shown in Table 5.

TABLE 5

| | Emitting layer | | | | |
|---|---|---|---|---|---|
| | Host | Dopant | | Chromaticity | |
| | material | material | LT95(h) | CIEx | CIEy |
| Example 5 | BH-5 | BD-1 | 145 | 0.139 | 0.090 |
| Comp. Ex. 5-1 | BH-5-a | BD-1 | 89 | 0.139 | 0.090 |
| Comp. Ex. 5-2 | BH-5-b | BD-1 | 85 | 0.139 | 0.090 |

Example 11, Comparative Example 11

Except that the compound shown in the following table was used as the host material and the dopant material of the emitting layer, the organic EL device was fabricated and evaluated in the same manner as in Example 1. The results are shown in Table 6.

TABLE 6

| | Emitting layer | | | | |
|---|---|---|---|---|---|
| | Host | Dopant | | Chromaticity | |
| | material | material | LT95(h) | CIEx | CIEy |
| Example 11 | BH-1 | BD-2 | 130 | 0.140 | 0.080 |
| Comp. Ex. 11 | BH-1-a | BD-2 | 83 | 0.140 | 0.080 |

Example 12, Comparative Example 12

Except that the compound shown in the following table was used as the host material and the dopant material of the emitting layer, the organic EL device was fabricated and evaluated in the same manner as in Example 1. The results are shown in Table 7.

TABLE 7

| | Emitting layer | | | | |
|---|---|---|---|---|---|
| | Host material | Dopant material | LT95(h) | Chromaticity CIEx | CIEy |
| Example 12 | BH-2 | BD-2 | 71 | 0.140 | 0.081 |
| Comp. Ex. 12 | BH-2-a | BD-2 | 45 | 0.140 | 0.080 |

Example 13, Comparative Example 13

Except that the compound shown in the following table was used as the host material and the dopant material of the emitting layer, the organic EL device was fabricated and evaluated in the same manner as in Example 1. The results are shown in Table 8.

TABLE 8

| | Emitting layer | | | | |
|---|---|---|---|---|---|
| | Host material | Dopant material | LT95(h) | Chromaticity CIEx | CIEy |
| Example 13 | BH-3 | BD-2 | 56 | 0.140 | 0.080 |
| Comp. Ex. 13 | BH-3-a | BD-2 | 36 | 0.140 | 0.080 |

Example 14, Comparative Example 14

Except that the compound shown in the following table was used as the host material and the dopant material of the emitting layer, the organic EL device was fabricated and evaluated in the same manner as in Example 1. The results are shown in Table 9.

TABLE 9

| | Emitting layer | | | | |
|---|---|---|---|---|---|
| | Host material | Dopant material | LT95(h) | Chromaticity CIEx | CIEy |
| Example 14 | BH-4 | BD-2 | 146 | 0.140 | 0.080 |
| Comp. Ex. 14 | BH-4-a | BD-2 | 82 | 0.140 | 0.080 |

Example 15, Comparative Example 15

Except that the compound shown in the following table was used as the host material and the dopant material of the emitting layer, the organic EL device was fabricated and evaluated in the same manner as in Example 1. The results are shown in Table 10.

TABLE 10

| | Emitting layer | | | | |
|---|---|---|---|---|---|
| | Host material | Dopant material | LT95(h) | Chromaticity CIEx | CIEy |
| Example 15 | BH-5 | BD-2 | 126 | 0.140 | 0.080 |
| Comp. Ex. 15 | BH-5-a | BD-2 | 78 | 0.140 | 0.080 |

Example 16, Comparative Example 16

Except that the compound shown in the following table was used as the host material and the dopant material of the emitting layer, the organic EL device was fabricated and evaluated in the same manner as in Example 1. The results are shown in Table 11.

TABLE 11

| | Emitting layer | | | | |
|---|---|---|---|---|---|
| | Host material | Dopant material | LT95(h) | Chromaticity CIEx | CIEy |
| Example 16 | BH-6 | BD-2 | 127 | 0.140 | 0.080 |
| Comp. Ex. 16 | BH-6-a | BD-2 | 80 | 0.140 | 0.080 |

Example 21, Comparative Example 21

Except that the compounds shown in the following table were used as the host material and the dopant material of the emitting layer, the organic EL devices were fabricated and evaluated in the same manner as in Example 1. The results are shown in Table 12.

TABLE 12

| | Emitting layer | | | | |
|---|---|---|---|---|---|
| | Host material | Dopant material | LT95(h) | Chromaticity CIEx | CIEy |
| Example 21 | BH-1 | BD-3 | 155 | 0.135 | 0.098 |
| Comp. Ex. 21 | BH-1-a | BD-3 | 96 | 0.135 | 0.098 |

Example 22, Comparative Example 22

Except that the compounds shown in the following table were used as the host material and the dopant material of the emitting layer, the organic EL devices were fabricated and evaluated in the same manner as in Example 1. The results are shown in Table 13.

TABLE 13

| | Emitting layer | | | | |
|---|---|---|---|---|---|
| | Host material | Dopant material | LT95(h) | Chromaticity CIEx | CIEy |
| Example 22 | BH-2 | BD-3 | 77 | 0.135 | 0.098 |
| Comp. Ex. 22 | BH-2-a | BD-3 | 50 | 0.135 | 0.099 |

Example 23, Comparative Example 23

Except that the compounds shown in the following table were used as the host material and the dopant material of the emitting layer, the organic EL devices were fabricated and evaluated in the same manner as in Example 1. The results are shown in Table 14.

TABLE 14

| | Emitting layer | | | Chromaticity | |
|---|---|---|---|---|---|
| | Host material | Dopant material | LT95(h) | CIEx | CIEy |
| Example 23 | BH-3 | BD-3 | 73 | 0.135 | 0.098 |
| Comp. Ex. 23 | BH-3-a | BD-3 | 43 | 0.135 | 0.098 |

Example 24, Comparative Example 24

Except that the compounds shown in the following table were used as the host material and the dopant material of the emitting layer, the organic EL devices were fabricated and evaluated in the same manner as in Example 1. The results are shown in Table 15.

TABLE 15

| | Emitting layer | | | Chromaticity | |
|---|---|---|---|---|---|
| | Host material | Dopant material | LT95(h) | CIEx | CIEy |
| Example 24 | BH-4 | BD-3 | 167 | 0.135 | 0.098 |
| Comp. Ex. 24 | BH-4-a | BD-3 | 105 | 0.135 | 0.098 |

Example 25, Comparative Example 25

Except that the compounds shown in the following table were used as the host material and the dopant material of the emitting layer, the organic EL devices were fabricated and evaluated in the same manner as in Example 1. The results are shown in Table 16.

TABLE 16

| | Emitting layer | | | Chromaticity | |
|---|---|---|---|---|---|
| | Host material | Dopant material | LT95(h) | CIEx | CIEy |
| Example 25 | BH-5 | BD-3 | 147 | 0.135 | 0.098 |
| Comp. Ex. 25 | BH-5-a | BD-3 | 92 | 0.135 | 0.098 |

Example 26, Comparative Example 26

Except that the compounds shown in the following table were used as the host material and the dopant material of the emitting layer, the organic EL devices were fabricated and evaluated in the same manner as in Example 1. The results are shown in Table 17.

TABLE 17

| | Emitting layer | | | Chromaticity | |
|---|---|---|---|---|---|
| | Host material | Dopant material | LT95(h) | CIEx | CIEy |
| Example 26 | BH-6 | BD-3 | 150 | 0.135 | 0.098 |
| Comp. Ex. 26 | BH-6-a | BD-3 | 96 | 0.135 | 0.098 |

Example 31, Comparative Example 31

Except that the compounds shown in the following table were used as the host material and the dopant material of the emitting layer, the organic EL devices were fabricated and evaluated in the same manner as in Example 1. The results are shown in Table 18.

TABLE 18

| | Emitting layer | | | Chromaticity | |
|---|---|---|---|---|---|
| | Host material | Dopant material | LT95(h) | CIEx | CIEy |
| Example 31 | BH-1 | BD-4 | 163 | 0.135 | 0.086 |
| Comp. Ex. 31 | BH-1-a | BD-4 | 98 | 0.135 | 0.086 |

Example 32, Comparative Example 32

Except that the compounds shown in the following table were used as the host material and the dopant material of the emitting layer, the organic EL devices were fabricated and evaluated in the same manner as in Example 1. The results are shown in Table 19.

TABLE 19

| | Emitting layer | | | Chromaticity | |
|---|---|---|---|---|---|
| | Host material | Dopant material | LT95(h) | CIEx | CIEy |
| Example 32 | BH-2 | BD-4 | 78 | 0.135 | 0.086 |
| Comp. Ex. 32 | BH-2-a | BD-4 | 51 | 0.135 | 0.086 |

Example 33, Comparative Example 33

Except that the compounds shown in the following table were used as the host material and the dopant material of the emitting layer, the organic EL devices were fabricated and evaluated in the same manner as in Example 1. The results are shown in Table 20.

TABLE 20

| | Emitting layer | | | Chromaticity | |
|---|---|---|---|---|---|
| | Host material | Dopant material | LT95(h) | CIEx | CIEy |
| Example 33 | BH-3 | BD-4 | 73 | 0.135 | 0.086 |
| Comp. Ex. 33 | BH-3-a | BD-4 | 39 | 0.135 | 0.086 |

Example 34, Comparative Example 34

Except that the compounds shown in the following table were used as the host material and the dopant material of the emitting layer, the organic EL devices were fabricated and evaluated in the same manner as in Example 1. The results are shown in Table 21.

TABLE 21

| | Emitting layer | | | Chromaticity | |
| | Host material | Dopant material | LT95(h) | CIEx | CIEy |
|---|---|---|---|---|---|
| Example 34 | BH-4 | BD-4 | 170 | 0.135 | 0.086 |
| Comp. Ex. 34 | BH-4-a | BD-4 | 105 | 0.135 | 0.086 |

Example 35, Comparative Example 35

Except that the compounds shown in the following table were used as the host material and the dopant material of the emitting layer, the organic EL devices were fabricated and evaluated in the same manner as in Example 1. The results are shown in Table 22.

TABLE 22

| | Emitting layer | | | Chromaticity | |
| | Host material | Dopant material | LT95(h) | CIEx | CIEy |
|---|---|---|---|---|---|
| Example 35 | BH-5 | BD-4 | 152 | 0.135 | 0.086 |
| Comp. Ex. 35 | BH-5-a | BD-4 | 89 | 0.135 | 0.086 |

Example 36, Comparative Example 36

Except that the compounds shown in the following table were used as the host material and the dopant material of the emitting layer, the organic EL devices were fabricated and evaluated in the same manner as in Example 1. The results are shown in Table 23.

TABLE 23

| | Emitting layer | | | Chromaticity | |
| | Host material | Dopant material | LT95(h) | CIEx | CIEy |
|---|---|---|---|---|---|
| Example 36 | BH-6 | BD-4 | 161 | 0.135 | 0.086 |
| Comp. Ex. 36 | BH-6-a | BD-4 | 102 | 0.135 | 0.086 |

Example 41, Comparative Example 41

Except that the compounds shown in the following table were used as the host material and the dopant material of the emitting layer, the organic EL devices were fabricated and evaluated in the same manner as in Example 1. The results are shown in Table 24.

TABLE 24

| | Emitting layer | | | Chromaticity | |
| | Host material | Dopant material | LT95(h) | CIEx | CIEy |
|---|---|---|---|---|---|
| Example 41 | BH-1 | BD-5 | 195 | 0.135 | 0.080 |
| Comp. Ex. 41 | BH-1-a | BD-5 | 123 | 0.135 | 0.080 |

Example 42, Comparative Example 42

Except that the compounds shown in the following table were used as the host material and the dopant material of the emitting layer, the organic EL devices were fabricated and evaluated in the same manner as in Example 1. The results are shown in Table 25.

TABLE 25

| | Emitting layer | | | Chromaticity | |
| | Host material | Dopant material | LT95(h) | CIEx | CIEy |
|---|---|---|---|---|---|
| Example 42 | BH-2 | BD-5 | 106 | 0.135 | 0.080 |
| Comp. Ex. 42 | BH-2-a | BD-5 | 66 | 0.135 | 0.080 |

Example 43, Comparative Example 43

Except that the compounds shown in the following table were used as the host material and the dopant material of the emitting layer, the organic EL devices were fabricated and evaluated in the same manner as in Example 1. The results are shown in Table 26.

TABLE 26

| | Emitting layer | | | Chromaticity | |
| | Host material | Dopant material | LT95(h) | CIEx | CIEy |
|---|---|---|---|---|---|
| Example 43 | BH-3 | BD-5 | 90 | 0.135 | 0.080 |
| Comp. Ex. 43 | BH-3-a | BD-5 | 53 | 0.135 | 0.080 |

Example 44, Comparative Example 44

Except that the compounds shown in the following table were used as the host material and the dopant material of the emitting layer, the organic EL devices were fabricated and evaluated in the same manner as in Example 1. The results are shown in Table 27.

TABLE 27

| | Emitting layer | | | Chromaticity | |
| | Host material | Dopant material | LT95(h) | CIEx | CIEy |
|---|---|---|---|---|---|
| Example 44 | BH-4 | BD-5 | 211 | 0.135 | 0.080 |
| Comp. Ex. 44 | BH-4-a | BD-5 | 133 | 0.135 | 0.081 |

Example 45, Comparative Example 45

Except that the compounds shown in the following table were used as the host material and the dopant material of the emitting layer, the organic EL devices were fabricated and evaluated in the same manner as in Example 1. The results are shown in Table 28.

TABLE 28

| | Emitting layer | | | | |
|---|---|---|---|---|---|
| | Host material | Dopant material | LT95(h) | Chromaticity CIEx | CIEy |
| Example 45 | BH-5 | BD-5 | 179 | 0.135 | 0.080 |
| Comp. Ex. 45 | BH-5-a | BD-5 | 112 | 0.135 | 0.080 |

Example 46, Comparative Example 46

Except that the compounds shown in the following table were used as the host material and the dopant material of the emitting layer, the organic EL devices were fabricated and evaluated in the same manner as in Example 1. The results are shown in Table 29.

TABLE 29

| | Emitting layer | | | | |
|---|---|---|---|---|---|
| | Host material | Dopant material | LT95(h) | Chromaticity CIEx | CIEy |
| Example 46 | BH-6 | BD-5 | 202 | 0.135 | 0.080 |
| Comp. Ex. 46 | BH-6-a | BD-5 | 125 | 0.135 | 0.080 |

Example 51, Comparative Example 51

Except that the compounds shown in the following table were used as the host material and the dopant material of the emitting layer, the organic EL devices were fabricated and evaluated in the same manner as in Example 1. The results are shown in Table 30.

TABLE 30

| | Emitting layer | | | | |
|---|---|---|---|---|---|
| | Host material | Dopant material | LT95(h) | Chromaticity CIEx | CIEy |
| Example 51 | BH-1 | BD-6 | 253 | 0.136 | 0.090 |
| Comp. Ex. 51 | BH-1-a | BD-6 | 146 | 0.136 | 0.090 |

Example 52, Comparative Example 52

Except that the compounds shown in the following table were used as the host material and the dopant material of the emitting layer, the organic EL devices were fabricated and evaluated in the same manner as in Example 1. The results are shown in Table 31.

TABLE 31

| | Emitting layer | | | | |
|---|---|---|---|---|---|
| | Host material | Dopant material | LT95(h) | Chromaticity CIEx | CIEy |
| Example 52 | BH-2 | BD-6 | 125 | 0.136 | 0.090 |
| Comp. Ex. 52 | BH-2-a | BD-6 | 73 | 0.136 | 0.090 |

Example 53, Comparative Example 53

Except that the compounds shown in the following table were used as the host material and the dopant material of the emitting layer, the organic EL devices were fabricated and evaluated in the same manner as in Example 1. The results are shown in Table 32.

TABLE 32

| | Emitting layer | | | | |
|---|---|---|---|---|---|
| | Host material | Dopant material | LT95(h) | Chromaticity CIEx | CIEy |
| Example 53 | BH-3 | BD-6 | 102 | 0.136 | 0.090 |
| Comp. Ex. 53 | BH-3-a | BD-6 | 64 | 0.136 | 0.090 |

Example 54, Comparative Example 54

Except that the compounds shown in the following table were used as the host material and the dopant material of the emitting layer, the organic EL devices were fabricated and evaluated in the same manner as in Example 1. The results are shown in Table 33.

TABLE 33

| | Emitting layer | | | | |
|---|---|---|---|---|---|
| | Host material | Dopant material | LT95(h) | Chromaticity CIEx | CIEy |
| Example 54 | BH-4 | BD-6 | 257 | 0.136 | 0.090 |
| Comp. Ex. 54 | BH-4-a | BD-6 | 161 | 0.136 | 0.091 |

Example 55, Comparative Example 55

Except that the compounds shown in the following table were used as the host material and the dopant material of the emitting layer, the organic EL devices were fabricated and evaluated in the same manner as in Example 1. The results are shown in Table 34.

TABLE 34

| | Emitting layer | | | | |
|---|---|---|---|---|---|
| | Host material | Dopant material | LT95(h) | Chromaticity CIEx | CIEy |
| Example 55 | BH-5 | BD-6 | 215 | 0.136 | 0.090 |
| Comp. Ex. 55 | BH-5-a | BD-6 | 137 | 0.136 | 0.090 |

Example 56, Comparative Example 56

Except that the compounds shown in the following table were used as the host material and the dopant material of the emitting layer, the organic EL devices were fabricated and evaluated in the same manner as in Example 1. The results are shown in Table 35.

TABLE 35

| | Emitting layer | | | Chromaticity | |
|---|---|---|---|---|---|
| | Host material | Dopant material | LT95(h) | CIEx | CIEy |
| Example 56 | BH-6 | BD-6 | 241 | 0.136 | 0.090 |
| Comp. Ex. 56 | BH-6-a | BD-6 | 141 | 0.136 | 0.090 |

Example 61, Comparative Example 61

Except that the compounds shown in the following table were used as the host material and the dopant material of the emitting layer, the organic EL devices were fabricated and evaluated in the same manner as in Example 1. The results are shown in Table 36.

TABLE 36

| | Emitting layer | | | Chromaticity | |
|---|---|---|---|---|---|
| | Host material | Dopant material | LT95(h) | CIEx | CIEy |
| Example 61 | BH-1 | BD-7 | 104 | 0.144 | 0.061 |
| Comp. Ex. 61 | BH-1-a | BD-7 | 65 | 0.144 | 0.061 |

Example 62, Comparative Example 62

Except that the compounds shown in the following table were used as the host material and the dopant material of the emitting layer, the organic EL devices were fabricated and evaluated in the same manner as in Example 1. The results are shown in Table 37.

TABLE 37

| | Emitting layer | | | Chromaticity | |
|---|---|---|---|---|---|
| | Host material | Dopant material | LT95(h) | CIEx | CIEy |
| Example 62 | BH-2 | BD-7 | 53 | 0.144 | 0.061 |
| Comp. Ex. 62 | BH-2-a | BD-7 | 37 | 0.144 | 0.061 |

Example 63, Comparative Example 63

Except that the compounds shown in the following table were used as the host material and the dopant material of the emitting layer, the organic EL devices were fabricated and evaluated in the same manner as in Example 1. The results are shown in Table 38.

TABLE 38

| | Emitting layer | | | Chromaticity | |
|---|---|---|---|---|---|
| | Host material | Dopant material | LT95(h) | CIEx | CIEy |
| Example 63 | BH-3 | BD-7 | 51 | 0.144 | 0.060 |
| Comp. Ex. 63 | BH-3-a | BD-7 | 32 | 0.144 | 0.061 |

Example 64, Comparative Example 64

Except that the compounds shown in the following table were used as the host material and the dopant material of the emitting layer, the organic EL devices were fabricated and evaluated in the same manner as in Example 1. The results are shown in Table 39.

TABLE 39

| | Emitting layer | | | Chromaticity | |
|---|---|---|---|---|---|
| | Host material | Dopant material | LT95(h) | CIEx | CIEy |
| Example 64 | BH-4 | BD-7 | 117 | 0.144 | 0.061 |
| Comp. Ex. 64 | BH-4-a | BD-7 | 75 | 0.144 | 0.061 |

Example 65, Comparative Example 65

Except that the compounds shown in the following table were used as the host material and the dopant material of the emitting layer, the organic EL devices were fabricated and evaluated in the same manner as in Example 1. The results are shown in Table 40.

TABLE 40

| | Emitting layer | | | Chromaticity | |
|---|---|---|---|---|---|
| | Host material | Dopant material | LT95(h) | CIEx | CIEy |
| Example 65 | BH-5 | BD-7 | 105 | 0.144 | 0.061 |
| Comp. Ex. 65 | BH-5-a | BD-7 | 65 | 0.144 | 0.061 |

Example 66, Comparative Example 66

Except that the compounds shown in the following table were used as the host material and the dopant material of the emitting layer, the organic EL devices were fabricated and evaluated in the same manner as in Example 1. The results are shown in Table 41.

TABLE 41

| | Emitting layer | | | Chromaticity | |
|---|---|---|---|---|---|
| | Host material | Dopant material | LT95(h) | CIEx | CIEy |
| Example 66 | BH-6 | BD-7 | 110 | 0.144 | 0.061 |
| Comp. Ex. 66 | BH-6-a | BD-7 | 66 | 0.144 | 0.061 |

Example 71, Comparative Example 71

Except that the compounds shown in the following table were used as the host material and the dopant material of the emitting layer, the organic EL devices were fabricated and evaluated in the same manner as in Example 1. The results are shown in Table 42.

TABLE 42

| | Emitting layer | | | | |
| | Host material | Dopant material | LT95(h) | Chromaticity CIEx | CIEy |
|---|---|---|---|---|---|
| Example 71 | BH-6 | BD-1 | 154 | 0.139 | 0.090 |
| Comp. Ex. 71 | BH-6-a | BD-1 | 90 | 0.139 | 0.090 |

Example 72, Comparative Example 72

Except that the compounds shown in the following table were used as the host material and the dopant material of the emitting layer, the organic EL devices were fabricated and evaluated in the same manner as in Example 1. The results are shown in Table 43.

TABLE 43

| | Emitting layer | | | | |
| | Host material | Dopant material | LT95(h) | Chromaticity CIEx | CIEy |
|---|---|---|---|---|---|
| Example 72 | BH-7 | BD-1 | 116 | 0.139 | 0.090 |
| Comp. Ex. 72 | BH-7-a | BD-1 | 70 | 0.139 | 0.090 |

Example 73, Comparative Example 73

Except that the compounds shown in the following table were used as the host material and the dopant material of the emitting layer, the organic EL devices were fabricated and evaluated in the same manner as in Example 1. The results are shown in Table 44.

TABLE 44

| | Emitting layer | | | | |
| | Host material | Dopant material | LT95(h) | Chromaticity CIEx | CIEy |
|---|---|---|---|---|---|
| Example 73 | BH-8 | BD-1 | 110 | 0.139 | 0.090 |
| Comp. Ex. 73 | BH-8-a | BD-1 | 75 | 0.139 | 0.090 |

Example 74, Comparative Example 74

Except that the compounds shown in the following table were used as the host material and the dopant material of the emitting layer, the organic EL devices were fabricated and evaluated in the same manner as in Example 1. The results are shown in Table 45.

TABLE 45

| | Emitting layer | | | | |
| | Host material | Dopant material | LT95(h) | Chromaticity CIEx | CIEy |
|---|---|---|---|---|---|
| Example 74 | BH-9 | BD-1 | 110 | 0.139 | 0.090 |
| Comp. Ex. 74 | BH-9-a | BD-1 | 70 | 0.139 | 0.090 |

Example 75, Comparative Example 75

Except that the compounds shown in the following table were used as the host material and the dopant material of the emitting layer, the organic EL devices were fabricated and evaluated in the same manner as in Example 1. The results are shown in Table 46.

TABLE 46

| | Emitting layer | | | | |
| | Host material | Dopant material | LT95(h) | Chromaticity CIEx | CIEy |
|---|---|---|---|---|---|
| Example 75 | BH-10 | BD-1 | 103 | 0.139 | 0.090 |
| Comp. Ex. 75 | BH-10-a | BD-1 | 58 | 0.139 | 0.090 |

Example 76, Comparative Example 76

Except that the compounds shown in the following table were used as the host material and the dopant material of the emitting layer, the organic EL devices were fabricated and evaluated in the same manner as in Example 1. The results are shown in Table 47.

TABLE 47

| | Emitting layer | | | | |
| | Host material | Dopant material | LT95(h) | Chromaticity CIEx | CIEy |
|---|---|---|---|---|---|
| Example 76 | BH-11 | BD-1 | 95 | 0.139 | 0.090 |
| Comp. Ex. 76 | BH-11-a | BD-1 | 50 | 0.139 | 0.090 |

Example 77, Comparative Example 77

Except that the compounds shown in the following table were used as the host material and the dopant material of the emitting layer, the organic EL devices were fabricated and evaluated in the same manner as in Example 1. The results are shown in Table 48.

TABLE 48

| | Emitting layer | | | | |
| | Host material | Dopant material | LT95(h) | Chromaticity CIEx | CIEy |
|---|---|---|---|---|---|
| Example 77 | BH-12 | BD-1 | 75 | 0.139 | 0.090 |
| Comp. Ex. 77 | BH-12-a | BD-1 | 51 | 0.139 | 0.090 |

Example 78, Comparative Example 78

Except that the compounds shown in the following table were used as the host material and the dopant material of the emitting layer, the organic EL devices were fabricated and evaluated in the same manner as in Example 1. The results are shown in Table 49.

TABLE 49

| | Emitting layer | | | | |
|---|---|---|---|---|---|
| | Host material | Dopant material | LT95(h) | Chromaticity CIEx | CIEy |
| Example 78 | BH-13 | BD-1 | 150 | 0.139 | 0.090 |
| Comp. Ex. 78 | BH-13-a | BD-1 | 83 | 0.139 | 0.090 |

Example 79, Comparative Example 79

Except that the compounds shown in the following table were used as the host material and the dopant material of the emitting layer, the organic EL devices were fabricated and evaluated in the same manner as in Example 1. The results are shown in Table 50.

TABLE 50

| | Emitting layer | | | | |
|---|---|---|---|---|---|
| | Host material | Dopant material | LT95(h) | Chromaticity CIEx | CIEy |
| Example 79 | BH-14 | BD-1 | 100 | 0.139 | 0.090 |
| Comp. Ex. 79 | BH-14-a | BD-1 | 63 | 0.139 | 0.090 |

Example 80, Comparative Example 80

Except that the compounds shown in the following table were used as the host material and the dopant material of the emitting layer, the organic EL devices were fabricated and evaluated in the same manner as in Example 1. The results are shown in Table 51.

TABLE 51

| | Emitting layer | | | | |
|---|---|---|---|---|---|
| | Host material | Dopant material | LT95(h) | Chromaticity CIEx | CIEy |
| Example 80 | BH-15 | BD-1 | 100 | 0.139 | 0.090 |
| Comp. Ex. 80 | BH-15-a | BD-1 | 60 | 0.139 | 0.090 |

Example 81, Comparative Example 81

Except that the compounds shown in the following table were used as the host material and the dopant material of the emitting layer, the organic EL devices were fabricated and evaluated in the same manner as in Example 1. The results are shown in Table 52.

TABLE 52

| | Emitting layer | | | | |
|---|---|---|---|---|---|
| | Host material | Dopant material | LT95(h) | Chromaticity CIEx | CIEy |
| Example 81 | BH-16 | BD-1 | 158 | 0.139 | 0.090 |
| Comp. Ex. 81 | BH-1-c | BD-1 | 103 | 0.139 | 0.090 |

Example 82, Comparative Example 82

Except that the compounds shown in the following table were used as the host material and the dopant material of the emitting layer, the organic EL devices were fabricated and evaluated in the same manner as in Example 1. The results are shown in Table 53.

TABLE 53

| | Emitting layer | | | | |
|---|---|---|---|---|---|
| | Host material | Dopant material | LT95(h) | Chromaticity CIEx | CIEy |
| Example 82 | BH-7 | BD-2 | 98 | 0.140 | 0.080 |
| Comp. Ex. 82 | BH-7-a | BD-2 | 64 | 0.140 | 0.080 |

Example 83, Comparative Example 83

Except that the compounds shown in the following table were used as the host material and the dopant material of the emitting layer, the organic EL devices were fabricated and evaluated in the same manner as in Example 1. The results are shown in Table 54.

TABLE 54

| | Emitting layer | | | | |
|---|---|---|---|---|---|
| | Host material | Dopant material | LT95(h) | Chromaticity CIEx | CIEy |
| Example 83 | BH-8 | BD-2 | 100 | 0.140 | 0.080 |
| Comp. Ex. 83 | BH-8-a | BD-2 | 64 | 0.140 | 0.080 |

Example 84, Comparative Example 84

Except that the compounds shown in the following table were used as the host material and the dopant material of the emitting layer, the organic EL devices were fabricated and evaluated in the same manner as in Example 1. The results are shown in Table 55.

TABLE 55

| | Emitting layer | | | | |
|---|---|---|---|---|---|
| | Host material | Dopant material | LT95(h) | Chromaticity CIEx | CIEy |
| Example 84 | BH-9 | BD-2 | 94 | 0.140 | 0.080 |
| Comp. Ex. 84 | BH-9-a | BD-2 | 58 | 0.140 | 0.080 |

Example 85, Comparative Example 85

Except that the compounds shown in the following table were used as the host material and the dopant material of the emitting layer, the organic EL devices were fabricated and evaluated in the same manner as in Example 1. The results are shown in Table 56.

TABLE 56

| | Emitting layer | | | Chromaticity | |
| --- | --- | --- | --- | --- | --- |
| | Host material | Dopant material | LT95(h) | CIEx | CIEy |
| Example 85 | BH-10 | BD-2 | 83 | 0.140 | 0.081 |
| Comp. Ex. 85 | BH-10-a | BD-2 | 50 | 0.140 | 0.080 |

Example 86, Comparative Example 86

Except that the compounds shown in the following table were used as the host material and the dopant material of the emitting layer, the organic EL devices were fabricated and evaluated in the same manner as in Example 1. The results are shown in Table 57.

TABLE 57

| | Emitting layer | | | Chromaticity | |
| --- | --- | --- | --- | --- | --- |
| | Host material | Dopant material | LT95(h) | CIEx | CIEy |
| Example 86 | BH-11 | BD-2 | 73 | 0.140 | 0.080 |
| Comp. Ex. 86 | BH-11-a | BD-2 | 45 | 0.140 | 0.080 |

Example 87, Comparative Example 87

Except that the compounds shown in the following table were used as the host material and the dopant material of the emitting layer, the organic EL devices were fabricated and evaluated in the same manner as in Example 1. The results are shown in Table 58.

TABLE 58

| | Emitting layer | | | Chromaticity | |
| --- | --- | --- | --- | --- | --- |
| | Host material | Dopant material | LT95(h) | CIEx | CIEy |
| Example 87 | BH-12 | BD-2 | 65 | 0.140 | 0.080 |
| Comp. Ex. 87 | BH-12-a | BD-2 | 40 | 0.140 | 0.080 |

Example 88, Comparative Example 88

Except that the compounds shown in the following table were used as the host material and the dopant material of the emitting layer, the organic EL devices were fabricated and evaluated in the same manner as in Example 1. The results are shown in Table 59.

TABLE 59

| | Emitting layer | | | Chromaticity | |
| --- | --- | --- | --- | --- | --- |
| | Host material | Dopant material | LT95(h) | CIEx | CIEy |
| Example 88 | BH-13 | BD-2 | 127 | 0.140 | 0.080 |
| Comp. Ex. 88 | BH-13-a | BD-2 | 75 | 0.140 | 0.080 |

Example 89, Comparative Example 89

Except that the compounds shown in the following table were used as the host material and the dopant material of the emitting layer, the organic EL devices were fabricated and evaluated in the same manner as in Example 1. The results are shown in Table 60.

TABLE 60

| | Emitting layer | | | Chromaticity | |
| --- | --- | --- | --- | --- | --- |
| | Host material | Dopant material | LT95(h) | CIEx | CIEy |
| Example 89 | BH-14 | BD-2 | 88 | 0.140 | 0.080 |
| Comp. Ex. 89 | BH-14-a | BD-2 | 54 | 0.140 | 0.080 |

Example 90, Comparative Example 90

Except that the compounds shown in the following table were used as the host material and the dopant material of the emitting layer, the organic EL devices were fabricated and evaluated in the same manner as in Example 1. The results are shown in Table 61.

TABLE 61

| | Emitting layer | | | Chromaticity | |
| --- | --- | --- | --- | --- | --- |
| | Host material | Dopant material | LT95(h) | CIEx | CIEy |
| Example 90 | BH-15 | BD-2 | 84 | 0.140 | 0.080 |
| Comp. Ex. 90 | BH-15-a | BD-2 | 52 | 0.140 | 0.080 |

Example 91, Comparative Examples 91-1, 91-2 and 91-3

Except that the compounds shown in the following table were used as the host material and the dopant material of the emitting layer, the organic EL devices were fabricated and evaluated in the same manner as in Example 1. The results are shown in Table 62.

TABLE 62

| | Emitting layer | | | Chromaticity | |
| --- | --- | --- | --- | --- | --- |
| | Host material | Dopant material | LT95(h) | CIEx | CIEy |
| Example 91 | BH-16 | BD-2 | 131 | 0.140 | 0.080 |
| Comp. Ex. 91-1 | BH-1-a | BD-2 | 83 | 0.140 | 0.080 |
| Comp. Ex. 91-2 | BH-1-b | BD-2 | 84 | 0.140 | 0.080 |
| Comp. Ex. 91-3 | BH-1-c | BD-2 | 86 | 0.140 | 0.080 |

Example 92, Comparative Example 92

Except that the compounds shown in the following table were used as the host material and the dopant material of the emitting layer, the organic EL devices were fabricated and evaluated in the same manner as in Example 1. The results are shown in Table 63.

TABLE 63

| | Emitting layer | | | | |
| | Host material | Dopant material | LT95(h) | Chromaticity CIEx | CIEy |
|---|---|---|---|---|---|
| Example 92 | BH-7 | BD-3 | 118 | 0.135 | 0.098 |
| Comp. Ex. 92 | BH-7-a | BD-3 | 75 | 0.135 | 0.098 |

Example 93, Comparative Example 93

Except that the compounds shown in the following table were used as the host material and the dopant material of the emitting layer, the organic EL devices were fabricated and evaluated in the same manner as in Example 1. The results are shown in Table 64.

TABLE 64

| | Emitting layer | | | | |
| | Host material | Dopant material | LT95(h) | Chromaticity CIEx | CIEy |
|---|---|---|---|---|---|
| Example 93 | BH-8 | BD-3 | 112 | 0.135 | 0.098 |
| Comp. Ex. 93 | BH-8-a | BD-3 | 72 | 0.135 | 0.098 |

Example 94, Comparative Example 94

Except that the compounds shown in the following table were used as the host material and the dopant material of the emitting layer, the organic EL devices were fabricated and evaluated in the same manner as in Example 1. The results are shown in Table 65.

TABLE 65

| | Emitting layer | | | | |
| | Host material | Dopant material | LT95(h) | Chromaticity CIEx | CIEy |
|---|---|---|---|---|---|
| Example 94 | BH-9 | BD-3 | 105 | 0.135 | 0.098 |
| Comp. Ex. 94 | BH-9-a | BD-3 | 66 | 0.135 | 0.098 |

Example 95, Comparative Example 95

Except that the compounds shown in the following table were used as the host material and the dopant material of the emitting layer, the organic EL devices were fabricated and evaluated in the same manner as in Example 1. The results are shown in Table 66.

TABLE 66

| | Emitting layer | | | | |
| | Host material | Dopant material | LT95(h) | Chromaticity CIEx | CIEy |
|---|---|---|---|---|---|
| Example 95 | BH-10 | BD-3 | 90 | 0.135 | 0.098 |
| Comp. Ex. 95 | BH-10-a | BD-3 | 60 | 0.135 | 0.098 |

Example 96, Comparative Example 96

Except that the compounds shown in the following table were used as the host material and the dopant material of the emitting layer, the organic EL devices were fabricated and evaluated in the same manner as in Example 1. The results are shown in Table 67.

TABLE 67

| | Emitting layer | | | | |
| | Host material | Dopant material | LT95(h) | Chromaticity CIEx | CIEy |
|---|---|---|---|---|---|
| Example 96 | BH-11 | BD-3 | 80 | 0.135 | 0.098 |
| Comp. Ex. 96 | BH-11-a | BD-3 | 53 | 0.135 | 0.098 |

Example 97, Comparative Example 97

Except that the compounds shown in the following table were used as the host material and the dopant material of the emitting layer, the organic EL devices were fabricated and evaluated in the same manner as in Example 1. The results are shown in Table 68.

TABLE 68

| | Emitting layer | | | | |
| | Host material | Dopant material | LT95(h) | Chromaticity CIEx | CIEy |
|---|---|---|---|---|---|
| Example 97 | BH-12 | BD-3 | 70 | 0.135 | 0.098 |
| Comp. Ex. 97 | BH-12-a | BD-3 | 46 | 0.135 | 0.099 |

Example 98, Comparative Example 98

Except that the compounds shown in the following table were used as the host material and the dopant material of the emitting layer, the organic EL devices were fabricated and evaluated in the same manner as in Example 1. The results are shown in Table 69.

TABLE 69

| | Emitting layer | | | | |
| | Host material | Dopant material | LT95(h) | Chromaticity CIEx | CIEy |
|---|---|---|---|---|---|
| Example 98 | BH-13 | BD-3 | 150 | 0.135 | 0.098 |
| Comp. Ex. 98 | BH-13-a | BD-3 | 92 | 0.135 | 0.098 |

Example 99, Comparative Example 99

Except that the compounds shown in the following table were used as the host material and the dopant material of the emitting layer, the organic EL devices were fabricated and evaluated in the same manner as in Example 1. The results are shown in Table 70.

TABLE 70

| | Emitting layer | | | | |
|---|---|---|---|---|---|
| | Host material | Dopant material | LT95(h) | Chromaticity CIEx | CIEy |
| Example 99 | BH-14 | BD-3 | 102 | 0.135 | 0.098 |
| Comp. Ex. 99 | BH-14-a | BD-3 | 64 | 0.135 | 0.098 |

Example 100, Comparative Example 100

Except that the compounds shown in the following table were used as the host material and the dopant material of the emitting layer, the organic EL devices were fabricated and evaluated in the same manner as in Example 1. The results are shown in Table 71.

TABLE 71

| | Emitting layer | | | | |
|---|---|---|---|---|---|
| | Host material | Dopant material | LT95(h) | Chromaticity CIEx | CIEy |
| Example 100 | BH-15 | BD-3 | 96 | 0.135 | 0.098 |
| Comp. Ex. 100 | BH-15-a | BD-3 | 60 | 0.135 | 0.098 |

Example 101, Comparative Examples 101-1, 101-2 and 101-3

Except that the compounds shown in the following table were used as the host material and the dopant material of the emitting layer, the organic EL devices were fabricated and evaluated in the same manner as in Example 1. The results are shown in Table 72.

TABLE 72

| | Emitting layer | | | | |
|---|---|---|---|---|---|
| | Host material | Dopant material | LT95(h) | Chromaticity CIEx | CIEy |
| Example 101 | BH-16 | BD-3 | 157 | 0.135 | 0.098 |
| Comp. Ex. 101-1 | BH-1-a | BD-3 | 96 | 0.135 | 0.098 |
| Comp. Ex. 101-2 | BH-1-b | BD-3 | 93 | 0.135 | 0.098 |
| Comp. Ex. 101-3 | BH-1-c | BD-3 | 100 | 0.135 | 0.098 |

Example 102, Comparative Example 102

Except that the compounds shown in the following table were used as the host material and the dopant material of the emitting layer, the organic EL devices were fabricated and evaluated in the same manner as in Example 1. The results are shown in Table 73.

TABLE 73

| | Emitting layer | | | | |
|---|---|---|---|---|---|
| | Host material | Dopant material | LT95(h) | Chromaticity CIEx | CIEy |
| Example 102 | BH-7 | BD-4 | 126 | 0.135 | 0.086 |
| Comp. Ex. 102 | BH-7-a | BD-4 | 80 | 0.135 | 0.086 |

Example 103, Comparative Example 103

Except that the compounds shown in the following table were used as the host material and the dopant material of the emitting layer, the organic EL devices were fabricated and evaluated in the same manner as in Example 1. The results are shown in Table 74.

TABLE 74

| | Emitting layer | | | | |
|---|---|---|---|---|---|
| | Host material | Dopant material | LT95(h) | Chromaticity CIEx | CIEy |
| Example 103 | BH-8 | BD-4 | 126 | 0.135 | 0.086 |
| Comp. Ex. 103 | BH-8-a | BD-4 | 76 | 0.135 | 0.086 |

Example 104, Comparative Example 104

Except that the compounds shown in the following table were used as the host material and the dopant material of the emitting layer, the organic EL devices were fabricated and evaluated in the same manner as in Example 1. The results are shown in Table 75.

TABLE 75

| | Emitting layer | | | | |
|---|---|---|---|---|---|
| | Host material | Dopant material | LT95(h) | Chromaticity CIEx | CIEy |
| Example 104 | BH-9 | BD-4 | 110 | 0.135 | 0.085 |
| Comp. Ex. 104 | BH-9-a | BD-4 | 70 | 0.135 | 0.086 |

Example 105, Comparative Example 105

Except that the compounds shown in the following table were used as the host material and the dopant material of the emitting layer, the organic EL devices were fabricated and evaluated in the same manner as in Example 1. The results are shown in Table 76.

TABLE 76

| | Emitting layer | | | | |
|---|---|---|---|---|---|
| | Host material | Dopant material | LT95(h) | Chromaticity CIEx | CIEy |
| Example 105 | BH-10 | BD-4 | 103 | 0.135 | 0.086 |
| Comp. Ex. 105 | BH-10-a | BD-4 | 60 | 0.135 | 0.086 |

Example 106, Comparative Example 106

Except that the compounds shown in the following table were used as the host material and the dopant material of the emitting layer, the organic EL devices were fabricated and evaluated in the same manner as in Example 1. The results are shown in Table 77.

TABLE 77

| Emitting layer | | | Chromaticity | |
|---|---|---|---|---|
| Host material | Dopant material | LT95(h) | CIEx | CIEy |
| Example 106 BH-11 | BD-4 | 90 | 0.135 | 0.086 |
| Comp. Ex. 106 BH-11-a | BD-4 | 56 | 0.135 | 0.086 |

Example 107, Comparative Example 107

Except that the compounds shown in the following table were used as the host material and the dopant material of the emitting layer, the organic EL devices were fabricated and evaluated in the same manner as in Example 1. The results are shown in Table 78.

TABLE 78

| Emitting layer | | | Chromaticity | |
|---|---|---|---|---|
| Host material | Dopant material | LT95(h) | CIEx | CIEy |
| Example 107 BH-12 | BD-4 | 80 | 0.135 | 0.086 |
| Comp. Ex. 107 BH-12-a | BD-4 | 50 | 0.135 | 0.086 |

Example 108, Comparative Example 108

Except that the compounds shown in the following table were used as the host material and the dopant material of the emitting layer, the organic EL devices were fabricated and evaluated in the same manner as in Example 1. The results are shown in Table 79.

TABLE 79

| Emitting layer | | | Chromaticity | |
|---|---|---|---|---|
| Host material | Dopant material | LT95(h) | CIEx | CIEy |
| Example 108 BH-13 | BD-4 | 157 | 0.135 | 0.085 |
| Comp. Ex. 108 BH-13-a | BD-4 | 92 | 0.135 | 0.086 |

Example 109, Comparative Example 109

Except that the compounds shown in the following table were used as the host material and the dopant material of the emitting layer, the organic EL devices were fabricated and evaluated in the same manner as in Example 1. The results are shown in Table 80.

TABLE 80

| Emitting layer | | | Chromaticity | |
|---|---|---|---|---|
| Host material | Dopant material | LT95(h) | CIEx | CIEy |
| Example 109 BH-14 | BD-4 | 110 | 0.135 | 0.086 |
| Comp. Ex. 109 BH-14-a | BD-4 | 65 | 0.135 | 0.086 |

Example 110, Comparative Example 110

Except that the compounds shown in the following table were used as the host material and the dopant material of the emitting layer, the organic EL devices were fabricated and evaluated in the same manner as in Example 1. The results are shown in Table 81.

TABLE 81

| Emitting layer | | | Chromaticity | |
|---|---|---|---|---|
| Host material | Dopant material | LT95(h) | CIEx | CIEy |
| Example 110 BH-15 | BD-4 | 100 | 0.135 | 0.086 |
| Comp. Ex. 110 BH-15-a | BD-4 | 60 | 0.135 | 0.086 |

Example 111, Comparative Examples 111-1, 111-2 and -3

Except that the compounds shown in the following table used as the host material and the dopant material of the emitting layer, the organ EL devices wreficated and evaluated in the samemannerasin Example 1. The results are shown in Table 82.

TABLE 82

| Emitting layer | | | Chromaticity | |
|---|---|---|---|---|
| Host material | Dopant material | LT95(h) | CIEx | CIEy |
| Example 111 BH-16 | BD-4 | 165 | 0.135 | 0.086 |
| Comp. Ex. 111-1 BH-1-a | BD-4 | 98 | 0.135 | 0.086 |
| Comp. Ex. 111-2 BH-1-b | BD-4 | 100 | 0.135 | 0.086 |
| Comp. Ex. 111-3 BH-1-c | BD-4 | 103 | 0.135 | 0.086 |

Example 112, Comparative Example 112

Except that the compounds shown in the following table were used as the host material and the dopant material of the emitting layer, the organic EL devices were fabricated and evaluated in the same manner as in Example 1. The results are shown in Table 83.

TABLE 83

| | Emitting layer | | | | |
|---|---|---|---|---|---|
| | Host material | Dopant material | LT95(h) | Chromaticity CIEx | CIEy |
| Example 112 | BH-7 | BD-5 | 150 | 0.135 | 0.080 |
| Comp. Ex. 112 | BH-7-a | BD-5 | 90 | 0.135 | 0.080 |

Example 113, Comparative Example 113

Except that the compounds shown in the following table were used as the host material and the dopant material of the emitting layer, the organic EL devices were fabricated and evaluated in the same manner as in Example 1. The results are shown in Table 84.

TABLE 84

| | Emitting layer | | | | |
|---|---|---|---|---|---|
| | Host material | Dopant material | LT95(h) | Chromaticity CIEx | CIEy |
| Example 113 | BH-8 | BD-5 | 155 | 0.135 | 0.080 |
| Comp. Ex. 113 | BH-8-a | BD-5 | 90 | 0.135 | 0.080 |

Example 114, Comparative Example 114

Except that the compounds shown in the following table were used as the host material and the dopant material of the emitting layer, the organic EL devices were fabricated and evaluated in the same manner as in Example 1. The results are shown in Table 85.

TABLE 85

| | Emitting layer | | | | |
|---|---|---|---|---|---|
| | Host material | Dopant material | LT95(h) | Chromaticity CIEx | CIEy |
| Example 114 | BH-9 | BD-5 | 143 | 0.135 | 0.080 |
| Comp. Ex. 114 | BH-9-a | BD-5 | 88 | 0.135 | 0.080 |

Example 115, Comparative Example 115

Except that the compounds shown in the following table were used as the host material and the dopant material of the emitting layer, the organic EL devices were fabricated and evaluated in the same manner as in Example 1. The results are shown in Table 86.

TABLE 86

| | Emitting layer | | | | |
|---|---|---|---|---|---|
| | Host material | Dopant material | LT95(h) | Chromaticity CIEx | CIEy |
| Example 115 | BH-10 | BD-5 | 124 | 0.135 | 0.080 |
| Comp. Ex. 115 | BH-10-a | BD-5 | 75 | 0.135 | 0.080 |

Example 116, Comparative Example 116

Except that the compounds shown in the following table were used as the host material and the dopant material of the emitting layer, the organic EL devices were fabricated and evaluated in the same manner as in Example 1. The results are shown in Table 87.

TABLE 87

| | Emitting layer | | | | |
|---|---|---|---|---|---|
| | Host material | Dopant material | LT95(h) | Chromaticity CIEx | CIEy |
| Example 116 | BH-11 | BD-5 | 106 | 0.135 | 0.080 |
| Comp. Ex. 116 | BH-11-a | BD-5 | 68 | 0.135 | 0.080 |

Example 117, Comparative Example 117

Except that the compounds shown in the following table were used as the host material and the dopant material of the emitting layer, the organic EL devices were fabricated and evaluated in the same manner as in Example 1. The results are shown in Table 88.

TABLE 88

| | Emitting layer | | | | |
|---|---|---|---|---|---|
| | Host material | Dopant material | LT95(h) | Chromaticity CIEx | CIEy |
| Example 117 | BH-12 | BD-5 | 90 | 0.135 | 0.081 |
| Comp. Ex. 117 | BH-12-a | BD-5 | 62 | 0.135 | 0.080 |

Example 118, Comparative Example 118

Except that the compounds shown in the following table were used as the host material and the dopant material of the emitting layer, the organic EL devices were fabricated and evaluated in the same manner as in Example 1. The results are shown in Table 89.

TABLE 89

| | Emitting layer | | | | |
|---|---|---|---|---|---|
| | Host material | Dopant material | LT95(h) | Chromaticity CIEx | CIEy |
| Example 118 | BH-13 | BD-5 | 195 | 0.135 | 0.080 |
| Comp. Ex. 118 | BH-13-a | BD-5 | 117 | 0.135 | 0.080 |

Example 119, Comparative Example 119

Except that the compounds shown in the following table were used as the host material and the dopant material of the emitting layer, the organic EL devices were fabricated and evaluated in the same manner as in Example 1. The results are shown in Table 90.

TABLE 90

| | Emitting layer | | | |
|---|---|---|---|---|
| | Host material | Dopant material | | Chromaticity |
| | | | LT95(h) | CIEx | CIEy |
| Example 119 | BH-14 | BD-5 | 138 | 0.135 | 0.080 |
| Comp. Ex. 119 | BH-14-a | BD-5 | 80 | 0.135 | 0.080 |

Example 120, Comparative Example 120

Except that the compounds shown in the following table were used as the host material and the dopant material of the emitting layer, the organic EL devices were fabricated and evaluated in the same manner as in Example 1. The results are shown in Table 91.

TABLE 91

| | Emitting layer | | | |
|---|---|---|---|---|
| | Host material | Dopant material | LT95(h) | CIEx | CIEy |
| Example 120 | BH-15 | BD-5 | 130 | 0.135 | 0.080 |
| Comp. Ex. 120 | BH-15-a | BD-5 | 77 | 0.135 | 0.080 |

Example 121, Comparative Examples 121-1, 121-2 and 121-3

Except that the compounds shown in the following table were used as the host material and the dopant material of the emitting layer, the organic EL devices were fabricated and evaluated in the same manner as in Example 1. The results are shown in Table 92.

TABLE 92

| | Emitting layer | | | |
|---|---|---|---|---|
| | Host material | Dopant material | LT95(h) | CIEx | CIEy |
| Example 121 | BH-16 | BD-5 | 200 | 0.135 | 0.080 |
| Comp. Ex. 121-1 | BH-1-a | BD-5 | 123 | 0.135 | 0.080 |
| Comp. Ex. 121-2 | BH-1-b | BD-5 | 125 | 0.135 | 0.080 |
| Comp. Ex. 121-3 | BH-1-c | BD-5 | 135 | 0.135 | 0.080 |

Example 122, Comparative Example 122

Except that the compounds shown in the following table were used as the host material and the dopant material of the emitting layer, the organic EL devices were fabricated and evaluated in the same manner as in Example 1. The results are shown in Table 93.

TABLE 93

| | Emitting layer | | | |
|---|---|---|---|---|
| | Host material | Dopant material | LT95(h) | CIEx | CIEy |
| Example 122 | BH-7 | BD-6 | 190 | 0.136 | 0.090 |
| Comp. Ex. 122 | BH-7-a | BD-6 | 114 | 0.136 | 0.090 |

Example 123, Comparative Example 123

Except that the compounds shown in the following table were used as the host material and the dopant material of the emitting layer, the organic EL devices were fabricated and evaluated in the same manner as in Example 1. The results are shown in Table 94.

TABLE 94

| | Emitting layer | | | |
|---|---|---|---|---|
| | Host material | Dopant material | LT95(h) | CIEx | CIEy |
| Example 123 | BH-8 | BD-6 | 179 | 0.136 | 0.090 |
| Comp. Ex. 123 | BH-8-a | BD-6 | 110 | 0.136 | 0.090 |

Example 124, Comparative Example 124

Except that the compounds shown in the following table were used as the host material and the dopant material of the emitting layer, the organic EL devices were fabricated and evaluated in the same manner as in Example 1. The results are shown in Table 95.

TABLE 95

| | Emitting layer | | | |
|---|---|---|---|---|
| | Host material | Dopant material | LT95(h) | CIEx | CIEy |
| Example 124 | BH-9 | BD-6 | 164 | 0.136 | 0.090 |
| Comp. Ex. 124 | BH-9-a | BD-6 | 98 | 0.136 | 0.090 |

Example 125, Comparative Example 125

Except that the compounds shown in the following table were used as the host material and the dopant material of the emitting layer, the organic EL devices were fabricated and evaluated in the same manner as in Example 1. The results are shown in Table 96.

TABLE 96

| | Emitting layer | | | |
|---|---|---|---|---|
| | Host material | Dopant material | LT95(h) | CIEx | CIEy |
| Example 125 | BH-10 | BD-6 | 147 | 0.136 | 0.090 |
| Comp. Ex. 125 | BH-10-a | BD-6 | 88 | 0.136 | 0.090 |

Example 126, Comparative Example 126

Except that the compounds shown in the following table were used as the host material and the dopant material of the emitting layer, the organic EL devices were fabricated and evaluated in the same manner as in Example 1. The results are shown in Table 97.

TABLE 97

| | Emitting layer | | | | |
|---|---|---|---|---|---|
| | Host material | Dopant material | LT95(h) | Chromaticity CIEx | CIEy |
| Example 126 | BH-11 | BD-6 | 122 | 0.136 | 0.090 |
| Comp. Ex. 126 | BH-11-a | BD-6 | 80 | 0.136 | 0.090 |

Example 127, Comparative Example 127

Except that the compounds shown in the following table were used as the host material and the dopant material of the emitting layer, the organic EL devices were fabricated and evaluated in the same manner as in Example 1. The results are shown in Table 98.

TABLE 98

| | Emitting layer | | | | |
|---|---|---|---|---|---|
| | Host material | Dopant material | LT95(h) | Chromaticity CIEx | CIEy |
| Example 127 | BH-12 | BD-6 | 118 | 0.136 | 0.090 |
| Comp. Ex. 127 | BH-12-a | BD-6 | 72 | 0.136 | 0.090 |

Example 128, Comparative Example 128

Except that the compounds shown in the following table were used as the host material and the dopant material of the emitting layer, the organic EL devices were fabricated and evaluated in the same manner as in Example 1. The results are shown in Table 99.

TABLE 99

| | Emitting layer | | | | |
|---|---|---|---|---|---|
| | Host material | Dopant material | LT95(h) | Chromaticity CIEx | CIEy |
| Example 128 | BH-13 | BD-6 | 242 | 0.136 | 0.090 |
| Comp. Ex. 128 | BH-13-a | BD-6 | 140 | 0.136 | 0.090 |

Example 129, Comparative Example 129

Except that the compounds shown in the following table were used as the host material and the dopant material of the emitting layer, the organic EL devices were fabricated and evaluated in the same manner as in Example 1. The results are shown in Table 100.

TABLE 100

| | Emitting layer | | | | |
|---|---|---|---|---|---|
| | Host material | Dopant material | LT95(h) | Chromaticity CIEx | CIEy |
| Example 129 | BH-14 | BD-6 | 155 | 0.136 | 0.090 |
| Comp. Ex. 129 | BH-14-a | BD-6 | 92 | 0.136 | 0.090 |

Example 130, Comparative Example 130

Except that the compounds shown in the following table were used as the host material and the dopant material of the emitting layer, the organic EL devices were fabricated and evaluated in the same manner as in Example 1. The results are shown in Table 101.

TABLE 101

| | Emitting layer | | | | |
|---|---|---|---|---|---|
| | Host material | Dopant material | LT95(h) | Chromaticity CIEx | CIEy |
| Example 130 | BH-15 | BD-6 | 146 | 0.136 | 0.090 |
| Comp. Ex. 130 | BH-15-a | BD-6 | 90 | 0.136 | 0.090 |

Example 131, Comparative Examples 131-1, 131-2 and 131-3

Except that the compounds shown in the following table were used as the host material and the dopant material of the emitting layer, the organic EL devices were fabricated and evaluated in the same manner as in Example 1. The results are shown in Table 102.

TABLE 102

| | Emitting layer | | | | |
|---|---|---|---|---|---|
| | Host material | Dopant material | LT95(h) | Chromaticity CIEx | CIEy |
| Example 131 | BH-16 | BD-6 | 245 | 0.136 | 0.090 |
| Comp. Ex. 131-1 | BH-1-a | BD-6 | 146 | 0.136 | 0.090 |
| Comp. Ex. 131-2 | BH-1-b | BD-6 | 142 | 0.136 | 0.090 |
| Comp. Ex. 131-3 | BH-1-c | BD-6 | 150 | 0.136 | 0.090 |

Example 132, Comparative Example 132

Except that the compounds shown in the following table were used as the host material and the dopant material of the emitting layer, the organic EL devices were fabricated and evaluated in the same manner as in Example 1. The results are shown in Table 103.

TABLE 103

| | Emitting layer | | | | |
|---|---|---|---|---|---|
| | Host material | Dopant material | LT95(h) | Chromaticity CIEx | CIEy |
| Example 132 | BH-7 | BD-7 | 82 | 0.144 | 0.061 |
| Comp. Ex. 132 | BH-7-a | BD-7 | 50 | 0.144 | 0.061 |

Example 133, Comparative Example 133

Except that the compounds shown in the following table were used as the host material and the dopant material of the emitting layer, the organic EL devices were fabricated and evaluated in the same manner as in Example 1. The results are shown in Table 104.

TABLE 104

| | Emitting layer | | | | |
|---|---|---|---|---|---|
| | Host material | Dopant material | LT95(h) | Chromaticity CIEx | CIEy |
| Example 133 | BH-8 | BD-7 | 82 | 0.144 | 0.061 |
| Comp. Ex. 133 | BH-8-a | BD-7 | 50 | 0.144 | 0.061 |

Example 134, Comparative Example 134

Except that the compounds shown in the following table were used as the host material and the dopant material of the emitting layer, the organic EL devices were fabricated and evaluated in the same manner as in Example 1. The results are shown in Table 105.

TABLE 105

| | Emitting layer | | | | |
|---|---|---|---|---|---|
| | Host material | Dopant material | LT95(h) | Chromaticity CIEx | CIEy |
| Example 134 | BH-9 | BD-7 | 74 | 0.144 | 0.060 |
| Comp. Ex. 134 | BH-9-a | BD-7 | 48 | 0.144 | 0.060 |

Example 135, Comparative Example 135

Except that the compounds shown in the following table were used as the host material and the dopant material of the emitting layer, the organic EL devices were fabricated and evaluated in the same manner as in Example 1. The results are shown in Table 106.

TABLE 106

| | Emitting layer | | | | |
|---|---|---|---|---|---|
| | Host material | Dopant material | LT95(h) | Chromaticity CIEx | CIEy |
| Example 135 | BH-10 | BD-7 | 63 | 0.144 | 0.061 |
| Comp. Ex. 135 | BH-10-a | BD-7 | 42 | 0.144 | 0.061 |

Example 136, Comparative Example 136

Except that the compounds shown in the following table were used as the host material and the dopant material of the emitting layer, the organic EL devices were fabricated and evaluated in the same manner as in Example 1. The results are shown in Table 107.

TABLE 107

| | Emitting layer | | | | |
|---|---|---|---|---|---|
| | Host material | Dopant material | LT95(h) | Chromaticity CIEx | CIEy |
| Example 136 | BH-11 | BD-7 | 61 | 0.144 | 0.061 |
| Comp. Ex. 136 | BH-11-a | BD-7 | 37 | 0.144 | 0.061 |

Example 137, Comparative Example 137

Except that the compounds shown in the following table were used as the host material and the dopant material of the emitting layer, the organic EL devices were fabricated and evaluated in the same manner as in Example 1. The results are shown in Table 108.

TABLE 108

| | Emitting layer | | | | |
|---|---|---|---|---|---|
| | Host material | Dopant material | LT95(h) | Chromaticity CIEx | CIEy |
| Example 137 | BH-12 | BD-7 | 55 | 0.144 | 0.061 |
| Comp. Ex. 137 | BH-12-a | BD-7 | 33 | 0.144 | 0.061 |

Example 138, Comparative Example 138

Except that the compounds shown in the following table were used as the host material and the dopant material of the emitting layer, the organic EL devices were fabricated and evaluated in the same manner as in Example 1. The results are shown in Table 109.

TABLE 109

| | Emitting layer | | | | |
|---|---|---|---|---|---|
| | Host material | Dopant material | LT95(h) | Chromaticity CIEx | CIEy |
| Example 138 | BH-13 | BD-7 | 105 | 0.144 | 0.060 |
| Comp. Ex. 138 | BH-13-a | BD-7 | 65 | 0.144 | 0.061 |

Example 139, Comparative Example 139

Except that the compounds shown in the following table were used as the host material and the dopant material of the emitting layer, the organic EL devices were fabricated and evaluated in the same manner as in Example 1. The results are shown in Table 110.

TABLE 110

| | Emitting layer | | | | |
|---|---|---|---|---|---|
| | Host material | Dopant material | LT95(h) | Chromaticity CIEx | CIEy |
| Example 139 | BH-14 | BD-7 | 75 | 0.144 | 0.061 |
| Comp. Ex. 139 | BH-14-a | BD-7 | 45 | 0.144 | 0.061 |

Example 140, Comparative Example 140

Except that the compounds shown in the following table were used as the host material and the dopant material of the emitting layer, the organic EL devices were fabricated and evaluated in the same manner as in Example 1. The results are shown in Table 111.

TABLE 111

| | Emitting layer | | | | |
|---|---|---|---|---|---|
| | Host material | Dopant material | LT95(h) | Chromaticity CIEx | CIEy |
| Example 140 | BH-15 | BD-7 | 70 | 0.144 | 0.061 |
| Comp. Ex. 140 | BH-15-a | BD-7 | 43 | 0.144 | 0.061 |

Example 141, Comparative Examples 141-1, 141-2 and 141-3

Except that the compounds shown in the following table were used as the host material and the dopant material of the emitting layer, the organic EL devices were fabricated and evaluated in the same manner as in Example 1. The results are shown in Table 112.

TABLE 112

| | Emitting layer | | | | |
|---|---|---|---|---|---|
| | Host material | Dopant material | LT95(h) | Chromaticity CIEx | CIEy |
| Example 141 | BH-16 | BD-7 | 107 | 0.144 | 0.061 |
| Comp. Ex. 141-1 | BH-1-a | BD-7 | 65 | 0.144 | 0.061 |
| Comp. Ex. 141-2 | BH-1-b | BD-7 | 66 | 0.144 | 0.061 |
| Comp. Ex. 141-3 | BH-1-c | BD-7 | 72 | 0.144 | 0.061 |

From the results of Tables 1 to 112, it can be recognized that, f the compound of the invention having a deuterium atom at the particular position is used in the emitting layer of the organic EL device, the lifetime of the organic EL device is prolonged compared with the case where the compound having no deuterium atom at the particular position is used. Moreover, comparison between Example 4 and Comparative Example 4-2 shows that even in compound having deuterium atom at a particular site, the driving voltages of organic EL device can be lowered by employing the structure of the invention.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The invention claimed is:
1. A compound having structures represented by the following formula (2):

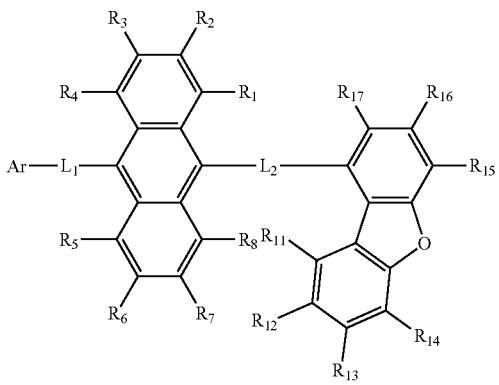

(2)

wherein in the formula (2),
$R_1$ to $R_8$ and $R_{11}$ to $R_{14}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{15}$ to $R_{17}$ are hydrogen atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ may be the same with or different from each other;
at least one of $R_1$ to $R_8$ is a deuterium atom;
two or more adjacent groups of $R_1$ to $R_4$, two or more adjacent groups of $R_5$ to $R_8$ and two or more adjacent groups of $R_{11}$ to $R_{14}$ do not form a ring;
$L_1$ is
a single bond,
a substituted or unsubstituted arylene group having 6 to 30 ring carbon atoms, or a substituted or unsubstituted divalent heterocyclic group having 5 to 30 ring atoms;

$L_2$ is a substituted or unsubstituted naphthalenediyl group;

Ar is selected from groups represented by the following formulas (a1) to (a4):

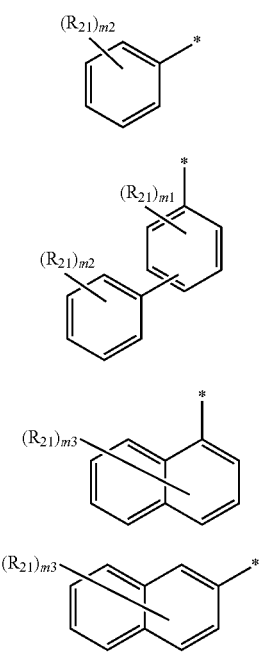

wherein in the formulas (a1) to (a4),

* is a single bond bonding to $L_1$;

$R_{21}$ is a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (2);

m1 is an integer of 0 to 4;

m2 is an integer of 0 to 5;

m3 is an integer of 0 to 7;

when each of m1 to m3 is 2 or more, the plural $R_{21}$s may be the same or different; and when each of m1 to m3 is 2 or more, adjacent plural $R_{21}$s are bonded with each other to form a substituted or unsubstituted, saturated or unsaturated ring, or do not form a substituted or unsubstituted, saturated or unsaturated ring.

2. The compound according to claim 1, wherein at least two of $R_1$ to $R_8$ are deuterium atoms.

3. The compound according to claim 1, wherein $R_1$ to $R_8$ are all deuterium atoms.

4. The compound according to claim 1, wherein $L_1$ is an unsubstituted arylene group having 6 to 30 ring carbon atoms in which at least one hydrogen atom is a deuterium atom, or an unsubstituted divalent heterocyclic group having 5 to 30 ring atoms in which at least one hydrogen atom is a deuterium atom.

5. The compound according to claim 1, wherein $L_1$ is independently a single bond, or a substituted or unsubstituted arylene group having 6 to 14 ring carbon atoms.

6. The compound according to claim 1, wherein $R_{11}$ to $R_{14}$ are hydrogen atoms.

7. The compound according to claim 1, wherein at least one of $R_{11}$ to $R_{17}$ is deuterium atom.

8. The compound according to claim 1, wherein the compound represented by the formula (2) is a compound represented by following formula (2-1):

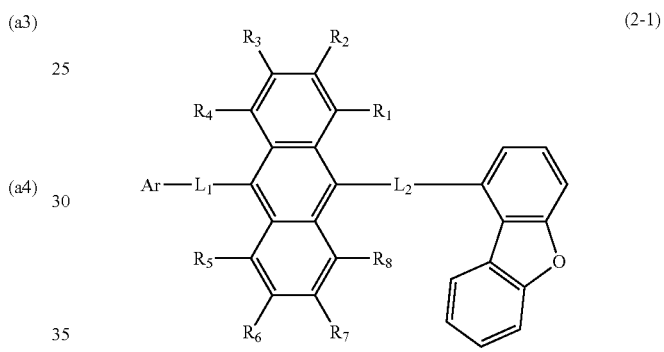

wherein in the formula (2-1), $R_1$ to $R_8$, Ar, $L_1$ and $L_2$ are as defined in the formula (2).

9. The compound according to claim 1, wherein the compound represented by the formula (2) is a compound represented by following formula (2-2):

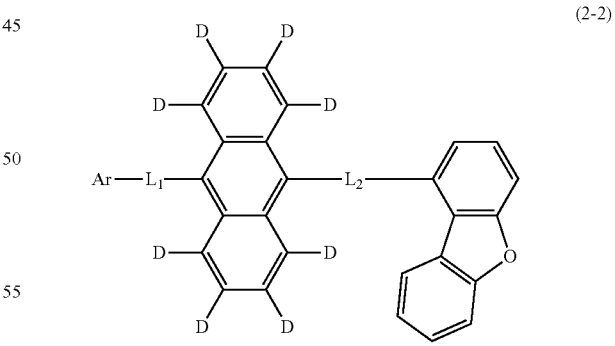

wherein in the formula (2-2), Ar, $L_1$ and $L_2$ are as defined in the formula (2).

10. The compound according to claim 1, wherein the compound is a material for an organic electroluminescence device.

11. A composition comprising the compound according to claim 1, wherein the content ratio of the protium compound having the same structure as formula (2) except that only protium atoms are contained as hydrogen atoms to the total of the compound represented by formula (2) and the protium compound is 99 mol % or less.

12. An organic electroluminescence device comprising:
a cathode,
an anode, and
one or two or more organic layer disposed between the cathode and the anode,
wherein at least one organic layer comprises the compound according to claim 1.

13. The organic electroluminescence device according to claim 12, wherein the organic layer comprises an emitting layer, and the emitting layer comprises the compound or the composition.

14. The organic electroluminescence device according to claim 12, wherein the emitting layer further comprises one or more compounds selected from the group consisting of compounds represented by the following formulas (11), (21), (31), (41), (51), (61), (71) and (81):

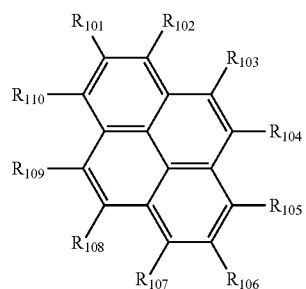

(11)

wherein, in the formula (11),
one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;
at least one of $R_{101}$ to $R_{110}$ is a monovalent group represented by the formula (12);
$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (2);

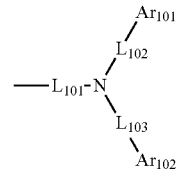

(12)

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;
$L_{101}$ to $L_{103}$ are independently
a single bond,
a substituted or unsubstituted arylene group having 6 to 30 ring carbon atoms, or
a substituted or unsubstituted divalent heterocyclic group having 5 to 30 ring atoms;

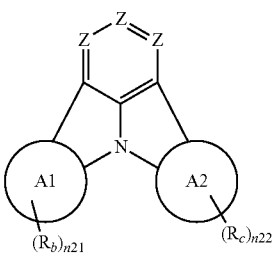

(21)

wherein, in the formula (21),
Zs are independently $CR_a$ or N;
A1 ring and A2 ring are independently a substituted or unsubstituted aromatic hydrocarbon ring having 6 to 50 ring carbon atoms, or a substituted or unsubstituted heterocyclic ring having 5 to 50 ring atoms;
when plural $R_a$s exist, one or more pairs of two or more adjacent groups of $R_a$ are bonded with each other to form a substituted or unsubstituted, saturated or unsaturated ring, or do not form a substituted or unsubstituted, saturated or unsaturated ring;
when plural $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;
when plural $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;
n21 and n22 are independently an integer of 0 to 4;
$R_a$ to $R_c$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms, a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
R$_{901}$ to R$_{907}$ are as defined in the formula (2);

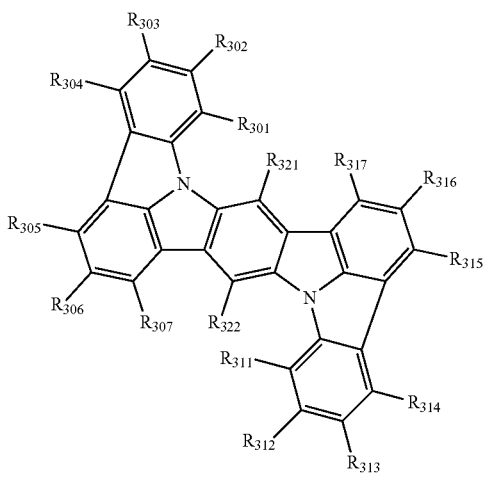

(31)

wherein, in the formula (31),
one or more pairs of two or more adjacent groups of R$_{301}$ to R$_{307}$ and R$_{311}$ to R$_{317}$ form a substituted or unsubstituted, saturated or unsaturated ring, or do not form a substituted or unsubstituted, saturated or unsaturated ring;
R$_{301}$ to R$_{307}$ and R$_{311}$ to R$_{317}$ that do not form the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
R$_{321}$ and R$_{322}$ are independently
a hydrogen atom,
a substituted or unsubstituted alkyl group having 1 to 50 carbon atoms,
a substituted or unsubstituted alkenyl group having 2 to 50 carbon atoms, a substituted or unsubstituted alkynyl group having 2 to 50 carbon atoms,
a substituted or unsubstituted cycloalkyl group having 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
R$_{901}$ to R$_{907}$ are as defined in the formula (2);

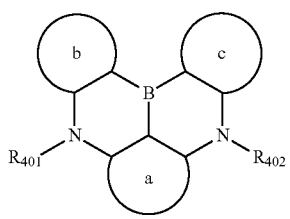

(41)

wherein, in the formula (41),
a ring, b ring and c ring are independently
a substituted or unsubstituted aromatic hydrocarbon ring having 6 to 50 ring carbon atoms, or
a substituted or unsubstituted heterocyclic ring having 5 to 50 ring atoms;
R$_{401}$ and R$_{402}$ are independently bonded to the a ring, the b ring or the c ring to form a substituted or unsubstituted heterocyclic ring or do not form a substituted or unsubstituted heterocyclic ring;
R$_{401}$ and R$_{402}$ that do not form the substituted or unsubstituted heterocyclic ring are independently a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;

p-q-r-s-t (51)

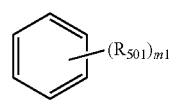

(52)

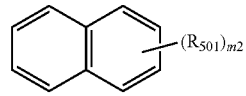

(53)

(54)

1031

-continued

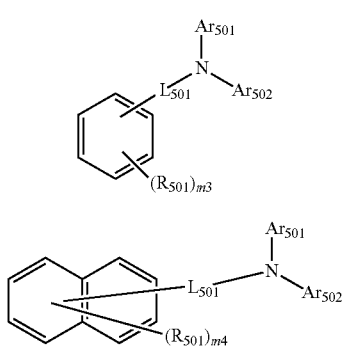

(55)

(56)

wherein, in the formula (51), r ring is a ring represented by the formula (52) or formula (53) which is fused to an adjacent ring at an arbitrary positon;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when plural $R_{501}$s exist, adjacent plural $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (2);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_5D$ is

1032 a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is independently an integer of 0 to 2, m2 is independently an integer of 0 to 4, m3 is independently an integer of 0 to 3, and m4 is independently an integer of 0 to 5; when plural $R_{501}$s exist, the plural $R_{501}$s may be the same or different;

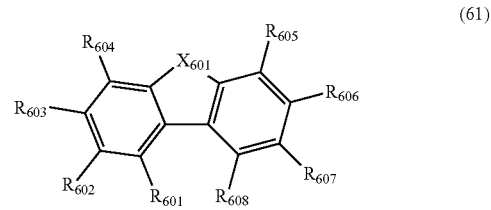

(61)

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

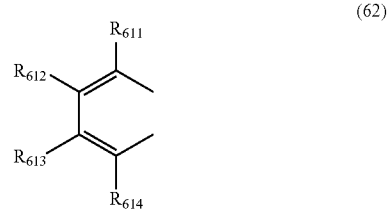

(62)

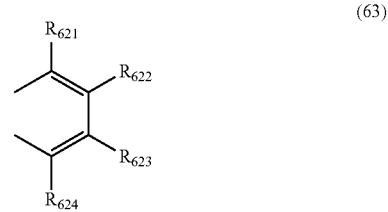

(63)

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (2);

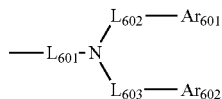

(64)

wherein, in the formula (64), $Ar_{601}$ and $Ar_{602}$ are independently
a substituted or unsubstituted aryl group having 6 to 50 ring carbon atoms, or
a substituted or unsubstituted monovalent heterocyclic group having 5 to 50 ring atoms;
$L_{601}$ to $L_{603}$ are independently
a single bond,
a substituted or unsubstituted arylene group having 6 to 30 ring carbon atoms,
a substituted or unsubstituted divalent heterocyclic group having 5 to 30 ring atoms, or
a divalent linking group formed by bonding 2 to 4 above mentioned groups;

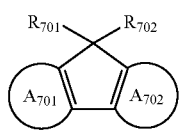

(71)

wherein, in the formula (71),
$A_{701}$ ring and $A_{702}$ ring are independently
a substituted or unsubstituted aromatic hydrocarbon ring having 6 to 50 ring carbon atoms, or
a substituted or unsubstituted heterocyclic ring having 5 to 50 ring atoms;
One or more rings selected from the group consisting of $A_{701}$ ring and $A_{702}$ ring are bonded to the bond * of the structure represented by the following formula (72);

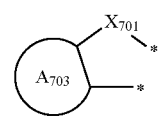

(72)

wherein, in the formula (72),
$A_{703}$ rings are independently
a substituted or unsubstituted aromatic hydrocarbon ring having 6 to 50 ring carbon atoms, or
a substituted or unsubstituted heterocyclic ring having 5 to 50 ring atoms;
$X_{701}$ is $NR_{703}$, $C(R_{704})(R_{705})$, $Si(R_{706})$ $(R_{707})$, $Ge(R_{708})$ $(R_{709})$, O, S or Se;
$R_{701}$ and $R_{702}$ are bonded with each other to form a substituted or unsubstituted, saturated or unsaturated ring or do not form a substituted or unsubstituted saturated or unsaturated ring;
$R_{701}$ and $R_{702}$ that do not form the substituted or unsubstituted, saturated or unsaturated ring, and $R_{703}$ to $R_{709}$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are as defined in the formula (2);

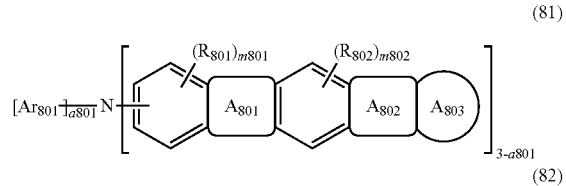

(81)

(82)

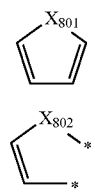

(83)

wherein, in the formula (81),
$A_{801}$ ring is a ring represented by the formula (82) which is fused to an adjacent ring at an arbitrary position;
$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{90})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (2);

m801 and m802 are independently an integer of 0 to 2; when these are 2, plural $R_{801}$s or $R_{802}$s may be the same or different;

a801 is an integer of 0 to 2; when a801 is 0 or 1, the structure in the parenthese indicated by "3-a801" may be the same or different from each other; when a801 is 2, $Ar_{801}$s may be the same or different from each other.

15. The organic electroluminescence device according to claim 14, wherein in the formula (11), two of $R_{101}$ to $R_{110}$ are the group represented by the formula (12).

16. The organic electroluminescence device according to claim 14, wherein the compound represented by the formula (11) is represented by the following formula (13):

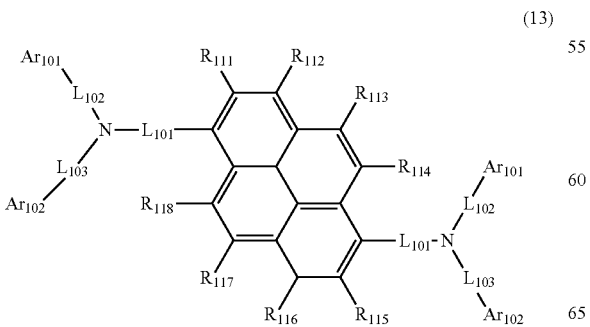

(13)

wherein, in the formula (13), $R_{111}$ to $R_{118}$ are the same as $R_{101}$ to $R_{110}$ that is not a monovalent group represented by the formula (12) in the formula (11); $Ar_{101}$, $Ar_{102}$, $L_{101}$, $L_{102}$ and $L_{103}$ are as defined in the formula (12).

17. The organic electroluminescence device according to claim 16, wherein the compound represented by the formula (13) is represented by the following formula (14):

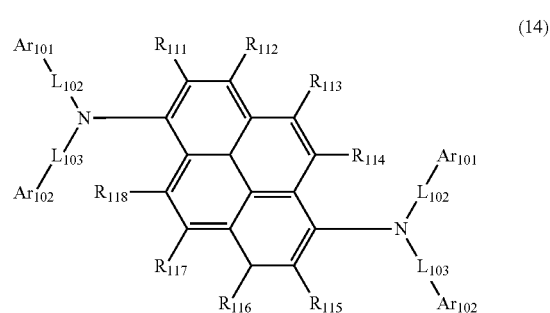

(14)

wherein, in the formula (14), $R_{111}$ to $R_{118}$ are as defined in the formula (13); $Ar_{101}$, $Ar_{102}$, $L_{102}$ and $L_{103}$ are as defined in the formula (12).

18. The organic electroluminescence device according to claim 16, wherein the compound represented by the formula (13) is represented by the following formula (15):

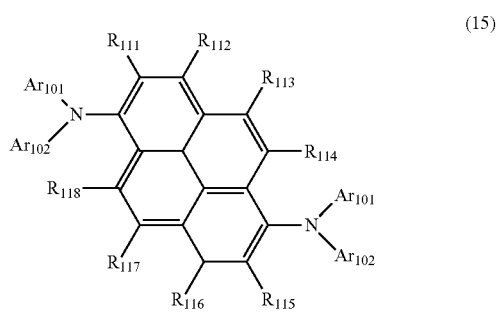

(15)

wherein, in the formula (15), $R_{111}$ to $R_{118}$ are as defined in the formula (13); $Ar_{101}$ and $Ar_{102}$ are as defined in the formula (12).

19. The organic electroluminescence device according to claim 16, wherein the compound represented by the formula (13) is represented by the following formula (17):

(17)

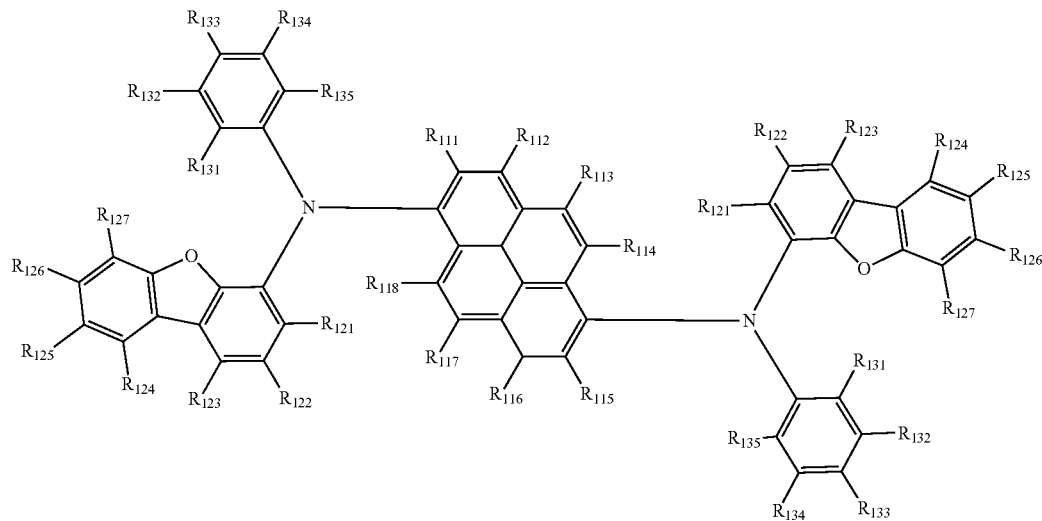

wherein, in the formula (17), $R_{111}$ to $R_{118}$ are as defined in the formula (13);

One or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:

$R_{121}$ to $R_{127}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (2);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (2).

20. The organic electroluminescence device according to claim 12, further comprising a hole-transporting layer between the anode and the emitting layer.

21. The organic electroluminescence device according to claim 12, further comprising an electron-transporting layer between the cathode and the emitting layer.

22. An electronic apparatus wherein the organic electroluminescence device according to claim 12 is provided.

23. An organic electroluminescence device comprising:
a cathode,
an anode, and
one or two or more organic layer disposed between the cathode and the anode,
wherein at least one organic layer comprises the composition according to claim 11.

* * * * *